(12) United States Patent
Phillips et al.

(10) Patent No.: US 11,524,949 B2
(45) Date of Patent: Dec. 13, 2022

(54) DEGRADERS AND DEGRONS FOR TARGETED PROTEIN DEGRADATION

(71) Applicant: C4 Therapeutics, Inc., Watertown, MA (US)

(72) Inventors: Andrew J. Phillips, Arlington, MA (US); Christopher G. Nasveschuk, Stoneham, MA (US); James A. Henderson, Weston, MA (US); Minsheng He, Andover, MA (US); Kiel Lazarski, Boston, MA (US)

(73) Assignee: C4 Therapeutics, Inc., Watertown, MA (US)

( * ) Notice: Subject to any disclaimer, the term of this patent is extended or adjusted under 35 U.S.C. 154(b) by 259 days.

(21) Appl. No.: 16/874,475

(22) Filed: May 14, 2020

(65) Prior Publication Data

US 2022/0251061 A1  Aug. 11, 2022

Related U.S. Application Data

(63) Continuation of application No. PCT/US2018/061573, filed on Nov. 16, 2018.

(60) Provisional application No. 62/587,303, filed on Nov. 16, 2017.

(51) Int. Cl.
*C07D 401/04* (2006.01)
*C07D 403/04* (2006.01)
*C07D 413/04* (2006.01)

(52) U.S. Cl.
CPC ......... *C07D 401/04* (2013.01); *C07D 403/04* (2013.01); *C07D 413/04* (2013.01)

(58) Field of Classification Search
CPC .. C07D 401/04; C07D 413/04; C07D 401/12; C07D 221/22
See application file for complete search history.

(56) References Cited

U.S. PATENT DOCUMENTS

| | | | |
|---|---|---|---|
| 2,763,652 A | 9/1956 | Safir et al. | |
| 2,948,723 A | 8/1963 | Bicking | |
| 5,635,517 A | 6/1997 | Muller et al. | |
| 6,045,501 A | 4/2000 | Elsayed et al. | |
| 6,306,663 B1 | 10/2001 | Kenten et al. | |
| 6,315,720 B1 | 11/2001 | Williams et al. | |
| 6,395,754 B1 | 5/2002 | Muller et al. | |
| 6,561,976 B2 | 5/2003 | Elsayed et al. | |
| 6,561,977 B2 | 5/2003 | Williams et al. | |
| 6,755,784 B2 | 6/2004 | Williams et al. | |
| 6,869,399 B2 | 3/2005 | Williams et al. | |
| 6,908,432 B2 | 6/2005 | Elsayed et al. | |
| 7,041,298 B2 | 5/2006 | Deshaies et al. | |
| 7,141,018 B2 | 11/2006 | Williams et al. | |
| 7,208,157 B2 | 4/2007 | Deshaies et al. | |
| 7,230,012 B2 | 6/2007 | D-Angio et al. | |
| 7,820,697 B2 | 10/2010 | Man et al. | |
| 7,874,984 B2 | 1/2011 | Elsayed et al. | |
| 7,959,566 B2 | 6/2011 | Williams et al. | |
| 8,204,763 B2 | 6/2012 | Elsayed et al. | |
| 8,315,886 B2 | 11/2012 | Williams et al. | |
| 8,589,188 B2 | 11/2013 | Elsayed et al. | |
| 8,626,531 B2 | 1/2014 | Williams et al. | |
| 8,673,939 B2 | 3/2014 | Zeldis | |
| 8,735,428 B2 | 5/2014 | Zeldis | |
| 8,741,929 B2 | 6/2014 | Zeldis | |
| 8,828,427 B2 | 9/2014 | Tutino et al. | |
| 9,056,120 B2 | 6/2015 | Zeldis | |
| 9,101,621 B2 | 8/2015 | Zeldis | |
| 9,101,622 B2 | 8/2015 | Zeldis | |
| 9,125,915 B2 | 9/2015 | Miyoshi et al. | |
| 9,249,161 B2 | 2/2016 | Albrecht et al. | |
| 10,351,568 B2 | 7/2019 | Finley et al. | |
| 10,646,575 B2 | 5/2020 | Phillips et al. | |
| 10,660,968 B2 | 5/2020 | Phillips et al. | |
| 10,849,982 B2 | 12/2020 | Phillips et al. | |
| 10,905,768 B1 | 2/2021 | Phillips et al. | |
| 2006/0069067 A1 | 3/2006 | Bhatnagar et al. | |
| 2013/0190340 A1 | 7/2013 | Hedstrom et al. | |
| 2014/0302523 A1 | 10/2014 | Crews et al. | |
| 2014/0356322 A1 | 12/2014 | Crews et al. | |
| 2015/0119435 A1 | 4/2015 | Crews et al. | |
| 2015/0274738 A1 | 10/2015 | Gray et al. | |
| 2015/0291562 A1 | 10/2015 | Crew et al. | |
| 2016/0016966 A1 | 1/2016 | Amans et al. | |
| 2016/0022642 A1 | 1/2016 | Crews et al. | |
| 2016/0045607 A1 | 2/2016 | Crew et al. | |
| 2016/0046661 A1 | 2/2016 | Gray et al. | |
| 2016/0058872 A1 | 3/2016 | Crew et al. | |
| 2016/0176916 A1 | 6/2016 | Bradner et al. | |
| 2016/0214972 A1 | 7/2016 | Jin et al. | |
| 2016/0272639 A1 | 9/2016 | Crew et al. | |
| 2017/0008904 A1 | 1/2017 | Crew et al. | |

(Continued)

FOREIGN PATENT DOCUMENTS

BR   PI1100318 A2   5/2013
CN   103421061 A   12/2013
(Continued)

OTHER PUBLICATIONS

Shi. Nature Reviews: Genetics, 2007, 8, 829-833 (Year: 2007).*
Lau. Journal of Cell Science, 2012, 125(12), 2815-2824 (Year: 2012).*
Yu. Mediators of Inflammation, 2014, article ID 950742, 1-10 (Year: 2014).*
Bornemann. Journal of Organic Chemistry, 2005, 70, 5862-5968. (Year: 2005).*
Burns.Archives of Toxicology, 2012, 86, 1491-1504 (Year: 2012).*
Shukla. Andrology, 2016, 4, 366-381 (Year: 2016).*

(Continued)

*Primary Examiner* — Noble E Jarrell

(74) *Attorney, Agent, or Firm* — Knowles Intellectual Property Strategies, LLC

(57) ABSTRACT

Pharmaceutical Degraders and Degrons for use in therapeutic applications are described herein.

18 Claims, 390 Drawing Sheets

(56) References Cited

U.S. PATENT DOCUMENTS

| | | |
|---|---|---|
| 2017/0037004 A1 | 2/2017 | Crew et al. |
| 2017/0065719 A1 | 3/2017 | Qian et al. |
| 2018/0015087 A1 | 1/2018 | Liu et al. |
| 2018/0085465 A1 | 3/2018 | Bradner et al. |
| 2020/0140456 A1 | 5/2020 | Phillips et al. |
| 2020/0207733 A1 | 7/2020 | Norcross et al. |
| 2020/0207764 A1 | 7/2020 | Norcross et al. |
| 2020/0207783 A1 | 7/2020 | Norcross et al. |
| 2020/0308171 A1 | 10/2020 | Jaeschke et al. |
| 2020/0361930 A1 | 11/2020 | Duplessis et al. |
| 2021/0009559 A1 | 1/2021 | Henderson et al. |
| 2021/0032245 A1 | 2/2021 | Nasveschuk et al. |

FOREIGN PATENT DOCUMENTS

| | | |
|---|---|---|
| WO | WO 1998/011111 A1 | 3/1998 |
| WO | WO 2002/059106 A1 | 8/2002 |
| WO | WO 2006/102557 A2 | 9/2006 |
| WO | WO 2007/031791 A1 | 3/2007 |
| WO | WO 2008/027542 A2 | 3/2008 |
| WO | WO 2008/033567 A1 | 3/2008 |
| WO | WO 2008/039489 A2 | 4/2008 |
| WO | WO 2008/115516 A2 | 9/2008 |
| WO | WO 2008/122038 A1 | 10/2008 |
| WO | WO 2009/042177 A1 | 4/2009 |
| WO | WO 2009/139880 A1 | 11/2009 |
| WO | WO 2009/145899 A1 | 12/2009 |
| WO | WO 2010/053732 A1 | 5/2010 |
| WO | WO 2010/107485 A1 | 9/2010 |
| WO | WO 2011/097218 A1 | 8/2011 |
| WO | WO 2011/143669 A2 | 11/2011 |
| WO | WO 2012/079022 A1 | 6/2012 |
| WO | WO 2012/178208 A2 | 12/2012 |
| WO | WO 2013/059215 A1 | 4/2013 |
| WO | WO 2013/089278 A1 | 6/2013 |
| WO | WO 2013/106646 A2 | 7/2013 |
| WO | WO 2013/170147 A1 | 11/2013 |
| WO | WO 2014/023081 A1 | 2/2014 |
| WO | WO 2014/145887 A1 | 9/2014 |
| WO | WO 2015/160845 A1 | 10/2015 |
| WO | WO 2016/065139 A1 | 4/2016 |
| WO | WO 2016/105518 A1 | 6/2016 |
| WO | WO 2016/118666 A1 | 7/2016 |
| WO | WO 2016/146985 A1 | 9/2016 |
| WO | WO 2016/149668 A1 | 9/2016 |
| WO | WO 2016/169989 A1 | 10/2016 |
| WO | WO 2016/191178 A1 | 12/2016 |
| WO | WO 2016/197032 A1 | 12/2016 |
| WO | WO 2016/197114 A1 | 12/2016 |
| WO | WO 2017/007612 A1 | 1/2017 |
| WO | WO 2017/024317 A2 | 2/2017 |
| WO | WO 2017/024318 A1 | 2/2017 |
| WO | WO 2017/024319 A1 | 2/2017 |
| WO | WO 2017/030814 A1 | 2/2017 |
| WO | WO 2017/046036 A1 | 3/2017 |
| WO | WO 2017/079267 A1 | 5/2017 |
| WO | WO 2017/161119 A1 | 9/2017 |
| WO | WO 2017/176708 A1 | 10/2017 |
| WO | WO 2017/176957 A1 | 10/2017 |
| WO | WO 2017/176958 A1 | 10/2017 |
| WO | WO 2017/180417 A1 | 10/2017 |
| WO | WO 2017/197036 A1 | 11/2017 |
| WO | WO 2017/197046 A1 | 11/2017 |
| WO | WO 2017/197051 A1 | 11/2017 |
| WO | WO 2017/197055 A1 | 11/2017 |
| WO | WO 2017/197056 A1 | 11/2017 |
| WO | WO 2017/197240 A1 | 11/2017 |
| WO | WO 2017/201069 A1 | 11/2017 |
| WO | WO 2017/201449 A1 | 11/2017 |
| WO | WO 2018/023029 A1 | 2/2018 |
| WO | WO 2018/051107 A1 | 3/2018 |
| WO | WO 2018/052945 A1 | 3/2018 |
| WO | WO 2018/052949 A1 | 3/2018 |
| WO | WO 2018/053354 A1 | 3/2018 |
| WO | WO 2018/071606 A1 | 4/2018 |
| WO | WO 2018/085247 A1 | 5/2018 |
| WO | WO 2018/102067 A2 | 6/2018 |
| WO | WO 2018/102725 A1 | 6/2018 |
| WO | WO 2018/118598 A1 | 6/2018 |
| WO | WO 2018/118947 A1 | 6/2018 |
| WO | WO 2018/119357 A1 | 6/2018 |
| WO | WO 2018/119441 A1 | 6/2018 |
| WO | WO 2018/119448 A1 | 6/2018 |
| WO | WO 2018/140809 A1 | 8/2018 |
| WO | WO 2018/144649 A1 | 8/2018 |
| WO | WO 2018/169777 A1 | 9/2018 |
| WO | WO 2018/183411 A1 | 10/2018 |
| WO | WO 2018/189554 A1 | 10/2018 |
| WO | WO 2018/191199 A1 | 10/2018 |
| WO | WO 2019/060693 A1 | 3/2019 |
| WO | WO 2019/060742 A1 | 3/2019 |
| WO | WO 2019/140387 A1 | 7/2019 |
| WO | WO 2019/152440 A1 | 8/2019 |
| WO | WO 2019/165229 A1 | 8/2019 |
| WO | WO 2019/199816 A1 | 10/2019 |
| WO | WO 2019/213005 A1 | 11/2019 |
| WO | WO 2020/006262 A1 | 1/2020 |
| WO | WO 2020/006264 A1 | 1/2020 |
| WO | WO 2020/006265 A1 | 1/2020 |
| WO | WO 2020/010227 A1 | 1/2020 |
| WO | WO 2020/023851 A1 | 1/2020 |
| WO | WO 2020/041331 A1 | 2/2020 |
| WO | WO 2020/051564 A1 | 3/2020 |
| WO | WO 2020/081450 A1 | 4/2020 |

OTHER PUBLICATIONS

U.S. Appl. No. 16/882,236, filed May 22, 2020, Phillips et al.
U.S. Appl. No. 17/103,621, filed Nov. 24, 2020, Nasveschuk et al.
U.S. Appl. No. 17/107,781, filed Nov. 30, 2020, Phillips et al.
U.S. Appl. No. 17/121,389, filed Dec. 14, 2020, Phillips et al.
U.S. Appl. No. 17/164,446, filed Feb. 1, 2021, Phillips et al.
Sakamoto, et al.; Solid State Photochemical Reaction of N-(α,β-Unsaturated carbonyl) benzoylformamides; Journal of Organic Chemistry, vol. 62, p. 6298-6308 (1997).
Stanek, et al.; Synthesis and Aromatase Inhibitory Activity of Novel 1-(4-Aminophenyl)-3-azabicyclo[3.1.0]heptane-2,4-diones; Journal of Medicinal Chemistry, vol. 34, p. 13291334 (1991).
Agafonov Roman et al., Poster Presentation titled "Quantitative and high throughput method for measuring complex formation between target proteins and E3 ubiquitin ligase", EMBO, Sep. 16, 2017.
Bartlett, et al., "The evolution of thalidomide and its IMiD derivatives as anticancer agents." Nat Rev Cancer 2004, 4(4):312-322.
Berndsen et al., "New insights into ubiquitin E3 ligase mechanism" Nat. Struct. Mol. Biol. 2014, 21:301-307.
Bondeson et al., "Catalytic in vivo protein knockdown by small-molecule PROTACs" Nature Chemical Biology 2015, 11:611-617.
Buckley et al., "HaloPROTACS: Use of Small Molecule PROTACS to Induce Degradation of HaloTag Fusion Proteins" ACS Chemical Biology 2015, 10:1831-1837.
Buckley et al., "Small-Molecule Control of Intracellular Protein Levels through Modulation of the Ubiquitin Proteasome System" Angewandte Reviews, 2014, 53:2312-2330.
Buckley et al., "Targeting the Von Hippel-Lindau E3 Ubiquitin Ligase Using Small Molecules to Disrupt the Vhl/Hif-1 alpha Interaction" J. Am. Chem. Soc. 2012, 134:4465-4468.
Burkhard et al., "Synthesis and Stability of Oxetane Analogs of Thalidomide and Lenalidomide" Organic Letters 2013, 15(7):4312-4315.
Chamberlain et al., "Structure of the human cereblon-DDB1-lenalidomide complex reveals basis for responsiveness to thalidomide analogs" Nature Structural and Molecule Biology, 2014, 21(9):803-809.
Chang, X. and Stewart, K. A., "What is the functional role of the thalidomide binding protein cereblon?" Int J Biochem Mol Bio. 2011, 2(3):287-294.
Contino-Pepin, et al., "Preliminary biological evaluations of new thalidomide analogues for multiple sclerosis application", Bioorganic & Medicinal Chemistry Letters, 2009, 19(3), 878-881.

(56) References Cited

OTHER PUBLICATIONS

Corson et al., "Design and applications of bifunctional small molecules: Why two heads are better than one" ACS Chemical Biology 2008, 3(11): 677-692.
Crews, C. M., "Targeting the undruggable proteome: the small molecules of my dreams" Chemistry and Biology 2010, 17(6):551-555.
Deshaies et al., "Ring domain E3 ubiquitin ligases." Ann. Rev. Biochem. 2009, 78:399-434.
Elam W.A., et al., Poster Presentation titled "Application of Biophysical Techniques to the Targeted Protein Degradation Therapeutic Strategy", Sep. 24, 2017.
Faden et al., "Generic tools for conditionally altering protein abundance and phenotypes on demain" Biol. Chem. 2014, 395(7-8):737-762.
Fischer et al., "Structure of the DDB1-CRBN E3 ubiquitin ligase in complex with thalidomide" Nature 2014, 512:49-53.
Fischer et al., "The Molecular Basis of CRL4DDB2/CSA Ubiquitin Ligase Architecture, Targeting, and Activation," Cell 2011, 147:1024-1039.
Fisher et al., "Targeted protein degradation and the enzymology of degraders", Current Opinion of Chemical Biology, 2018, 44, 47-55.
Grant, Johnathan W. et al., "Toward the Development of a Cephalosporin-Based Dual-Release Prodrug for Use in ADEPT", Journal of Organic Chemistry, vol. 69, No. 23, Nov. 1, 2004, pp. 7965-7970. XP55639681, US ISSN: 0022-3263, DOI: 10.1021/jo048970i *5-Thia-1-azabicyclo[4.2.0]oct-2-ene-2-carboxylic acid, 3-[[[[4-[(3R)-ethyl-2,6-dioxo-3-piperidinyl)phenyl]amino]-8-oxo-, diphenylmethyl ester, (6R, 7E)*.
Gosink et al., "Redirecting the Specificity of Ubiquitination by Modifying Ubiquitin-Conjugating Enzymes" Proc. Natl. Acad. Sci. USA 1995, 92:9117-9121.
Gustafson et al., "Small-Molecule-Mediated Degradation of the Androgen Receptor through Hydrophobic Tagging" Angewandte Chemie, 2015, 54:9659-9662.
Hines et al., "Posttranslational protein knockdown couple to receptor tyrosine kinase activation with phosphoPROTACs" PNAS 2013, 110(22):8942-8947.
International Search Report and Written Opinion for PCT/US2018/61573 dated May 3, 2019.
Henderson C., Presentation titled "Development of AchillesTAG degradation systems and their application to control CAR-T activity", ChemBio in the hub, Cambridge, MA. Oct. 22, 2018.
Ito et al., "Identification of a Primary Target of Thalidomide Teratogenicity" Science 2010, 327(5971):1345-1350.
Itoh et al., "Protein knockdown using methyl bestatin-ligand hybrid molecules: design and synthesis of inducers of ubiquitination-mediated degradation of cellular retinoic acid-binding proteins" Journal of the American Chemical Society 2010, 132(16), 5820-5826.
Jacques et al., "Differentiation of anti-inflammatory and antitumorigenic properties of stabilized enantiomers of thalidomide analogs" PNAS 2015, 112:E1471-E1479.
Jarman, M. et al., "Selective inhibition of cholesterol side-chain cleavage by potential pro-drug forms of aminoglutethimide", Anti-Cancer Drug Design, vol. 3, 1988, pp. 185-190, XPOO9517051, *N-{4-{3-ethyl-2,6-dioxo-3-piperidinyl)-4-methyl-4-(4-methylphenyl)-2,5-dioxo-1-imidazolidineacetamide*.
Kronke et al., "Lenalidomide Causes Selective Degradation of IKZF1 and IKZF3 in Multiple Myeloma Cells" Science 2014, 343(6168):301-305.
Kronke et al., "Lenalidomide induces ubiquitination and degradation of CDK1[alpha] in del(5q) MDS" Nature 2015, 523(7559):183-188.
Lai et al., "Modular PROTAC Design for the Degradation of Oncogenic BCR-ABL" Angewandte Chemie International Edition 2016, 55:807-810.
Lee et al., "Targeted Degradation of the Aryl Hydrocarbon Receptor by the PROTAC Approach: A Useful Chemical Genetic Tool" ChemBioChem 2007, 8:2058-2062.

Li et al., "Genome-wide and functional annotation of human E3 ubiquitin ligases identifies MULAN, a mitochondrial E3 that regulates the organelle's dynamics and signaling" PLOS One 2008, 3:1487.
Liu et al., "Design and biological characterization of hybrid compounds of curcumin and thalidomide for multiple myeloma" Organic and Biomolecular Chemistry, 2013, 11:4757.
Lu et al., "Hijacking the E3 Ubiquitin Ligase Cereblon to Efficiently Target BRD4" Chemistry and Biology 2015, 22(6):755-763.
Lu et al., "The myeloma drug lenalidomide promotes the cereblon-dependent destruction of Ikaros proteins" Science, 2014, 343:305-309.
Martiniani, R. et al., "Biological activity of lenalidomide and its underlying therapeutic effects in multiple myeloma", Adv Hematol, 2012, 2012:842945.
Nasveschuk C., Presentation titled "Advances in the Medicinal Chemistry of Targeted Protein Degradation", Aug. 7, 2018.
Nawaz et al., "Proteasome-Dependent Degradation of the Human Estrogen Receptor" Proc. Natl. Acad. Sci. USA 1999, 96:1858-1862.
Neklesa et al., "Small-molecule hydrophobic tagging-induced degradation of HaloTag fusion proteins." Nat Chem Biol 2011, 7(8):538-543.
Patel, J., Poster Presentation titled "Diverse Utility of Targeted Protein Degradation at C4 Therapeutics", Sep. 17, 2017.
Phillips A., Presentation titled "Targeted Protein Degradation", Applied Pharmaceutical Chemistry, Cambridge, MA. Apr. 5, 2018.
Phillips A., Presentation titled "Small molecule driven targeted protein degradation", ChemBio in the hub, Cambridge, MA. Oct. 22, 2018.
PubChem-CID: 14872634 Create Date Feb. 9, 2007, pp. 1-7, structure 2.
Raina et al., "Chemical Inducers of Targeted Protein Degradation" Journal of Biological Chemistry 2010, 285:11057-11060.
Rodriguez-Gonzalez et al., "Targeting steroid hormone receptors for ubiquitination and degradation in breast and prostate cancer" Oncogene, 2008, 27:7201-7211.
Ruchelman et al., "Isosteric analogs of lenalidomide and pomalidomide: Synthesis and biological activity", Bioorganic and Medicinal Chemistry Letters, 2012, 23:360-365.
Sakamoto et al., "Development of Protacs to Target Cancer-Promoting Proteins for Ubiquitination and Degradation" Molecular and Cellular Proteomics, 2003, 2(12):1350-1357.
Sakamoto et al., "Protacs: chimeric molecules that target proteins to the Skp1-Cullin-F box complex for ubiquitination and degradation" PNAS, 2001, 98(15):8554-8559.
Schneekloth et al., "Chemical approaches to controlling intracellular protein degradation" Chembiochem., 2005, 6(1):40-46.
Schneekloth et al., "Chemical Genetic Control of Protein Levels: Selective in Vivo Targeted Degradation" Journal of the American Chemical Society, 2004, 126(12):3748-3754.
Schneekloth et al., "Targeted Intracellular Protein Degradation Induced by a Small Molecule: En Route to Chemical Proteomics" Bioorganic and Medicinal Chemistry Letters, 2008, 18:5904-5908.
Shoji, et al., "Modified DNA Aptamer That Binds the (R)-Isomer of a Thalidomide Derivative with High Enantioselectivity", J. Am. Chem. Soc., 2007, 129, 1456-1464.
Smith et al., "Targeted Intracellular Protein Degradation Induced by a Small Molecule: En Route to Chemical Proteomics" Bioorg. Med. Chem. Lett. 2008, 18(22):5904-5908.
Spratt et al., "RBR E3 ubiquitin ligases: new structures, new insights, new questions." Biochem. 2014, 458:421-437.
Terpos, E. et al., "Pomalidomide: a novel drug to treat relapsed and refractory multiple myeloma", Oncotargets and Therapy, 2013, 6:531.
Toure et al., "Small-Molecule PROTACs: New Approaches to Protein Degradation" Angewandte Chemie International Edition 2016, 55:1966-1973.
Vassilev et al., "In Vivo Activation of the P53 Pathway by Small-Molecule Antagonists of MDM2" Science, 2004, 303:844-848.
Vieux Ellen et al., Poster Presentation titled "Measuring Small Molecule Induced Ubiquitination of Proteins", EMBO, Sep. 18, 2017.

(56) References Cited

OTHER PUBLICATIONS

Wang et al., "Roles of F-box proteins in cancer." Nat. Rev. Cancer 2014, 14:233-347.

Winter et al., "Phthalimide conjugation as a strategy for in vivo target protein degradation", Science 2015, 348(6241):1376-1381.

Zeid Rhamy Presentation titled "Targeted protein degradation as a novel therapeutic approach", Gordon Research Conference, Jun. 26, 2017.

Zengerle et al., "Selective Small Molecule Induced Degradation of the BET Bromodomain Protein BRD4" ACS Chem. Biol. 2015, 10:1770-1777.

Zhou et al., "Harnessing the Ubiquitination Machinery to Target the Degradation of Specific Cellular Proteins" Molecular Cell 2000, 6:751-756.

US, 2020/0207764, A1, U.S. Appl. No. 16/809,325, Norcross et al., Jul. 2, 2020.

US, 2020/0207783, A1, U.S. Appl. No. 16/809,336, Norcross et al., Jul. 2, 2020.

US, 2020/0207733, A1, U.S. Appl. No. 16/809,345, Norcross et al., Jul. 2, 2020.

US, 2021/0009559, A1, U.S. Appl. No. 17/031,550, Henderson et al., Jan. 14, 2021.

US, 2020/0140456, A1, U.S. Appl. No. 16/721,650, Phillips et al., May 7, 2020.

US, 2021/0032245, A1, U.S. Appl. No. 17/072,896, Nasveschuk et al., Feb. 4, 2021.

US, 2021/0070763, A1, U.S. Appl. No. 17/103,621, Nasveschuk et al, Mar. 11, 2021.

US, 2021/0106688, A1, U.S. Appl. No. 16/882,236, Phillips et al., Apr. 15, 2021.

US, 2021/0198256, A1, U.S. Appl. No. 17/192,634, Nasveschuk et al, Jul. 1, 2021.

U.S. Appl. No. 17/351,935, filed Jun. 18, 2021, Phillips et al.

* cited by examiner

FIG. 1Q
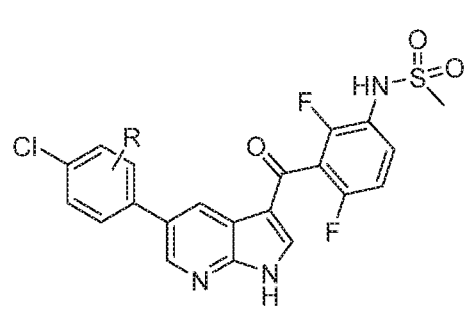
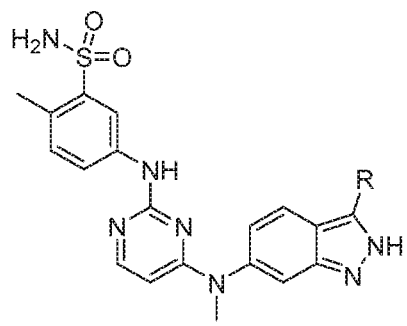
FIG. 1R
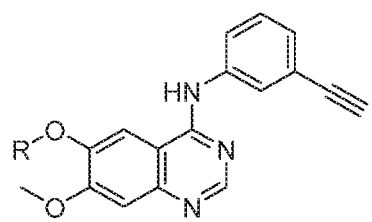
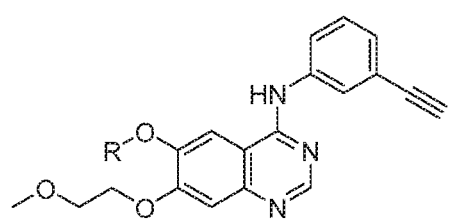
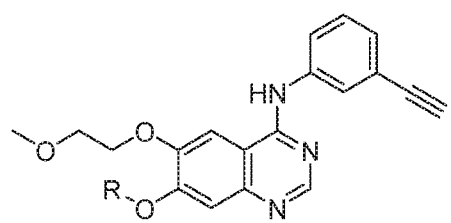
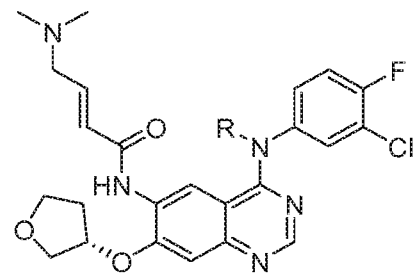
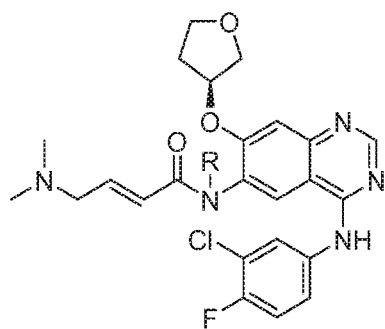
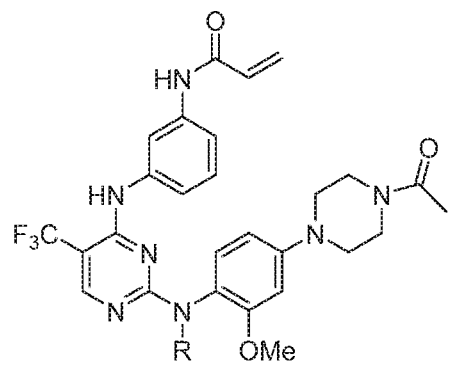

FIG. 1EE
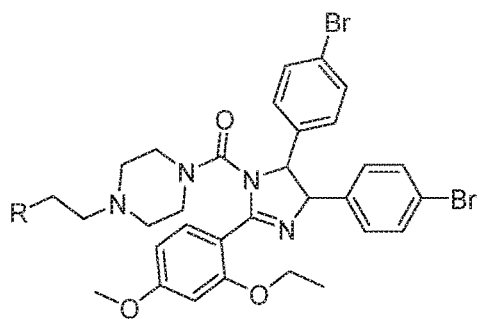
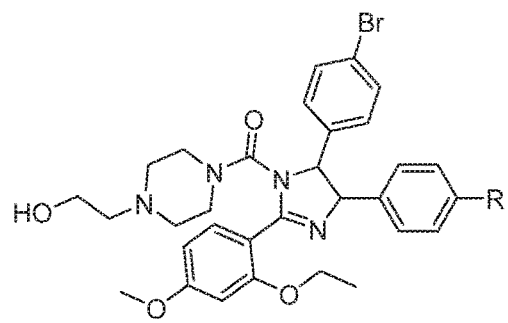
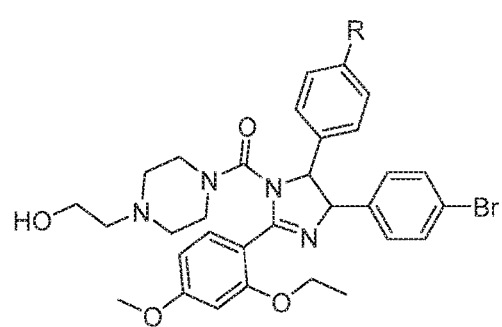
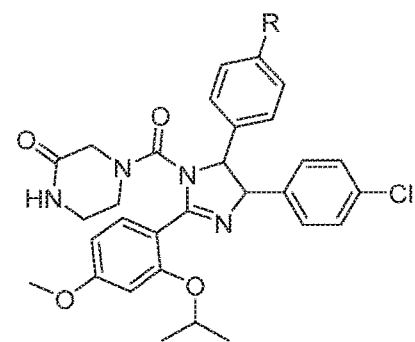
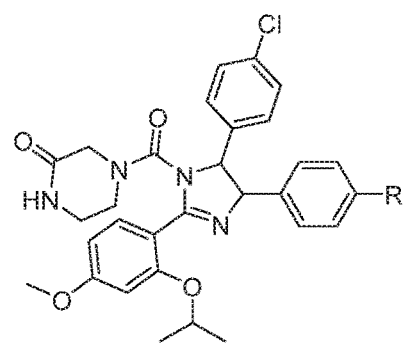
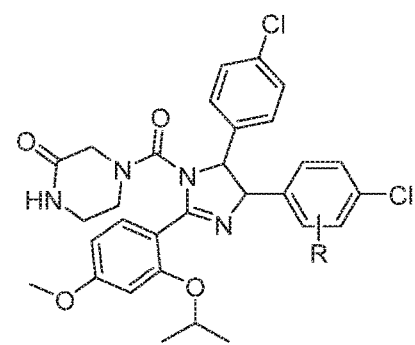
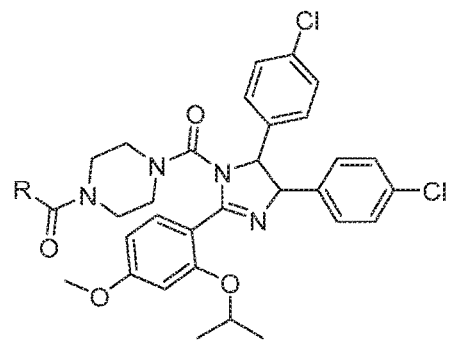
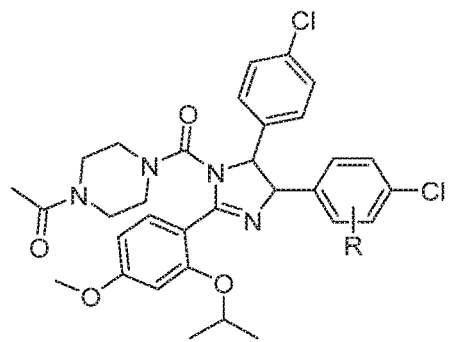

FIG. 1LL
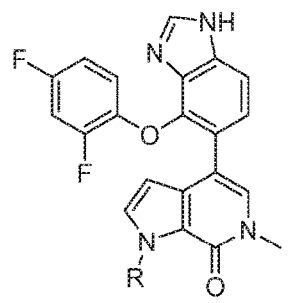
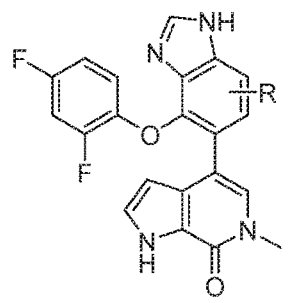
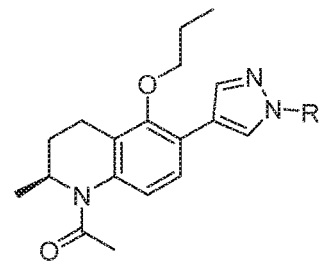
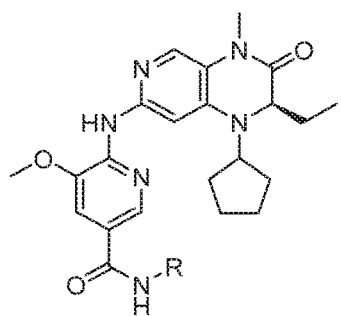
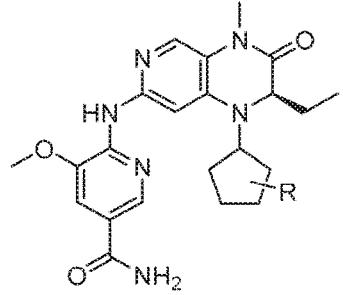
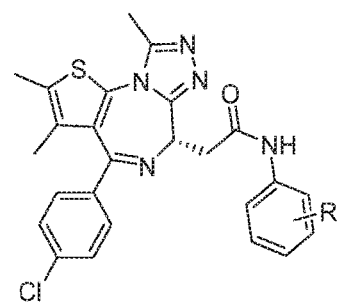
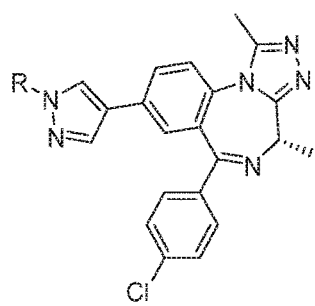
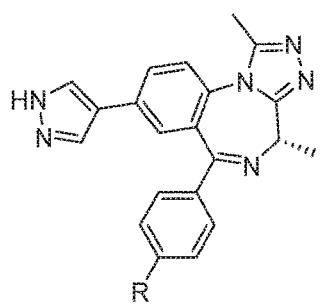
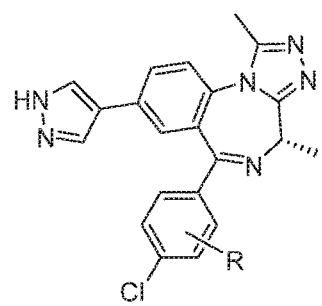
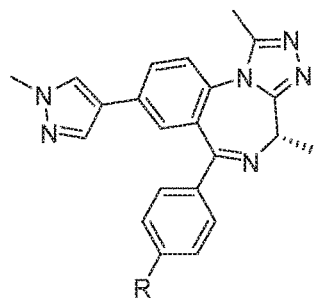
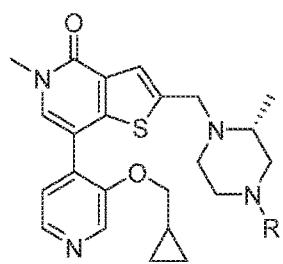
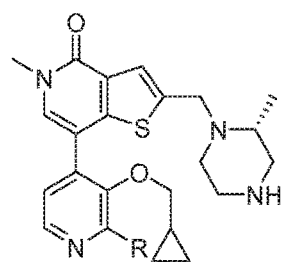

FIG. 1PP
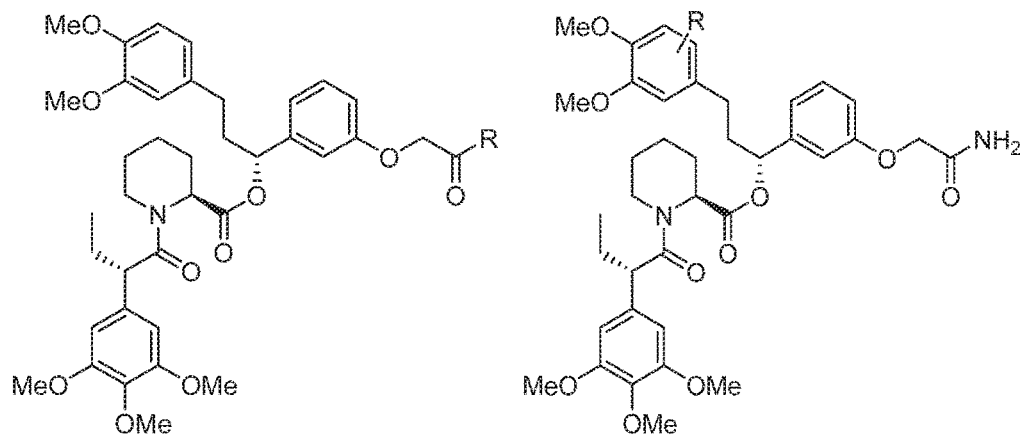
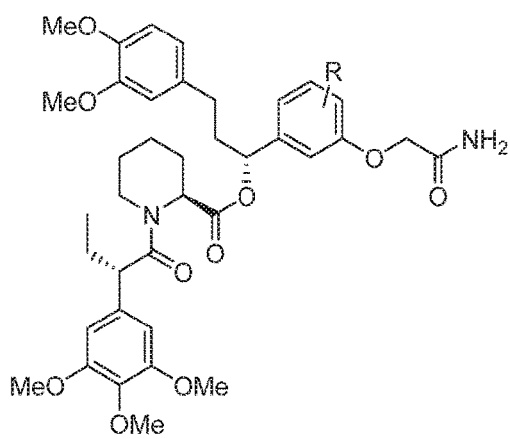
FIG. 1QQ
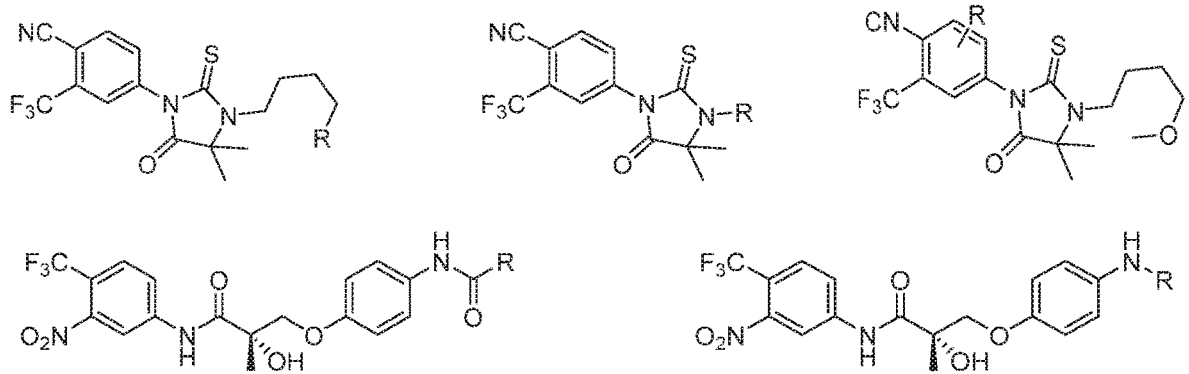

FIG. 1TT
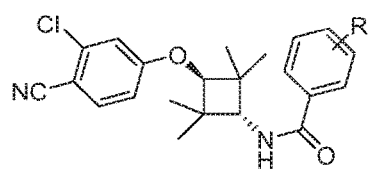
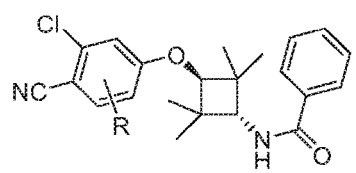
FIG. 1UU
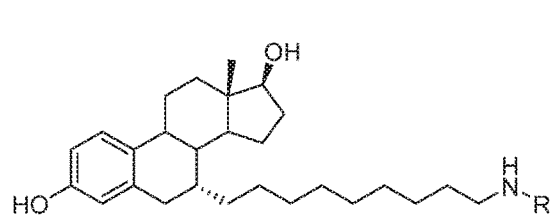
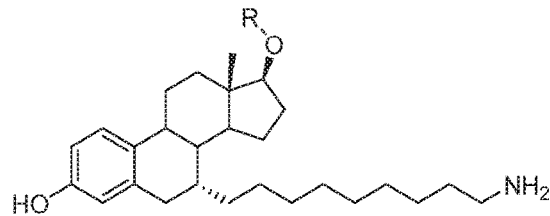
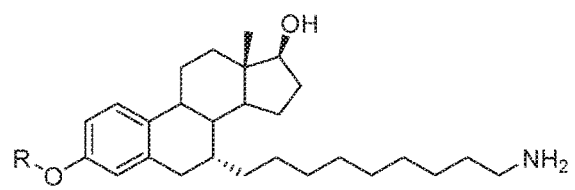
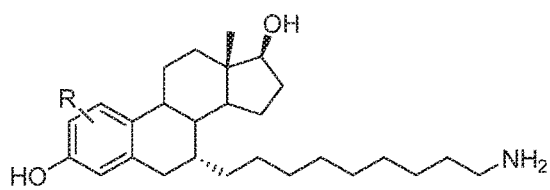
FIG. 1VV
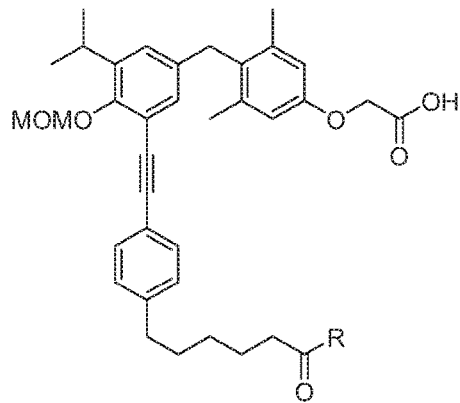
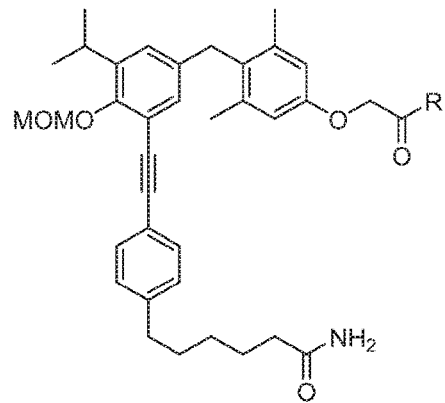

FIG. 1WW
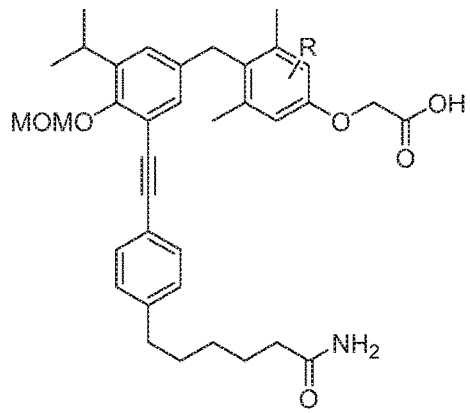
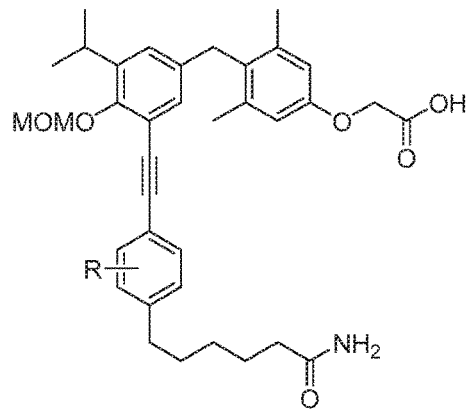
FIG. 1XX
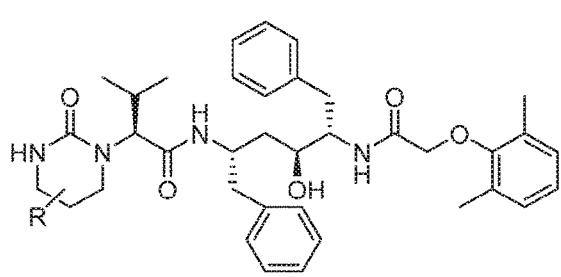
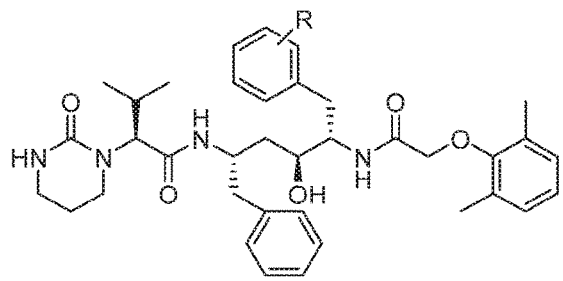
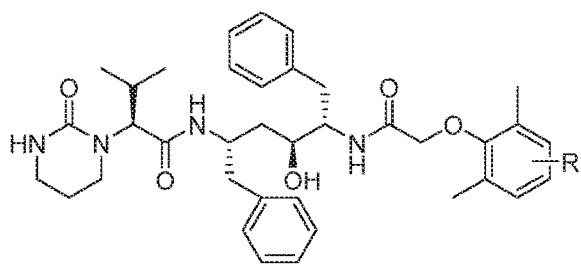
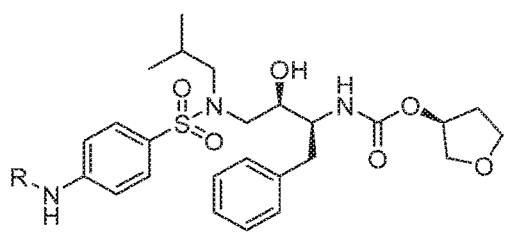
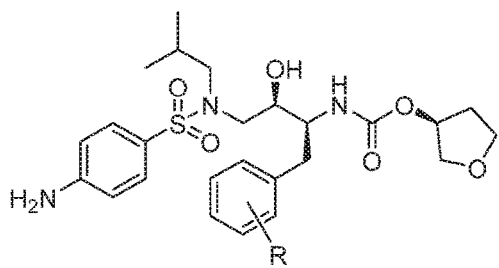
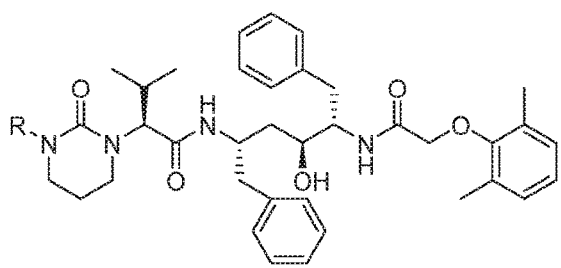

FIG. 1AAA
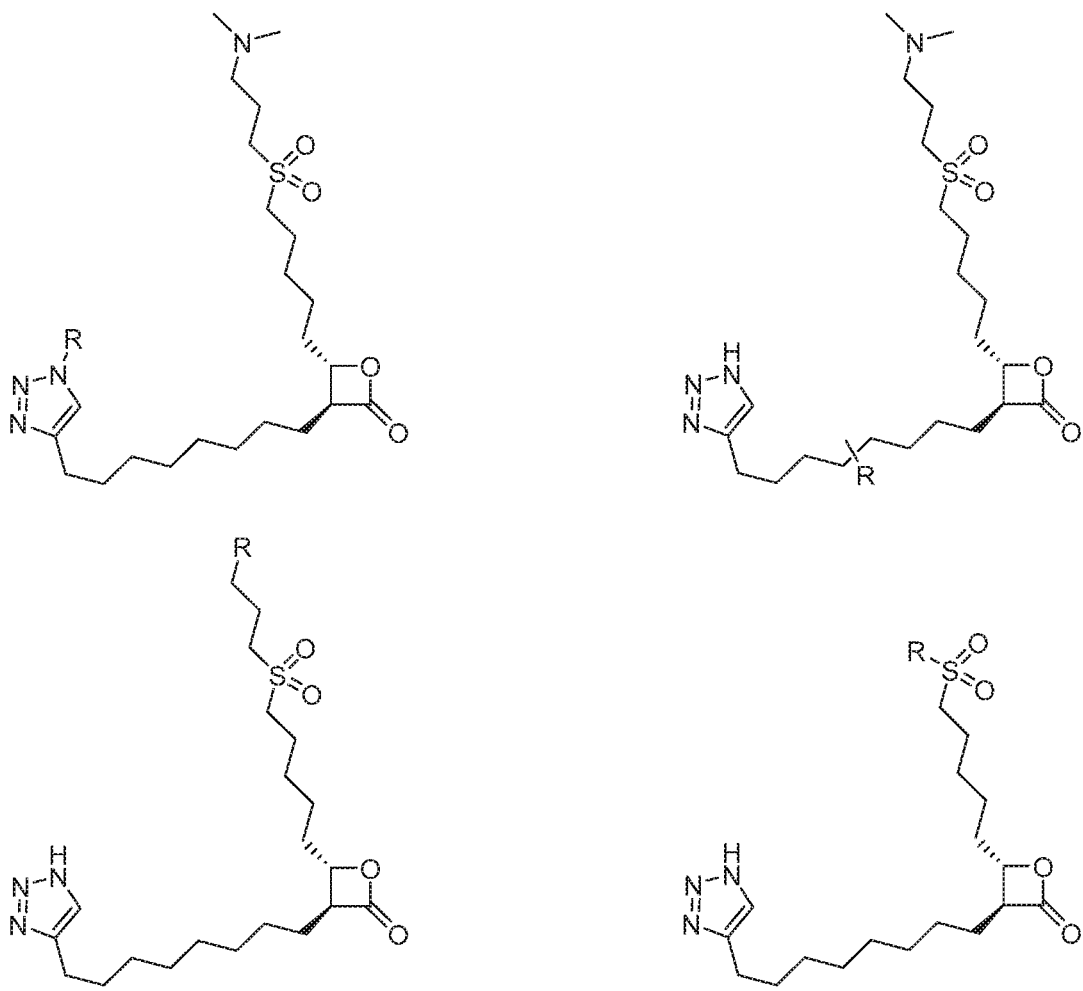
FIG. 1BBB
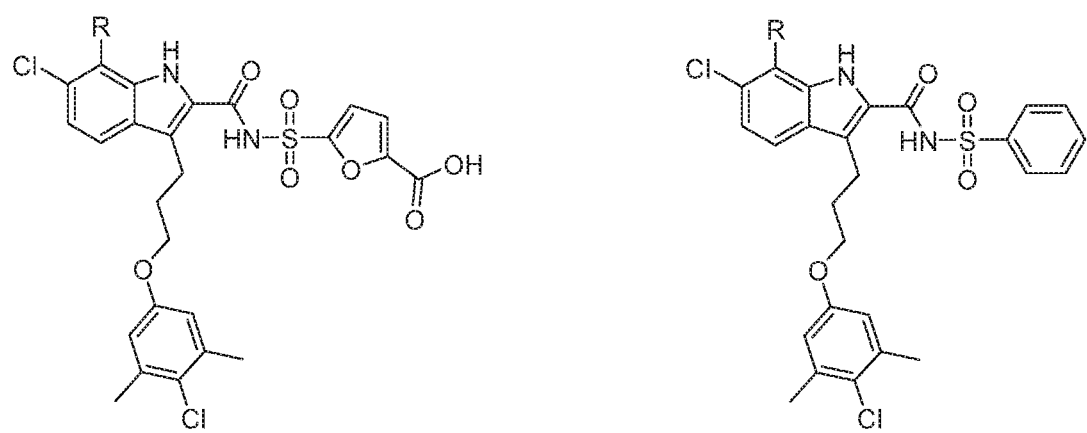

FIG. 1CCC
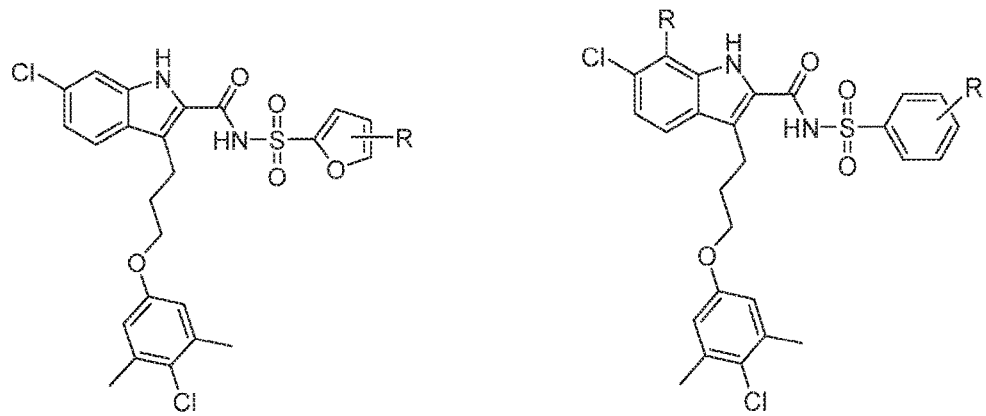
FIG. 1DDD
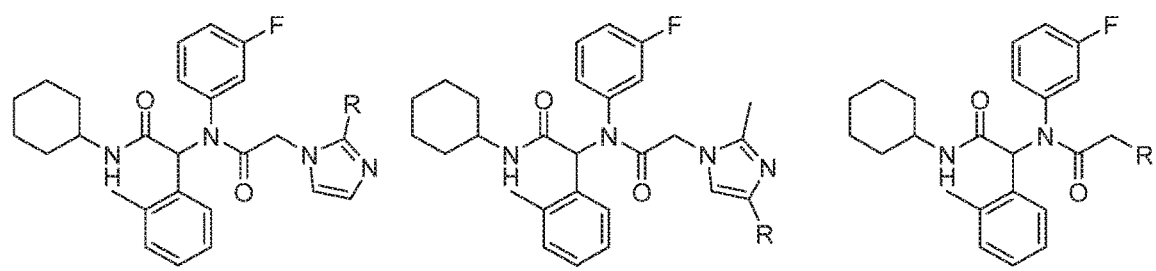
FIG. 1EEE
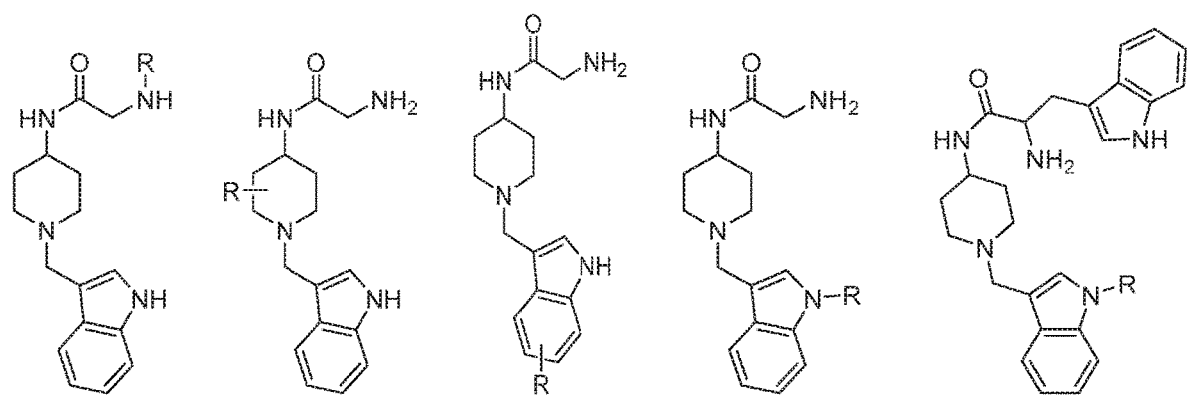

FIG. 1FFF
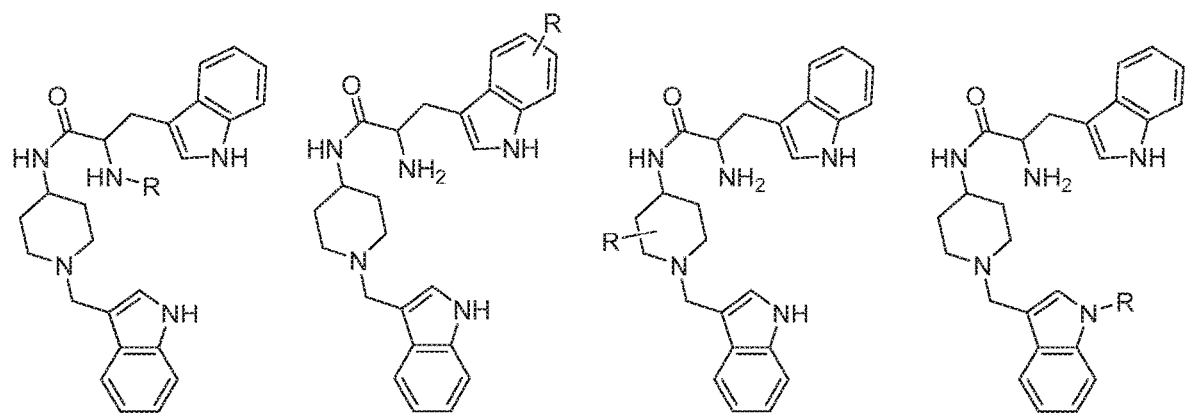
FIG. 1GGG
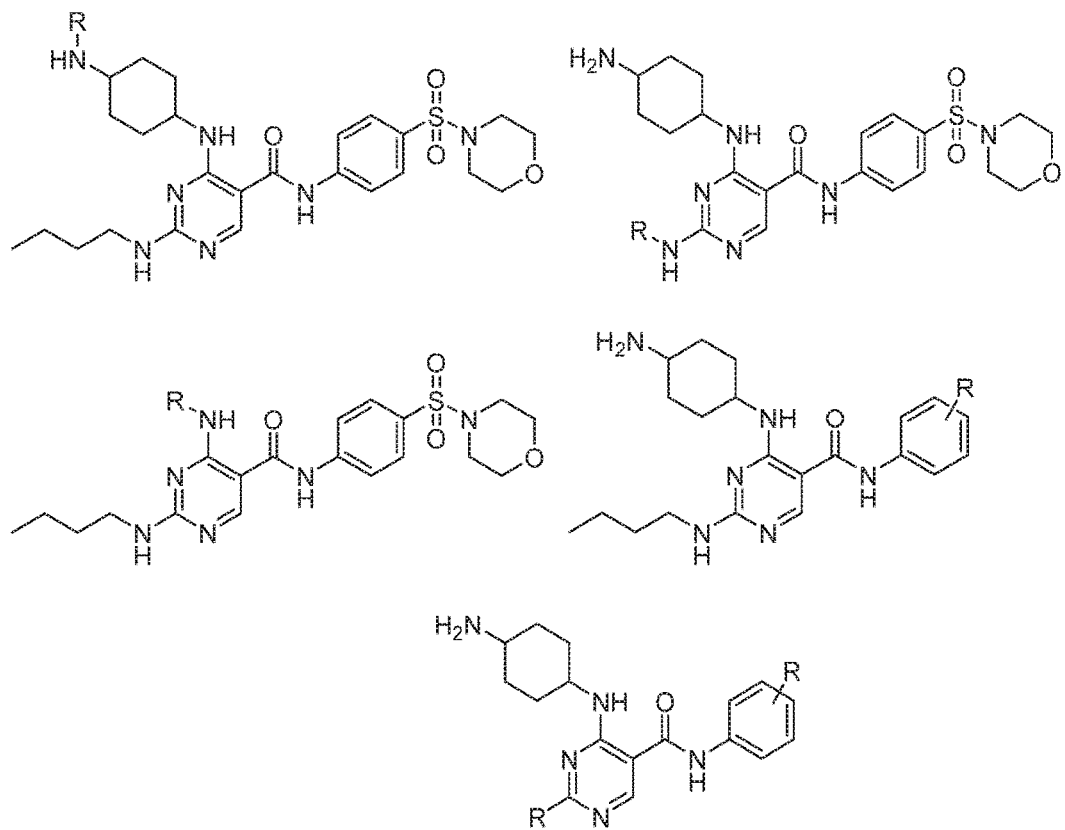

FIG. 1HHH
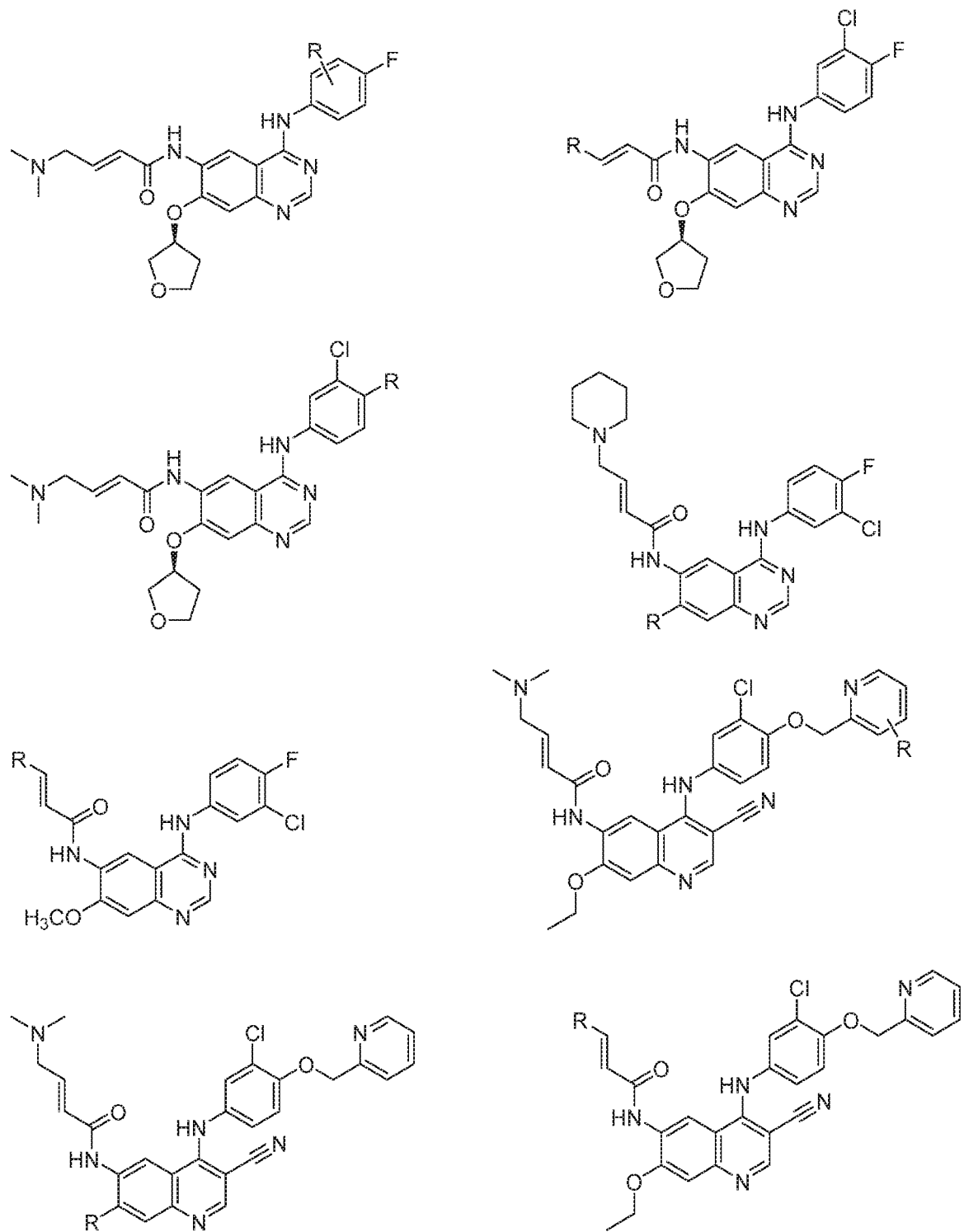

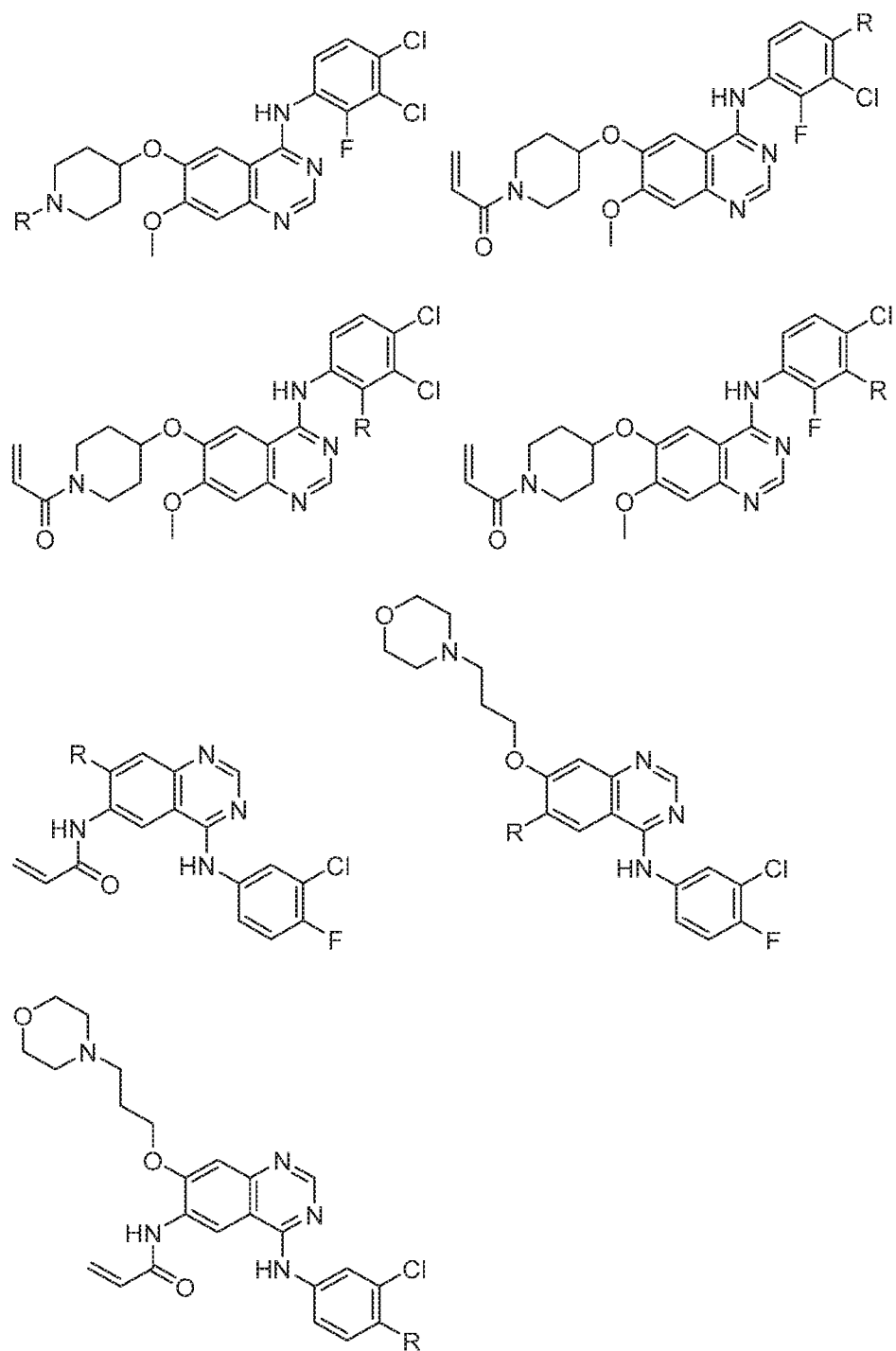
FIG. 1III

FIG. 1JJJ
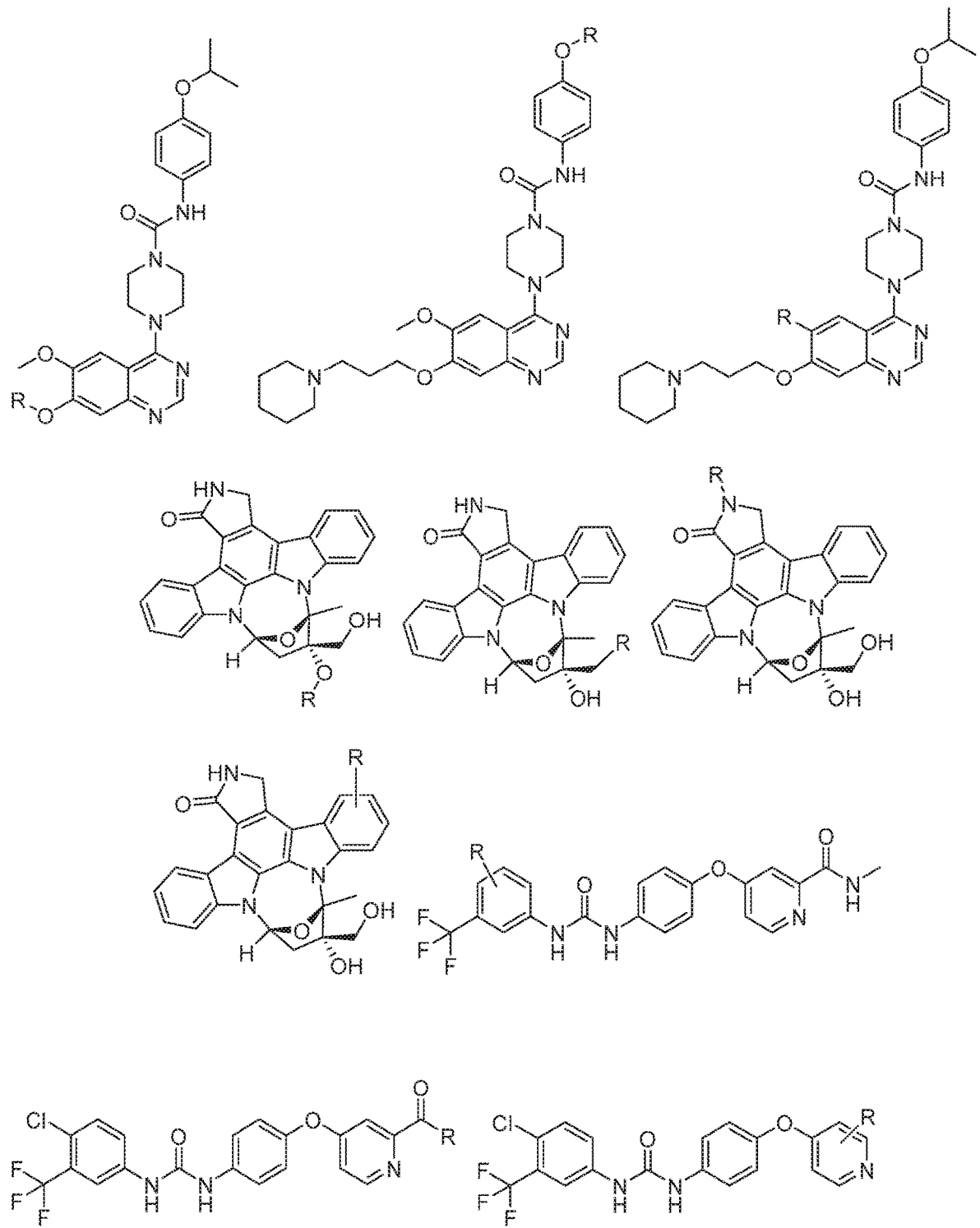

FIG. 1KKK
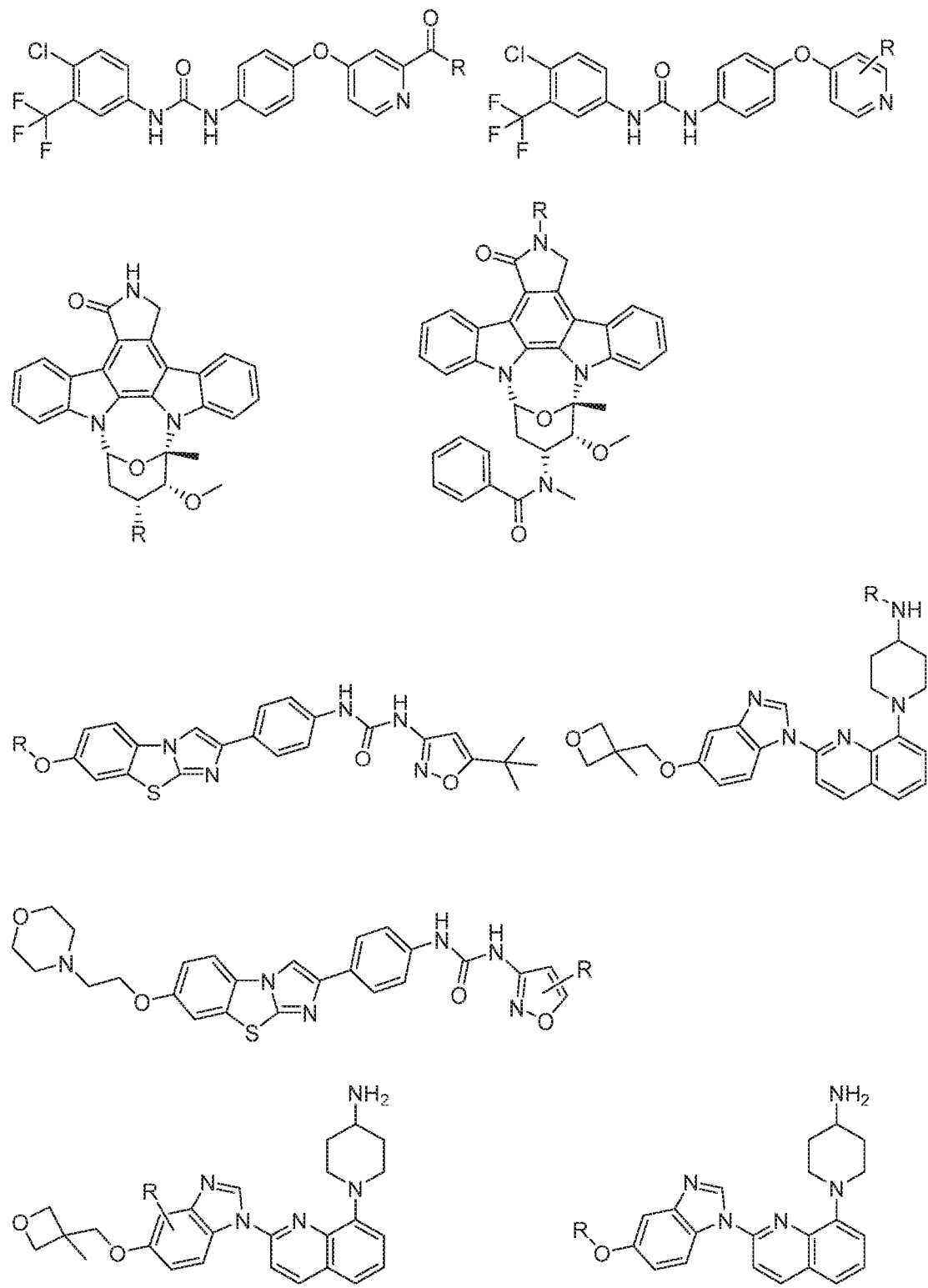

FIG. 1LLL
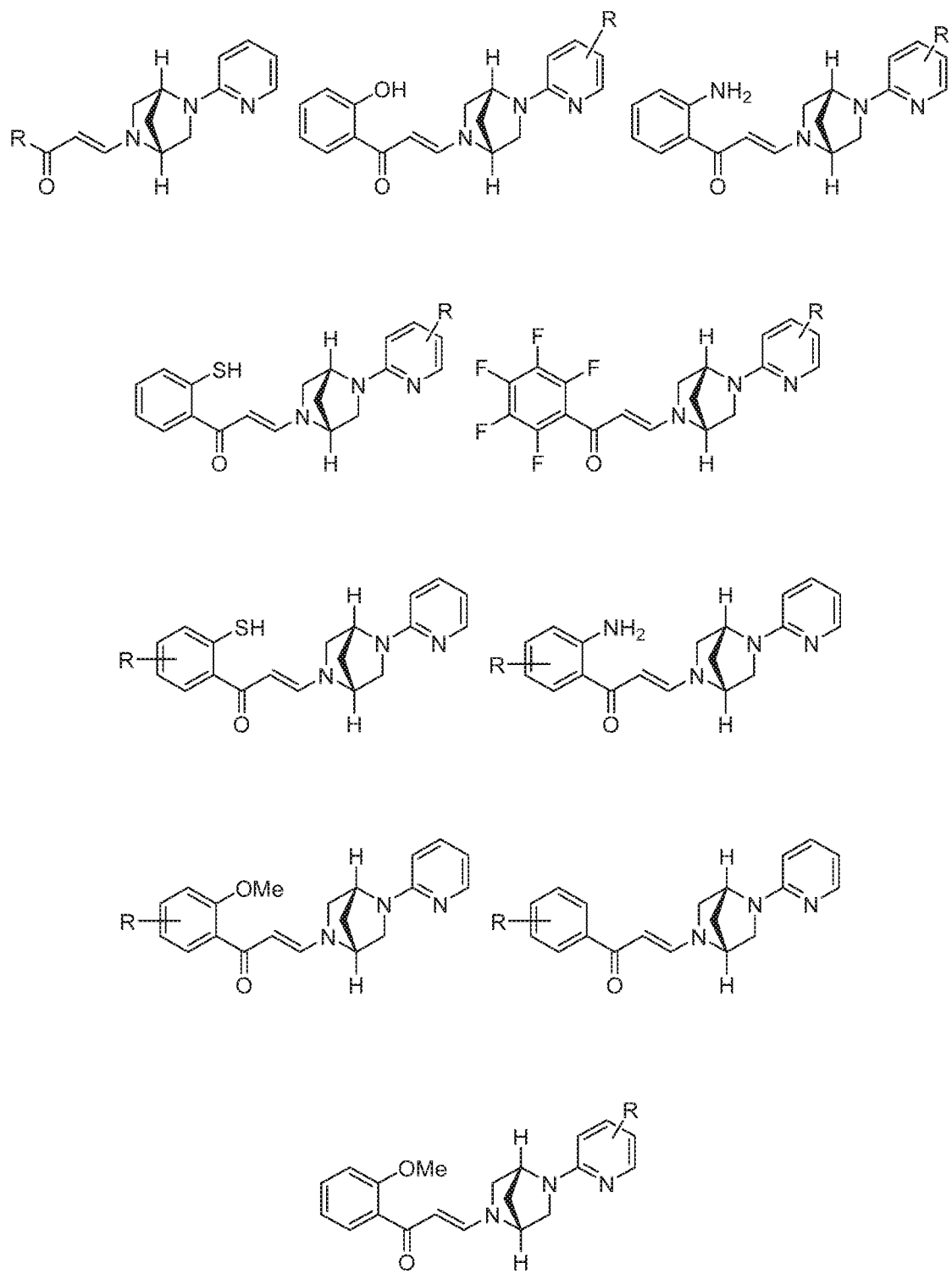

FIG. 2F
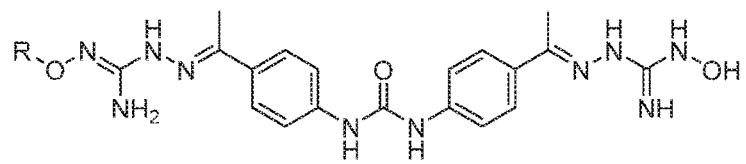
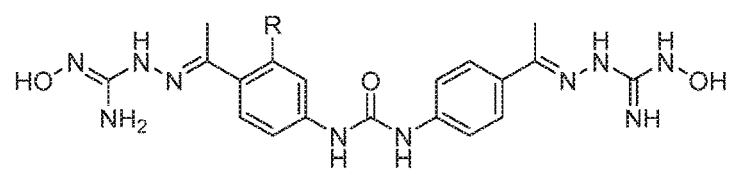
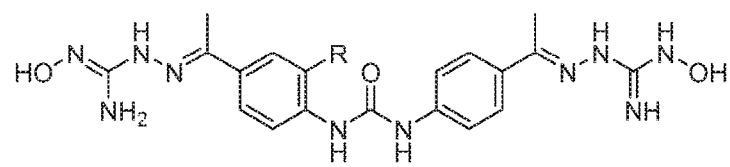
FIG. 2G
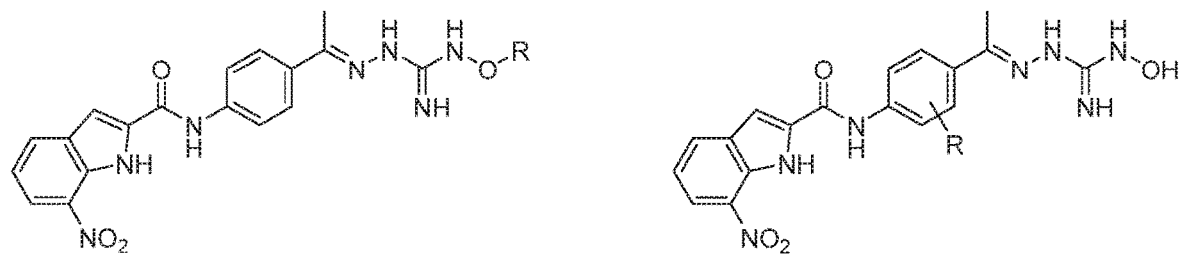
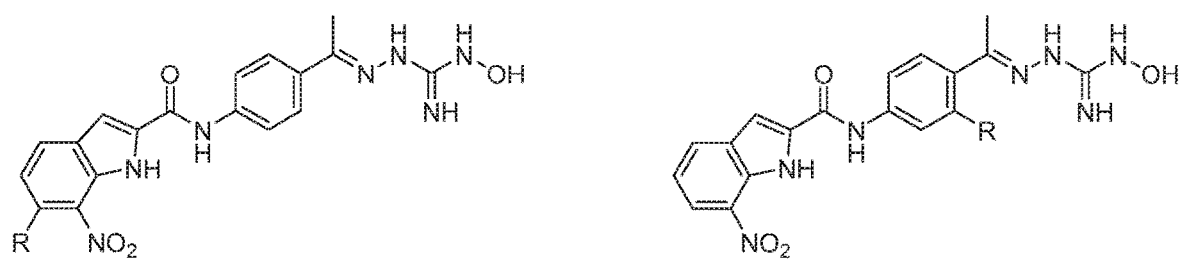
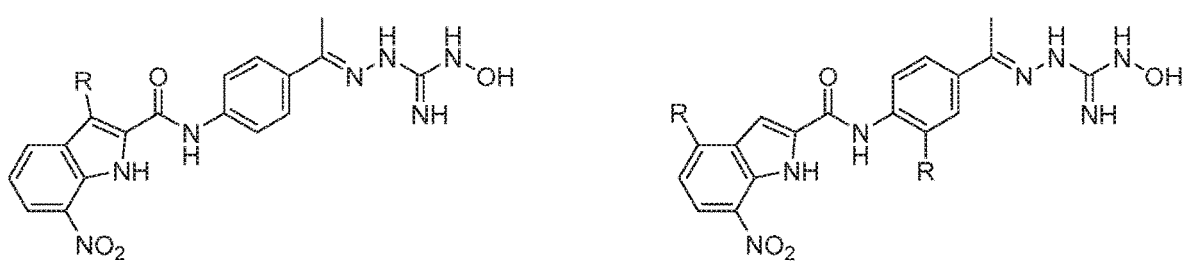

FIG. 2W
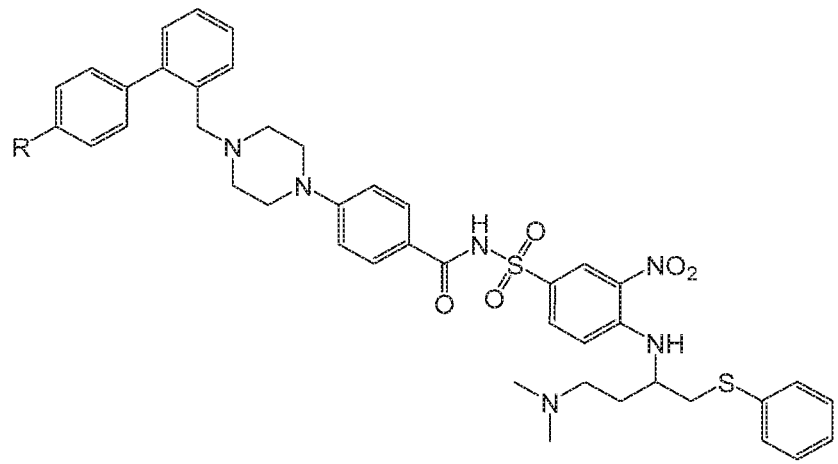
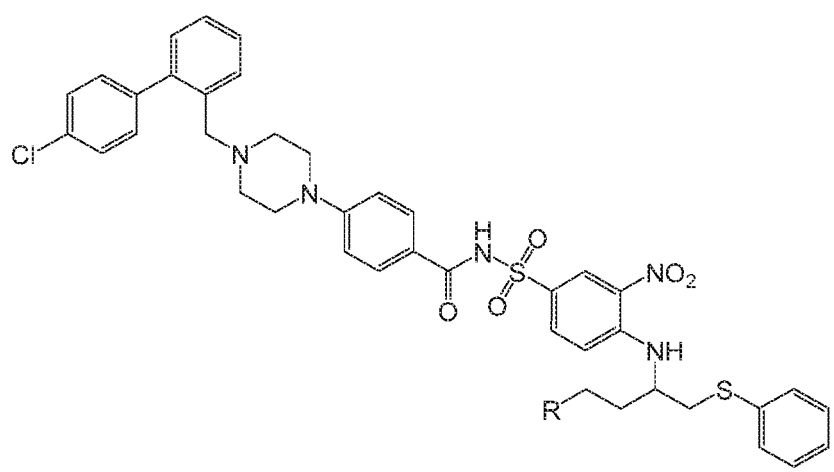
FIG. 2X
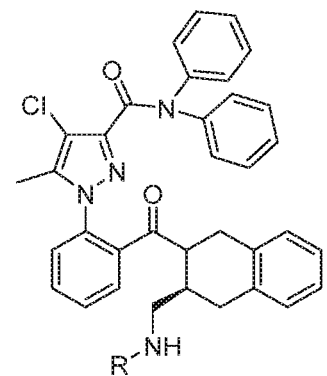

FIG. 2Y
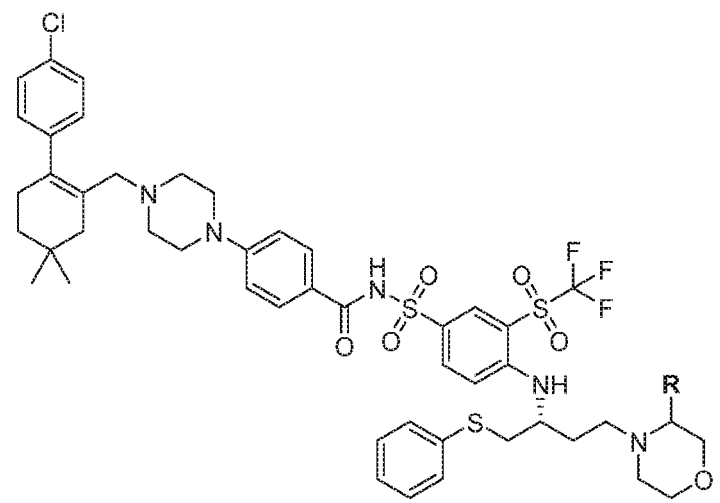
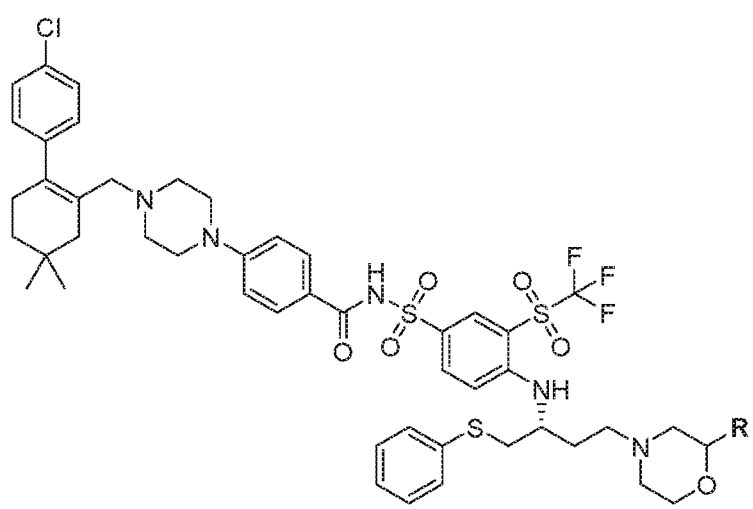
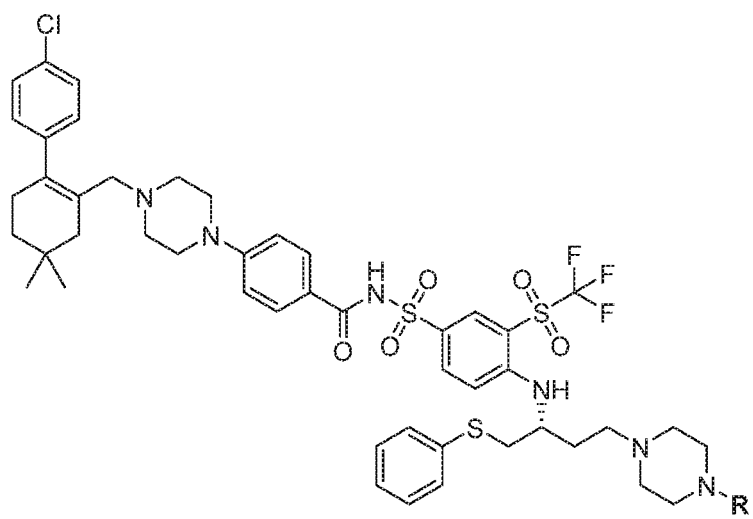

FIG. 2RR
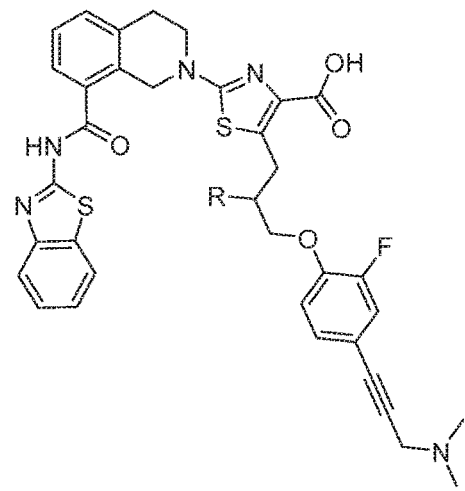
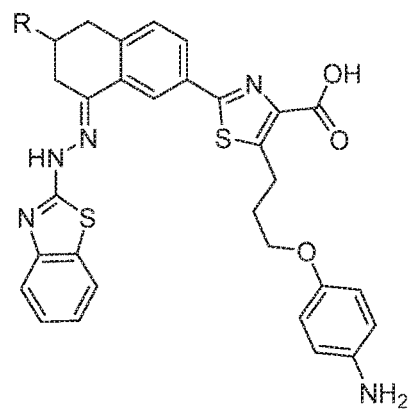
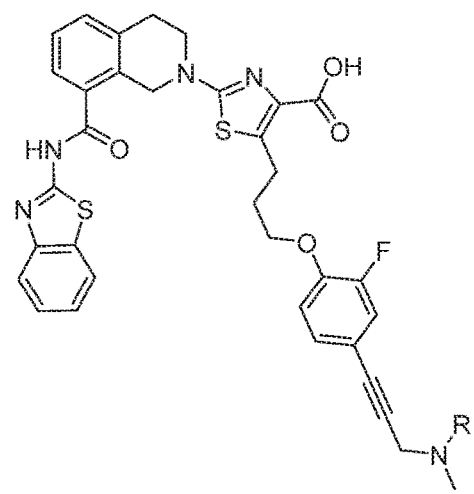
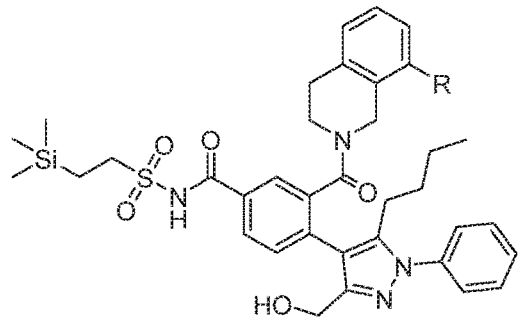
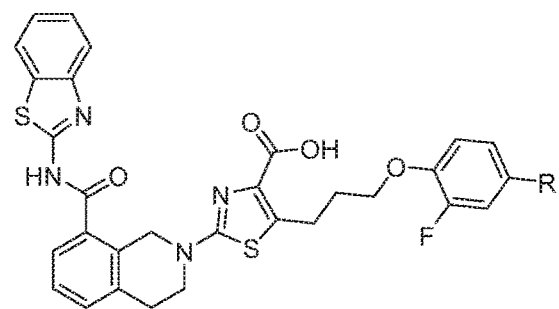
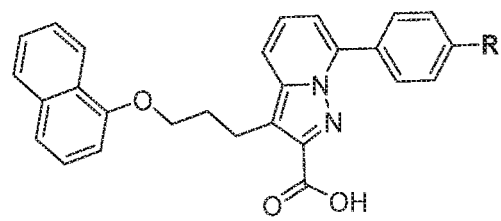

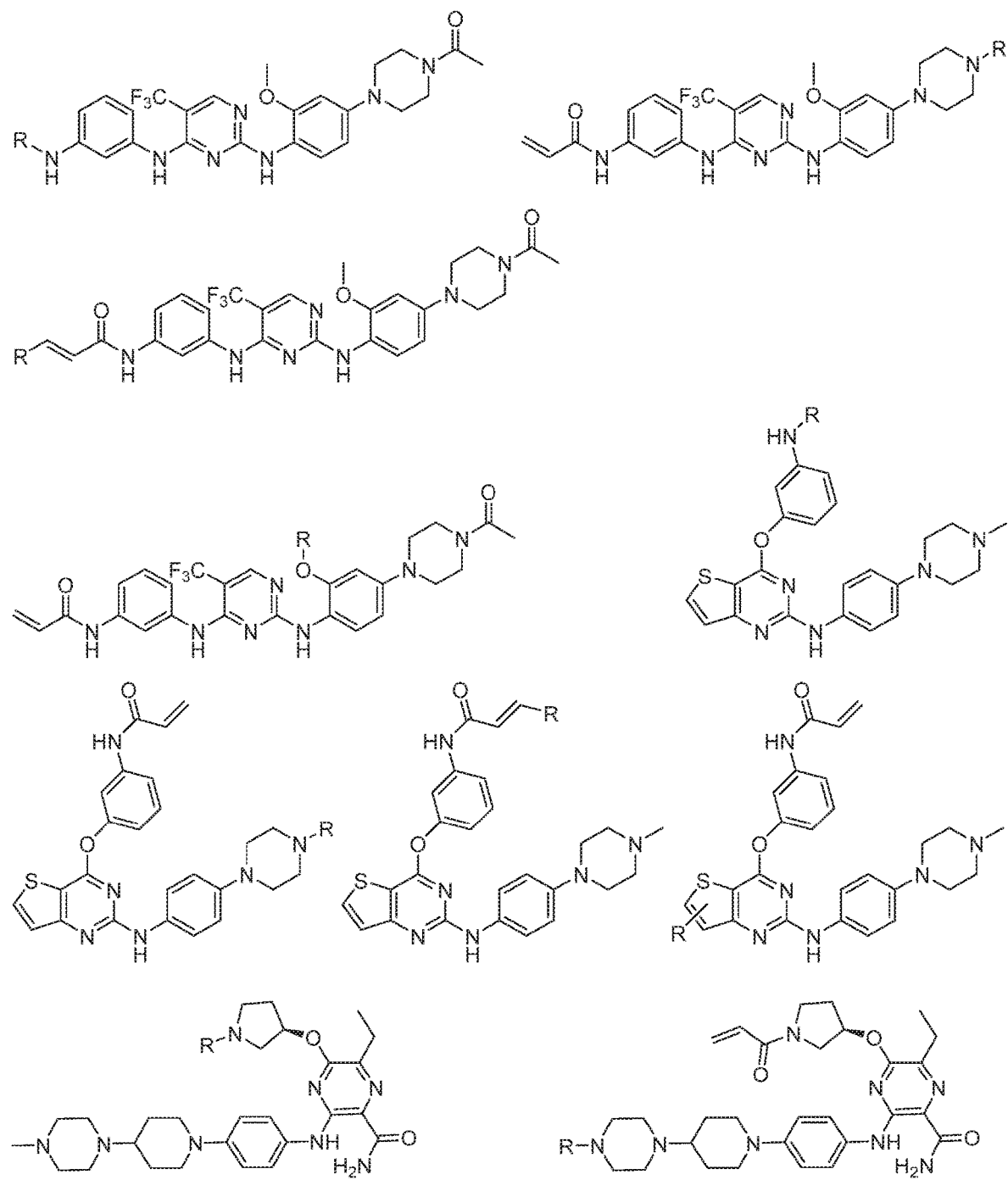
FIG. 2AAA

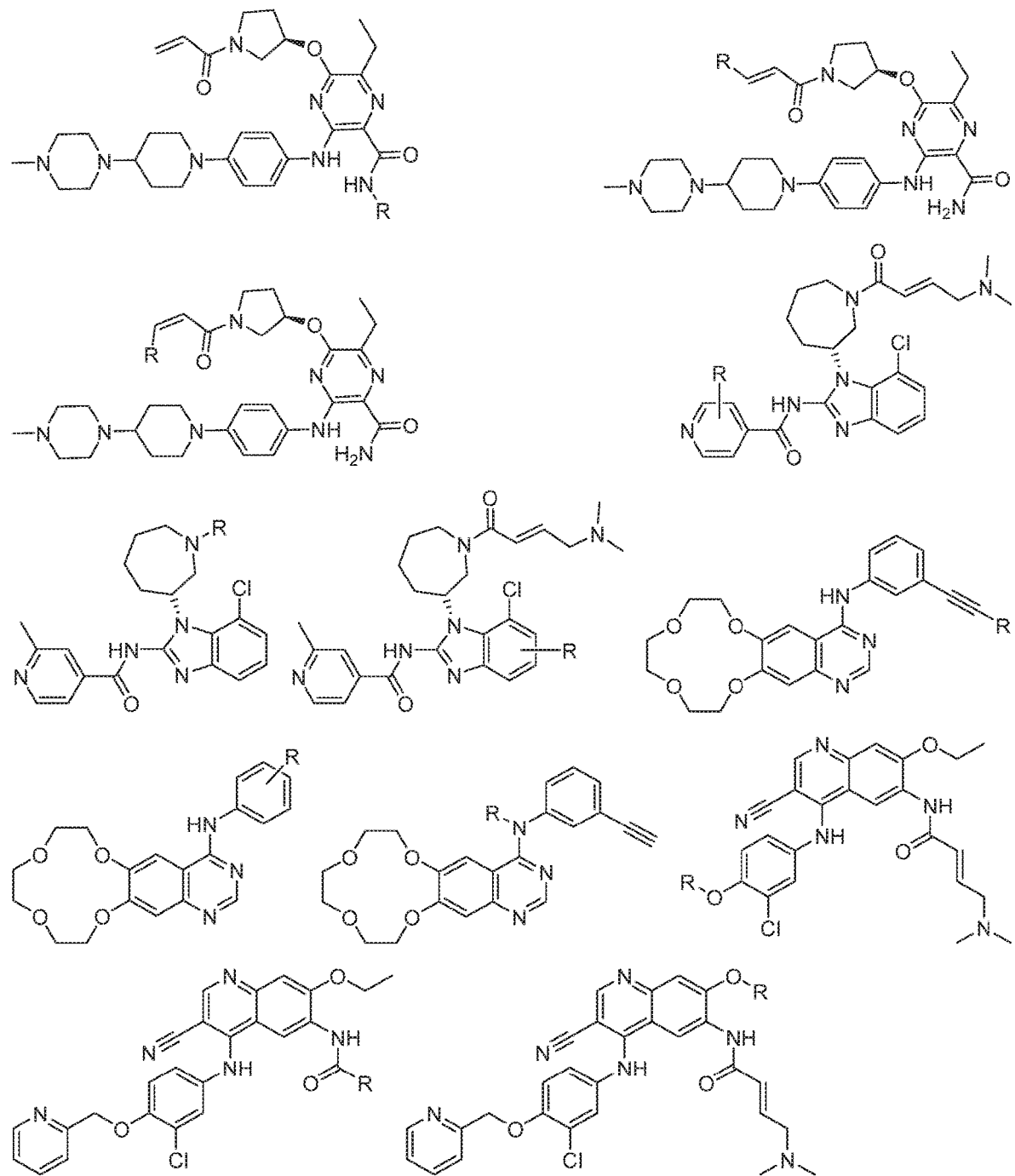
FIG. 2BBB

FIG. 2CCC
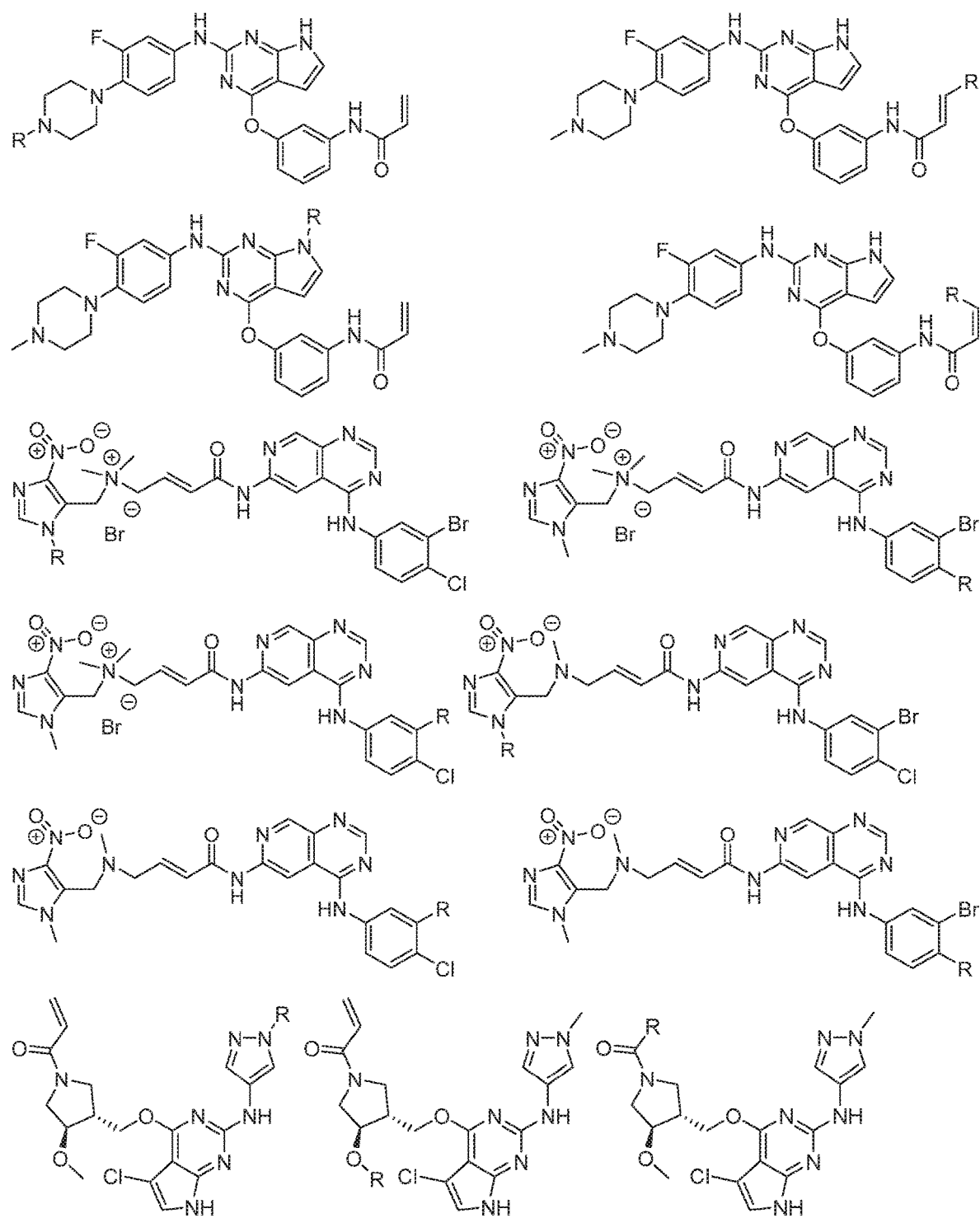

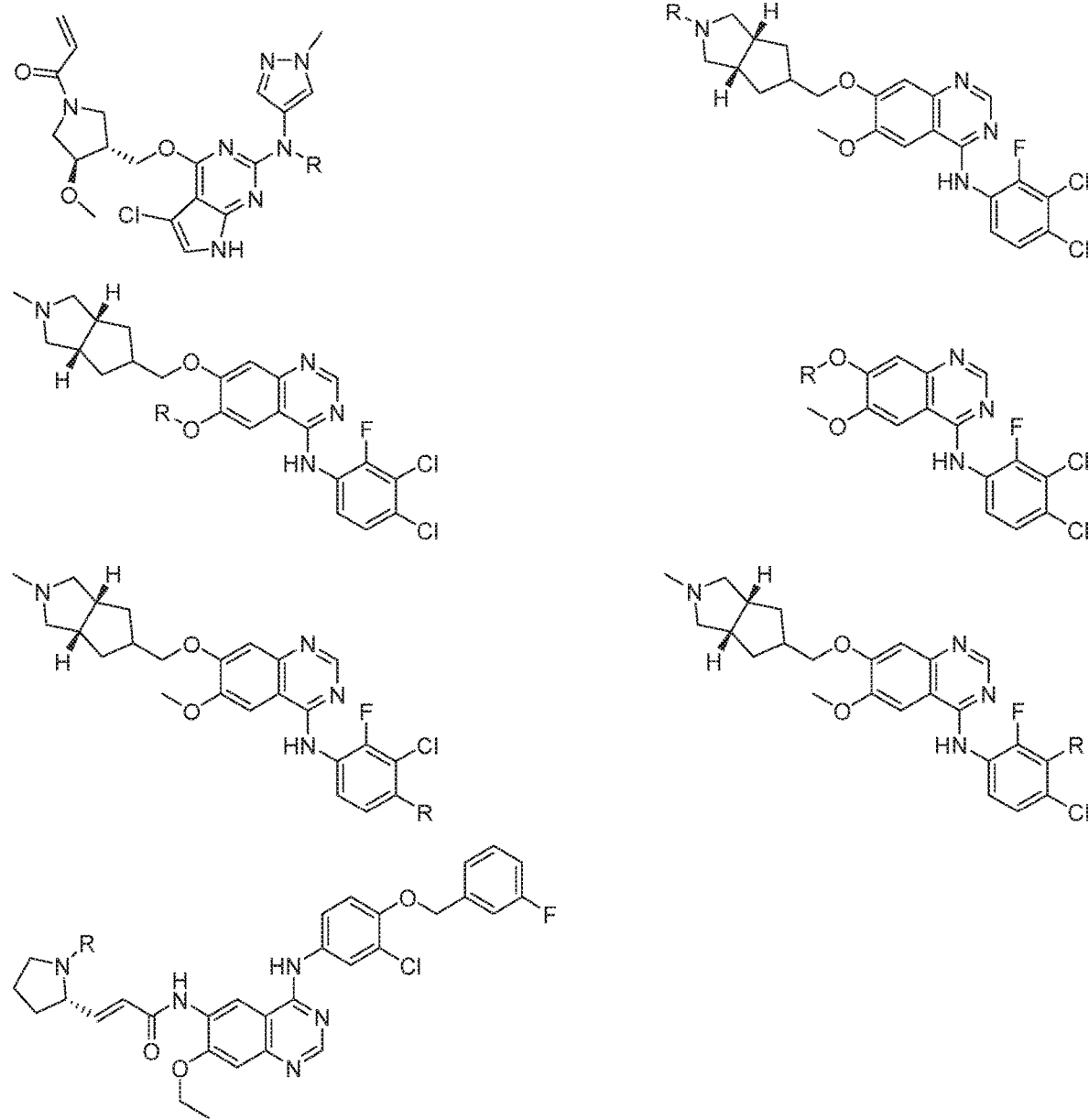
FIG. 2DDD

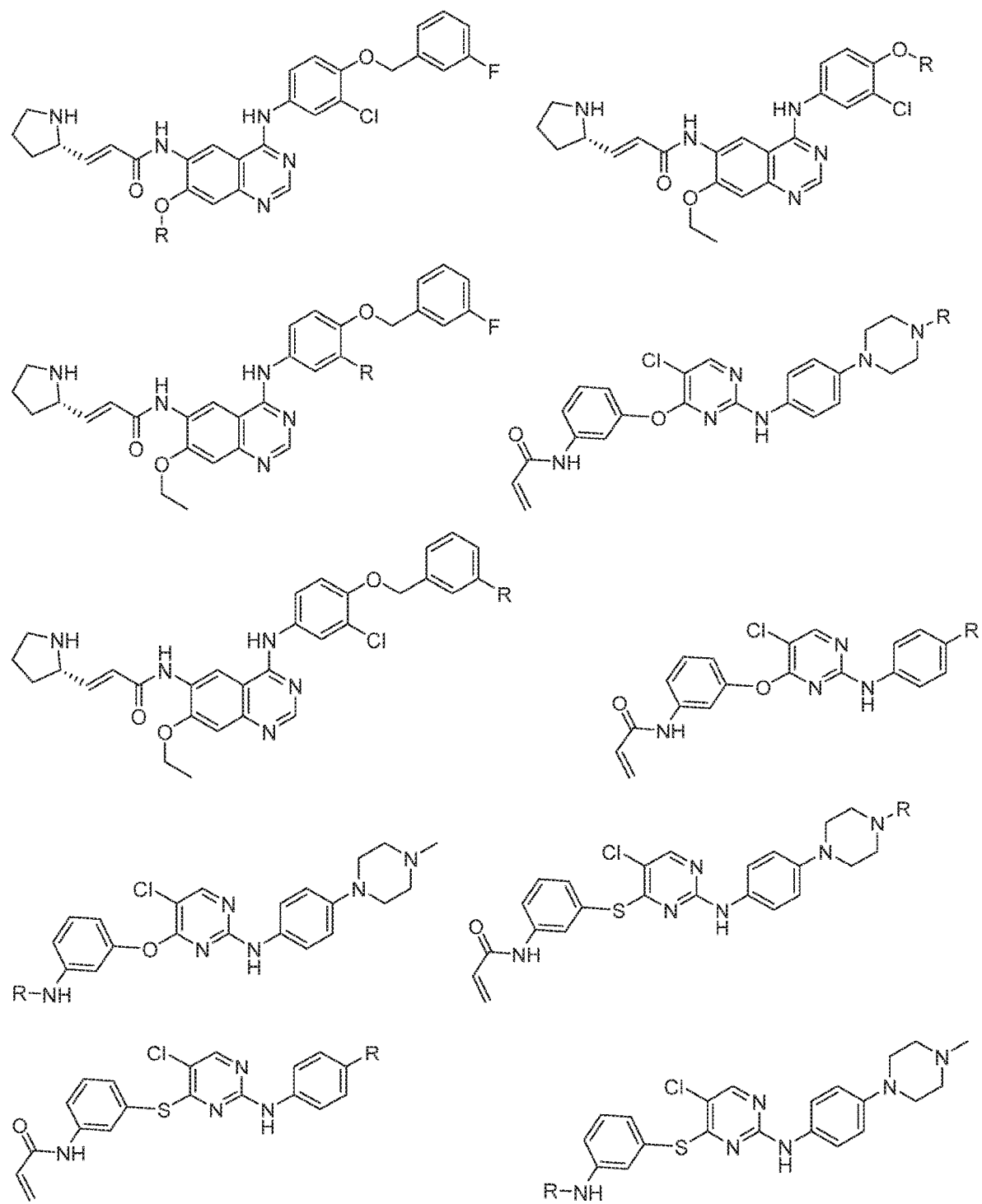
FIG. 2EEE

FIG. 2FFF
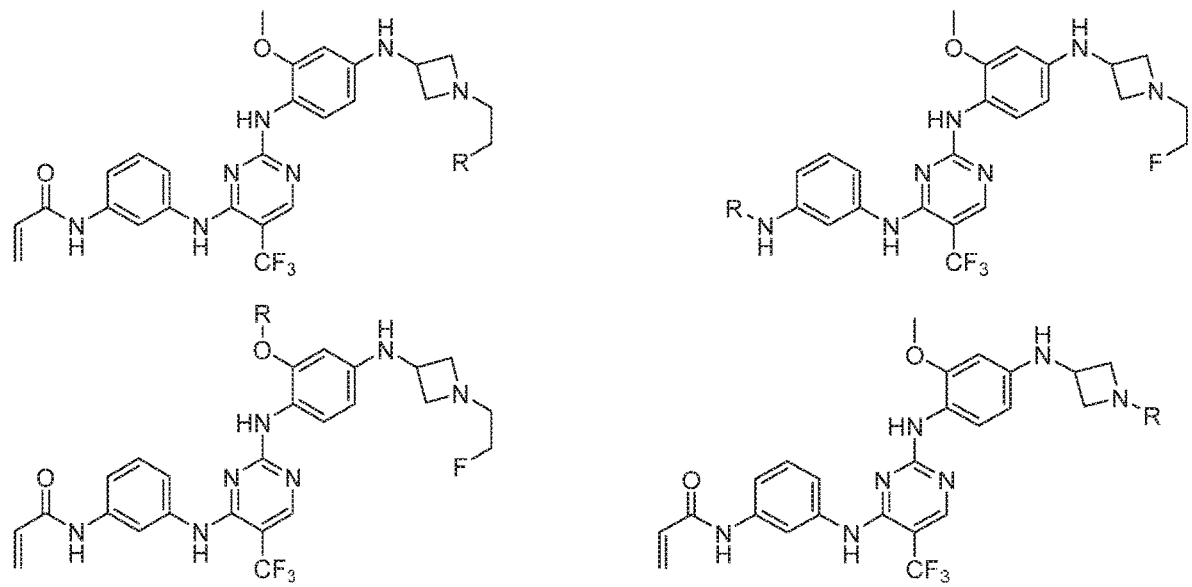
FIG. 2GGG
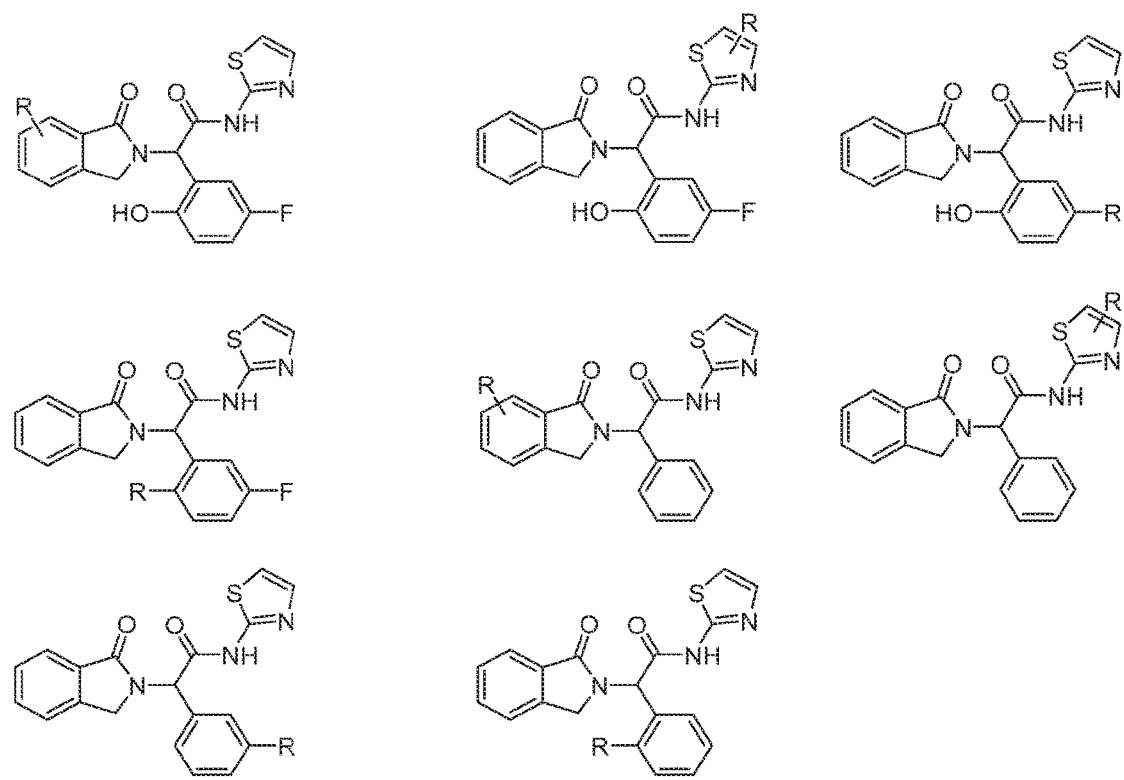

FIG. 2HHH
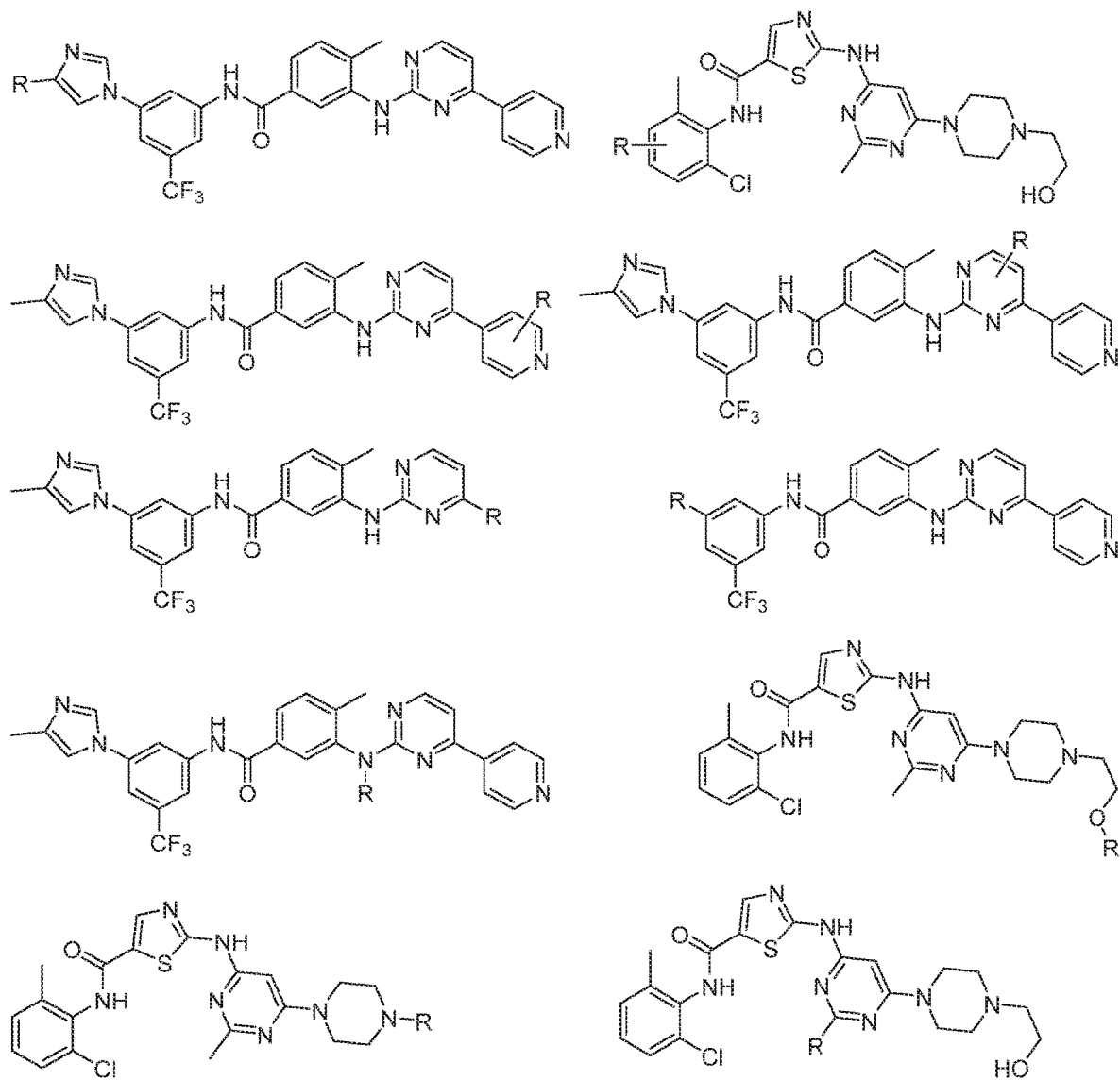

FIG. 2III
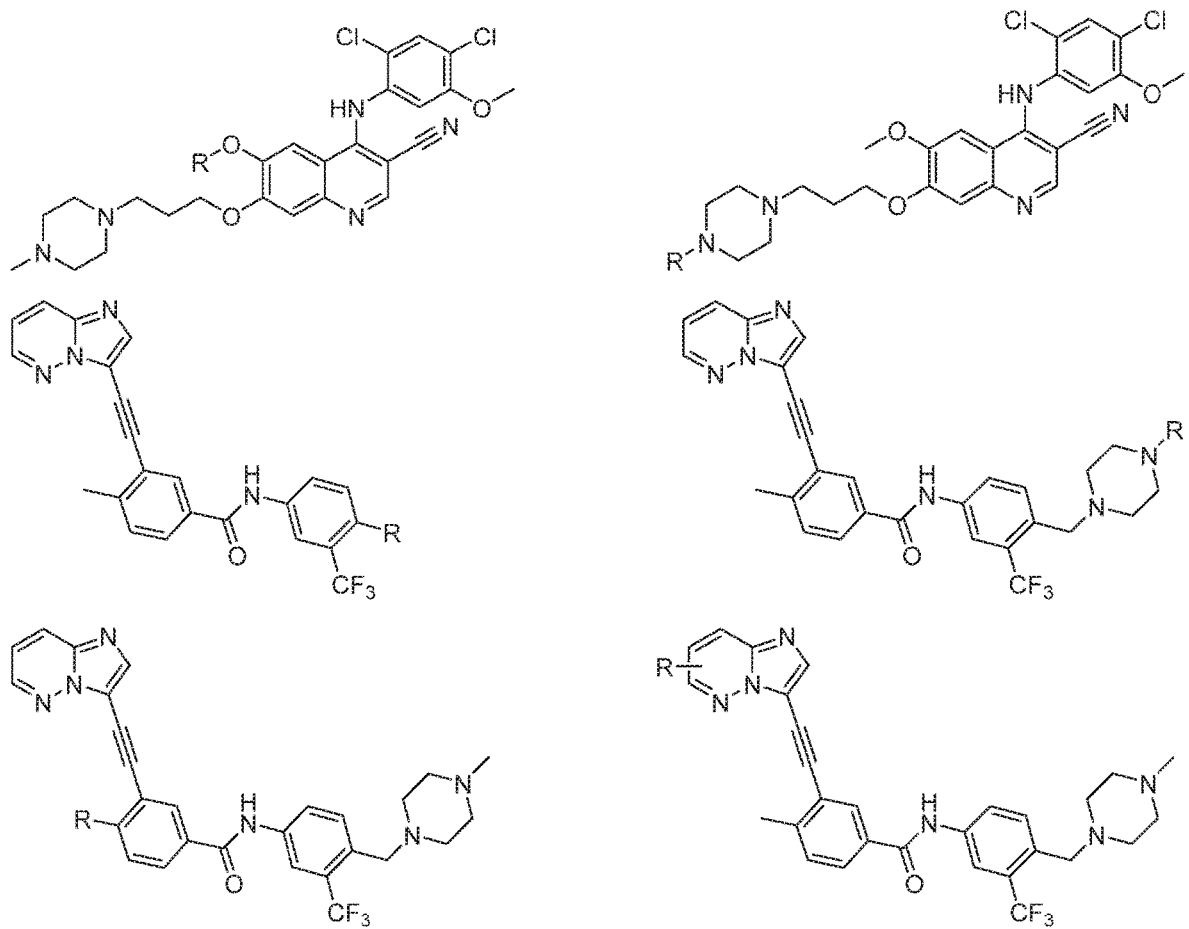
FIG. 2JJJ
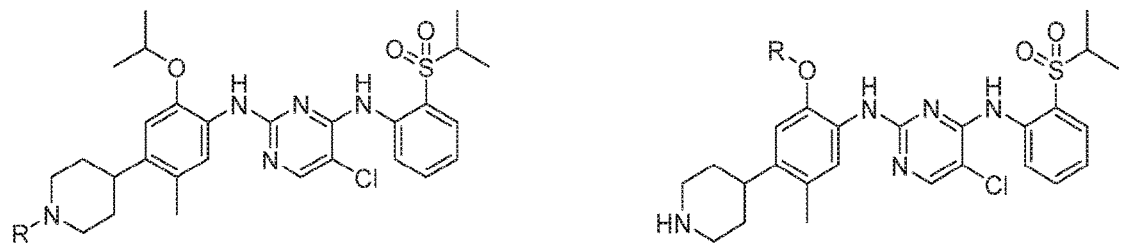

FIG. 2KKK
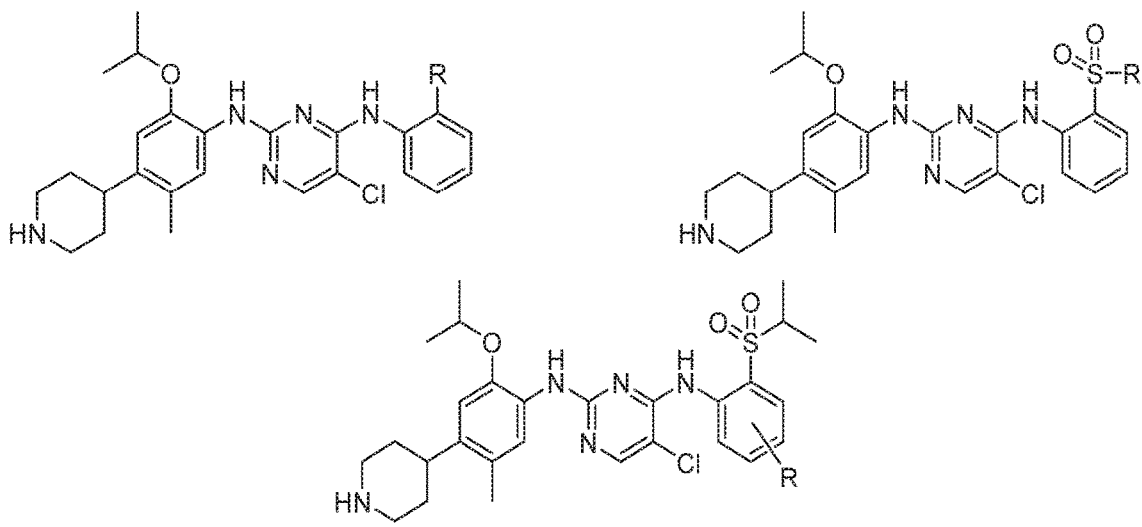
FIG. 2LLL
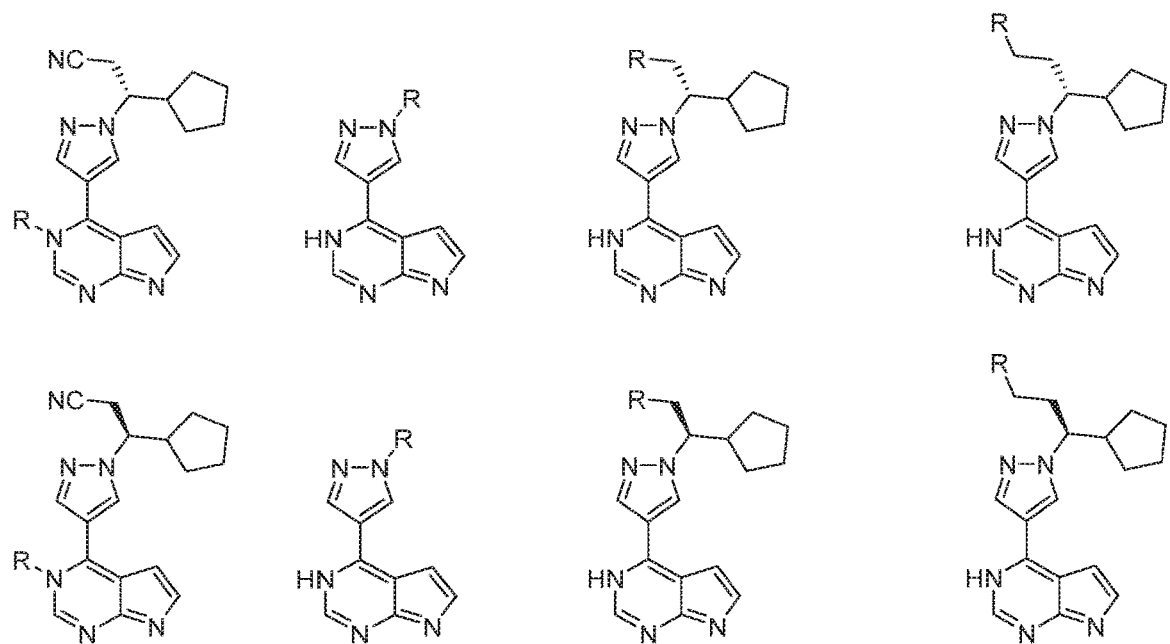

FIG. 2MMM
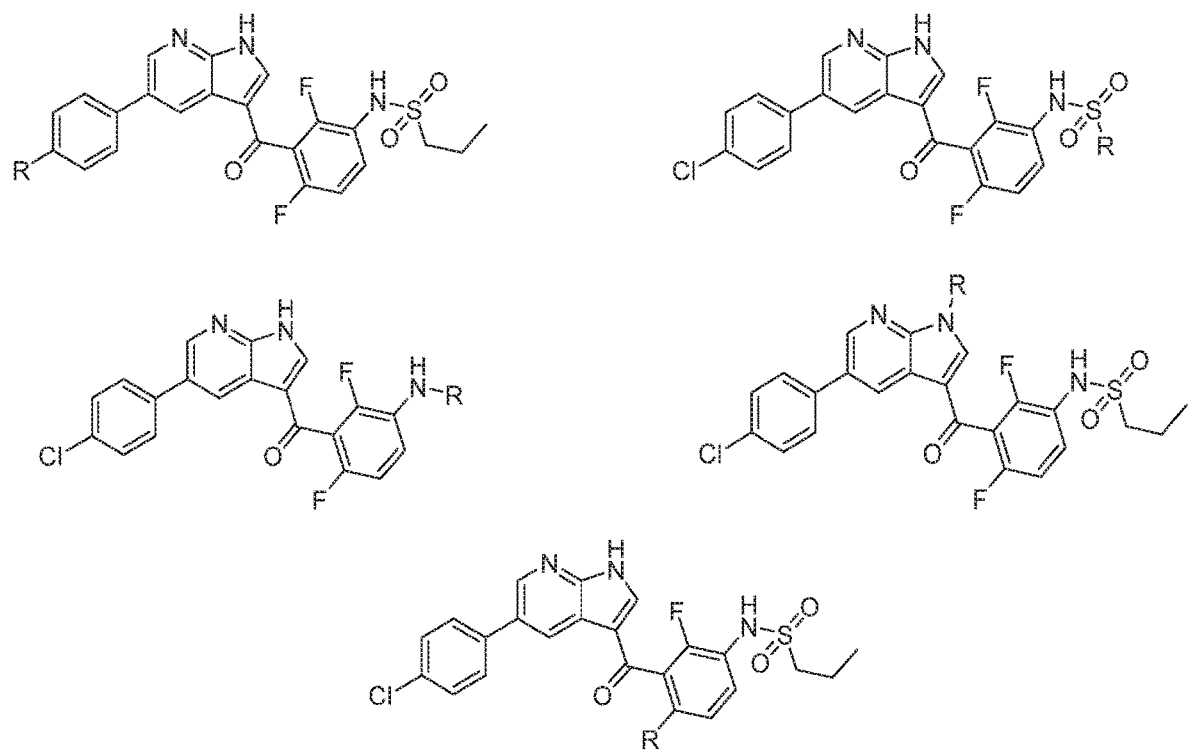
FIG. 2NNN
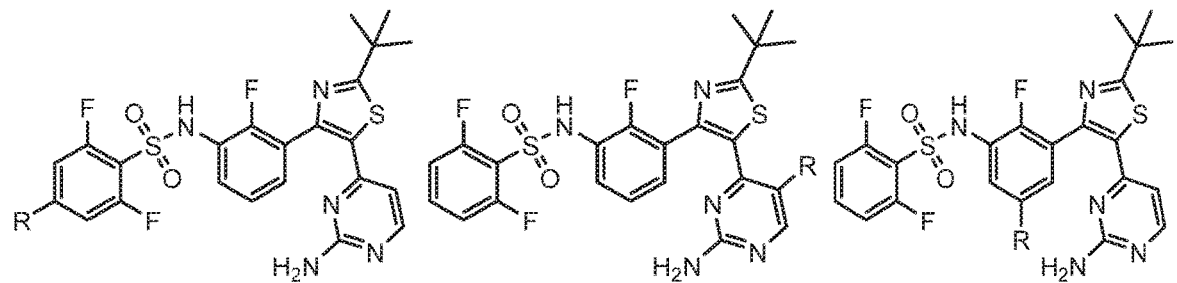

FIG. 2OOO
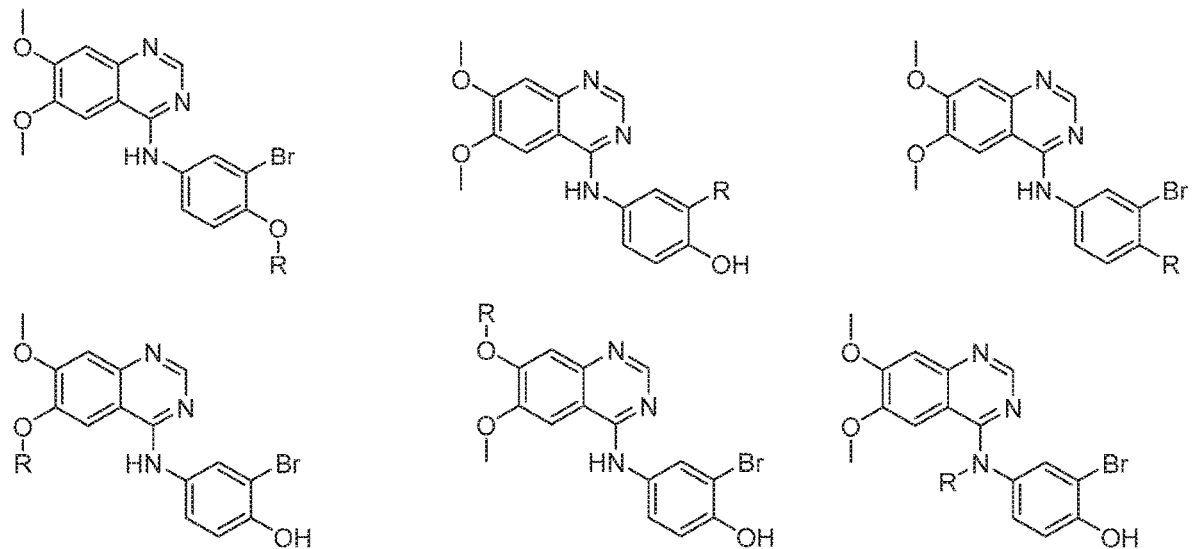
FIG. 2PPP
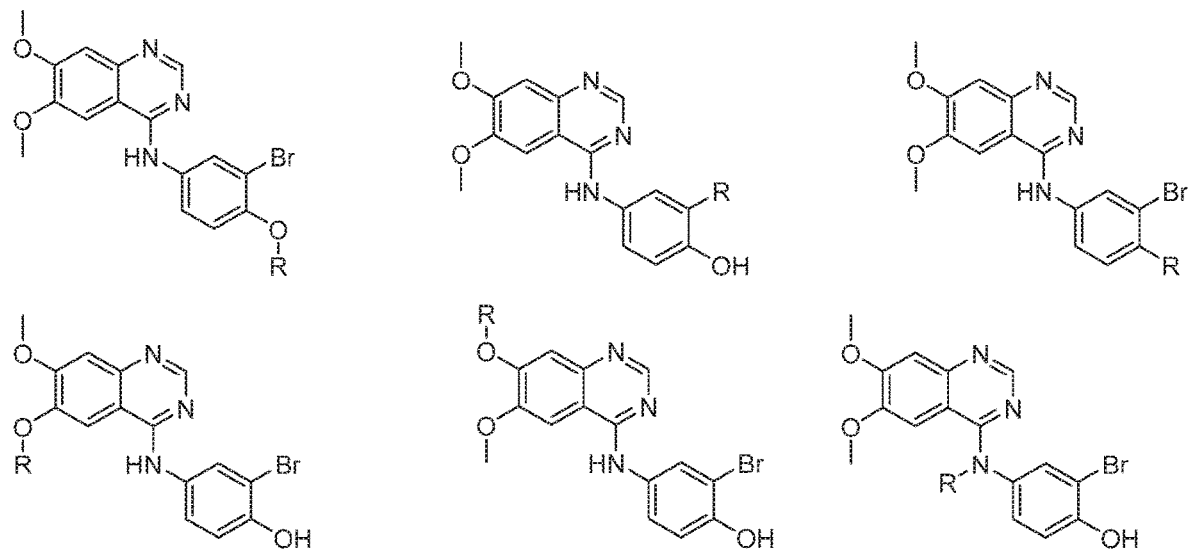

FIG. 2QQQ
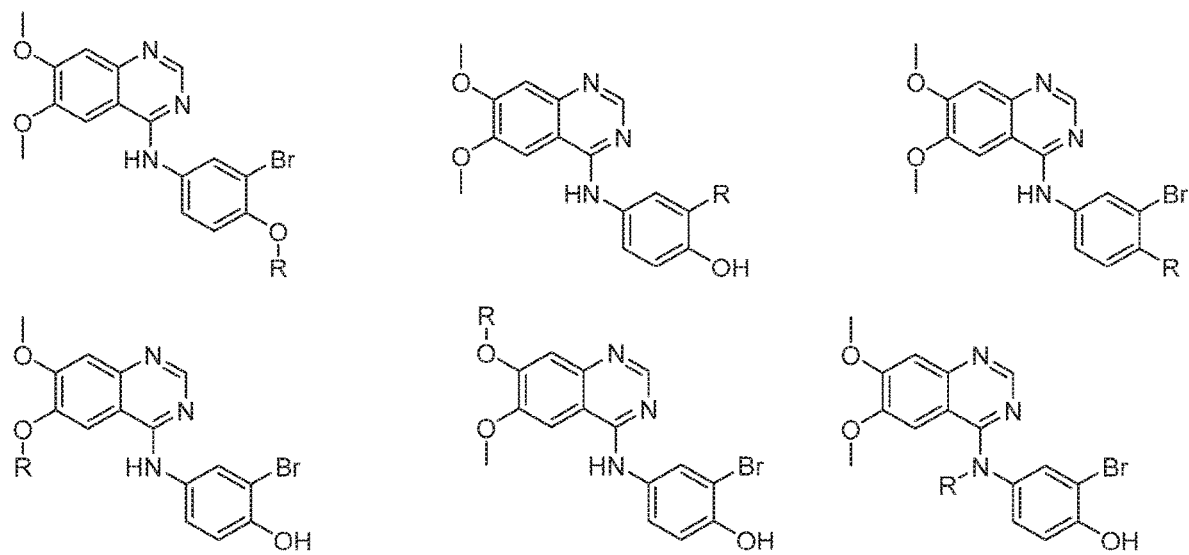
FIG. 2RRR
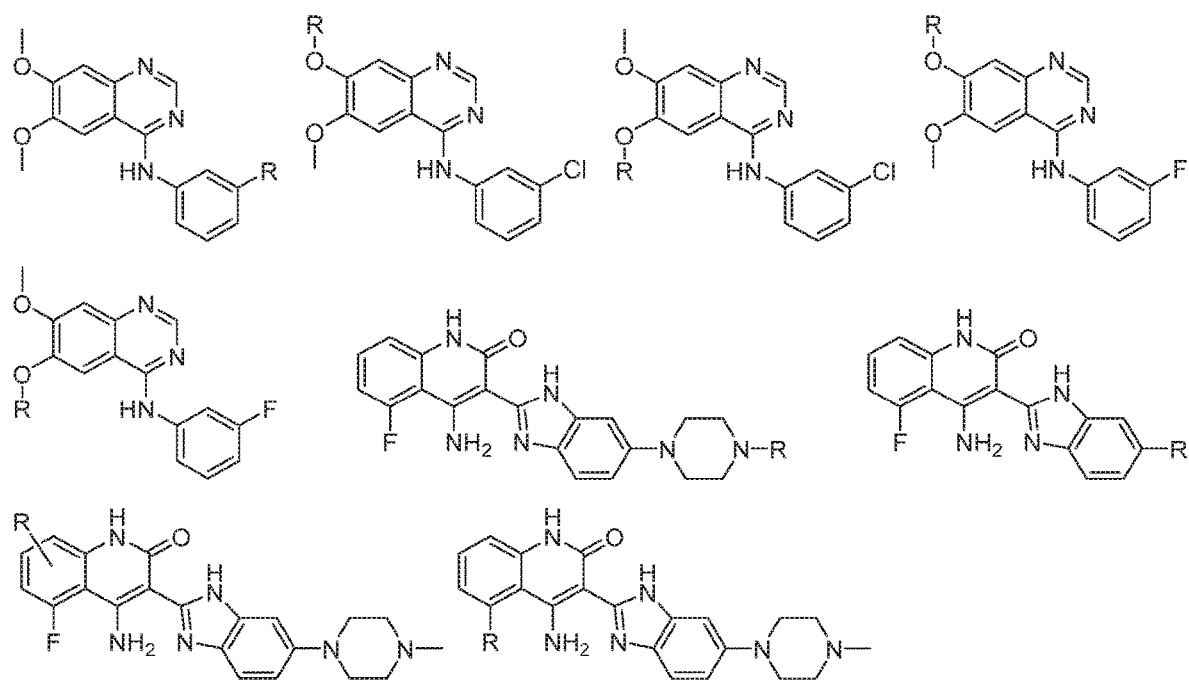

FIG. 2SSS
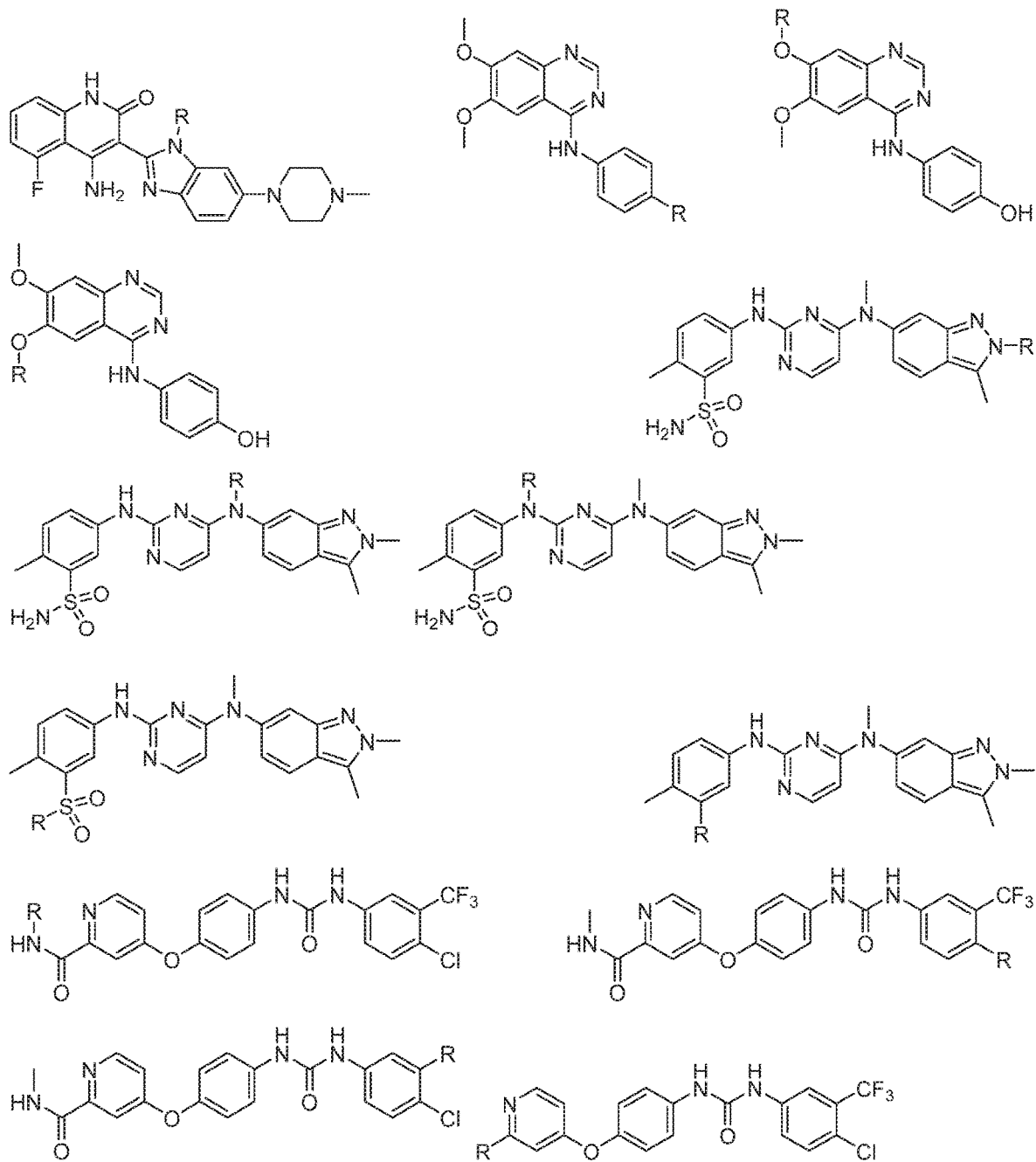

FIG. 2TTT
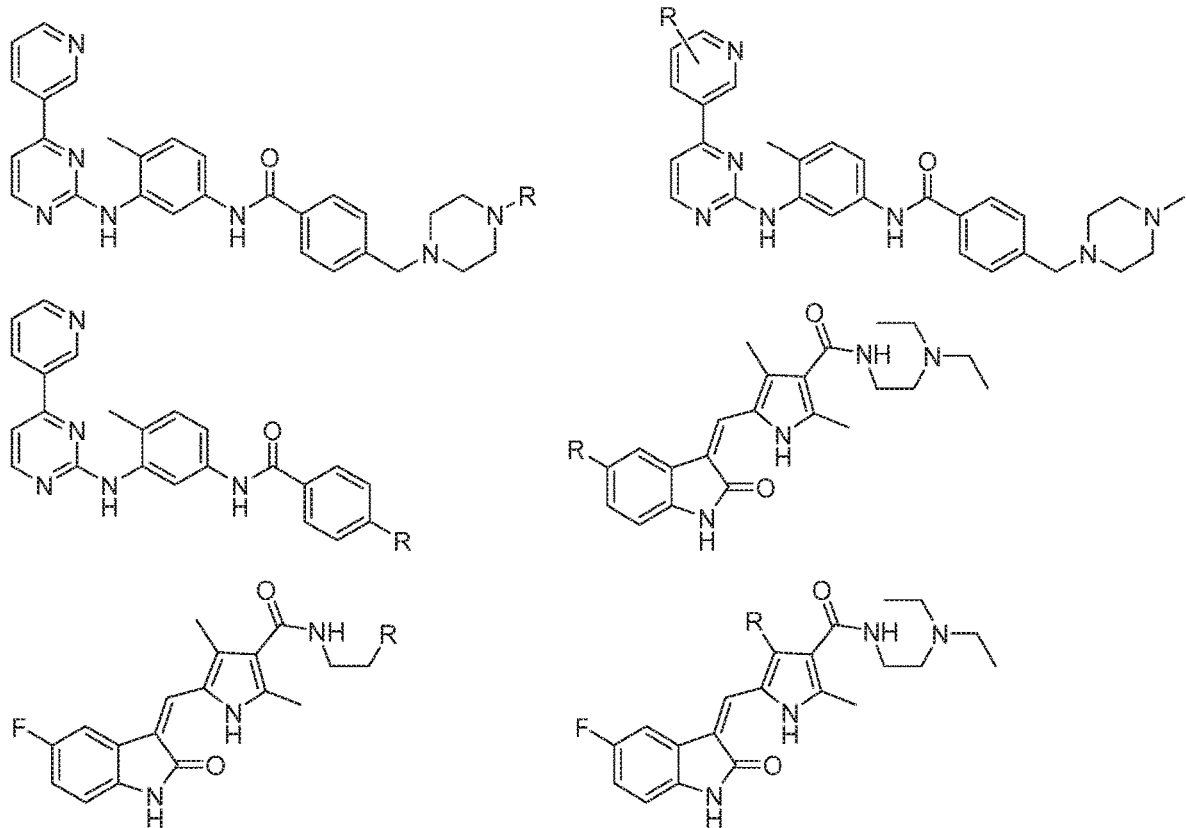
FIG. 2UUU
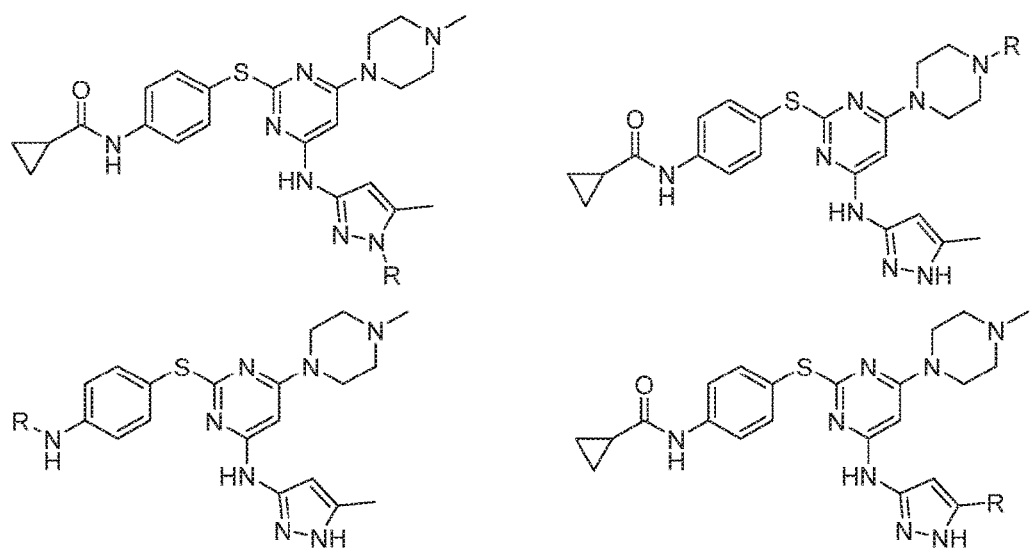

FIG. 2VVV
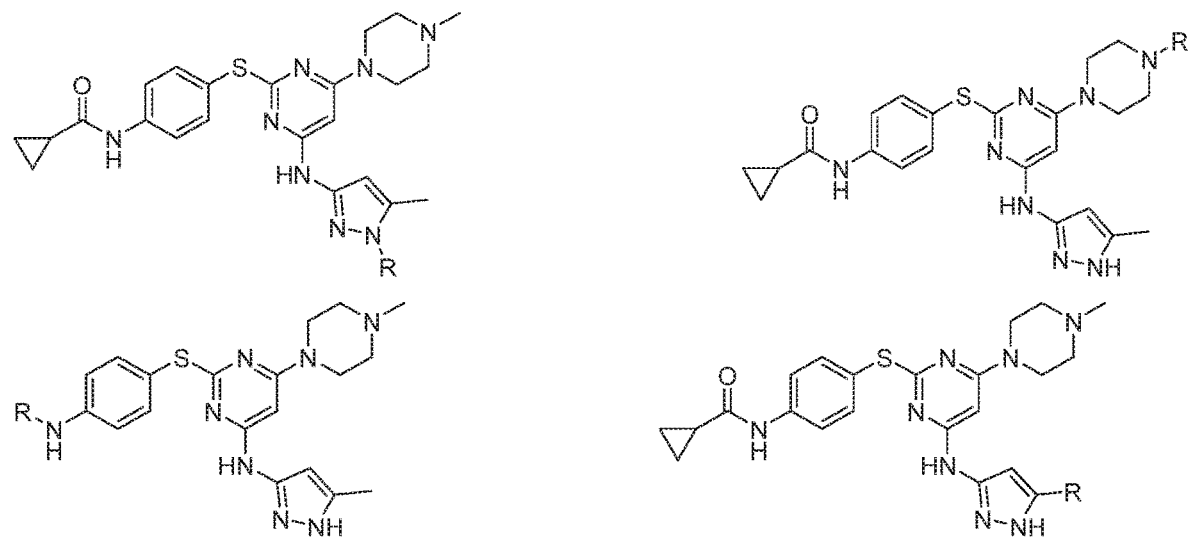
FIG. 2WWW
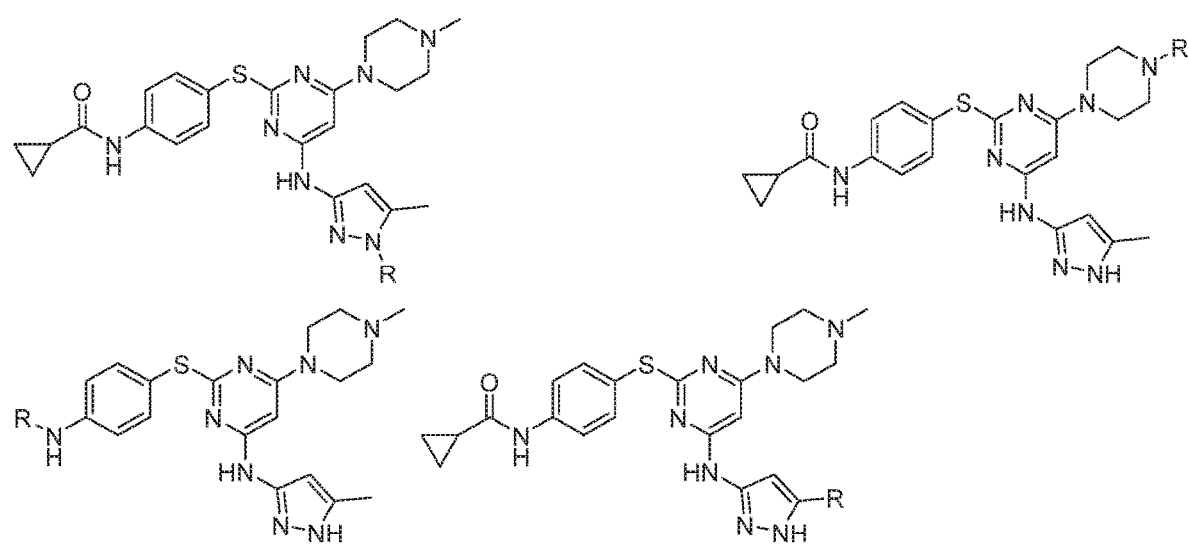

FIG. 2XXX
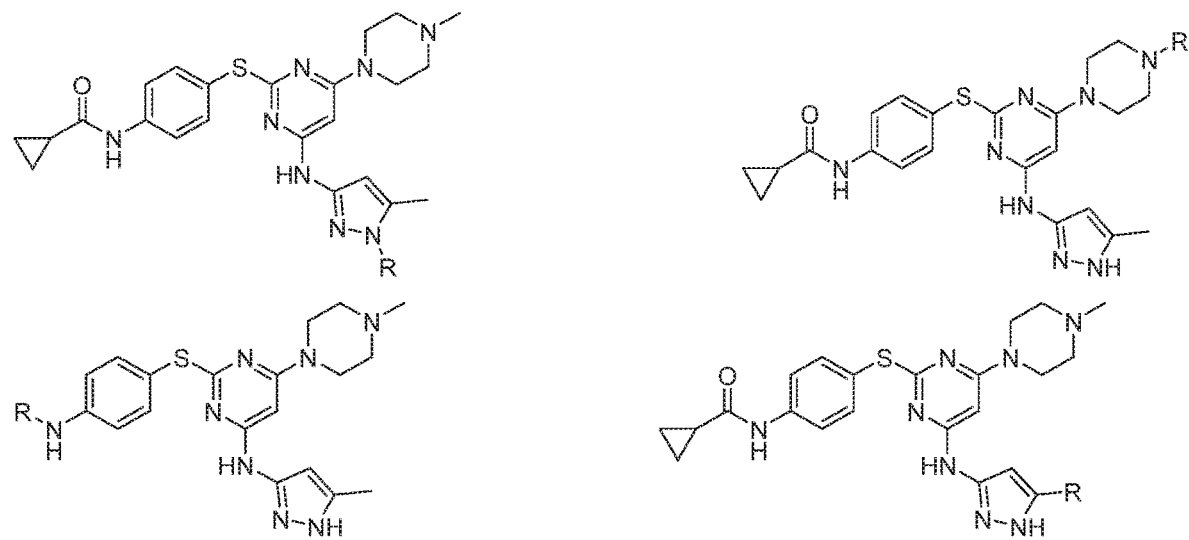
FIG. 2YYY
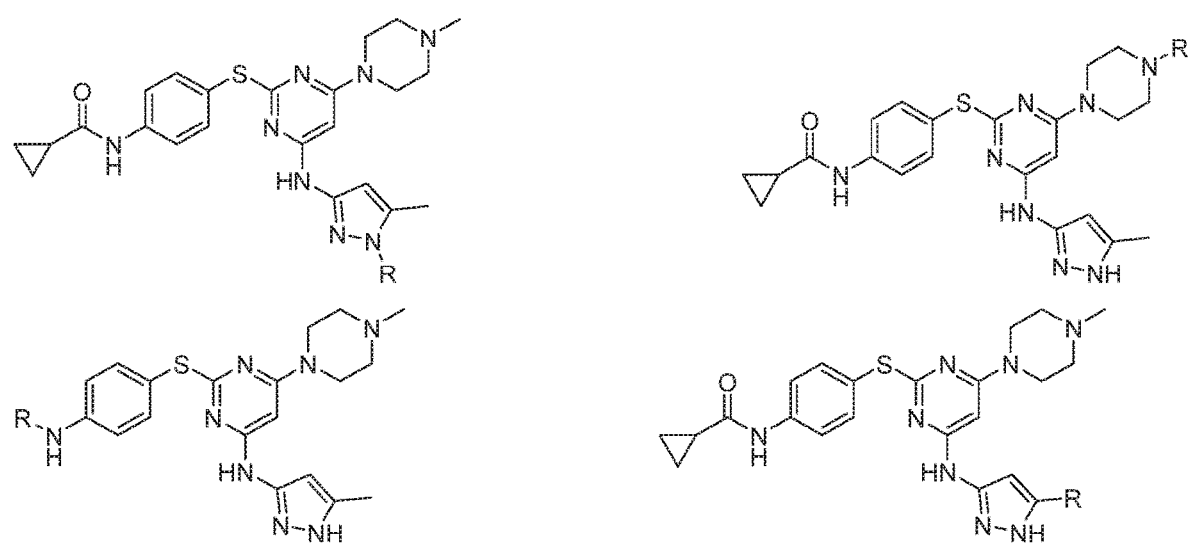

FIG. 2ZZZ
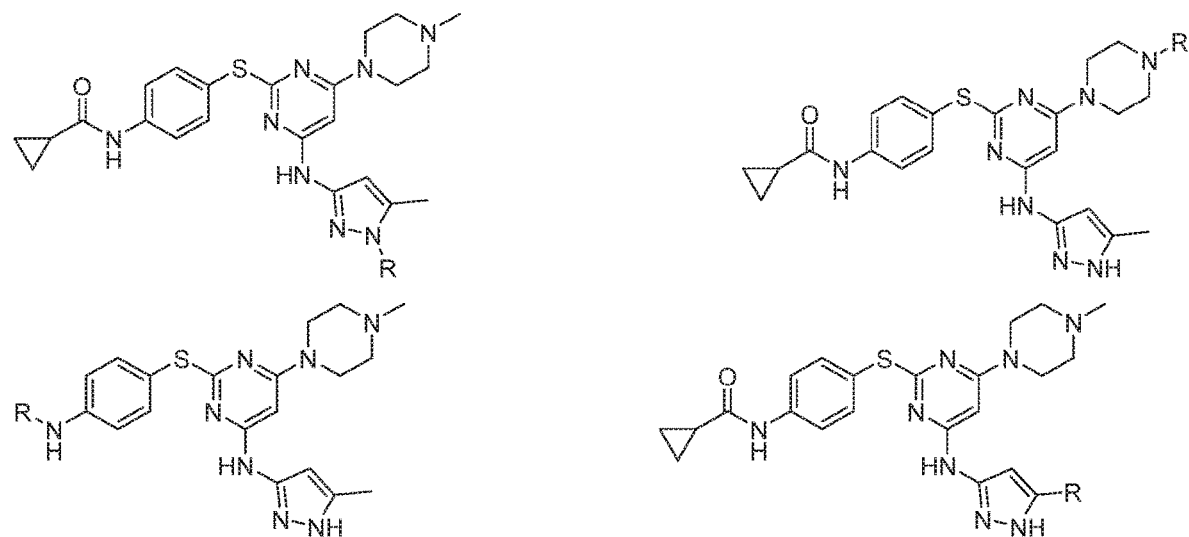
FIG. 2AAAA
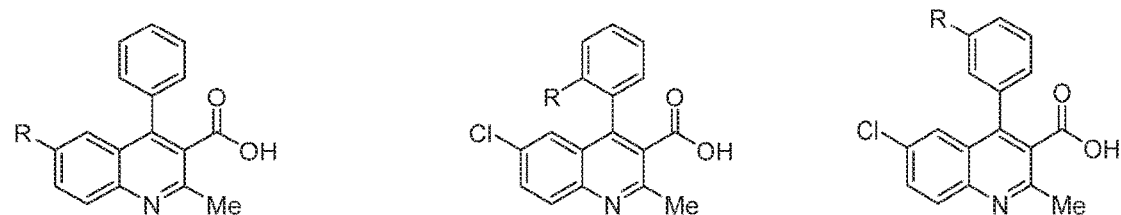
FIG. 2BBBB
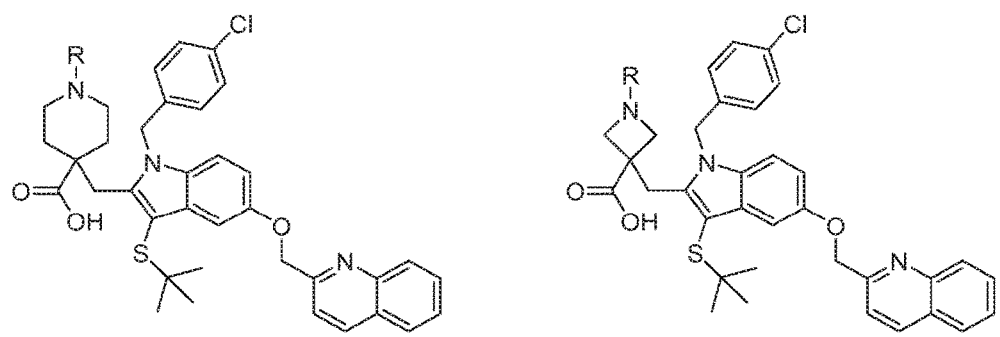

FIG. 2CCCC
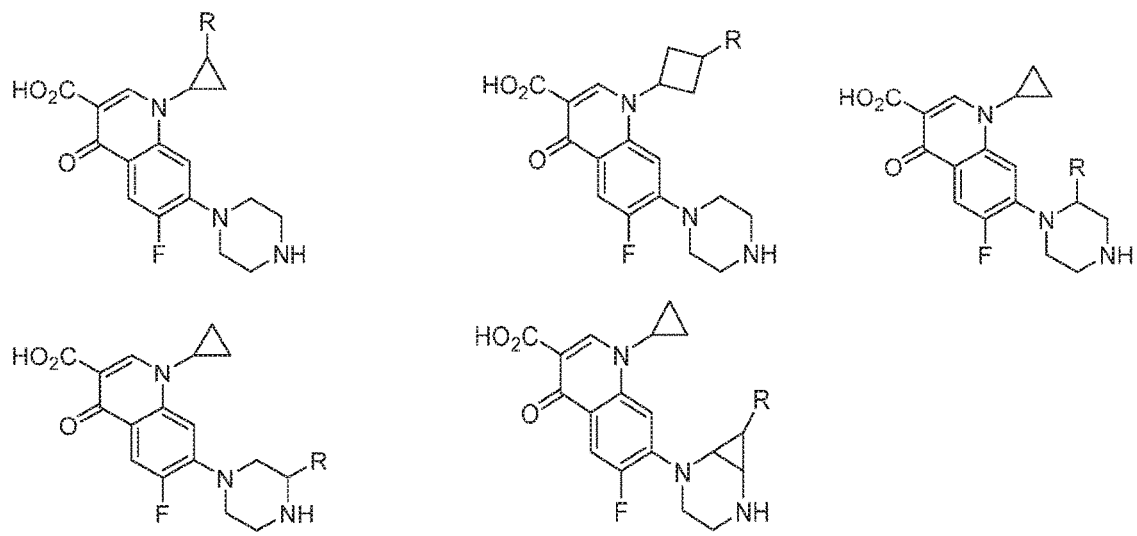
FIG. 2DDDD
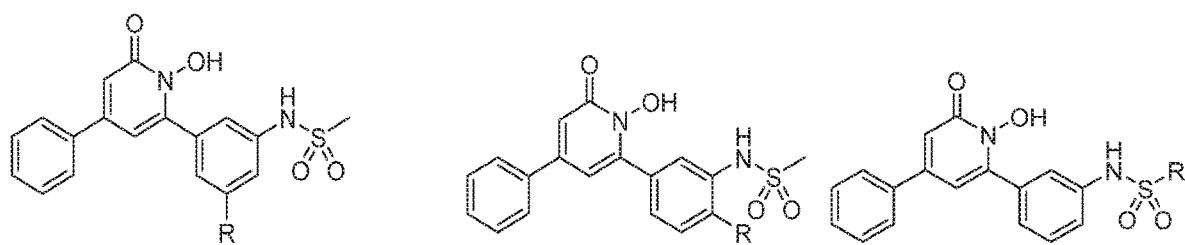
FIG. 2EEEE
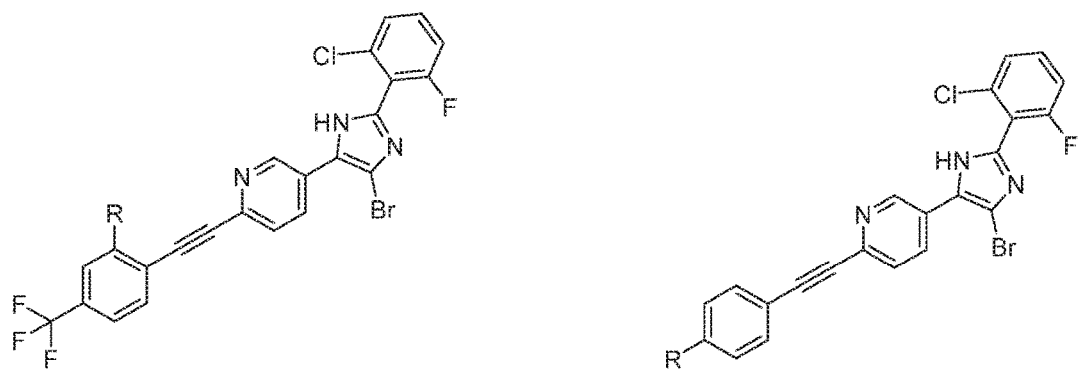

FIG. 2FFFF
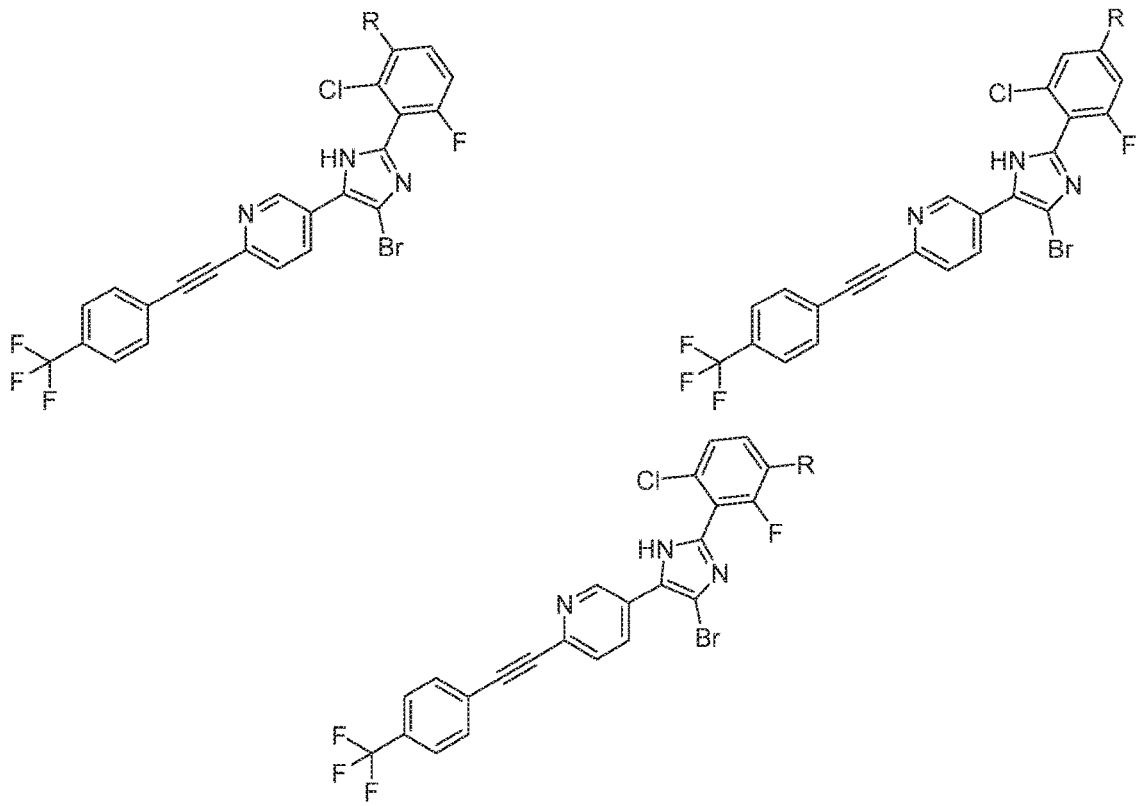
FIG. 2GGGG
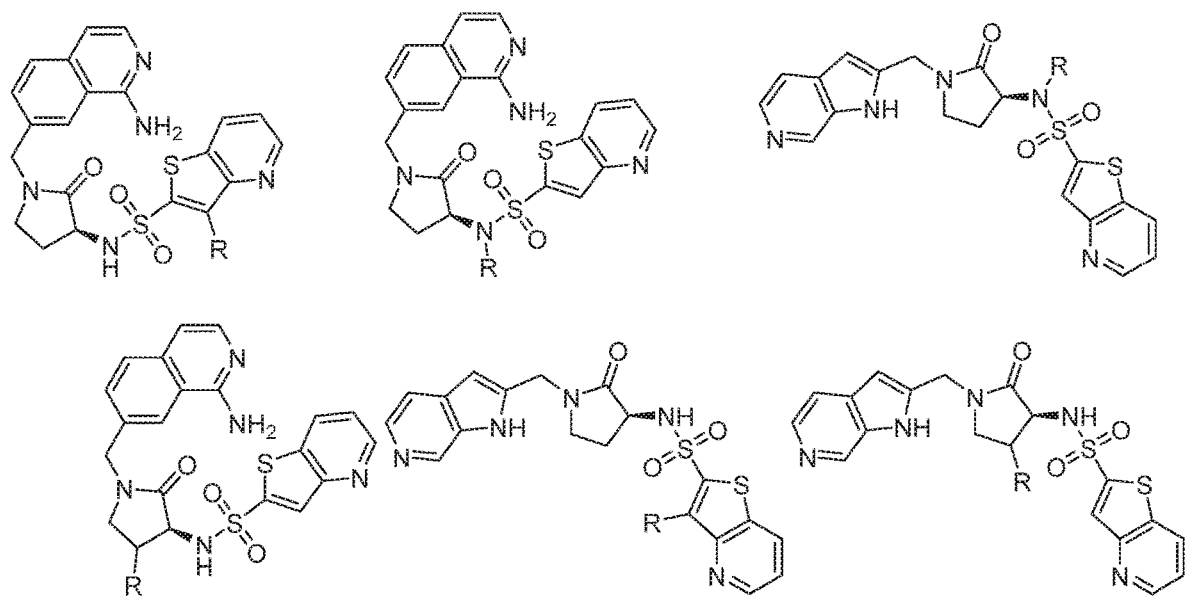

FIG. 2HHHH
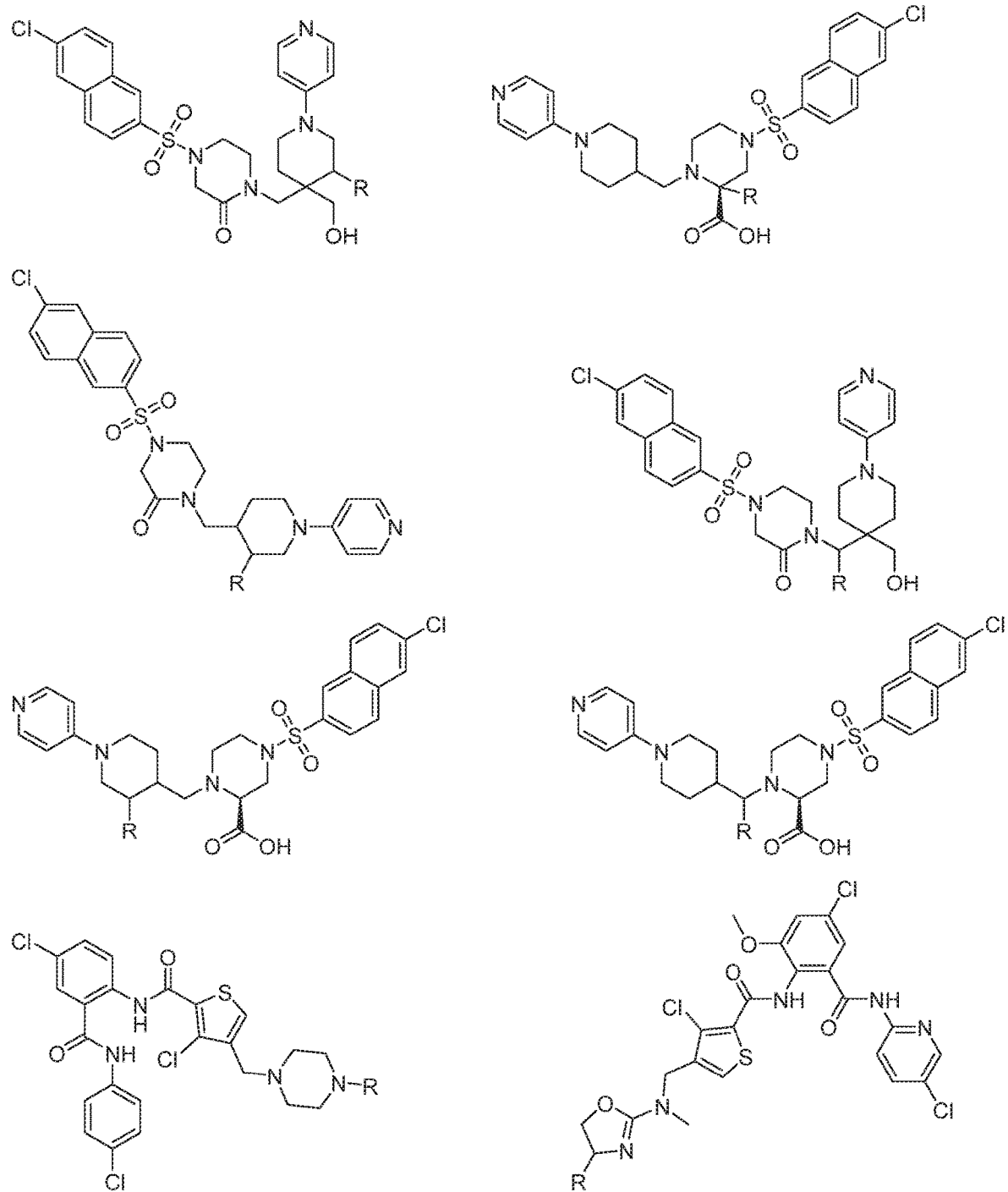

FIG. 2IIII
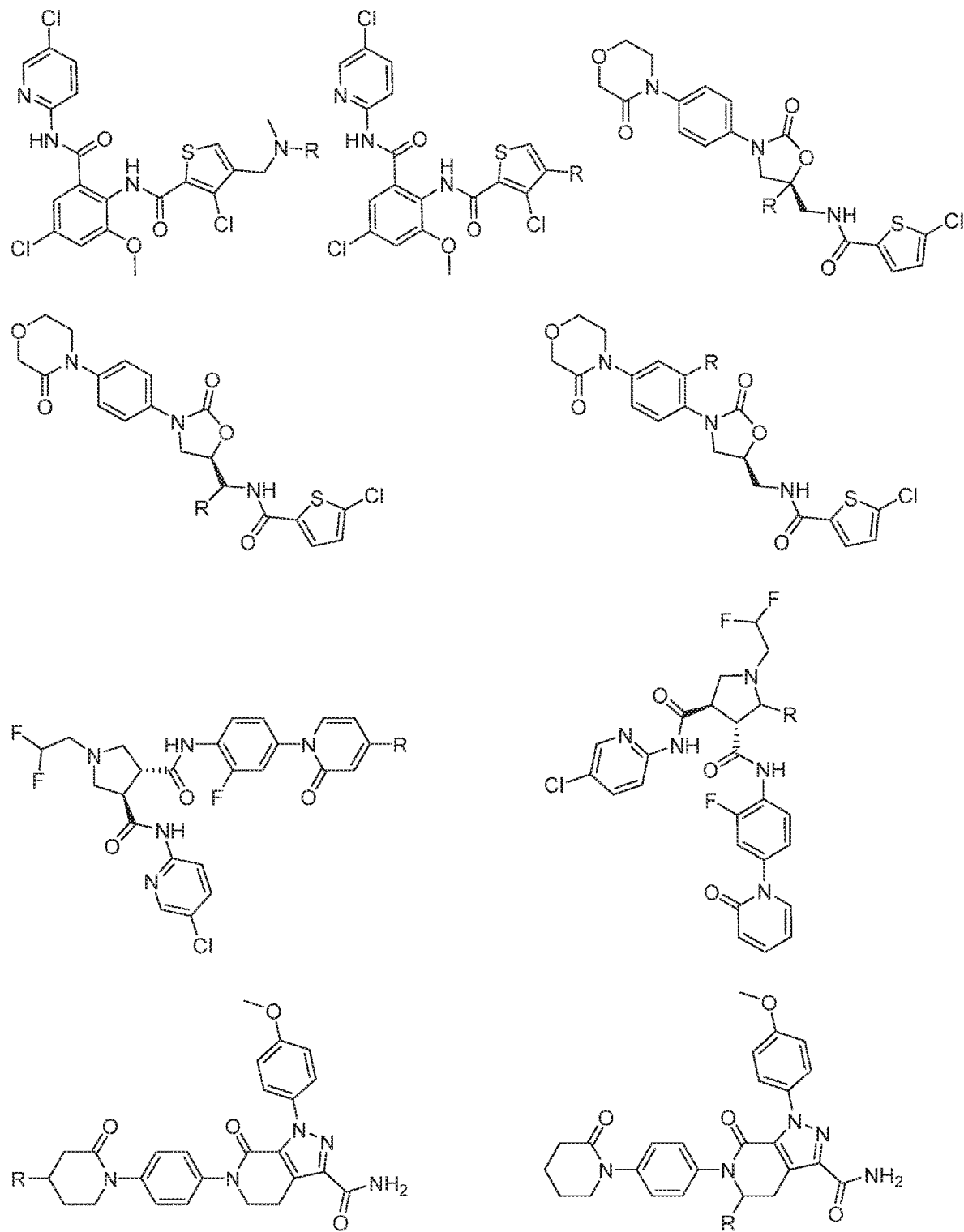

FIG. 2JJJJ
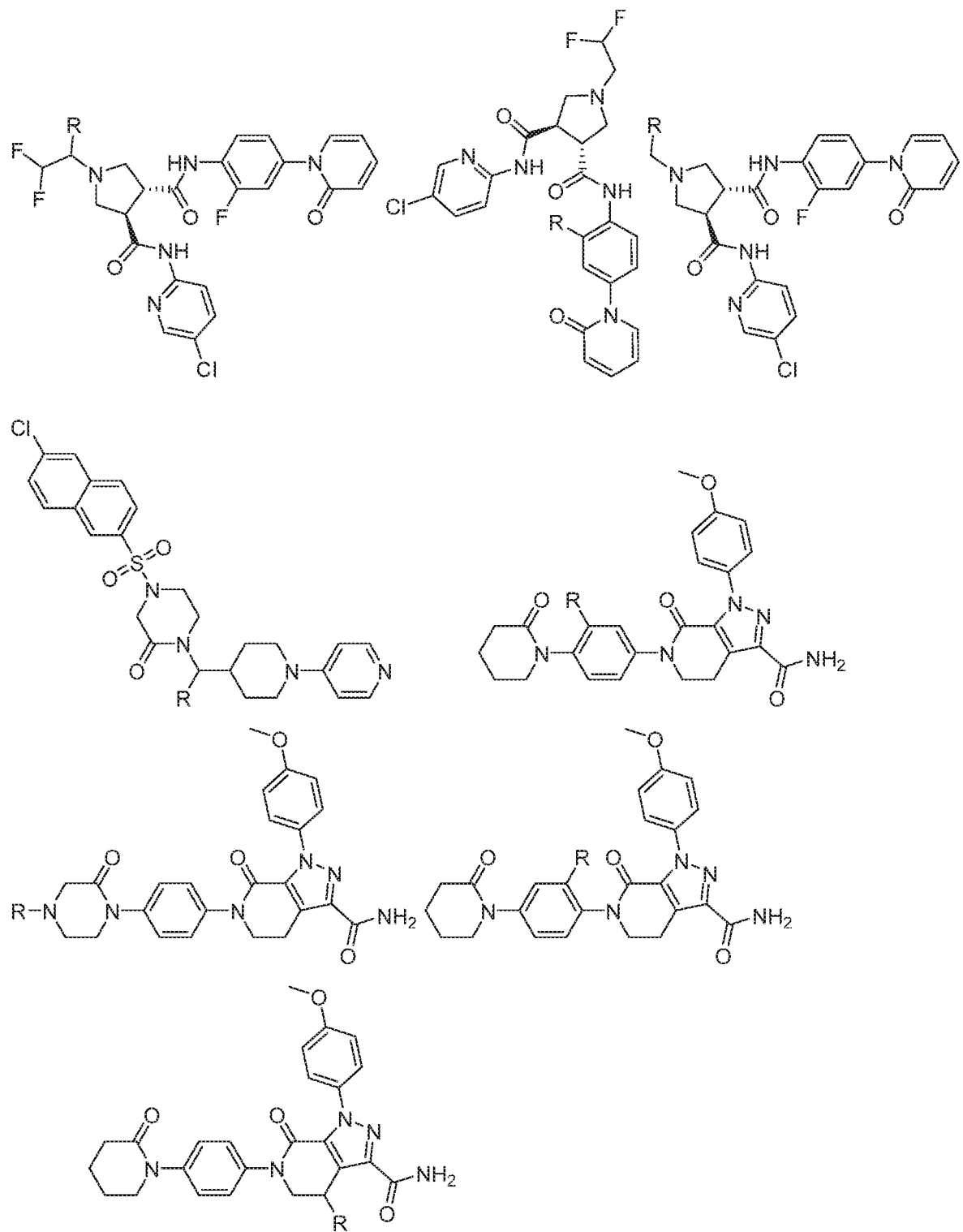

FIG. 2KKKK
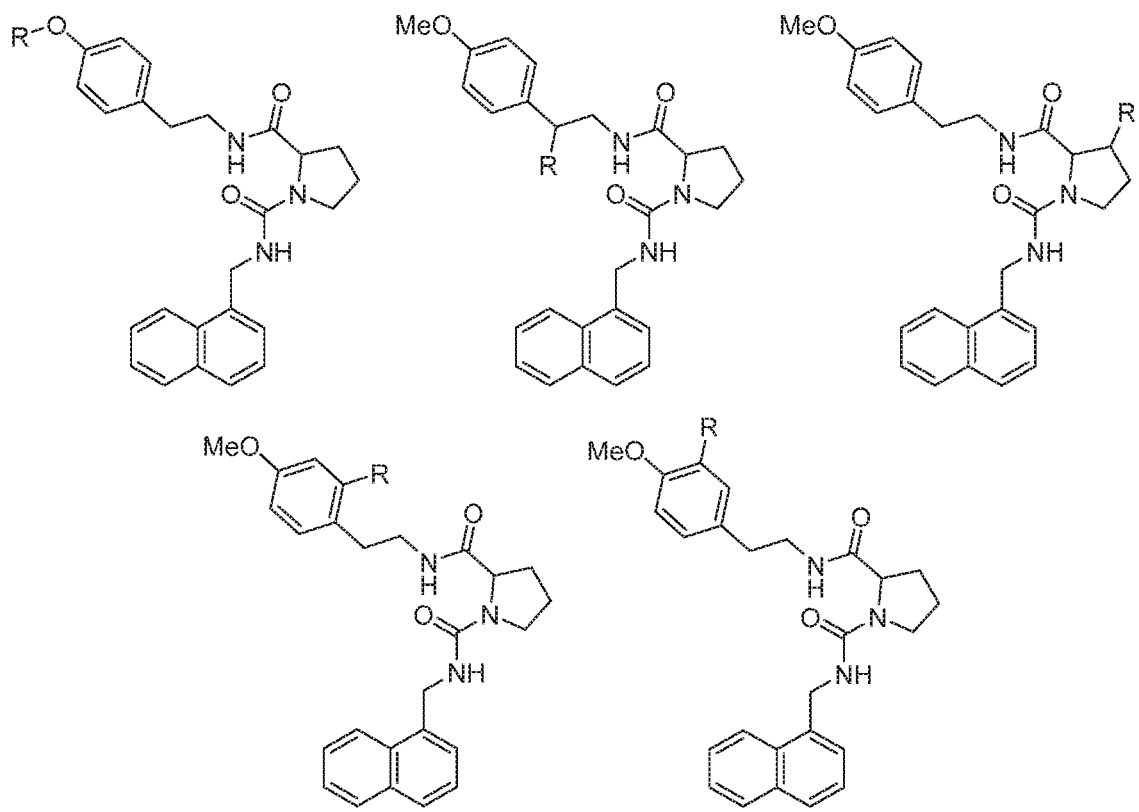
FIG. 2LLLL
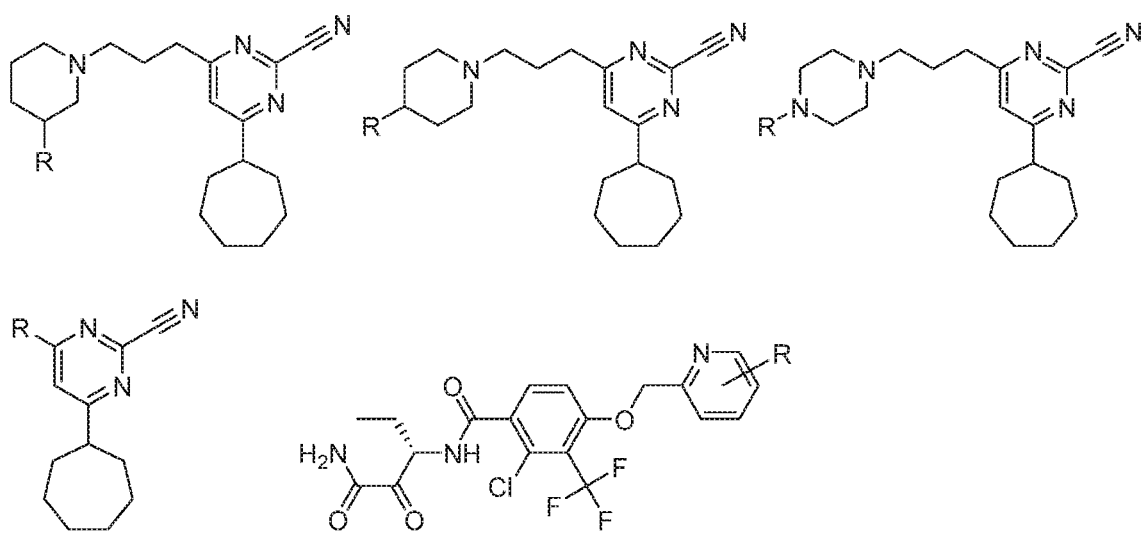

FIG. 2MMMM
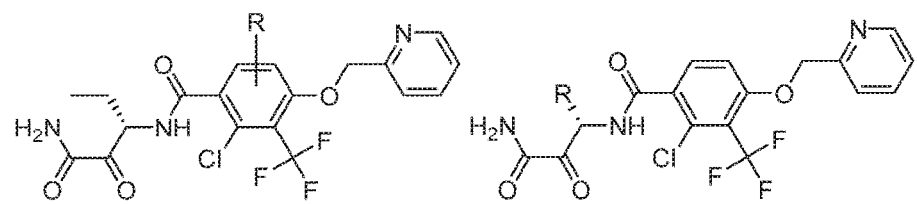
FIG. 2NNNN
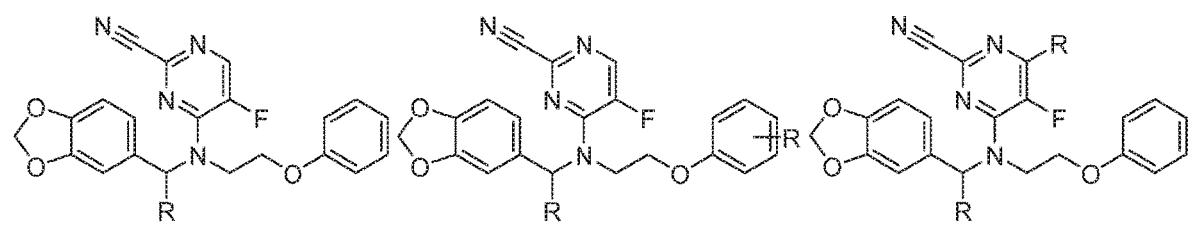
FIG. 2OOOO
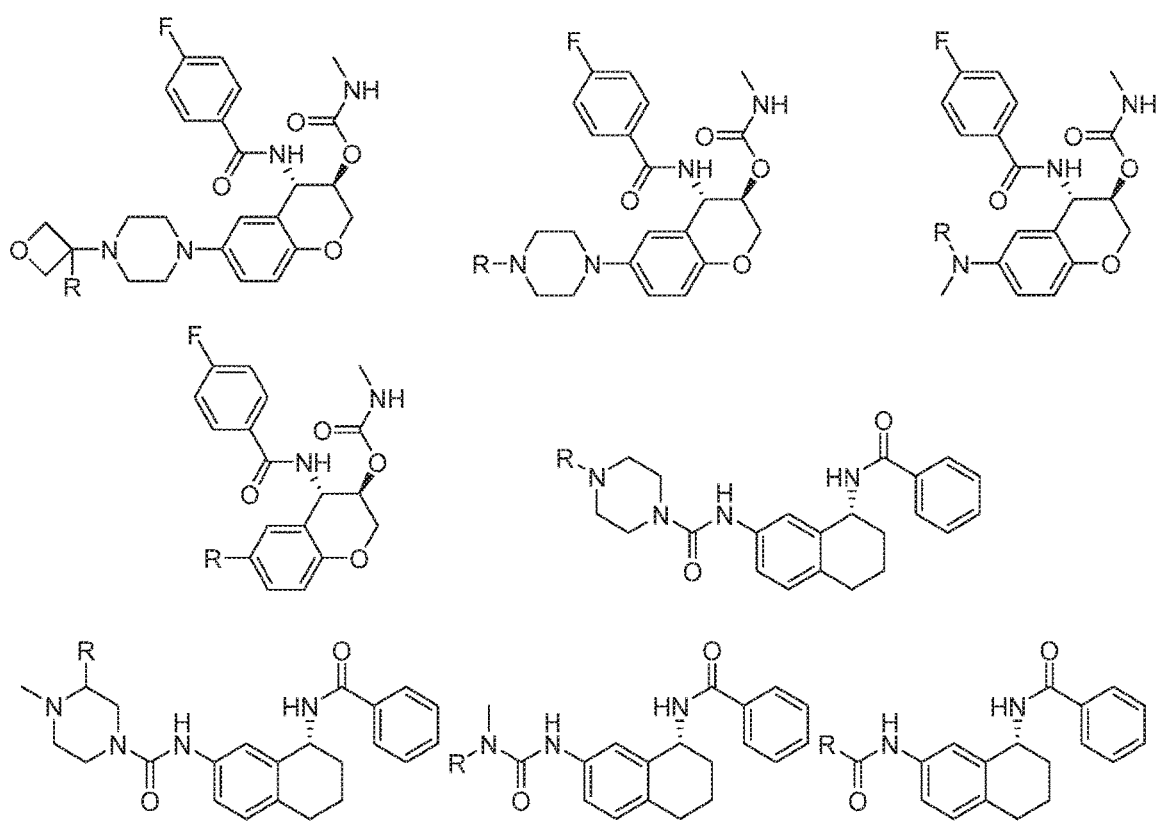

FIG. 2PPPP
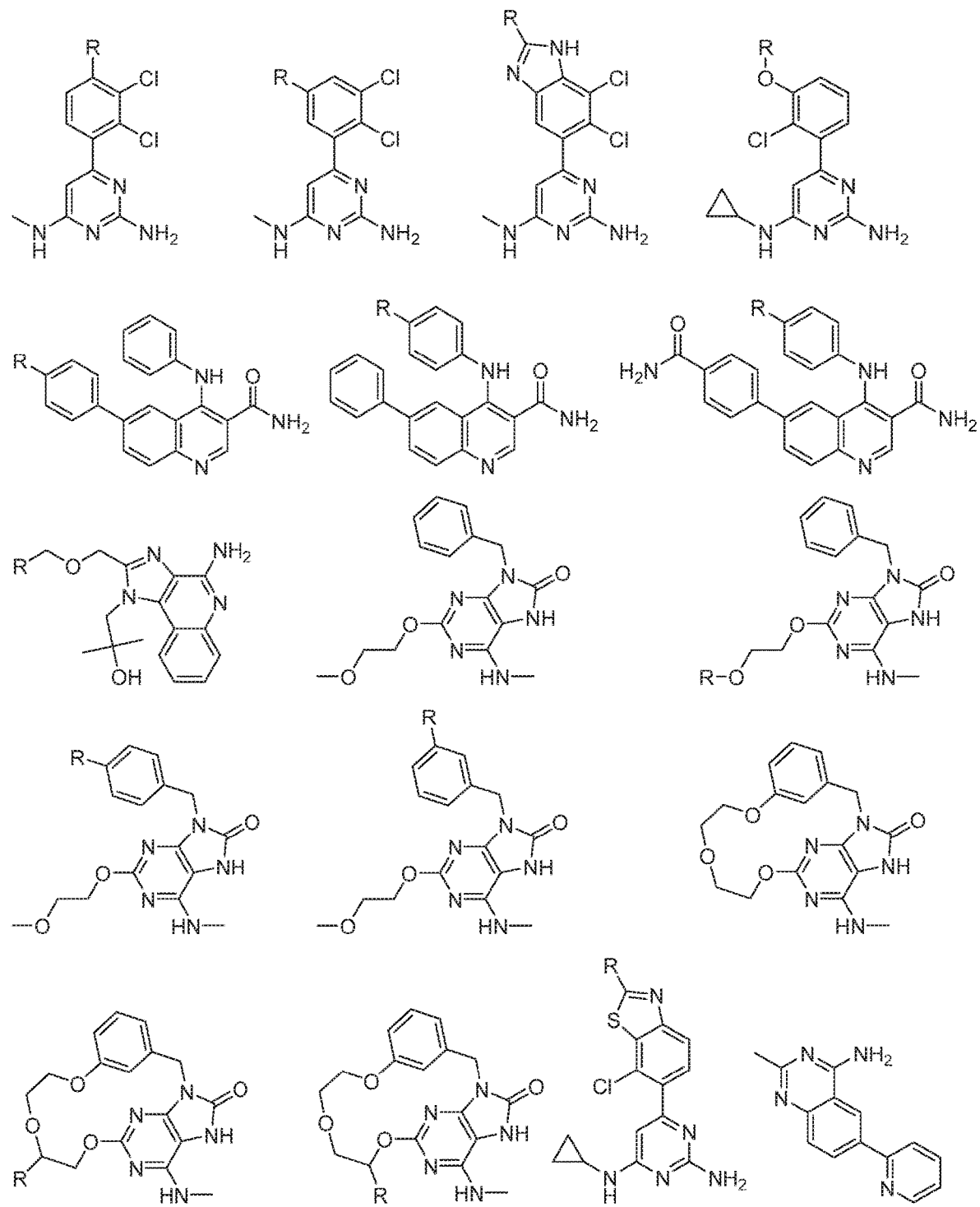

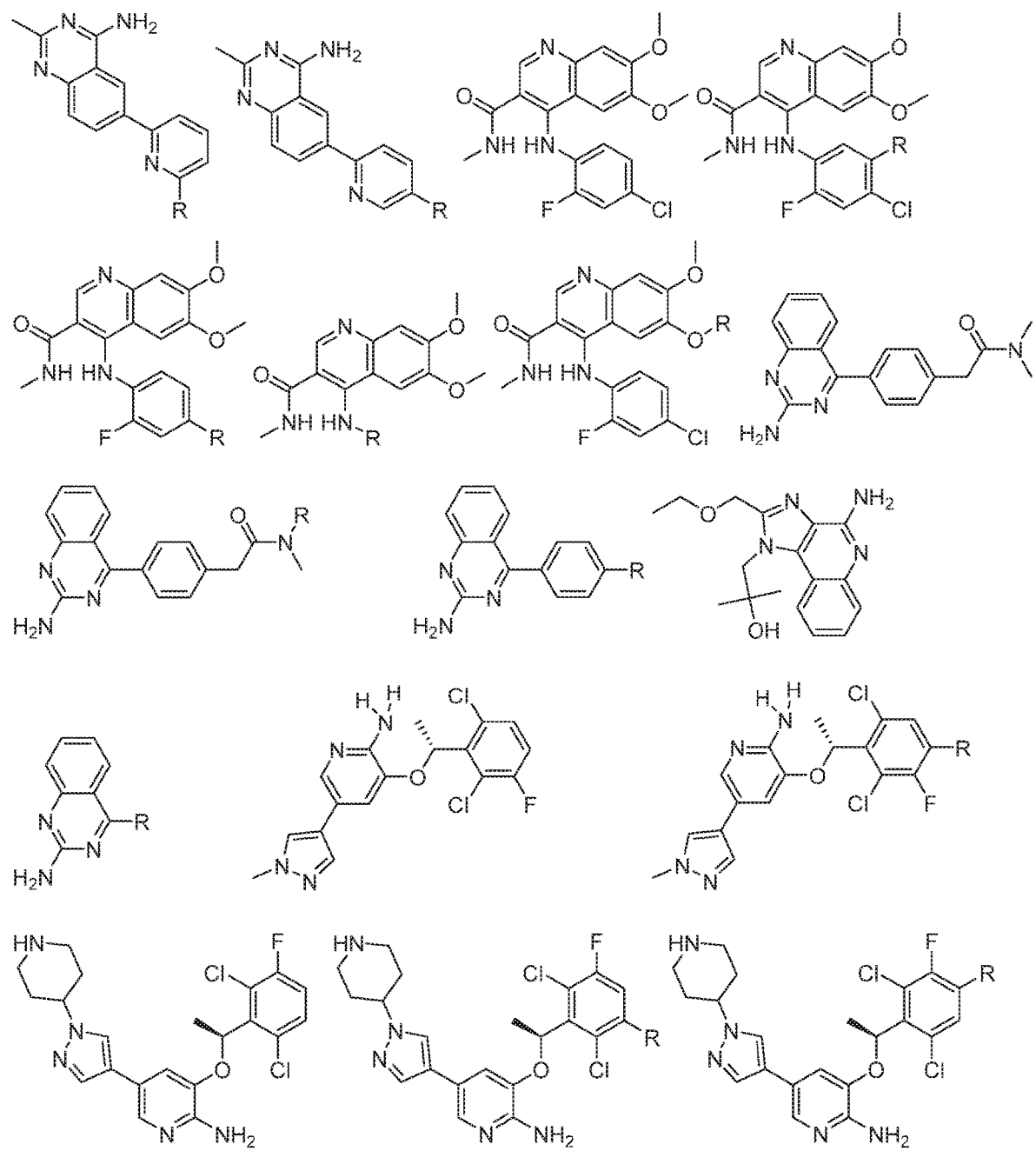
FIG. 2QQQQ

FIG. 2RRRR
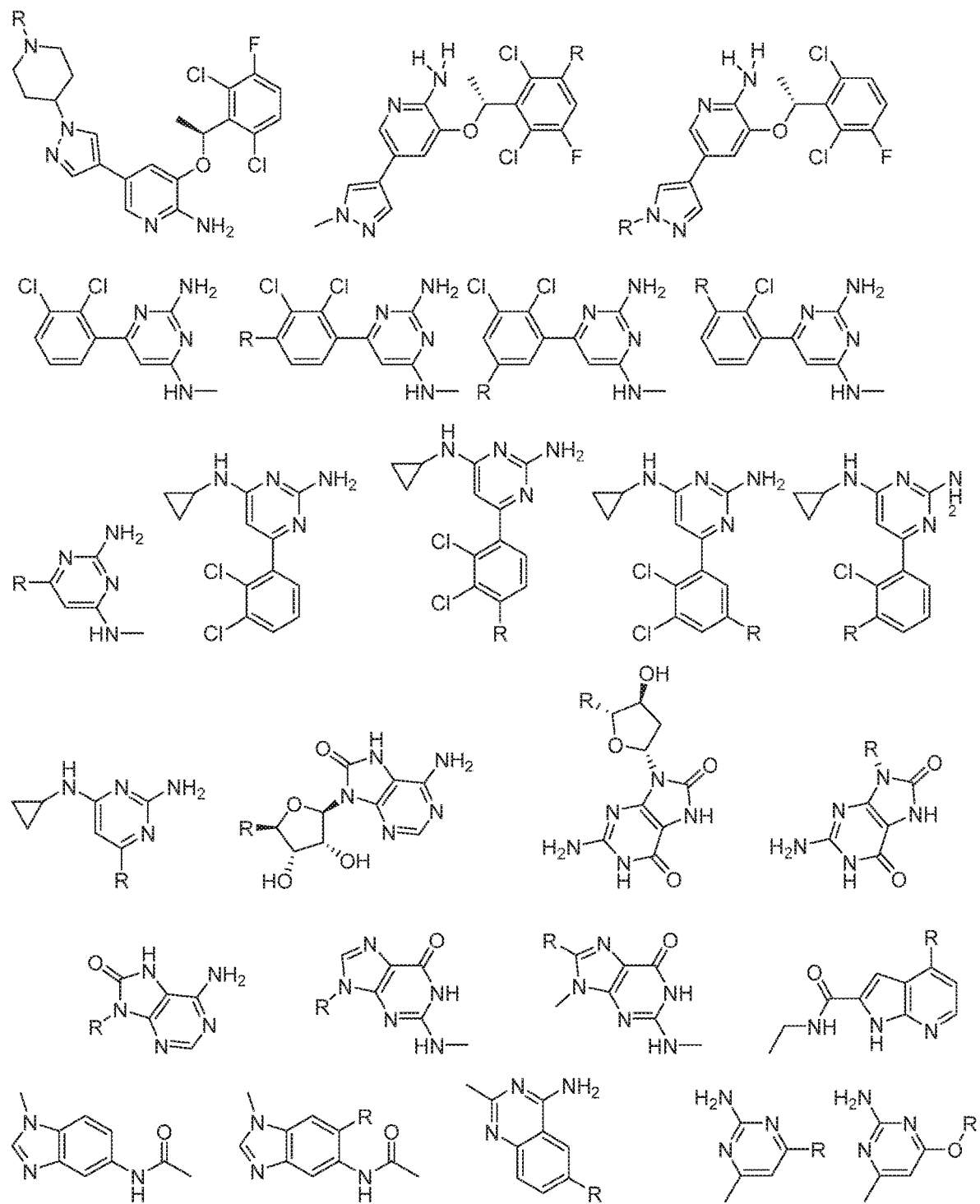

FIG. 2SSSS
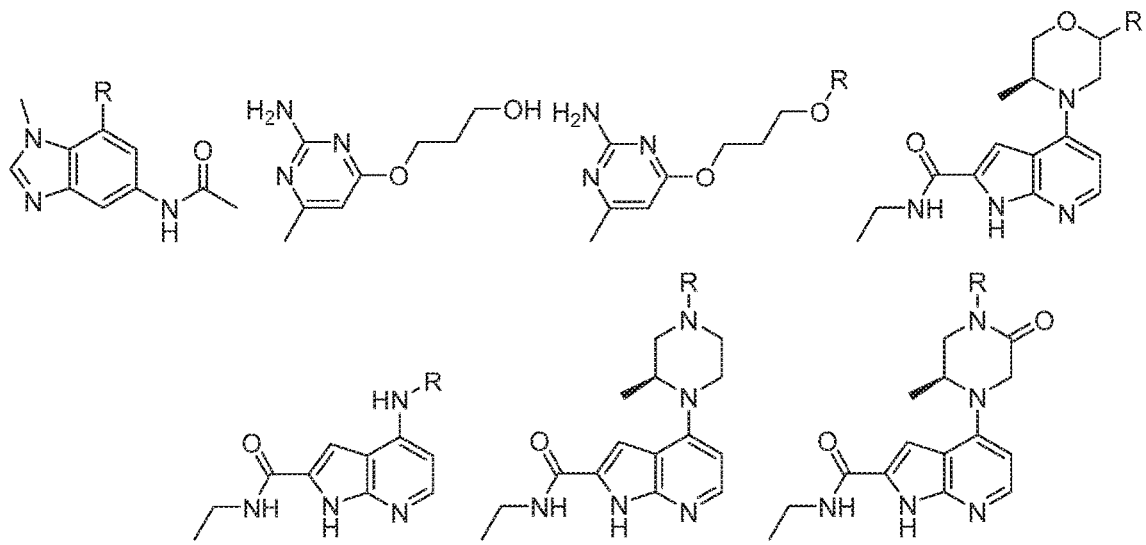
FIG. 2TTTT
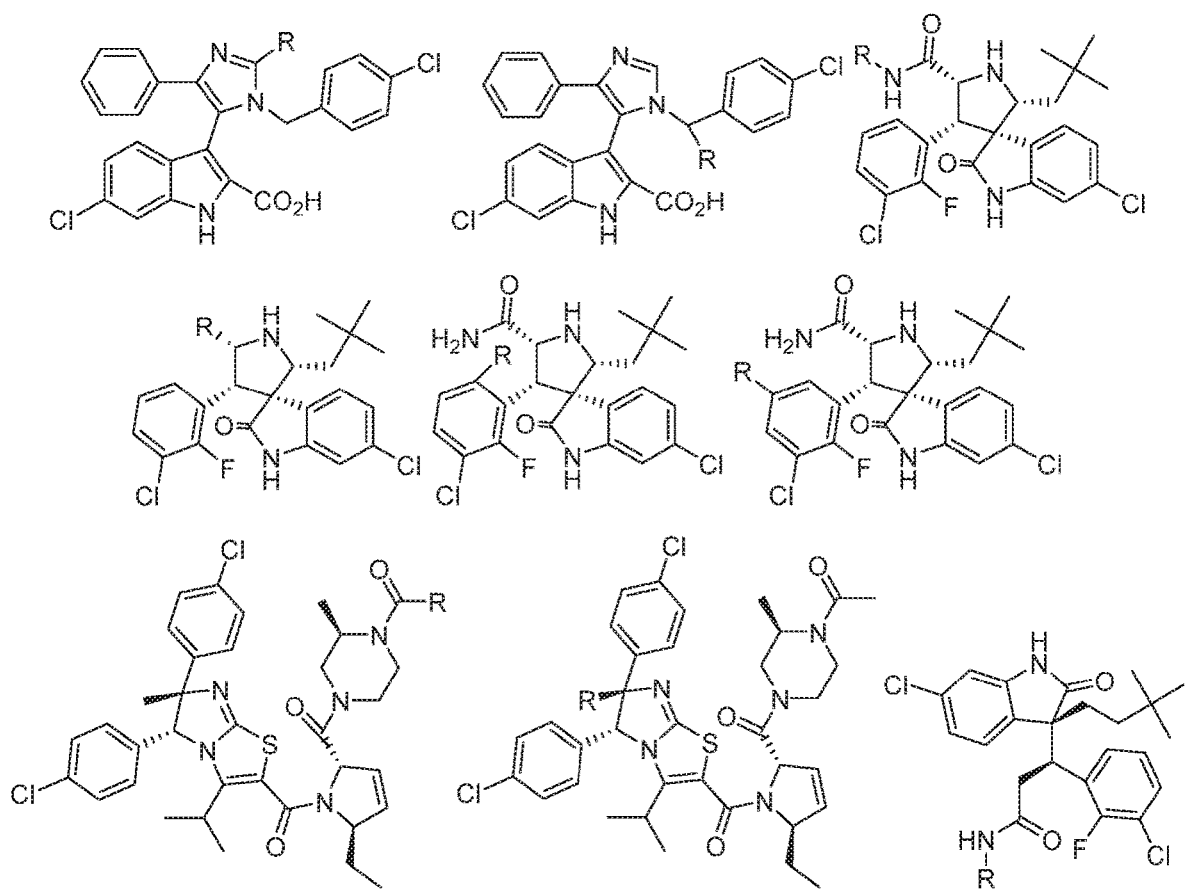

FIG. 2UUUU
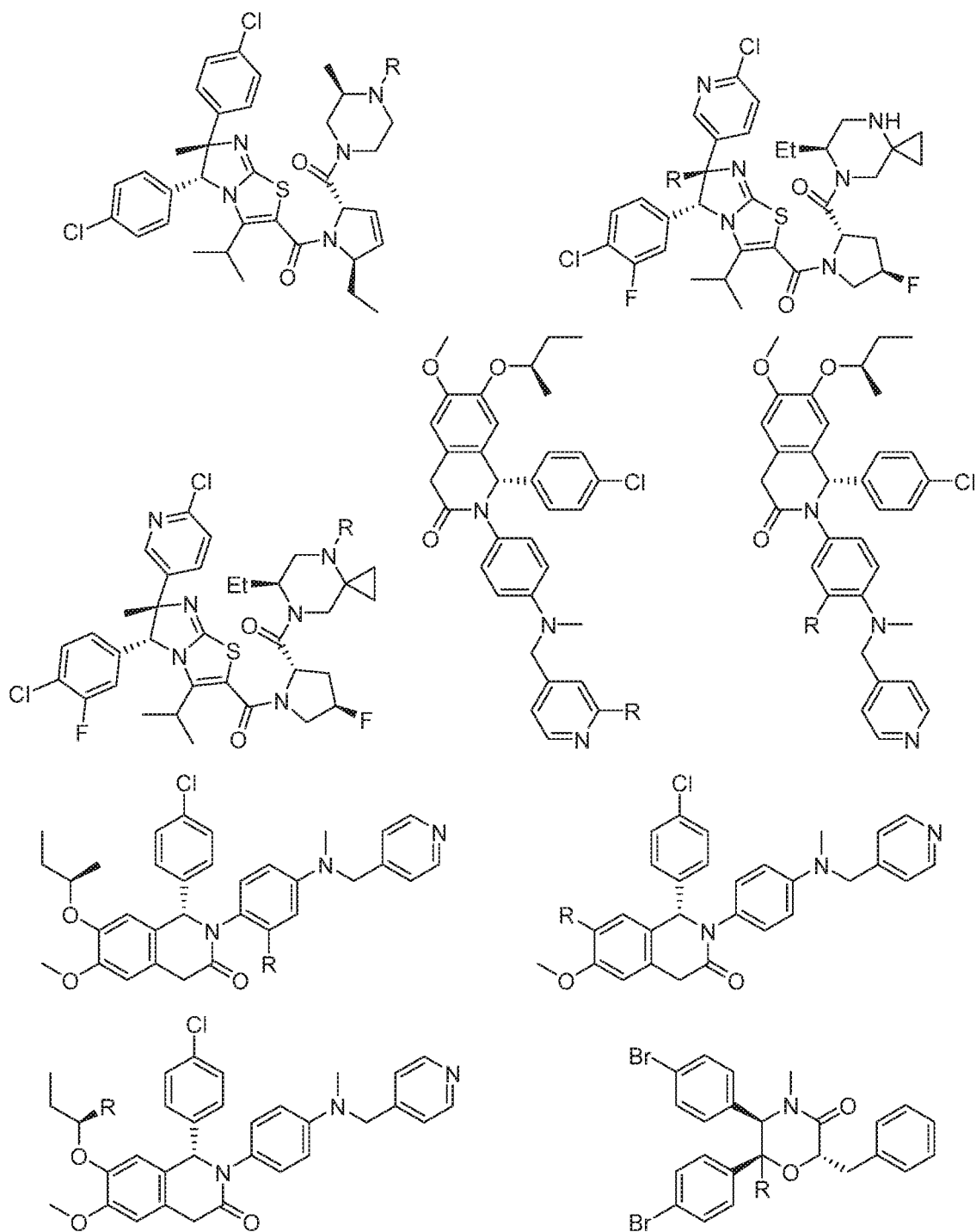

FIG. 2VVVV
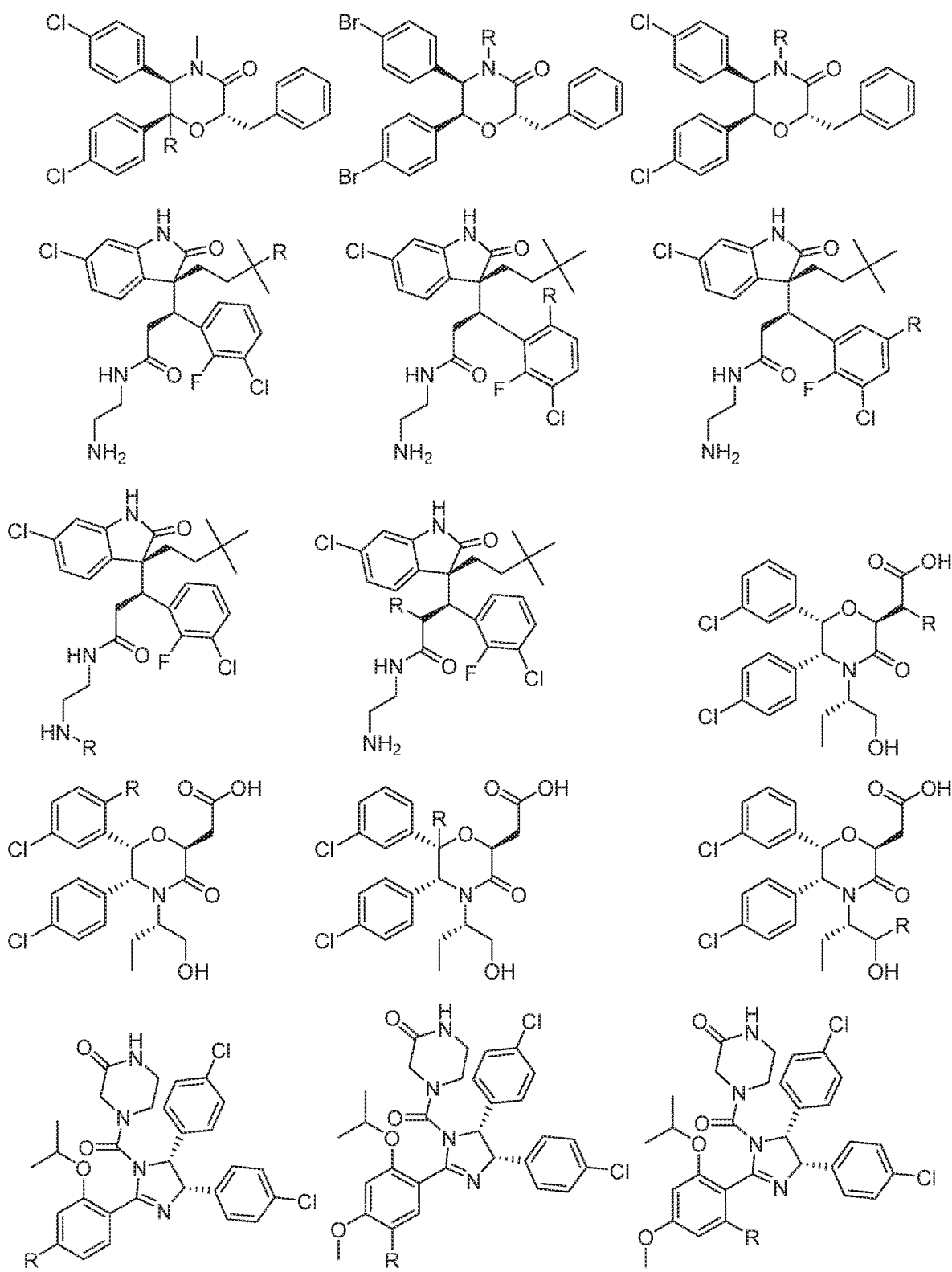

FIG. 2WWWW
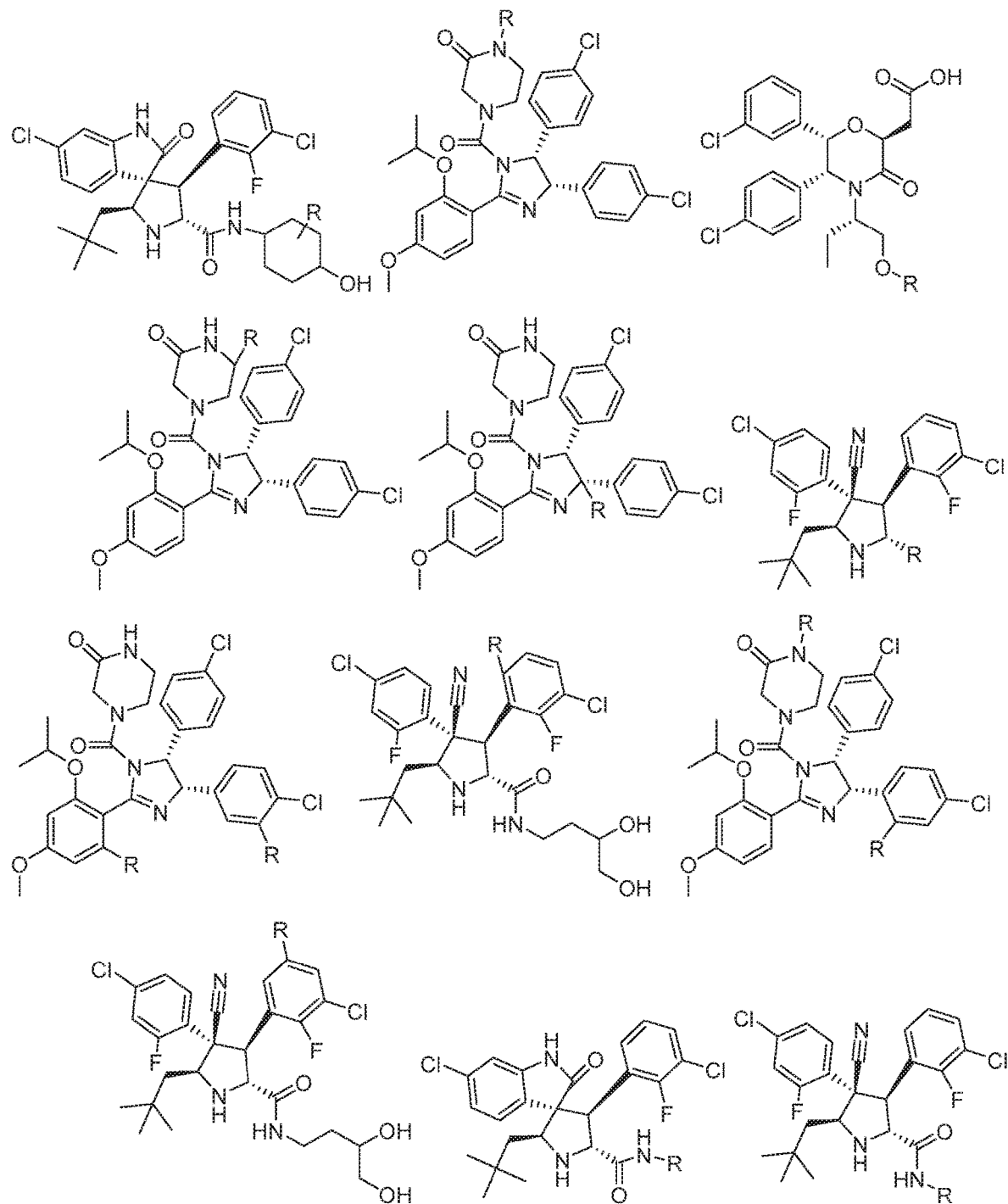

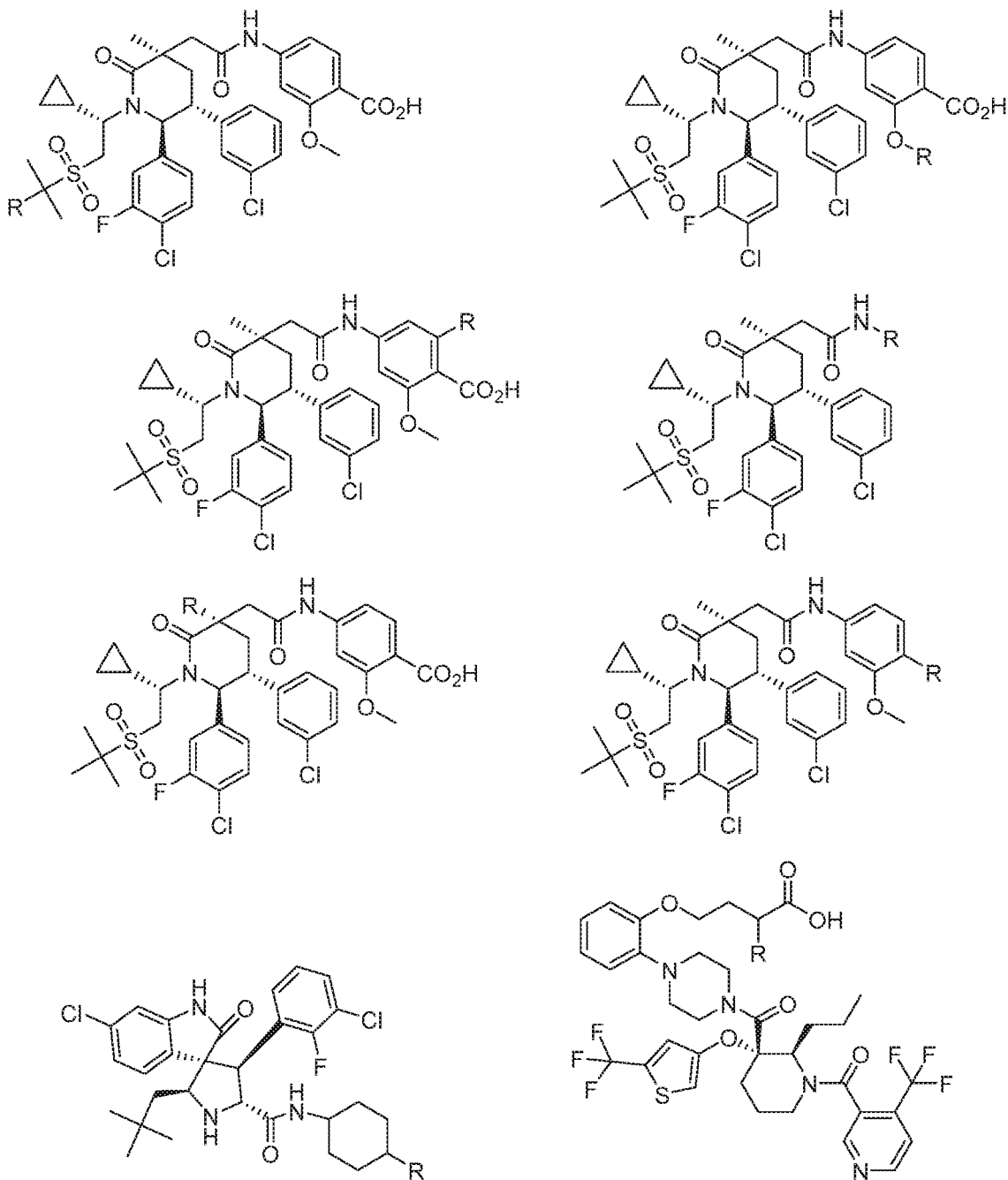
FIG. 2XXXX

FIG. 2YYYY
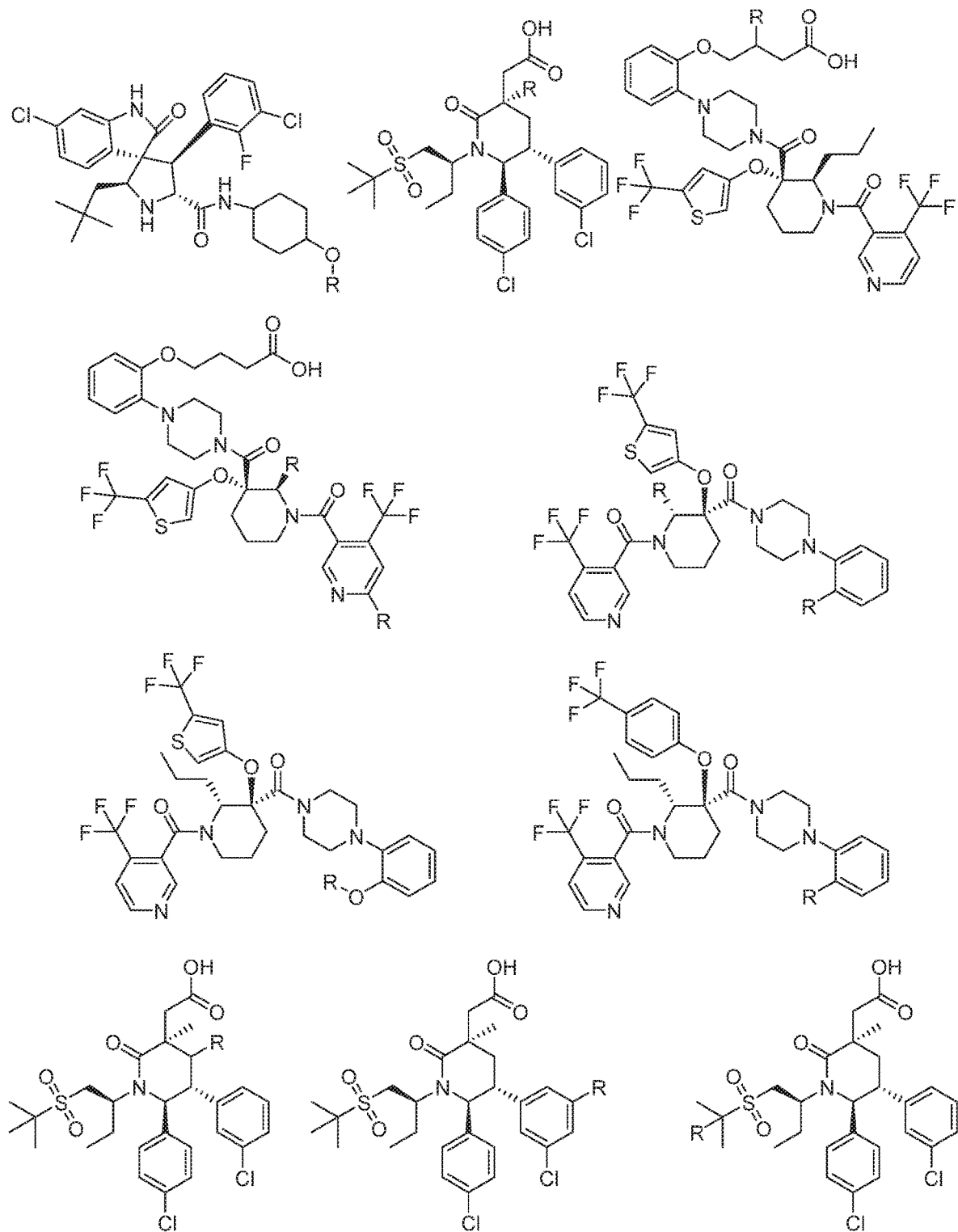

FIG. 2ZZZZ
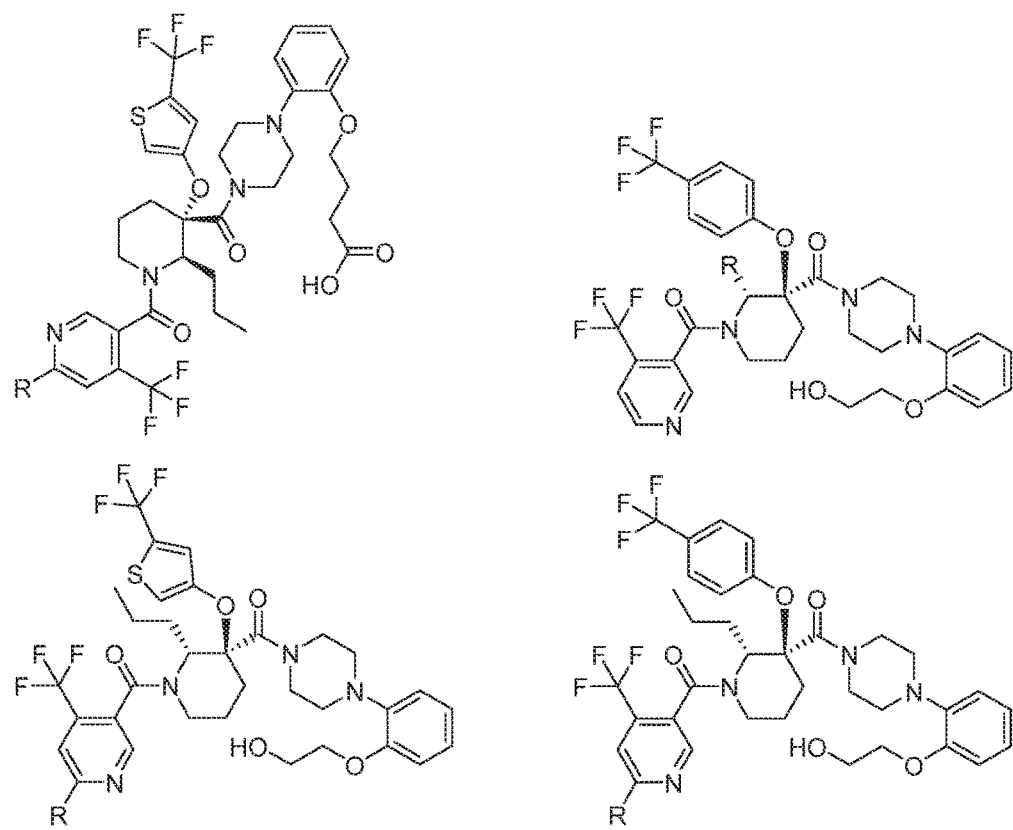
FIG. 2AAAAA
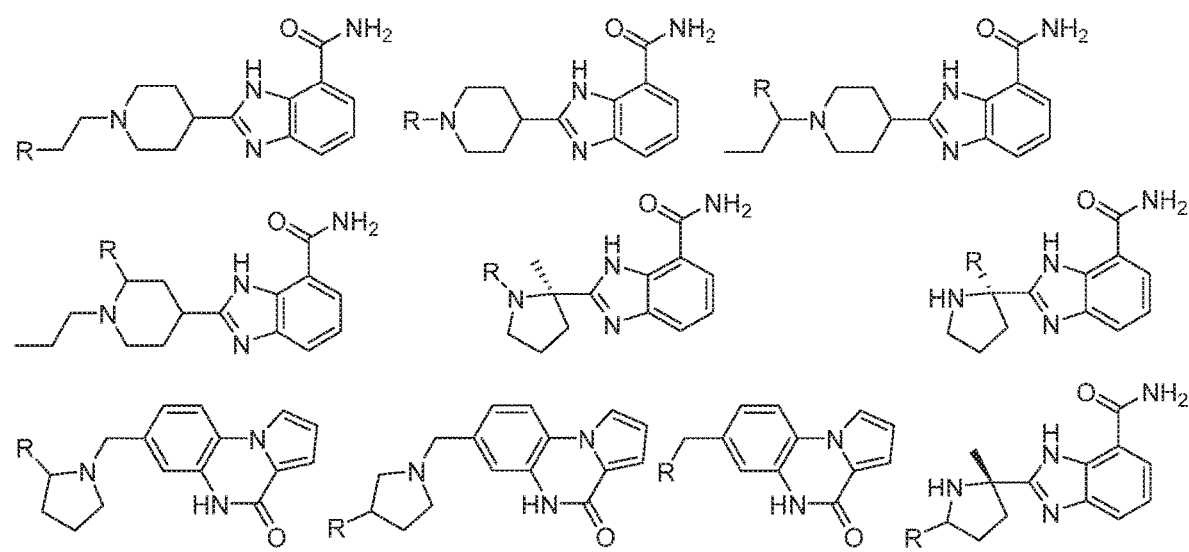

FIG. 2BBBBB
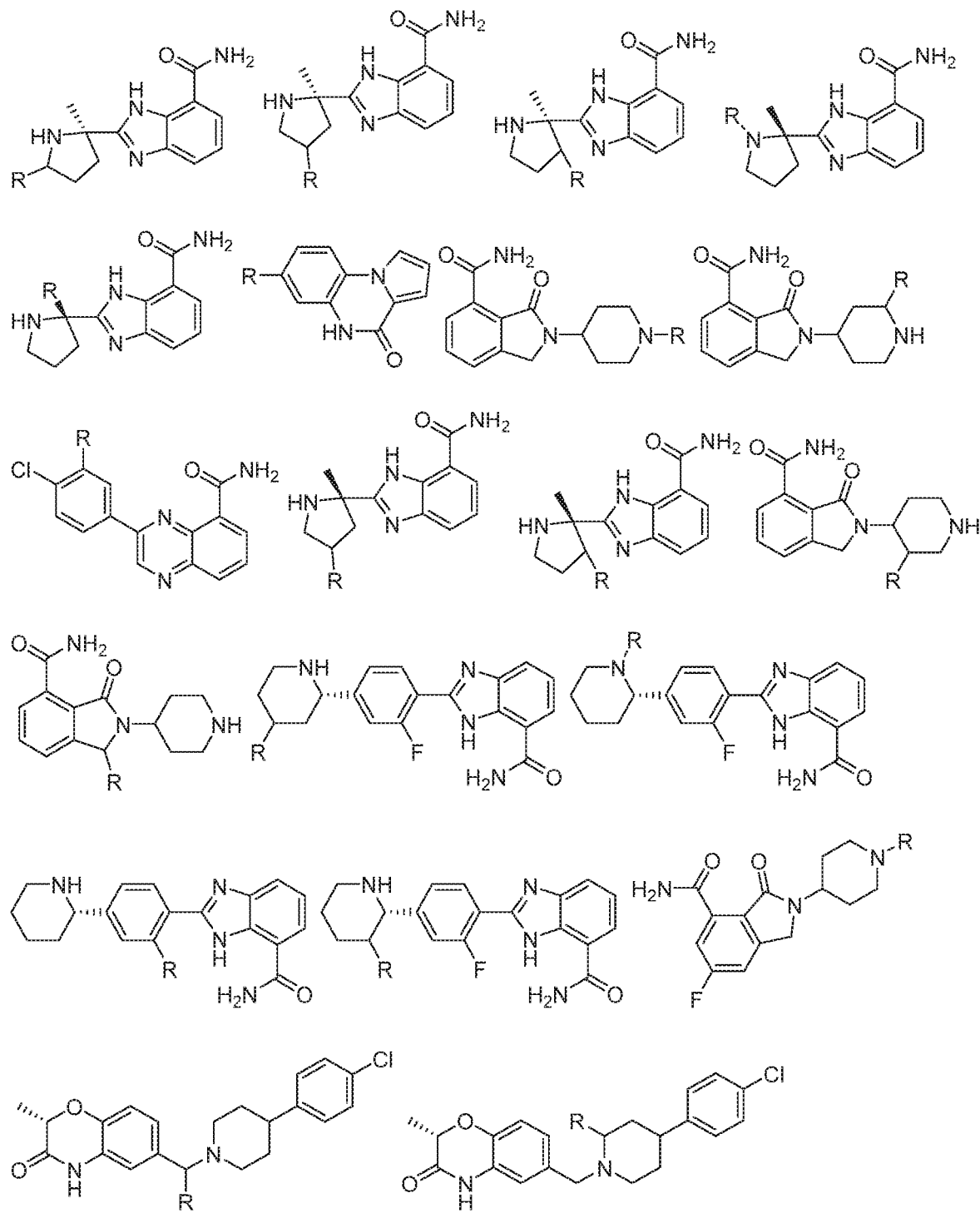

FIG. 2CCCCC
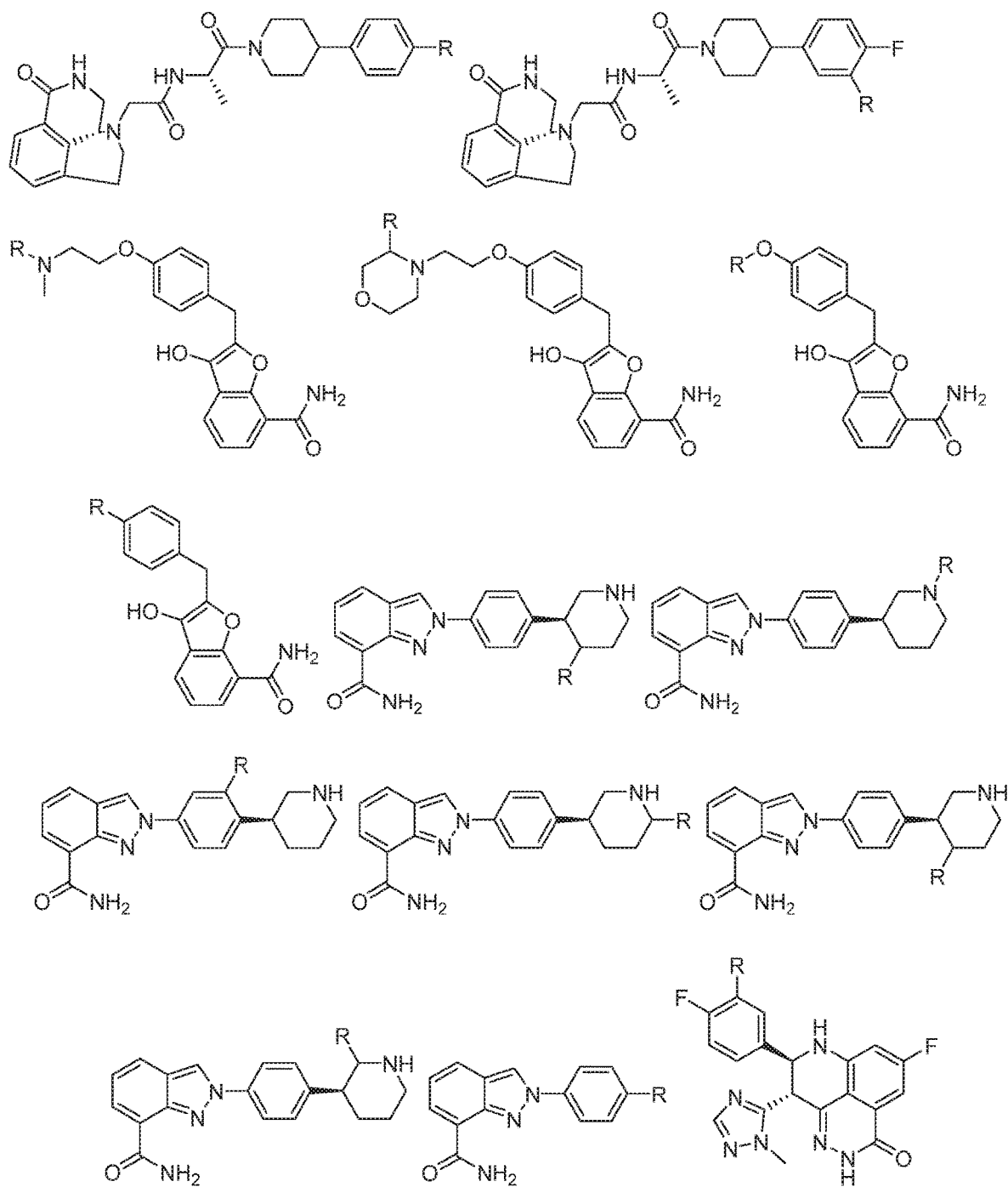

FIG. 2DDDDD
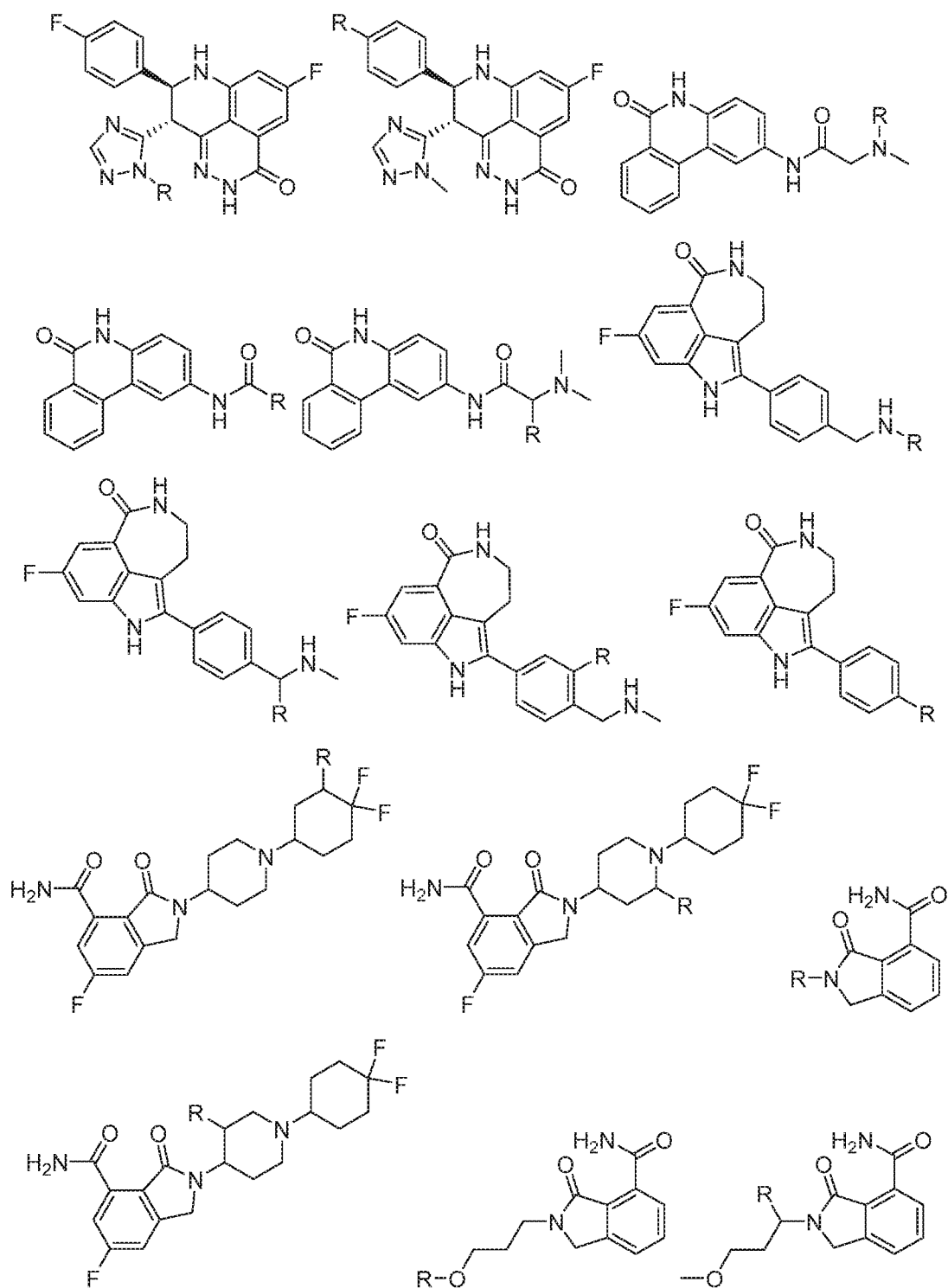

FIG. 2EEEEE
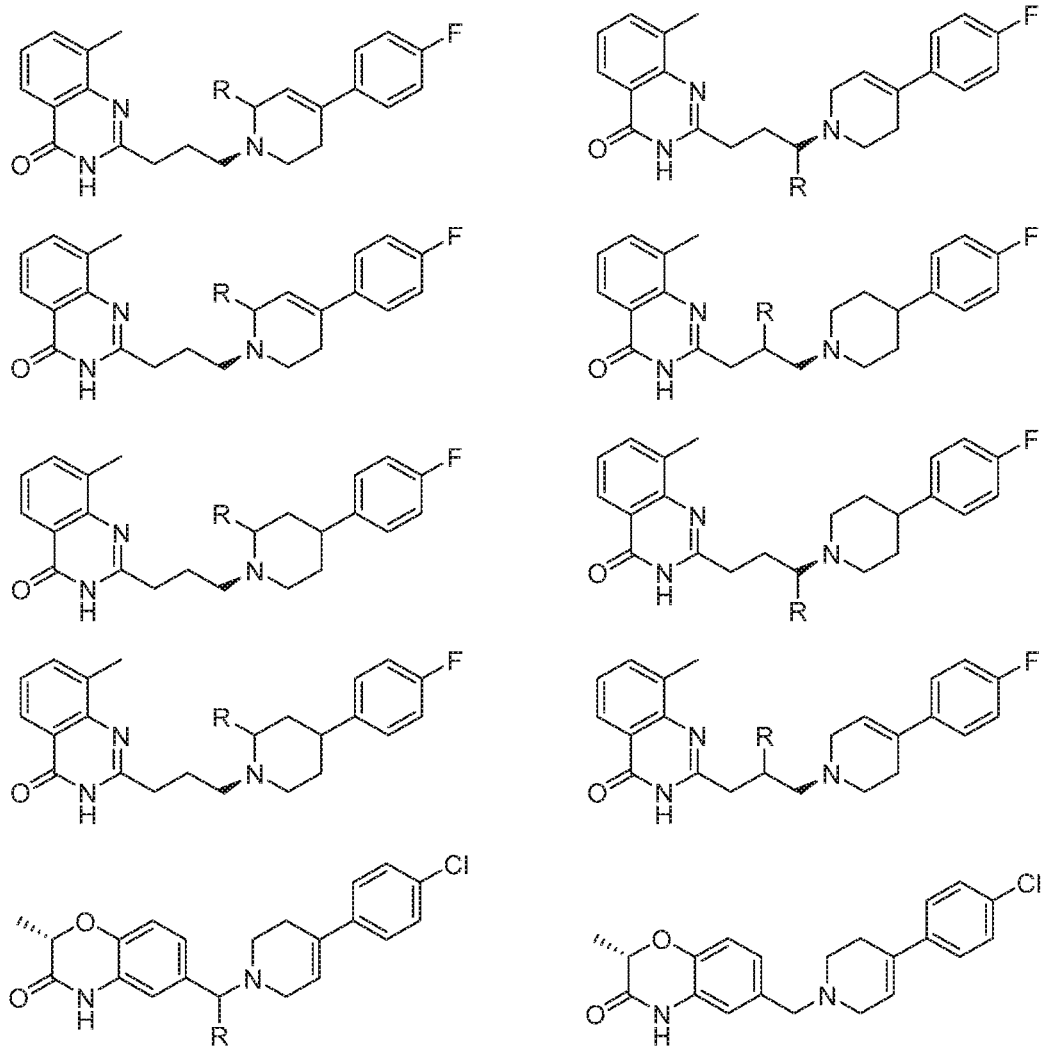
FIG. 2FFFFF
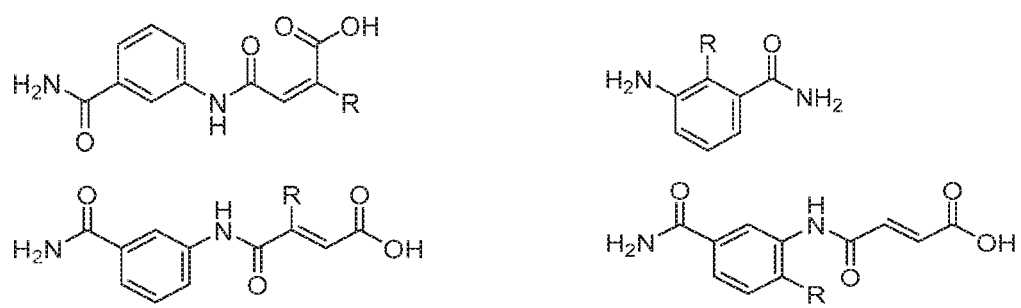

FIG. 2GGGGG
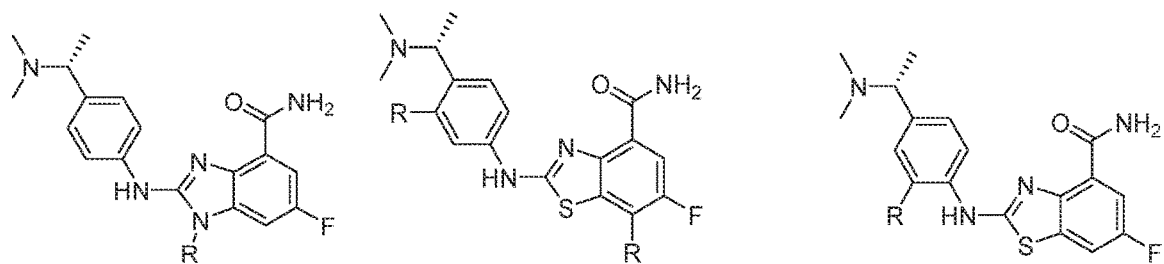
FIG. 2HHHHH
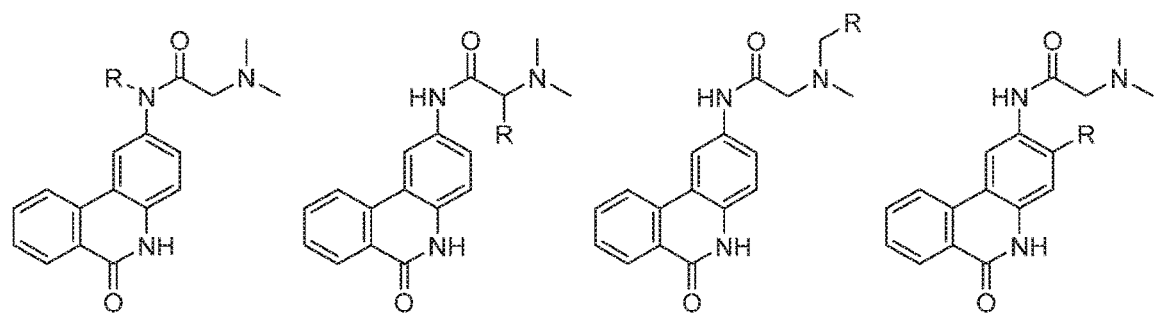
FIG. 2IIIII
FIG. 2JJJJJ
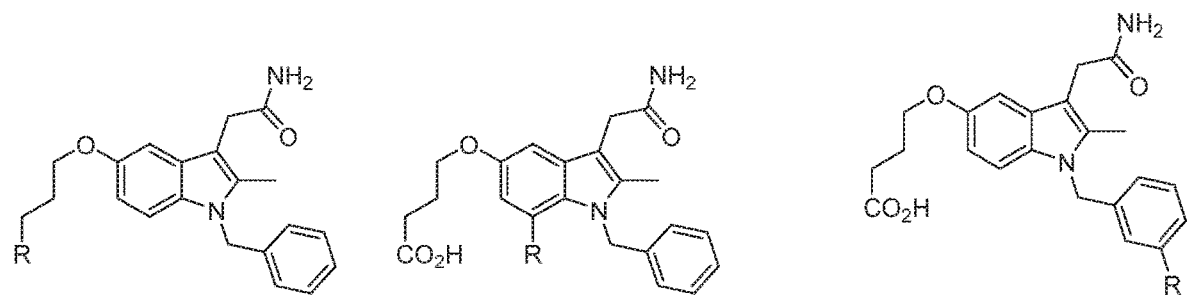

FIG. 2KKKKK
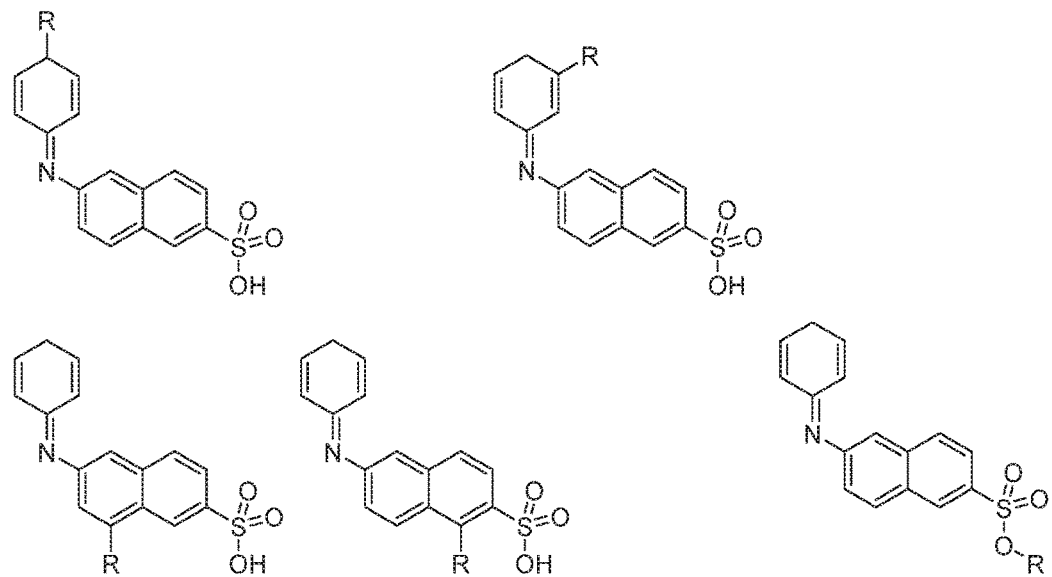
FIG. 2LLLLL
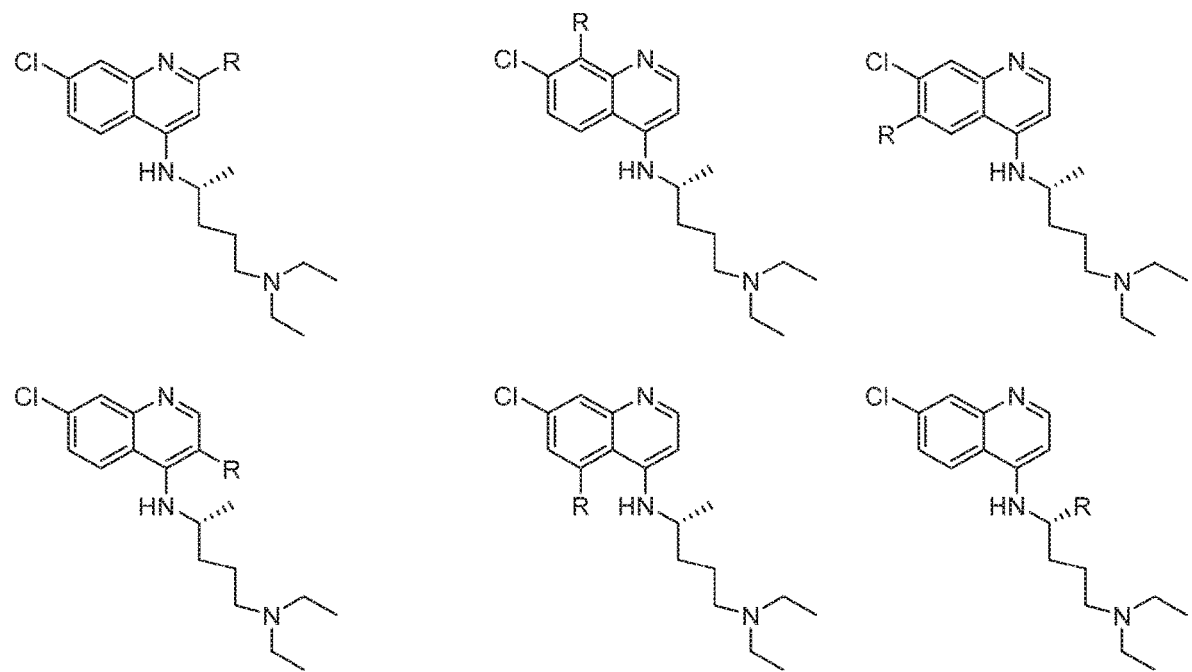

FIG. 2MMMMM
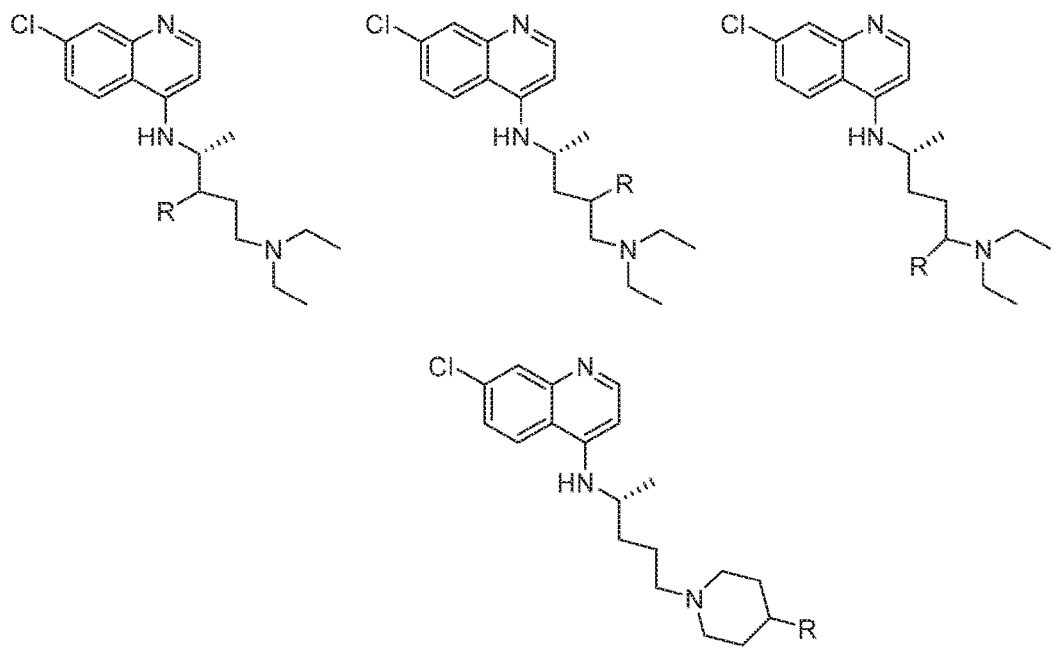
FIG. 2NNNNN
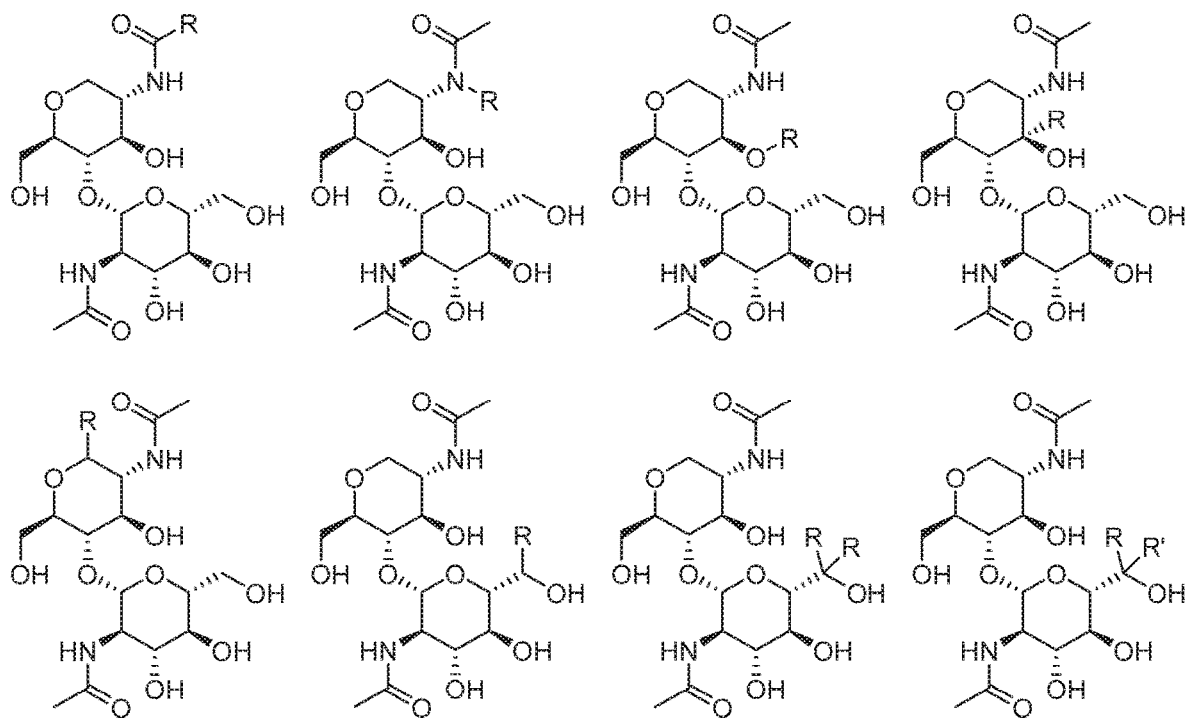

FIG. 2OOOOO
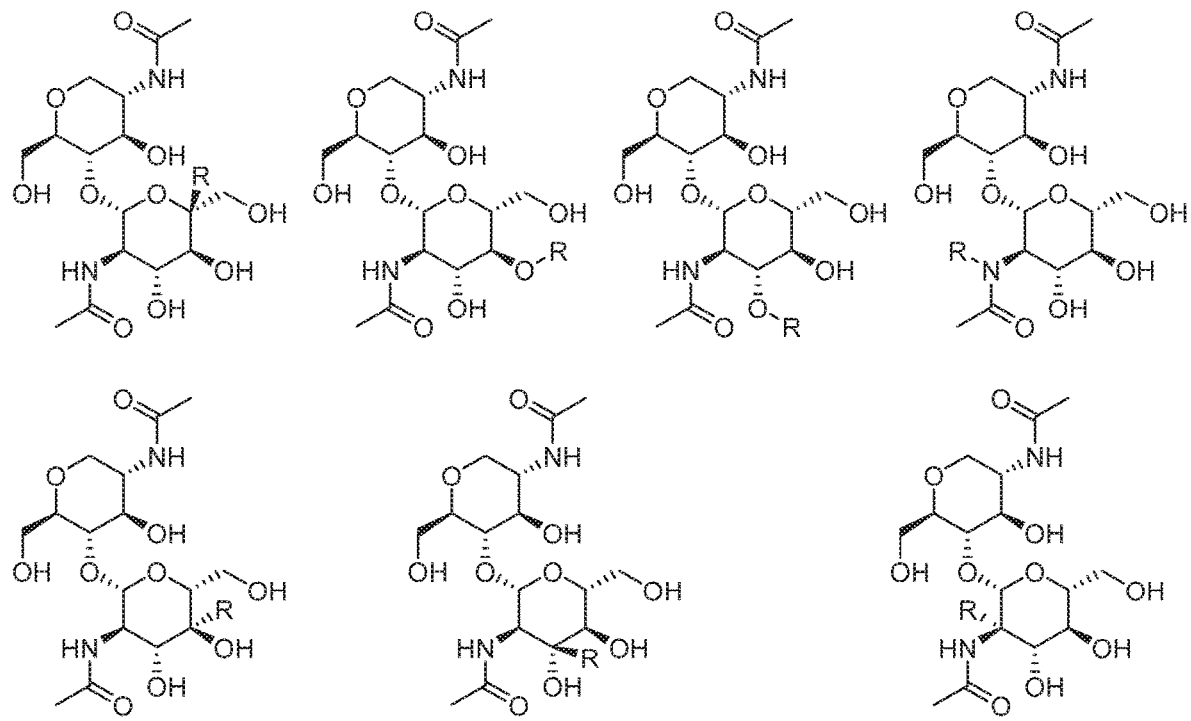
FIG. 2PPPPP
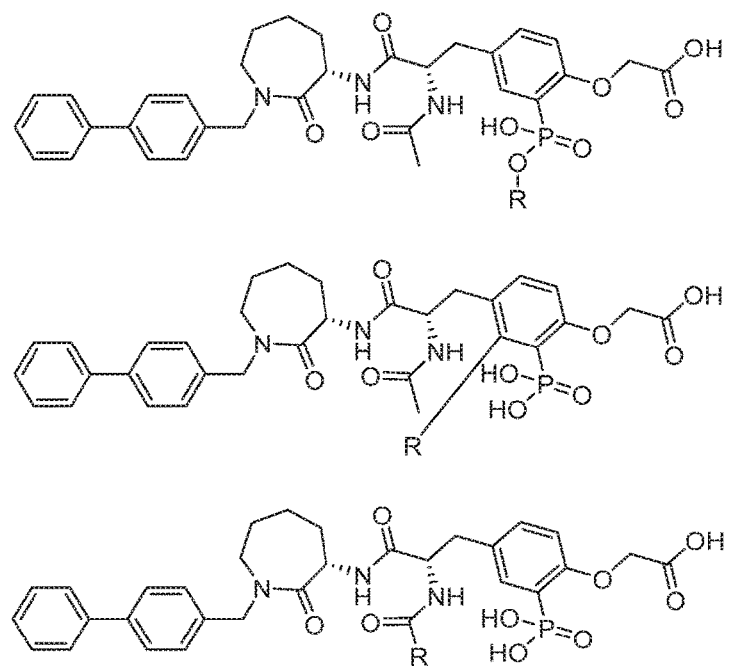

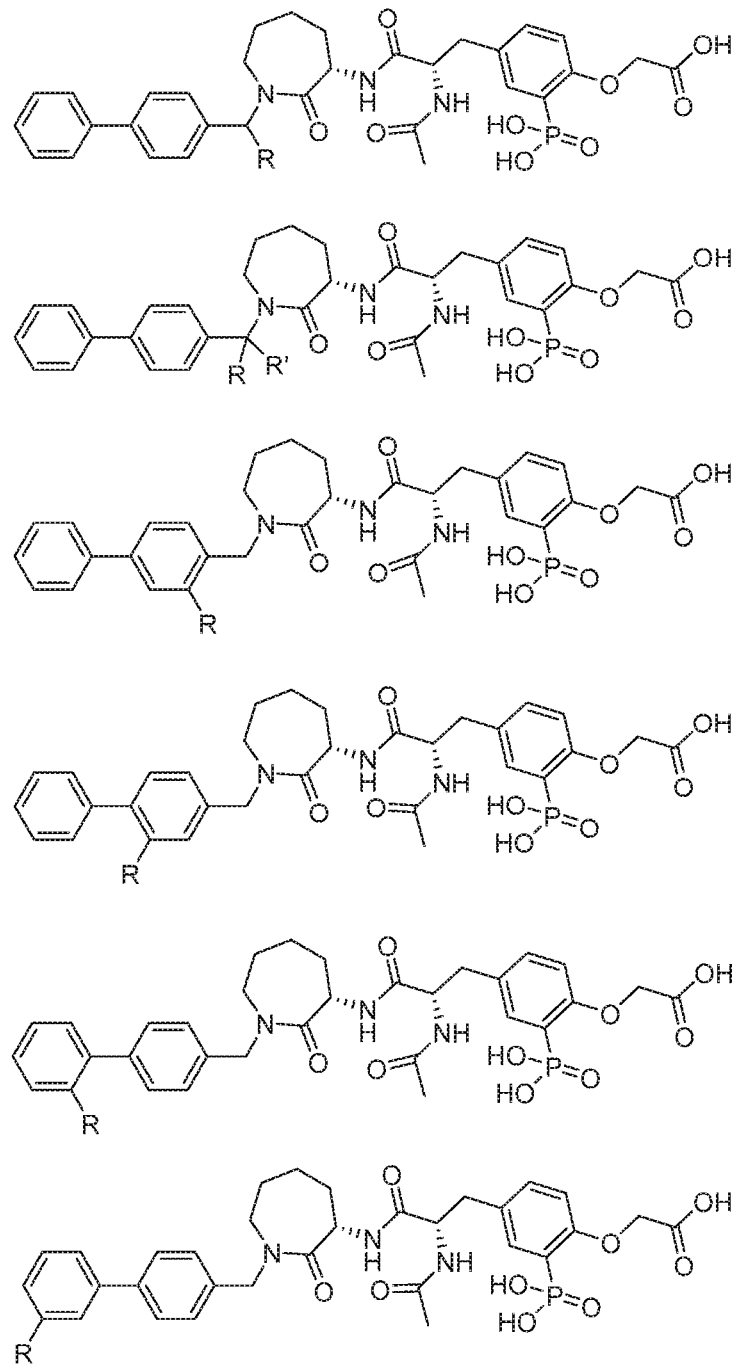
FIG. 2QQQQQ

FIG. 2RRRRR
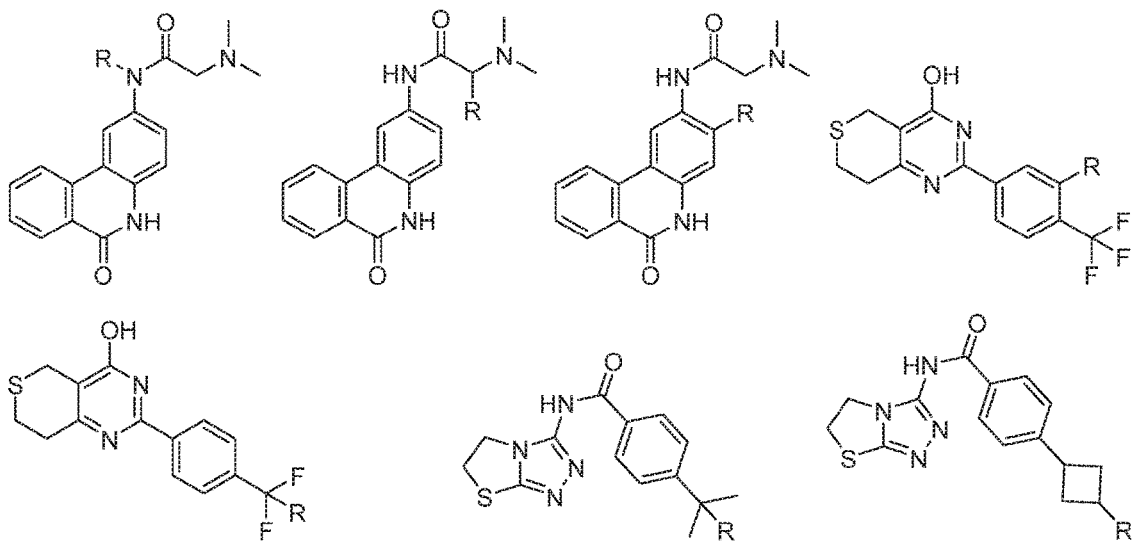
FIG. 2SSSSS
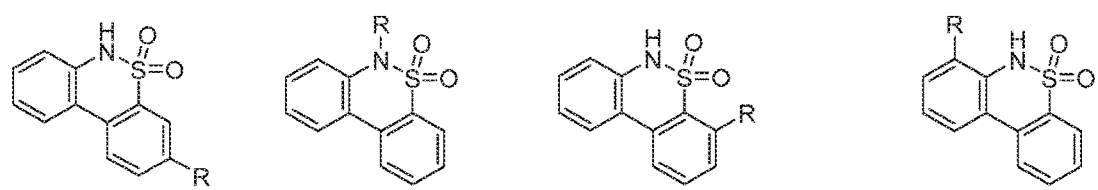
FIG. 2TTTTT
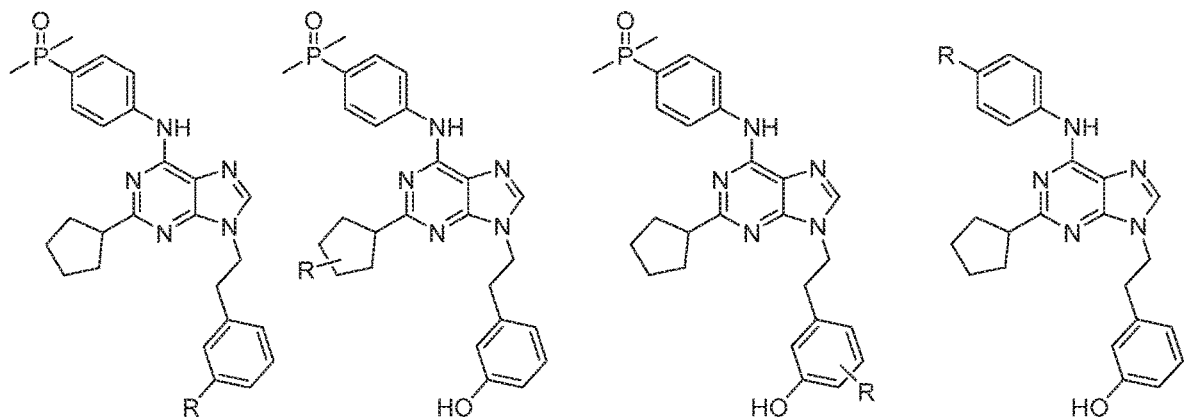

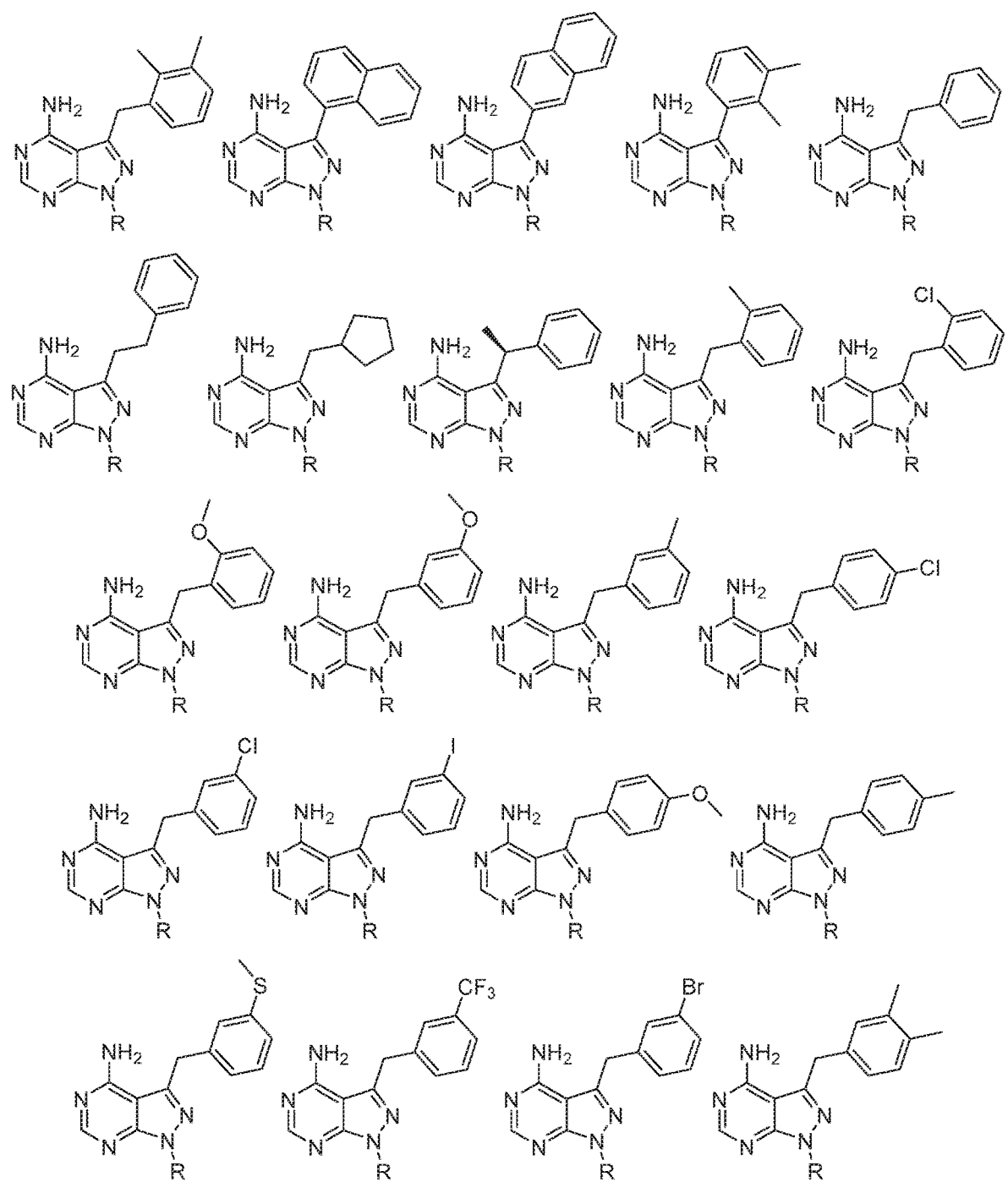
FIG. 2UUUUU

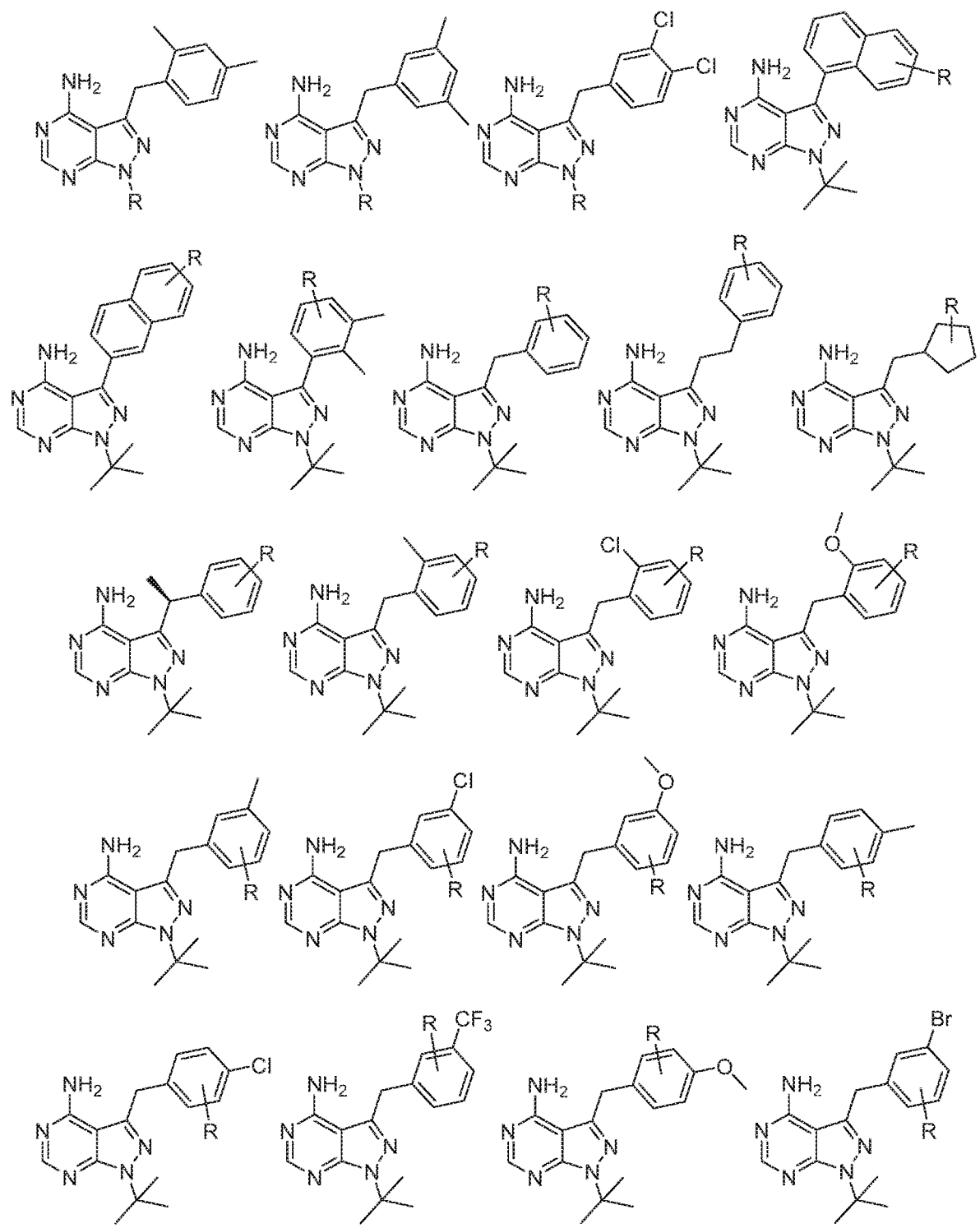
FIG. 2VVVVV

FIG. 2WWWWW
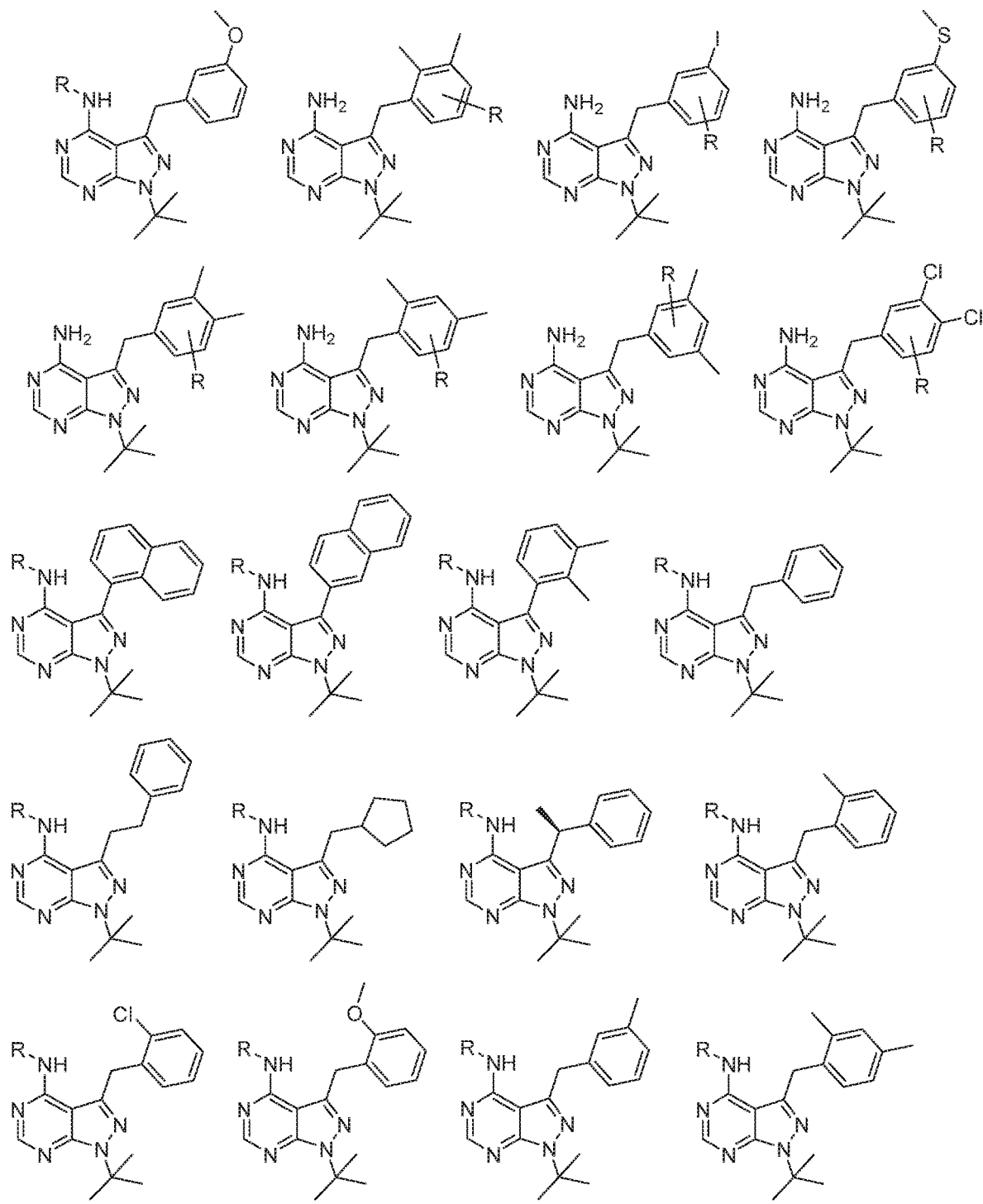

FIG. 2XXXXX
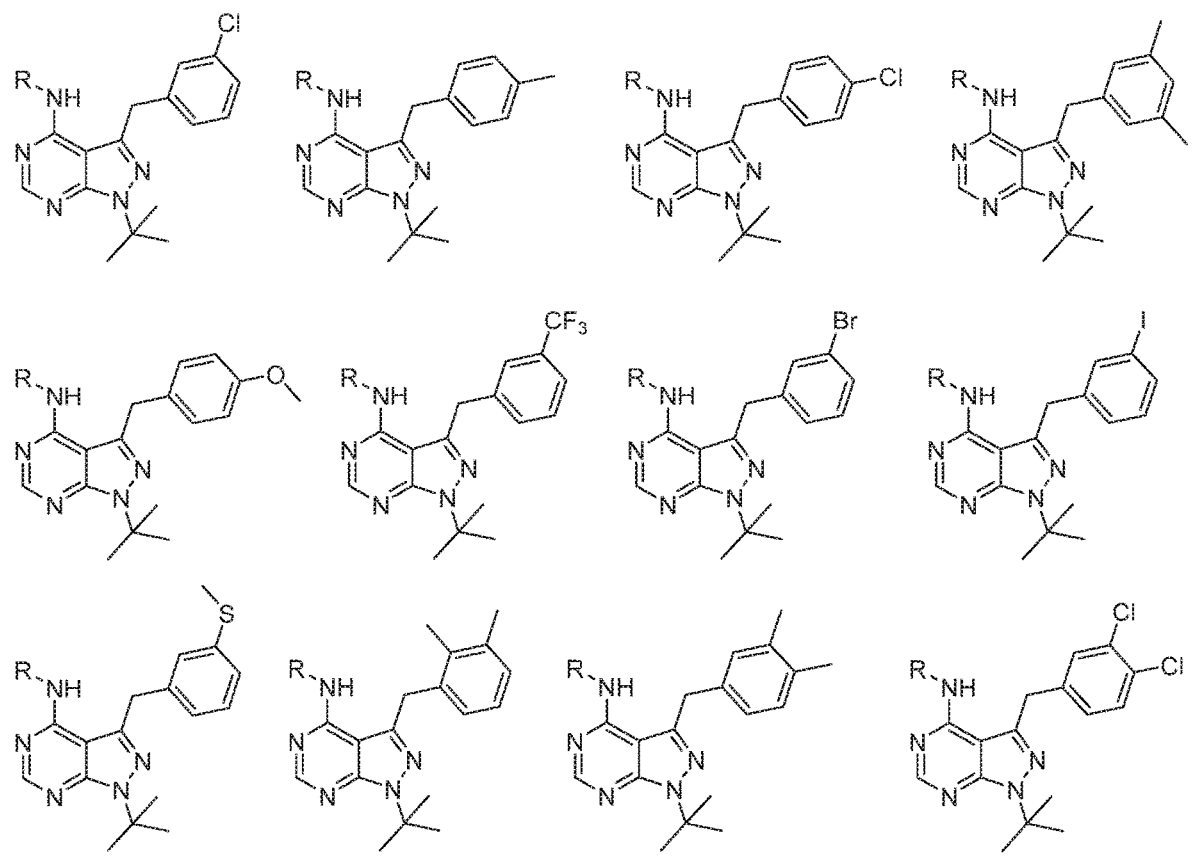
FIG. 2YYYYY
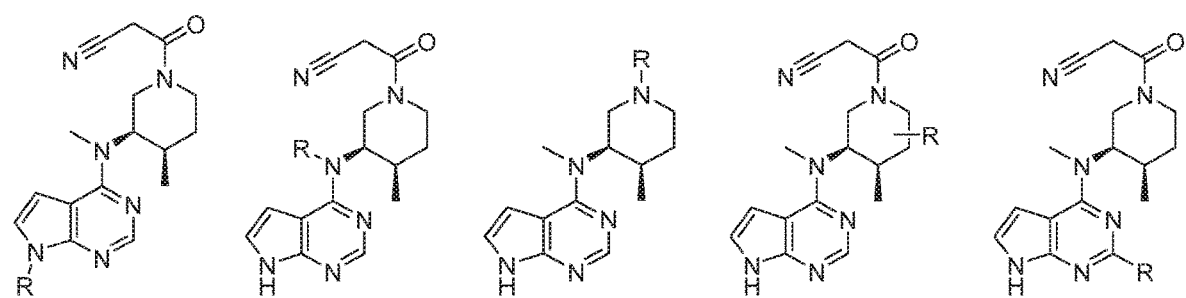

FIG. 2ZZZZZ
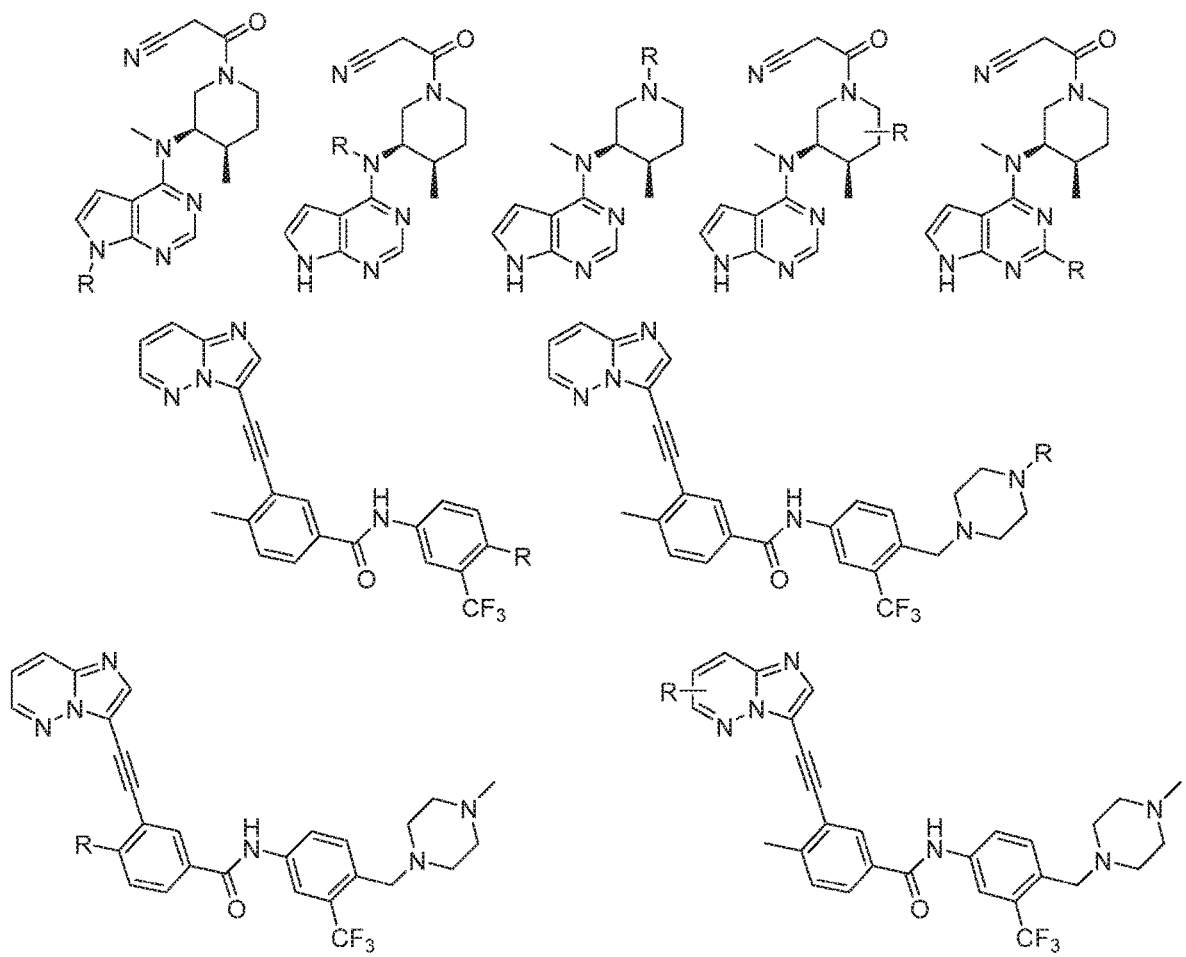
FIG. 3A
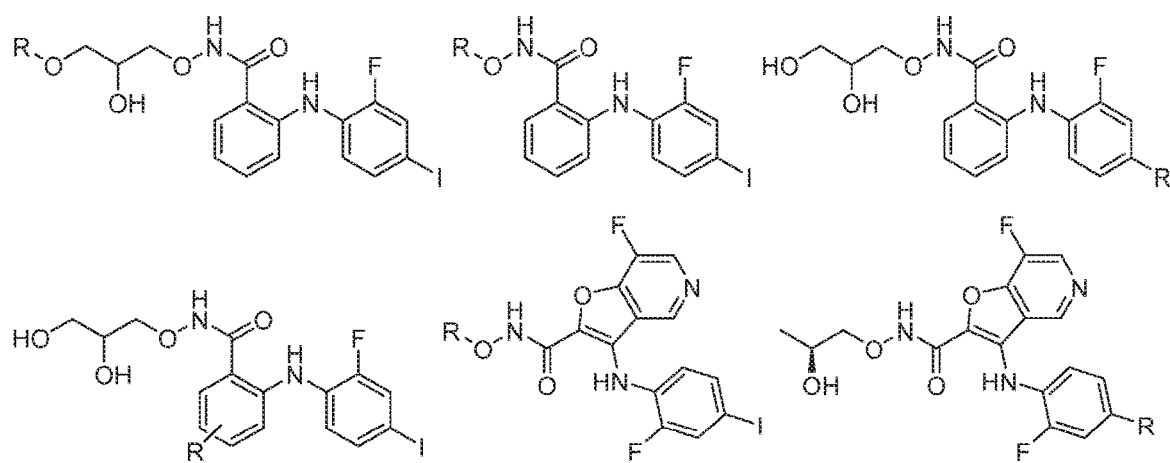

FIG. 3I
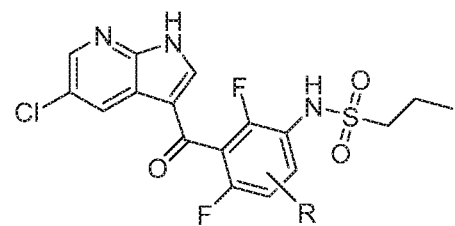 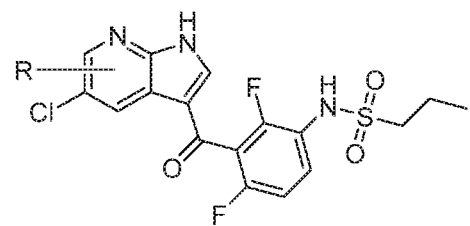
FIG. 3J
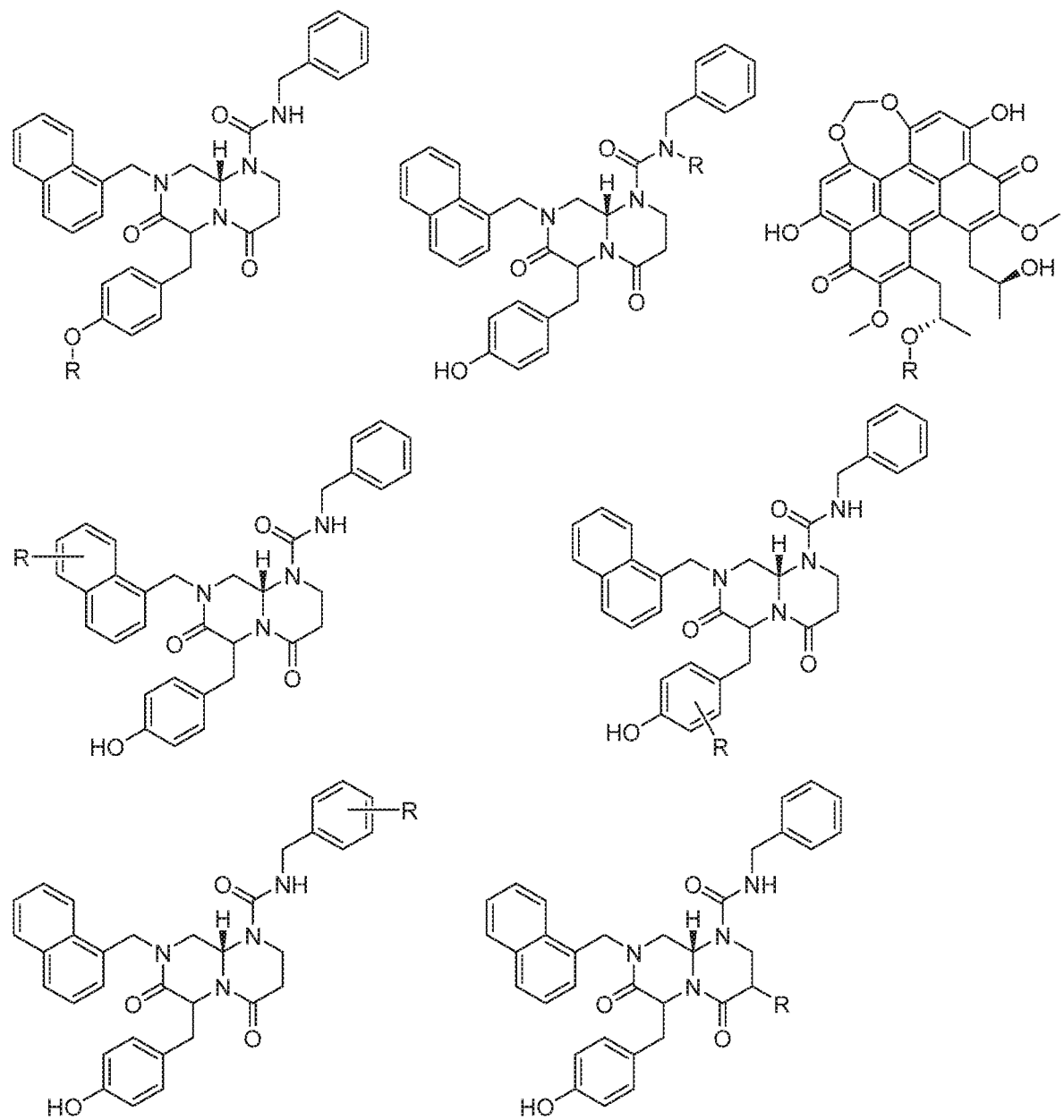

FIG. 3CC
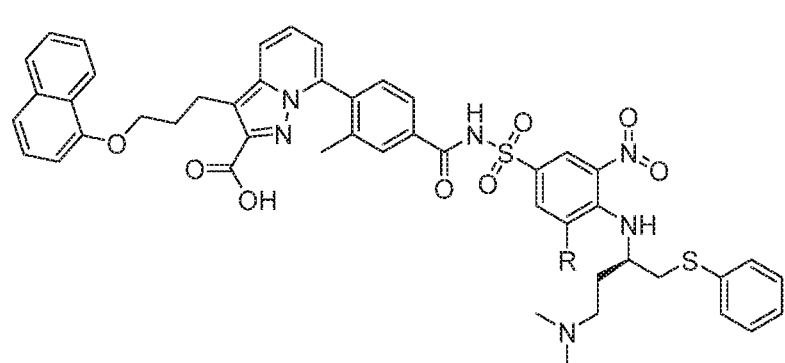 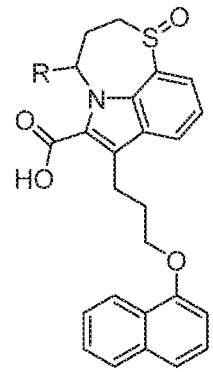
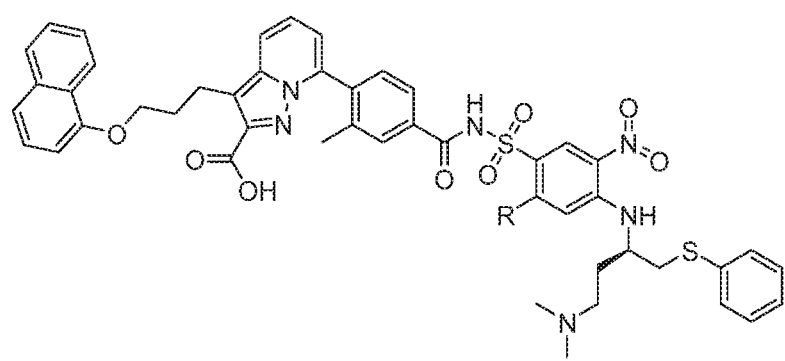 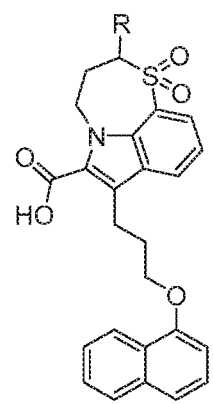
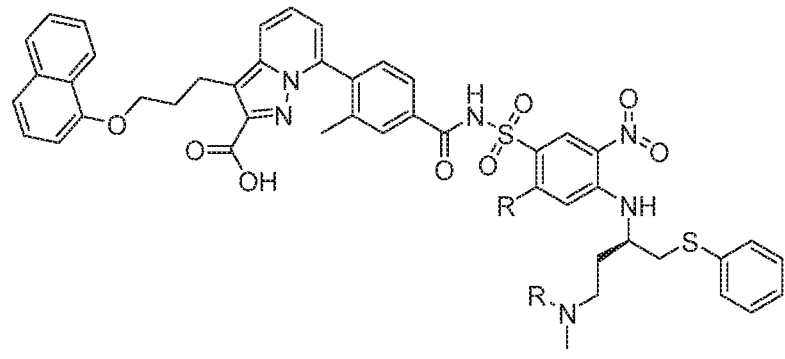 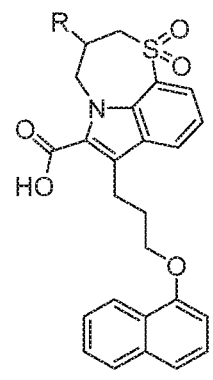
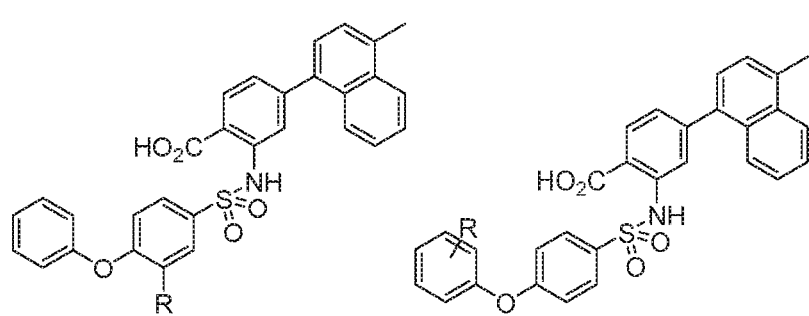 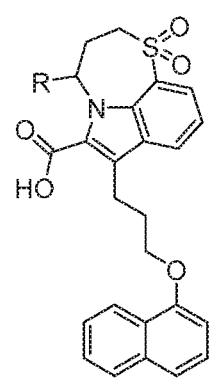

FIG. 3FF
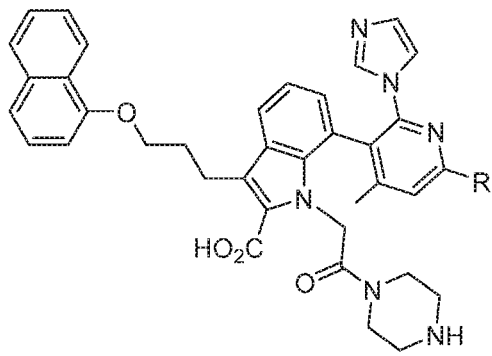
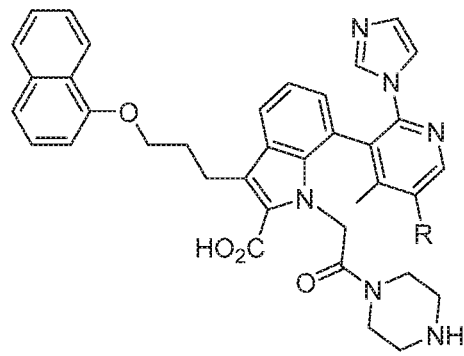
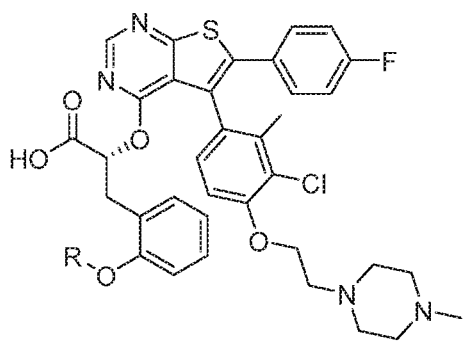
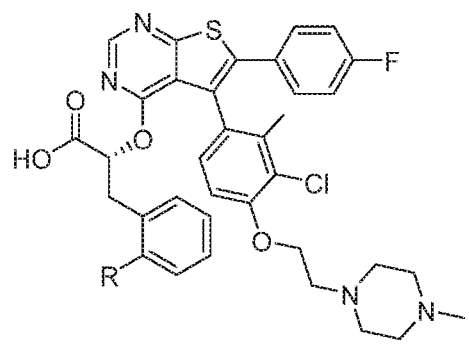
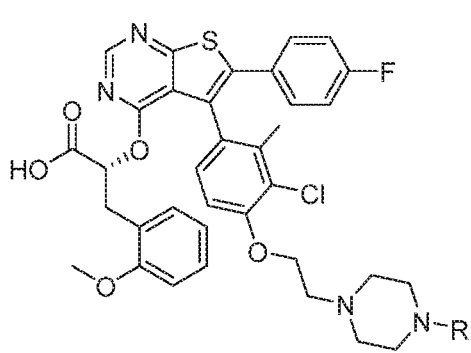
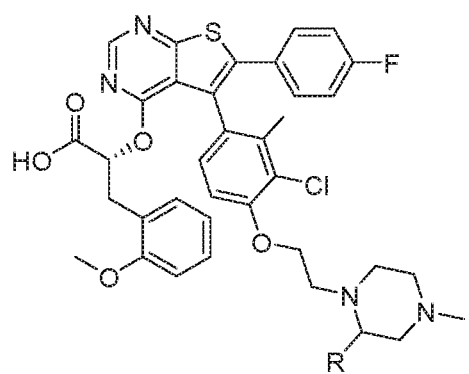
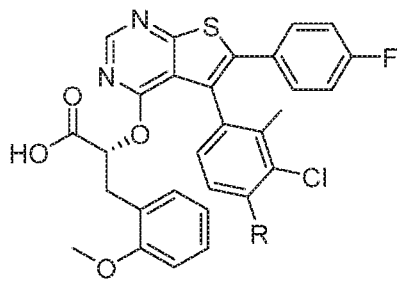
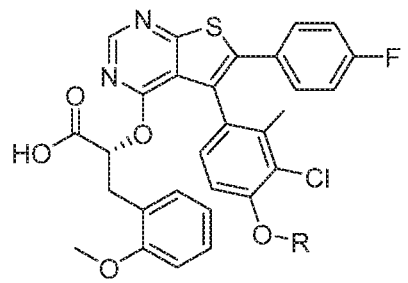

FIG. 3GG
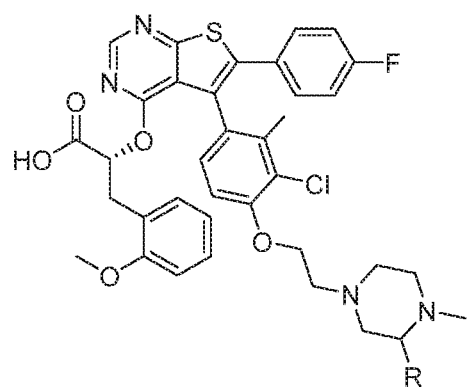 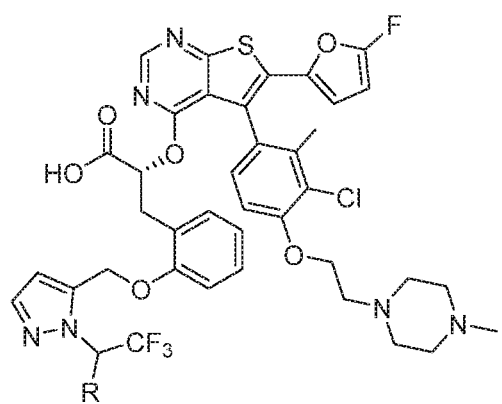
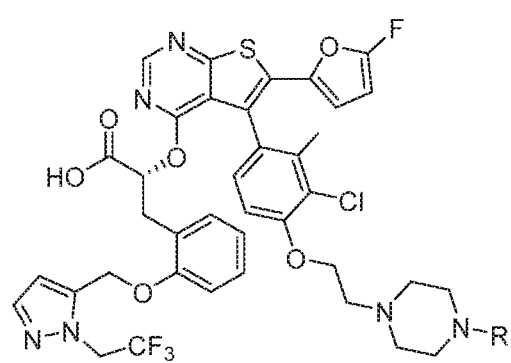 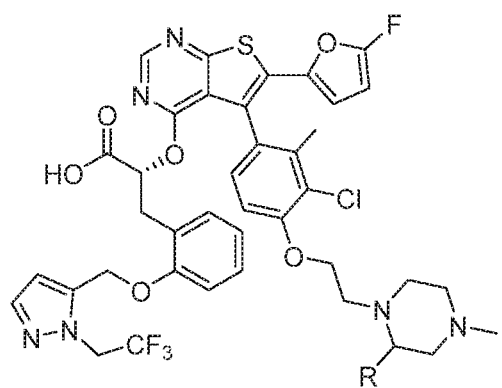
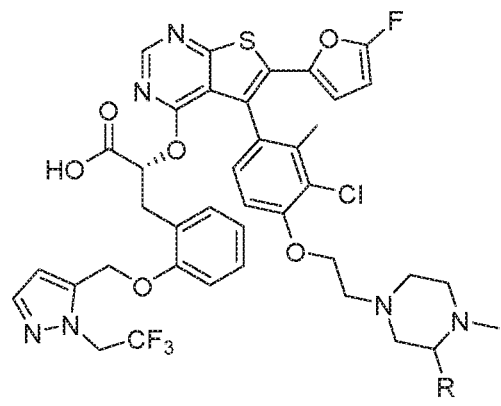 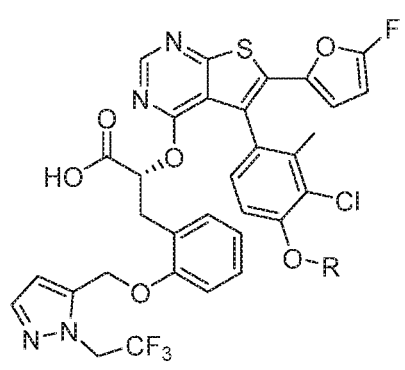

FIG. 3JJ
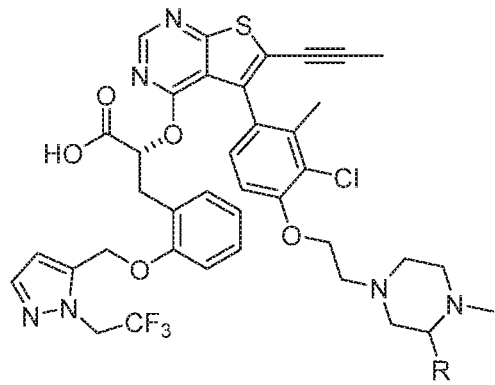
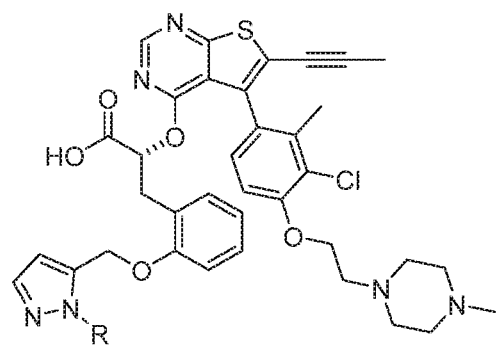
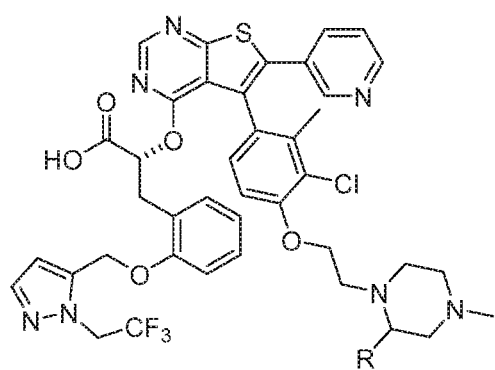
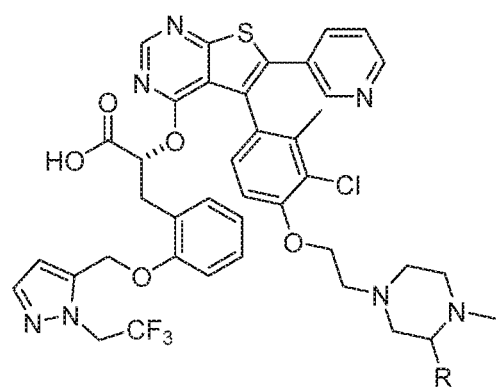
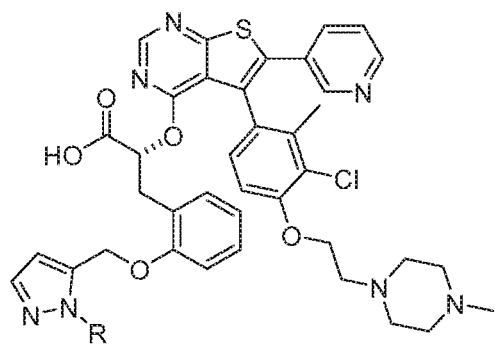
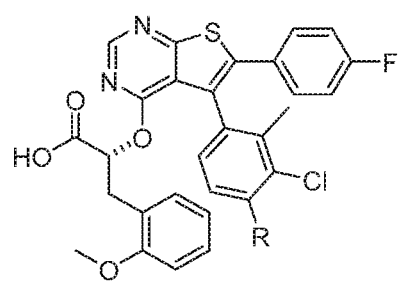
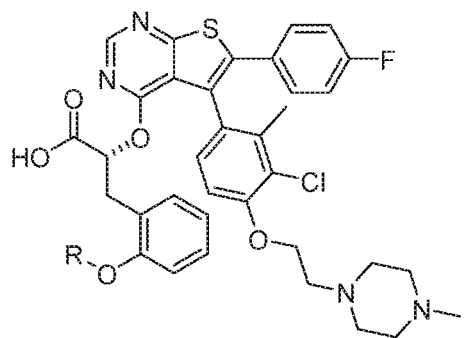
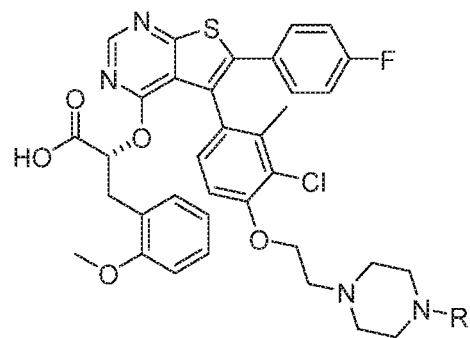

FIG. 3KK
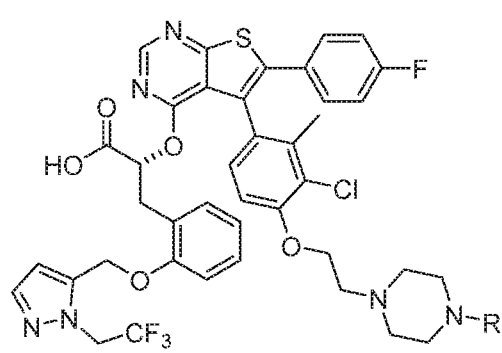
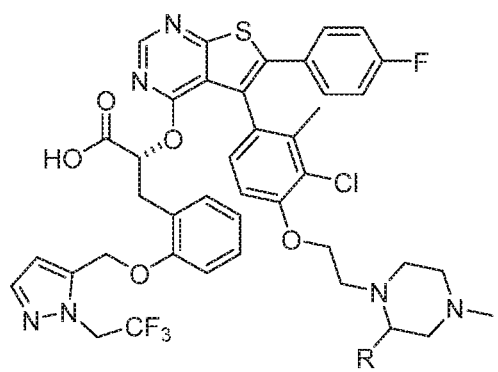
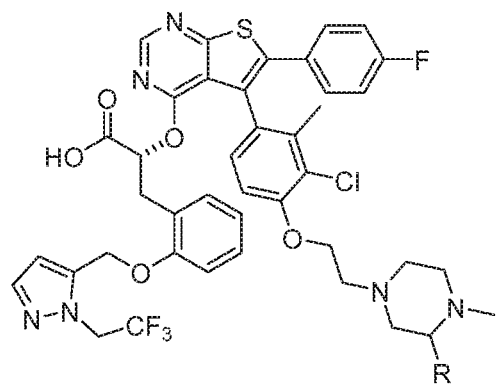
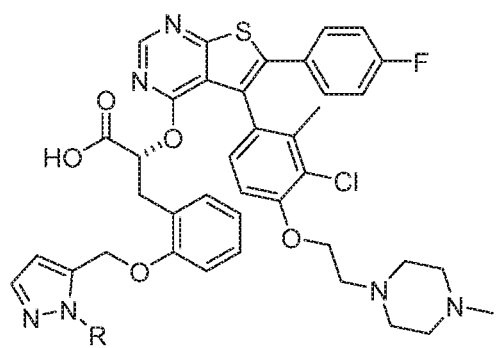
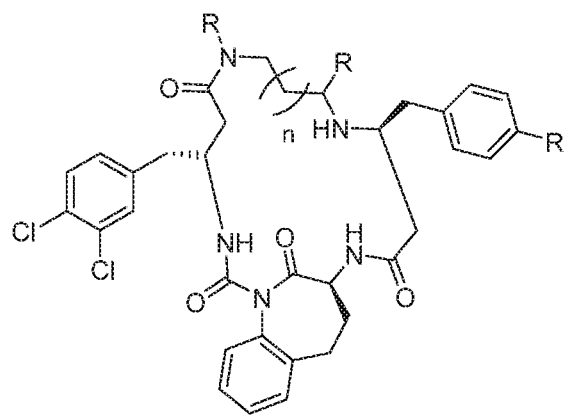
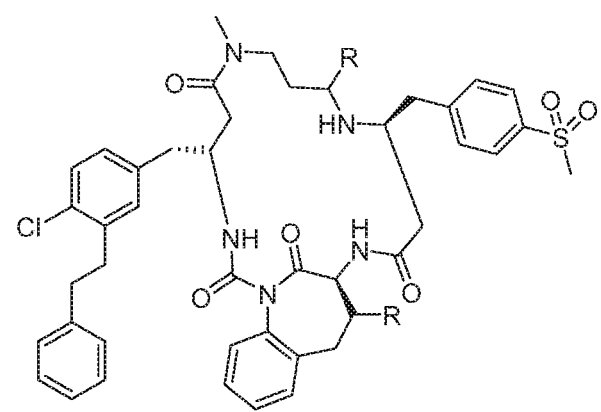

FIG. 3NN
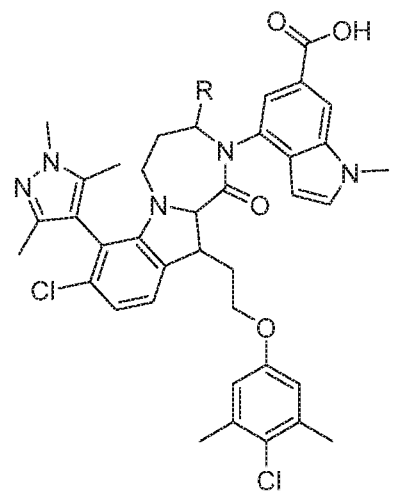
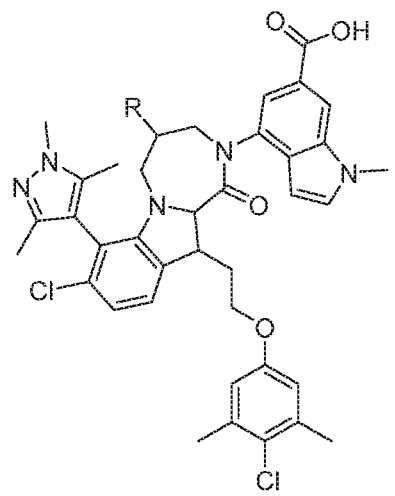
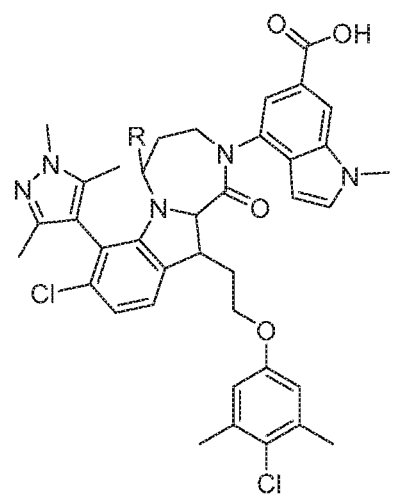
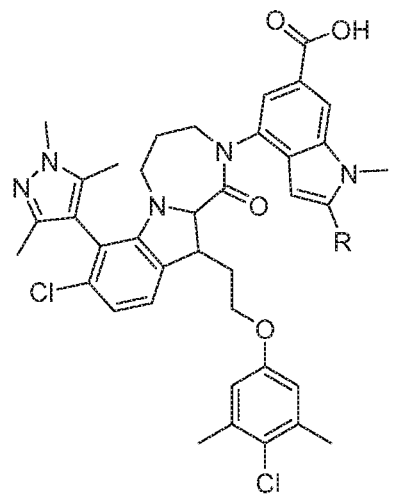
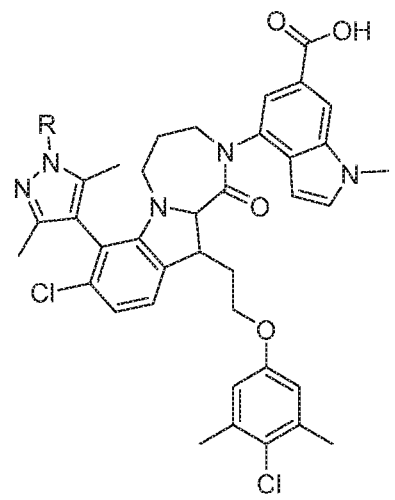
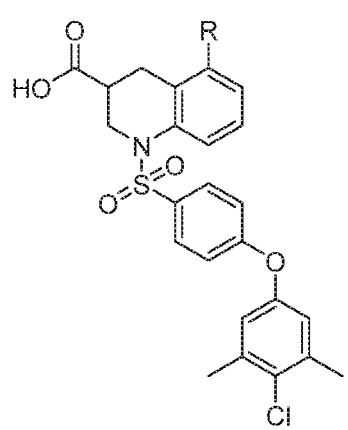

FIG. 3AAA
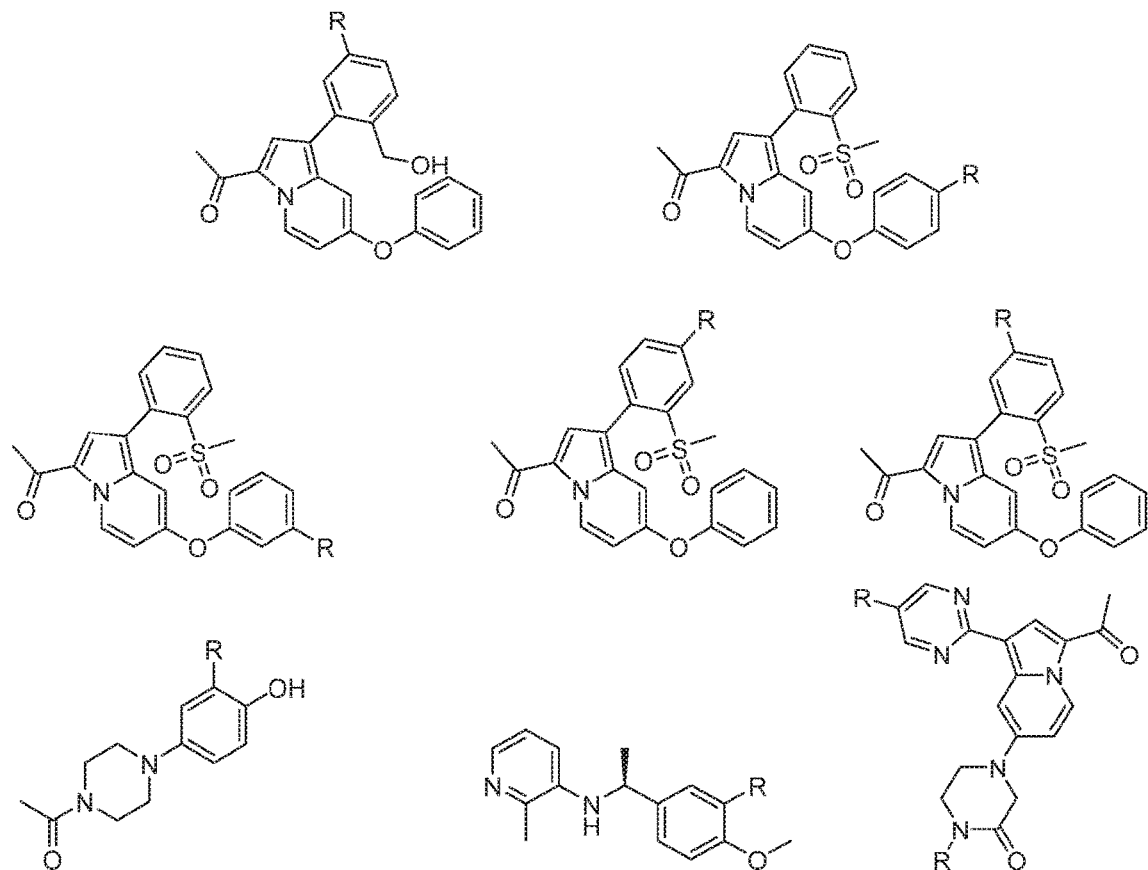
FIG. 3BBB
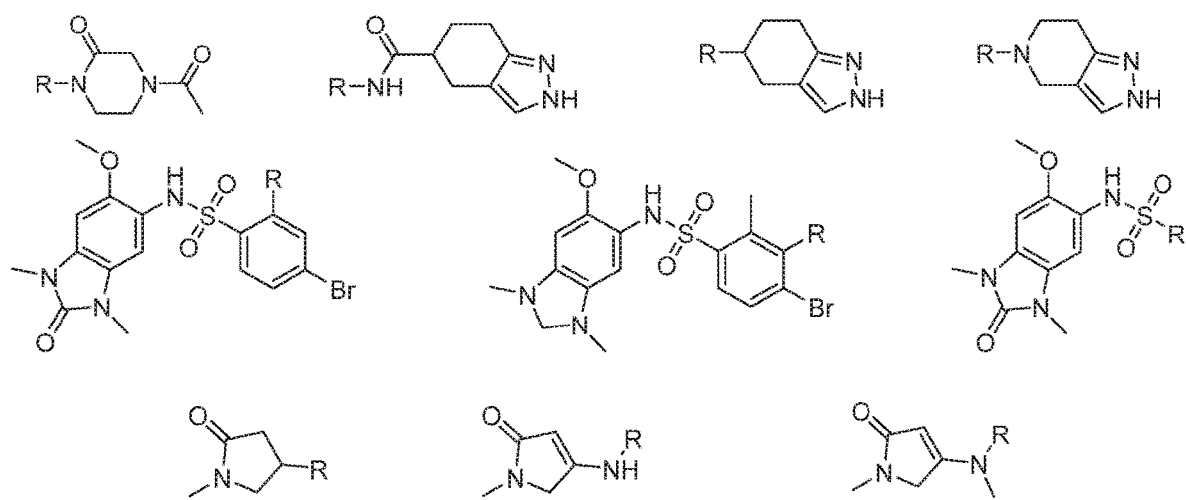

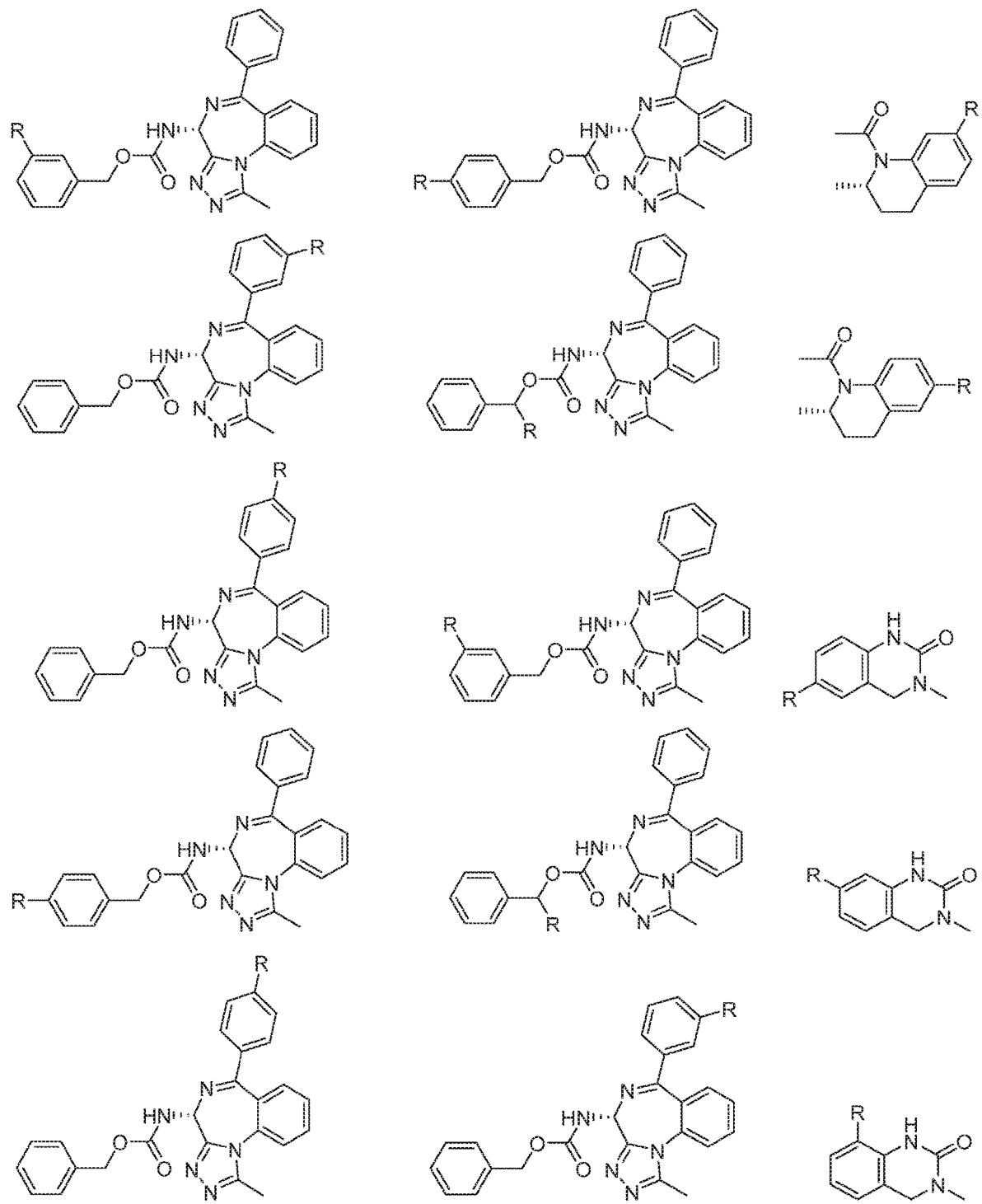
FIG. 3CCC

FIG. 3DDD
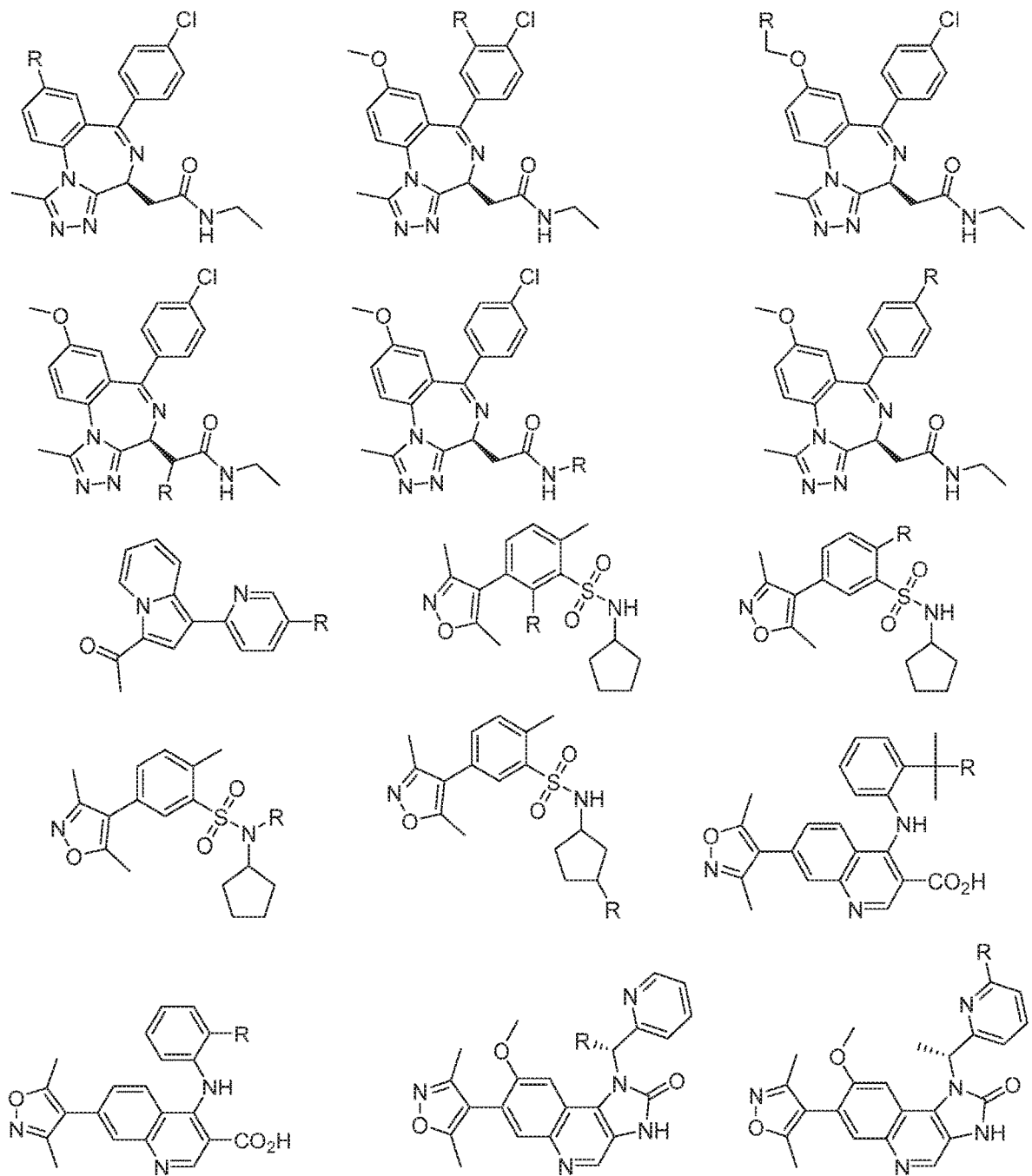

FIG. 3EEE
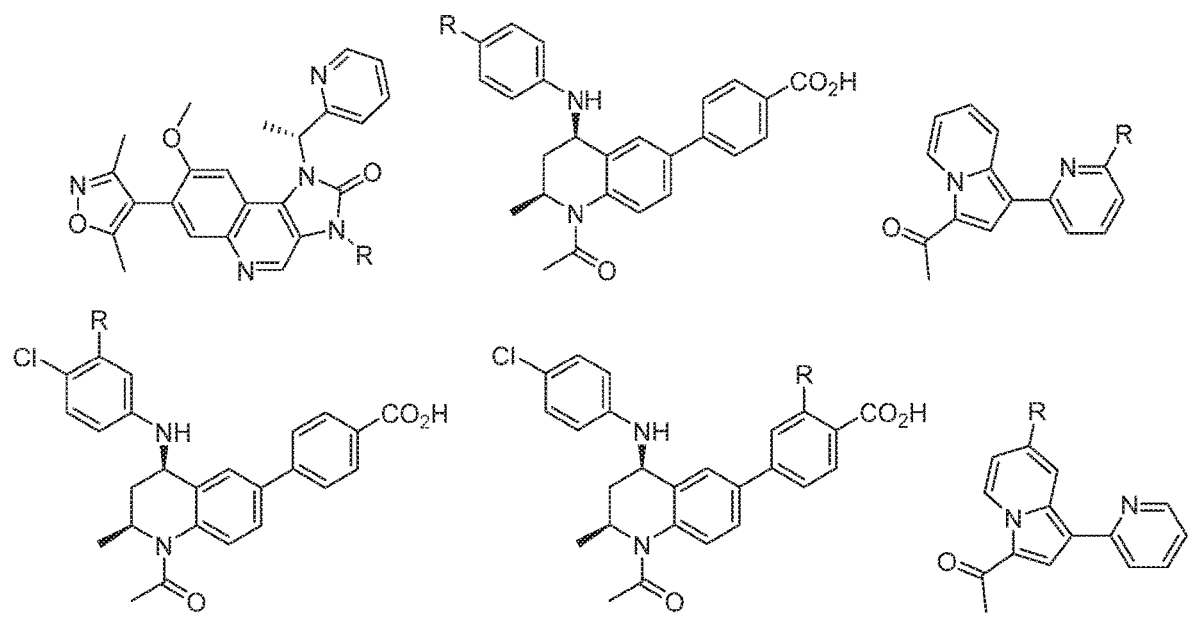
FIG. 3FFF
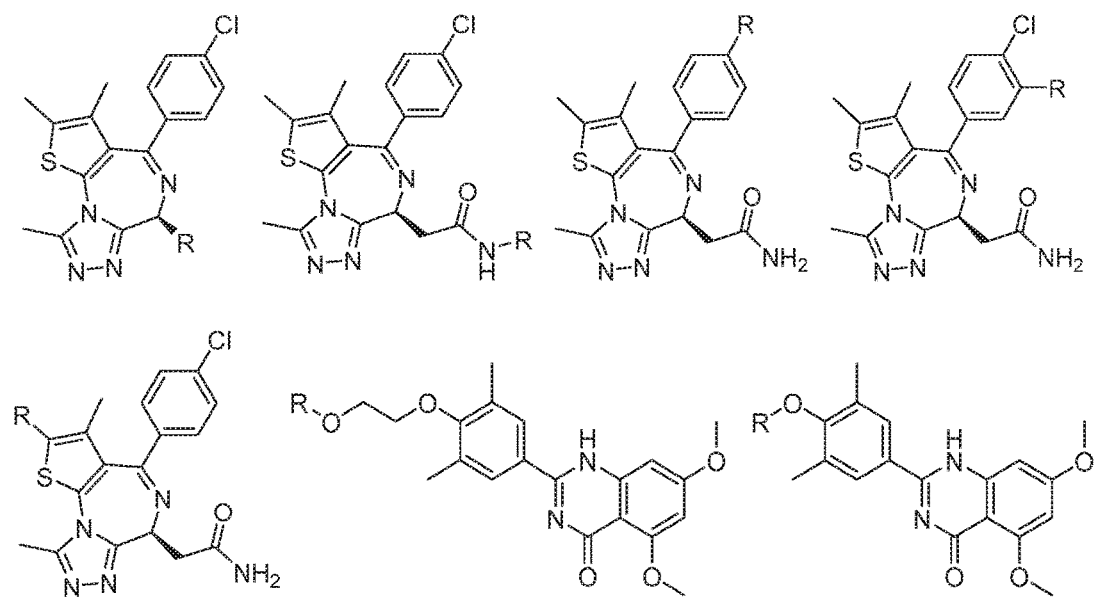

FIG. 3GGG
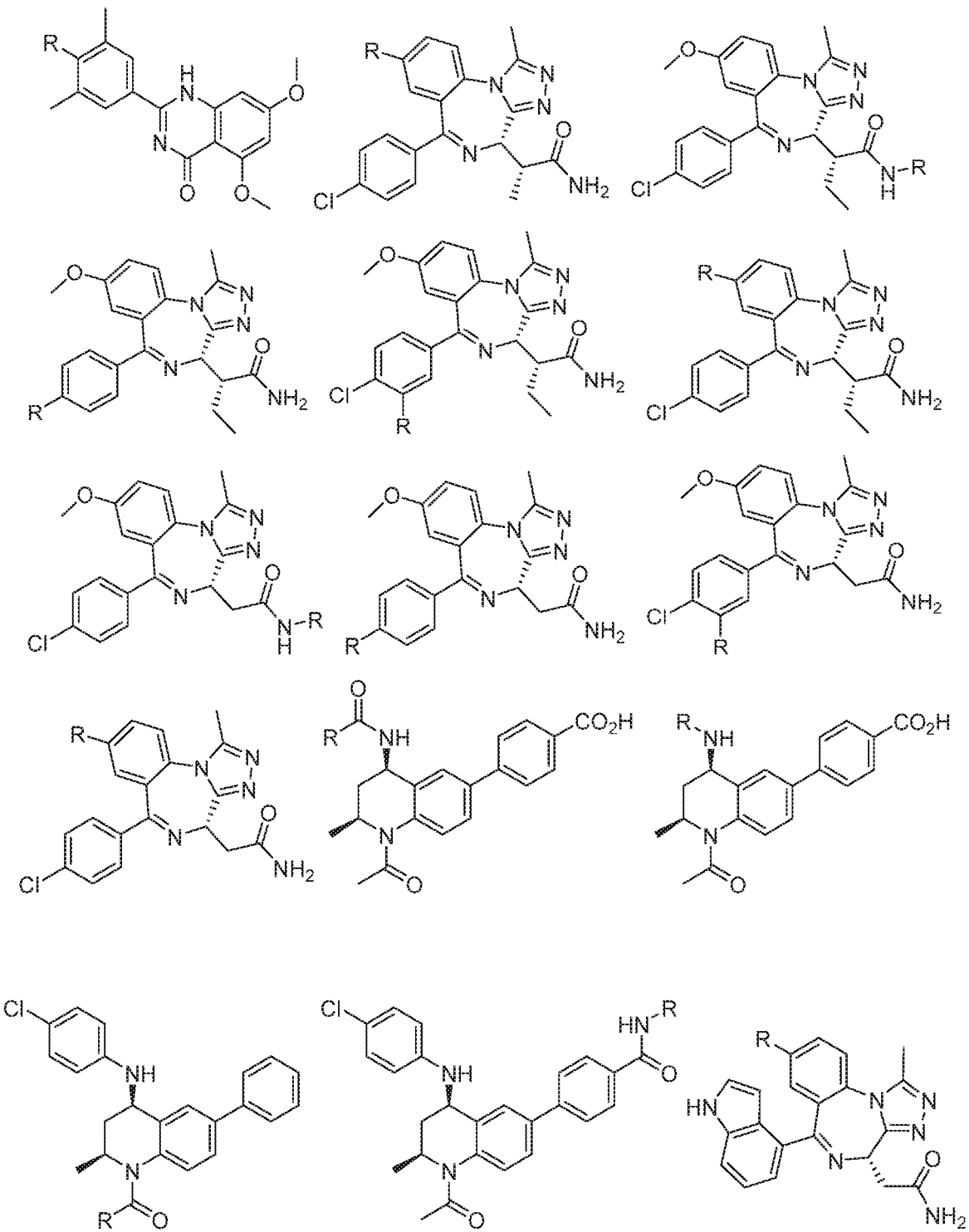

FIG. 3HHH
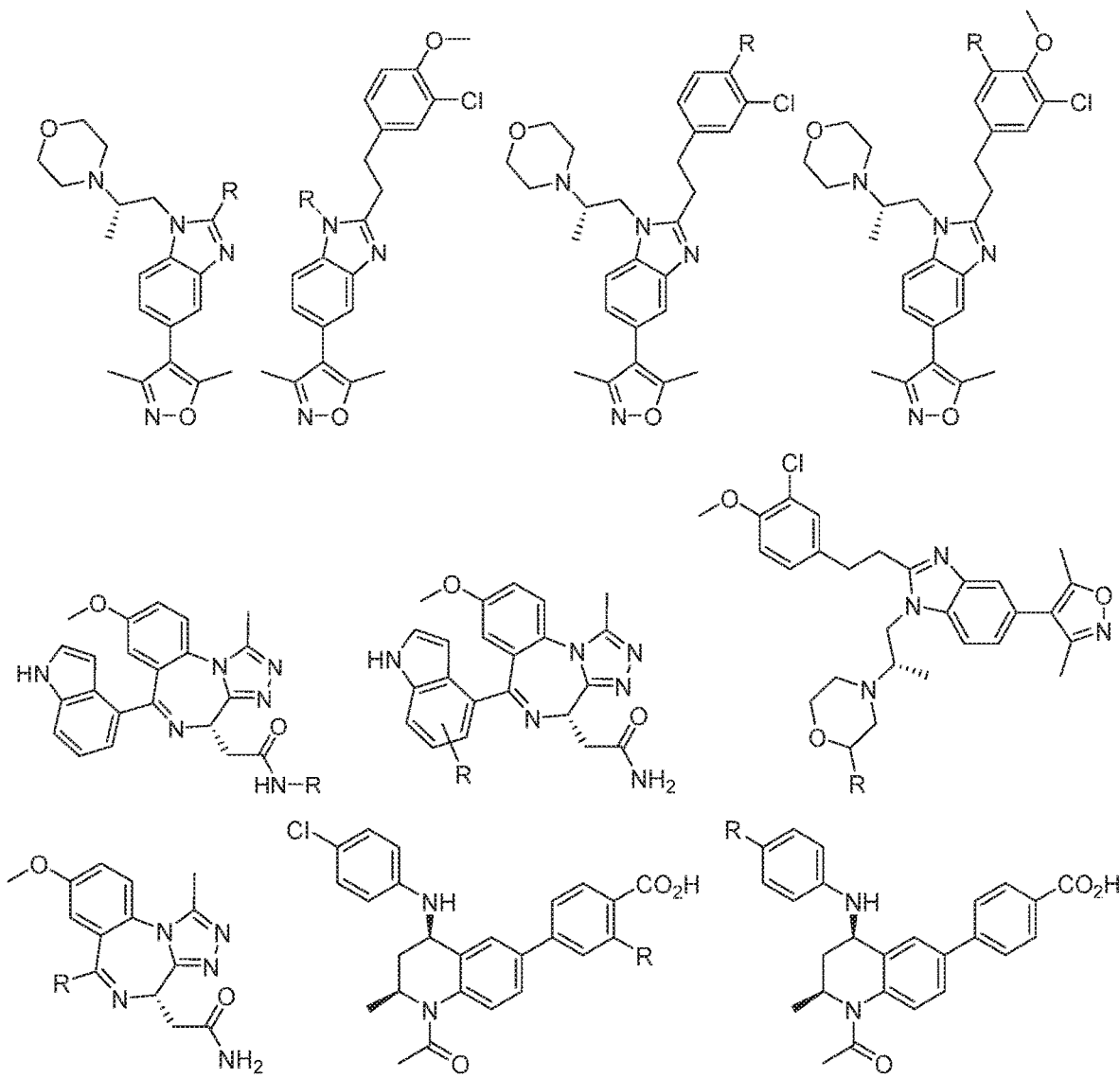
FIG. 3III
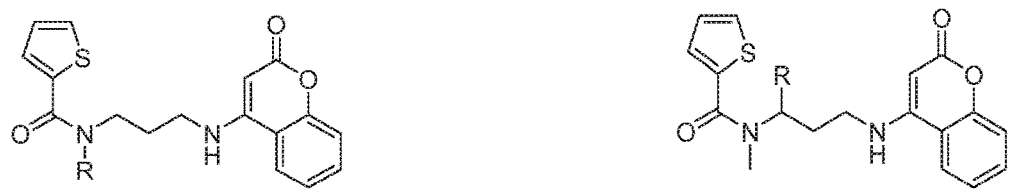

FIG. 3JJJ
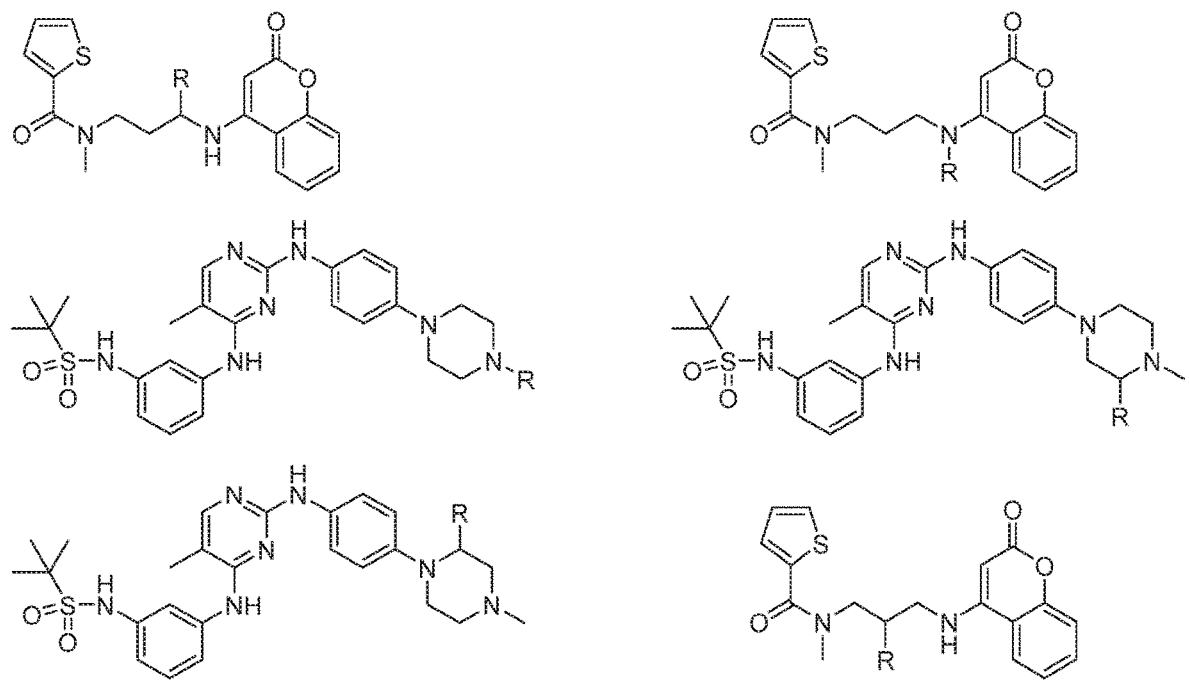
FIG. 3KKK
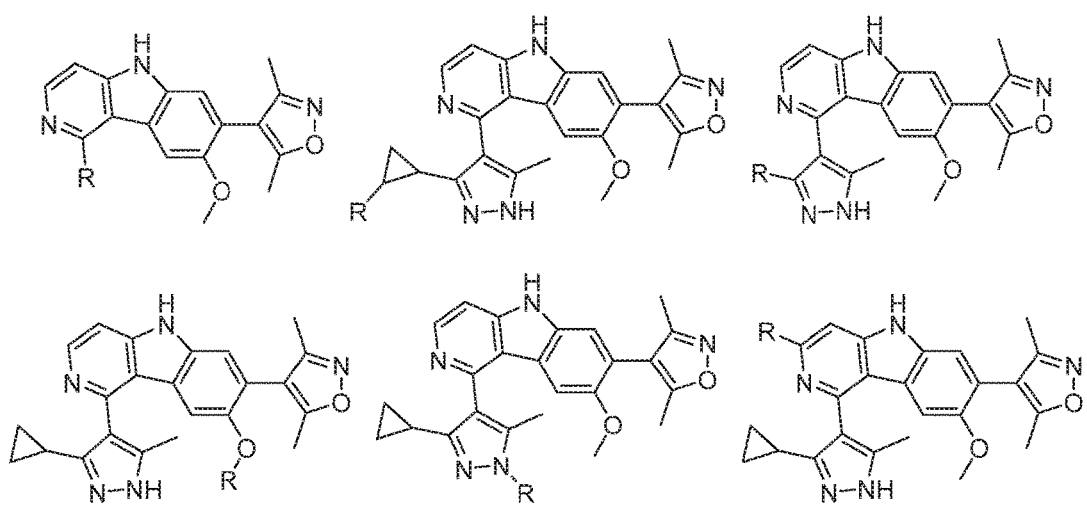

FIG. 3LLL
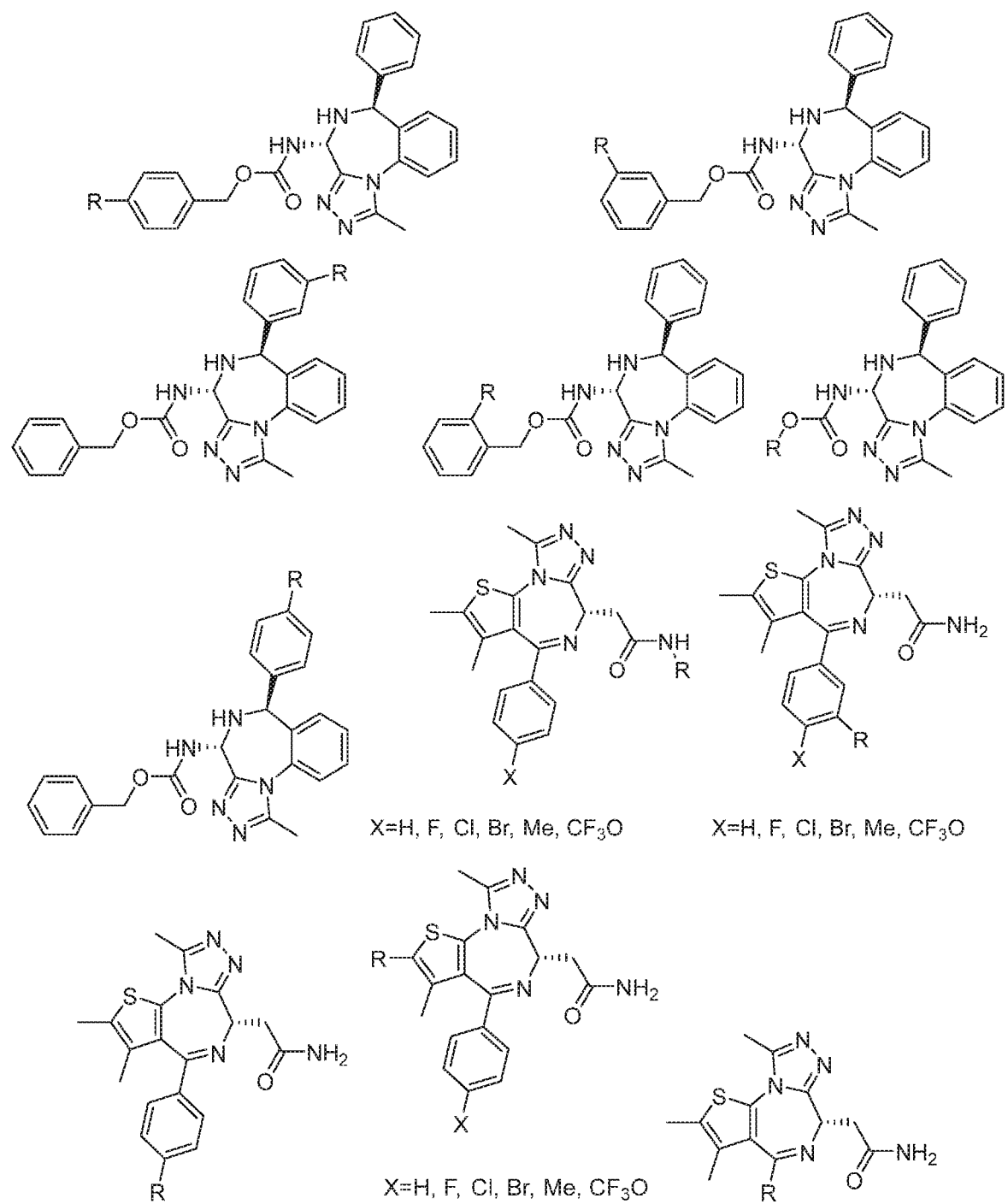

FIG. 3MMM
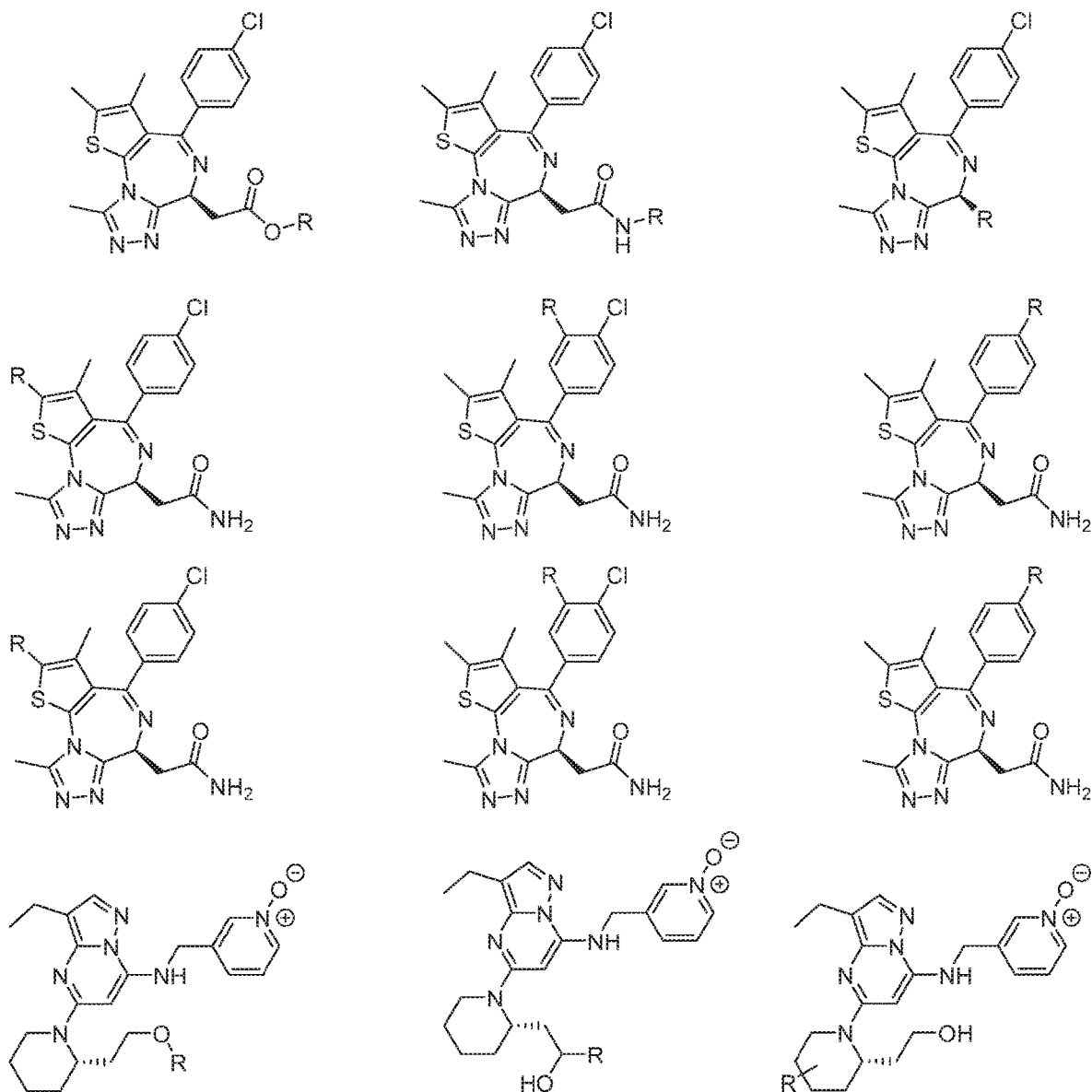
FIG. 3NNN
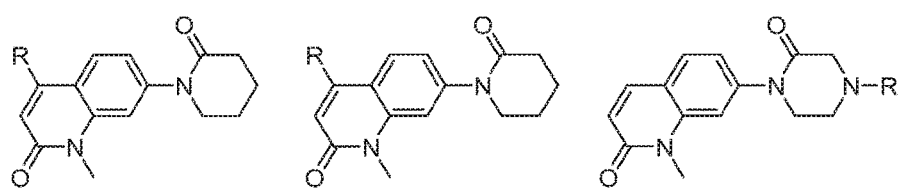

FIG. 3OOO
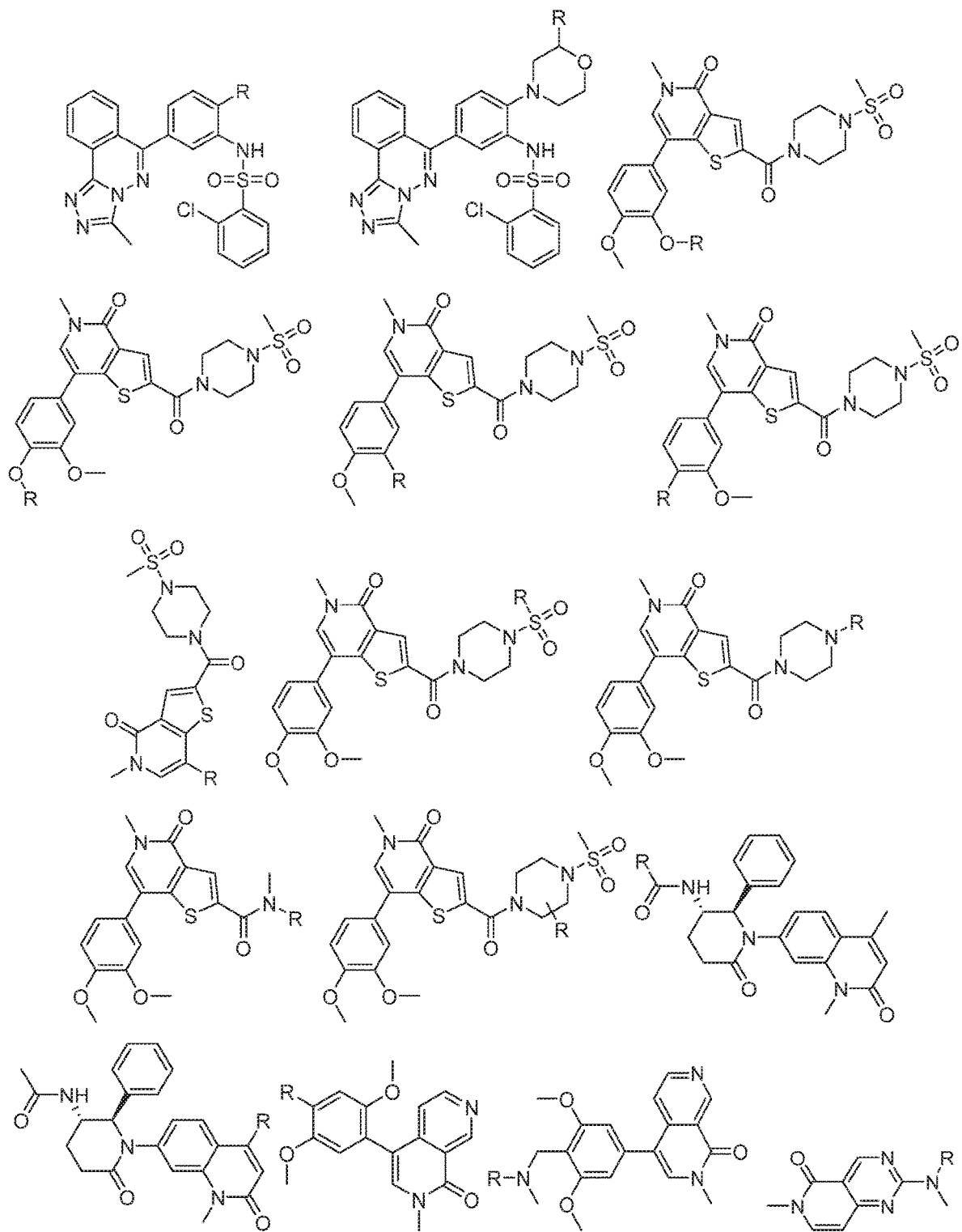

FIG. 3PPP
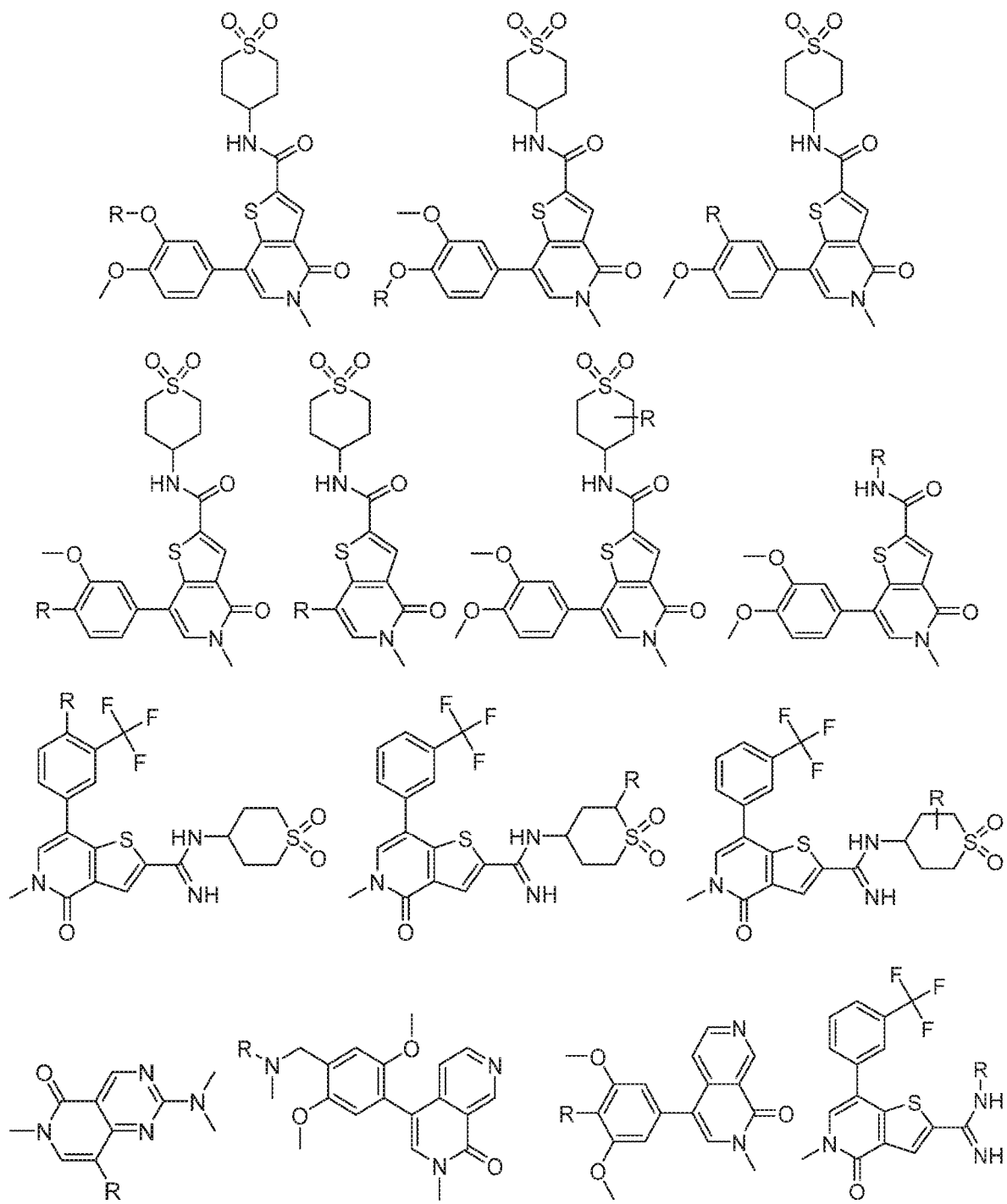

FIG. 3QQQ
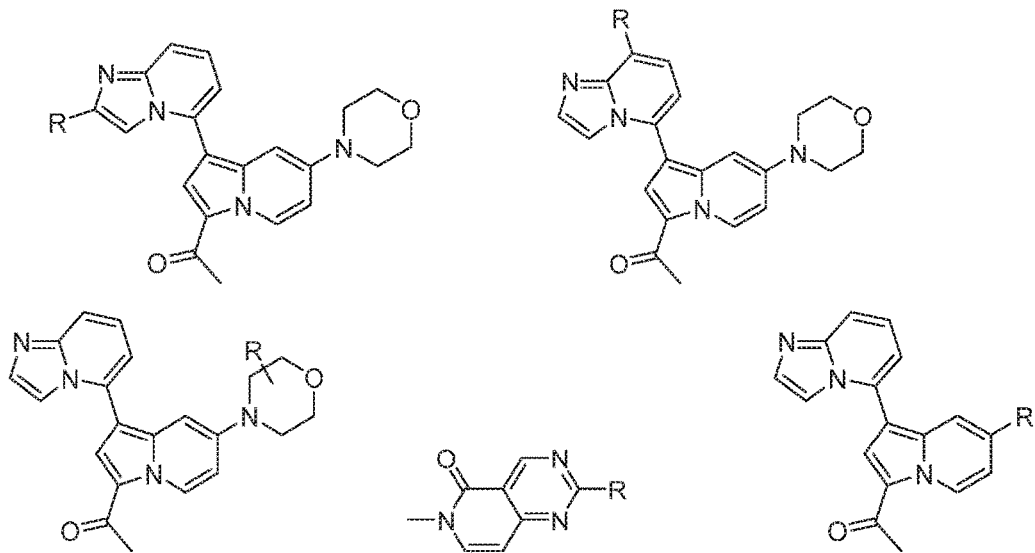
FIG. 3RRR
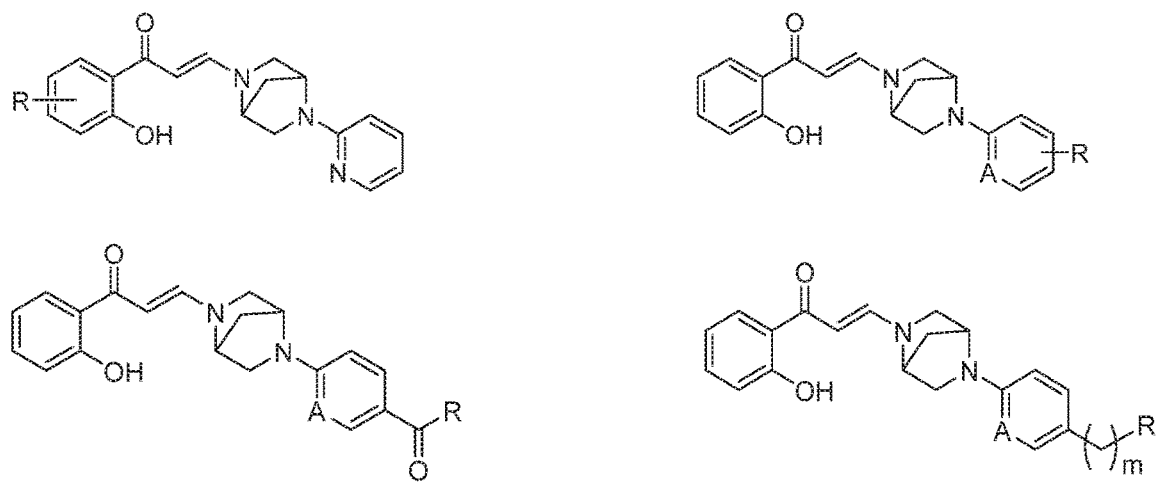
FIG. 3SSS
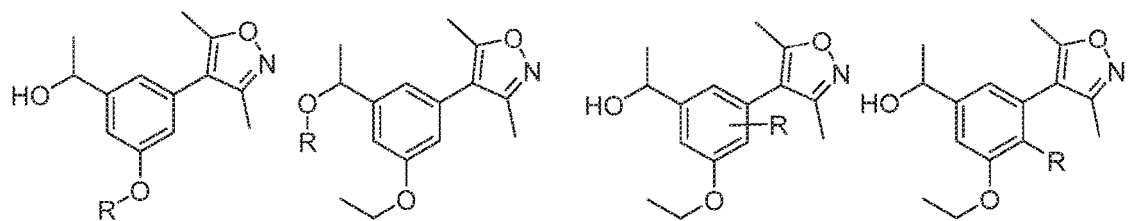

FIG. 3TTT
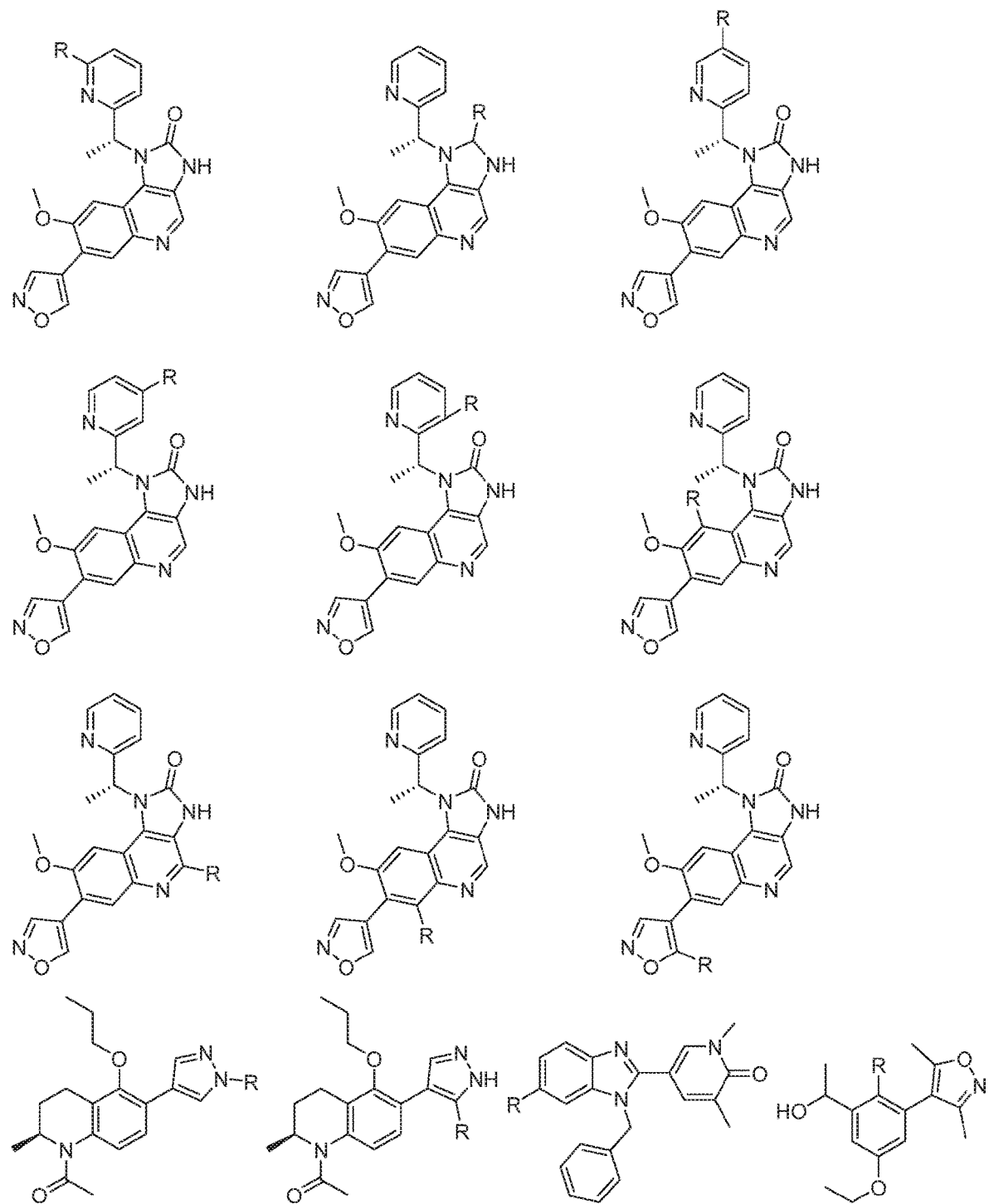

FIG. 3UUU
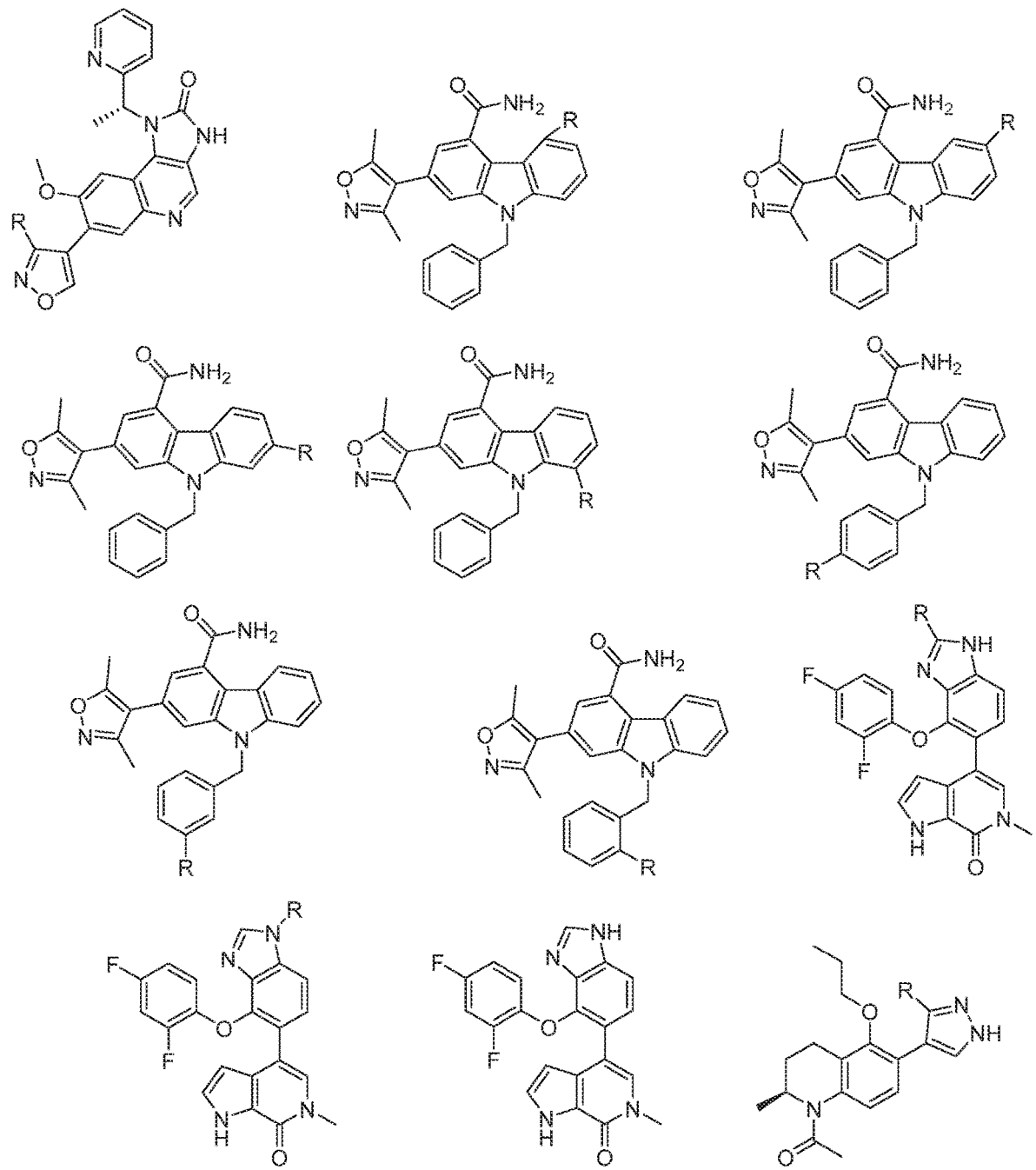

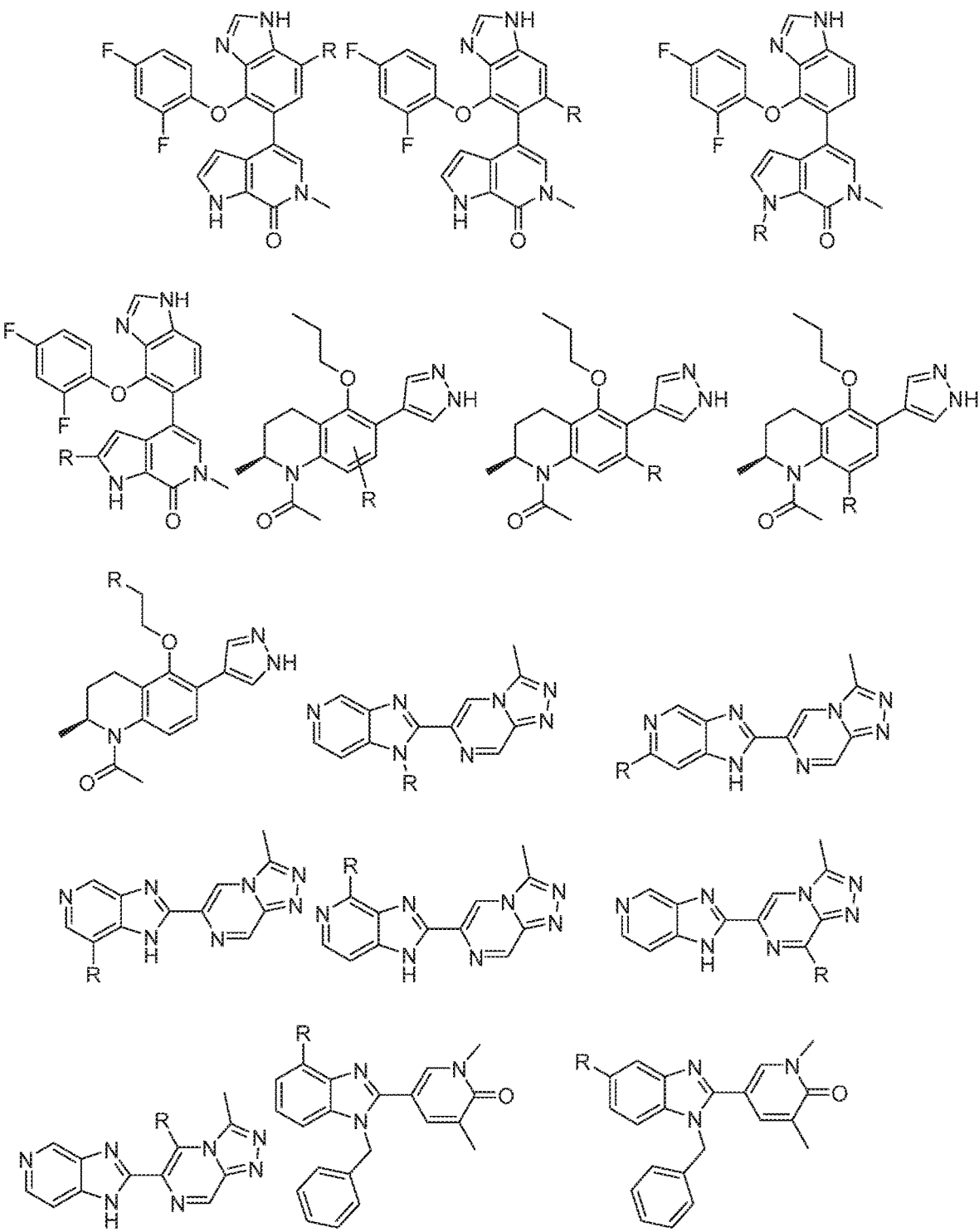
FIG. 3VVV

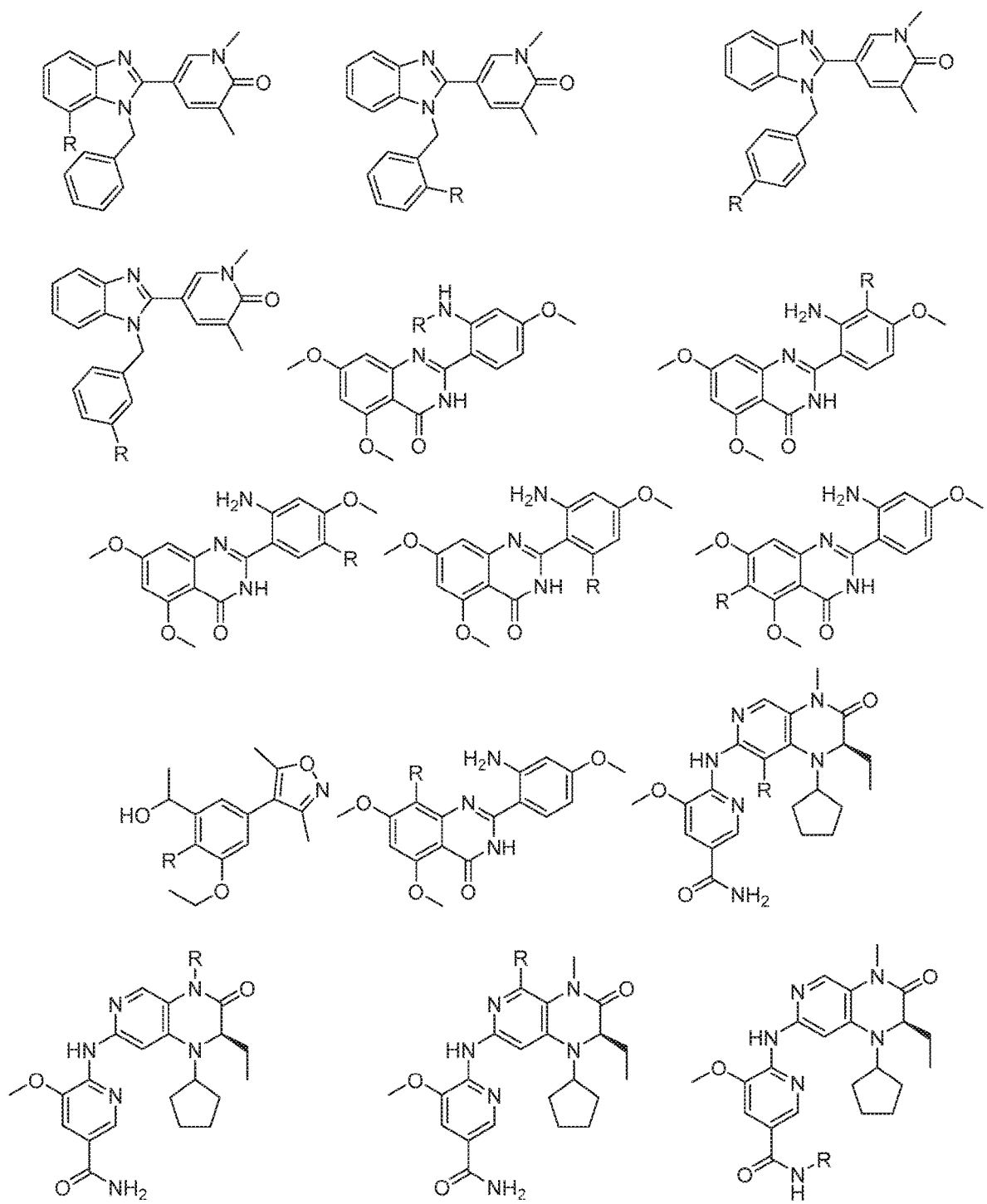
FIG. 3WWW

FIG. 3XXX
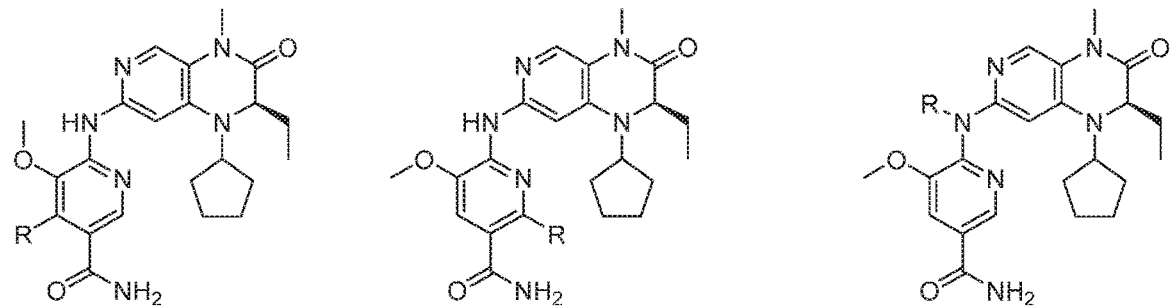
FIG. 3YYY
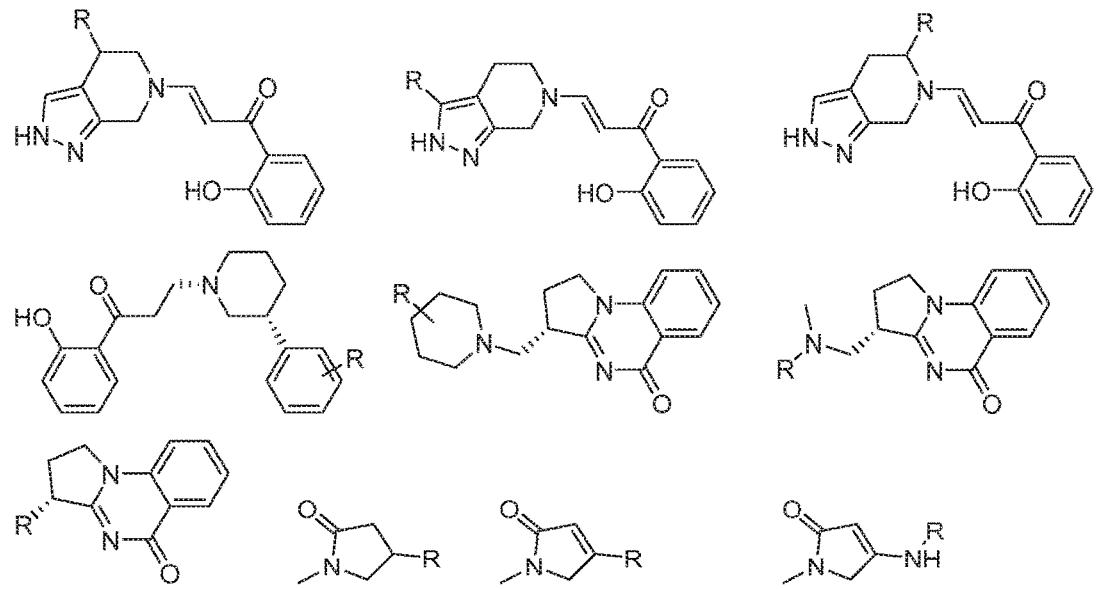
FIG. 3ZZZ
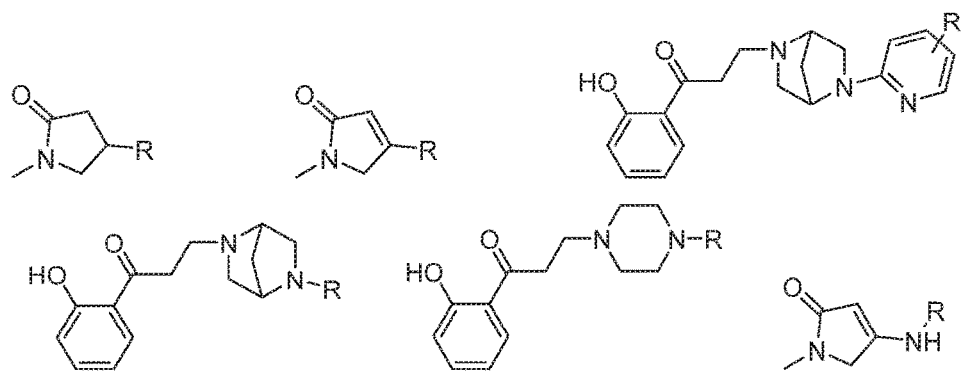

FIG. 3AAAA
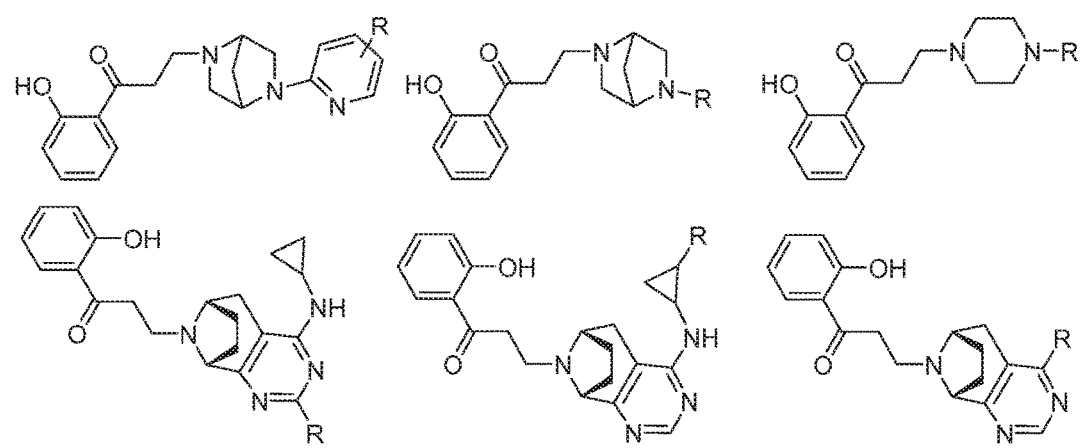
FIG. 3BBBB
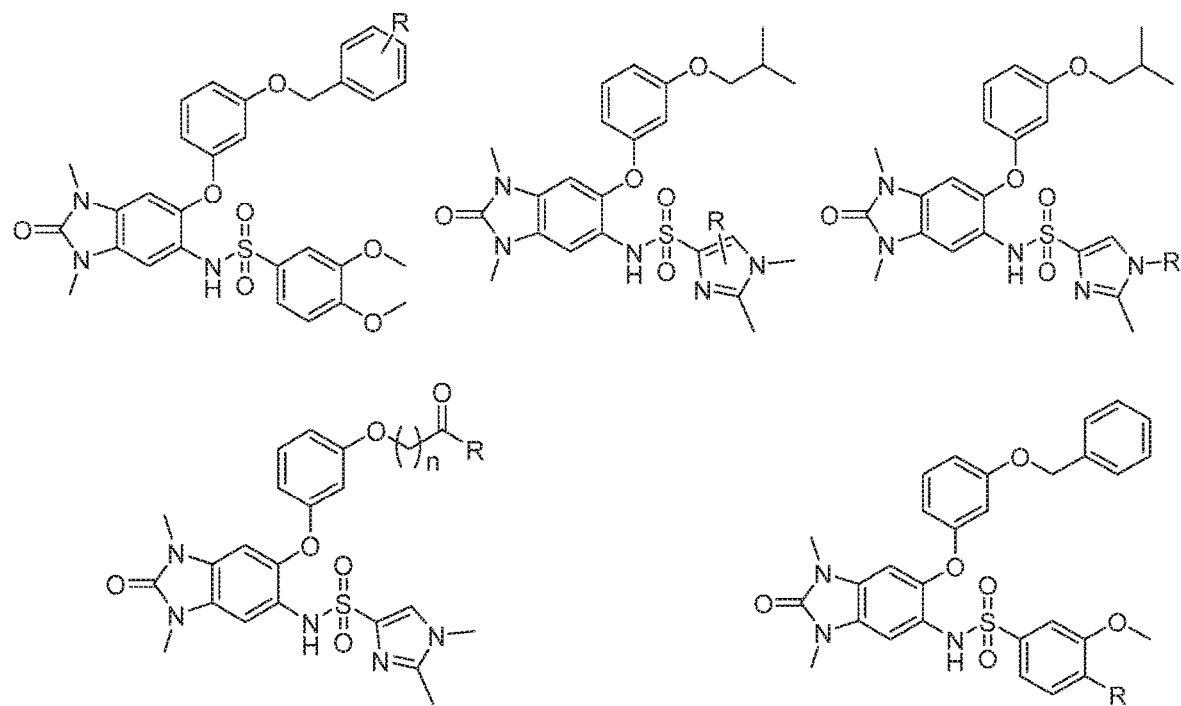

FIG. 3CCCC
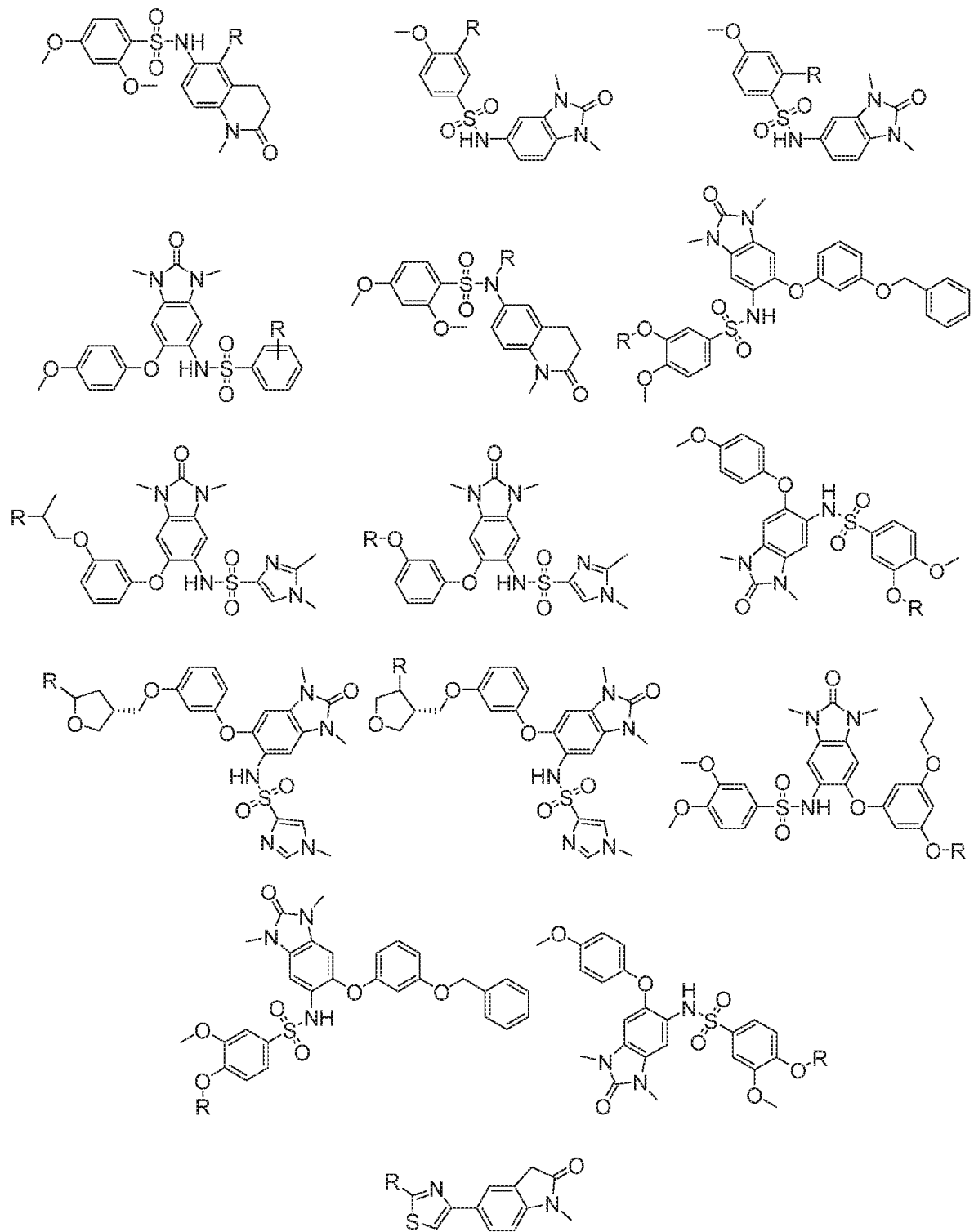

FIG. 3DDDD
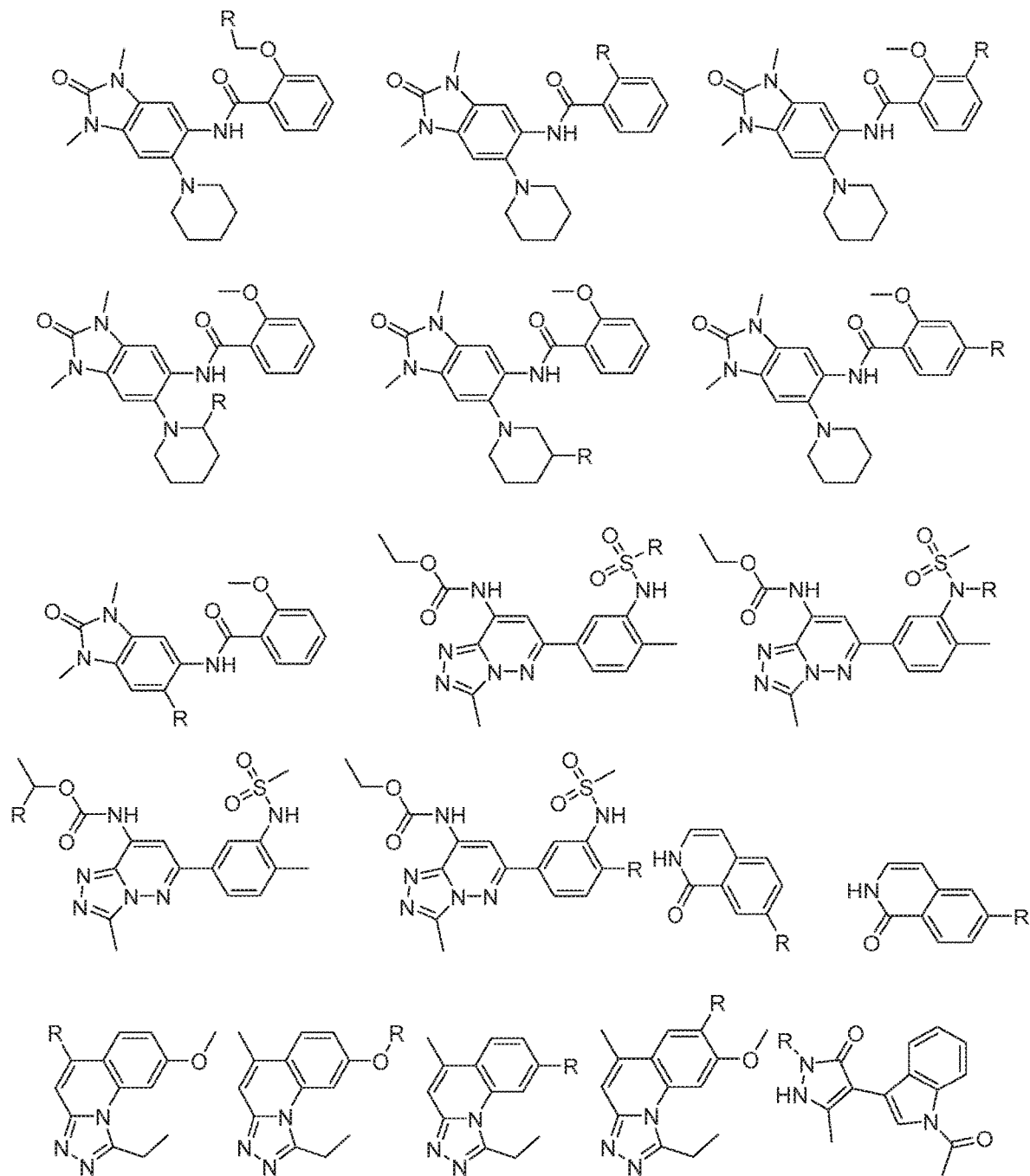

FIG. 3EEEE
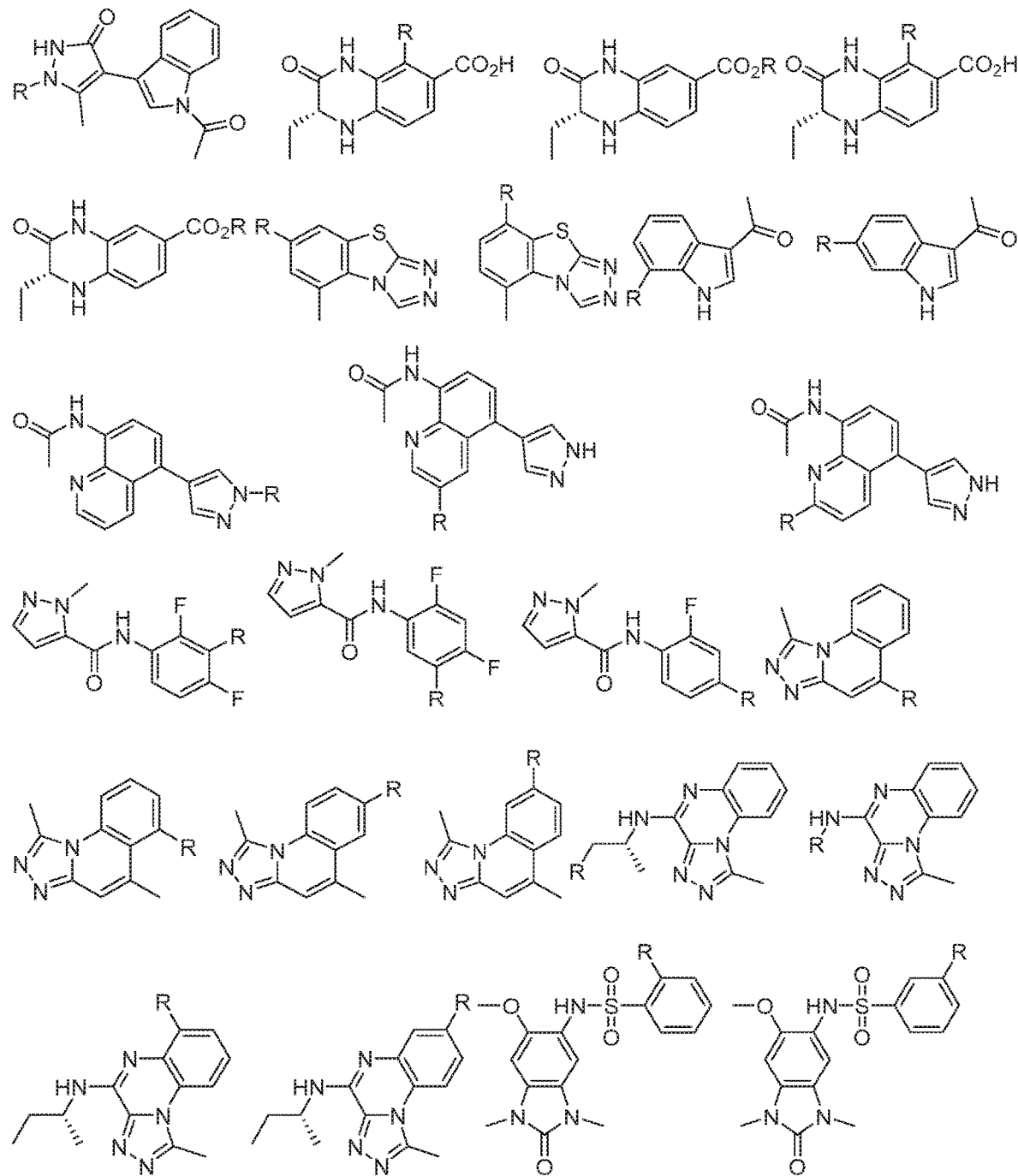

FIG. 3FFFF
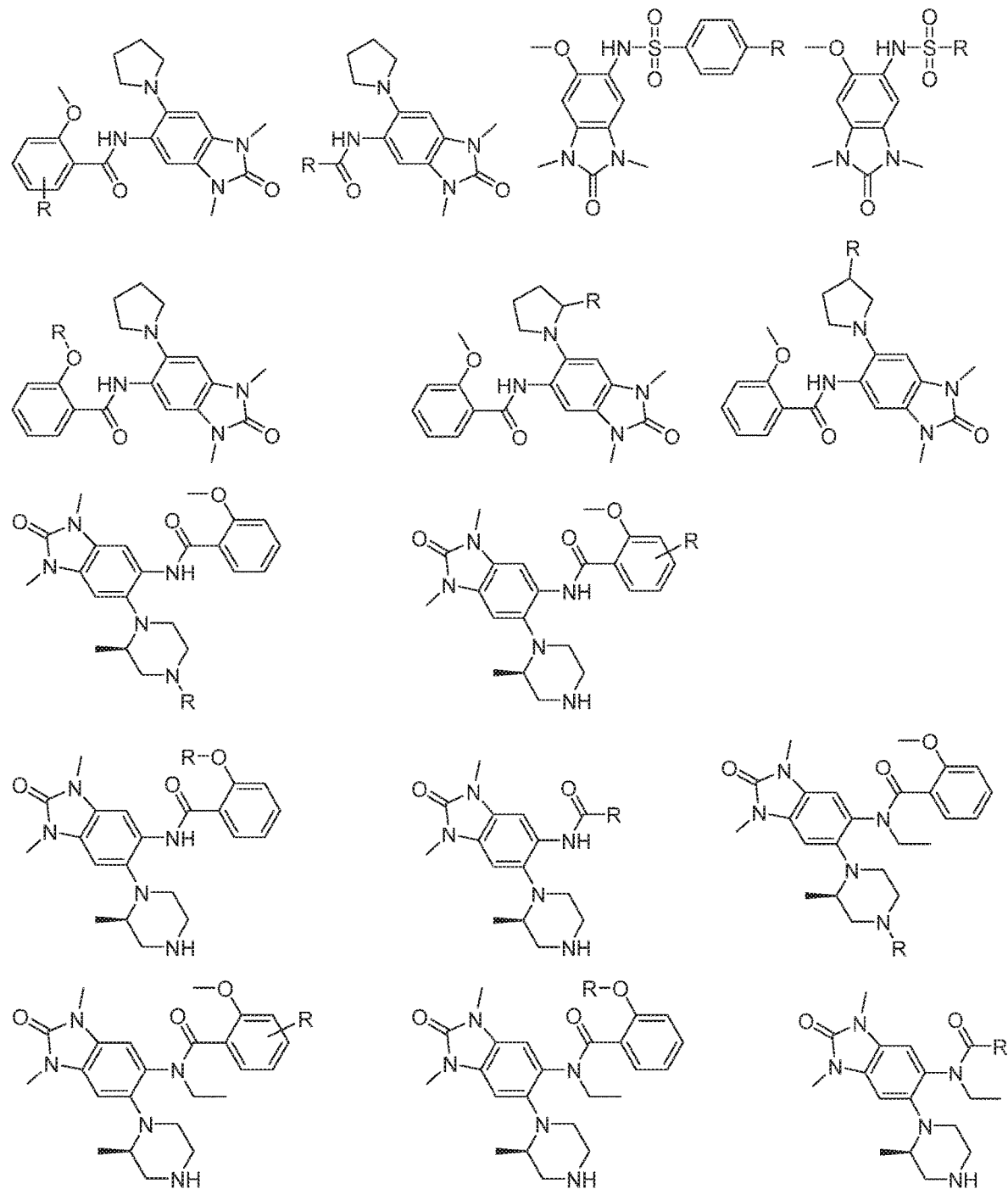

FIG. 3GGGG
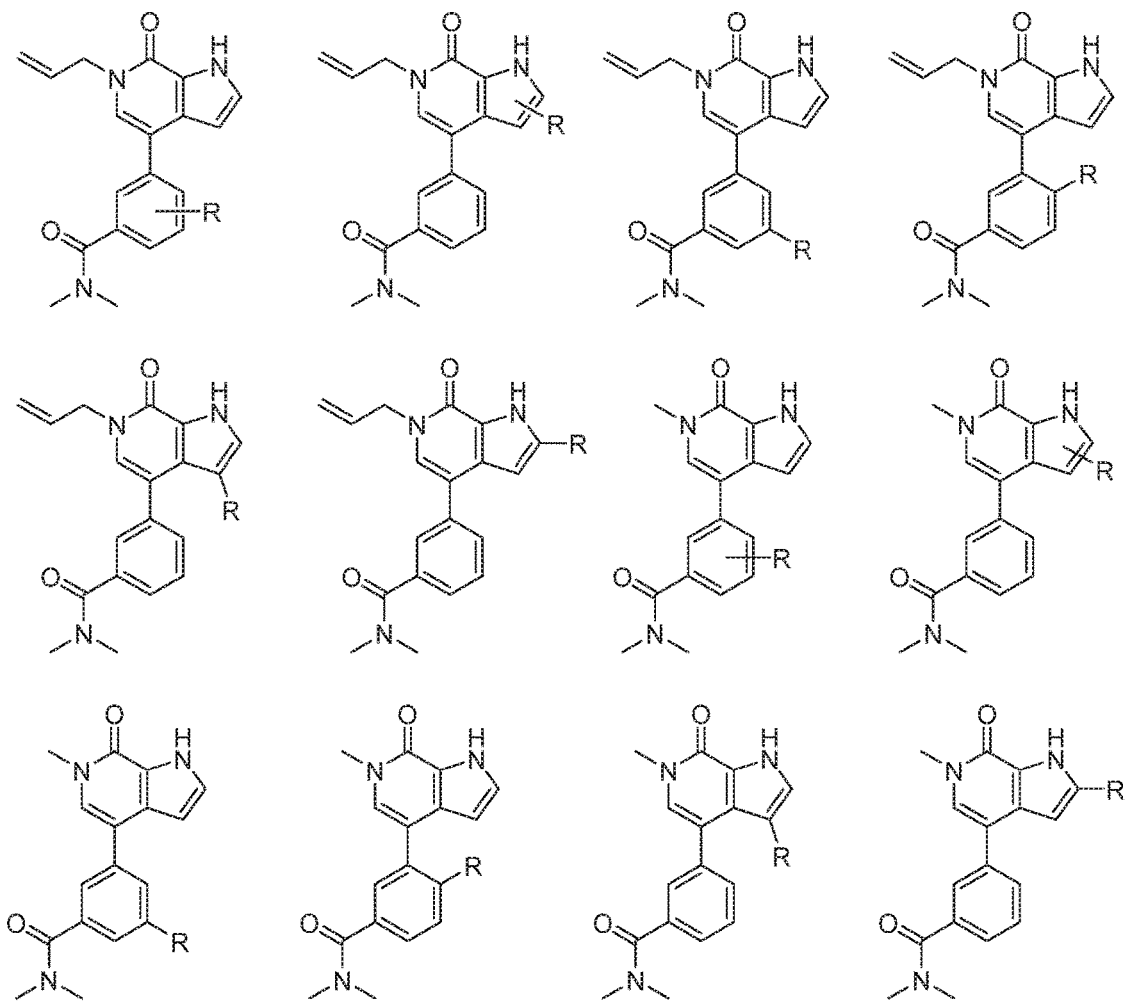
FIG. 3HHHH
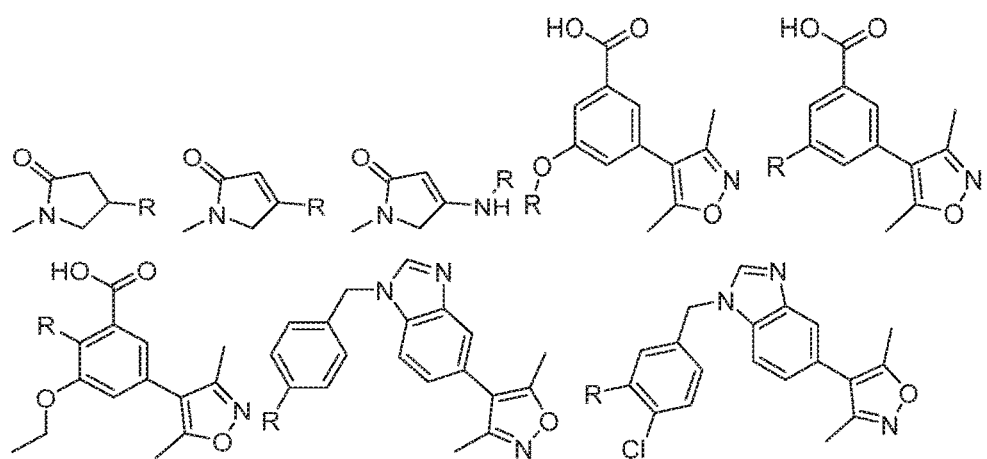

FIG. 3IIII
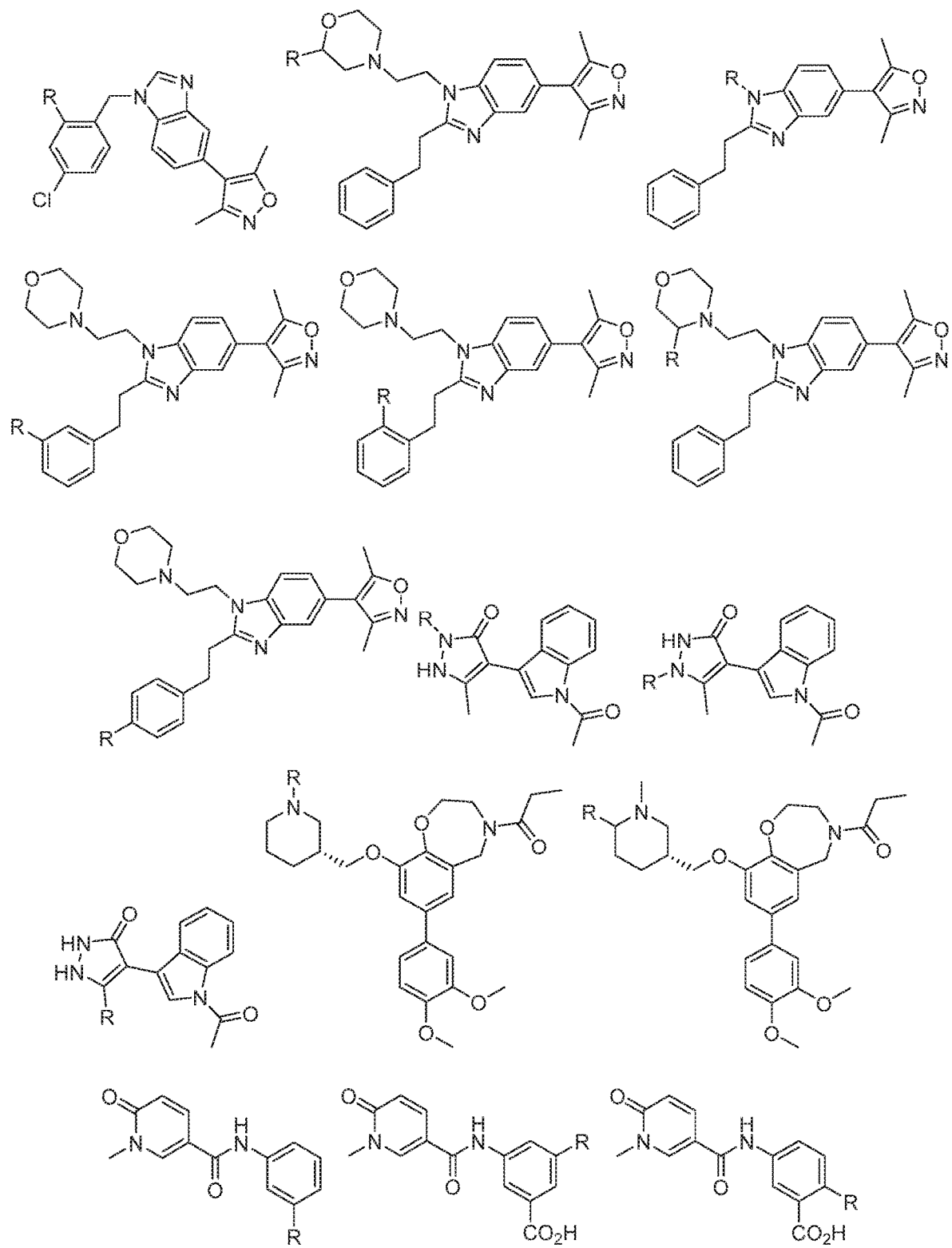

FIG. 3JJJJ
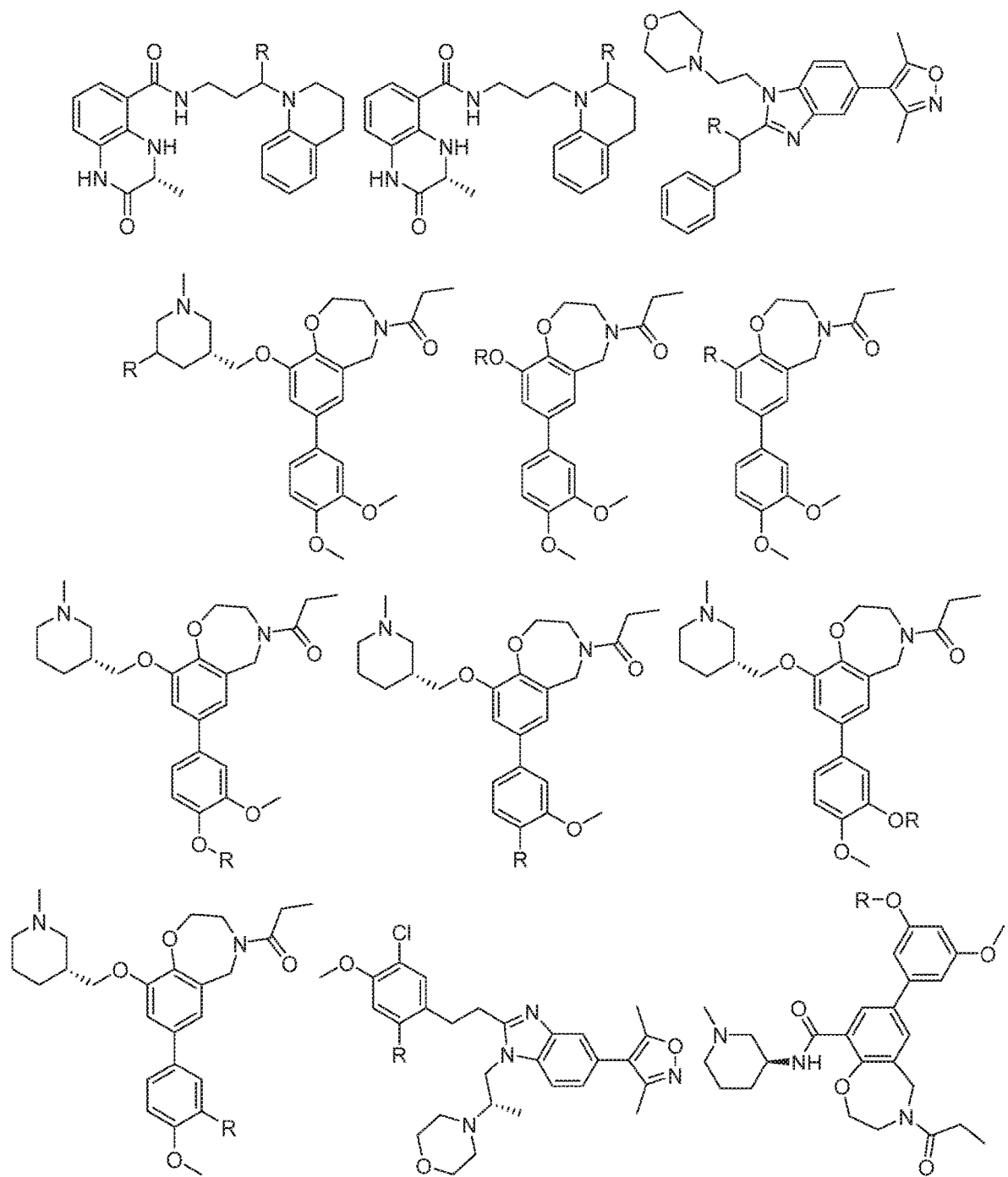

FIG. 3KKKK
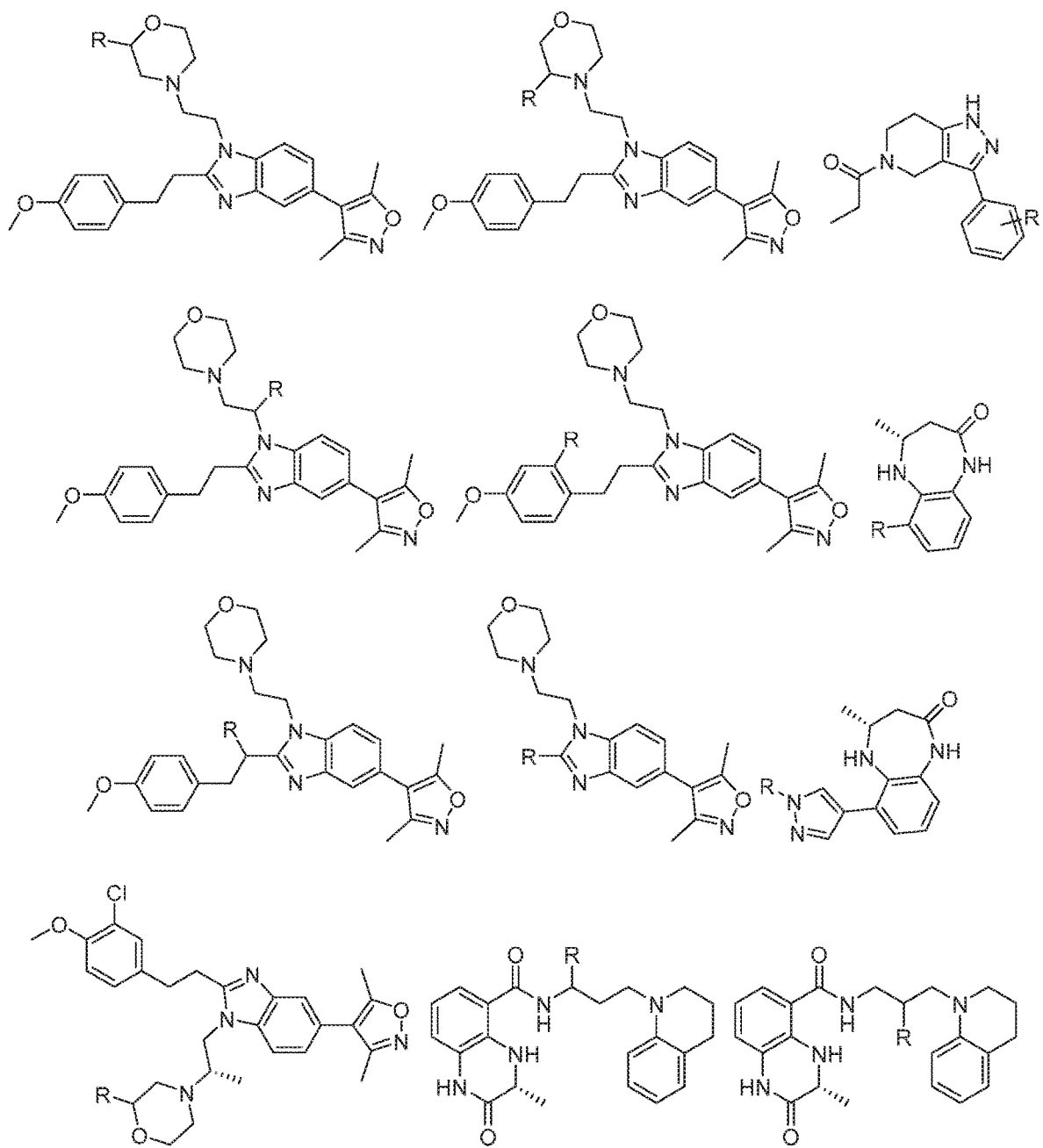

FIG. 3LLLL
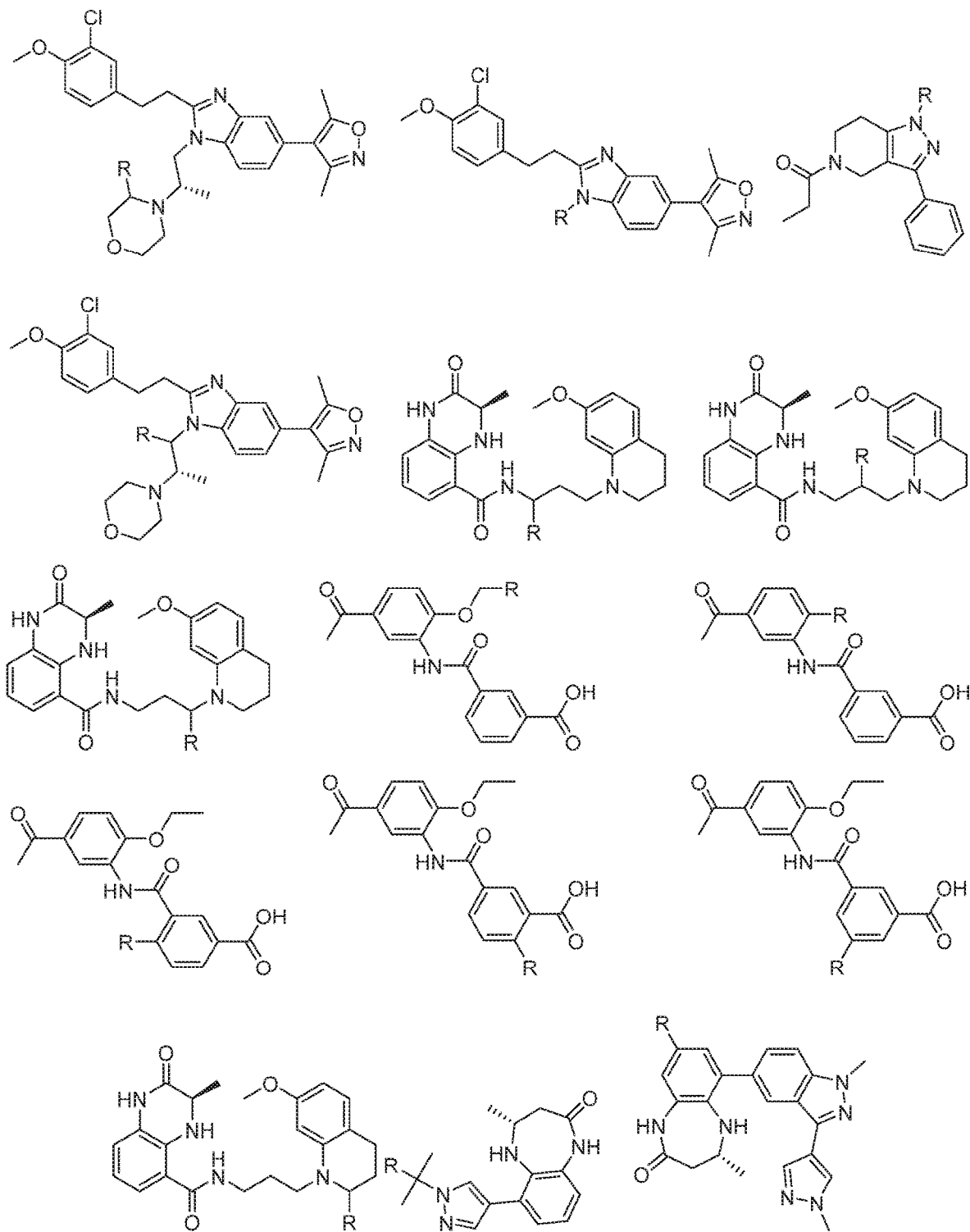

FIG. 3MMMM
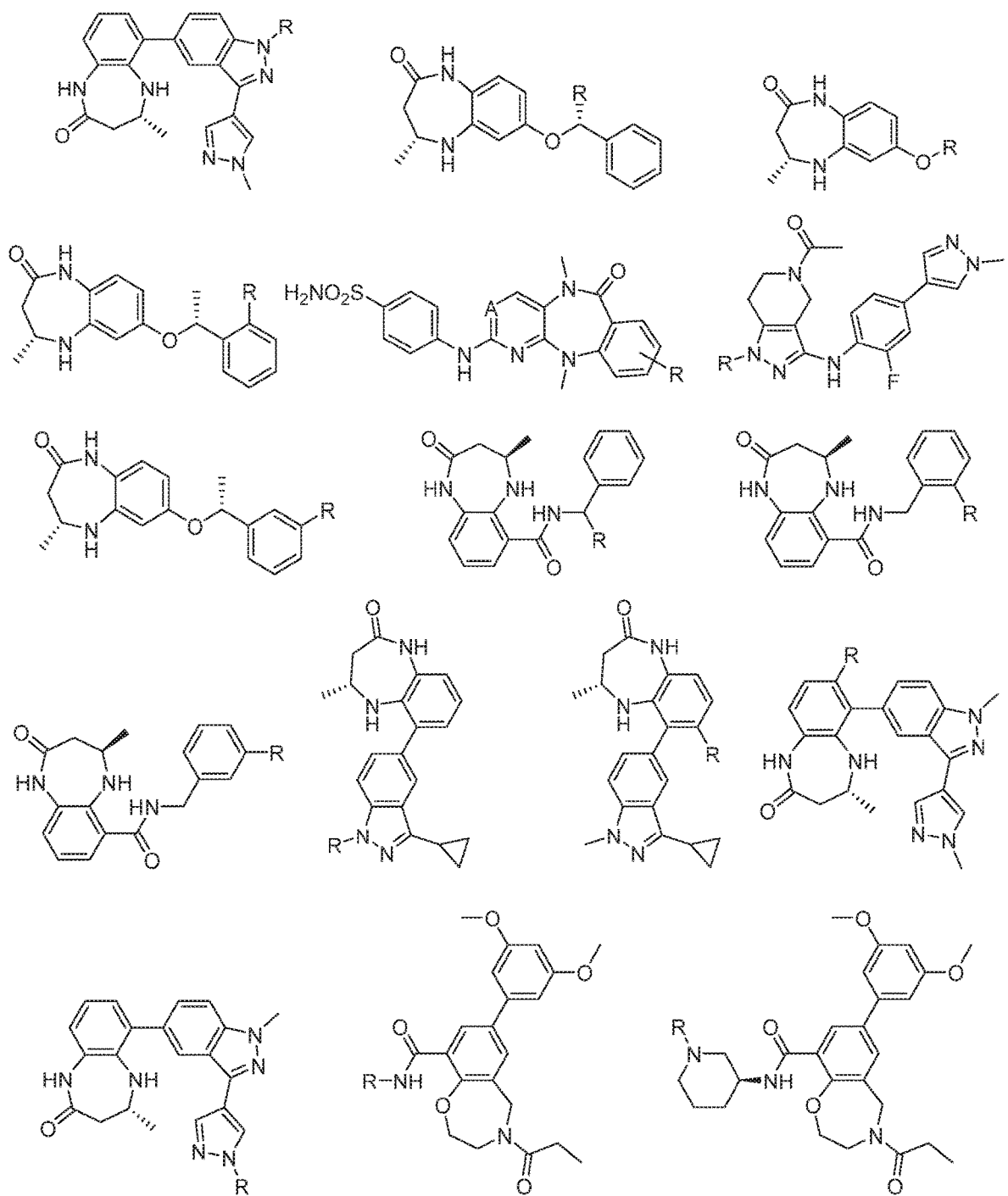

FIG. 3NNNN
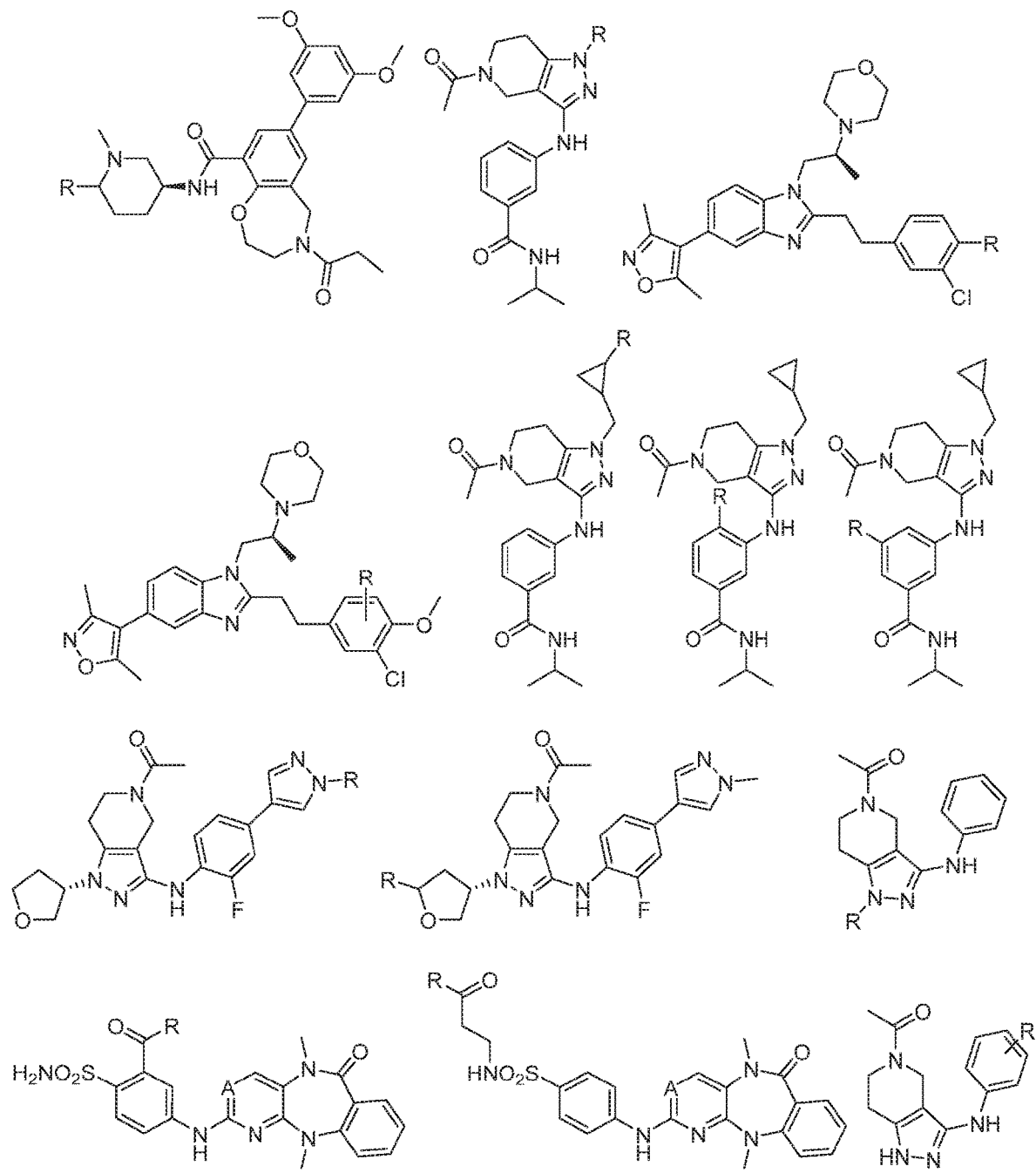

FIG. 3OOOO
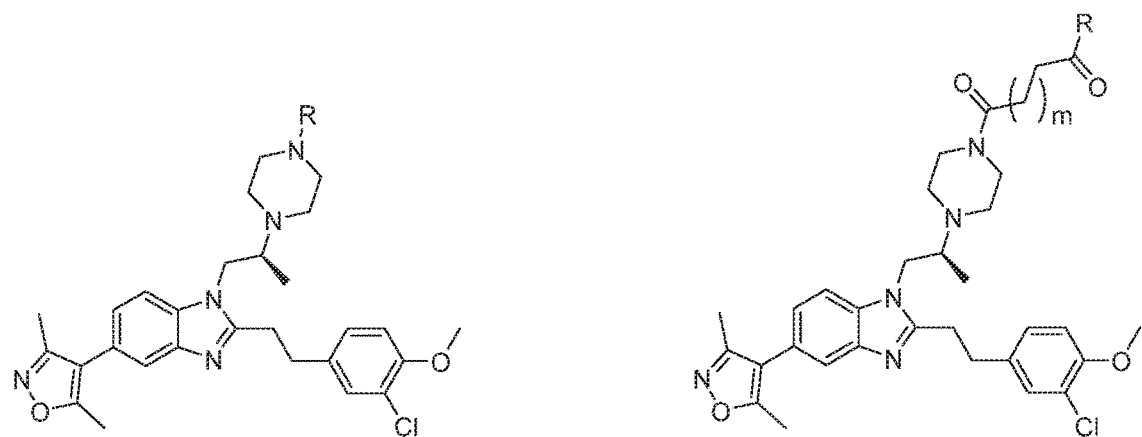
FIG. 3PPPP
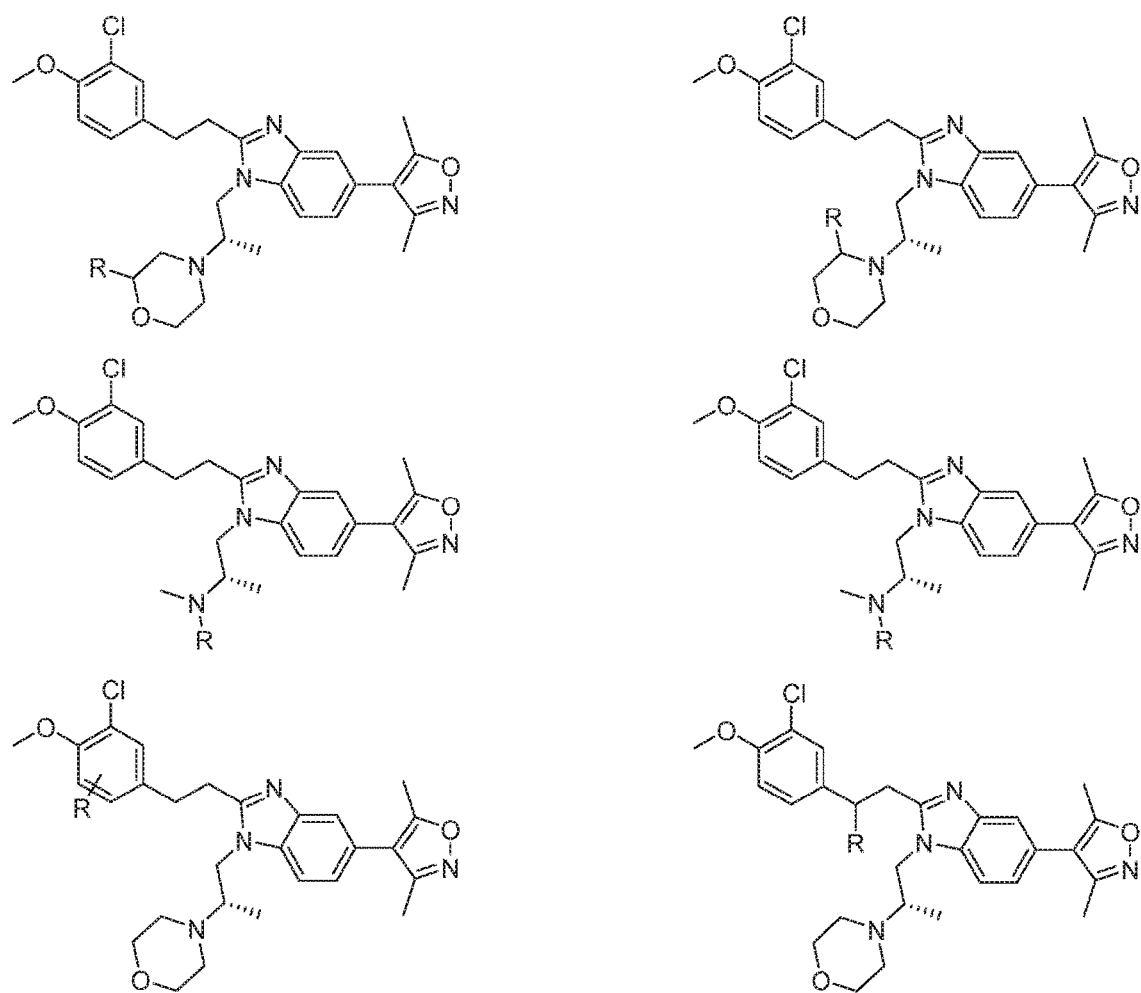

FIG. 3QQQQ
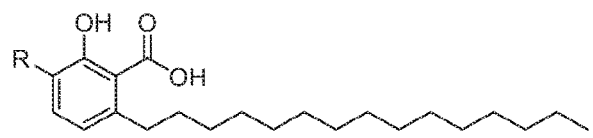
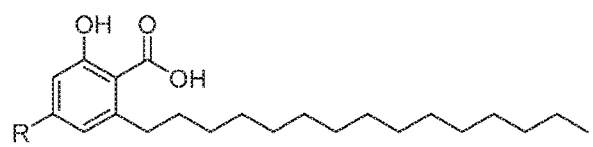
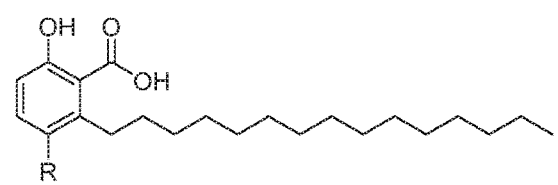
FIG. 3RRRR
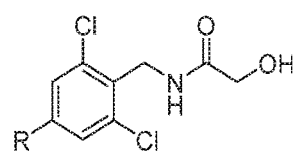
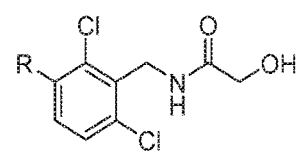
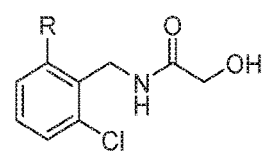
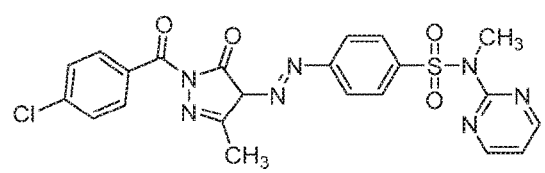
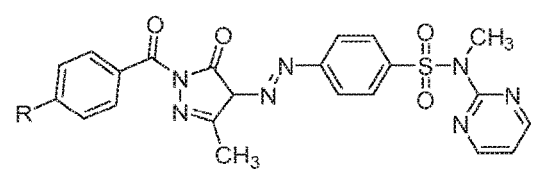
FIG. 3SSSS
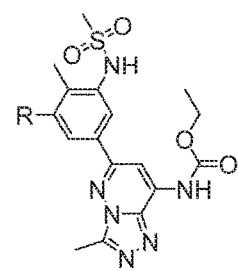
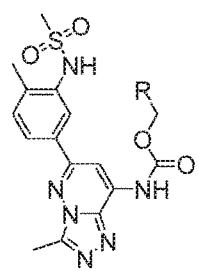
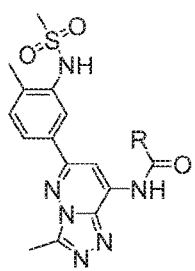
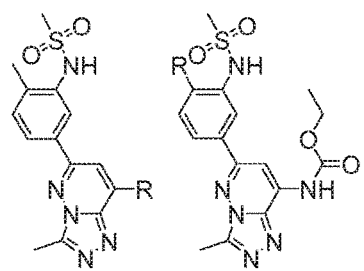

FIG. 3TTTT
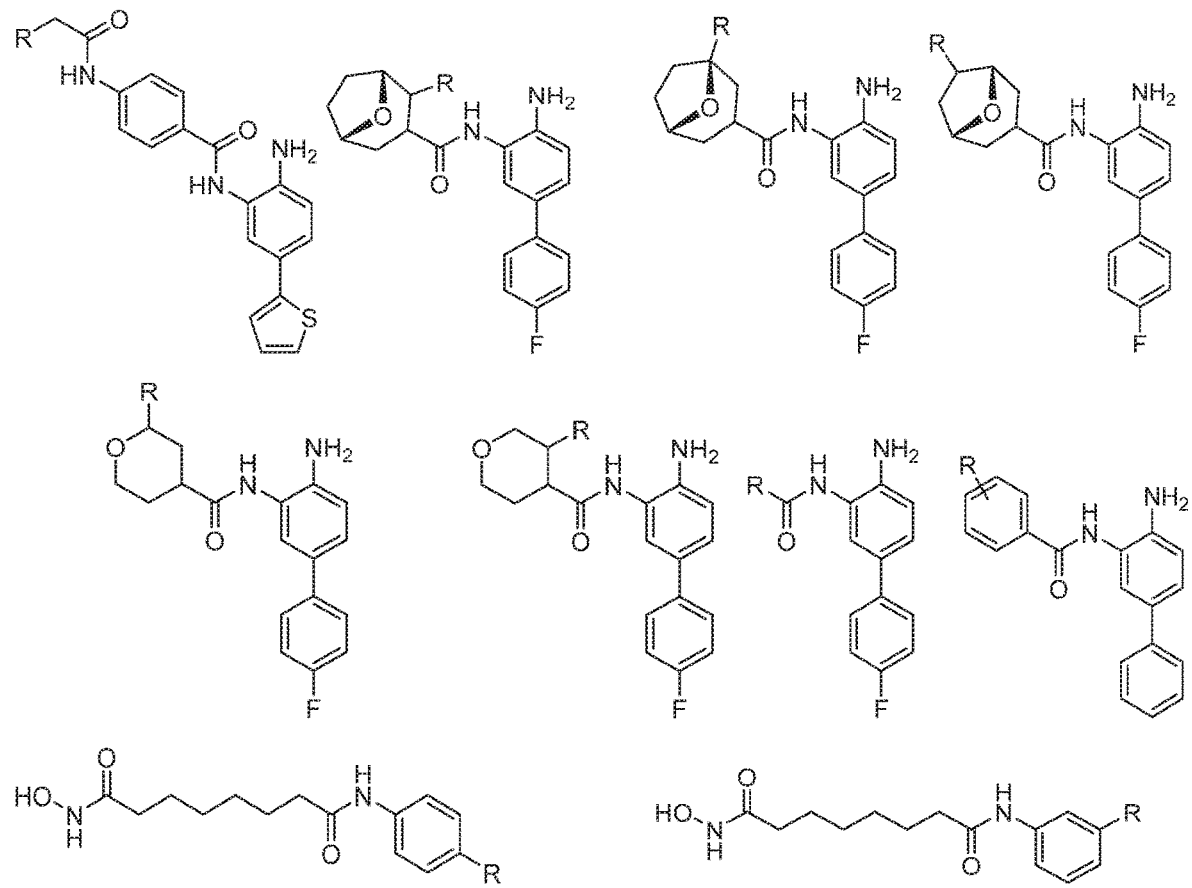
FIG. 3UUUU
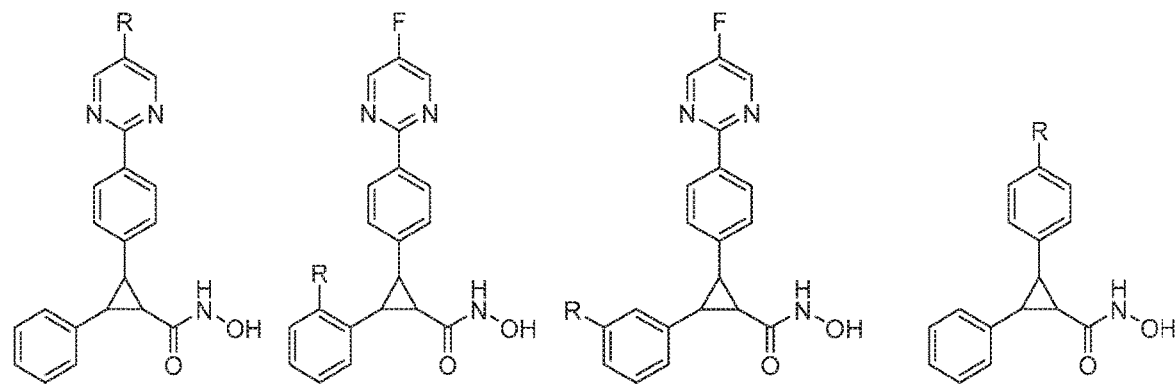

FIG. 3VVVV
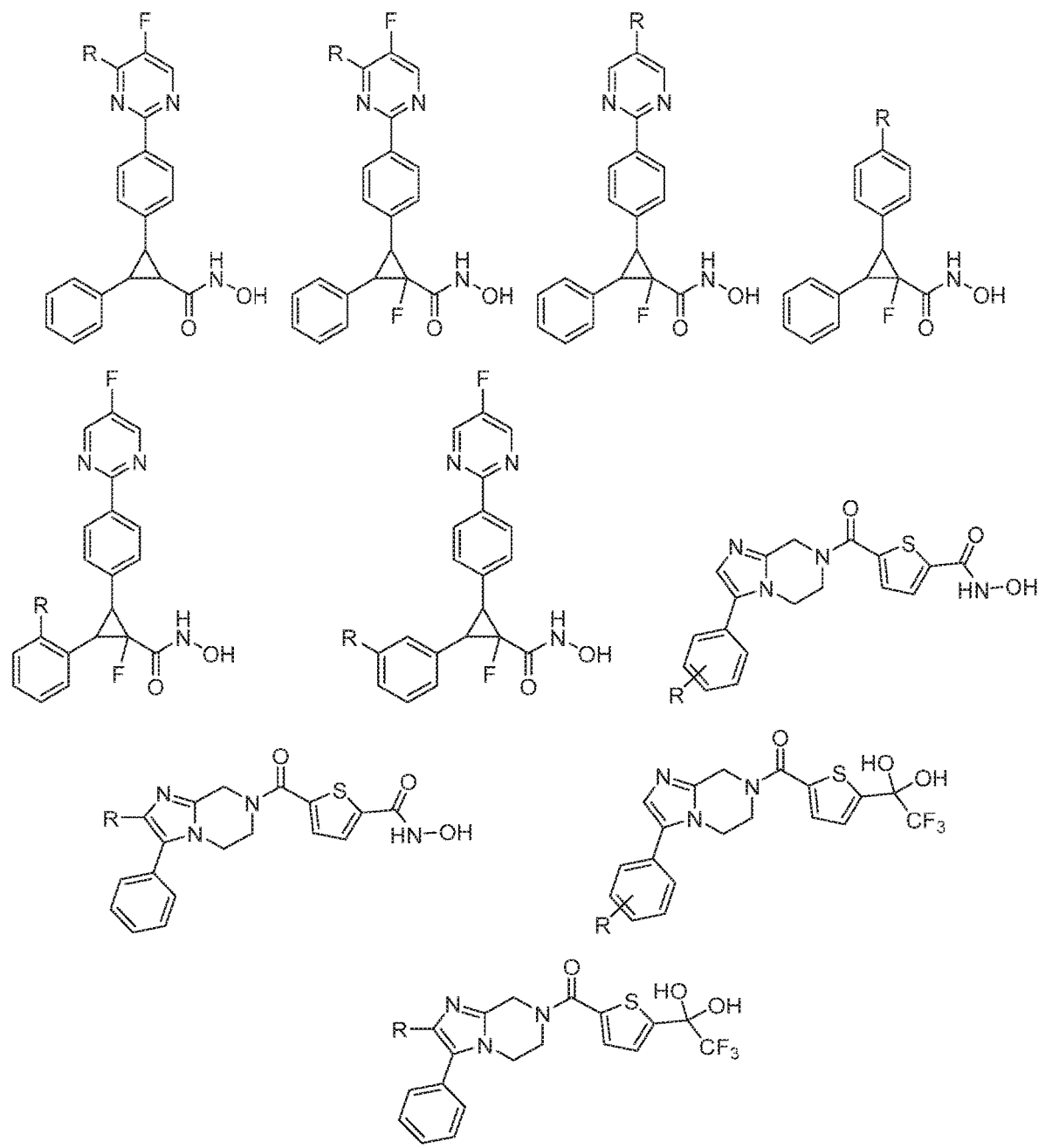

FIG. 3WWWW
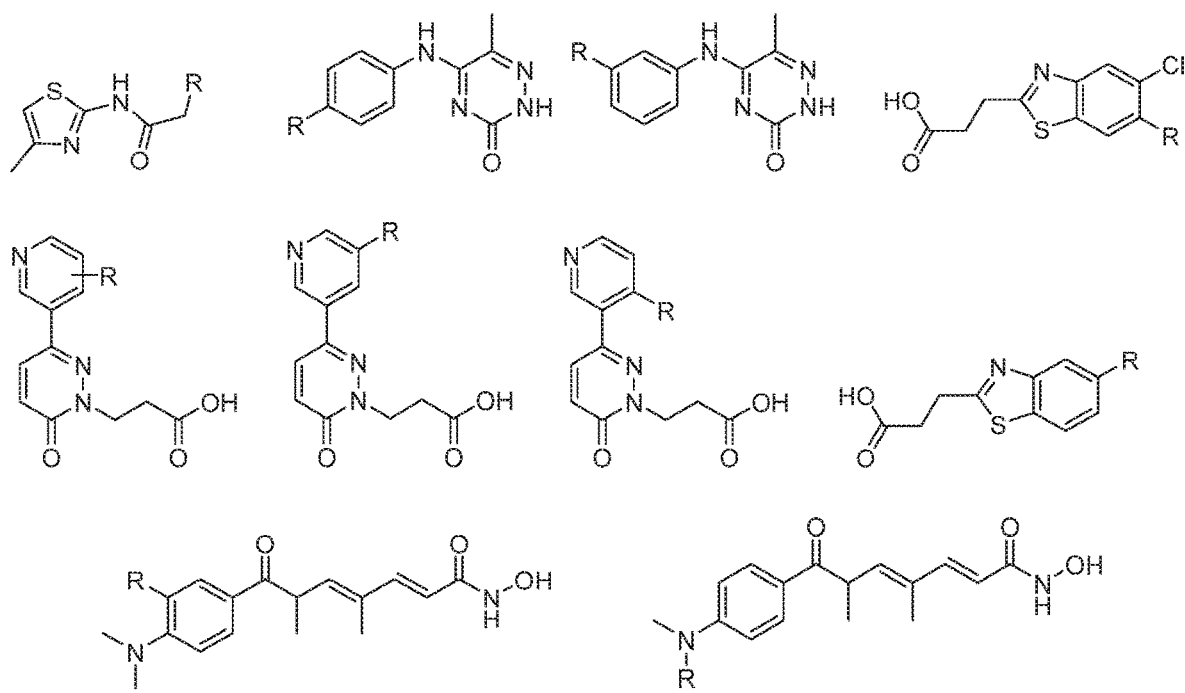
FIG. 3XXXX
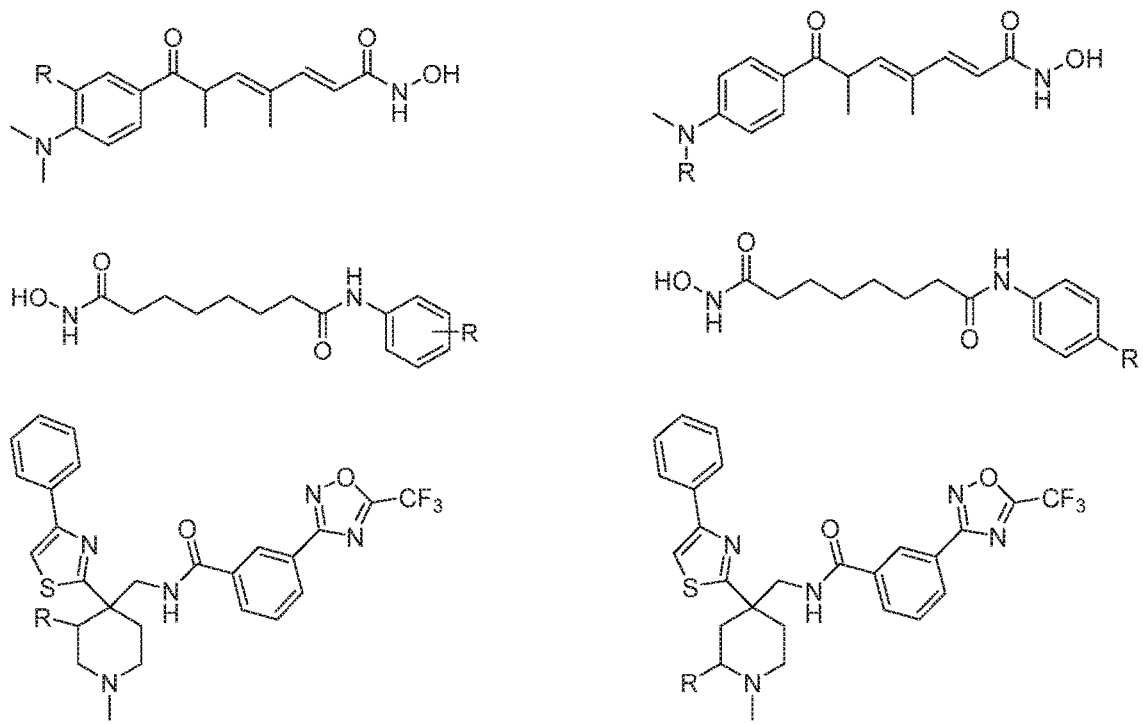

FIG. 3YYYY
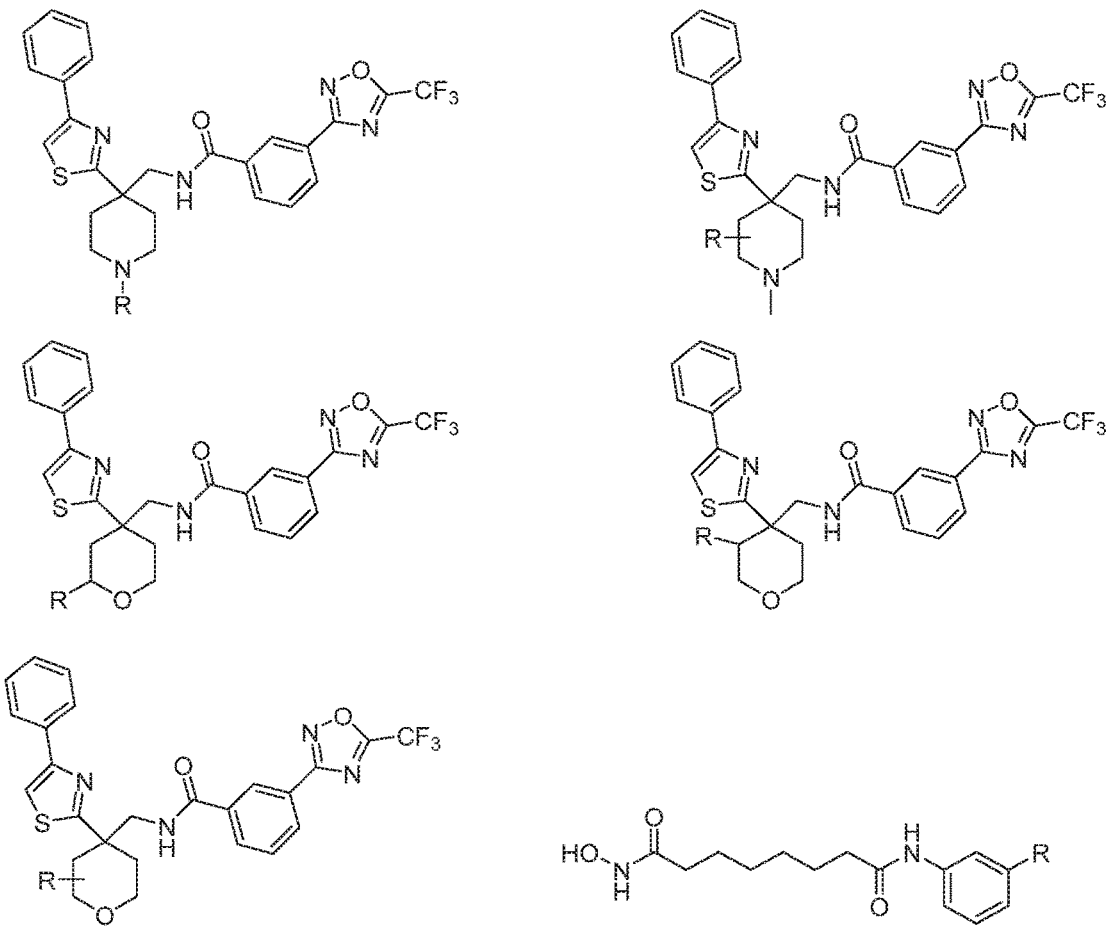
FIG. 3ZZZZ
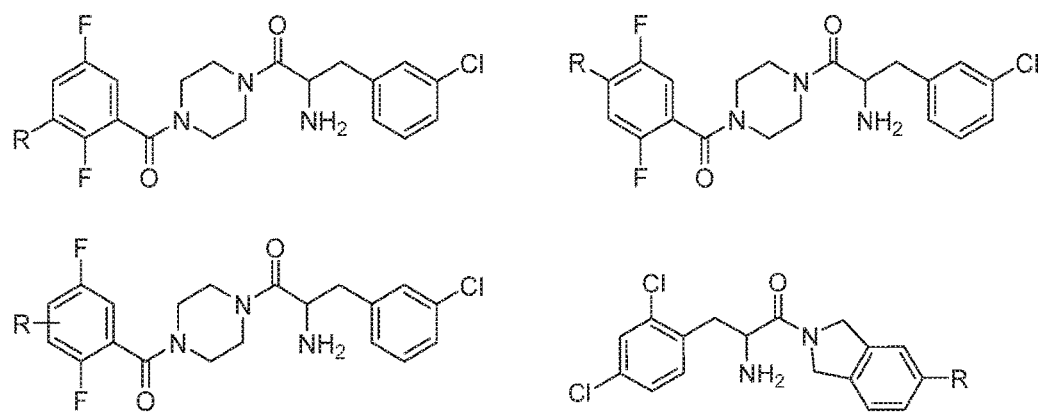

FIG. 3AAAAA
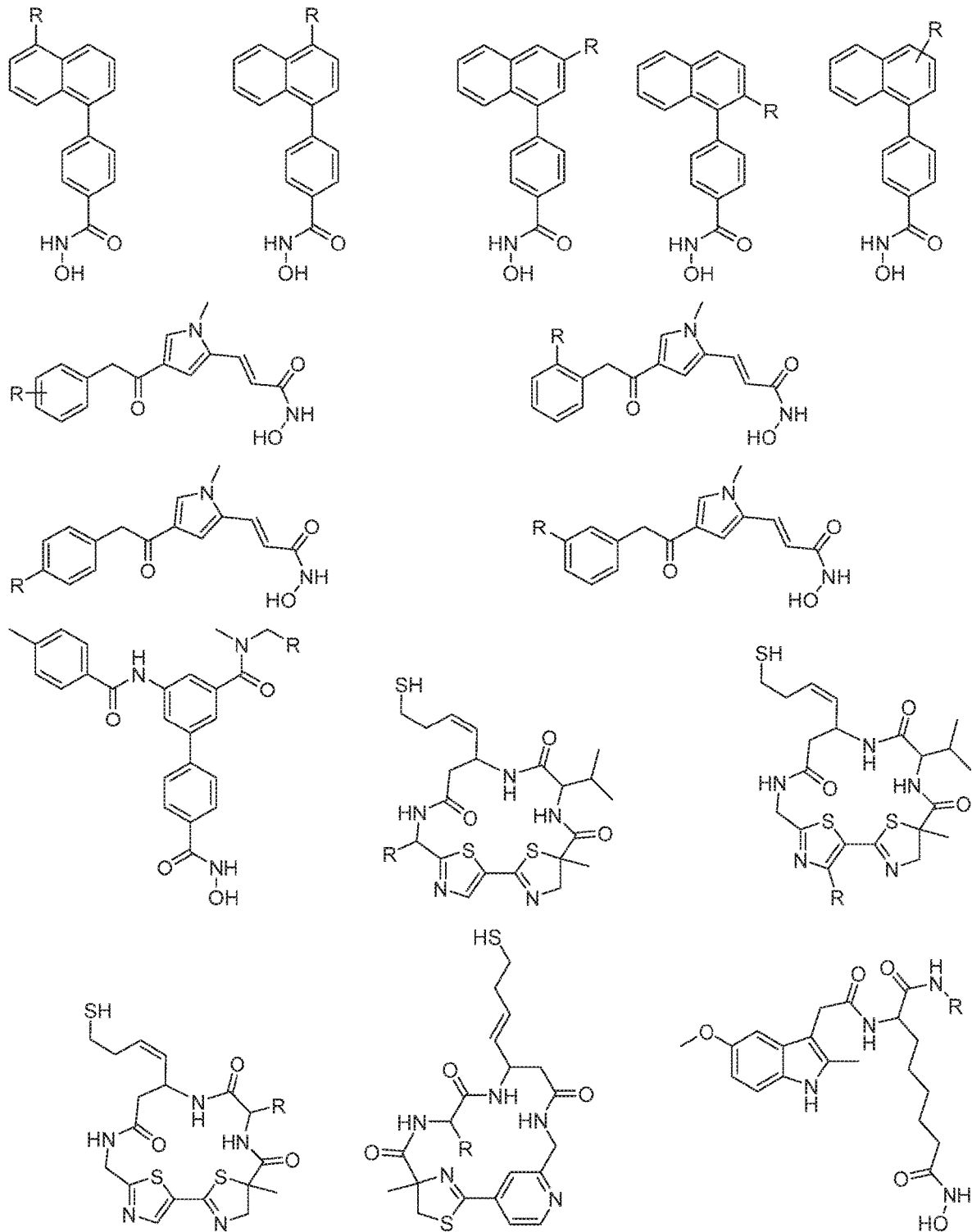

FIG. 3BBBBB
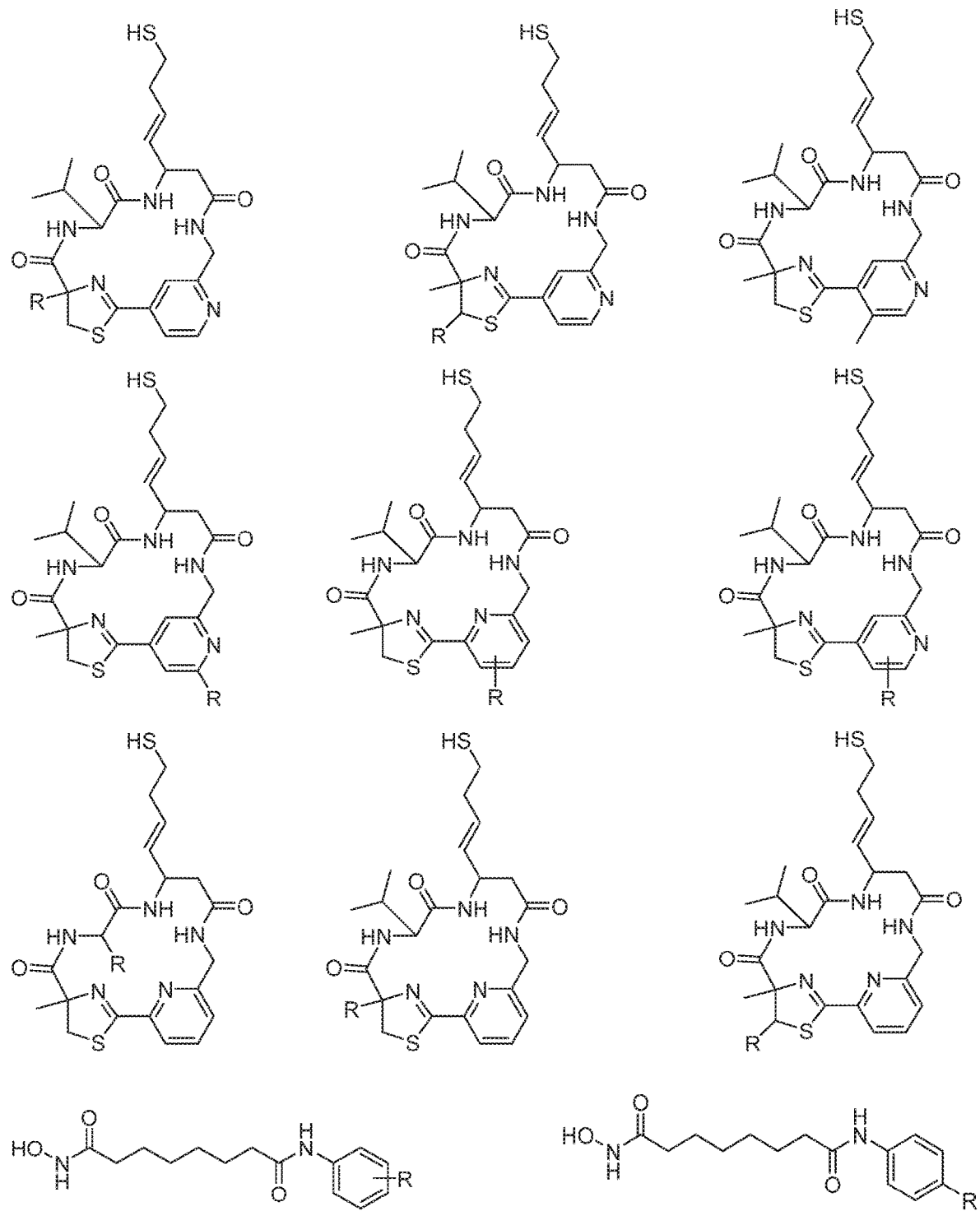

FIG. 3CCCCC
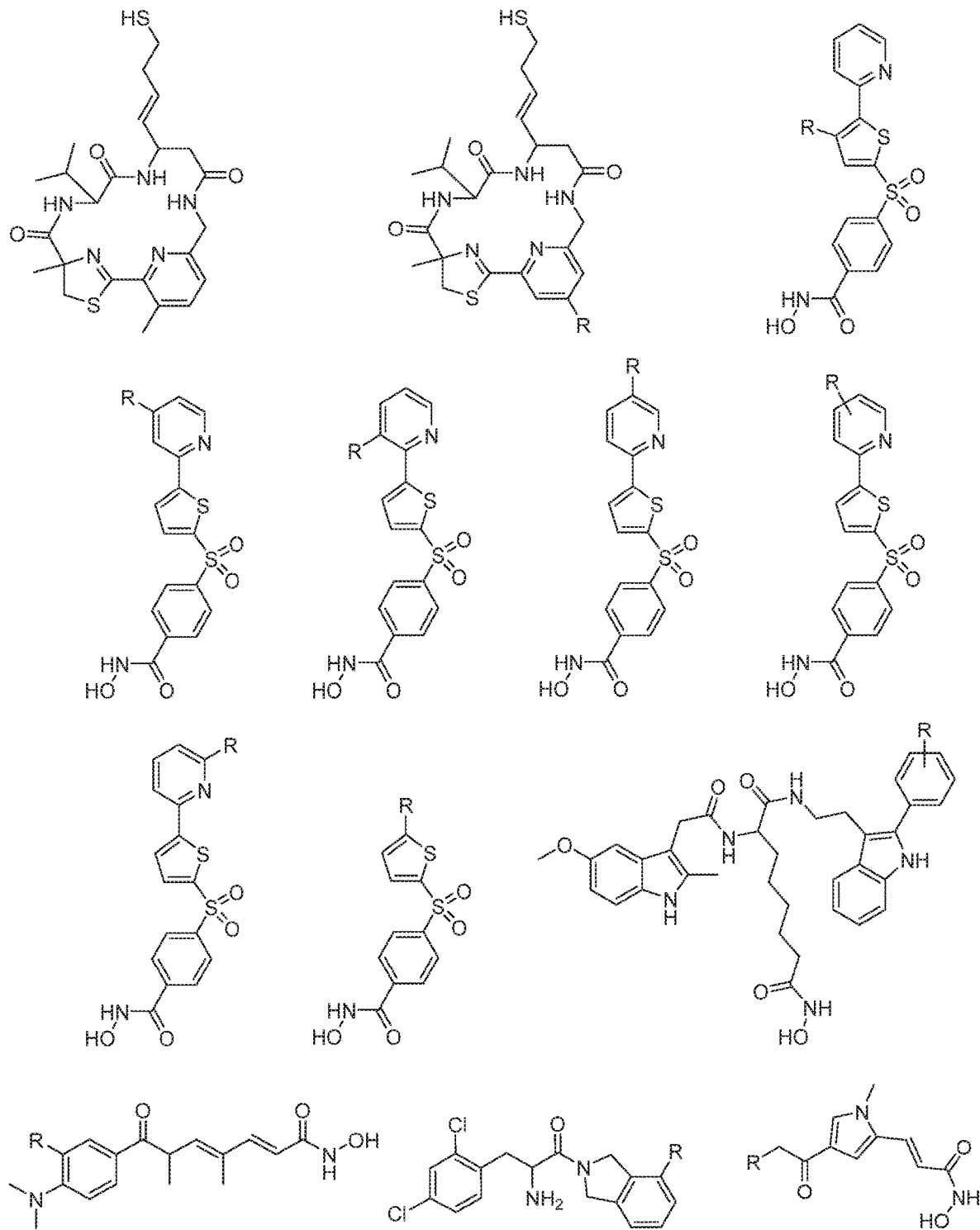

FIG. 3DDDDD
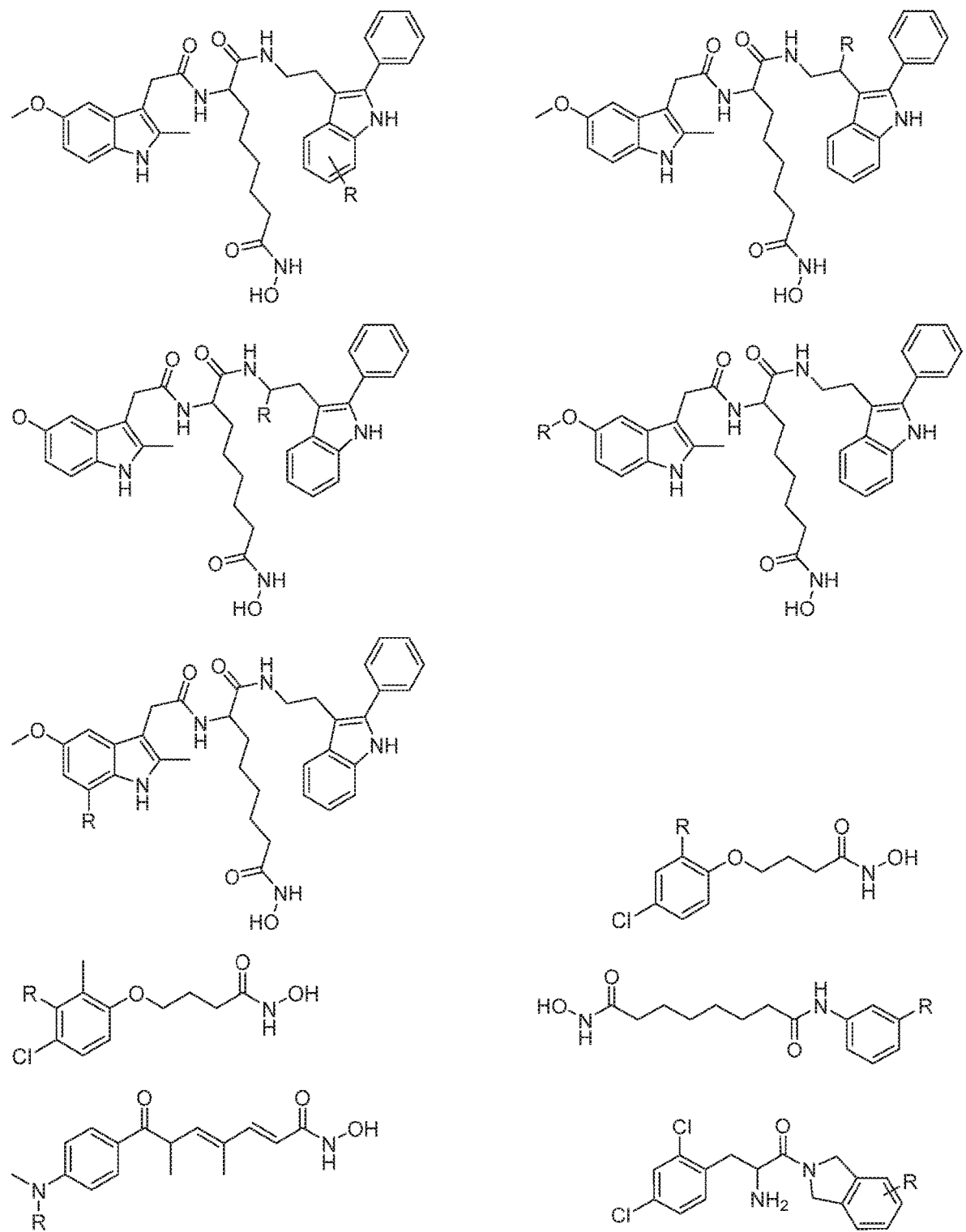

FIG. 3EEEEE
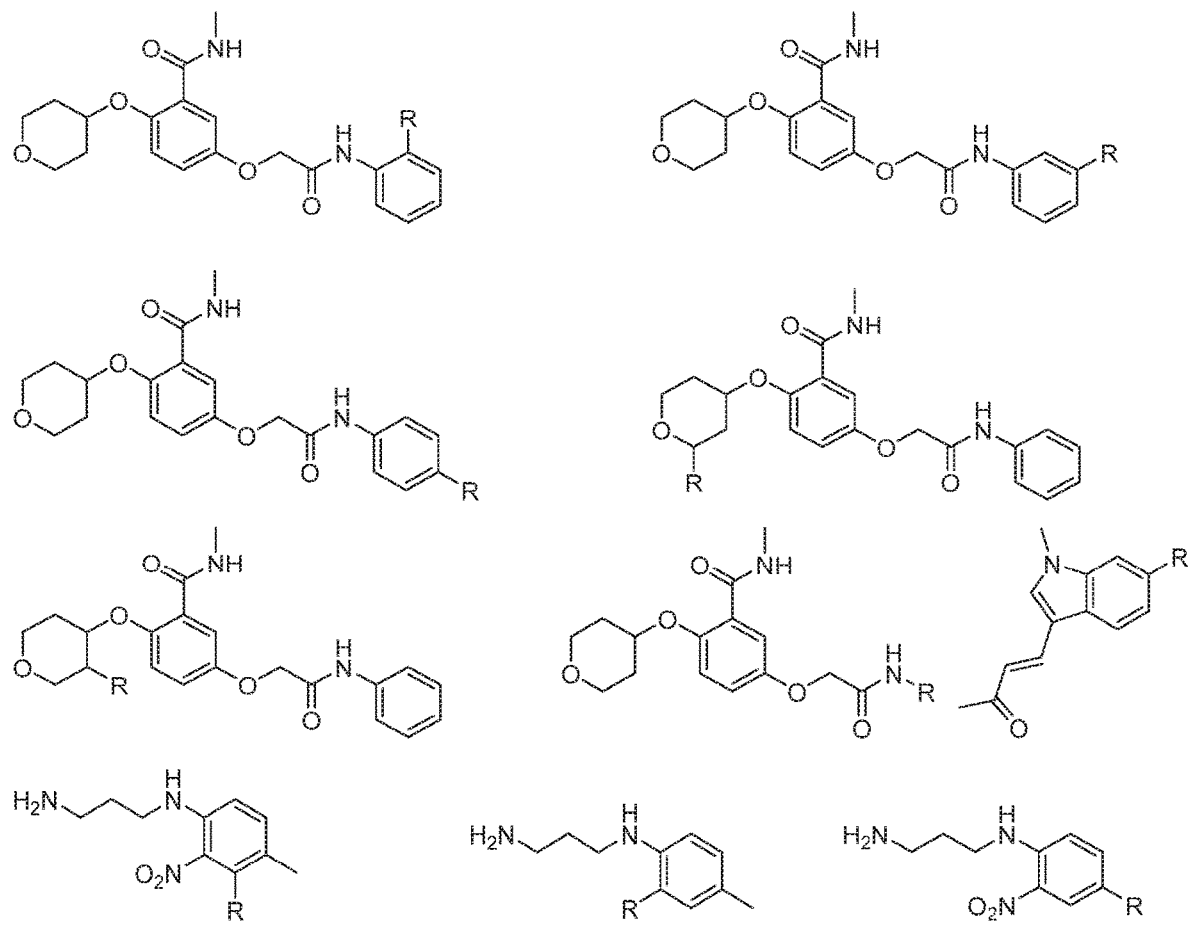
FIG. 3FFFFF
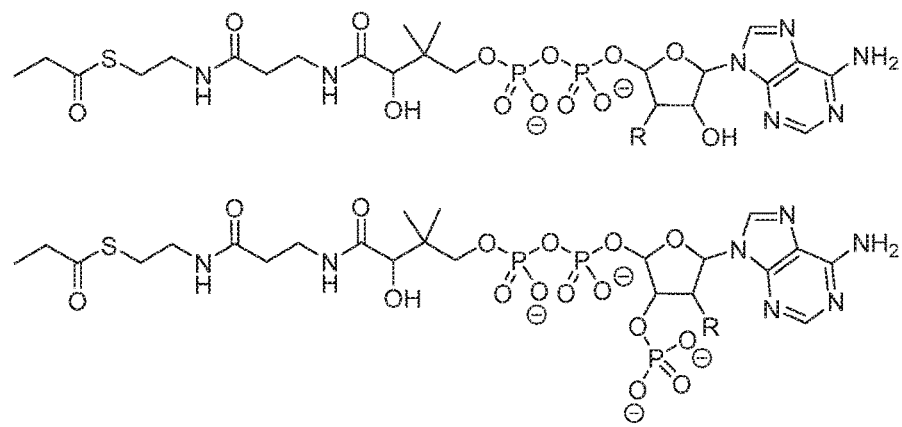

FIG. 3GGGGG
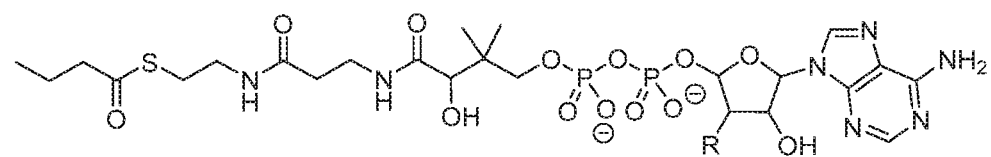
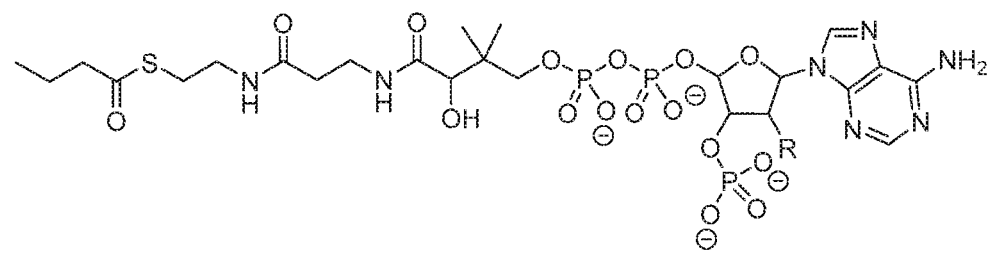
FIG. 3HHHHH
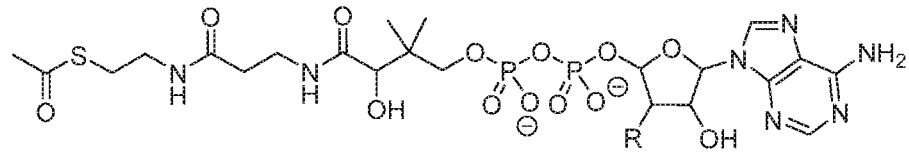
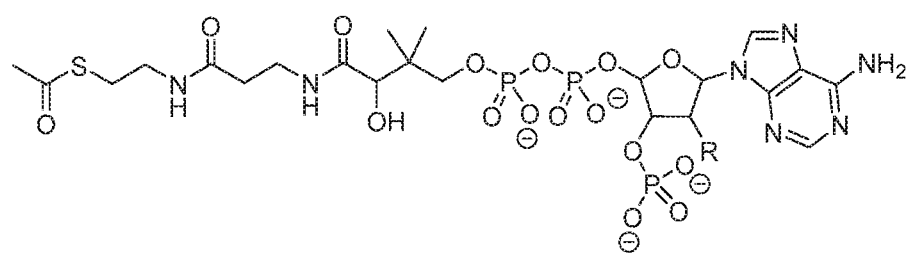
FIG. 3IIIII
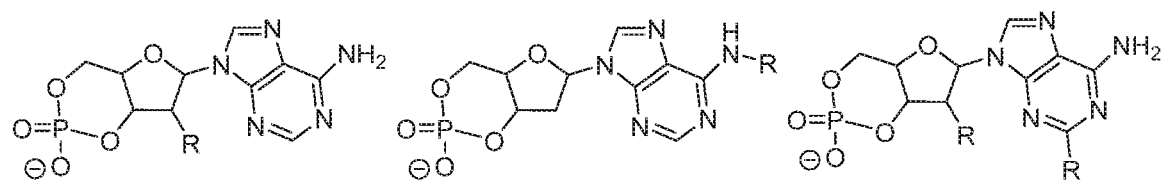

FIG. 3JJJJJ
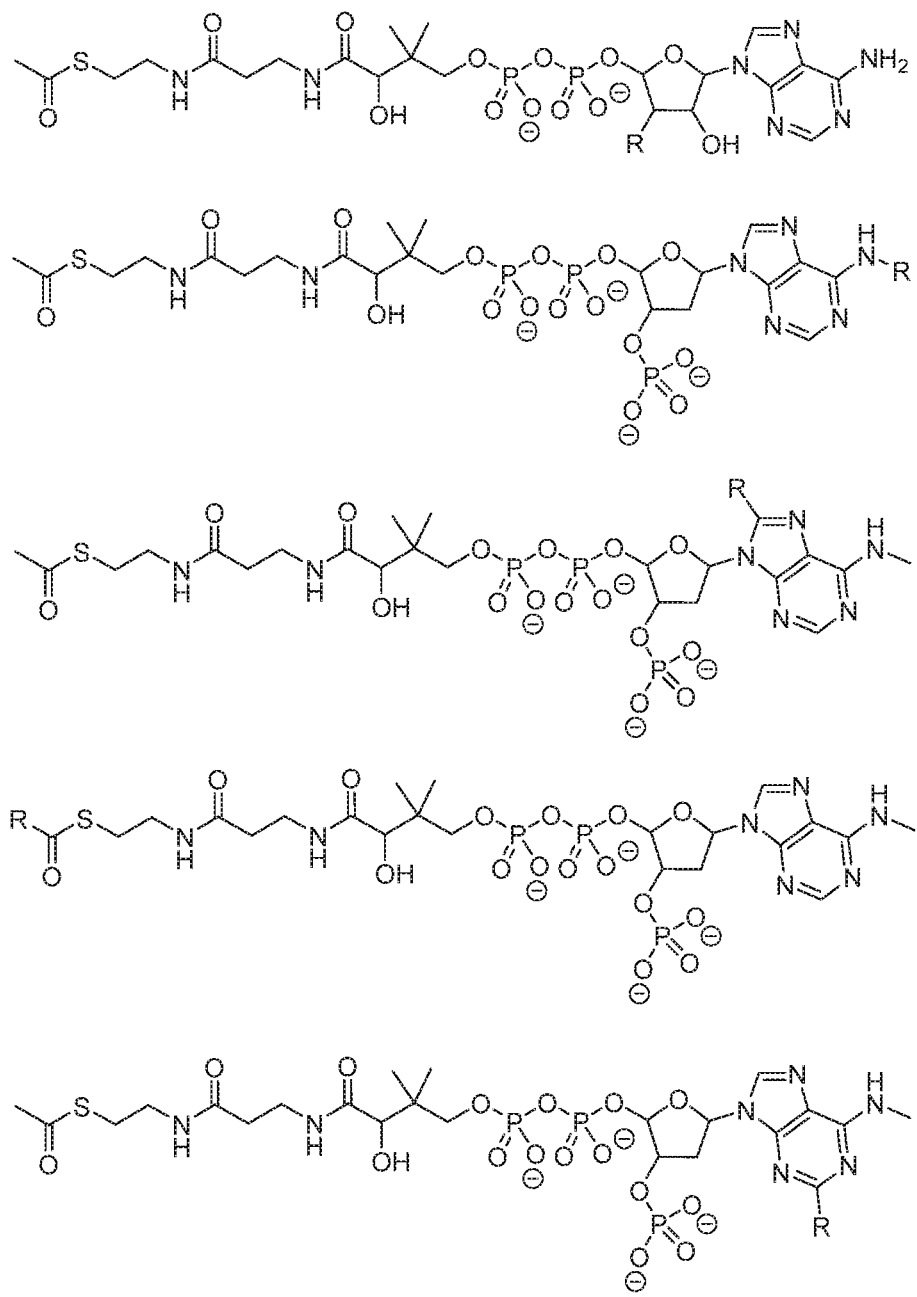

FIG. 3KKKKK
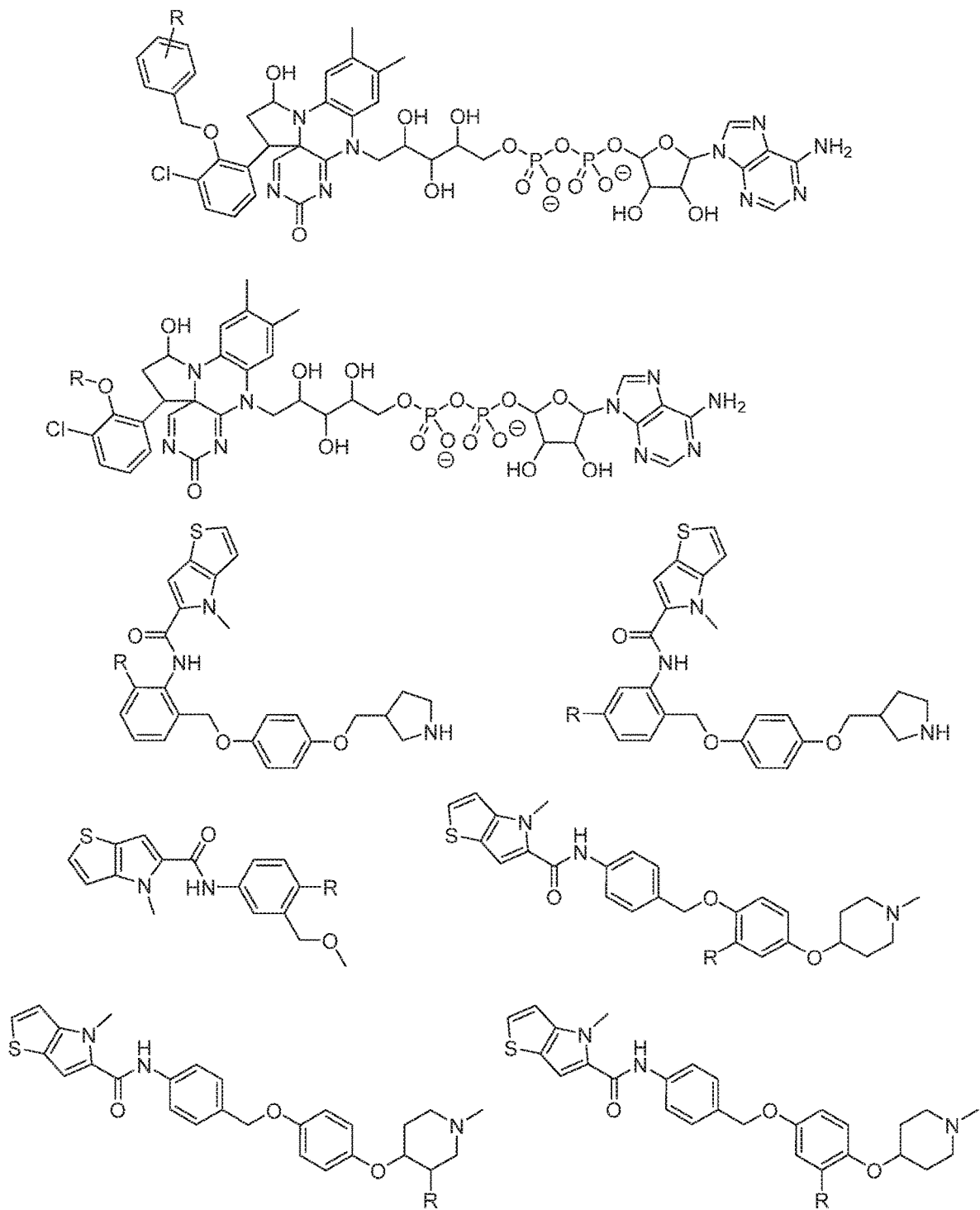

FIG. 3LLLLL
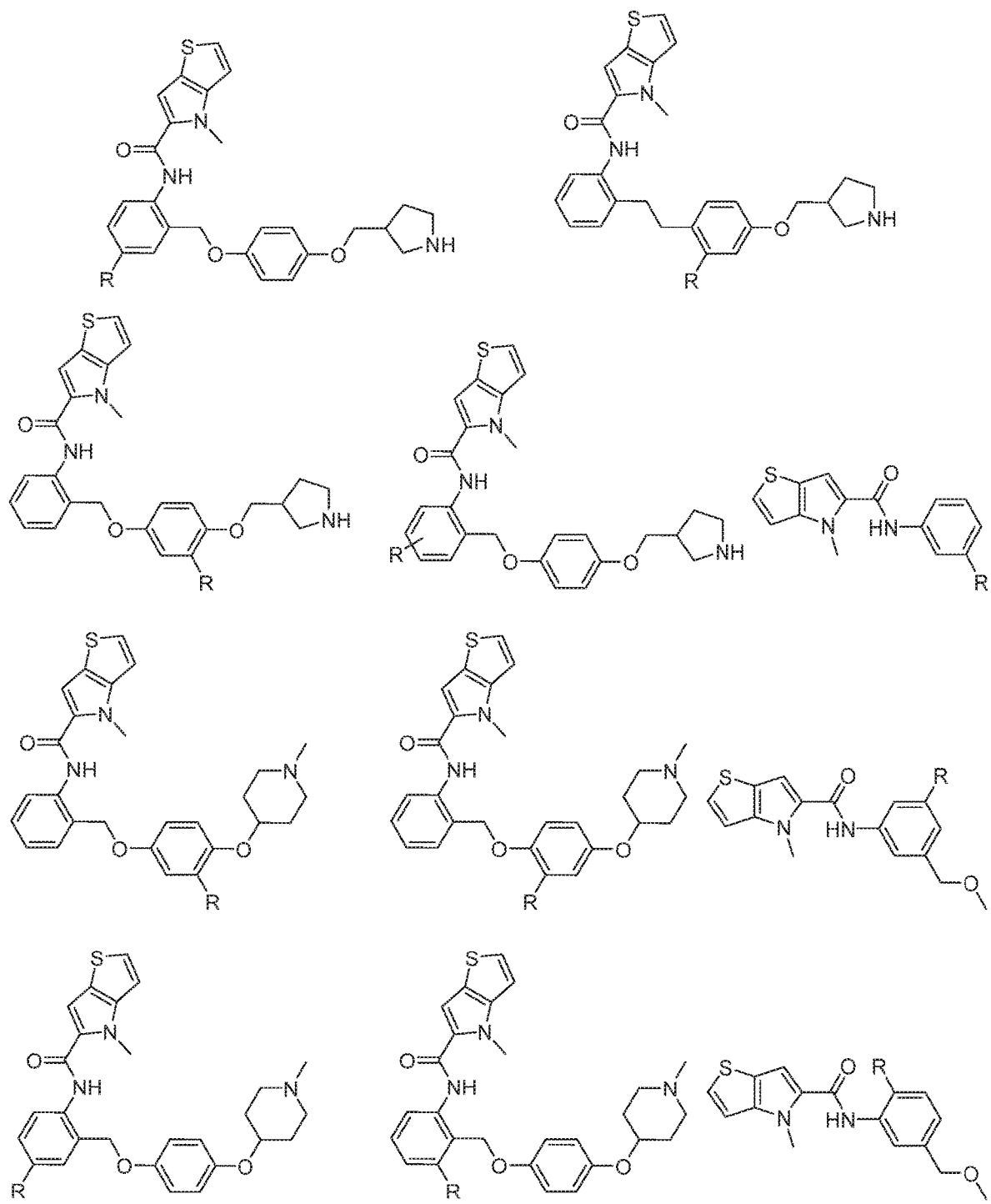

FIG. 3MMMMM
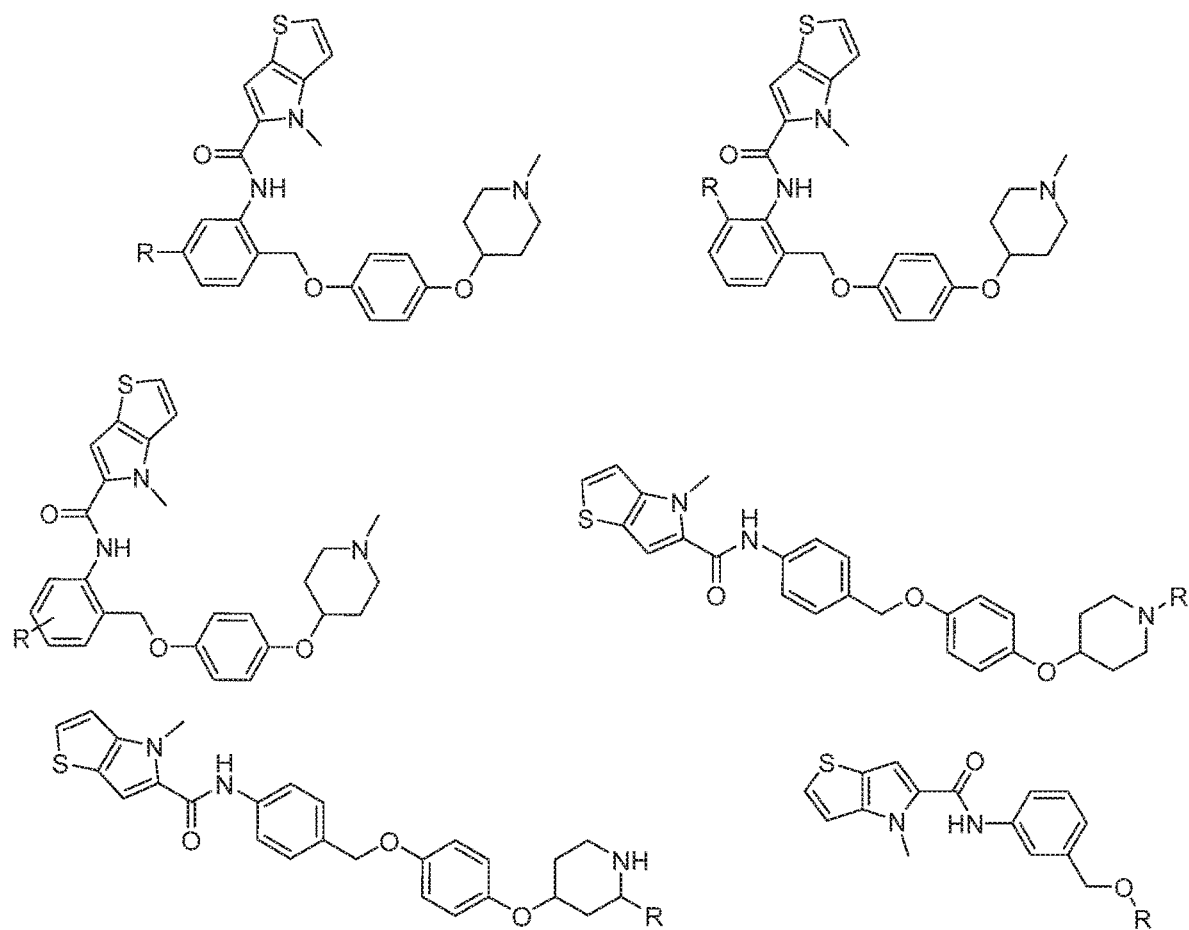
FIG. 3NNNNN
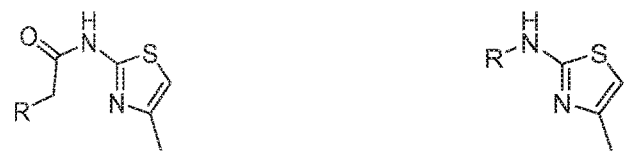

FIG. 300000
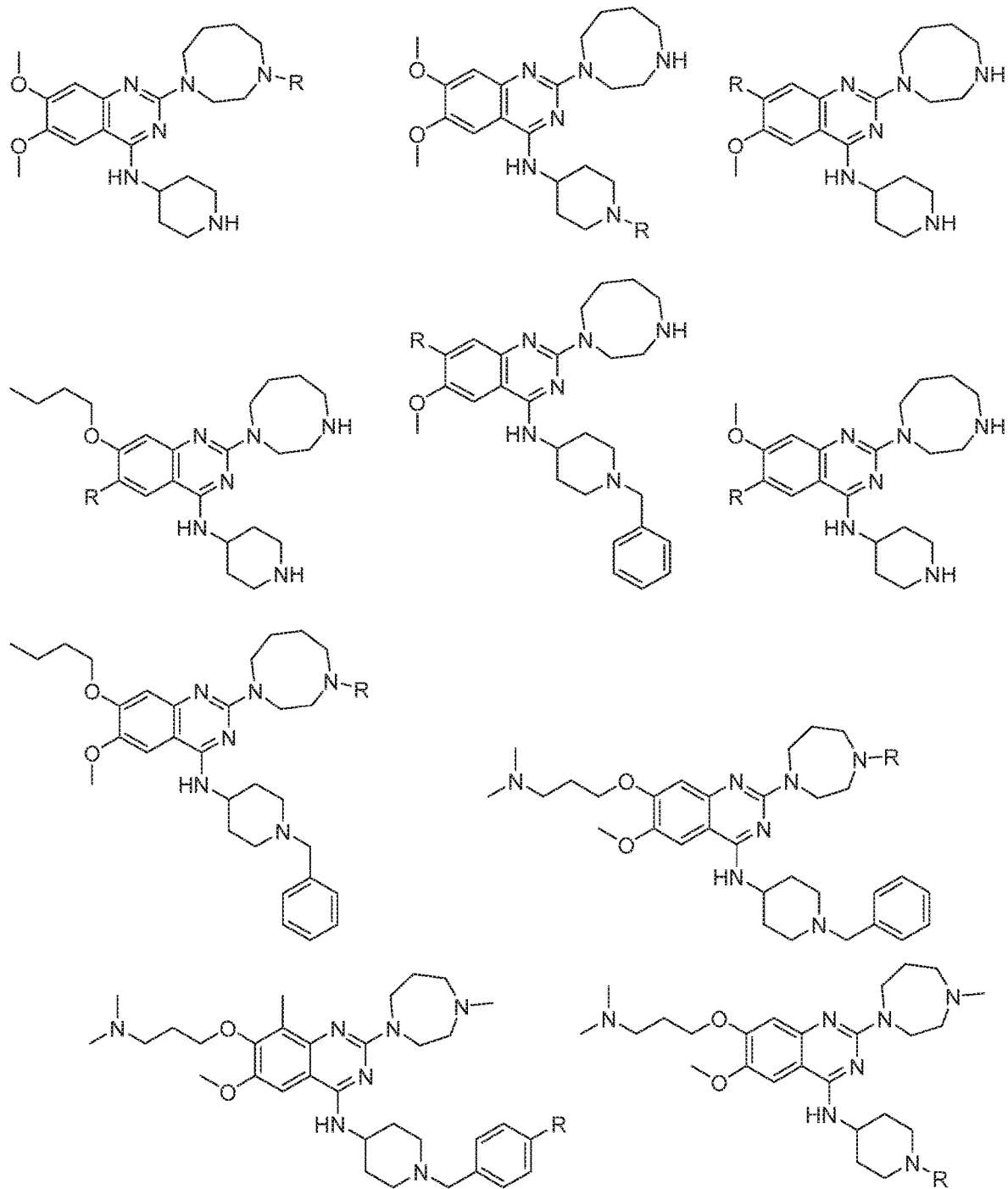

FIG. 3PPPPP
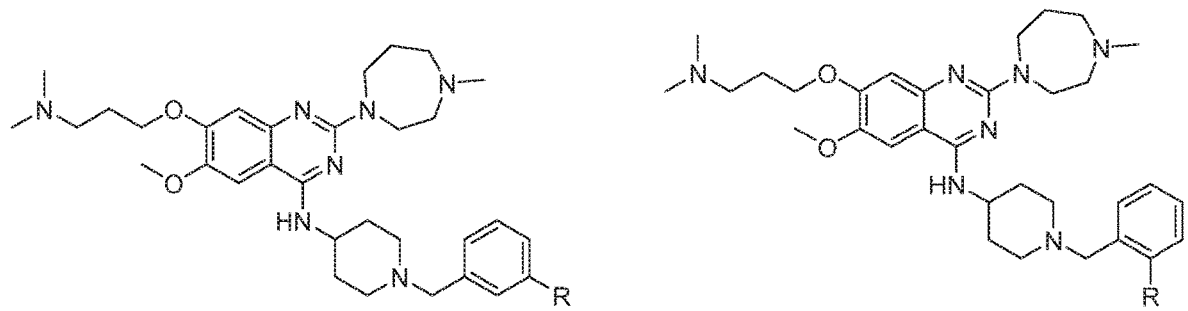
FIG. 3QQQQQ
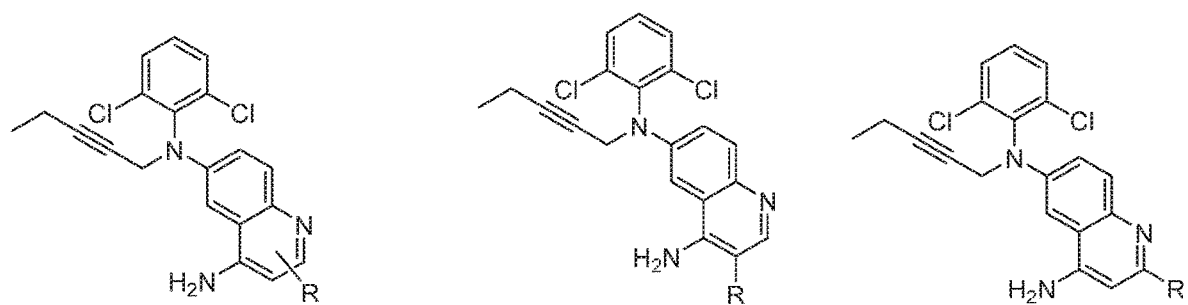
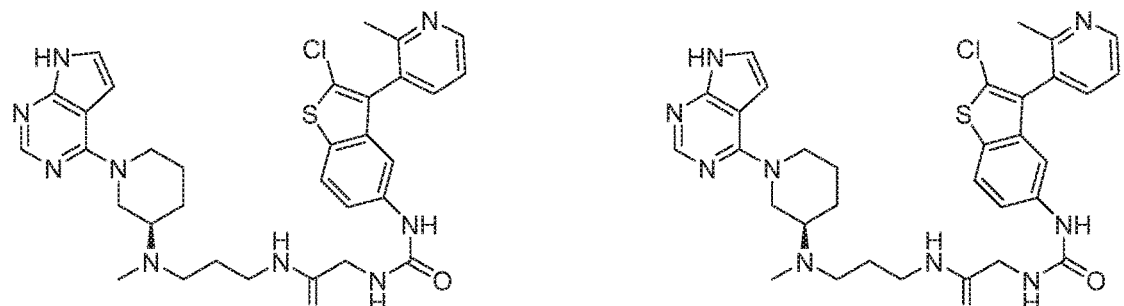
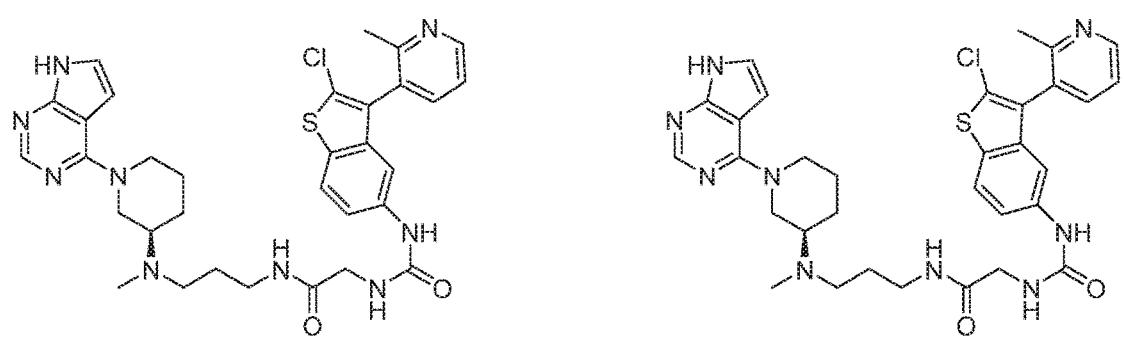

FIG. 3RRRRR
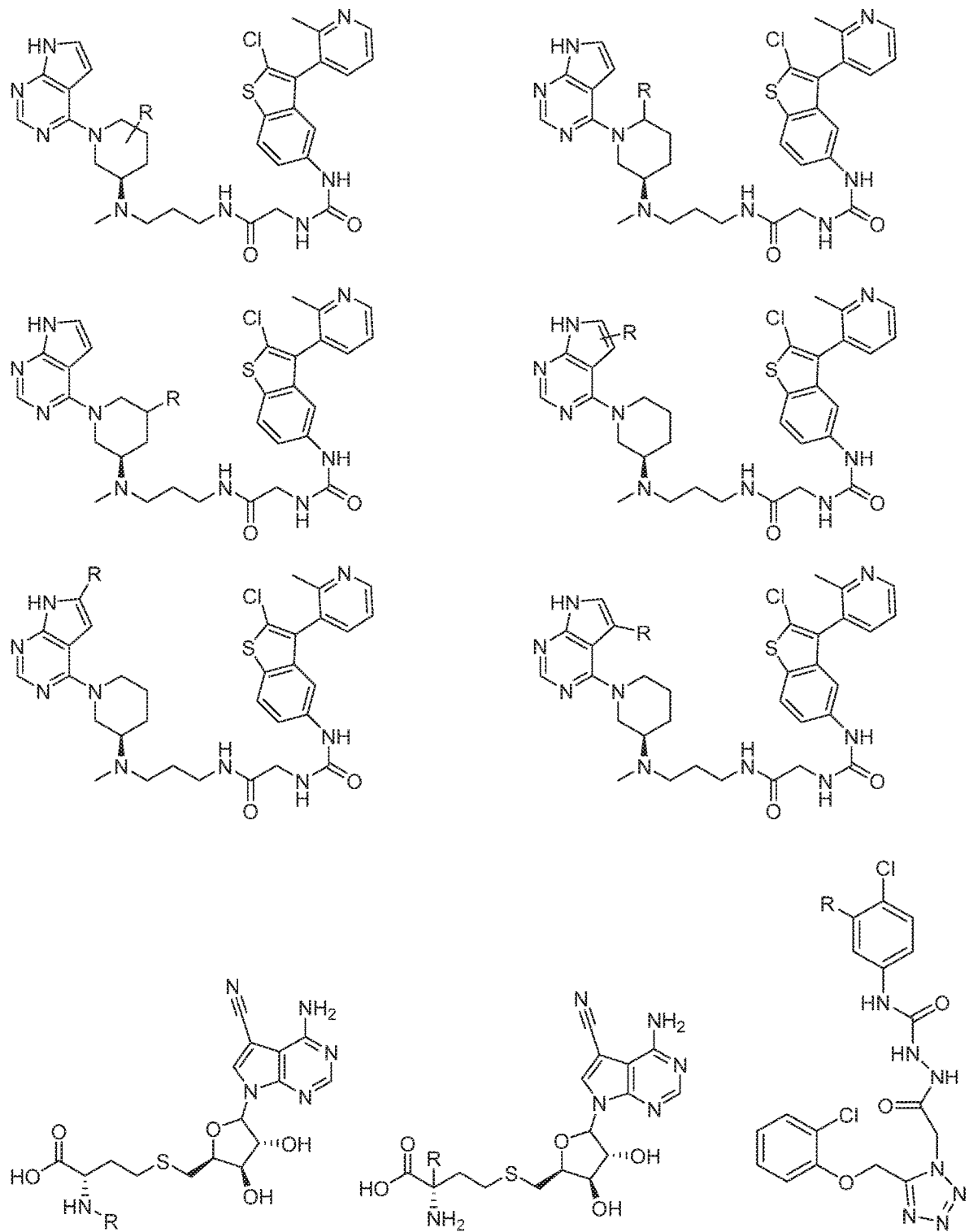

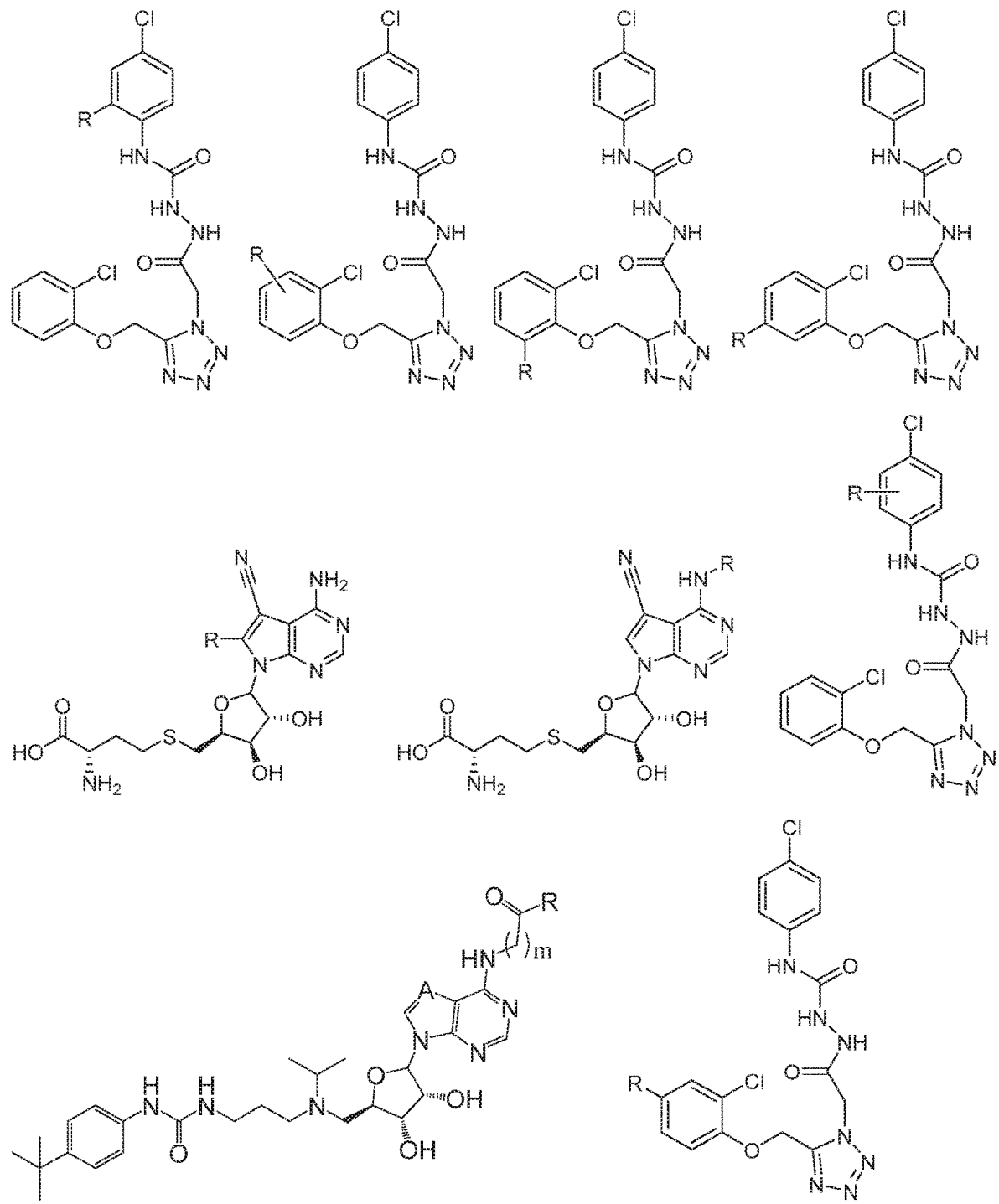
FIG. 3SSSSS

FIG. 3TTTTT
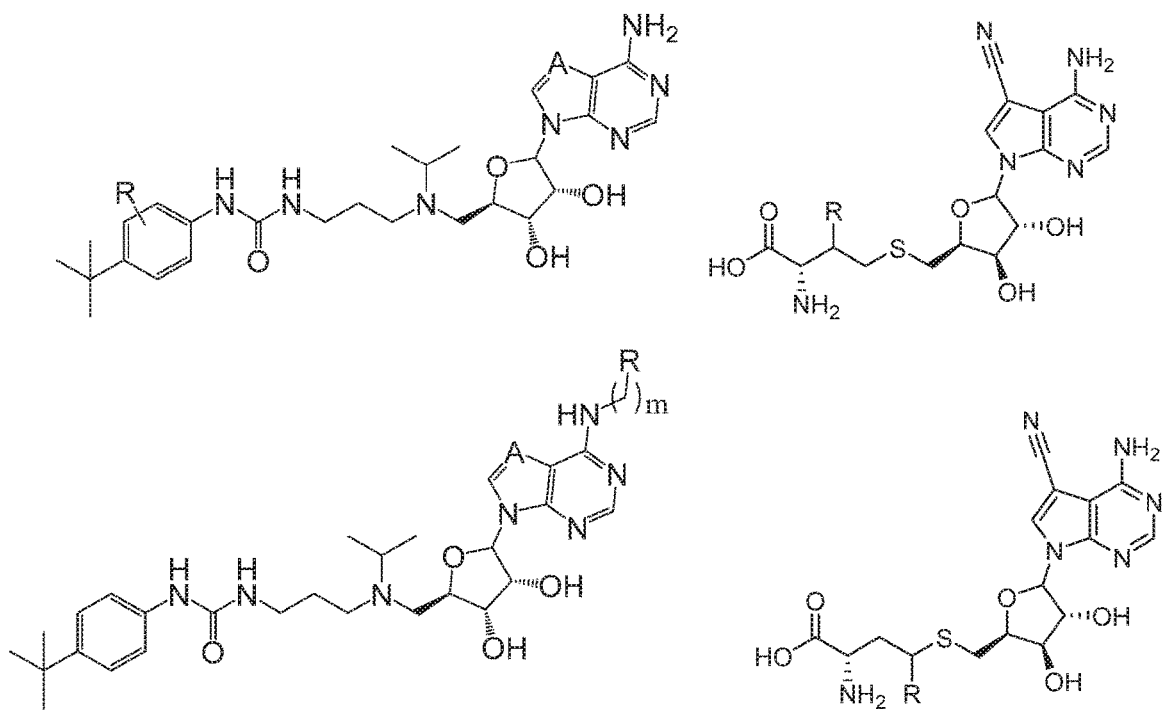
FIG. 3UUUUU
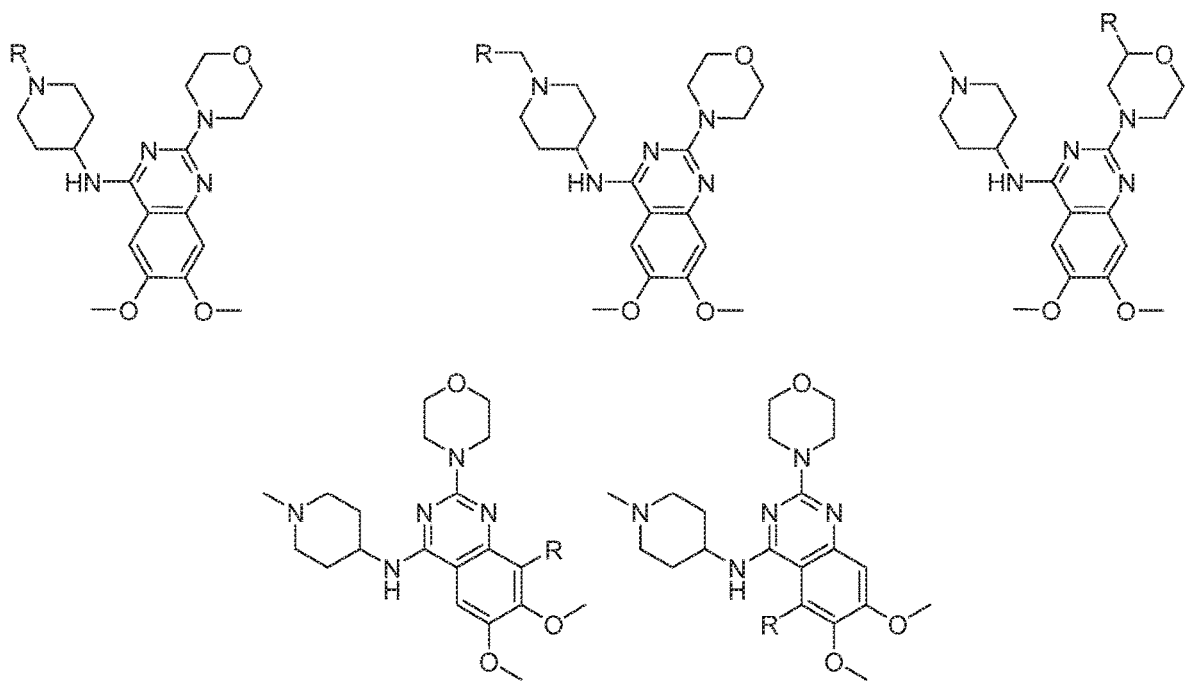

FIG. 3VVVVV
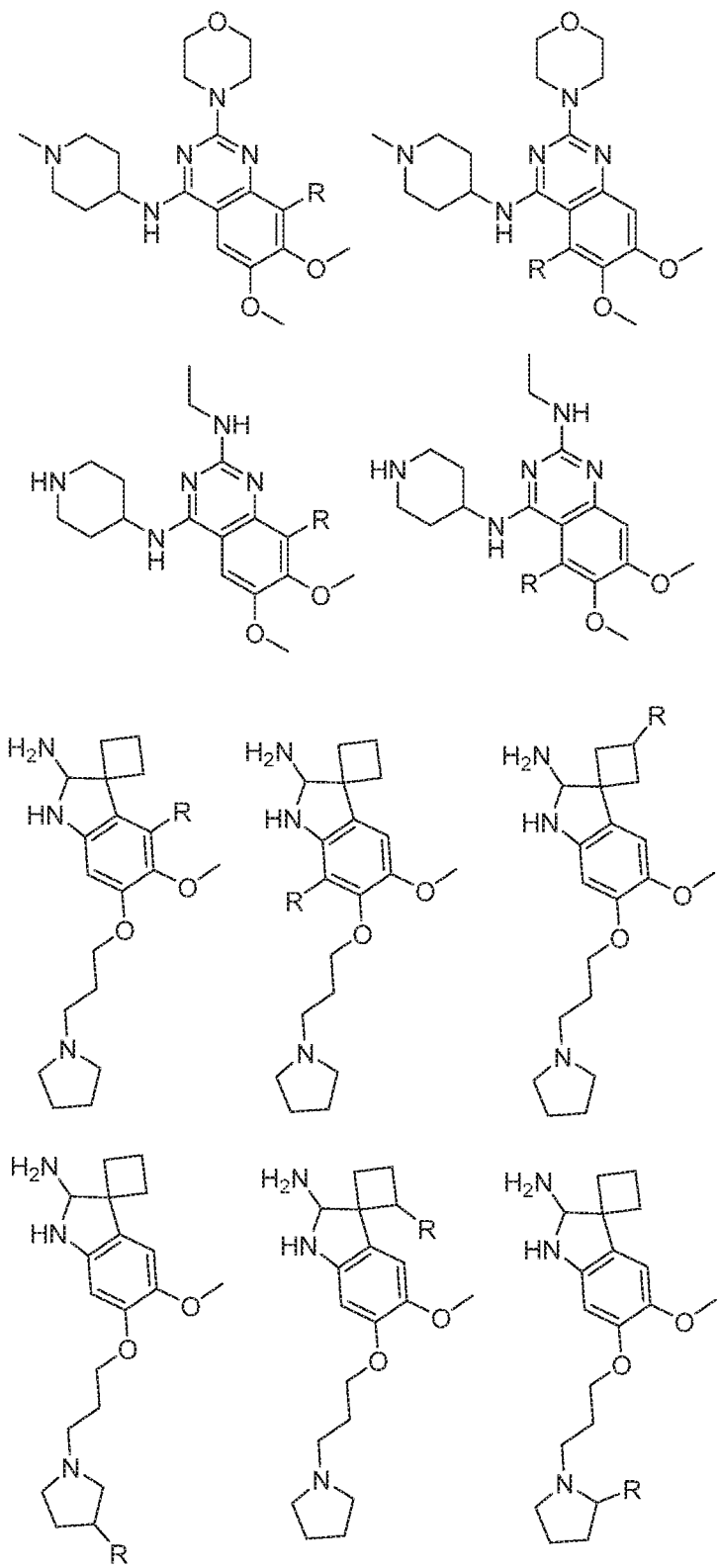

FIG. 3WWWWW
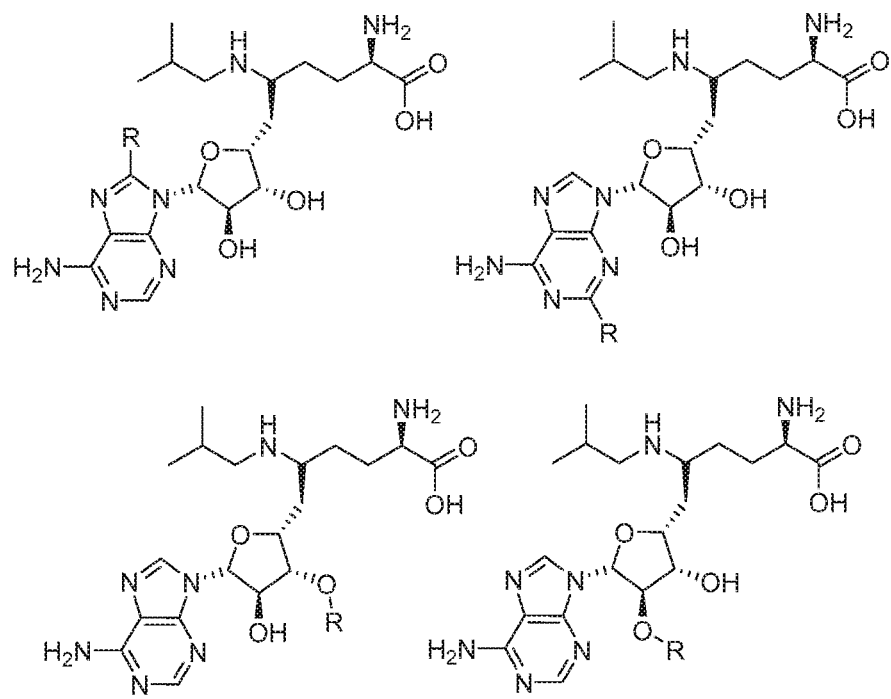
FIG. 3XXXXX
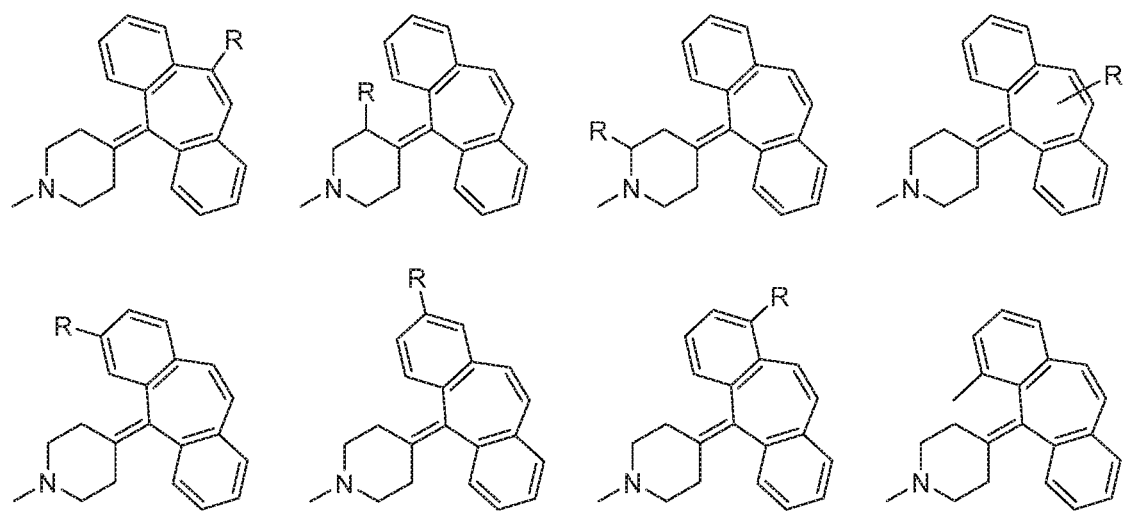

FIG. 3YYYYY
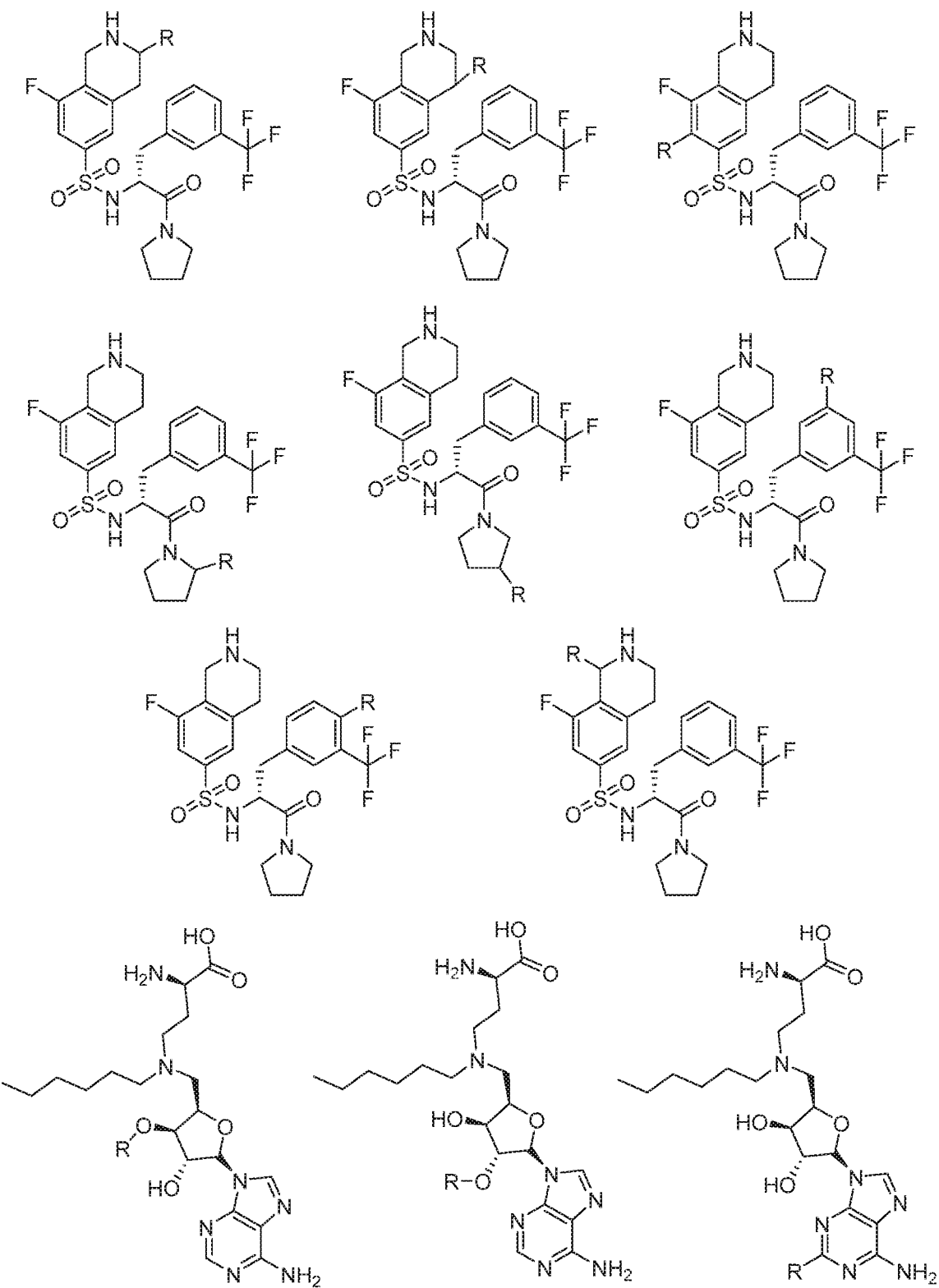

FIG. 3ZZZZZ
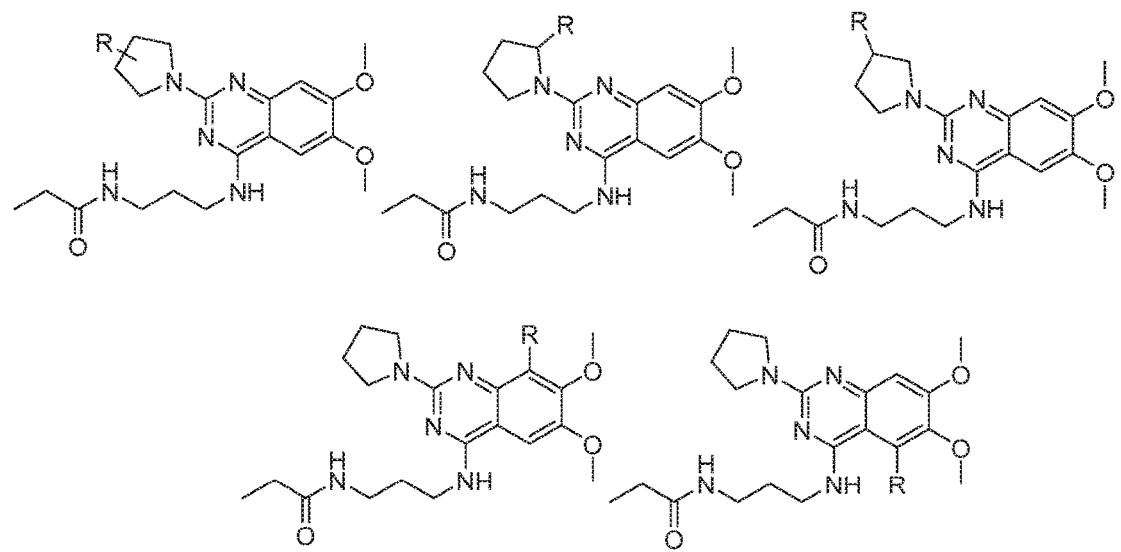
FIG. 4A
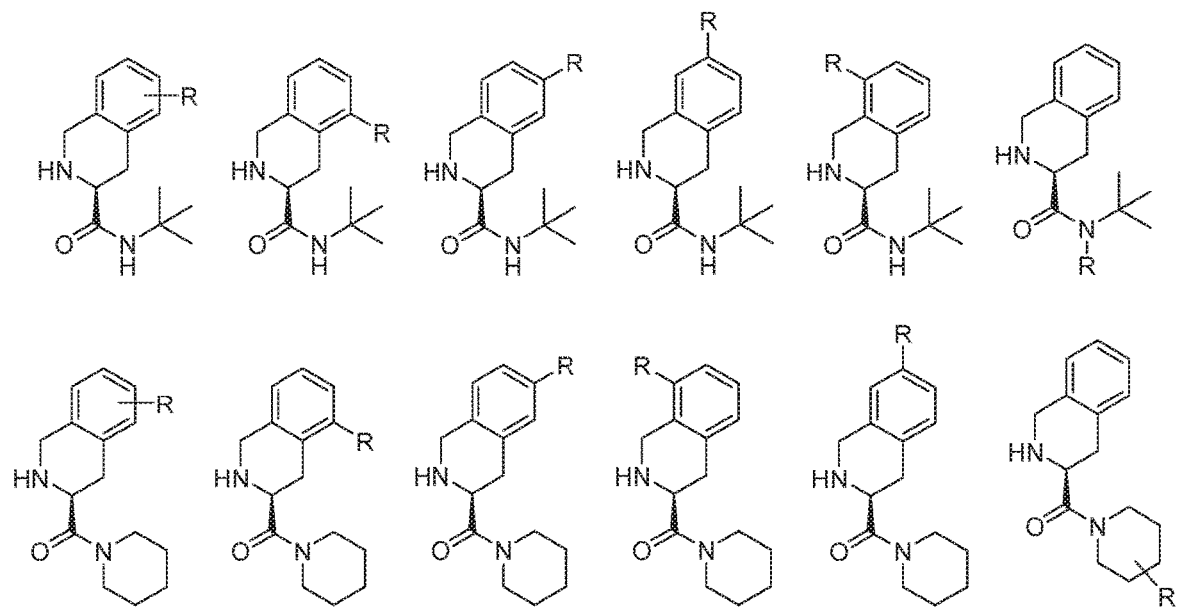

FIG. 5B
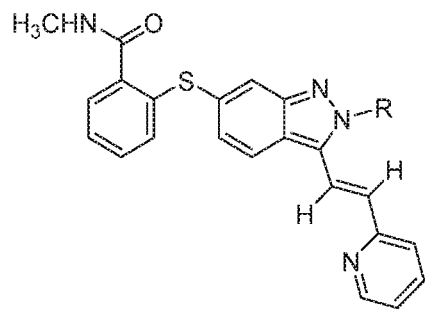
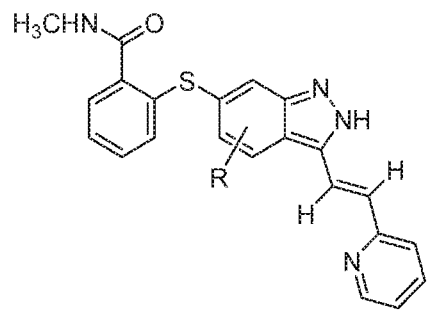
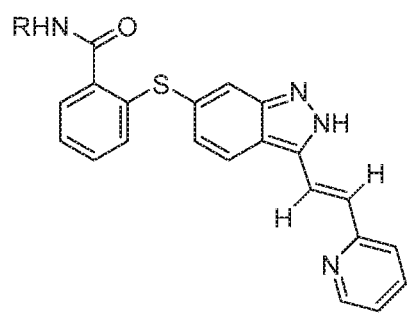
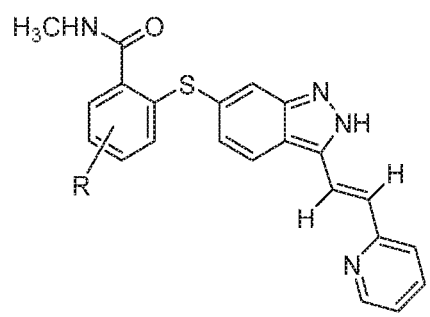
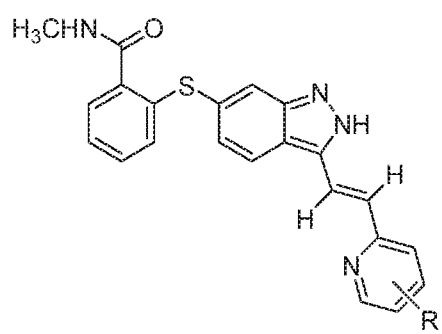
FIG. 5C
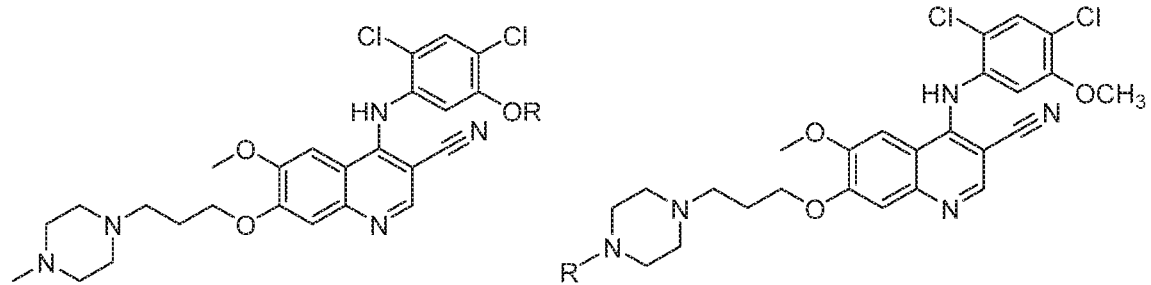

FIG. 5L
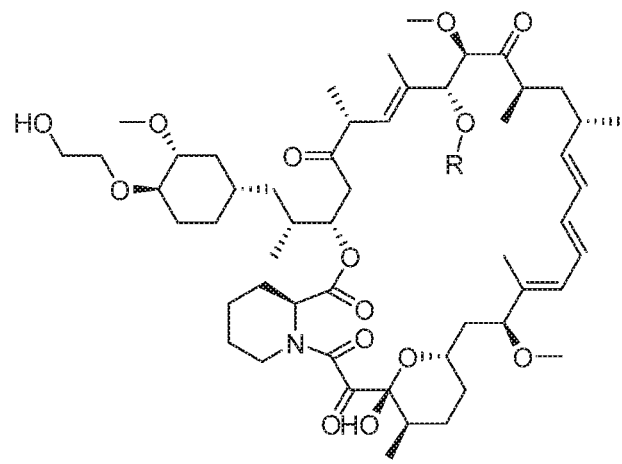
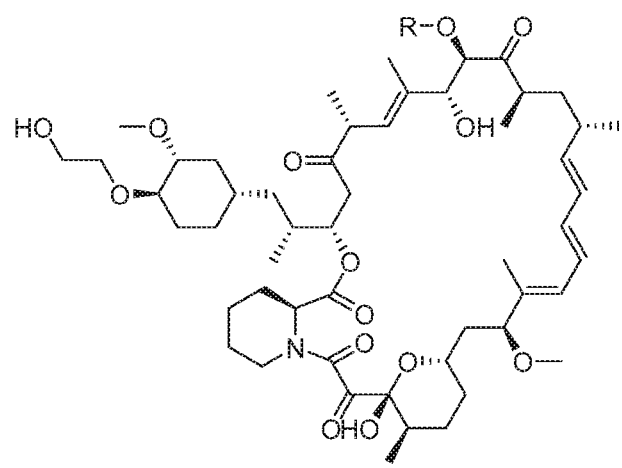
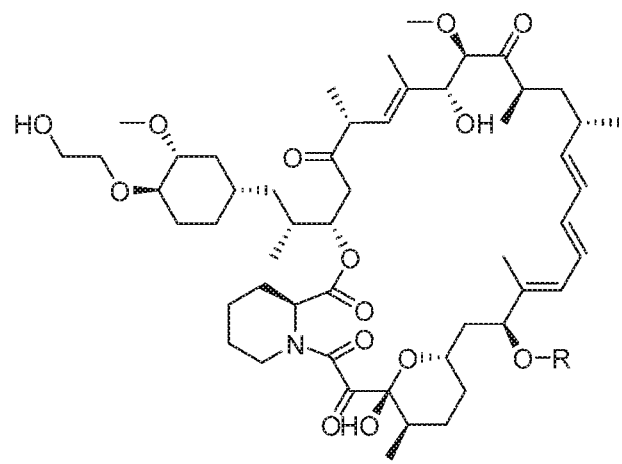

FIG. 5M
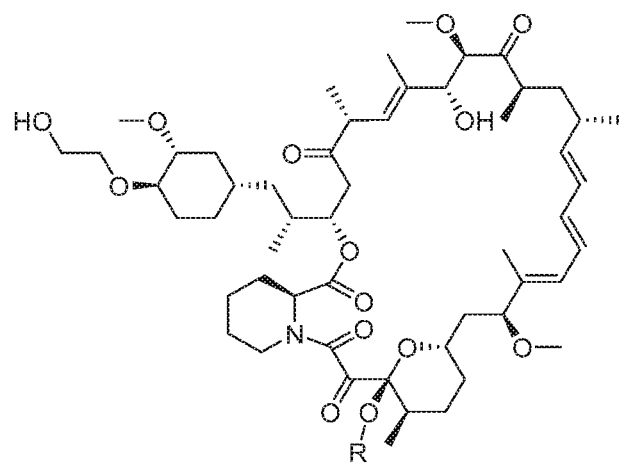
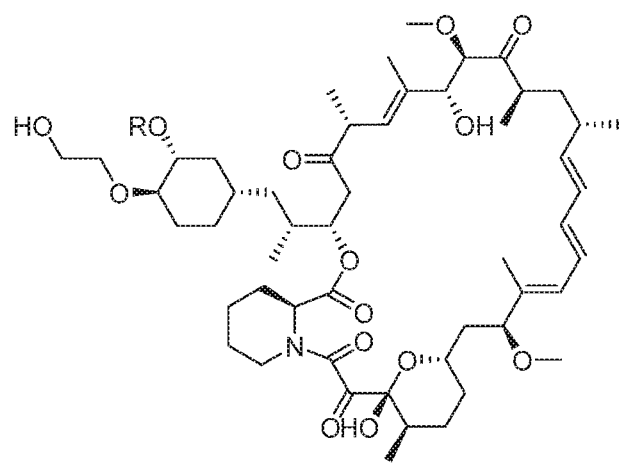
FIG. 5N
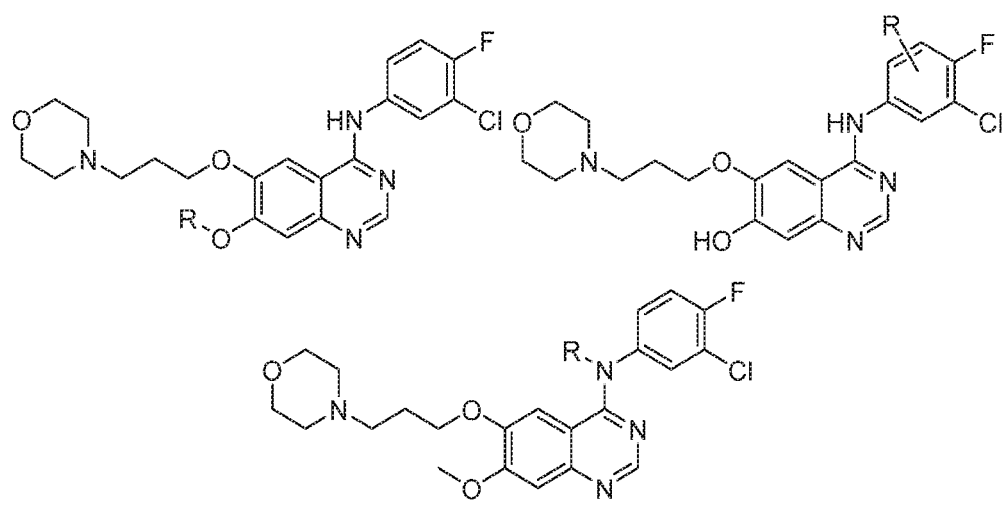

FIG. 5JJ
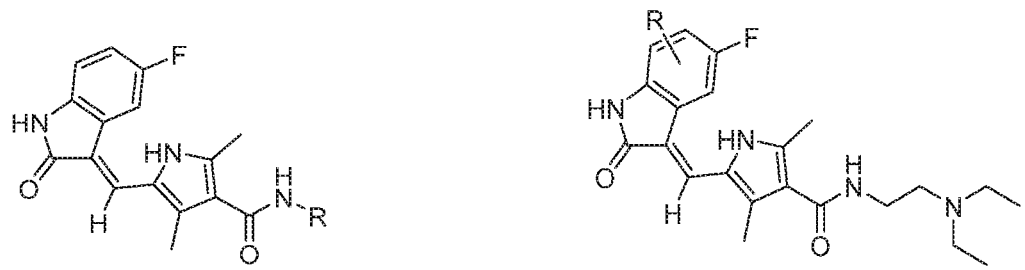
FIG. 5KK
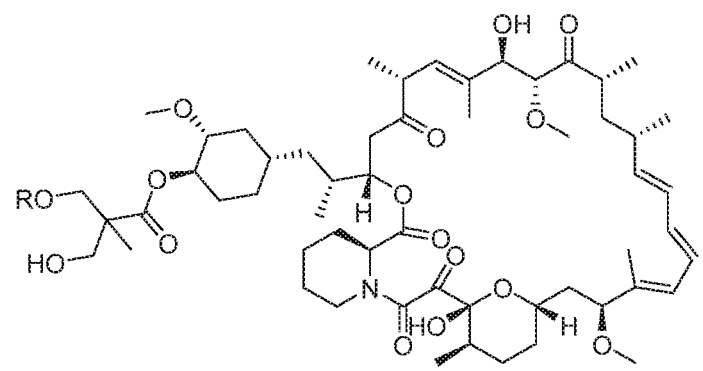
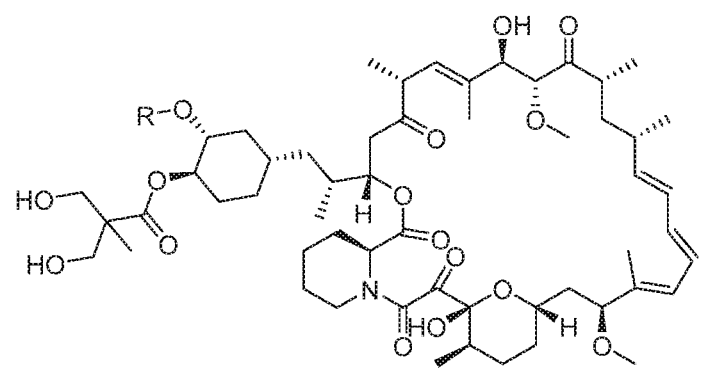

FIG. 6N
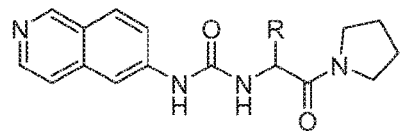
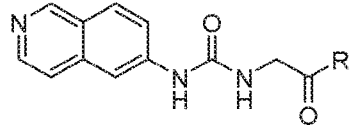
FIG. 6O
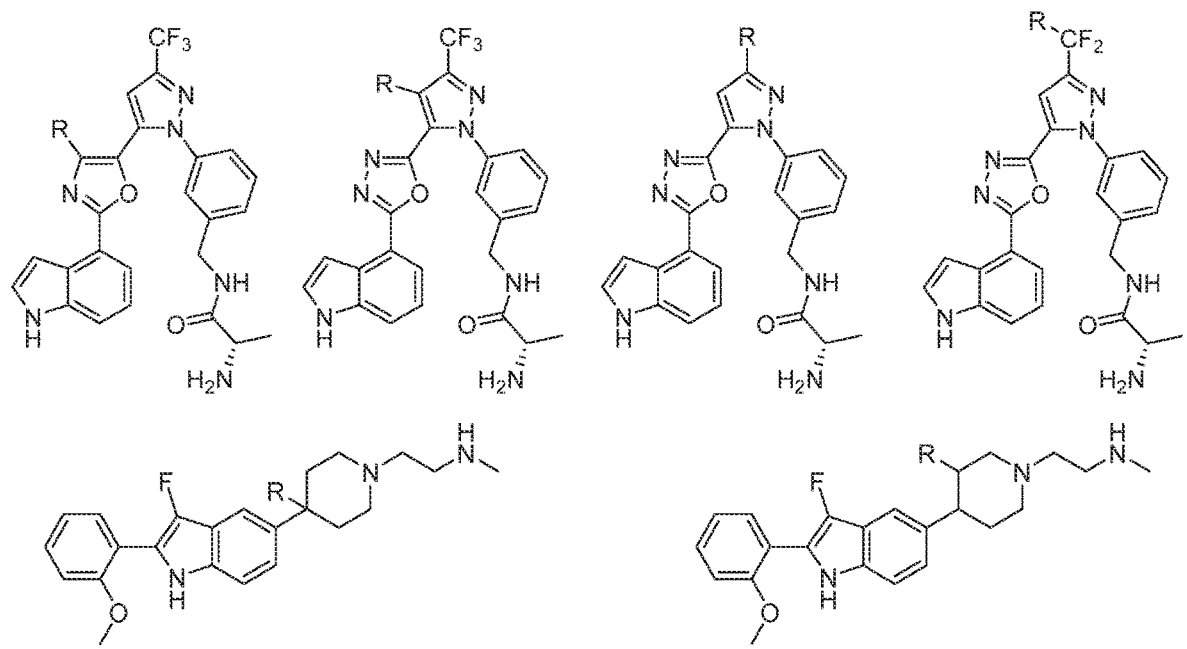
FIG. 6P
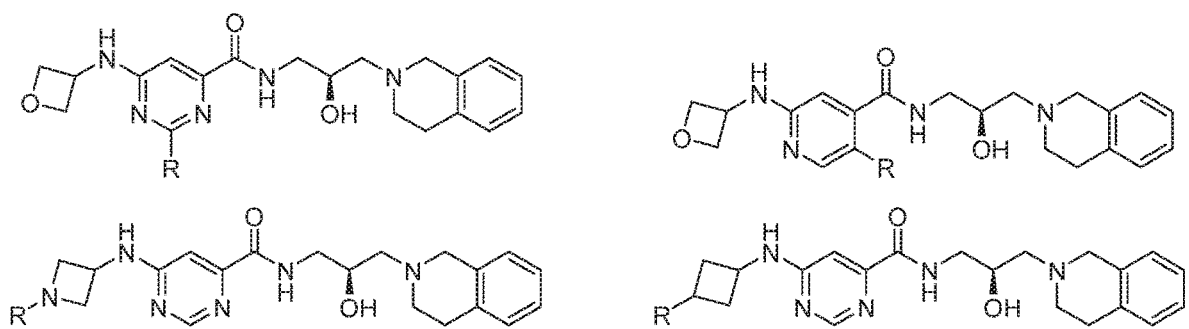

FIG. 7E
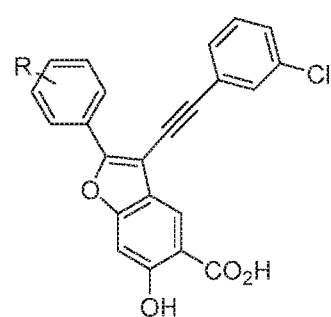
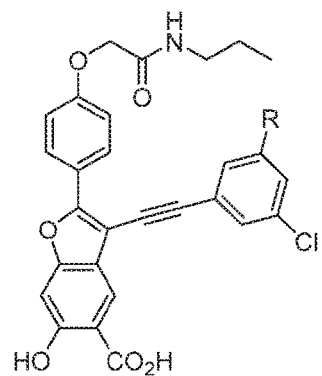
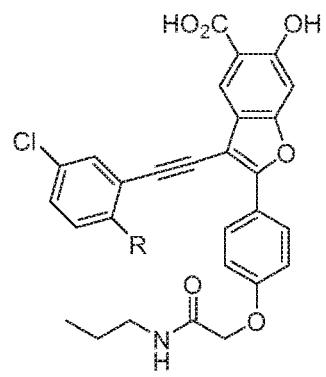
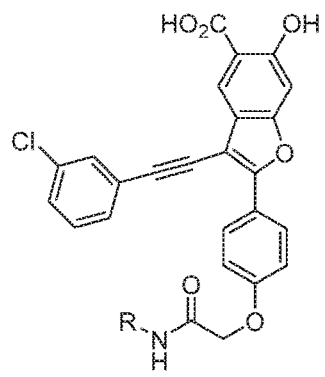
FIG 7F
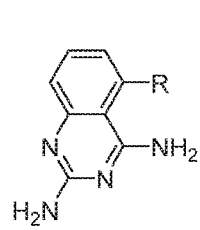
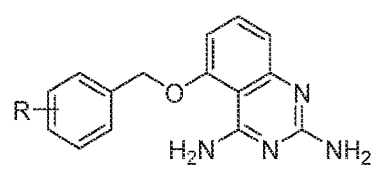
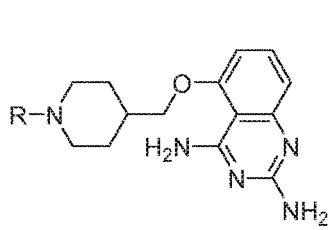
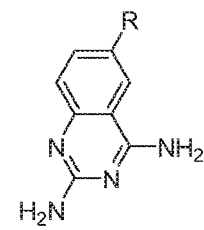

X=H, F, Cl, Br, Me, CF₃O

FIG. 8S
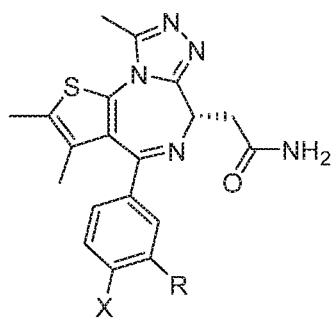
X=H, F, Cl, Br, Me, CF₃O
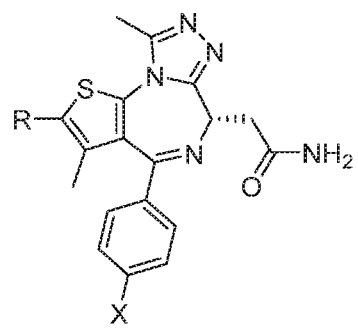
X=H, F, Cl, Br, Me, CF₃O
FIG. 8T
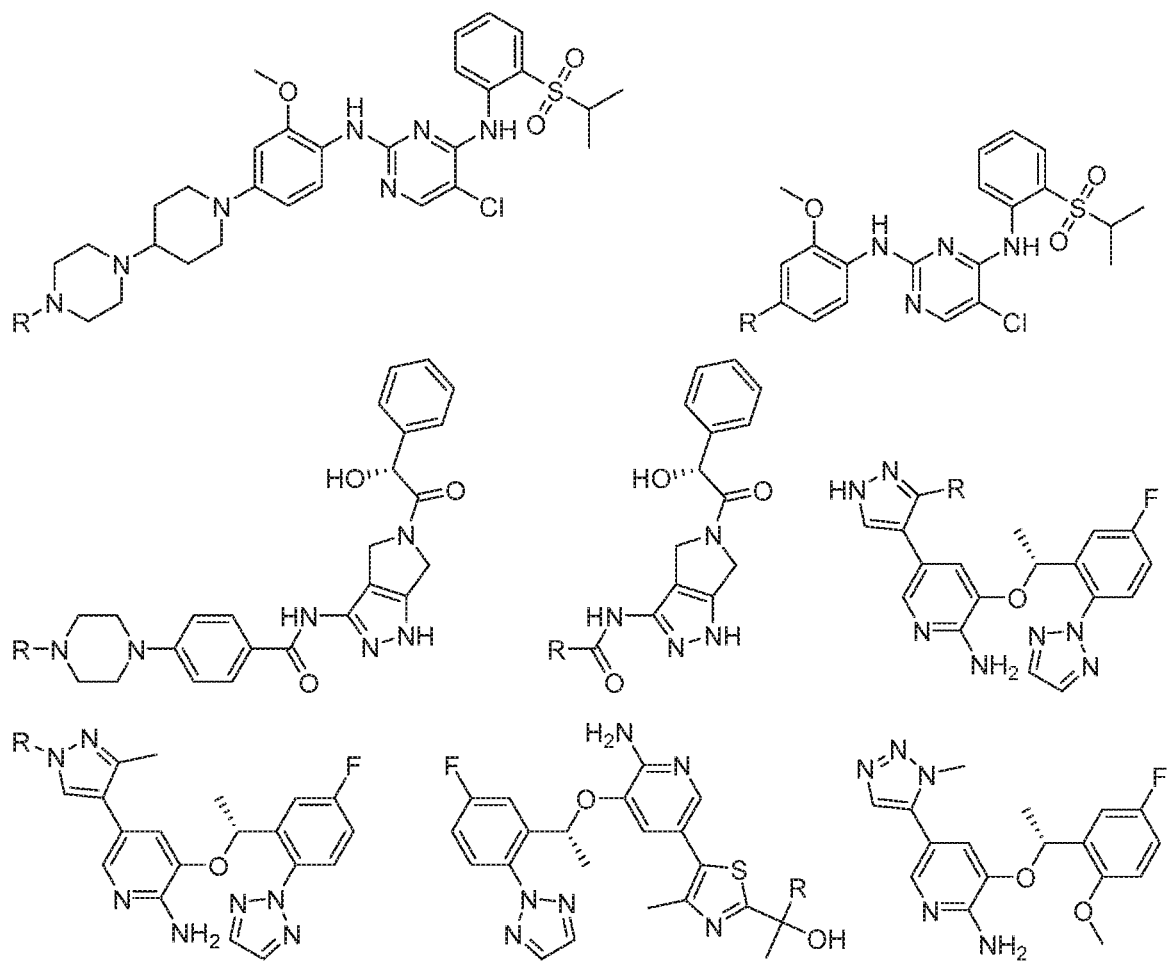

FIG. 8AAA
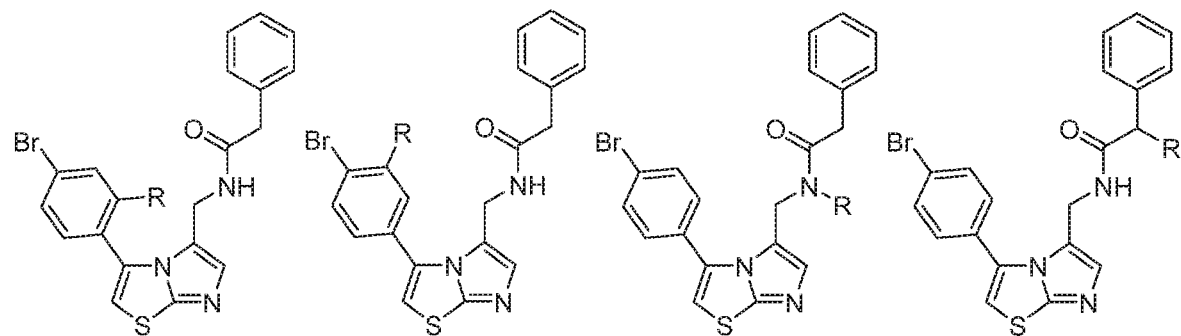
FIG. 8BBB
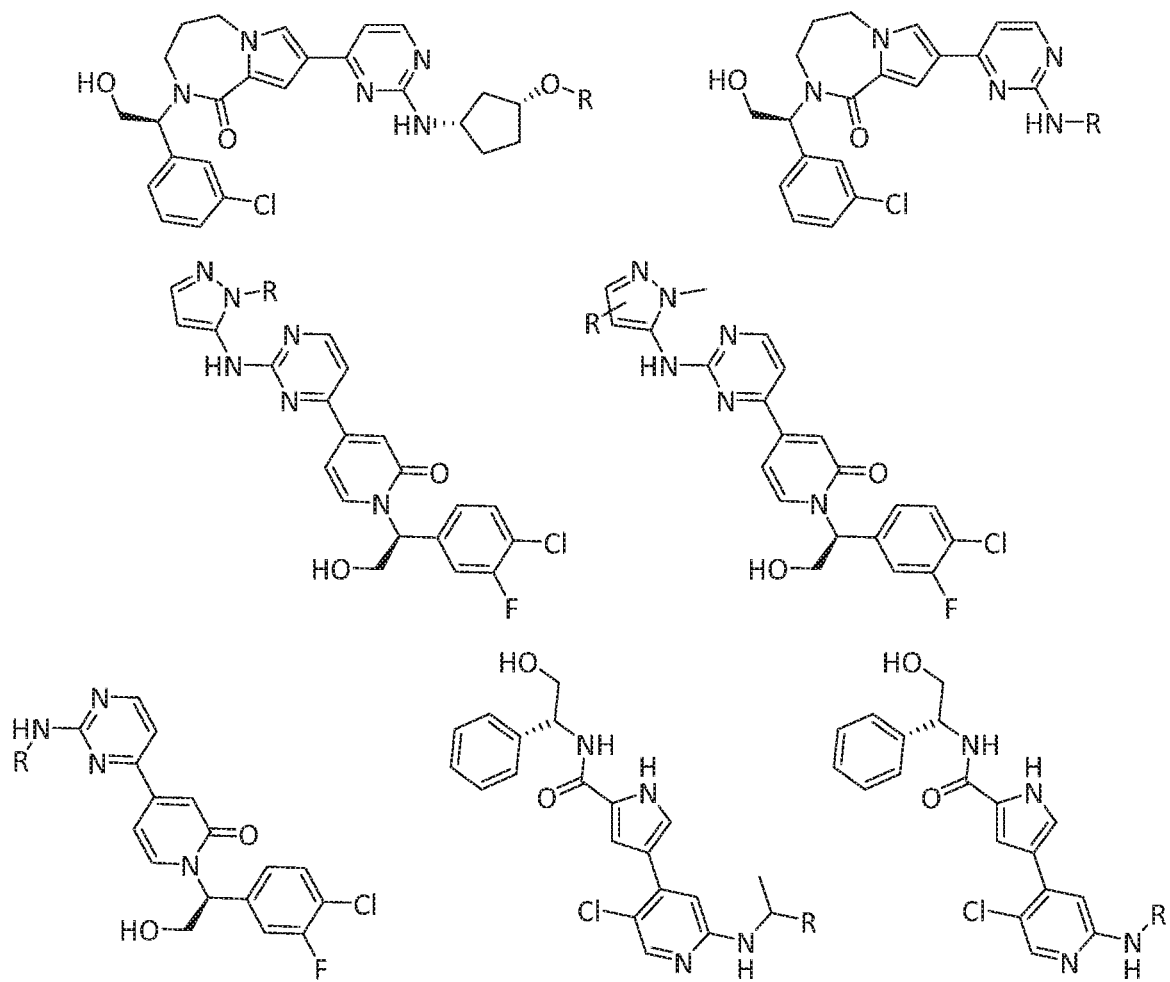

FIG. 8CCC
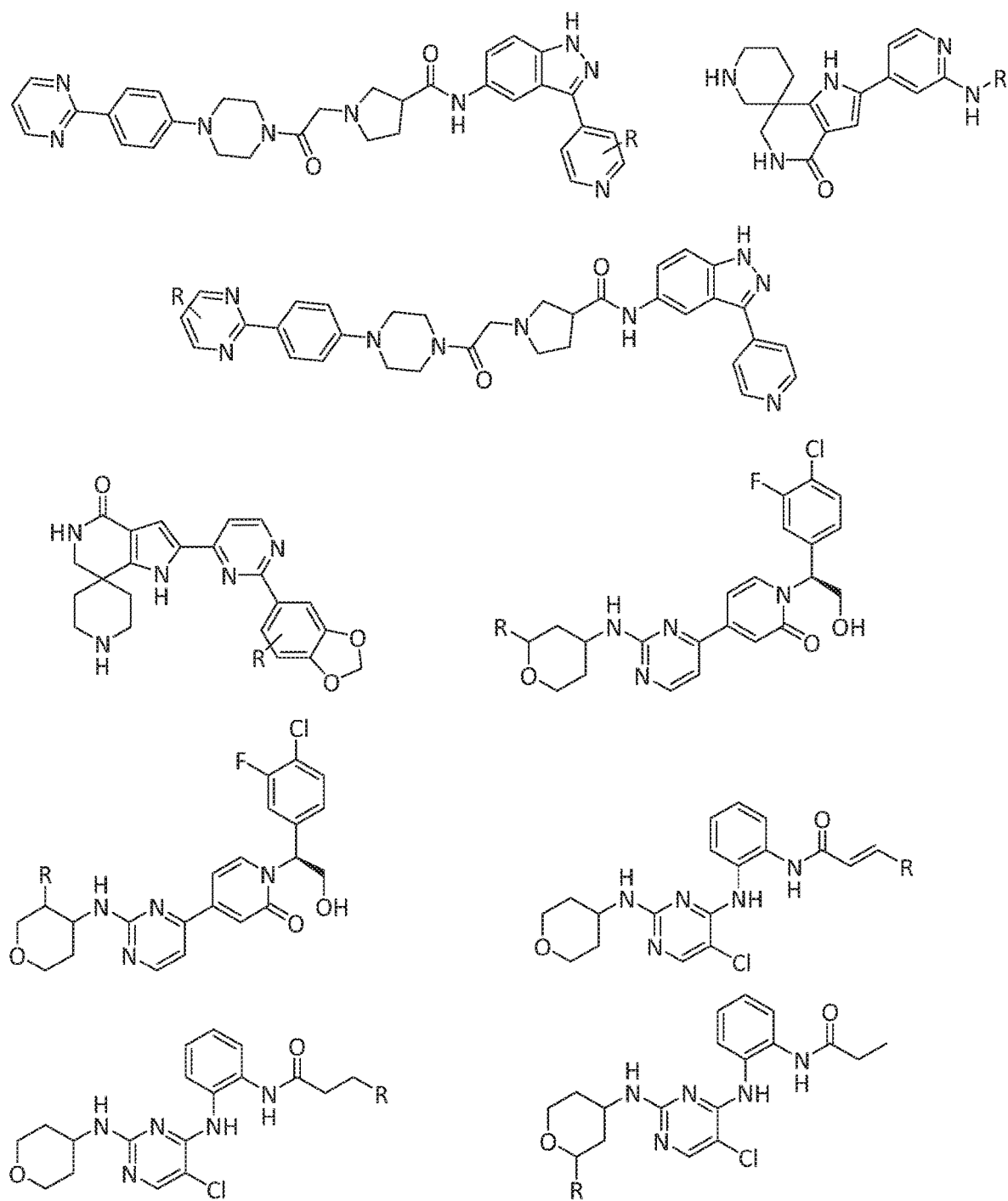

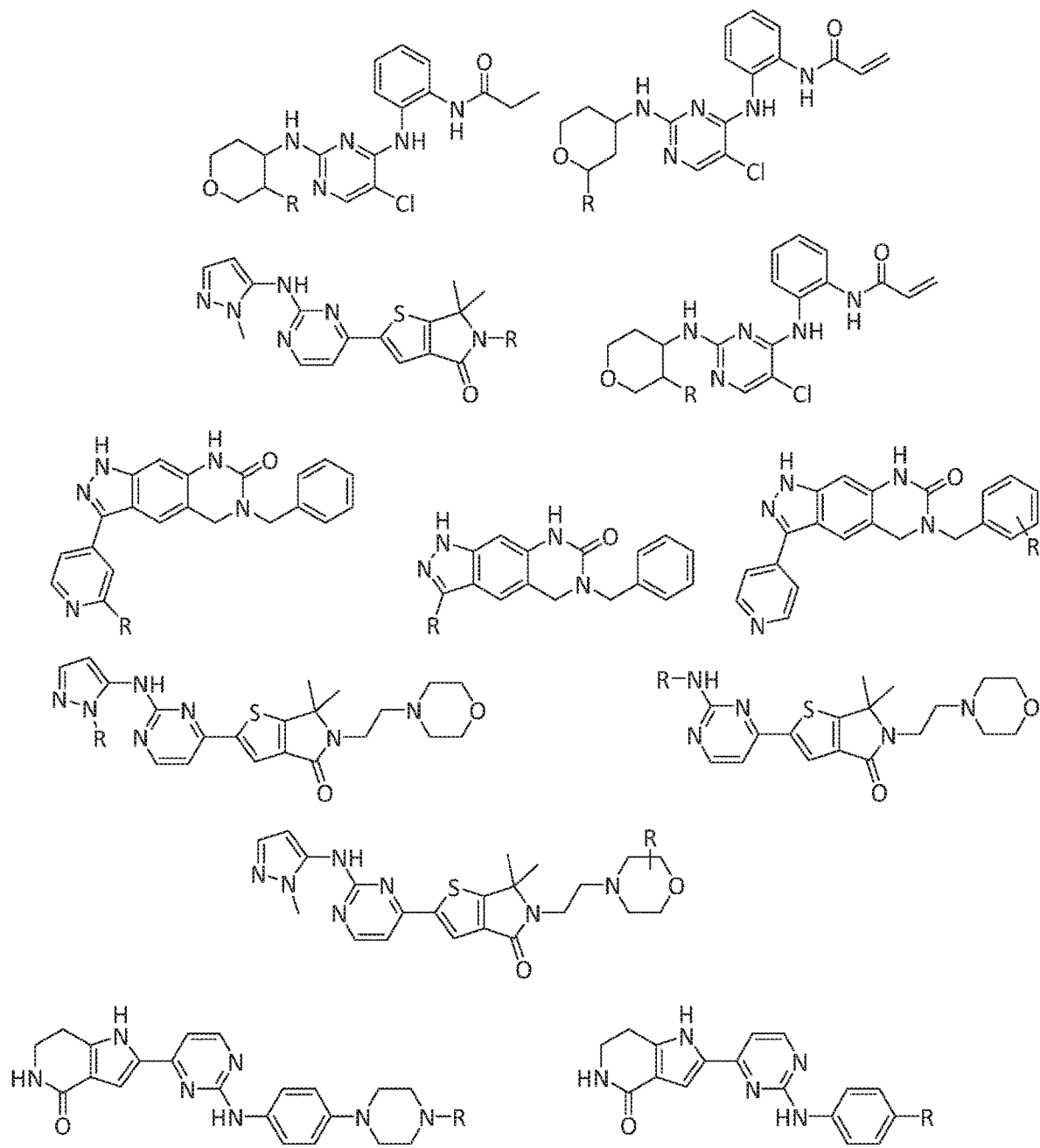
FIG. 8DDD

FIG. 8EEE
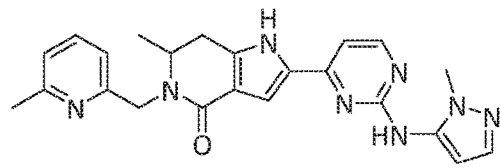
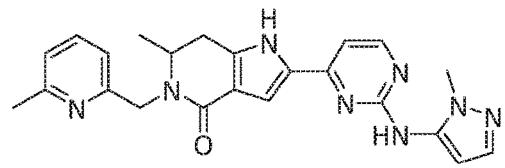
FIG. 8FFF
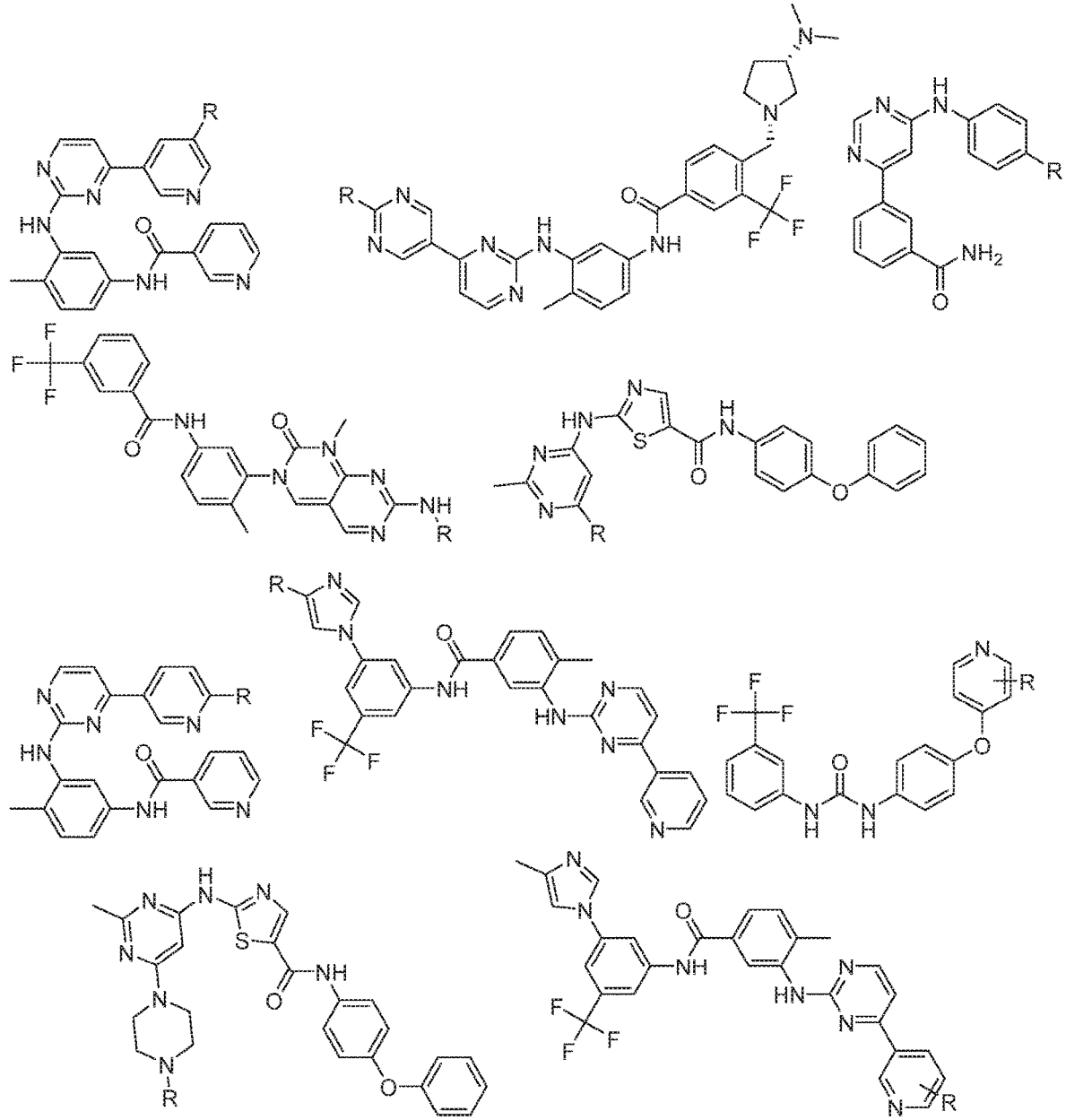

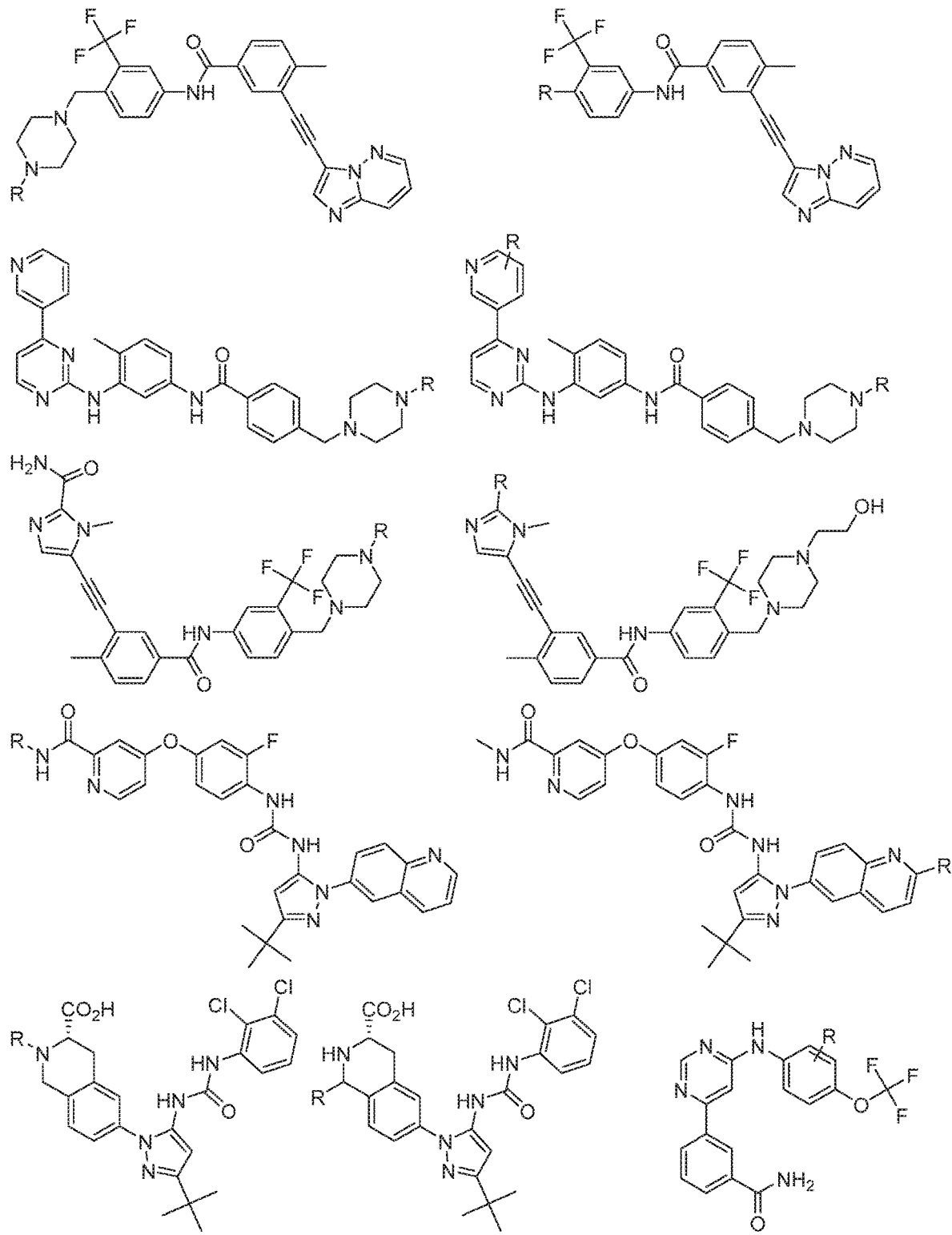
FIG. 8GGG

FIG. 8HHH
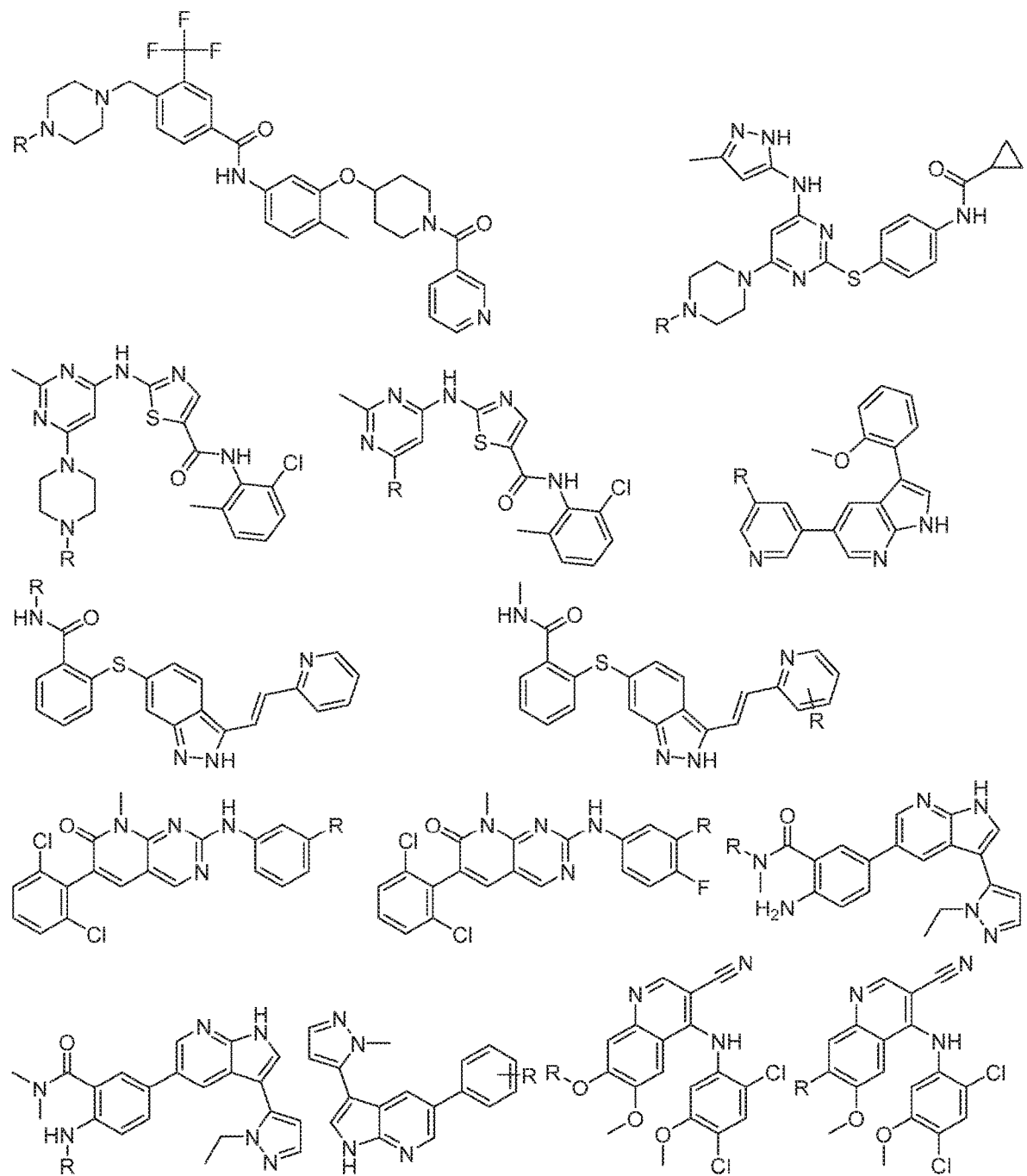

FIG. 8III
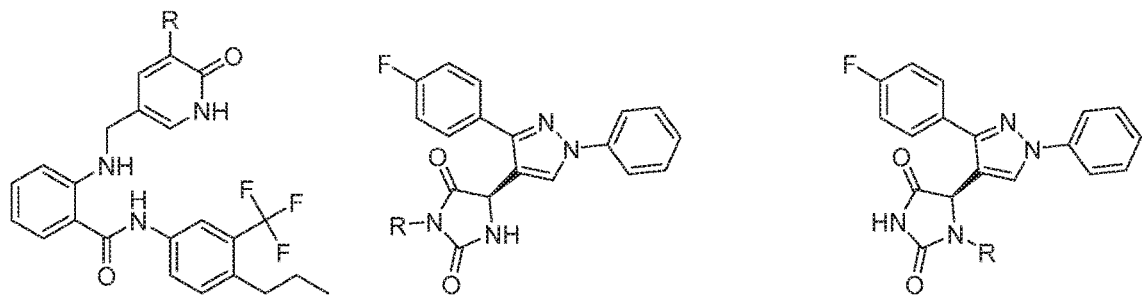
FIG. 8JJJ
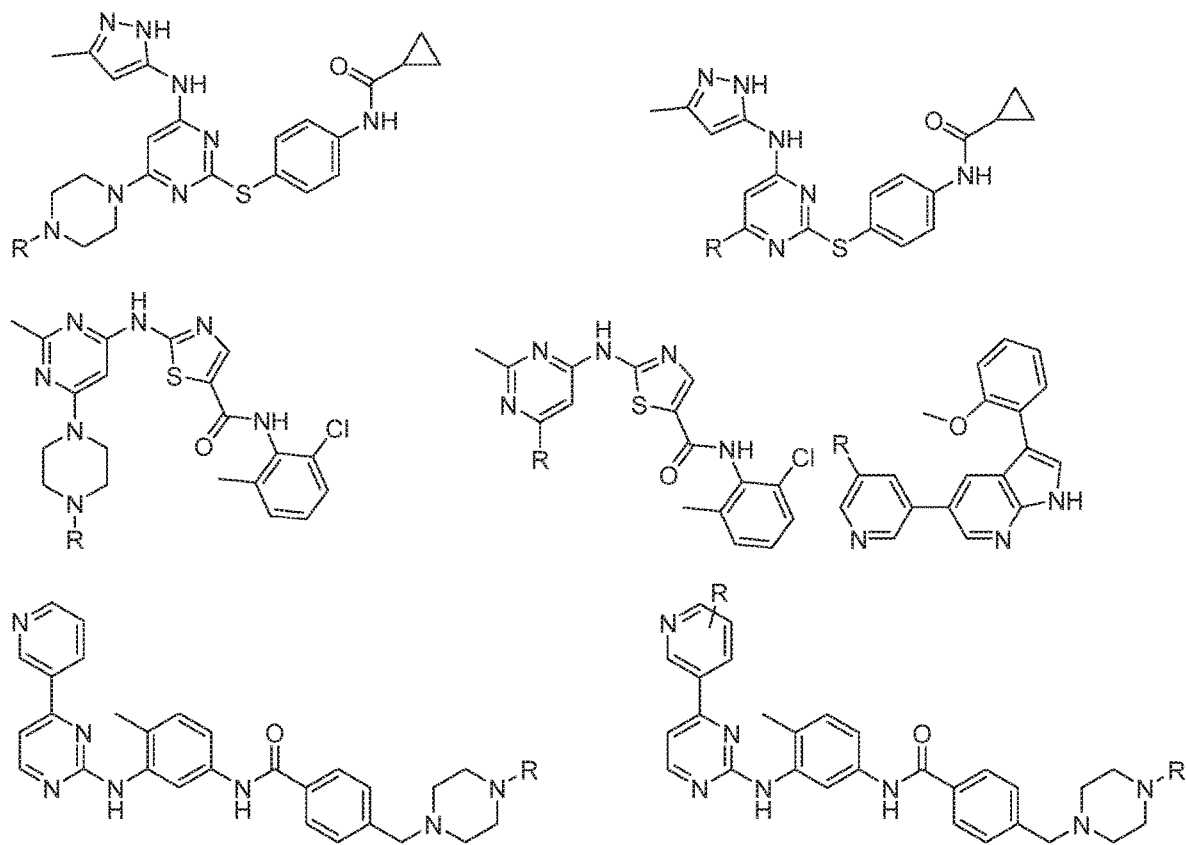

FIG. 8KKK
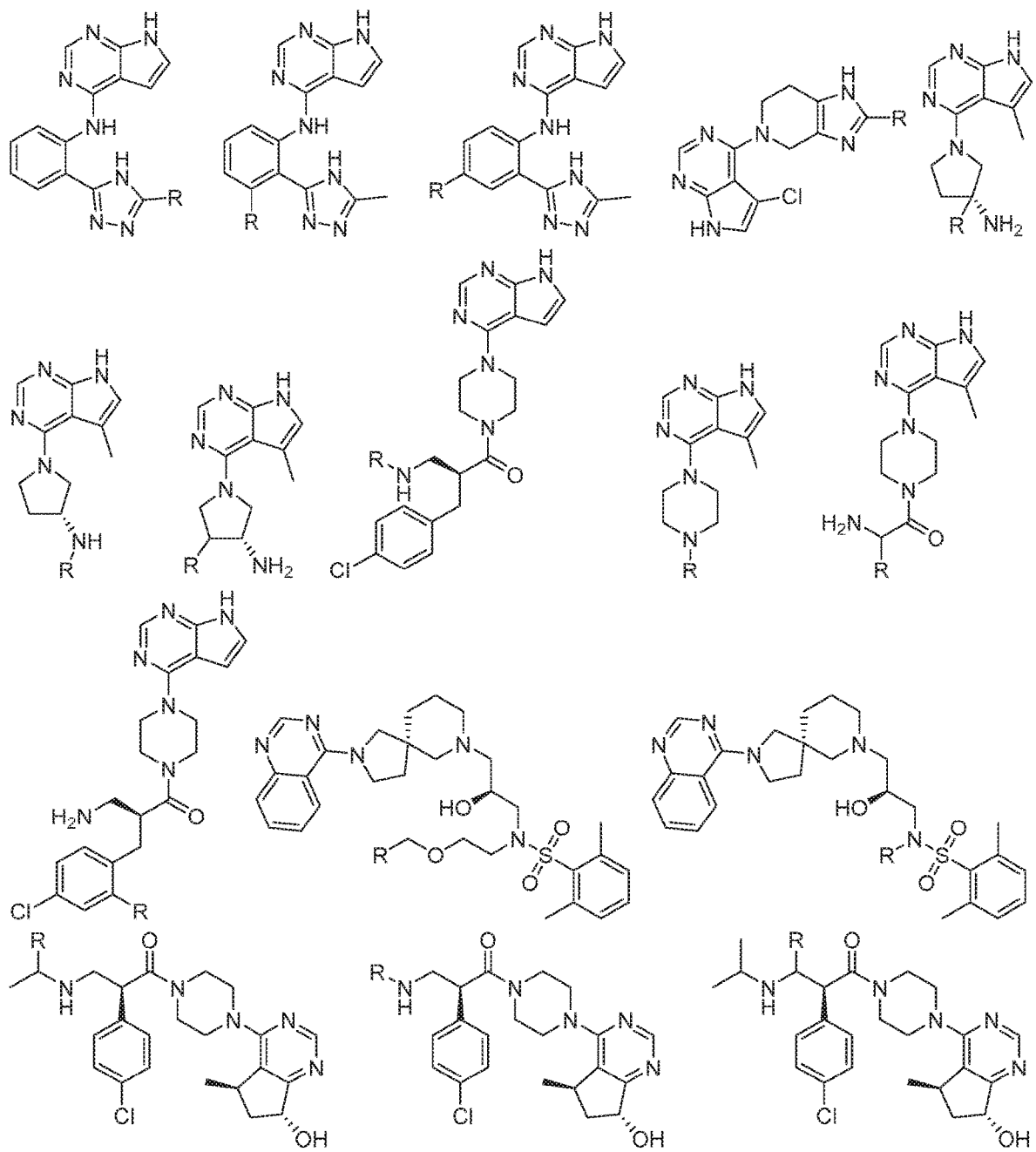

FIG. 8LLL
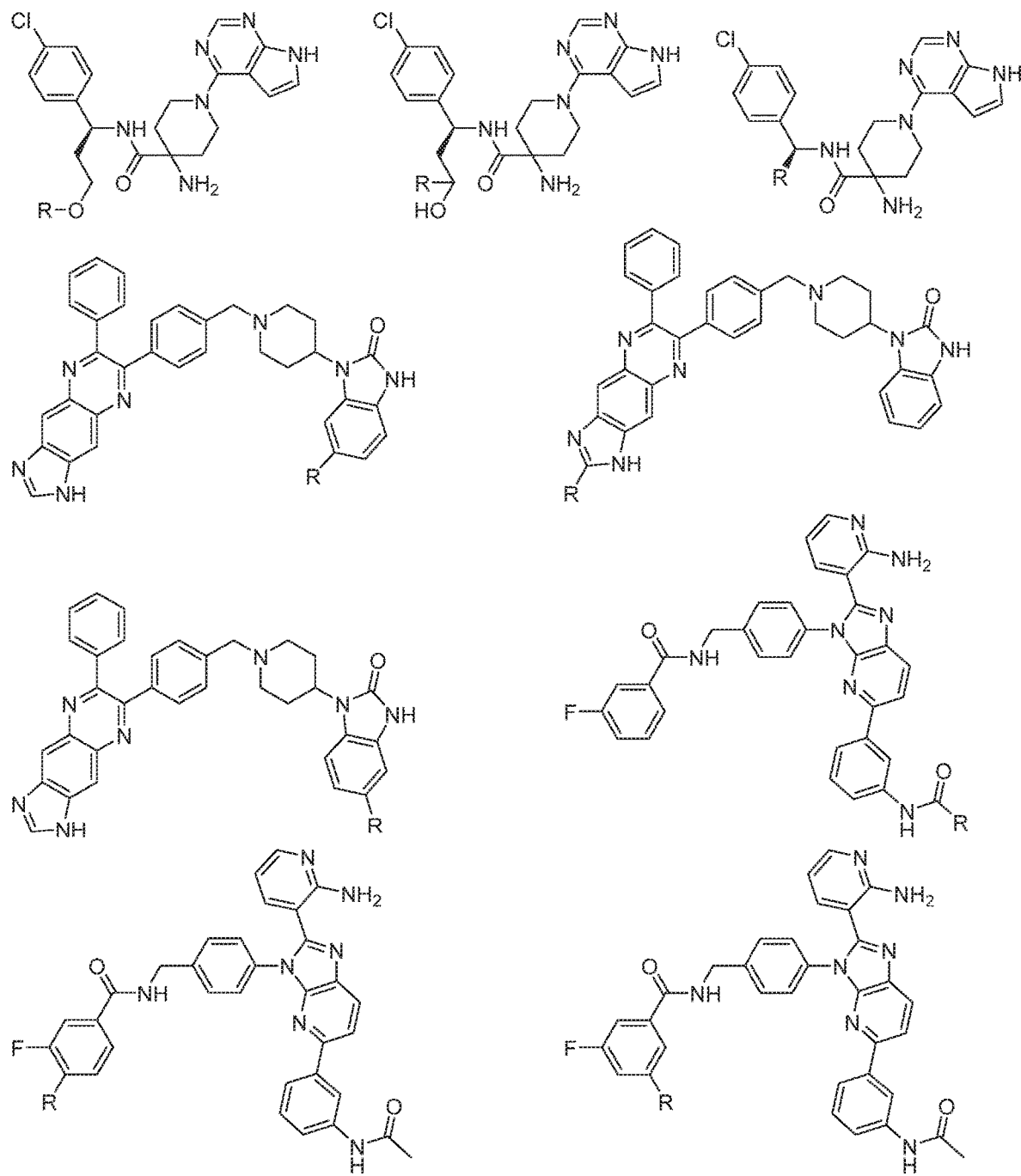

FIG. 8MMM
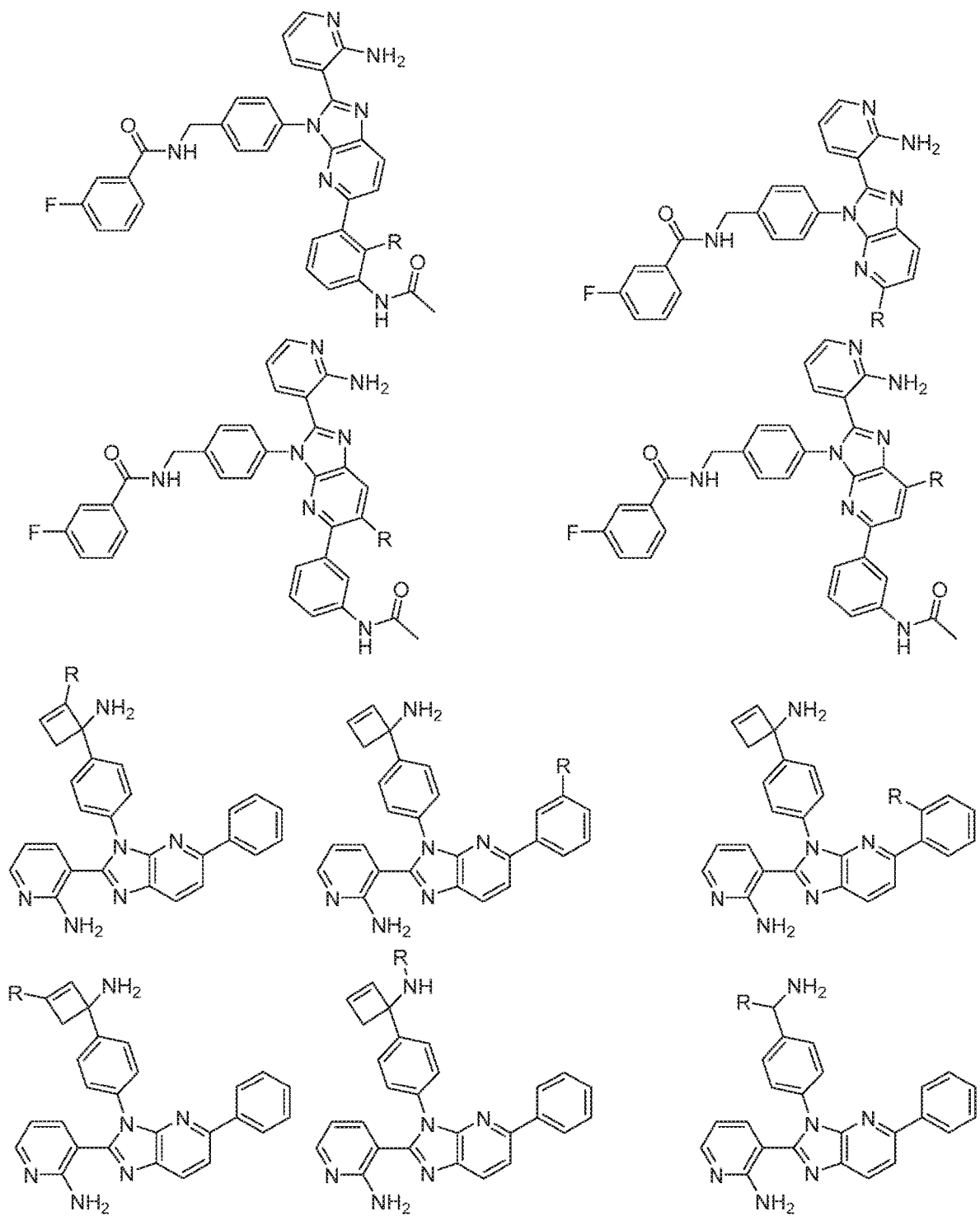

FIG. 8NNN
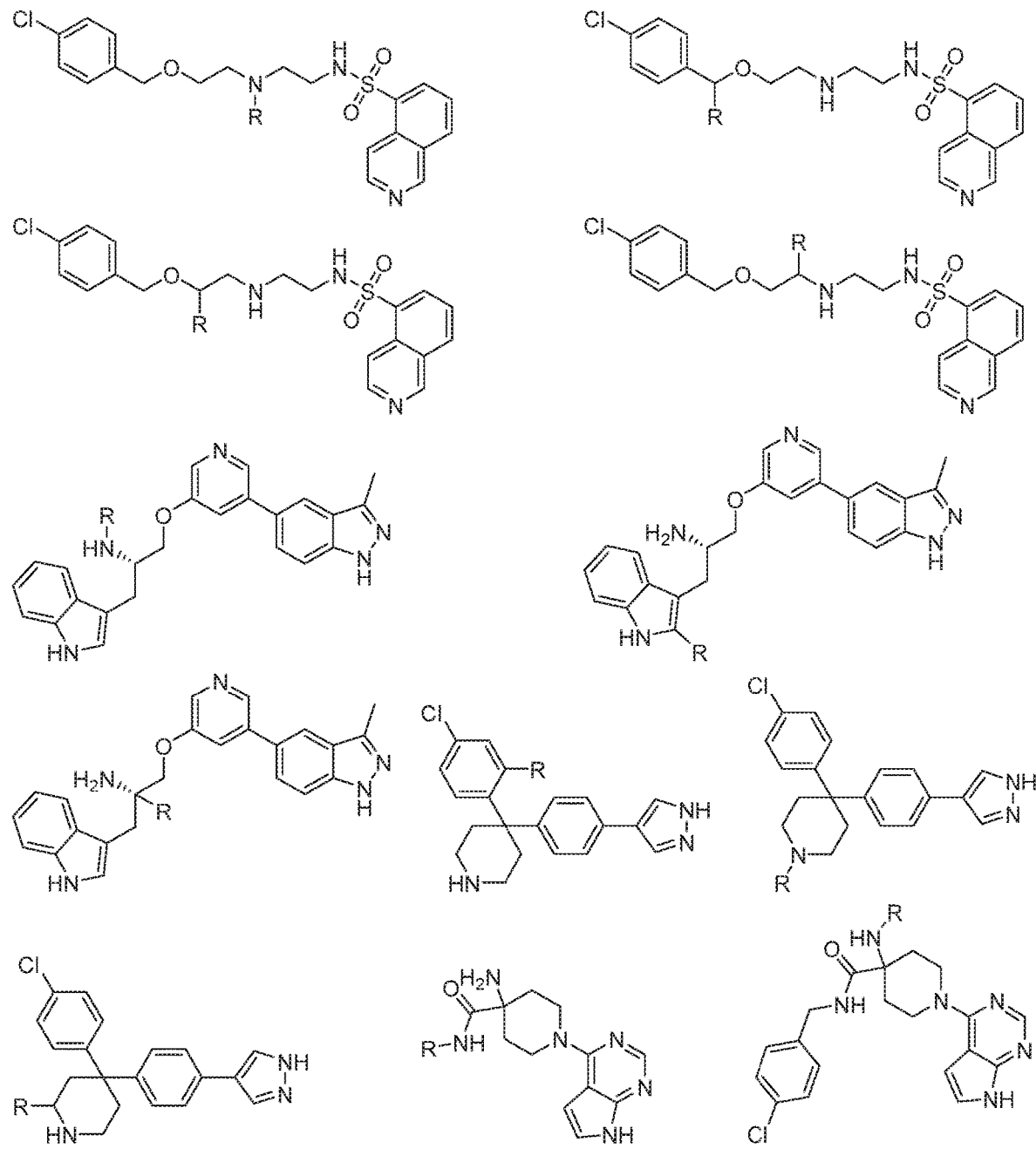

FIG. 8OOO
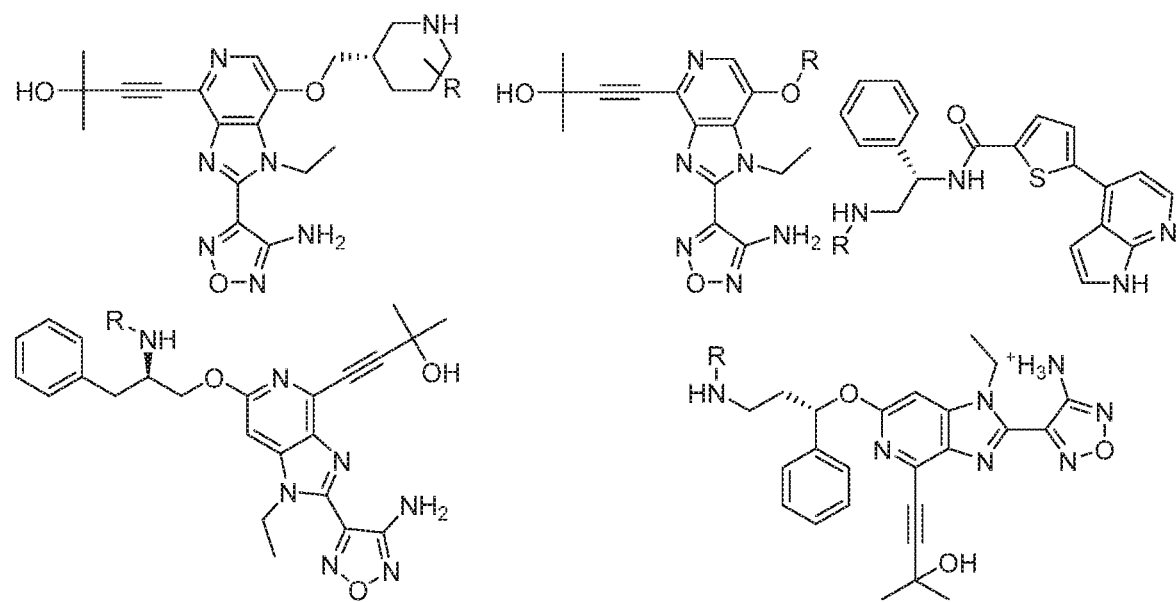
FIG. 8PPP
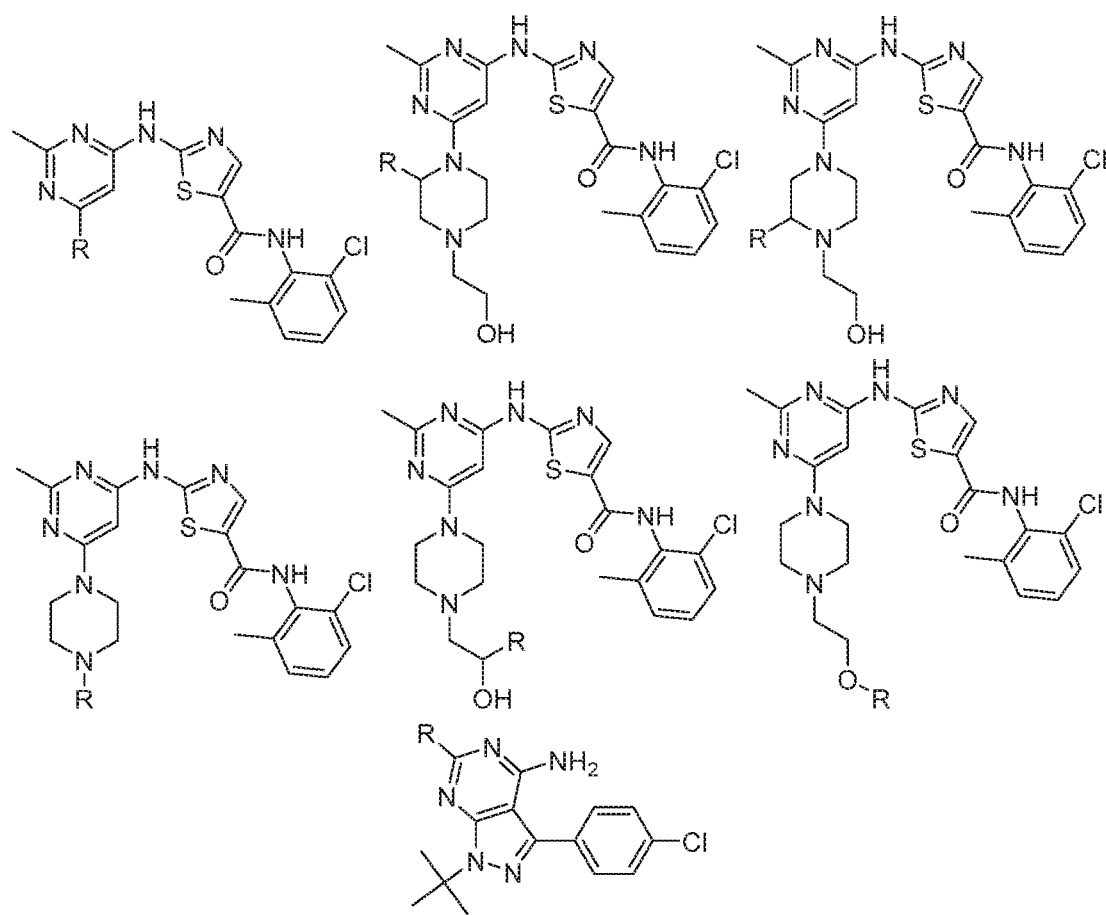

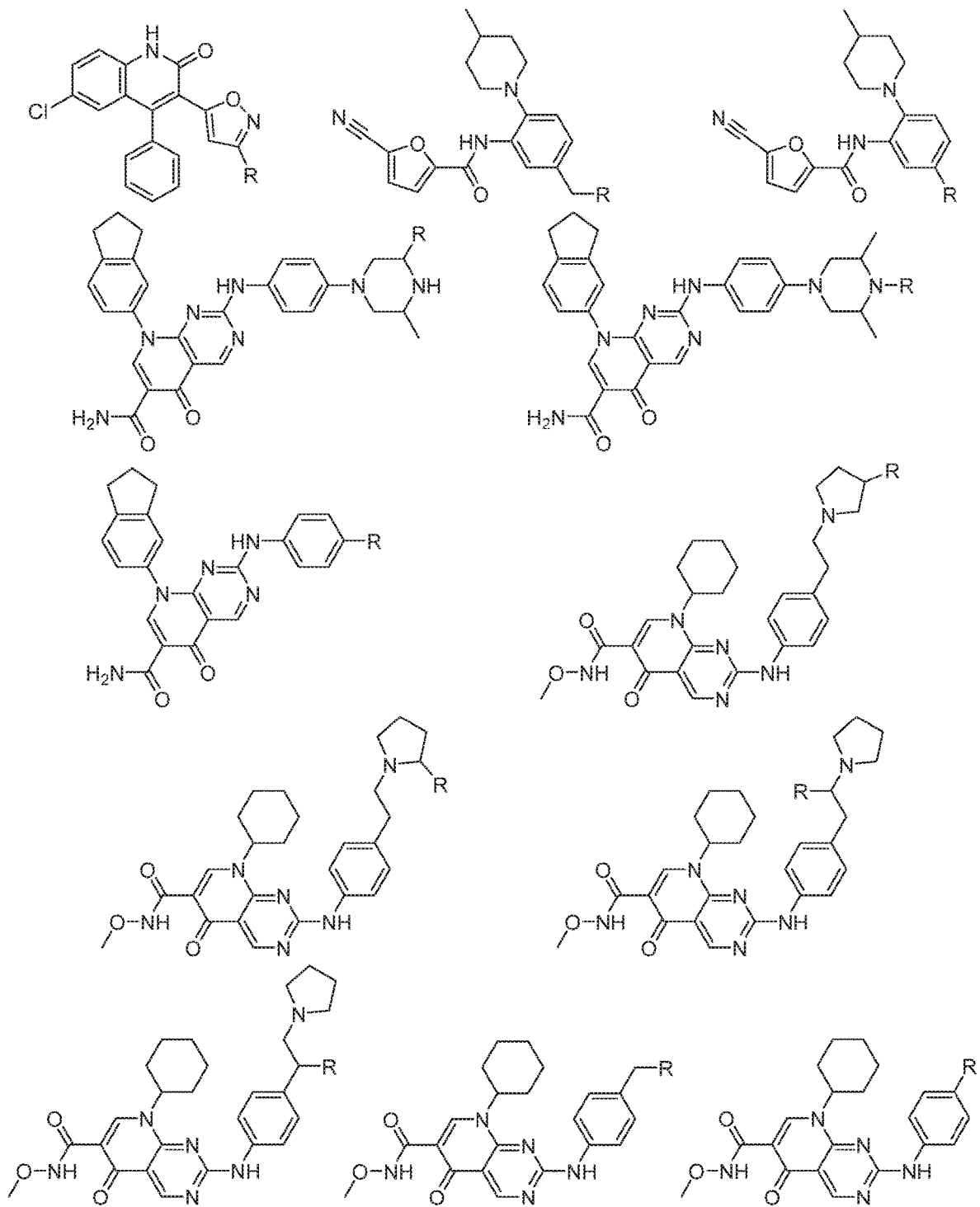
FIG. 8QQQ

FIG. 8RRR
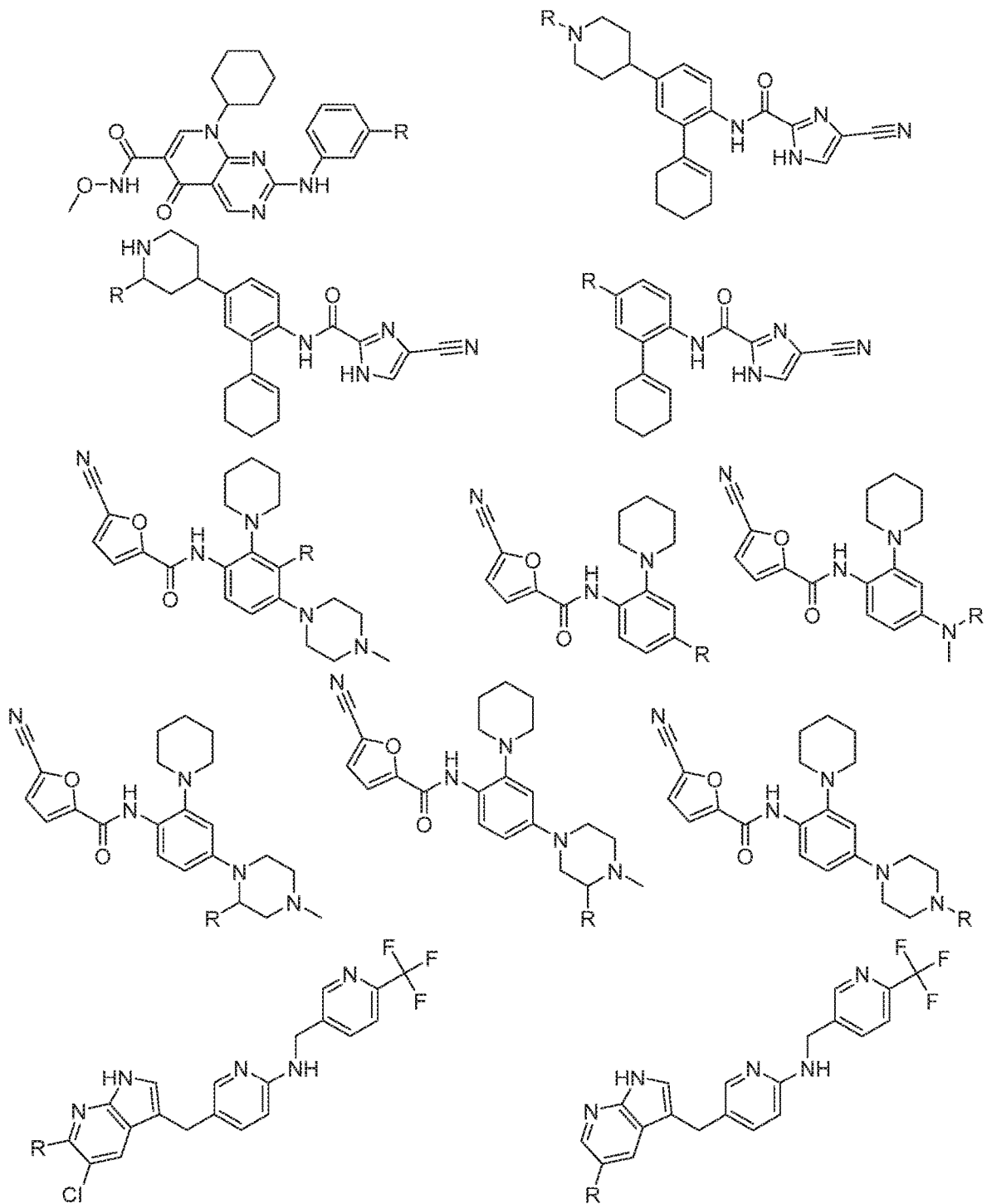

FIG. 8SSS
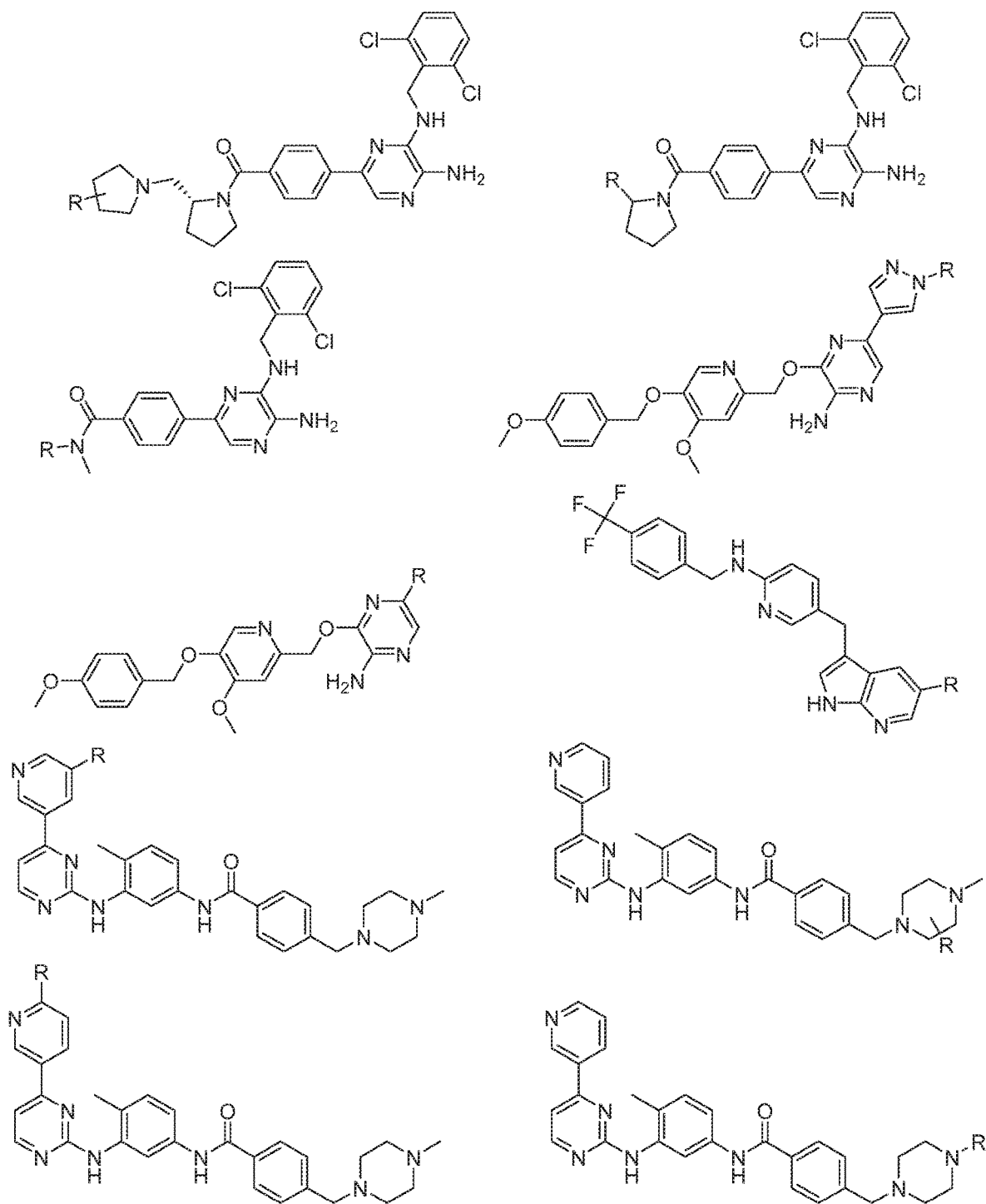

FIG. 8TTT
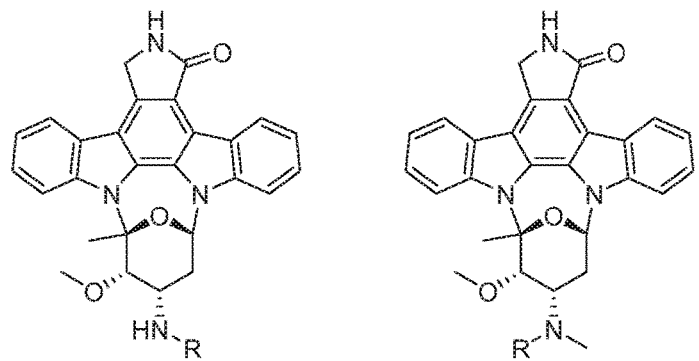
FIG. 8UUU
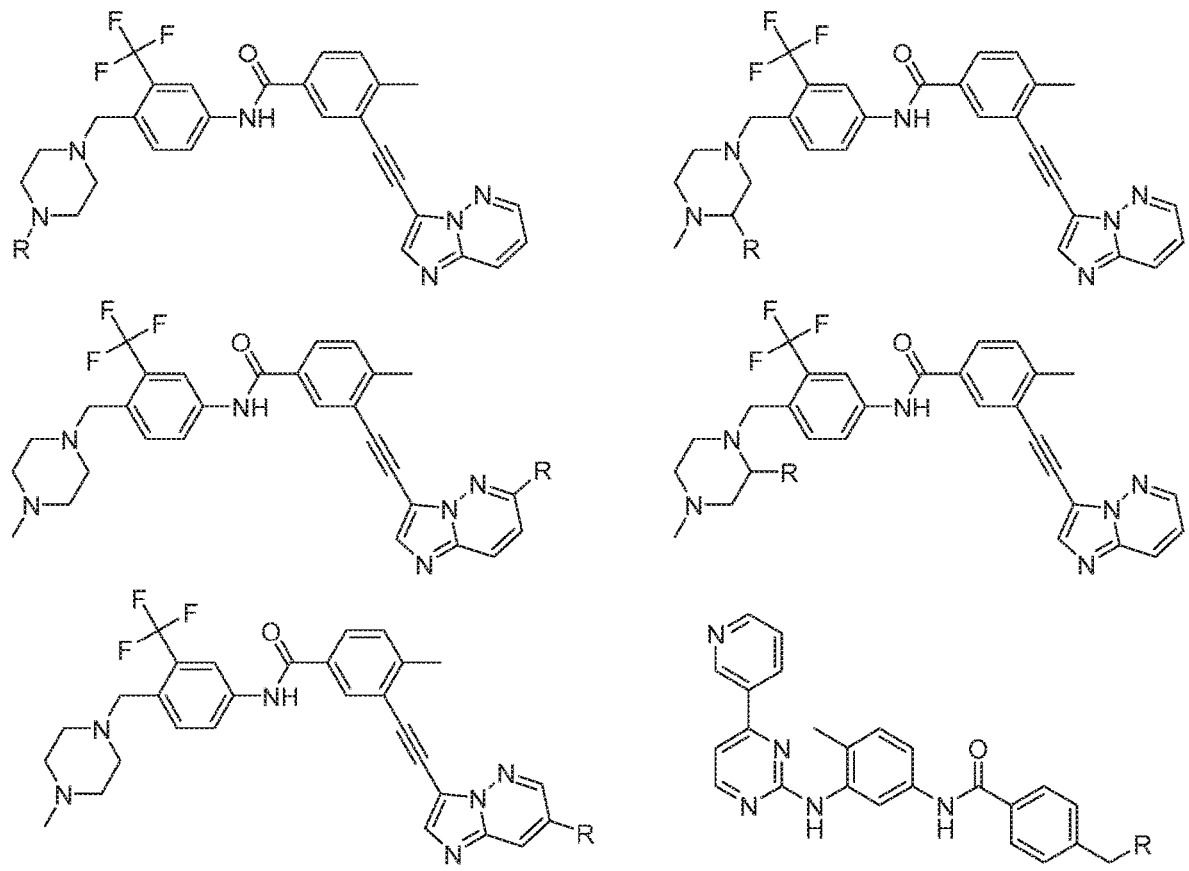

FIG. 8VVV
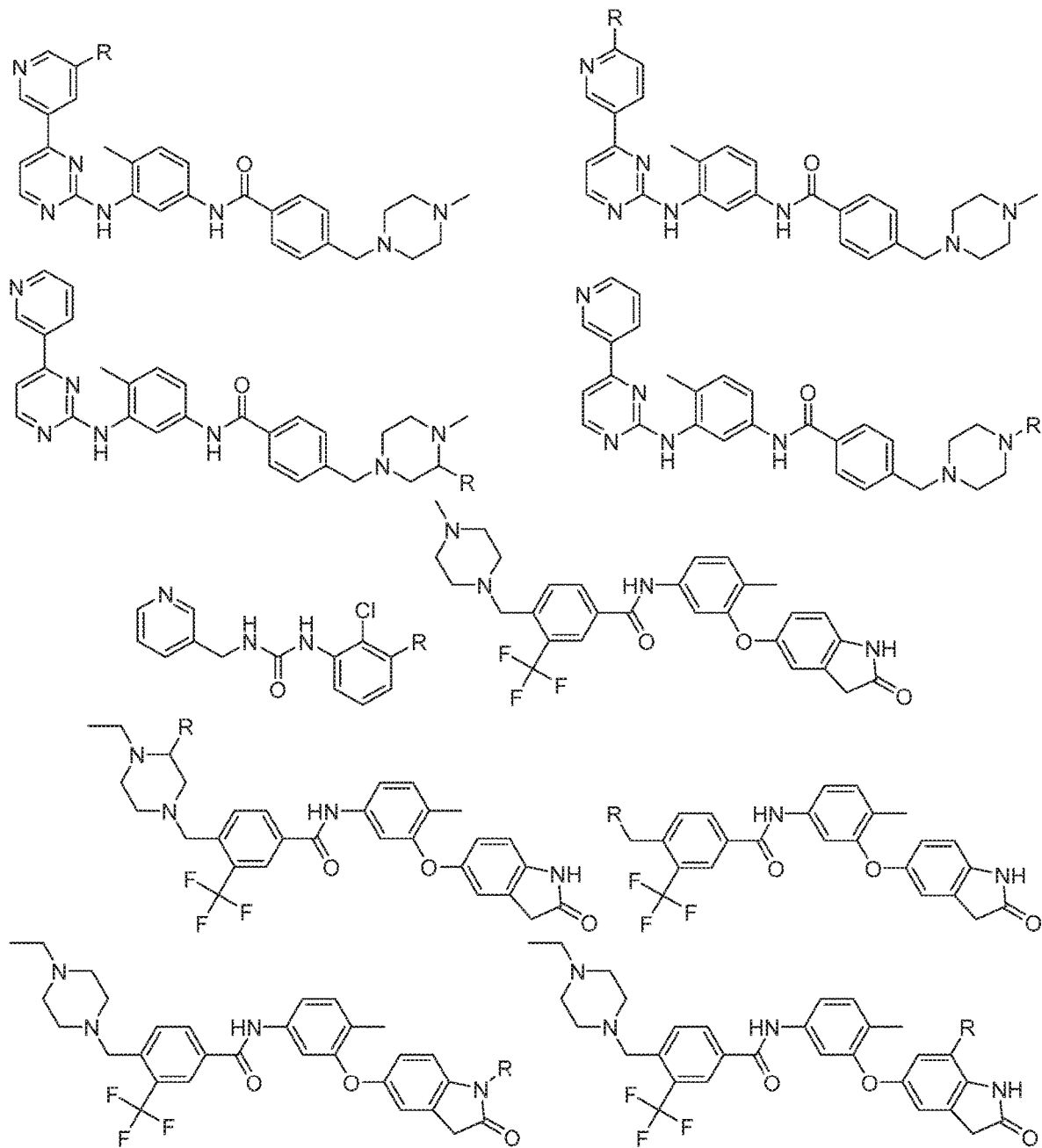

FIG. 8WWW
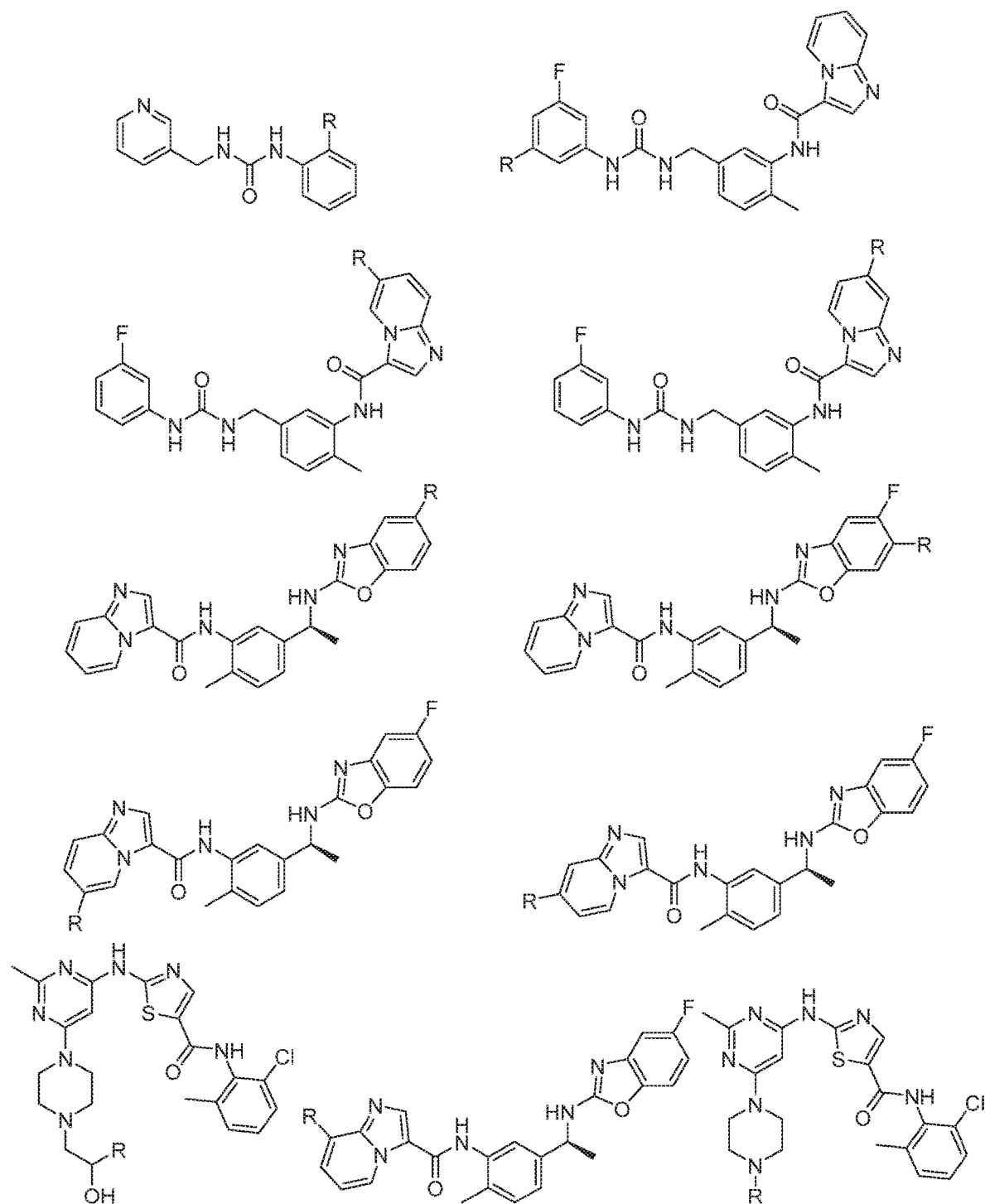

FIG. 8XXX
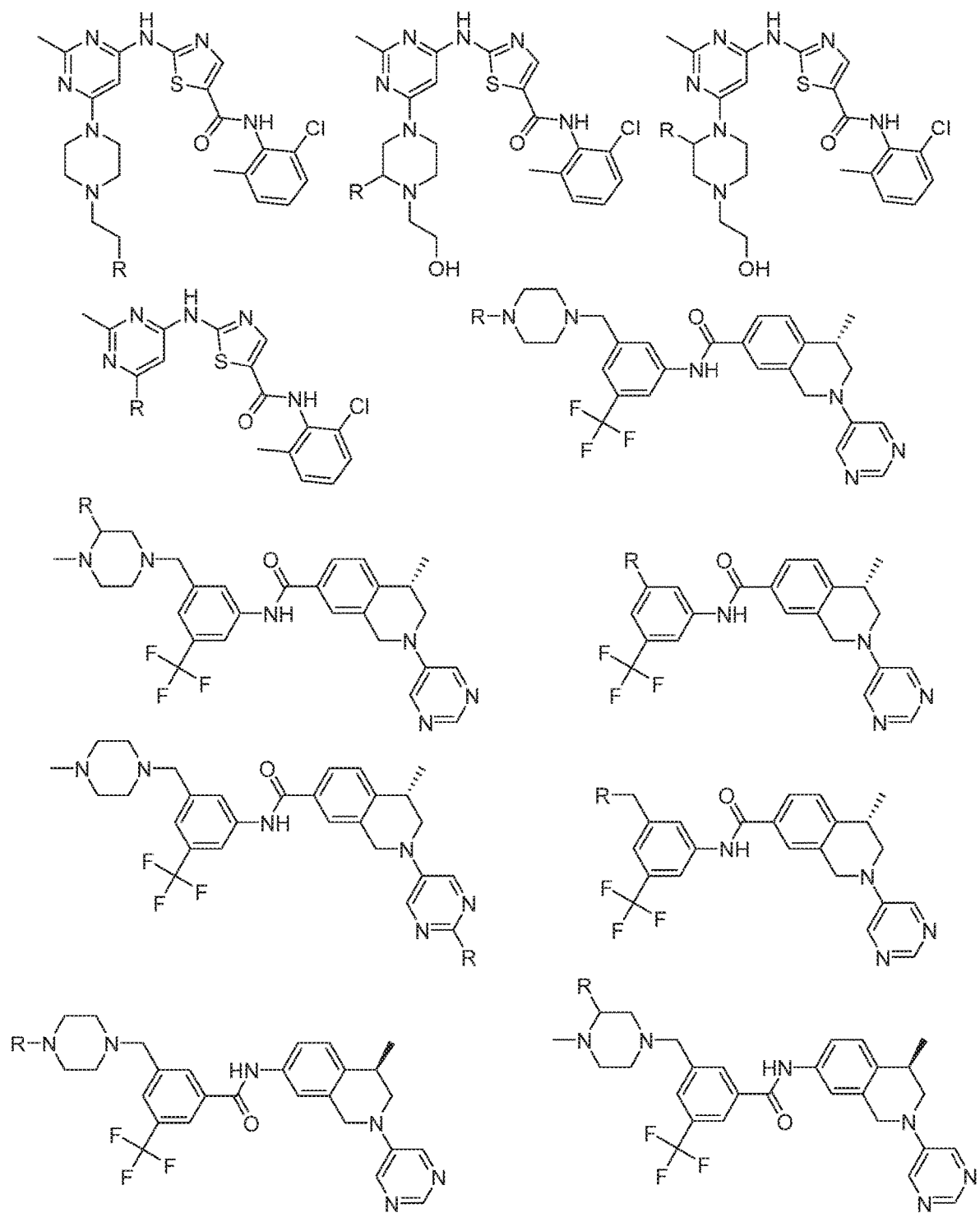

FIG. 8YYY
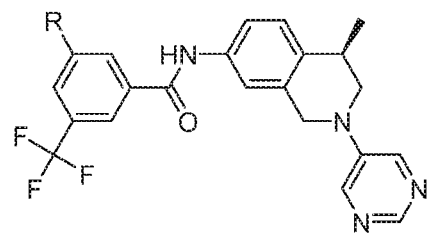
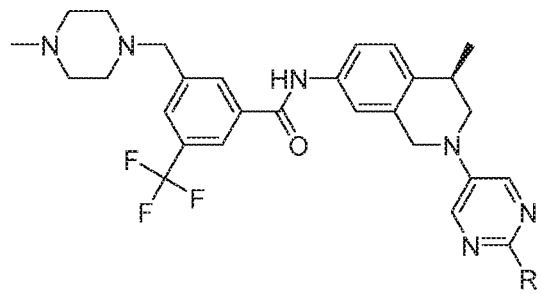
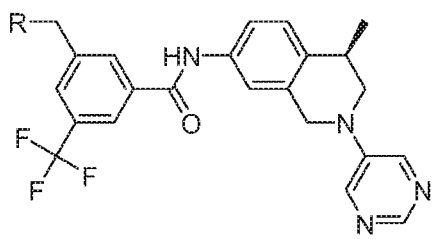
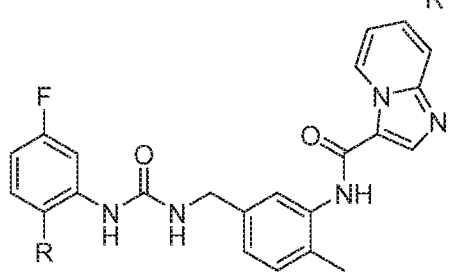
FIG. 8ZZZ
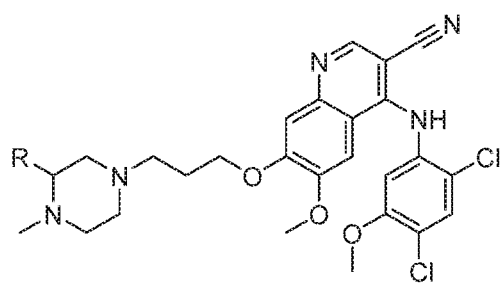
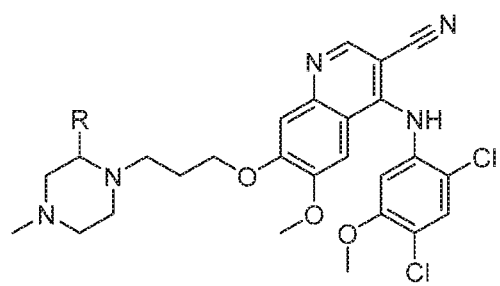
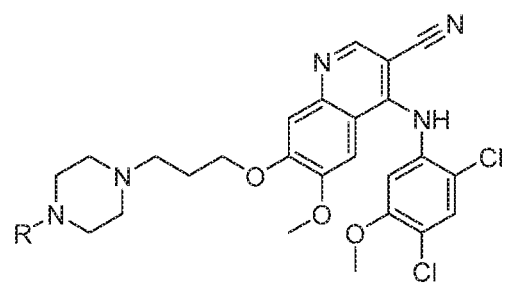
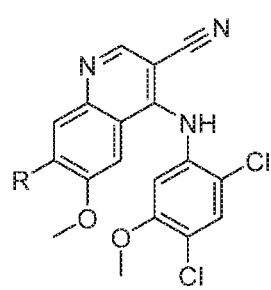
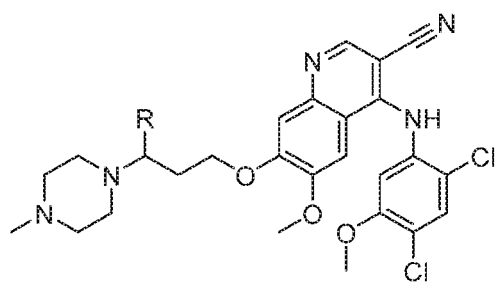
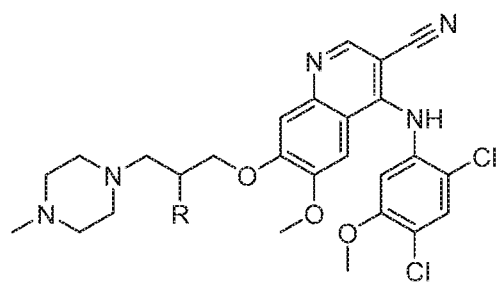

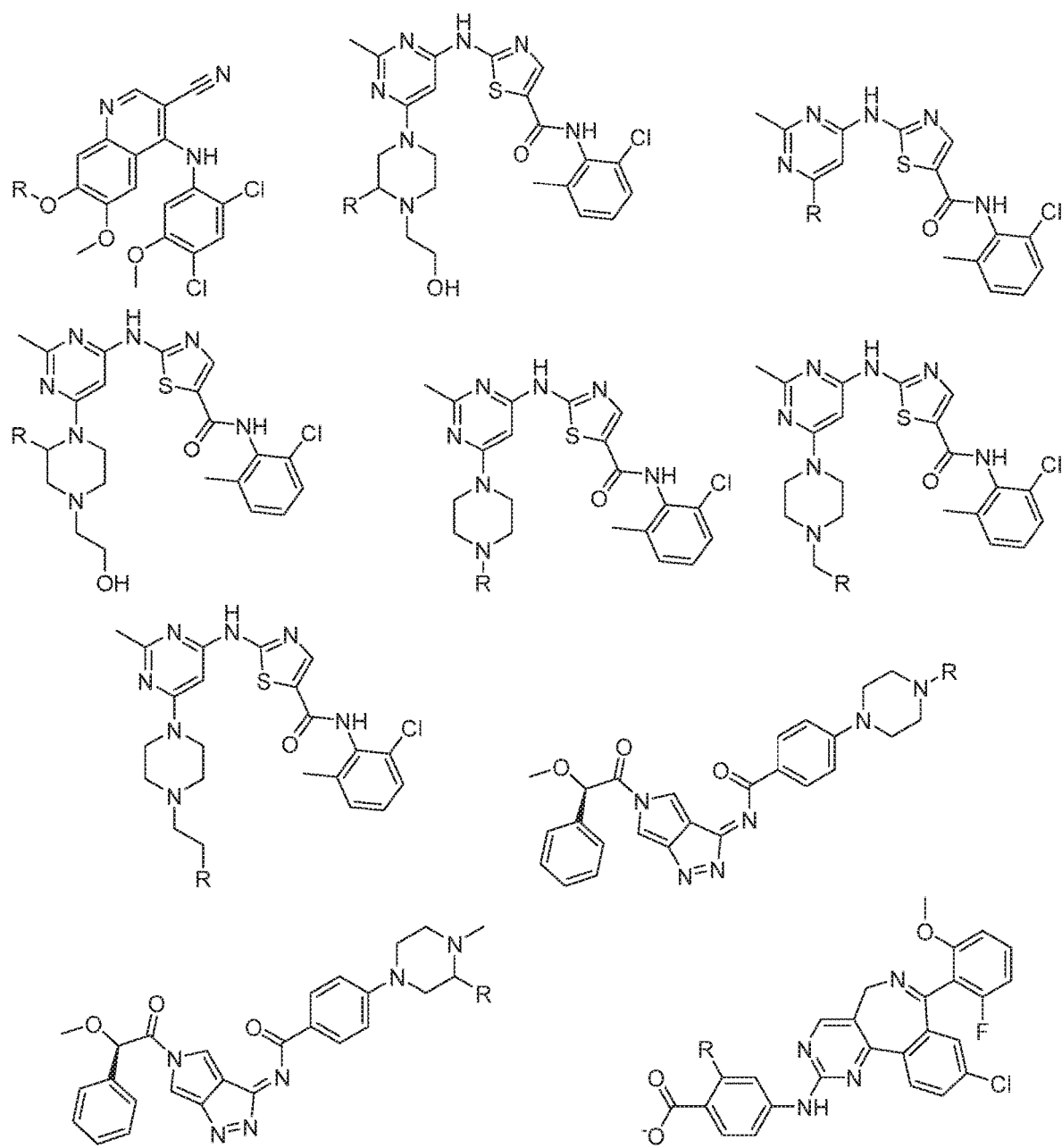
FIG. 8AAAA

FIG. 8BBBB
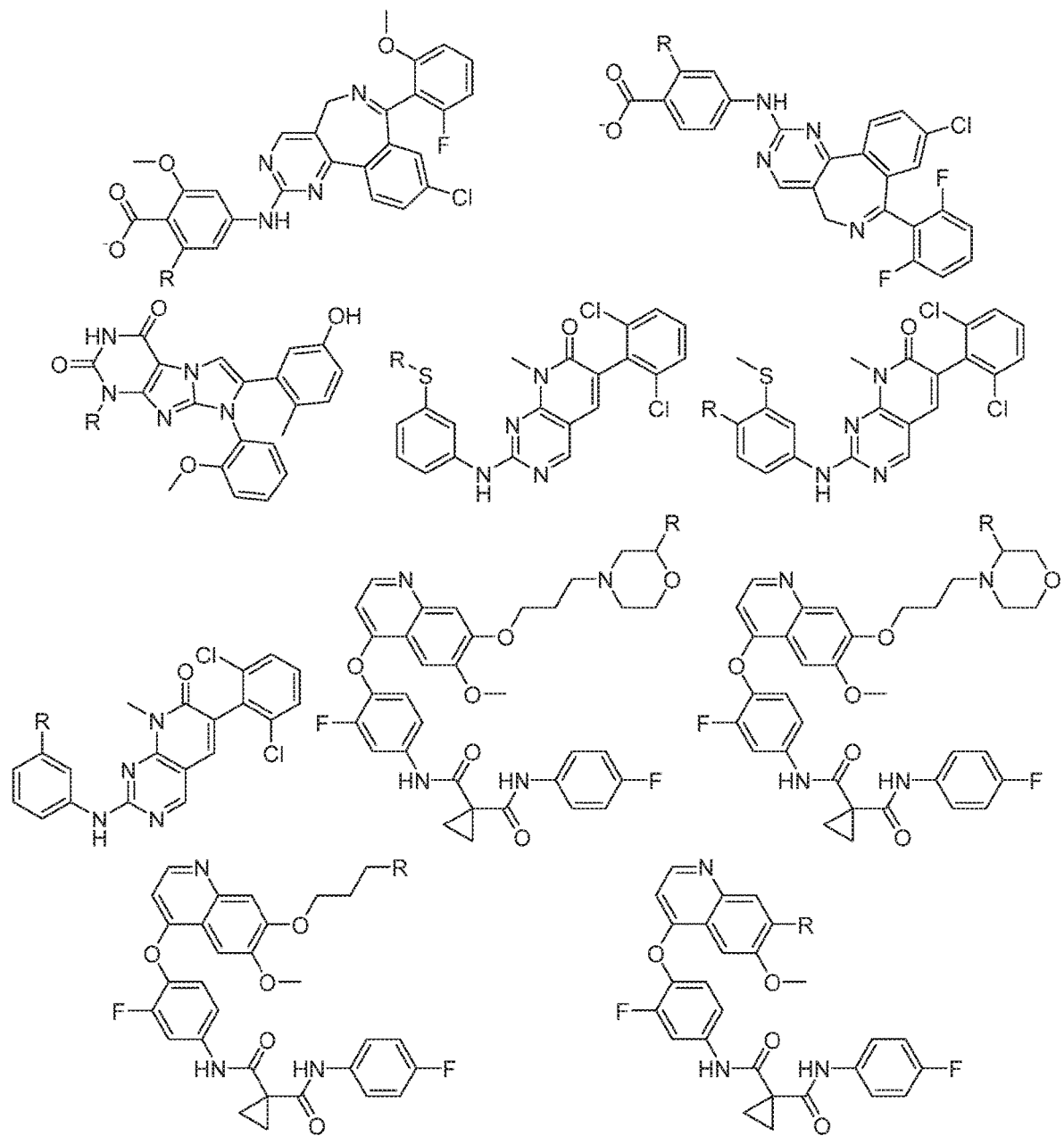

FIG. 8CCCC
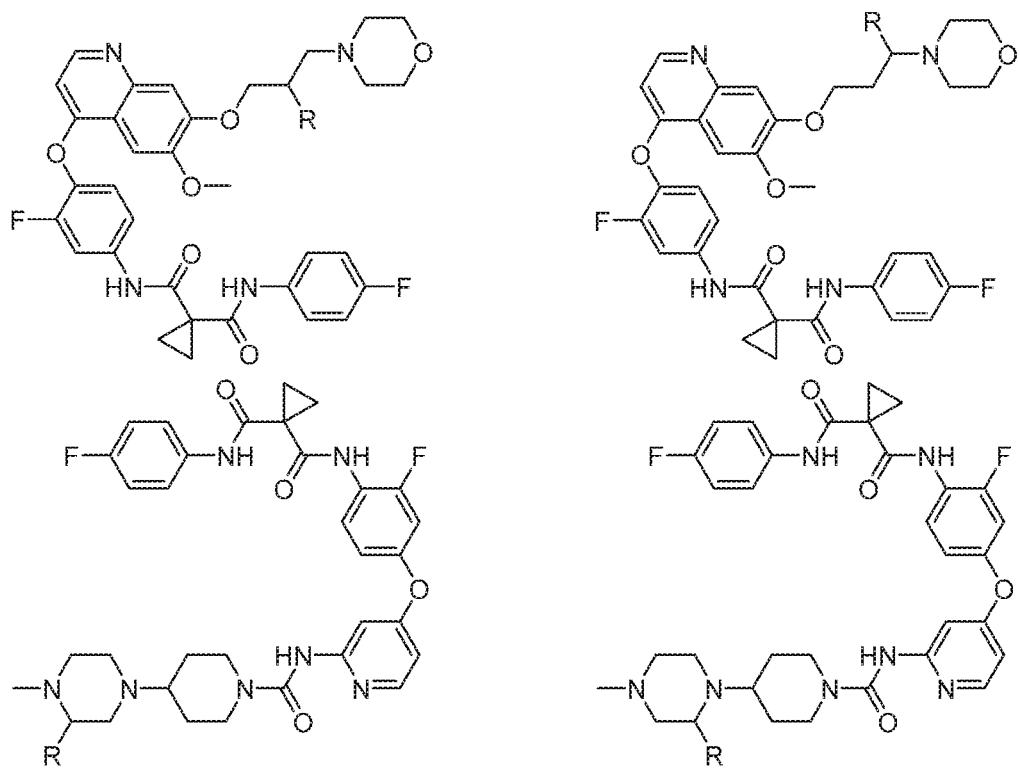
FIG. 8DDDD
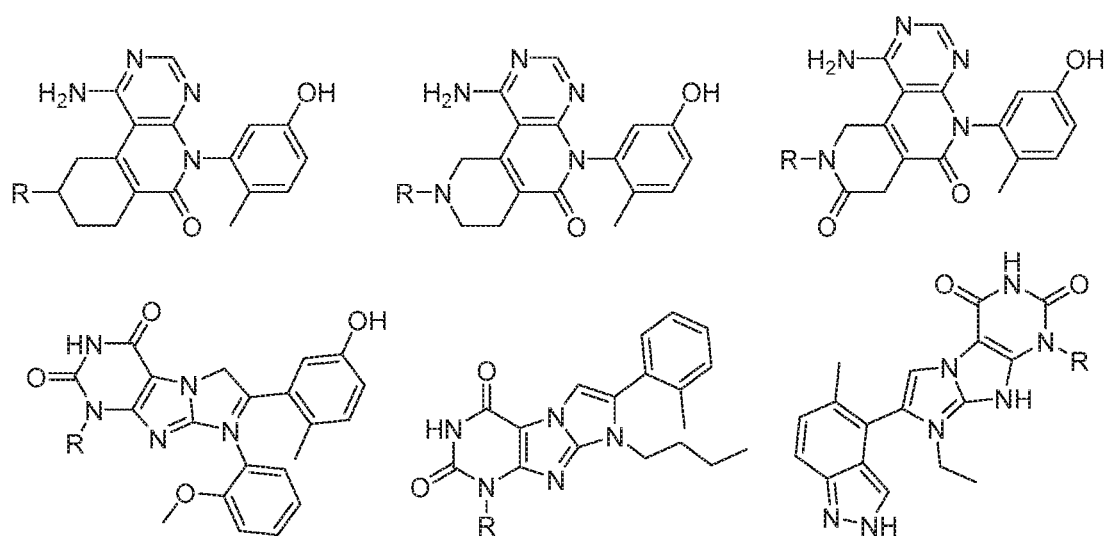

FIG. 8EEEE
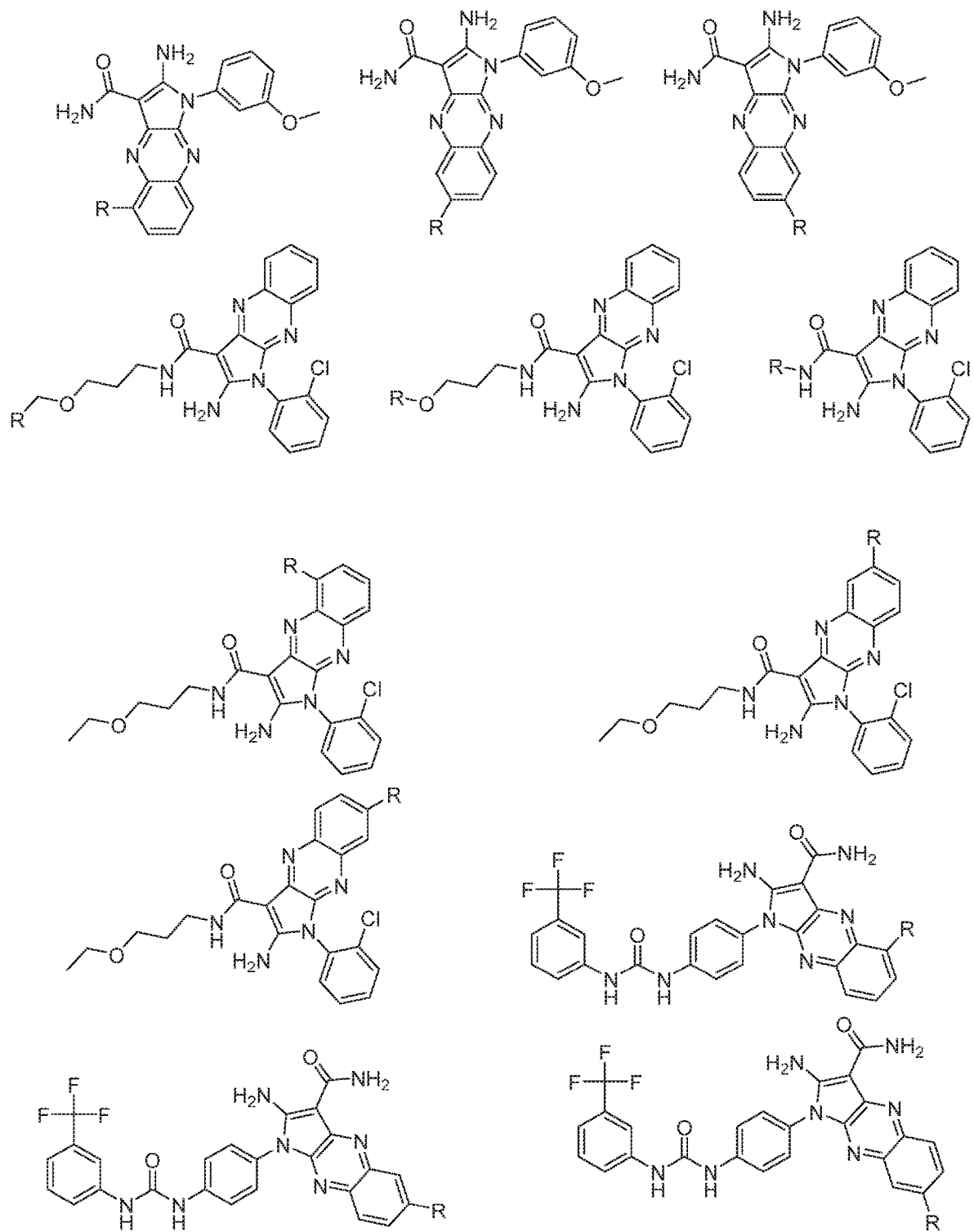

FIG. 8FFFF
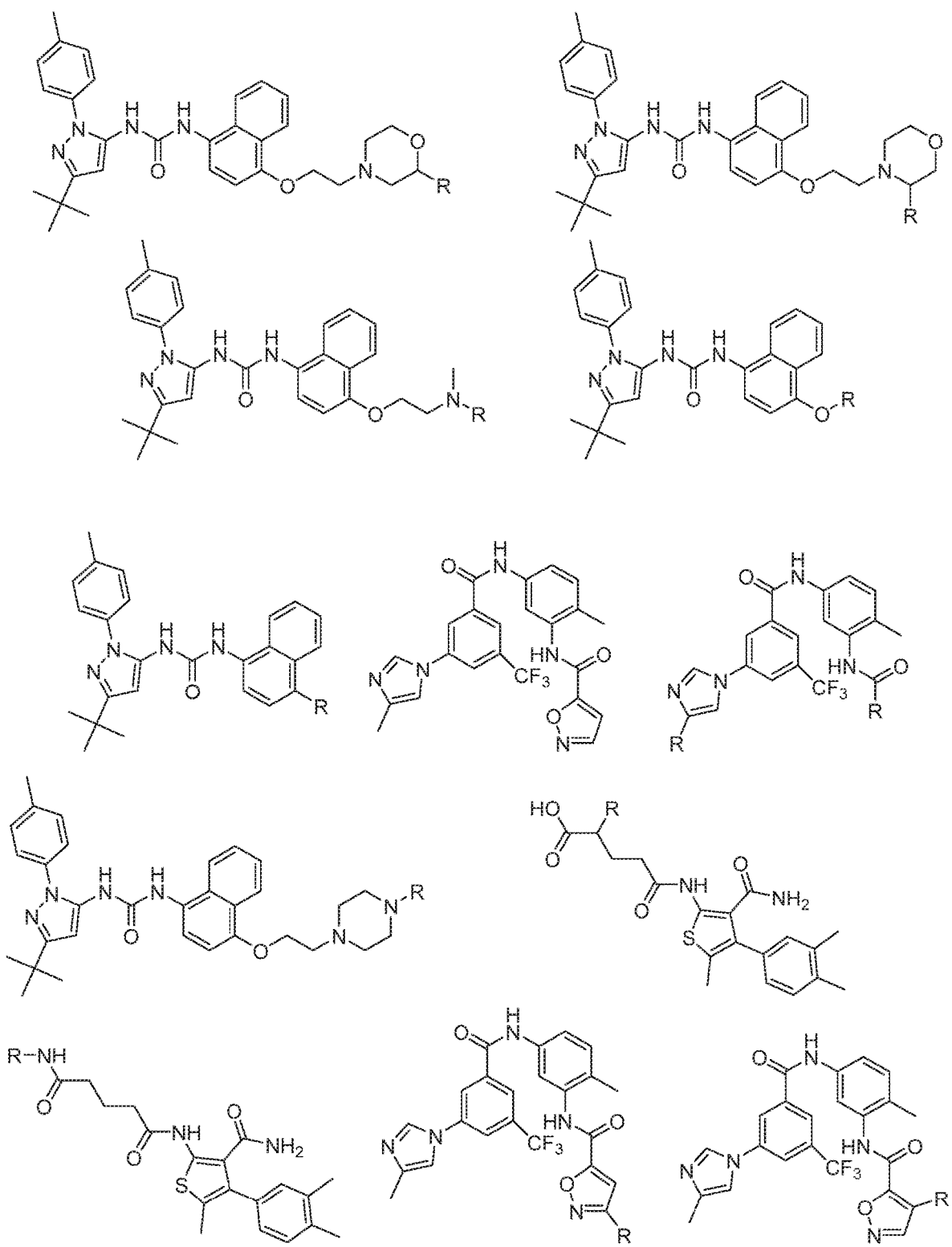

FIG. 8GGGG
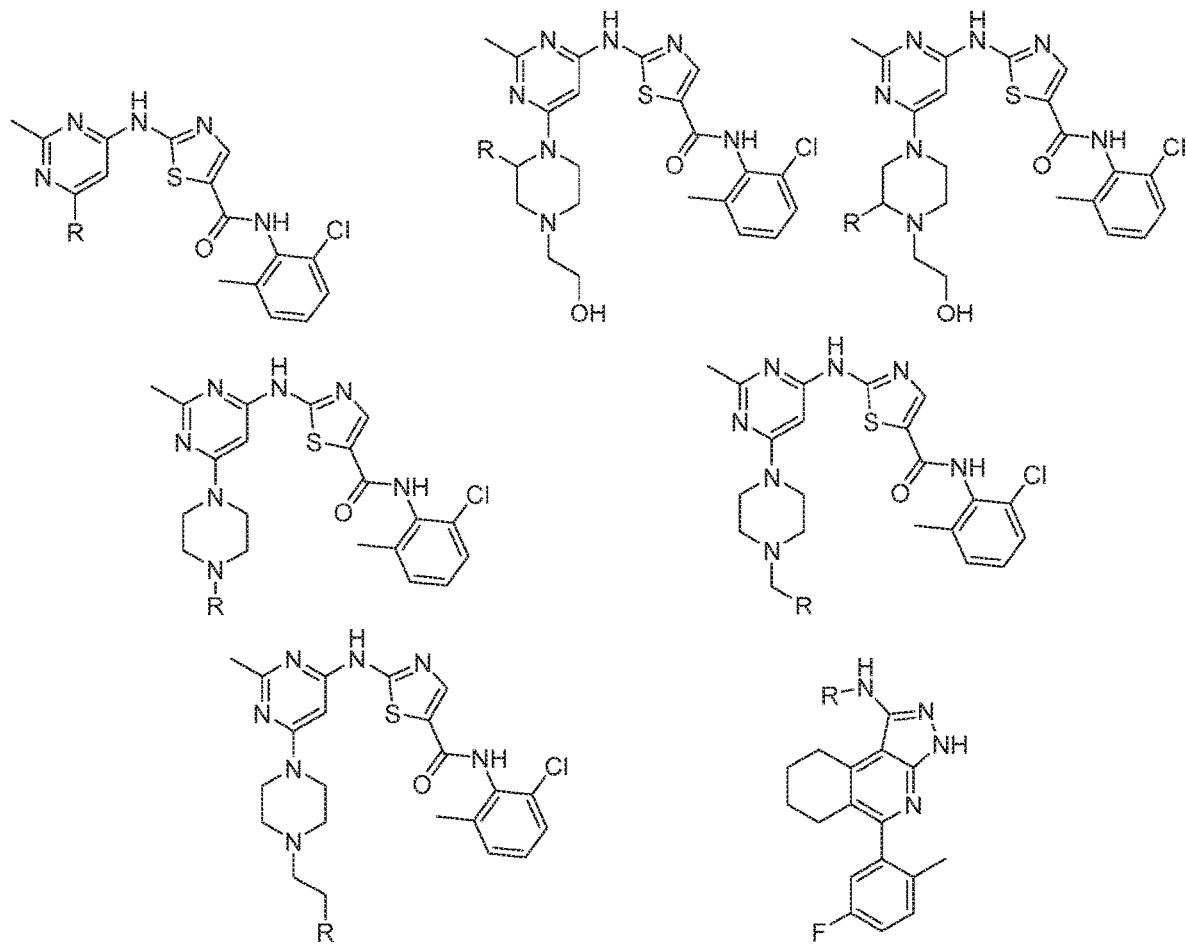
FIG. 8HHHH
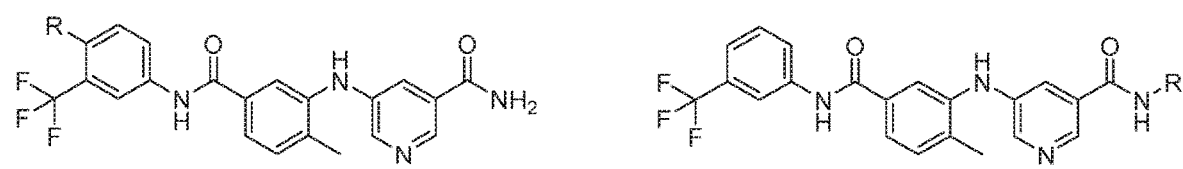
FIG. 8IIII
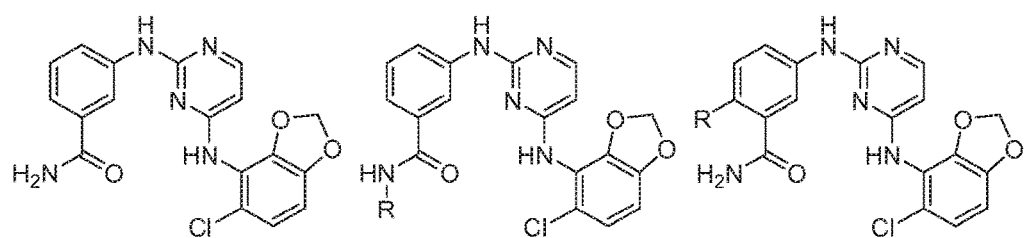

FIG. 8JJJJ
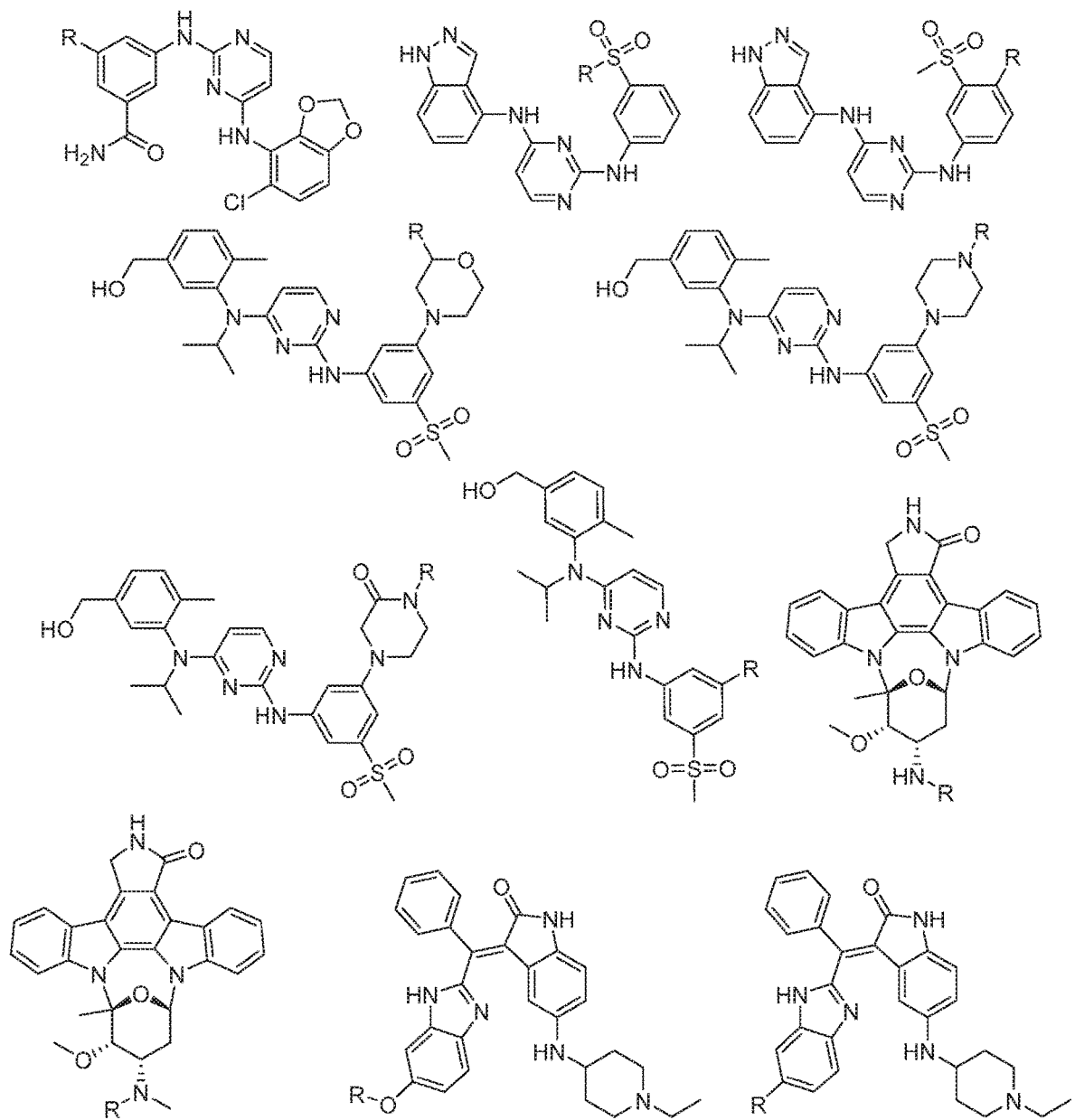

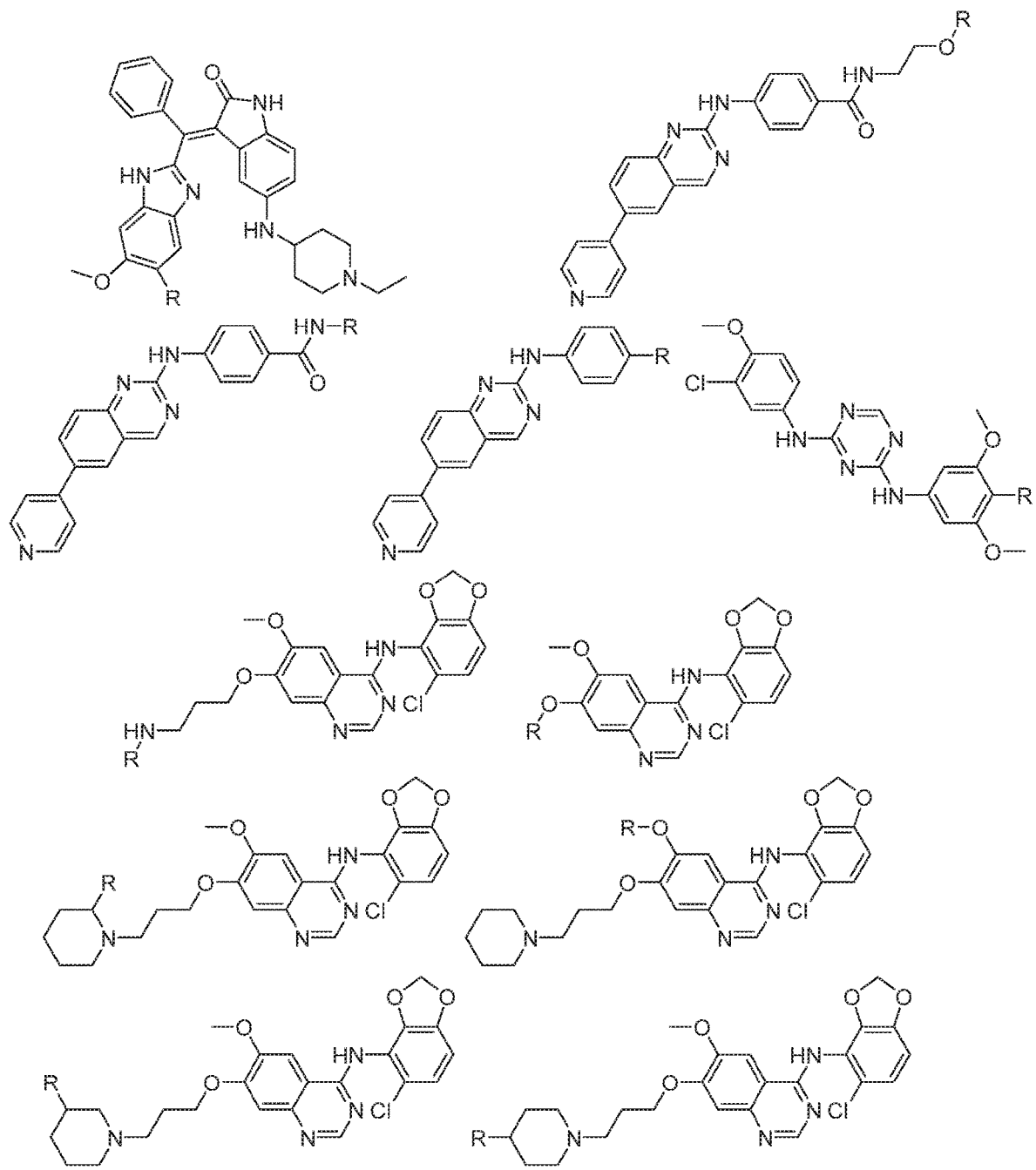
FIG. 8KKKK

FIG. 8LLLL
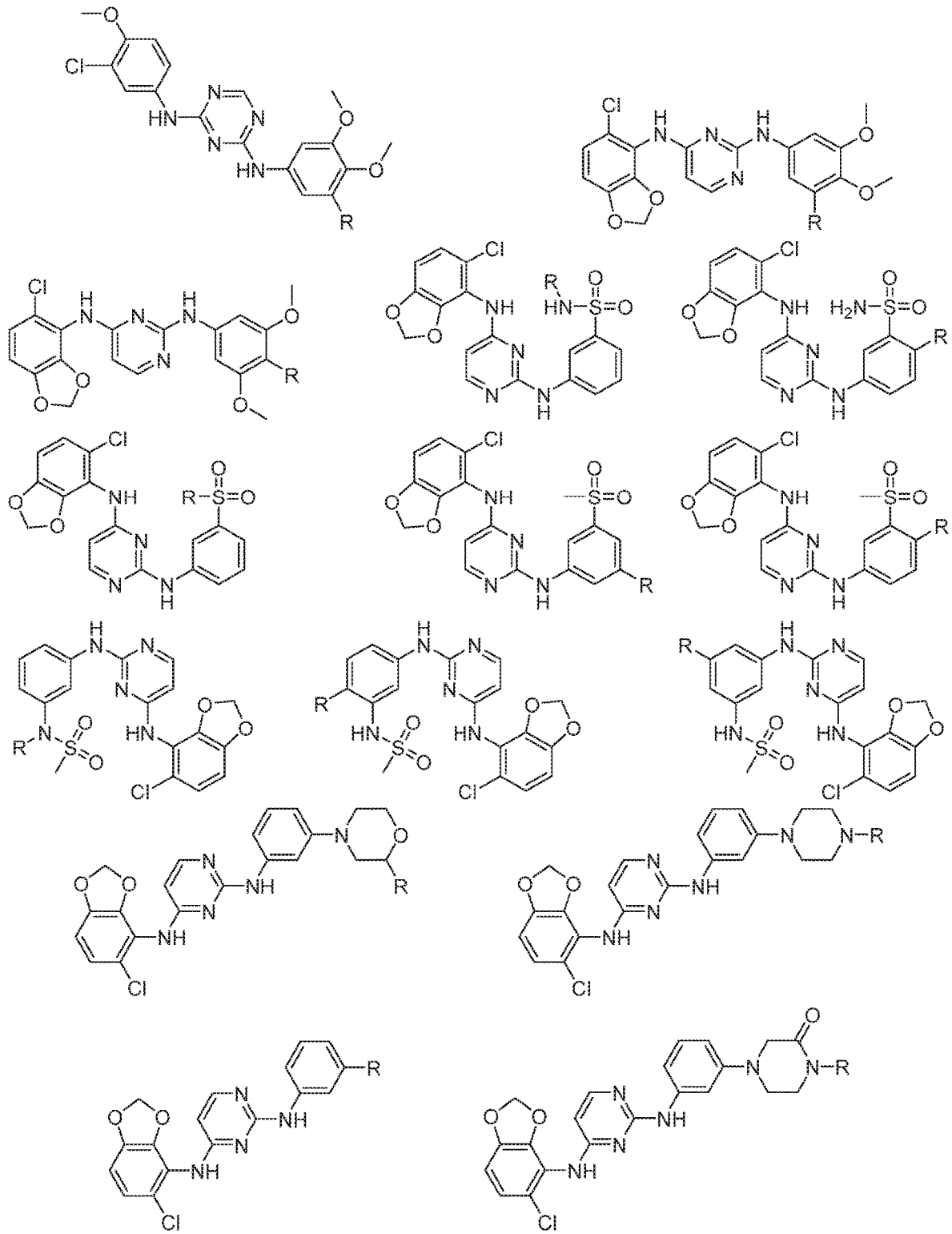

FIG. 8MMMM
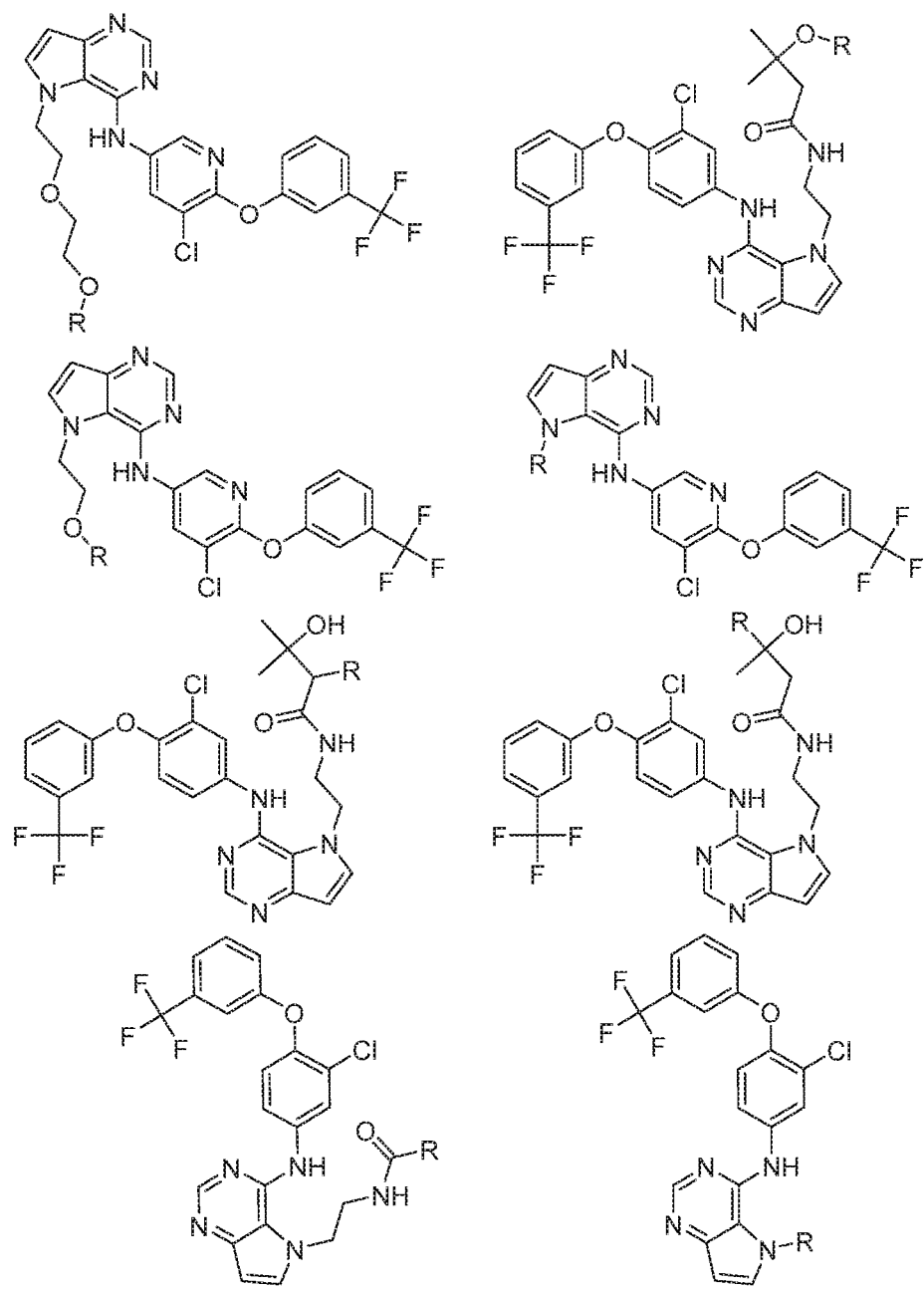

FIG. 8NNNN
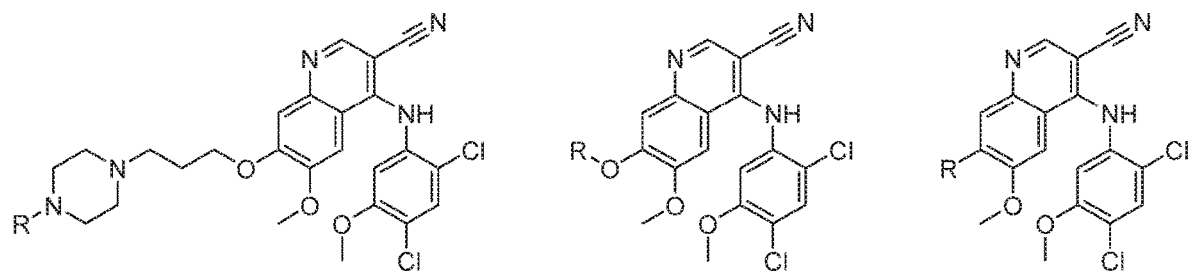
FIG. 8OOOO
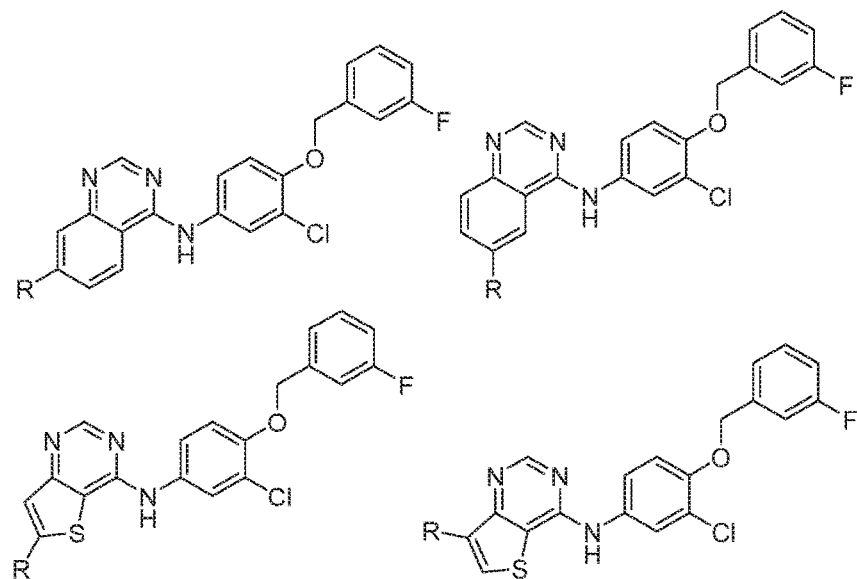
FIG. 8PPPP
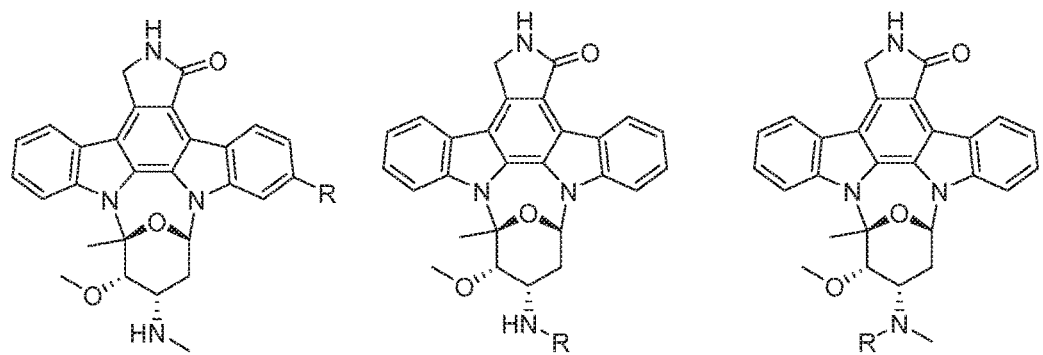

FIG. 8QQQQ
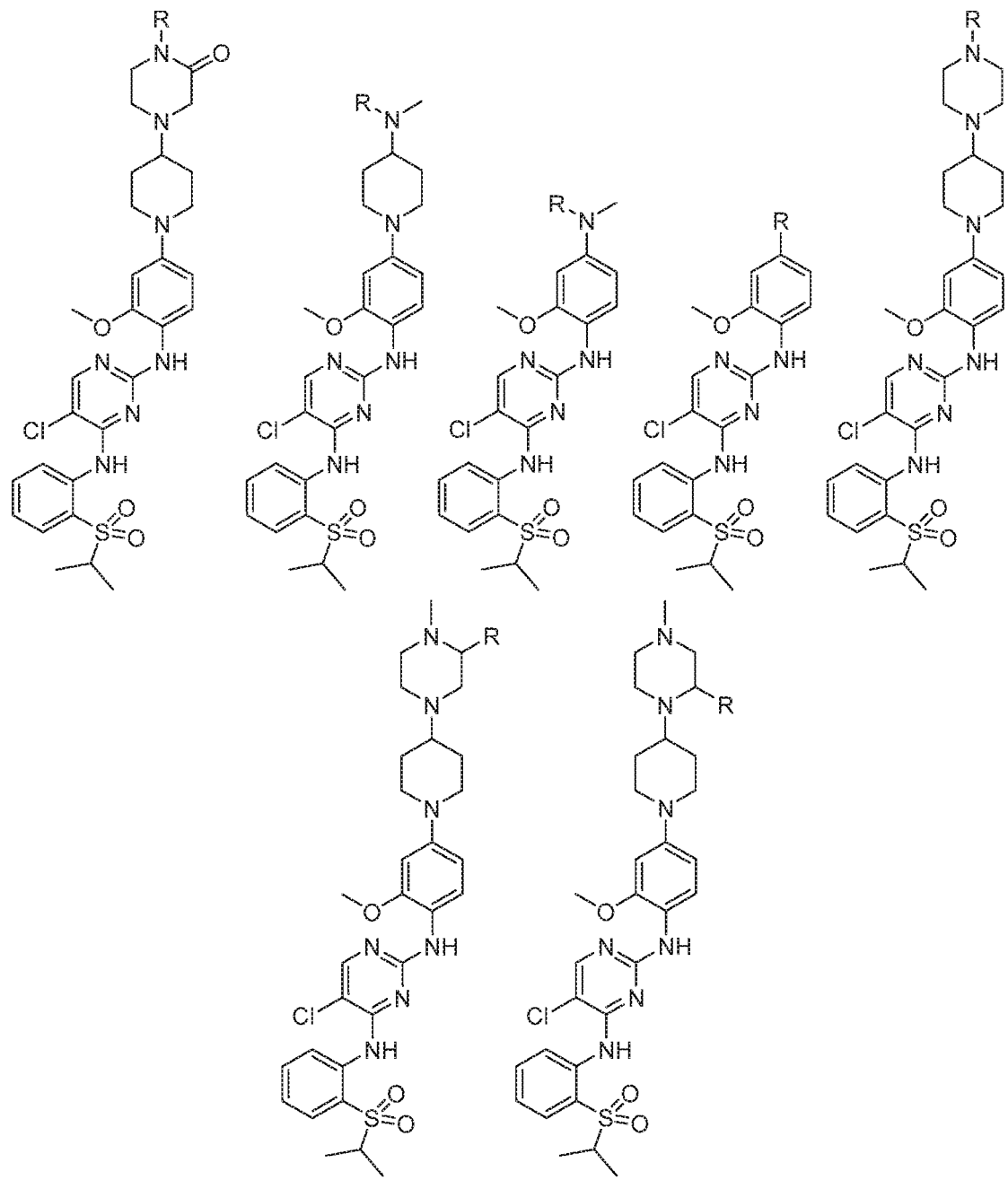

FIG. 8RRRR
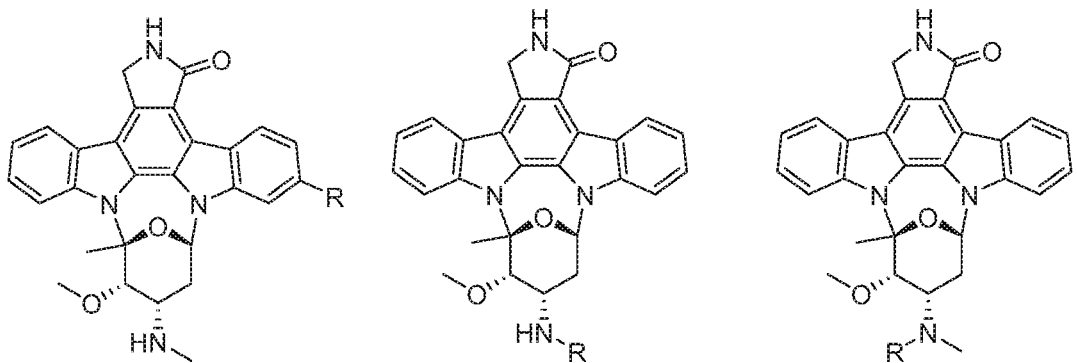
FIG. 8SSSS
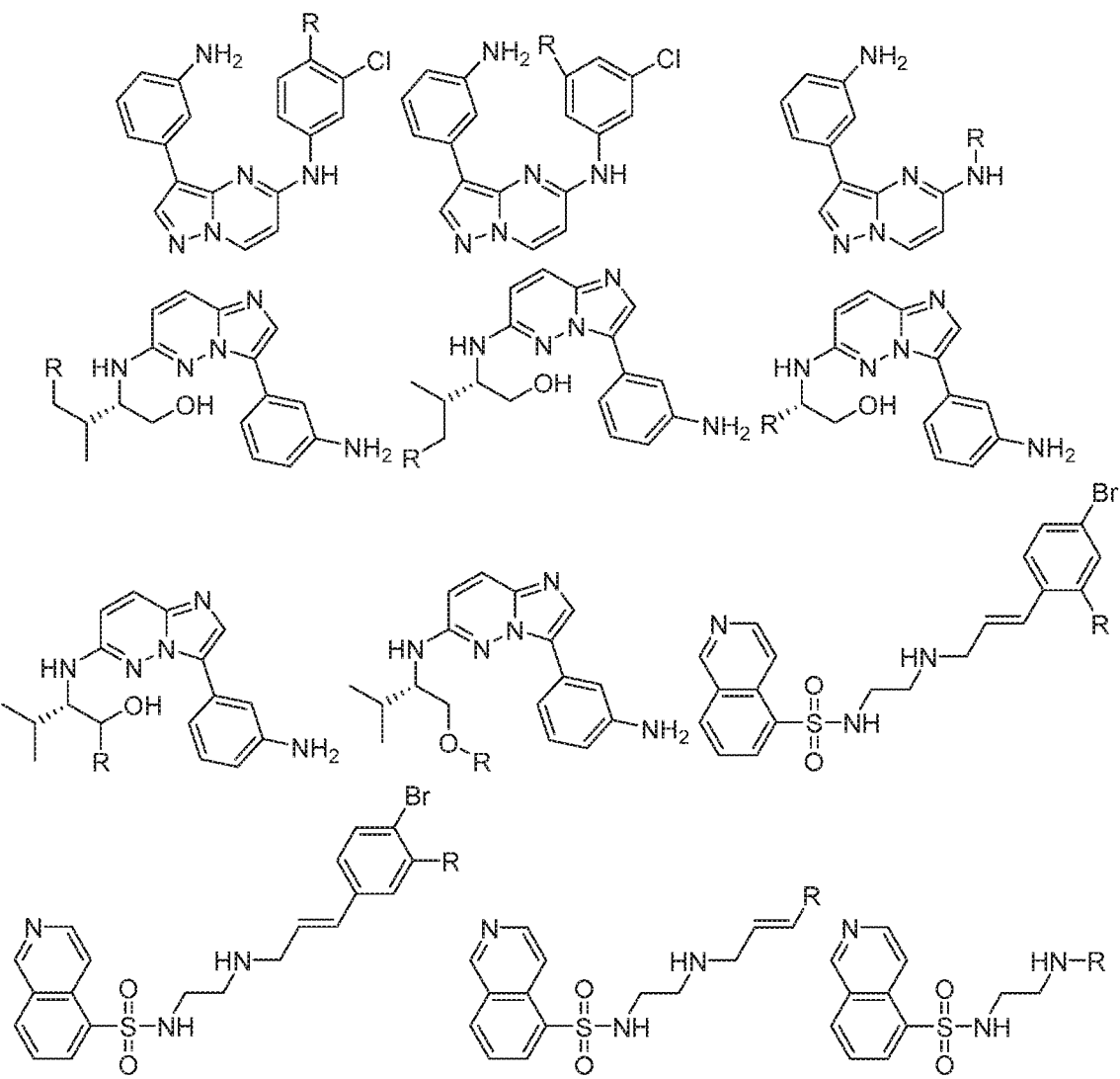

FIG. 8TTTT
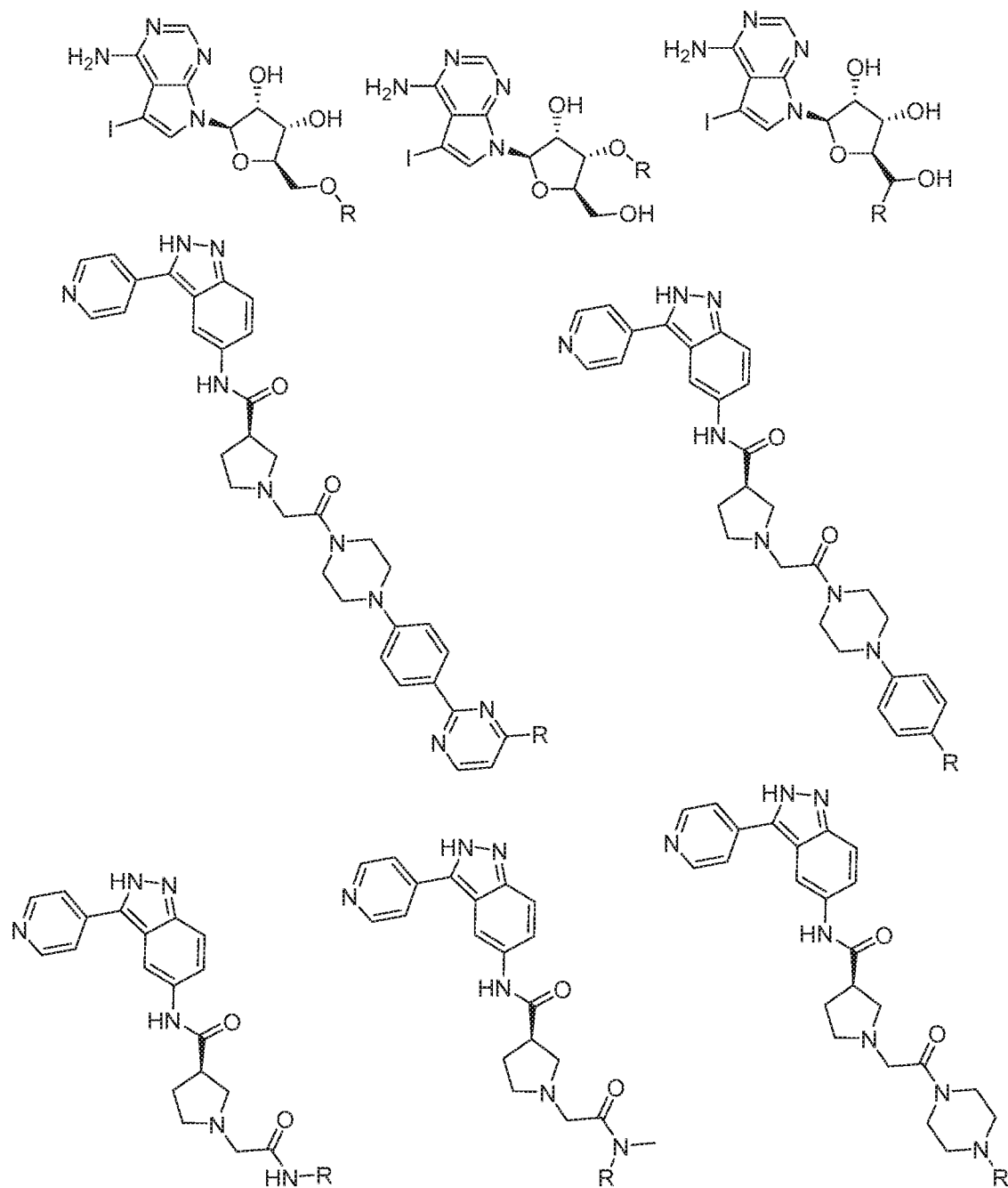

FIG. 8UUUU
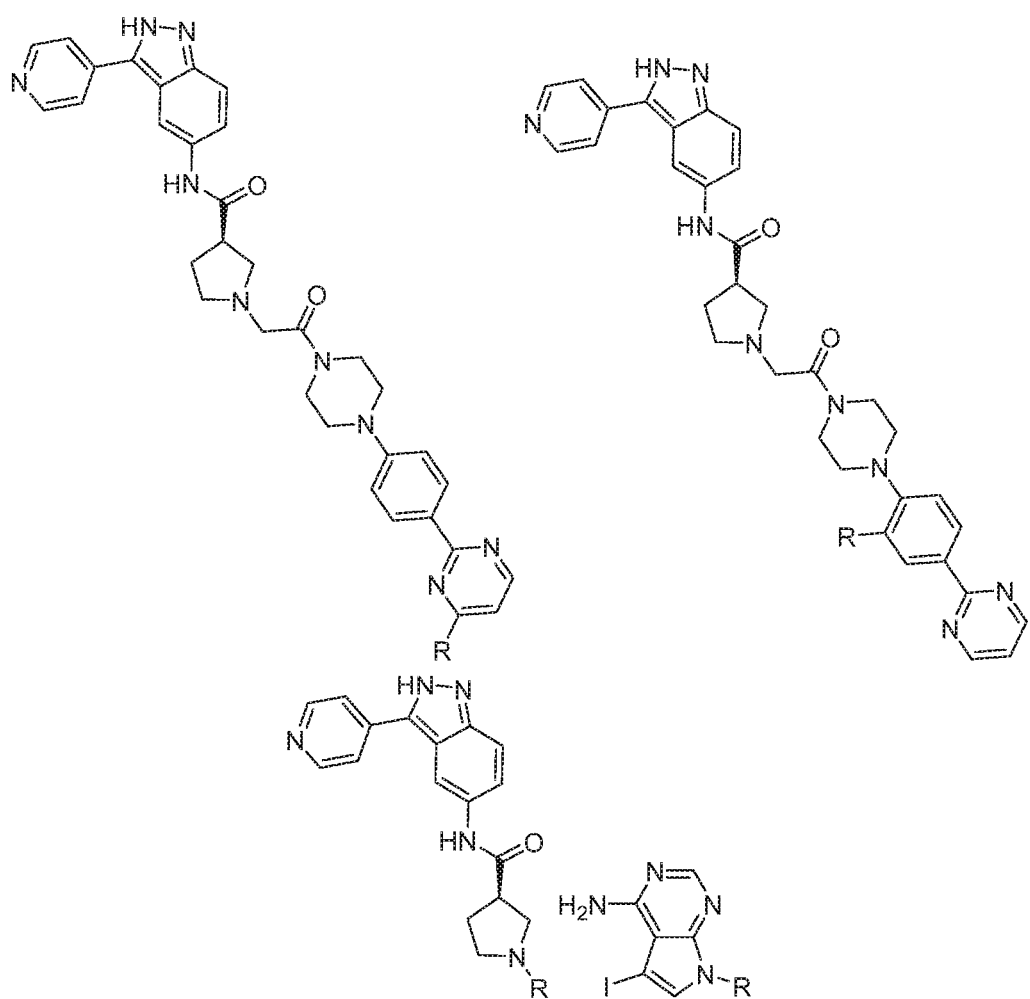

FIG. 8VVVV
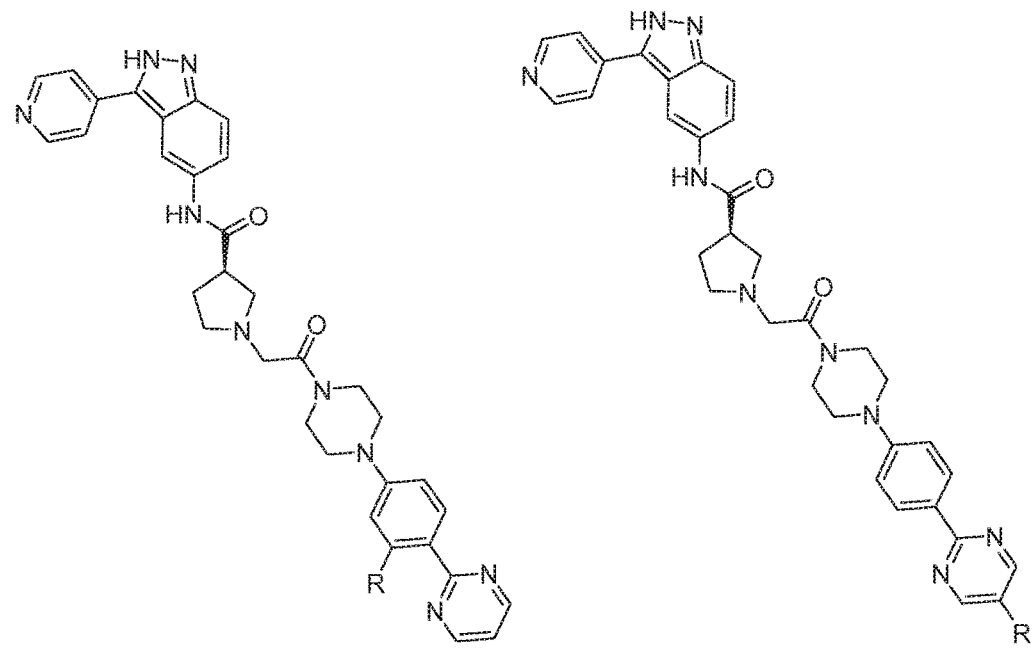
FIG. 8WWWW
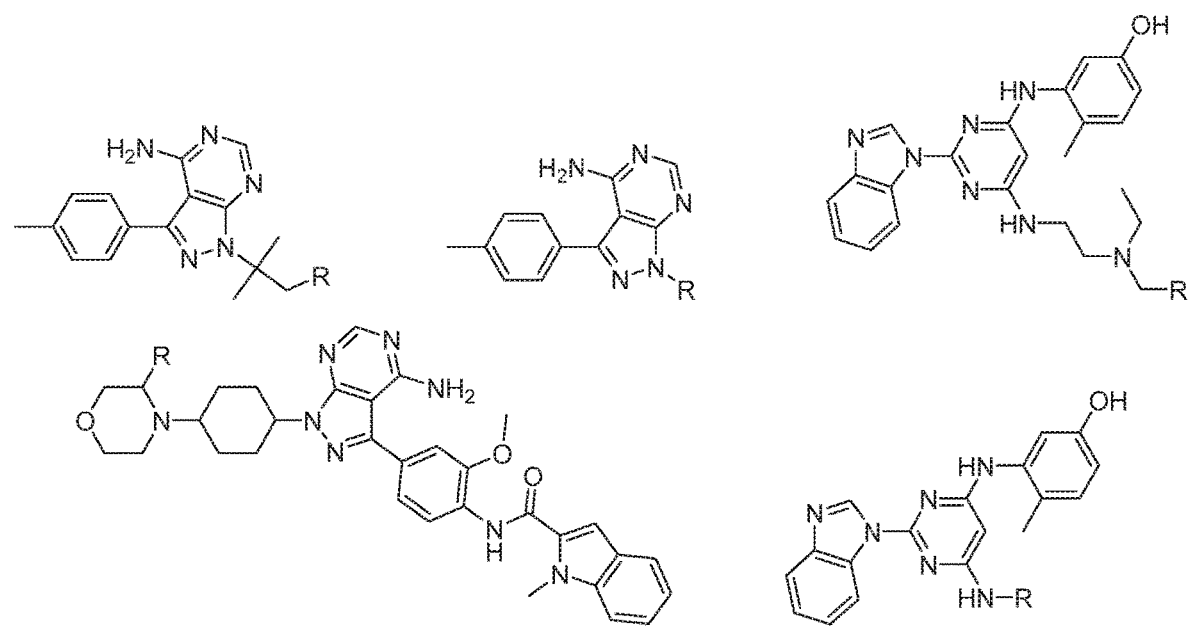

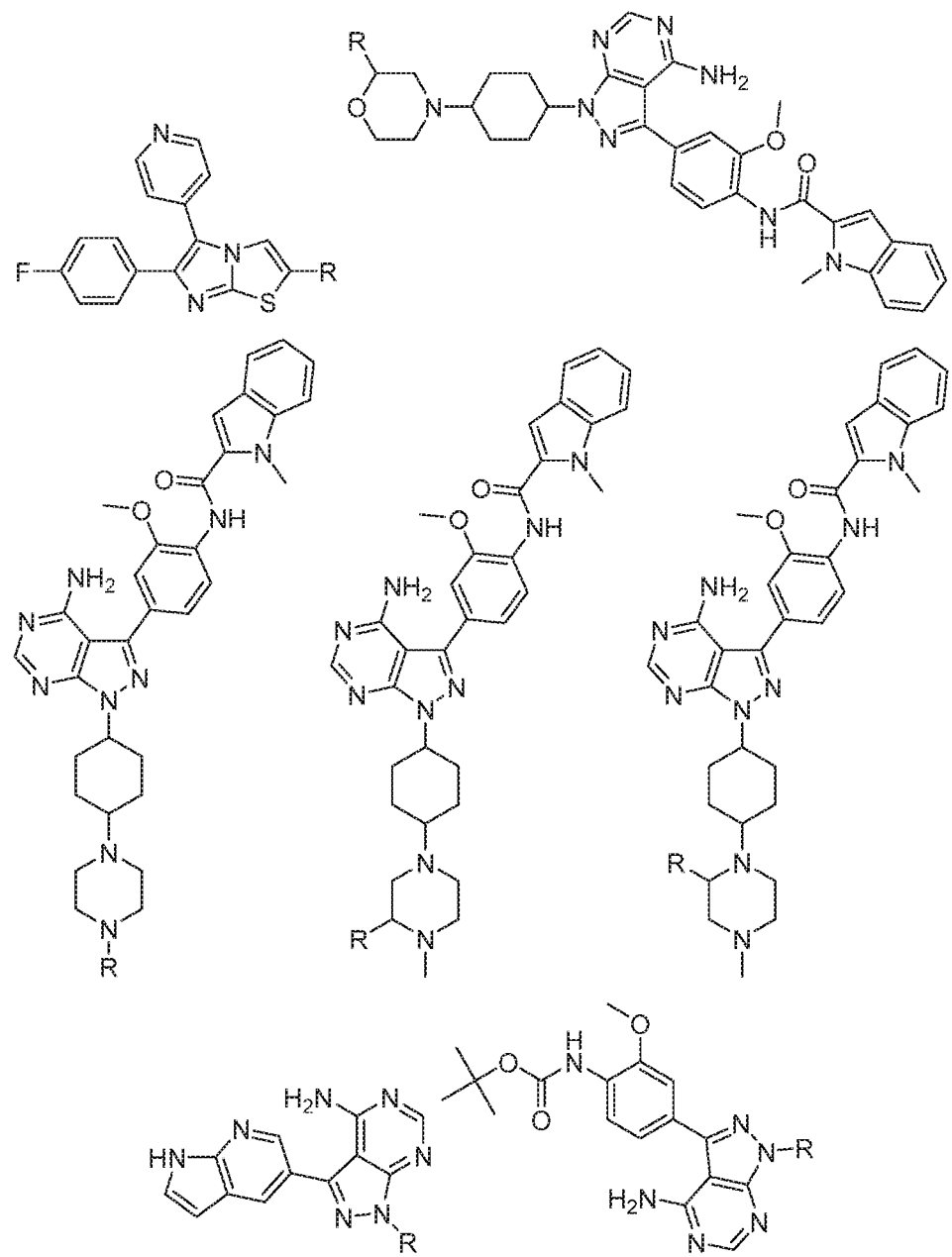
FIG. 8XXXX

FIG. 8YYYY
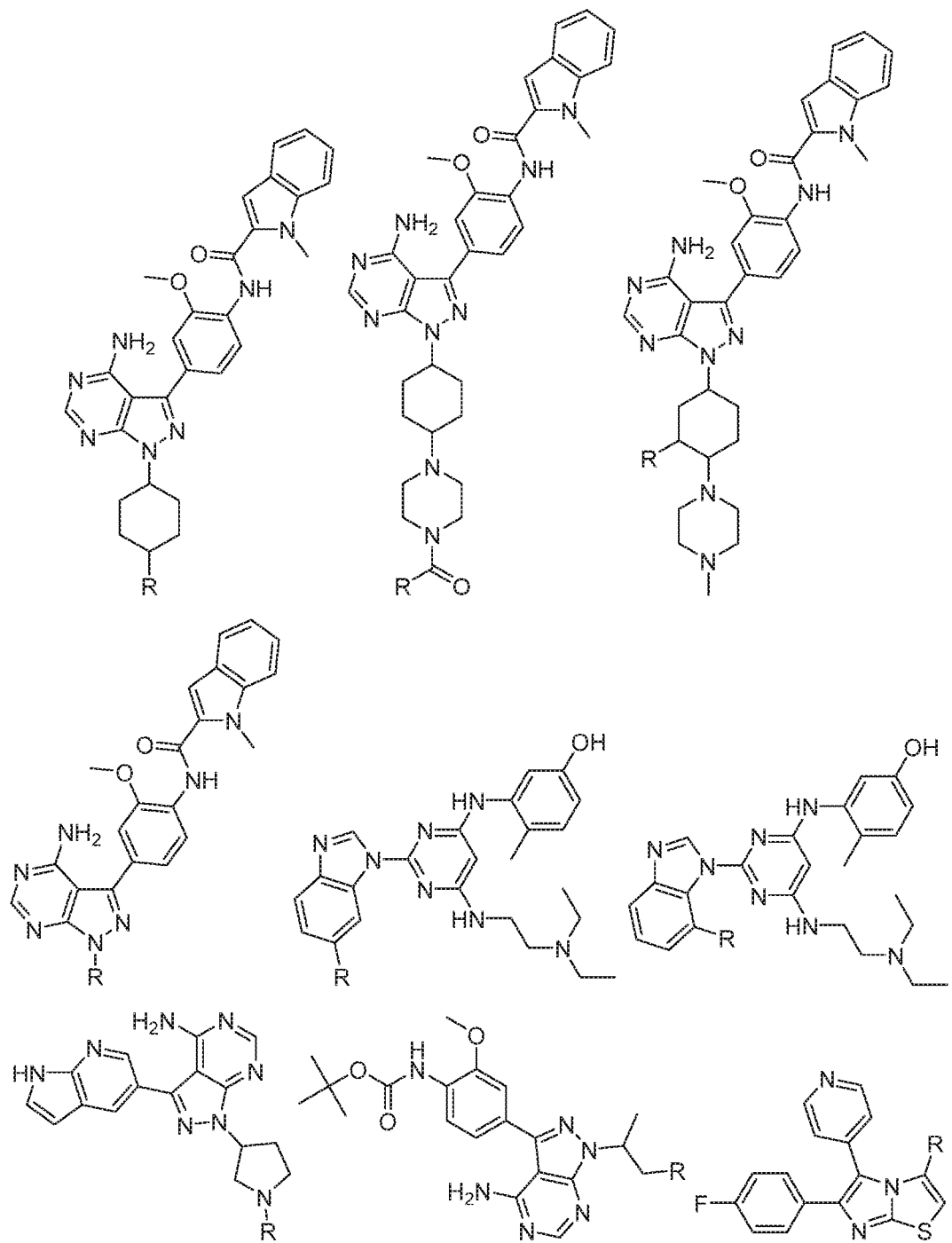

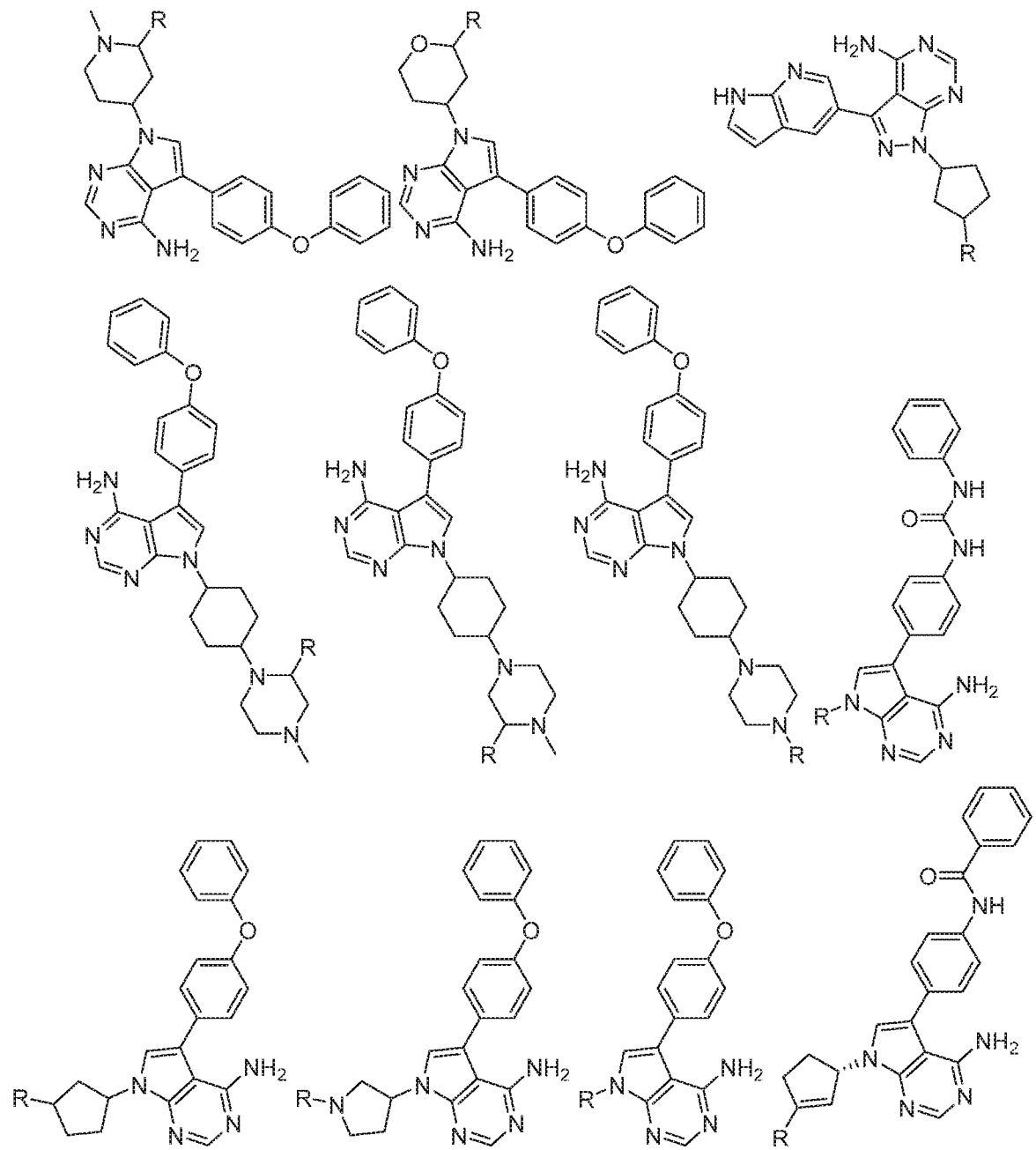
FIG. 8ZZZZ

FIG. 8AAAAA
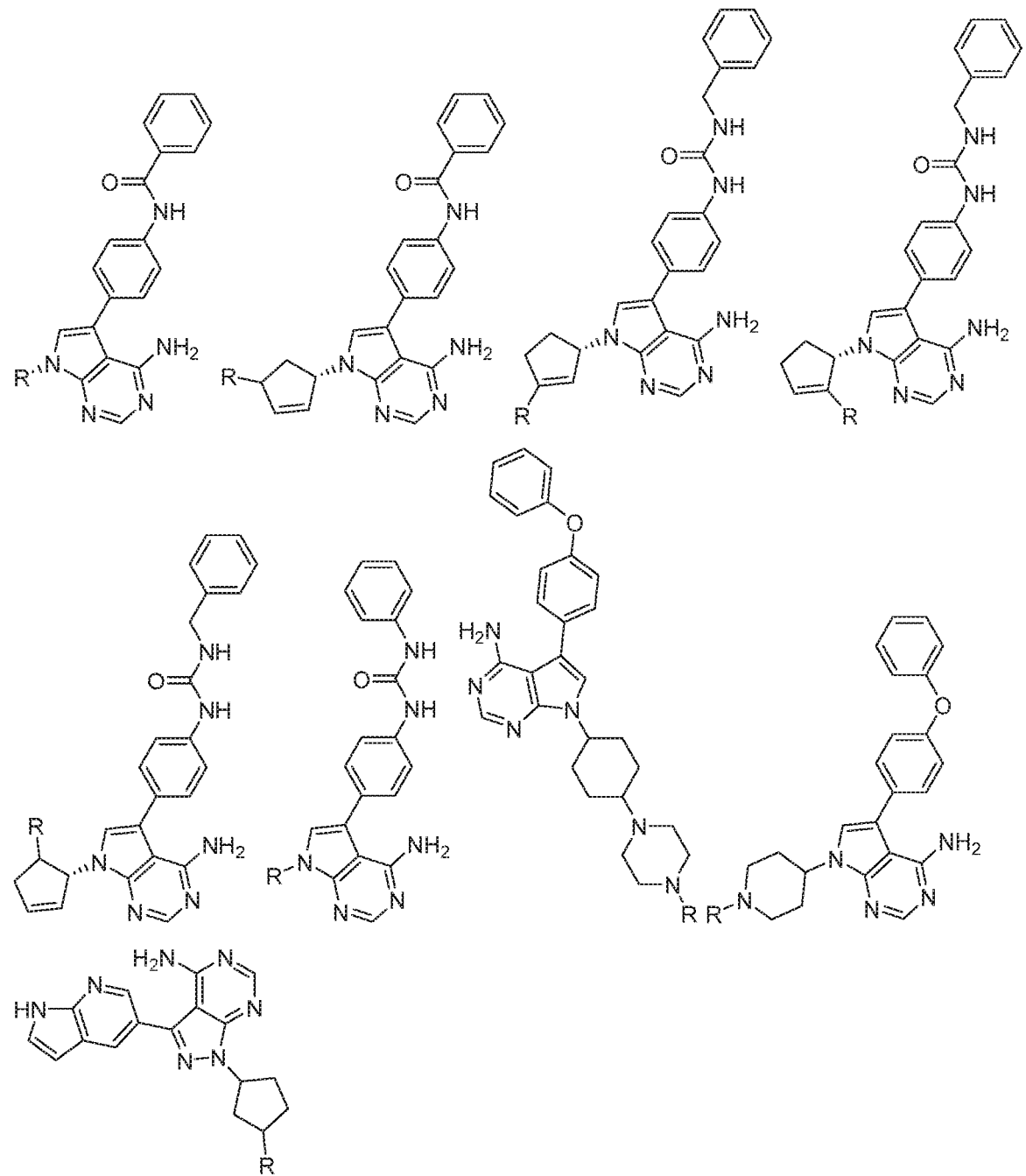

FIG. 8BBBBB
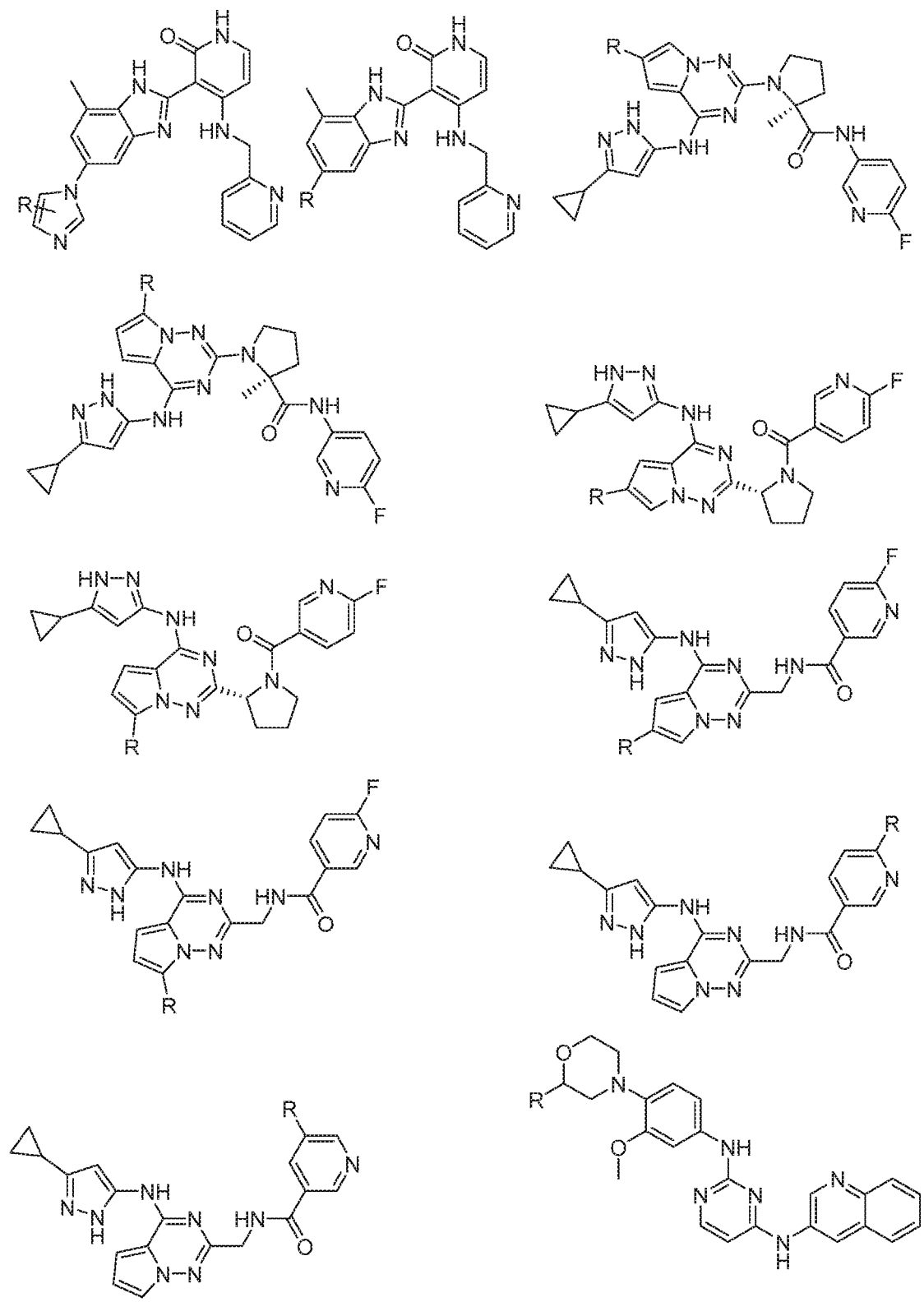

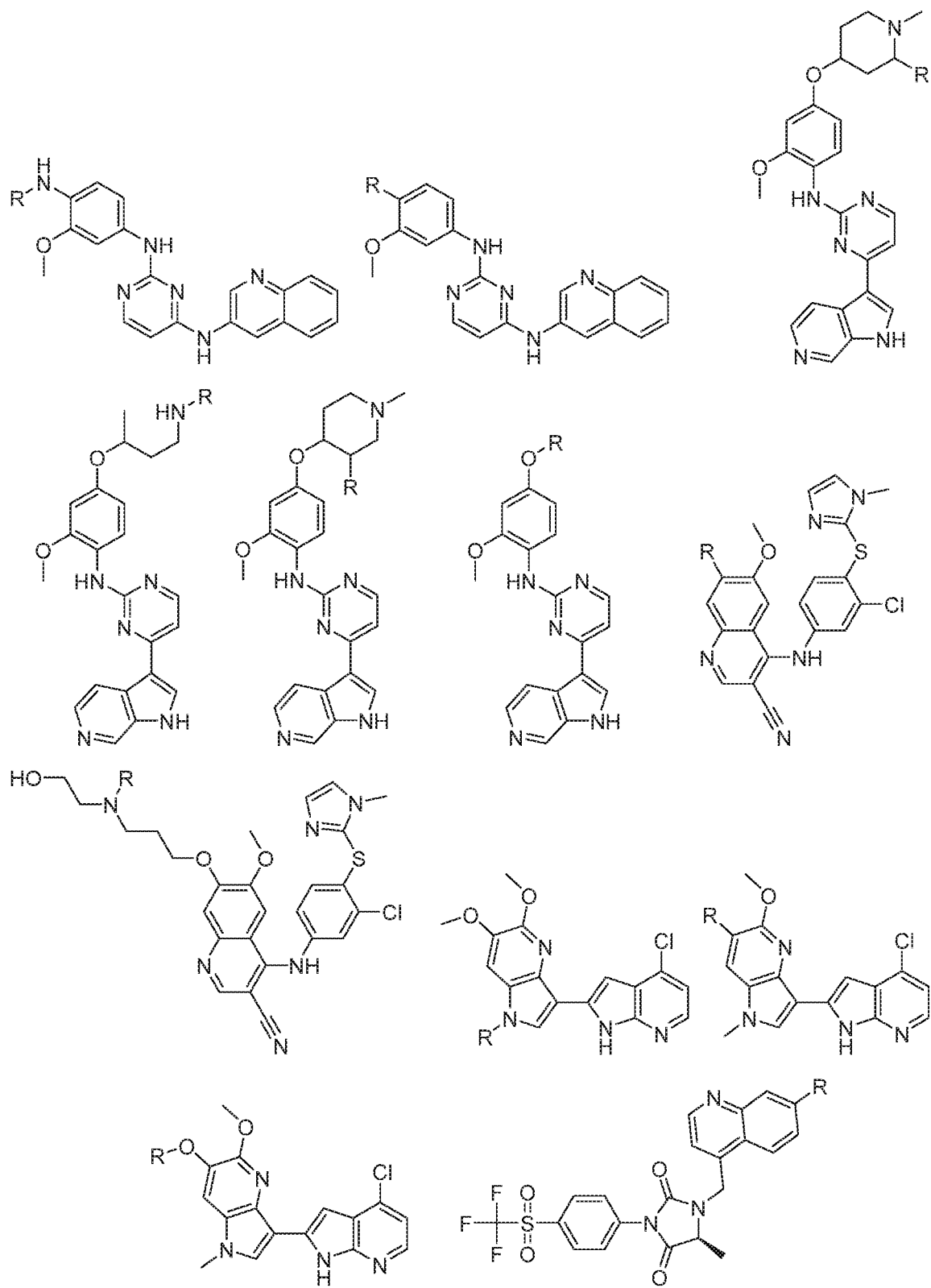
FIG. 8CCCCC

FIG. 8DDDDD
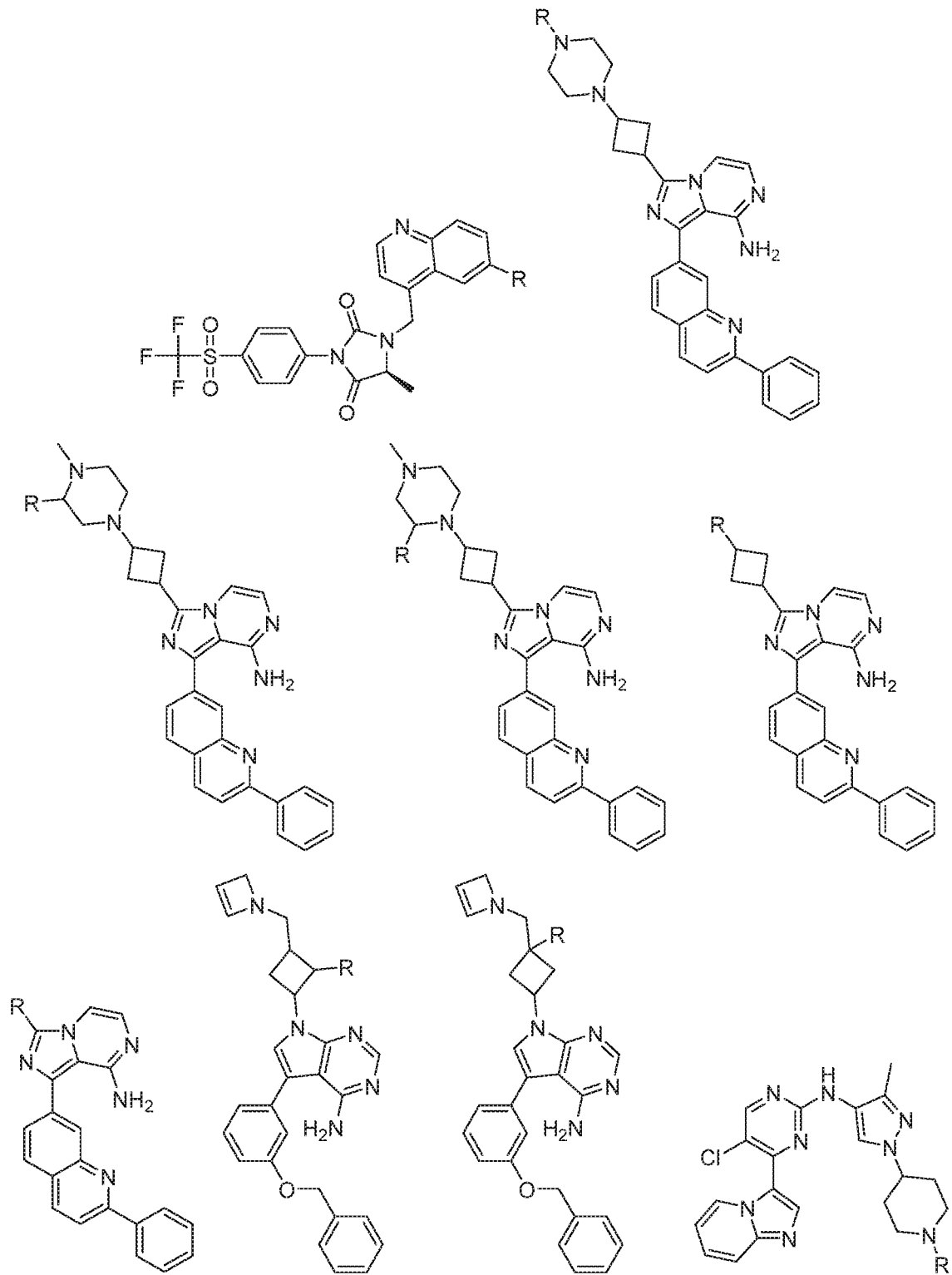

FIG. 8EEEEE
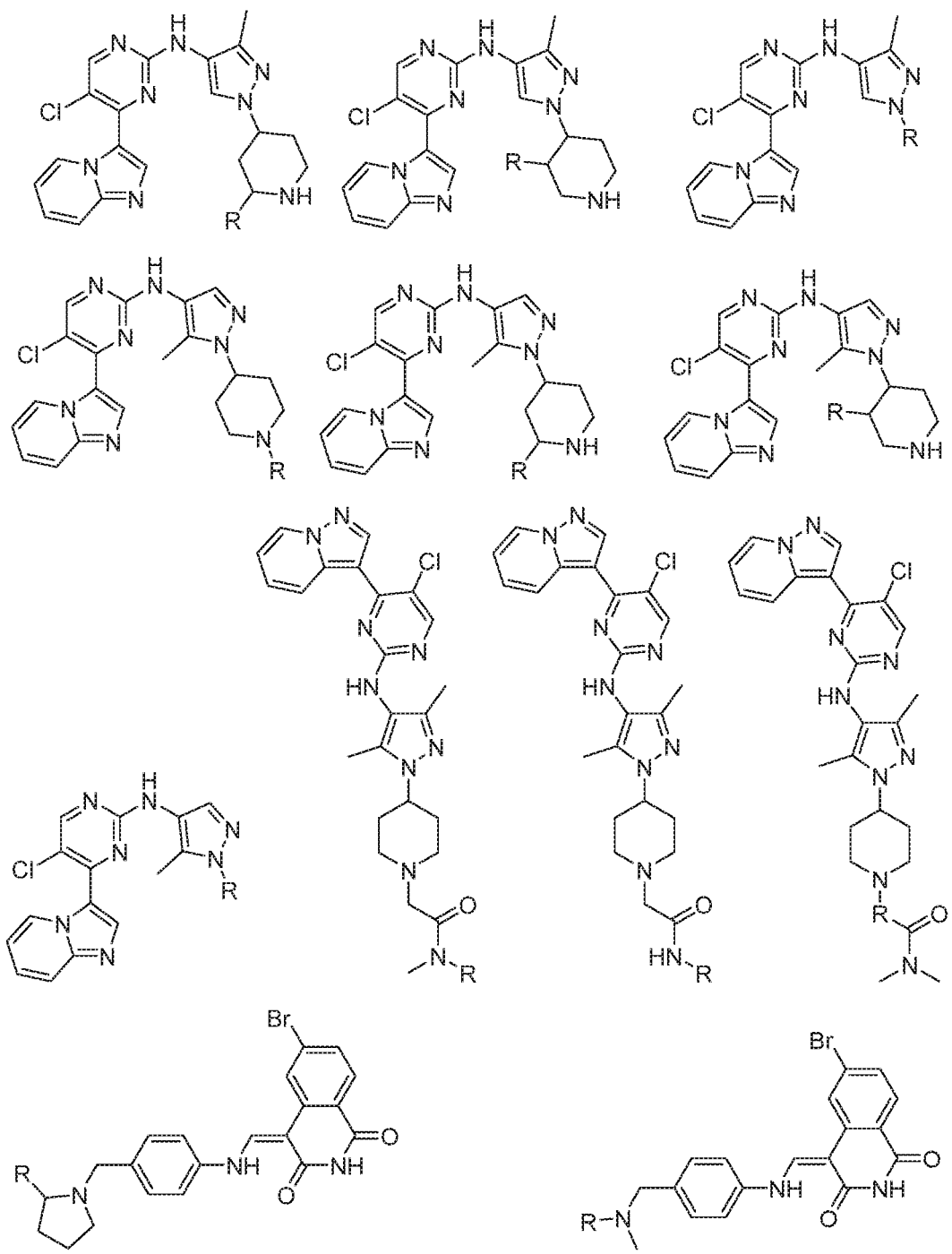

FIG. 8FFFFF
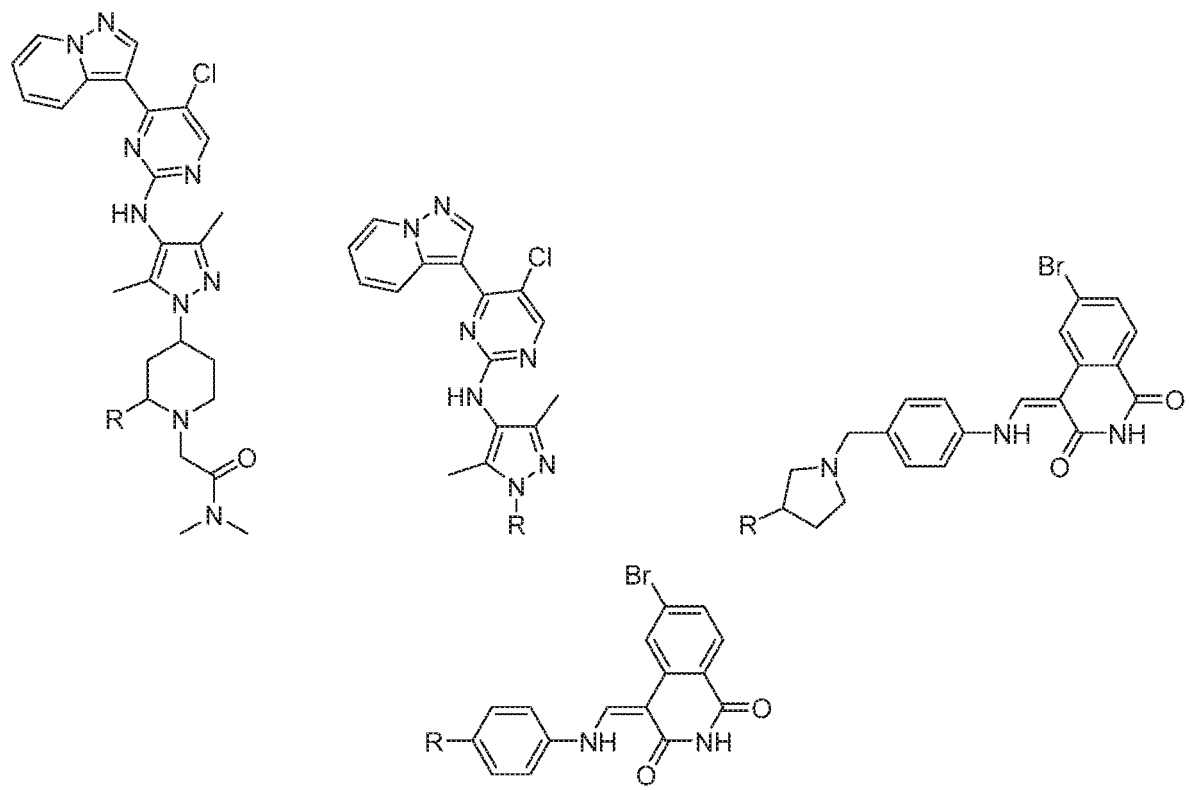
FIG. 8GGGGG
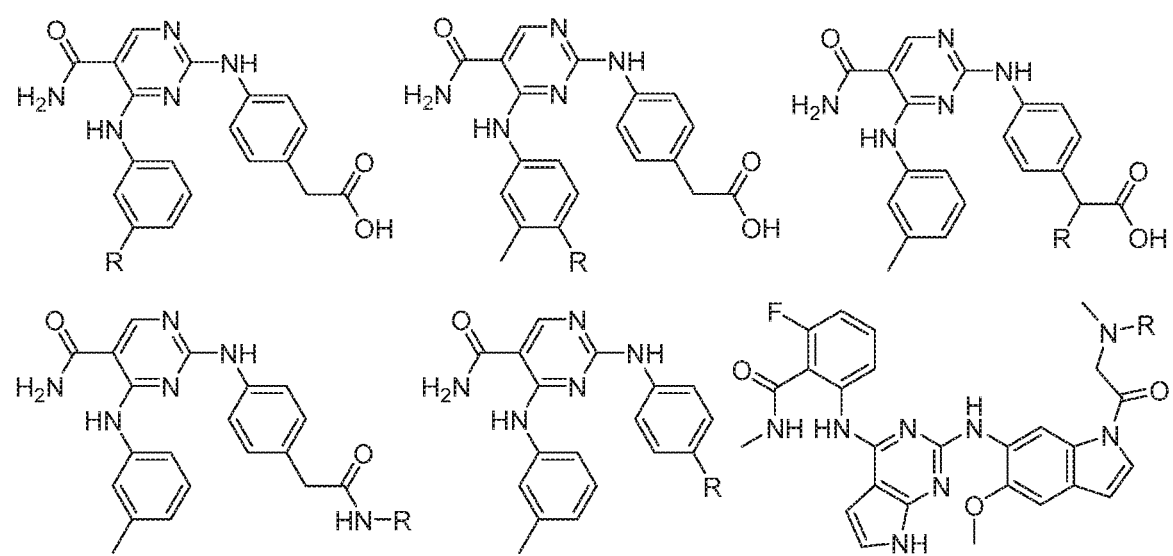

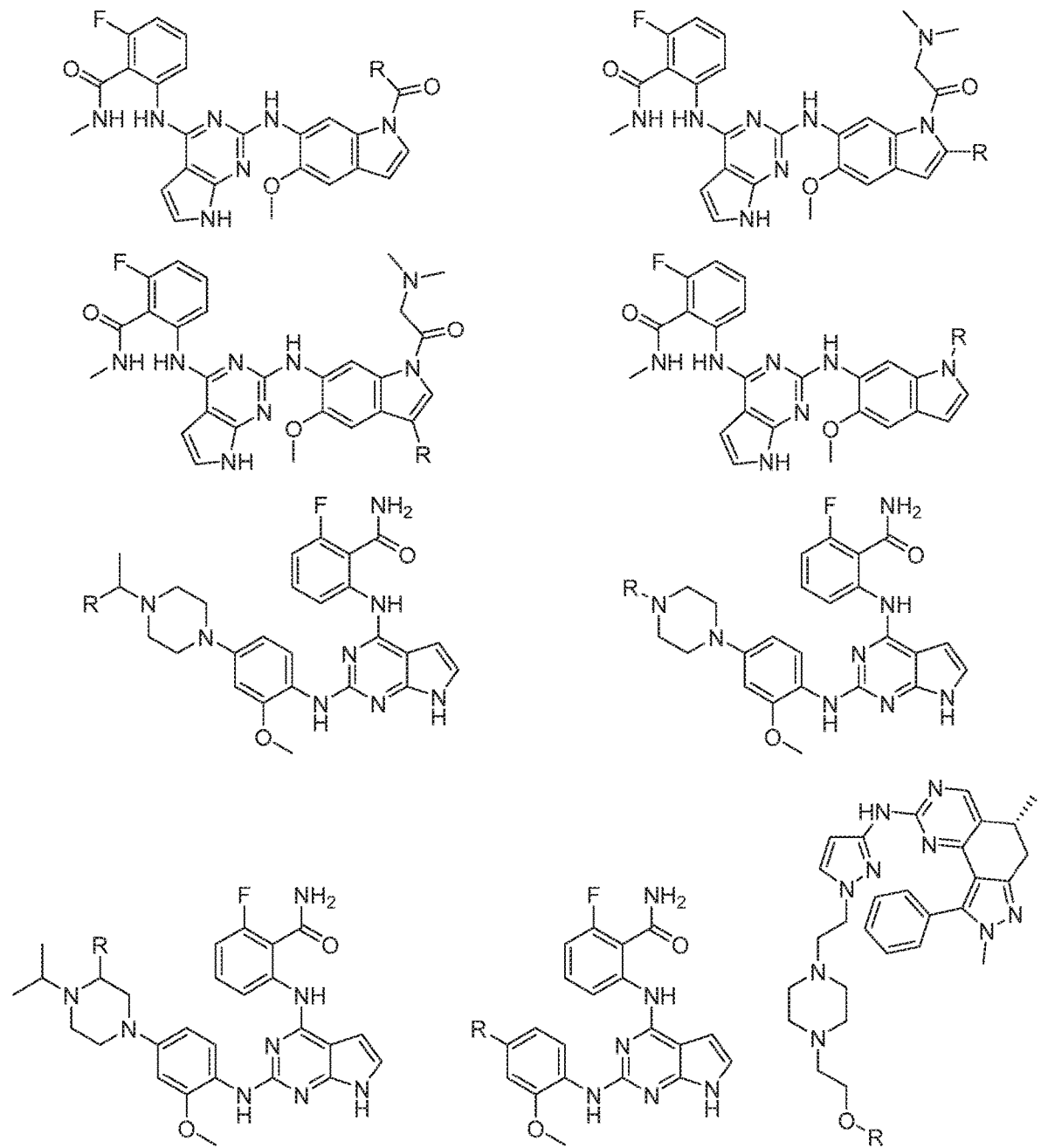
FIG. 8HHHHH

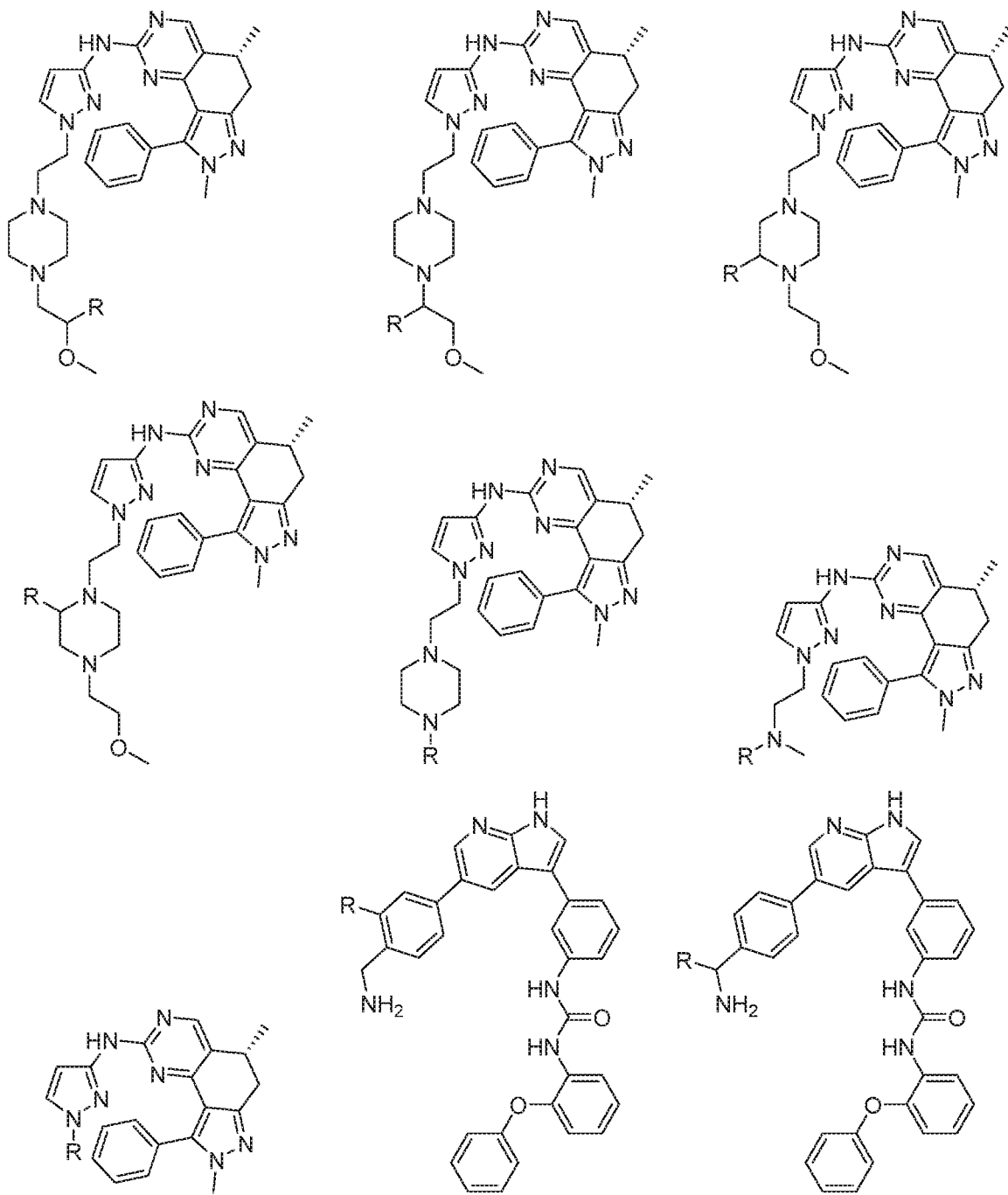
FIG. 8IIIII

FIG. 8JJJJJ
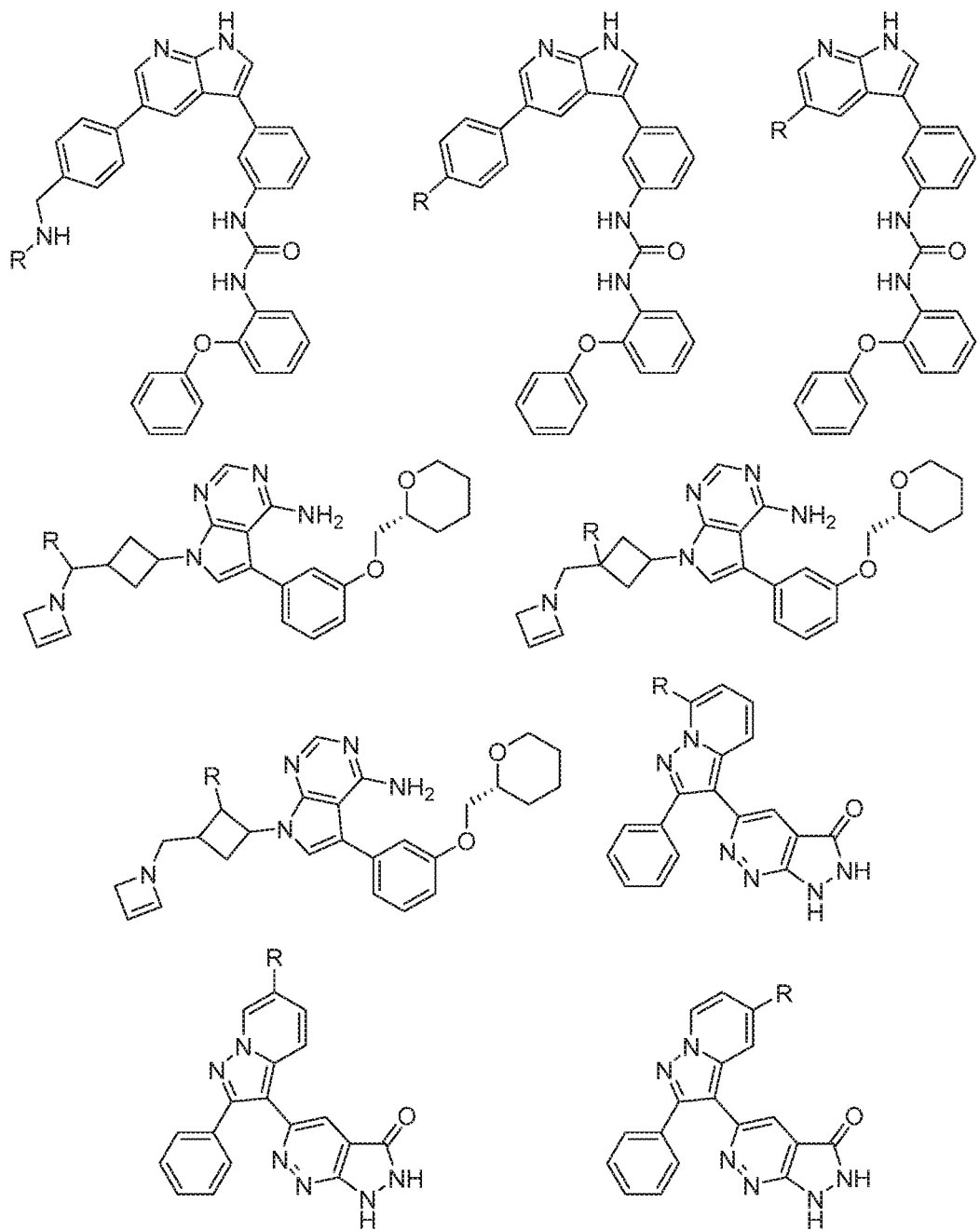

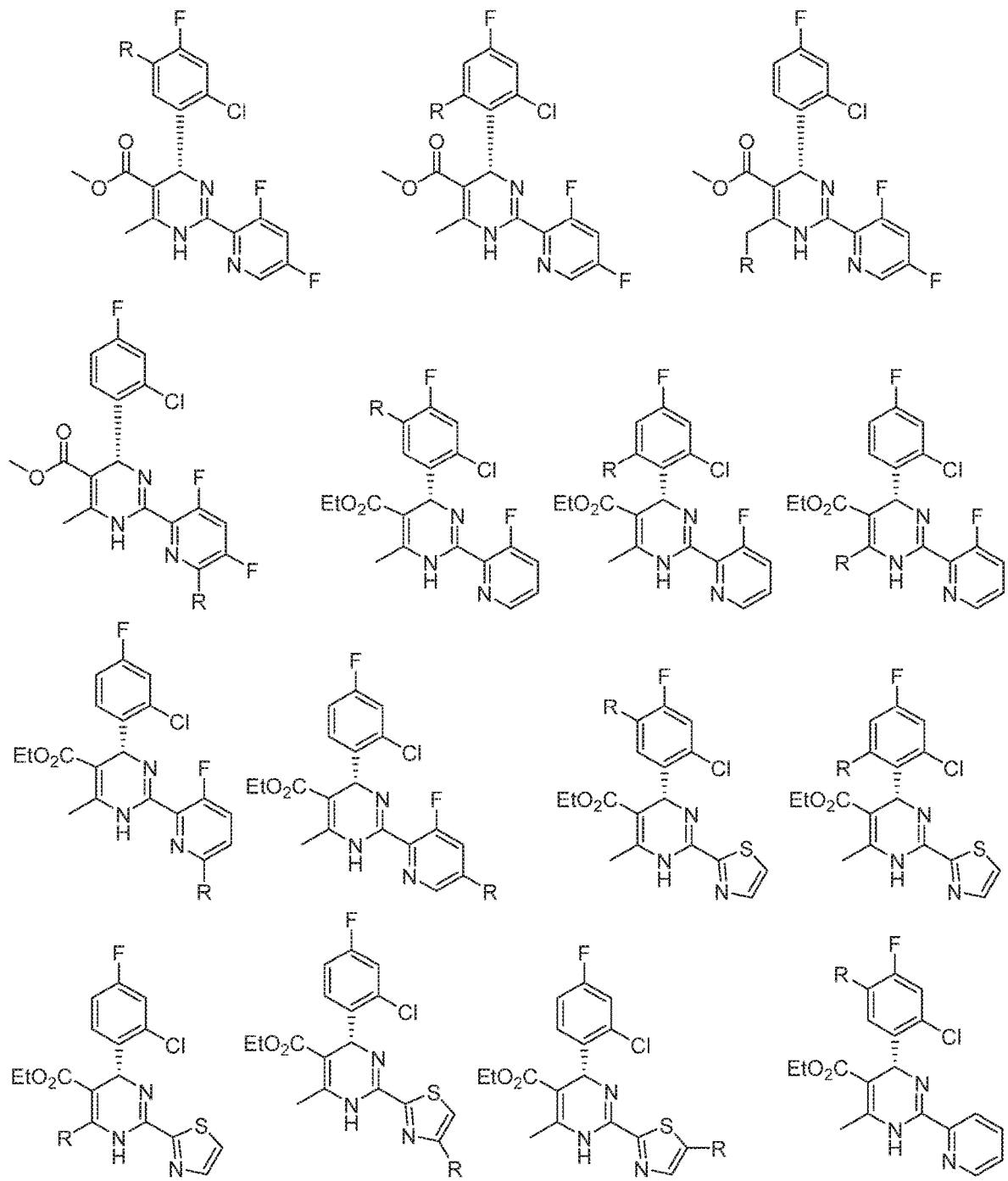
FIG. 8KKKKK

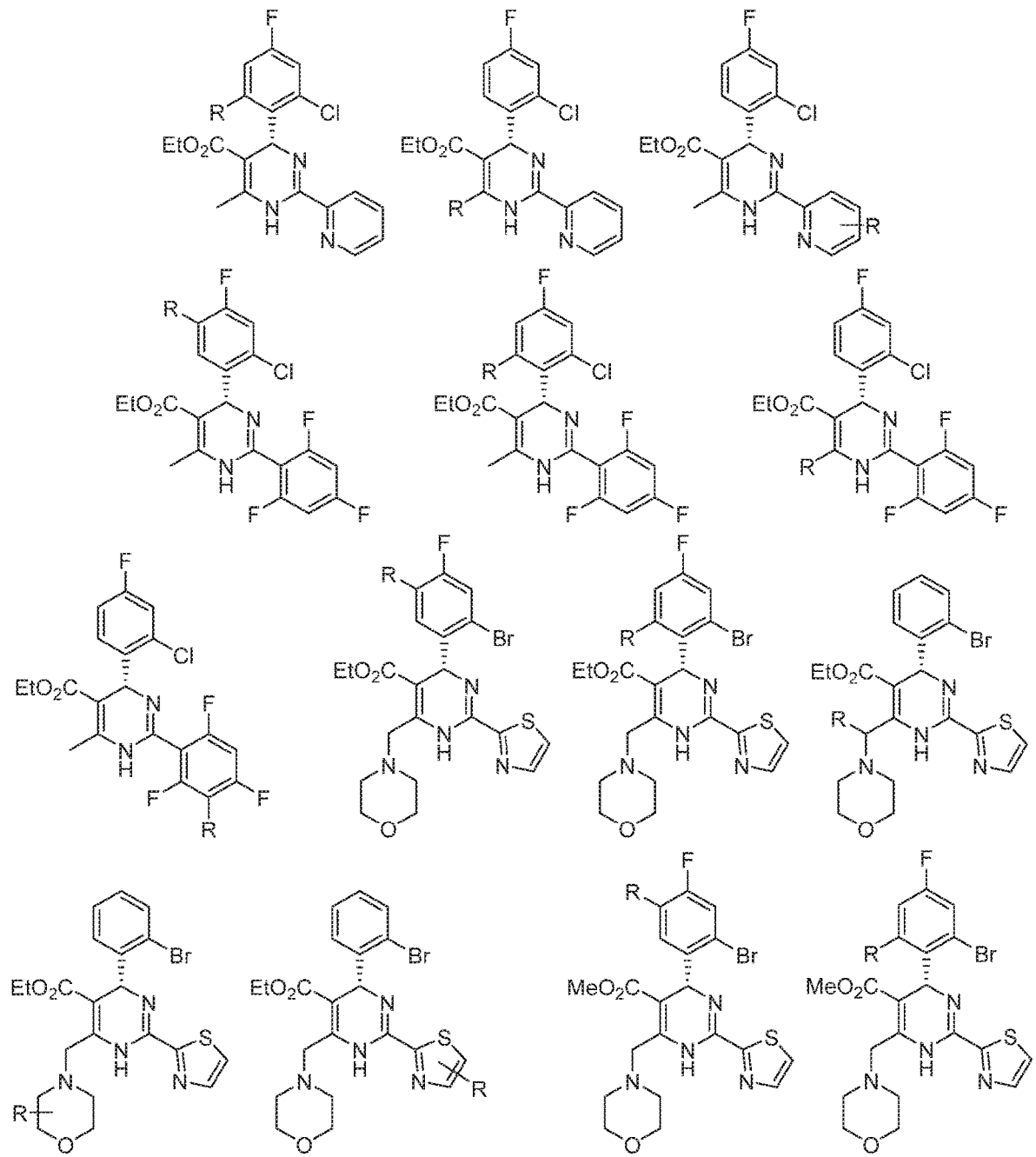
FIG. 8LLLLL

FIG. 8MMMMM
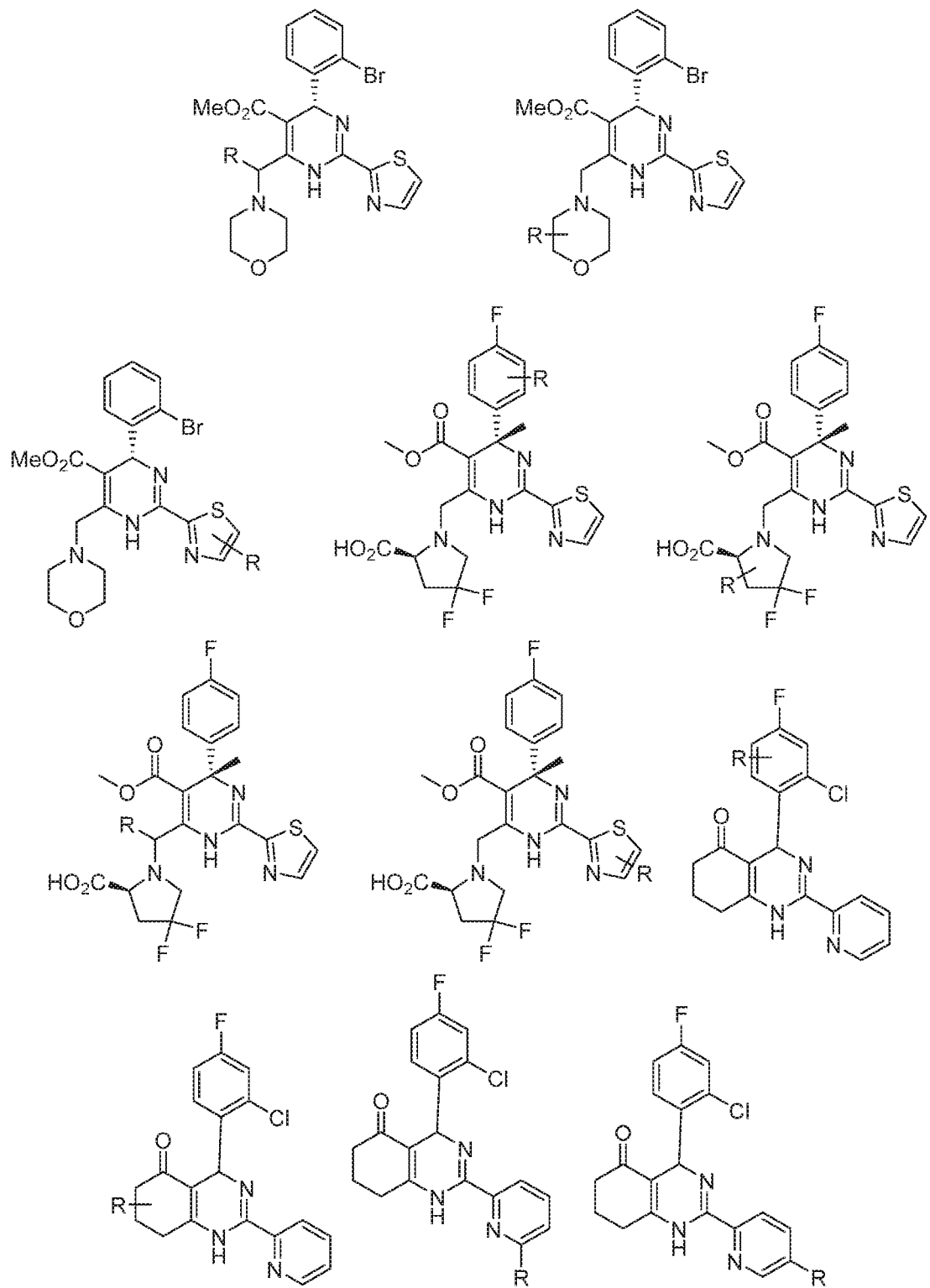

FIG. 8NNNNN
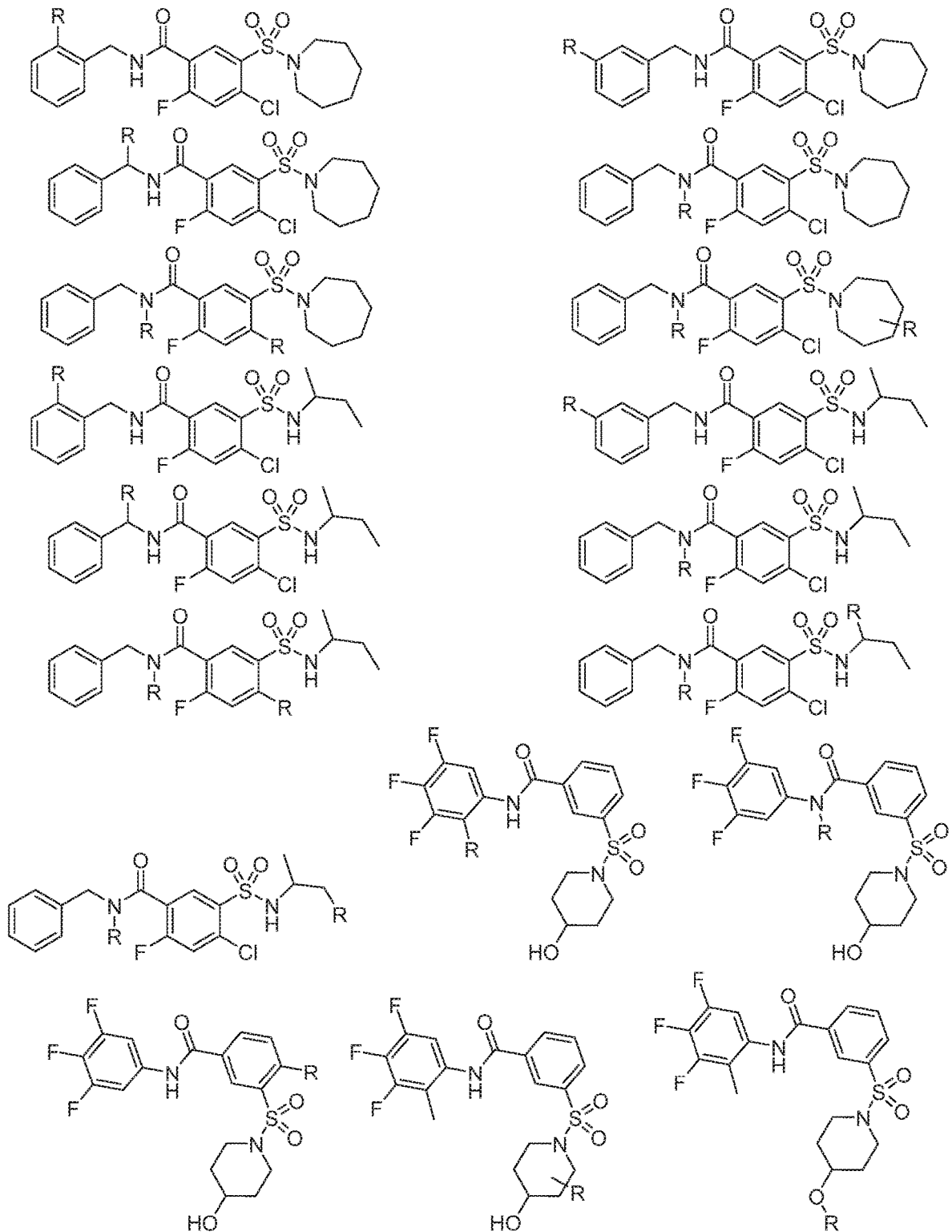

FIG. 800000
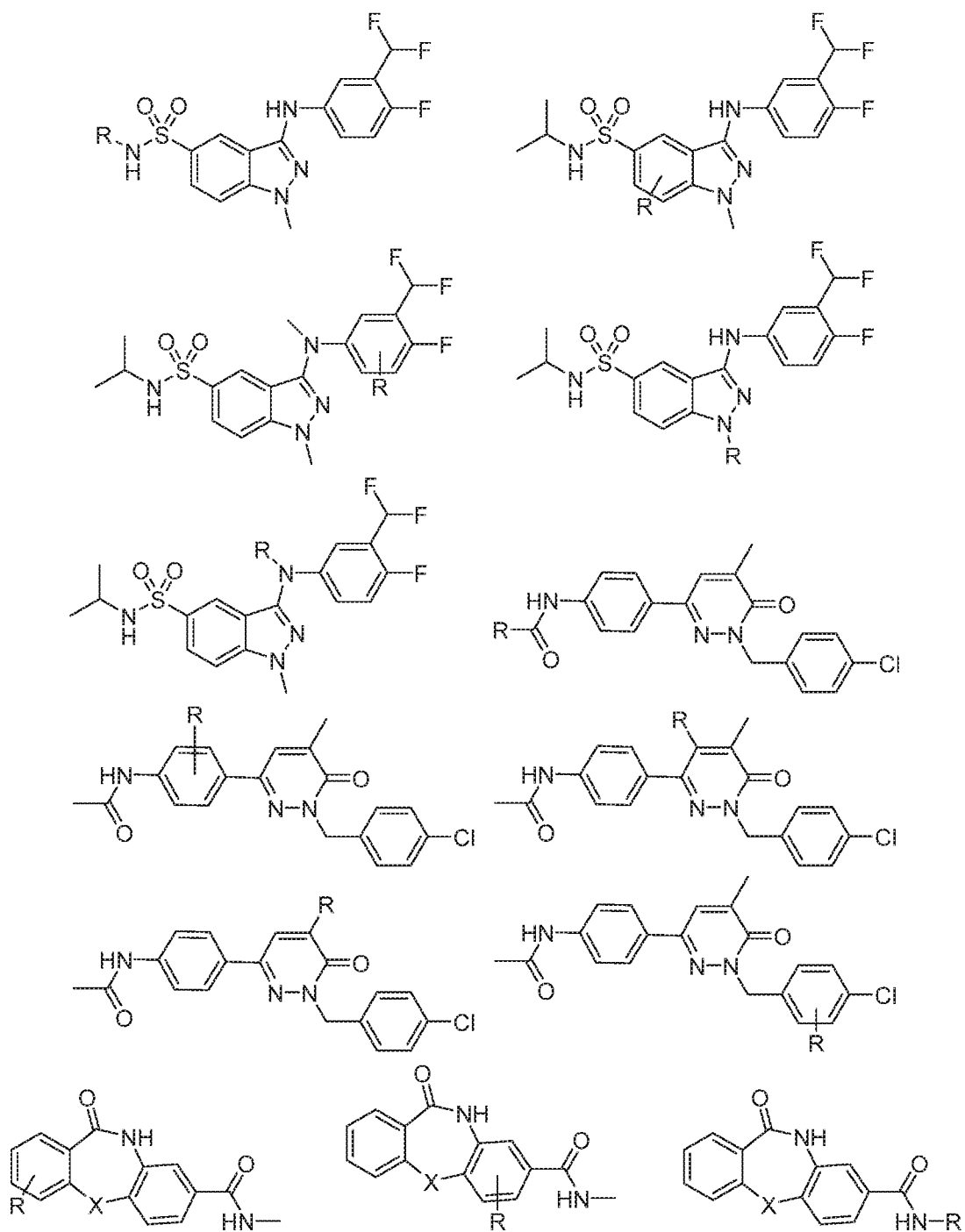

FIG. 8PPPPP
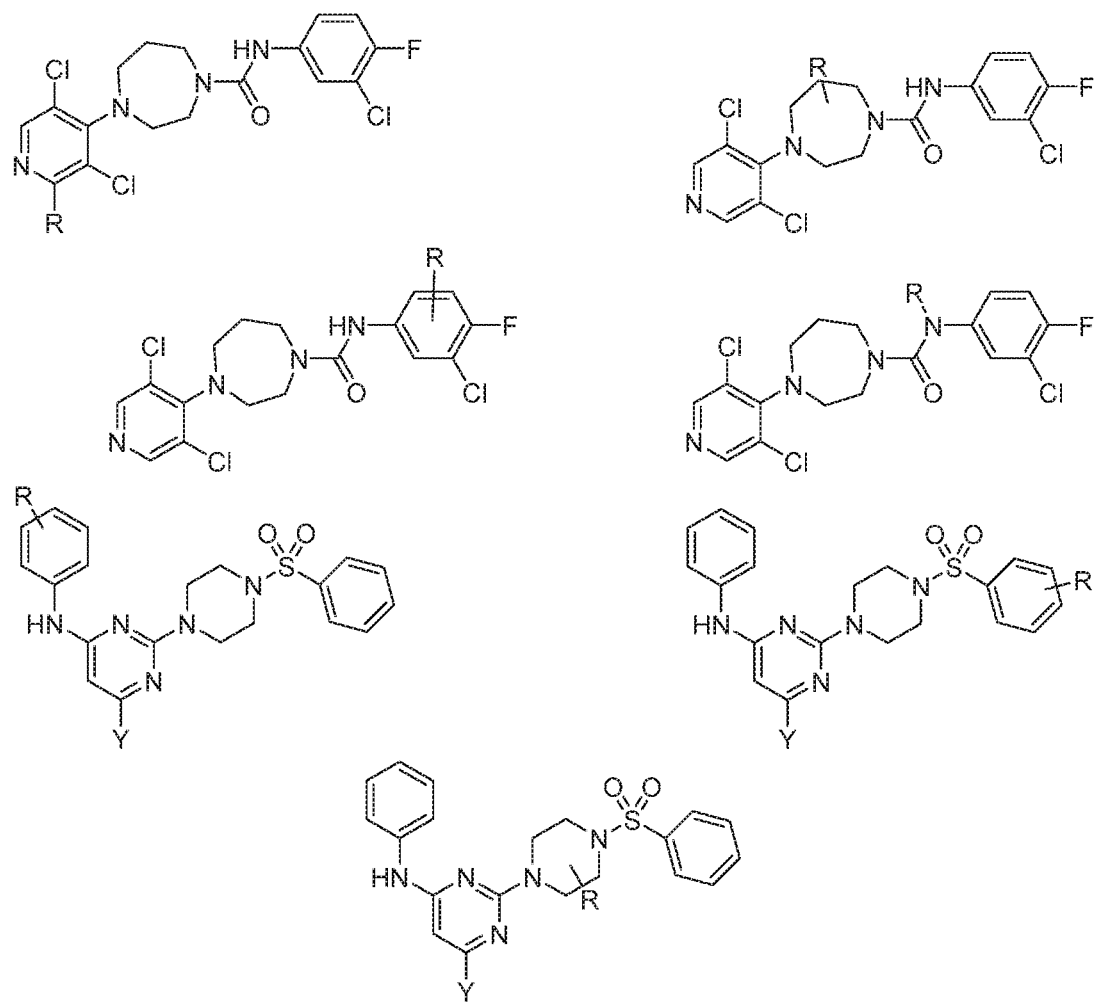

FIG. 10
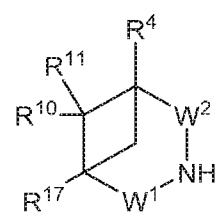
Formula I
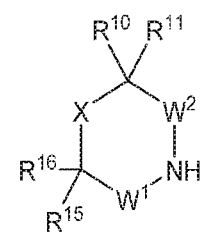
Formula II
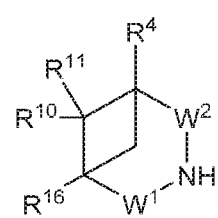
Formula III
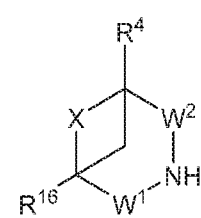
Formula IV

DEGRADERS AND DEGRONS FOR TARGETED PROTEIN DEGRADATION

CROSS-REFERENCE TO RELATED APPLICATIONS

This application is a continuation of International Application No. PCT/US2018/061573, filed in the U.S. Receiving Office on Nov. 16, 2018, which claims claims the benefit of U.S. Provisional Application No. 62/587,303 filed Nov. 16, 2017, the entirety of each of these applications is incorporated herein for all purposes.

FIELD OF THE INVENTION

This invention provides pharmaceutical Degraders and Degrons for therapeutic applications as described further herein.

BACKGROUND

Protein degradation is a highly regulated and essential process that maintains cellular homeostasis. The selective identification and removal of damaged, misfolded, or excess proteins is achieved via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer among others.

The drug thalidomide and its analogs lenalidomide and pomalidomide have garnered interest as immunomodulators and antineoplastics, especially in multiple myeloma (see Martiniani, R. et al. "Biological activity of lenalidomide and its underlying therapeutic effects in multiple myeloma" Adv Hematol, 2012, 2012:842945; and Terpos, E. et al. "Pomalidomide: a novel drug to treat relapsed and refractory multiple myeloma" Oncotargets and Therapy, 2013, 6:531). While the exact therapeutic mechanism of action of thalidomide, lenalidomide and pomalidomide is unknown, the compounds are used in the treatment of some cancers including multiple myeloma. There are also clinical and preclinical studies related to the treatment of renal cell carcinoma, glioblastoma, prostate cancer, melanoma, colorectal cancer, crohns disease, rheumatoid arthritis, Behcet's syndrome, breast cancer, head and neck cancer, ovarian cancer, chronic heart failure, graft-versus-host disease, and tuberculous meningitis.

Thalidomide and its analogues have been found to bind to the ubiquitin ligase cereblon and redirect its ubiquitination activity (see Ito, T. et al. "Identification of a primary target of thalidomide teratogenicity" Science, 2010, 327:1345). Cereblon forms part of an E3 ubiquitin ligase complex which interacts with damaged DNA binding protein 1, forming an E3 ubiquitin ligase complex with Cullin 4 and the E2-binding protein ROC1 (known as RBX1) where it functions as a substrate receptor to select proteins for ubiquitination. The binding of lenalidomide to cereblon facilitates subsequent binding of cereblon to Ikaros and Aiolos, leading to their ubiquitination and degradation by the proteasome (see Lu, G. et al. "The myeloma drug lenalidomide promotes the cereblon-dependent destruction of Ikaros proteins" Science, 2014, 343:305-309; Kronke, J. et al. "Lenalidomide causes selective degradation of IKZF1 and IKZF3 in multiple myeloma cells" Science, 2014, 343:301-305).

The disclosure that thalidomide binds to the cereblon E3 ubiquitin ligase led to research to investigate incorporating thalidomide and certain derivatives into compounds for the targeted destruction of proteins. Celgene has disclosed imides for similar uses, including those in U.S. Pat. Nos. 6,045,501; 6,315,720; 6,395,754; 6,561,976; 6,561,977; 6,755,784; 6,869,399; 6,908,432; 7,141,018; 7,230,012; 7,820,697; 7,874,984; 7,959,566; 8,204,763; 8,315,886; 8,589,188; 8,626,531; 8,673,939; 8,735,428; 8,741,929; 8,828,427; 9,056,120; 9,101,621; and 9,101,622.

Patent applications filed by C4 Therapeutics, Inc., that describe compounds capable of binding to an E3 ubiquitin ligase and a target protein for degradation include: WO 2017/197051 titled "Amine-Linked C3-Glutarimide Degronimers for Target Protein Degradation"; WO 2017/197055 titled "Heterocyclic Degronimers for Target Protein Degradation"; WO 2017/197036 titled "Spirocyclic Degronimers for Target Protein Degradation"; WO 2017/197046 titled "C3-Carbon Linked Glutarimide Degronimers for Target Protein Degradation"; and WO 2017/197056 titled "Bromodomain Targeting Degronimers for Target Protein Degradation."

Other patent applications that describe protein degrading compounds include: WO 2015/160845; WO 2016/105518; WO 2016/118666; WO 2016/149668; WO 2016/197032; WO 2016/197114; WO 2017/007612; WO 2017/030814; WO 2017/046036; WO 2017/176708; WO 2017/176957; WO 2017/180417; WO 2018/053354; WO 2018/071606; WO 2018/102067; WO 2018/102725; WO 2018/118598; WO 2018/119357; WO 2018/119441; and WO 2018/140809.

Additional publications in this area include the following: Lu et al. (*Chem. Biol.* 2015, 22, 755-763) titled "Hijacking the E3 Ubiquitin Ligase Cereblon to Efficiently Target Brd4"; Bondeson et al. (*Nat. Chem. Biol.* 2015, 11, 611-617) titled "Catalytic in Vivo Protein Knockdown by Small-Molecule Protacs"; Gustafson et al. (*Angewandte Chemie, International Edition in English* 2015, 54, 9659-9662) titled "Small-Molecule-Mediated Degradation of the Androgen Receptor through Hydrophobic Tagging"; Lai et al. (*Angewandte Chemie, International Edition in English* 2016, 55, 807-810) titled "Modular Protac Design for the Degradation of Oncogenic Bcr-Abl"; Toure et al. (*Angew. Chem. Int. Ed.* 2016, 55, 1966-1973) titled "Small-Molecule Protacs: New Approaches to Protein Degradation"; and Winter et al. (*Science* 2015, 348, 1376-1381) titled "Drug Development. Phthalimide Conjugation as a Strategy for in Vivo Target Protein Degradation."

It is an object of the present invention to provide new compounds, methods, compositions, and methods of manufacture that are useful to degrade selected proteins in vivo.

SUMMARY OF THE INVENTION

Compounds and their uses and manufacture are provided that cause degradation of a selected protein via the ubiquitin proteasome pathway (UPP). Compounds are described (Degrons) of Formula V, Formula VI, Formula VII, Formula VIII, and Formula XII that bind an E3 ligase (typically a cereblon subunit). Degraders are disclosed of Formula I, Formula II, Formula III, Formula IV, Formula IX, Formula X, and Formula XI that include a "Targeting Ligand" that binds to a selected Target Protein, a "Degron" which binds to a E3 Ligase (typically via a cereblon subunit), and optionally a Linker that covalently links the Targeting Ligand to the Degron.

A Degrader provided herein or its pharmaceutically acceptable salt and/or its pharmaceutically acceptable composition can be used to treat a disorder which is mediated by the selected Target Protein that binds to the Targeting Ligand. Therefore, in some embodiments a method to treat a host with a disorder mediated by the Target Protein is provided that includes administering an effective amount of the Degrader or its pharmaceutically acceptable salt described herein to the host, typically a human, optionally in a pharmaceutically acceptable composition.

In one embodiment, the selected Target Protein is derived from a gene that has undergone an amplification, translocation, rearrangement, a copy number variation, alteration, deletion, mutation, or inversion event which causes or is caused by a medical disorder. In certain aspects, the selected Target Protein has been post-translationally modified by one, or combinations, of phosphorylation, acetylation, acylation including propionylation and crotylation, N-linked glycosylation, amidation, hydroxylation, methylation, poly-methylation, O-linked glycosylation, pyroglutamoylation, myristoylation, farnesylation, geranylation, ubiquitination, sumoylation, or sulfation which causes or is caused by a medical disorder. In an alternative embodiment, the Target Protein can be covalently modified by a Targeting Ligand that has been functionalized to create a covalent bond with the Target Protein, and the covalent bond can be irreversible or reversible.

In one aspect, the present invention includes a compound of Formula I:

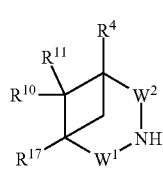

(Formula I)

or a pharmaceutically acceptable salt, N-oxide, isotopic derivative, or prodrug thereof, optionally in a pharmaceutically acceptable carrier to form a composition;
wherein:
$W^1$ is $CR^6R^7$, C=O, C=S, C=CH$_2$, SO$_2$, S(O), P(O)OH, or P(O)NH$_2$;
$W^2$ is $CR^8R^9$, C=O, C=S, C=CH$_2$, SO$_2$, S(O), P(O)OH, or P(O)NH$_2$;
in a typical embodiment, $W^1$ is C=O;
in another typical embodiment, $W^2$ is C=O;
$R^2$ is selected at each instance from hydrogen, alkyl, heteroalkyl, aliphatic, heteroaliphatic, heterocyclic, aryl, heteroaryl, —C(O)H, —C(O)OH, —C(O)alkyl, —C(O)Oalkyl, —C(O)(aliphatic, aryl, heteroaliphatic or heteroaryl), —C(O)O(aliphatic, aryl, heteroaliphatic, or heteroaryl), alkene, and alkyne;

$R^4$ is selected from hydrogen, aliphatic, and heteroaliphatic; or
in one embodiment, $R^4$ may be heterocyclic;
$R^5$ is selected at each instance from hydrogen, alkyl, alkene, alkyne, halogen, hydroxyl, alkylhydroxyl, alkoxy, azide, amino, alkylamino, cyano, —NH(aliphatic, including alkyl), —N(aliphatic, including alkyl)$_2$, —NHSO$_2$(aliphatic, including alkyl), —N(aliphatic, including alkyl)SO$_2$alkyl, —NHSO$_2$(aryl, heteroaryl, or heterocyclic), —N(alkyl)SO$_2$(aryl, heteroaryl, or heterocyclic), —NHSO$_2$alkenyl, —N(alkyl)SO$_2$alkenyl, —NHSO$_2$alkynyl, —N(alkyl)SO$_2$alkynyl, haloalkyl, aliphatic, heteroaliphatic, heteroalkyl, carbocyclic, C(O)R$^{40}$, aryl, aryloxy, heterocyclo, heteroaryl, arylalkyl, O-arylalkyl, nitro, nitroso, sulfone, sulfoxide, thioalkyl, thiol, haloalkyl, and cycloalkyl;
$R^6$, $R^7$, $R^8$, $R^9$, $R^{10}$, and $R^{11}$ are independently selected from hydrogen, alkyl, aliphatic, heteroaliphatic, carbocyclic, heterocyclic, aryl, heteroaryl, halo, azide, cyano, hydroxyl, alkoxy, amine, —NH(aliphatic, including alkyl), and —N(aliphatic, including alkyl)$_2$;
or $R^{10}$ and $R^{11}$ together with the carbon to which they are bound form a 3-, 4-, 5-, or 6-membered spirocarbocycle, or a 4-, 5-, or 6-membered spiroheterocycle comprising 1 or 2 heteroatoms selected from N, O, and S;
$R^{17}$ is selected from $R^{17a}$, $R^{17b}$, and $R^{17c}$;
$R^{17a}$ is selected from:

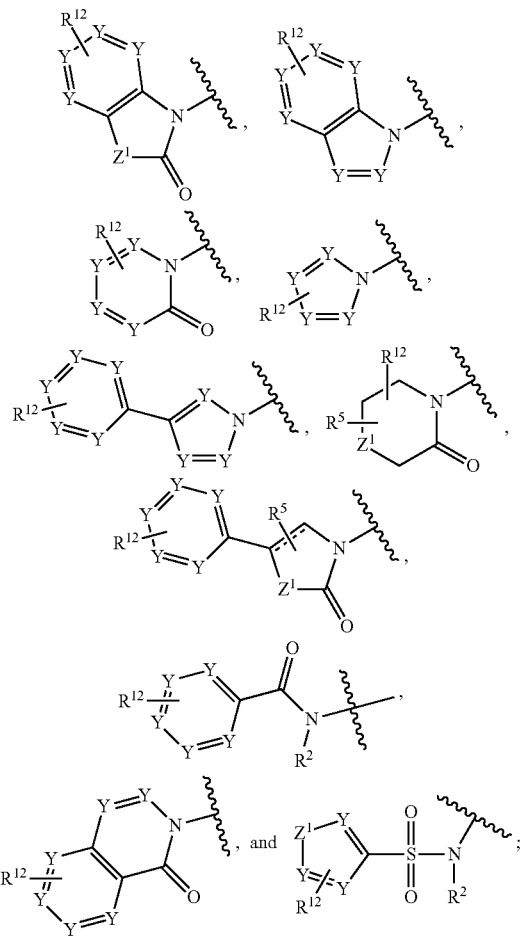

or $R^{17a}$ is selected from

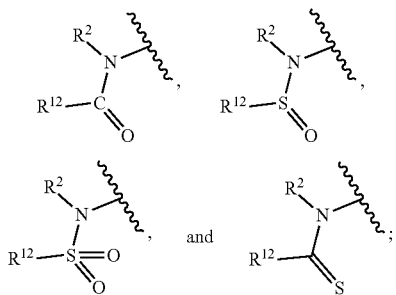

or $R^{17a}$ is a 3, 4, 5, 6, 7, 8, or 10 membered heterocyclo or heteroaryl moiety containing at least one nitrogen atom through which it is directly attached, wherein the heterocyclo or heteroaryl moiety is substituted with $R^{12}$ at any desired position, wherein the heterocyclo or heteroaryl moiety is optionally further substituted with one or more, for example 1, 2, 3, or 4, substituents selected from $R^5$; and in an additional alternative embodiment the heterocyclo or heteroaryl moiety is optionally further substituted with one or more oxo groups at a position allowed by valence;

or $R^{17a}$ is selected from:

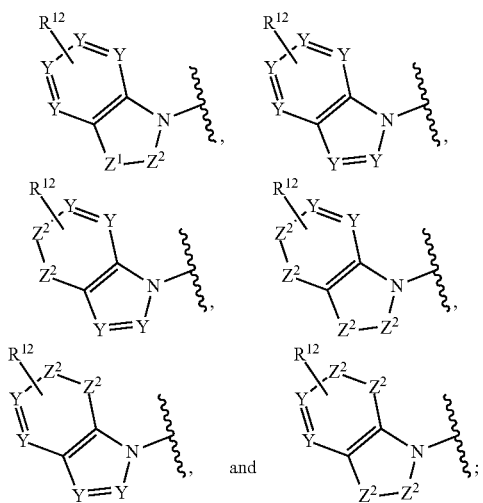

in an alternative embodiment, $R^{17a}$ is selected from:

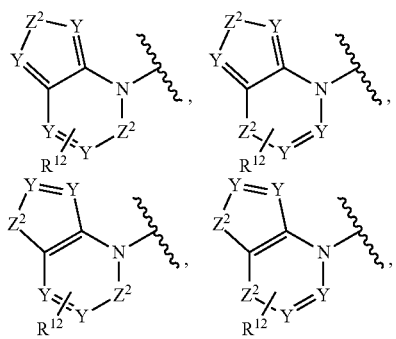

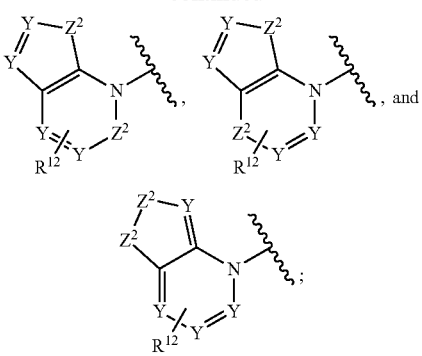

$R^{17b}$ is selected from

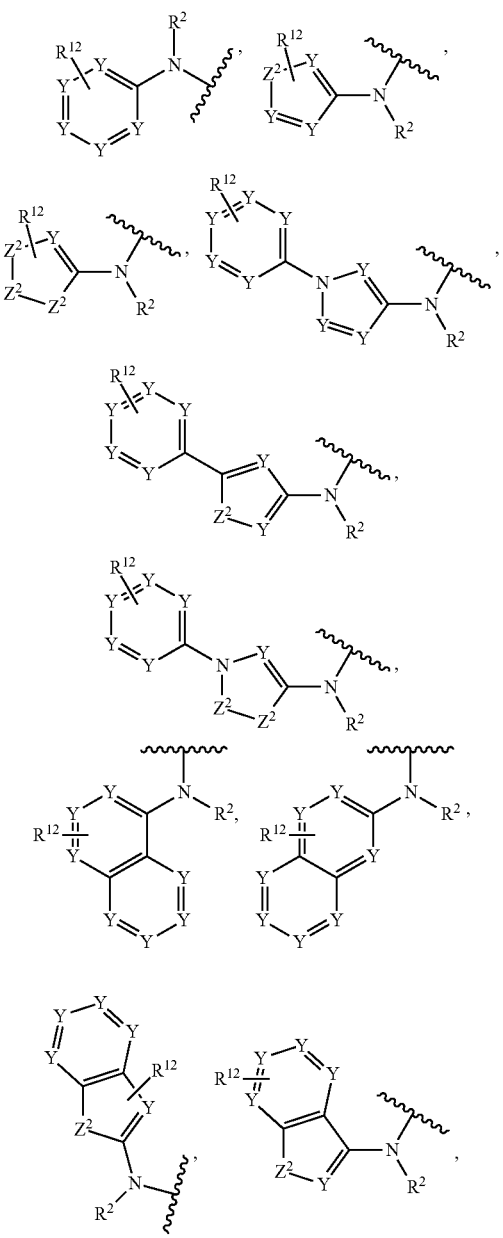

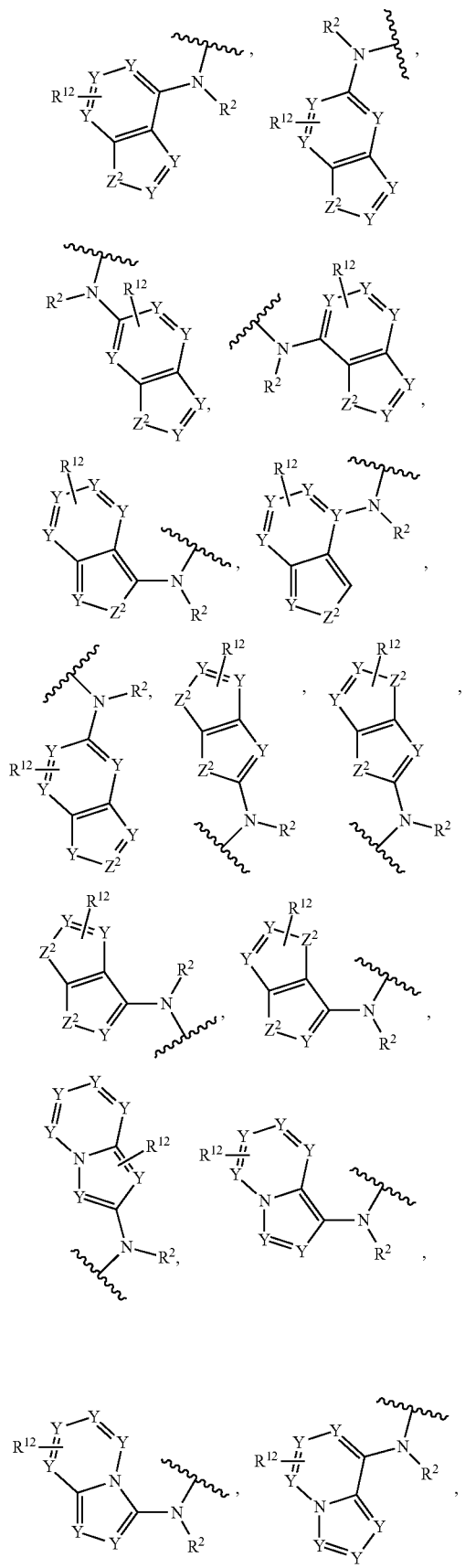

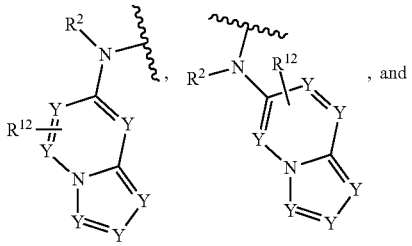

or R[17b] is selected from

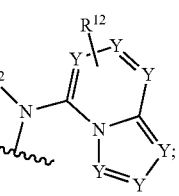

or R[17b] is —NR[2]aryl, —NR[2]heteroaryl, or NR[2]carbocycle, wherein the aryl, heteroaryl, and carbocycle moieties are substituted with a R[12] at any desired position, wherein the aryl, heteroaryl, and carbocycle moieties are optionally further substituted with one or more, for example 1, 2, 3, or 4, substituents selected from R[5]; and in an additional alternative embodiment the aryl, heteroaryl, and carbocycle moieties are optionally further substituted with one or more oxo groups at a position allowed by valence;

R[17c] is selected from

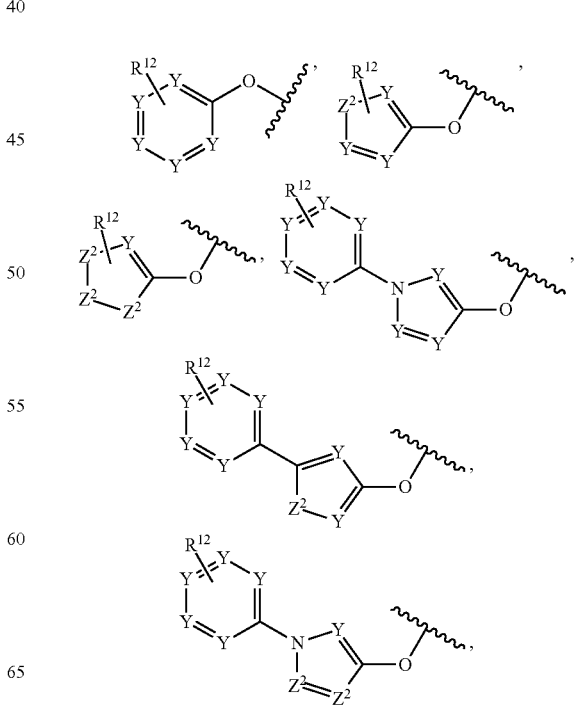

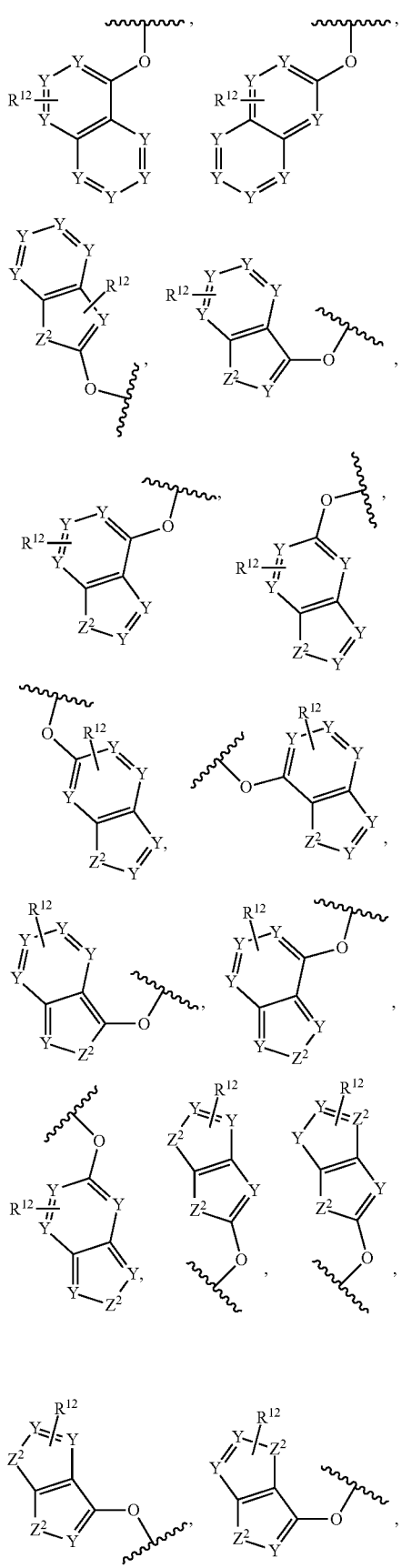
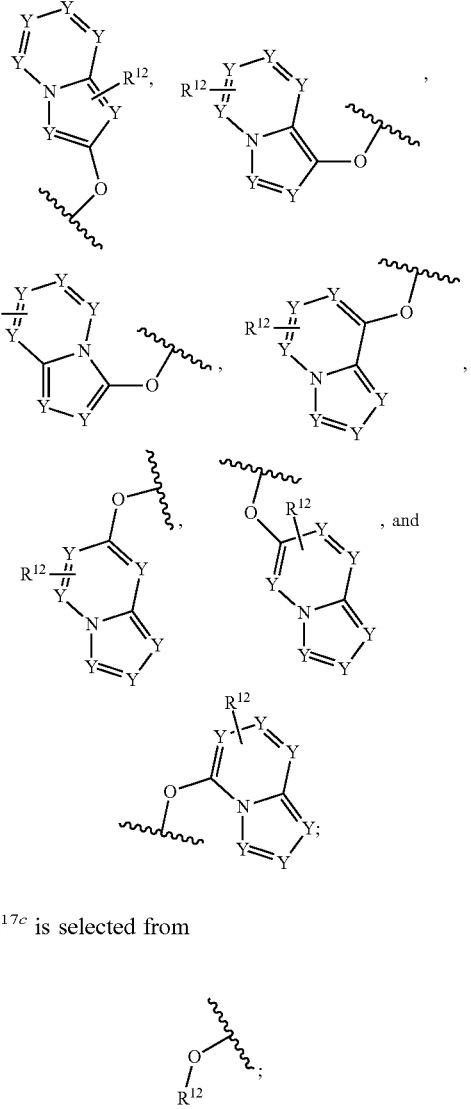

or R$^{17c}$ is selected from or R$^{17c}$ is —O-aryl, —O-heteroaryl, or —O-carbocycle, wherein the aryl, heteroaryl, and carbocycle moieties are substituted with a R$^{12}$ at any desired position, wherein the aryl, heteroaryl, and carbocycle moieties are optionally further substituted with one or more, for example 1, 2, 3, or 4, substituents selected from R$^5$; and in an additional alternative embodiment the aryl, heteroaryl, and carbocycle moieties are optionally further substituted with one or more oxo groups at a position allowed by valence;

═══ is selected from a single or double bond;

Y is independently selected from N, CH, or CR$^5$, wherein 0, 1, 2, 3, or 4 (as context allows) instances of Y are selected to be N and are selected to produce a stable ring as well known to those skilled in the art and that forms a pharmaceutically acceptable compound;

Z$^1$ is selected from CH$_2$, CHR$^2$, C(R$^2$)$_2$, NR$^2$, O, and S;

Z$^2$ is selected from NH, O, S, NR$^2$, C═O, S═O, and SO$_2$;

when R$^{12}$ is bonded to a Y, then Y is CR$^{12}$; when R$^{12}$ is bonded to a Z$^1$ that is nitrogen, then Z$^1$ is NR$^{12}$; when R$^{12}$ is bonded to Z$^1$ that is carbon, then Z$^1$ is CR$^2$R$^{12}$; when R$^{12}$ is bonded to a Z$^2$, then Z$^2$ is NR$^{12}$; wherein these variables are selected such that a stable compound results;

for example

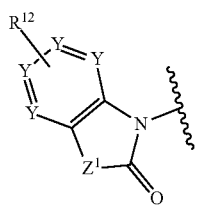

corresponds to

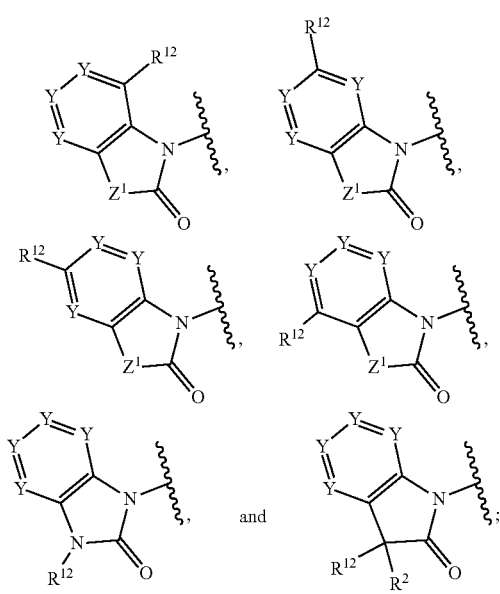

$R^{12}$ is -(Linker)$^A$-Targeting Ligand or -(Linker)$^B$;

(Linker)$^A$ is a bivalent chemical group that attaches a Degron to a Targeting Ligand; for example, (Linker)$^A$ can be any bivalent moiety described in Section IV;

in one embodiment, (Linker)$^A$ is selected from

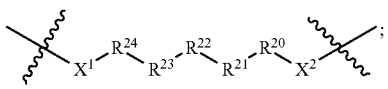

(Linker)$^B$ is a monovalent chemical group that is attached to a Degron; for example, (Linker)$^A$ can be any monovalent moiety described in Section IV;

in one embodiment, (Linker)$^B$ is selected from

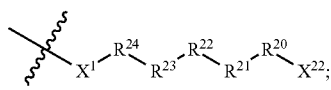

or in an alternative embodiment, $R^{12}$ is -(Linker)$^C$;

-(Linker)$^C$ is a chemical group that is covalently attached to a Targeting Ligand and one or more additional Targeting Ligands or Degrons;

$X^1$ and $X^2$ are independently selected from bond, NH, $NR^2$, $CH_2$, $CHR^2$, $C(R^2)_2$, O, and S;

$R^{20}$, $R^{21}$, $R^{22}$, $R^{23}$, and $R^{24}$ are independently selected from bond, alkyl, —C(O)—, —C(O)O—, —OC(O)—, —C(O)alkyl, —C(O)Oalkyl, —C(S)—, —SO$_2$—, —S(O)—, —C(S)—, —C(O)NH—, —NHC(O)—, —N(alkyl)C(O)—, —C(O)N(alkyl)-, —O—, —S—, —NH—, —N(alkyl)-, —CH(—O—R$^{26}$)—, —CH(—NHR$^2$)—, —CH(—NH$_2$)—, —CH(—NR$^2_2$)—, —C(—O—R$^{26}$)alkyl-, —C(—NHR$^2$)alkyl-, —C(—NH$_2$)alkyl-, —C(—NR$^2_2$)alkyl-, —C(R$^{40}$R$^{40}$)—, -alkyl(R$^{27}$)-alkyl(R$^{28}$)—, —C(R$^{27}$R$^{28}$)—, —P(O)(OR$^{26}$)O—, —P(O)(OR$^{26}$)—, —NHC(O)NH—, —N(R$^2$)C(O)N(R$^2$)—, —N(H)C(O)N(R$^2$)—, alkene, haloalkyl, alkoxy, alkyneheteroarylalkyl, aryl, arylalkyl, heterocycle, aliphatic, heteroaliphatic, heteroaryl, lactic acid, glycolic acid, carbocycle, —O—(CH$_2$)$_{1-12}$—O—, —NH—(CH$_2$)$_{1-12}$—NH—, —NH—(CH$_2$)$_{1-12}$—O—, —O—(CH$_2$)$_{1-12}$—NH—, —S—(CH$_2$)$_{1-12}$—O—, —O—(CH$_2$)$_{1-12}$—S—, —S—(CH$_2$)$_{1-12}$—S—, —S—(CH$_2$)$_{1-12}$—NH—, and —NH—(CH$_2$)$_{1-12}$—S—, wherein the 1-12 can be independently 1, 2, 3, 4, 5, 6, 7, 8, 9, 10, 11 or 12, and wherein one or more of the CH$_2$ or NH groups can be modified by substitution of a H for a methyl, ethyl, cyclopropyl, F (if on carbon), etc, as described herein, and optionally, a heteroatom, heteroalkyl, aryl, heteroaryl or cycloaliphatic group is interspersed in the chain. Certain non-limiting examples include —O—CH(CH$_3$)—CH(CH$_3$)CH—O—, —O—CH$_2$—CH(CH$_3$)CH—O—, —O—CH(CH$_3$)—CH$_2$CH—O—, etc. in an alternative embodiment, $R^{20}$, $R^{21}$, $R^{22}$, $R^{23}$, or $R^{24}$ may independently be selected from polyethylene glycol, poly (lactic-co-glycolic acid), or polypropylene glycol;

each of which $R^{20}$, $R^{21}$, $R^{22}$, $R^{23}$, and $R^{24}$ is optionally substituted with one or more substituents selected from $R^{101}$ or alternatively as described in Section 1. Definitions;

$R^{101}$ is independently selected at each occurrence from hydrogen, alkyl, alkene, alkyne, haloalkyl, alkoxy, hydroxyl, aryl, heteroaryl, heterocycle, arylalkyl, heteroarylalkyl, heterocycloalkyl, aryloxy, heteroaryloxy, CN, —COOalkyl, COOH, NO$_2$, F, Cl, Br, I, CF$_3$, NH$_2$, NHalkyl, N(alkyl)$_2$, aliphatic, and heteroaliphatic;

$X^{22}$ is $X^{22a}$ or $X^{22b}$;

$X^{22a}$ is selected from halo, —NH$_2$, —NHR$^2$, —N(R$^2$)$_2$, hydroxyl, thiol, —B(OH)$_2$, —Sn(R$^2$)$_3$, —Si(R$^2$)$_3$, —OS(O)$_2$alkyl, —OS(O)$_2$haloalkyl, alkenyl, alkynyl, ethynyl, ethenyl, —C(O)H, —NR$^2$C(O)alkene, —NR$^2$C(O)alkyne, cyano, —SC(O)alkyln, OC(O)alkyl, and —C(O)OH;

$X^{22b}$ is selected from hydrogen, alkyl, —CH$_2$R$^2$, —CH(R$^2$)$_2$, —C(R$^2$)$_3$, aryl, heteroaryl, aliphatic, heteroaliphatic, carbocyclic, and heterocyclyl;

$R^{26}$ is selected from hydrogen, alkyl, silane, arylalkyl, heteroarylalkyl, alkene, alkyne, aryl, heteroaryl, heterocyclic, aliphatic and heteroaliphatic;

$R^{27}$ and $R^{28}$ are independently selected from hydrogen, alkyl, amine, or together with the carbon atom to which they are attached, form C(O), C(S), C=CH$_2$, a C$_3$-C$_6$ spirocarbocycle, or a 4-, 5-, or 6-membered spiroheterocycle comprising 1 or 2 heteroatoms selected from N and O, or form a 1 or 2 carbon bridged ring;

$R^{40}$ is selected at each instance from: hydrogen, alkyl, alkene, alkyne, halogen, hydroxyl, alkoxy, azide, amino, cyano, —NH(aliphatic, including alkyl), —N(aliphatic, including alkyl)$_2$, —NHSO$_2$(aliphatic, including alkyl), —N(aliphatic, including alkyl)SO$_2$alkyl, —NHSO$_2$(aryl, heteroaryl or heterocyclic), —N(alkyl)SO$_2$(aryl, heteroaryl or heterocyclic) —NHSO$_2$alkenyl, —N(alkyl)SO$_2$alkenyl, —NHSO$_2$alkynyl, —N(alkyl)SO$_2$alkynyl, haloalkyl, aliphatic, heteroaliphatic, aryl, heteroaryl, heteroalkyl and carbocyclic; or in one embodiment, $R^{40}$ may be heterocyclic; and Targeting Ligand is a molecule that binds to a Target Protein, wherein the Target Protein is a mediator of disease in a host.

In another aspect of the present invention, a compound is provided wherein $(Linker)^B$ is covalently attached to a ubiquitin binding moiety (Degron) that is described in WO2017/197036, WO2017/197046, WO2017/197051, WO2017/197055, or WO2017/197056, wherein $(Linker)^B$ is attached at a location as described in these applications. In one embodiment $(Linker)^B$ replaces the Linker-Targeting Ligand moiety in any of the compounds described in any of these applications, to form a "capped" compound of formula Degron-Linker$^B$. WO2017/197036, WO2017/197046, WO2017/197051, WO2017/197055, and WO2017/197056 are each specifically incorporated by reference herein.

In one embodiment the Degron is described in WO2017/197036.

In another embodiment the Degron is described in WO2017/197046.

In another embodiment the Degron is described in WO2017/197051.

In another embodiment the Degron is described in WO2017/197055.

In another embodiment the Degron is described in WO2017/197056.

In another aspect, the present invention includes a compound of Formula II:

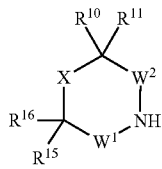

(Formula II)

or a pharmaceutically acceptable salt, N-oxide, isotopic derivative, or prodrug thereof, optionally in a pharmaceutically acceptable carrier to form a composition;

wherein:

X is selected from NH, $NR^2$, O, S(O), $S(O)_2$, and S;

$R^{15}$ is selected from hydrogen, alkyl, aliphatic, heteroaliphatic, heterocyclic, carbocyclic, aryl, heteroaryl, hydroxyl, halo, azide, cyano, alkoxy, amine, NH(aliphatic, including alkyl), and N(aliphatic, including alkyl);

$R^{16}$ is selected from:

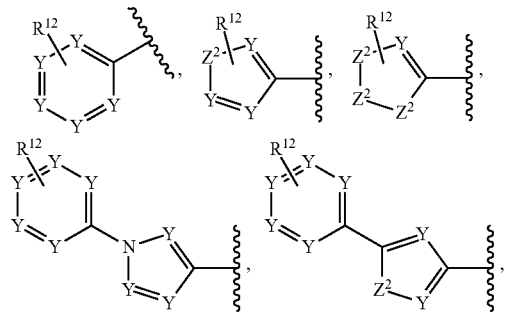

-continued

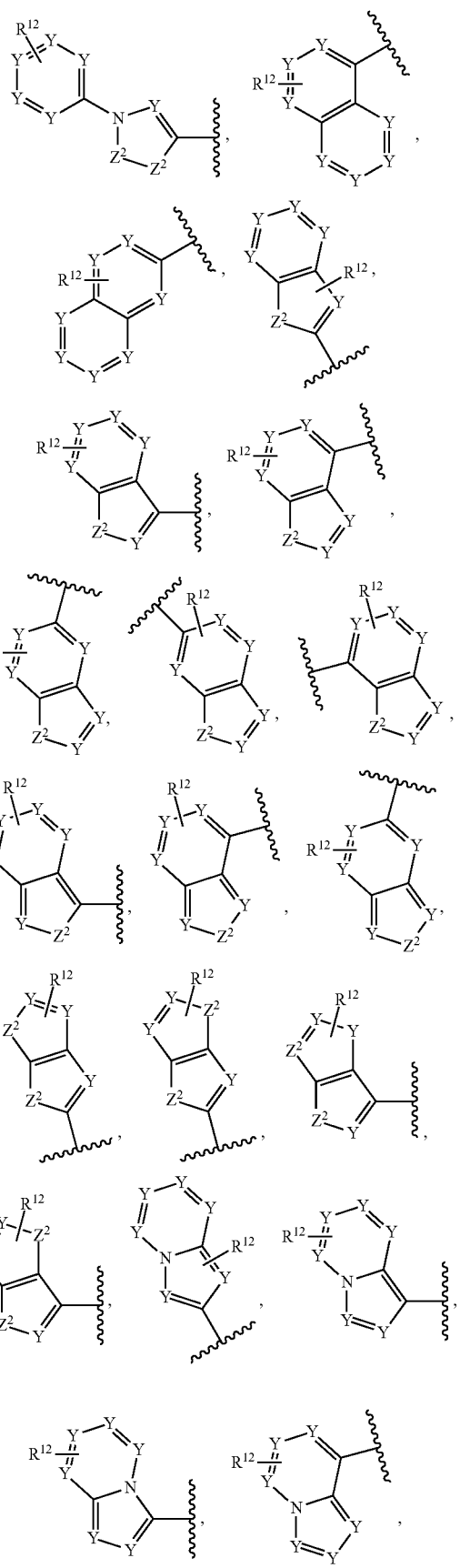

-continued

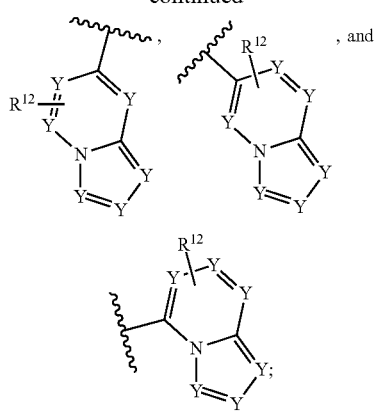

or $R^{16}$ is a 4, 5, 6, 7, 8, 9, or 10 membered carbocyclo or aryl moiety, wherein the carbocyclo or aryl moiety is substituted with $R^{12}$ at any desired position; wherein the carbocyclo or aryl moiety is optionally further substituted with one or more substituents selected from $R^5$; and wherein the carbocyclo or aryl moiety is attached through a carbon atom; or $R^{16}$ is

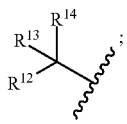

In any of the fused rings that have an $R^{12}$, the $R^{12}$ can be placed on any available ring atom on either of the fused rings, except when excluded by context (such as where valency precludes), for example as shown in the formulas:

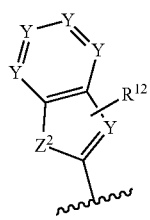

includes compounds of structure

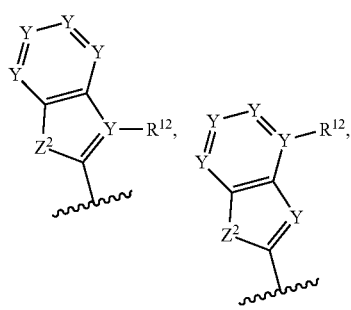

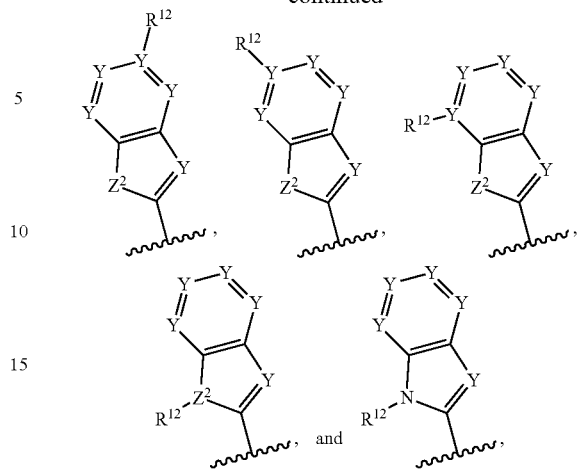

and, and each is considered specifically and independently described.

$R^{13}$ and $R^{14}$ are independently selected from hydrogen, alkyl, alkenyl, alkynyl, alkoxy, haloalkoxy, hydroxy, amino, —NHalkyl, and —N(alkyl)$_2$, each of which is optionally substituted as described in the Definition section, if desired to achieve the target effect and results in a stable compound that makes chemical sense to the routineer;

or $R^{13}$ and $R^{14}$ together with the carbon atom to which they are attached form C(O), C(S), C=CH$_2$, a 3-, 4-, 5-, or 6-membered spirocarbocycle, or a 4-, 5-, or 6-membered spiroheterocycle comprising 1 or 2 heteroatoms selected from N and O;

$Z^2$ is selected from NH, O, S, NR$^2$, C=O, S=O, and SO$_2$; and all other variables are defined as above.

In an additional aspect, the present invention includes a compound of Formula III or Formula IV:

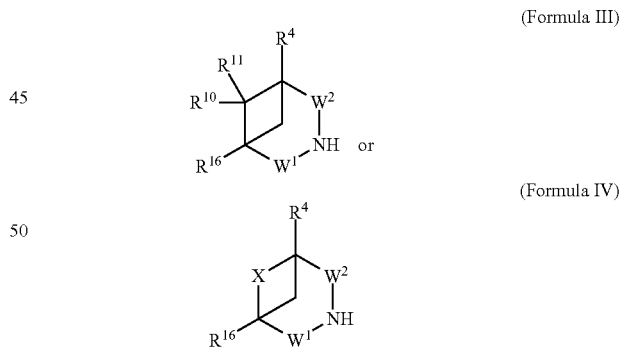

or a pharmaceutically acceptable salt, N-oxide, derivative, or prodrug thereof, optionally in a pharmaceutically acceptable carrier to form a composition;

wherein all variables are defined as above.

The structure of the Degrader is typically selected such that it is sufficiently stable to sustain a shelf life of at least two, three, four, or five months under ambient conditions. To accomplish this, each of the R groups described herein must be sufficiently stable to sustain the corresponding desired shelf life of at least two, three, four, or five months under ambient conditions. One of ordinary skill in the art is well aware of the stability of chemical moieties and can avoid those that are not stable or are too reactive under appropriate conditions.

The Degrader (Degron, Linker and Targeting Ligand), including any of the "R" groups defined herein, may be optionally substituted as described below in Section I. Definitions, if desired to achieve the target effect, results in a stable R moiety and final compound that makes chemical sense to the routineer, and if a final compound for therapy, is pharmaceutically acceptable. Also, all R groups, with or without optional substituents, should be interpreted in a manner that does not include redundancy (i.e., as known in the art, alkyl substituted with alkyl is redundant; however, for example, alkoxy substituted with alkoxy is not redundant).

In one aspect, Degraders of Formula I, Formula II, Formula III, Formula IV, Formula IX, Formula X, and Formula XI are bifunctional compounds with an E3 Ubiquitin Ligase targeting moiety (Degron) linked to protein Targeting Ligand (described in more detail below), which function to recruit a Target Protein, typically via a cereblon-containing E3 Ubiquitin Ligase for degradation. One non-limiting example of a disorder treatable by such compounds is abnormal cellular proliferation, such as a tumor or cancer, wherein the Target Protein is an oncogenic protein or a signaling mediator of an abnormal cellular proliferative pathway and its degradation decreases abnormal cell growth.

Based on this discovery, compounds and methods are presented for the treatment of a patient with a disorder mediated by a protein that is targeted for selective degradation that includes administering an effective amount of one or a combination of the Degraders of Formula I, Formula II, Formula III, Formula IV, Formula IX, Formula X, and Formula XI described herein to a patient (typically a human) in need thereof, optionally in a pharmaceutically acceptable carrier (composition). In certain embodiments, the disorder is selected from a benign growth, neoplasm, tumor, cancer, abnormal cellular proliferation, immune disorder, inflammatory disorder, graft-versus-host rejection, viral infection, bacterial infection, an amyloid-based proteinopathy, a proteinopathy, or fibrotic disorder. In a typical embodiment, the patient is a human.

In one embodiment, the present invention provides Degrons thereof which are covalently linked to a Targeting Ligand through -(Linker)$^A$- which can be of varying length and functionality.

In another embodiment, the present invention provides Degrons which are monovalently linked to -(Linker)$^B$, wherein in one embodiment -(Linker)$^B$ contains a reactive functional group ($X^{22a}$) for optional later attachment to an appropriate Targeting Ligand and in another embodiment -(Linker)$^B$ contains a non-reactive group ($X^{22b}$). In one embodiment the resulting Degron-(Linker)$^B$ compound is used to treat a disorder described herein. In one embodiment the resulting Degron-(Linker)$^A$-Targeting Ligand compound is used to treat a disorder described herein. In one embodiment, the Degron is linked directly to the Targeting Ligand (i.e., -(Linker)$^A$- is a bond).

In certain embodiments, -(Linker)$^A$- can be any chemically stable group that attaches the Degron to the Targeting Ligand. The Linker can be any of the linkers described in Section IV (Linkers). In certain embodiment, -(Linker)$^B$ is a monovalent group attached to the Degron. In a typical embodiment, -(Linker)$^A$- or -(Linker)$^B$ has a chain of 2 to 14, 15, 16, 17, 18, 19, or 20 or more carbon atoms of which one or more carbon atoms can be replaced by a heteroatom such as O, N, S, or P, as long as the resulting molecule has a stable shelf life for at least two months, three months, six months, or one year as part of a pharmaceutically acceptable dosage form, and itself is pharmaceutically acceptable. In certain embodiments, the chain has 2, 3, 4, 5, 6, 7, 8, 9, 10, 11, 12, 13, or 14 contiguous atoms in the chain. For example, the chain may include 1 or more ethylene glycol units, and in some embodiments, may have at least 2, 3, 4, 5, 6, 7, 8, 9, or 10 or more contiguous, partially contiguous, or non-contiguous ethylene glycol units in -(Linker)$^A$- or -(Linker)$^B$. In certain embodiments, the chain has at least 1, 2, 3, 4, 5, 6, 7, or 8 branches which can be independently alkyl, heteroalkyl, aryl, heteroaryl, alkenyl, or alkynyl substituents, which in one embodiment, each branch has 10, 8, 6, 4, 3, 2, or 1 carbon.

In one embodiment, the Target Protein is a protein that is not druggable in the classic sense in that it does not have a binding pocket or an active site that can be inhibited or otherwise bound, and cannot be easily allosterically controlled. In another embodiment, the Target Protein is a protein that is druggable in the classic sense. Examples of Target Proteins are provided below.

In another embodiment, a Degron as described herein can be used alone (i.e., not as part of a Degrader) as an in vivo binder of cereblon, which can be administered to a host, for example, a human, in need thereof, in an effective amount, optionally as a pharmaceutically acceptable salt, and optionally in a pharmaceutically acceptable composition, for any therapeutic indication which can be treated by modulating the function or activity of the cereblon-containing E3 Ubiquitin Ligase Protein Complex, including but not limited to uses known for the cereblon binders thalidomide, pomalidomide, and lenalidomide. In certain embodiments, the Degron as described herein can activate, decrease, or change the natural activity of cereblon. Non-limiting examples of uses for cereblon binders are multiple myeloma, a hematological disorder such as myelodysplastic syndrome, cancer, tumors, abnormal cellular proliferation, HIV/AIDS, Crohn's disease, sarcoidosis, graft-versus-host disease, rheumatoid arthritis, Behcet's disease, tuberculosis, and myelofibrosis.

Thus, in another aspect a compound of Formula V is provided:

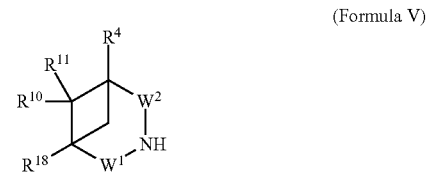

(Formula V)

or a pharmaceutically acceptable salt, N-oxide, isotopic derivative, or prodrug thereof, optionally in a pharmaceutically acceptable carrier to form a composition;
wherein:
$R^{18}$ is $R^{18a}$, $R^{18b}$, or $R^{18c}$.
$R^{18a}$ is selected from:

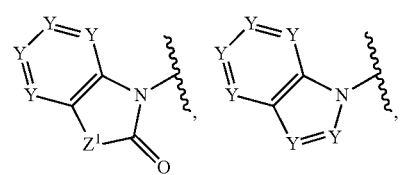

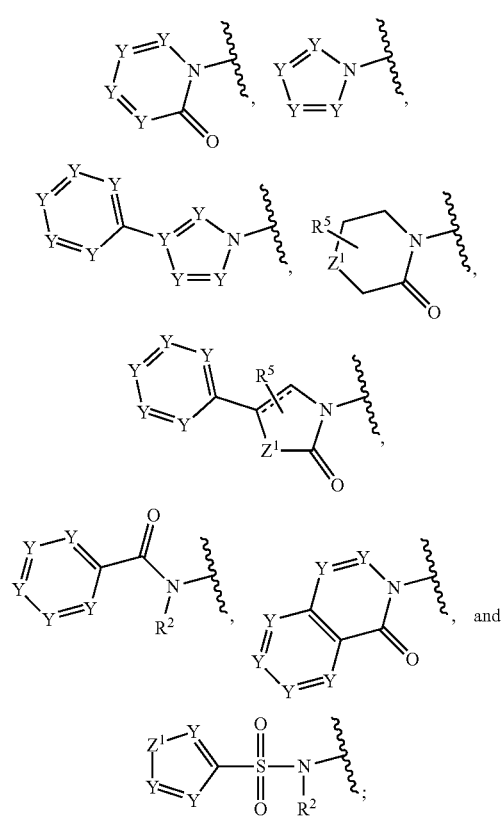
$R^{18b}$ is selected from:
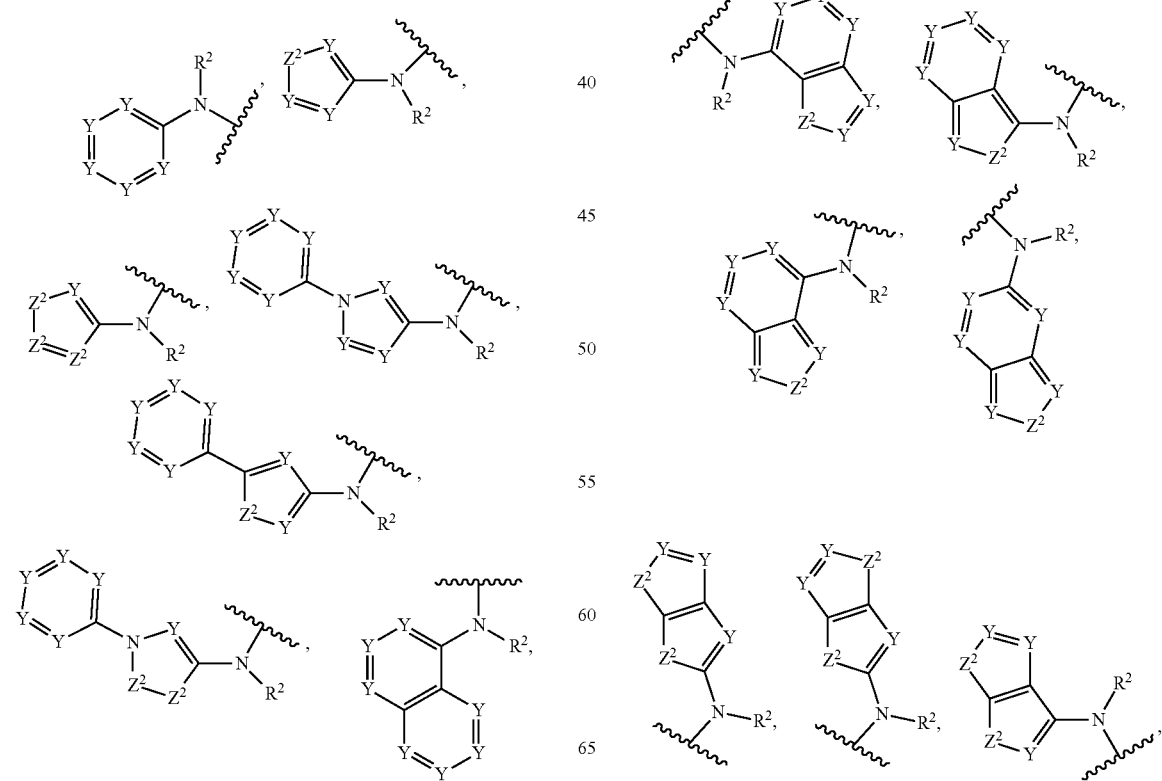

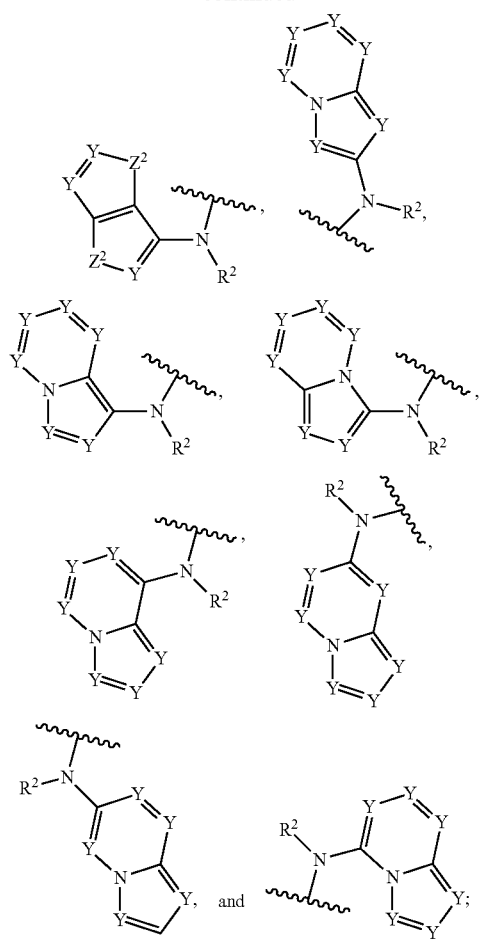
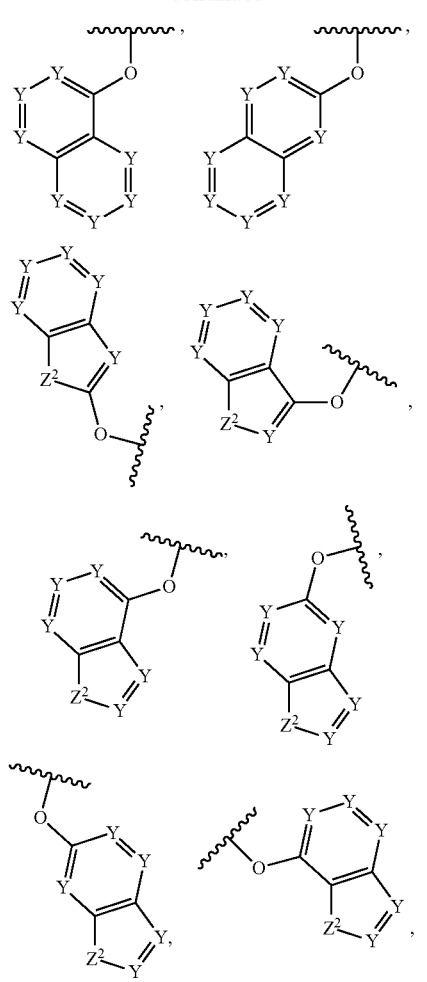
R[18c] is selected from:
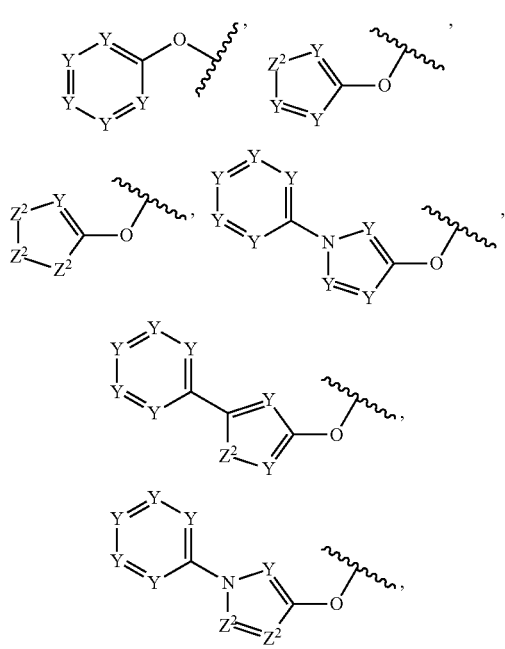
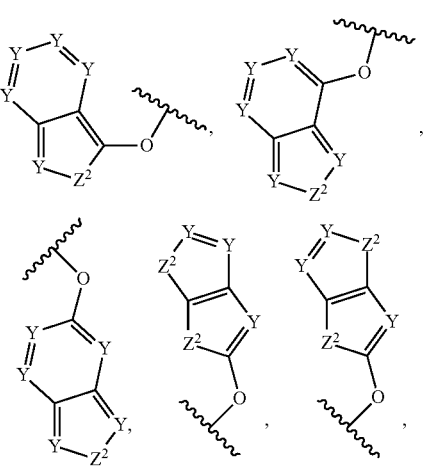
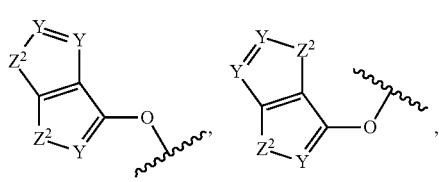

-continued

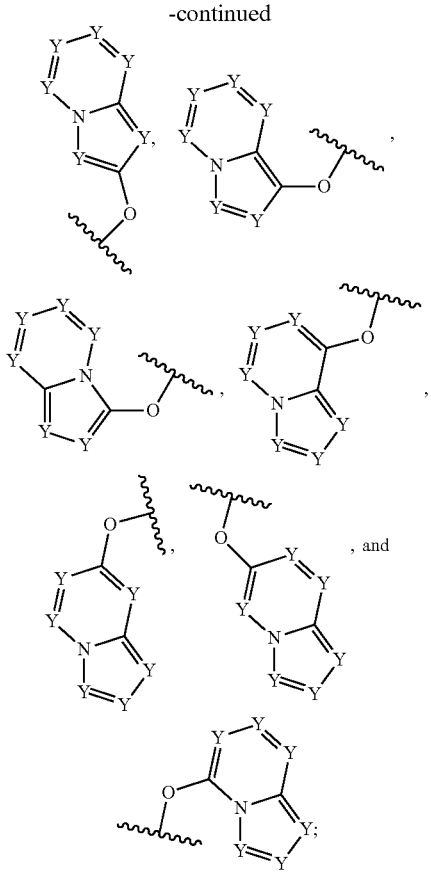

or
in an alternative embodiment, $R^{18a}$ is selected from:

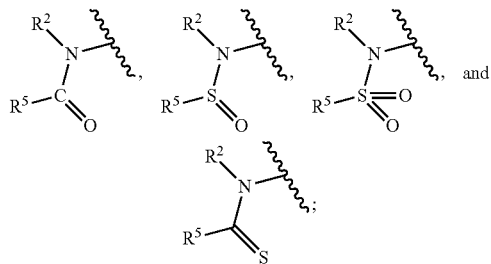

in another alternative embodiment, $R^{18a}$ is a 4, 5, 6, 7, 8, 9, or 10 membered heterocyclo or heteroaryl moiety containing at least one nitrogen atom through which it is directly attached, wherein the heterocyclo or heteroaryl moiety is optionally further substituted with one or more substituents selected from $R^5$; or in an alternative embodiment. $R^{18b}$ is selected from

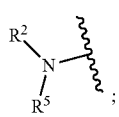

or in another alternative embodiment. $R^{18b}$ is —NR²aryl, —NR²heteroaryl, or NR²carbocycle, wherein the aryl, heteroaryl, and carbocycle moiety are optionally substituted with one or more, for example 1, 2, 3, or 4, substituents selected from $R^5$; and in an additional alternative embodiment the aryl, heteroaryl, and carbocycle moiety are optionally further substituted with one or more oxo groups at a position allowed by valence; or in an alternative embodiment. $R^{18c}$ is selected from

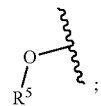

or $R^{18c}$ is —O-aryl, —O-heteroaryl, or —O-carbocycle, wherein the aryl, heteroaryl, and carbocycle moiety are optionally substituted with one or more, for example 1, 2, 3, or 4, substituents selected from $R^5$; and in an additional alternative embodiment the aryl, heteroaryl, and carbocycle moiety are optionally further substituted with one or more oxo groups at a position allowed by valence; and all other variables are defined as above.

In yet another aspect, a compound of Formula VI is provided:

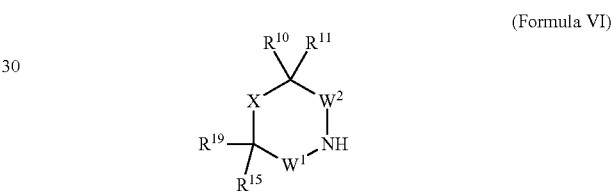

(Formula VI)

or a pharmaceutically acceptable salt, N-oxide, isotopic derivative, or prodrug thereof, optionally in a pharmaceutically acceptable carrier to form a composition;

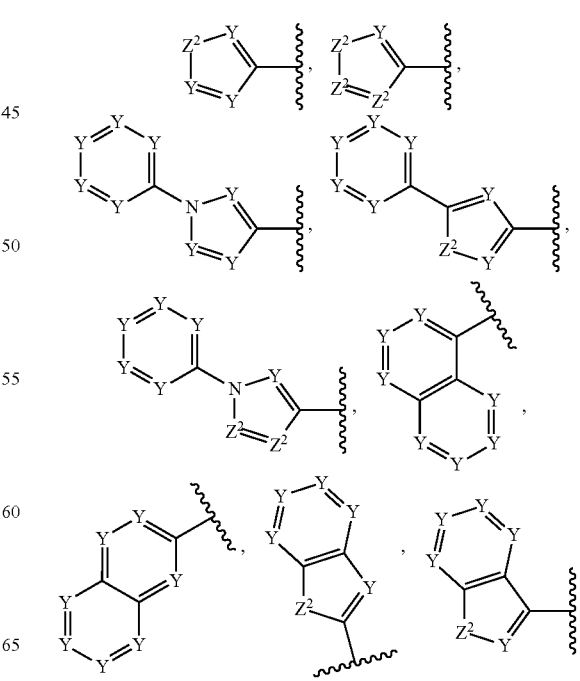

-continued

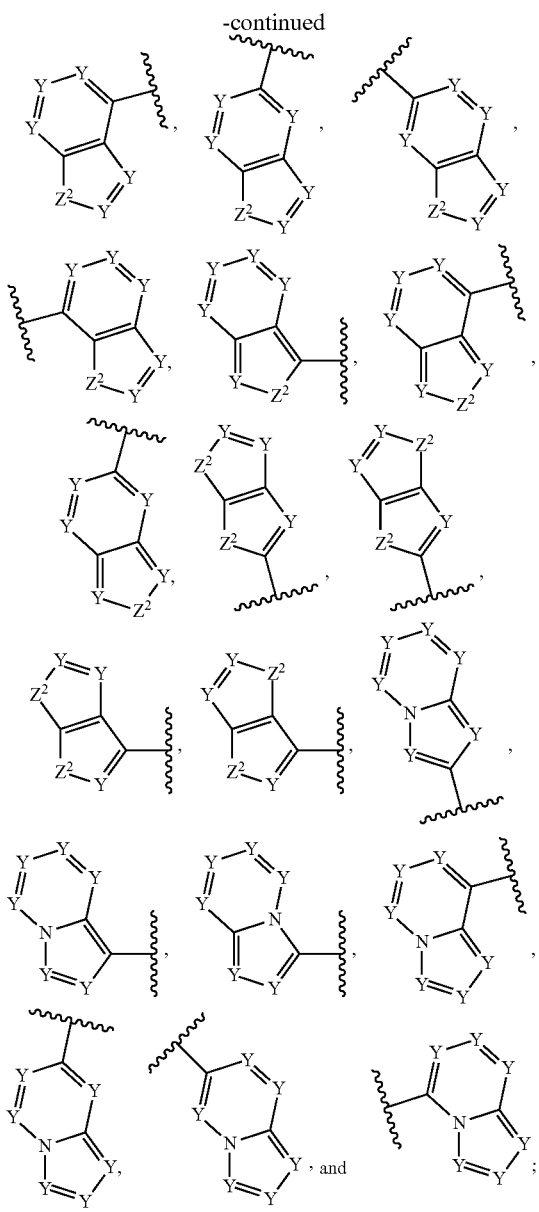

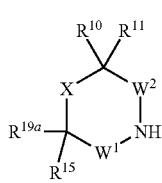

or in an alternative embodiment $R^{19}$ is a 4, 5, 6, 7, 8, 9, or 10 membered carbocyclo or aryl moiety, wherein the carbocyclo or aryl moiety is optionally further substituted with one or more substituents selected from $R^5$; and all other variables are defined as above.

In another aspect, the present invention includes a compound of Formula VIa:

(Formula VIa)

or a pharmaceutically acceptable salt, N-oxide, isotopic derivative, or prodrug thereof, optionally in a pharmaceutically acceptable carrier to form a composition;

wherein:

$R^{19a}$ is selected from:

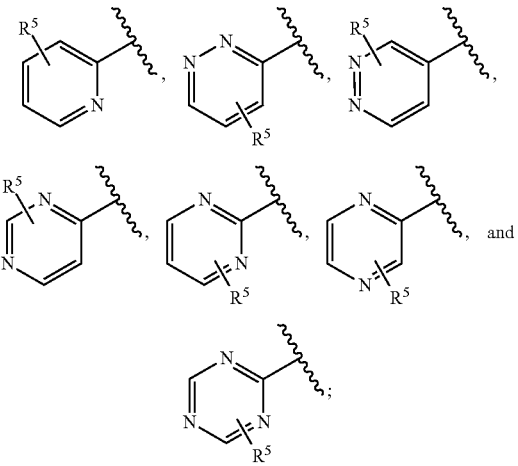

and all other variables are defined as above.

In another aspect, the present invention includes a compound of Formula VIb:

(Formula VIb)

or a pharmaceutically acceptable salt, N-oxide, isotopic derivative, or prodrug thereof, optionally in a pharmaceutically acceptable carrier to form a composition;

wherein:

$R^{19b}$ is selected from:

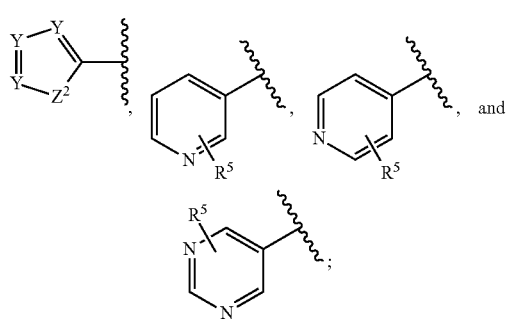

$X^A$ is selected from O or S; and all other variables are defined as above.

In an additional aspect, a compound of Formula VII or Formula VIII is provided:

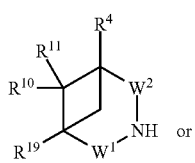
(Formula VII)

or

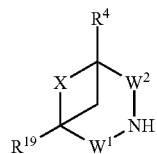
(Formula VIII)

or a pharmaceutically acceptable salt, N-oxide, derivative, or prodrug thereof, optionally in a pharmaceutically acceptable carrier to form a composition;

wherein all variables are defined as above.

In another aspect, the present invention includes a compound of Formula IX or Formula X:

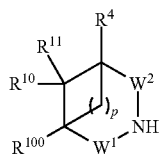
(Formula IX)

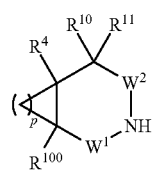
(Formula X)

or a pharmaceutically acceptable salt, N-oxide, isotopic derivative, or prodrug thereof, optionally in a pharmaceutically acceptable carrier to form a composition;

wherein:
p is 1, 2, 3, or 4;
$R^{100}$ is selected from $R^{16}$, $R^{17}$, $R^{18}$, and $R^{19}$; and
all other variables are defined as above.

In an alternative aspect, the present invention includes a compound of Formula XI:

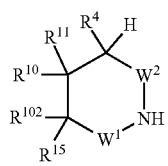
(Formula XI)

or a pharmaceutically acceptable salt, N-oxide, isotopic derivative, or prodrug thereof, optionally in a pharmaceutically acceptable carrier to form a composition;

wherein:
$R^{102}$ is selected from

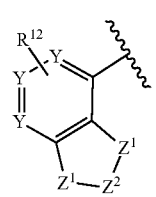 and 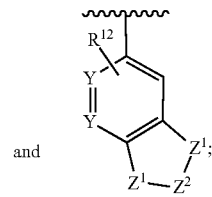;

In any of the fused rings that have an $R^{12}$, the $R^{12}$ can be placed on any available ring atom on either of the fused rings, except when excluded by context (such as where valency precludes), for example as shown in the formulas:

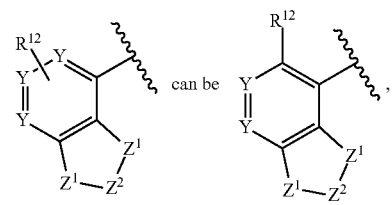 can be 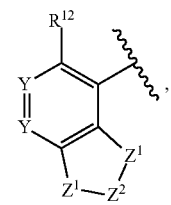,

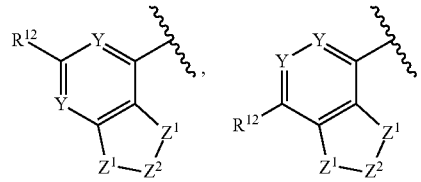,

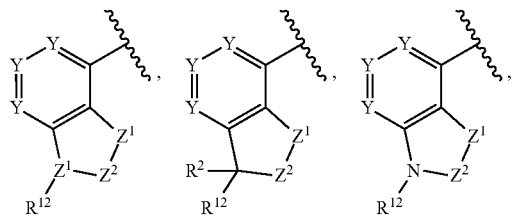,

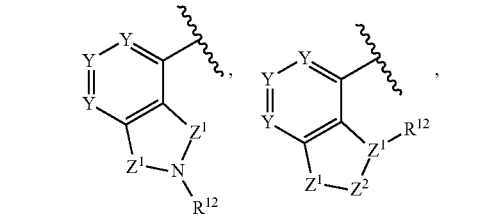,

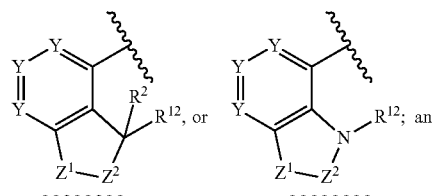, or 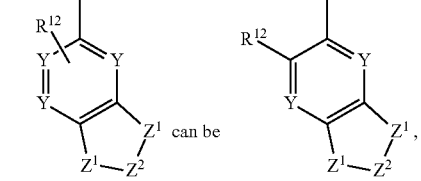; and

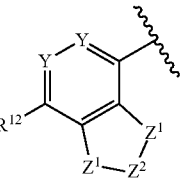 can be

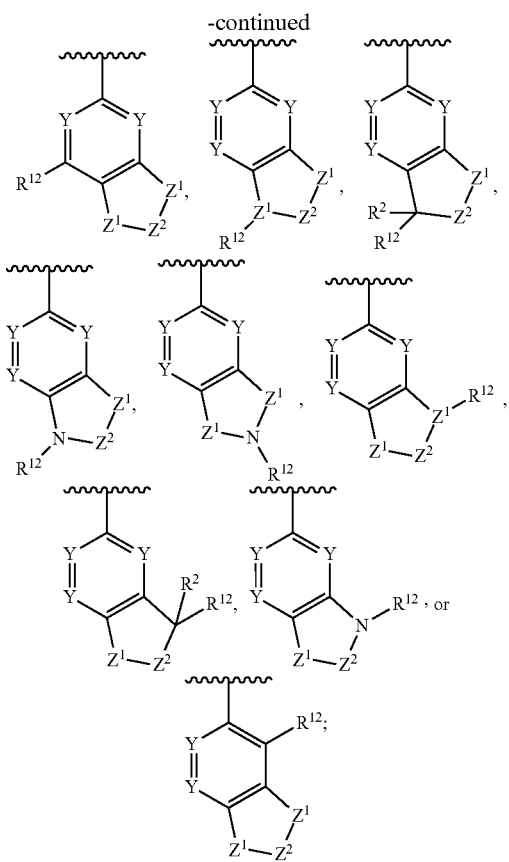

or $R^{102}$ is a 3, 4, 5, 6, 7, 8, or 10 membered heterocycle moiety containing at least one nitrogen atom, wherein the heterocycle moiety is attached through a carbon atom, wherein the heterocycle moiety is substituted with $R^{12}$ at any desired position, and wherein the heterocycle moiety is optionally further substituted with one or more, for example 1, 2, 3, or 4, substituents selected from $R^5$; and all other variables are defined as above.

In an alternative aspect, the present invention includes a compound of Formula XII:

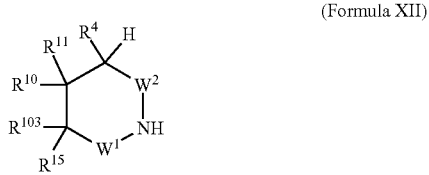

(Formula XII)

or a pharmaceutically acceptable salt, N-oxide, isotopic derivative, or prodrug thereof, optionally in a pharmaceutically acceptable carrier to form a composition;

wherein:

$R^{103}$ is a 3, 4, 5, 6, 7, 8, or 10 membered heterocycle moiety containing at least one nitrogen atom, wherein the heterocycle moiety is attached through a carbon atom, and wherein the heterocycle moiety is optionally further substituted with one or more, for example 1, 2, 3, or 4, substituents selected from $R^5$; and all other variables are defined as above.

In an alternative embodiment of any one of Formulas I, II, III, IV, IX, X, or XI, $R^2$ may additionally be selected from $R^{12}$ at each occurrence.

In another alternative embodiment of any one of Formulas I, II, III, IV, IX, X, or XI, $R^5$ may additionally be selected from $R^{12}$ at each occurrence.

The compounds of Formula V, Formula VI, Formula VII, Formula VIII, and Formula XII do not include a Targeting Ligand. In certain embodiments, the compound of Formula V, Formula VI, Formula VII, Formula VIII, or Formula XII can activate, decrease, or change the natural activity of cereblon. These compounds of Formula V, Formula VI, Formula VII, Formula VIII, and Formula XII are useful as therapeutic agents when administered in an effective amount to a host, typically a human, for the treatment of a medical disorder that can be treated with thalidomide, pomalidomide, or lenalidomide, and/or including, but not limited to, abnormal cell proliferation, including a tumor or cancer, or a myelo- or lymphoproliferative disorder such as B- or T-cell lymphomas, multiple myeloma, Waldenstrom's macroglobulinemia, Wiskott-Aldrich syndrome, or a post-transplant lymphoproliferative disorder; an immune disorder, including autoimmune disorders such as Addison disease, Celiac disease, dermatomyositis, Graves disease, thyroiditis, multiple sclerosis, pernicious anemia, reactive arthritis, lupus, or type I diabetes; a disease of cardiologic malfunction including hypercholesterolemia; an infectious disease including viral or bacterial infections; and inflammatory conditions including asthma, chronic peptic ulcers, tuberculosis, rheumatoid arthritis, periodontitis, ulcerative colitis, Crohn's disease, or hepatitis.

In certain embodiments, the present invention provides the administration of an effective amount of a compound of Formula I, Formula II, Formula III, Formula IV, Formula V, Formula VI, Formula VII, Formula VIII, Formula IX, Formula X, Formula XI, or Formula XII to treat a patient, for example, a human, having an infectious disease, wherein the therapy targets a Target Protein of the infectious agent or a Target Protein of the host (Formula I, Formula II, Formula III, Formula IV, Formula IX, Formula X, or Formula XI), or acts via binding to cereblon or its E3 Ubiquitin Ligase (Formula V, Formula VI, Formula VII, Formula VIII, or Formula XII), or acts through an independent mechanism, optionally in combination with another bioactive agent. The disease state or condition may be caused by a microbial agent or other exogenous agent such as a virus (as non-limiting examples, HIV, HBV, HCV, HSV, HPV, RSV, CMV, Ebola, Flavivirus, Pestivirus, Rotavirus, Influenza, Coronavirus, EBV, viral pneumonia, drug-resistant viruses, Bird Flu, RNA virus, DNA virus, adenovirus, poxvirus, Picornavirus, Togavirus, Orthomyxovirus, Retrovirus, or Hepadnovirus), bacteria (including but not limited to Gram-negative, Gram-positive, Atypical, Staphylococcus, Streptococcus, E. Coli, Salmonella, Helicobacter pylori, meningitis, gonorrhea, Chlamydiaceae, Mycoplasmataceae, etc.), fungus, protozoa, helminth, worm, prion, parasite, or other microbe.

In certain embodiments, the compound of Formula I, Formula II, Formula III, Formula IV, Formula V, Formula VI, Formula VII, Formula VIII, Formula IX, Formula X, Formula XI, or Formula XII has at least one desired isotopic substitution of an atom, at an amount above the natural abundance of the isotope, i. e., enriched. In one embodiment, the compound of Formula I, Formula II, Formula III, Formula IV, Formula V, Formula VI, Formula VII, Formula VIII, Formula IX, Formula X, Formula XI, or Formula XII includes a deuterium or multiple deuterium atoms.

Compounds of the present invention may offer important clinical benefits to patients, in particular for the treatment of the disease states and conditions modulated by the proteins of interest.

Unless otherwise defined, all technical and scientific terms used herein have the same meaning as commonly understood by one of ordinary skill in the art to which this application belongs. In the specification, singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

Other features and advantages of the present application will be apparent from the following detailed description and claims.

The present invention thus includes at least the following features:

(a) A Degrader of Formula I, Formula II, Formula III, Formula IV, Formula IX, Formula X, or Formula XI as described herein, or a pharmaceutically acceptable salt, isotopic derivative (including a deuterated derivative), or prodrug thereof;

(b) A Degron of Formula V, Formula VI, Formula VII, Formula VIII, Formula IX, Formula X, or Formula XII as described herein, or a pharmaceutically acceptable salt, isotopic derivative (including a deuterated derivative), or prodrug thereof;

(c) A Degrader of Formula I, Formula II, Formula III, Formula IV, Formula IX, Formula X, or Formula XI, or a pharmaceutically acceptable salt, isotopic derivative (including a deuterated derivative), or prodrug thereof for the treatment of a disorder that is mediated by a Target Protein, wherein the compound includes a Targeting Ligand for the Target Protein, and wherein the Degron is optionally linked to the Targeting Ligand through a linker;

(d) Use of a Degrader of Formula I, Formula II, Formula III, Formula IV, Formula IX, Formula X, or Formula XI in an effective amount in the treatment of a patient, typically a human, with any of the disorders described herein mediated by a Target Protein, including abnormal cellular proliferation such as a tumor or cancer, an immune or autoimmune disorder or inflammatory disorder, a cardiologic disorder, an infectious disease, or other disorder that responds to such treatment;

(e) Use of a compound of Formula V, Formula VI, Formula VII, Formula VIII, or Formula XII in an effective amount in the treatment of a patient, typically a human, with a disorder that responds to such treatment, including by decreasing the cereblon-based ubiquitination of a protein, such as for example, abnormal cellular proliferation such as a tumor or cancer, an immune or autoimmune disorder or inflammatory disorder, a cardiac disorder, an infectious disease, or other disorder that responds to such treatment;

(f) Use of a compound of Formula I, Formula II, Formula III, Formula IV, Formula V, Formula VI, Formula VII, Formula VIII, Formula IX, Formula X, Formula XI, or Formula XII or a pharmaceutically acceptable salt, isotopic derivative (including a deuterated derivative), or prodrug thereof in the manufacture of a medicament for the treatment of a medical disorder, as further described herein;

(g) A method for manufacturing a medicament intended for the therapeutic treatment of a disorder in a host characterized in that a compound of Formula I, Formula II, Formula III, Formula IV, Formula V, Formula VI, Formula VII, Formula VIII, Formula IX, Formula X, Formula XI, or Formula XII as described herein is used in the manufacture;

(h) A compound of Formula I, Formula II, Formula III, Formula IV, Formula V, Formula VI, Formula VII, Formula VIII, Formula IX, Formula X, Formula XI, or Formula XII as described herein, or a pharmaceutically acceptable salt, isotopic derivative (including a deuterated derivative), or prodrug thereof that are useful in the treatment of an abnormal cellular proliferation such as cancer in a host, including any of the cancers described herein;

(i) Use of a compound of Formula I, Formula II, Formula III, Formula IV, Formula V, Formula VI, Formula VII, Formula VIII, Formula IX, Formula X, Formula XI, or Formula XII as described herein, or a pharmaceutically acceptable salt, isotopic derivative (including a deuterated derivative), or prodrug thereof in the manufacture of a medicament for the treatment of an abnormal cellular proliferation such as cancer, including any of the cancers described herein;

(j) A method for manufacturing a medicament intended for the therapeutic use of treating an abnormal cellular proliferation such as cancer, including any of the cancers in a host described herein, characterized in that a compound of Formula I, Formula II, Formula III, Formula IV, Formula V, Formula VI, Formula VII, Formula VIII, Formula IX, Formula X, Formula XI, or Formula XII as described herein is used in the manufacture;

(k) A compound of Formula I, Formula II, Formula III, Formula IV, Formula V, Formula VI, Formula VII, Formula VIII, Formula IX, Formula X, Formula XI, or Formula XII as described herein, or a pharmaceutically acceptable salt, isotopic derivative (including a deuterated derivative), or prodrug thereof that are useful in the treatment of a tumor in a host, including any of the tumors described herein;

(l) Use of a compound of Formula I, Formula II, Formula III, Formula IV, Formula V, Formula VI, Formula VII, Formula VIII, Formula IX, Formula X, Formula XI, or Formula XII as described herein, or a pharmaceutically acceptable salt, isotopic derivative (including a deuterated derivative), or prodrug thereof in the manufacture of a medicament for the treatment of a tumor, including any of the cancers described herein;

(m) A method for manufacturing a medicament intended for the therapeutic treatment of a tumor in a host, including any of the tumors described herein, characterized in that a compound of Formula I, Formula II, Formula III, Formula IV, Formula V, Formula VI, Formula VII, Formula VIII, Formula IX, Formula X, Formula XI, or Formula XII as described herein is used in the manufacture;

(n) A compound of Formula I, Formula II, Formula III, Formula IV, Formula V, Formula VI, Formula VII, Formula VIII, Formula IX, Formula X, Formula XI, or Formula XII as described herein, or a pharmaceutically acceptable salt, isotopic derivative (including a deuterated derivative), or prodrug thereof that is useful in the treatment of an immune, autoimmune, or inflammatory disorder in a host;

(o) Use of a compound of Formula I, Formula II, Formula III, Formula IV, Formula V, Formula VI, Formula VII, Formula VIII, Formula IX, Formula X, Formula XI, or Formula XII as described herein, or a pharmaceutically acceptable salt, isotopic derivative (including a deuterated derivative), or prodrug thereof in the manufacture of a medicament for the treatment an immune, autoimmune, or inflammatory disorder in a host;

(p) A method for manufacturing a medicament intended for the therapeutic treatment of an immune, autoimmune, or inflammatory disorder in a host, characterized in that a compound of Formula I, Formula II, Formula III, Formula IV, Formula V, Formula VI, Formula VII, Formula VIII, Formula IX, Formula X, Formula XI, or Formula XII as described herein is used in the manufacture;

(q) A compound of Formula I, Formula II, Formula III, Formula IV, Formula V, Formula VI, Formula VII, Formula VIII, Formula IX, Formula X, Formula XI, or Formula XII as described herein, and pharmaceutically acceptable salts, isotopic derivatives, and prodrugs thereof that are useful in the treatment of an infection, including a viral infection in a host, for example HIV, HBV, HCV, and RSV;

(r) Use of a compound of Formula I, Formula II, Formula III, Formula IV, Formula V, Formula VI, Formula VII, Formula VIII, Formula IX, Formula X, Formula XI, or Formula XII as described herein, or a pharmaceutically acceptable salt, isotopic derivative (including a deuterated derivative), or prodrug thereof in the manufacture of a medicament for treatment of an infection, including a viral infection in a host, for example HIV, HBV, HCV, and RSV;

(s) A method for manufacturing a medicament intended for the therapeutic treatment of an infection, including a viral infection in a host, for example HIV, HBV, HCV, and RSV, characterized in that a compound of Formula I, Formula II, Formula III, Formula IV, Formula V, Formula VI, Formula VII, Formula VIII, Formula IX, Formula X, Formula XI, or Formula XII as described herein is used in the manufacture;

(t) A pharmaceutical formulation comprising an effective host-treating amount of a compound of Formula I, Formula II, Formula III, Formula IV, Formula V, Formula VI, Formula VII, Formula VIII, Formula IX, Formula X, Formula XI, or Formula XII, or a pharmaceutically acceptable salt, isotopic derivative, or prodrug thereof together with a pharmaceutically acceptable carrier or diluent;

(u) A compound of Formula I, Formula II, Formula III, Formula IV, Formula V, Formula VI, Formula VII, Formula VIII, Formula IX, Formula X, Formula XI, or Formula XII as described herein as a mixture of enantiomers or diastereomers (as relevant), including as a racemate;

(v) A compound of Formula I, Formula II, Formula III, Formula IV, Formula V, Formula VI, Formula VII, Formula VIII, Formula IX, Formula X, Formula XI, or Formula XII as described herein in enantiomerically or diastereomerically (as relevant) enriched form, including an isolated enantiomer or diastereomer (i.e., greater than 85, 90, 95, 97, or 99% pure); and (w) A process for the preparation of therapeutic products that contain an effective amount of a compound of Formula I, Formula II, Formula III, Formula IV, Formula V, Formula VI, Formula VII, Formula VIII, Formula IX, Formula X, Formula XI, or Formula XII as described herein.

BRIEF DESCRIPTION OF THE FIGURES

FIG. 1K-1Q present examples of General Kinase and Phosphatase Targeting Ligands wherein R is the point at which the Linker is attached.

FIG. 1AA presents examples of mTORC1 and/or mTORC2 Targeting Ligands wherein R is the point at which the Linker is attached.

FIG. 1BB-1CC present examples of Mast/stem cell growth factor receptor (SCFR), also known as c-KIT receptor, Targeting Ligands wherein R is the point at which the Linker is attached.

FIG. 1DD presents examples of IGF1R and/or IR Targeting Ligands wherein R is the point at which the Linker is attached.

FIG. 1EE-1FF present examples of HDM2 and/or MDM2 Targeting Ligands wherein R is the point at which the Linker is attached.

FIG. 1GG-1MM present examples of BET Bromodomain-Containing Protein Targeting Ligands wherein R is the point at which the Linker is attached.

FIG. 1NN presents examples of HDAC Targeting Ligands wherein R is the point at which the Linker is attached.

FIG. 1OO presents examples of RAF Receptor Targeting Ligands wherein R is the point at which the Linker is attached.

FIG. 1PP presents examples of FKBP Receptor Targeting Ligands wherein R is the point at which the Linker is attached.

FIG. 1QQ-1TT present examples of Androgen Receptor Targeting Ligands wherein R is the point at which the Linker is attached.

FIG. 1UU presents examples of Estrogen Receptor Targeting Ligands wherein R is the point at which the Linker is attached.

FIG. 1VV-1WW present examples of Thyroid Hormone Receptor Targeting Ligands wherein R is the point at which the Linker is attached.

FIG. 1XX presents examples of HIV Protease Targeting Ligands wherein R is the point at which the Linker is attached.

FIG. 1YY presents examples of HIV Integrase Targeting Ligands wherein R is the point at which the Linker is attached.

FIG. 1ZZ presents examples of HCV Protease Targeting Ligands wherein R is the point at which the Linker is attached.

FIG. 1AAA presents examples of AP1 and/or AP2 Targeting Ligands wherein R is the point at which the Linker is attached.

FIG. 1BBB-1CCC present examples of MCL-1 Targeting Ligands wherein R is the point at which the Linker is attached.

FIG. 1DDD presents examples of IDH1 Targeting Ligands wherein R is the point at which the Linker is attached.

FIG. 1EEE-1FFF present examples of RAS or RASK Targeting Ligands wherein R is the point at which the Linker is attached.

FIG. 1GGG presents examples of MERTK or MER Targeting Ligands wherein R is the point at which the linker is attached.

FIG. 1HHH-1III present examples of EGFR Targeting Ligands wherein R is the point at which the Linker is attached.

FIG. 1JJJ-1KKK present examples of FLT3 Targeting Ligands wherein R is the point at which the Linker is attached.

FIG. 1LLL presents examples of SMRCA2 Targeting Ligands wherein R is the point at which the Linker is attached.

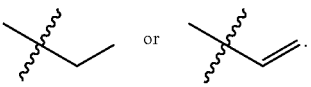

Figure 2A:
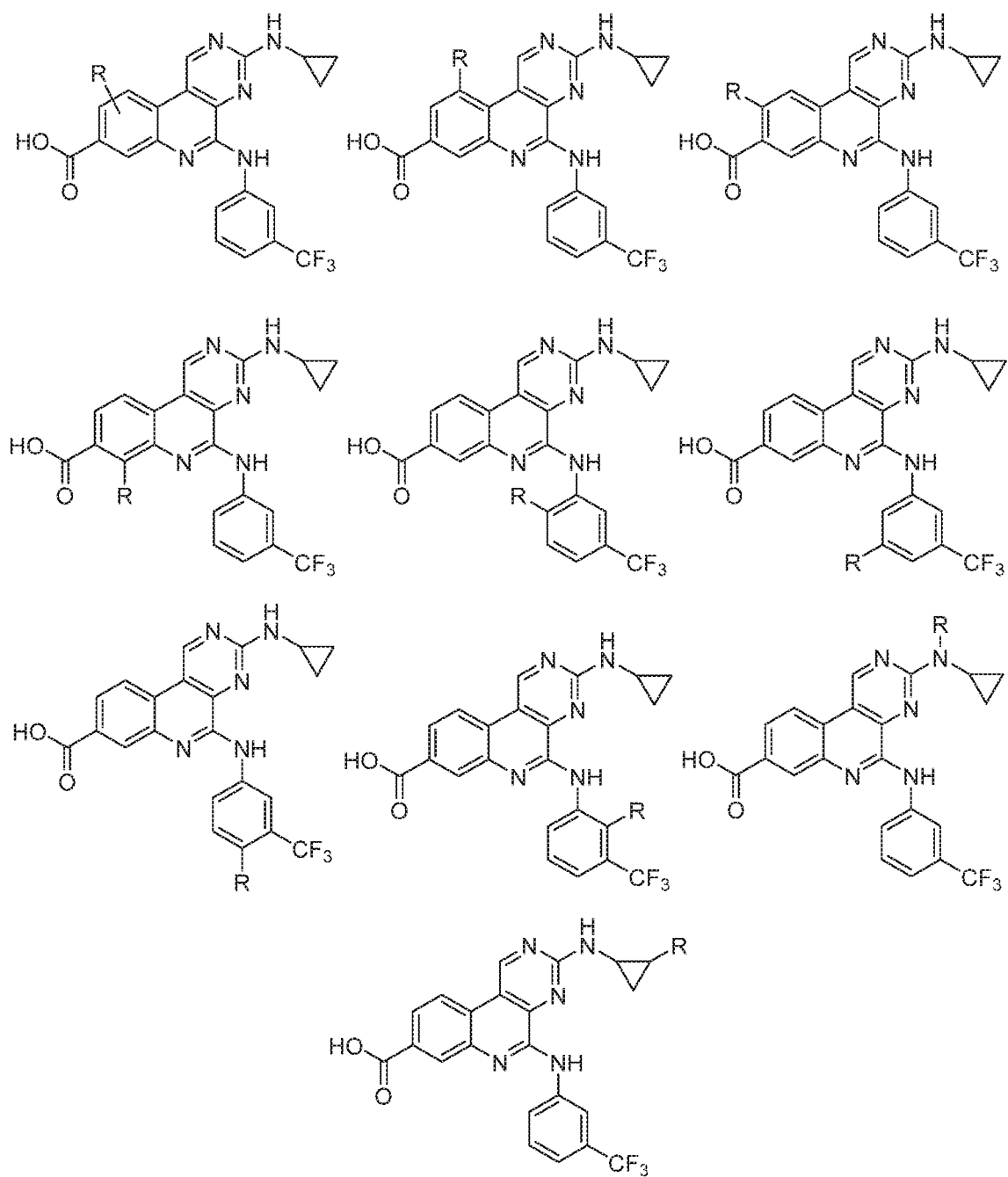
FIG. 2A presents examples of the kinase inhibitor Targeting Ligands U09-CX-5279 (derivatized) wherein R is the point at which the Linker is attached.
Figure 2B:
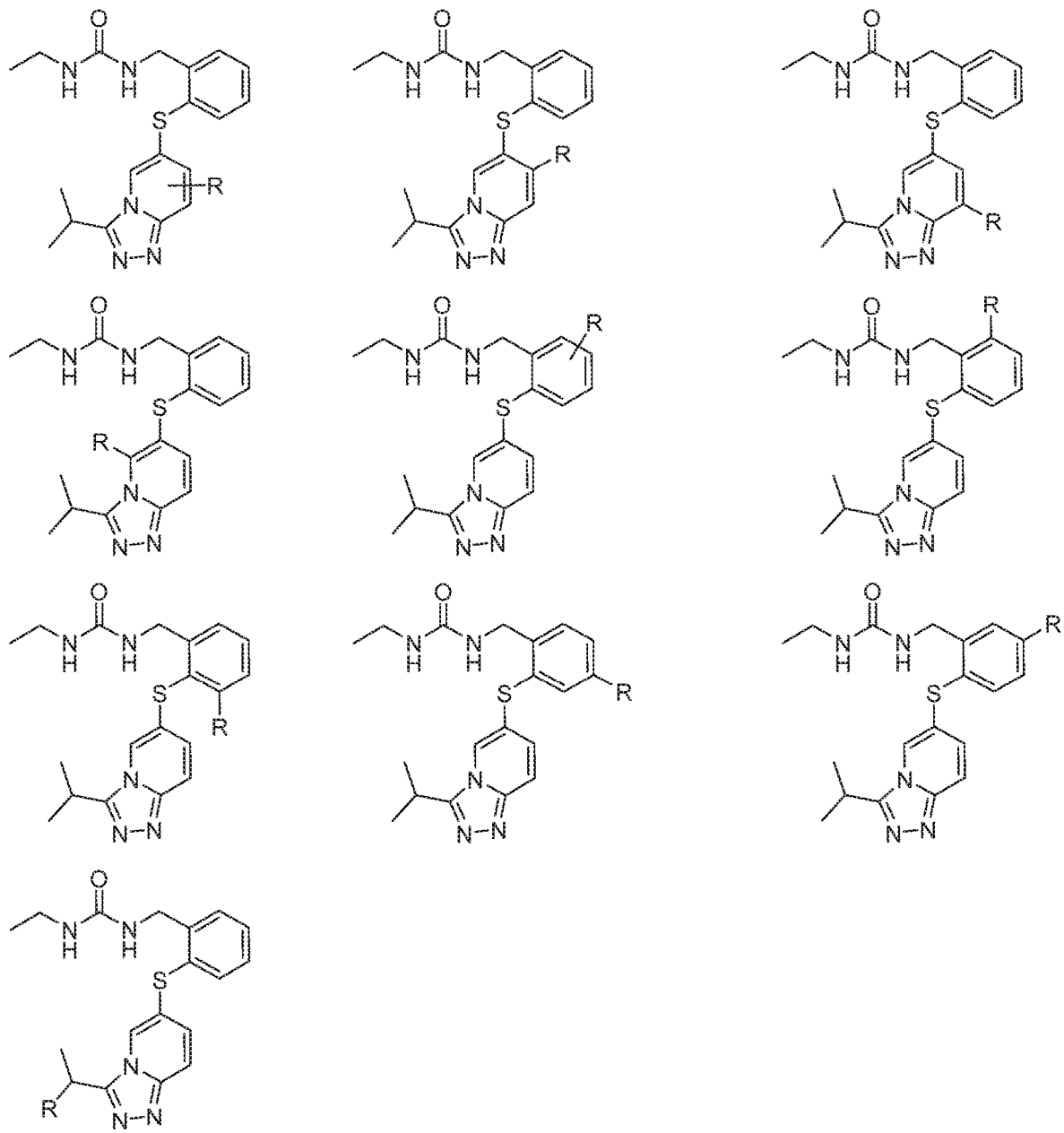
FIG. 2B-2C present examples of kinase inhibitor Targeting Ligands, including the kinase inhibitor compounds Y1W and Y1X (derivatized) wherein R is the point at which the Linker is attached. For additional examples and related ligands, see, the kinase inhibitors identified in Millan et al. "Design and Synthesis of Inhaled P38 Inhibitors for the Treatment of Chronic Obstructive Pulmonary Disease" *J. Med. Chem.*, 54: 7797 (2011).
Figure 2C:
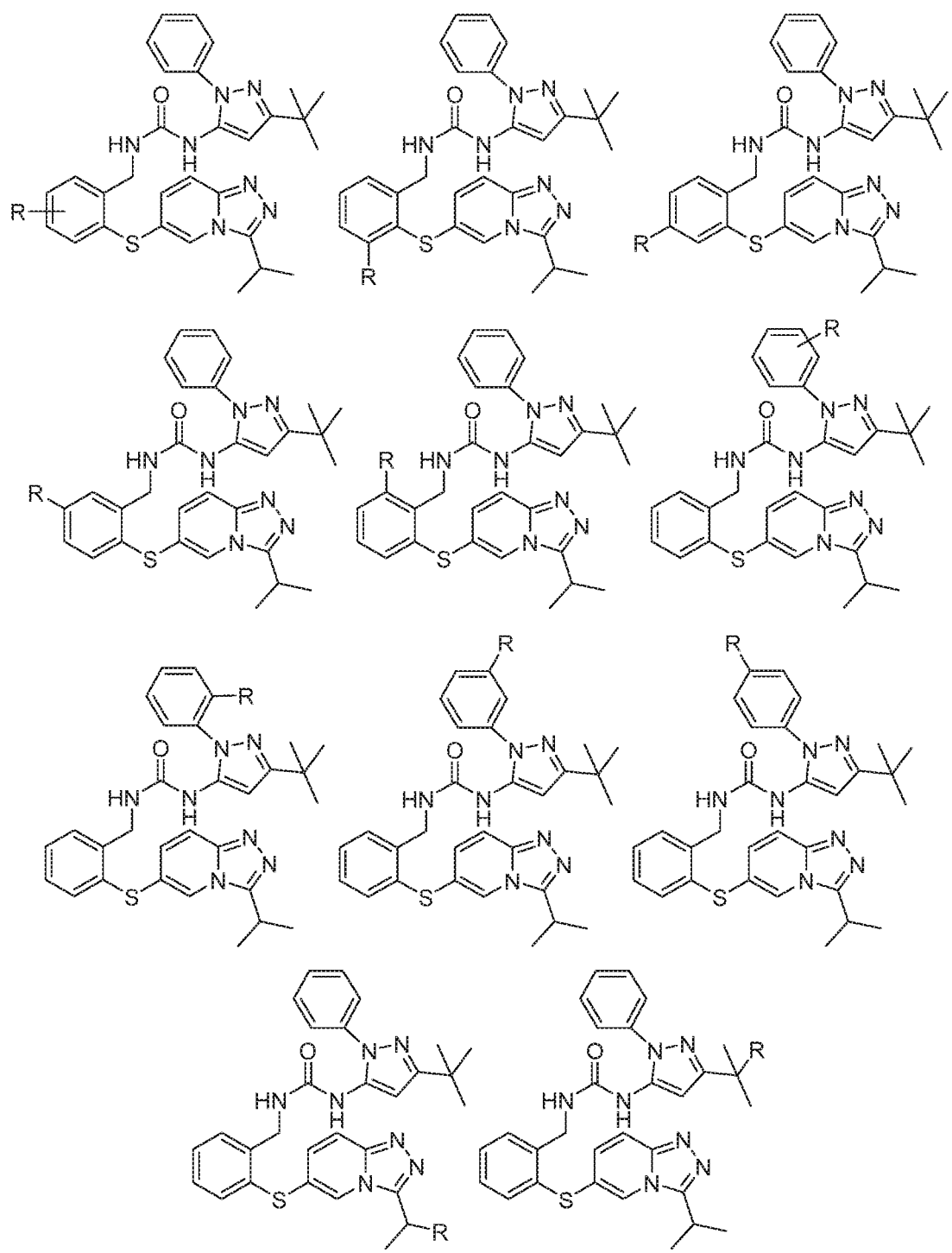
Figure 2D:
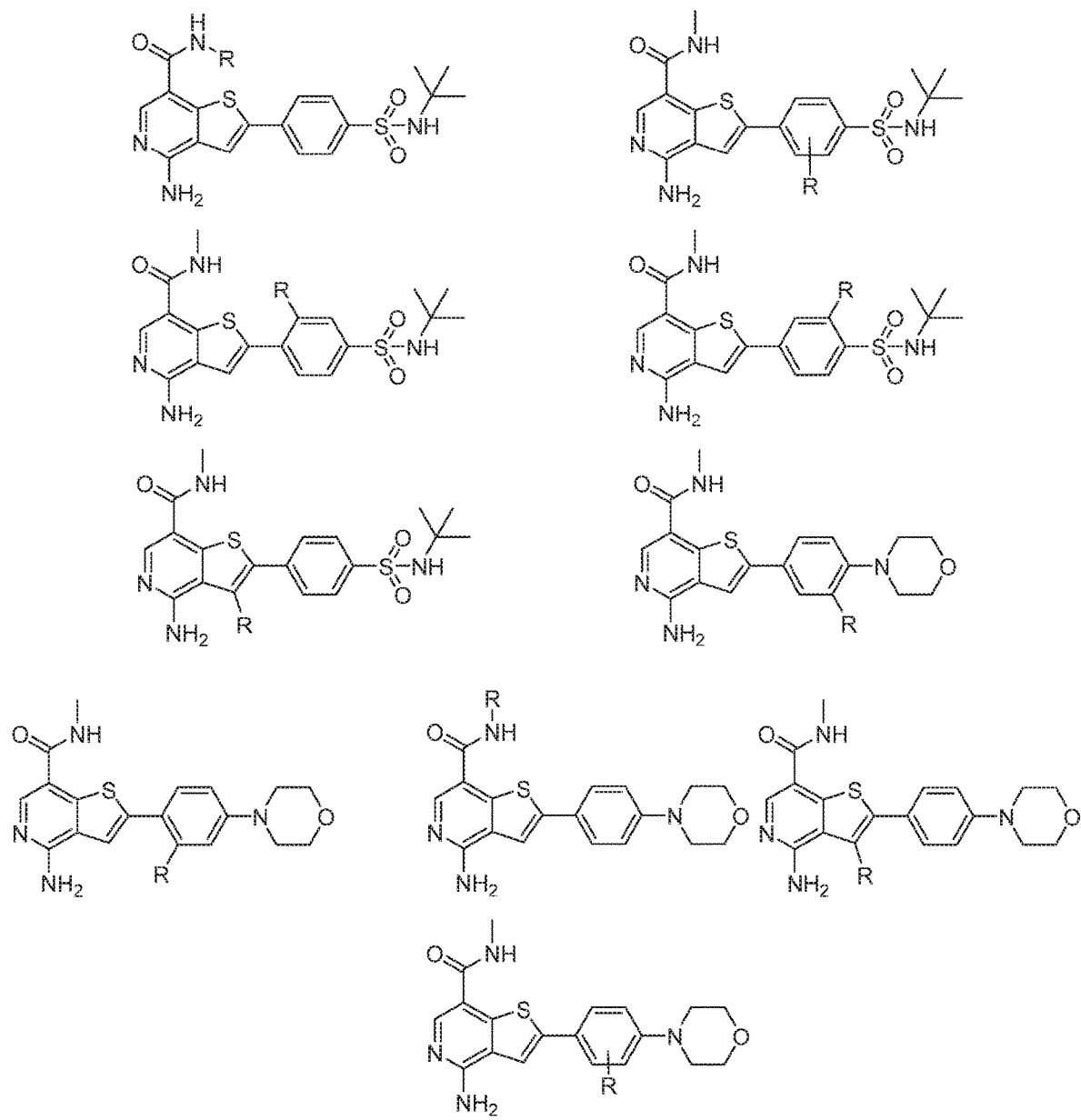
FIG. 2D presents examples of kinase inhibitor Targeting Ligands, including the kinase inhibitor compounds 6TP and OTP (derivatized) wherein R is the point at which the Linker is attached. For additional examples and related ligands, see, the kinase inhibitors identified in Schenkel et al. "Discovery of Potent and Highly Selective Thienopyridine Janus Kinase 2 Inhibitors" *J. Med. Chem.*, 54 (24): 8440-8450 (2011).
Figure 2E:
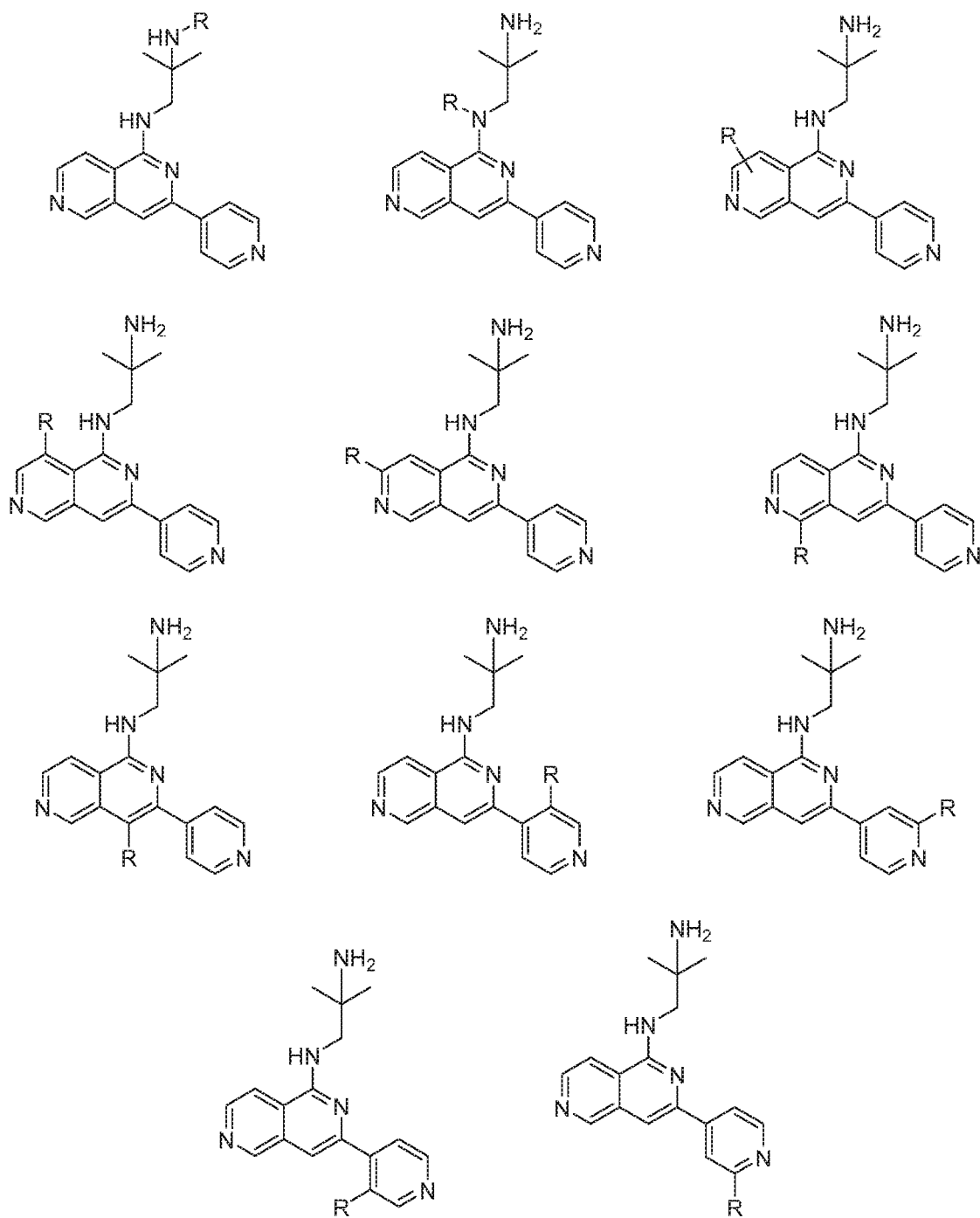
FIG. 2E presents examples of kinase inhibitor Targeting Ligands, including the kinase inhibitor compound 07U wherein R is the point at which the Linker is attached. For additional examples and related ligands, see, the kinase inhibitors identified in Van Eis et al. "2 6-Naphthyridines as potent and selective inhibitors of the novel protein kinase C isozymes" *Biorg. Med. Chem. Lett.*, 21(24): 7367-72 (2011).
Figure 2H:
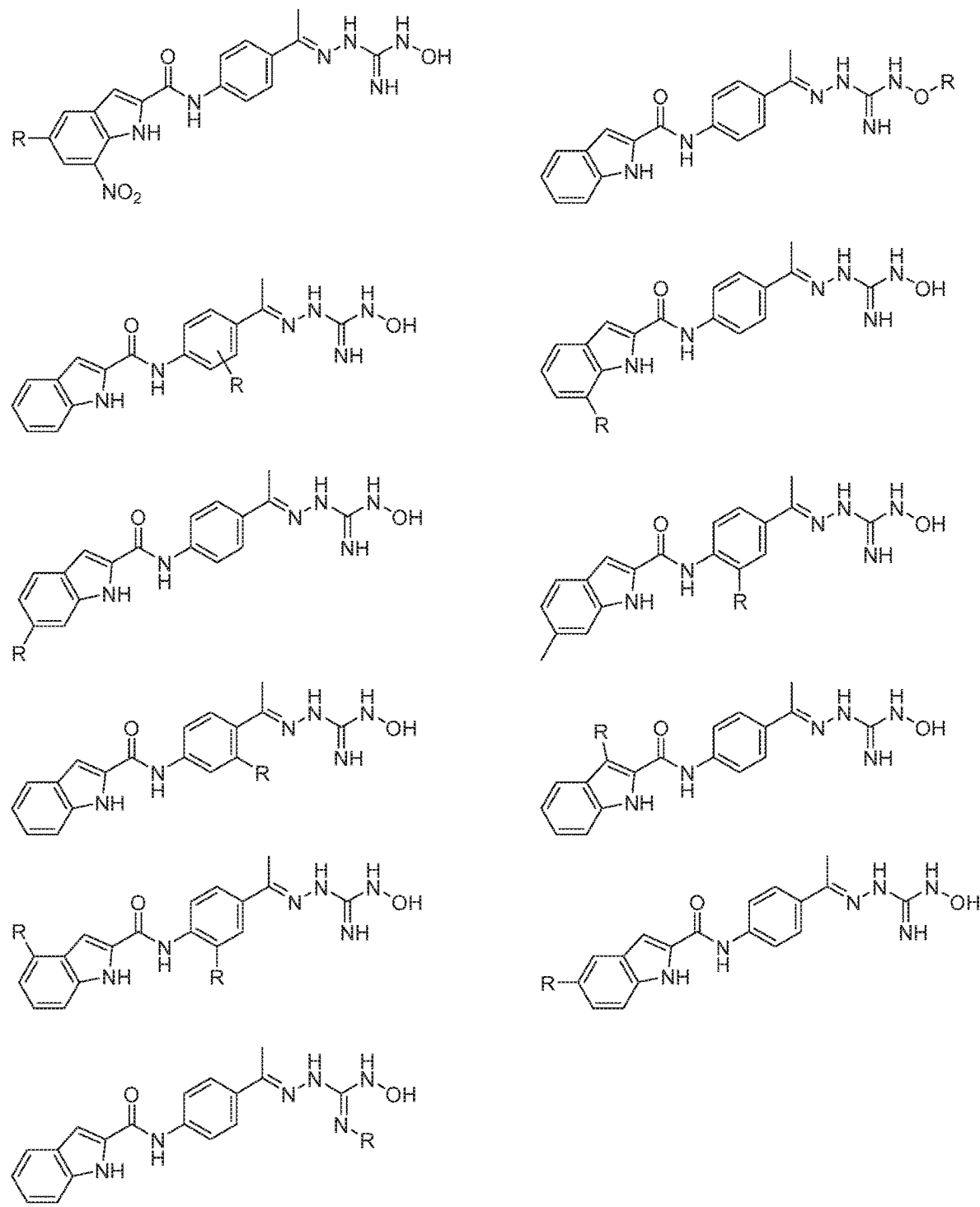
FIG. 2G-2H present examples of kinase inhibitor Targeting Ligands, including the kinase inhibitors XK9 and NXP (derivatized) wherein R is the point at which the Linker is attached. For additional examples and related ligands, see, the kinase inhibitors identified in Lountos et al. "Structural Characterization of Inhibitor Complexes with Checkpoint Kinase 2 (Chk2) a Drug Target for Cancer Therapy" *J. Struct. Biol.*, 176: 292 (2011).
Figure 2I:
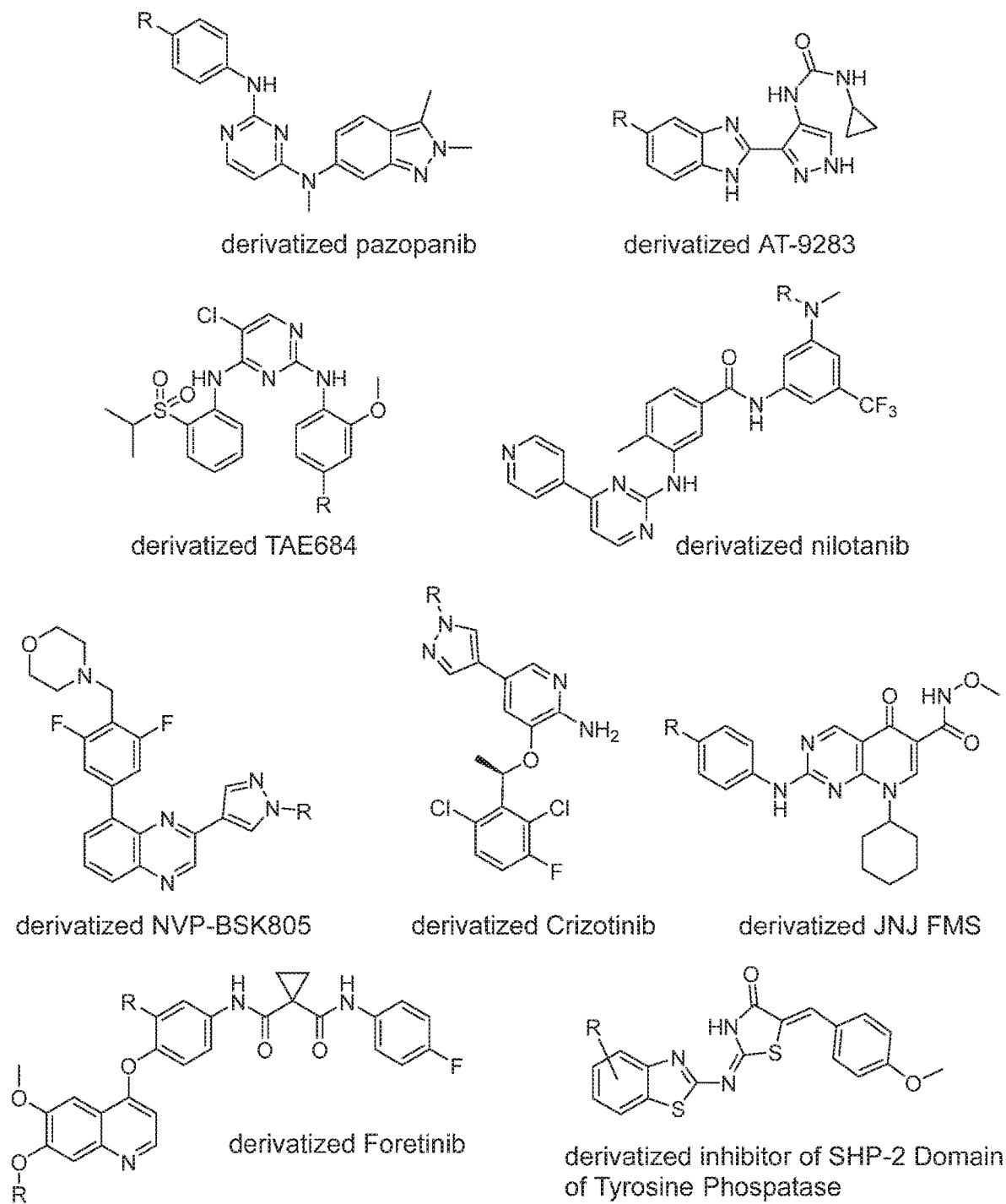
FIG. 2I-2J present examples of kinase inhibitor Targeting Ligands wherein R is the point at which the Linker r is attached.
Figure 2J:
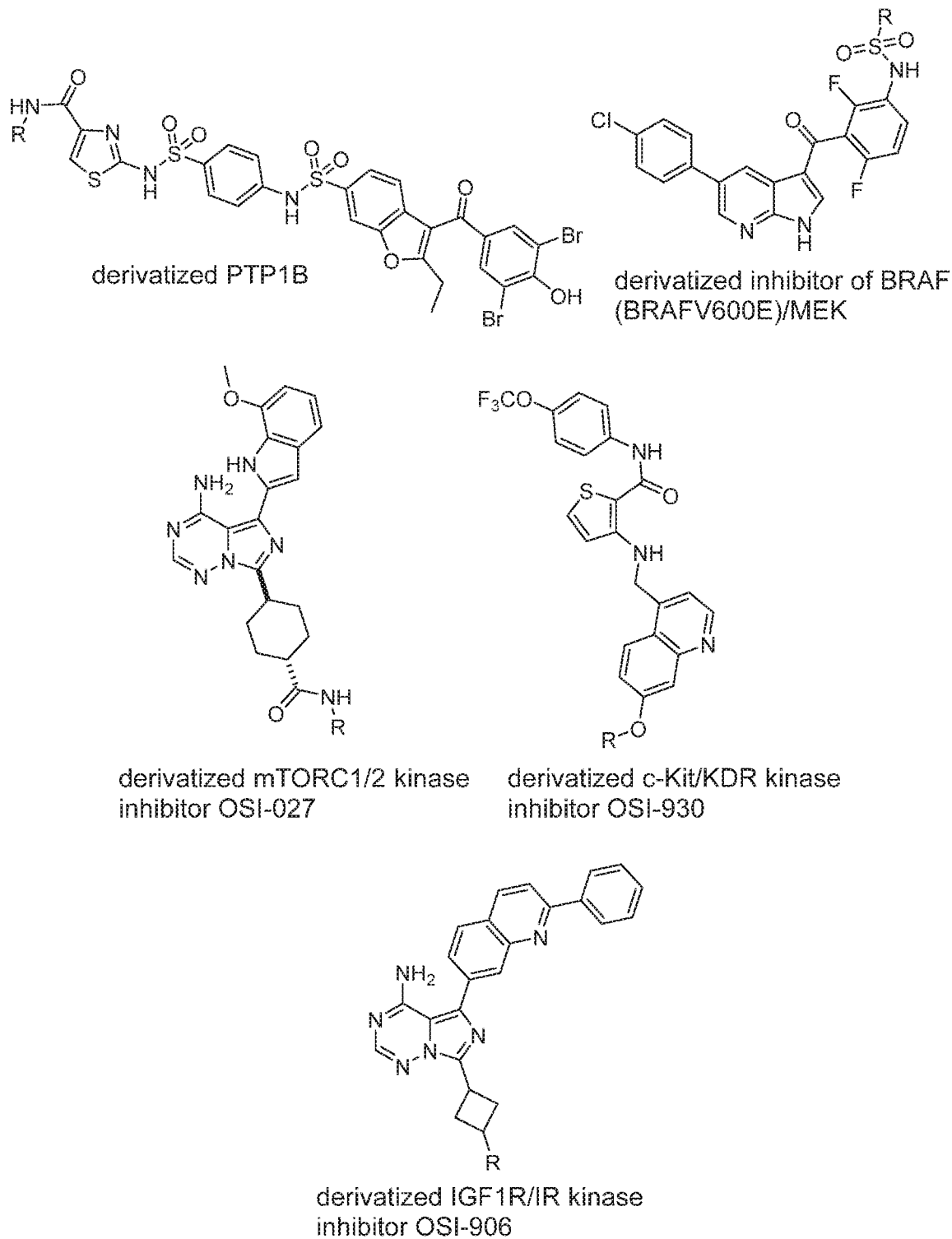
Figure 2K:
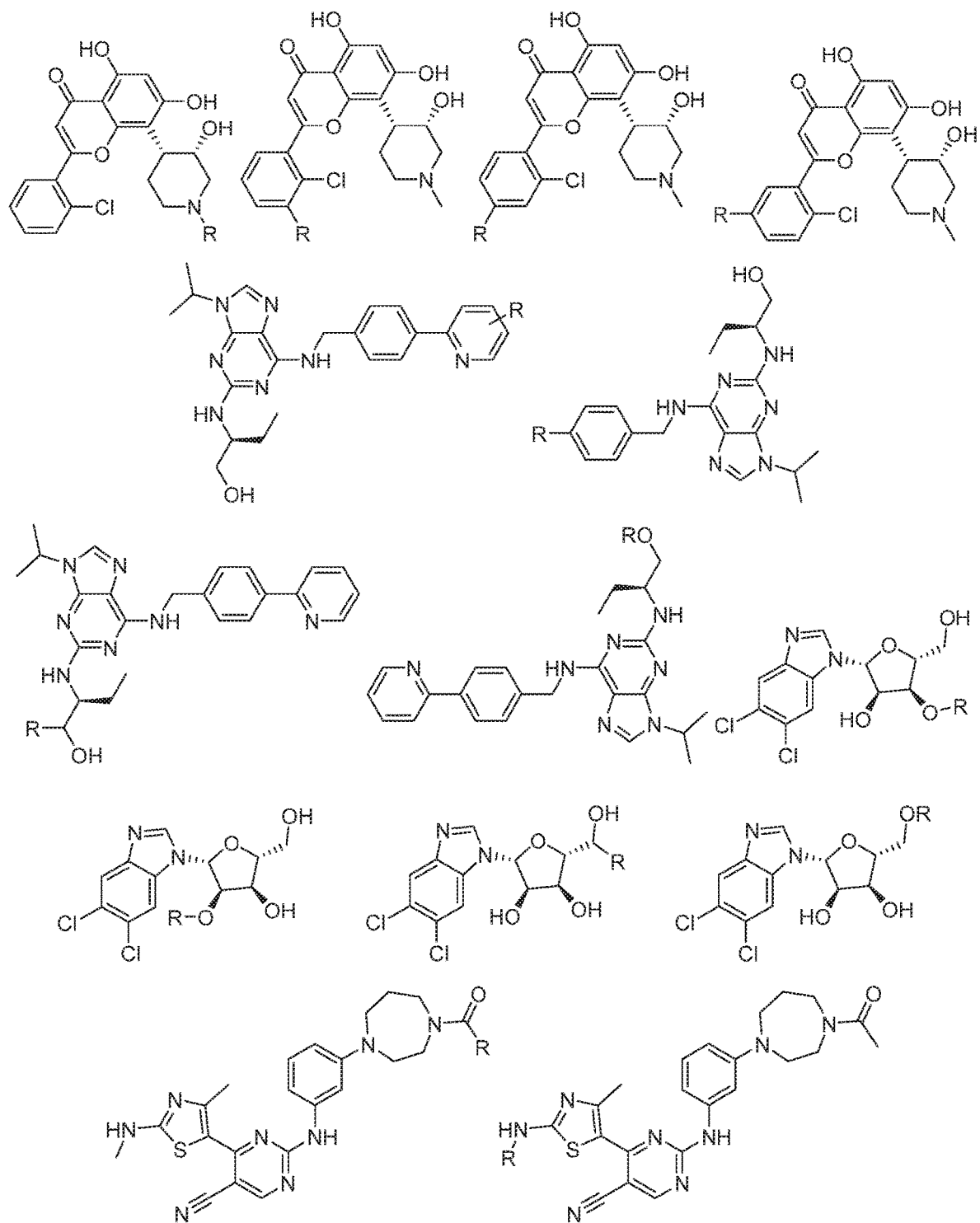
FIG. 2K-2M present examples of Cyclin Dependent Kinase 9 (CDK9) Targeting Ligands wherein R is the point at which the Linker is attached. For additional examples and related ligands, see, Baumli et al. "The structure of P-TEFb (CDK9/cyclin Ti) its complex with flavopiridol and regulation by phosphorylation." *Embo J.*, 27: 1907-1918 (2008); Bettayeb et al. "CDK Inhibitors Roscovitine and CR8 Trigger Mcl-1 Down-Regulation and Apoptotic Cell Death in Neuroblastoma Cells." *Genes Cancer*, 1: 369-380 (2010); Baumli et al. "Halogen bonds form the basis for selective P-TEFb inhibition by DRB." *Chem. Biol.* 17: 931-936 (2010); Hole et al. "Comparative Structural and Functional Studies of 4-(Thiazol-5-Yl)-2-(Phenylamino)Pyrimidine-5-Carbonitrile Cdk9 Inhibitors Suggest the Basis for Isotype Selectivity." *J. Med. Chem.* 56: 660 (2013); Lücking et al. "Identification of the potent and highly selective PTEFb inhibitor BAY 1251152 for the treatment of cancer—From p.o. to i.v. application via scaffold hops." Licking et al. *U. AACR Annual Meeting*, Apr. 1-5, 2017 Washington, D.C. USA.
Figure 2L:
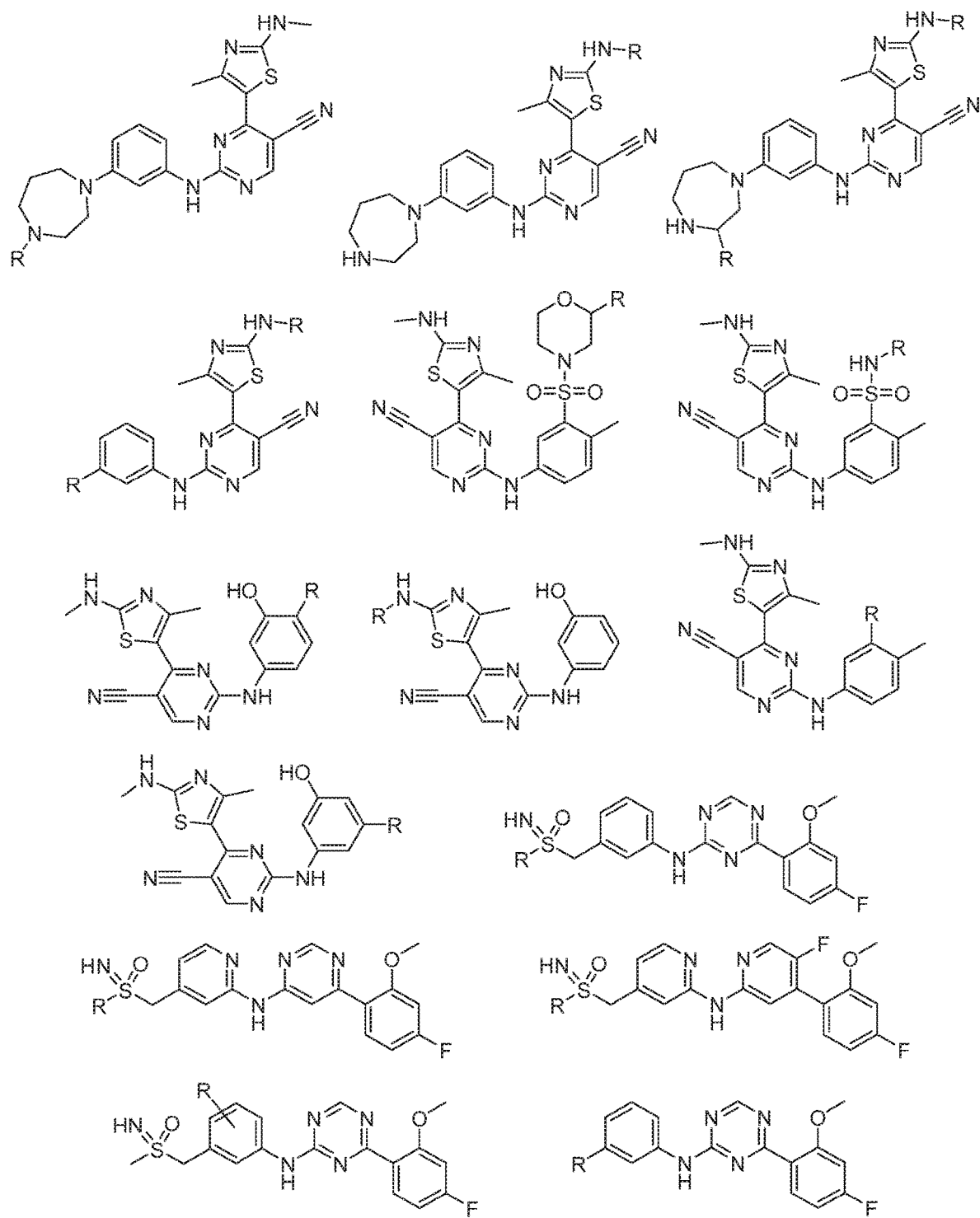
Figure 2M:
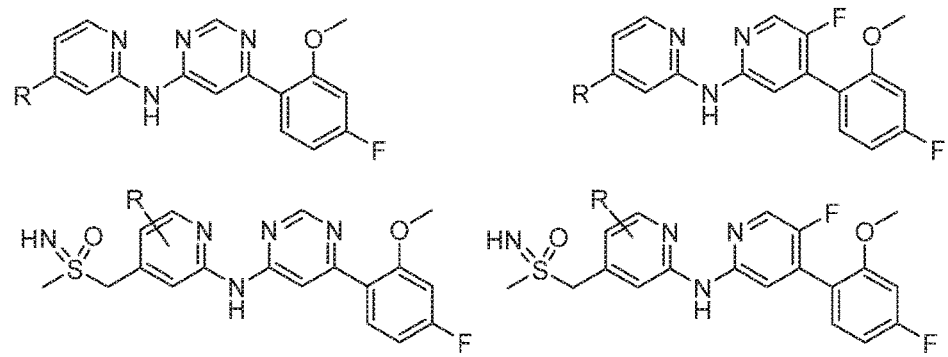
Figure 2N:
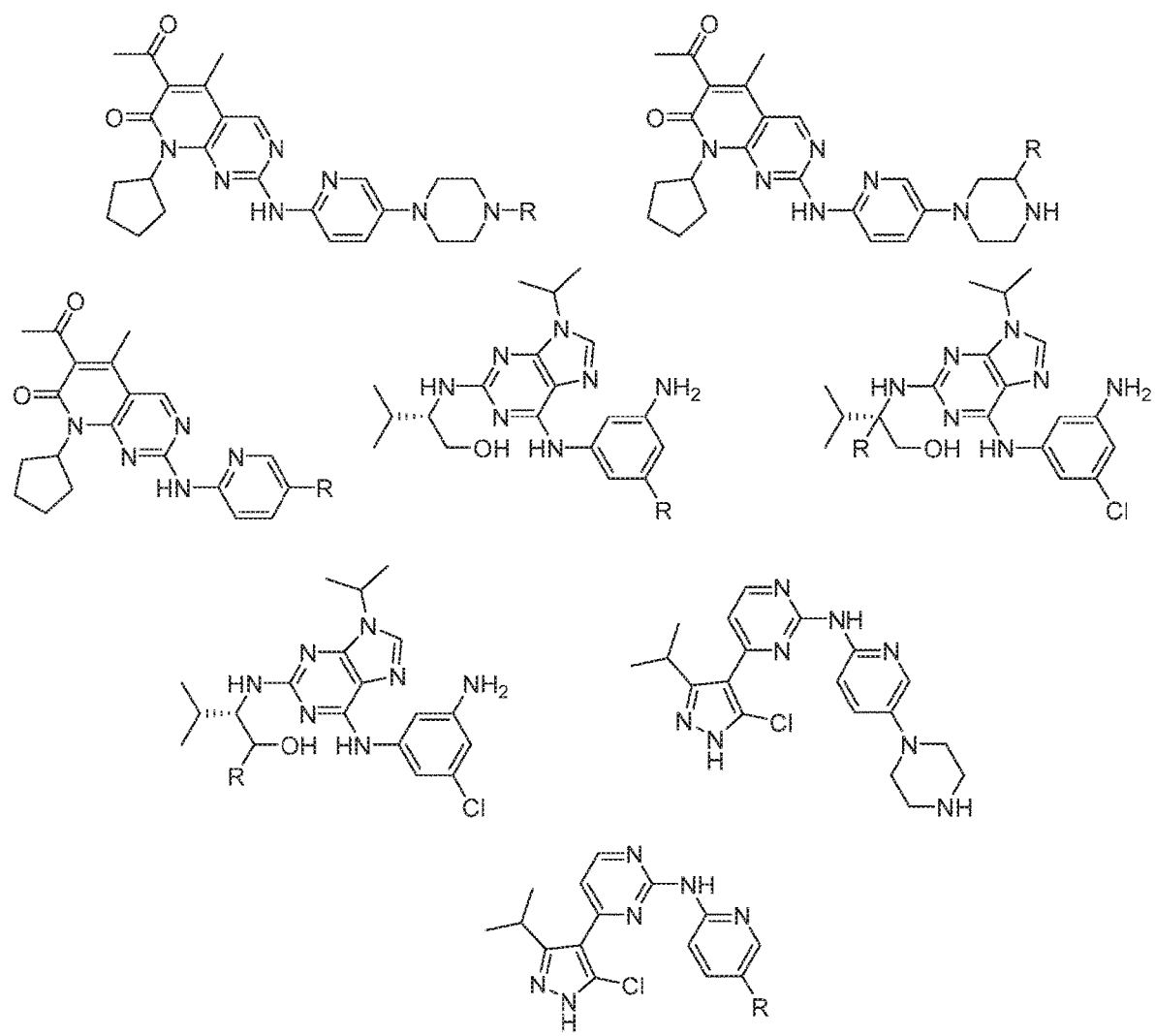
FIG. 2N-2P present examples of Cyclin Dependent Kinase 4/6 (CDK4/6) Targeting Ligands wherein R is the point at which the Linker is attached. For additional examples and related ligands, see, Lu H.; Schulze-Gahmen U.; "Toward understanding the structural basis of cyclin-dependent kinase 6 specific inhibition." *J. Med. Chem.*, 49: 3826-3831 (2006); 4-(Pyrazol-4-yl)-pyrimidines as selective inhibitors of cyclin-dependent kinase 4/6. Cho et al. (2010) J. Med. Chem. 53: 7938-7957; Cho Y. S. et al. "Fragment-Based Discovery of 7-Azabenzimidazoles as Potent Highly Selective and Orally Active CDK4/6 Inhibitors." *ACS Med Chem Lett* 3: 445-449 (2012); Li Z. et al. "Discovery of AMG 925 a FLT3 and CDK4 dual kinase inhibitor with preferential affinity for the activated state of FLT3." *J. Med. Chem.* 57: 3430-3449 (2014); Chen P. et al. "Spectrum and Degree of CDK Drug Interactions Predicts Clinical Performance." *Mol. Cancer Ther.* 15: 2273-2281 (2016).
Figure 2O:
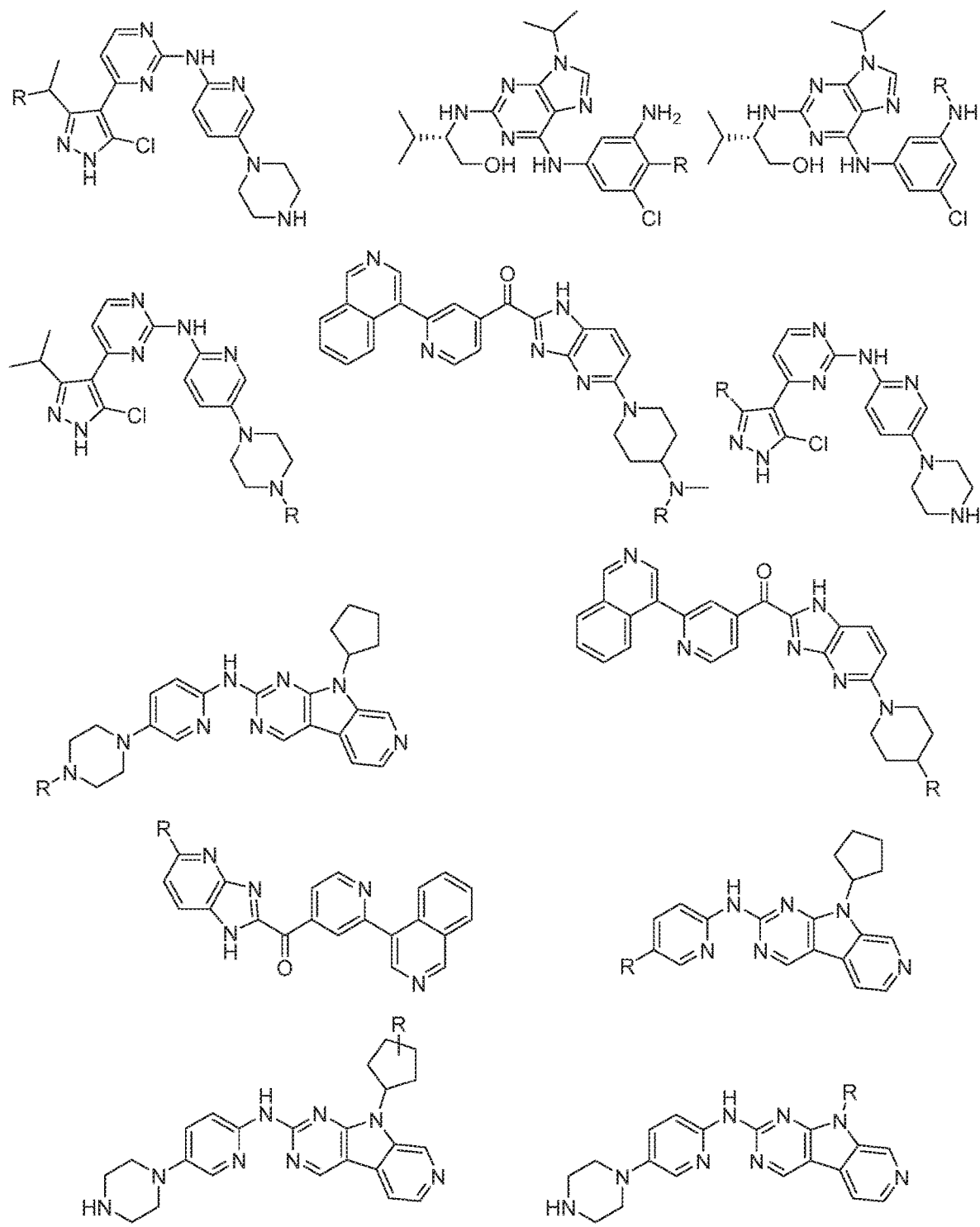
Figure 2P:
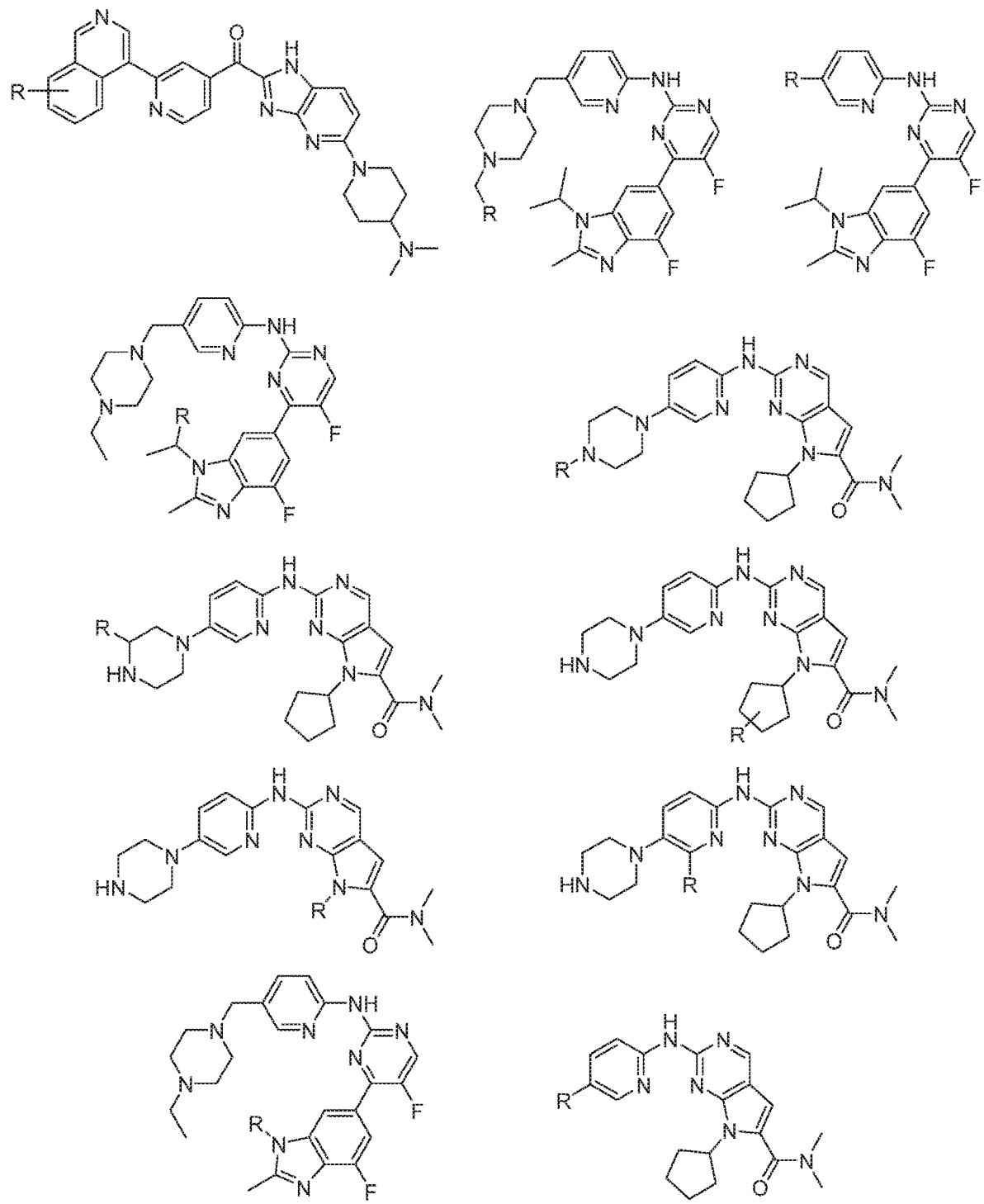
Figure 2Q:
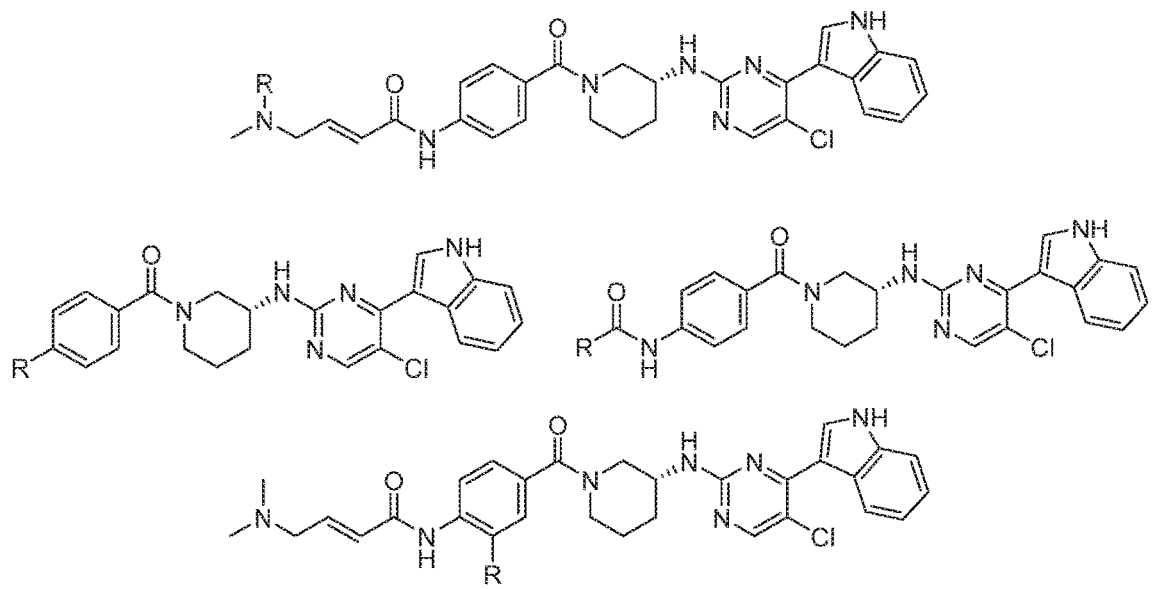
FIG. 2Q presents examples of Cyclin Dependent Kinase 12 and/or Cyclin Dependent Kinase 13 Targeting Ligands wherein R is the point at which the Linker is attached. For additional examples and related ligands, see, Zhang T. et al. "Covalent Targeting of Remote Cysteine Residues to Develop Cdk12 and Cdk13 Inhibitors." *Nat. Chem. Biol.* 12: 876 (2016).
Figure 2R:
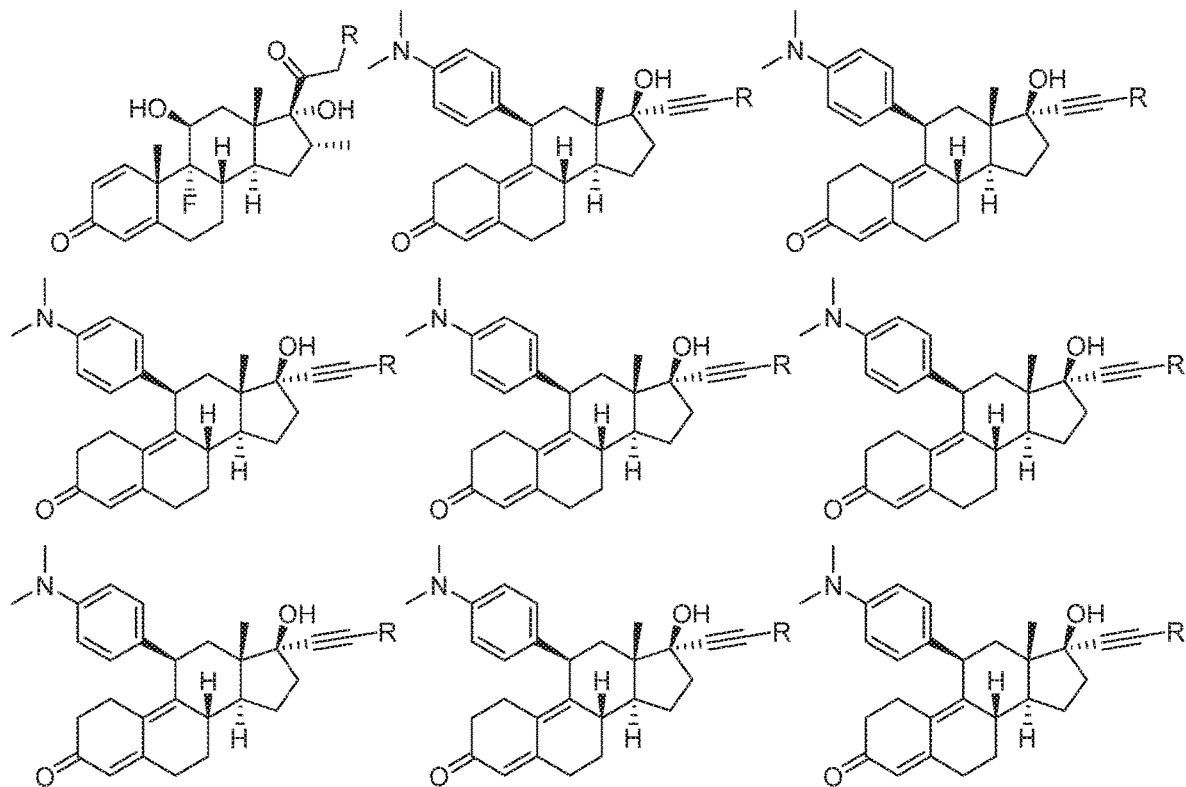
FIG. 2R-2S present examples of Glucocorticoid Receptor Targeting Ligands wherein R is the point at which the Linker is attached.
Figure 2S:
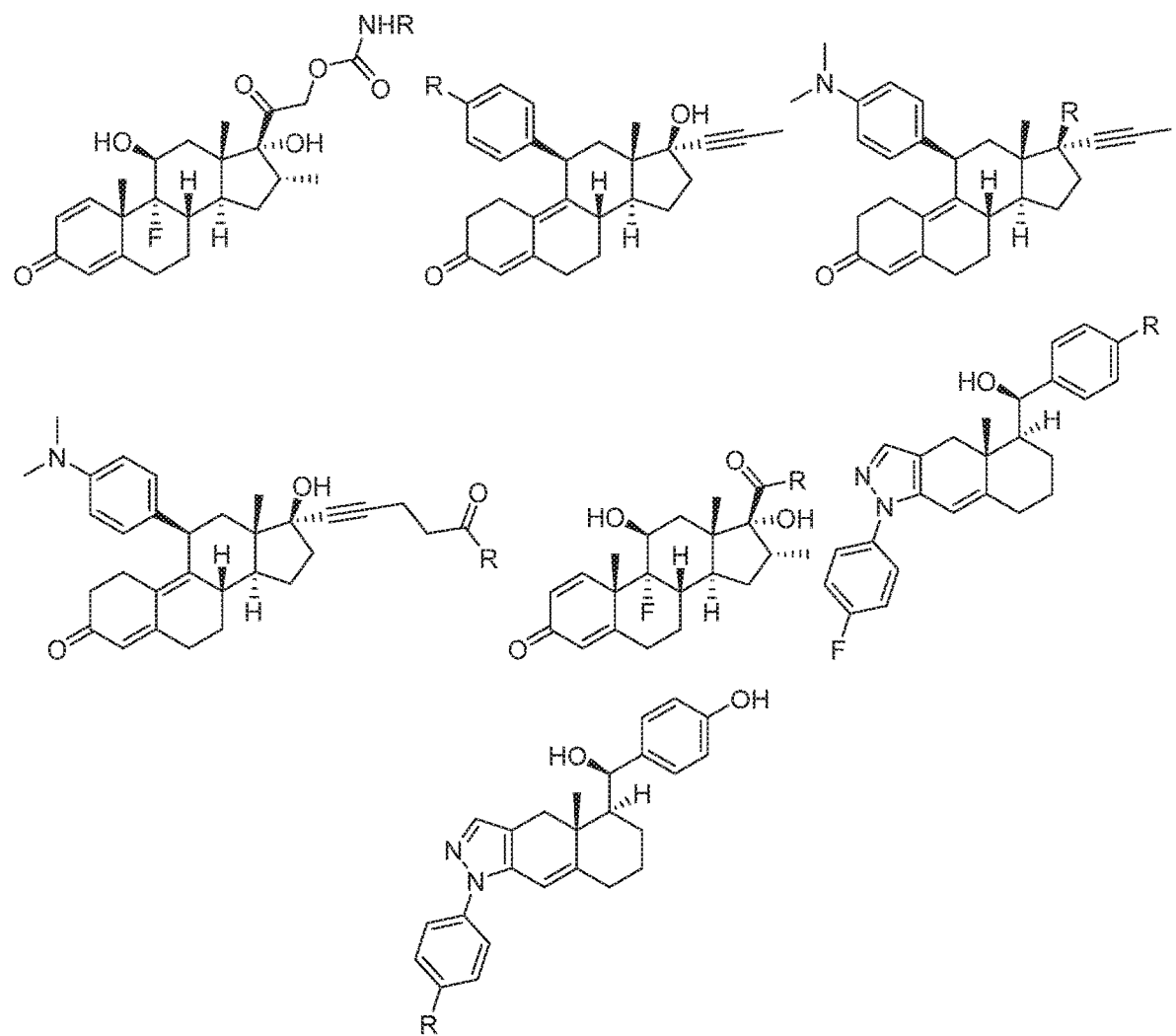
Figure 2T:
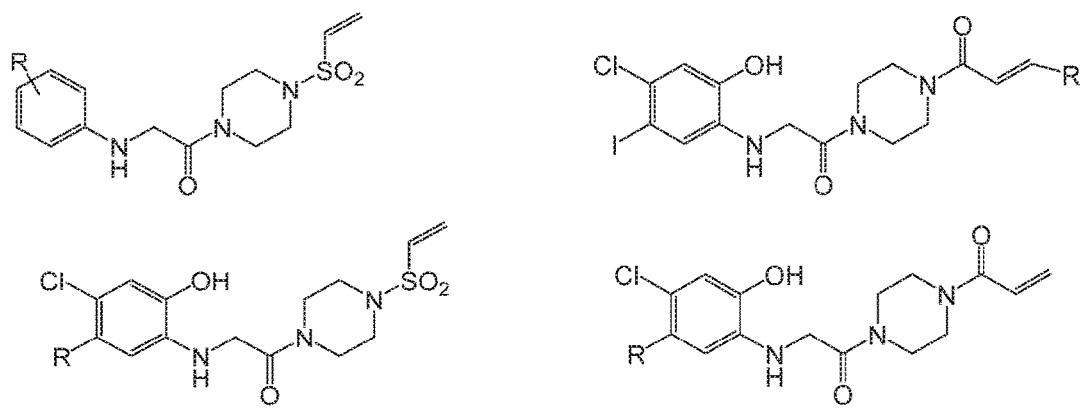
FIG. 2T-2U present examples of RasG12C Targeting Ligands wherein R is the point at which the Linker is attached.
Figure 2U:
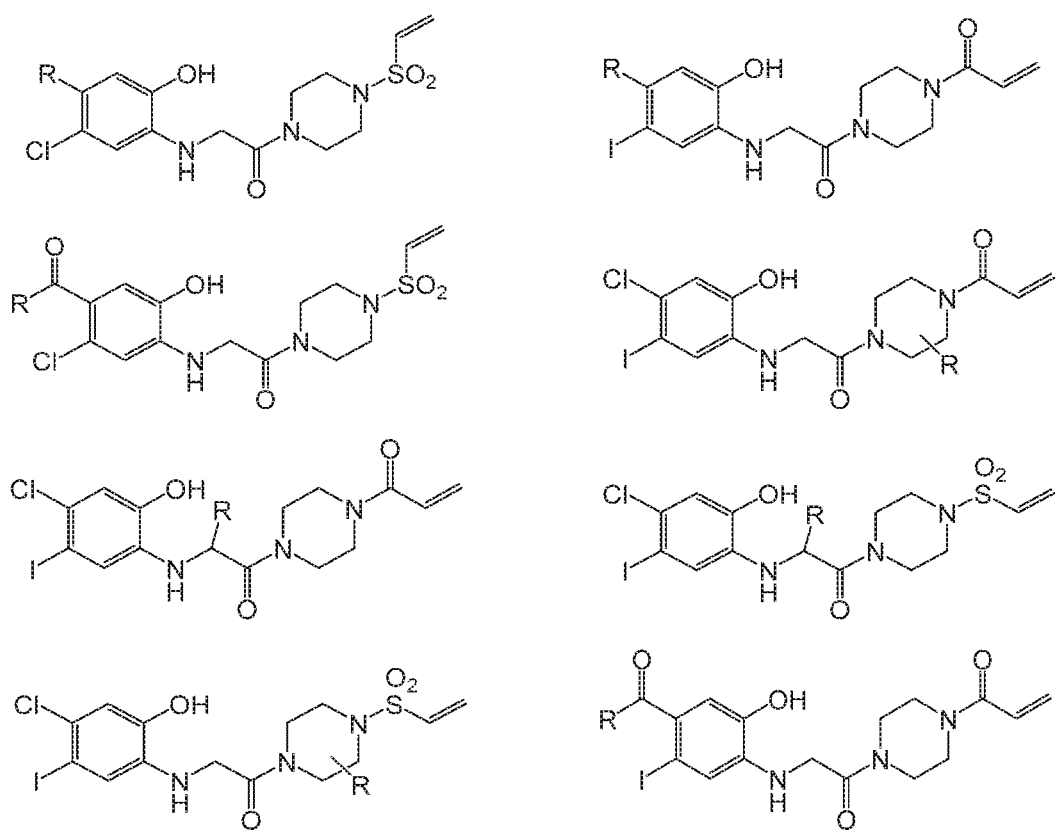
Figure 2V:
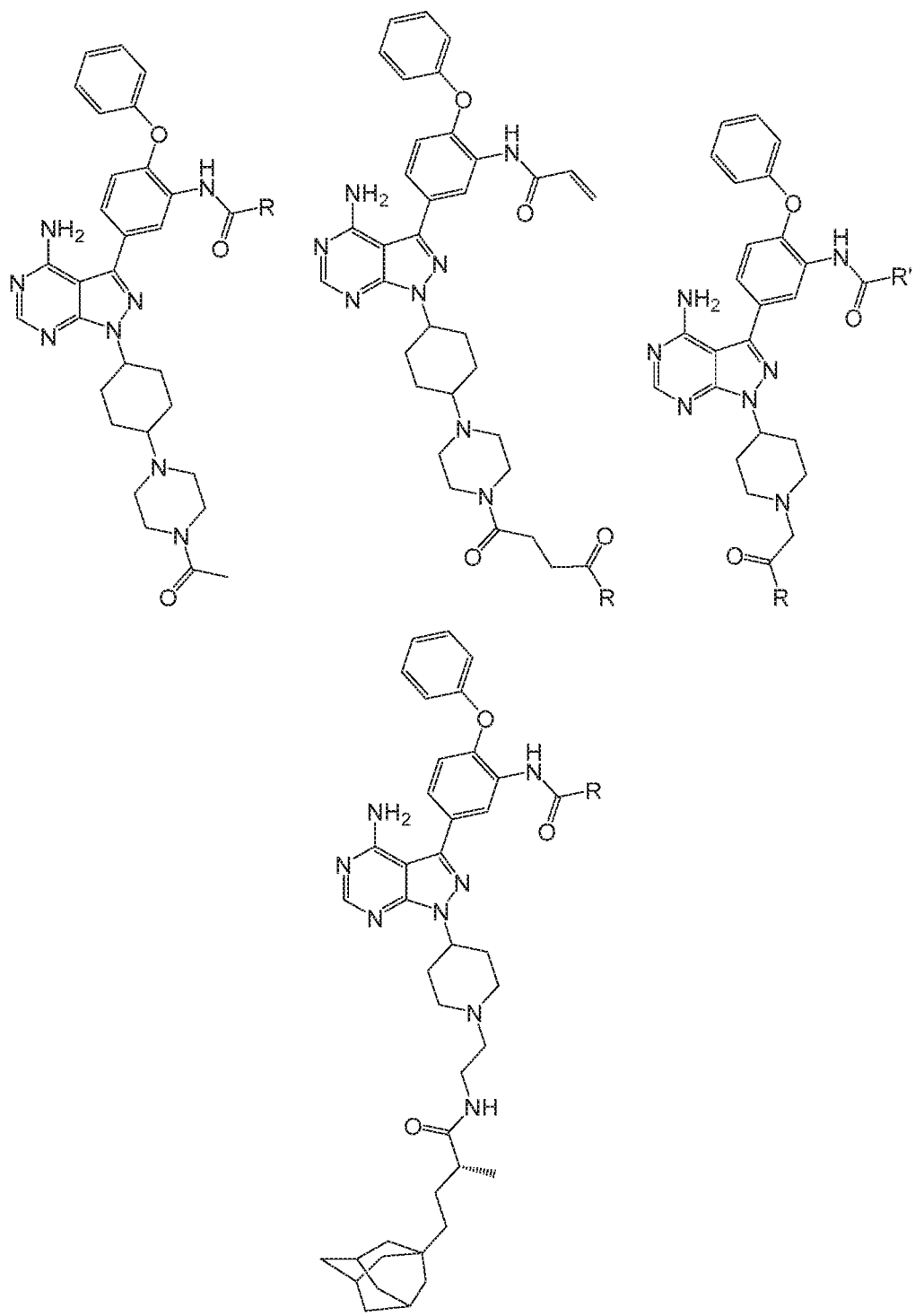
FIG. 2V presents examples of Her3 Targeting Ligands wherein R is the point at which the Linker is attached and R' is
Figure 2Z:
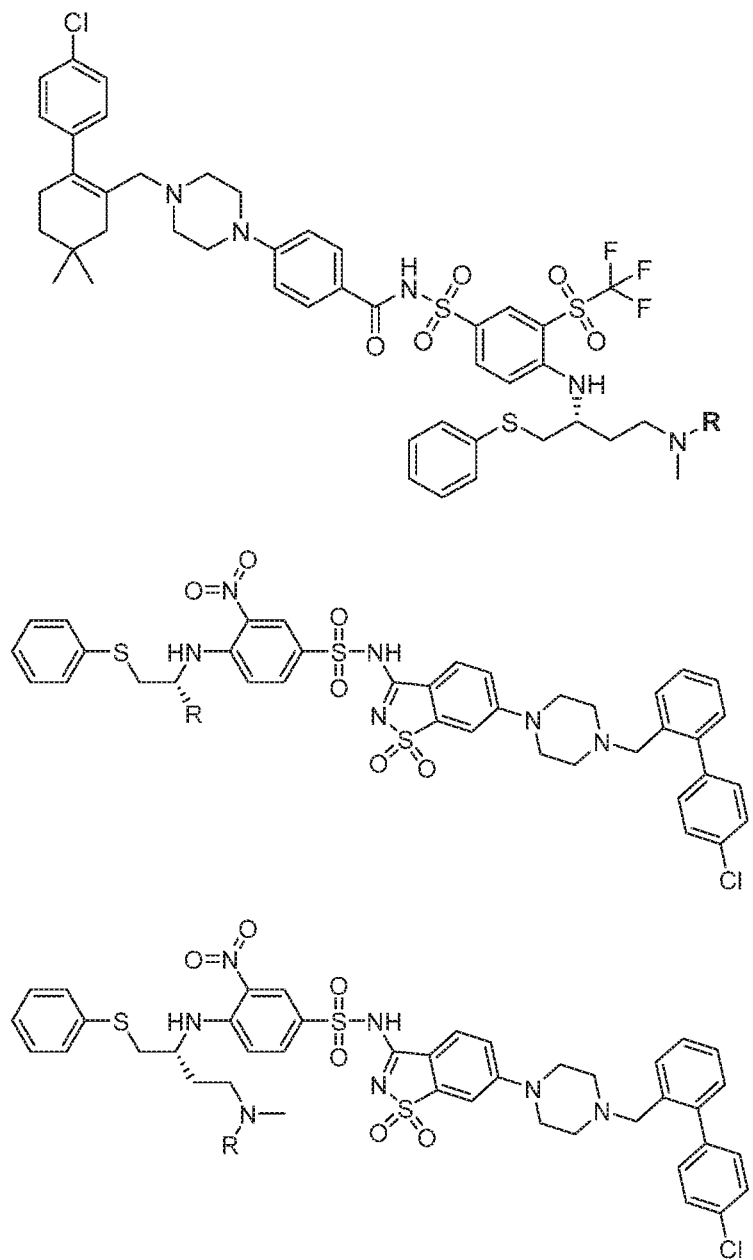
FIG. 2F presents examples of kinase inhibitor Targeting Ligands, including the kinase inhibitor compound YCF, wherein R is the point at which the Linker is attached. For additional examples and related ligands, see, the kinase inhibitors identified in Lountos et al. "Structural Characterization of Inhibitor Complexes with Checkpoint Kinase 2 (Chk2) a Drug Target for Cancer Therapy" *J. Struct. Biol.*, 176: 292 (2011).
Figure 2A:
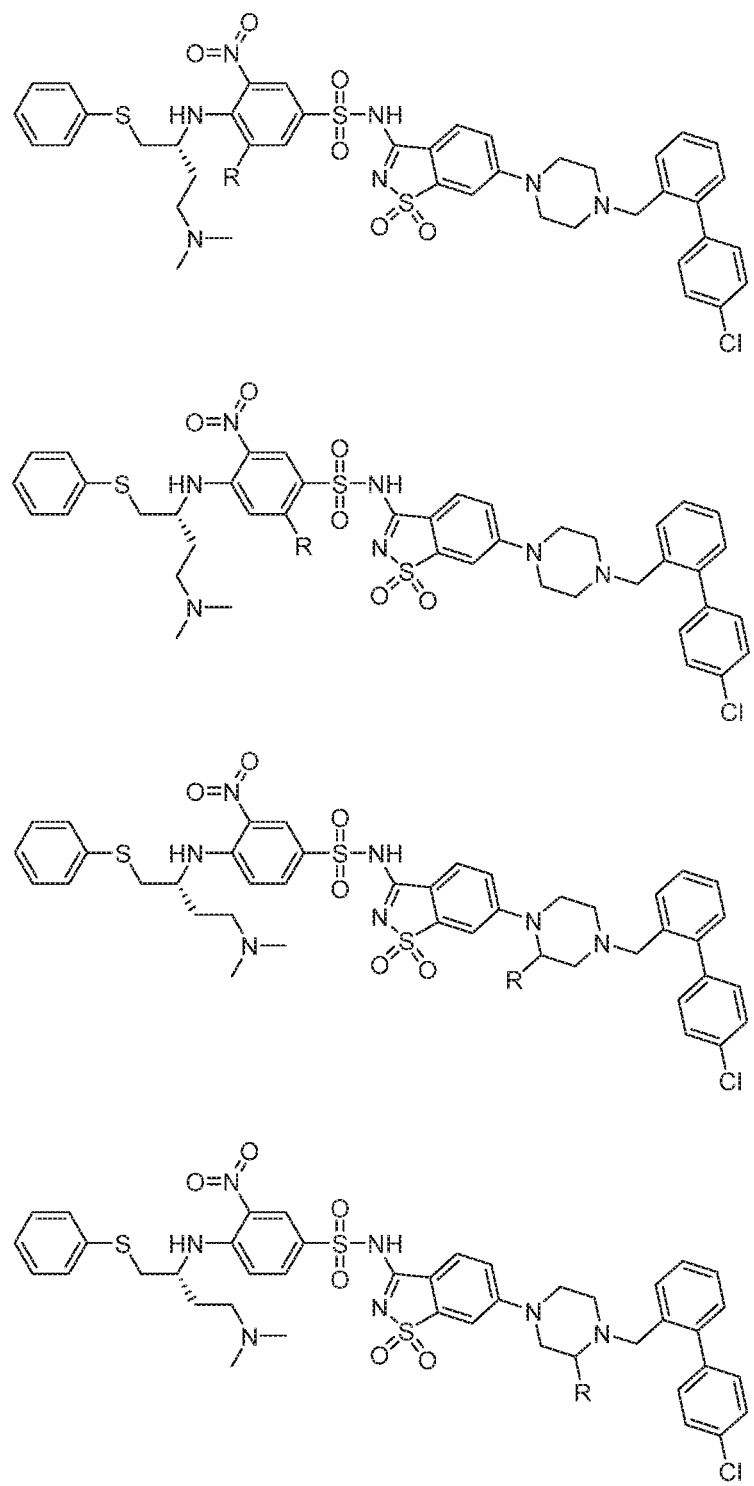
Figure 2B:
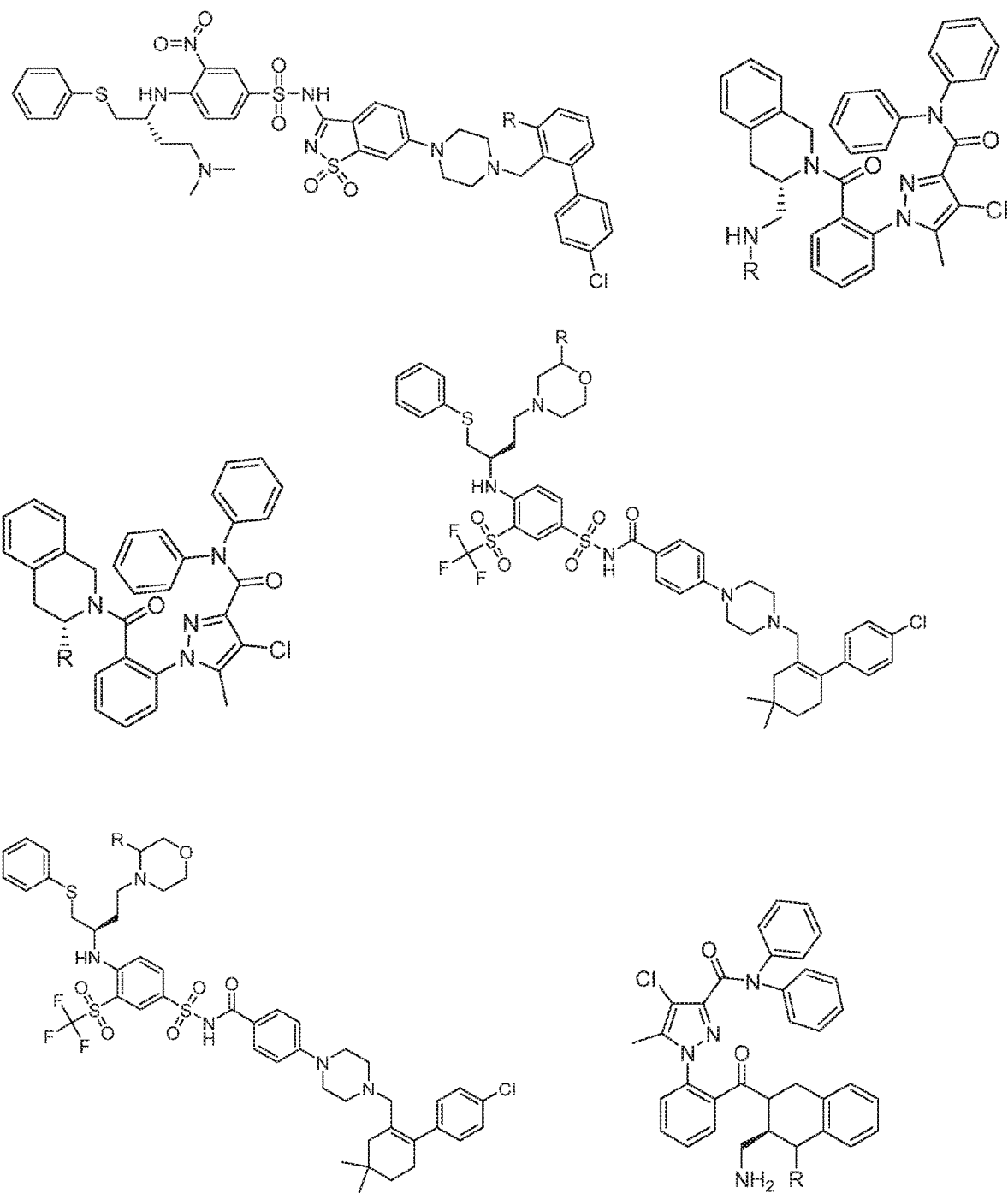
Figure 2C:
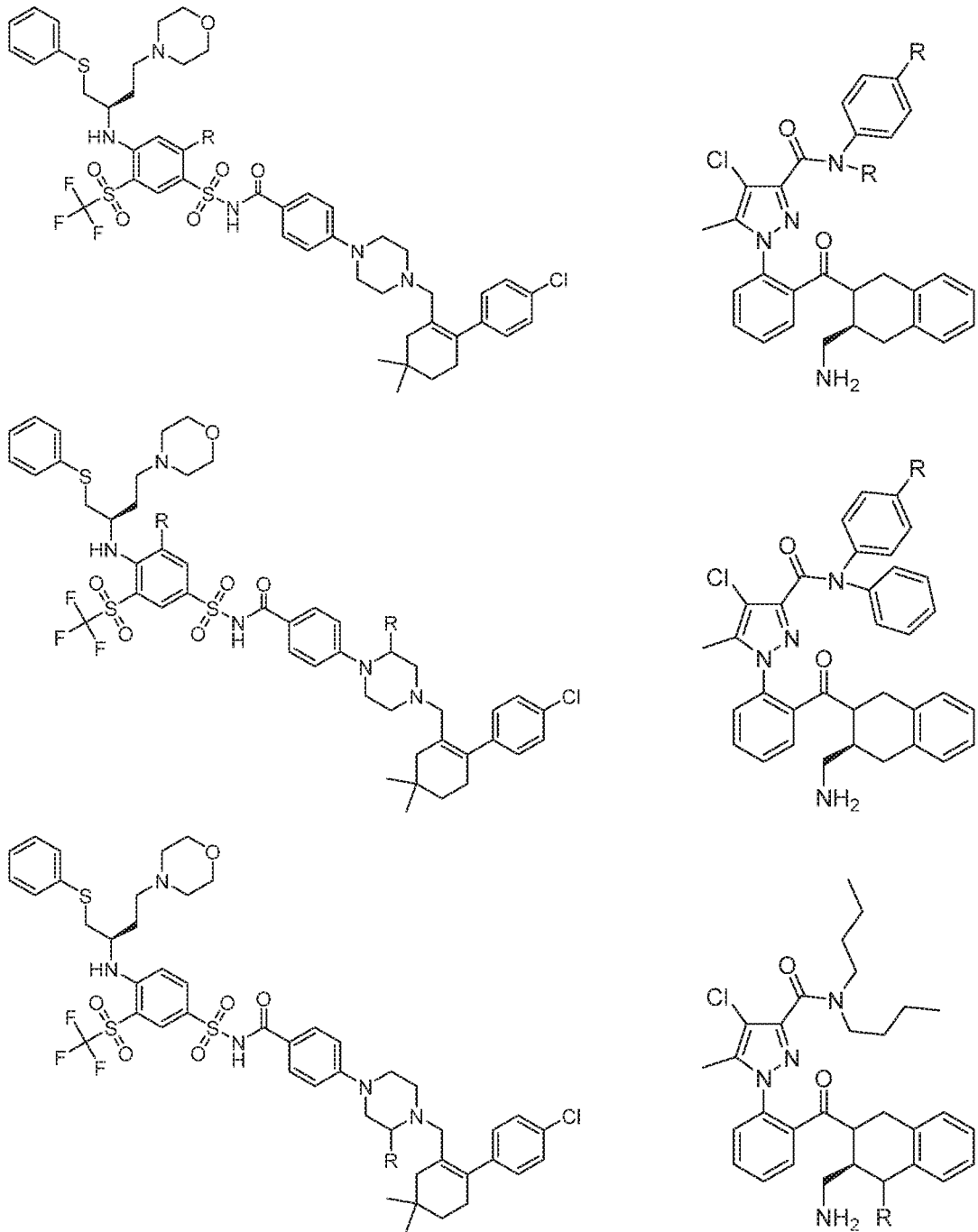
Figure 2D:
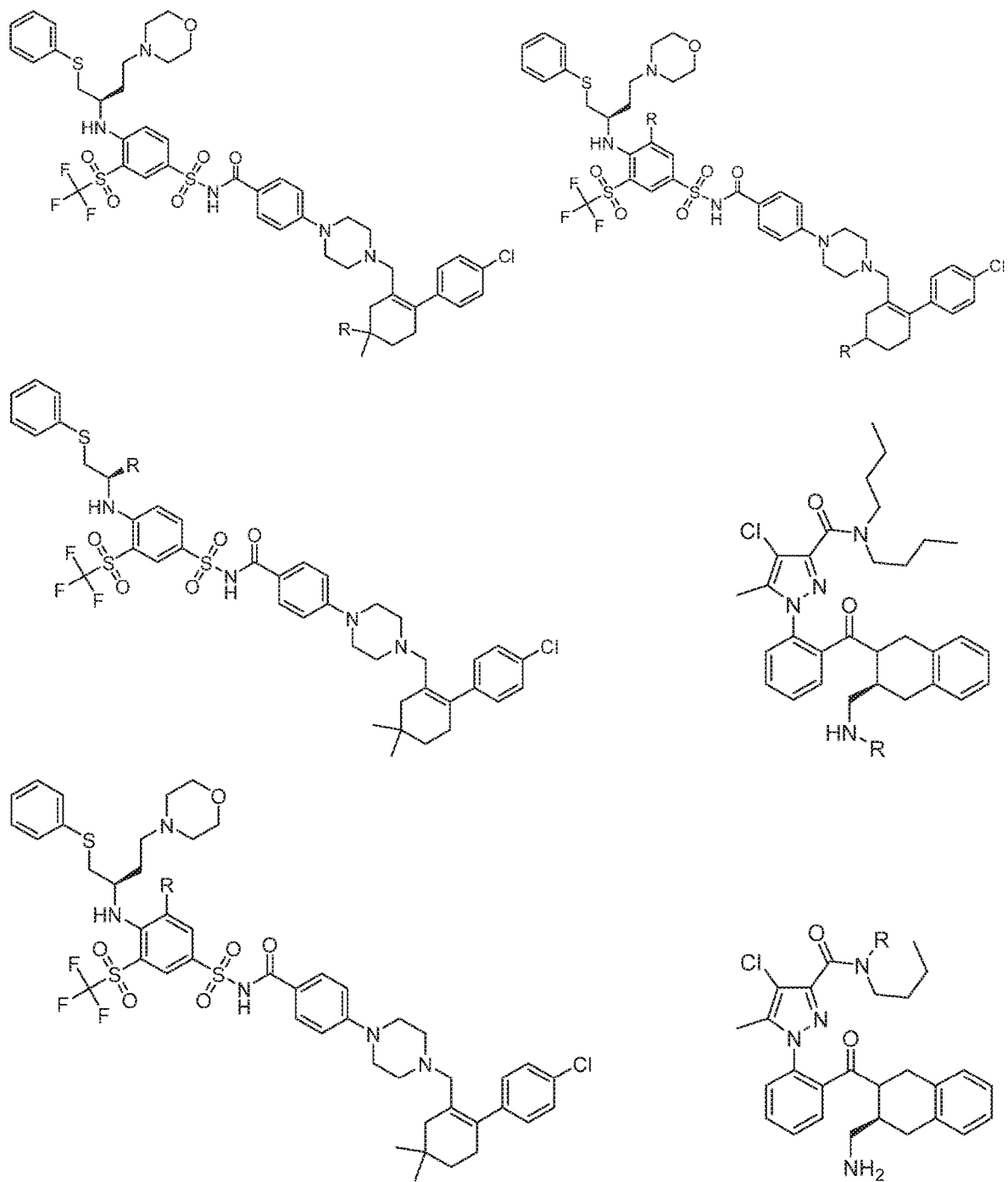
Figure 2E:
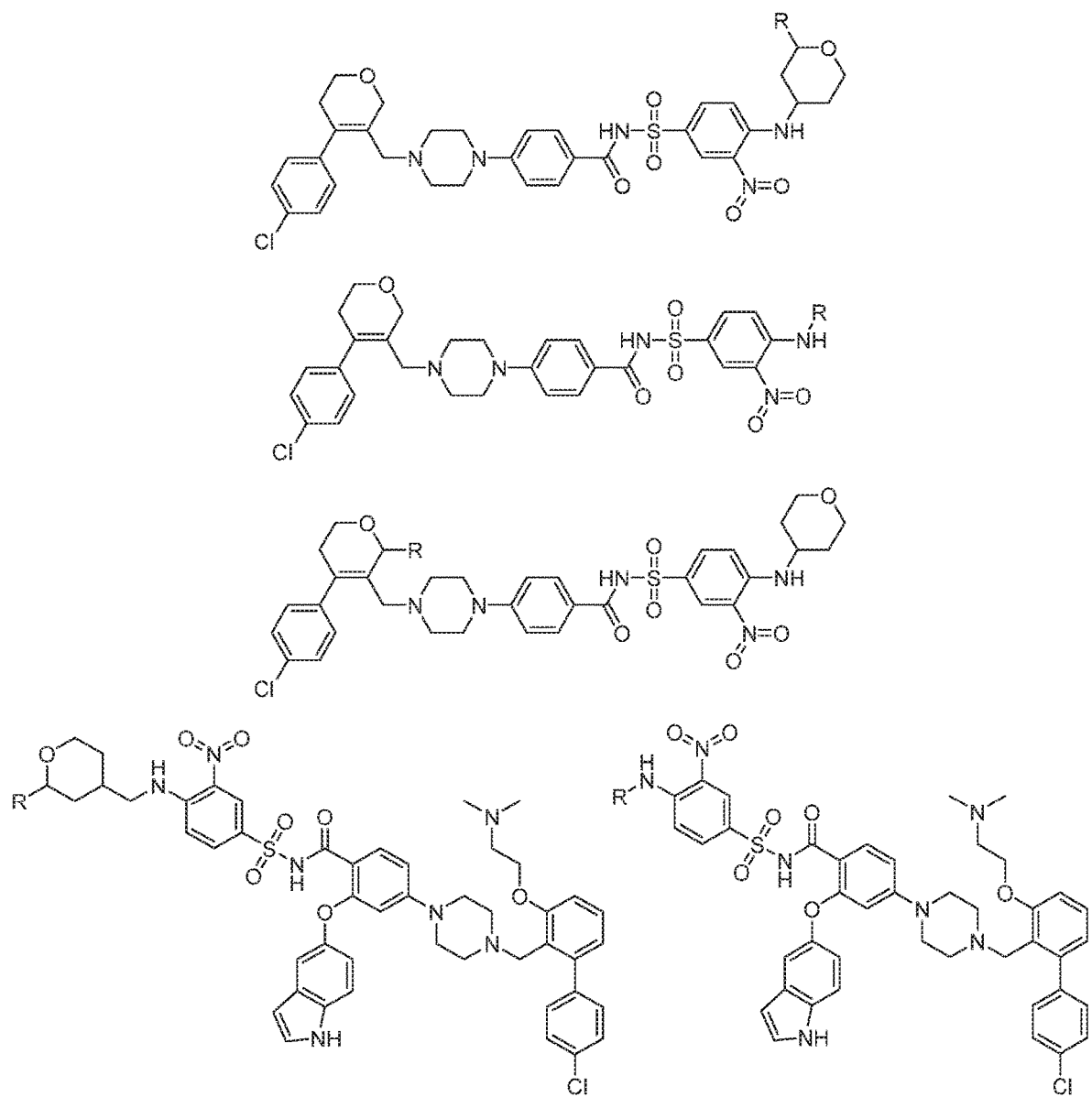
Figure 2F:
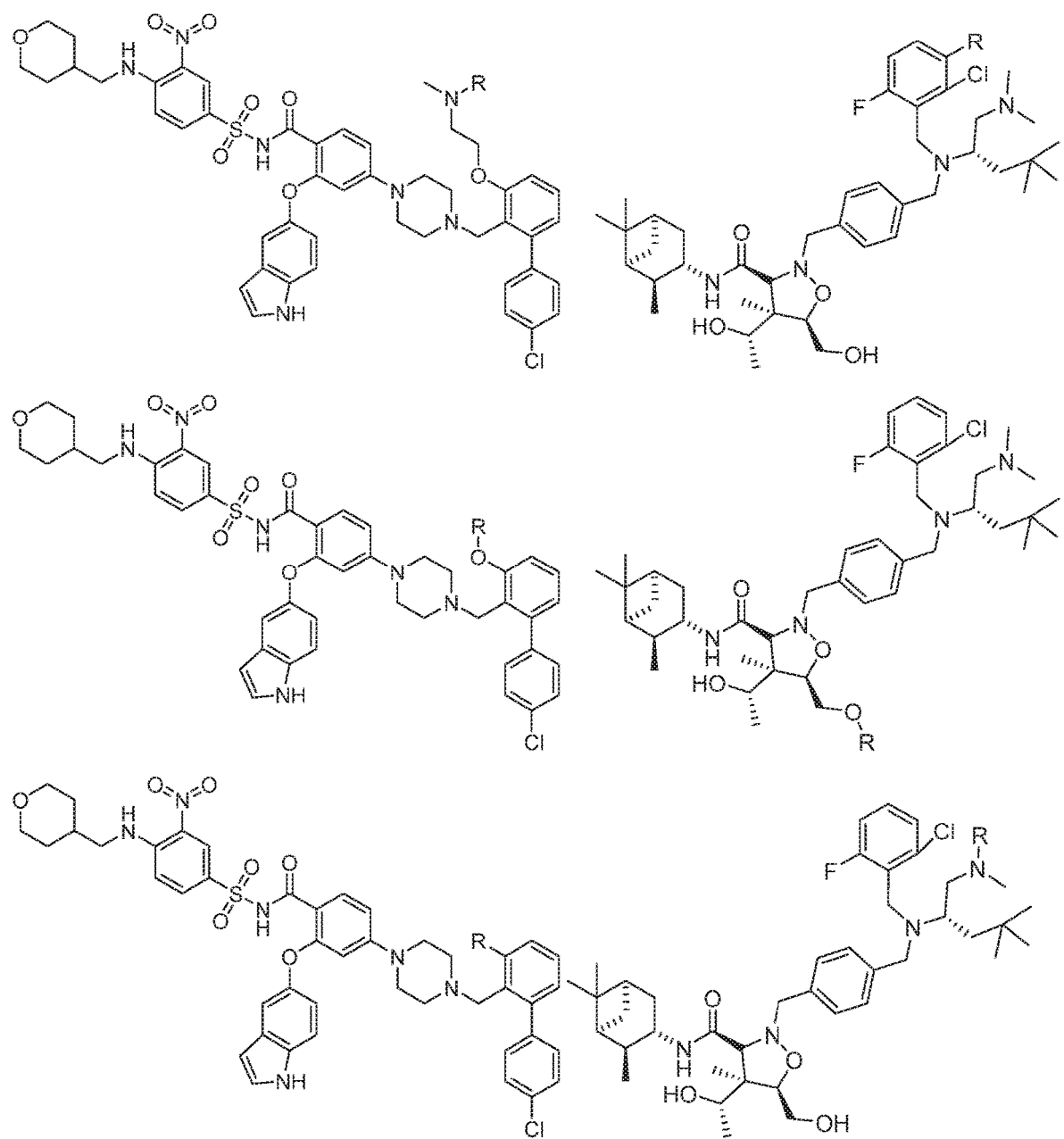
Figure 2G:
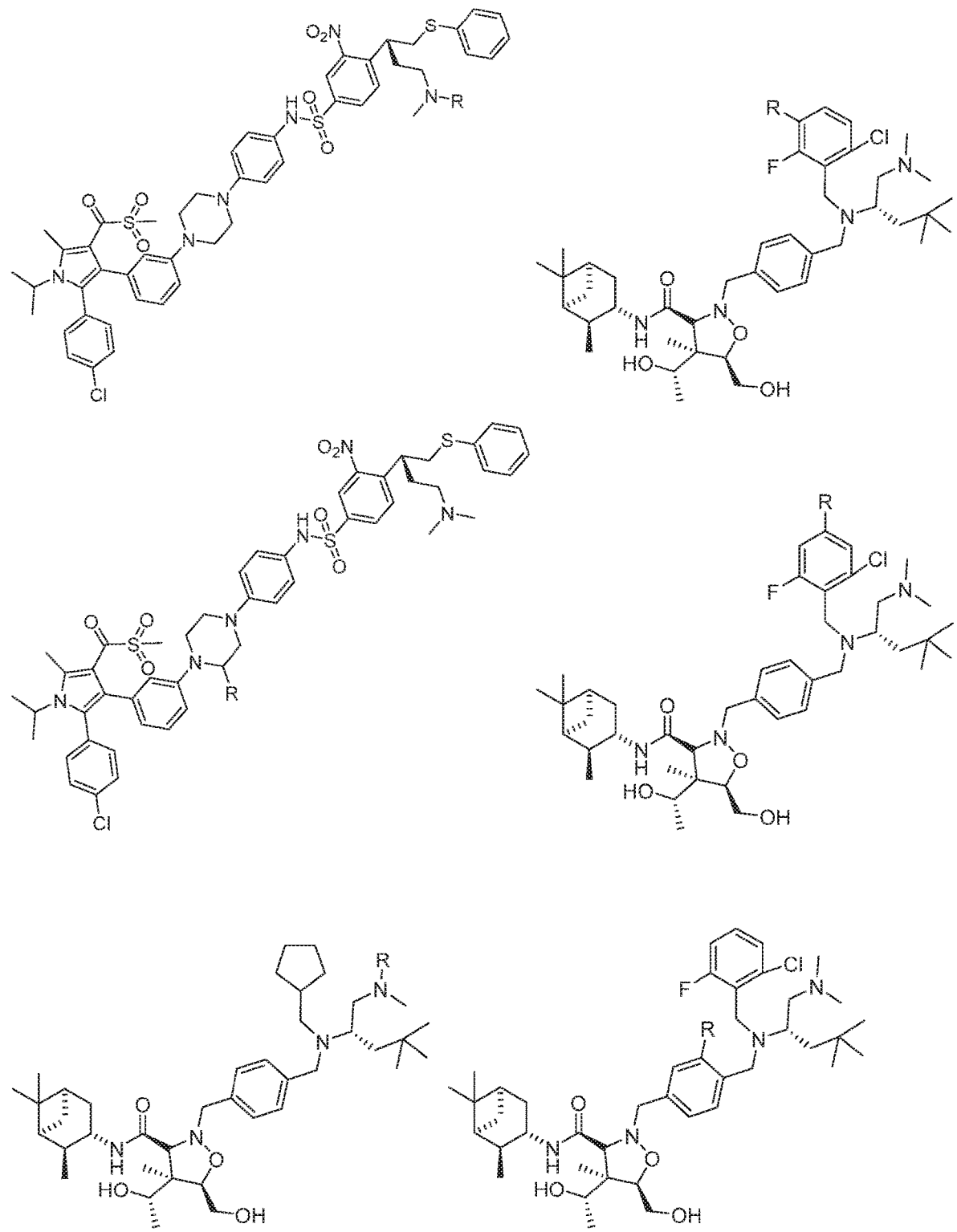
Figure 2H:
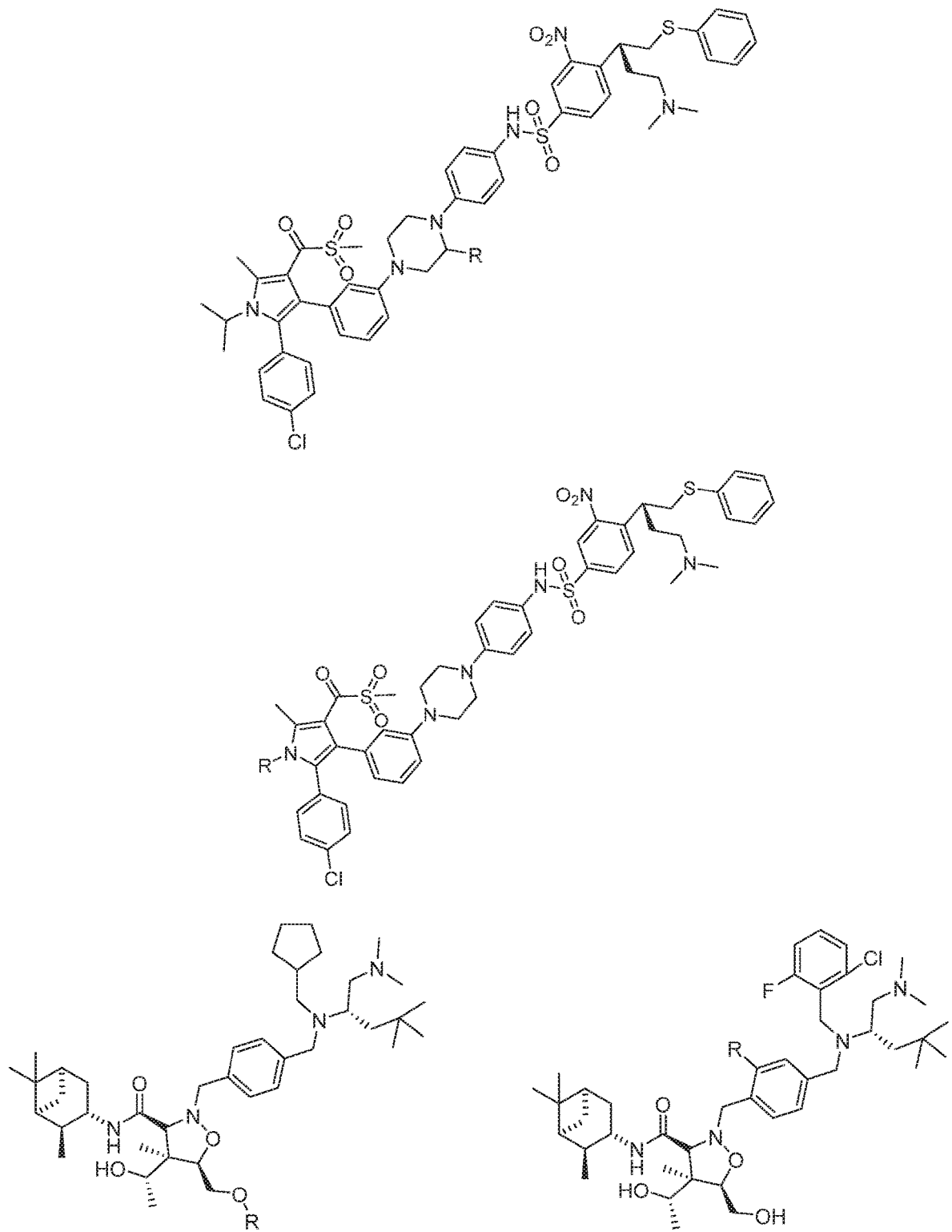
Figure 2I:
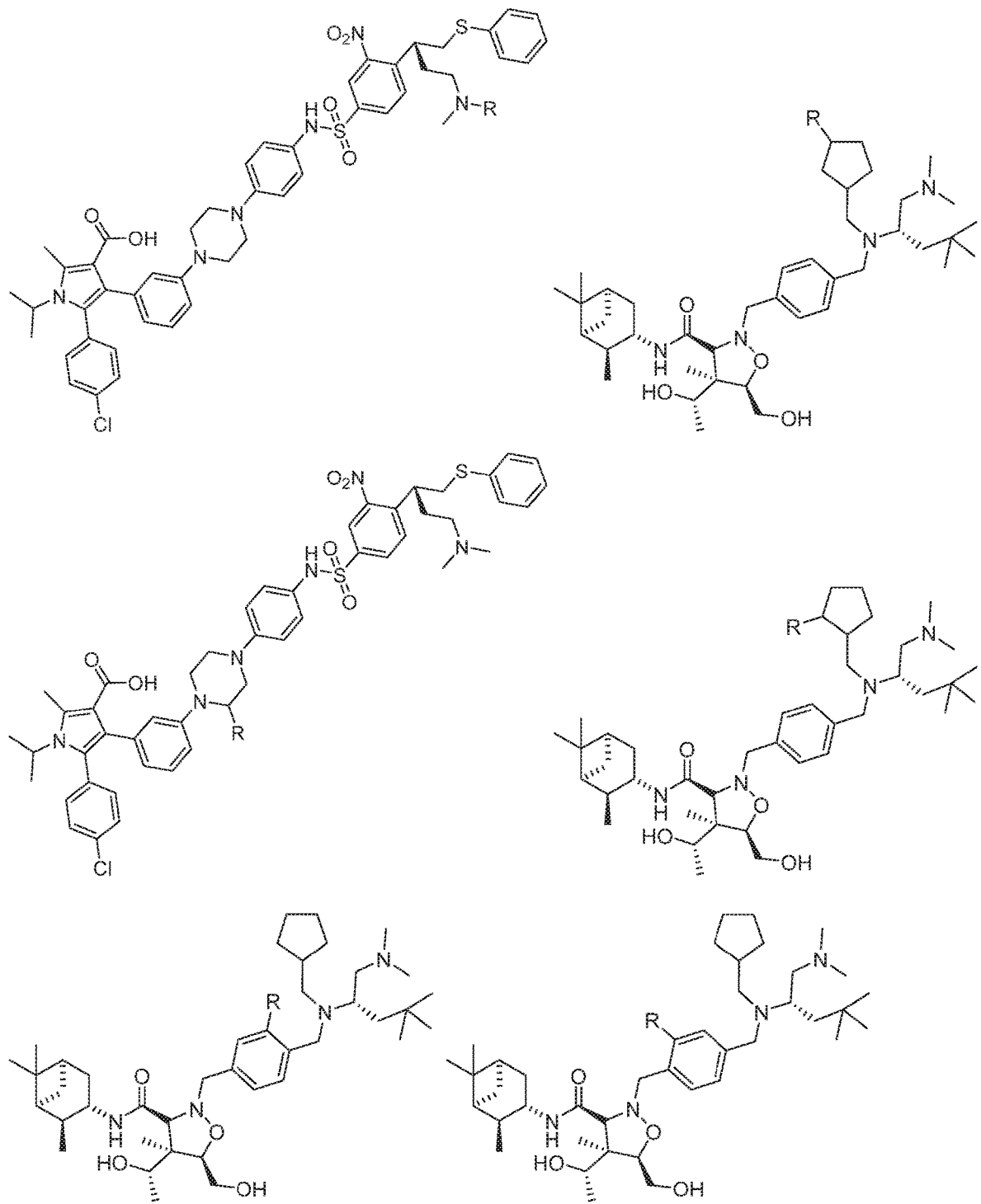
Figure 2J:
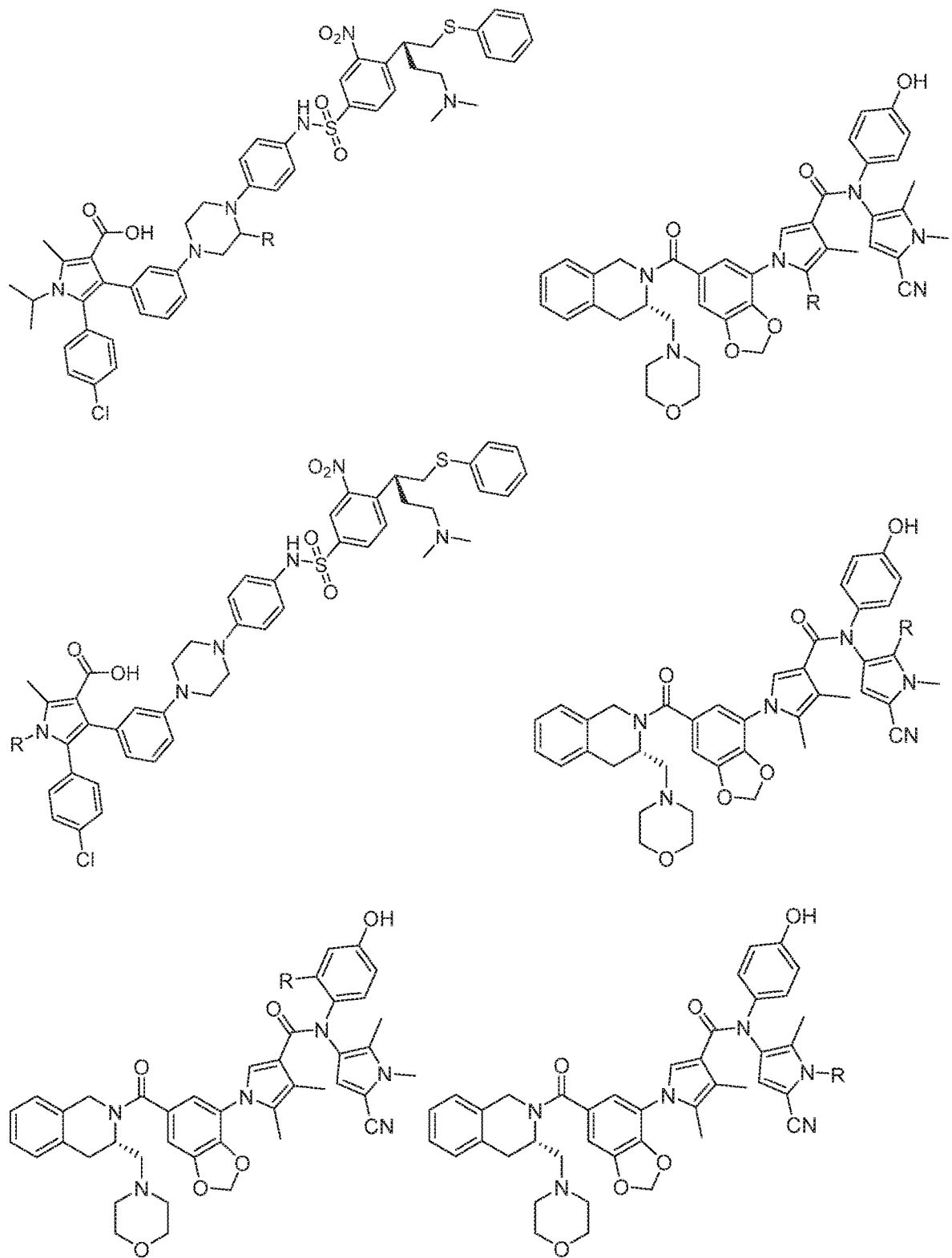
Figure 2K:
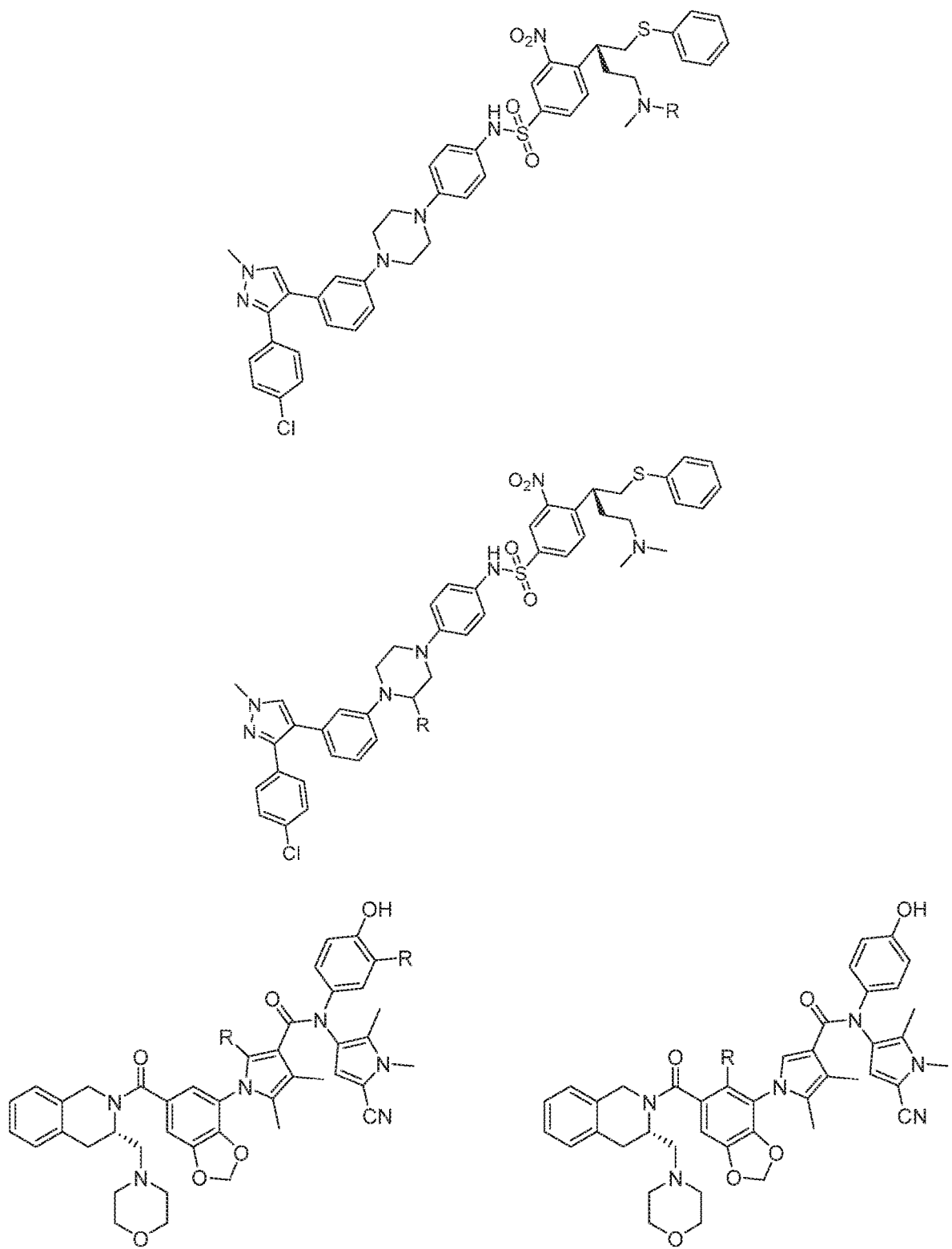
Figure 2L:
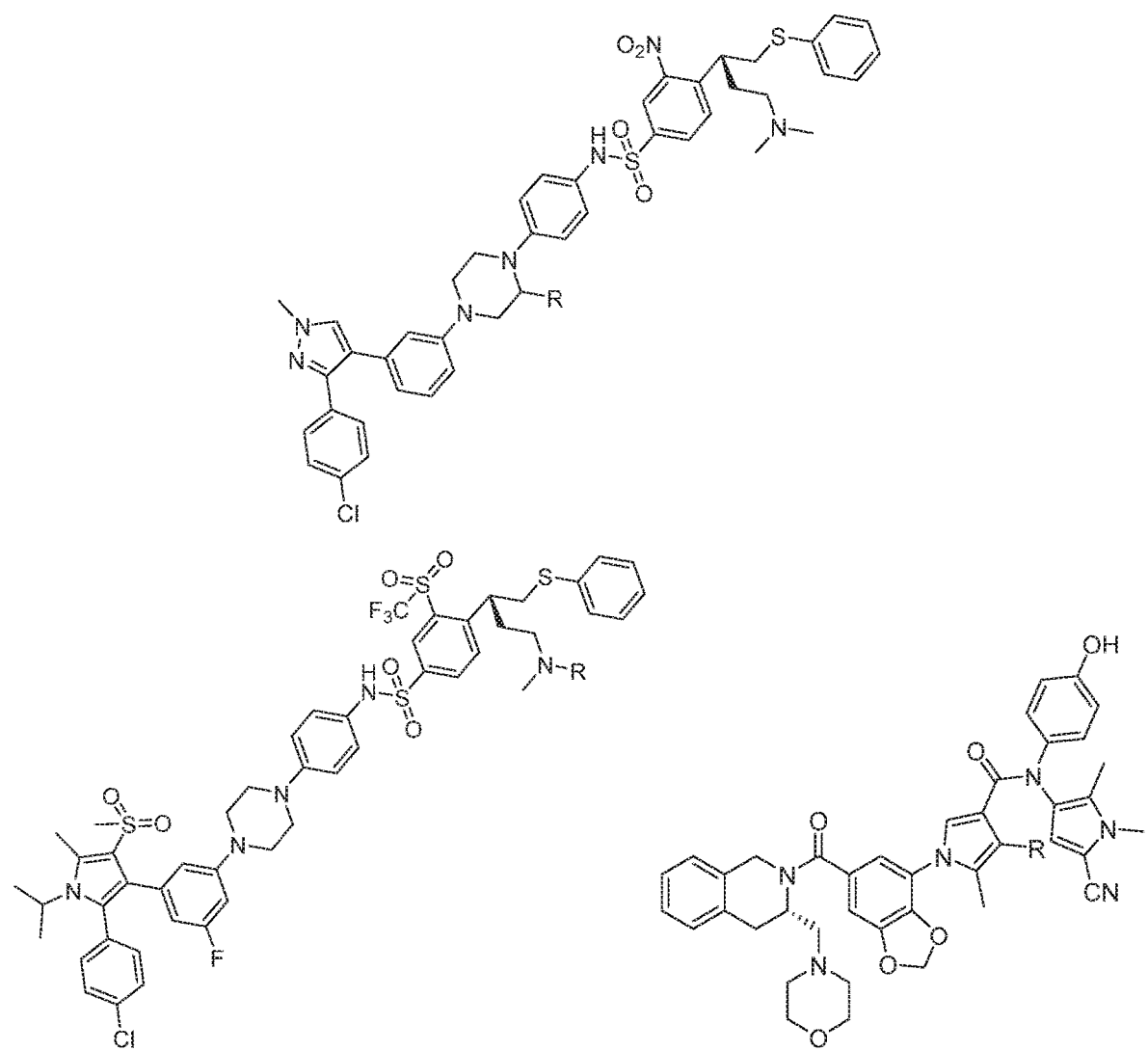
Figure 2M:
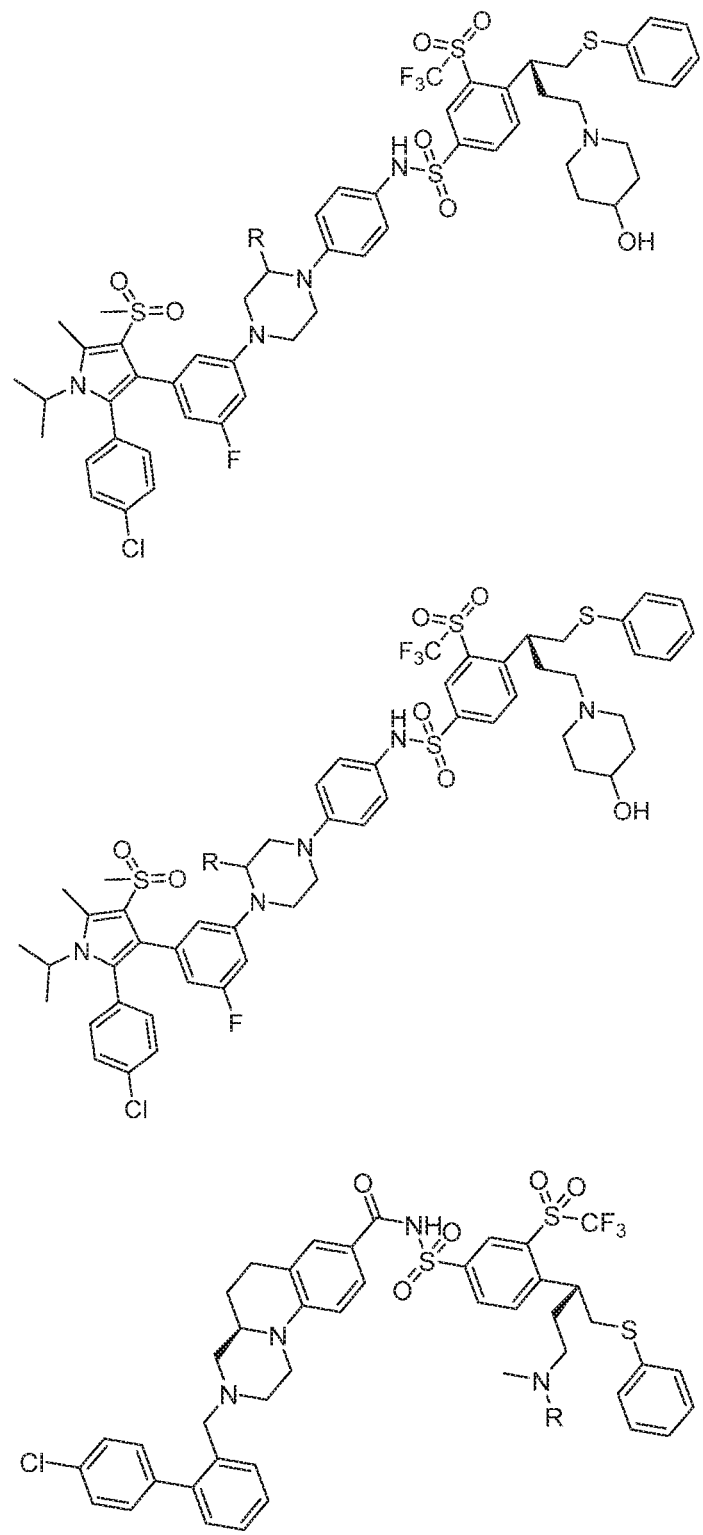
Figure 2N:
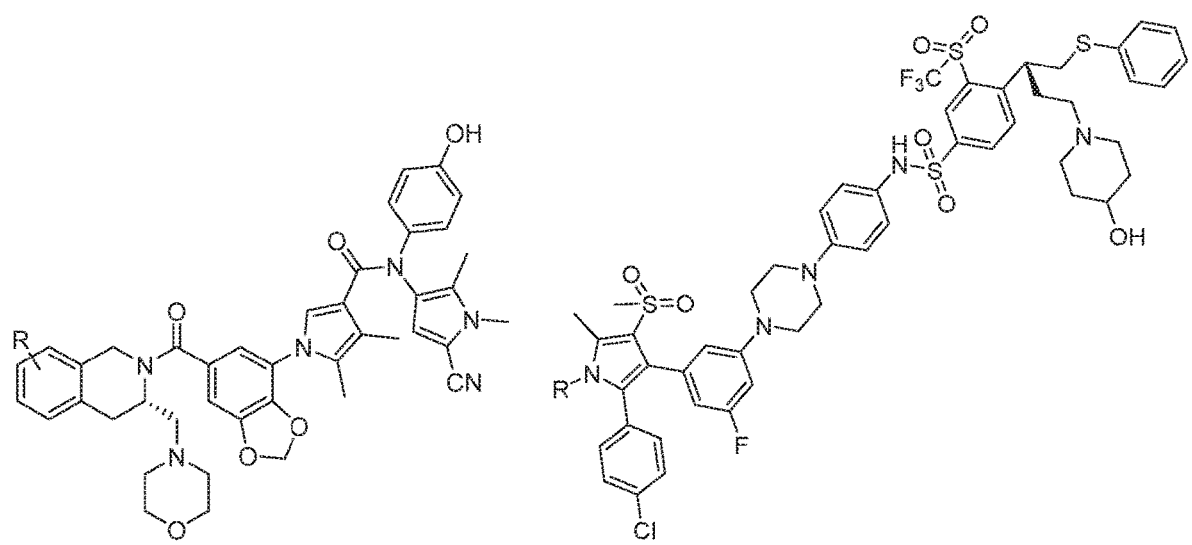
Figure 2O:
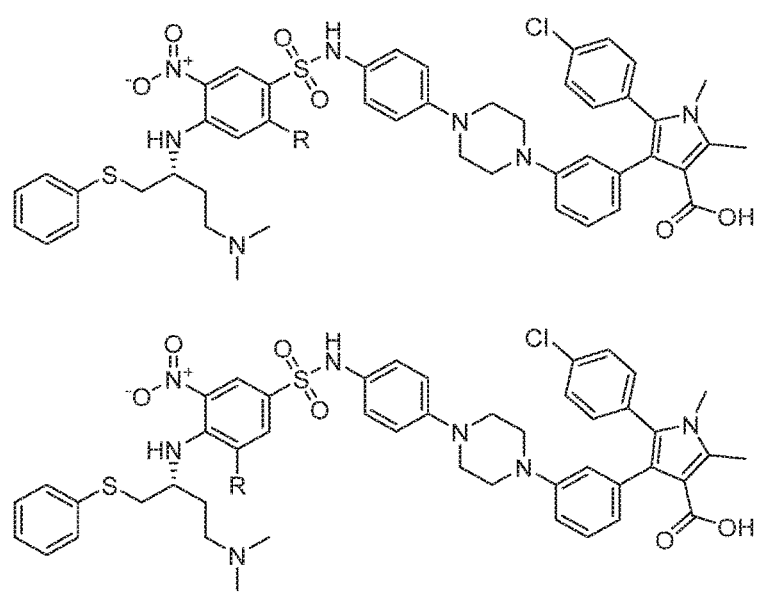
Figure 2P:
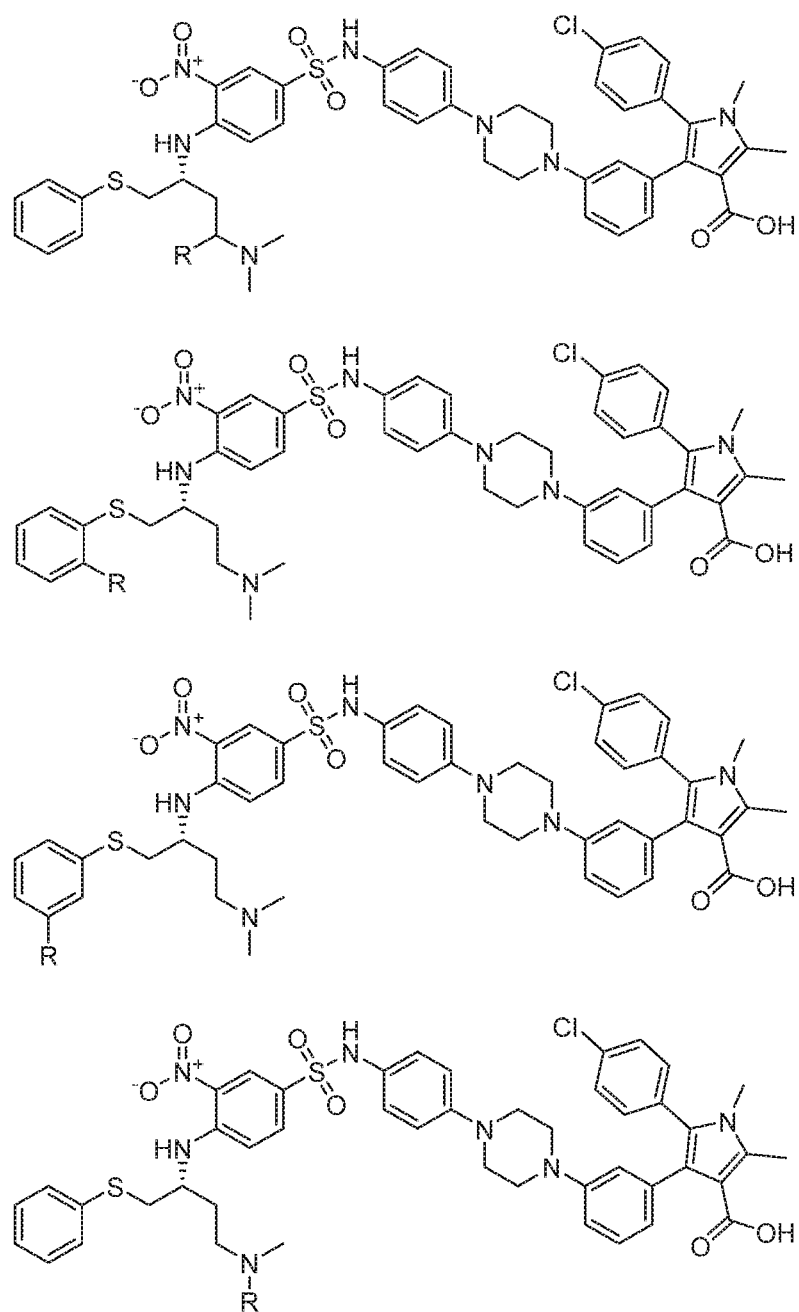
Figure 2Q:
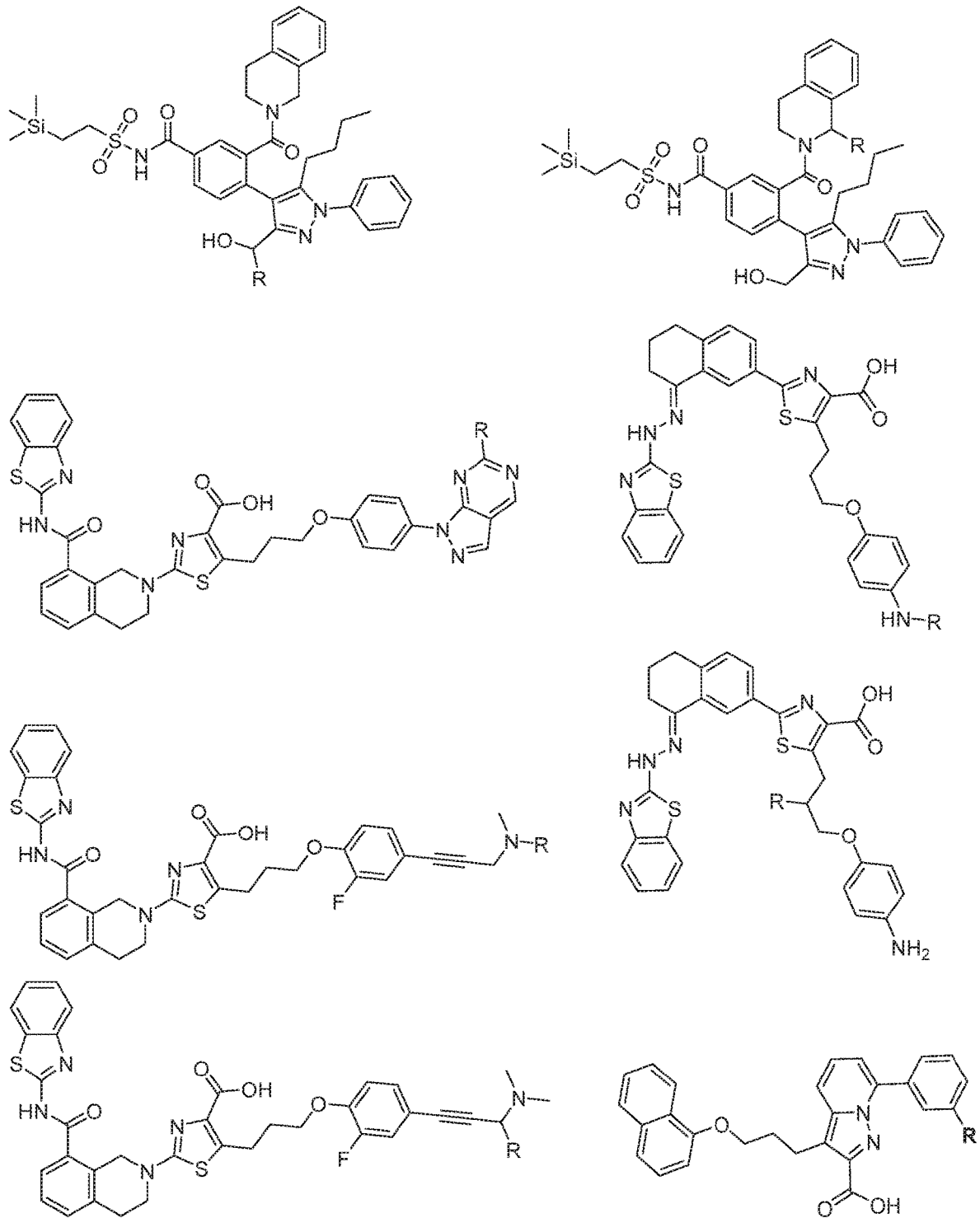
Figure 2S:
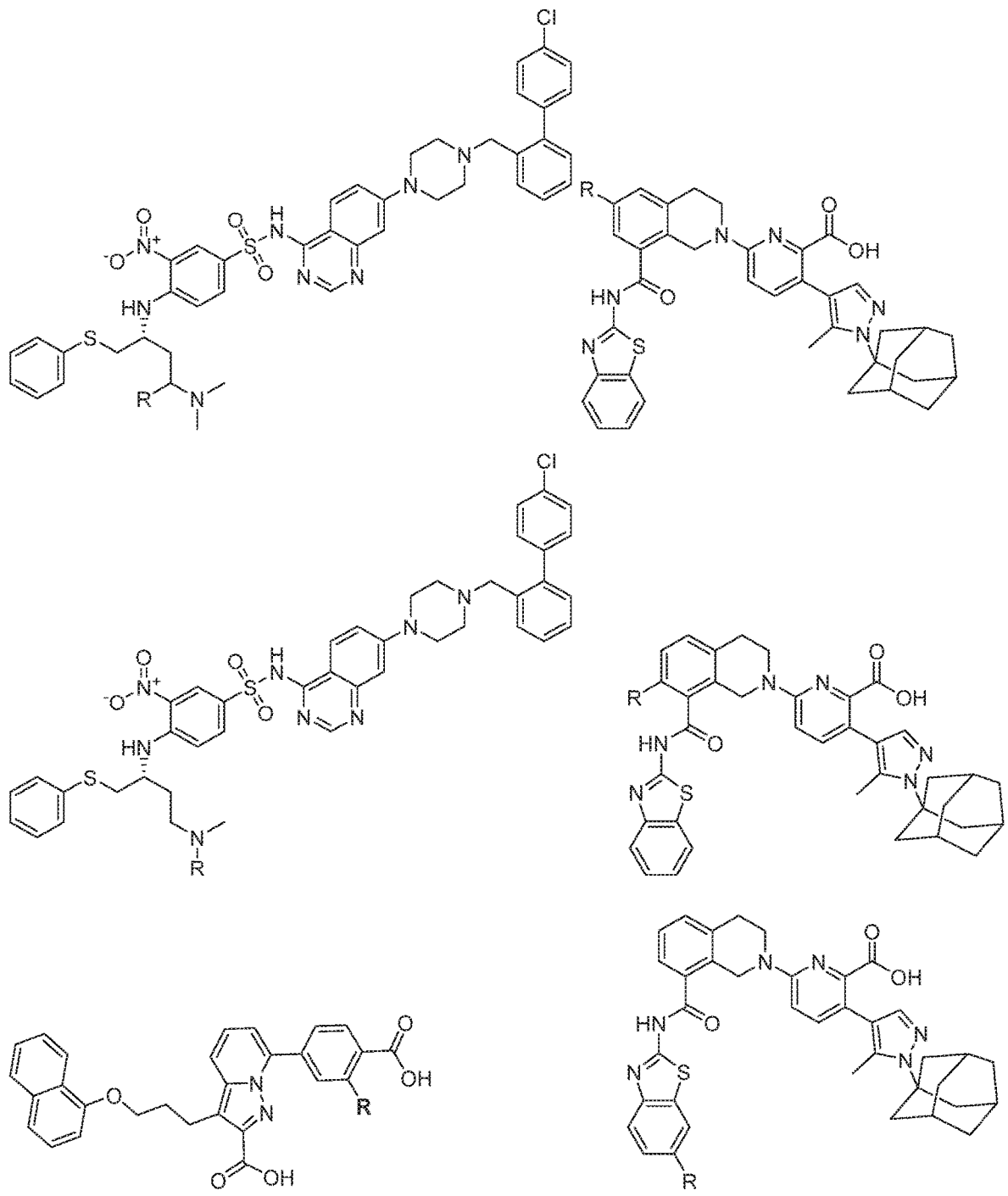
Figure 2T:
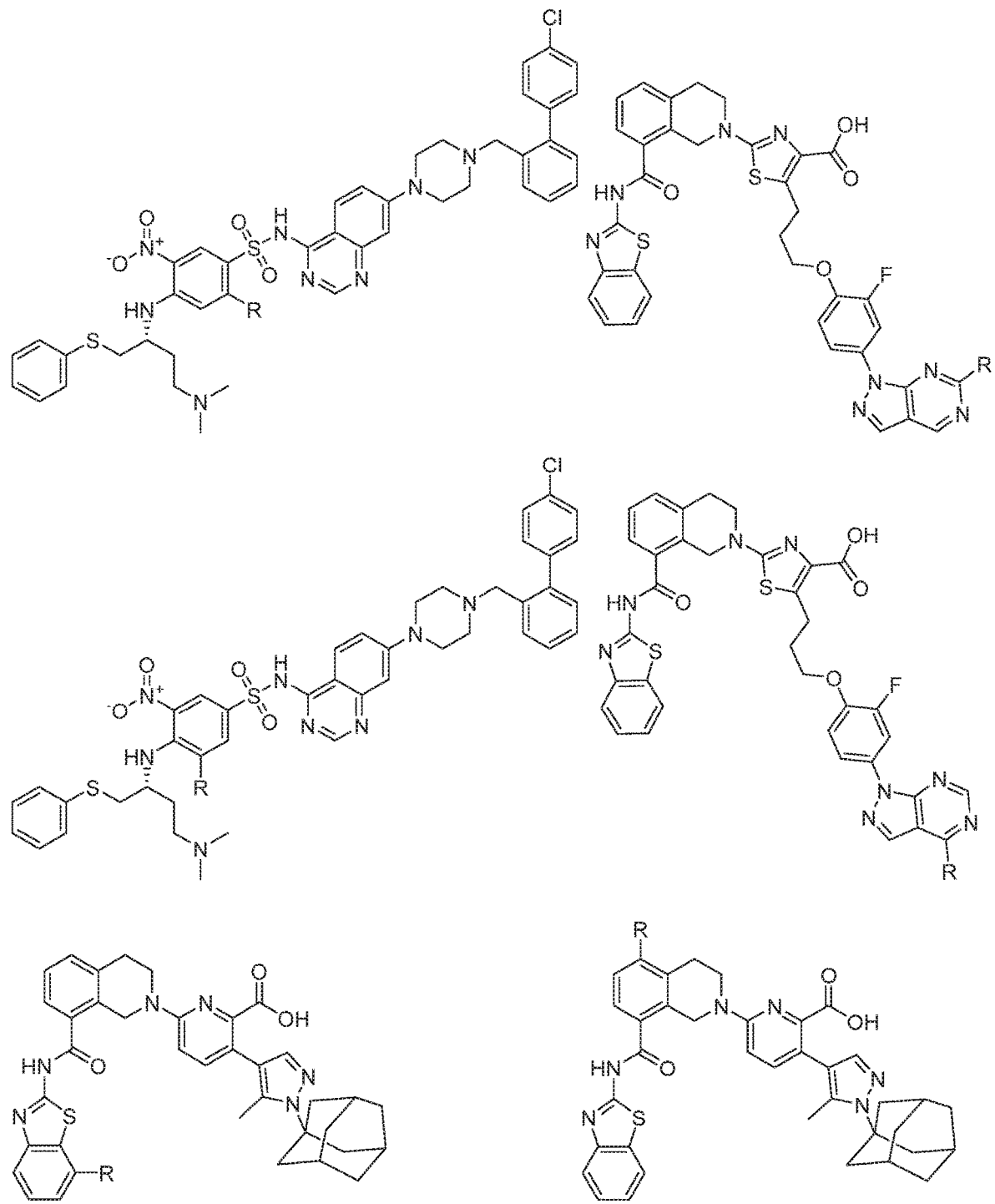
Figure 2U:
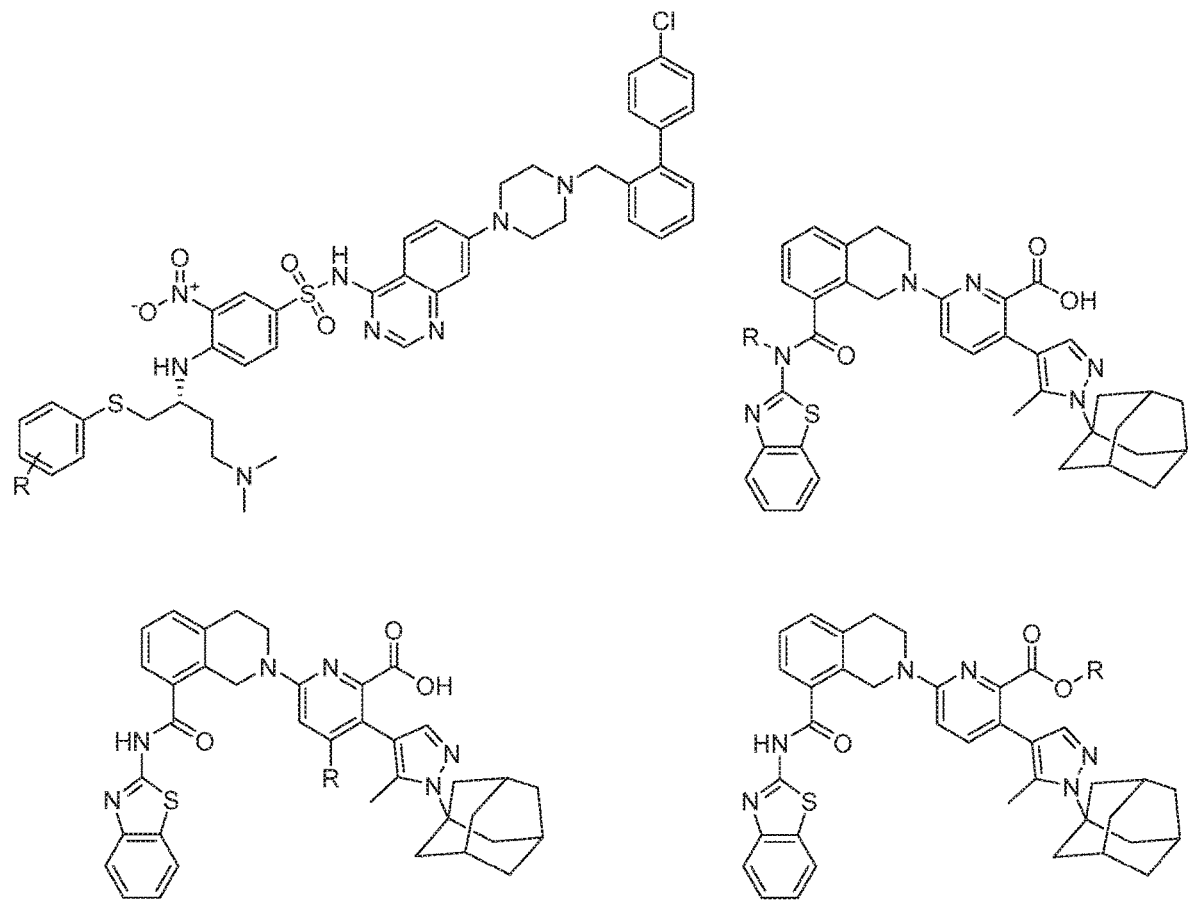
Figure 2V:
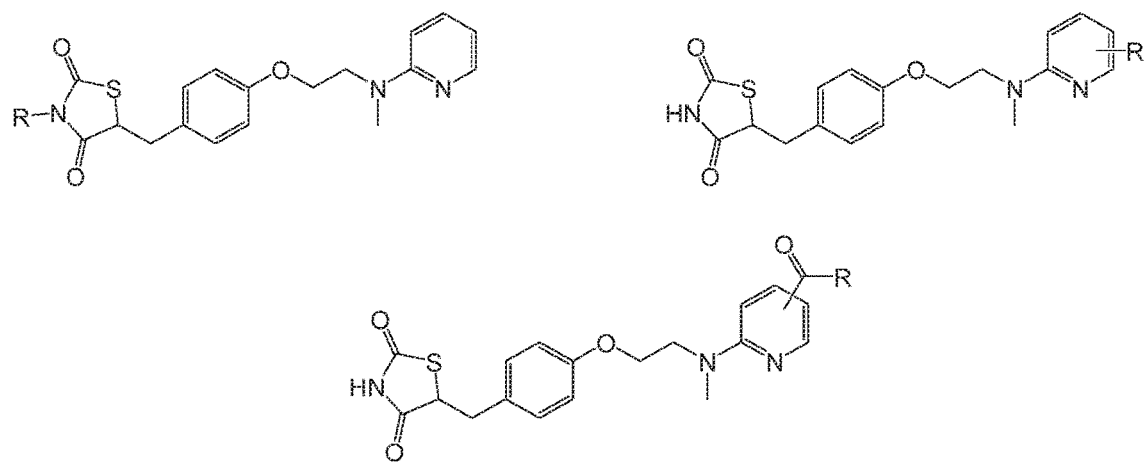
Figure 2W:
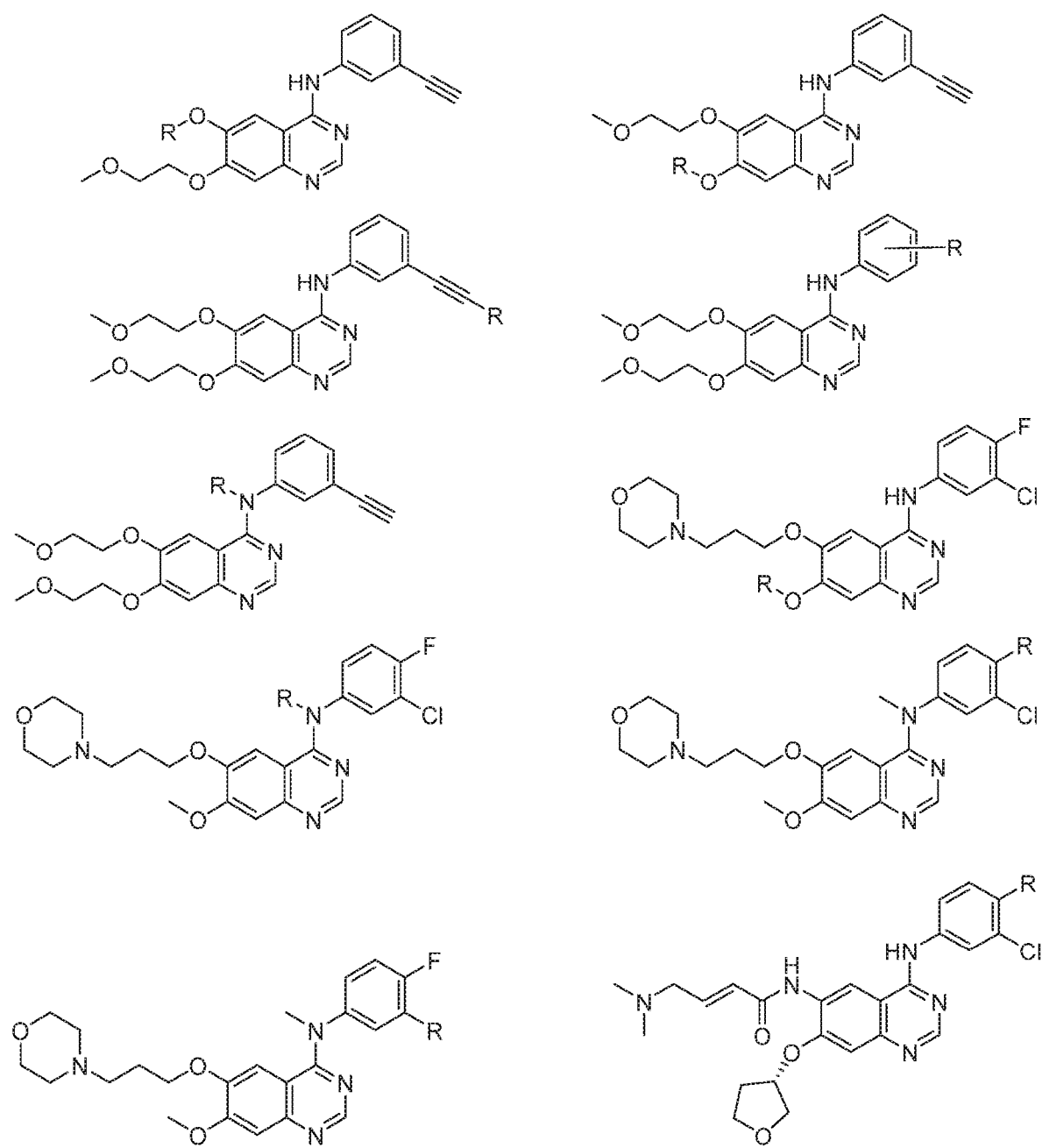

FIG. 2W presents examples of Bcl-2 or Bcl-XL Targeting Ligands wherein R is the point at which the Linker is attached.

Figure 2X:
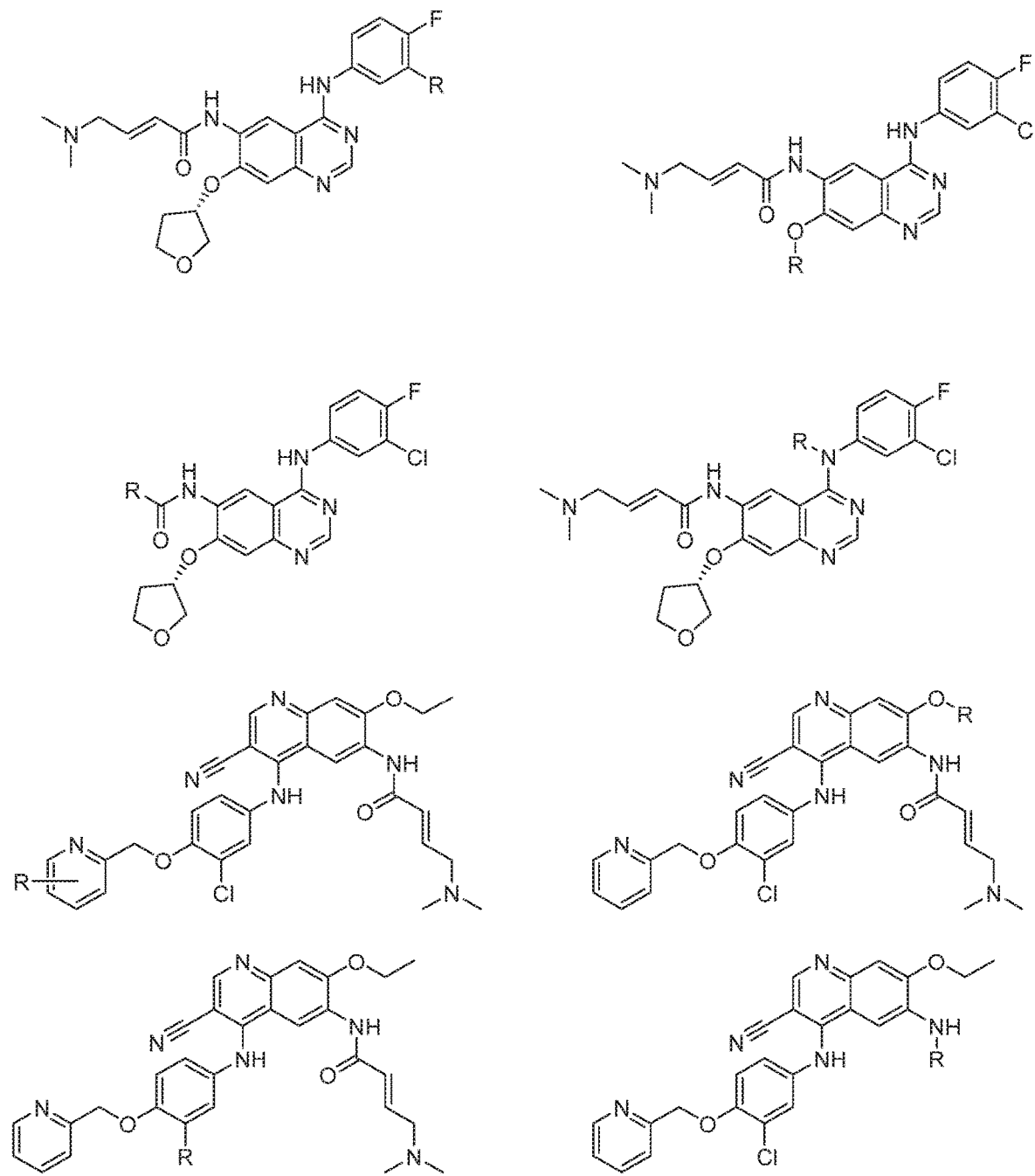

FIG. 2X-2NN present examples of BCL2 Targeting Ligands wherein R is the point at which the Linker is attached. For additional examples and related ligands, see, Toure B. B. et al. "The role of the acidity of N-heteroaryl sulfonamides as inhibitors of bcl-2 family protein-protein interactions." *ACS Med Chem Lett*, 4: 186-190 (2013); Porter J. et al. "Tetrahydroisoquinoline Amide Substituted Phenyl Pyrazoles as Selective Bcl-2 Inhibitors" *Bioorg. Med. Chem. Lett.* 19: 230 (2009); Souers A. J. et al. "ABT-199 a potent and selective BCL-2 inhibitor achieves antitumor activity while sparing platelets." *Nature Med.* 19: 202-208 (2013); Angelo Aguilar et al. "A Potent and Highly Efficacious Bcl-2/Bcl-xL Inhibitor" *J Med Chem.* 56(7): 3048-3067 (2013); Longchuan Bai et al. "BM-1197: A Novel and Specific Bcl-2/Bcl-xL Inhibitor Inducing Complete and Long-Lasting Tumor Regression In Vivo" *PLoS ONE* 9(6): e99404; Fariba Ne'matil et al. "Targeting Bcl-2/Bcl-XL Induces Antitumor Activity in Uveal Melanoma Patient-Derived Xenografts" *PLoS ONE* 9(1): e80836; WO2015011396 titled "Novel derivatives of indole and pyrrole method for the production thereof and pharmaceutical compositions containing same"; WO2008060569A1 titled "Compounds and methods for inhibiting the interaction of Bcl proteins with binding partners"; "Inhibitors of the anti-apoptotic Bcl-2 proteins: a patent review" *Expert Opin. Ther. Patents* 22(1):2008 (2012); and, Porter et al. "Tetrahydroisoquinoline amide substituted phenyl pyrazoles as selective Bcl-2 inhibitors" *Bioorg Med Chem Lett.*, 19(1): 230-3 (2009).

FIG. 2OO-2UU present examples of BCL-XL Targeting Ligands wherein R is the point at which the Linker is attached. For additional examples and related ligands, see, Zhi-Fu Tao et al. "Discovery of a Potent and Selective BCL-XL Inhibitor with in Vivo Activity" *ACSMed. Chem. Lett.*, 5: 1088-1093 (2014); Joel D. Leverson et al. "Exploiting selective BCL-2 family inhibitors to dissect cell survival dependencies and define improved strategies for cancer therapy" *Science Translational Medicine*, 7:279ra40 (2015); and, the crystal structure PDB 3ZK6 (Guillaume Lessene et al. "Structure-guided design of a selective BCL-XL inhibitor" *Nature Chemical Biology* 9: 390-397 (2013))

FIG. 2VV presents examples of PPAR-gamma Targeting Ligands wherein R is the point at which the Linker is attached.

FIG. 2WW-2YY present examples of EGFR Targeting Ligands that target the EGFR L858R mutant, including erlotnib, gefitnib, afatinib, neratinib, and dacomitinib, wherein R is the point at which the Linker is attached.

FIG. 2ZZ-2FFF present examples of EGFR Targeting Ligands that target the EGFR T790M mutant, including osimertinib, rociletinib, olmutinib, naquotinib, nazartinib, PF-06747775, Icotinib, Neratinib Avitinib, Tarloxotinib, PF-0645998, Tesevatinib, Transtinib, WZ-3146, WZ8040, and CNX-2006, wherein R is the point at which the Linker is attached.

FIG. 2GGG presents examples of EGFR Targeting Ligands that target the EGFR C797S mutant, including EAI045, wherein R is the point at which the Linker is attached.

FIG. 2HHH presents examples of BCR-ABL Targeting Ligands that target the BCR-ABL T315I mutantm including Nilotinib and Dasatinib, wherein R is the point at which the Linker is attached. See for example, the crystal structure PDB 3CS9.

FIG. 2III presents examples of Targeting Ligands that target BCR-ABL, including Nilotinib, Dasatinib Ponatinib and Bosutinib, wherein R is the point at which the Linker is attached.

FIG. 2JJJ-2KKK present examples of ALK Targeting Ligands that target the ALK L1196M mutant including Ceritinib, wherein R is the point at which the Linker is attached. See for example, the crystal structure PDB 4MKC.

FIG. 2LLL presents examples of JAK2 Targeting Ligands that target the JAK2V617F mutant, including Ruxolitinib, wherein R is the point at which the Linker is attached.

FIG. 2MMM presents examples of BRAF Targeting Ligands that target the BRAF V600E mutant including Vemurafenib, wherein R is the point at which the Linker is attached. For additional examples and related ligands, see, the crystal structure PBD 3OG7.

FIG. 2NNN presents examples of BRAF Targeting Ligands, including Dabrafenib, wherein R is the point at which the Linker is attached.

FIG. 2OOO presents examples of LRRK2 Targeting Ligands that target the LRRK2 R1441C mutant wherein R is the point at which the Linker is attached.

FIG. 2PPP presents examples of LRRK2 Targeting Ligands that target the LRRK2 G2019S mutant wherein R is the point at which the Linker is attached.

FIG. 2QQQ presents examples of LRRK2 Targeting Ligands that target the LRRK2 I2020T mutant wherein R is the point at which the Linker is attached.

FIG. 2RRR-2TTT present examples of PDGFRα Targeting Ligands that target the PDGFRα T674I mutant, including AG-1478, CHEMBL94431, Dovitinib, erlotinib, gefitinib, imatinib, Janex 1, Pazopanib, PD153035, Sorafenib, Sunitinib, and WHI-P180, wherein R is the point at which the Linker is attached.

FIG. 2UUU presents examples of RET Targeting Ligands that target the RET G691S mutant, including tozasertib, wherein R is the point at which the Linker is attached.

FIG. 2VVV presents examples of RET Targeting Ligands that target the RET R749T mutant, including tozasertib, wherein R is the point at which the Linker is attached.

FIG. 2WWW presents examples of RET Targeting Ligands that target the RET E762Q mutant, including tozasertib, wherein R is the point at which the Linker is attached.

FIG. 2XXX presents examples of RET Targeting Ligands that target the RET Y791F mutant, including tozasertib, wherein R is the point at which the Linker is attached.

Figure 2Y:
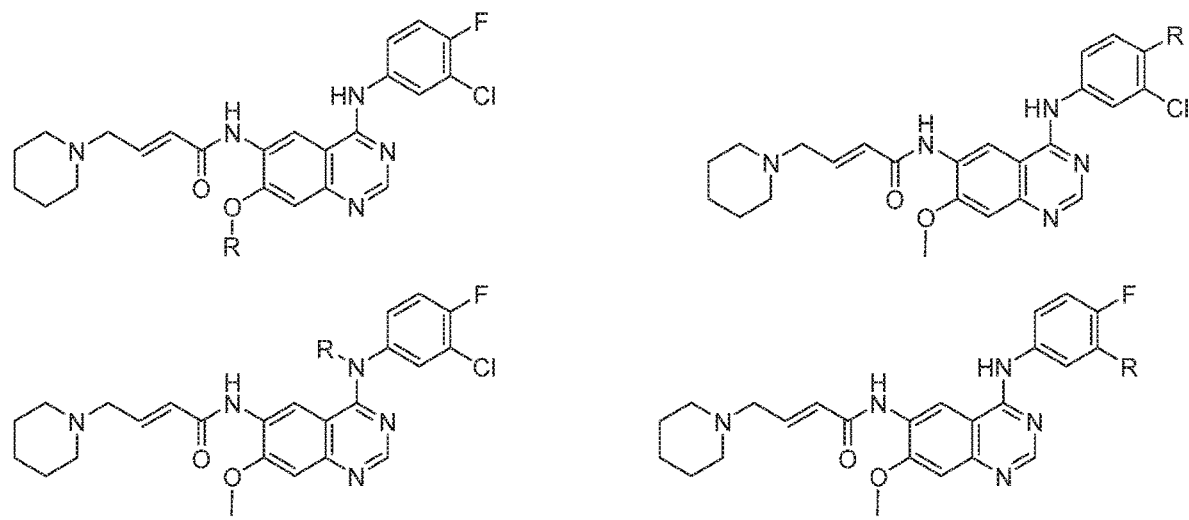
Figure 2Z:
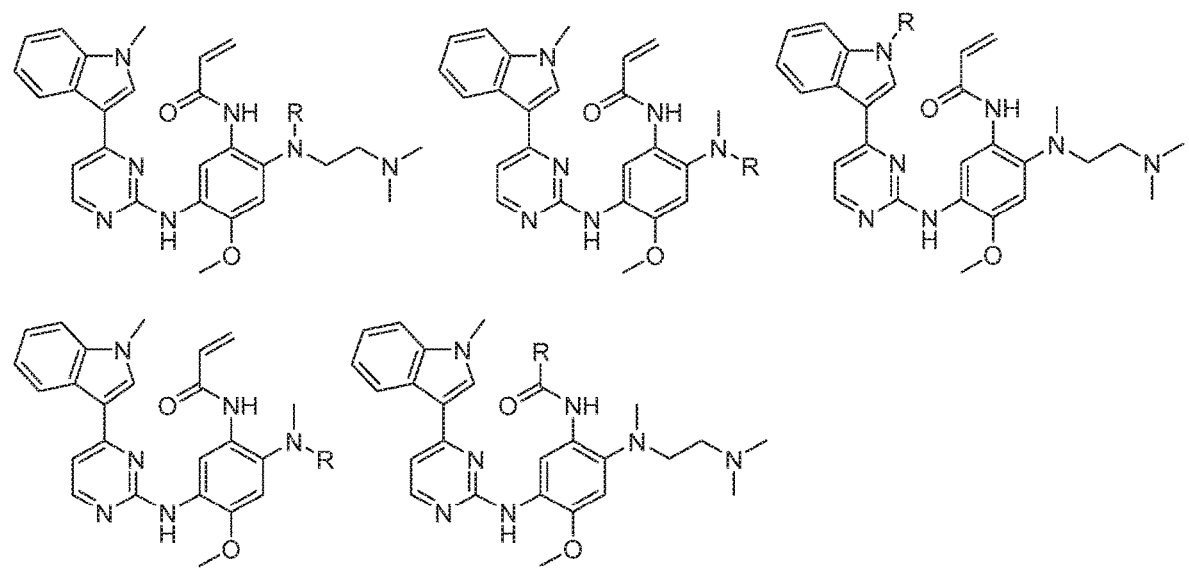

FIG. 2YYY presents examples of RET Targeting Ligands that target the RET V804M mutant, including tozasertib, wherein R is the point at which the Linker is attached.

FIG. 2ZZZ presents examples of RET Targeting Ligands that target the RET M918T mutant, including tozasertib, wherein R is the point at which the Linker is attached.

FIG. 2AAAA presents examples of Fatty Acid Binding Protein Targeting Ligands wherein R is the point at which the Linker is attached.

FIG. 2BBBB presents examples of 5-Lipoxygenase Activating Protein (FLAP) Targeting Ligands wherein R is the point at which the Linker is attached.

FIG. 2CCCC presents examples of Kringle Domain V 4BVV Targeting Ligands wherein R is the point at which the Linker is attached.

FIG. 2DDDD presents examples of Lactoylglutathione Lyase Targeting Ligands wherein R is the point at which the Linker is attached.

FIG. 2EEEE-2FFFF present examples of mPGES-1 Targeting Ligands wherein R is the point at which the Linker is attached.

FIG. 2GGGG-2JJJJ present examples of Factor Xa Targeting Ligands wherein R is the point at which the Linker is attached. For additional examples and related ligands, see, Maignan S. et al. "Crystal structures of human factor Xa complexed with potent inhibitors." *J. Med. Chem.* 43: 3226-3232 (2000); Matsusue T. et al. "Factor Xa Specific Inhibitor that Induces the Novel Binding Model in Complex with Human Fxa." (to be published); the crystal structures PDB 1iqh, 1iqi, 1iqk, and 1iqm; Adler M. et al. "Crystal Structures of Two Potent Nonamidine Inhibitors Bound to Factor Xa." *Biochemistry* 41: 15514-15523 (2002); Roehrig S. et al. "Discovery of the Novel Antithrombotic Agent 5-Chloro-N-({(5S)-2-Oxo-3-[4-(3-Oxomorpholin-4-Y1)Phenyl]-1 3-Oxazolidin-5-Yl}Methyl)Thiophene-2-Carboxamide (Bay 59-7939): An Oral Direct Factor Xa Inhibitor." *J. Med. Chem.* 48: 5900 (2005); Anselm L. et al. "Discovery of a Factor Xa Inhibitor (3R 4R)-1-(2 2-Difluoro-Ethyl)-Pyrrolidine-3 4-Dicarboxylic Acid 3-[(5-Chloro-Pyridin-2-Y1)-Amide] 4-{[2-Fluoro-4-(2-Oxo-2H-Pyridin-1-Y1)-Phenyl]-Amide} as a Clinical Candidate." *Bioorg. Med. Chem.* 20: 5313 (2010); and, Pinto D. J. et al. "Discovery of 1-(4-Methoxyphenyl)-7-oxo-6-(4-(2-oxopiperidin-1-yl)phenyl)-4 5 6 7-tetrahydro-1H-pyrazolo[3 4-c]pyridine-3-carboxamide (Apixaban BMS-562247) a Highly Potent Selective Efficacious and Orally Bioavailable Inhibitor of Blood Coagulation Factor Xa." *J. Med. Chem.* 50: 5339-5356 (2007).

FIG. 2KKKK presents examples of Kallikrein 7 Targeting Ligands wherein R is the point at which the Linker is attached. For additional examples and related ligands, see, Maibaum J. et al. "Small-molecule factor D inhibitors targeting the alternative complement pathway." *Nat. Chem. Biol.* 12: 1105-1110 (2016).

FIG. 2LLLL-2MMMM present examples of Cathepsin K Targeting Ligands wherein R is the point at which the Linker is attached. For additional examples and related ligands, see, Rankovic Z. et al. "Design and optimization of a series of novel 2-cyano-pyrimidines as cathepsin K inhibitors" *Bioorg. Med. Chem. Lett.* 20: 1524-1527 (2010); and, Cai J. et al. "Trifluoromethylphenyl as P2 for ketoamide-based cathepsin S inhibitors." *Bioorg. Med. Chem. Lett.* 20: 6890-6894 (2010).

FIG. 2NNNN presents examples of Cathepsin L Targeting Ligands wherein R is the point at which the Linker is attached. For additional examples and related ligands, see, Kuhn B. et al. "Prospective Evaluation of Free Energy Calculations for the Prioritization of Cathepsin L Inhibitors." *J. Med. Chem.* 60: 2485-2497 (2017).

FIG. 2OOOO presents examples of Cathepsin S Targeting Ligands wherein R is the point at which the Linker is attached. For additional examples and related ligands, see, Jadhav P. K. et al. "Discovery of Cathepsin S Inhibitor LY3000328 for the Treatment of Abdominal Aortic Aneurysm" *ACSMed. Chem. Lett.* 5: 1138-1142." (2014).

FIG. 2PPPP-2SSSS present examples of MTH1 Targeting Ligands wherein R is the point at which the Linker is attached. For additional examples and related ligands, see, Kettle J. G. et al. "Potent and Selective Inhibitors of Mth1 Probe its Role in Cancer Cell Survival." *J. Med. Chem.* 59: 2346 (2016); Huber K. V. M. et al. "Stereospecific Targeting of Mth1 by (S)-Crizotinib as an Anticancer Strategy." *Nature* 508: 222 (2014); Gad H. et al. "MTH1 inhibition eradicates cancer by preventing sanitation of the dNTP pool." *Nature* 508: 215-221 (2014); Nissink J. W. M. et al. "Mth1 Substrate Recognition—an Example of Specific Promiscuity." *Plos One* 11: 51154 (2016); and, Manuel Ellermann et al. "Novel class of potent and selective inhibitors efface MTH1 as broad-spectrum cancer target." AACR National Meeting Abstract 5226, 2017.

FIG. 2TTTT-2ZZZZ present examples of MDM2 and/or MDM4 Targeting Ligands wherein R is the point at which the Linker is attached. For additional examples and related ligands, see, Popowicz G. M. et al. "Structures of low molecular weight inhibitors bound to MDMX and MDM2 reveal new approaches for p53-MDMX/MDM2 antagonist drug discovery." *Cell Cycle,* 9 (2010); Miyazaki M. et al. "Synthesis and evaluation of novel orally active p53-MDM2 interaction inhibitors." *Bioorg. Med. Chem.* 21: 4319-4331 (2013); Miyazaki M. et al. "Discovery of DS-5272 as a promising candidate: A potent and orally active p53-MDM2 interaction inhibitor." *Bioorg Med Chem.* 23: 2360-7 (2015); Holzer P. et al. "Discovery of a Dihydroisoquinolinone Derivative (NVP-CGM097): A Highly Potent and Selective MDM2 Inhibitor Undergoing Phase 1 Clinical Trials in p53 wt Tumors." *J. Med. Chem.* 58: 6348-6358 (2015); Gonzalez-Lopez de Turiso F. et al. "Rational Design and Binding Mode Duality of MDM2-p53 Inhibitors." *J. Med. Chem.* 56: 4053-4070 (2013); Gessier F. et al. "Discovery of dihydroisoquinolinone derivatives as novel inhibitors of the p53-MDM2 interaction with a distinct binding mode." *Bioorg. Med. Chem. Lett.* 25: 3621-3625 (2015); Fry D. C. et al. "Deconstruction of a nutlin: dissecting the binding determinants of a potent protein-protein interaction inhibitor." *ACS Med Chem Lett* 4: 660-665 (2013); Ding Q. et al. "Discovery of RG7388 a Potent and Selective p53-MDM2 Inhibitor in Clinical Development." *J. Med. Chem.* 56: 5979-5983 (2013); Wang S. et al. "SAR405838: an optimized inhibitor of MDM2-p53 interaction that induces complete and durable tumor regression." *Cancer Res.* 74: 5855-5865 (2014); Rew Y. et al. "Discovery of AM-7209 a Potent and Selective 4-Amidobenzoic Acid Inhibitor of the MDM2-p53 Interaction." *J. Med. Chem.* 57: 10499-10511 (2014); Bogen S. L. et al. "Discovery of Novel 3 3-Disubstituted Piperidines as Orally Bioavailable Potent and Efficacious HDM2-p53 Inhibitors." ACSMed. *Chem. Lett.* 7: 324-329 (2016); and, Sun D. et al. "Discovery of AMG 232 a Potent Selective and Orally Bioavailable MDM2-p53 Inhibitor in Clinical Development." *J. Med. Chem.* 57: 1454-1472 (2014).

FIG. 2AAAAA-2EEEEE present examples of PARP1, PARP2, and/or PARP3 Targeting Ligands wherein R is the point at which the Linker is attached. For additional examples and related ligands, see, Iwashita A. et al. "Discovery of quinazolinone and quinoxaline derivatives as potent and selective poly(ADP-ribose) polymerase-1/2 inhibitors." *Febs Lett.* 579: 1389-1393 (2005); the crystal structure PDB 2RCW (PARP complexed with A861695, Park C. H.); the crystal structure PDB 2RD6 (PARP complexed with A861696, Park C. H.); the crystal structure PDB 3GN7; Miyashiro J. et al. "Synthesis and SAR of novel tricyclic quinoxalinone inhibitors of poly(ADP-ribose)polymerase-1 (PARP-1)" Bioorg. Med. Chem. Lett. 19: 4050-4054 (2009); Gandhi V. B. et al. "Discovery and SAR of substituted 3-oxoisoindoline-4-carboxamides as potent inhibitors of poly(ADP-ribose) polymerase (PARP) for the treatment of cancer." Bioorg. Med. Chem. Lett. 20: 1023-1026 (2010); Penning T. D. et al. "Optimization of phenyl-substituted benzimidazole carboxamide poly(ADP-ribose) polymerase inhibitors: identification of (S)-2-(2-fluoro-4-(pyrrolidin-2-yl)phenyl)-1H-benzimidazole-4-carboxamide (A-966492) a highly potent and efficacious inhibitor." J. Med. Chem. 53: 3142-3153 (2010); Ye N. et al. "Design, Synthesis, and Biological Evaluation of a Series of Benzo[de][1 7]naphthyridin-7(8H)-ones Bearing a Functionalized Longer Chain Appendage as Novel PARP1 Inhibitors." J. Med. Chem. 56: 2885-2903 (2013); Patel M. R. et al. "Discovery and Structure-Activity Relationship of Novel 2 3-Dihydrobenzofuran-7-carboxamide and 2 3-Dihydrobenzofuran-3(2H)-one-7-carboxamide Derivatives as Poly (ADP-ribose)polymerase-1 Inhibitors." J. Med. Chem. 57: 5579-5601 (2014);

Thorsell A. G. et al. "Structural Basis for Potency and Promiscuity in Poly(ADP-ribose) Polymerase (PARP) and Tankyrase Inhibitors." J. Med. Chem. 60:1262-1271 (2012); the crystal structure PDB 4RV6 ("Human ARTD1 (PARP1) catalytic domain in complex with inhibitor Rucaparib", Karlberg T. et al.); Papeo G. M. E. et al. "Discovery of 2-[1-(4 4-Difluorocyclohexyl)Piperidin-4-Y1]-6-Fluoro-3-Oxo-2 3-Dihydro-1H-Isoindole-4-Carboxamide (Nms-P118): A Potent Orally Available and Highly Selective Parp-1 Inhibitor for Cancer Therapy." J. Med. Chem. 58: 6875 (2015); Kinoshita T. et al. "Inhibitor-induced structural change of the active site of human poly(ADP-ribose) polymerase." Febs Lett. 556: 43-46 (2004); and, Gangloff A. R. et al. "Discovery of novel benzo[b][1 4]oxazin-3(4H)-ones as poly(ADP-ribose)polymerase inhibitors." Bioorg. Med. Chem. Lett. 23: 4501-4505 (2013).

FIG. 2FFFFF-2GGGGG present examples of PARP14 Targeting Ligands wherein R is the point at which the Linker is attached.

FIG. 2HHHHH presents examples of PARP15 Targeting Ligands wherein R is the point at which the Linker is attached.

FIG. 2IIIII presents examples of PDZ domain Targeting Ligands wherein R is the point at which the Linker(s) are attached.

FIG. 2JJJJJ presents examples of Phospholipase A2 domain Targeting Ligands wherein R is the point at which the Linker is attached.

FIG. 2KKKKK presents examples of Protein S 100-A7 2WOS Targeting Ligands wherein R is the point at which the Linker is attached.

FIG. 2LLLLL-2MMMMM present examples of Saposin-B Targeting Ligands wherein R is the point at which the Linker is attached.

FIG. 2NNNNN-2OOOOO present examples of Sec7 Targeting Ligands wherein R is the point at which the Linker is attached.

FIG. 2PPPPP-2QQQQQ present examples of SH2 domain of pp60 Src Targeting Ligands wherein R is the point at which the Linker is attached.

FIG. 2RRRRR presents examples of Tank1 Targeting Ligands wherein R is the point at which the Linker is attached.

FIG. 2SSSSS presents examples of Ubc9 SUMO E2 ligase SF6D Targeting Ligands wherein R is the point at which the Linker is attached.

FIG. 2TTTTT presents examples of Src Targenting Ligands, including AP23464, wherein R is the point at which the Linker is attached.

FIG. 2UUUUU-2XXXXX present examples of Src-AS1 and/or Src AS2 Targeting Ligands wherein R is the point at which the Linker is attached.

FIG. 2YYYYY presents examples of JAK3 Targeting Ligands, including Tofacitinib, wherein R is the point at which the Linker is attached.

FIG. 2ZZZZZ presents examples of ABL Targeting Ligands, including Tofacitinib and Ponatinib, wherein R is the point at which the Linker is attached.

Figure 3B:
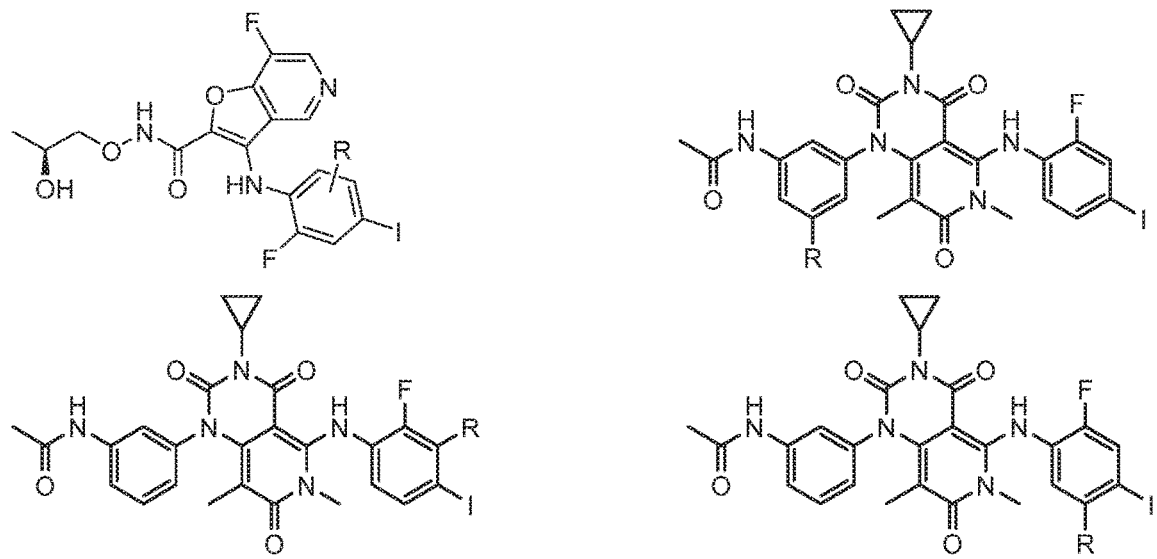
Figure 3C:
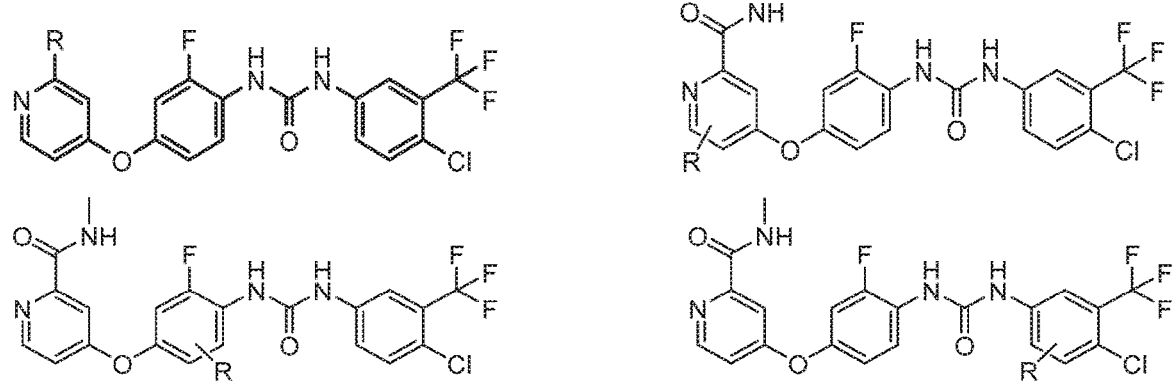
Figure 3D:
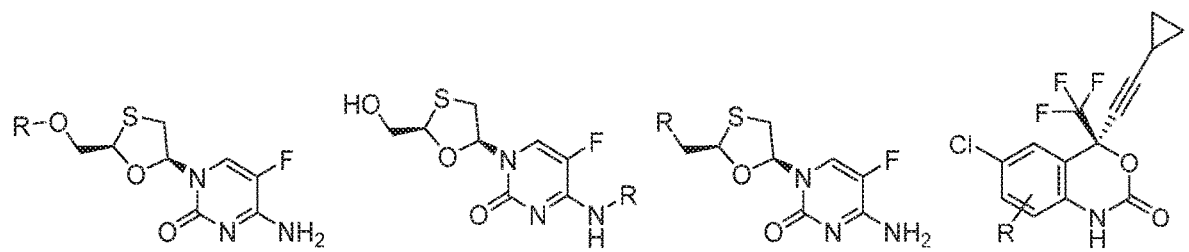
Figure 3E:
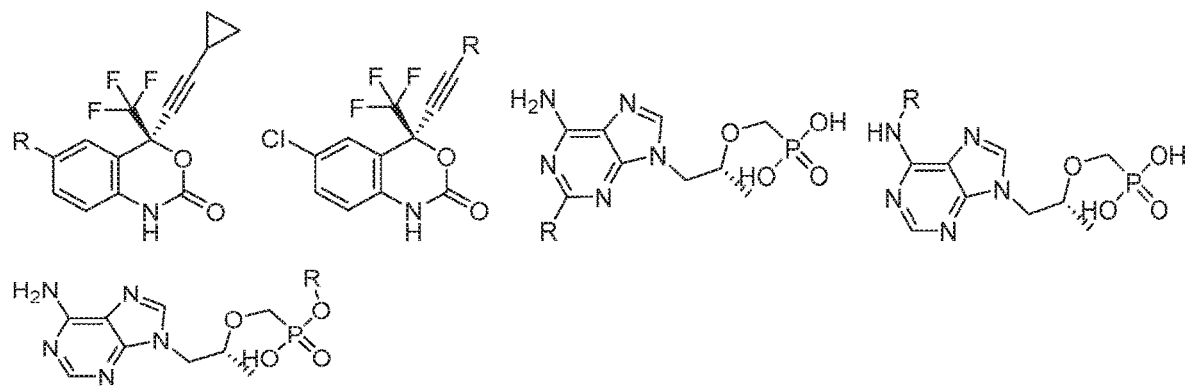
Figure 3F:
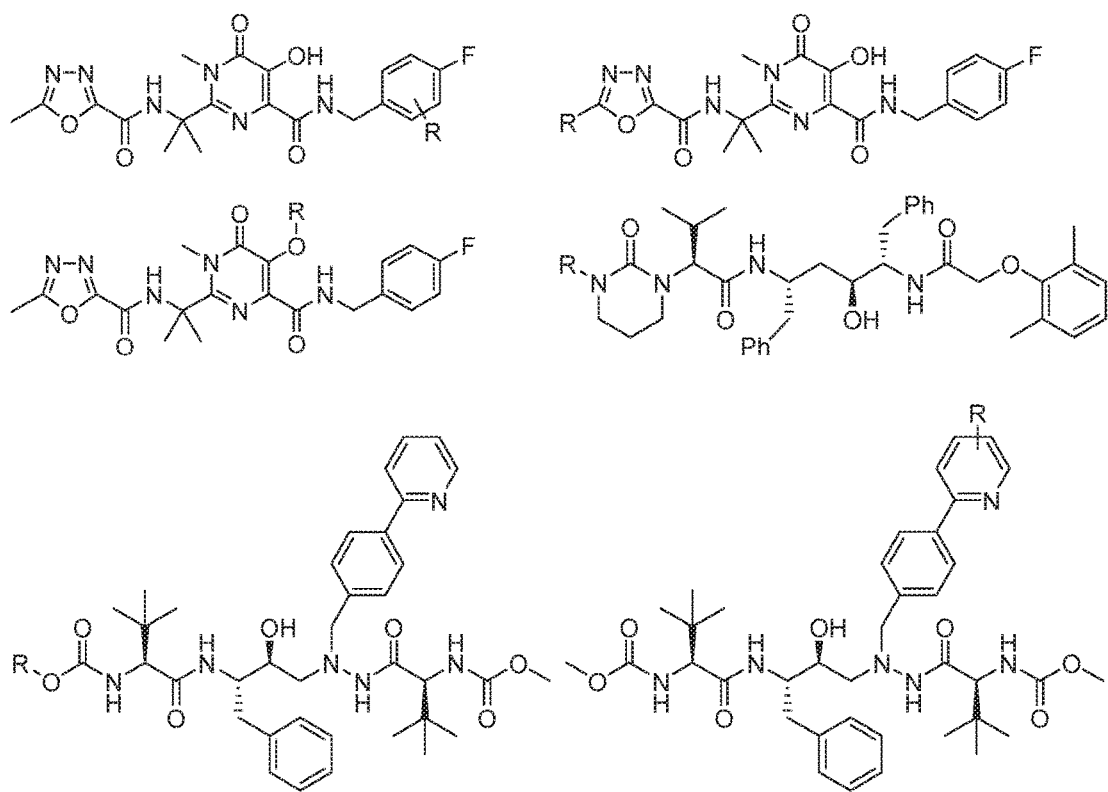
Figure 3G:
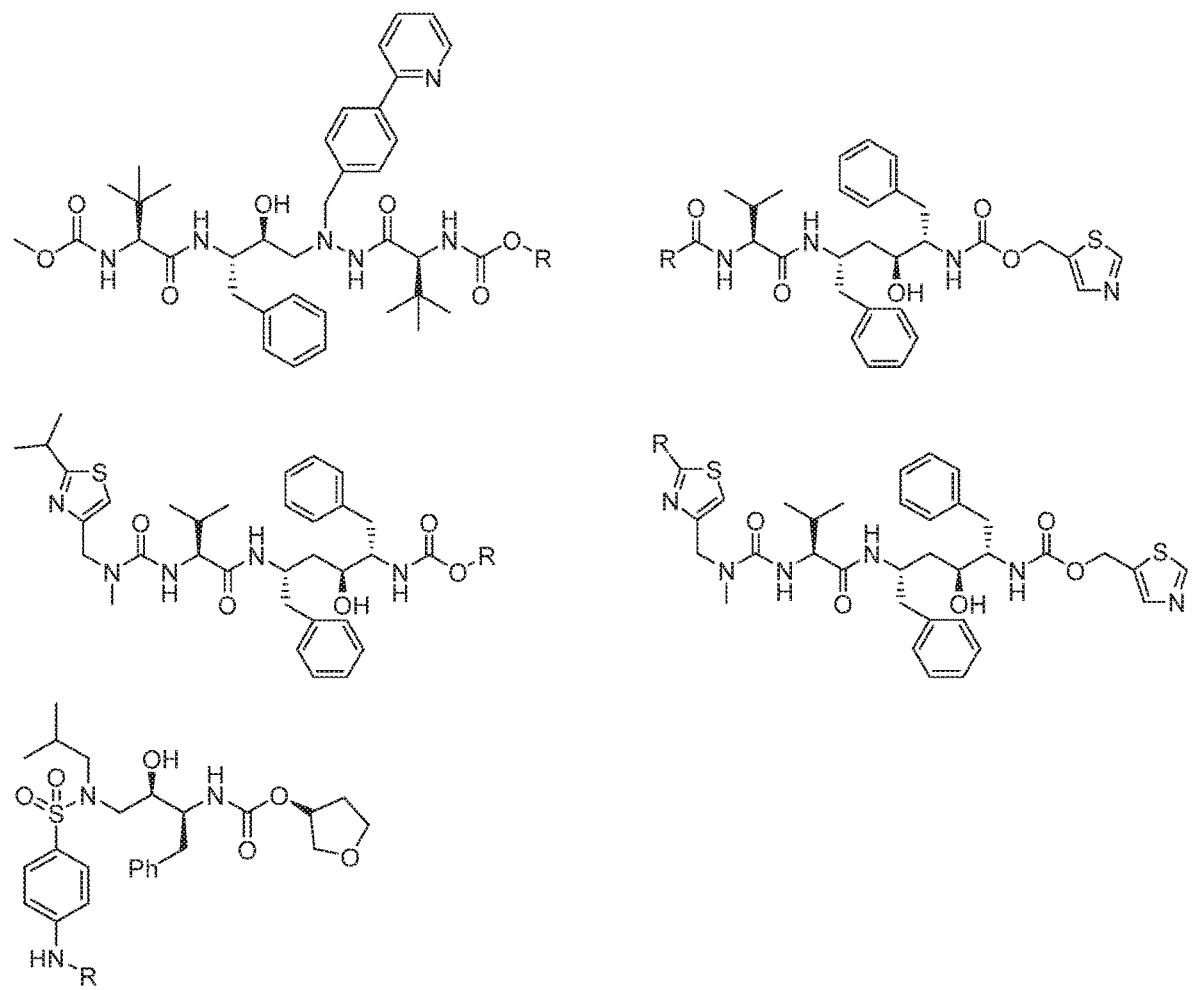
Figure 3H:
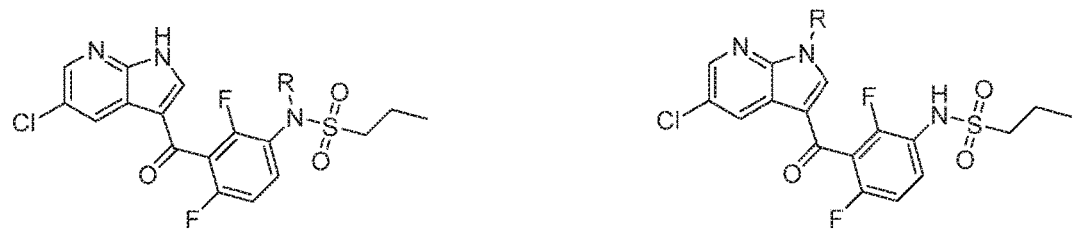
Figure 3K:
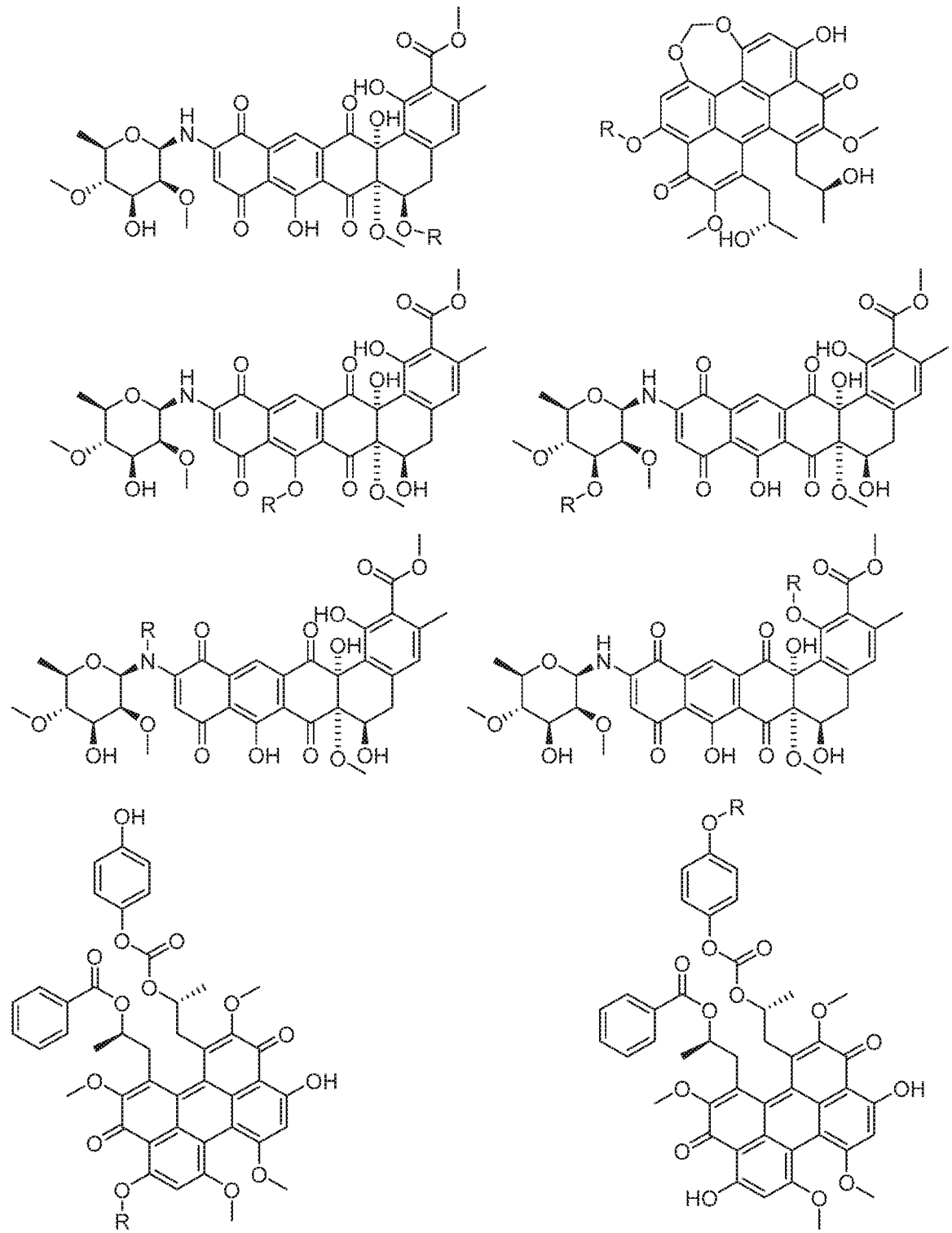
Figure 3L:
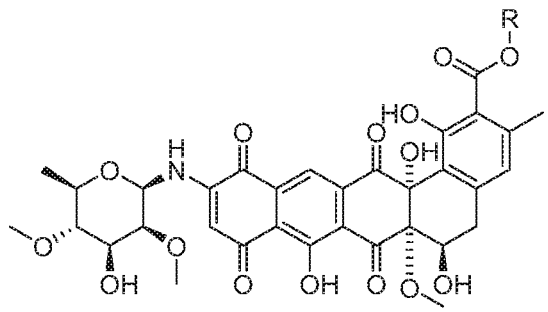
Figure 3M:
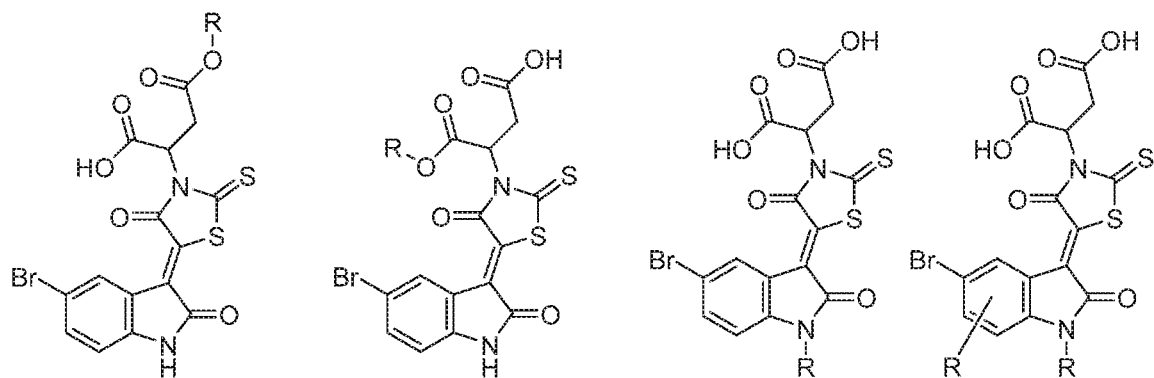
Figure 3N:
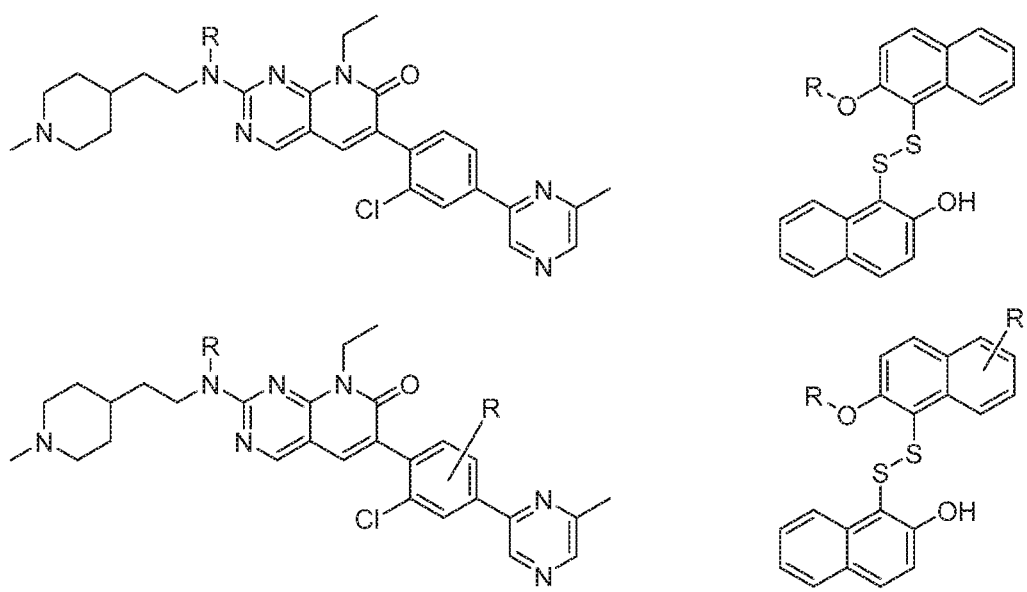
Figure 3O:
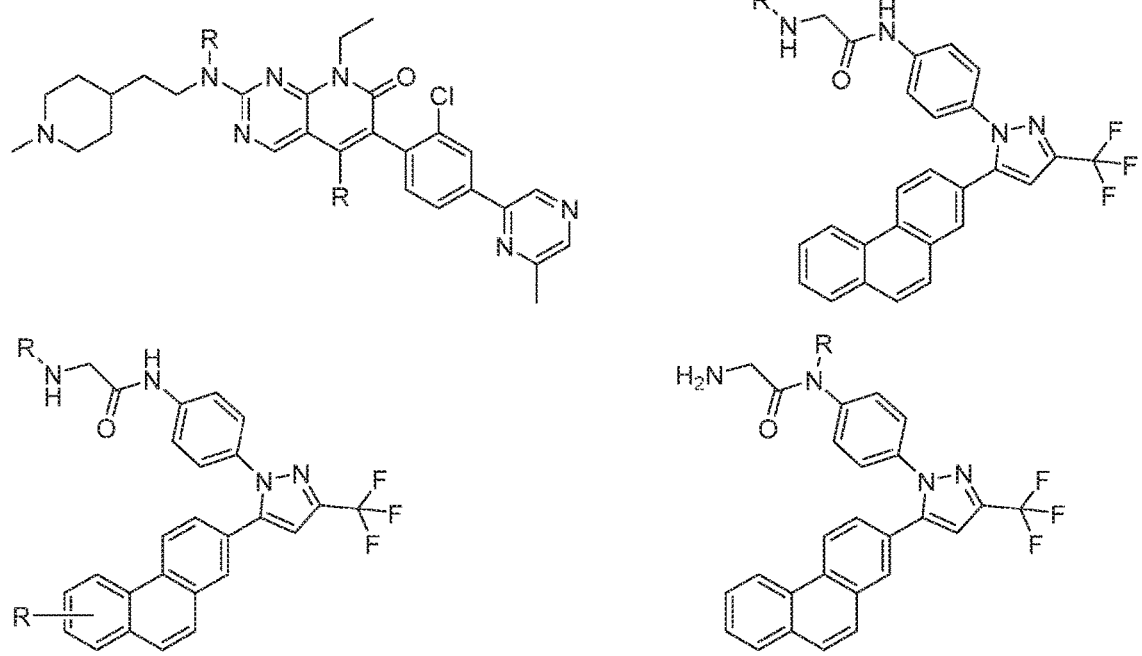
Figure 3P:
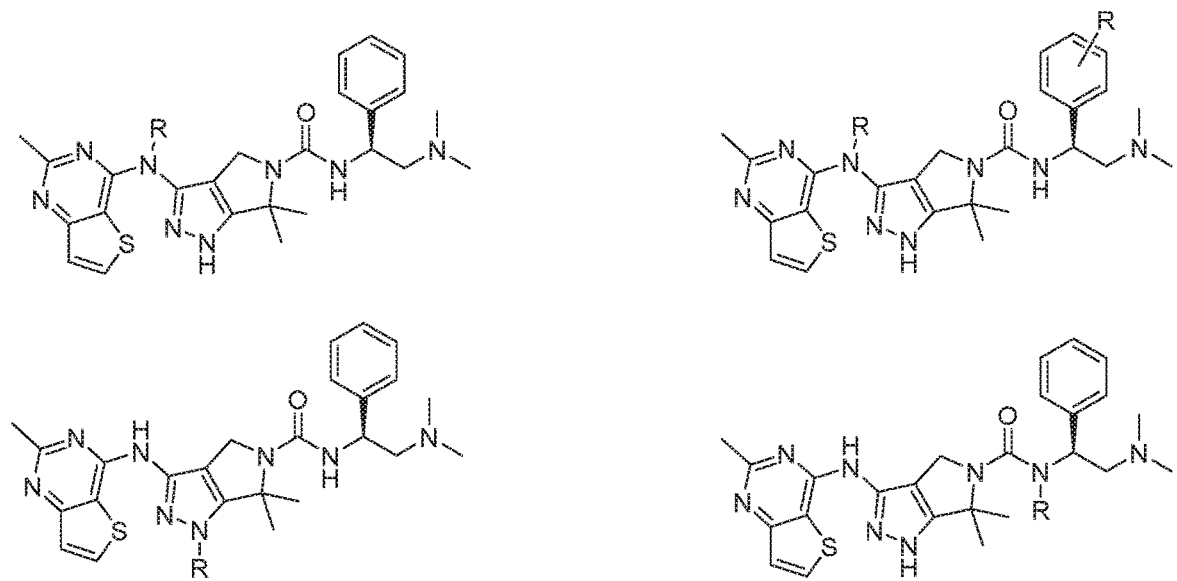
Figure 3Q:
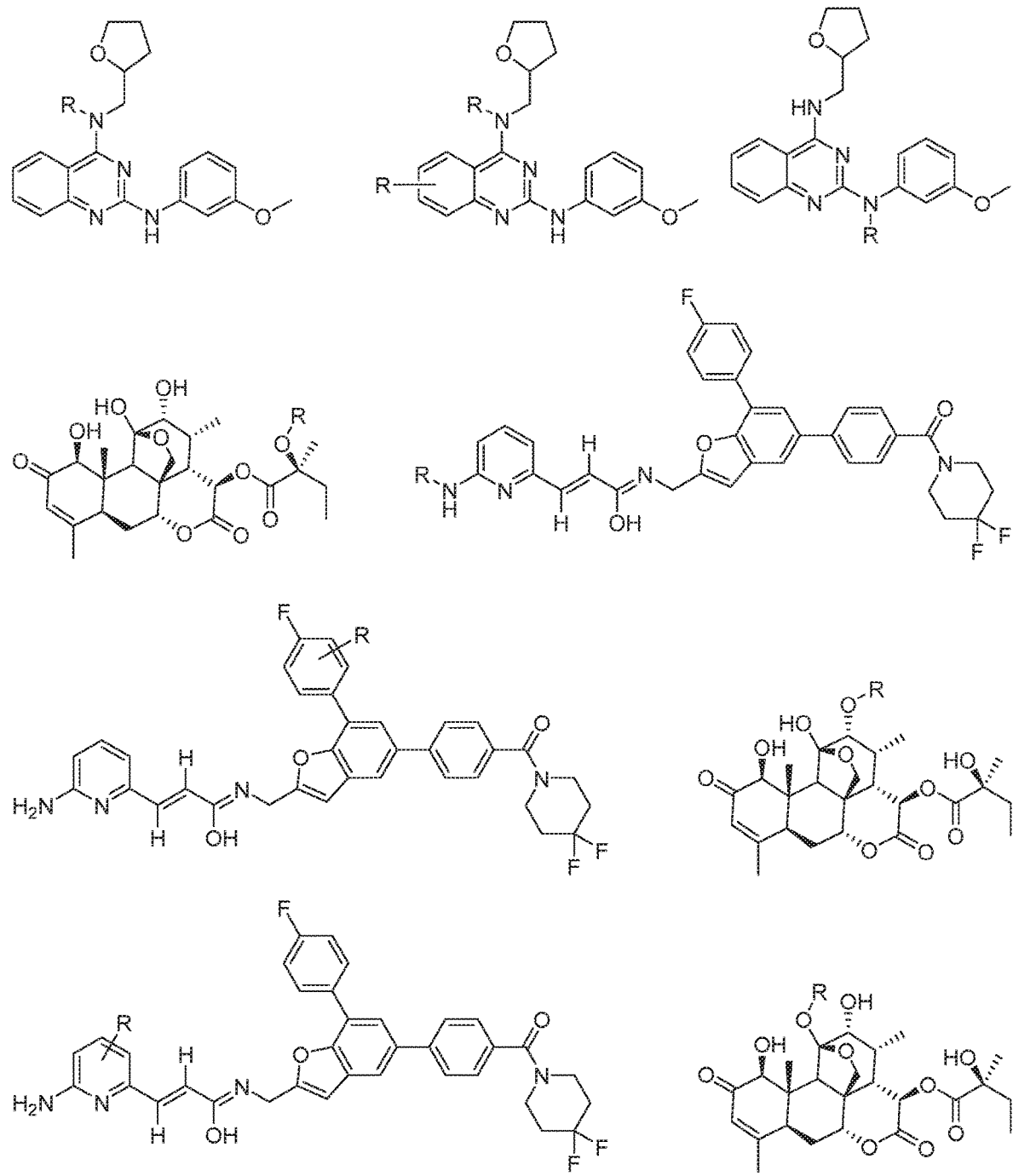
Figure 3R:
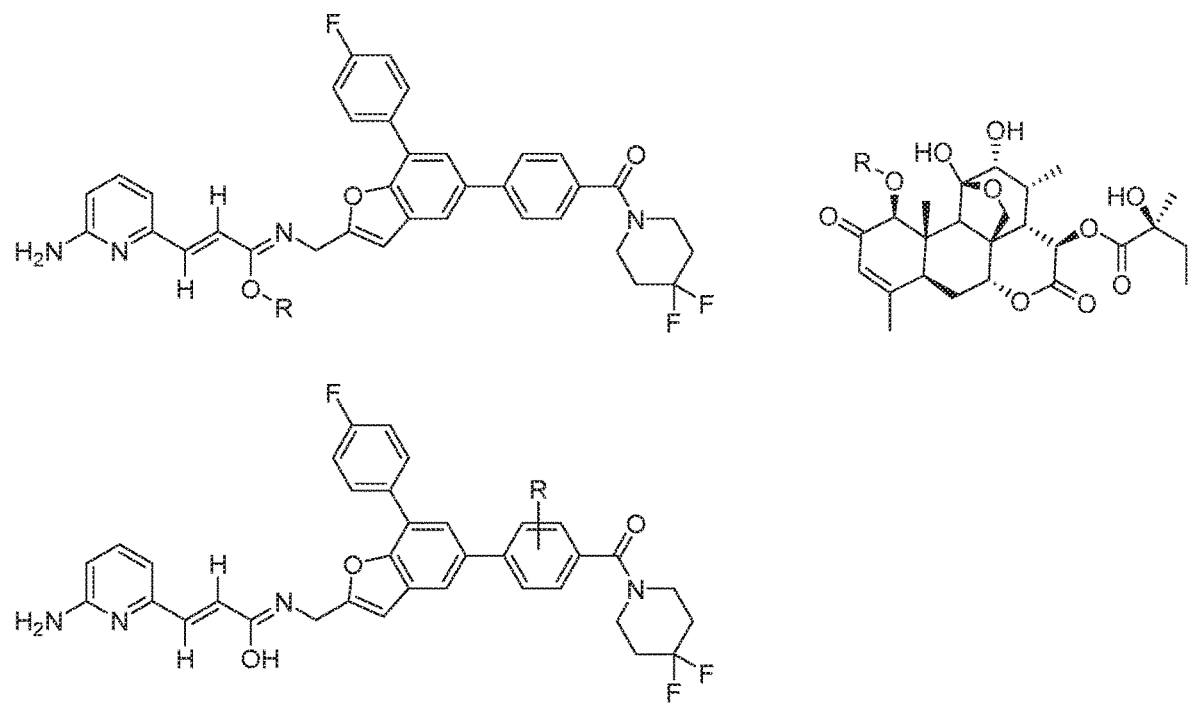
Figure 3S:
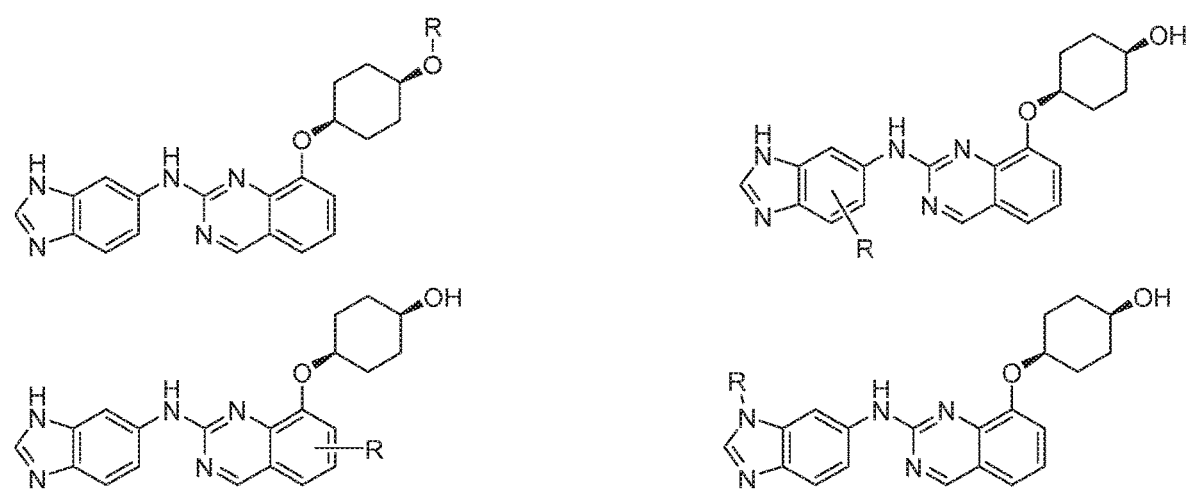
Figure 3T:
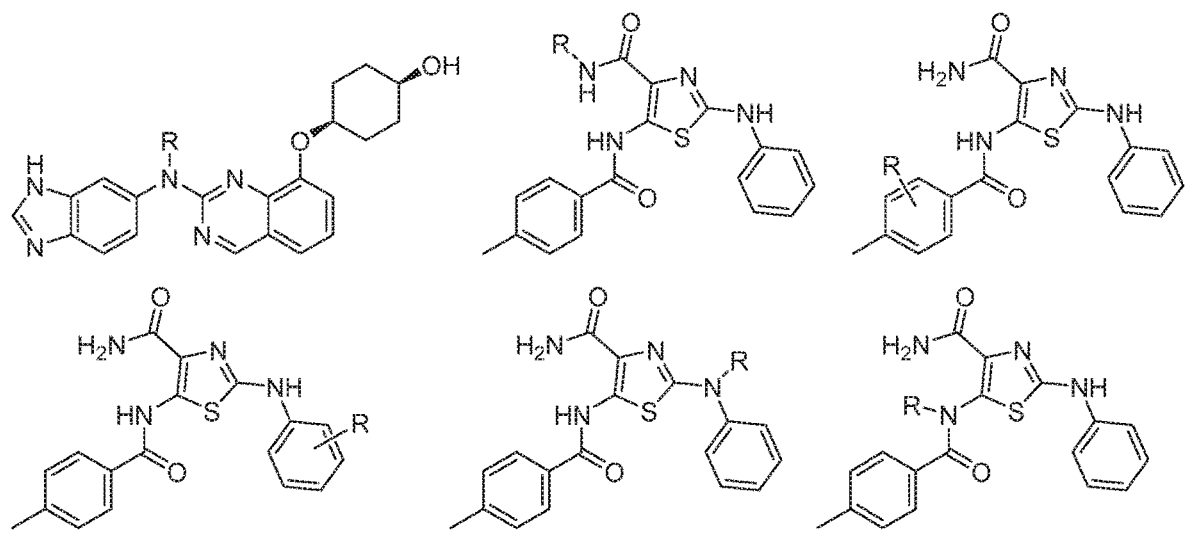
Figure 3U:
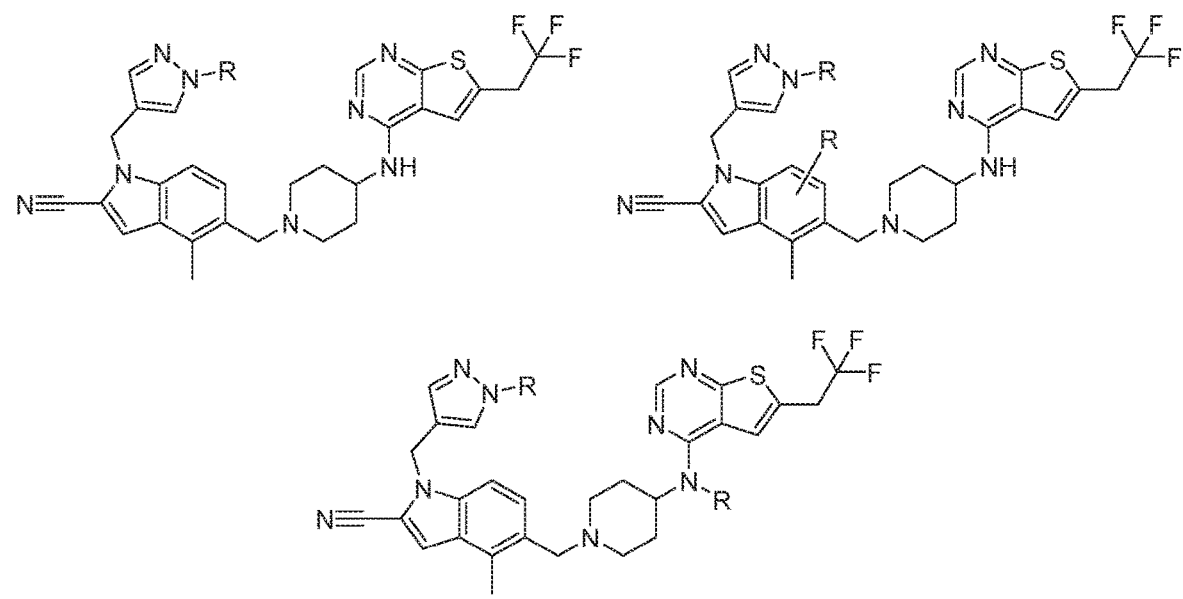
Figure 3V:
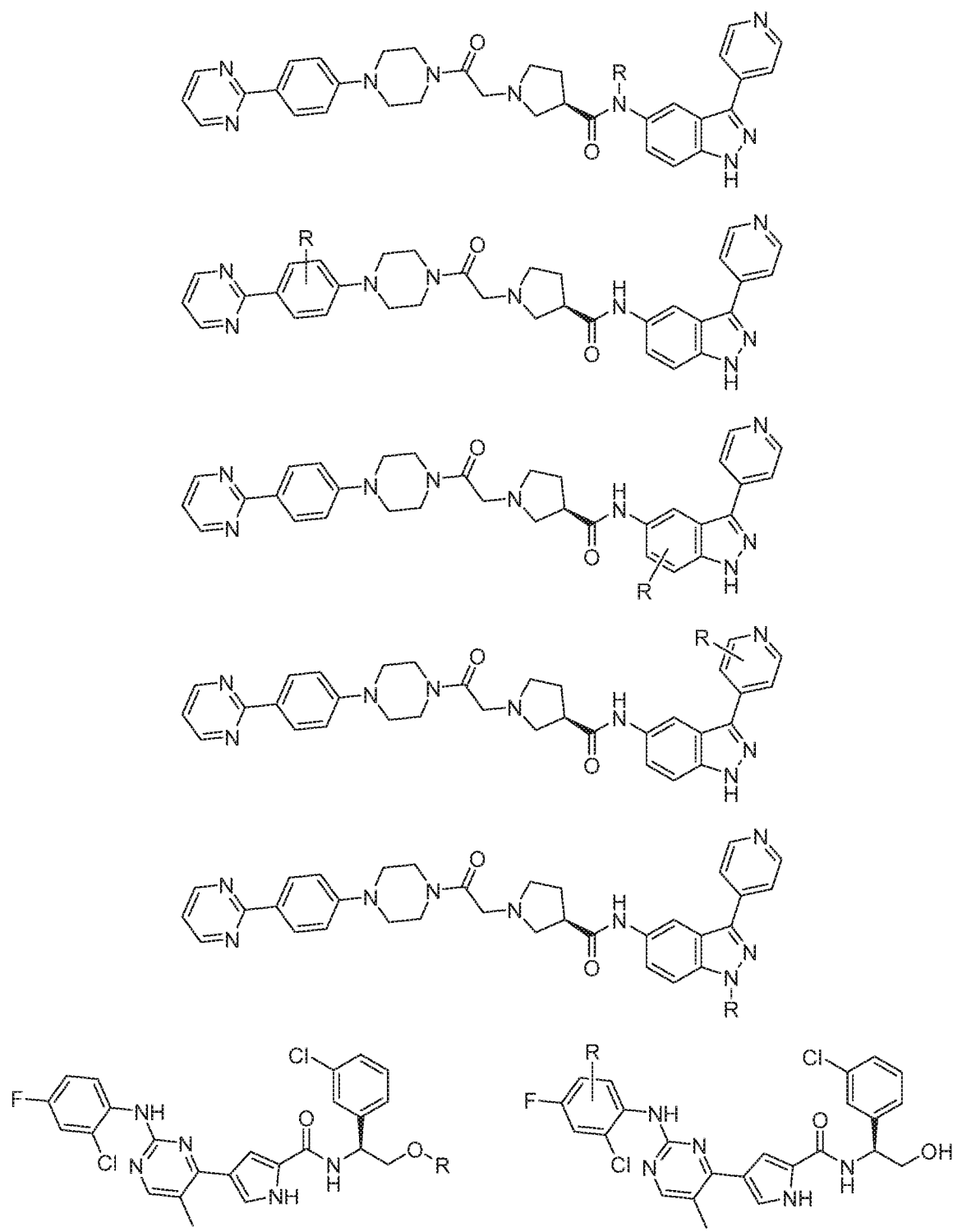
Figure 3W:
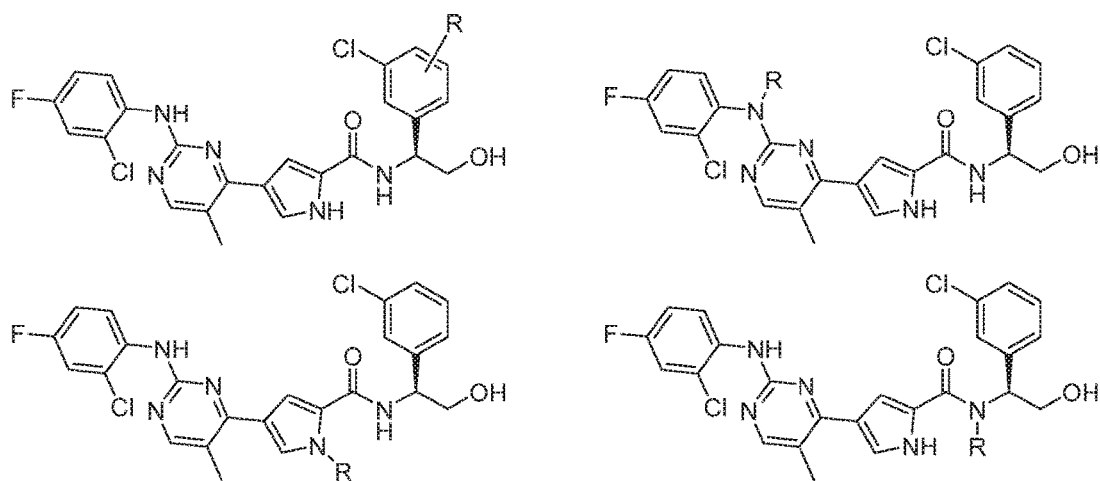
Figure 3X:
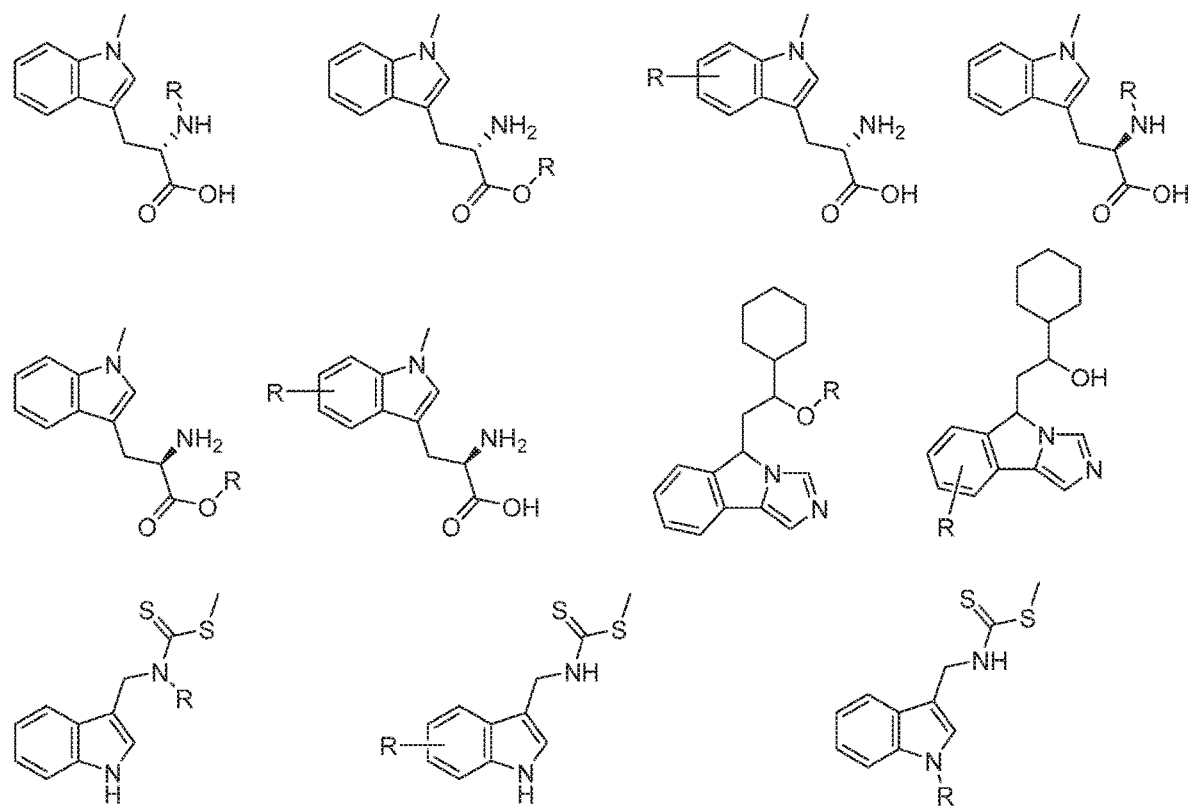
Figure 3Y:
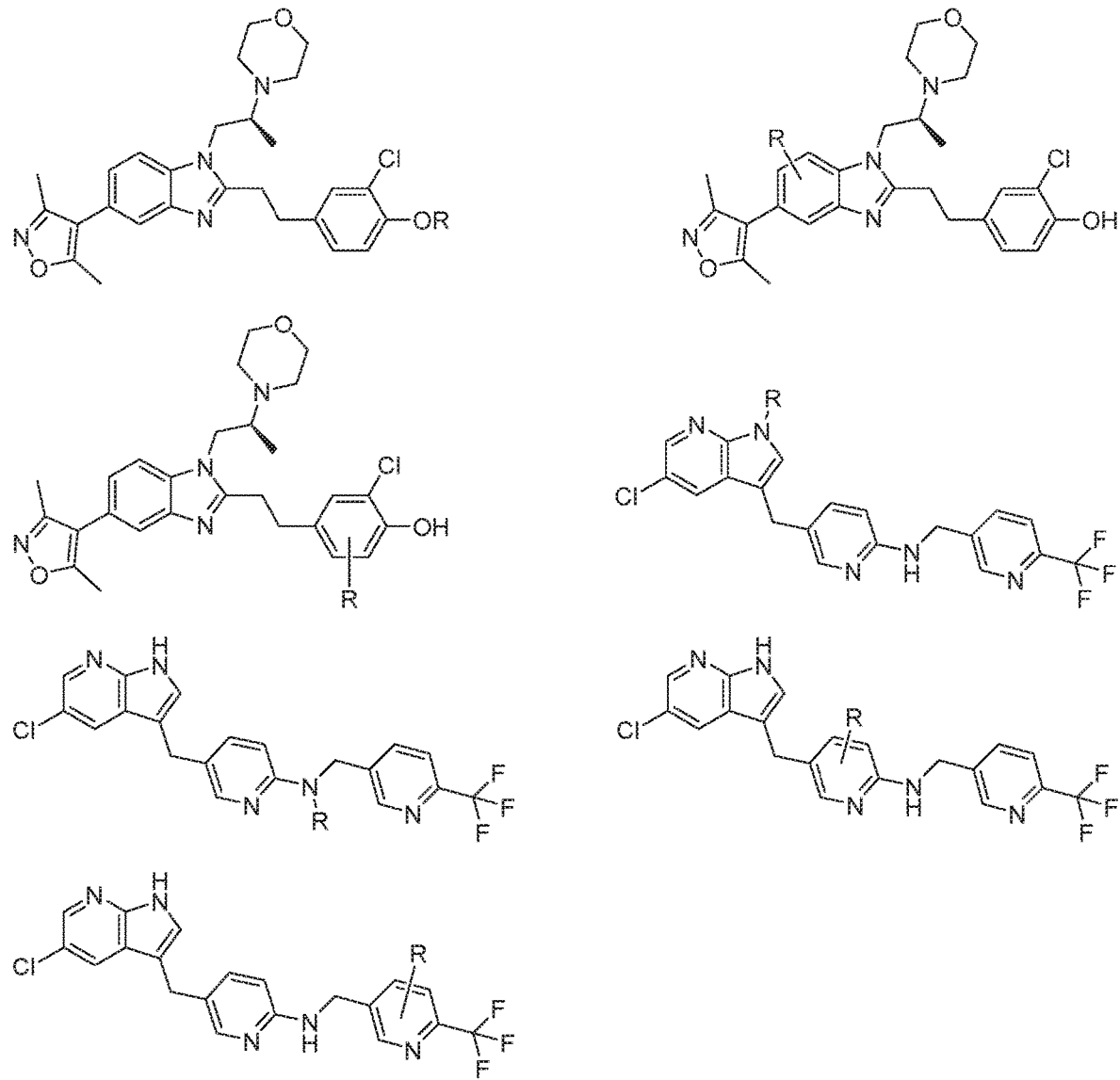
Figure 3Z:
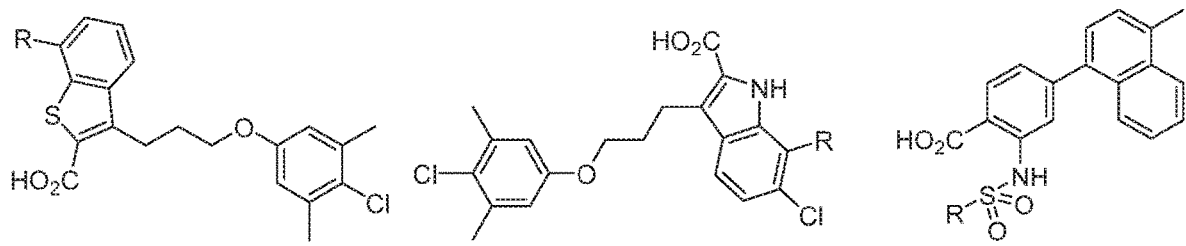
Figure 3A:
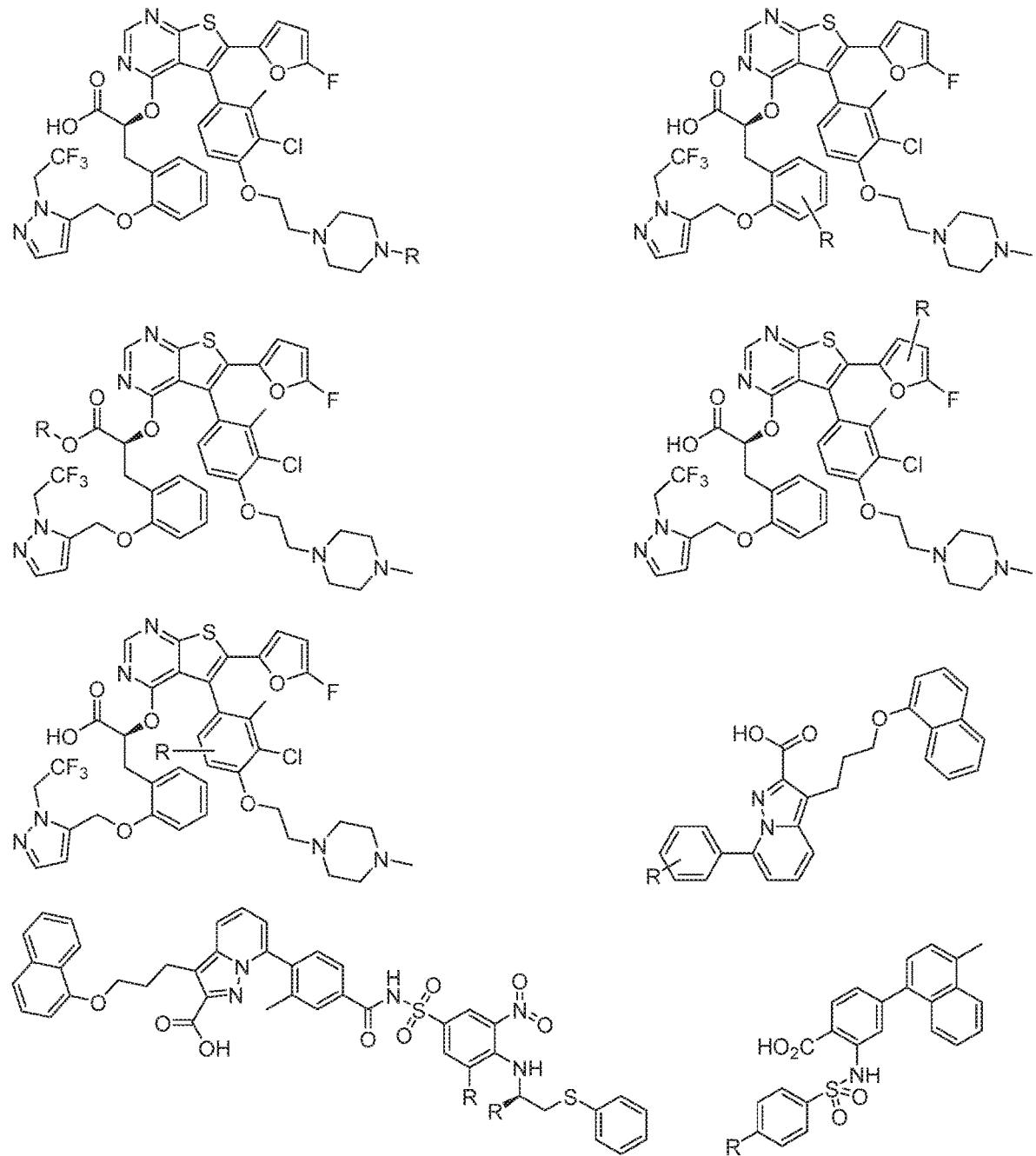
Figure 3B:
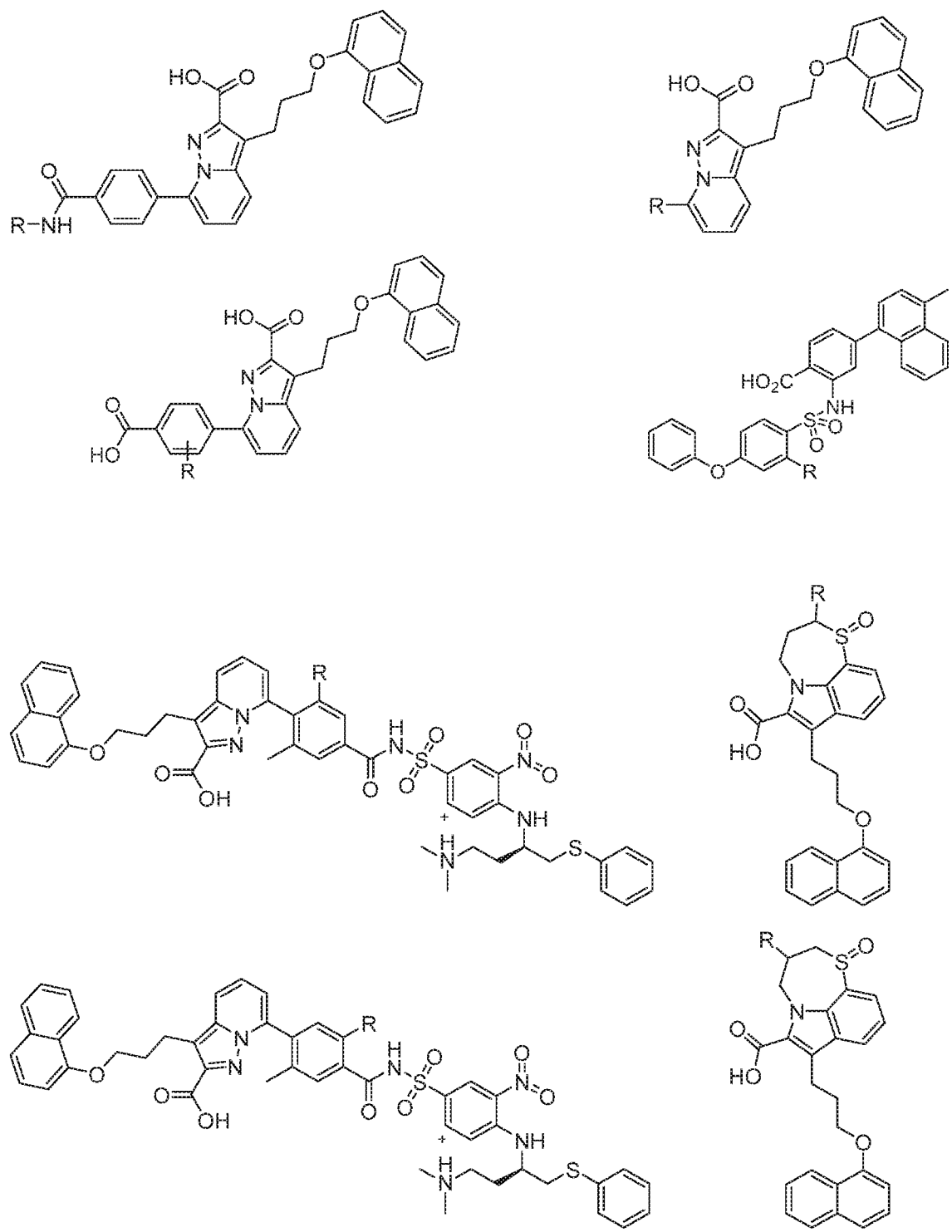
Figure 3D:
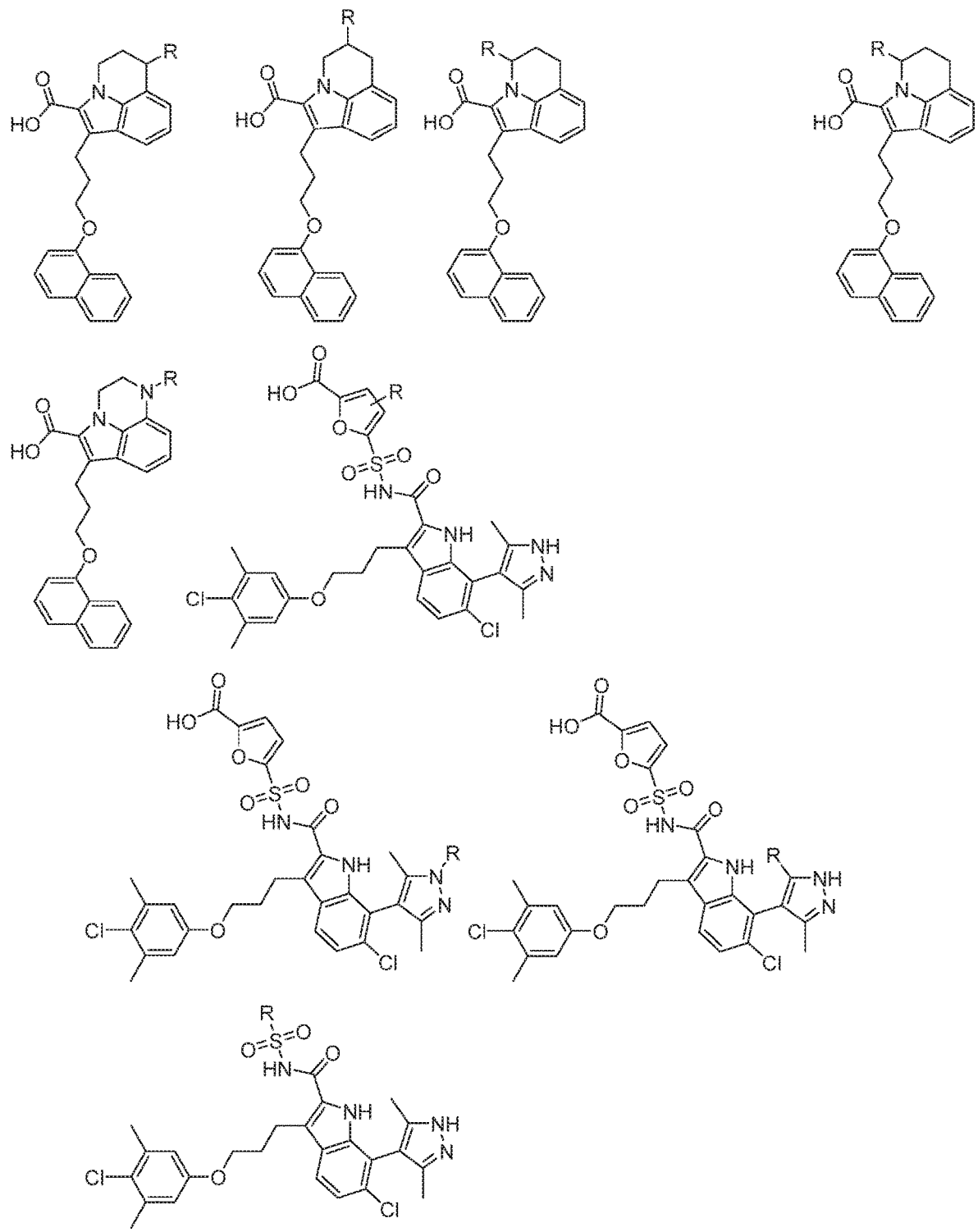
Figure 3E:
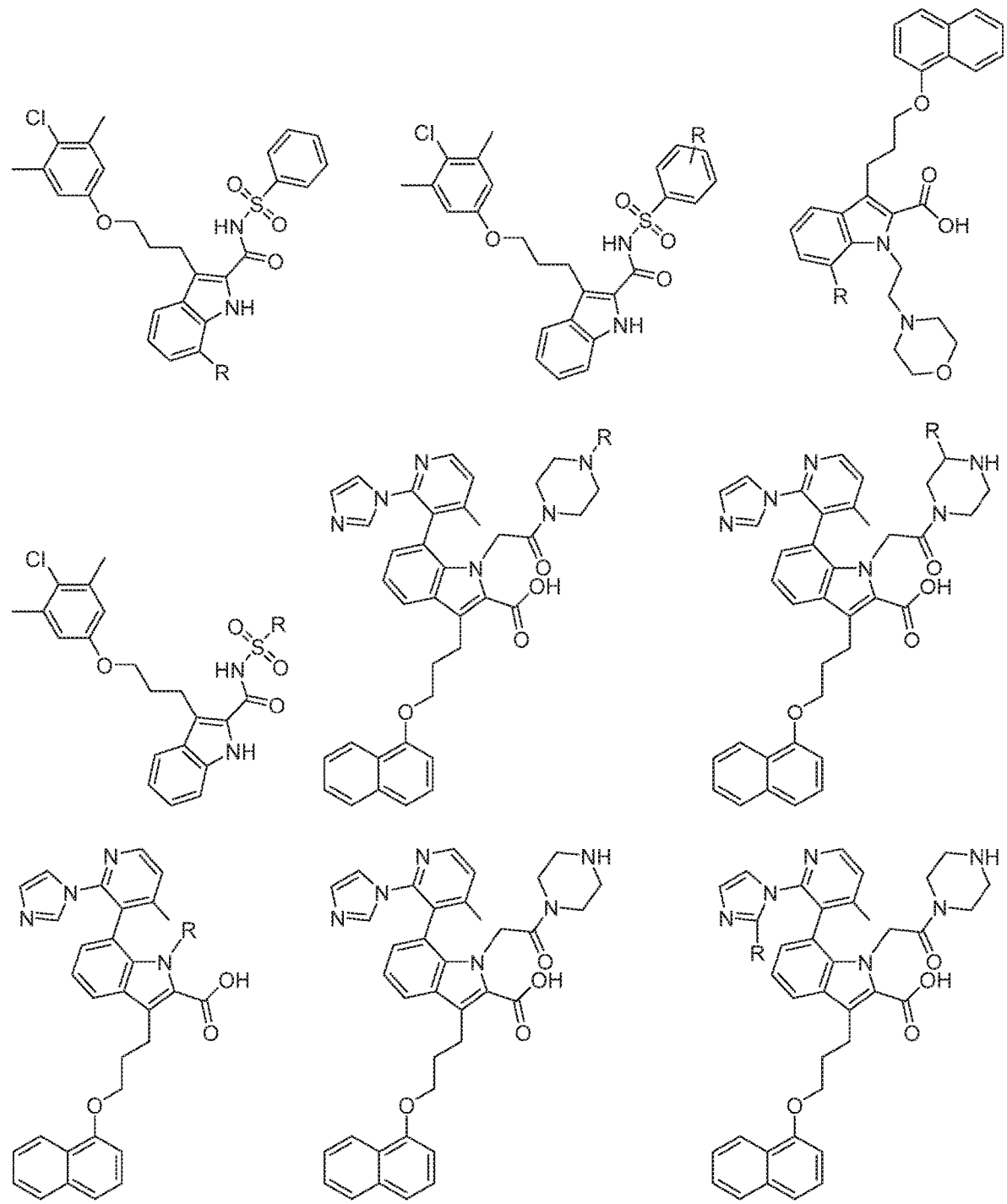
Figure 3H:
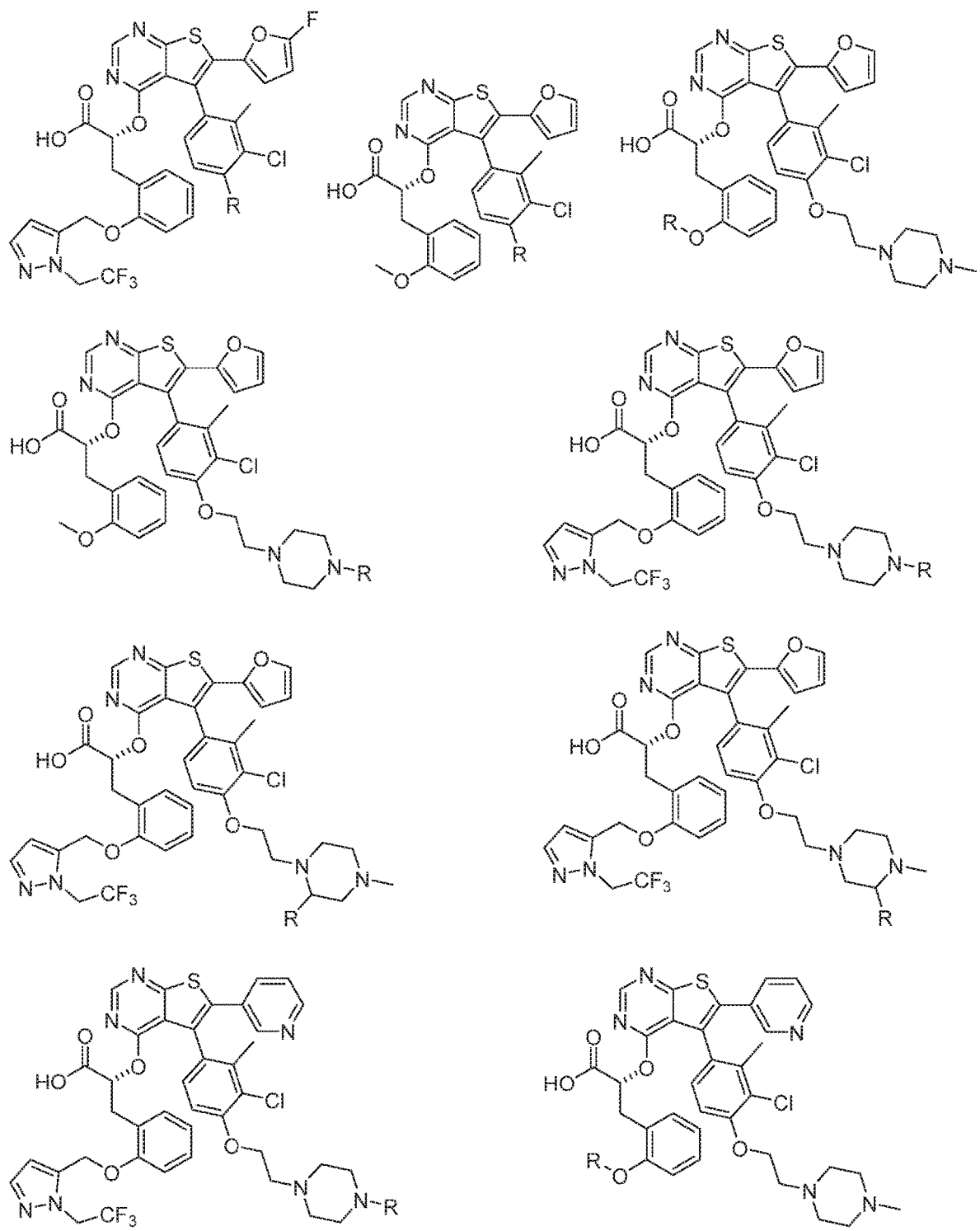

FIG. 3A-3B present examples of MEK1 Targeting Ligands, including PD318088, Trametinib and G-573, wherein R is the point at which the Linker is attached.

FIG. 3C presents examples of KIT Targeting Ligands, including Regorafenib, wherein R is the point at which the Linker is attached.

FIG. 3D-3E present examples of HIV Reverse Transcriptase Targeting Ligands, including Efavirenz, Tenofovir, Emtricitabine, Ritonavir, Raltegravir, and Atazanavir, wherein R is the point at which the Linker is attached.

FIG. 3F-3G present examples of HIV Protease Targeting Ligands, including Ritonavir, Raltegravir, and Atazanavir, wherein R is the point at which the Linker is attached.

Figure 3I:
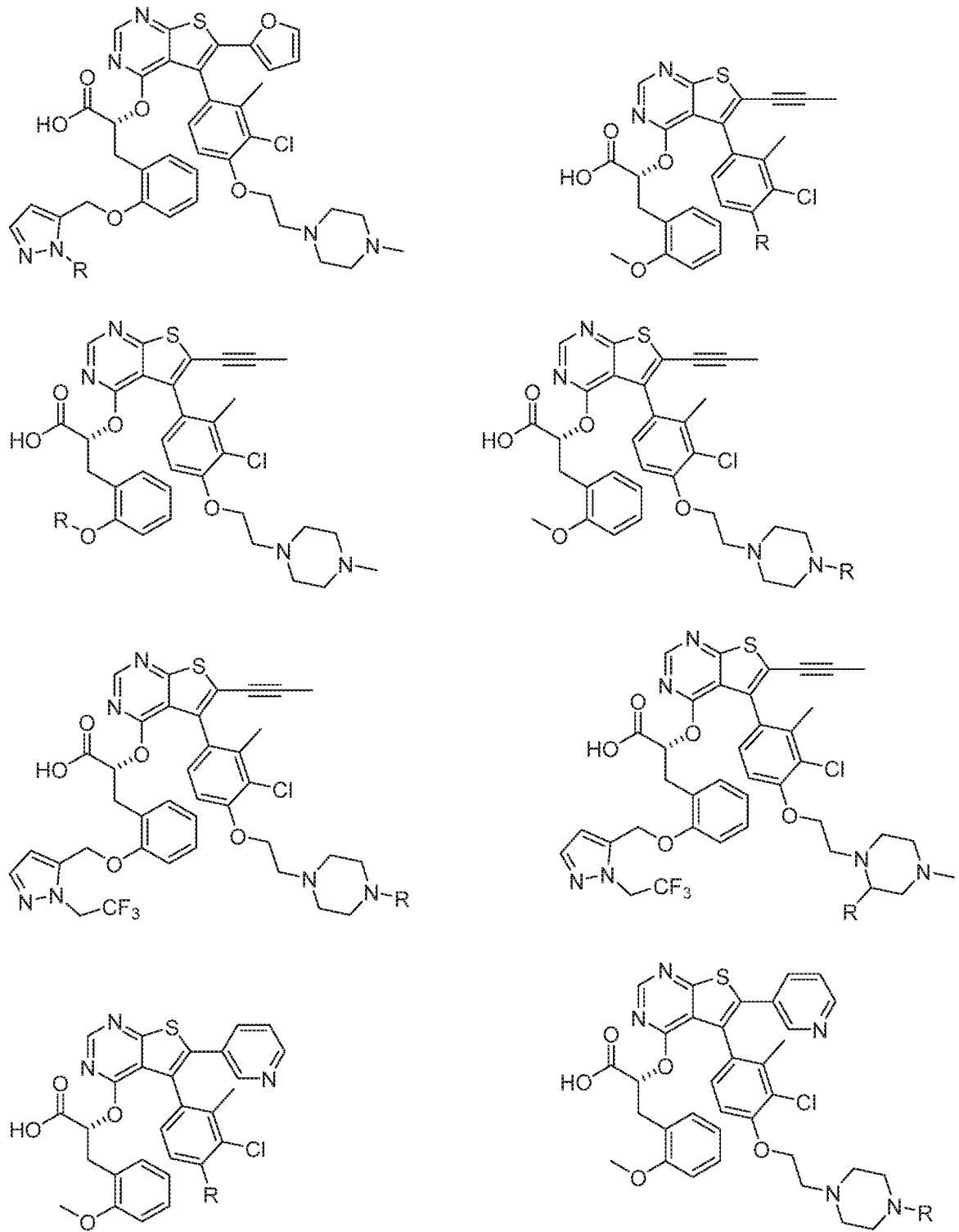
Figure 3L:
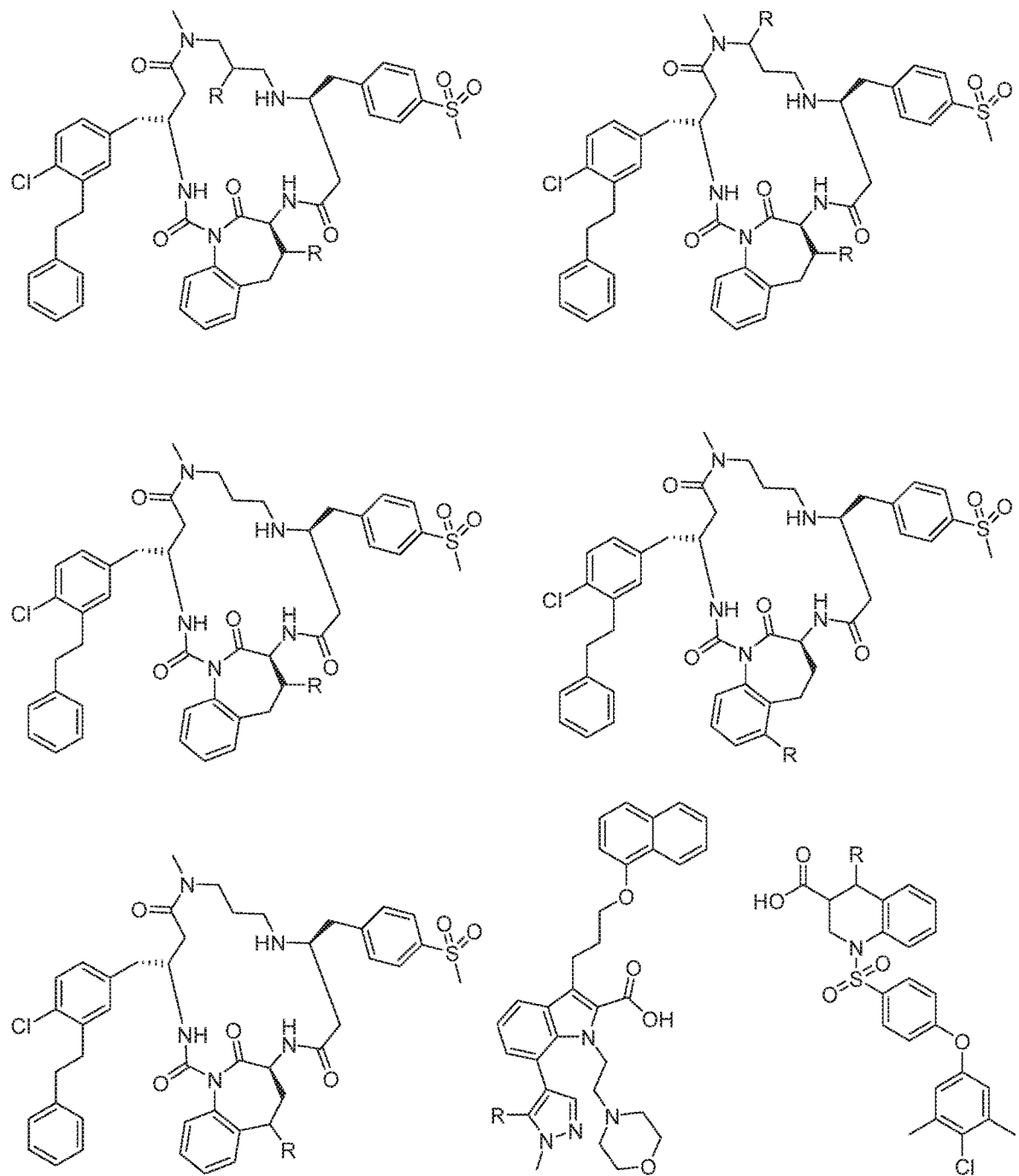
Figure 3M:
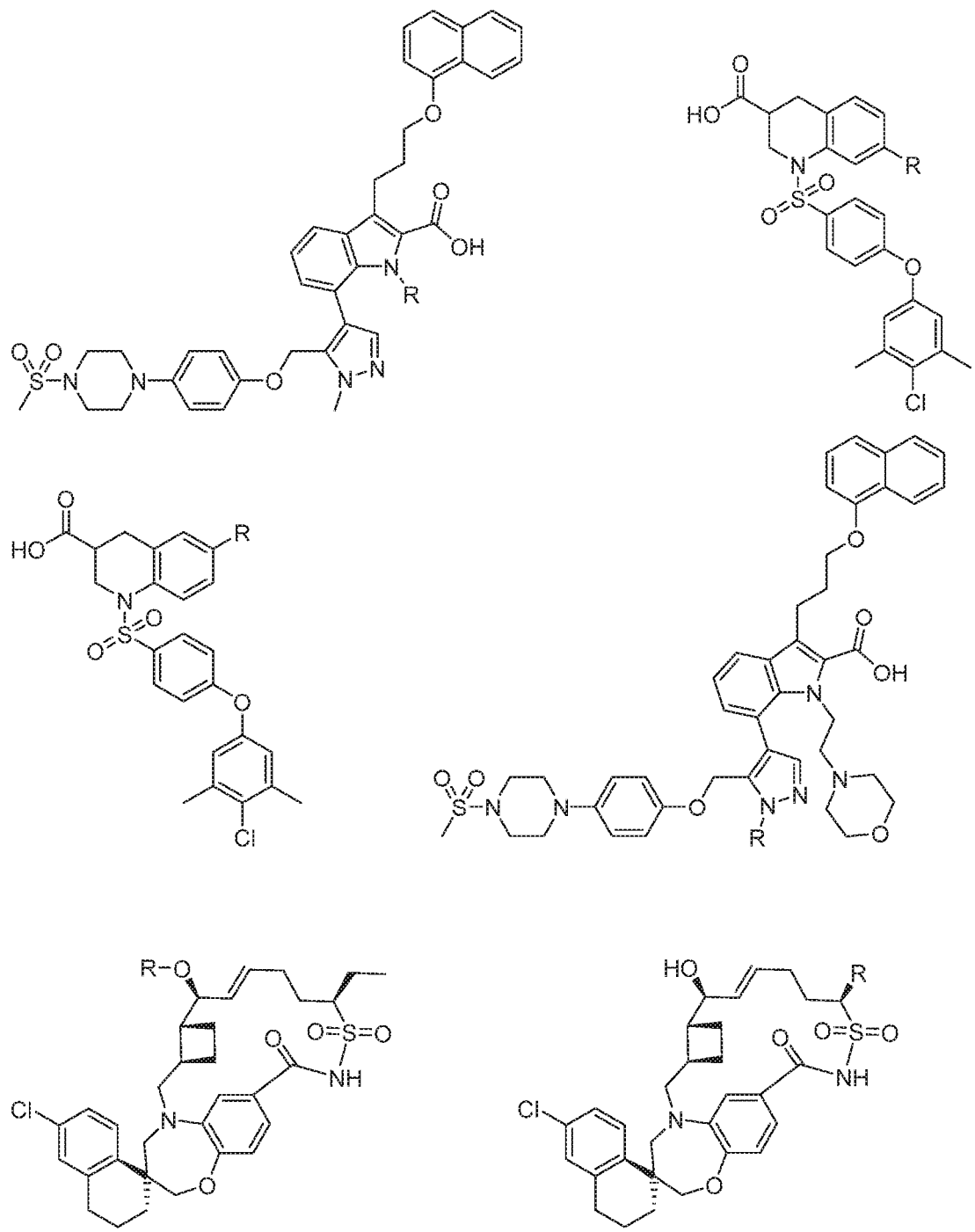
Figure 3O:
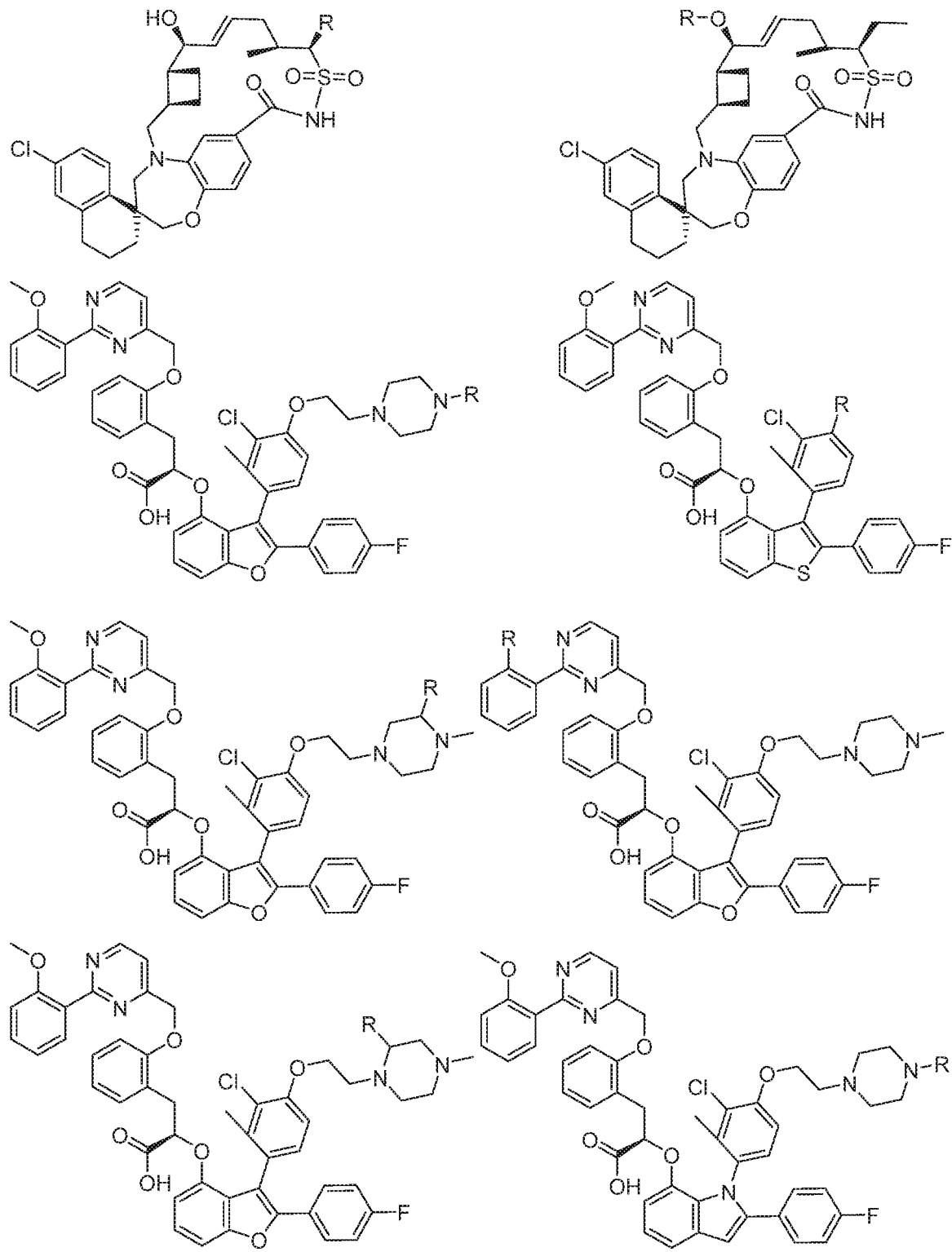
Figure 3P:
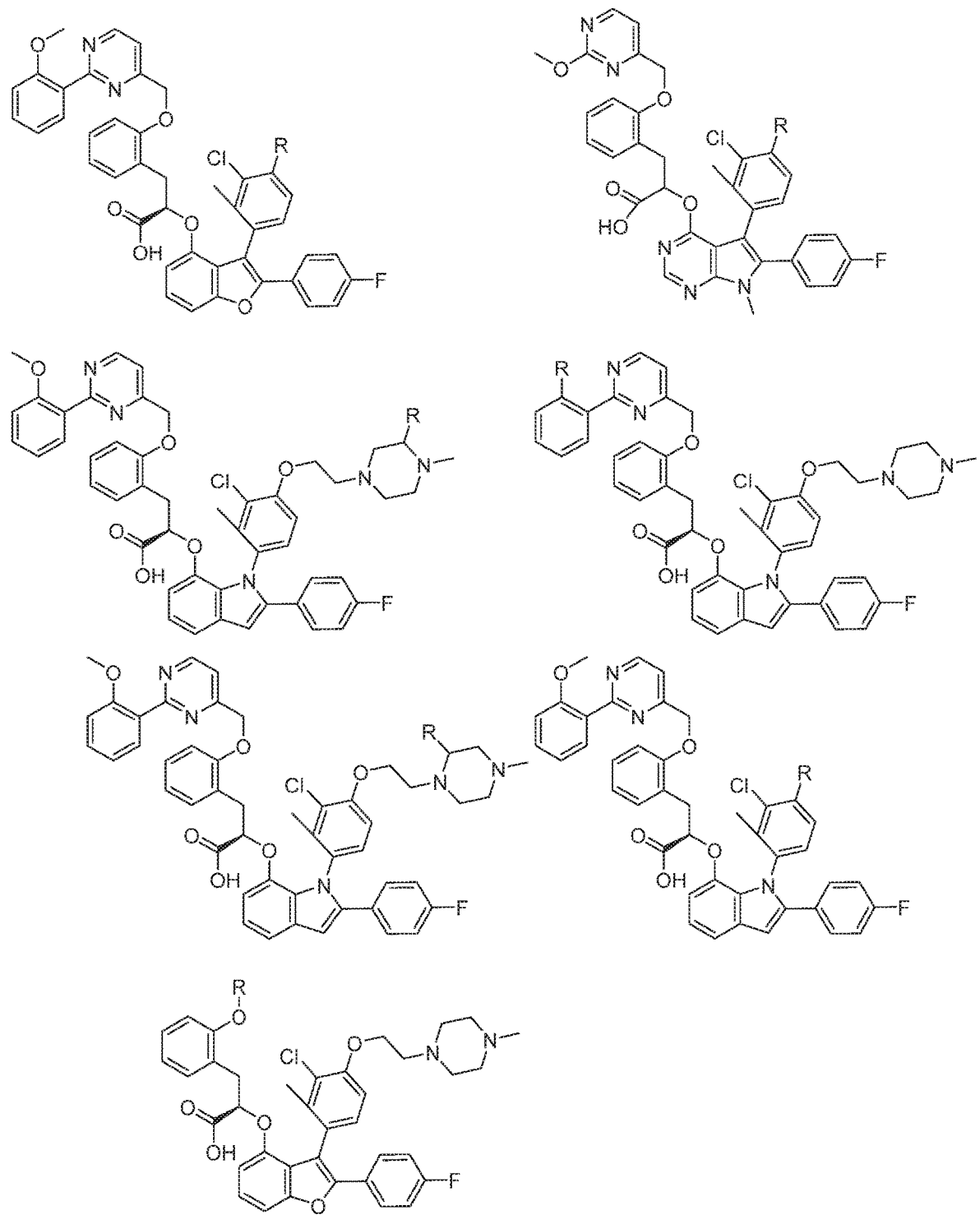
Figure 3Q:
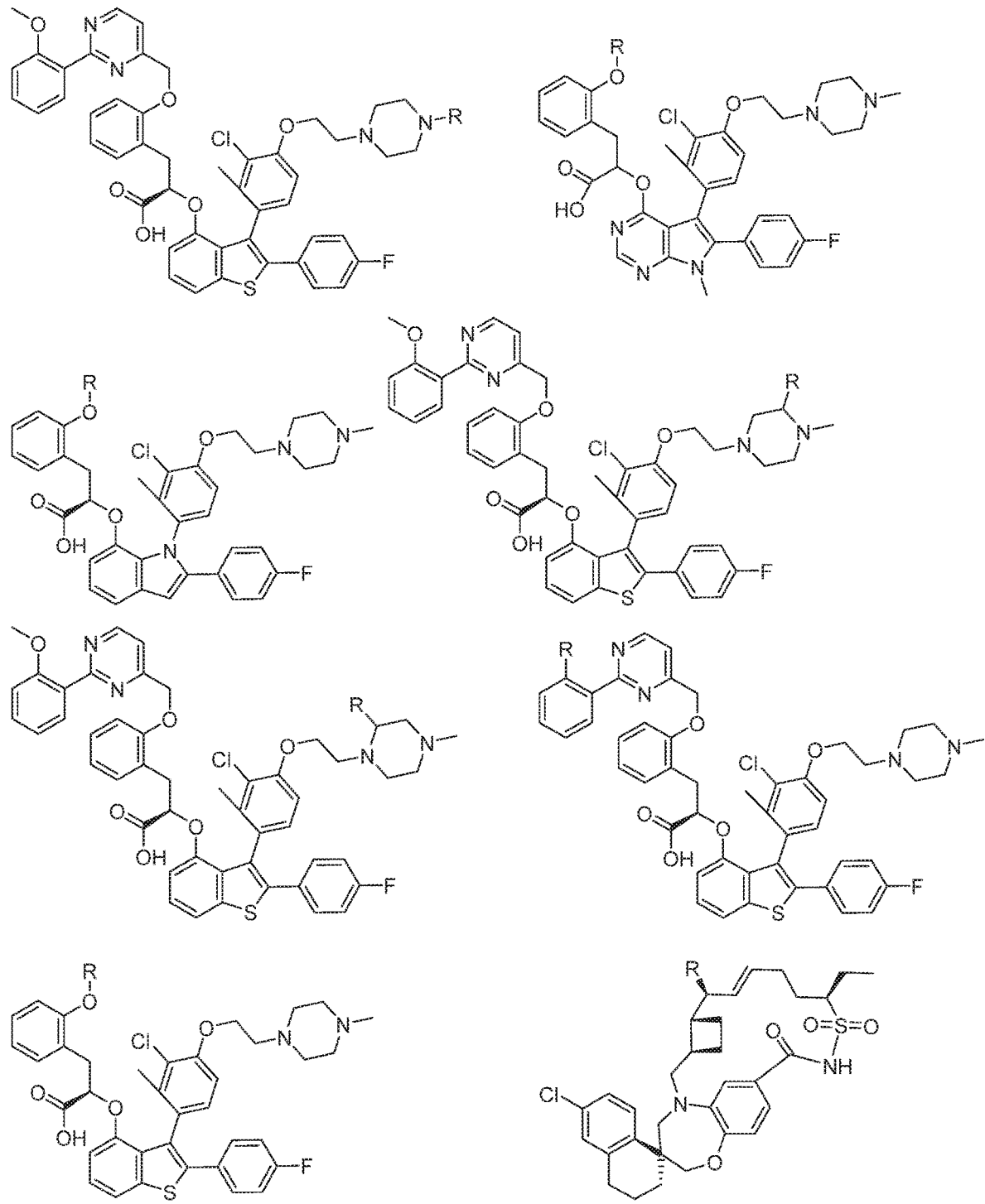
Figure 3R:
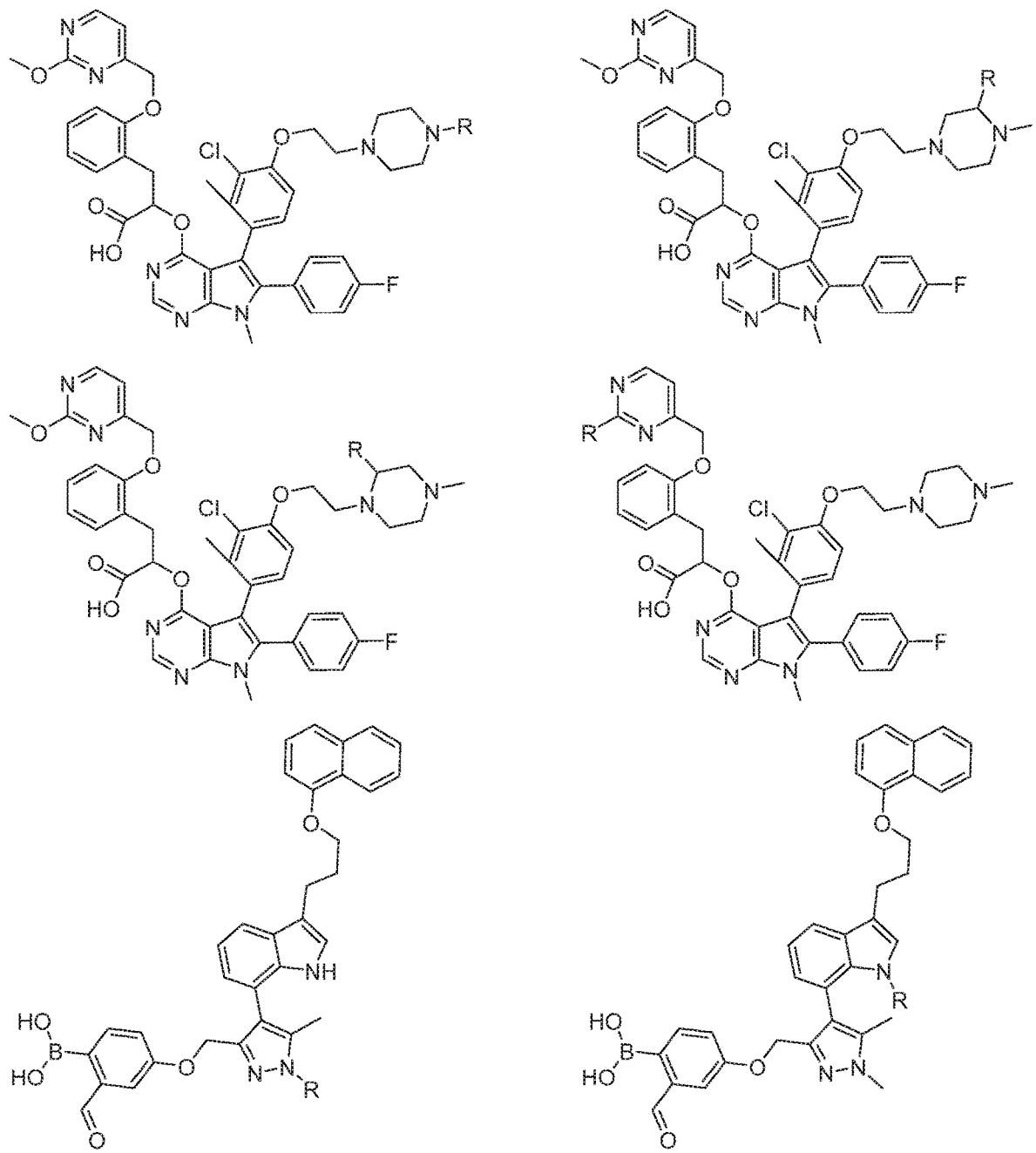
Figure 3S:
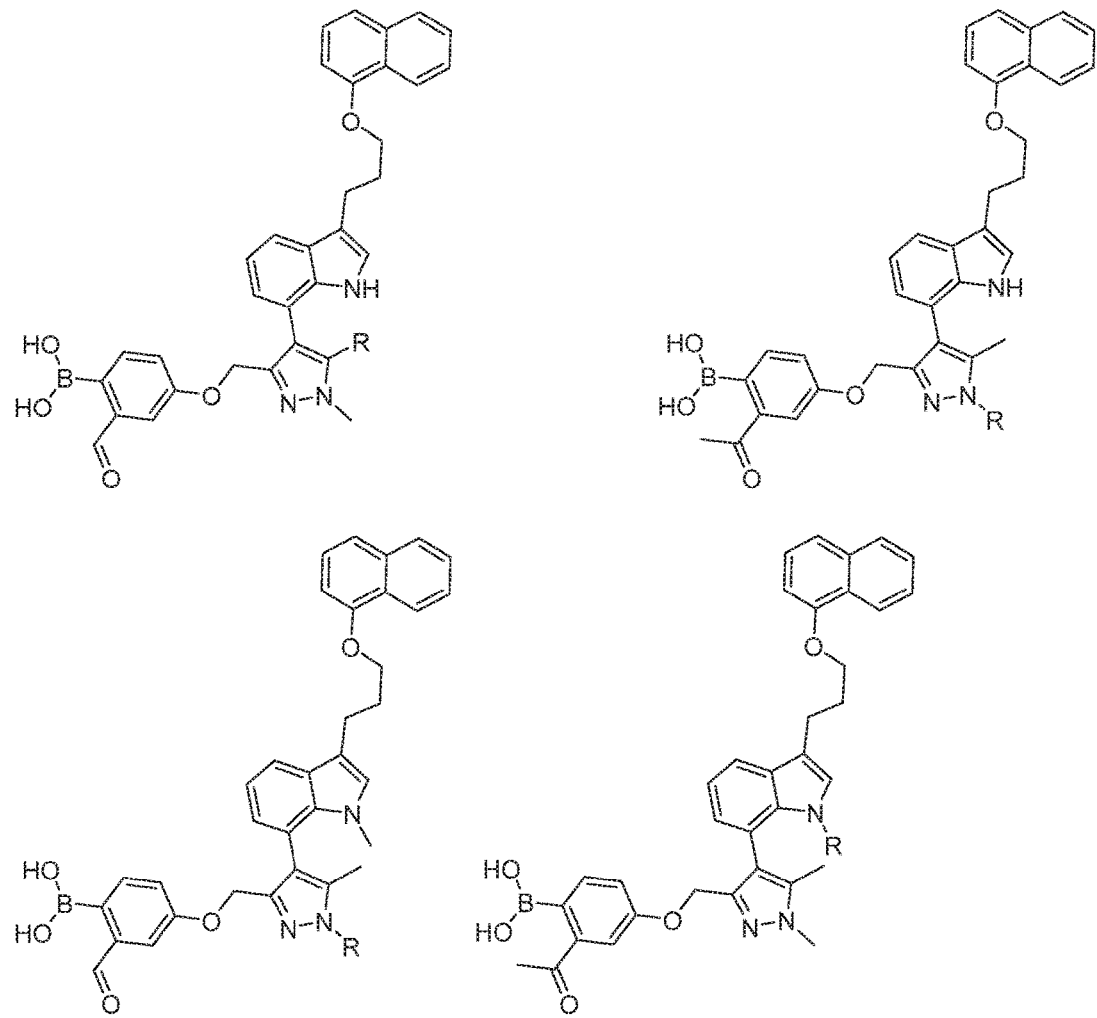
Figure 3T:
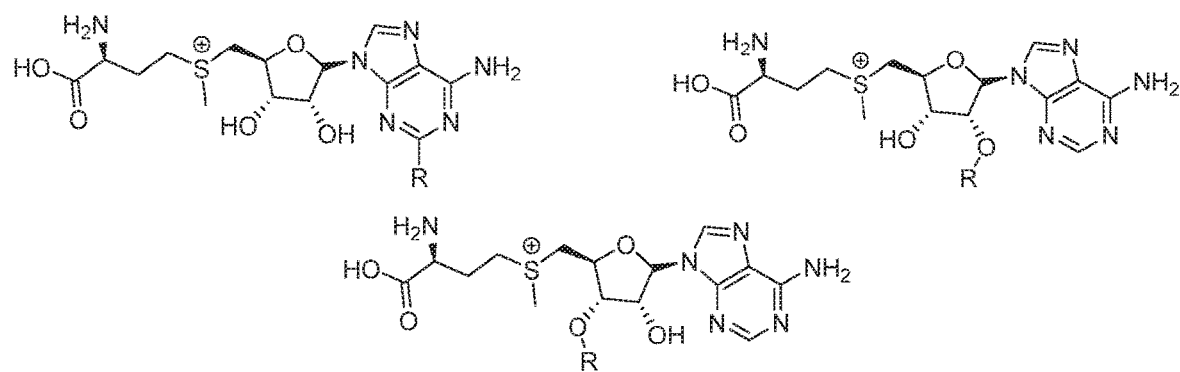
Figure 3U:
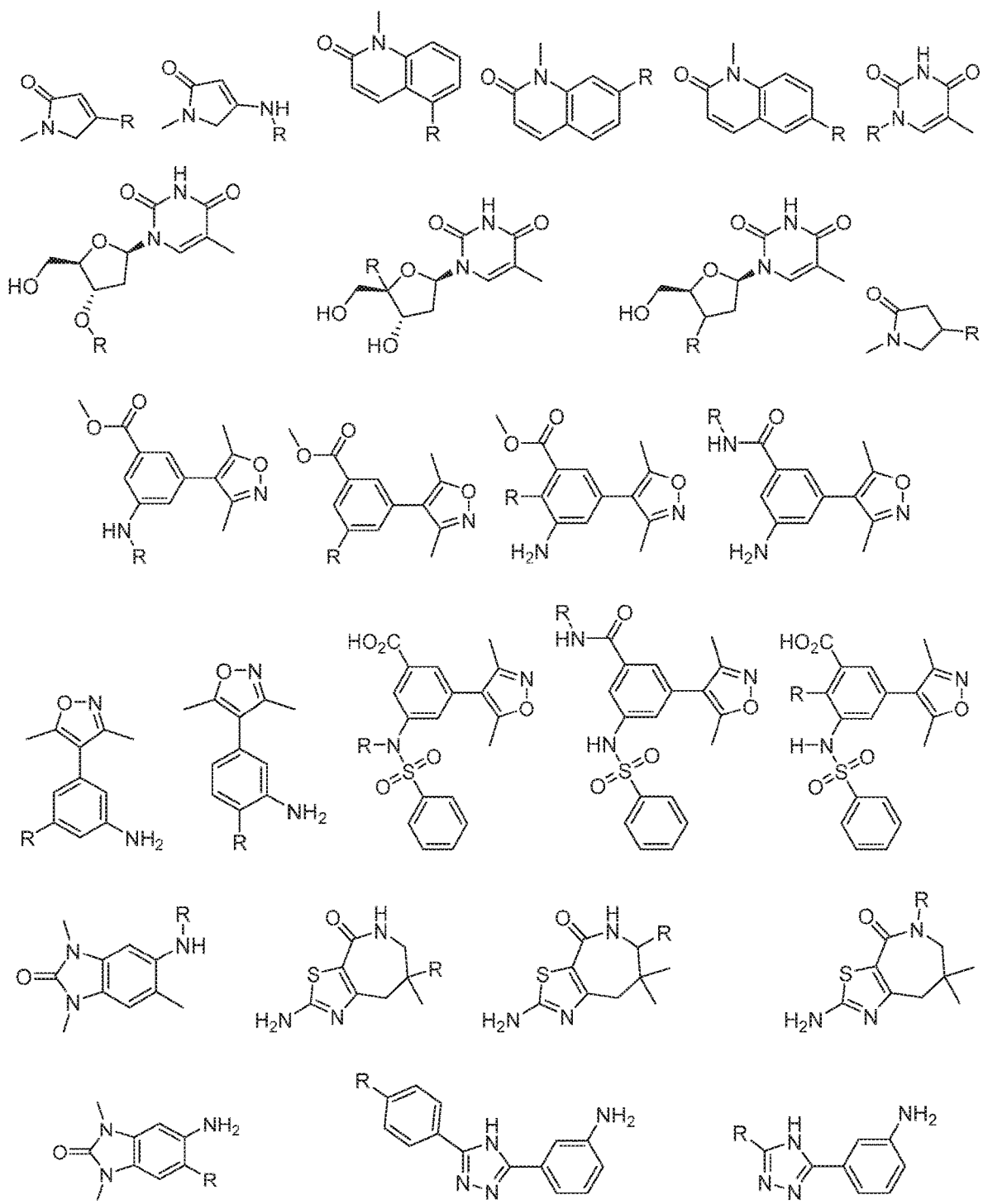
Figure 3V:
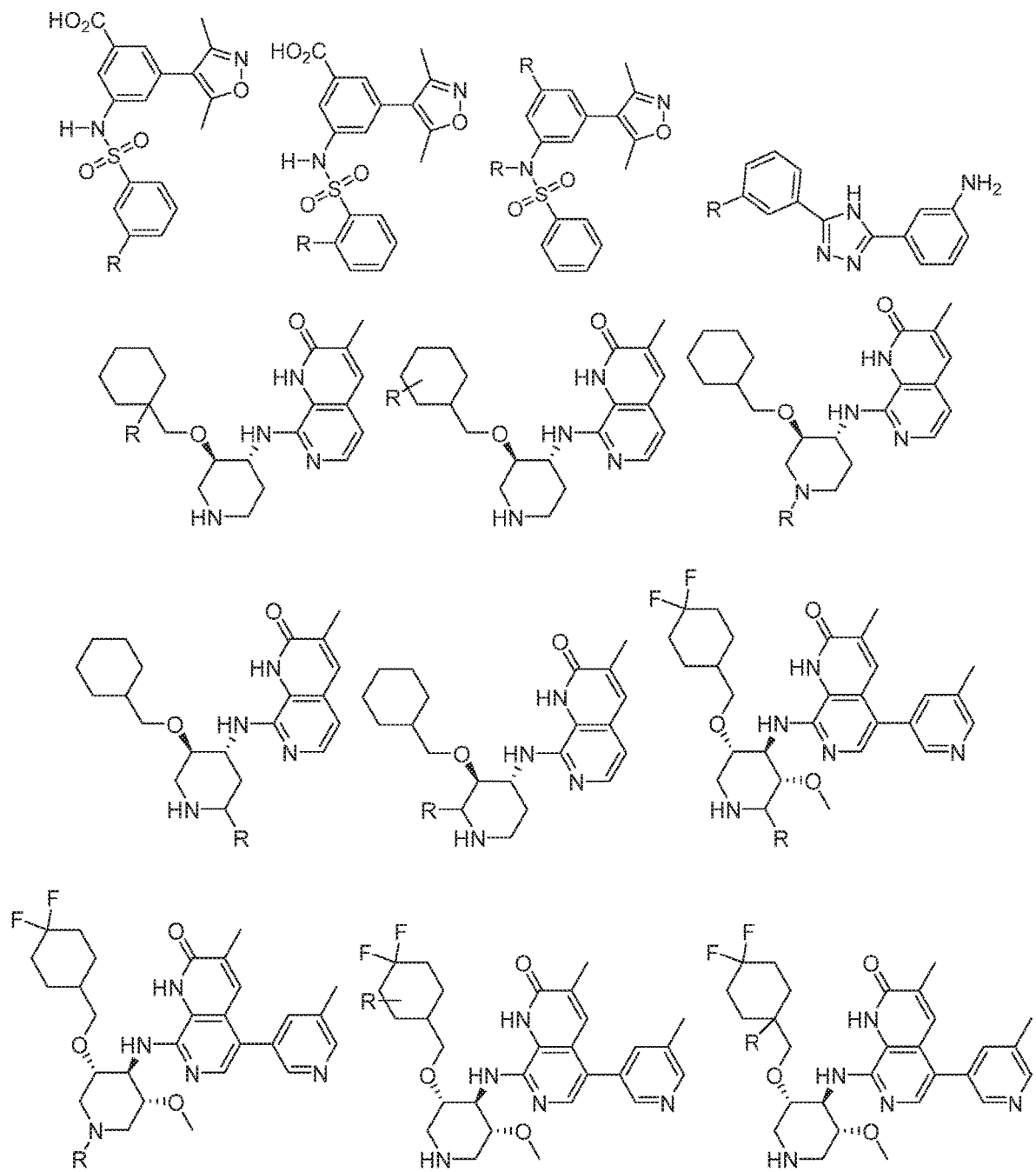
Figure 3W:
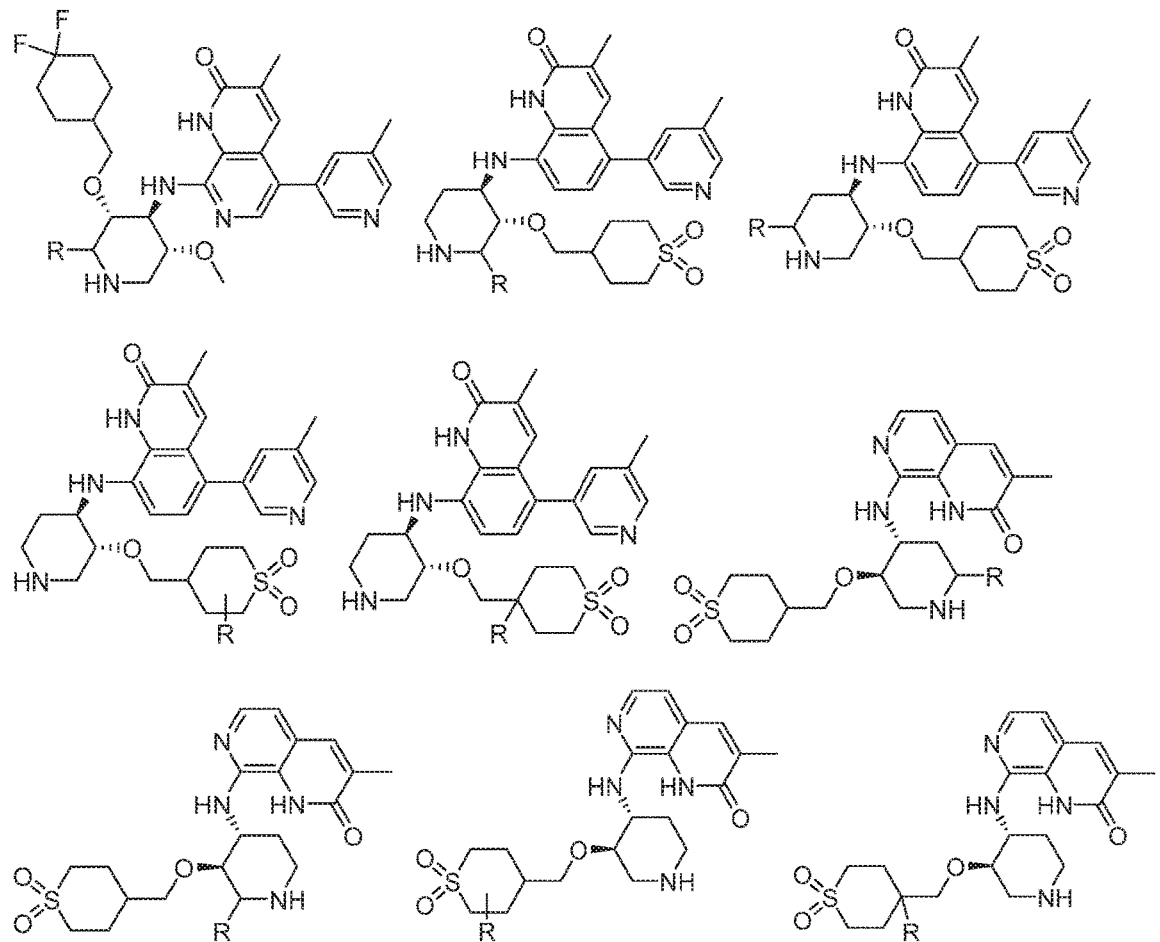
Figure 3X:
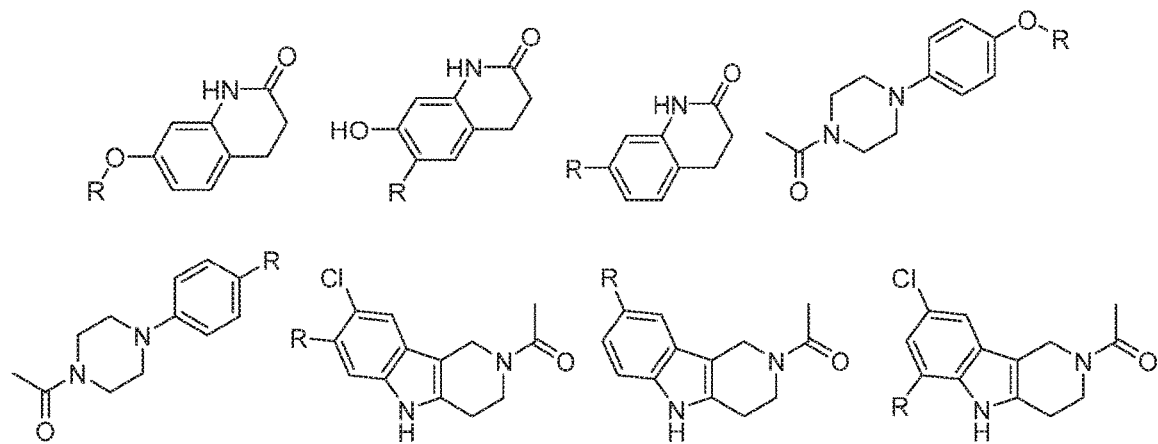
Figure 3Y:
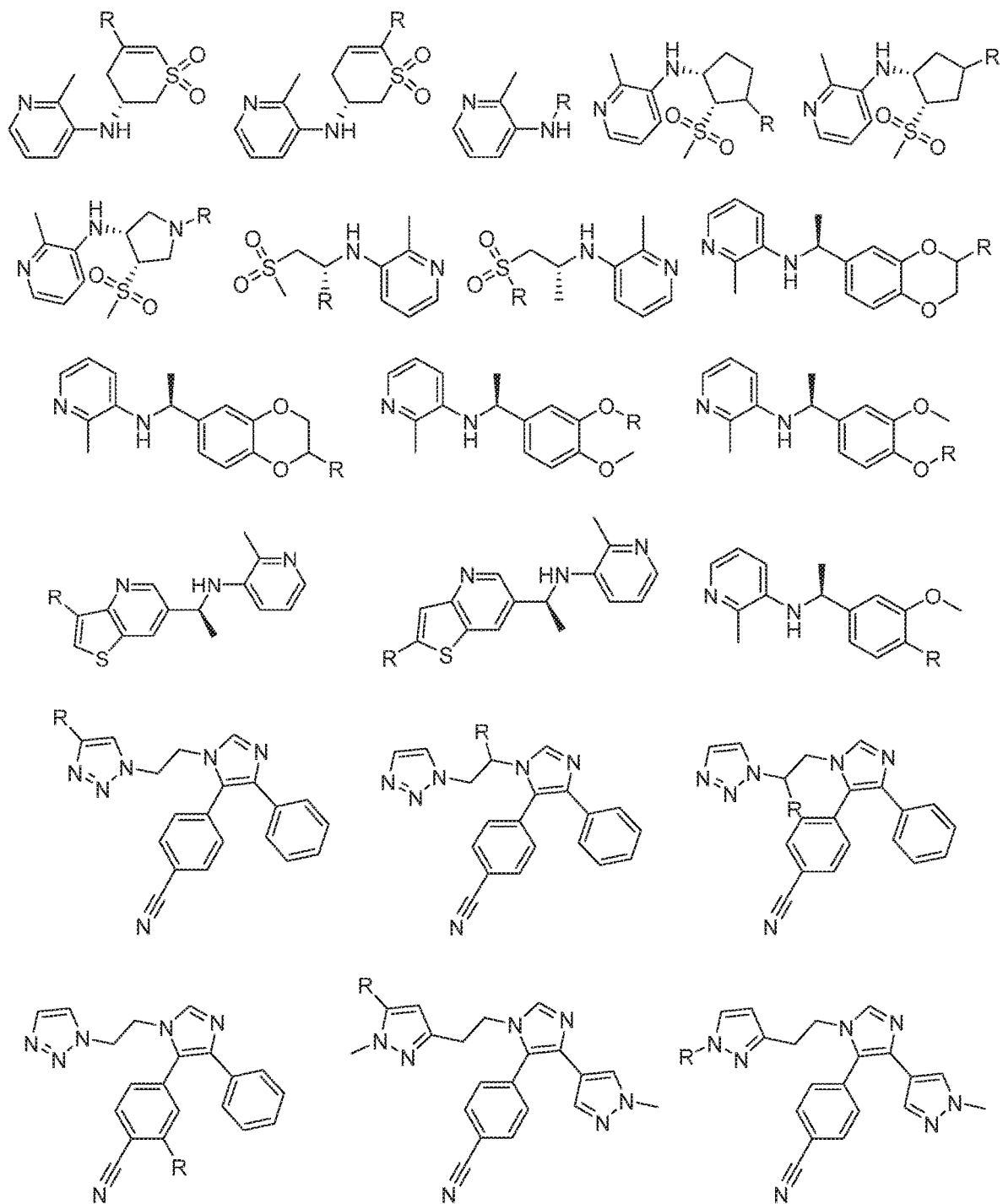
Figure 3Z:
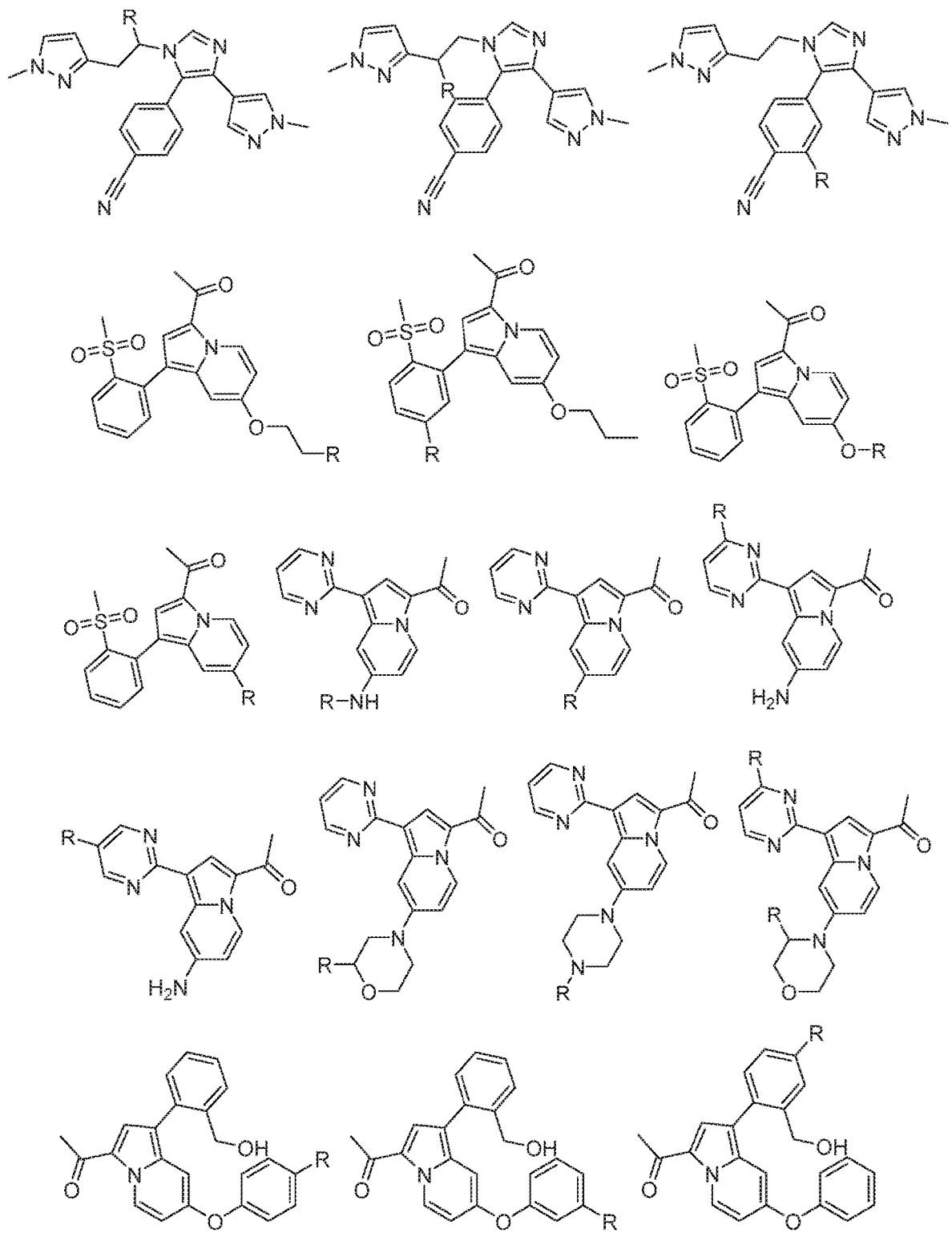

FIG. 3H-3I present examples of KSR1 Targeting Ligands wherein R is the point at which the Linker is attached.

FIG. 3J-3L present examples of CNNTB1 Targeting Ligands wherein R is the point at which the Linker is attached.

FIG. 3M presents examples of BCL6 Targeting Ligands wherein R is the point at which the Linker is attached.

FIG. 3N-3O present examples of PAK1 Targeting Ligands wherein R is the point at which the Linker is attached.

FIG. 3P-3R present examples of PAK4 Targeting Ligands wherein R is the point at which the Linker is attached.

FIG. 3S-3T present examples of TNIK Targeting Ligands wherein R is the point at which the Linker is attached.

FIG. 3U presents examples of MEN1 Targeting Ligands wherein R is the point at which the Linker is attached.

FIG. 3V-3W present examples of ERK1 Targeting Ligands wherein R is the point at which the Linker is attached.

FIG. 3X presents examples of IDO1 Targeting Ligands wherein R is the point at which the Linker is attached.

FIG. 3Y presents examples of CBP Targeting Ligands wherein R is the point at which the Linker is attached.

FIG. 3Z-3SS present examples of MCL1 Targeting Ligands wherein R is the point at which the Linker is attached. For additional examples and related ligands, see, Tanaka Y. et al "Discovery of potent Mcl-1/Bcl-xL dual inhibitors by using a hybridization strategy based on structural analysis of target proteins." J. Med. Chem. 56: 9635-9645 (2013); Friberg A. et al. "Discovery of potent myeloid cell leukemia 1 (Mcl-1) inhibitors using fragment-based methods and structure-based design." J. Med. Chem. 56: 15-30 (2013); Petros A. M. et al "Fragment-based discovery of potent inhibitors of the anti-apoptotic MCL-1 protein." Bioorg. Med. Chem. Lett. 24: 1484-1488 (2014); Burke J. P. et al. "Discovery of tricyclic indoles that potently inhibit mcl-1 using fragment-based methods and structure-based design." J. Med. Chem. 58: 3794-3805 (2015); Pelz N. F. et al. "Discovery of 2-Indole-acylsulfonamide Myeloid Cell Leukemia 1 (Mcl-1) Inhibitors Using Fragment-Based Methods." J. Med. Chem. 59: 2054-2066 (2016); Clifton M. C. et al. "A Maltose-Binding Protein Fusion Construct Yields a Robust Crystallography Platform for MCL1." Plos

*One* 10: e0125010-e0125010 (2015); Kotschy A et al. "The MCL1 inhibitor S63845 is tolerable and effective in diverse cancer models. *Nature* 538:477-482 (2016); EP 2886545 A1 titled "New thienopyrimidine derivatives a process for their preparation and pharmaceutical compositions containing them"; Jeffrey W. Johannes et al. "Structure Based Design of Non-Natural Peptidic Macrocyclic Mcl-1 Inhibitors" *ACS Med. Chem. Lett.* (2017); DOI: 10.1021/acsmedchemlett.6b00464; Bruncko M. et al. "Structure-Guided Design of a Series of MCL-1 Inhibitors with High Affinity and Selectivity." *J. Med. Chem.* 58: 2180-2194 (2015); Taekyu Lee et al. "Discovery and biological characterization of potent myeloid cell leukemia-1 inhibitors." *FEBS Letters* 591: 240-251 (2017); Chen L. et al. "Structure-Based Design of 3-Carboxy-Substituted 1 2 3 4-Tetrahydroquinolines as Inhibitors of Myeloid Cell Leukemia-1 (Mcl-1)." *Org. Biomol. Chem.* 14:5505-5510 (2016); US 2016/0068545 titled "Tetrahydronaphthalene derivatives that inhibit mcl-1 protein"; WO 2016207217 A1 titled "Preparation of new bicyclic derivatives as pro-apoptotic agents"; Gizem Akgay et al. "Inhibition of Mcl-1 through covalent modification of a noncatalytic lysine side chain" *Nature Chemical Biology* 12: 931-936 (2016).

FIG. 3TT presents examples of ASH1L Targeting Ligands wherein R is the point at which the Linker is attached. See for example, the crystal structure PDB 4YNM ("Human ASH1L SET domain in complex with S-adenosyl methionine (SAM)" Rogawski D. S. et al.) FIG. 3UU-3WW present examples of ATAD2 Targeting Ligands wherein R is the point at which the Linker is attached. For additional examples and related ligands, see, Chaikuad A. et al. "Structure-based approaches towards identification of fragments for the low-druggability ATAD2 bromodomain" *Med Chem Comm* 5: 1843-1848 (2014); Poncet-Montange G. et al. "Observed bromodomain flexibility reveals histone peptide- and small molecule ligand-compatible forms of ATAD2." *Biochem. J.* 466: 337-346 (2015); Harner M. J. et al. "Fragment-Based Screening of the Bromodomain of ATAD2." *J. Med. Chem.* 57: 9687-9692 (2014); Demont E. H. et al. "*Fragment-Based Discovery of Low-Micromolar Atad2 Bromodomain Inhibitors.*" *J. Med. Chem.* 58: 5649 (2015); and, Bamborough P. et al. "Structure-Based Optimization of Naphthyridones into Potent Atad2 Bromodomain Inhibitors." *J. Med. Chem.* 58: 6151 (2015).

FIG. 3XX-3AAA present examples of BAZ2A and BAZ2B Targeting Ligands wherein R is the point at which the Linker is attached. For additional examples and related ligands, see, the crystal structure PDB 4CUU ("Human Baz2B in Complex with Fragment-6 N09645" Bradley A. et al.); the crystal structure PDB 5CUA ("Second Bromodomain of Bromodomain Adjacent to Zinc Finger Domain Protein 2B (BAZ2B) in complex with 1-Acetyl-4-(4-hydroxyphenyl)piperazine". Bradley A. et al.); Ferguson F. M. et al. "Targeting low-druggability bromodomains: fragment based screening and inhibitor design against the BAZ2B bromodomain." *J. Med. Chem.* 56: 10183-10187 (2013); Marchand J. R. et al. "Derivatives of 3-Amino-2-methylpyridine as BAZ2B Bromodomain Ligands: In Silico Discovery and in Crystallo Validation." *J. Med. Chem.* 59: 9919-9927 (2016); Drouin L. et al. "Structure Enabled Design of BAZ2-ICR A Chemical Probe Targeting the Bromodomains of BAZ2A and BAZ2B." *J. Med. Chem.* 58: 2553-2559 (2015); Chen P. et al. "Discovery and characterization of GSK2801 a selective chemical probe for the bromodomains BAZ2A and BAZ2B." *J. Med. Chem.* 59:1410-1424 (2016).

FIG. 3BBB presents examples of BRD1 Targeting Ligands wherein R is the point at which the Linker is attached. For additional examples and related ligands, see, the crystal structure PDB SAME ("the Crystal Structure of the Bromodomain of Human Surface Epitope Engineered Brd1A in Complex with 3D Consortium Fragment 4-Acetyl-Piperazin-2-One Pearce", N. M. et al.); the crystal structure PDB 5AMF ("Crystal Structure of the Bromodomain of Human Surface Epitope Engineered Brd1A in Complex with 3D Consortium Fragment Ethyl 4 5 6 7-Tetrahydro-1H-Indazole-5-Carboxylate", Pearce N. M. et al.); the crystal structure PDB 5FG6 ("the Crystal structure of the bromodomain of human BRD1 (BRPF2) in complex with OF-1 chemical probe.", Tallant C. et al.); Filippakopoulos P. et al. "Histone recognition and large-scale structural analysis of the human bromodomain family." *Cell,* 149: 214-231 (2012).

FIG. 3CCC-3EEE present examples of BRD2 Bromodomain 1 Targeting Ligands wherein R is the point at which the Linker is attached. For additional examples and related ligands, see, the crystal structure PDB 2ydw; the crystal structure PDB 2yek; the crystal structure PDB 4a9h; the crystal structure PDB 4a9f; the crystal structure PDB 4a9i; the crystal structure PDB 4a9m; the crystal structure PDB 4akn; the crystal structure PDB 4alg, and the crystal structure PDB 4uyf.

FIG. 3FFF-3HHH present examples of BRD2 Bromodomain 2 Targeting Ligands wherein R is the point at which the Linker is attached. For additional examples and related ligands, see, the crystal structure PDB 3oni; Filippakopoulos P. et al. "Selective Inhibition of BET Bromodomains." *Nature* 468: 1067-1073 (2010); the crystal structure PDB 4j1p; McLure K. G. et al. "RVX-208: an Inducer of ApoA-I in Humans is a BET Bromodomain Antagonist." *Plos One* 8: e83190-e83190 (2013); Baud M. G. et al. "Chemical biology. A bump-and-hole approach to engineer controlled selectivity of BET bromodomain chemical probes" *Science* 346: 638-641 (2014); Baud M. G. et al. "New Synthetic Routes to Triazolo-benzodiazepine Analogues: Expanding the Scope of the Bump-and-Hole Approach for Selective Bromo and Extra-Terminal (BET) Bromodomain Inhibition" *J. Med. Chem.* 59: 1492-1500 (2016); Gosmini R. et al. "The Discovery of I-Bet726 (Gsk1324726A) a Potent Tetrahydroquinoline Apoa1 Up-Regulator and Selective Bet Bromodomain Inhibitor" *J. Med. Chem.* 57: 8111 (2014); the crystal structure PDB 5EK9 ("Crystal structure of the second bromodomain of human BRD2 in complex with a hydroquinolinone inhibitor", Tallant C. et al); the crystal structure PDB 5BT5; the crystal structure PDB 5dfd; Baud M. G. et al. "New Synthetic Routes to Triazolo-benzodiazepine Analogues: Expanding the Scope of the Bump-and-Hole Approach for Selective Bromo and Extra-Terminal (BET) Bromodomain Inhibition" *J. Med. Chem.* 59: 1492-1500 (2016).

FIG. 3III-3JJJ present examples of BRD4 Bromodomain 1 Targeting Ligands wherein R is the point at which the Linker is attached. For additional examples and related ligands, see, the crystal structure PDB 5WUU and the crystal structure PDB 5F5Z.

FIG. 3KKK-3LLL present examples of BRD4 Bromodomain 2 Targeting Ligands wherein R is the point at which the Linker is attached. For additional examples and related ligands, see, Chung C. W. et al. "Discovery and Characterization of Small Molecule Inhibitors of the Bet Family Bromodomains" *J. Med. Chem.* 54: 3827 (2011) and Ran X. et al. "Structure-Based Design of gamma-Carboline Analogues as Potent and Specific BET Bromodomain Inhibitors" *J. Med. Chem.* 58: 4927-4939 (2015).

FIG. 3MMM presents examples of BRDT Targeting Ligands wherein R is the point at which the Linker is attached. For additional examples and related ligands, see, the crystal structure PDB 4flp and the crystal structure PDB 4kcx.

FIG. 3NNN-3QQQ present examples of BRD9 Targeting Ligands wherein R is the point at which the Linker is attached. For additional examples and related ligands, see, the crystal structure PDB 4nqn; the crystal structure PDB 4uit; the crystal structure PDB 4uiu; the crystal structure PDB 4uiv; the crystal structure PDB 4z6h; the crystal structure PDB 4z6i; the crystal structure PDB 5e9v; the crystal structure PDB 5eul; the crystal structure PDB 5flh; and, the crystal structure PDB 5fp2.

FIG. 3RRR presents examples of SMARCA4 PB1 and/or SMARCA2 Targeting Ligands wherein R is the point at which the Linker is attached, A is N or CH, and m is 0 1 2 3 4 5 6 7 or 8.

FIG. 3SSS-3XXX present examples of additional Bromodomain Targeting Ligands wherein R is the point at which the Linker is attached. For additional examples and related ligands, see, Hewings et al. "3 5-Dimethylisoxazoles Act as Acetyl-lysine Bromodomain Ligands." *J. Med. Chem.* 54 6761-6770 (2011); Dawson et al. "Inhibition of BET Recruitment to Chromatin as an Effective Treatment for MLL-fusion Leukemia." *Nature*, 478, 529-533 (2011); US 2015/0256700; US 2015/0148342; WO 2015/074064; WO 2015/067770; WO 2015/022332; WO 2015/015318; and, WO 2015/011084.

FIG. 3YYY presents examples of PB1 Targeting Ligands wherein R is the point at which the Linker is attached. For additional examples and related ligands, see, the crystal structure PDB 3mb4; the crystal structure PDB 4q0n; and, the crystal structure PDB 5fh6.

FIG. 3ZZZ presents examples of SMARCA4 Targeting Ligands wherein R is the point at which the Linker is attached. For additional examples and related ligands, see, the crystal structure 3uvd and the crystal structure 5dkd.

FIG. 3AAAA presents examples of SMARCA2 Targeting Ligands wherein R is the point at which the Linker is attached. For additional examples and related ligands, see, the crystal structure 5dkc and the crystal structure 5dkh.

FIG. 3BBBB presents examples of TRIM24 (TIF1a) and/or BRPF1 Targeting Ligands wherein R is the point at which the Linker is attached and m is 0 1 2 3 4 5 6 7 or 8.

FIG. 3CCCC presents examples of TRIM24 (TIF1a) Targeting Ligands wherein R is the point at which the Linker is attached. For additional examples and related ligands, see, Palmer W. S. et al. "Structure-Guided Design of IACS-9571: a Selective High-Affinity Dual TRIM24-BRPF1 Bromodomain Inhibitor." *J. Med. Chem.* 59: 1440-1454 (2016).

FIG. 3DDDD-3FFFF presents examples of BRPF1 Targeting Ligands wherein R is the point at which the Linker is attached. For additional examples and related ligands, see, the crystal structure PDB 4uye; the crystal structure PDB 5c7n; the crystal structure PDB 5c87; the crystal structure PDB 5c89; the crystal structure PDB 5d7x; the crystal structure PDB 5dya; the crystal structure PDB 5epr; the crystal structure PDB 5eq1; the crystal structure PDB 5etb; the crystal structure PDB 5ev9; the crystal structure PDB 5eva; the crystal structure PDB 5ewv; the crystal structure PDB 5eww; the crystal structure PDB 5ffy; the crystal structure PDB 5fg5; and, the crystal structure PDB 5g4r.

FIG. 3GGGG presents examples of CECR2 Targeting Ligands wherein R is the point at which the Linker is attached. For additional examples and related ligands, see, Moustakim M. et al. *Med. Chem. Comm.* 7:2246-2264 (2016) and Crawford T. et al. Journal of *Med. Chem.* 59; 5391-5402 (2016).

FIG. 3HHHH-3OOOO present examples of CREBBP Targeting Ligands wherein R is the point at which the Linker is attached, A is N or CH, and m is 0 1 2 3 4 5 6 7 or 8. For additional examples and related ligands, see, the crystal structure PDB 3p1d; the crystal structure PDB 3svh; the crystal structure PDB 4nr4; the crystal structure PDB 4nr5; the crystal structure PDB 4ts8; the crystal structure PDB 4nr6; the crystal structure PDB 4nr7; the crystal structure PDB 4nyw; the crystal structure PDB 4nyx; the crystal structure PDB 4tqn; the crystal structure PDB 5cgp; the crystal structure PDB 5dbm; the crystal structure PDB 5ep7; the crystal structure PDB 5i83; the crystal structure PDB 5i86; the crystal structure PDB 5i89; the crystal structure PDB 5i8g; the crystal structure PDB 5j0d; the crystal structure PDB 5ktu; the crystal structure PDB 5ktw; the crystal structure PDB 5ktx; the crystal structure PDB 5tb6.

FIG. 3PPPP presents examples of EP300 Targeting Ligands wherein R is the point at which the Linker is attached. For additional examples and related ligands, see, the crystal structure PDB 5BT3.

FIG. 3QQQQ presents examples of PCAF Targeting Ligands wherein R is the point at which the Linker is attached. See for example, M. Ghizzoni et al. *Bioorg. Med. Chem.* 18: 5826-5834 (2010).

FIG. 3RRRR presents examples of PHIP Targeting Ligands wherein R is the point at which the Linker is attached. For additional examples and related ligands, see, *Mol Cancer Ther.* 7(9): 2621-2632 (2008).

FIG. 3SSSS presents examples of TAF1 and TAF1L Targeting Ligands wherein R is the point at which the Linker is attached. For additional examples and related ligands, see, Picaud S. et al. *Sci Adv* 2: e1600760-e1600760 (2016).

FIG. 3TTTT presents examples of Histone Deacetylase 2 (HDAC2) Targeting Ligands wherein R is the point at which the Linker is attached. For additional examples and related ligands, see, Lauffer B. E. *J. Biol. Chem.* 288: 26926-26943 (2013); Wagner F. F. *Bioorg. Med. Chem.* 24: 4008-4015 (2016); Bressi J. C. *Bioorg. Med. Chem. Lett.* 20: 3142-3145 (2010); and, Lauffer B. E. *J. Biol. Chem.* 288: 26926-26943 (2013).

FIG. 3UUUU-3VVVV present examples of Histone Deacetylase 4 (HDAC4) Targeting Ligands wherein R is the point at which the Linker is attached. For additional examples and related ligands, see, Burli R. W. *J. Med. Chem.* 56: 9934 (2013); Luckhurst C. A. *ACS Med. Chem. Lett.* 7: 34 (2016); Bottomley M. J. *J Biol. Chem.* 283: 26694-26704 (2008).

FIG. 3WWWW presents examples of Histone Deaceytlase 6 Targeting Ligands wherein R is the point at which the Linker is attached. For additional examples and related ligands, see, Harding R. J. (to be published); Hai Y. *Nat. Chem. Biol.* 12: 741-747, (2016); and, Miyake Y. *Nat. Chem. Biol.* 12: 748 (2016).

FIG. 3XXXX-3YYYY presents examples of Histone Deacetylase 7 Targeting Ligands wherein R is the point at which the Linker is attached. For additional examples and related ligands, see, Lobera M. *Nat. Chem. Biol.* 9: 319 (2013) and Schuetz A. *J Biol. Chem.* 283: 11355-11363 (2008).

FIG. 3ZZZZ-3DDDDD present examples of Histone Deacetylase 8 Targeting Ligands wherein R is the point at which the Linker is attached. For additional examples and related ligands, see, Whitehead L. *Biol. Med. Chem.* 19:

4626-4634 (2011); Tabackman A. A. *J. Struct. Biol.* 195: 373-378 (2016); Dowling D. P. *Biochemistry* 47, 13554-13563 (2008); Somoza J. R. *Biochemistry* 12, 1325-1334 (2004); Decroos C. *Biochemistry* 54: 2126-2135 (2015); Vannini A. *Proc. Natl Acad. Sci.* 101: 15064 (2004); Vannini A. *EMBO Rep.* 8: 879 (2007); the crystal structure PDB 5BWZ; Decroos A. *ACS Chem. Biol.* 9: 2157-2164 (2014); Somoza J. R. *Biochemistry* 12: 1325-1334 (2004); Decroos C. *Biochemistry* 54: 6501-6513 (2015); Decroos A. *ACS Chem. Biol.* 9: 2157-2164 (2014); and, Dowling D. P. *Biochemistry* 47: 13554-13563 (2008).

FIG. 3EEEEE presents examples of Histone Acetyltransferase (KAT2B) Targeting Ligands wherein R is the point at which the Linker is attached. For additional examples and related ligands, see, Chaikuad A. *J. Med. Chem.* 59: 1648-1653 (2016); the crystal structure PDB 1ZS5; and, Zeng L. *J. Am. Chem. Soc.* 127: 2376-2377 (2005).

FIG. 3FFFFF-3GGGGG present examples of Histone Acetyltransferase (KAT2A) Targeting Ligands wherein R is the point at which the Linker is attached. For additional examples and related ligands, see, Ringel A. E. *Acta Crystallogr. D. Struct. Biol.* 72: 841-848 (2016).

FIG. 3HHHHH presents examples of Histone Acetyltransferase Type B Catalytic Unit (HAT1) Targeting Ligands wherein R is the point at which the Linker is attached. For additional examples and related ligands, see, the crystal structure PDB 2POW.

FIG. 3IIIII presents examples of Cyclic AMP-dependent Transcription Factor (ATF2) Targeting Ligands wherein R is the point at which the Linker is attached.

FIG. 3JJJJJ presents examples of Histone Acetyltransferase (KAT5) Targeting Ligands wherein R is the point at which the Linker is attached.

FIG. 3KKKKK-3MMMMM present examples of Lysine-specific histone demethylase 1A (KDM1A) Targeting Ligands wherein R is the point at which the Linker is attached. For additional examples and related ligands, see, Mimasu S. *Biochemistry* 49: 6494-6503 (2010); Sartori L. *J. Med. Chem.* 60:1673-1693 (2017); and, Vianello P. *J. Med. Chem.* 60: 1693-1715 (2017).

FIG. 3NNNNN presents examples of HDAC6 Zn Finger Domain Targeting Ligands wherein R is the point at which the Linker is attached.

FIG. 3OOOOO-3PPPPP present examples of general Lysine Methyltransferase Targeting Ligands wherein R is the point at which the Linker is attached.

FIG. 3QQQQQ-3TTTTT present examples of DOT1L Targeting Ligands wherein R is the point at which the Linker is attached, A is N or CH, and m is 0 1 2 3 4 5 6 7 or 8. For additional examples and related ligands, see, the crystal structure PDB 5MVS ("Dot1L in complex with adenosine and inhibitor CPD1" Be C. et al.); the crystal structure PDB 5MW4 ("Dot1L in complex inhibitor CPD7" Be C. et al.); the crystal structure PDB 5DRT ("Dot1L in complex inhibitor CPD2" Be C. et al.); Be C. et al. *ACSMed. Lett.* 8: 338-343 (2017); the crystal structure PDB 5JUW "(Dot1L in complex with SS148" Yu W. et al. Structural Genomics Consortium).

FIG. 3UUUUU presents examples of EHMT1 Targeting Ligands wherein R is the point at which the Linker is attached. For additional examples and related ligands, see, the crystal structure PDB 5TUZ ("EHMT1 in complex with inhibitor MS0124", Babault N. et al.).

FIG. 3VVVVV presents examples of EHMT2 Targeting Ligands wherein R is the point at which the Linker is attached. For additional examples and related ligands, see, the crystal structure PDB 5TUY ("EHMT2 in complex with inhibitor MS0124", Babault N. et al.); the PDB crystal structure 5TTF ("EHMT2 in complex with inhibitor MS012", Dong A. et al.); the PDB crystal structure 3RJW (Dong A. et al., Structural Genomics Consortium); the PDB crystal structure 3K5K; Liu F. et al. *J. Med. Chem.* 52: 7950-7953 (2009); and, the PDB crystal structure 4NVQ ("EHMT2 in complex with inhibitor A-366" Sweis R. F. et al.).

FIG. 3WWWWW presents examples of SETD2 Targeting Ligands wherein R is the point at which the Linker is attached. For additional examples and related ligands, see, the PDB crystal structure 5LSY ("SETD2 in complex with cyproheptadine", Tisi D. et al.); Tisi D. et al. *ACS Chem. Biol.* 11: 3093-3105 (2016); the crystal structures PDB 5LSS, 5LSX, 5LSZ, 5LT6, 5LT7, and 5LT8; the PDB crystal structure 4FMU; and, Zheng W. et al. *J. Am. Chem. Soc.* 134: 18004-18014 (2012).

FIG. 3XXXXX-3YYYYY present examples of SETD7 Targeting Ligands wherein R is the point at which the Linker is attached. For additional examples and related ligands, see, the PDB crystal structure 5AYF ("SETD7 in complex with cyproheptadine." Niwa H. et al.); the PDB crystal structure 4JLG ("SETD7 in complex with (R)-PFI-2", Dong A. et al.); the PDB crystal structure 4JDS (Dong A. et. al Structural Genomics Consortium); the PDB crystal structure 4E47 (Walker J. R. et al. Structural Genomics Consortium; the PDB crystal structure 3VUZ ("SETD7 in complex with AAM-1." Niwa H. et al.); the PDB crystal structure 3VVO; and, Niwa H et al. *Acta Crystallogr. Sect.D* 69: 595-602 (2013).

FIG. 3ZZZZZ presents examples of SETD8 Targeting Ligands wherein R is the point at which the Linker is attached. For additional examples and related ligands, see, the PDB crystal structure 5TH7 ("SETD8 in complex with MS453", Yu W. et al.) and the PDB crystal structure 5T5G (Yu W et. al.; to be published).

Figure 4B:
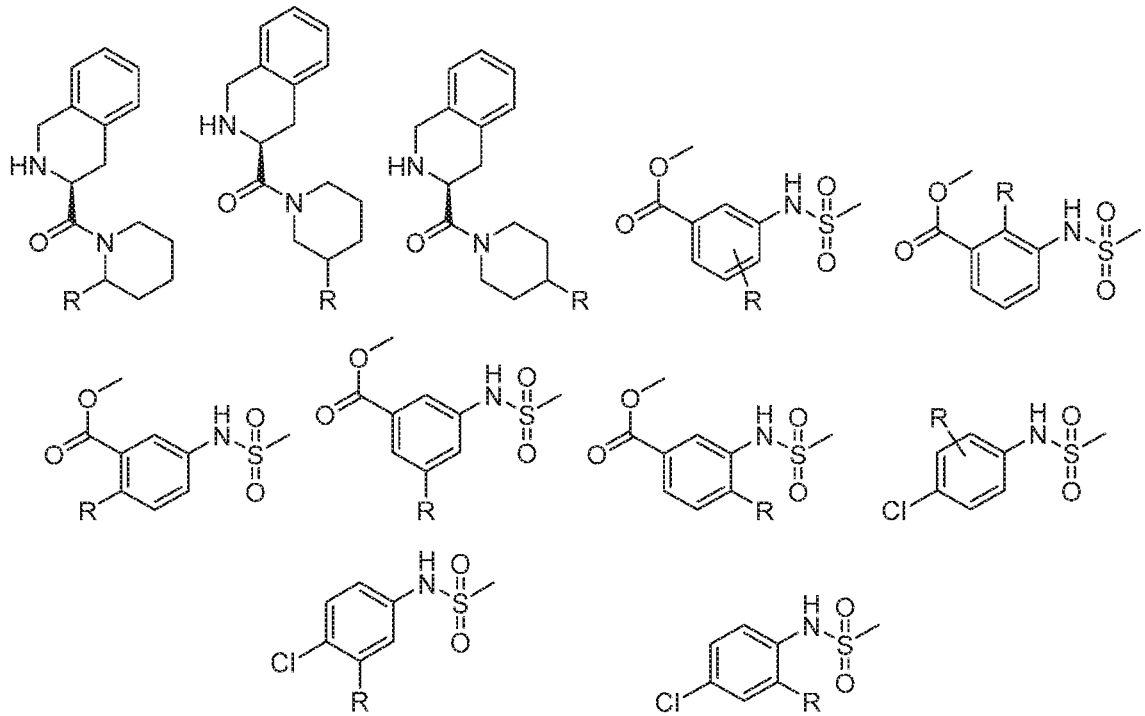
Figure 4C:
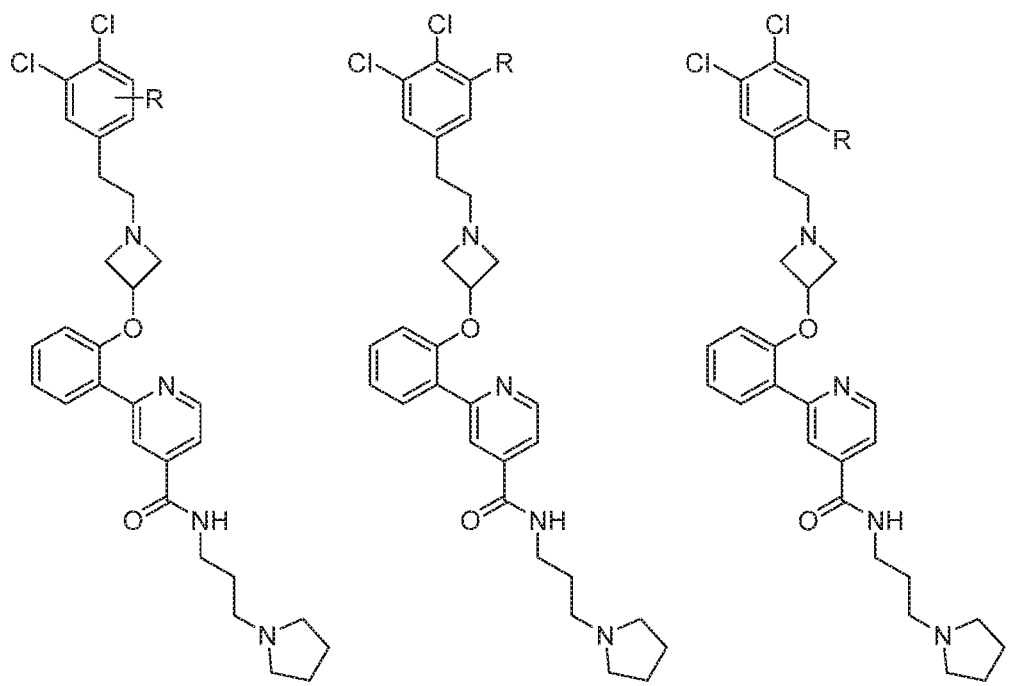
Figure 4D:
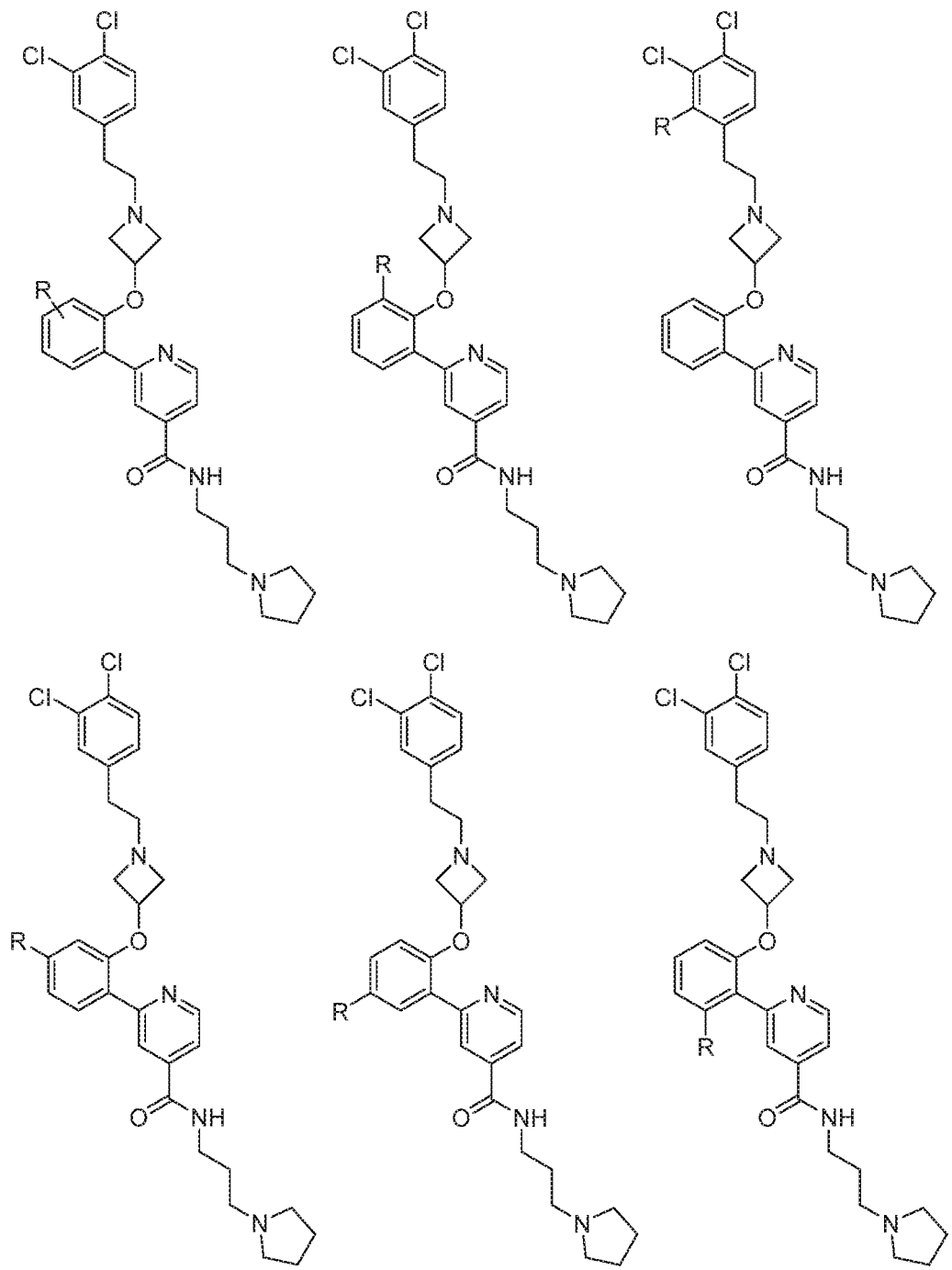
Figure 4E:
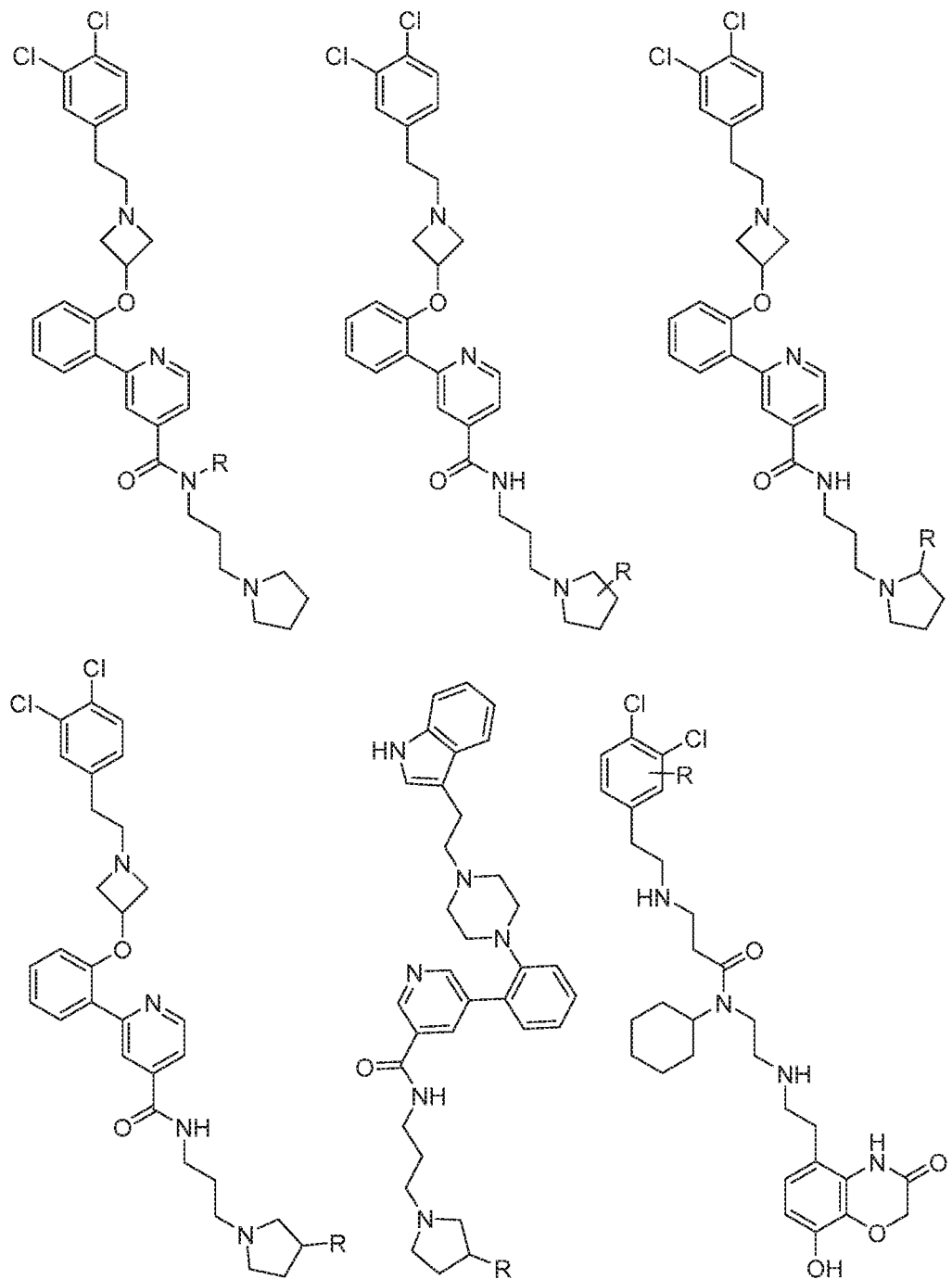
Figure 4F:
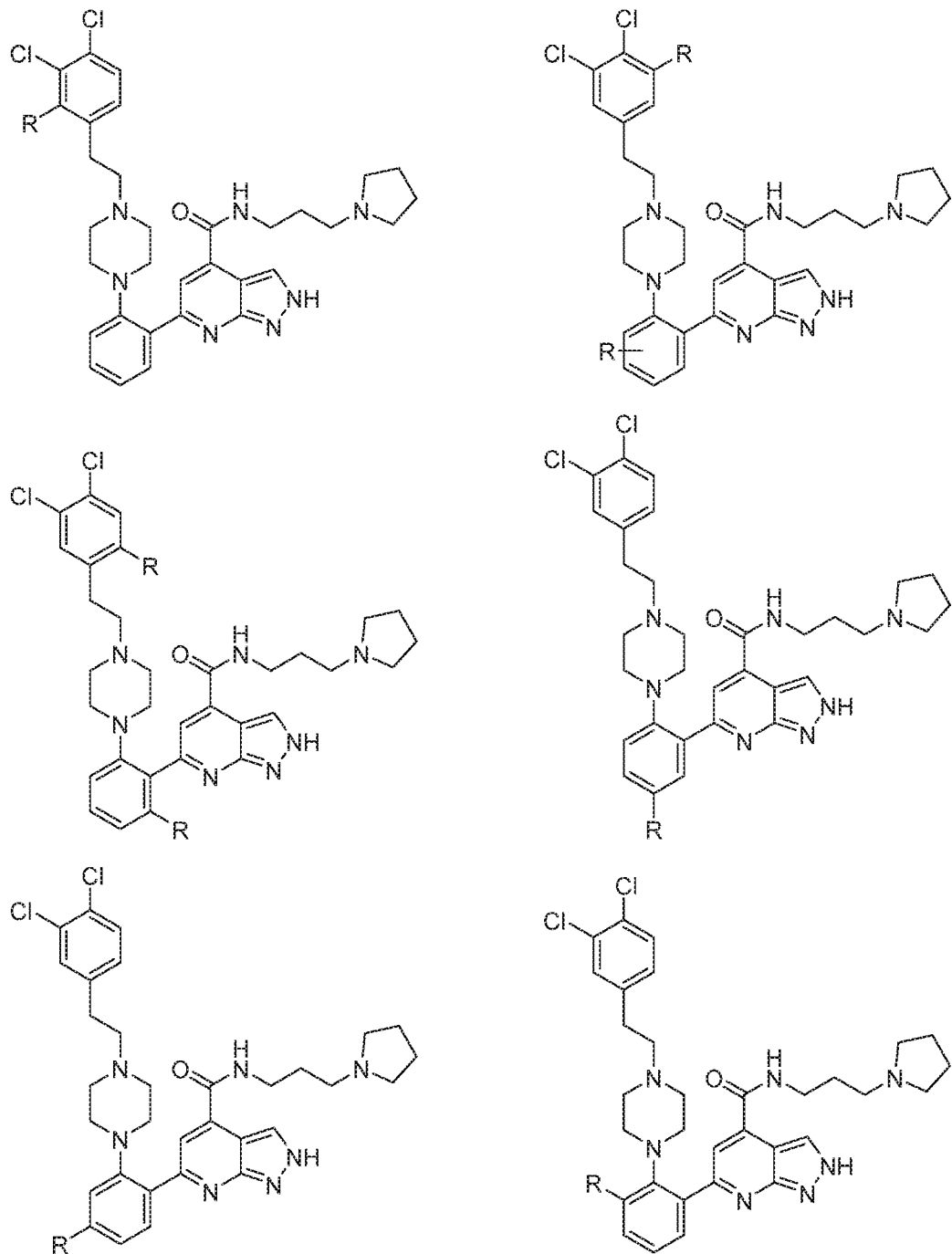
Figure 4G:
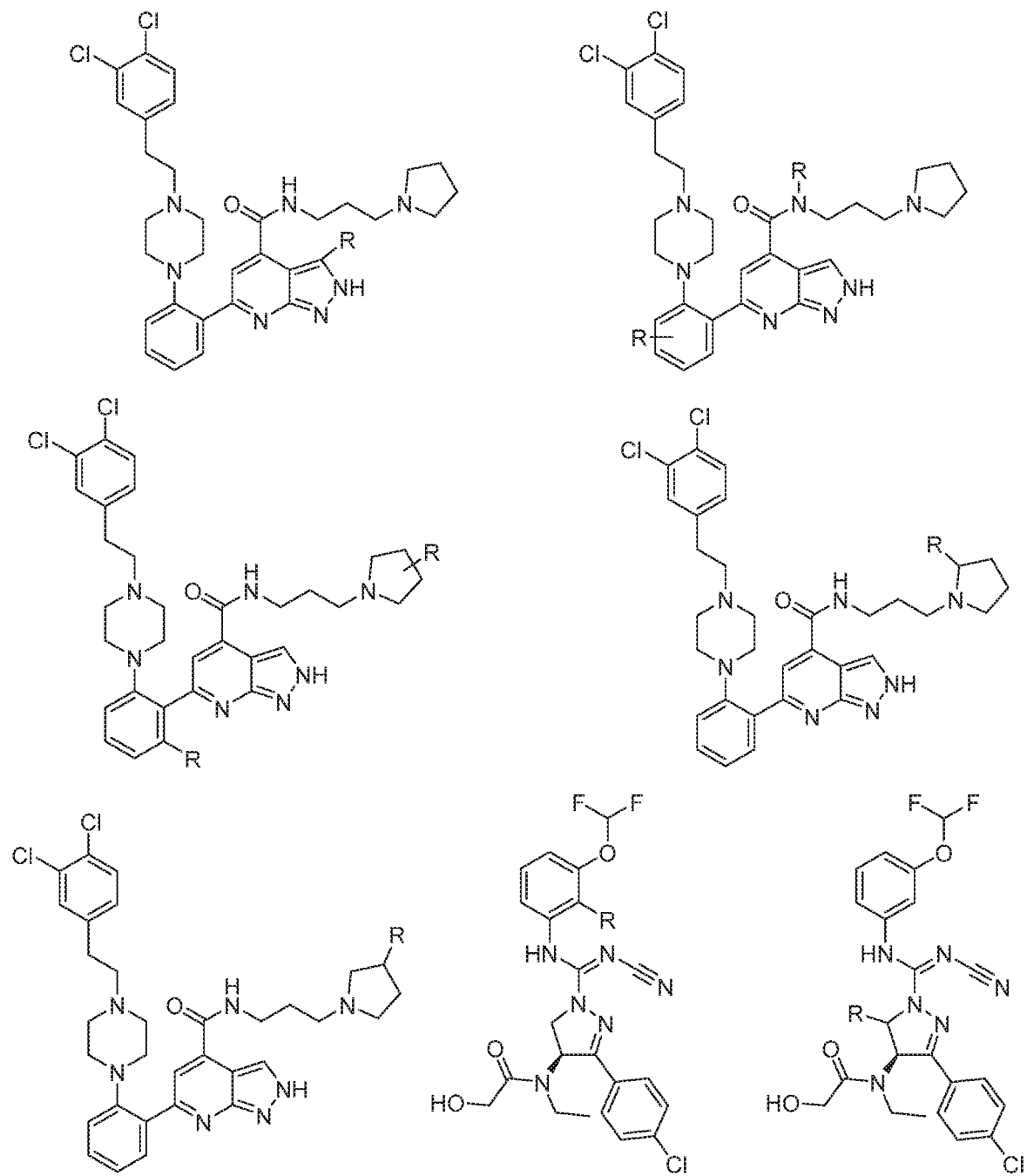
Figure 4H:
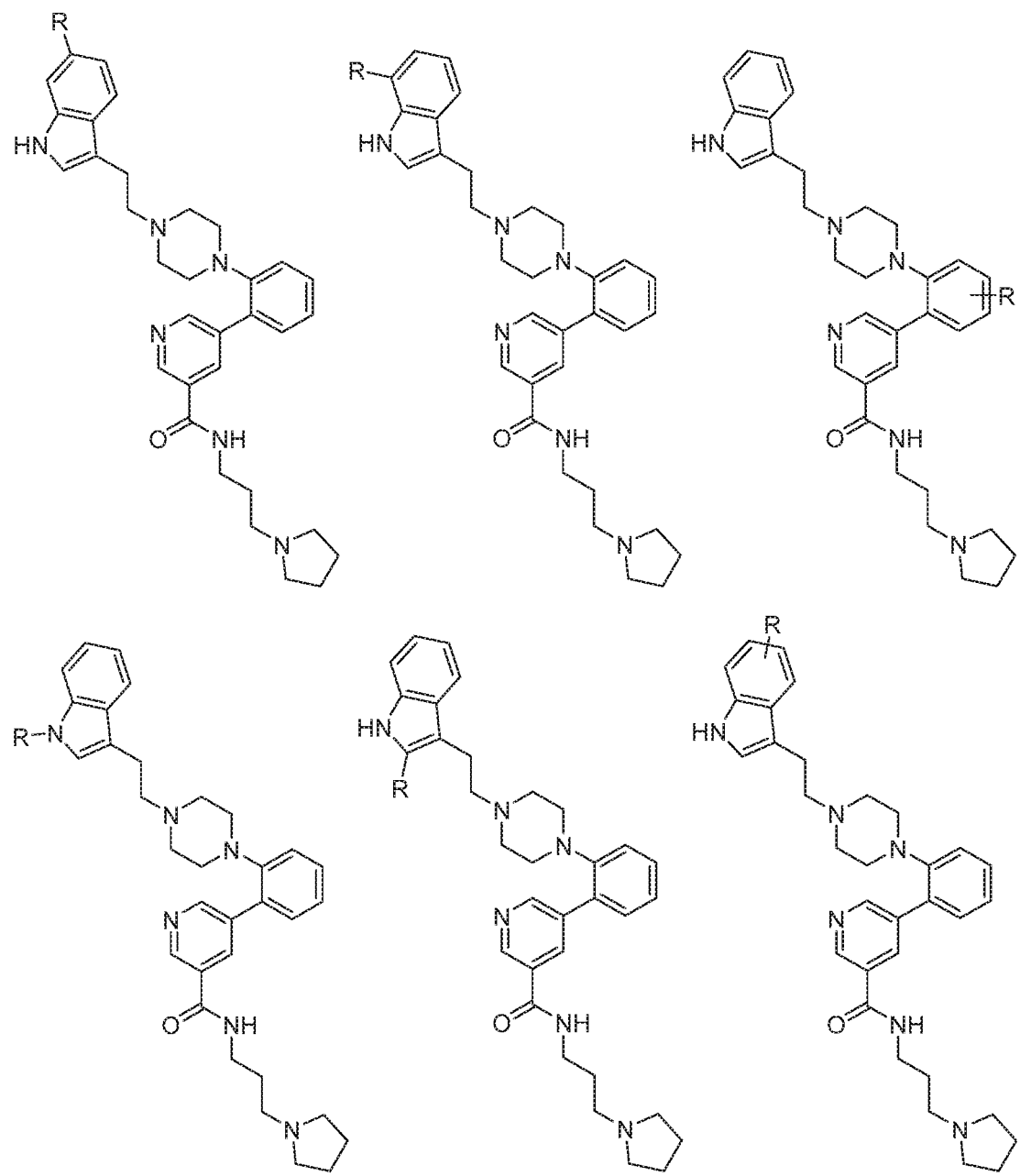
Figure 4I:
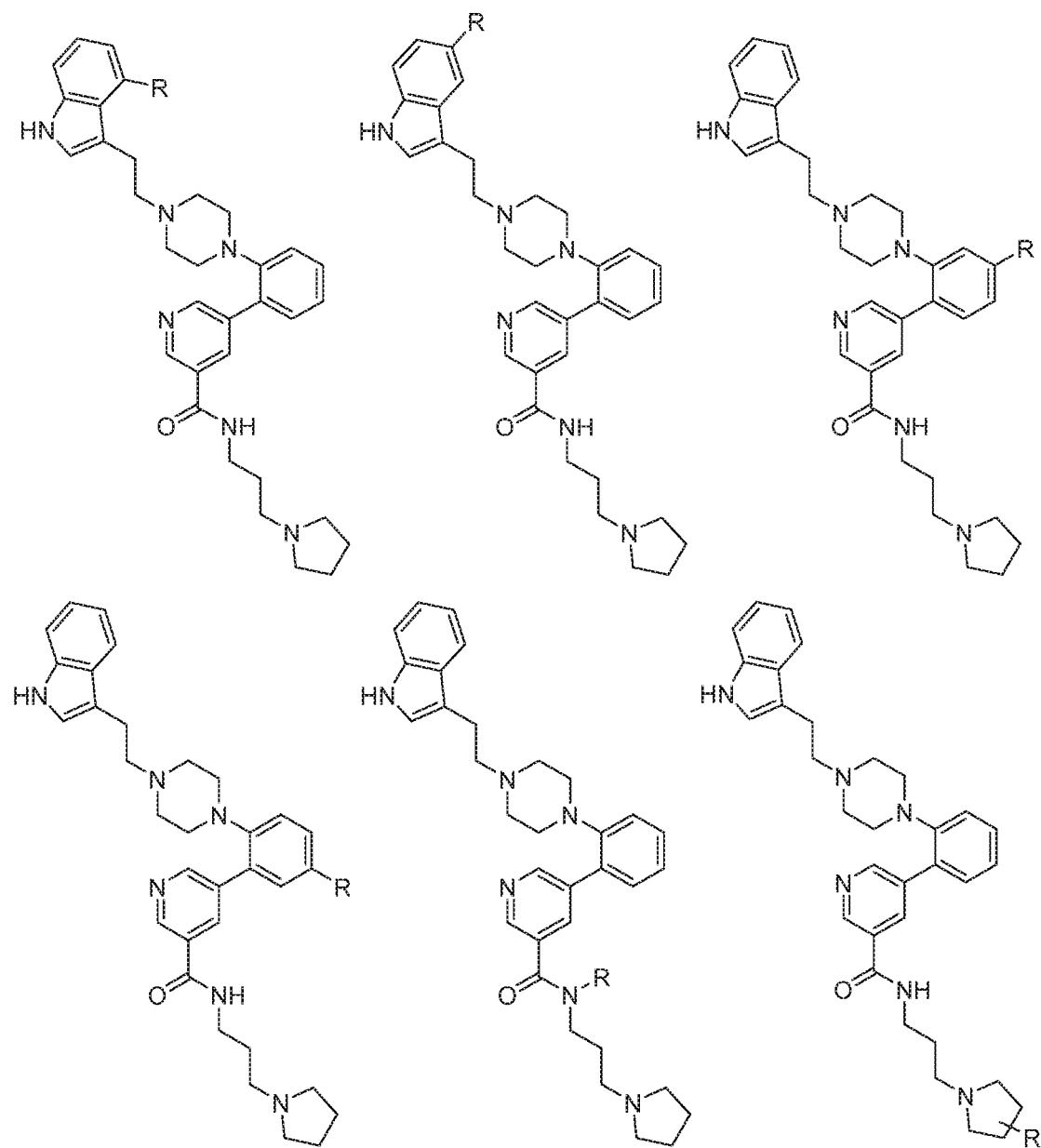
Figure 4J:
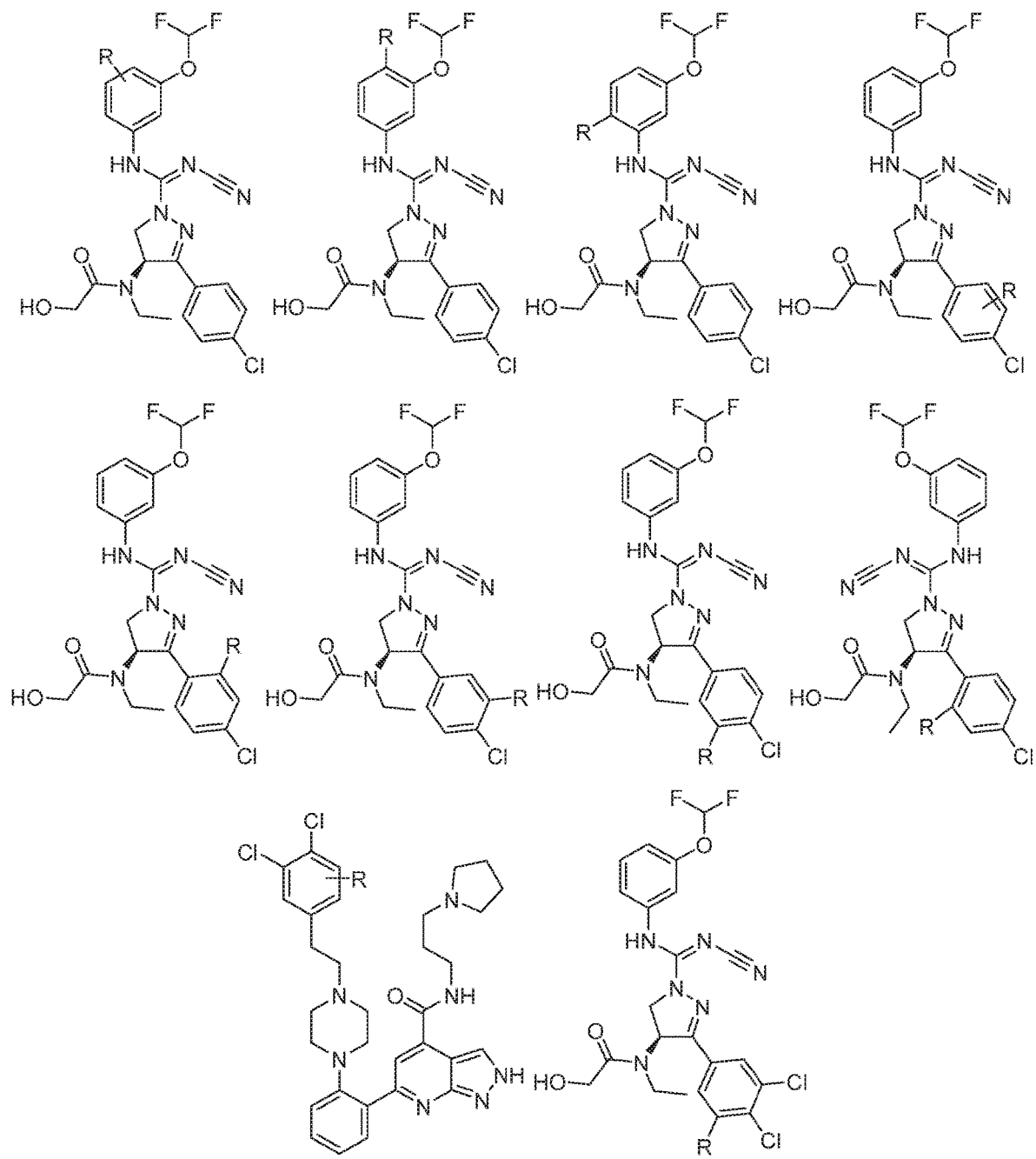
Figure 4K:
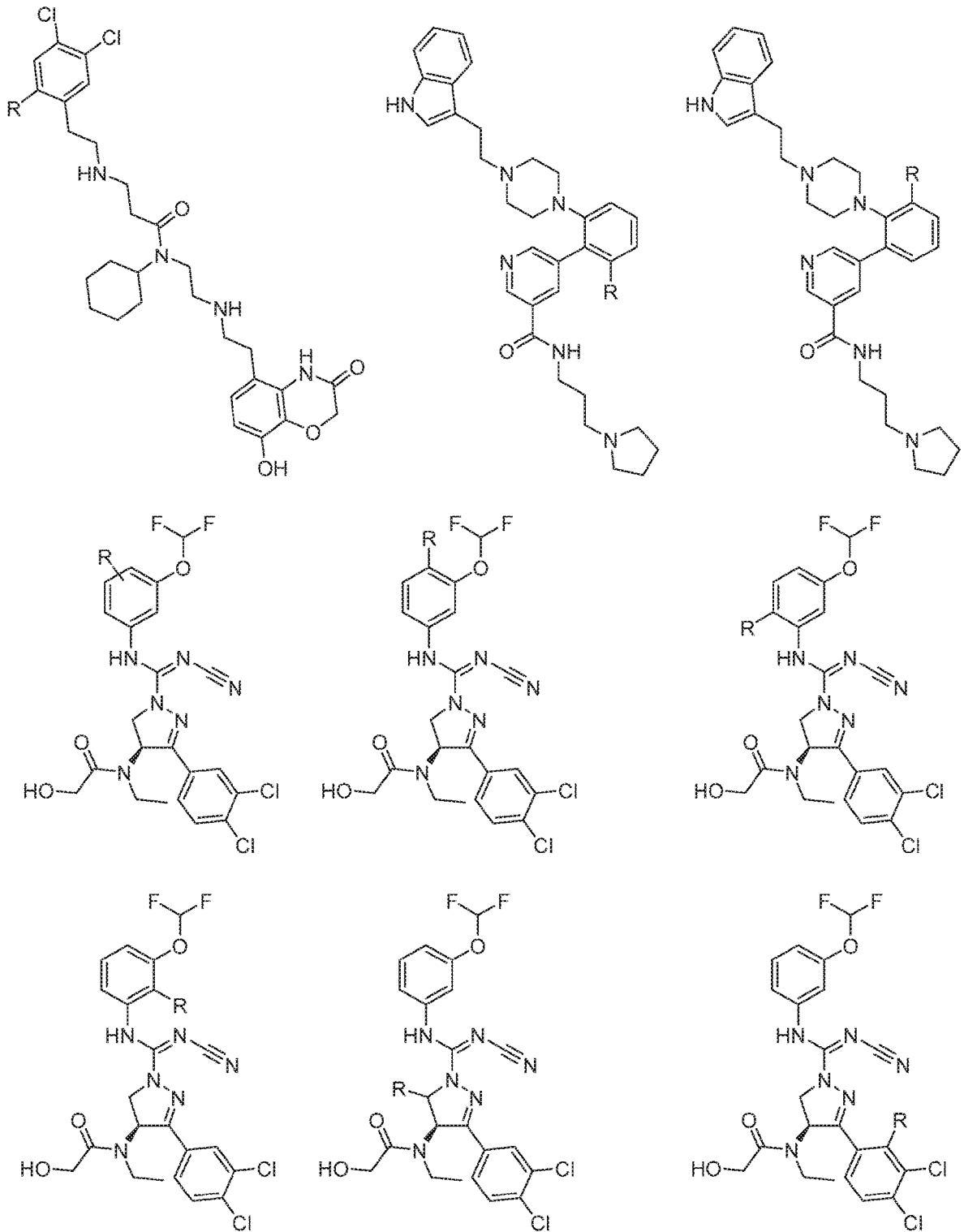
Figure 4L:
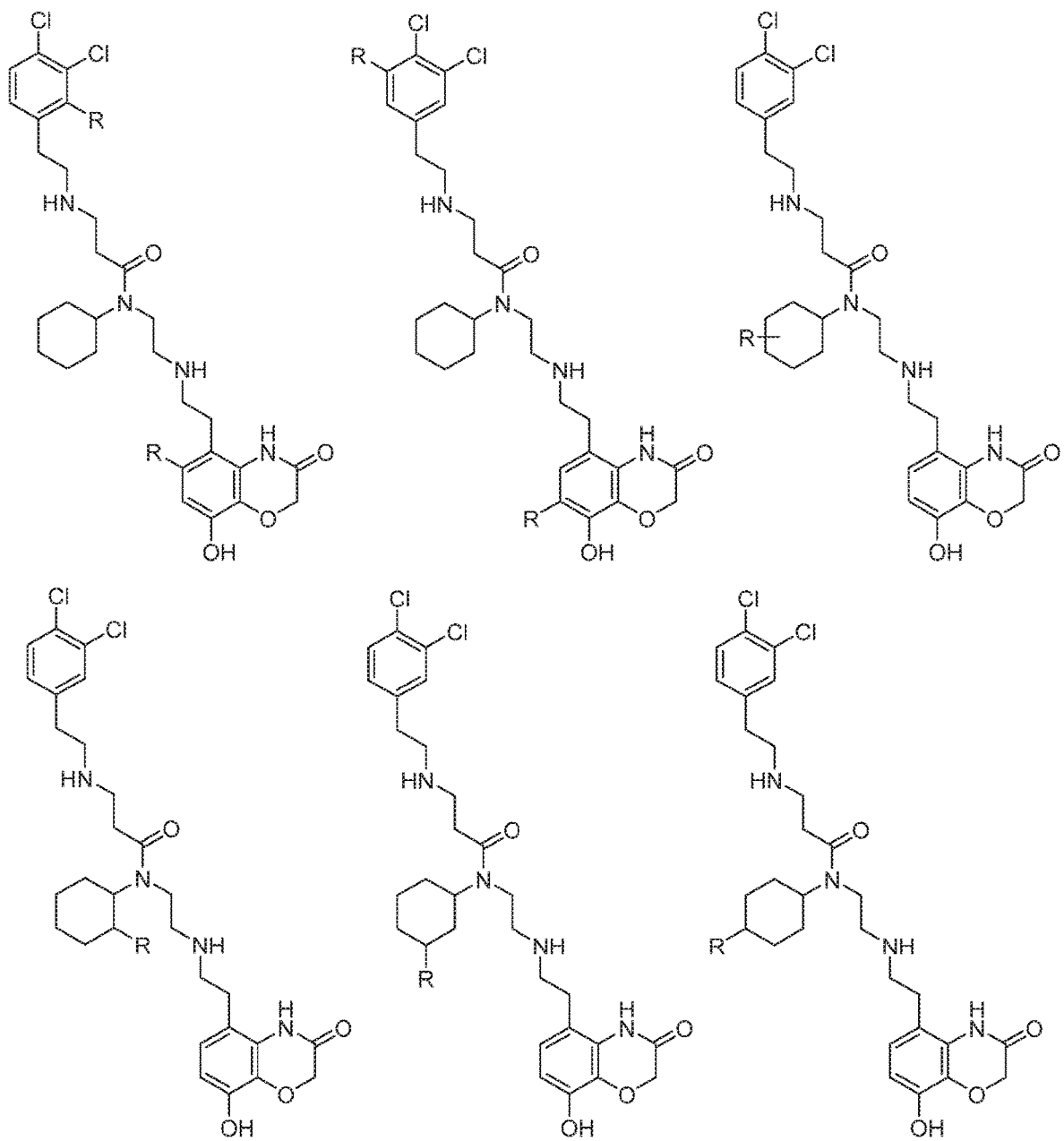
Figure 4M:
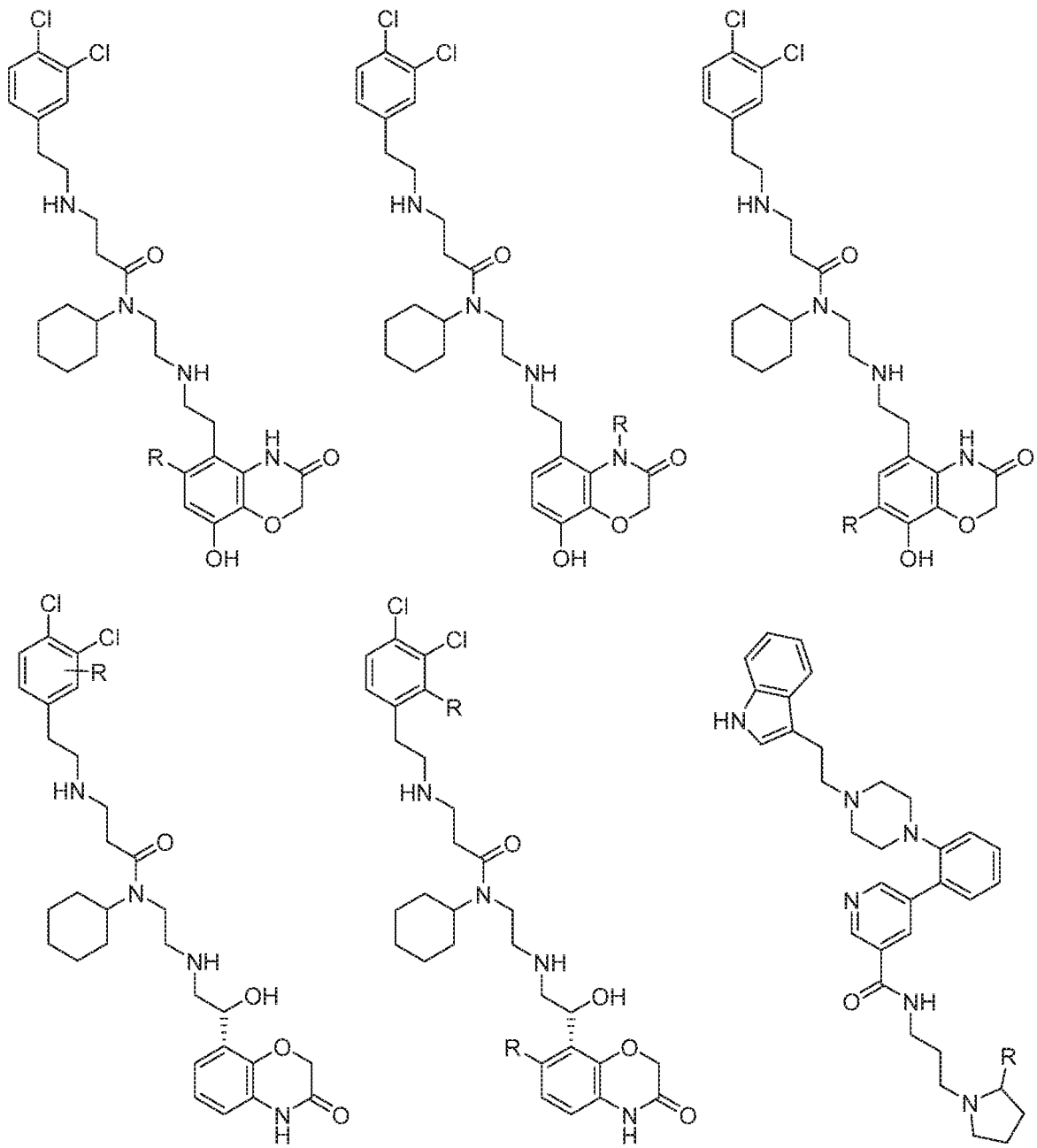
Figure 4N:
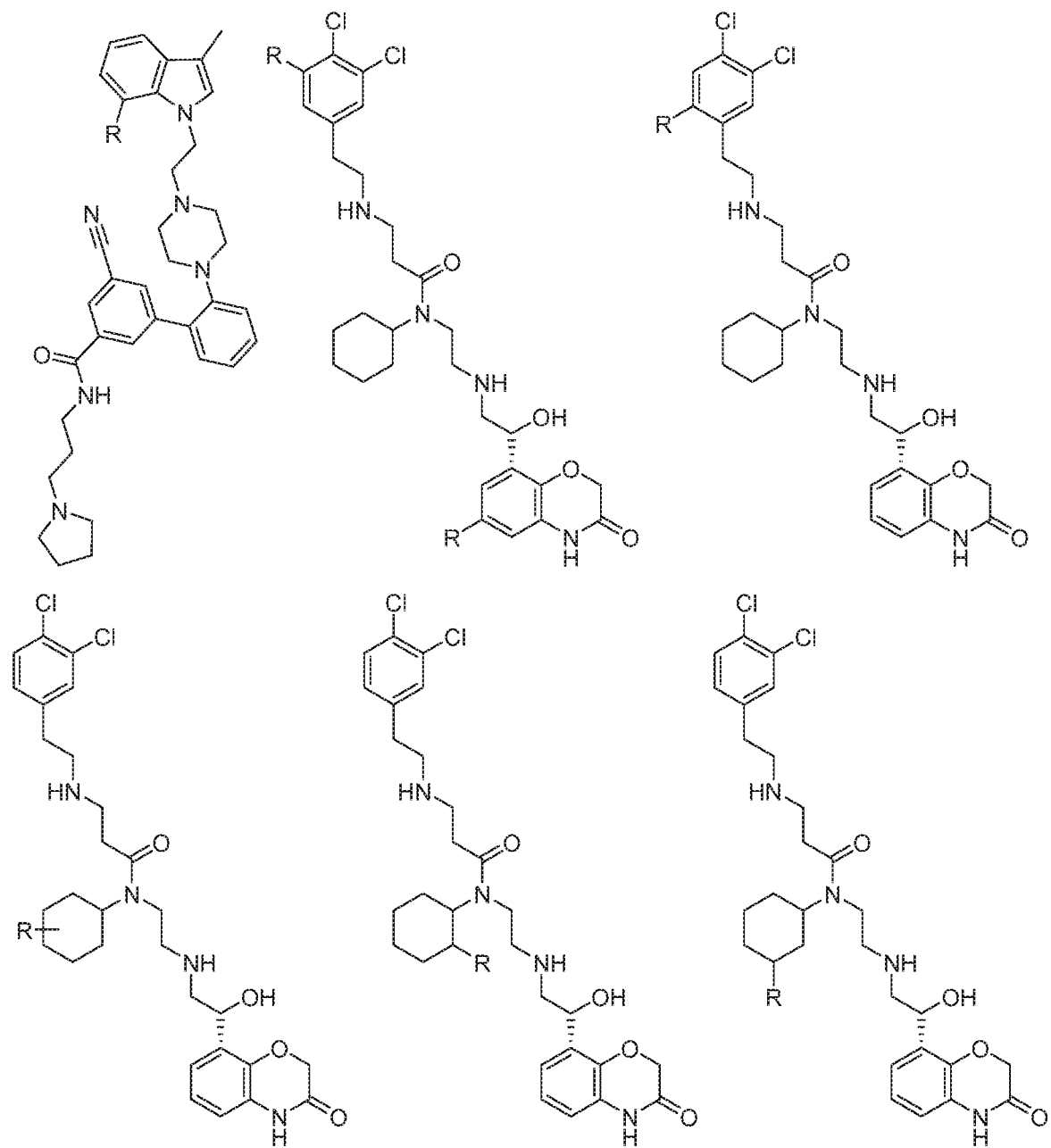
Figure 4O:
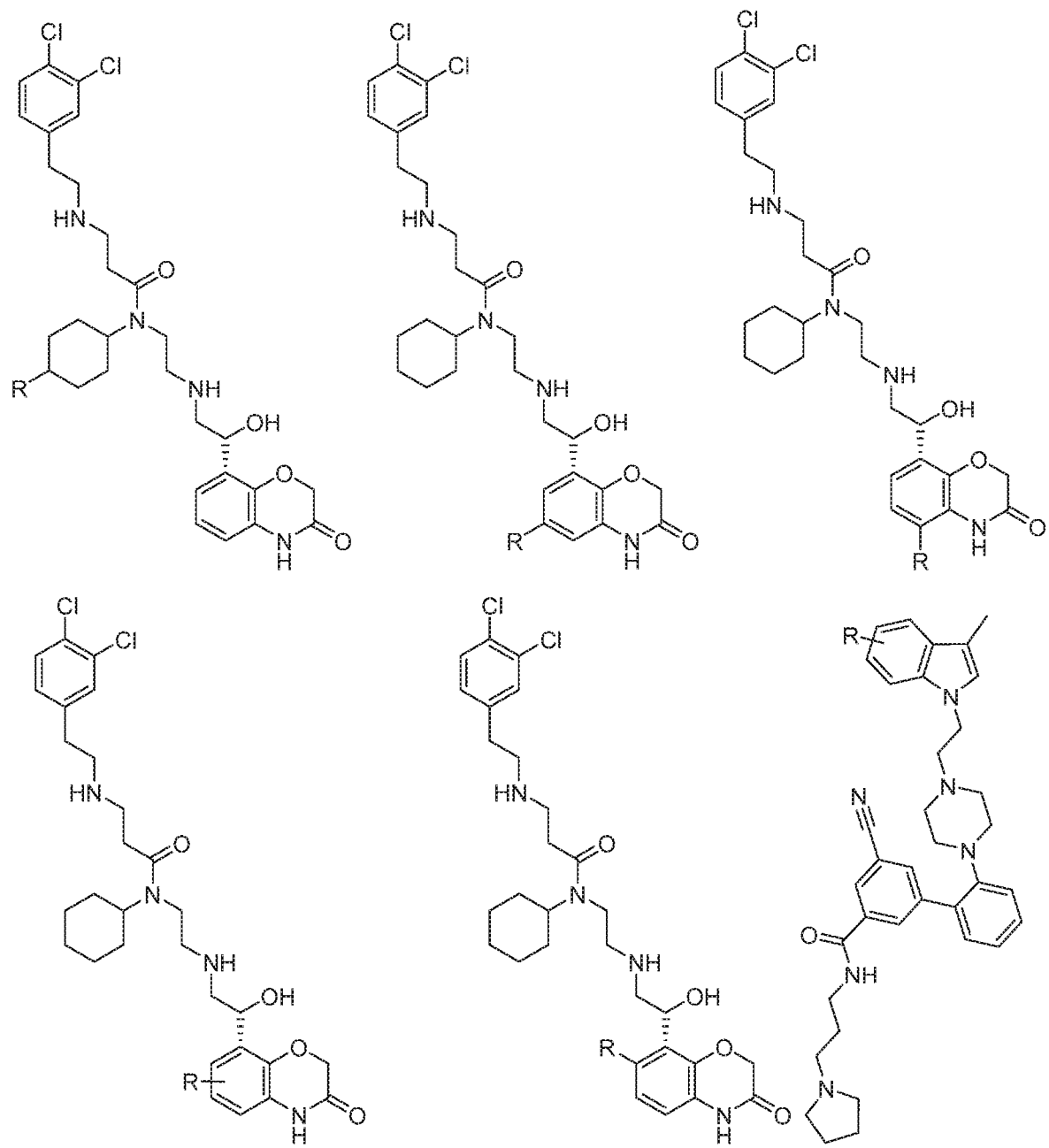
Figure 4P:
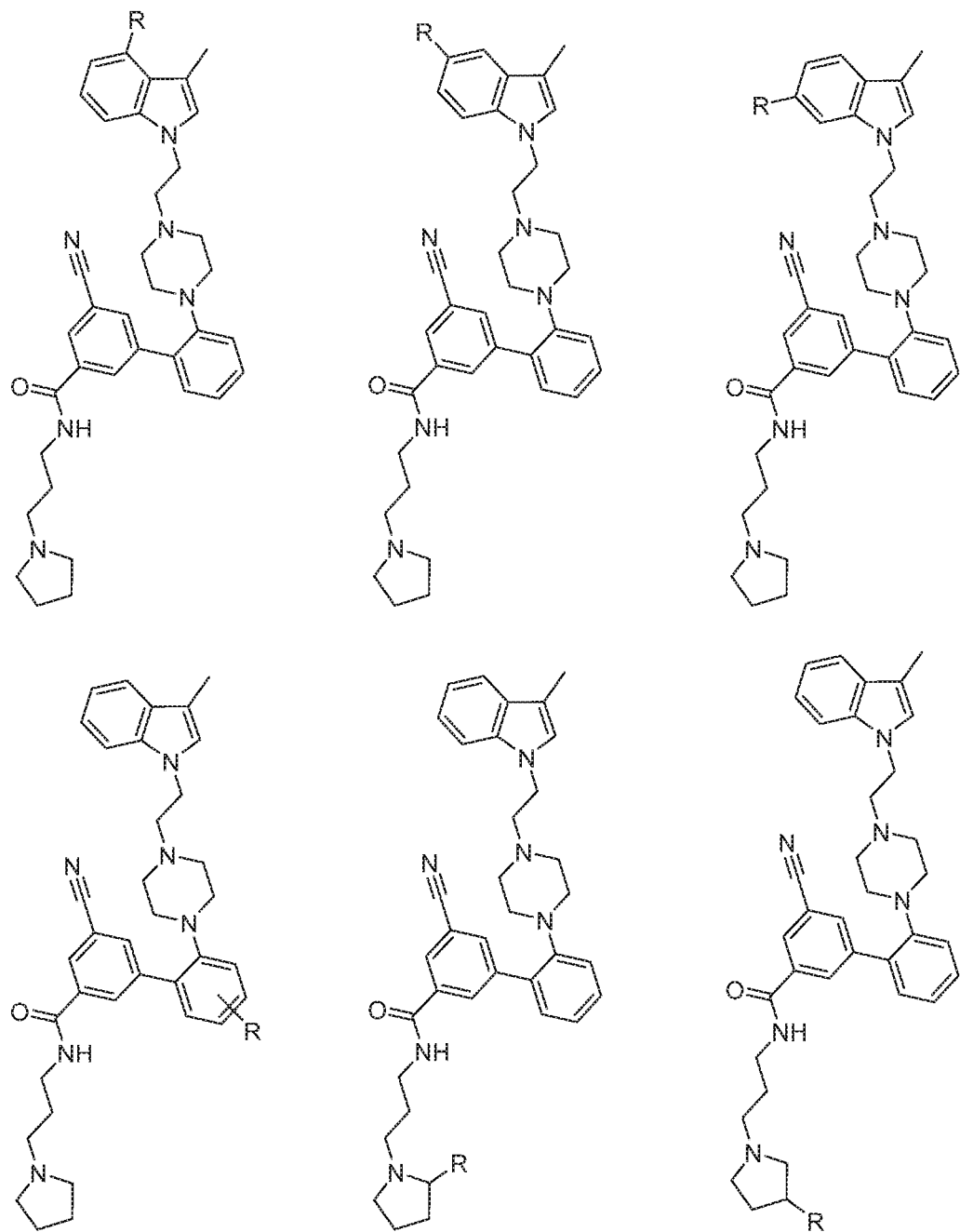
Figure 4Q:
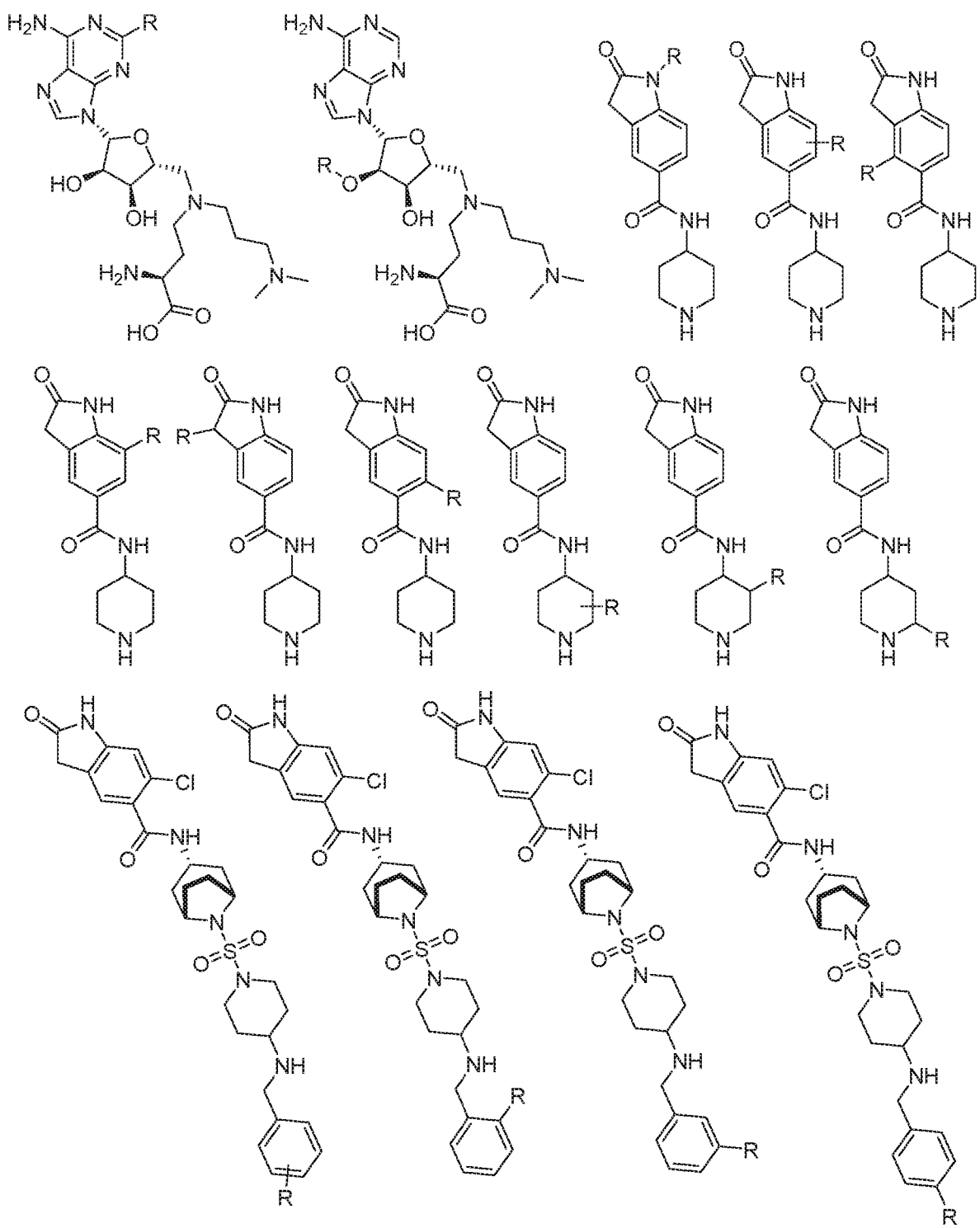
Figure 4R:
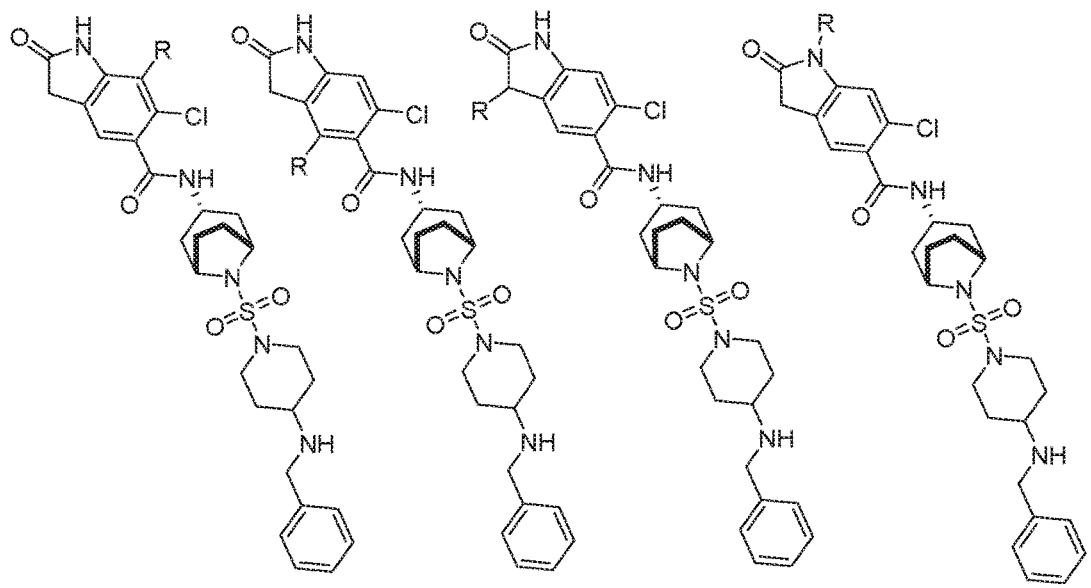
Figure 4S:
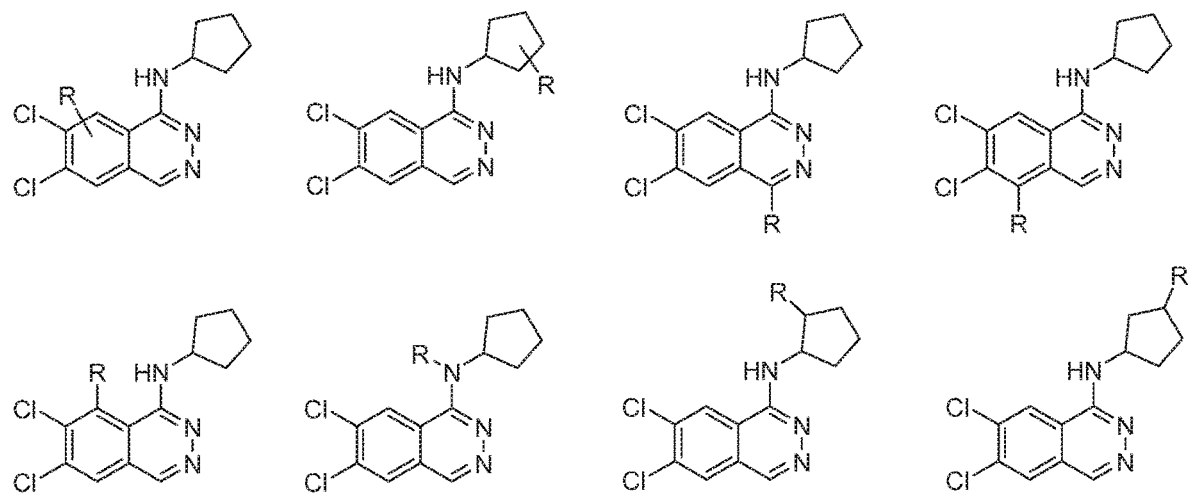
Figure 4T:
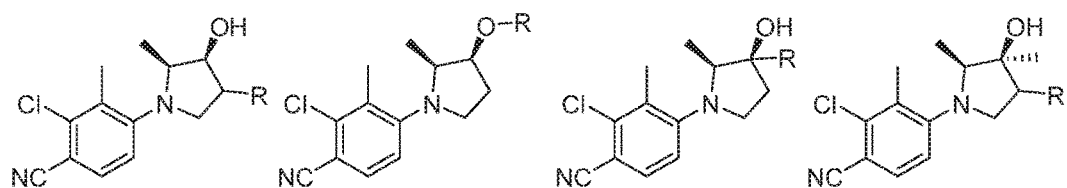
Figure 4U:
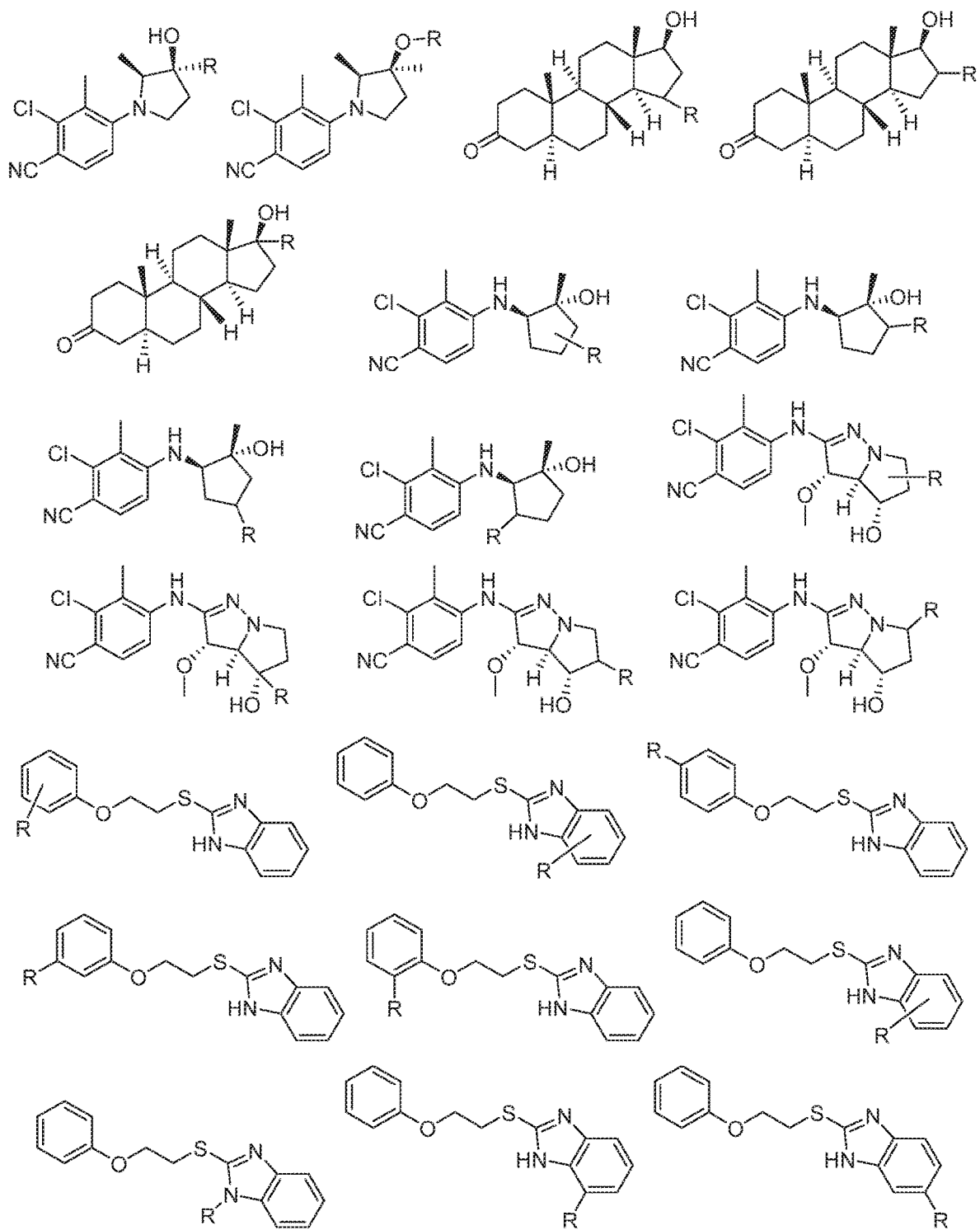
Figure 4V:
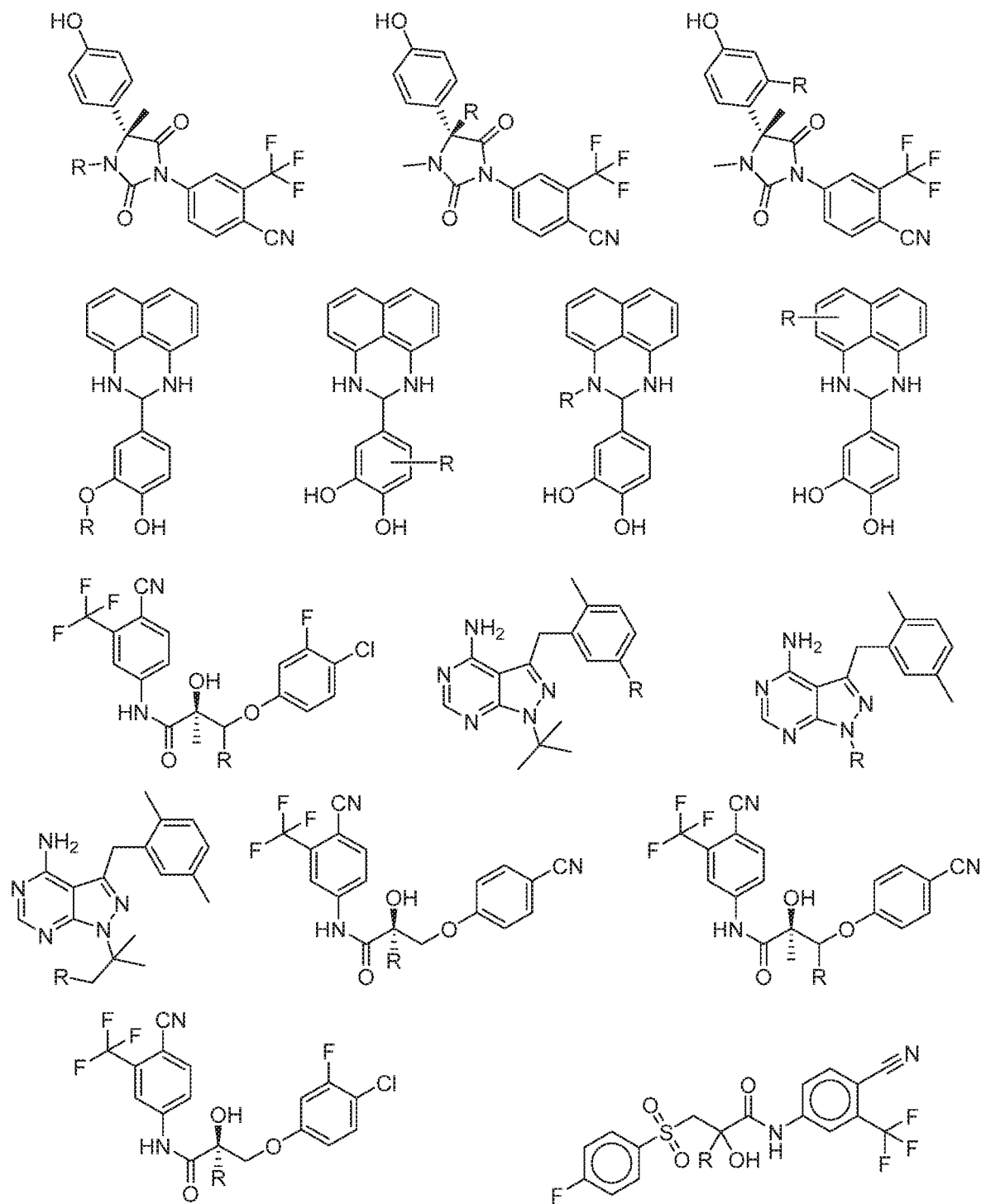
Figure 4W:
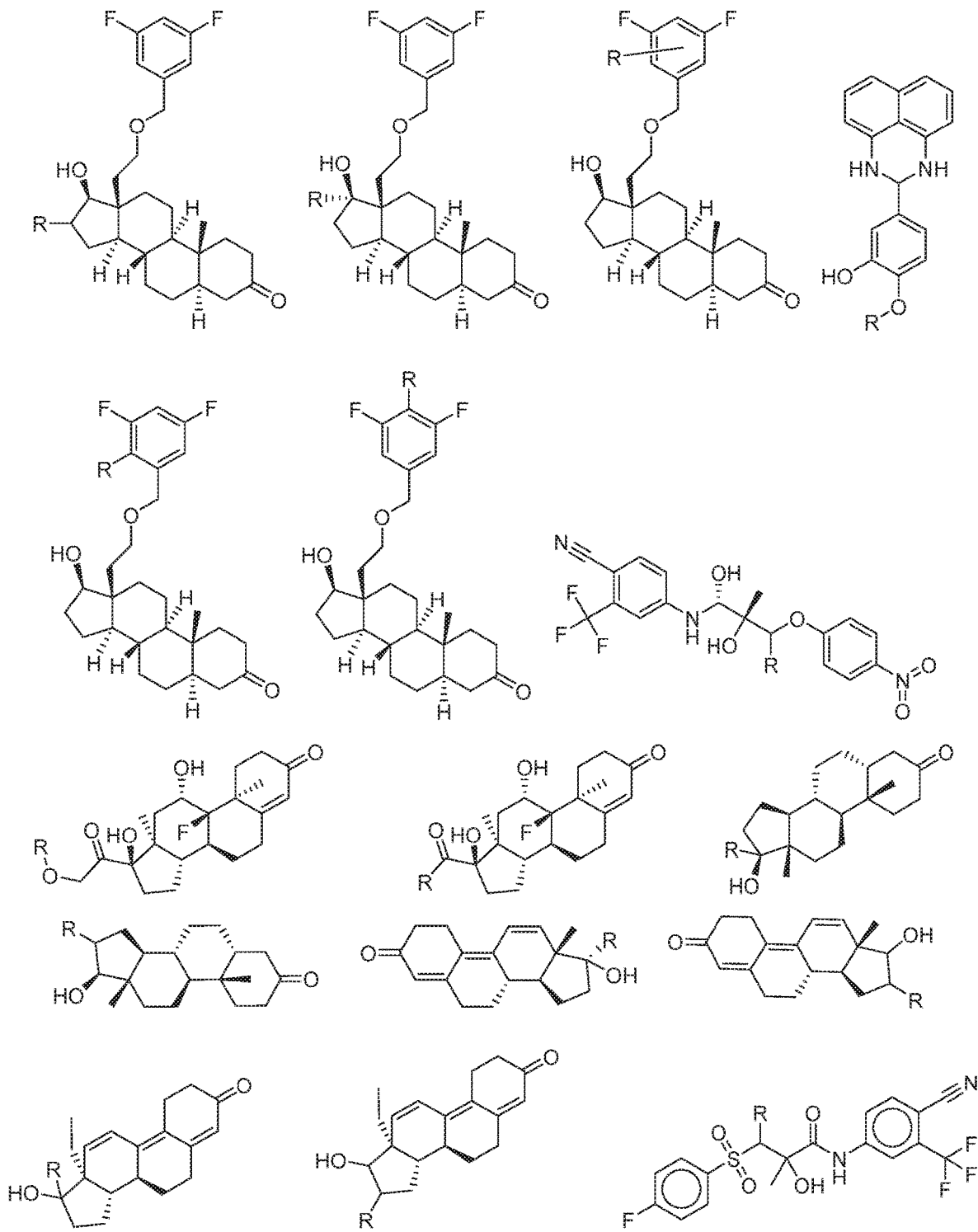
Figure 4X:
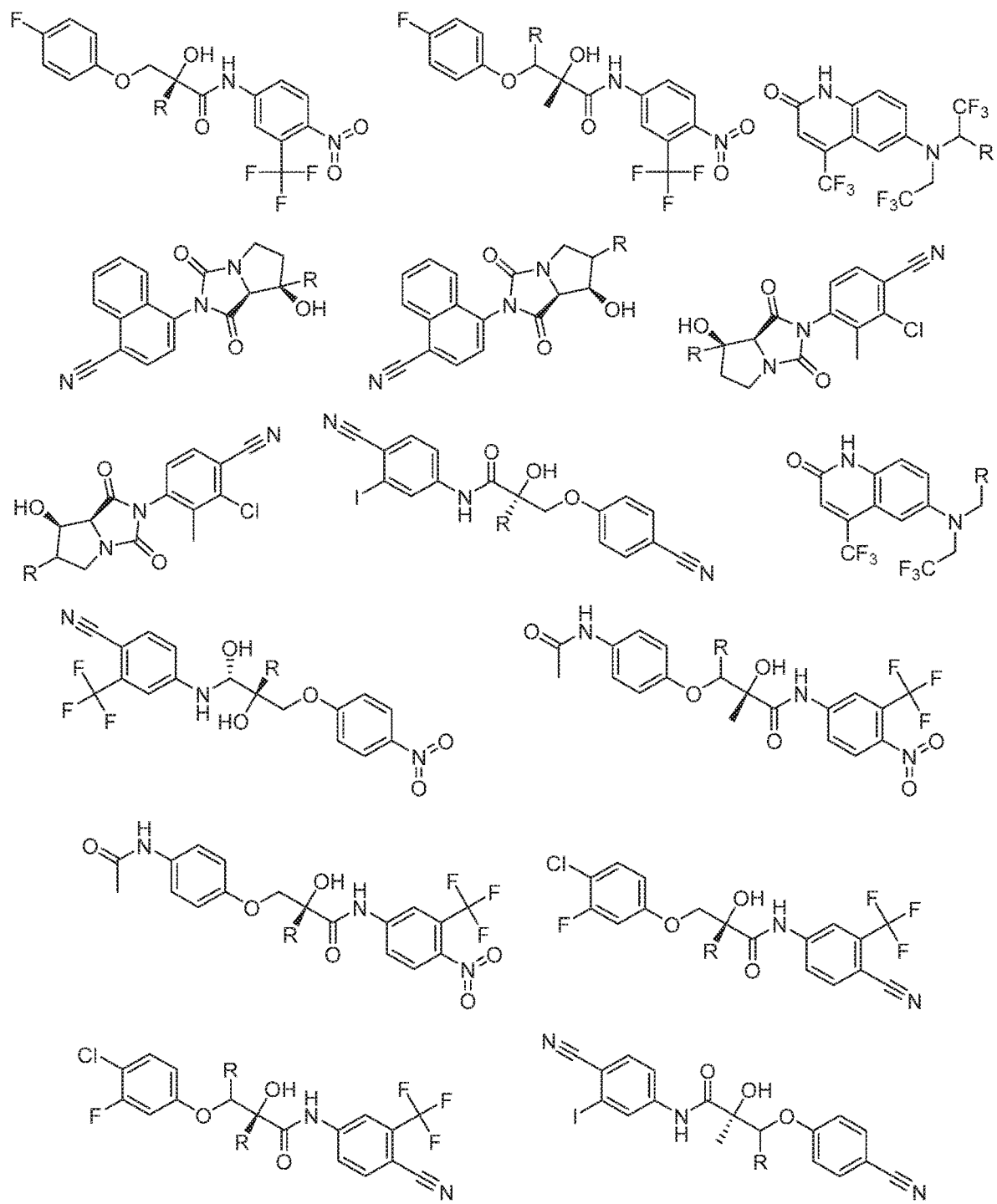
Figure 4Y:
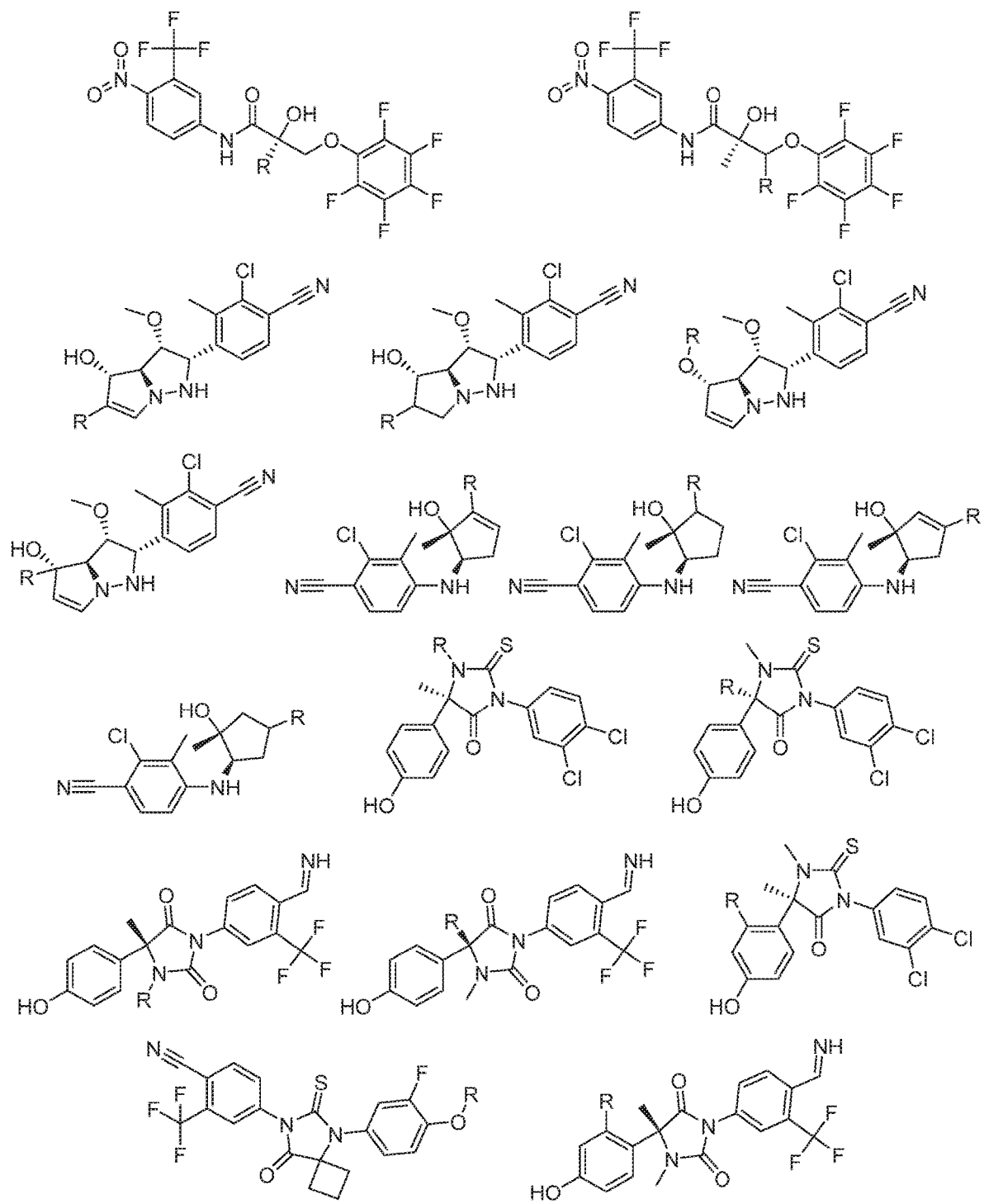
Figure 4Z:
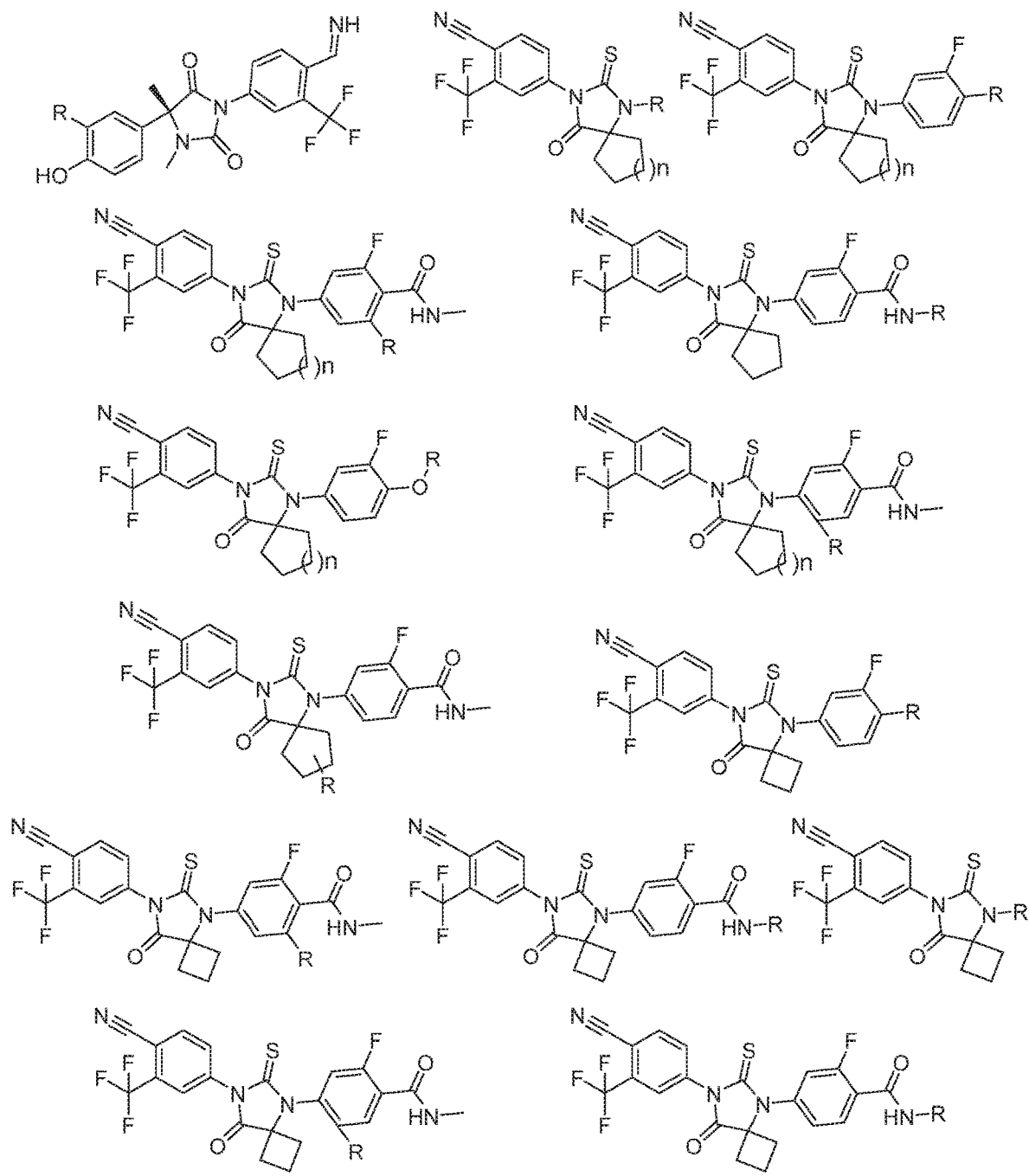
Figure 4A:
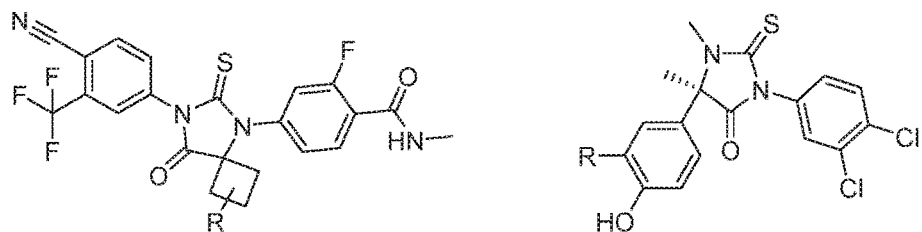
Figure 4B:
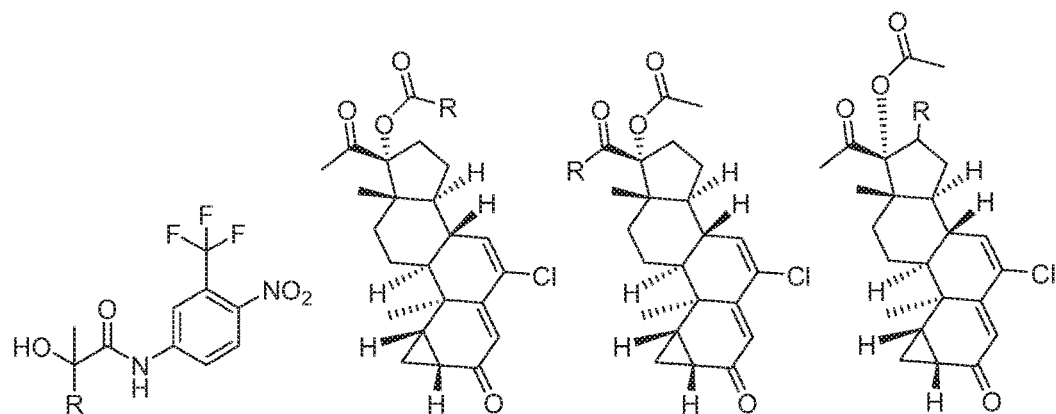
Figure 4C:
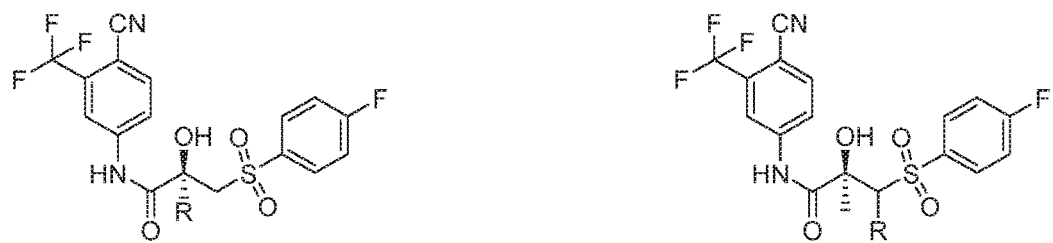
Figure 4D:
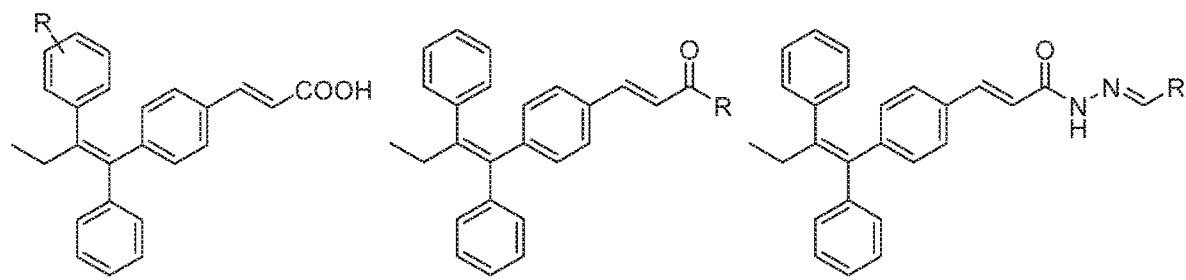
Figure 4E:
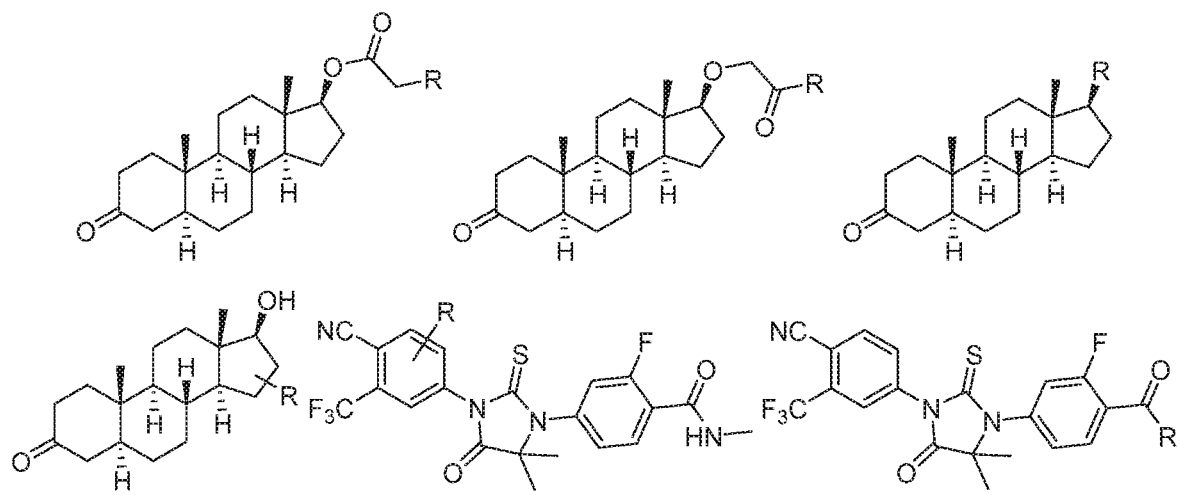

FIG. 4A-4B present examples of SETDB1 Targeting Ligands wherein R is the point at which the Linker is attached. For additional examples and related ligands, see, the PDB crystal structure 5KE2 ("SETDB1 in complex with inhibitor XST06472A", Iqbal A. et al.); the PDB crystal structure 5KE3 ("SETDB1 in complex with fragment MRT0181a", Iqbal A. et al.); the PDB crystal structure 5KH6 ("SETDB1 in complex with fragment methyl 3-(methylsulfonylamino)benzoate", Walker J. R. et al. Structural Genomics Consortium); and, the PDB crystal structure 5KCO ("SETDB1 in complex with [N]-(4-chlorophenyl)methanesulfonamide", Walker J. R. et al.)

FIG. 4C-4P present examples of SMYD2 Targeting Ligands wherein R is the point at which the Linker is attached. For additional examples and related ligands, see, the PDB crystal structure 5KJK ("SMYD2 in complex with inhibitor AZ13450370", Cowen S. D. et al.); the PDB crystal structure 5KJM ("SMYD2 in complex with AZ931", Cowen S. D. et al.); the PDB crystal structure 5KJN ("SMYD2 in complex with AZ506", Cowen S. D. et al.); the PDB crystal structure 5ARF ("SMYD2 in complex with N-[3-(4-chlorophenyl)-1-{N'-cyano-N-[3-(difluoromethoxy)phenyl] carbamimidoyl}-4 5-dihydro-1H-pyrazol-4-YL]-N-ethyl-2-hydroxyacetamide", Eggert E. et al.); the PDB crystal structure 5ARG ("SMYD2 in complex with BAY598", Eggert E. et al.); the PDB crystal structure 4YND ("SMYD2 in complex with A-893", Sweis R. F. et al.); the PDB crystal structure 4WUY ("SMYD2 in complex with LLY-507", Nguyen H. et al.); and, the PDB crystal structure 3S7B ("N-cyclohexyl-N~3~-[2-(3 4-dichlorophenyl)ethyl]-N-(2-{[2-(5-hydroxy- 3-oxo-3 4-dihydro-2H-1 4-benzoxazin-8-yl)ethyl] amino}ethyl)-beta-alaninamide", Ferguson A. D. et al.).

FIG. 4Q-4R present examples of SMYD3 Targeting Ligands wherein R is the point at which the Linker is attached. For additional examples and related ligands, see, the crystal structure 5H17 ("SMYD3 in complex with 5'-{[(3S)-3-amino-3-carboxypropyl][3-(dimethylamino)propyl]amino}-5'-deoxyadenosine", Van Aller G. S. et al.); the crystal structure 5CCL ("SMYD3 in complex with oxindole compound", Mitchell L. H. et al.); and, the crystal structure 5CCM ("Crystal structure of SMYD3 with SAM and EPZ030456").

FIG. 4S presents examples of SUV4-20H1 Targeting Ligands wherein R is the point at which the Linker is attached. For additional examples and related ligands, see, the PDB crystal structure 5CPR ("SUV4-20H1 in complex with inhibitor A-196", Bromberg K. D. et al.).

FIG. 4T-4AA present examples of Wild Type Androgen Receptor Targeting Ligands wherein R is the point at which the Linker is attached. For additional examples and related ligands, see, the PDB crystal structures 5T8E and 5T8J ("Androgen Receptor in complex with 4-(pyrrolidin-1-yl) benzonitrile derivatives", Asano M. et al.); Asano M. et al. *Bioorg. Med. Chem. Lett.* 27: 1897-1901 (2017); the PDB crystal structure 5JJM ("Androgen Receptor", Nadal M. et al.); the PDB crystal structure 5CJ6 ("Androgen Receptor in complex with 2-Chloro-4-[[(1R 2R)-2-hydroxy-2-methyl-cyclopentyl]amino]-3-methyl-benzonitrile derivatives", Saeed A. et al.); the PDB crystal structure 4QL8 ("Androgen Receptor in complex with 3-alkoxy-pyrrolo[1 2-b]pyrazolines derivatives", Ullrich T. et al.); the PDB crystal structure 4HLW ("Androgen Receptor Binding Function 3 (BF3) Site of the Human Androgen Receptor through Virtual Screening", Munuganti R. S. et al.); the PDB crystal structure 3V49 ("Androgen Receptor lbd with activator peptide and sarm inhibitor 1", Nique F. et al.); Nique F. et al. *J. Med. Chem.* 55: 8225-8235 (2012); the PDB crystal structure 2YHD ("Androgen Receptor in complex with AF2 small molecule inhibitor", Axerio-Cilies P. et al.); the PDB crystal structure 3RLJ ("Androgen Receptor ligand binding domain in complex with SARM S-22", Bohl C. E. et al.); Bohl C. E. et al. *J. Med. Chem.* 54: 3973-3976 (2011); the PDB crystal structure 3B5R ("Androgen Receptor ligand binding domain in complex with SARM C-31", Bohl C. E. et al.); Bohl C. E. et al. *Bioorg. Med. Chem. Lett.* 18: 5567-5570 (2008); the PDB crystal structure 2PIP ("Androgen Receptor ligand binding domain in complex with small molecule", Estebanez-Perpina E. et al.); Estebanez-Perpina. E. *Proc. Natl. Acad. Sci.* 104:16074-16079 (2007); the PDB crystal structure 2PNU ("Androgen Receptor ligand binding domain in complex with EM5744", Cantin L. et al.); and, the PDB crystal structure 2HVC ("Androgen Receptor ligand binding domain in complex with LGD2226", Wang F. et al.). For additional related ligands, see, Matias P. M. et al. "Structural Basis for the Glucocorticoid Response in a Mutant Human Androgen Receptor (Ar(Ccr)) Derived from an Androgen-Independent Prostate Cancer." *J. Med. Chem.* 45: 1439 (2002); Sack J. S. et al. "Crystallographic structures of the ligand-binding domains of the androgen receptor and its T877A mutant complexed with the natural agonist dihydrotestosterone." *Proc. Natl. Acad. Sci.* 98: 4904-4909 (2001); He B. et al. "Structural basis for androgen receptor interdomain and coactivator interactions suggests a transition in nuclear receptor activation function dominance." *Mol. Cell* 16: 425-438 (2004); Pereira de Jesus-Tran K. "Comparison of crystal structures of human androgen receptor ligand-binding domain complexed with various agonists reveals molecular determinants responsible for binding affinity." *Protein Sci.* 15: 987-999 (2006); Bohl C. E. et al. "Structural Basis for Accommodation of Nonsteroidal Ligands in the Androgen Receptor." *Mol Pharmacol.* 63(1): 211-23 (2003); Sun C. et al. "Discovery of potent orally-active and muscle-selective androgen receptor modulators based on an N-aryl-hydroxybicyclohydantoin scaffold." *J. Med. Chem.* 49: 7596-7599 (2006); Nirschl A. A. et al. "N-aryl-oxazolidin-2-imine muscle selective androgen receptor modulators enhance potency through pharmacophore reorientation." *J. Med. Chem.* 52: 2794-2798 (2009); Bohl C. E. et al. "Effect of B-ring substitution pattern on binding mode of propionamide selective androgen receptor modulators." *Bioorg. Med. Chem. Lett.* 18: 5567-5570 (2008); Ullrich T. et al. "3-alkoxy-pyrrolo[1 2-b]pyrazolines as selective androgen receptor modulators with ideal physicochemical properties for transdermal administration." *J. Med. Chem.* 57: 7396-7411 (2014); Saeed A. et al. "2-Chloro-4-[[(1R 2R)-2-hydroxy-2-methyl-cyclopentyl]amino]-3-methyl-benzonitrile: A Transdermal Selective Androgen Receptor Modulator (SARM) for Muscle Atrophy." *J. Med. Chem.* 59: 750-755 (2016); Nique et al. "Discovery of diarylhydantoins as new selective androgen receptor modulators." *J. Med. Chem.* 55: 8225-8235 (2012); and, Michael E. Jung et al. "Structure-Activity Relationship for Thiohydantoin Androgen Receptor Antagonists for Castration-Resistant Prostate Cancer (CRPC)." *J. Med. Chem.* 53: 2779-2796 (2010).

FIG. 4BB presents examples of Mutant T877A Androgen Receptor Targeting Ligands wherein R is the point at which the Linker is attached. For additional examples and related ligands, see, the PDB crystal structure 4OGH ("Androgen Receptor T877A-AR-LBD", Hsu C. L. et al.) and the PDB crystal structure 2OZ7 ("Androgen Receptor T877A-AR-LBD", Bohl C. E. et al.).

FIG. 4CC presents examples of Mutant W741L Androgen Receptor Targeting Ligands wherein R is the point at which the Linker is attached. For additional examples and related ligands, see, the PDB crystal structure 4OJB ("Androgen Receptor T877A-AR-LBD", Hsu C. L. et al.).

FIG. 4DD-4EE presents examples of Estrogen and/or Andregon Targeting Ligands wherein R is the point at which the Linker is attached.

Figure 5A:
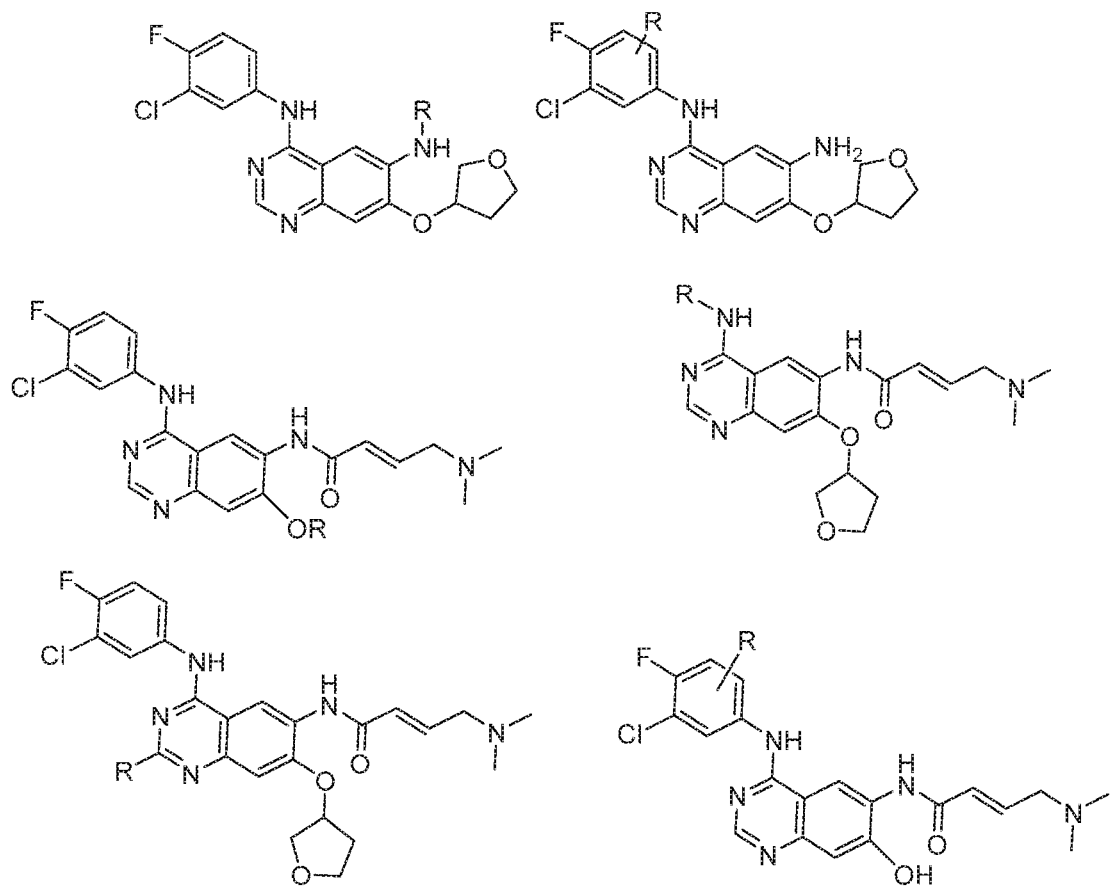

FIG. 5A presents examples of Afatinib, a Targeting Ligands for the EGFR and ErbB2/4 receptors. R is the point at which the Linker is attached.

Figure 5D:
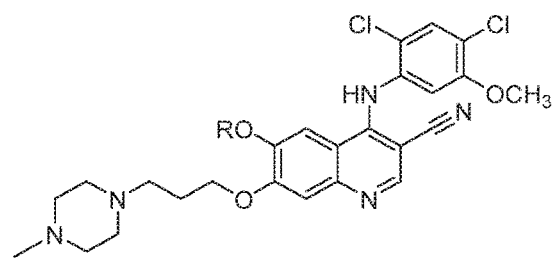
Figure 5E:
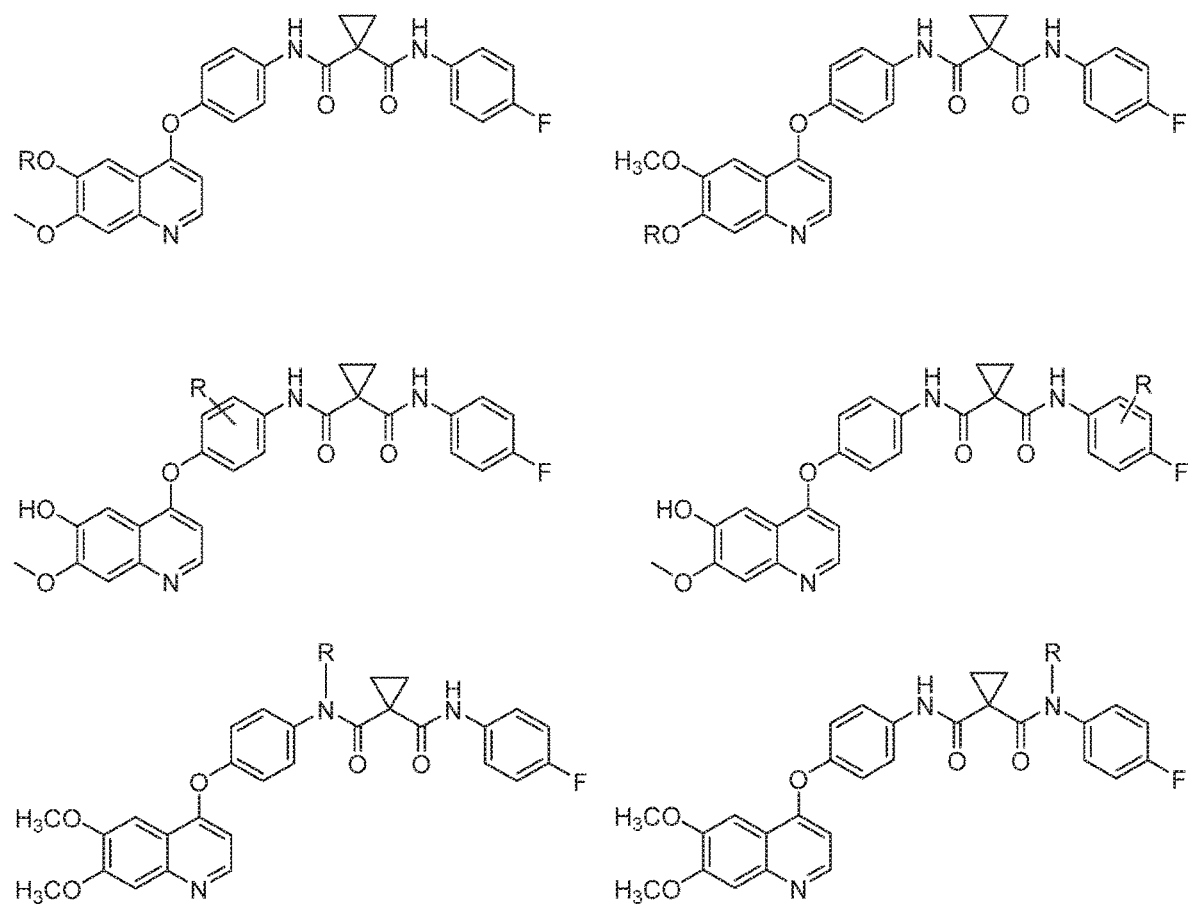
Figure 5F:
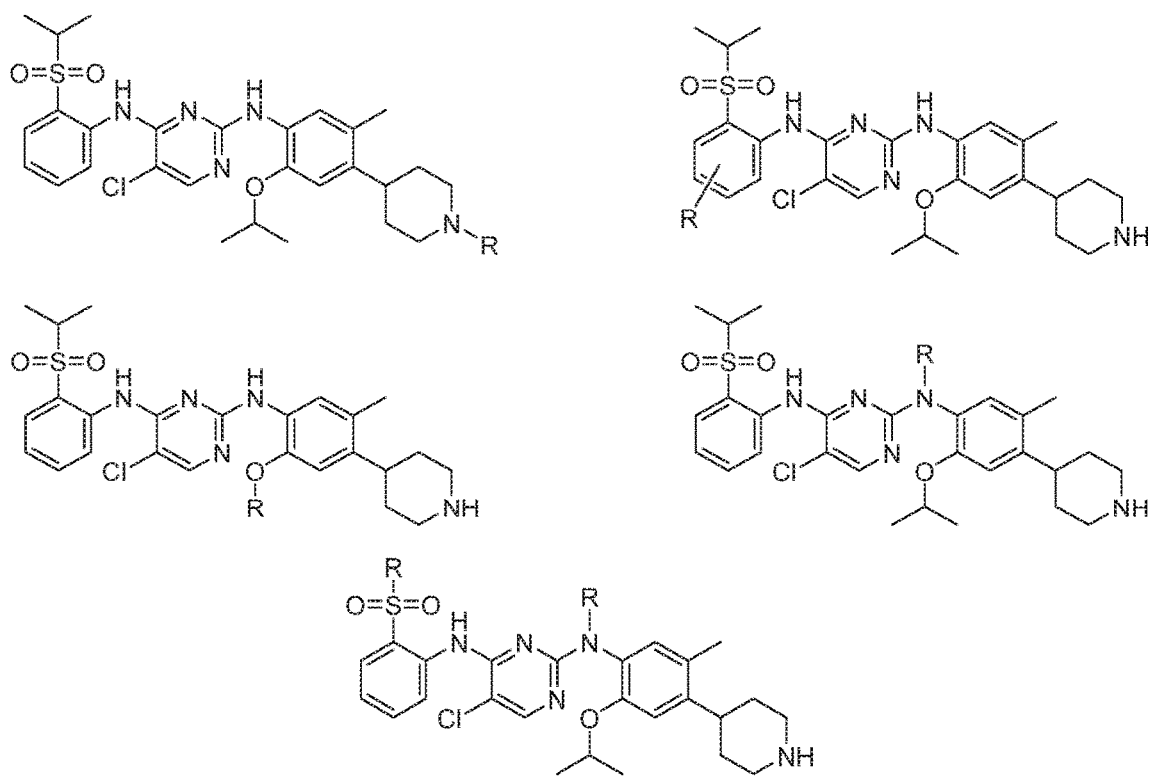
Figure 5G:
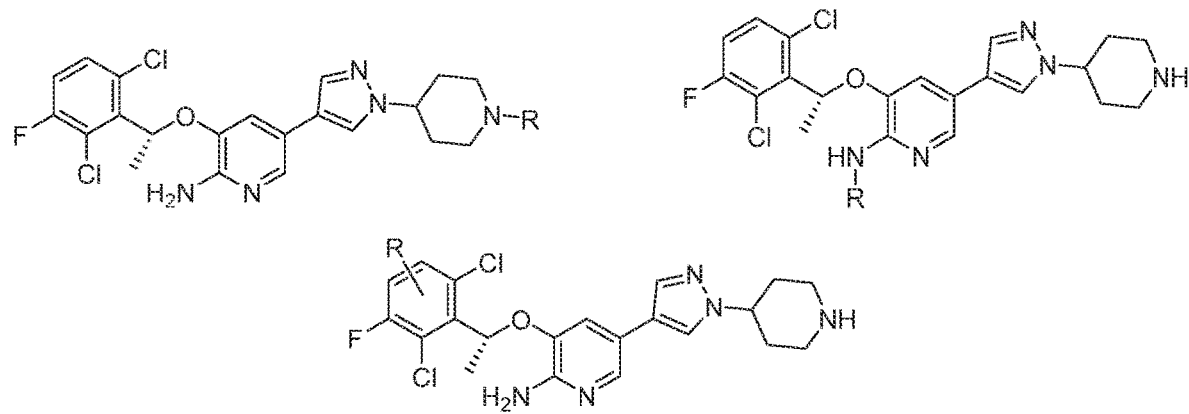
Figure 5H:
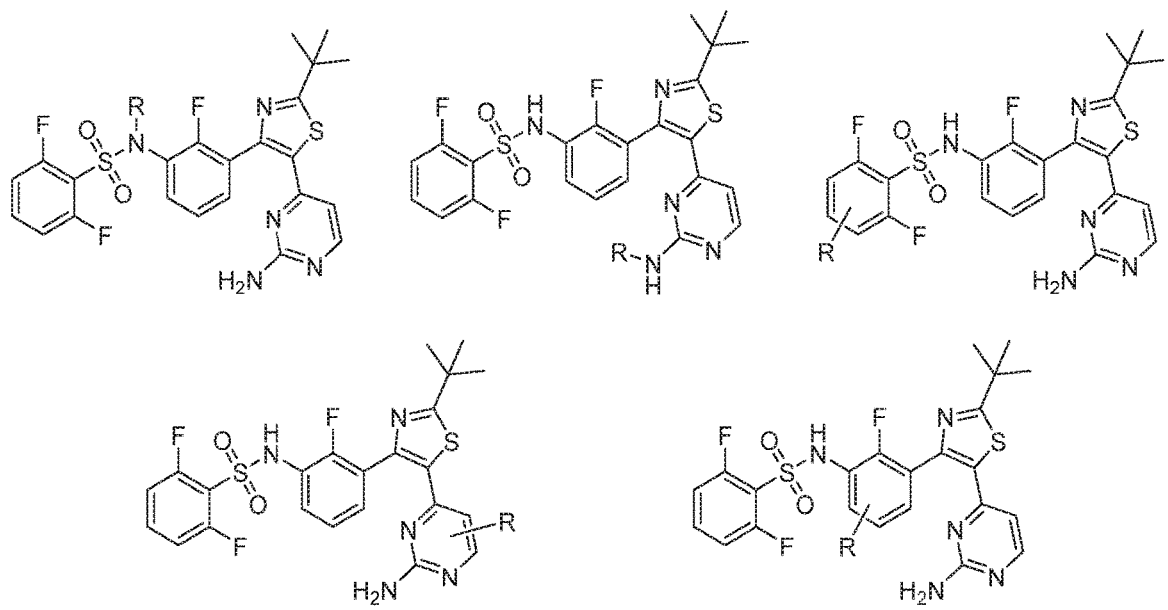
Figure 5I:
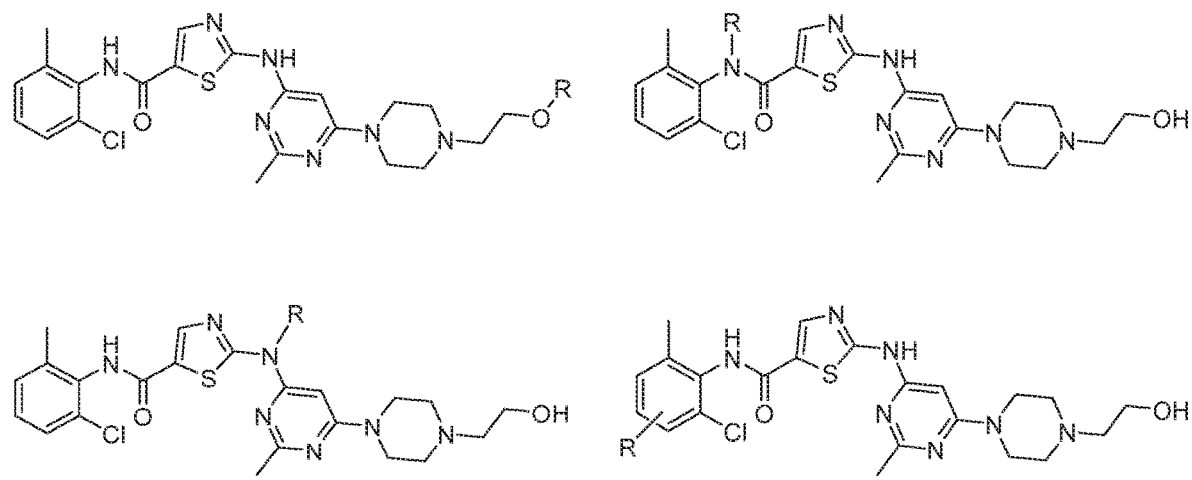
Figure 5J:
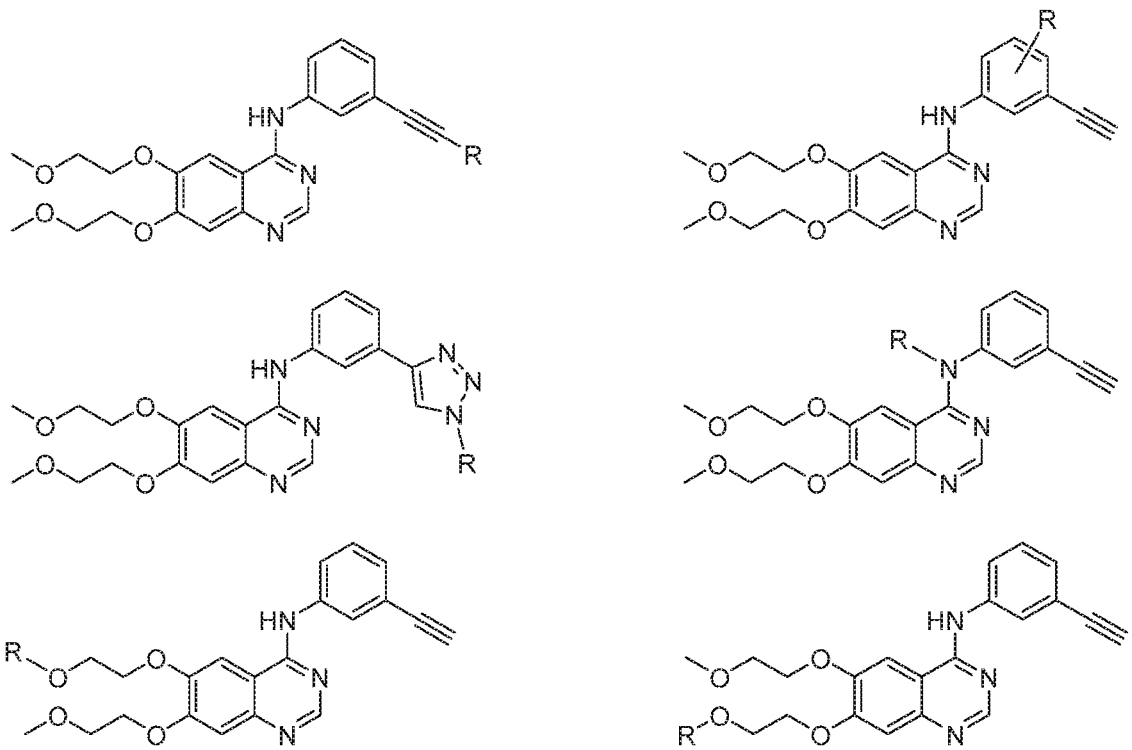
Figure 5K:
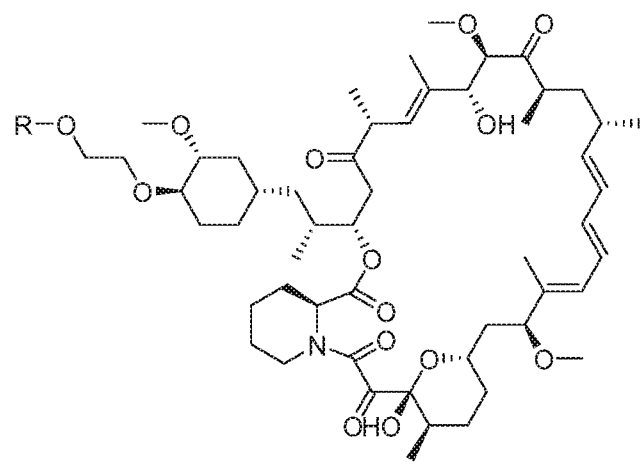
Figure 5O:
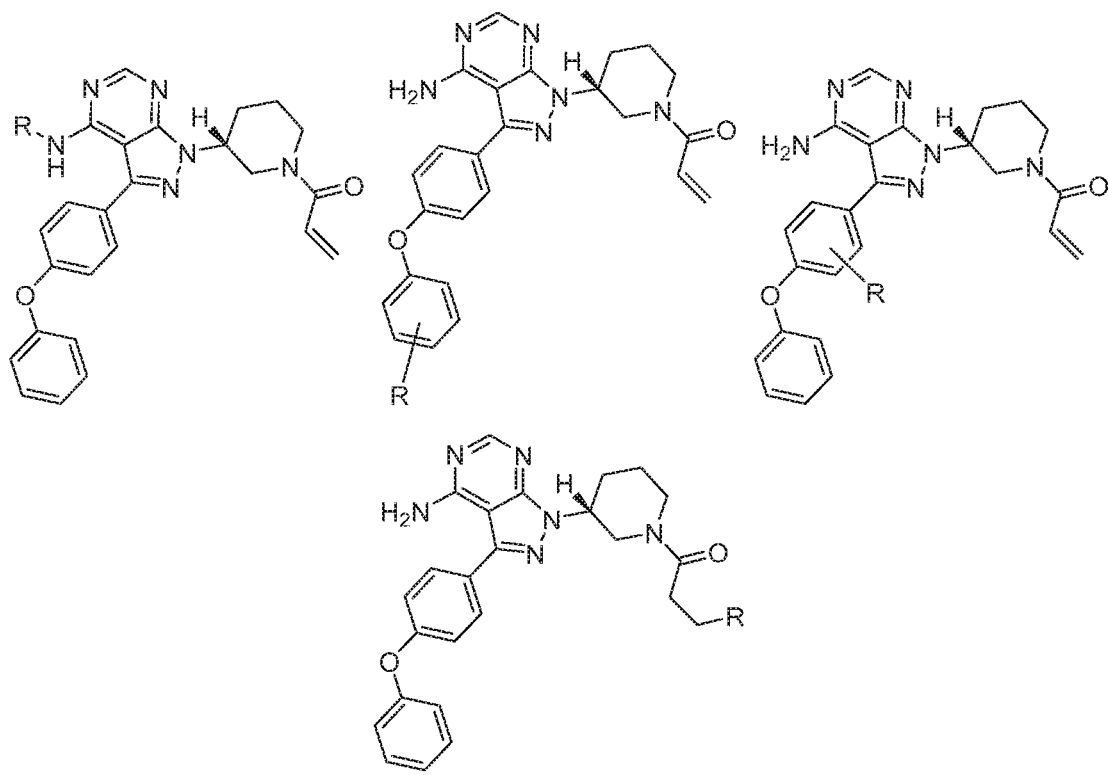
Figure 5P:
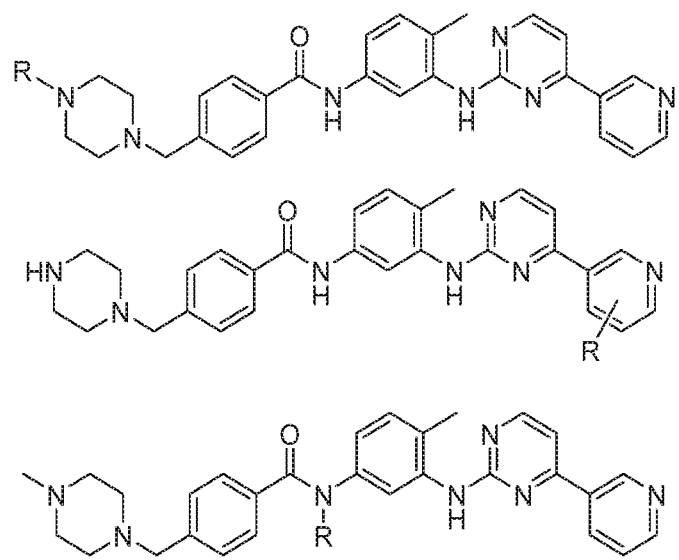
Figure 5Q:
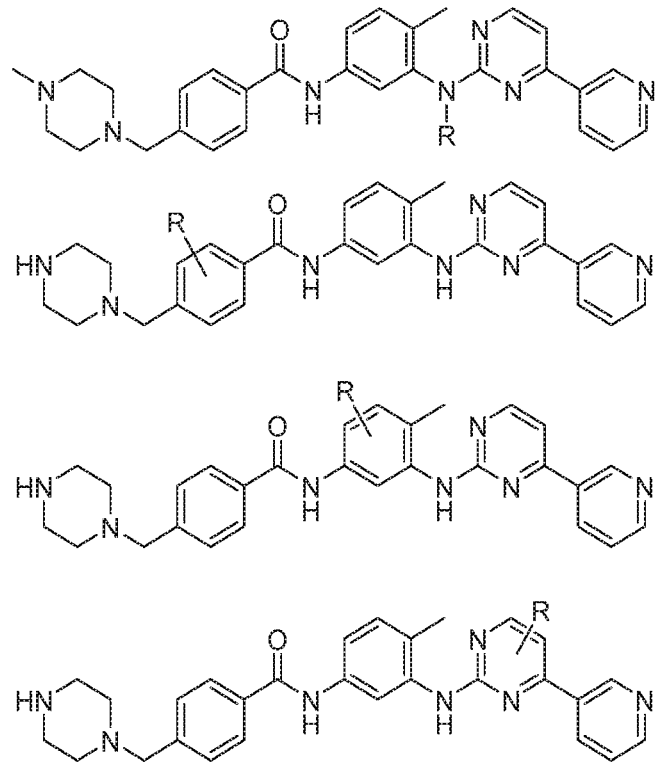
Figure 5R:
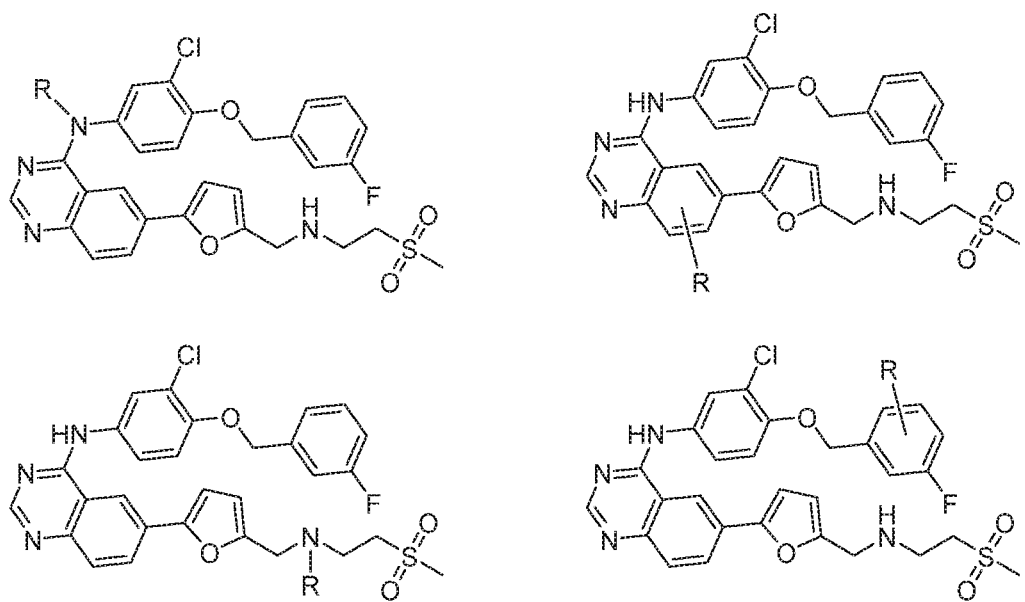
Figures 5S, 5T, 5U:
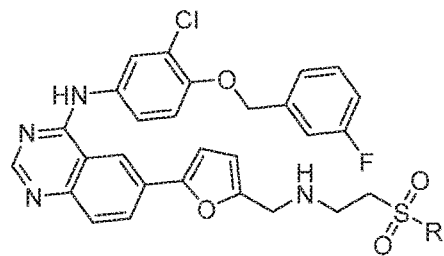
Figure 5V:
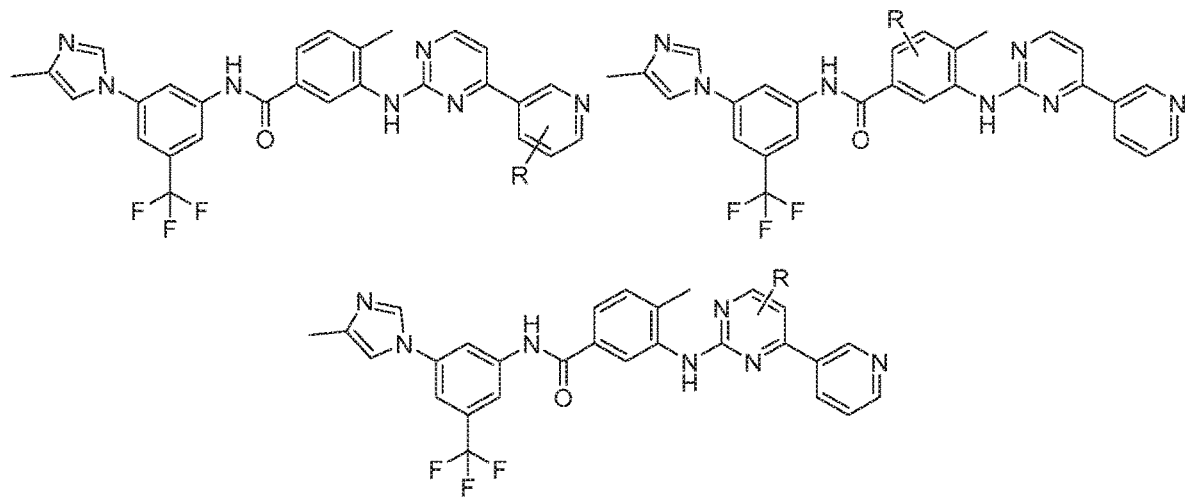
Figure 5W:
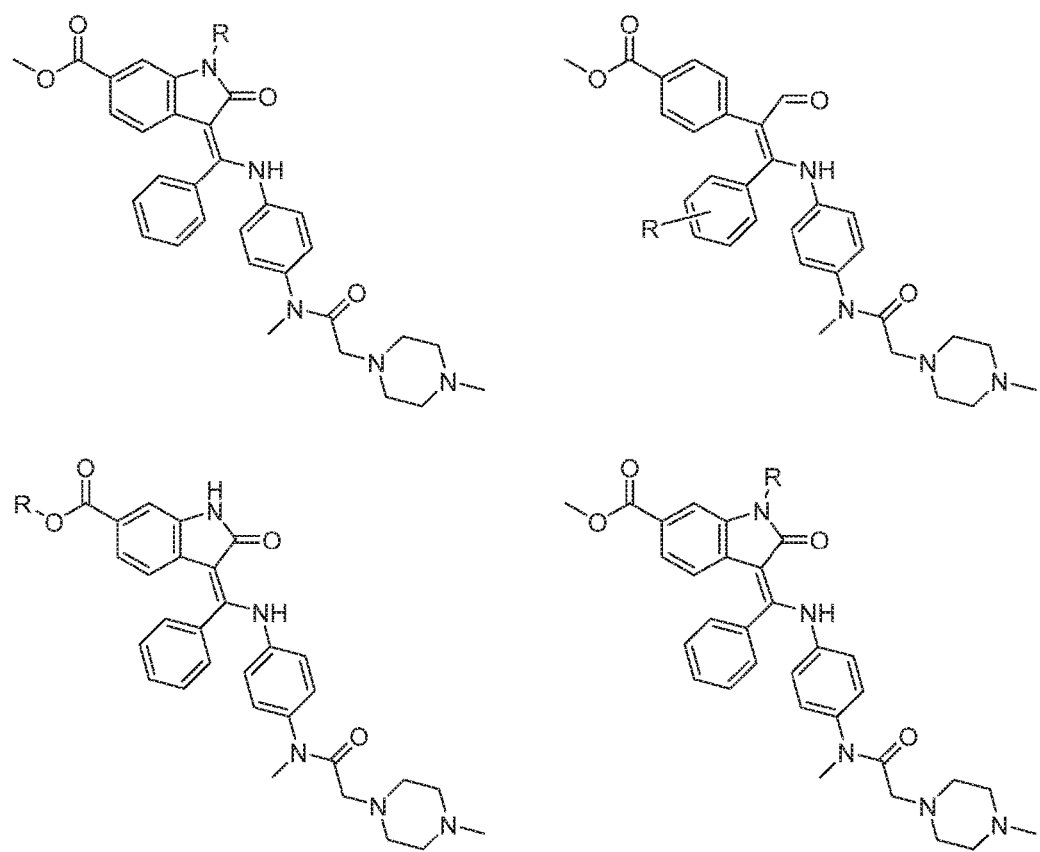
Figure 5X:
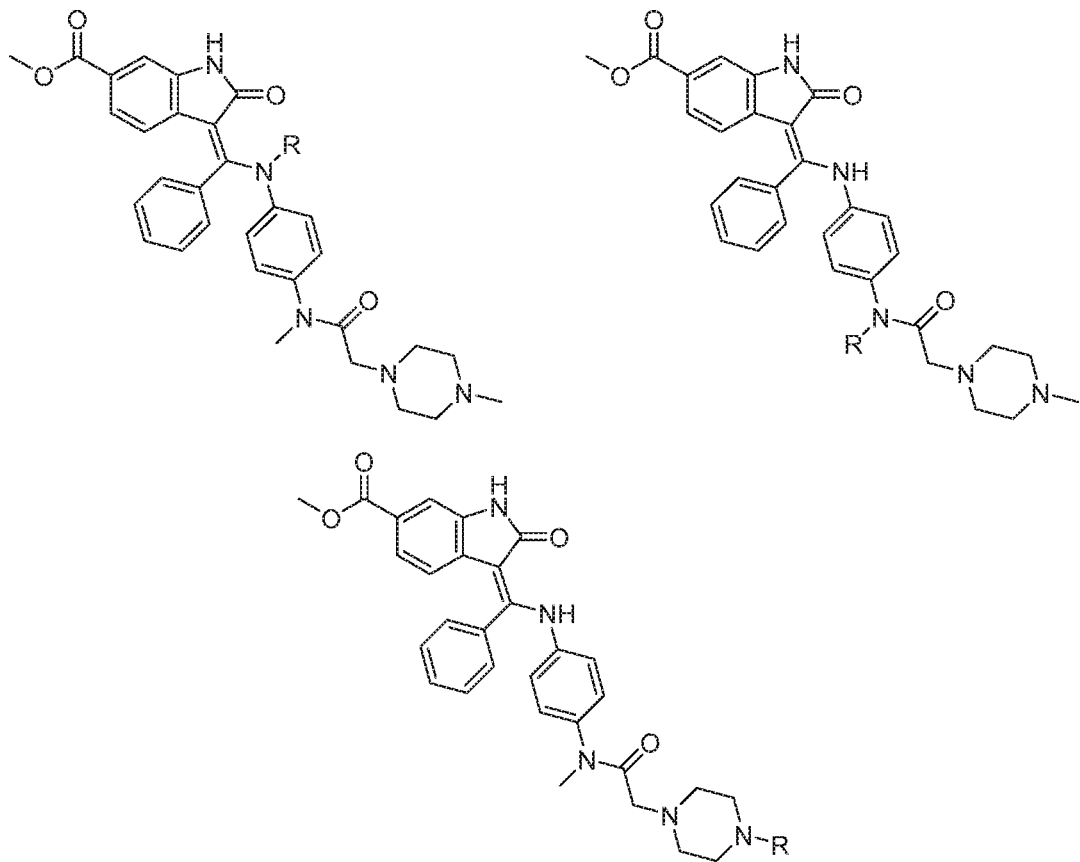
Figure 5Y:
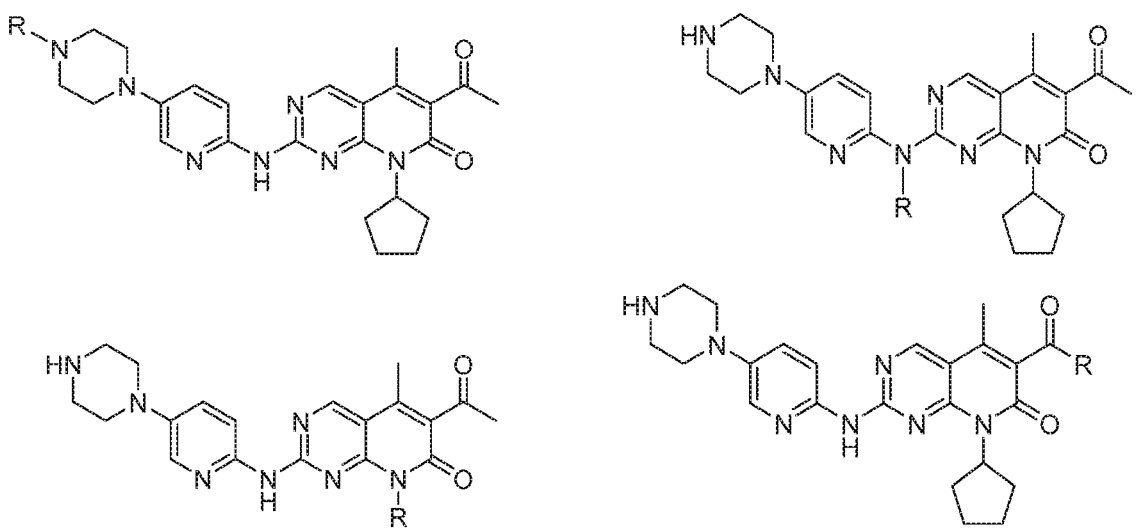
Figure 5Z:
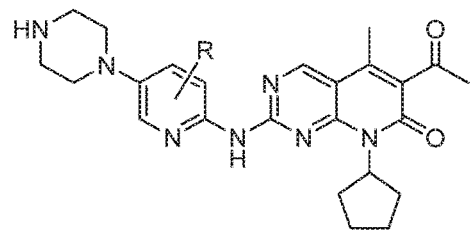
Figure 5A:
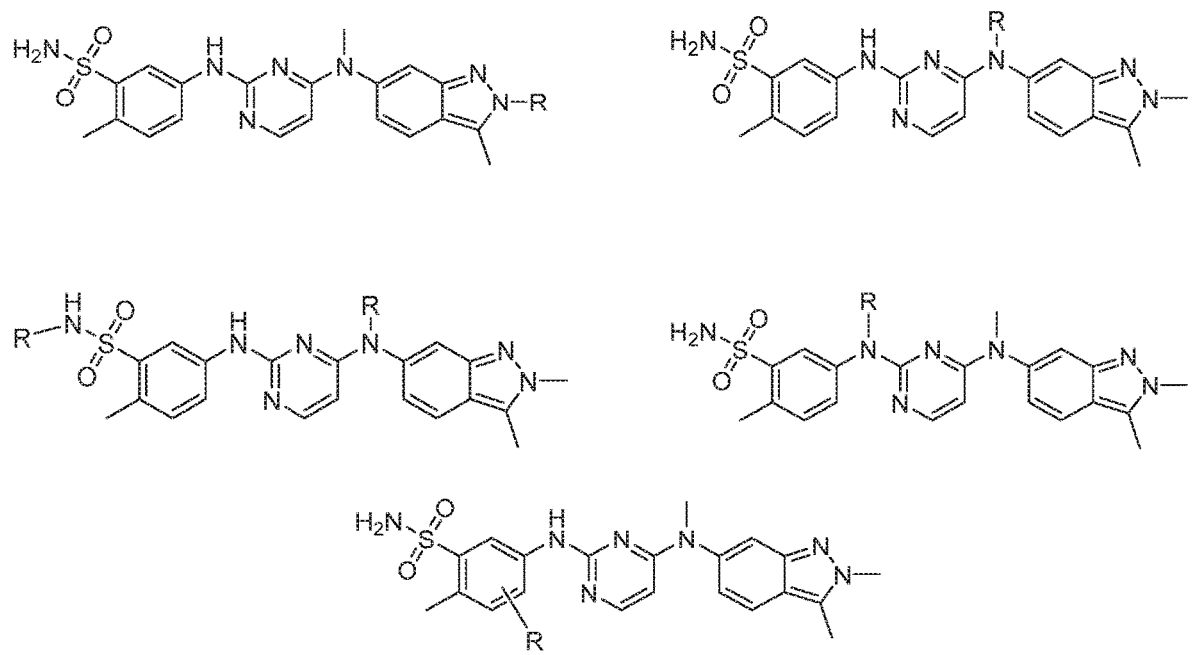
Figure 5B:
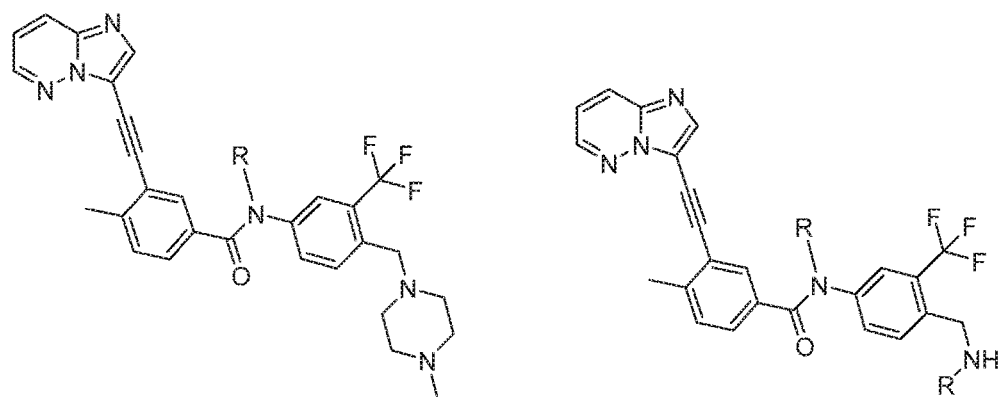

FIG. 5B presents examples of Axitinib, a Targeting Ligands for the VEGFR1/2/3, PDGFRP3, and Kit receptors. R is the point at which the Linker is attached.

Figure 5C:
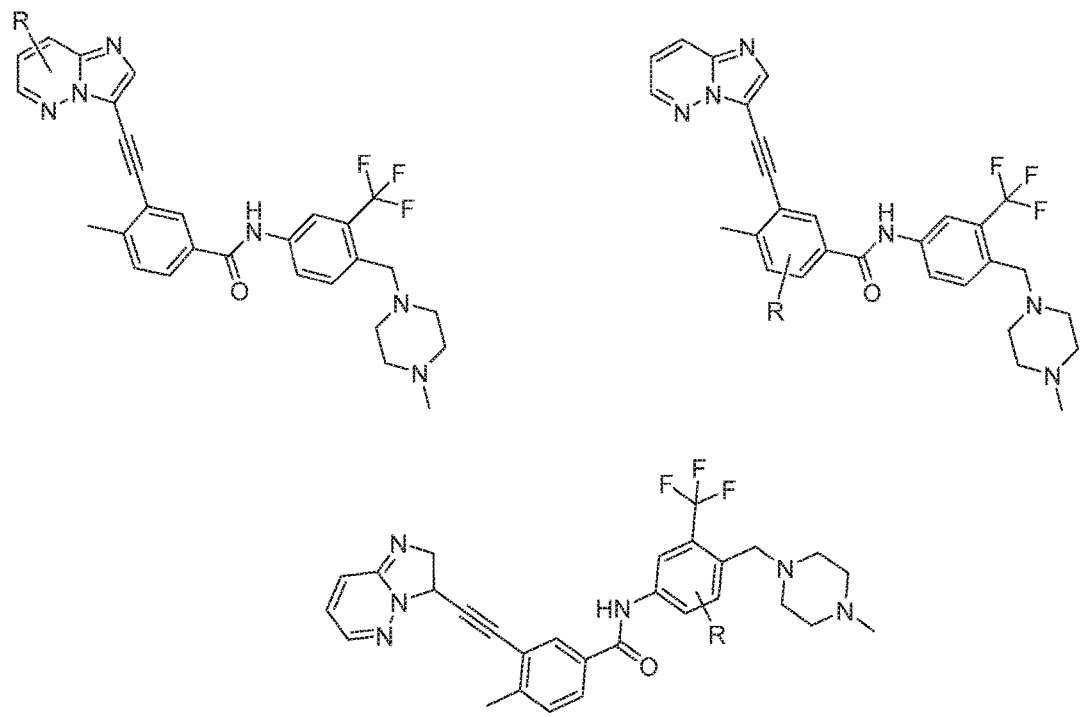
Figure 5D:
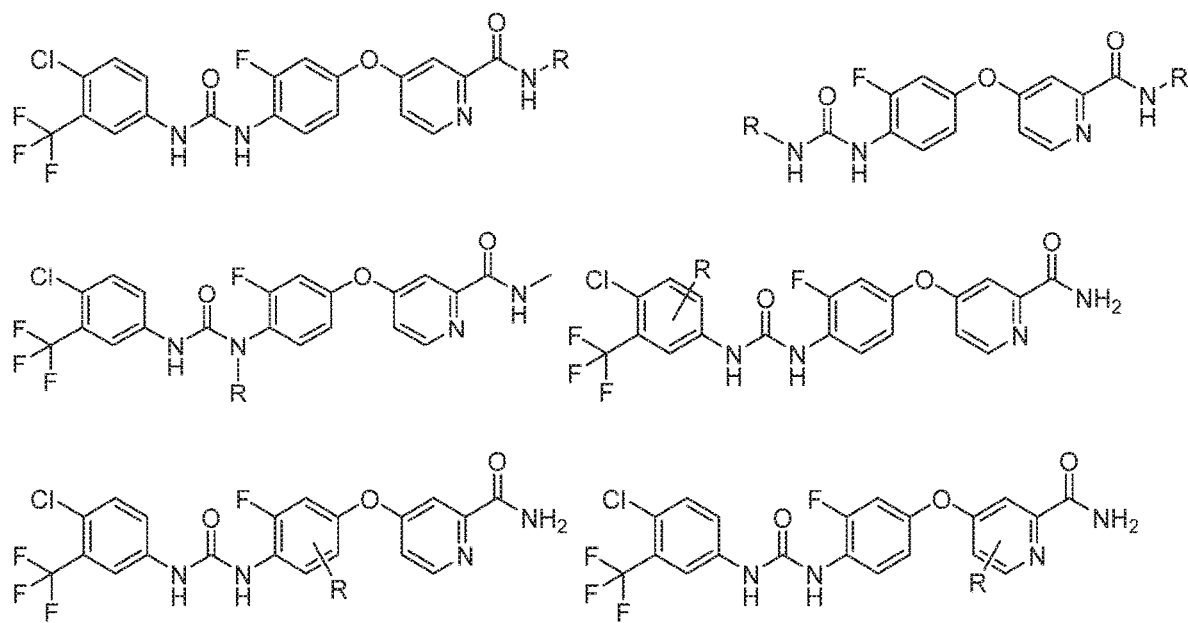
Figure 5E:
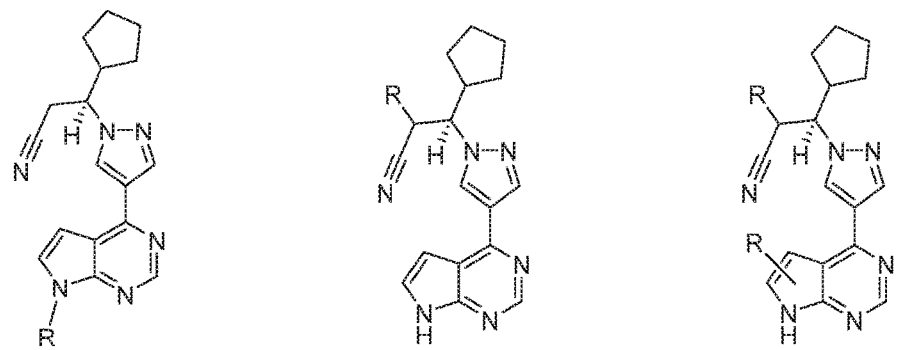
Figure 5F:
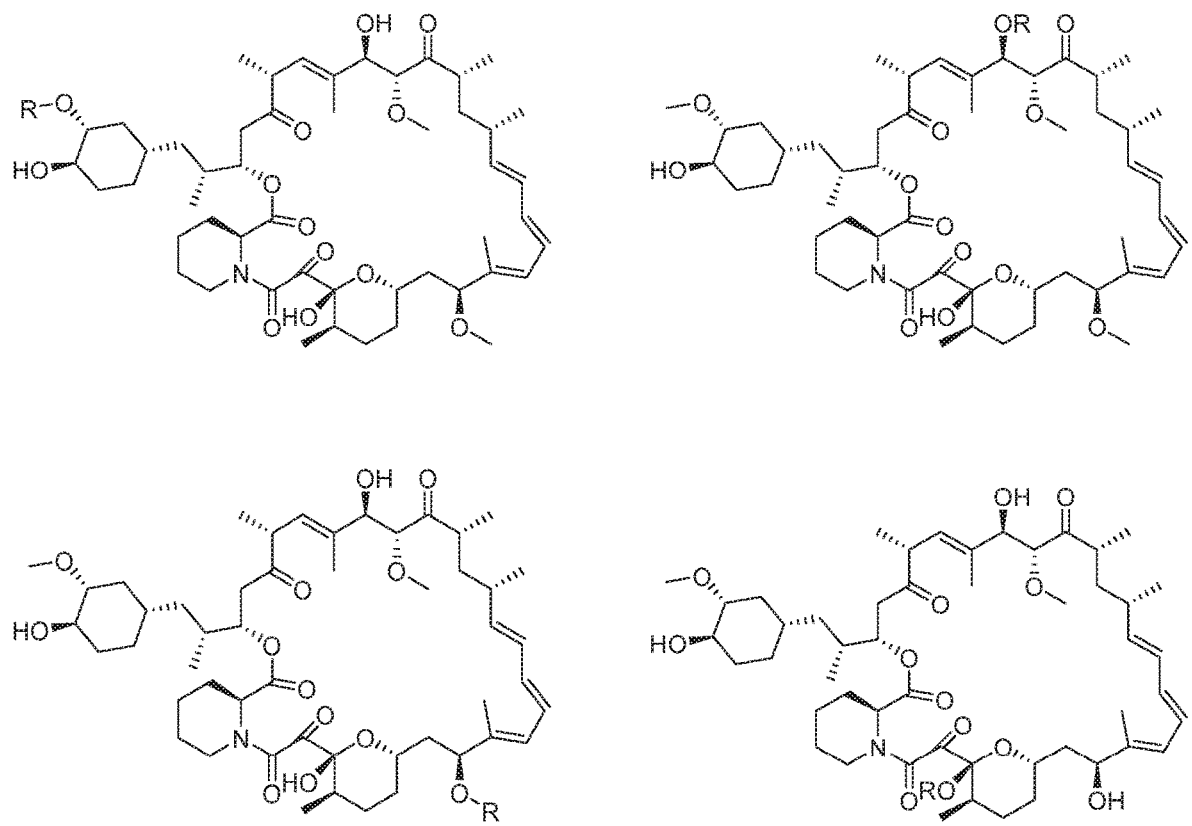
Figure 5G:
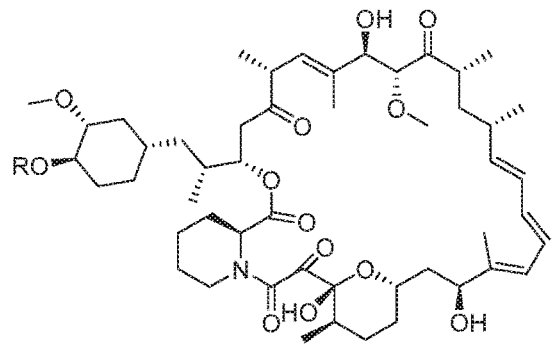
Figure 5H:
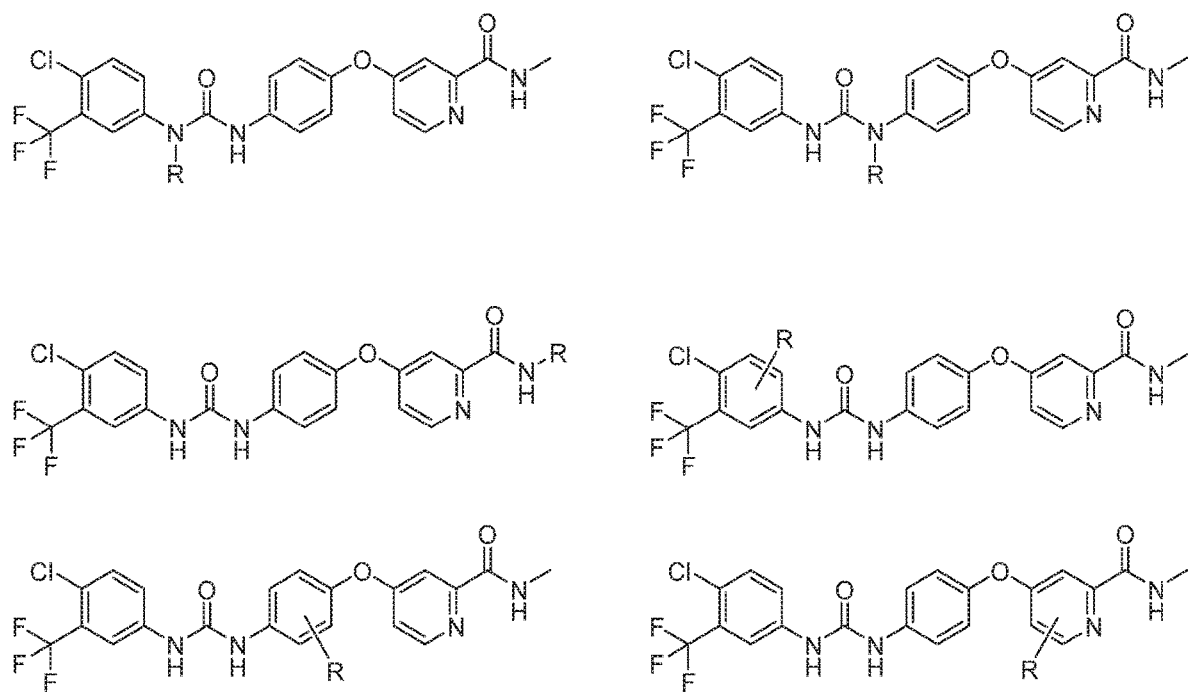
Figure 5I:
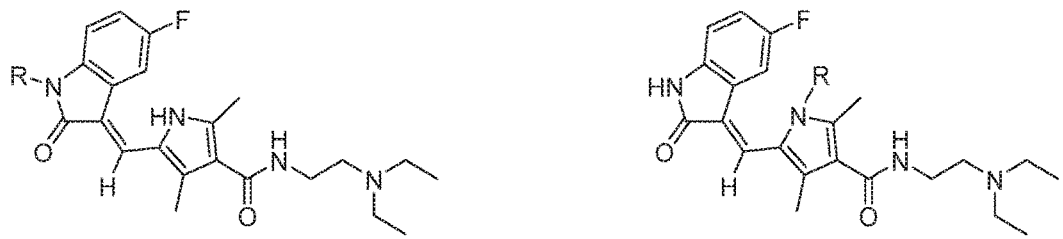

FIG. 5C-5D present examples of Bosutinib, a Targeting Ligands for the BCR-Abl, Src, Lyn and Hck receptors. R is the point at which the Linker is attached.

FIG. 5E presents examples of Cabozantinib, a Targeting Ligands for the RET, c-Met, VEGFR1/2/3, Kit, TrkB, Flt3, Axl, and Tie 2 receptors. R is the point at which the Linker is attached.

FIG. 5F presents examples of Ceritinib, a Targeting Ligands for the ALK, IGF-1R, InsR, and ROS1 receptors. R is the point at which the Linker is attached.

FIG. 5G presents examples of Crizotinib, a Targeting Ligands for the ALK, c-Met, HGFR, ROS1, and MST1R receptors. R is the point at which the Linker is attached.

FIG. 5H presents examples of Dabrafenib, a Targeting Ligands for the B-Raf receptor. R is the point at which the Linker is attached.

FIG. 5I presents examples of Dasatinib, a Targeting Ligands for the BCR-Abl, Src, Lck, Lyn, Yes, Fyn, Kit, EphA2, and PDGFRP3 receptors. R is the point at which the Linker is attached.

FIG. 5J presents examples of Erlotinib, a Targeting Ligands for the EGFR receptor. R is the point at which the Linker is attached.

Figure 5L:
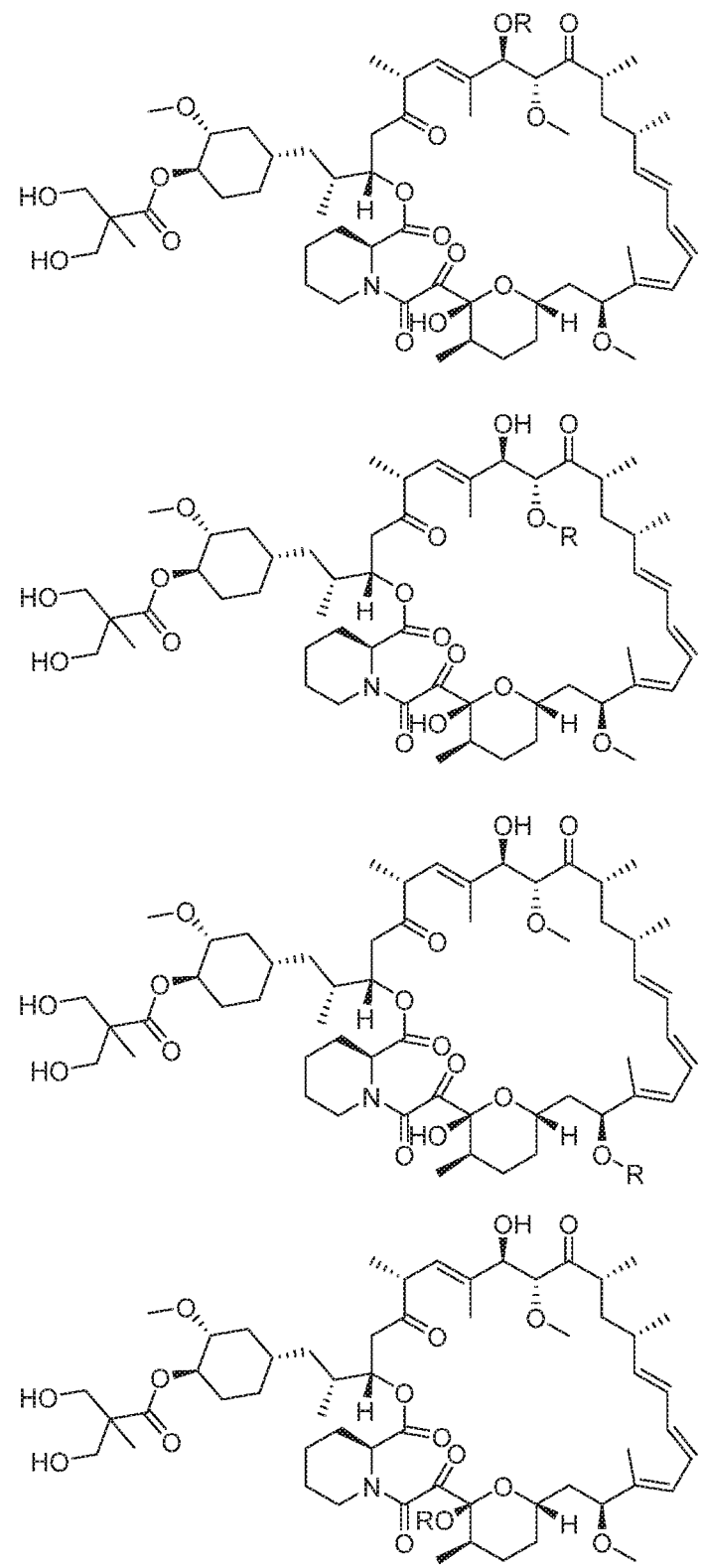
Figure 5M:
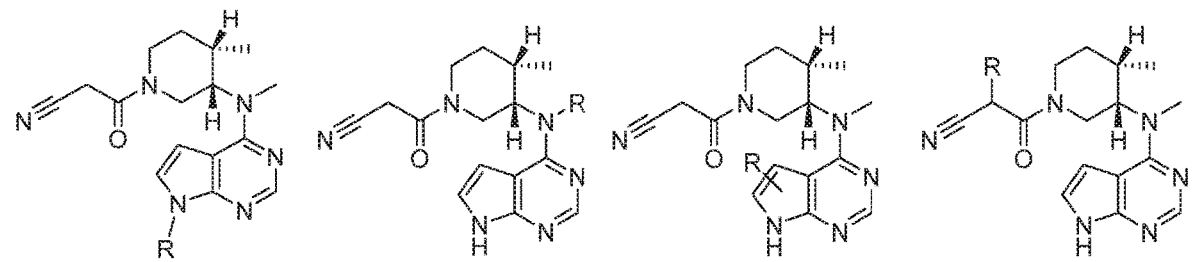

FIG. 5K-5M presents examples of Everolimus, a Targeting Ligands for the HER2 breast cancer receptor, the PNET receptor, the RCC receptors, the RAML receptor, and the SEGA receptor. R is the point at which the Linker is attached.

Figure 5N:
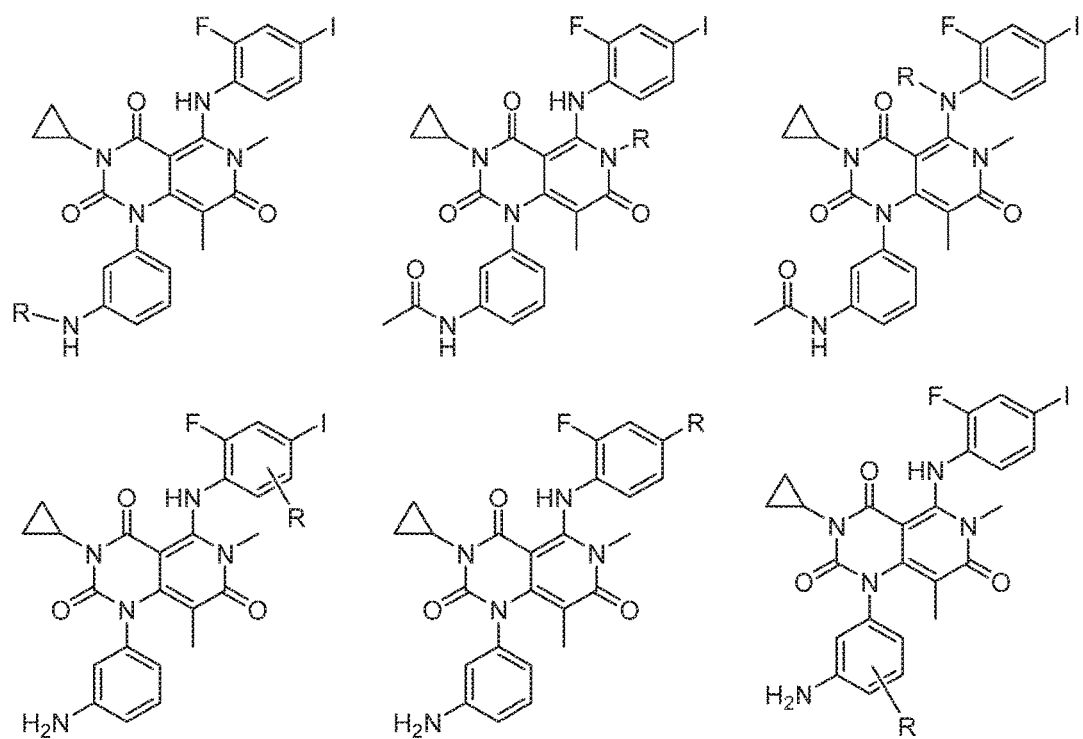
Figure 5O:
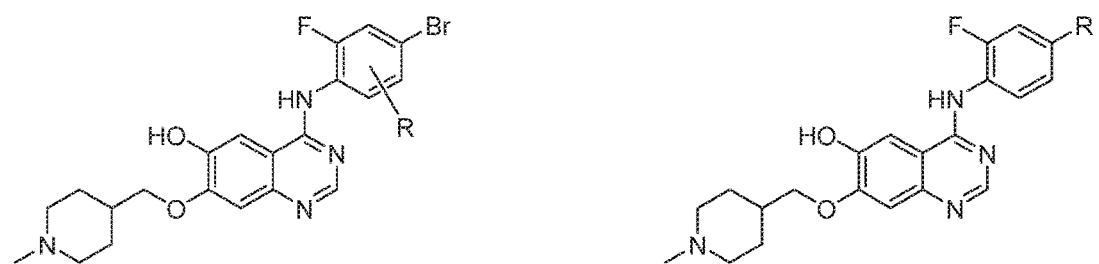
Figure 5P:
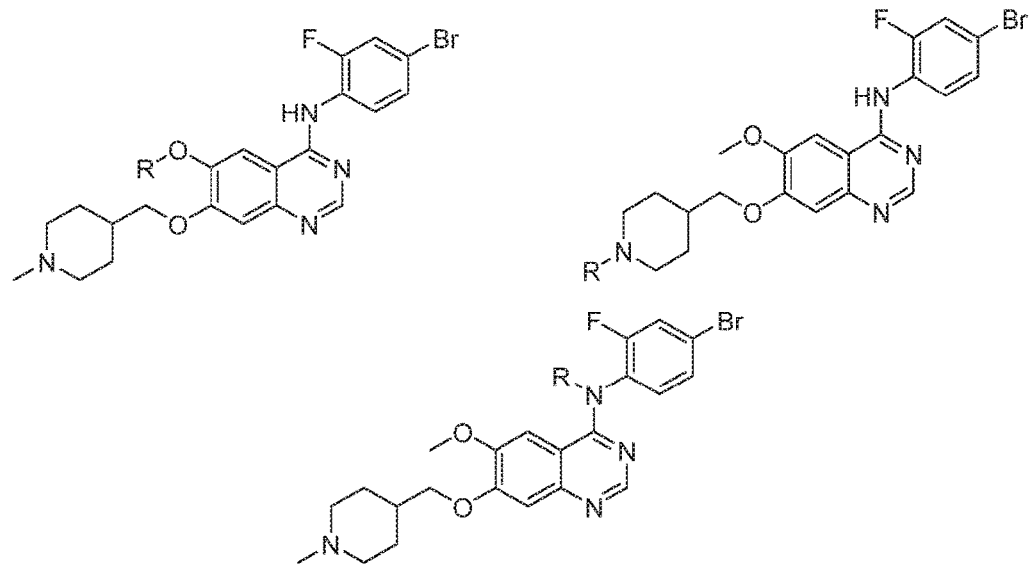
Figure 5Q:
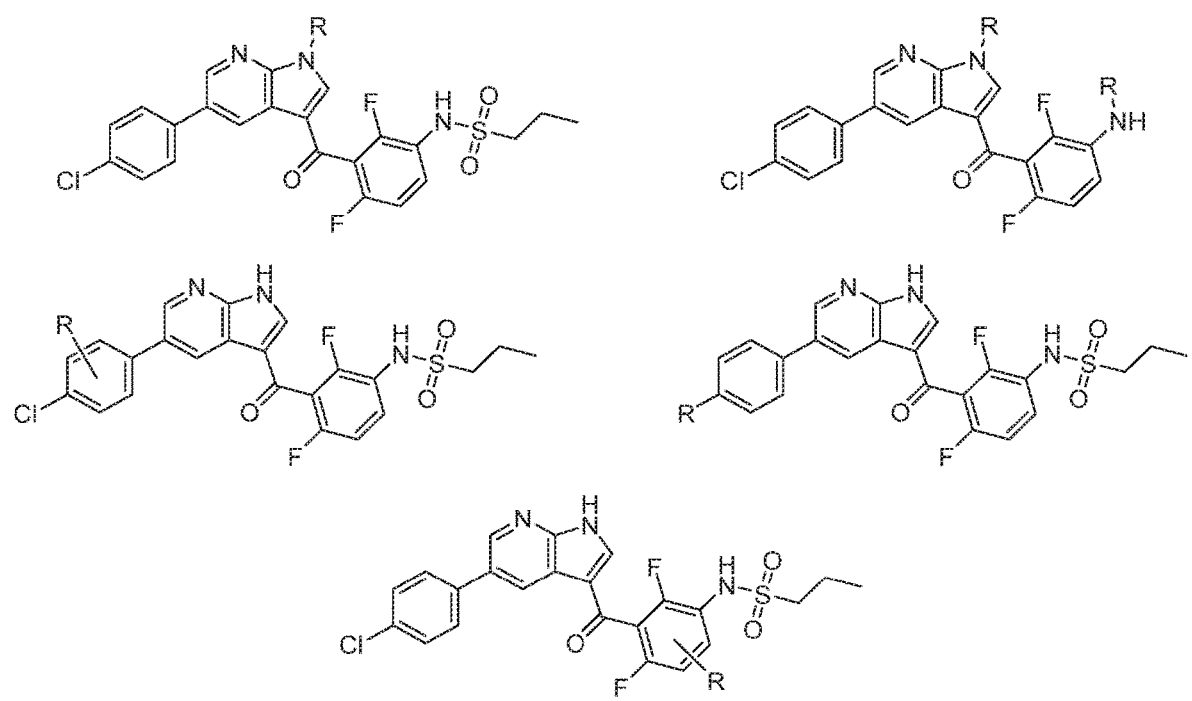
Figure 5R:
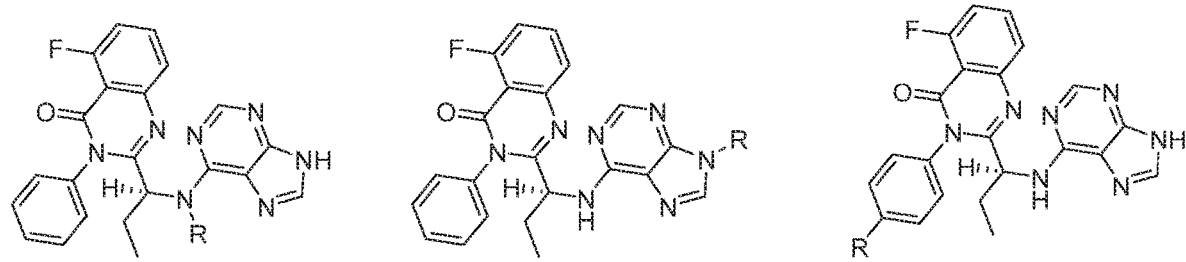
Figure 5S:
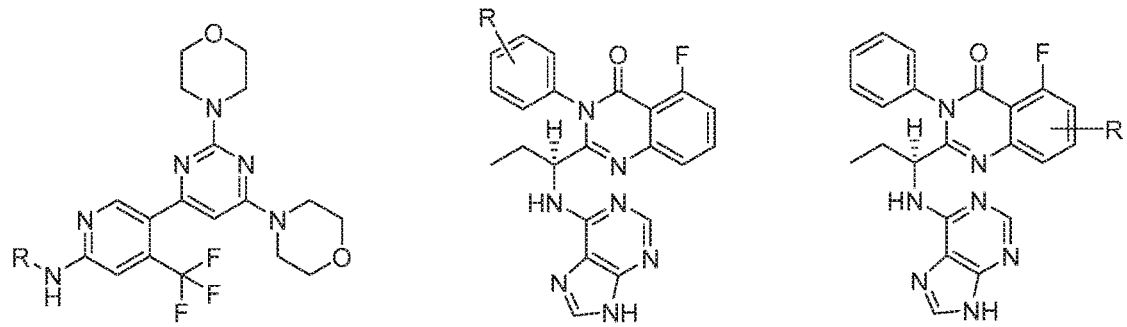
Figure 5T:
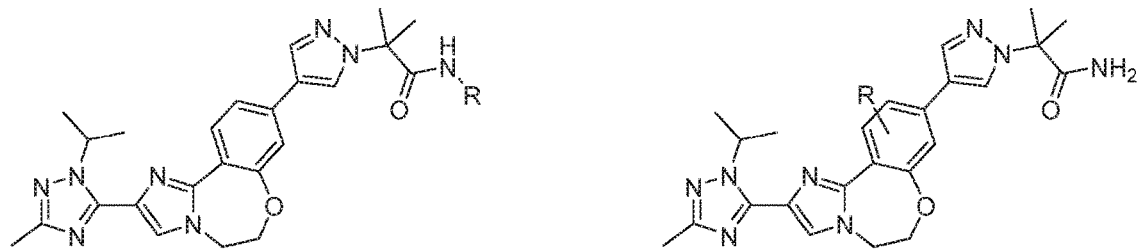
Figure 5U:
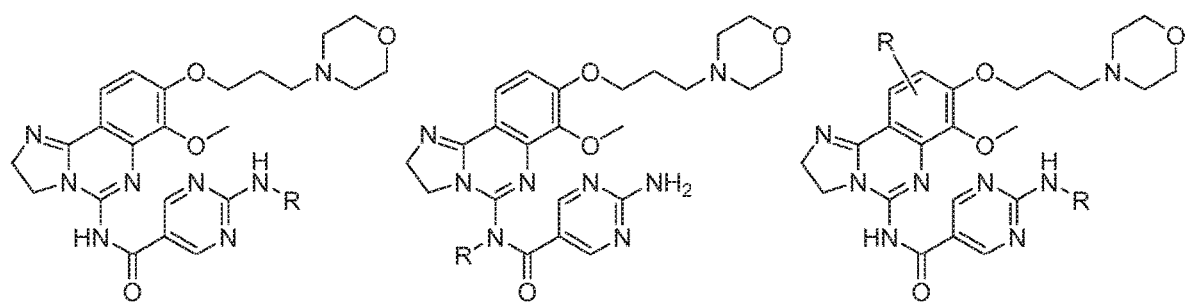
Figure 5V:
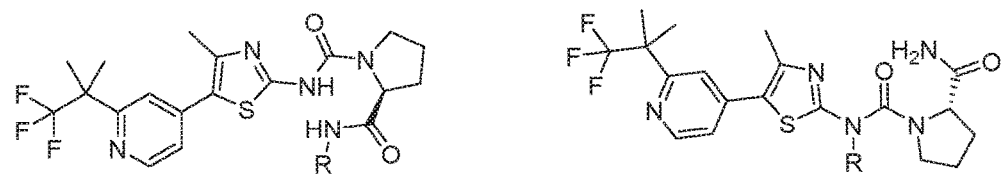
Figure 5W:
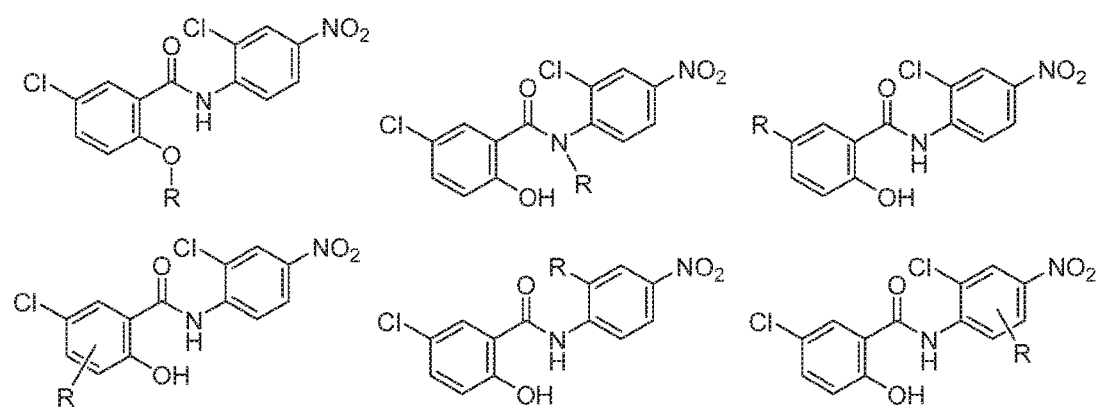

FIG. 5N presents examples of Gefitinib, a Targeting Ligands for the EGFR and PDGFR receptors. R is the point at which the Linker is attached.

FIG. 5O presents examples of Ibrutinib, a Targeting Ligands for the BTK receptor. R is the point at which the Linker is attached.

FIG. 5P-5Q present examples of Imatinib, a Targeting Ligands for the BCR-Abl, Kit, and PDGFR receptors. R is the point at which the Linker is attached.

FIG. 5R-5S present examples of Lapatinib, a Targeting Ligands for the EGFR and ErbB2 receptors. R is the point at which the Linker is attached.

FIG. 5T presents examples of Lenvatinib, a Targeting Ligands for the VEGFR1/2/3, FGFR1/2/3/4, PDGFRα, Kit, and RET receptors. R is the point at which the Linker is attached.

FIG. 5U-5V a present examples of Nilotinib, a Targeting Ligands for the BCR-Abl, PDGRF, and DDR1 receptors. R is the point at which the Linker is attached.

FIG. 5W-5X present examples of Nintedanib, a Targeting Ligands for the FGFR1/2/3, Flt3, Lck, PDGFRα/β, and VEGFR1/2/3 receptors. R is the point at which the Linker is attached.

FIG. 5Y-5Z present examples of Palbociclib, a Targeting Ligands for the CDK4/6 receptor. R is the point at which the Linker is attached.

FIG. 5AA presents examples of Pazopanib, a Targeting Ligands for the VEGFR1/2/3, PDGFRα/β, FGFR1/3, Kit, Lck, Fms, and Itk receptors. R is the point at which the Linker is attached.

FIG. 5BB-5CC present examples of Ponatinib, a Targeting Ligands for the BCR-Abl, T315I VEGFR, PDGFR, FGFR, EphR, Src family kinases, Kit, RET, Tie2, and Flt3 receptors. R is the point at which the Linker is attached.

FIG. 5DD presents examples of Regorafenib, a Targeting Ligands for the VEGFR1/2/3, BCR-Abl, B-Raf, B-Raf (V600E), Kit, PDGFRα/β, RET, FGFR1/2, Tie2, and Eph2A. R is the point at which the Linker is attached.

FIG. 5EE presents examples of Ruxolitinib, a Targeting Ligands for the JAK1/2 receptors. R is the point at which the Linker is attached.

FIG. 5FF-5GG present examples of Sirolimus, a Targeting Ligands for the FKBP12/mTOR receptors. R is the point at which the Linker is attached.

FIG. 5HH presents examples of Sorafenib, a Targeting Ligands for the B-Raf, CDK8, Kit, Flt3, RET, VEGFR1/2/3, and PDGFR receptors. R is the point at which the Linker is attached.

FIG. 5II-5JJ present examples of Sunitinib, a Targeting Ligands for PDGFRα/β, VEGFR1/2/3, Kit, Flt3, CSF-1R, RET. R is the point at which the Linker is attached.

FIG. 5KK-5LL present examples of Temsirolimus, a Targeting Ligands FKBP12/mTOR. R is the point at which the Linker is attached.

FIG. 5MM presents examples of Tofacitinib, a Targeting Ligands for JAK3 receptors. R is the point at which the Linker is attached.

FIG. 5NN presents examples of Trametinib, a Targeting Ligands for the MEK1/2 receptors. R is the point at which the Linker is attached.

FIG. 5OO-5PP presents examples of Vandetanib, a Targeting Ligands for the EGFR, VEGFR, RET, Tie2, Brk, and EphR. R is the point at which the Linker is attached.

FIG. 5QQ presents examples of Vemurafenib, a Targeting Ligands for the A/B/C-Raf, KSR1, and B-Raf (V600E) receptors. R is the point at which the Linker is attached.

FIG. 5RR presents examples of Idelasib, a Targeting Ligands for the PI3Ka receptor. R is the point at which the Linker is attached.

FIG. 5SS presents examples of Buparlisib, a Targeting Ligands for the PI3Ka receptor. R is the point at which the Linker is attached.

FIG. 5TT presents examples of Taselisib, a Targeting Ligands for the PI3Ka receptor. R is the point at which the Linker is attached.

FIG. 5UU presents examples of Copanlisib, a Targeting Ligands for the PI3Ka. R is the point at which the Linker is attached.

FIG. 5VV presents examples of Alpelisib, a Targeting Ligands for the PI3Ka. R is the point at which the Linker is attached.

FIG. 5WW presents examples of Niclosamide, a Targeting Ligands for the CNNTB1. R is the point at which the Linker is attached.

Figure 6A:
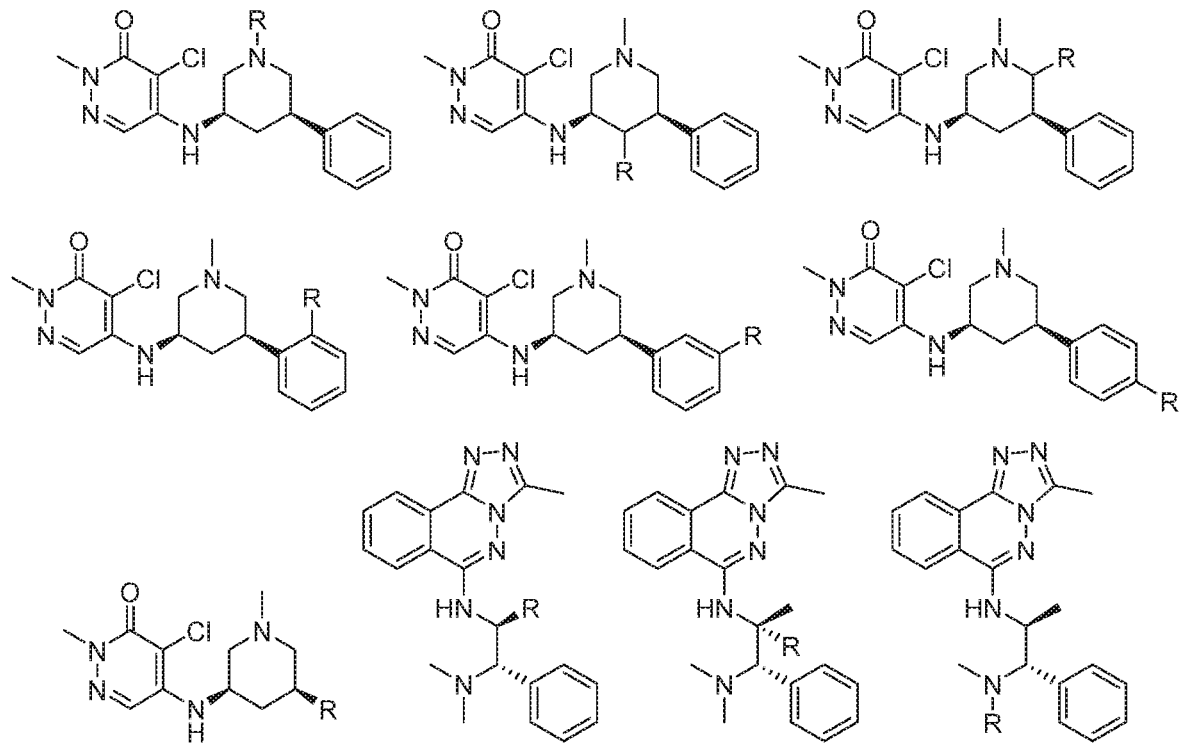
Figure 6B:
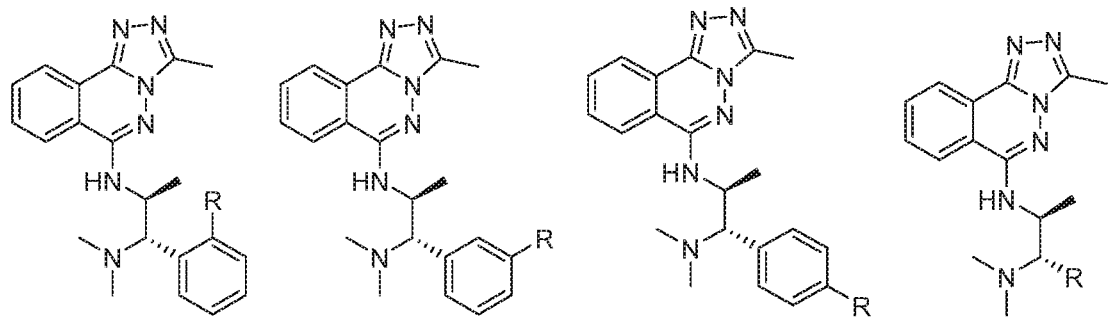

FIG. 6A-6B present examples of the BRD4 Bromodomains of PCAF and GCN5 receptors 1 Targeting Ligands wherein R is the point at which the Linker is attached. For additional examples and related ligands, see, the PDB crystal structure 5tpx ("Discovery of a PCAF Bromodomain Chemical Probe"); Moustakim, M., et al. *Angew. Chem. Int. Ed. Engl.* 56: 827 (2017); the PDB crystal structure 5mlj ("Discovery of a Potent, Cell Penetrant, and Selective p300/CBP-Associated Factor (PCAF)/General Control Nonderepressible 5 (GCN5) Bromodomain Chemical Probe"); and, Humphreys, P. G. et al. *J. Med. Chem.* 60: 695 (2017).

Figure 6C:
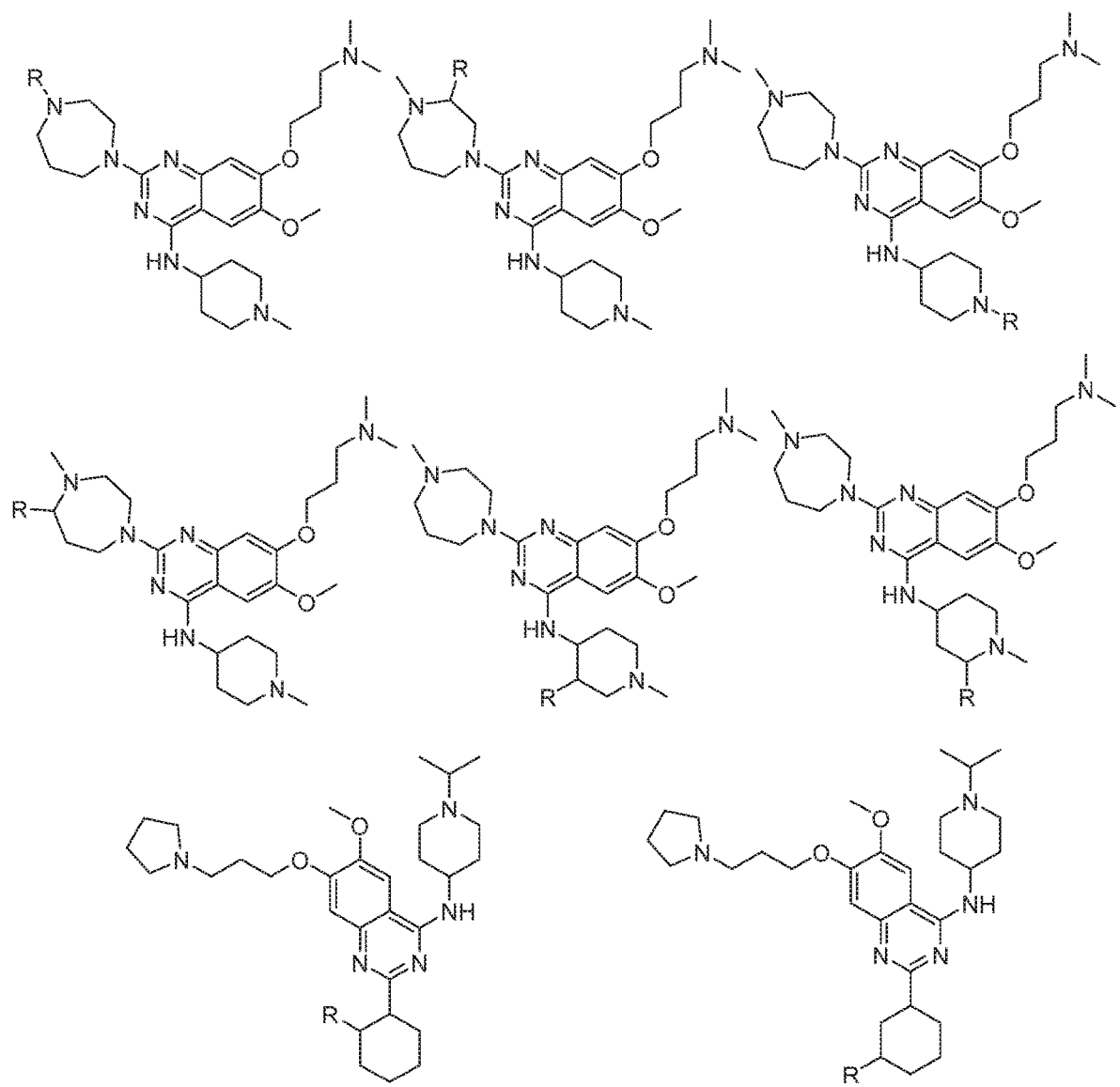
Figure 6D:
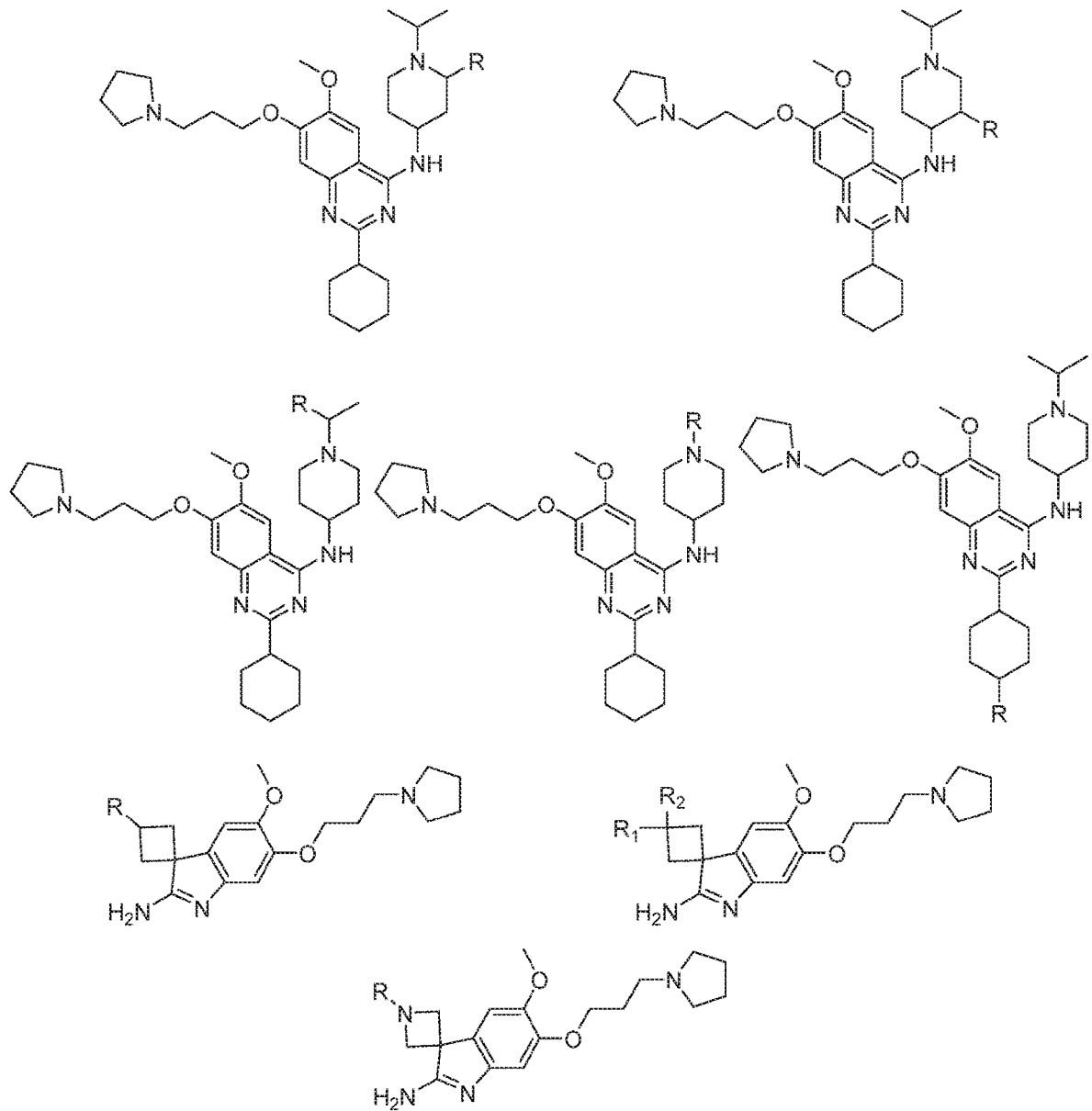

FIG. 6C-6D present examples of G9a (EHMT2) Targeting Ligands wherein R is the point at which the Linker is attached. For additional examples and related ligands, see, the PDB crystal structure 3k5k; ("Discovery of a 2,4-diamino-7-aminoalkoxyquinazoline as a potent and selective inhibitor of histone lysine methyltransferase G9a"); Liu, F. et al. *J. Med. Chem.* 52: 7950 (2009); the PDB crystal structure 3rjw ("A chemical probe selectively inhibits G9a and GLP methyltransferase activity in cells"); Vedadi, M. et al. *Nat. Chem. Biol.* 7: 566 (2011); the PDB crystal structure 4nvq ("Discovery and development of potent and selective inhibitors of histone methyltransferase g9a"); and, Sweis, R. F. et al. *ACSMed Chem Lett* 5: 205 (2014).

Figure 6E:
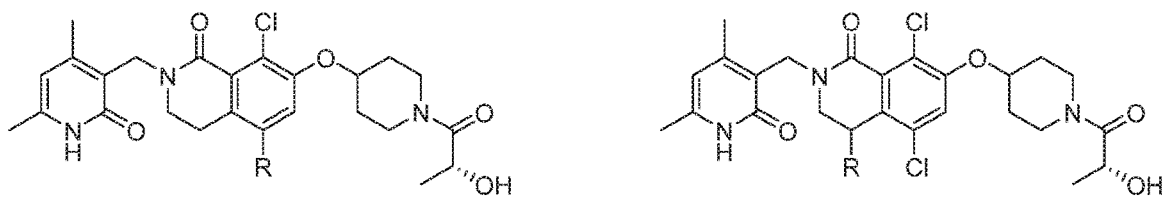
Figure 6F:
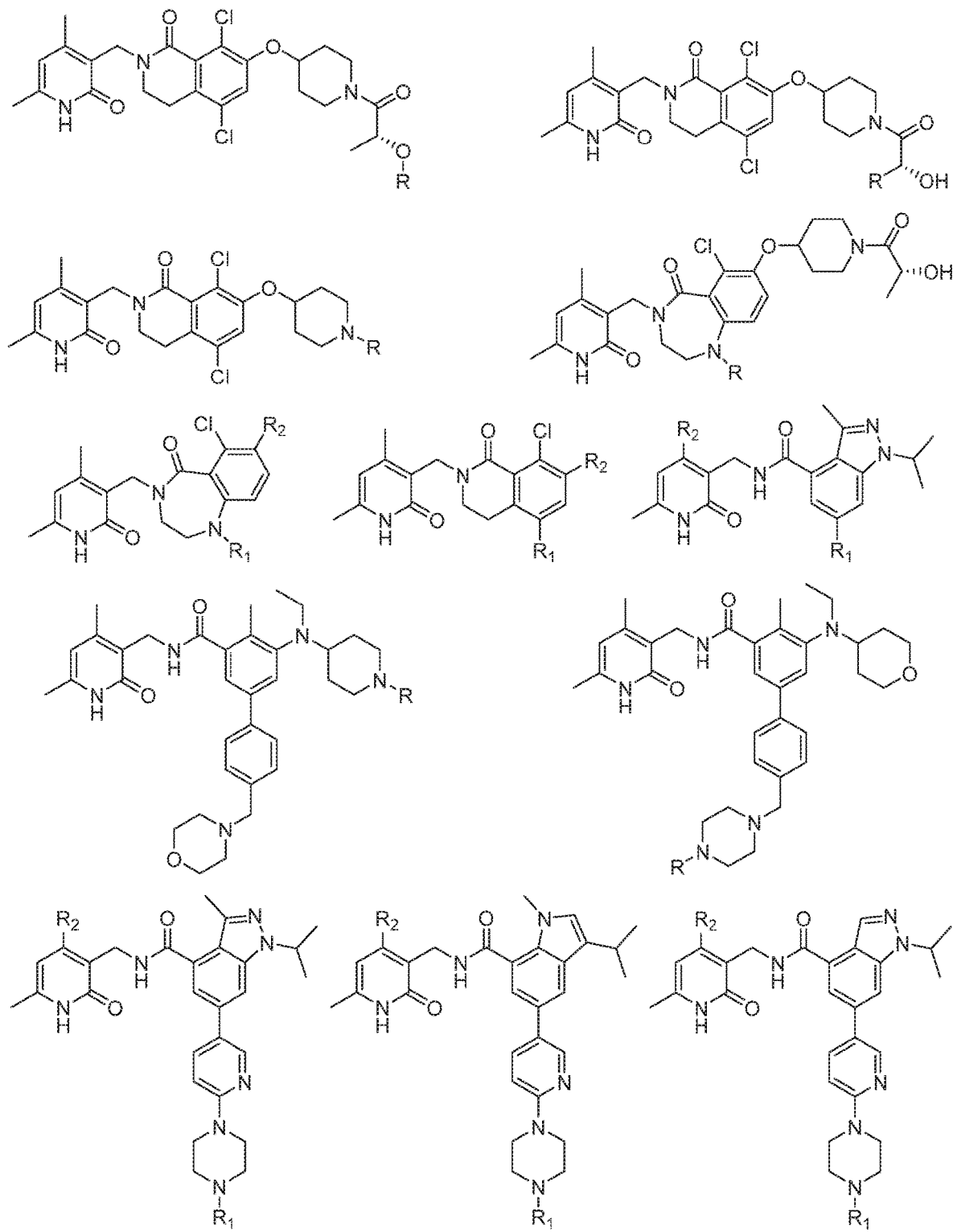
Figure 6G:
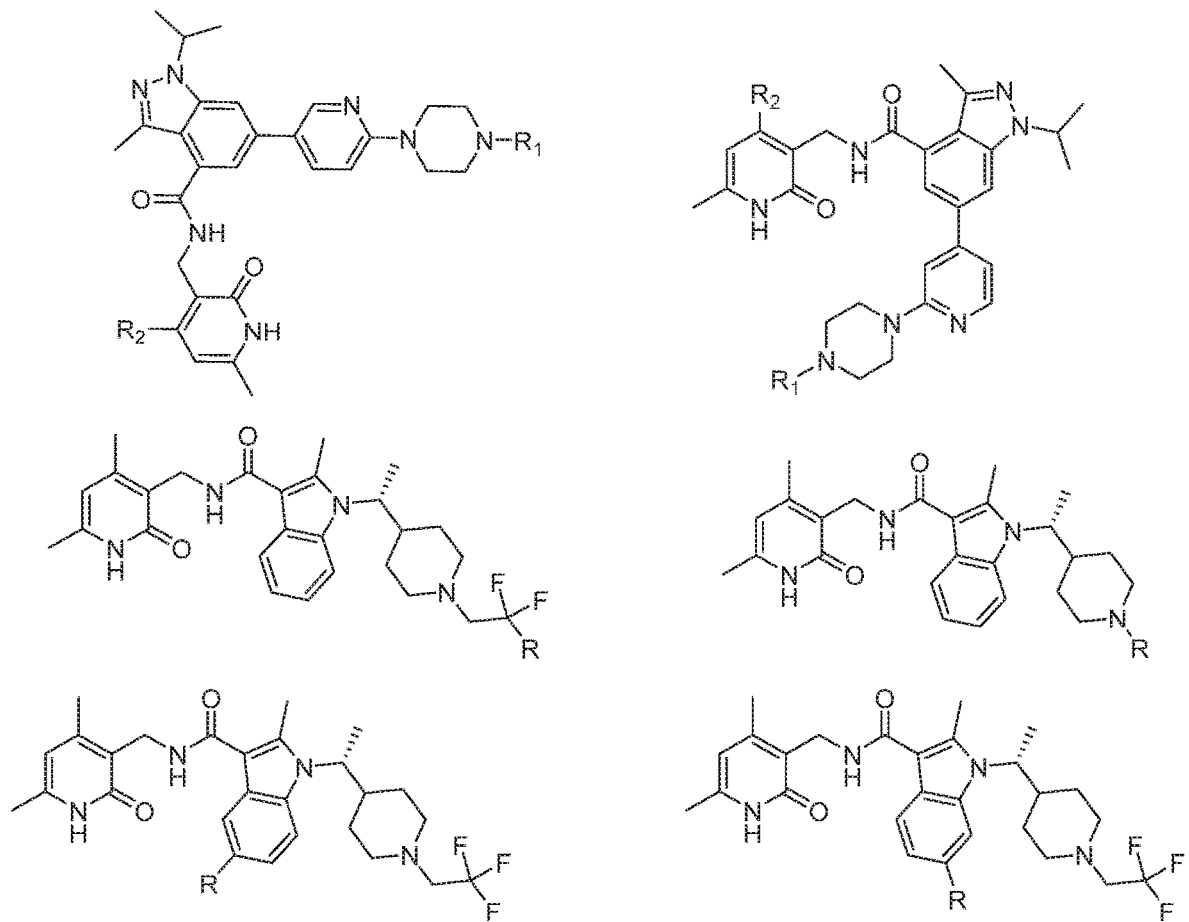

FIG. 6E-6G present examples of EZH2 Targeting Ligands wherein R is the point at which the Linker is attached. For additional examples and related ligands, see, the PDB crystal structure 5ij8 ("Polycomb repressive complex 2 structure with inhibitor reveals a mechanism of activation and drug resistance"); Brooun, A. et al. *Nat Commun* 7: 11384 (2016); the PDB crystal structure 5ls6 ("Identification of (R)—N-((4-Methoxy-6-methyl-2-oxo-1,2-dihydropyridin-3-yl) methyl)-2-methyl-1-(1-(1-(2,2,2-trifluoroethyl)piperidin-4-yl)ethyl)-1H-indole-3-carboxamide (CPI-1205), a Potent and Selective Inhibitor of Histone Methyltransferase EZH2, Suitable for Phase I Clinical Trials for B-Cell Lymphomas");

Vaswani, R. G. et al. *J. Med. Chem.* 59: 9928 (2016); and, the PDB crystal structures 5ij8 and 5ls6.

Figure 6H:
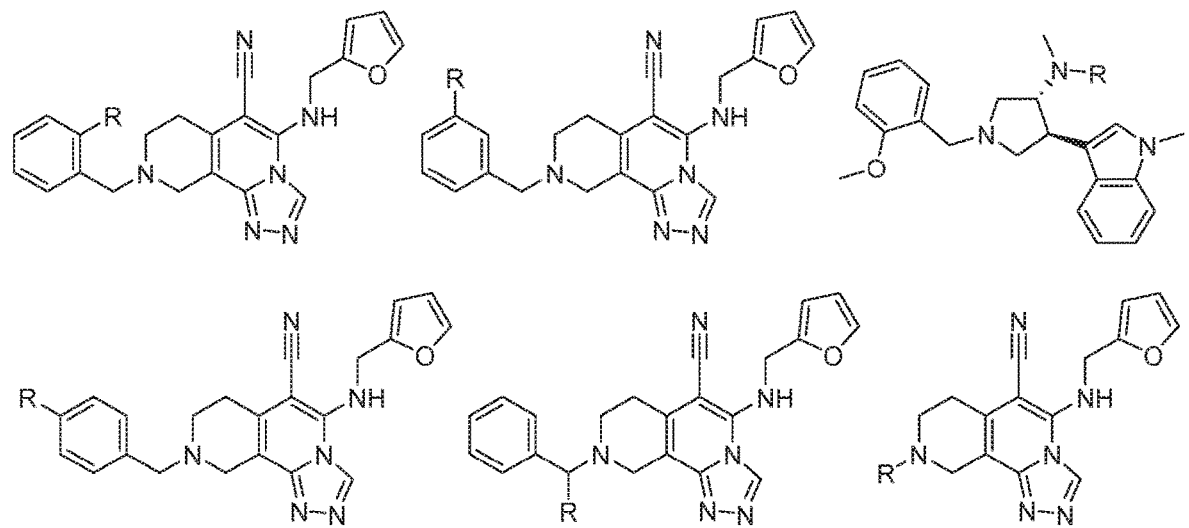
Figure 6I:
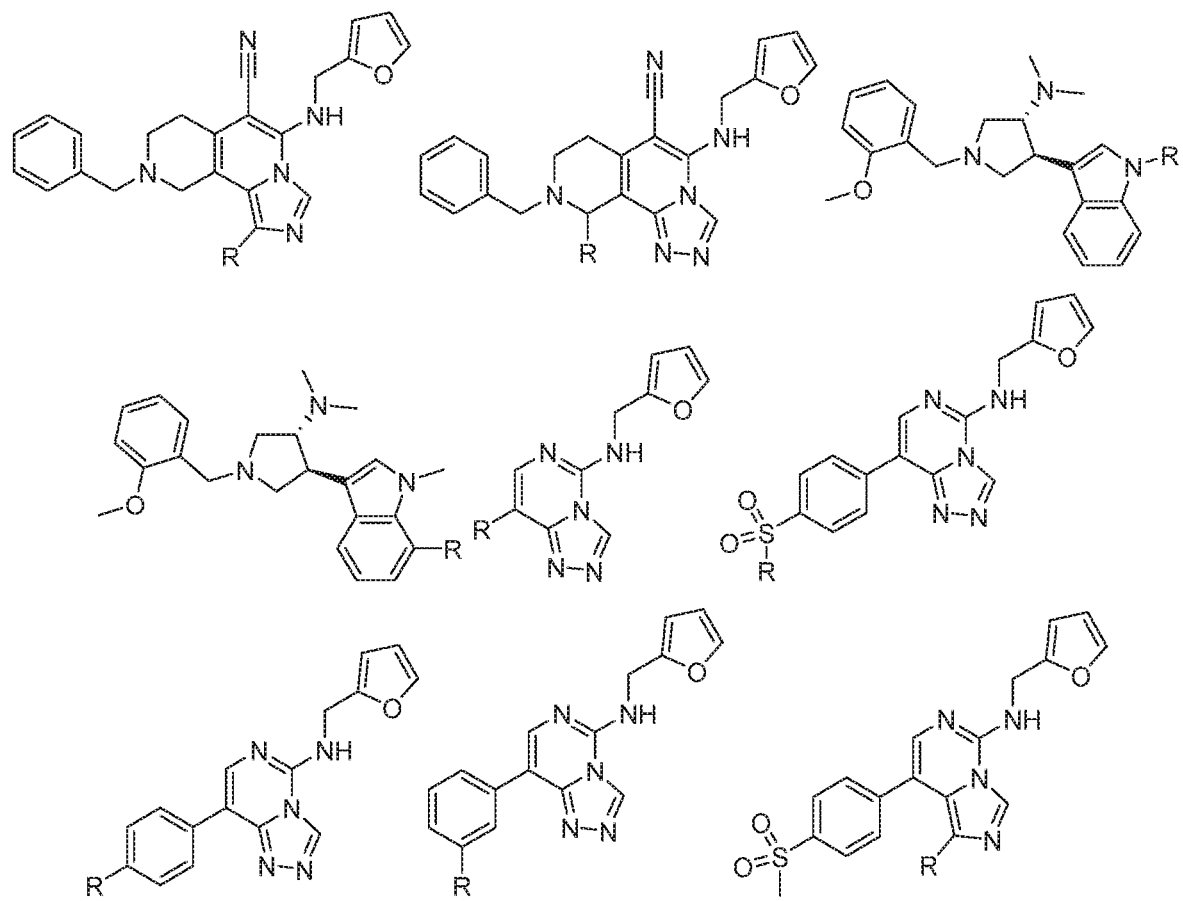

FIG. 6H-6I present examples of EED Targeting Ligands wherein R is the point at which the Linker is attached. For additional examples and related ligands, see, the PDB crystal structures 5h15 and 5h19 ("Discovery and Molecular Basis of a Diverse Set of Polycomb Repressive Complex 2 Inhibitors Recognition by EED"); Li, L. et al. *PLoS ONE* 12: e0169855 (2017); and, the PDB crystal structure 5h19.

Figure 6J:
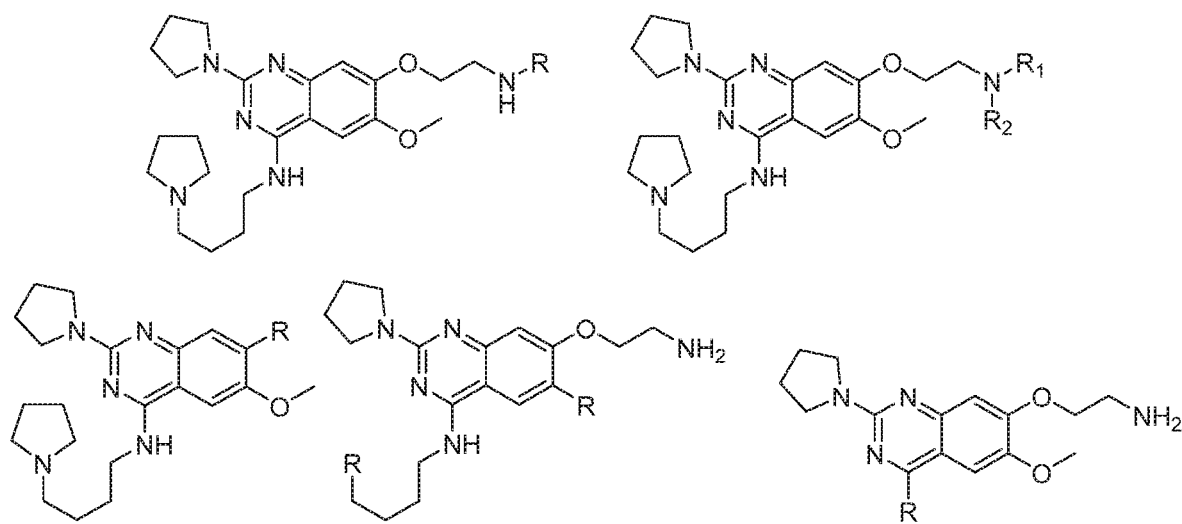

FIG. 6J presents examples of KMT5A (SETD8) Targeting Ligands wherein R is the point at which the Linker is attached. See for example, the PDB crystal structure 5t5g.

Figure 6K:
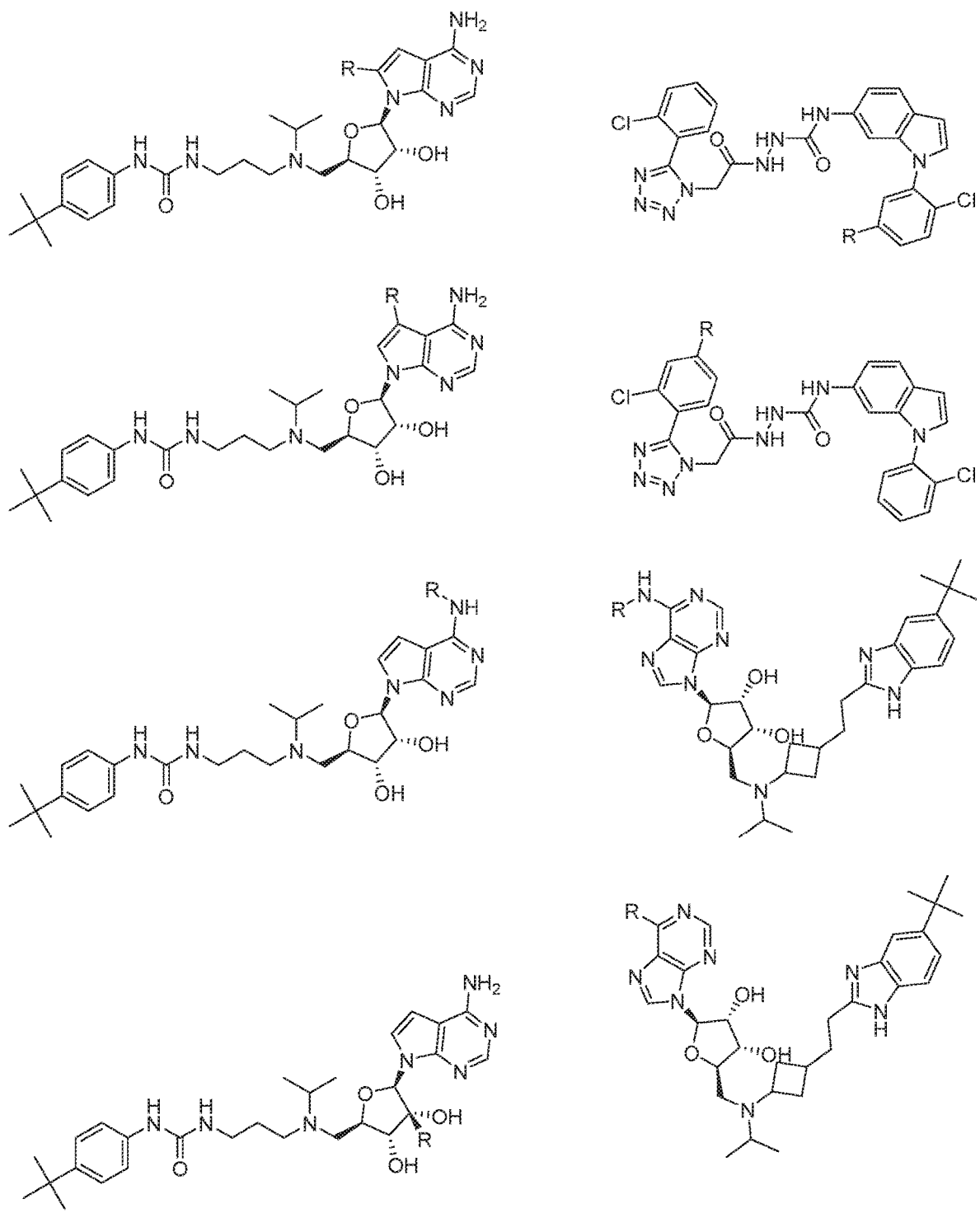
Figure 6L:
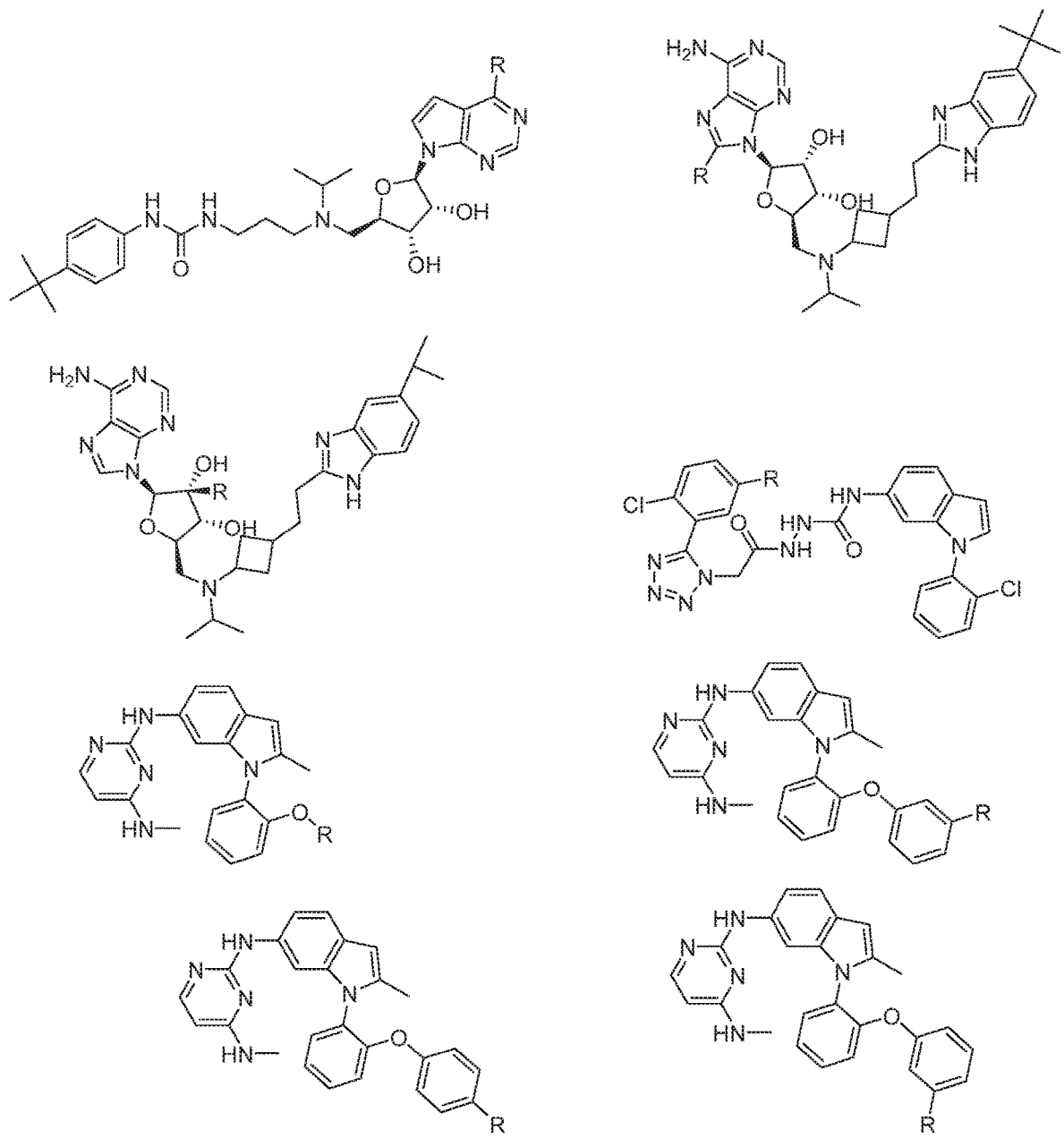

FIG. 6K-6L present examples of DOT1L Targeting Ligands wherein R is the point at which the Linker is attached. For additional examples and related ligands, see, the PDB crystal structure 4eki ("Conformational adaptation drives potent, selective and durable inhibition of the human protein methyltransferase DOT1L"); Basavapathruni, A. et al. *Chem. Biol. Drug Des.* 80: 971 (2012); the PDB crystal structure 4hra ("Potent inhibition of DOT1L as treatment of MLL-fusion leukemia"); Daigle, S. R. et al. *Blood* 122: 1017 (2013); the PDB crystal structure 5dry ("Discovery of Novel Dot1L Inhibitors through a Structure-Based Fragmentation Approach") Chen, C. et al. *ACSMed. Chem. Lett.* 7: 735 (2016); the PDB crystal structure 5dt2 ("Discovery of Novel Dot1L Inhibitors through a Structure-Based Fragmentation Approach"); and, Chen, C. et al. *ACS Med. Chem. Lett.* 7: 735 (2016).

Figure 6M:
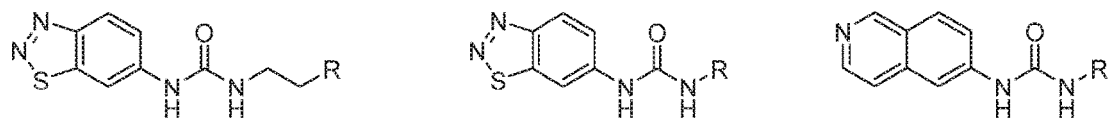

FIG. 6M-6N present examples of PRMT3 Targeting Ligands wherein R is the point at which the Linker is attached. For additional examples and related ligands, see, the PDB crystal structure 3smq ("An allosteric inhibitor of protein arginine methyltransferase 3"); Siarheyeva, A. et al. *Structure* 20: 1425 (2012); PDB crystal structure 4ryl ("A Potent, Selective and Cell-Active Allosteric Inhibitor of Protein Arginine Methyltransferase 3 (PRMT3)"); and Kaniskan, H. U. et al. *Angew. Chem. Int. Ed. Engl.* 54: 5166 (2015).

FIG. 6O presents examples of CARM 1 (PRMT4) Targeting Ligands wherein R is the point at which the Linker is attached. For additional examples and related ligands, see, the PDB crystal structures 2ylx and 2ylw and related ligands described in "Structural Basis for Carm1 Inhibition by Indole and Pyrazole Inhibitors." Sack, J. S. et al. *Biochem. J.* 436: 331 (2011).

FIG. 6P presents examples of PRMT5 Targeting Ligands wherein R is the point at which the Linker is attached. For additional examples and related ligands, see, the PDB crystal structure 4x61 and related ligands described in "A selective inhibitor of PRMT5 with in vivo and in vitro potency in MCL models". Chan-Penebre, E. *Nat. Chem. Biol.* 11: 432 (2015).

Figure 6Q:
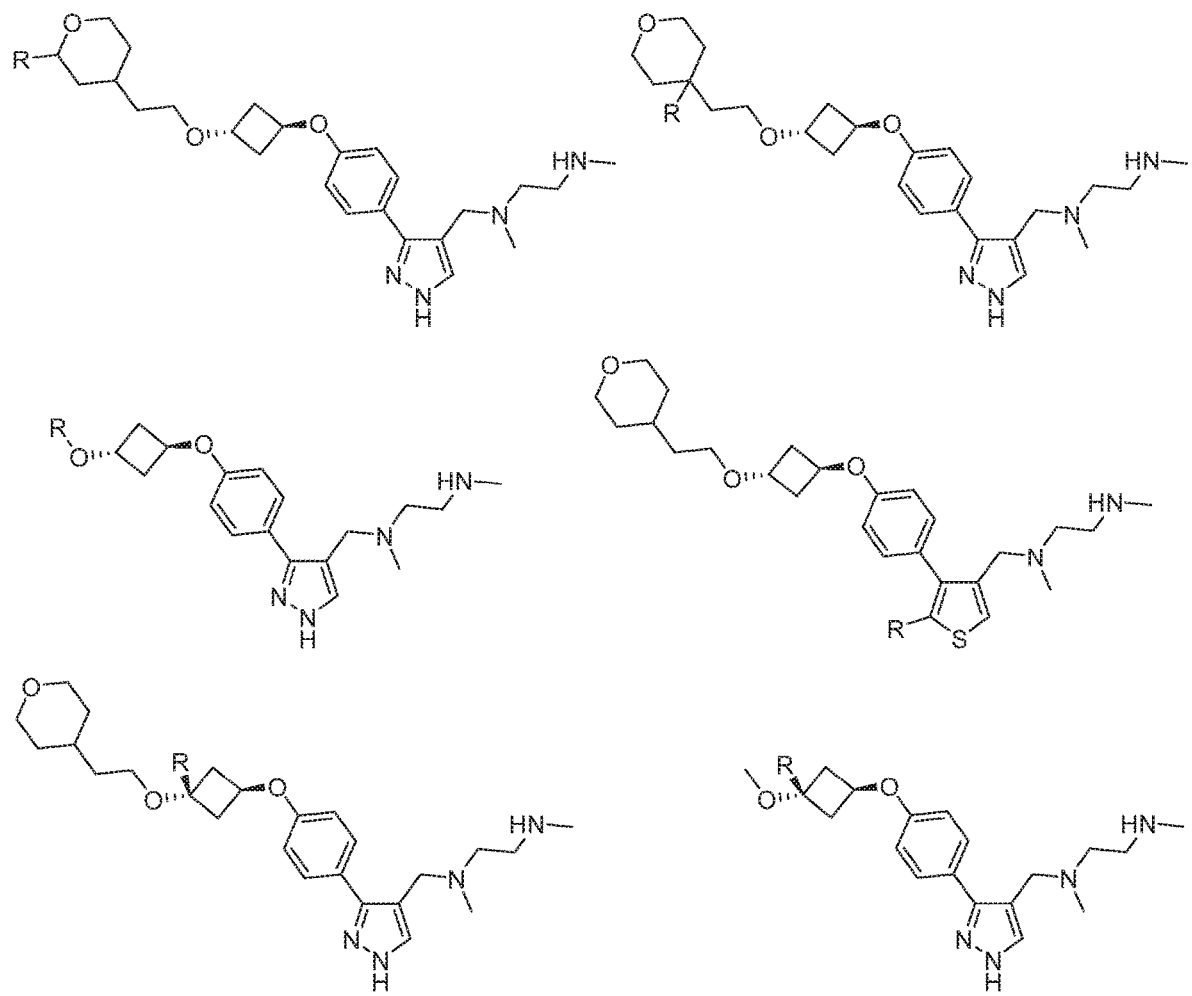

FIG. 6Q presents examples of PRMT6 Targeting Ligands wherein R is the point at which the Linker is attached. For additional examples and related ligands, see, the PDB crystal structure 4y30 and related ligands described in "Aryl Pyrazoles as Potent Inhibitors of Arginine Methyltransferases: Identification of the First PRMT6 Tool Compound". Mitchell, L. H. et al. *ACS Med. Chem. Lett.* 6: 655 (2015).

Figure 6R:
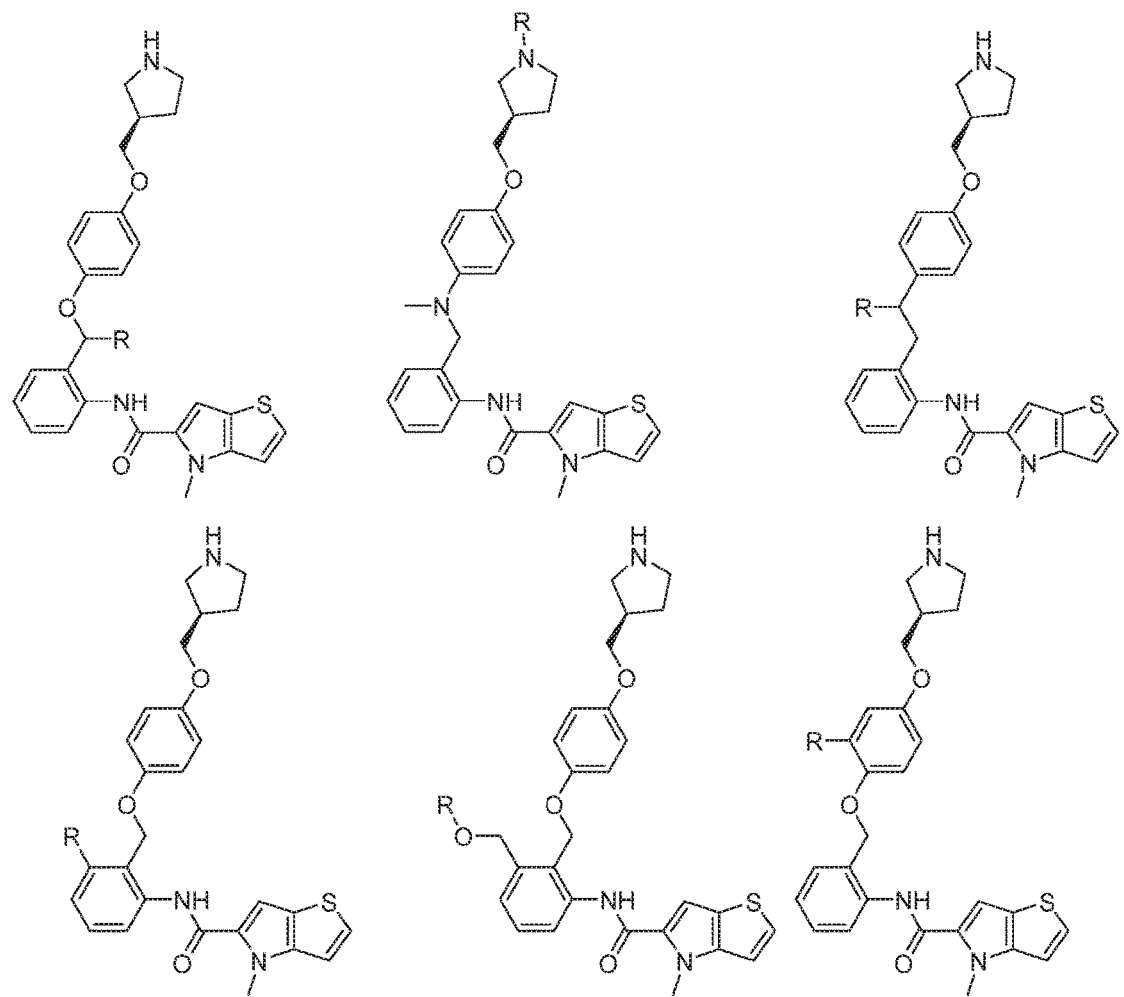

FIG. 6R presents examples of LSD1 (KDM1A) Targeting Ligands wherein R is the point at which the Linker is attached. For additional examples and related ligands, see, the PDB crystal structure 5lgu and related ligands described in "Thieno[3,2-b]pyrrole-5-carboxamides as New Reversible Inhibitors of Histone Lysine Demethylase KDM1A/ LSD1. Part 2: Structure-Based Drug Design and Structure-Activity Relationship". Vianello, P. et al. *J. Med. Chem.* 60: 1693 (2017).

Figure 6S:
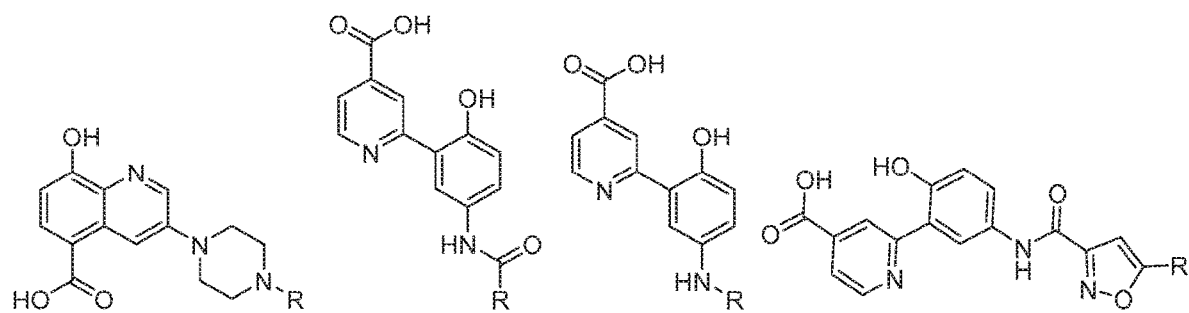
Figure 6T:
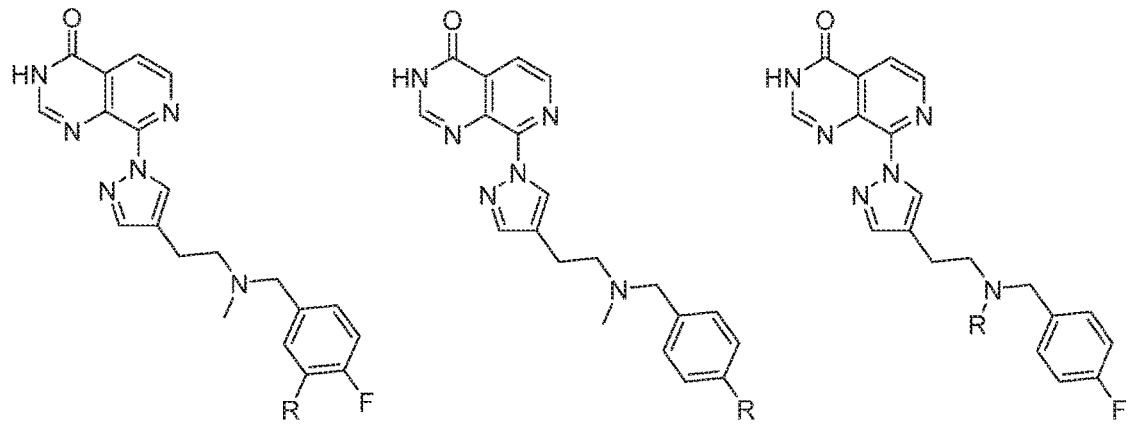

FIG. 6S-6T present examples of KDM4 Targeting Ligands wherein R is the point at which the Linker is attached. For additional examples and related ligands, see, the PDB crystal structure 3rvh; the PDB crystal structure 5a7p and related ligands described in "Docking and Linking of Fragments to Discover Jumonji Histone Demethylase Inhibitors." Korczynska, M., et al. *J. Med. Chem.* 59: 1580 (2016); and, the PDB crystal structure 3f3c and related ligands described in "8-Substituted Pyrido[3,4-d]pyrimidin-4(3H)-one Derivatives As Potent, Cell Permeable, KDM4 (JMJD2) and KDM5 (JARID1) Histone Lysine Demethylase Inhibitors." Bavetsias, V. et al. *J. Med. Chem.* 59: 1388 (2016).

Figure 6U:
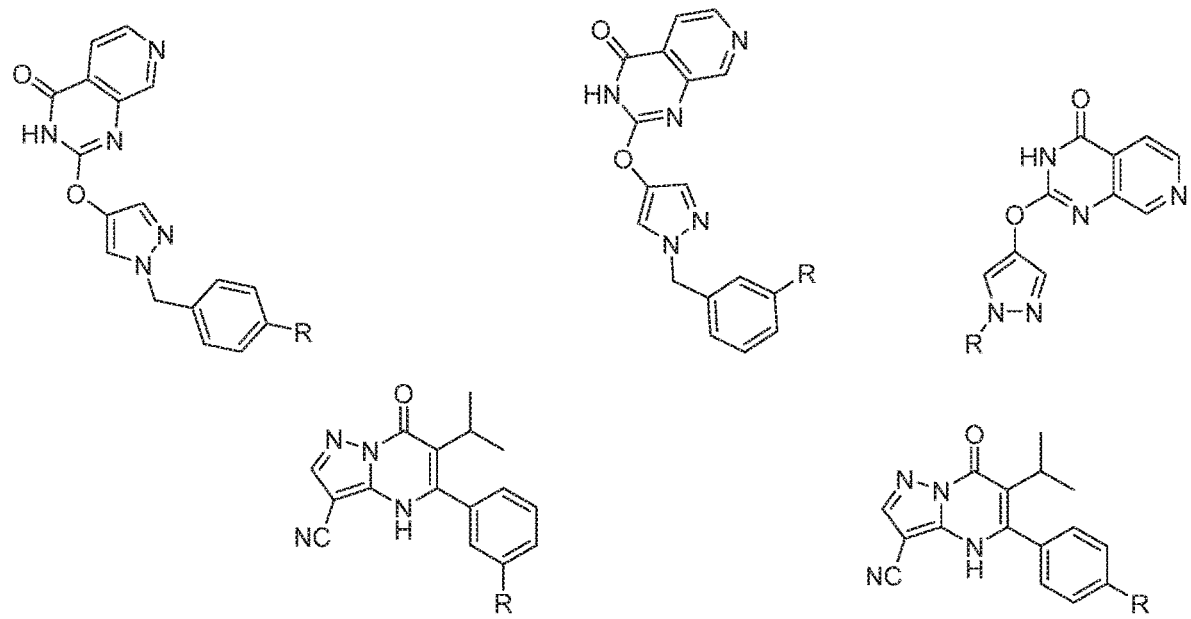

FIG. 6U presents examples of KDM5 Targeting Ligands wherein R is the point at which the Linker is attached. For additional examples and related ligands, see, the PDB crystal structure 3fun and related ligands described in "Structural Analysis of Human Kdm5B Guides Histone Demethylase Inhibitor Development". Johansson, C. et al. *Nat. Chem. Biol.* 12: 539 (2016) and the PDB crystal structure 5ceh and related ligands described in "An inhibitor of KDM5 demethylases reduces survival of drug-tolerant cancer cells". Vinogradova, M. et al. *Nat. Chem. Biol.* 12: 531 (2016).

Figure 6V:
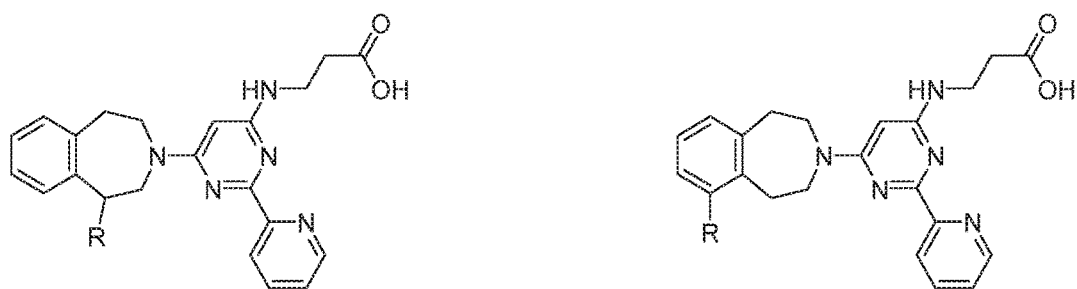
Figure 6W:
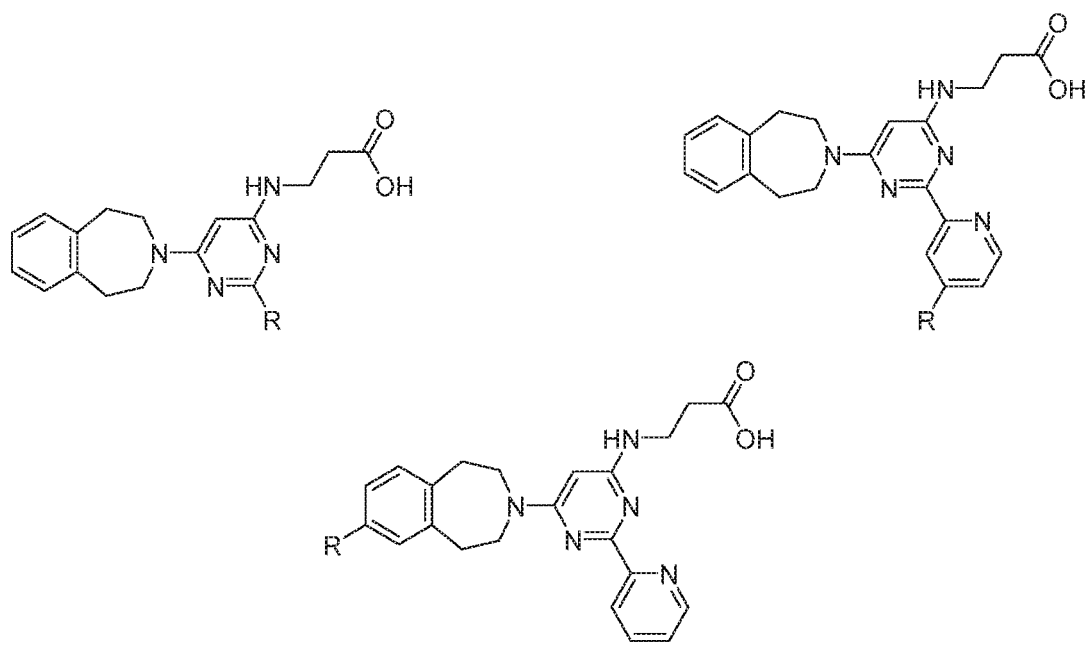

FIG. 6V-6W present examples of KDM6 Targeting Ligands wherein R is the point at which the Linker is attached. For additional examples and related ligands, see, the PDB crystal structure 4ask and related ligands described in "A Selective Jumonji H3K27 Demethylase Inhibitor Modulates the Proinflammatory Macrophage Response". Kruidenier, L. et al. *Nature* 488: 404 (2012).

Figure 6X:
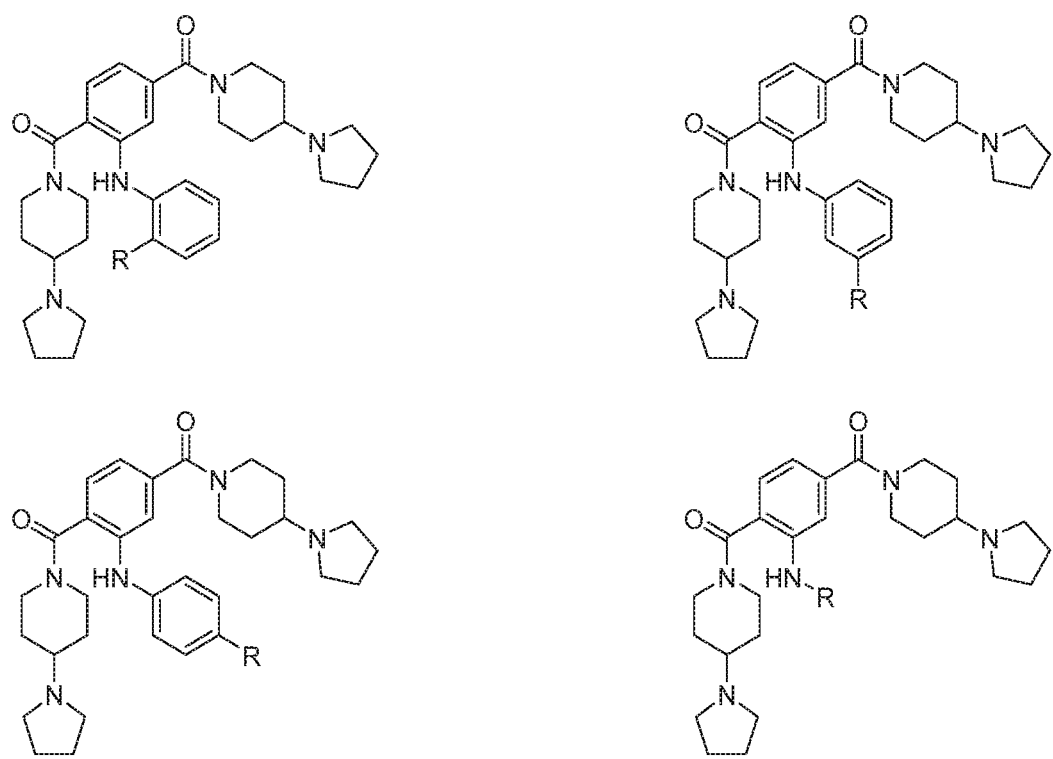

FIG. 6X presents examples of L3MBTL3 targeting ligands wherein R is the point at which the Linker is attached. See for example, the PDB crystal structure 4fl6.

Figure 6Y:
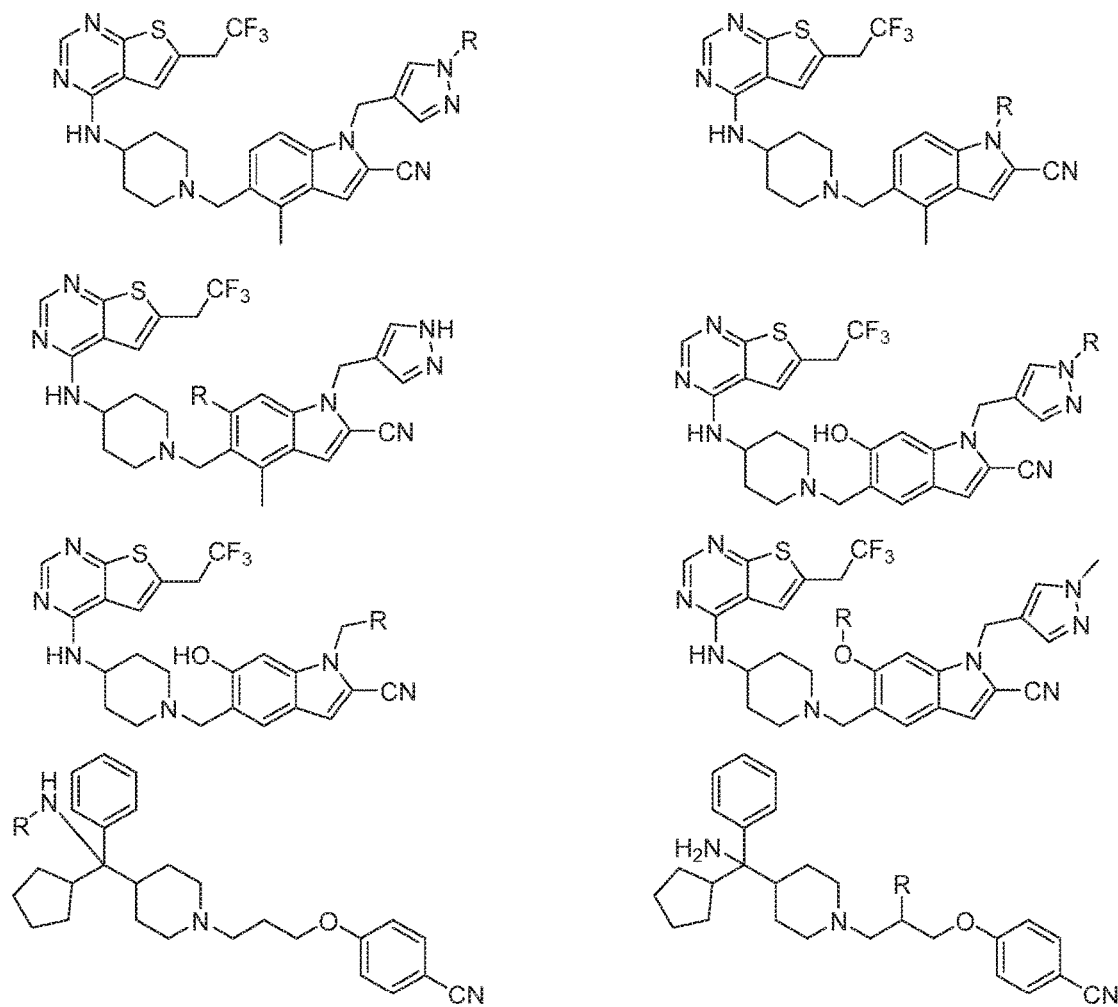

FIG. 6Y presents examples of Menin Targeting Ligands wherein R is the point at which the Linker is attached. For additional examples and related ligands, see, the PDB crystal structure 4x5y and related ligands described in "Pharmacologic Inhibition of the Menin-MLL Interaction Blocks Progression of MLL Leukemia In Vivo" Borkin, D. et al. *Cancer Cell* 27: 589 (2015) and the PDB crystal structure 4og8 and related ligands described in "High-Affinity Small-Molecule Inhibitors of the Menin-Mixed Lineage Leukemia (MLL) Interaction Closely Mimic a Natural Protein-Protein Interaction" He, S. et al. *J. Med. Chem.* 57: 1543 (2014).

Figure 6Z:
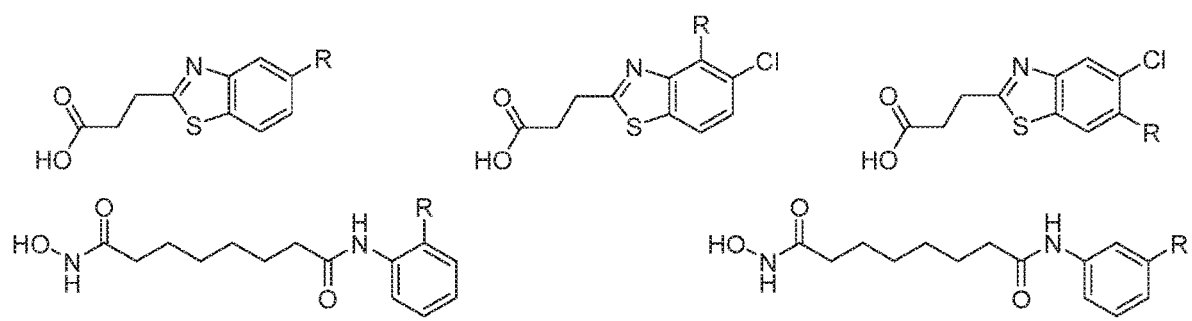
Figure 6A:
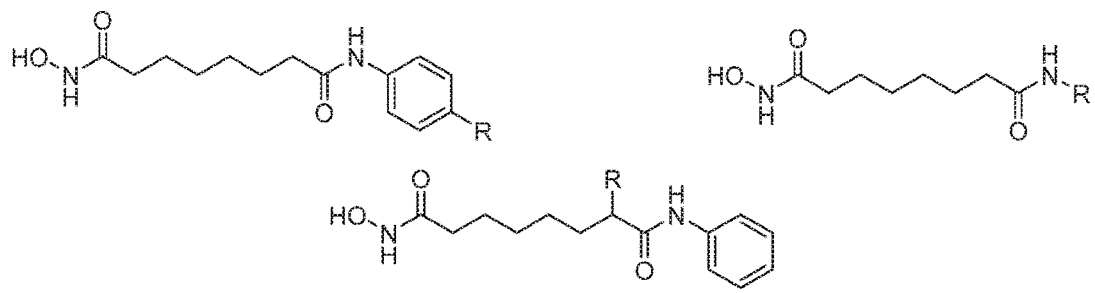
Figure 6B:
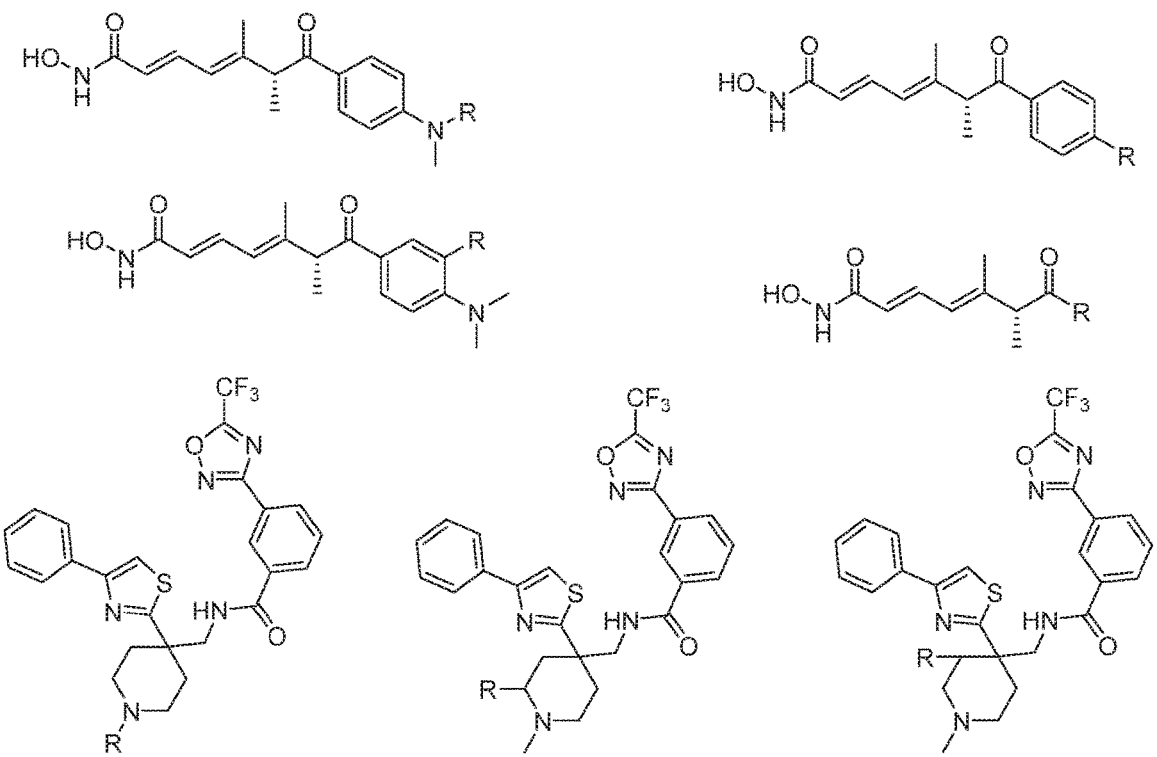

FIG. 6Z-6AA present examples of HDAC6 Targeting Ligands wherein R is the point at which the Linker is attached. See for example, the PDB crystal structures 5kh3 and 5eei.

FIG. 6BB presents examples of HDAC7 Targeting Ligands wherein R is the point at which the Linker is attached. For additional examples and related ligands, see, the PDB crystal structure 3c10 and related ligands described in "Human HDAC7 harbors a class IIa histone deacetylase-specific zinc binding motif and cryptic deacetylase activity." Schuetz, A. et al. *J. Biol. Chem.* 283: 11355 (2008) and the PDB crystal structure PDB 3zns and related ligands described in "Selective Class Iia Histone Deacetylase Inhibition Via a Non-Chelating Zinc Binding Group". Lobera, M. et al. *Nat. Chem. Biol.* 9: 319 (2013).

Figure 7A:
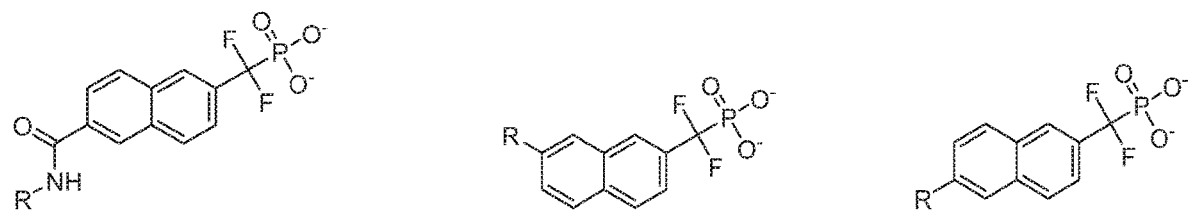
Figure 7B:
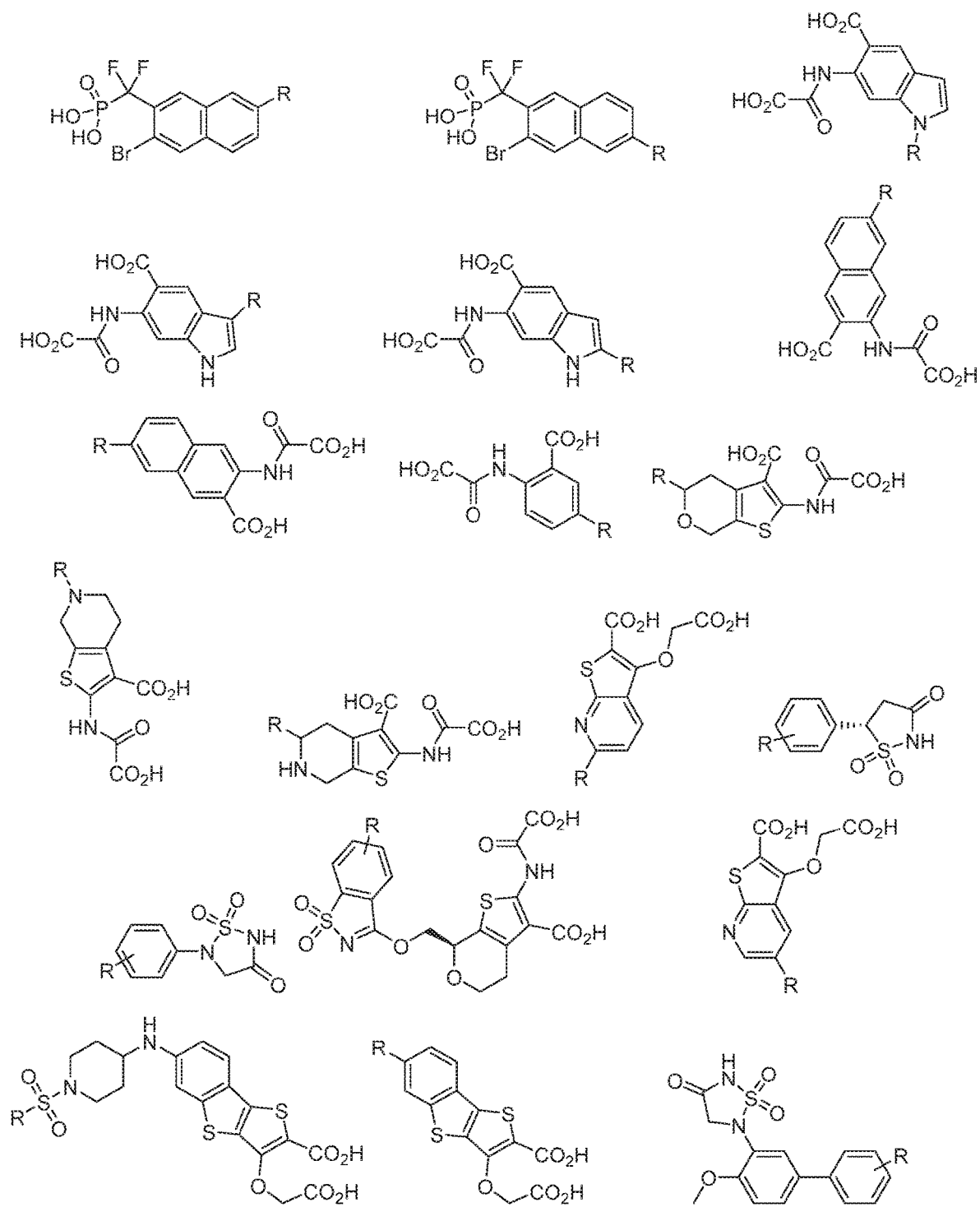
Figure 7C:
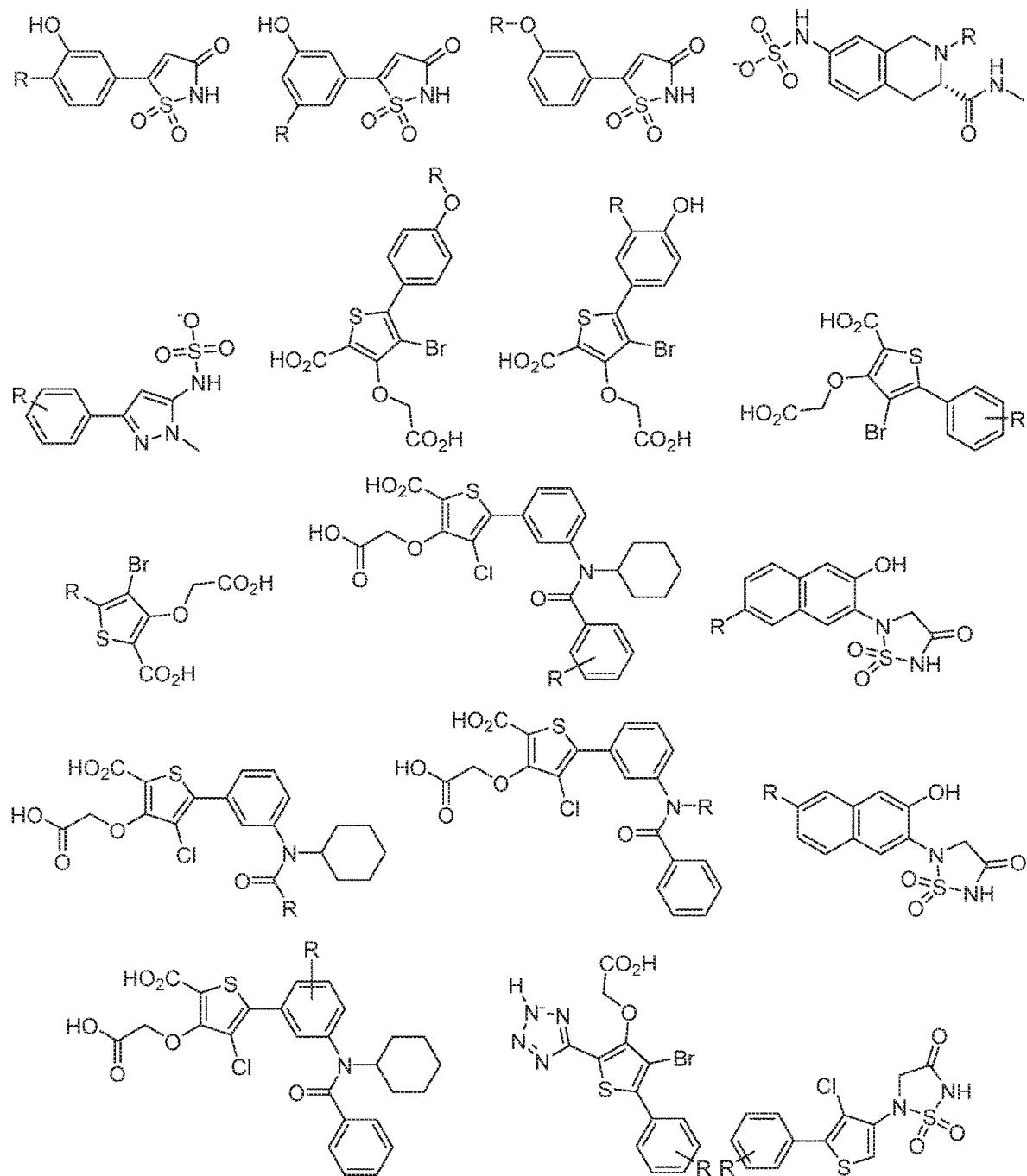

FIG. 7A-7C present examples of Protein Tyrosine Phosphatase, Non-Receptor Type 1, PTP1B Targeting Ligands wherein R is the point at which the Linker is attached. For additional examples and related ligands, see, the PDB crystal structure 1bzj described in "Structural basis for inhibition of the protein tyrosine phosphatase 1B by phosphotyrosine peptide mimetics" Groves, M. R. et al. *Biochemistry* 37: 17773-17783 (1998); the PDB crystal structure 3cwe described in "Discovery of [(3-bromo-7-cyano-2-naphthyl)(difluoro)methyl]phosphonic acid, a potent and orally active small molecule PTP1B inhibitor". Han Y, *Bioorg Med Chem Lett.* 18:3200-5 (2008); the PDB crystal structures 2azr and 2b07 described in "Bicyclic and tricyclic thiophenes as protein tyrosine phosphatase 1B inhibitors." Moretto, A. F. et al. *Bioorg. Med. Chem.* 14: 2162-2177 (2006); the PDB crystal structures PDB 2bgd, 2bge, 2cm7, 2cm8, 2cma, 2cmb, 2cmc described in ""Structure-Based Design of Protein Tyrosine Phosphatase-1B Inhibitors". Black, E. et al. *Bioorg. Med. Chem. Lett.* 15: 2503 (2005) and "Structural Basis for Inhibition of Protein-Tyrosine Phosphatase 1B by Isothiazolidinone Heterocyclic Phosphonate Mimetics." Ala, P. J. et al. *J. Biol. Chem.* 281: 32784 (2006); the PDB crystal structures 2f6t and 2f6w described in "1,2,3,4-Tetrahydroisoquinolinyl sulfamic acids as phosphatase PTP1B inhibitors". Klopfenstein, S. R. et al. *Bioorg. Med. Chem. Lett.* 16: 1574-1578 (2006); the PDB crystal structures 2h4g, 2h4k, 2hb1 described in ""Monocyclic thiophenes as protein tyrosine phosphatase 1B inhibitors: Capturing interactions with Asp48." Wan, Z. K. et al. *Bioorg. Med. Chem. Lett.* 16: 4941-4945 (2006); the PDB crystal structures 2zn7 described in "Structure-based optimization of protein tyrosine phosphatase-1 B inhibitors: capturing interactions with arginine 24". Wan, Z. K. et al. *Chem Med Chem.* 3:1525-9 (2008); the PDB crystal structure 2nt7, 2nta described in "Probing acid replacements of thiophene PTP1B inhibitors." Wan, Z. K. et al. *Bioorg. Med. Chem. Lett.* 17: 2913-2920 (2007); and, WO 2008148744 A1 assigned to Novartis AG titled "Thiadiazole derivatives as antidiabetic agents". See also, the PDB crystal structures 1c84, 1c84, 1c85, 1c86, 1c88, 118g and described in ""2-(oxalylamino)-benzoic acid is a general, competitive inhibitor of protein-tyrosine phosphatases". Andersen, H. S. et al. *J. Biol. Chem.* 275: 7101-7108 (2000); "Structure-based design of a low molecular weight, nonphosphorus, nonpeptide, and highly selective inhibitor of protein-tyrosine phosphatase 1B." Iversen, L. F. et al. *J Biol. Chem.* 275: 10300-10307 (2000); and, "Steric hindrance as a basis for structure-based design of selective inhibitors of protein-tyrosine phosphatases". Iversen, L. F. et al. *Biochemistry* 40: 14812-14820 (2001).

Figure 7D:
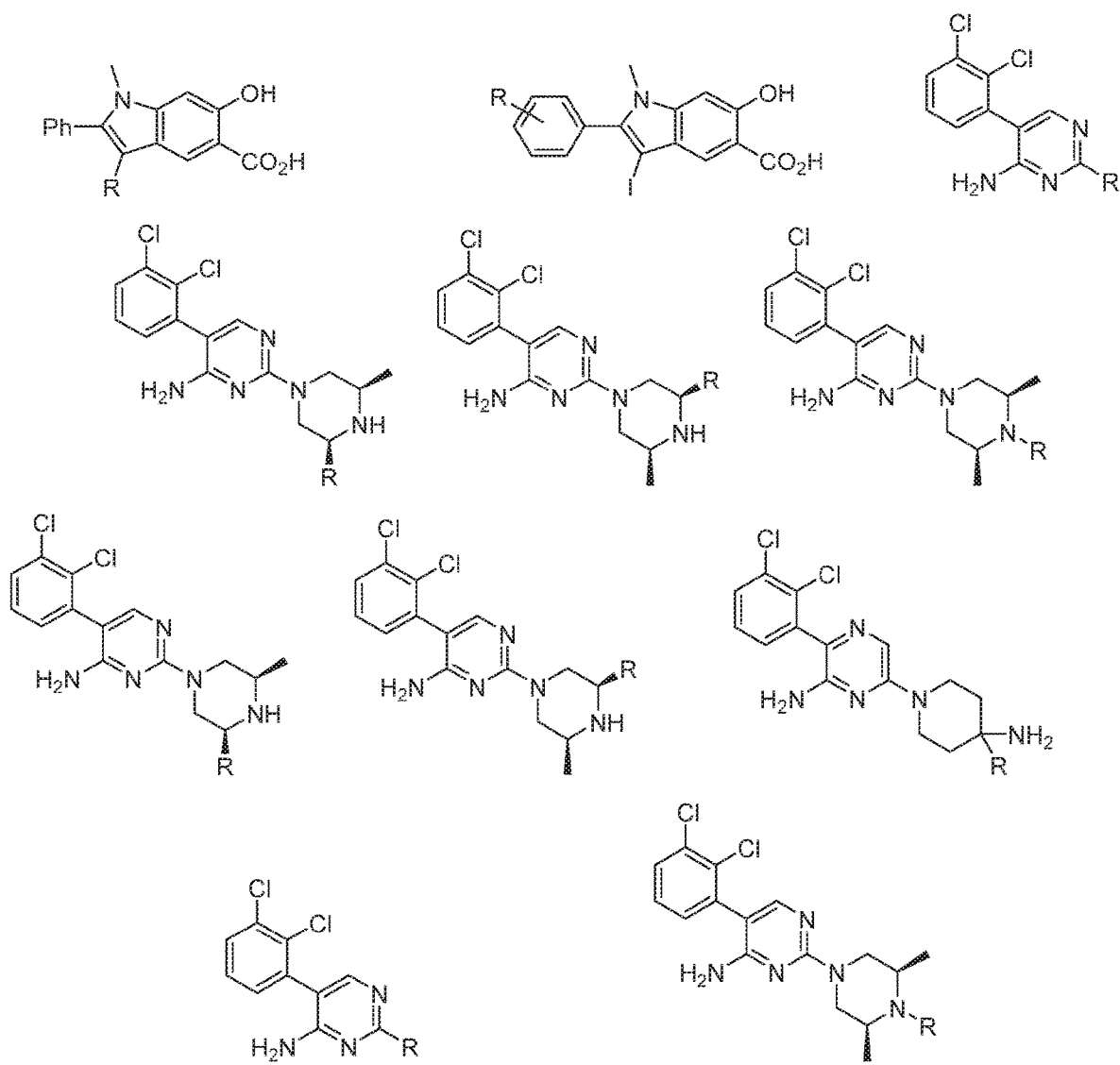

FIG. 7D presents examples of Tyrosine-protein phosphatase non-receptor type 11, SHP2 Targeting Ligands wherein R is the point at which the Linker is attached. For additional examples and related ligands, see, the crystal structures PDB 4pvg and 3o5x and described in "Salicylic acid based small molecule inhibitor for the oncogenic Src homology-2 domain containing protein tyrosine phosphatase-2 (SHP2)." Zhang, X. et al. *J. Med. Chem.* 53: 2482-2493 (2010); and, the crystal structure PDB 5ehr and related ligands described in "Allosteric Inhibition of SHP2: Identification of a Potent, Selective, and Orally Efficacious Phosphatase Inhibitor." Garcia Fortanet, J. et al. *J. Med. Chem.* 59: 7773-7782 (2016). Also, see the crystal structure PDB 5ehr described in "Allosteric Inhibition of SHP2: Identification of a Potent, Selective, and Orally Efficacious Phosphatase Inhibitor." Garcia Fortanet, J. et al. *J. Med. Chem.* 59: 7773-7782 (2016) and "Allosteric inhibition of SHP2 phosphatase inhibits cancers driven by receptor tyrosine kinases." Chen, Y. P. et al. *Nature* 535: 148-152 (2016).

FIG. 7E presents examples of Tyrosine-protein phosphatase non-receptor type 22 Targeting Ligands wherein R is the point at which the Linker is attached. For additional examples and related ligands, see, the crystal structure PDB 4j 51 described in "A Potent and Selective Small-Molecule Inhibitor for the Lymphoid-Specific Tyrosine Phosphatase (LYP), a Target Associated with Autoimmune Diseases." He, Y. et al. *J. Med. Chem.* 56: 4990-5008 (2013).

FIG. 7F presents examples of Scavenger mRNA-decapping enzyme DcpS Targeting Ligands wherein R is the point at which the Linker is attached. For additional examples and related ligands, see, the crystal structures PDB 3b17, 3b19, 3bla, 4qde, 4qdv, 4qeb and related ligands described in "DcpS as a therapeutic target for spinal muscular atrophy." Singh, J. et al. *ACS Chem. Biol.* 3: 711-722 (2008).

Figure 8A:
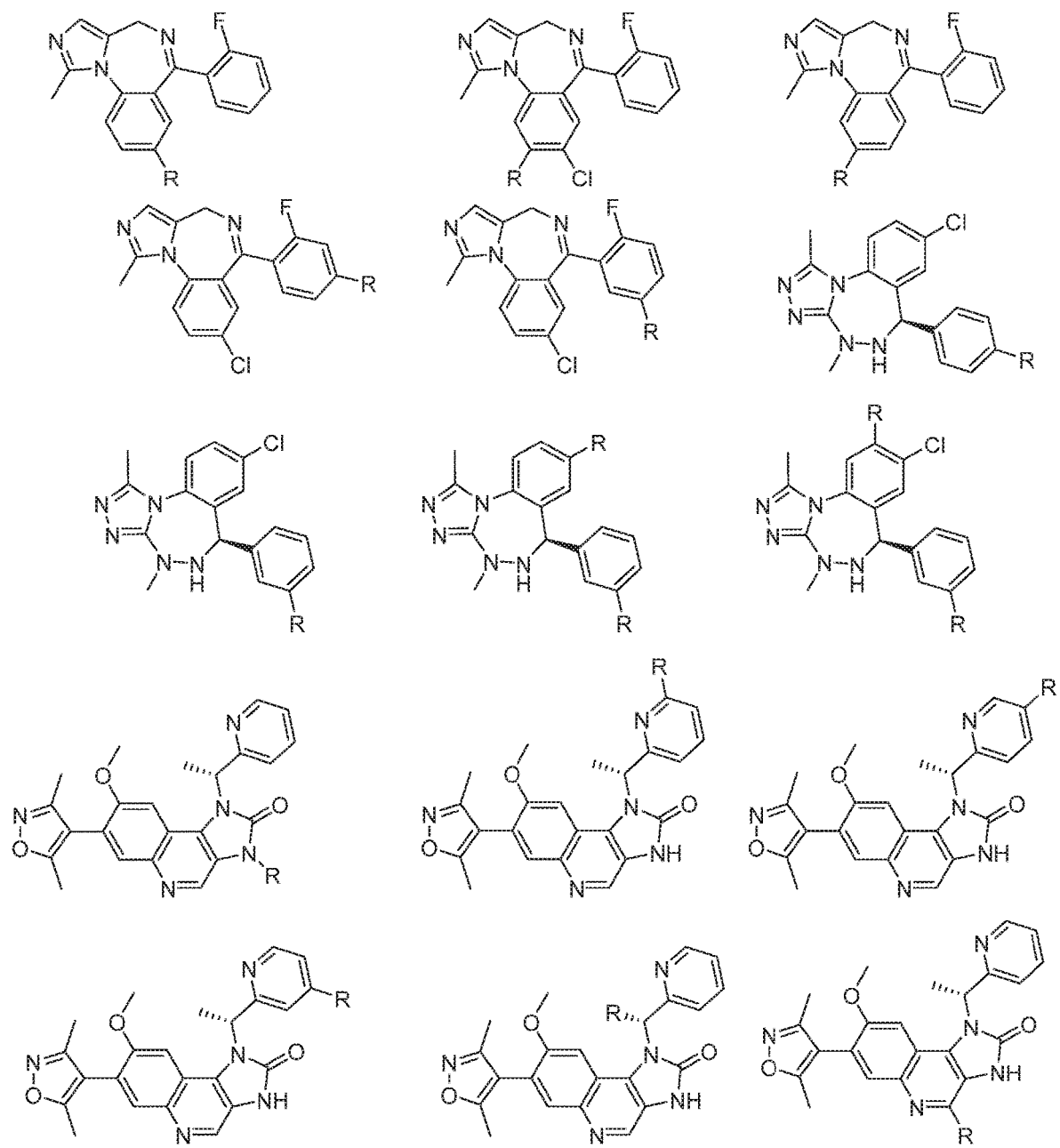
Figure 8B:
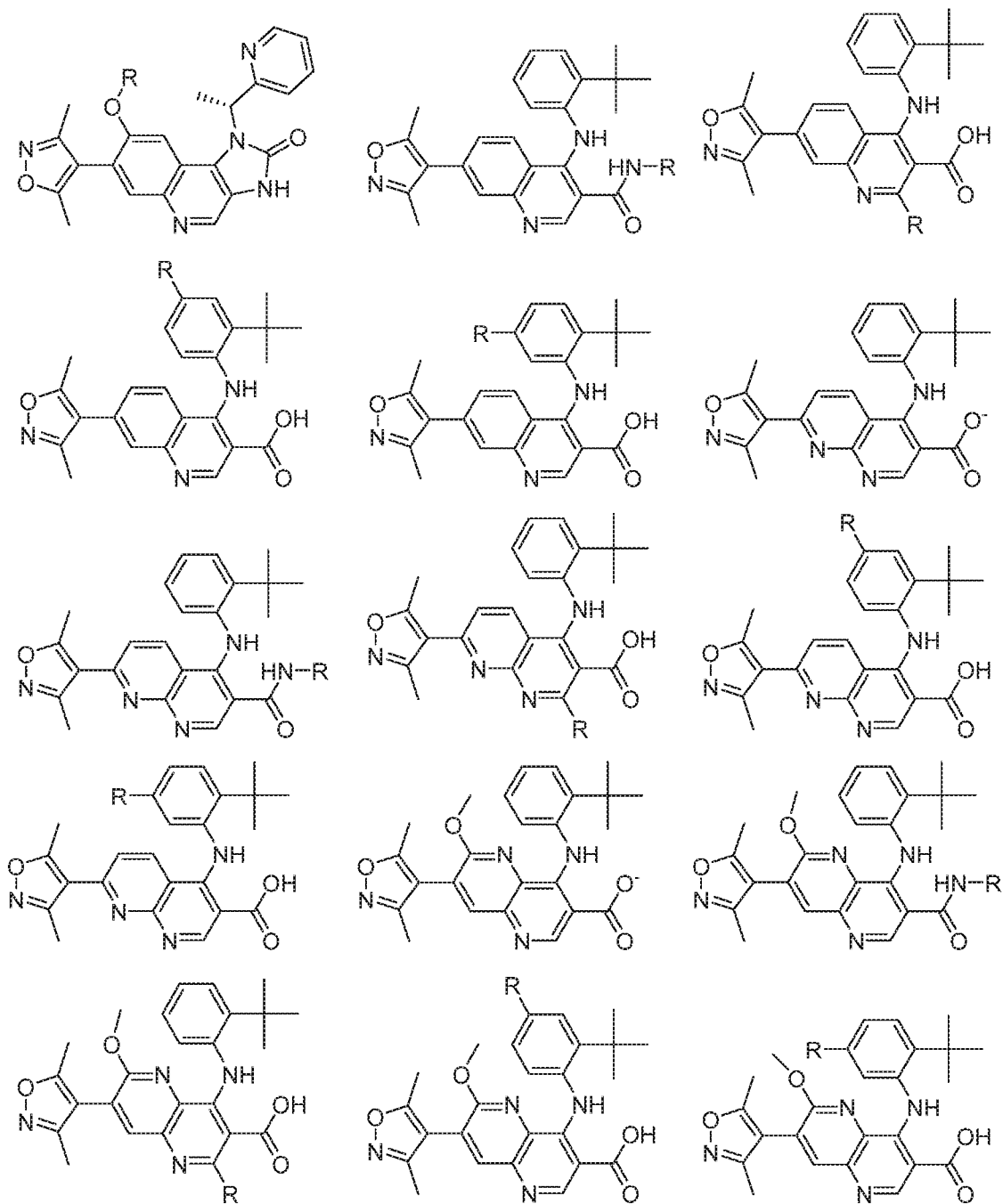
Figure 8C:
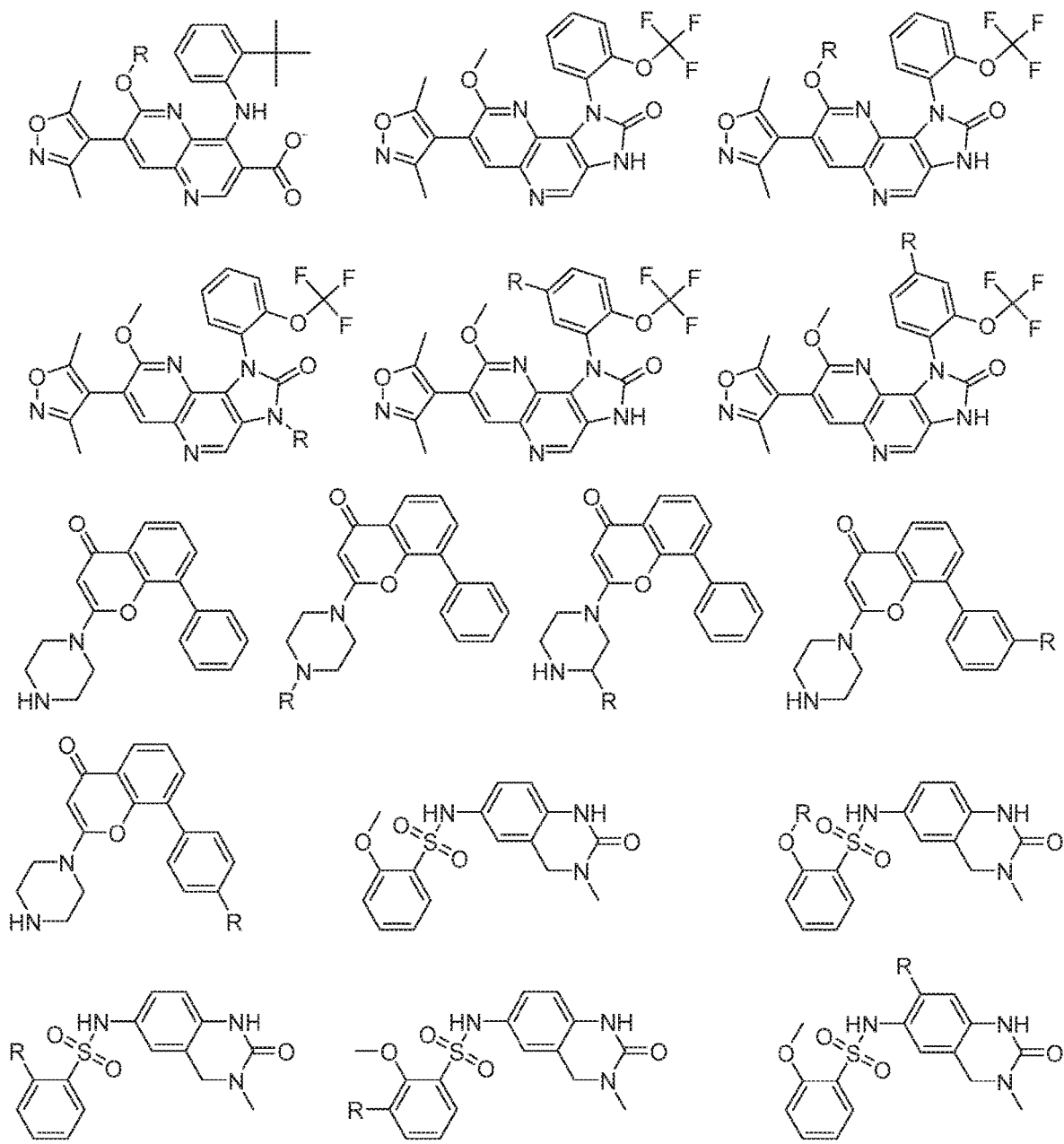
Figure 8D:
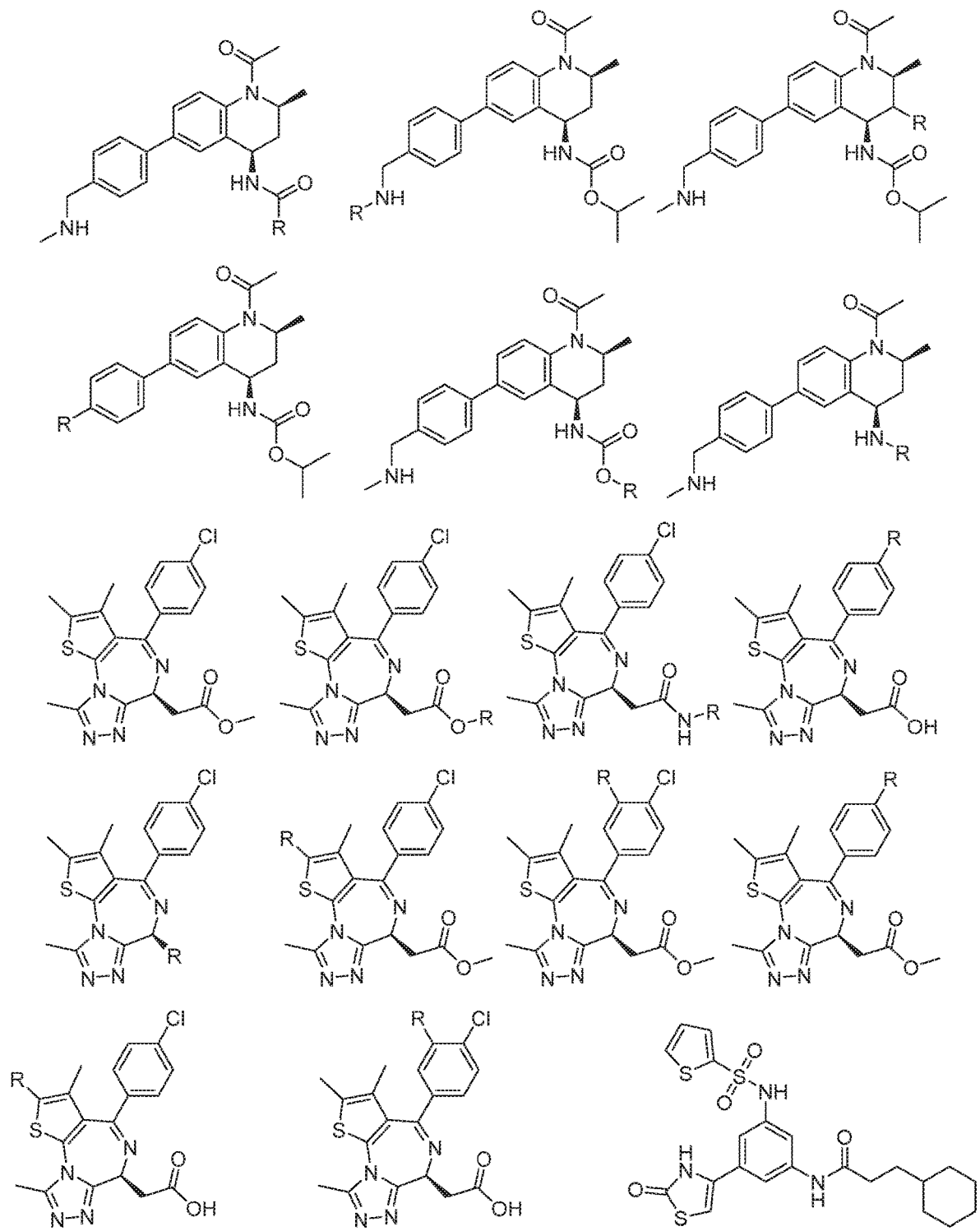
Figure 8E:
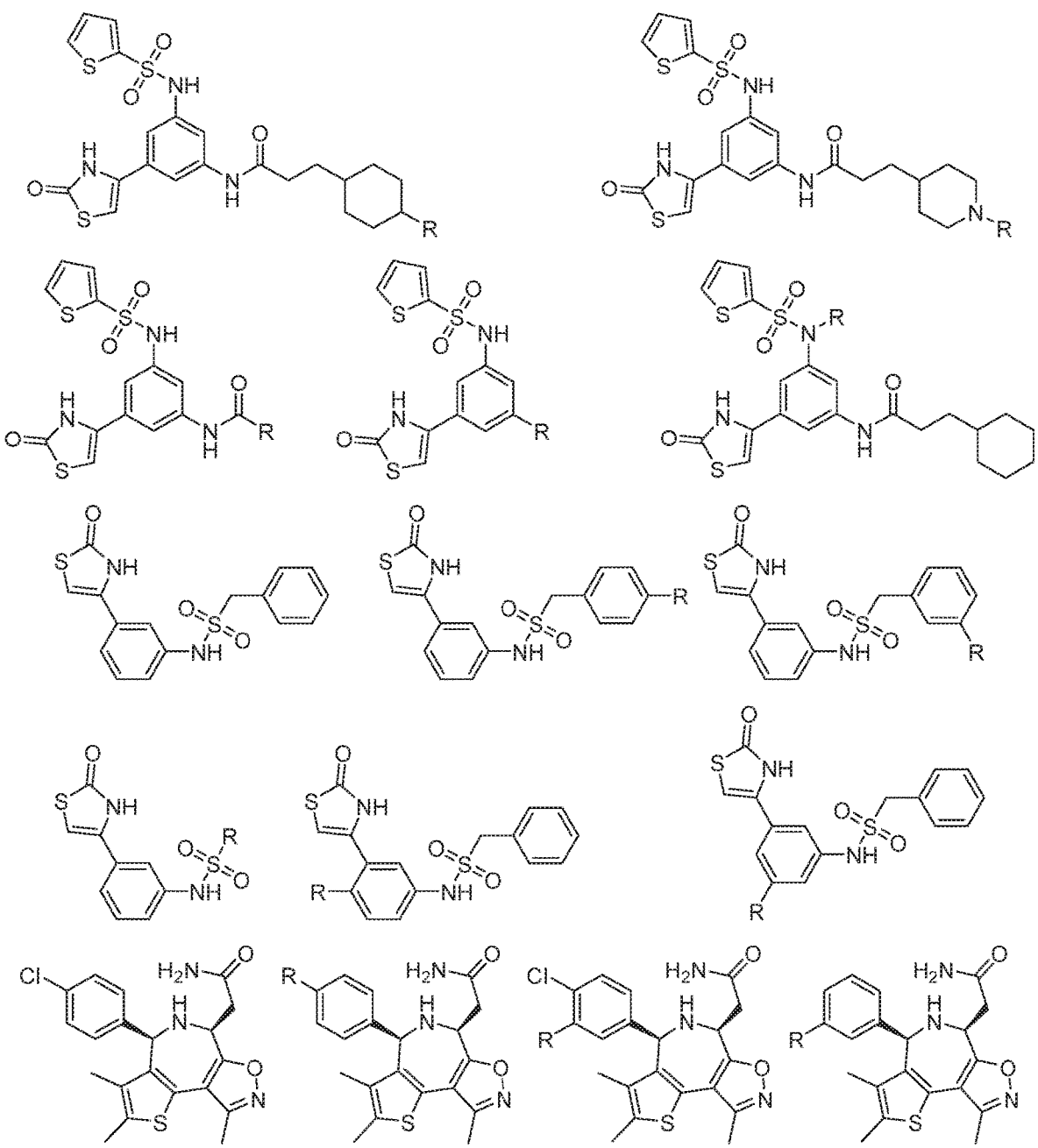
Figure 8F:
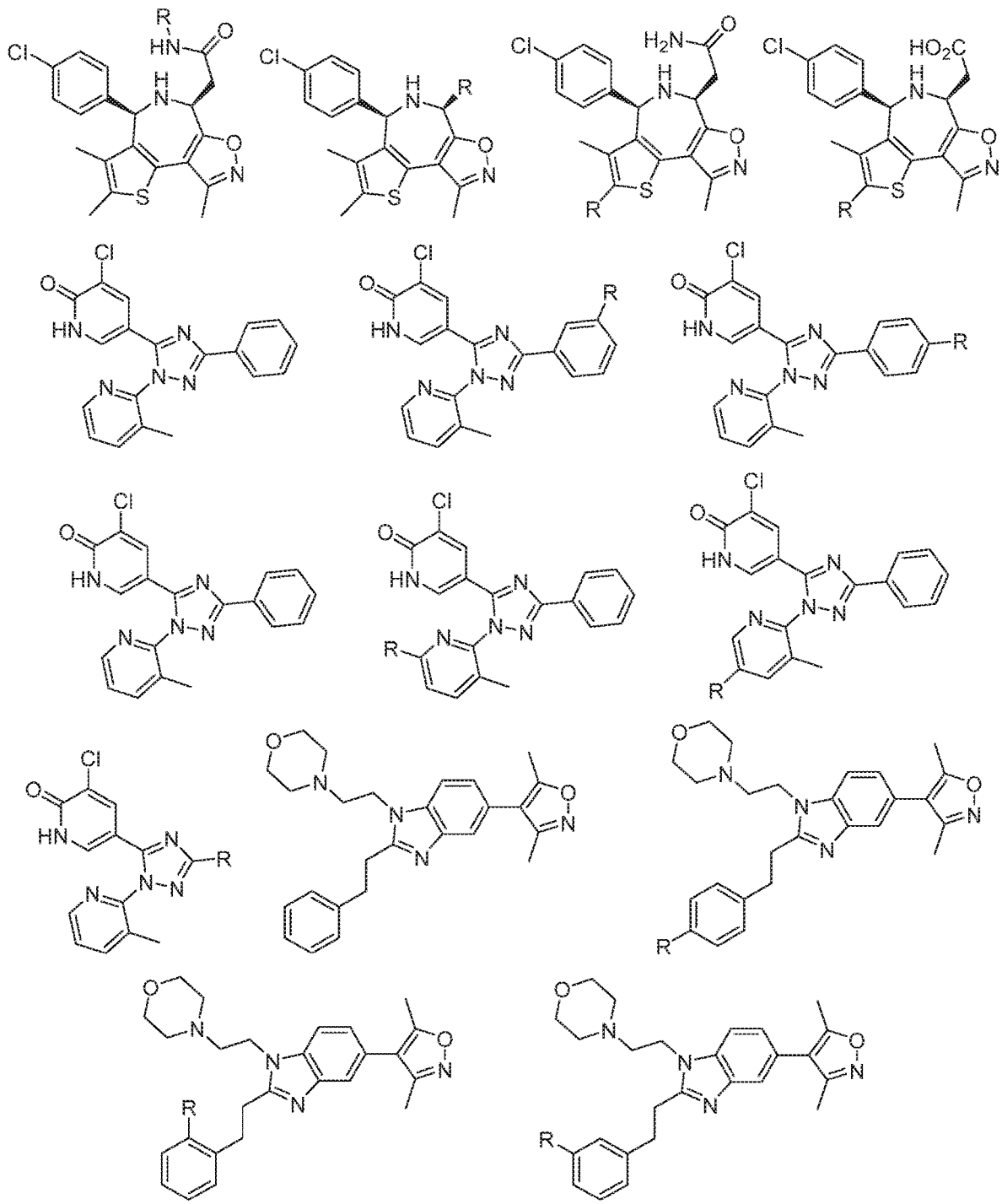
Figure 8G:
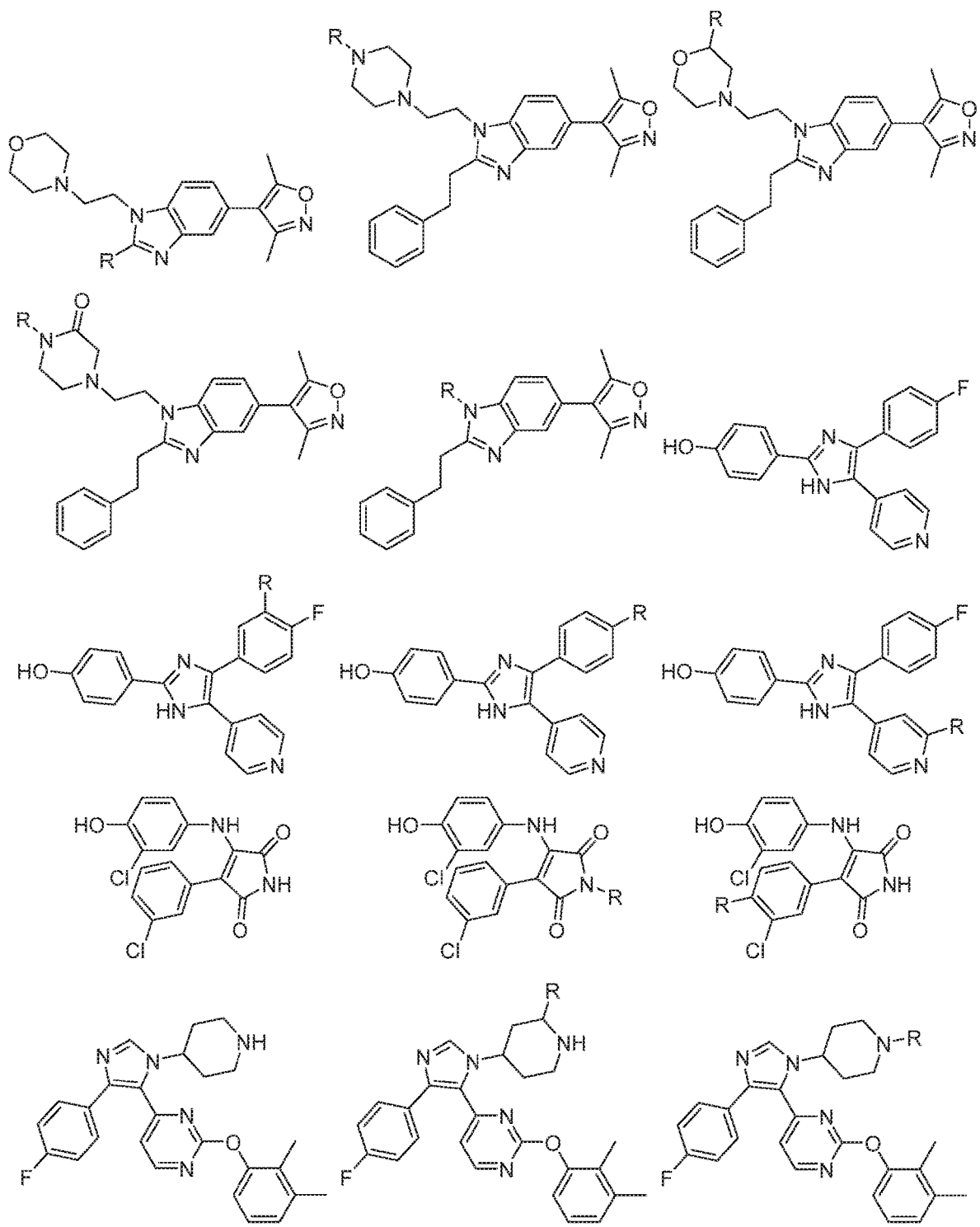
Figure 8H:
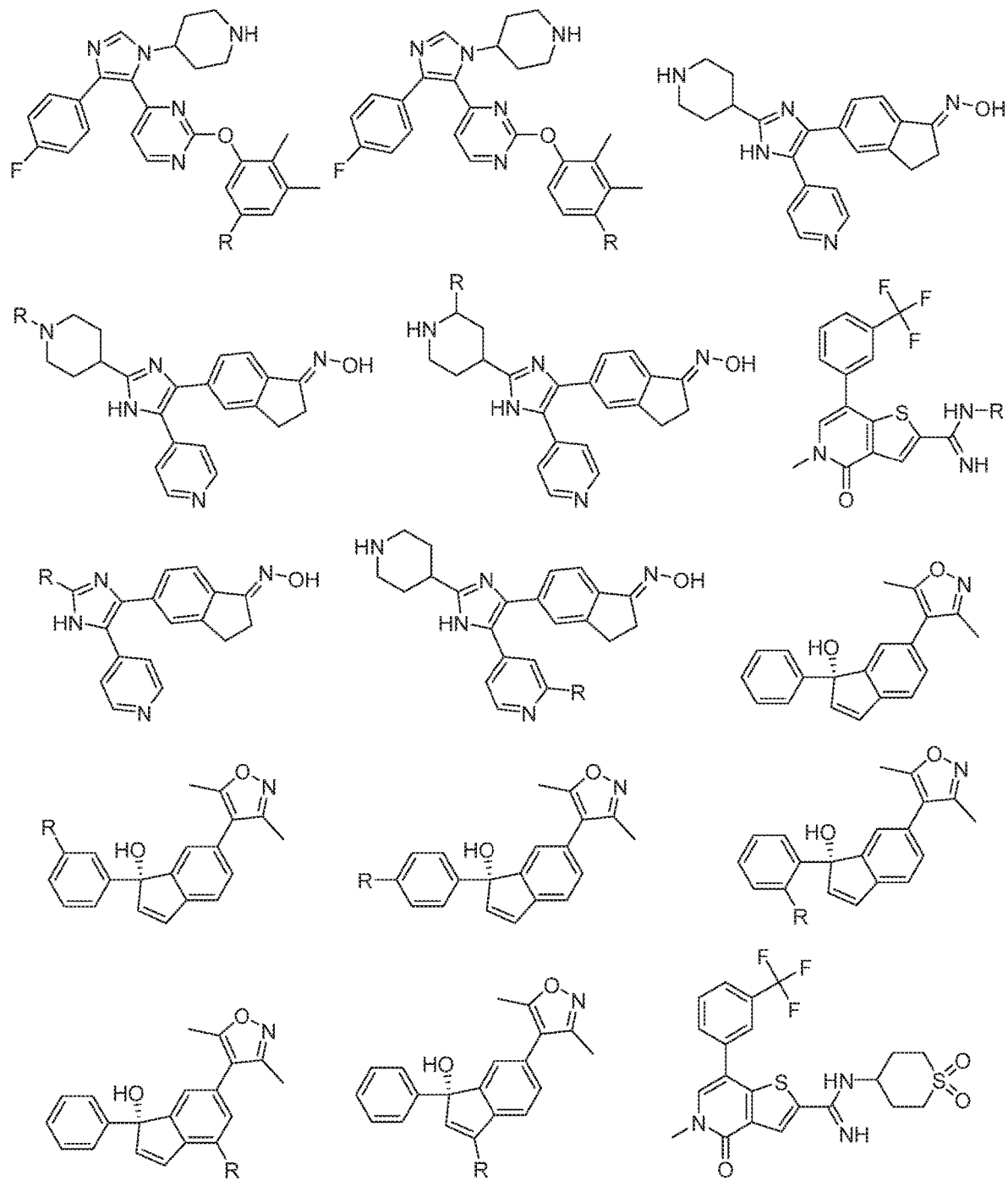
Figure 8I:
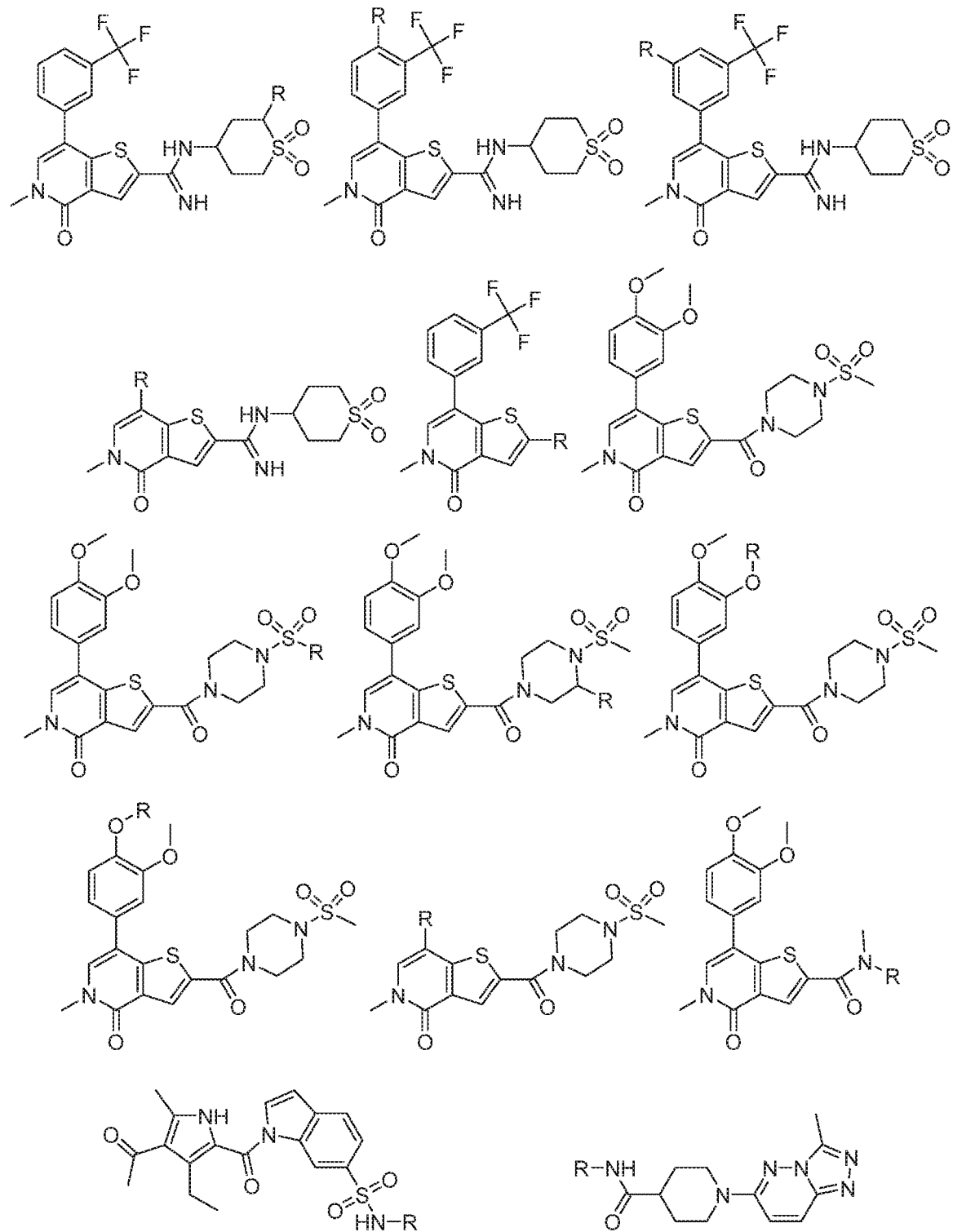
Figure 8J:
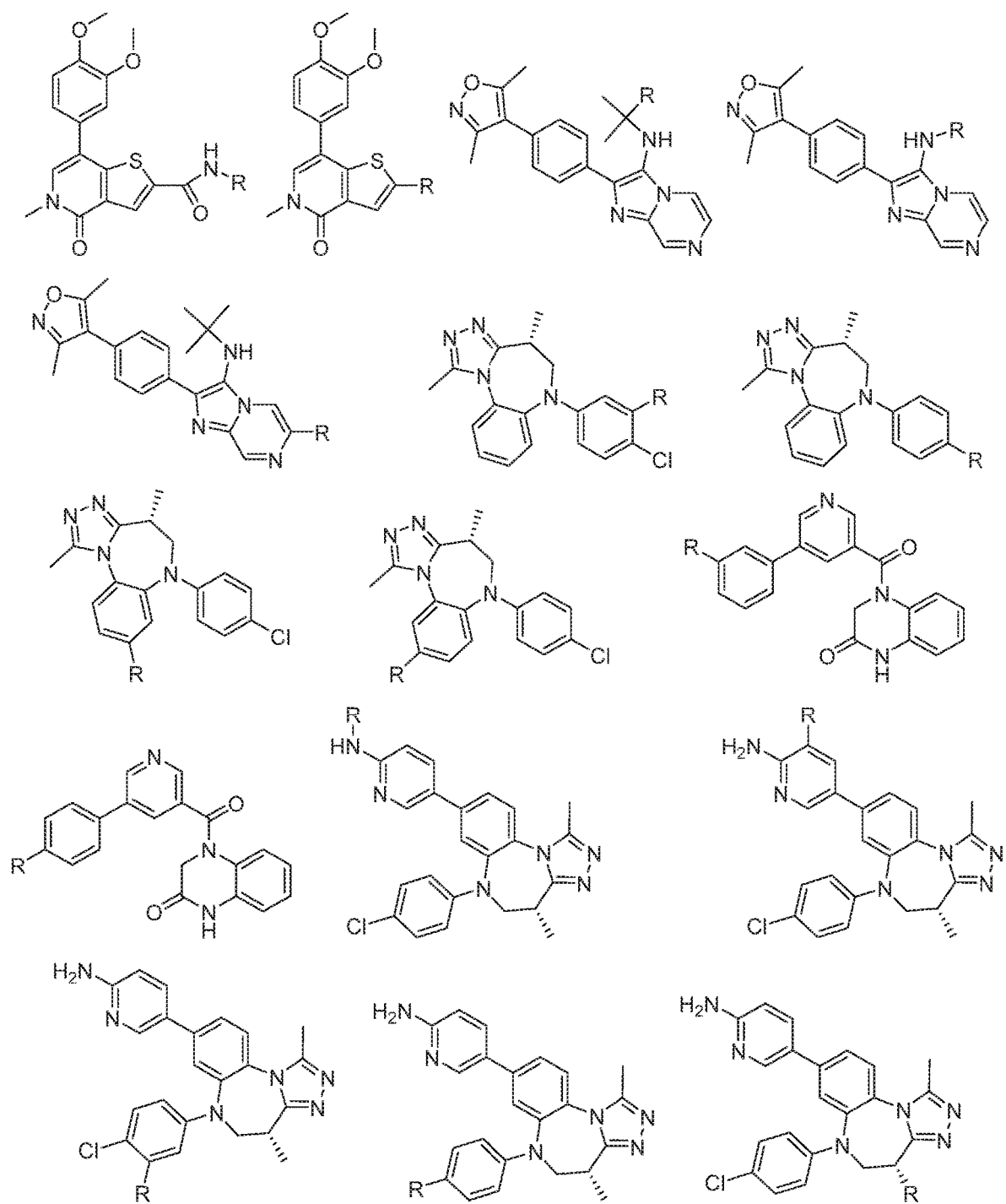
Figure 8K:
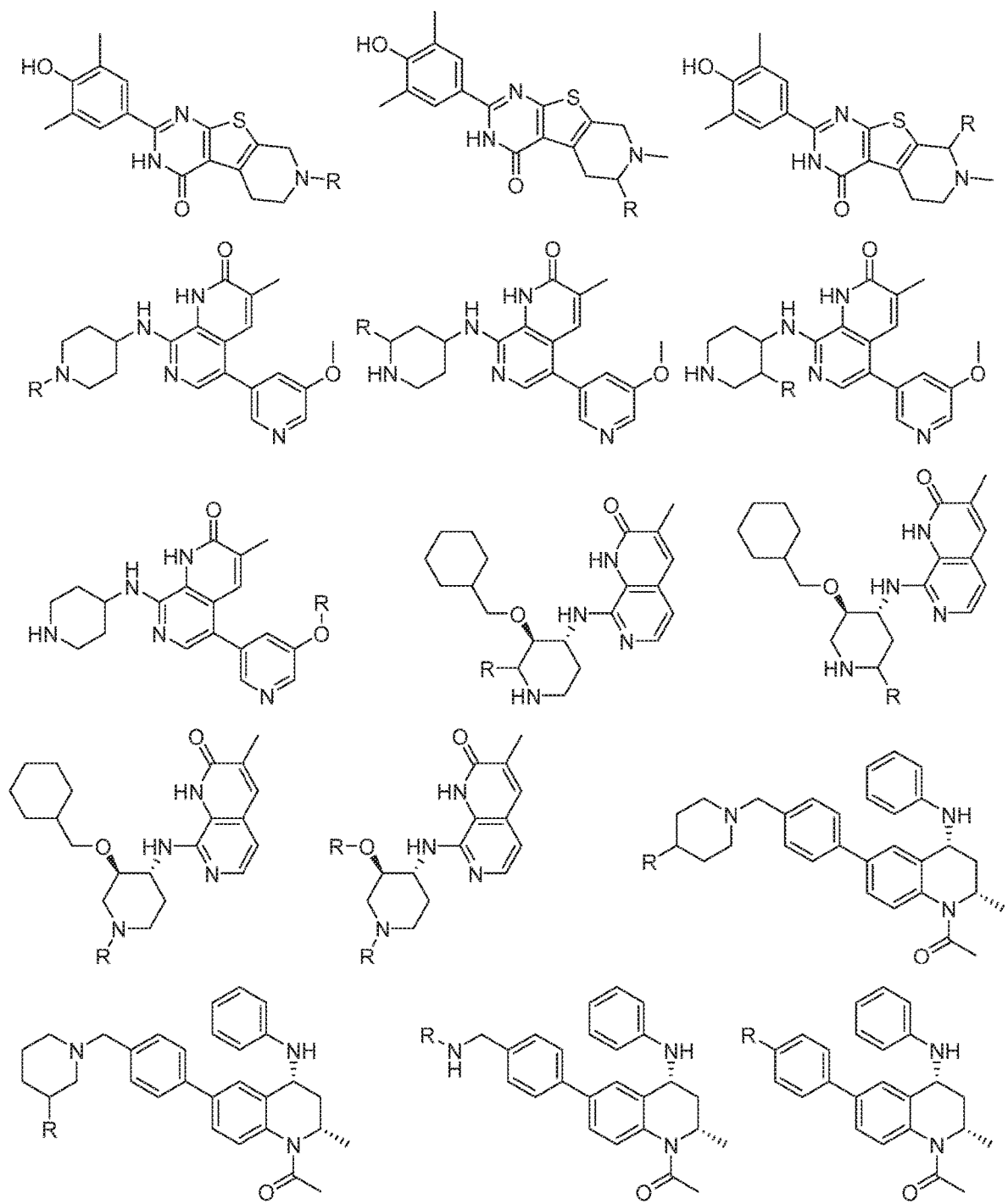
Figure 8L:
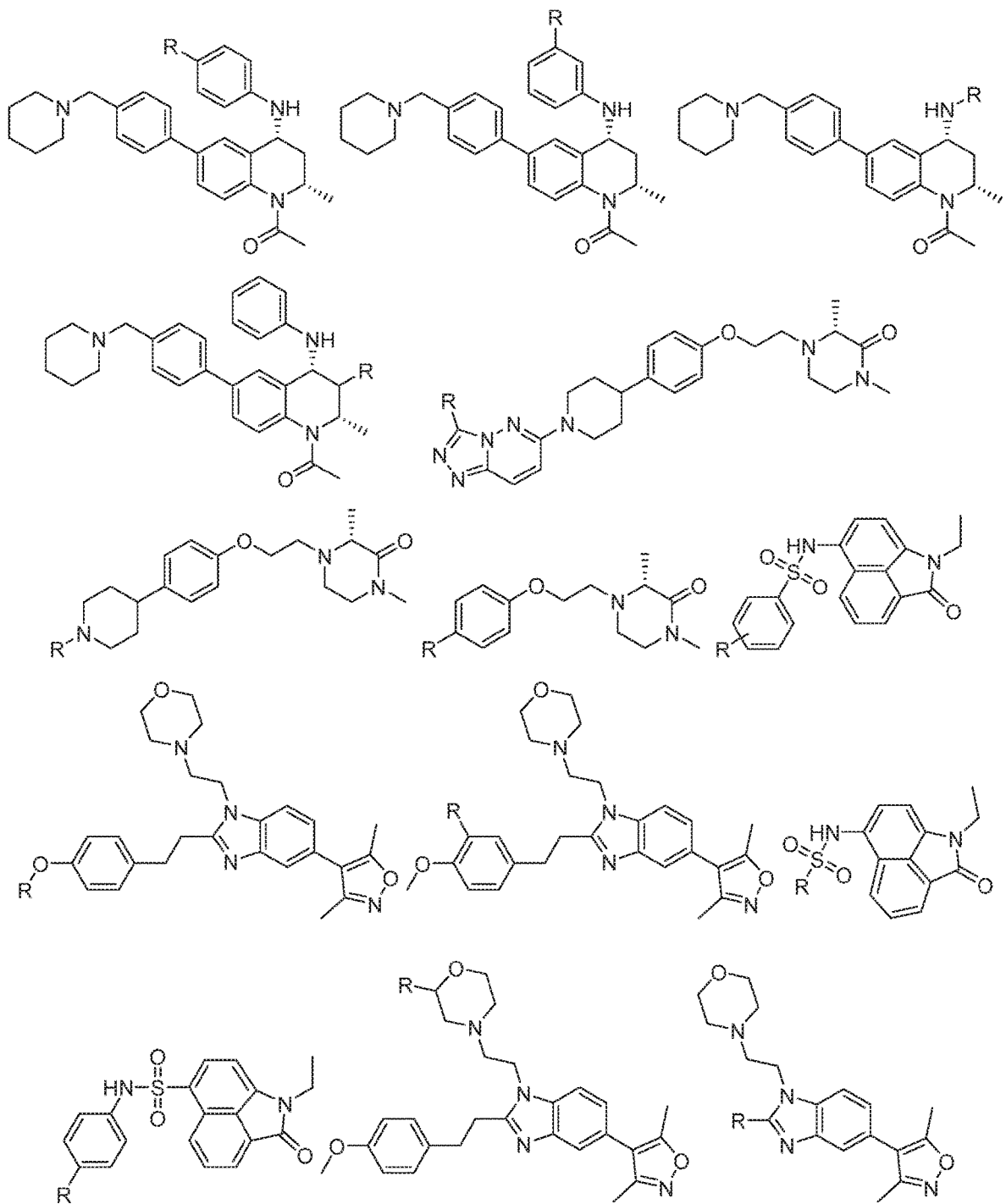
Figure 8M:
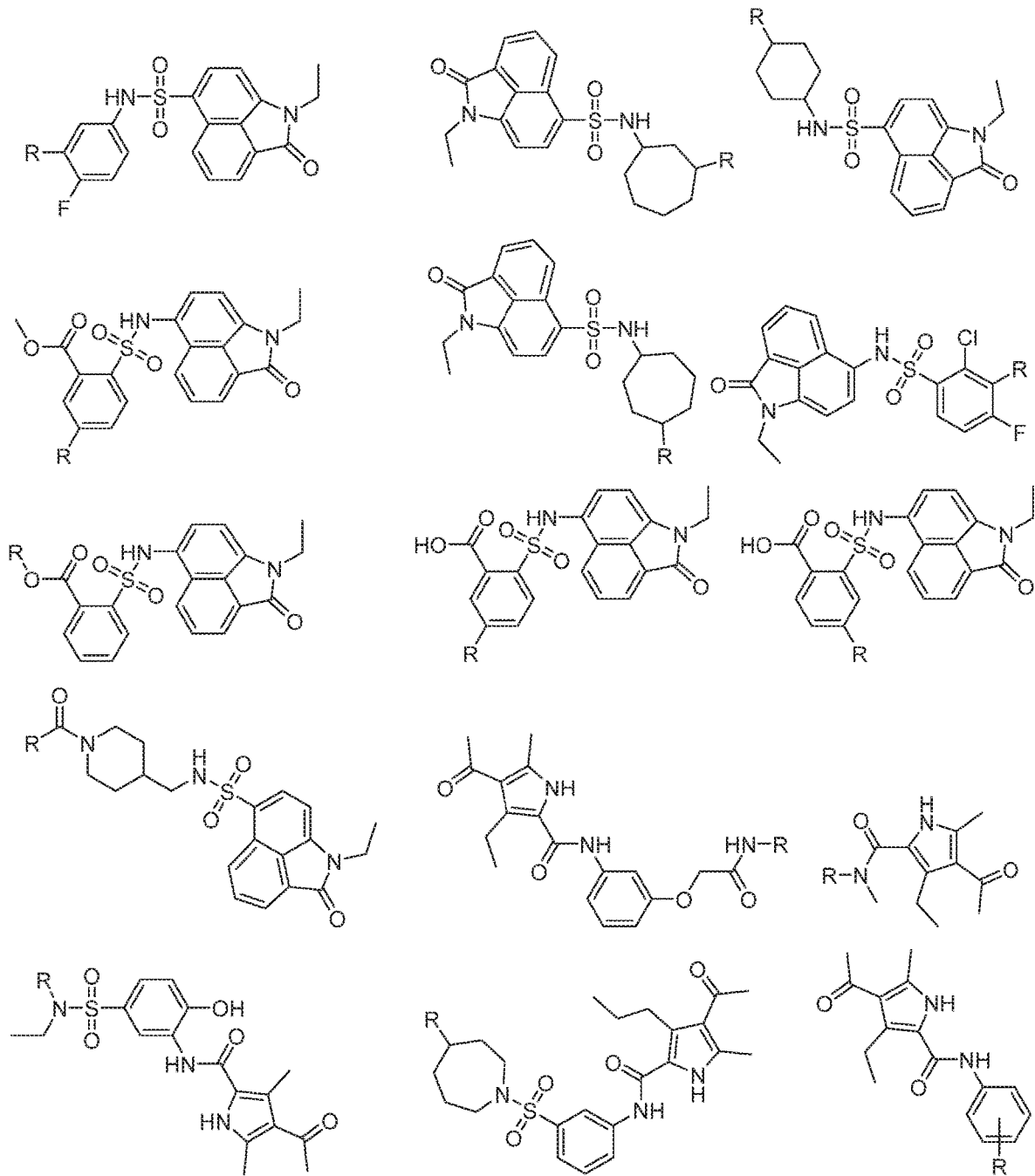
Figure 8N:
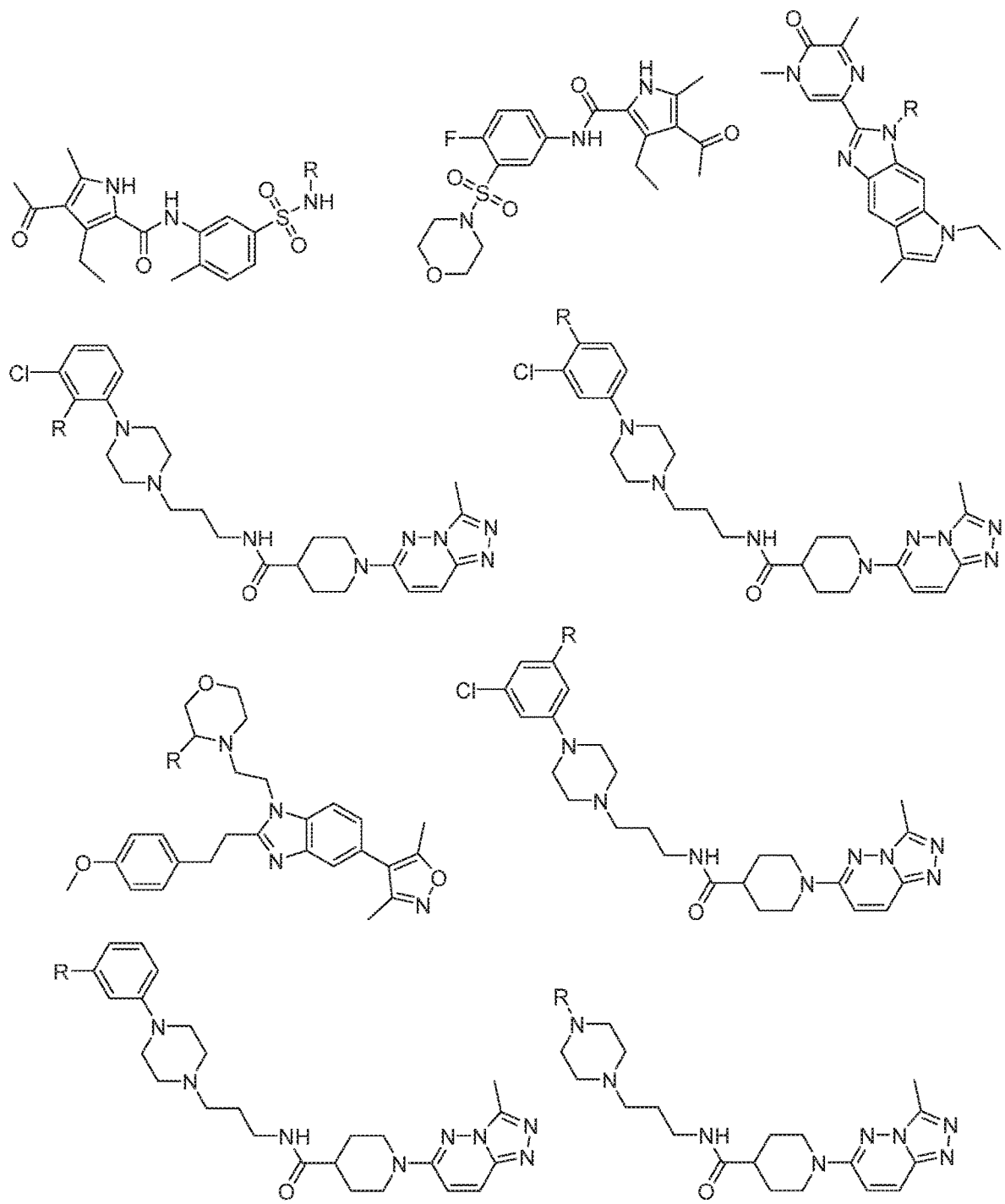
Figure 8O:
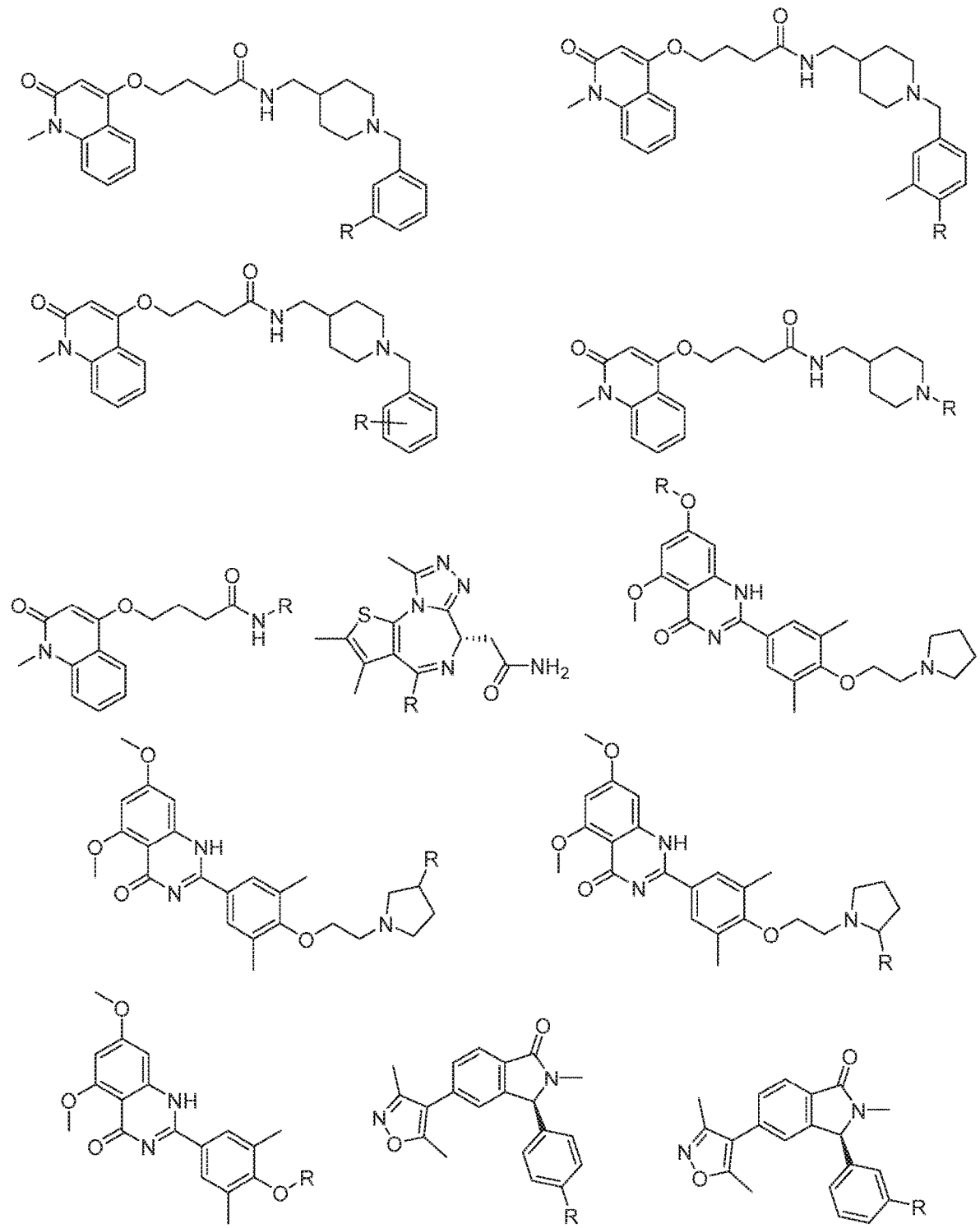
Figure 8P:
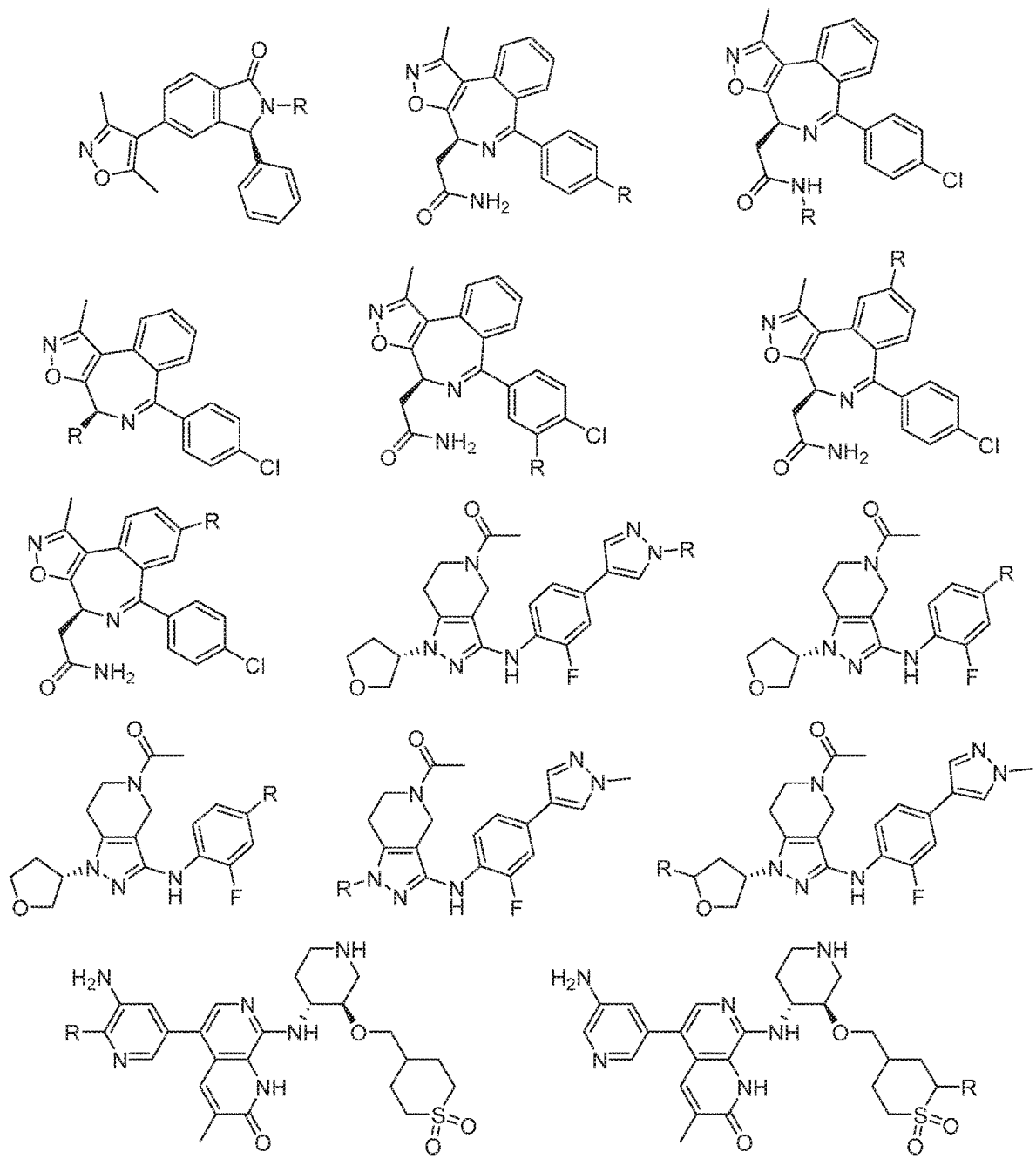
Figure 8Q:
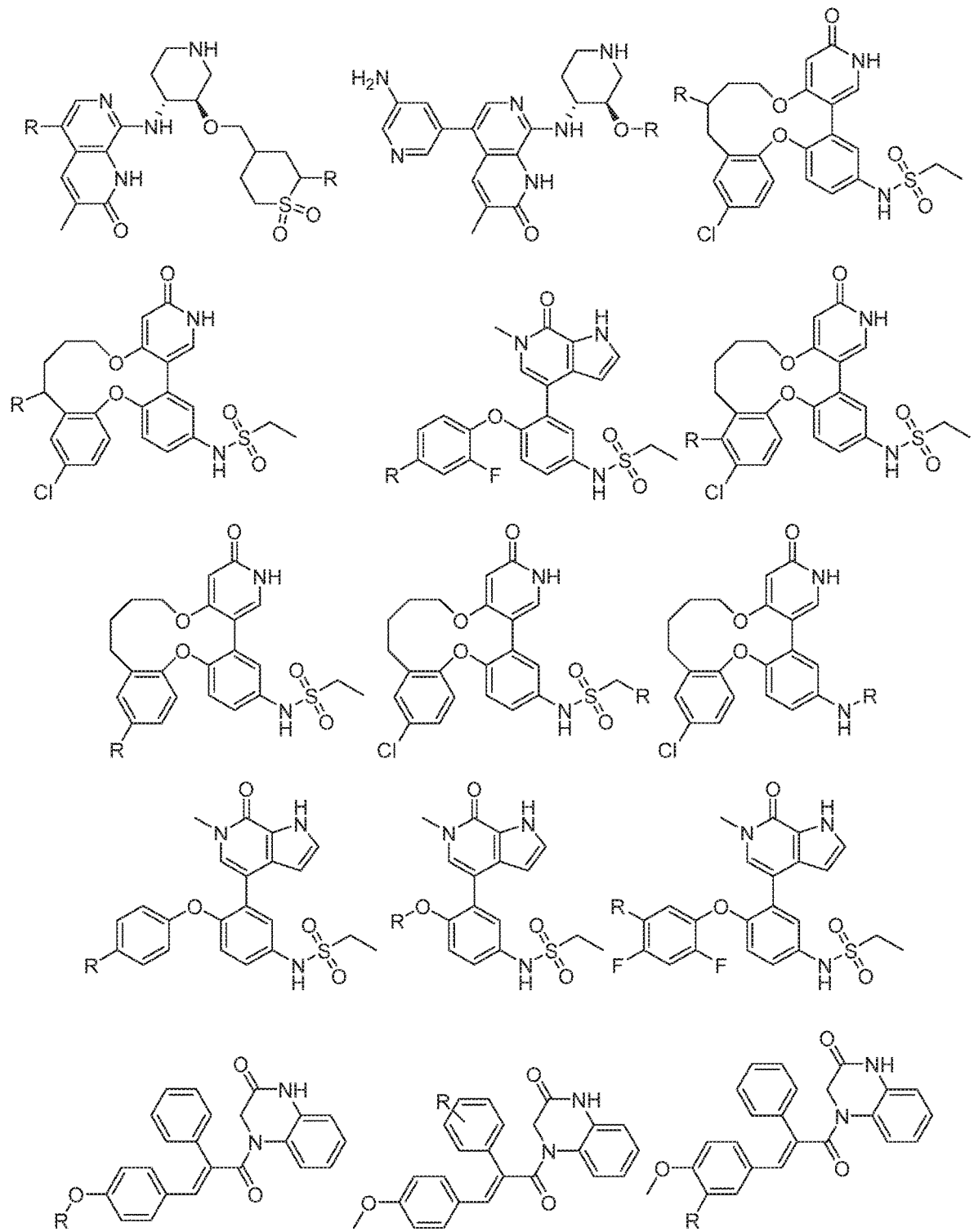
Figure 8R:
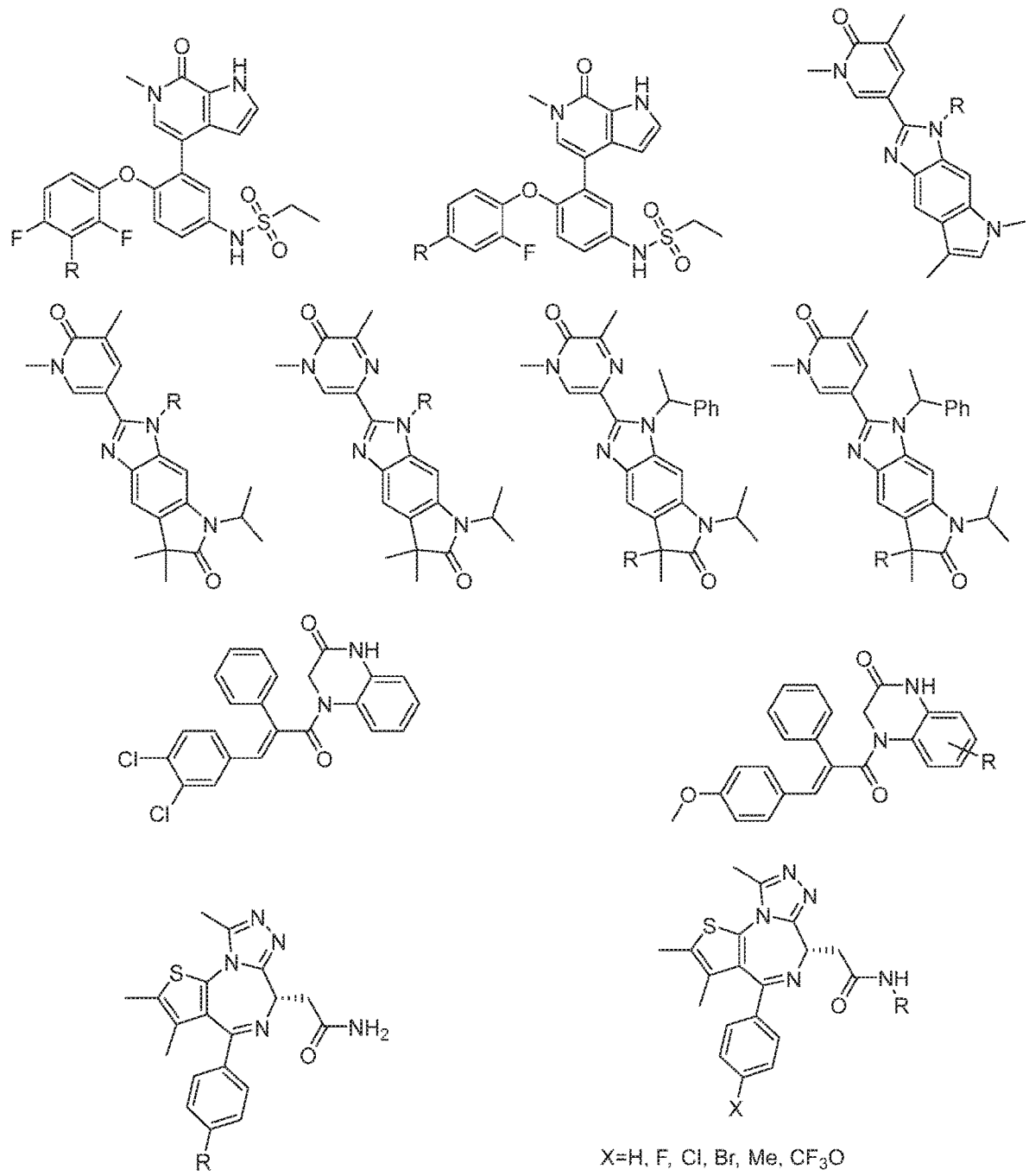
Figure 8U:
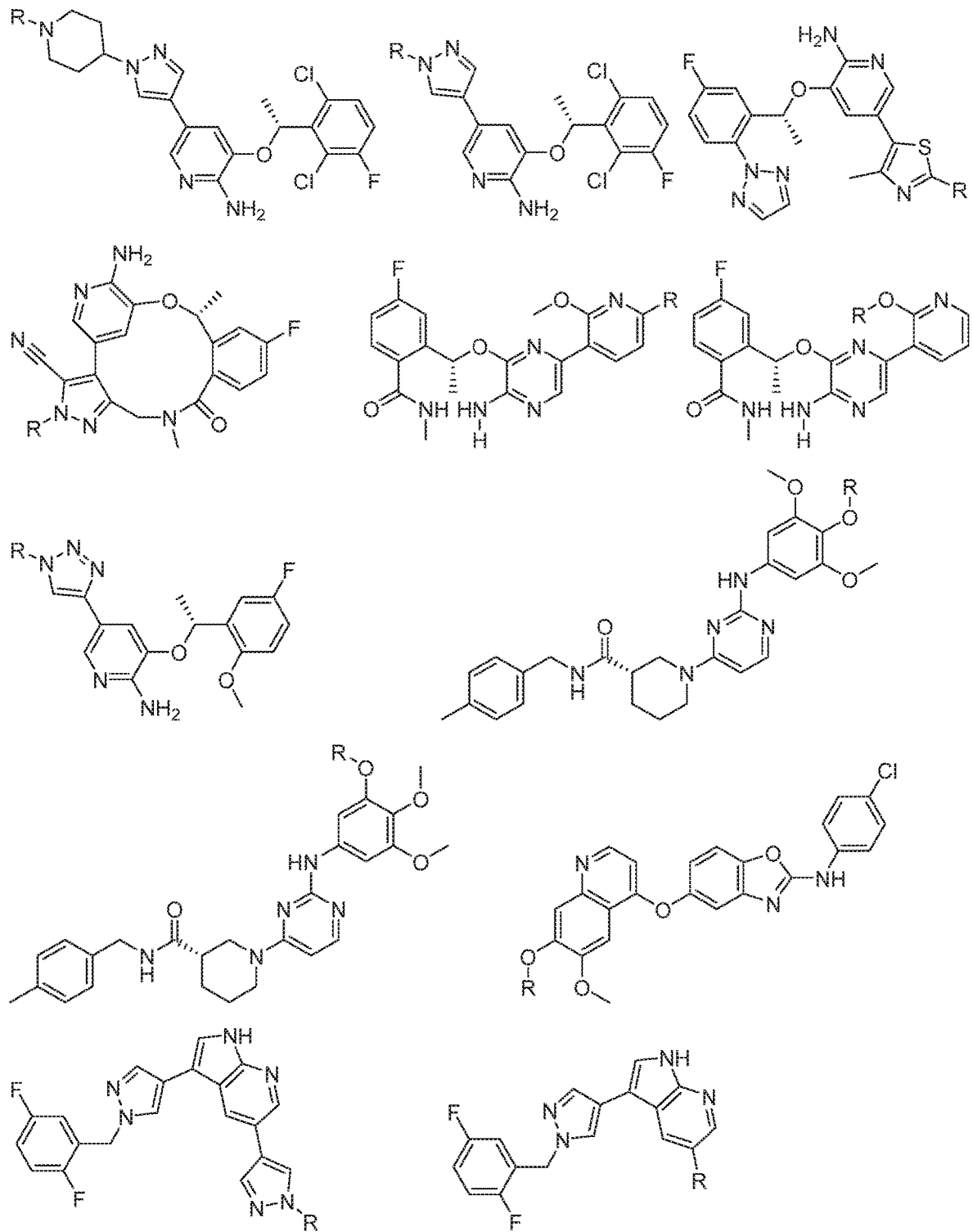
Figure 8V:
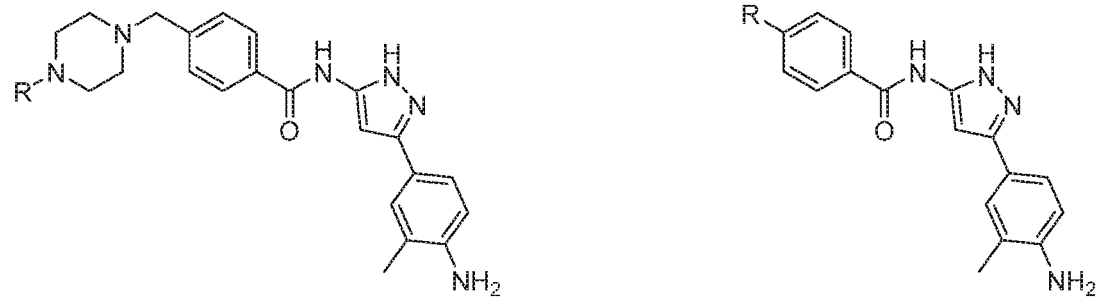
Figure 8W:
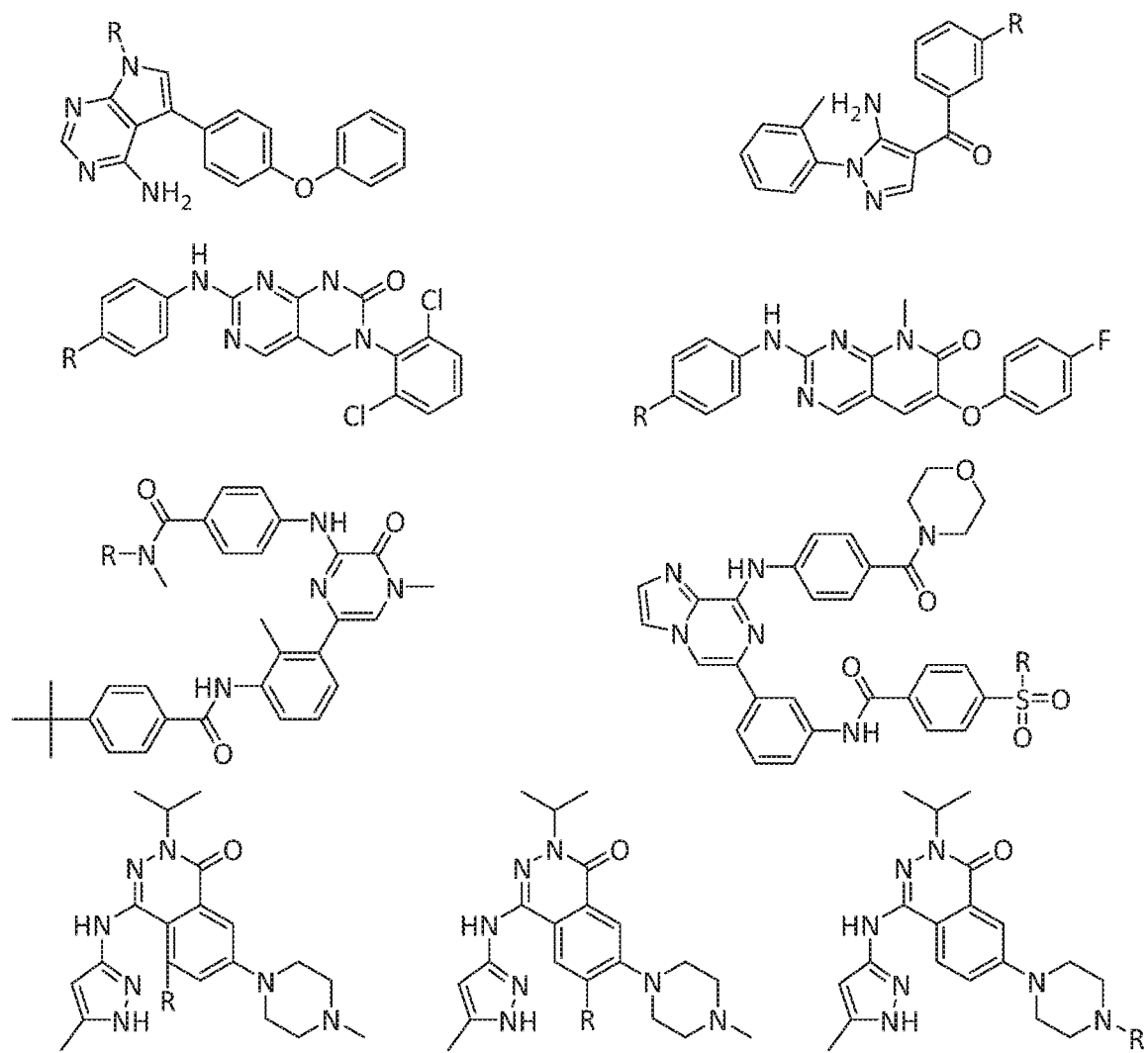
Figure 8X:
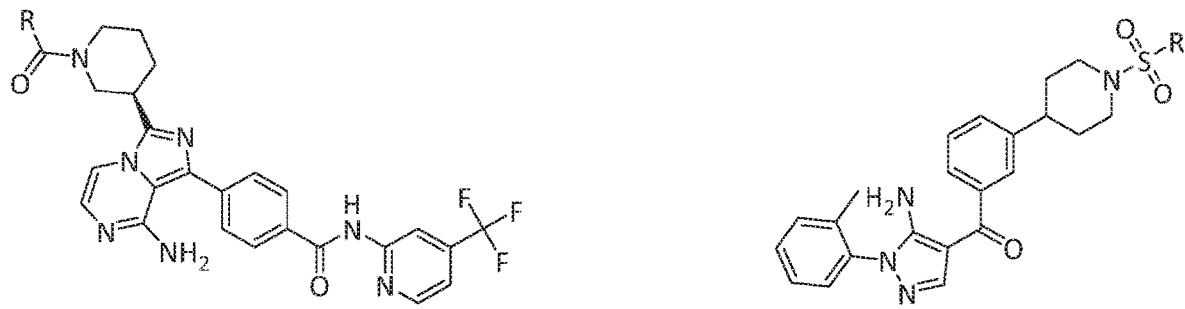
Figure 8Y:
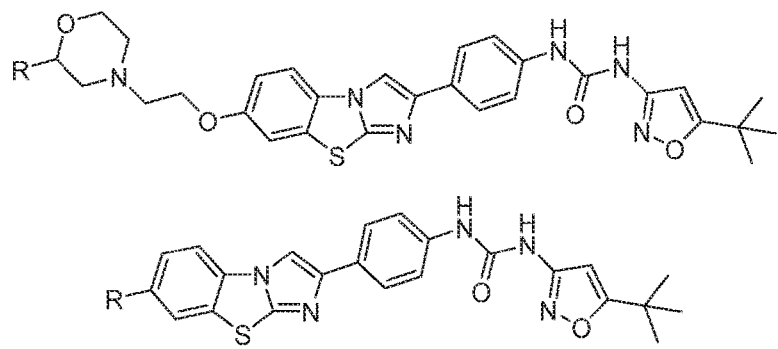
Figure 8Z:
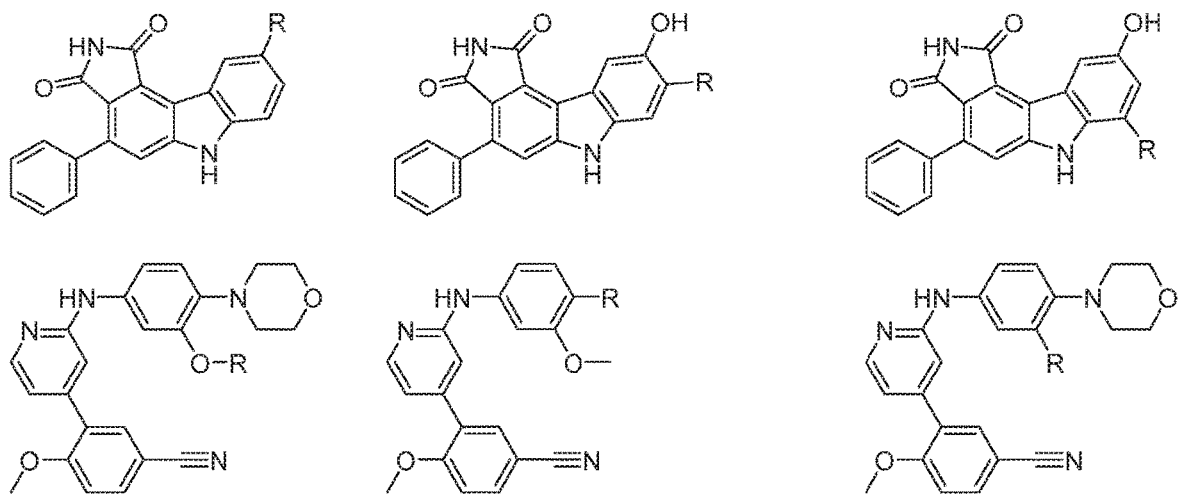
Figure 8A:
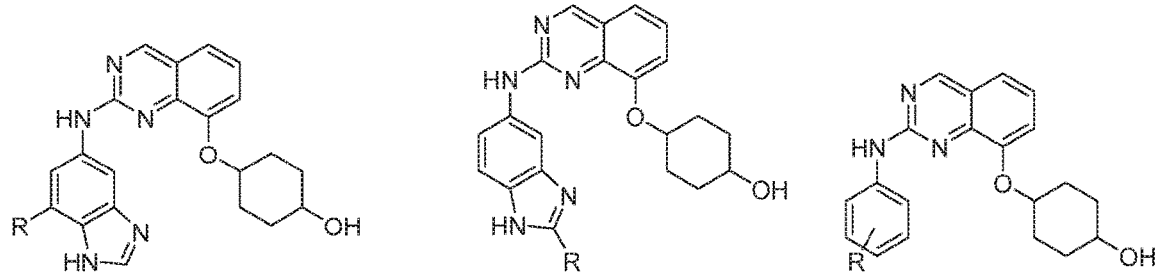
Figure 8B:
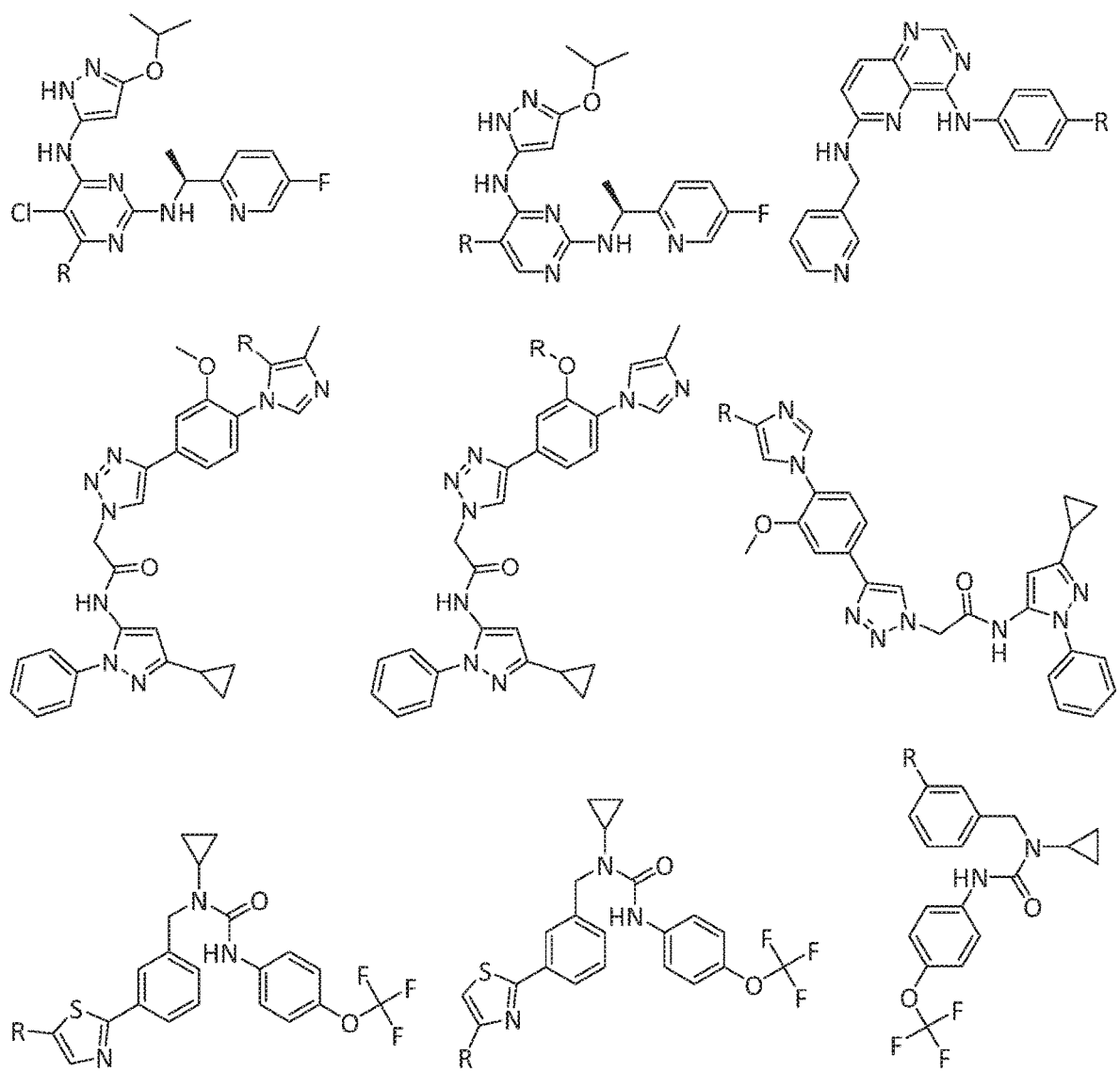
Figure 8C:
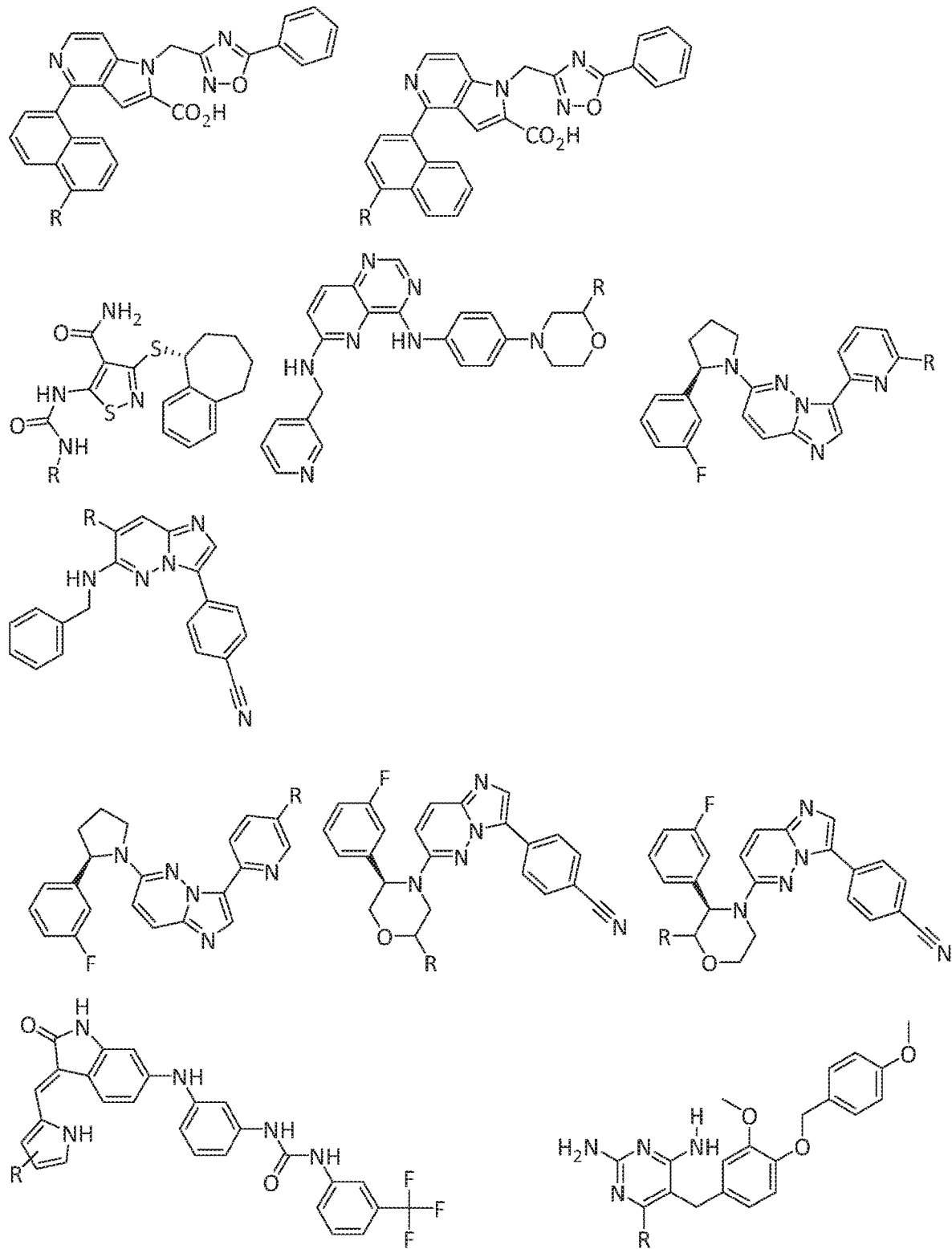
Figure 8D:
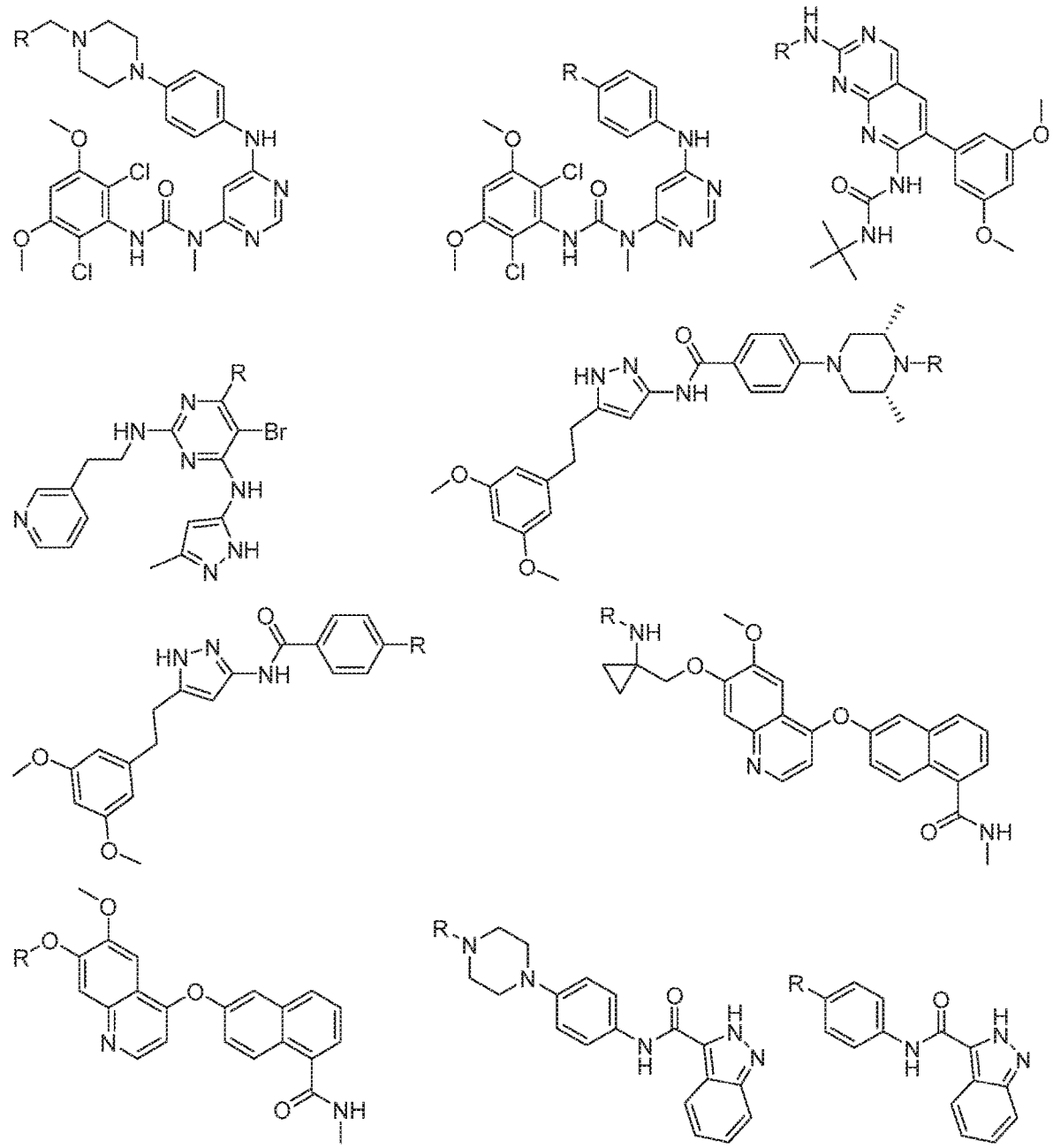
Figure 8E:
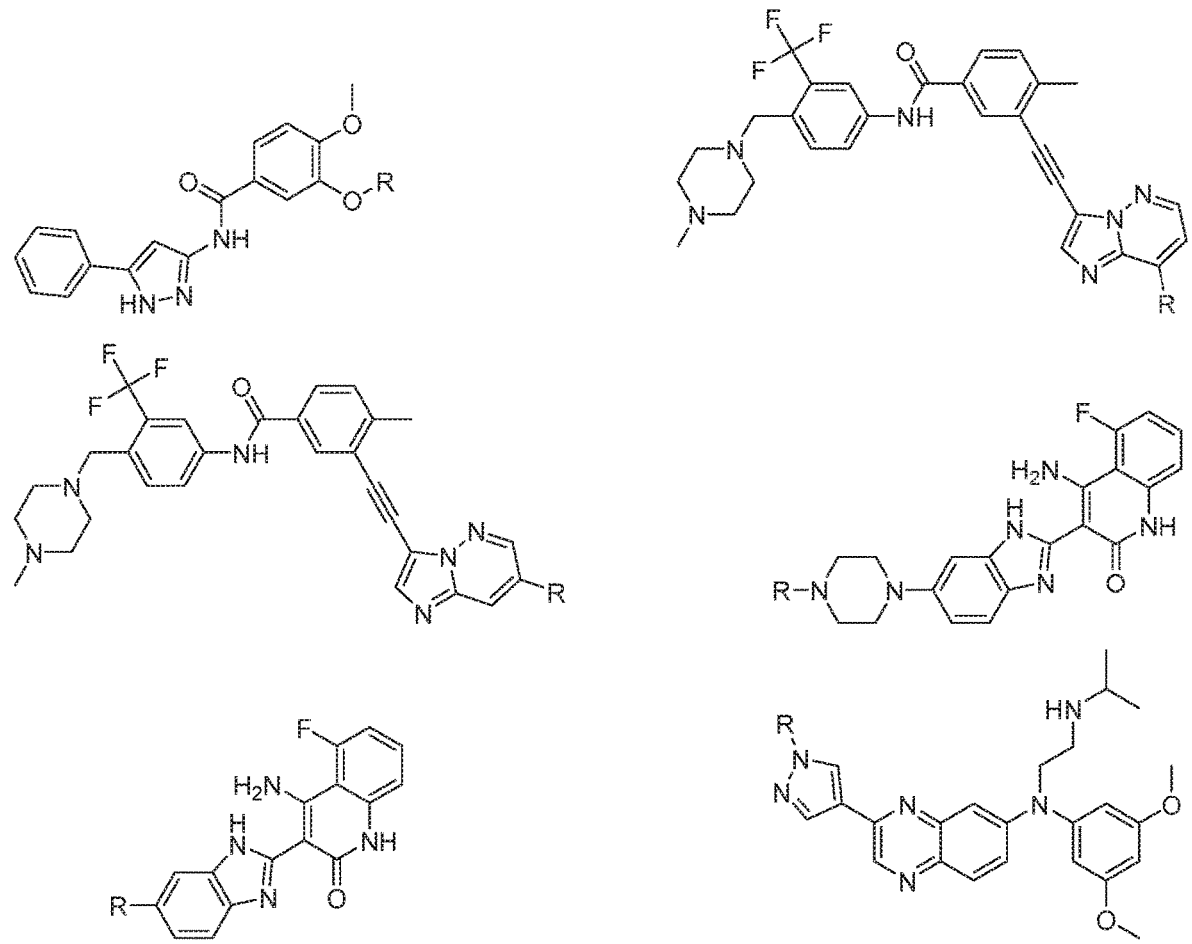
Figure 8F:
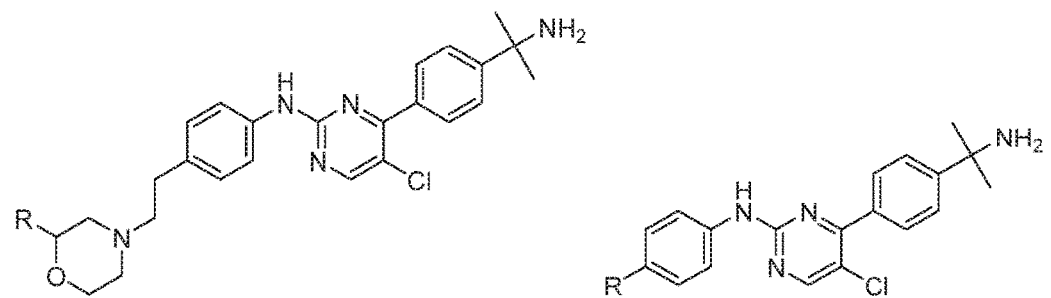
Figure 8G:
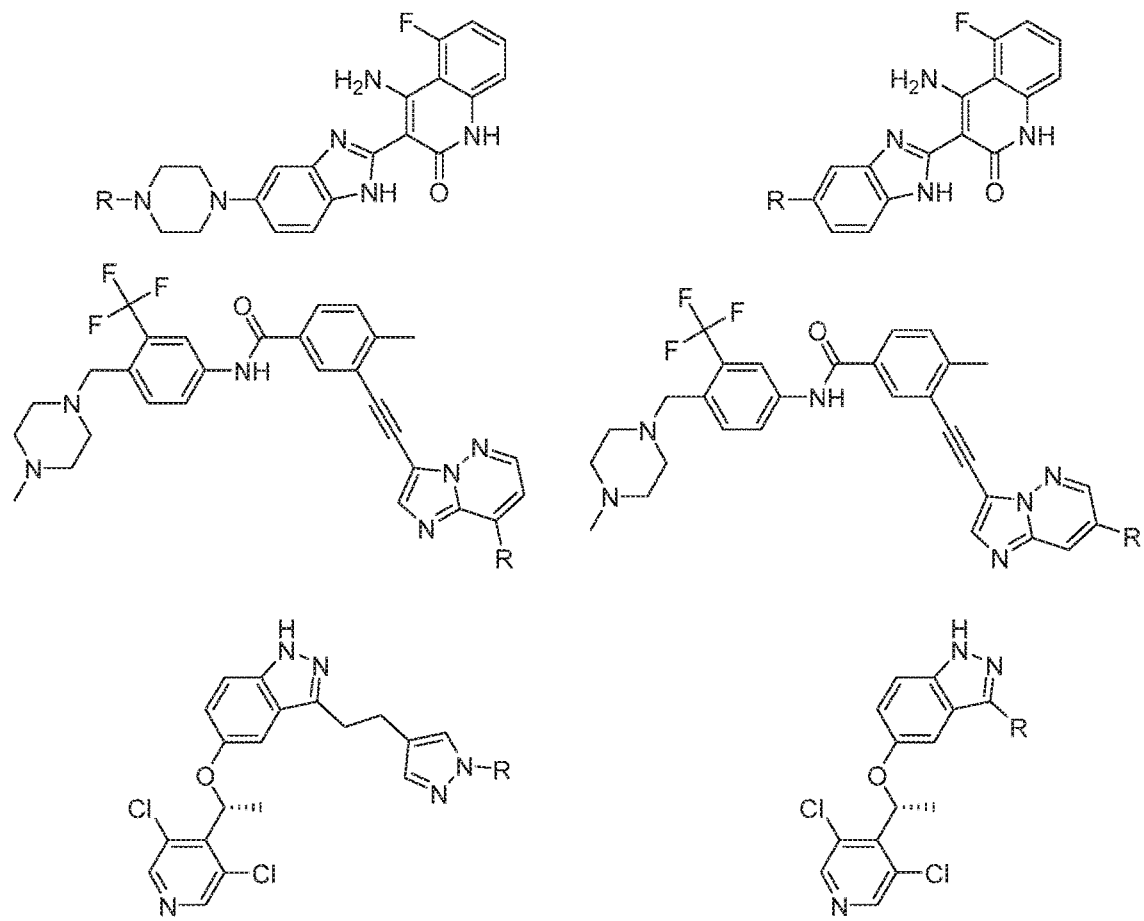
Figure 8H:
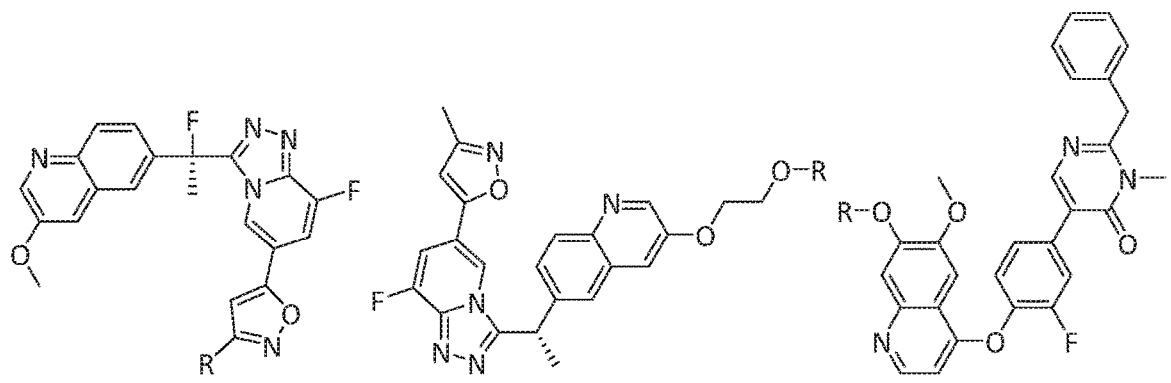
Figure 8I:
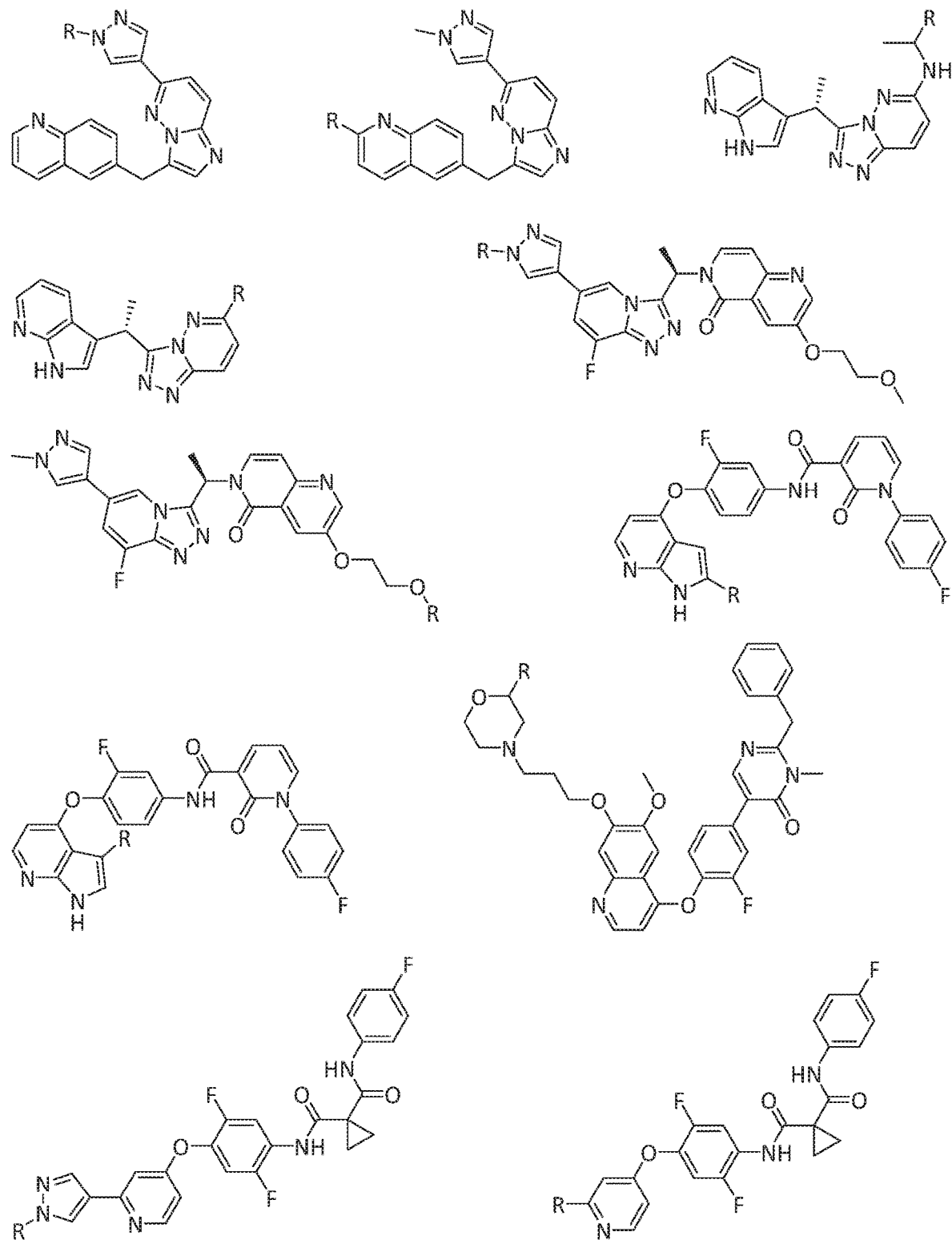
Figure 8J:
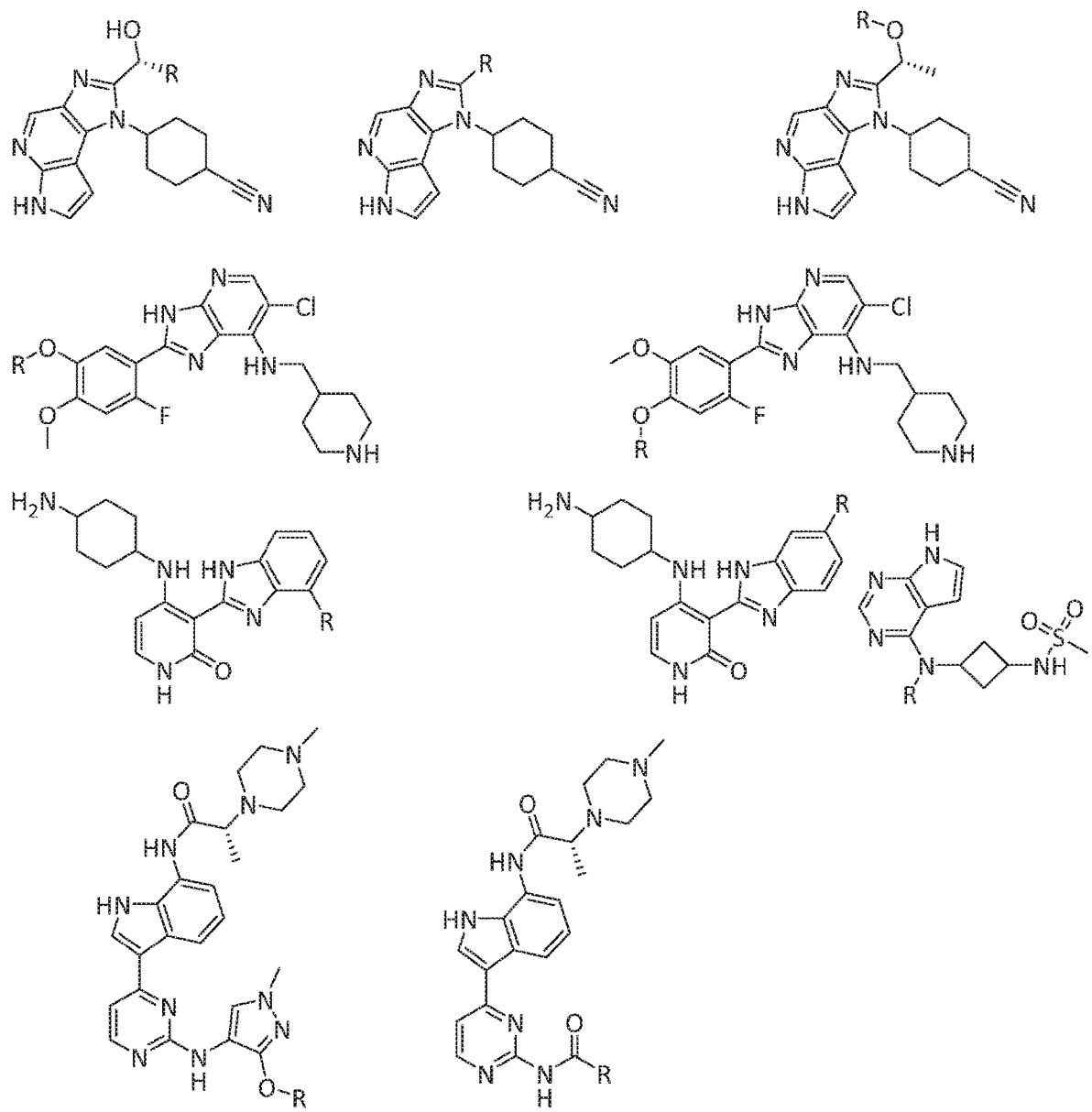
Figure 8K:
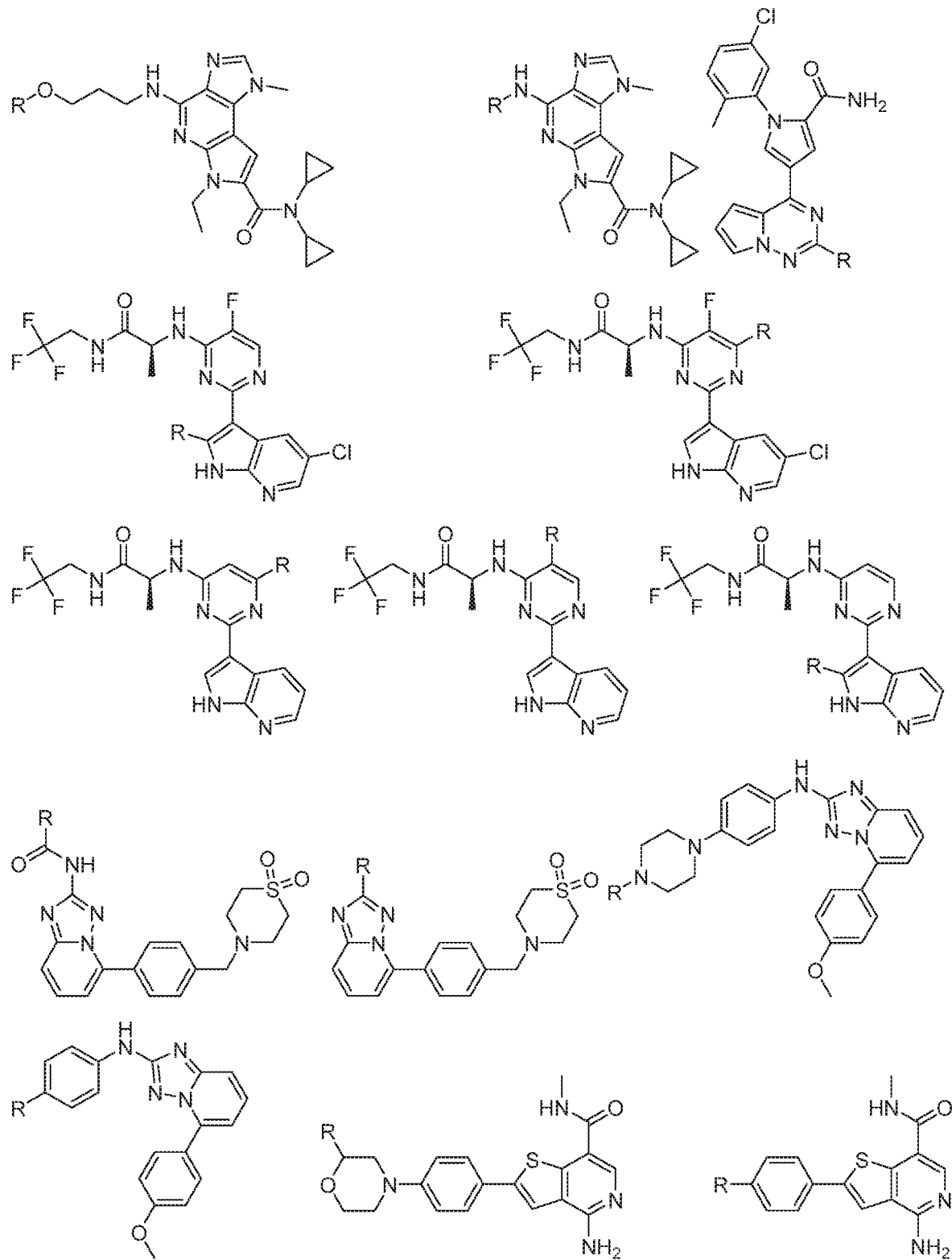
Figure 8L:
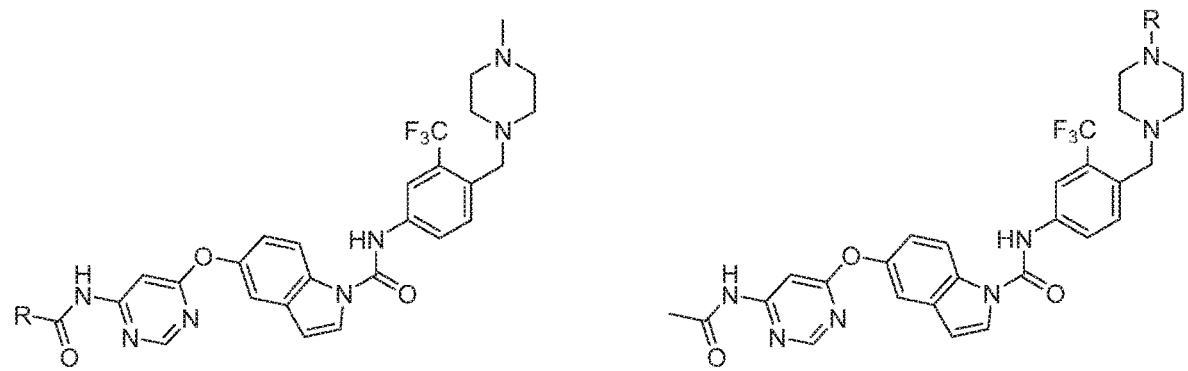
Figure 8M:
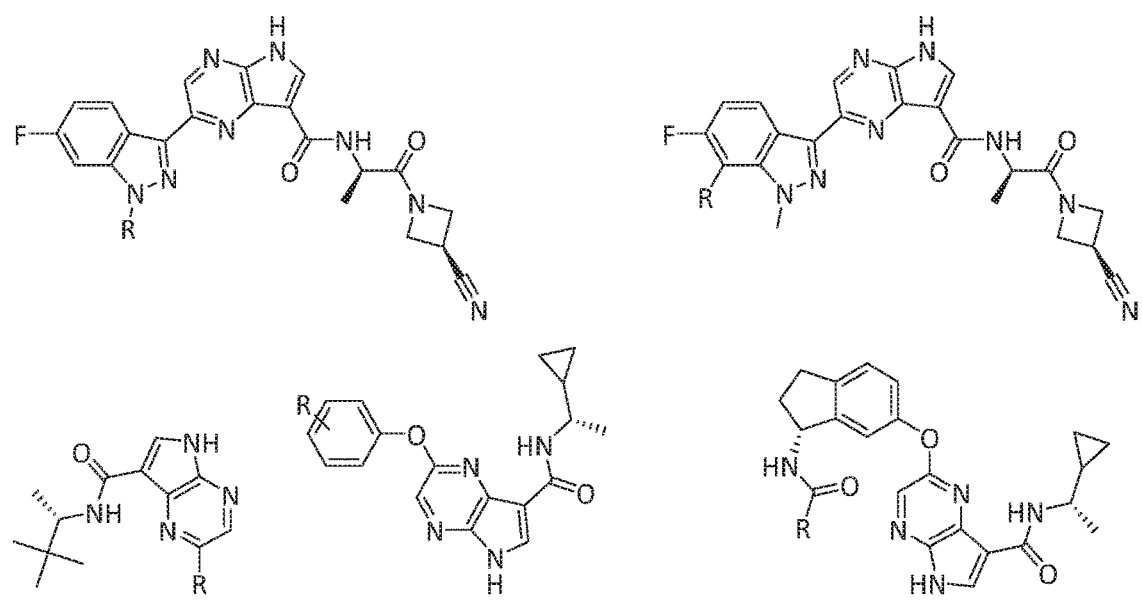
Figure 8N:
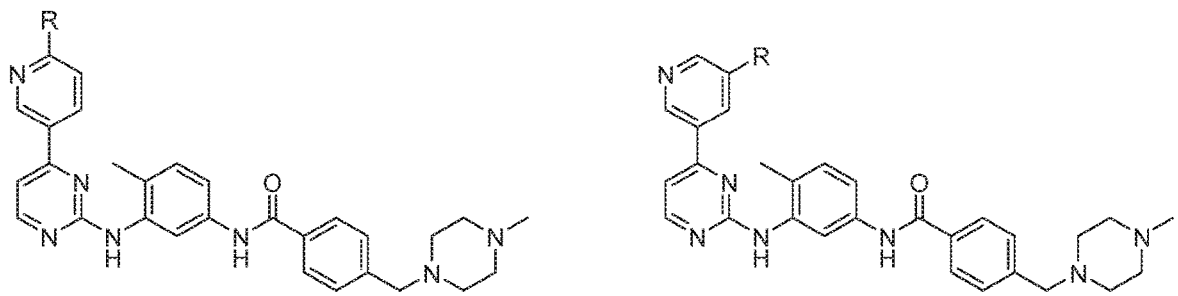
Figure 8O:
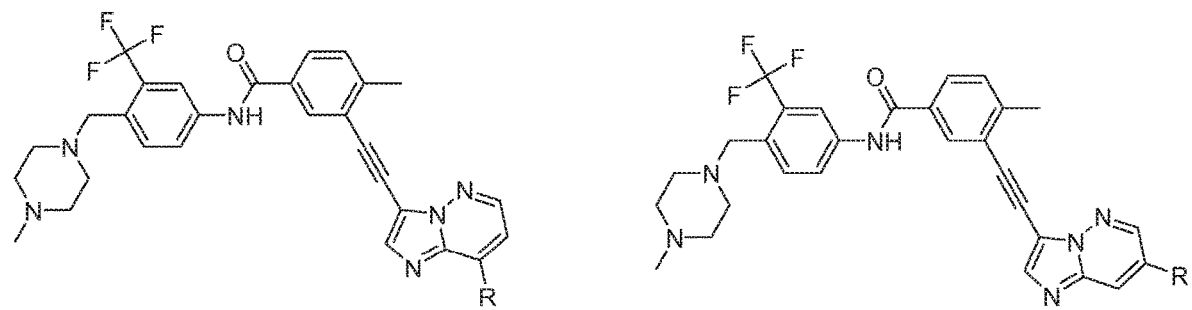
Figure 8P:
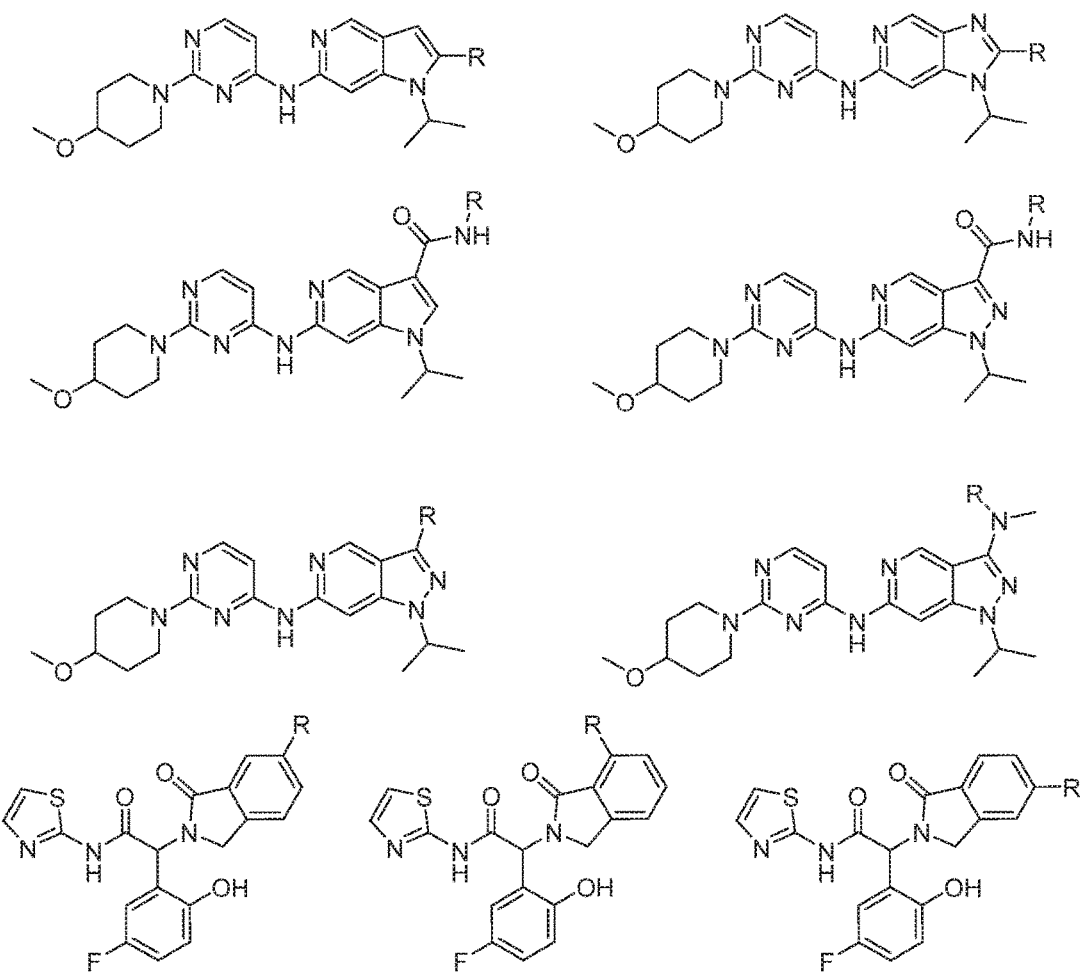
Figure 8Q:
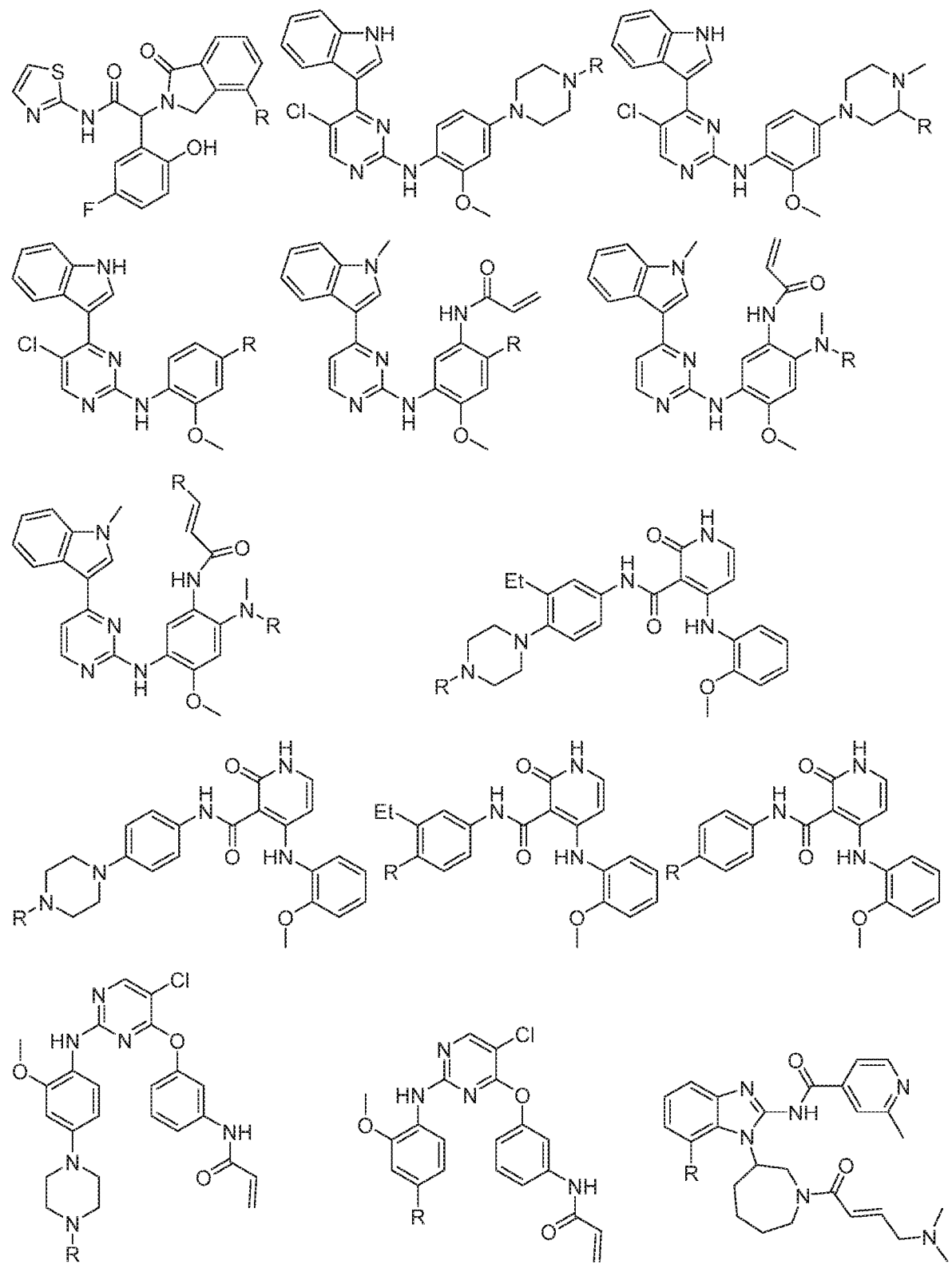
Figure 8R:
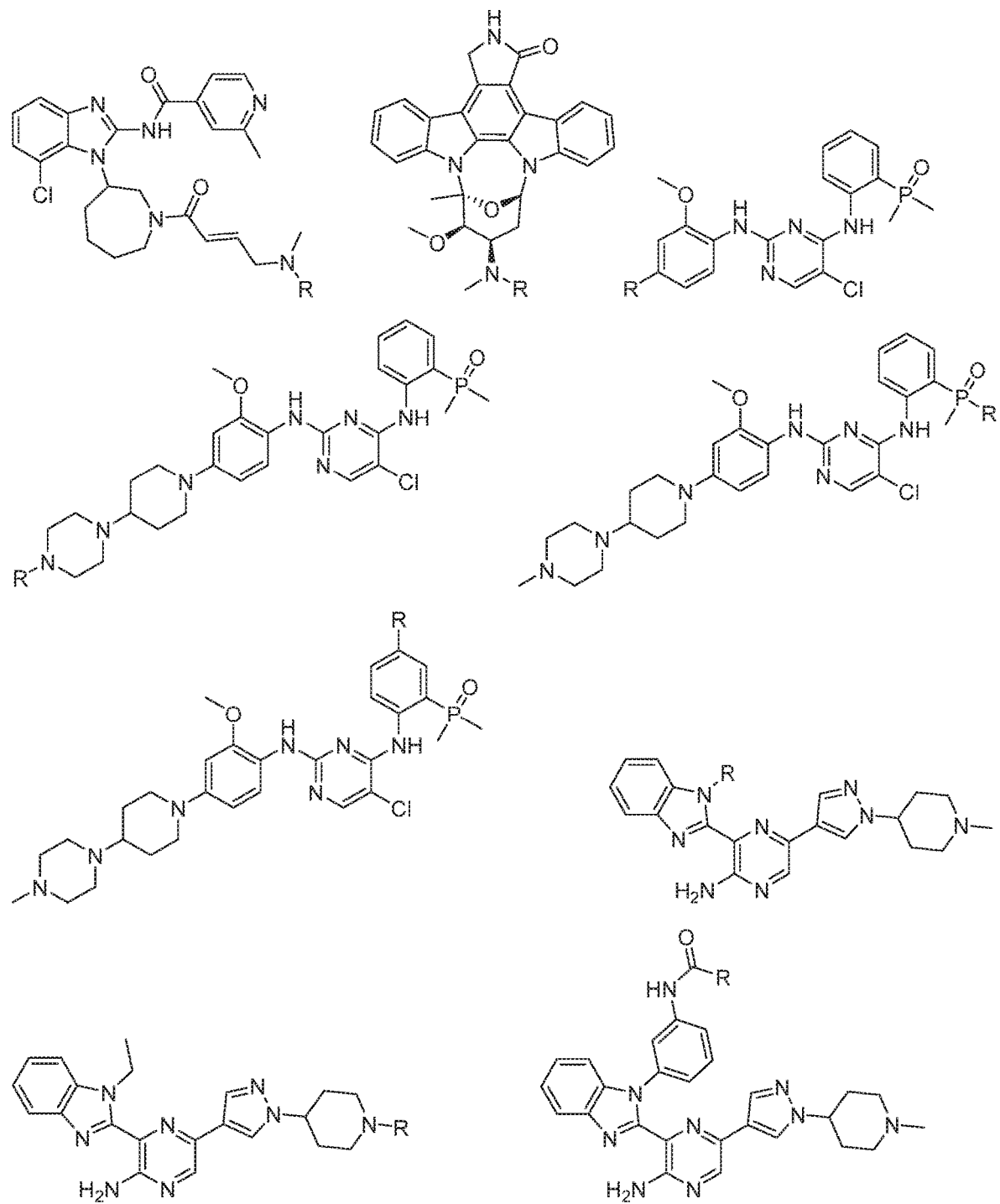
Figure 8S:
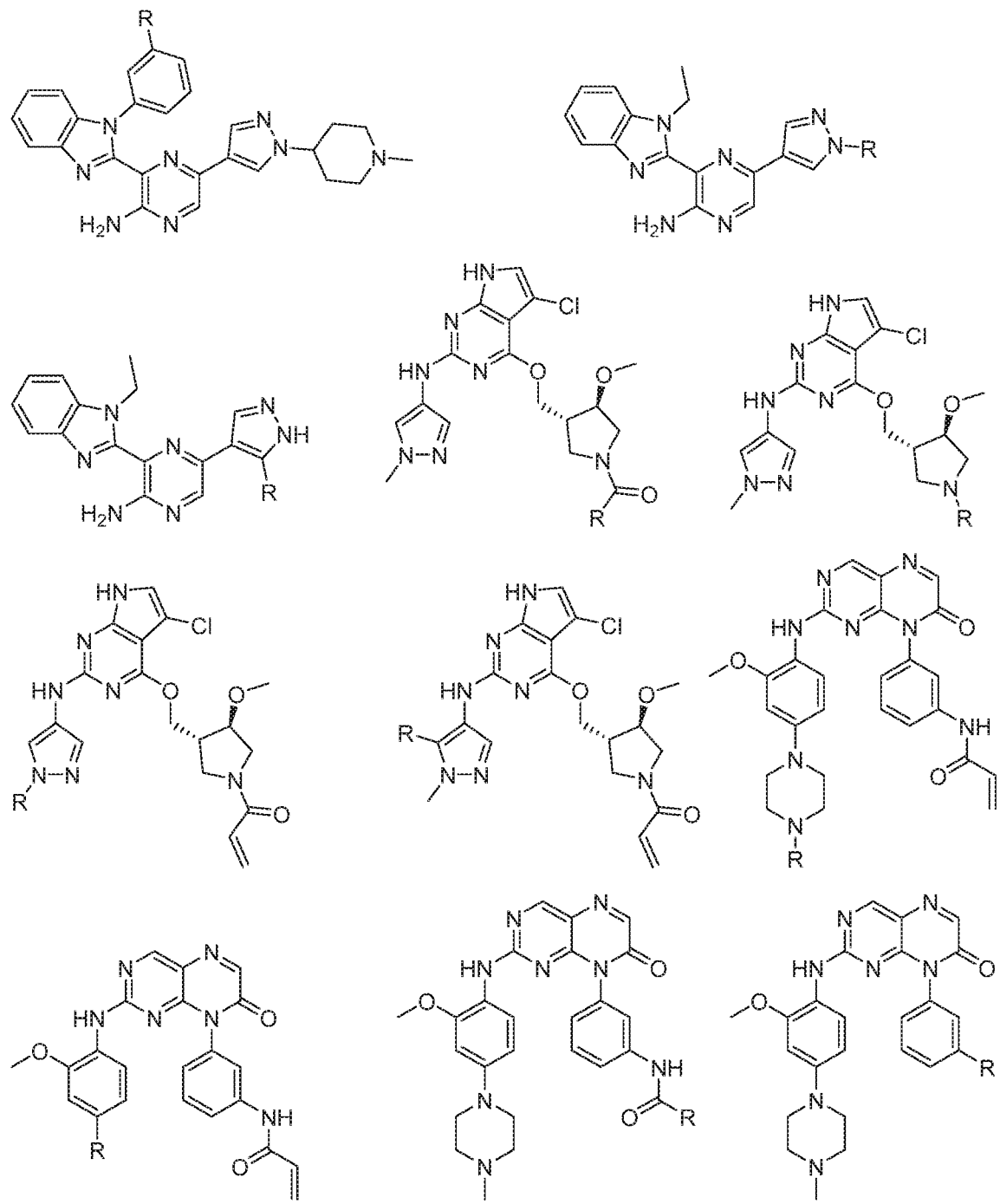

FIG. 8A-8S present examples of BRD4 Bromodomain 1 Targeting Ligands wherein R is the point at which the Linker is attached. For additional examples and related ligands, see, the crystal structures PDB 3u5k and 3u5l and related ligands in Filippakopoulos, P. et al. "Benzodiazepines and benzotriazepines as protein interaction inhibitors targeting bromodomains of the BET family", *Bioorg. Med. Chem.* 20: 1878-1886 (2012); the crystal structure PDB 3u5l; the crystal structure PDB 3zyu and related ligands described in Dawson, M. A. et al. "Inhibition of Bet Recruitment to Chromatin as an Effective Treatment for Mll-Fusion Leukaemia." *Nature* 478: 529 (2011); the crystal structure PDB 4bw1 and related ligands described in Mirguet, O. et al. "Naphthyridines as Novel Bet Family Bromodomain Inhibitors." *Chemmedchem* 9: 589 (2014); the crystal structure PDB 4cfl and related ligands described in Dittmann, A. et al. "The Commonly Used Pi3-Kinase Probe Ly294002 is an Inhibitor of Bet Bromodomains" *ACS Chem. Biol.* 9: 495 (2014); the crystal structure PDB 4e96 and related ligands described in Fish, P. V. et al. "Identification of a chemical probe for bromo and extra C-terminal bromodomain inhibition through optimization of a fragment-derived hit." *J. Med. Chem.* 55: 9831-9837 (2012); the crystal structure PDB 4clb and related ligands described in Atkinson, S. J. et al. "The Structure Based Design of Dual Hdac/Bet Inhibitors as Novel Epigenetic Probes." *Medchemcomm* 5: 342 (2014); the crystal structure PDB 4f3i and related ligands described in Zhang, G. et al. "Down-regulation of NF-{kappa}B Transcriptional Activity in HIV-associated Kidney Disease by BRD4 Inhibition." *J. Biol. Chem.* 287: 28840-28851 (2012); the crystal structure PDB 4hxl and related ligands described in Zhao, L. "Fragment-Based Drug Discovery of 2-Thiazolidinones as Inhibitors of the Histone Reader BRD4 Bromodomain." *J. Med. Chem.* 56: 3833-3851 (2013); the crystal structure PDB 4hxs and related ligands described in Zhao, L. et al. "Fragment-Based Drug Discovery of 2-Thiazolidinones as Inhibitors of the Histone Reader BRD4 Bromodomain." *J. Med. Chem.* 56: 3833-3851 (2013); the crystal structure PDB 4lrg and related ligands described in Gehling, V. S. et al. "Discovery, Design, and Optimization of Isoxazole Azepine BET Inhibitors." *ACS Med Chem Lett* 4: 835-840 (2013); the crystal structure PDB 4mep and related ligands described in Vidler, L. R. "Discovery of Novel Small-Molecule Inhibitors of BRD4 Using Structure-Based Virtual Screening." et al. *J. Med. Chem.* 56: 8073-8088 (2013); the crystal structures PDB 4nr8 and PDB 4c77 and related ligands described in Ember, S. W. et al. "Acetyl-lysine Binding Site of Bromodomain-Containing Protein 4 (BRD4) Interacts with Diverse Kinase Inhibitors". *ACS Chem. Biol.* 9: 1160-1171 (2014); the crystal structure PDB 4o7a and related ligands described in Ember, S. W. et al. "Acetyl-lysine Binding Site of Bromodomain-Containing Protein 4 (BRD4) Interacts with Diverse Kinase Inhibitors." *ACS Chem. Biol.* 9: 1160-1171 (2014); the crystal structure PDB 4o7b and related ligands described in "Acetyl-lysine Binding Site of Bromodomain-Containing Protein 4 (BRD4)

Interacts with Diverse Kinase Inhibitors." Ember, S. W. et al. (2014) *ACS Chem. Biol.* 9: 1160-1171; the crystal structure PDB 4o7c and related ligands described in Ember, S. W. et al. "Acetyl-lysine Binding Site of Bromodomain-Containing Protein 4 (BRD4) Interacts with Diverse Kinase Inhibitors". *ACS Chem. Biol.* 9: 1160-1171 (2014); the crystal structure PDB 4gpj; the crystal structure PDB 4uix and related ligands described in Theodoulou, N. H. et al. "The Discovery of I-Brd9, a Selective Cell Active Chemical Probe for Bromodomain Containing Protein 9 Inhibition". *J. Med. Chem.* 59: 1425 (2016); the crystal structure PDB 4uiz and related ligands described in Theodoulou, N. H., et al. "The Discovery of I-Brd9, a Selective Cell Active Chemical Probe for Bromodomain Containing Protein 9 Inhibition". *J. Med. Chem.* 59: 1425 (2016); the crystal structure PDB 4wiv and related ligands described in McKeown, M. R. et al. "Biased multicomponent reactions to develop novel bromodomain inhibitors." *J. Med. Chem.* 57: 9019-9027 (2014); the crystal structure PDB 4x2i and related ligands described in Taylor, A. M. et al. "Discovery of Benzotriazolo[4,3-d][1,4]diazepines as Orally Active Inhibitors of BET Bromodomains." ACSMed. *Chem. Lett.* 7: 145-150 (2016); the crystal structure PDB 4yh3; And related ligands described in Duffy, B. C. "Discovery of a new chemical series of BRD4(1) inhibitors using protein-ligand docking and structure-guided design." *Bioorg. Med. Chem. Lett.* 25: 2818-2823 (2015); the crystal structure PDB 4yh4 and related ligands described in Duffy, B. C. "Discovery of a new chemical series of BRD4(1) inhibitors using protein-ligand docking and structure-guided design." *Bioorg. Med. Chem. Lett.* 25: 2818-2823 (2015); the crystal structure PDB 4zlq and related ligands described in Taylor, A. M. "Discovery of Benzotriazolo[4,3-d][1,4]diazepines as Orally Active Inhibitors of BET Bromodomains." ACSMed. *Chem. Lett.* 7: 145-150 (2016); the crystal structure PDB 4zw1; the crystal structure PDB 5a5s and related ligands described in Demont, E. H. "Fragment-Based Discovery of Low-Micromolar Atad2 Bromodomain Inhibitors. *J. Med. Chem.* 58: 5649 (2015); the crystal structure PDB 5a85 and related ligands described in Bamborough, P. "Structure-Based Optimization of Naphthyridones Into Potent Atad2 Bromodomain Inhibitors" *J. Med. Chem.* 58: 6151 (2015); the crystal structure PDB 5acy and related ligands described in Sullivan, J. M. "Autism-Like Syndrome is Induced by Pharmacological Suppression of Bet Proteins in Young Mice." *J. Exp. Med.* 212: 1771 (2015); the crystal structure PDB 5ad2 and related ligands described in Waring, M. J. et al. "Potent and Selective Bivalent Inhibitors of Bet Bromodomains". *Nat. Chem. Biol.* 12: 1097 (2016); the crystal structure PDB 5cfw and related ligands described in Chekler, E. L. et al. "Transcriptional Profiling of a Selective CREB Binding Protein Bromodomain Inhibitor Highlights Therapeutic Opportunities." *Chem. Biol.* 22: 1588-1596 (2015); the crystal structure PDB 5cqt and related ligands described in Xue, X. et al. "Discovery of Benzo[cd]indol-2(1H)-ones as Potent and Specific BET Bromodomain Inhibitors: Structure-Based Virtual Screening, Optimization, and Biological Evaluation". *J. Med. Chem.* 59: 1565-1579 (2016); the crystal structure PDB 5d3r and related ligands described in Hugle, M. et al. "4-Acyl Pyrrole Derivatives Yield Novel Vectors for Designing Inhibitors of the Acetyl-Lysine Recognition Site of BRD4(1)". *J. Med. Chem.* 59: 1518-1530 (2016); the crystal structure PDB 5dlx and related ligands described in Milhas, S. et al. "*Protein-Protein Interaction Inhibition (2P2I)-Oriented Chemical Library Accelerates Hit Discovery.*" (2016) *ACS Chem. Biol.* 11: 2140-2148; the crystal structure PDB 5dlz and related ligands described in Milhas, S. et al. "Protein-Protein Interaction Inhibition (2P2I)-Oriented Chemical Library Accelerates Hit Discovery." *ACS Chem. Biol.* 11: 2140-2148 (2016); the crystal structure PDB 5dw2 and related ligands described in Kharenko, O. A. et al. "RVX-297—a novel BD2 selective inhibitor of BET bromodomains." *Biochem. Biophys. Res. Commun.* 477: 62-67 (2016); the crystal structure PDB 5dlx; the crystal structure PDB Shis and related ligands described in Albrecht, B. K. et al. "Identification of a Benzoisoxazoloazepine Inhibitor (CPI-0610) of the Bromodomain and Extra-Terminal (BET) Family as a Candidate for Human Clinical Trials." *J. Med. Chem.* 59: 1330-1339 (2016); the crystal structure PDB 5ku3 and related ligands described in Crawford, T. D. et al. "Discovery of a Potent and Selective in Vivo Probe (GNE-272) for the Bromodomains of CBP/EP300*". J. Med. Chem.* 59: 10549-10563 (2016); the crystal structure PDB 5lj2 and related ligands described in Bamborough, P. et al. "A Chemical Probe for the ATAD2 Bromodomain." *Angew. Chem. Int. Ed. Engl.* 55: 11382-11386 (2016); the crystal structure PDB 5dlx and related ligands described in Wang, L. "Fragment-based, structure-enabled discovery of novel pyridones and pyridone macrocycles as potent bromodomain and extra-terminal domain (BET) family bromodomain inhibitors". *J. Med. Chem.* 10.1021/acs.jmedchem.7b00017 (2017); WO 2015169962 A1 titled "Benzimidazole derivatives as BRD4 inhibitors and their preparation and use for the treatment of cancer" assigned to Boehringer Ingelheim International GmbH, Germany; and, WO 2011143669 A2 titled "Azolodiazepine derivatives and their preparation, compositions and methods for treating neoplasia, inflammatory disease and other disorders" assigned to Dana-Farber Cancer Institute, Inc, USA.

Figure 8T:
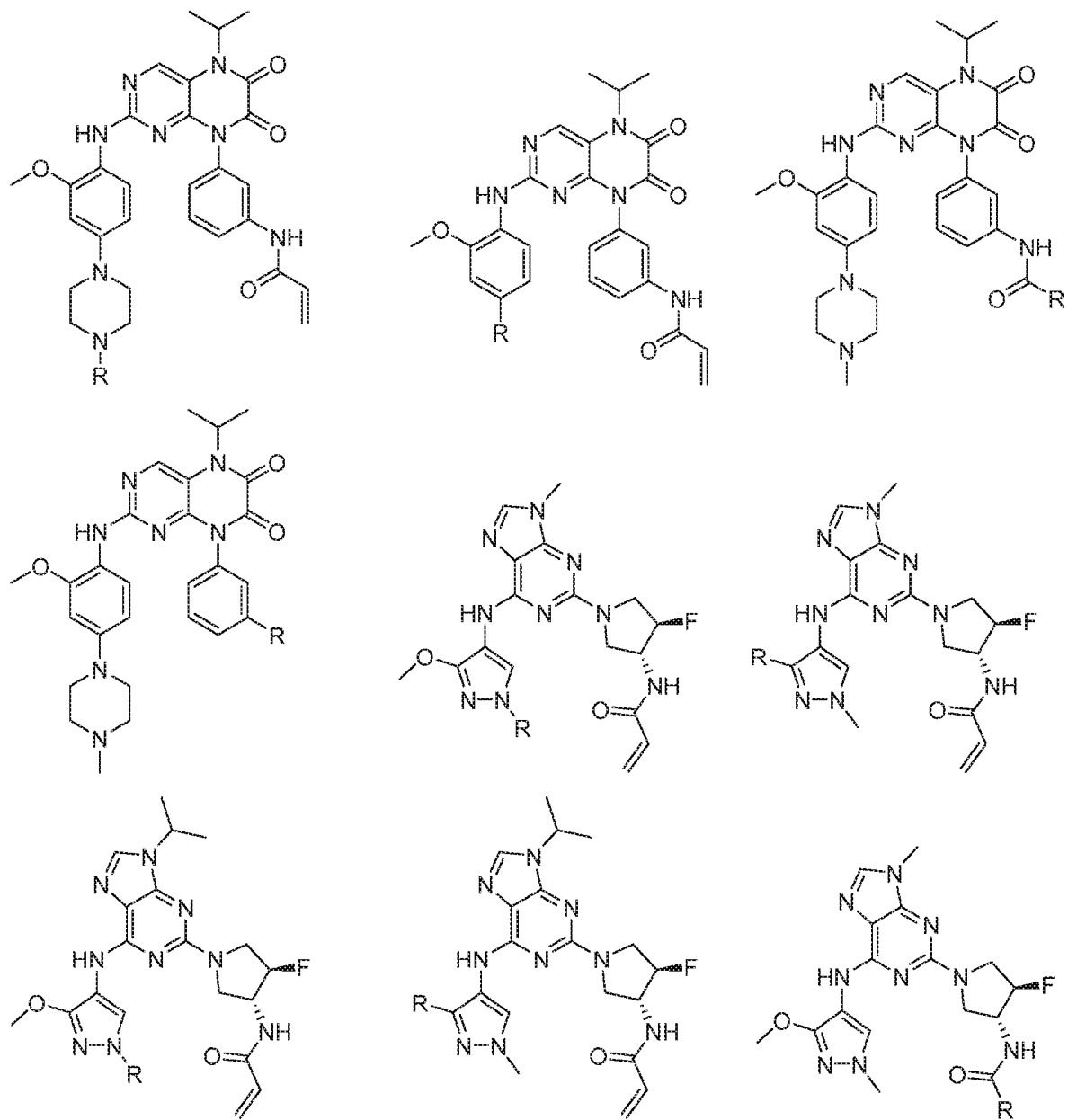
Figure 8U:
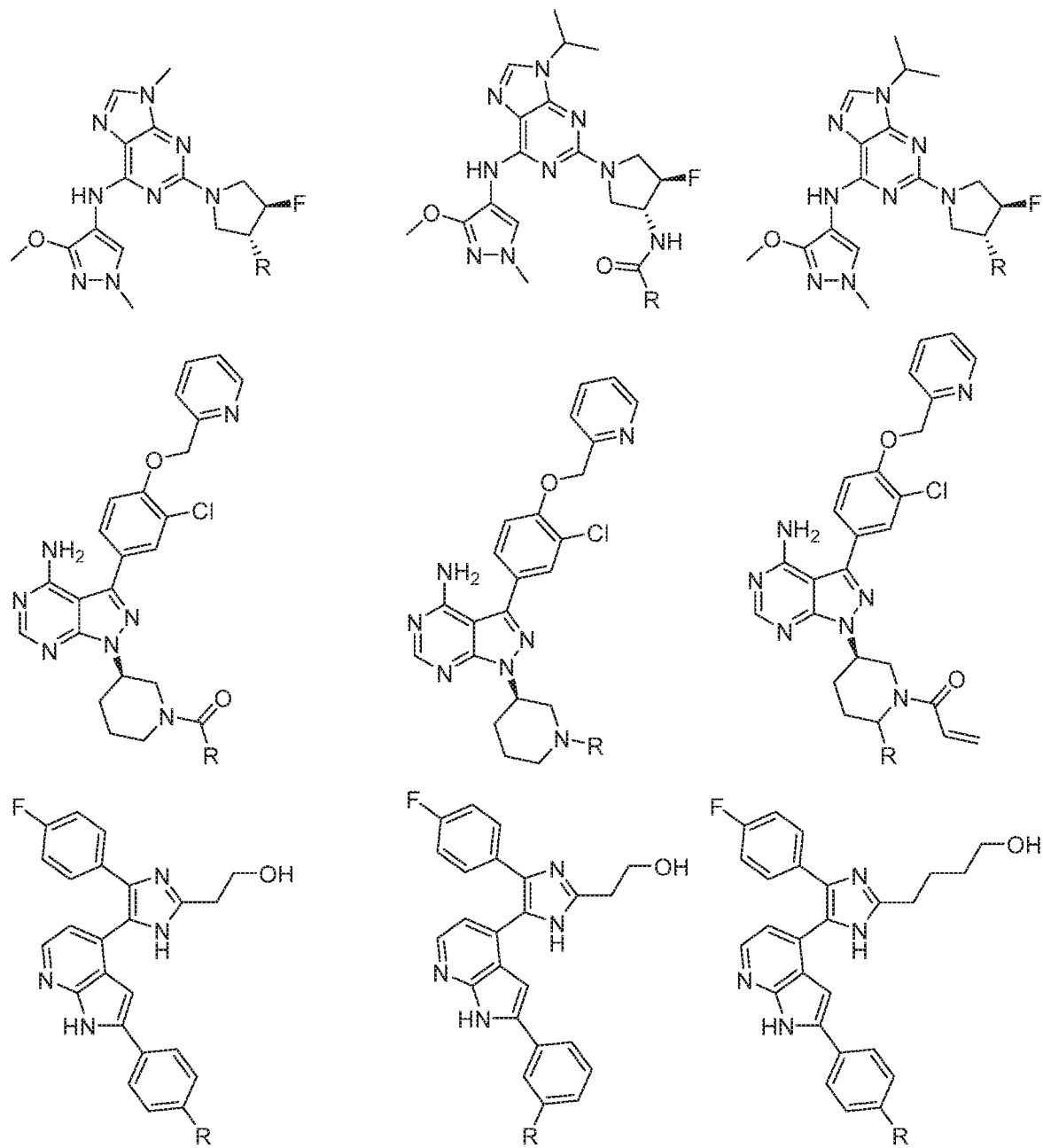
Figure 8V:
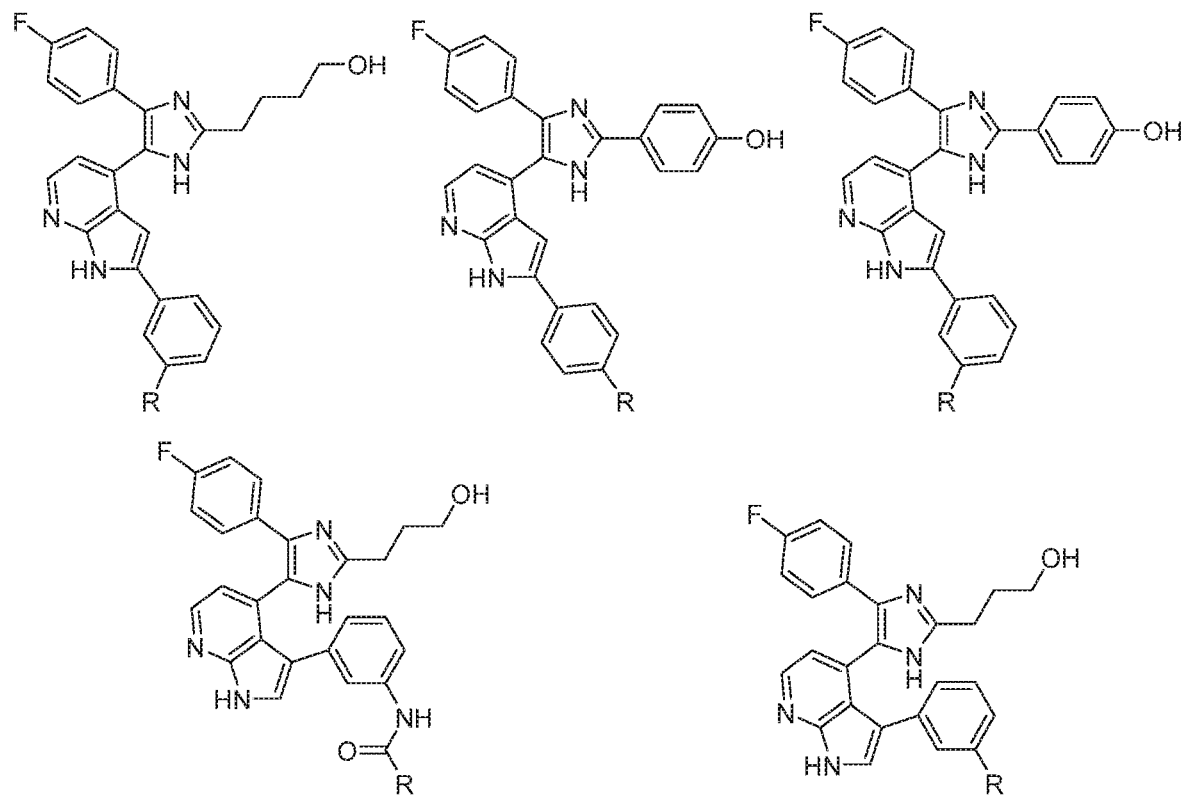
Figure 8W:
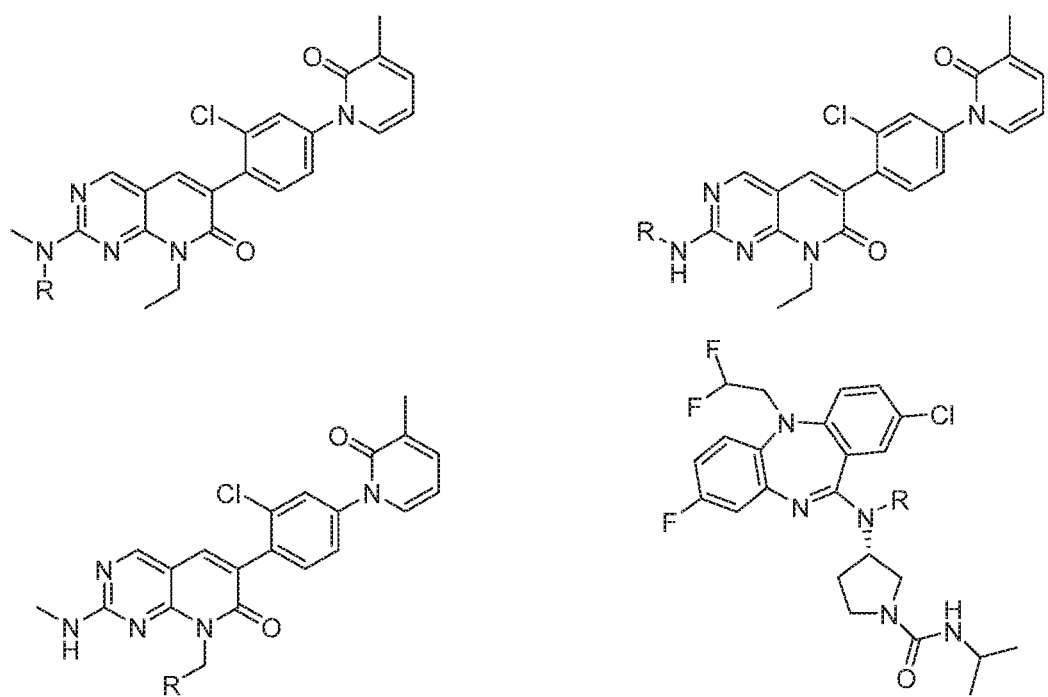
Figure 8X:
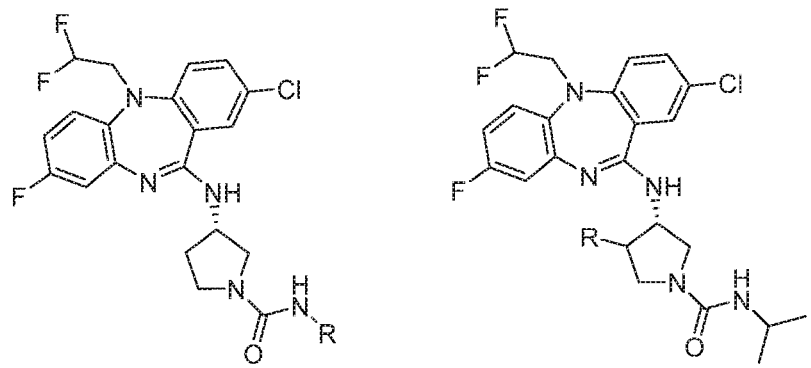
Figure 8Y:
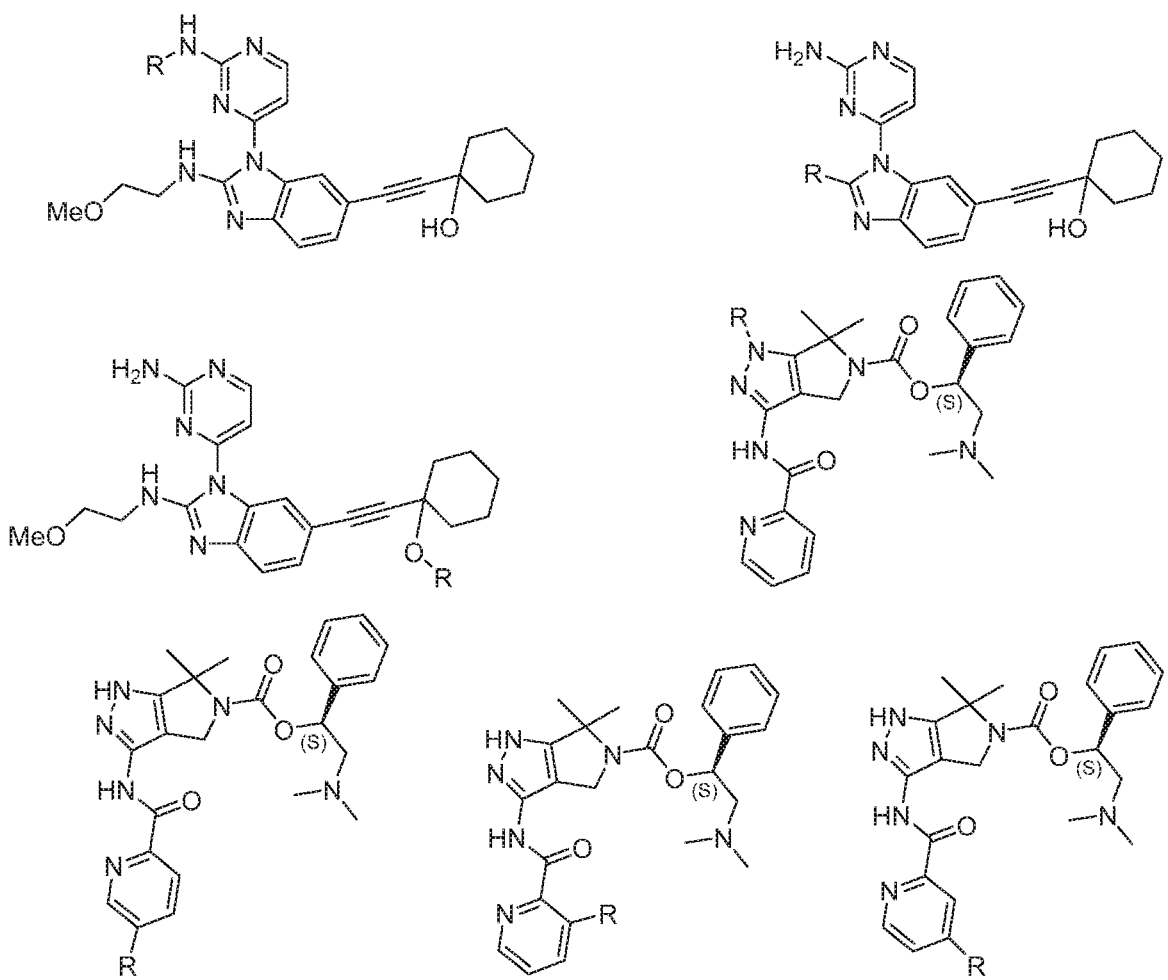
Figure 8Z:
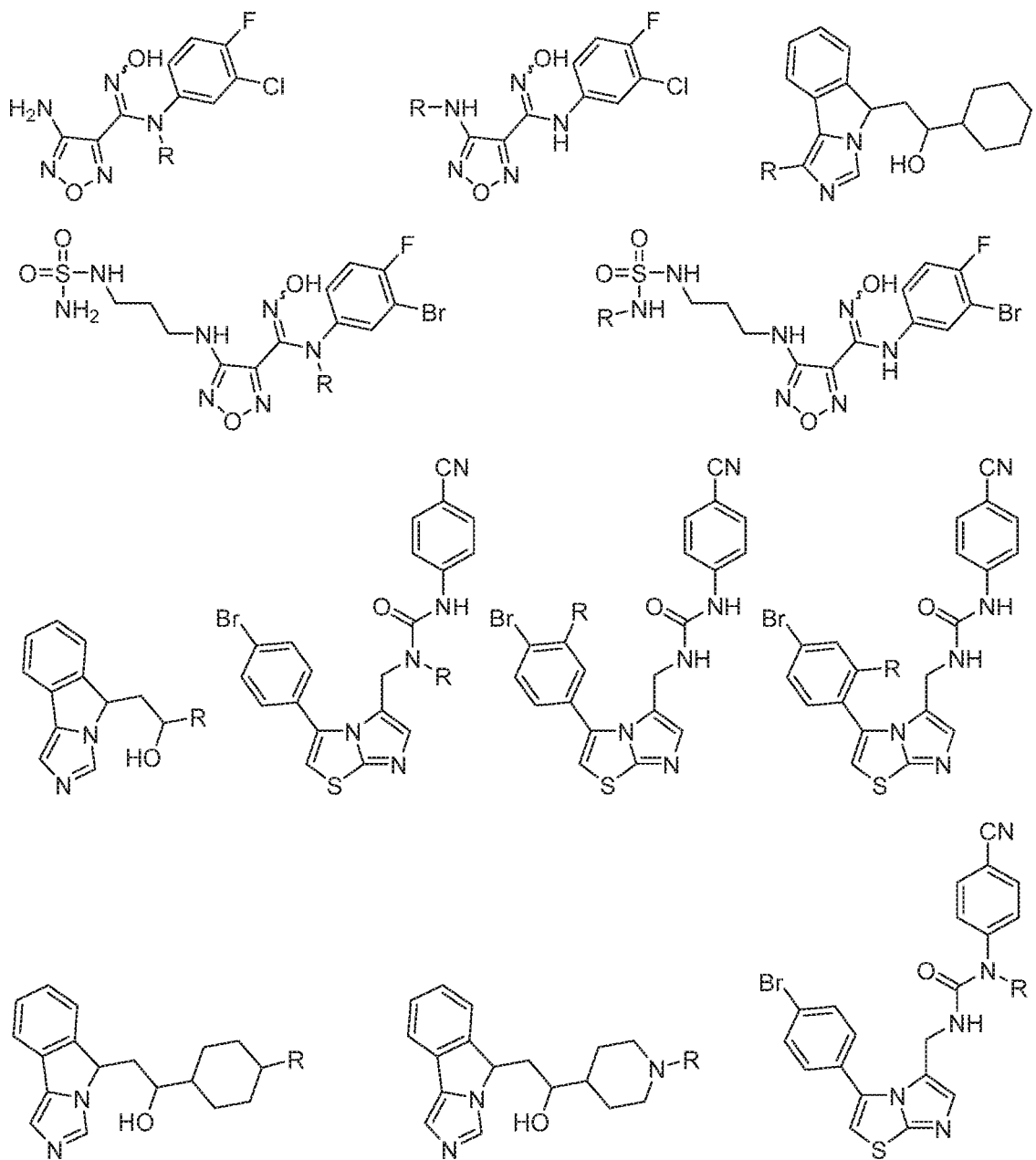

FIG. 8T-8V present examples of ALK Targeting Ligands wherein R is the point at which the Linker is attached. For additional examples and related ligands, see, the crystal structures PDB 2xb7 and 2xba and related ligands described in Bossi, R. T. et al. "Crystal Structures of Anaplastic Lymphoma Kinase in Complex with ATP Competitive Inhibitors" *Biochemistry* 49: 6813-6825 (2010); the crystal structures PDB 2yfx, 4ccb, 4ccu, amd 4cd0 snd related ligands described in Huang, Q. et al. "Design of Potent and Selective Inhibitors to Overcome Clinical Anaplastic Lymphoma Kinase Mutations Resistant to Crizotinib." *J. Med. Chem.* 57: 1170 (2014); the crystal structures PDB, 4cli, 4cmo, and 4cnh and related ligands described in Johnson, T. W. et al. "Discovery of (10R)-7-Amino-12-Fluoro-2,10,16-Trimethyl-15-Oxo-10,15,16,17-Tetrahydro-2H-8,4-(Metheno)Pyrazolo[4,3-H][2,5,11]Benzoxadiazacyclotetradecine-3-Carbonitrile (Pf-06463922), a Macrocyclic Inhibitor of Alk/Ros1 with Pre-Clinical Brain Exposure and Broad Spectrum Potency Against Alk-Resistant Mutations." *J. Med. Chem.* 57: 4720 (2014); the crystal structure PDB 4fny and related ligands described in Epstein, L. F. et al. "The R1275Q Neuroblastoma Mutant and Certain ATP-competitive Inhibitors Stabilize Alternative Activation Loop Conformations of Anaplastic Lymphoma Kinase." *J. Biol. Chem.* 287: 37447-37457 (2012). the crystal structure PDB 4dce and related ligands described in Bryan, M. C. et al "Rapid development of piperidine carboxamides as potent and selective anaplastic lymphoma kinase inhibitors." *J. Med. Chem.* 55: 1698-1705 (2012); the crystal structure PDB 4joa and related ligands described in Gummadi, V. R. et al. "Discovery of 7-azaindole based anaplastic lymphoma kinase (ALK) inhibitors: wild type and mutant (L1196M) active compounds with unique binding mode." (2013) *Bioorg. Med. Chem. Lett.* 23: 4911-4918; and, the crystal structure PDB 5iui and related ligands described in Tu, C. H.

et al. "Pyrazolylamine Derivatives Reveal the Conformational Switching between Type I and Type II Binding Modes of Anaplastic Lymphoma Kinase (ALK)." *J. Med. Chem.* 59: 3906-3919 (2016).

FIG. 8W-8X present examples of BTK Targeting Ligands wherein R is the point at which the Linker is attached. For additional examples and related ligands, see, the crystal structure PDB 3gen, 3piz and related ligands described in Marcotte, D. J. et al. "Structures of human Bruton's tyrosine kinase in active and inactive conformations suggest a mechanism of activation for TEC family kinases." *Protein Sci.* 19: 429-439 (2010) and Kuglstatter, A. et al. "Insights into the conformational flexibility of Bruton's tyrosine kinase from multiple ligand complex structures" *Protein Sci.* 20: 428-436" (2011); the crystal structure PDB 3ocs, 4ot6 and related ligands described in Lou, Y. et al. "Structure-Based Drug Design of RN486, a Potent and Selective Bruton's Tyrosine Kinase (BTK) Inhibitor, for the Treatment of Rheumatoid Arthritis" *J. Med. Chem.* 58: 512-516 (2015); the crystal structures PDB 5fbn and 5fbo and related ligands described in Liu, J. et al. "Discovery of 8-Amino-imidazo [1,5-a]pyrazines as Reversible BTK Inhibitors for the Treatment of Rheumatoid Arthritis." *ACS Med. Chem. Lett.* 7: 198-203 (2016); the crystal structure PDB 3pix and related ligands described in Kuglstatter, A. et al. "Insights into the conformational flexibility of Bruton's tyrosine kinase from multiple ligand complex structures." *Protein Sci.* 20: 428-436 (2011); and, the crystal structure PDB 3pij and related ligands described in Bujacz, A. et al. "Crystal structures of the apo form of beta-fructofuranosidase from *Bifidobacterium longum* and its complex with fructose." *Febs J.* 278: 1728-1744 (2011).

FIG. 8Y presents examples of FLT3 Targeting Ligands wherein R is the point at which the Linker is attached. For additional examples and related ligands, see, the crystal structures PDB 4xuf and 4rt7 and related ligands described in Zorn, J. A. et al. "Crystal Structure of the FLT3 Kinase Domain Bound to the Inhibitor Quizartinib (AC220)". *Plos One* 10: e0121177-e0121177 (2015).

FIG. 8Z-8AA present examples of TNIK Targeting Ligands wherein R is the point at which the Linker is attached. For additional examples and related ligands, see, the crystal structure PDB 2x7f; the crystal structures PDB 5ax9 and 5d7a; and, related ligands described in Masuda, M. et al. "TNIK inhibition abrogates colorectal cancer stemness." *Nat Commun* 7: 12586-12586 (2016).

FIG. 8BB-8CC present examples of NTRK1, NTRK2, and NTRK3 Targeting Ligands wherein R is the point at which the Linker is attached. For additional examples and related ligands, see, the crystal structure PDB 4aoj and related ligands described in Wang, T. et al. "Discovery of Disubstituted Imidazo[4,5-B]Pyridines and Purines as Potent Trka Inhibitors." *ACS Med. Chem. Lett.* 3: 705 (2012); the crystal structures PDB 4pmm, 4pmp, 4pms and 4pmt and related ligands described in Stachel, S. J. et al. "Maximizing diversity from a kinase screen: identification of novel and selective pan-Trk inhibitors for chronic pain." *J. Med. Chem.* 57: 5800-5816 (2014); the crystal structures PDB 4yps and 4yne snd related ligands described in Choi, H. S. et al. "(R)-2-Phenylpyrrolidine Substituted Imidazopyridazines: A New Class of Potent and Selective Pan-TRK Inhibitors." *ACS Med. Chem. Lett.* 6: 562-567 (2015); the crystal structures PDB 4at5 and 4at3 and related ligands described in Bertrand, T. et al. "The Crystal Structures of Trka and Trkb Suggest Key Regions for Achieving Selective Inhibition." *J. Mol. Biol.* 423: 439 (2012); and, the crystal structures PDB 3v5q and 4ymj and related ligands described in Albaugh, P. et al. "Discovery of GNF-5837, a selective TRK Inhibitor with efficacy in rodent cancer tumor models." *ACS Med. Chem. Lett.* 3: 140-145 (2012) and Choi, H. S. et al. "(R)-2-Phenylpyrrolidine Substitute Imidazopyridazines: a New Class of Potent and Selective Pan-TRK Inhibitors." *ACS Med Chem Lett* 6: 562-567 (2015).

FIG. 8DD-8EE present examples of FGFR1 Targeting Ligands wherein R is the point at which the Linker is attached. For additional examples and related ligands, see, the crystal structures PDB 3tto and 2fgi and related ligands described in Brison, Y. et al. "Functional and structural characterization of alpha-(1-2) branching sucrase derived from DSR-E glucansucrase." *J. Biol. Chem.* 287: 7915-7924 (2012) and Mohammadi, M. et al. "Crystal structure of an angiogenesis inhibitor bound to the FGF receptor tyrosine kinase domain." *EMBO J.* 17: 5896-5904 (1998); the crystal structure PDB 4fb3; the crystal structure PDB 4rwk and related ligands described in Harrison, C. et al. "Polyomavirus large T antigen binds symmetrical repeats at the viral origin in an asymmetrical manner." *J. Virol.* 87: 13751-13759 (2013); the crystal structure PDB 4rwl and related ligands described in Sohl, C. D. et al. "Illuminating the Molecular Mechanisms of Tyrosine Kinase Inhibitor Resistance for the FGFR1 Gatekeeper Mutation: The Achilles' Heel of Targeted Therapy." *ACS Chem. Biol.* 10: 1319-1329 (2015); the crystal structure PDB 4uwc; the crystal structure PDB 4v01 and related ligands described in Tucker, J. A. et al. "Structural Insights Into Fgfr Kinase Isoform Selectivity: Diverse Binding Modes of Azd4547 and Ponatinib in Complex with Fgfr1 and Fgfr4." Structure 22: 1764 (2014).; the crystal structure PDB 5a46 and related ligands described in Klein, T. et al. "Structural and Dynamic Insights Into the Energetics of Activation Loop Rearrangement in Fgfr1 Kinase." *Nat. Commun.* 6: 7877 (2015); and, the crystal structure PDB 5ew8 and related ligands described in Patani, H. et al. "Landscape of activating cancer mutations in FGFR kinases and their differential responses to inhibitors in clinical use." *Oncotarget* 7: 24252-24268 (2016).

FIG. 8FF presents examples of FGFR2 Targeting Ligands wherein R is the point at which the Linker is attached. For additional examples and related ligands, see, the crystal structure PDB 2pvf and related ligands described in Chen, H. et al. "A molecular brake in the kinase hinge region regulates the activity of receptor tyrosine kinases." *Mol. Cell* 27: 717-730 (2007).

FIG. 8GG presents examples of FGFR4 Targeting Ligands wherein R is the point at which the Linker is attached. For additional examples and related ligands, see, the crystal structure PDB 4tyi and related ligands described in Lesca, E. et al. "Structural analysis of the human fibroblast growth factor receptor 4 kinase." *J. Mol. Biol.* 426: 3744-3756 (2014).

FIG. 8HH-8II present examples of MET Targeting Ligands wherein R is the point at which the Linker is attached. For additional examples and related ligands, see, the crystal structures PDB 3qti and 3zcl; the crystal structures PDB 4xmo, 4xyf, and 3zcl and related ligands described in Peterson, E. A. et al. "Discovery of Potent and Selective 8-Fluorotriazolopyridine c-Met Inhibitors." *J. Med. Chem.* 58: 2417-2430 (2015) and Cui, J. J. et al. "Lessons from (S)-6-(1-(6-(1-Methyl-1H-Pyrazol-4-Y1)-[1, 2, 4]Triazolo[4,3-B]Pyridazin-3-Y1)Ethyl)Quinoline (Pf-04254644), an Inhibitor of Receptor Tyrosine Kinase C-met with High Protein Kinase Selectivity But Broad Phosphodiesterase Family Inhibition Leading to Myocardial Degeneration in Rats." *J. Med. Chem.* 56: 6651 (2013); the crystal structure PDB Seyd and related ligands described in Boezio, A. A. et al. "Discovery of (R)-6-(1-(8-Fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one (AMG 337), a Potent and Selective Inhibitor of MET with High Unbound Target Coverage and Robust In Vivo Antitumor Activity." *J. Med. Chem.* 59: 2328-2342 (2016); the crystal structure PDB 3ce3 and related ligands described in Kim, K. S. et al. "Discovery of pyrrolopyridine-pyridone based inhibitors of Met kinase: synthesis, X-ray crystallographic analysis, and biological activities." *J. Med. Chem.* 51: 5330-5341 (2008); the crystal structure PDB 2rfn and related ligands described in Bellon, S. F. et al. "c-Met inhibitors with novel binding mode show activity against several hereditary papillary renal cell carcinoma-related mutations." *J. Biol. Chem.* 283: 2675-2683 (2008); and, the crystal structure PDB 5dg5 and related ligands described in Smith, B. D. et al "Altiratinib Inhibits Tumor Growth, Invasion, Angiogenesis, and Microenvironment-Mediated Drug Resistance via Balanced Inhibition of MET, TIE2, and VEGFR2." *Mol. Cancer Ther.* 14: 2023-2034 (2015).

FIG. 8JJ presents examples of JAK1 Targeting Ligands wherein R is the point at which the Linker is attached. For additional examples and related ligands, see, the crystal structure PDB 4ivd and related ligands described in Zak, M. et al. "Identification of C-2 Hydroxyethyl Imidazopyrrolo-pyridines as Potent JAK1 Inhibitors with Favorable Physicochemical Properties and High Selectivity over JAK2." *J. Med. Chem.* 56: 4764-4785 (2013); the crystal structure PDB 5e1e and related ligands described in Vasbinder, M. M. et al. "Identification of azabenzimidazoles as potent JAK1 selective inhibitors." *Bioorg. Med. Chem. Lett.* 26: 60-67 (2016); the crystal structure PDB 5hx8 and related ligands described in Simov, V., et al. "Structure-based design and development of (benz)imidazole pyridones as JAK1-selective kinase inhibitors." *Bioorg. Med. Chem. Lett.* 26: 1803-1808 (2016); the crystal structure PDB 5hx8 and related ligands described in Caspers, N. L. et al. "Development of a high-throughput crystal structure-determination platform for JAK1 using a novel metal-chelator soaking system". *Acta Crystallogr. Sect. F* 72: 840-845 (2016); and, Kettle, J. G. "Discovery of the JAK1 selective kinase inhibitor AZD4205", AACR National Meeting, April 2017.

FIG. 8KK-8LL present examples of JAK2 Targeting Ligands wherein R is the point at which the Linker is attached. For additional examples and related ligands, see, the crystal structure PDB 3ugc and related ligands described in Andraos, R. et al. "Modulation of activation-loop phosphorylation by JAK inhibitors is binding mode dependent." *Cancer Discov* 2: 512-523 (2012); the crystal structures PDB 5cf4, 5cf5, 5cf6 and 5cf8 and related ligands described in Hart, A. C. et al. "Structure-Based Design of Selective Janus Kinase 2 Imidazo[4,5-d]pyrrolo[2,3-b]pyridine Inhibitors." *ACSMed. Chem. Lett.* 6: 845-849 (2015); the crystal structure PDB 5aep and related ligands described in Brasca, M. G. et al "Novel Pyrrole Carboxamide Inhibitors of Jak2 as Potential Treatment of Myeloproliferative Disorders" *Bioorg. Med. Chem.* 23: 2387 (2015); the crystal structures PDB 4ytf, 4yth and 4yti and related ligands described in Farmer, L. J. et al. "Discovery of VX-509 (Decernotinib): A Potent and Selective Janus Kinase 3 Inhibitor for the Treatment of Autoimmune Diseases." *J. Med. Chem.* 58: 7195-7216 (2015); the crystal structure PDB 4ytf, 4yth, 4yti and related ligands described in Menet, C. J. et al. "Triazolopyridines as Selective JAK1 Inhibitors: From Hit Identification to GLPG0634." *J. Med. Chem.* 57: 9323-9342 (2014); the crystal structure PDB 4ji9 and related ligands described in Siu, M. et al. "2-Amino-[1,2,4]triazolo[1,5-a]pyridines as JAK2 inhibitors." *Bioorg. Med. Chem. Lett.* 23: 5014-5021 (2013); and, the crystal structures PDB 3io7 and 3iok and related ligands described in Schenkel, L. B. et al. "Discovery of potent and highly selective thieno-pyridine janus kinase 2 inhibitors." *J. Med. Chem.* 54: 8440-8450 (2011).

FIG. 8MM presents examples of JAK3 Targeting Ligands wherein R is the point at which the Linker is attached. For additional examples and related ligands, see, the crystal structure PDB 3zc6 and related ligands described in Lynch, S. M. et al. "Strategic Use of Conformational Bias and Structure Based Design to Identify Potent Jak3 Inhibitors with Improved Selectivity Against the Jak Family and the Kinome." *Bioorg. Med. Chem. Lett.* 23: 2793 (2013); and, the crystal structures PDB 4hvd, 4i6q, and 3zep and related ligands described in Soth, M. et al. "3-Amido Pyrrolopyrazine JAK Kinase Inhibitors: Development of a JAK3 vs JAK1 Selective Inhibitor and Evaluation in Cellular and in Vivo Models." *J. Med. Chem.* 56: 345-356 (2013) and Jaime-Figueroa, S. et al. "Discovery of a series of novel 5H-pyrrolo[2,3-b]pyrazine-2-phenyl ethers, as potent JAK3 kinase inhibitors." *Bioorg. Med. Chem. Lett.* 23: 2522-2526 (2013).

FIG. 8NN-800 present examples of KIT Targeting Ligands wherein R is the point at which the Linker is attached. For additional examples and related ligands, see, the crystal structure PDB 1t46 and related ligands described in Mol, C. D. et al. "Structural basis for the autoinhibition and STI-571 inhibition of c-Kit tyrosine kinase." *J. Biol. Chem.* 279: 31655-31663 (2004); and, the crystal structure PDB 4u0i and related ligands described in Garner, A. P. et al. "Ponatinib Inhibits Polyclonal Drug-Resistant KIT Oncoproteins and Shows Therapeutic Potential in Heavily Pre-treated Gastrointestinal Stromal Tumor (GIST) Patients." *Clin. Cancer Res.* 20: 5745-5755 (2014).

FIG. 88PP-8VV present examples of EGFR Targeting Ligands wherein R is the point at which the Linker is attached. For additional examples and related ligands, see, the crystal structures PDB 5hcy, 4rj4, and 5cav; Heald, R., "Noncovalent Mutant Selective Epidermal Growth Factor Receptor Inhibitors: A Lead Optimization Case Study", *J. Med. Chem.* 58, 8877-8895 (2015); Hanano, E. J., "Discovery of Selective and Noncovalent Diaminopyrimidine-Based Inhibitors of Epidermal Growth Factor Receptor Containing the T790M Resistance Mutation." *J. Med. Chem.*, 57, 10176-10191 (2014); Chan, B. K. et al. "Discovery of a Noncovalent, Mutant-Selective Epidermal Growth Factor Receptor Inhibitor" *J. Med. Chem.* 59, 9080 (2016); the crystal structure PDB 5d41 and related ligands described in Jia, Y. et al., "Overcoming EGFR(T790M) and EGFR (C797S) resistance with mutant-selective allosteric inhibitors" *Nature* 534, 129 (2016); Ward, R. A. "Structure- and reactivity-based development of covalent inhibitors of the activating and gatekeeper mutant forms of the epidermal growth factor receptor (EGFR)" *J. Med. Chem.* 56, 7025-7048 (2013); the crystal structure PDB 4zau and related ligands described in "Discovery of a Potent and Selective EGFR Inhibitor (AZD9291) of Both Sensitizing and T790M Resistance Mutations That Spares the Wild Type Form of the Receptor" *J. Med. Chem.*, 57 (20), 8249-8267 (2014); the crystal structure PDB 5em7 and related ligands described in Bryan, M. C. et al. "Pyridones as Highly Selective, Noncovalent Inhibitors of T790M Double Mutants of EGFR" *ACS Med. Chem. Lett.*, 7 (1), 100-104 (2016); the crystal structure PDB 3IKA and related ligands described in Zhou, W. et al. "Novel mutant-selective EGFR kinase inhibitors against EGFR T790M" *Nature* 462(7276), 1070-1074 (2009); the crystal structure see PDB 5feq and related ligands described in Lelais, G., J. "Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a Novel, Potent, and WT Sparing Covalent Inhibitor of Oncogenic (L858R, ex19del) and Resistant (T790M) EGFR Mutants for the Treatment of EGFR Mutant Non-Small-Cell Lung Cancers" *Med. Chem.*, 59 (14), 6671-6689 (2016); Lee, H.-J. "Noncovalent Wild-type-Sparing Inhibitors of EGFR T790M" *Cancer Discov.* 3(2): 168-181 (2013); the crystal structure PDB 5j7h and related ligands described in Huang, W-S. et al. "Discovery of Brigatinib (AP26113), a Phosphine Oxide-Containing, Potent, Orally Active Inhibitor of Anaplastic Lymphoma Kinase." *J. Med. Chem.* 59: 4948-4964 (2016); the crystal structure PDB 4v0g and related ligands described in Hennessy, E. J. et al. "Utilization of Structure-Based Design to Identify Novel, Irreversible Inhibitors of EGFR Harboring the T790M Mutation." *ACS. Med. Chem. Lett.* 7: 514-519 (2016); the crystal structure PDB 5hg7 and related ligands described in Cheng, H. "Discovery of 1-{(3R,4R)-3-[({5-Chloro-2-[(1-methyl-1H-pyrazol-4-yl)amino]-7H-pyrrolo[2,3-d]pyrimidin-4-yl}oxy)methyl]-4-methoxypyrrolidin-1-yl}prop-2-en-1-one (PF-06459988), a Potent, WT Sparing, Irreversible Inhibitor of T790M-Containing EGFR Mutants." *J. Med. Chem.* 59: 2005-2024 (2016); Hao, Y. "Discovery and Structural Optimization of N5-Substituted 6,7-Dioxo-6,7-dihydropteridines as Potent and Selective Epidermal Growth Factor Receptor (EGFR) Inhibitors against L858R/T790M Resistance Mutation." *J. Med. Chem.* 59: 7111-7124 (2016); the crystal structure PDB 5ug8, 5ug9, and 5ugc and related ligands described in Planken, S. "Discovery of N-((3R,4R)-4-Fluoro-1-(6-((3-methoxy-1-methyl-1H-pyrazol-4-yl)amino)-9-methyl-9H-purin-2-yl)pyrrolidine-3-yl)acrylamide (PF-06747775) through Structure-Based Drug Design: A High Affinity Irreversible Inhibitor Targeting Oncogenic EGFR Mutants with Selectivity over Wild-Type EGFR." *J. Med. Chem.* 60: 3002-3019 (2017); the crystal structure PDB 5gnk and related ligands described in Wang, A. "Discovery of (R)-1-(3-(4-Amino-3-(3-chloro-4-(pyridin-2-ylmethoxy)phenyl)-1H-pyrazolo[3,4-d]pyrimidin-1-yl)piperidin-1-yl)prop-2-en-1-one (CHMFL-EGFR-202) as a Novel Irreversible EGFR Mutant Kinase Inhibitor with a Distinct Binding Mode." *J. Med. Chem.* 60: 2944-2962 (2017); and, Juchum, M. "Trisubstituted imidazoles with a rigidized hinge binding motif act as single digit nM inhibitors of clinically relevant EGFR L858R/T790M and L858R/T790M/C797S mutants: An example of target hopping." *J. Med. Chem.* DOI: 10.1021/acs.jmedchem.7b00178 (2017).

FIG. 8WW-8XX present examples of PAK1 Targeting Ligands wherein R is the point at which the Linker is attached. For additional examples and related ligands, see, Rudolph, J. et al. "Chemically Diverse Group I p21-Activated Kinase (PAK) Inhibitors Impart Acute Cardiovascular Toxicity with a Narrow Therapeutic Window." *J. Med. Chem.* 59, 5520-5541 (2016) and Karpov A S, et al. ACSMed *Chem Lett.* 22; 6(7):776-81 (2015).

FIG. 8YY presents examples of PAK4 Targeting Ligands wherein R is the point at which the Linker is attached. For additional examples and related ligands, see, Staben S T, et al. *J Med Chem.* 13; 57(3):1033-45 (2014) and Guo, C. et al. "Discovery of pyrroloaminopyrazoles as novel PAK inhibitors" *J. Med. Chem.* 55, 4728-4739 (2012).

FIG. 8ZZ-8AAA present examples of IDO Targeting Ligands wherein R is the point at which the Linker is attached. For additional examples and related ligands, see, Yue, E. W.; et al. "Discovery of potent competitive inhibitors of indoleamine 2,3-dioxygenase with in vivo pharmacodynamic activity and efficacy in a mouse melanoma model." *J. Med. Chem.* 52, 7364-7367 (2009); Tojo, S.; et al. "Crystal structures and structure, and activity relationships of imidazothiazole derivatives as IDO1 inhibitors." *ACS Med. Chem. Lett.* 5, 1119-1123 (2014); Mautino, M. R. et al. "NLG919, a novel indoleamine-2,3-dioxygenase (IDO)-pathway inhibitor drug candidate for cancer therapy" Abstract 491, AACR 104th Annual Meeting 2013; Apr. 6-10, 2013; Washington, D.C.; and, WO2012142237 titled "Fused imidazole derivatives useful as IDO inhibitors".

FIG. 8BBB-8EEE present examples of ERK1 and ERK2 Targeting Ligands wherein R is the point at which the Linker is attached. For additional examples and related ligands, see, the crystal structures PDB 5K4I and 5K4J and related ligands described in Blake, J. F. et al. "Discovery of (S)-1-(1-(4-Chloro-3-fluorophenyl)-2-hydroxyethyl)-4-(2-((1-methyl-1H-pyrazol-5-yl)amino)pyrimidin-4-yl)pyridin-2 (1H)-one (GDC-0994), an Extracellular Signal-Regulated Kinase 1/2 (ERK1/2) Inhibitor in Early Clinical Development" *J. Med. Chem.* 59: 5650-5660 (2016); the crystal structure PDB 5BVF and related ligands described in Bagdanoff, J. T. et al. "Tetrahydropyrrolo-diazepenones as inhibitors of ERK2 kinase" *Bioorg. Med. Chem. Lett.* 25, 3788-3792 (2015); the crystal structure PDB 4QYY and related ligands described in Deng, Y. et al. "Discovery of Novel, Dual Mechanism ERK Inhibitors by Affinity Selection Screening of an Inactive Kinase" *J. Med. Chem.* 57: 8817-8826 (2014); the crystal structures PDB 5HD4 and 5HD7 and the related ligands described in Jha, S. et al. "Dissecting Therapeutic Resistance to ERK Inhibition" *Mol. Cancer Ther.* 15: 548-559 (2016); the crystal structure PDB 4XJ0 and related ligands described in Ren, L. et al. "Discovery of highly potent, selective, and efficacious small molecule inhibitors of ERK1/2." *J. Med. Chem.* 58: 1976-1991 (2015); the crystal structures PDB 4ZZM, 4ZZN, 4ZZO and related ligands described in Ward, R. A. et al. "Structure-Guided Design of Highly Selective and Potent Covalent Inhibitors of Erk1/2." *J. Med. Chem.* 58: 4790 (2015); Burrows, F. et al. "KO-947, a potent ERK inhibitor with robust preclinical single agent activity in MAPK pathway dysregulated tumors" Poster #5168, AACR National Meeting 2017; Bhagwat, S. V. et al. "Discovery of LY3214996, a selective and novel ERK1/2 inhibitor with potent antitumor activities in cancer models with MAPK pathway alterations." AACR National Meeting 2017; the crystal structures PDB 3FHR and 3FXH and related ligands described in Cheng, R. et al. "High-resolution crystal structure of human Mapkap kinase 3 in complex with a high affinity ligand" *Protein Sci.* 19: 168-173 (2010); the crystal structures PDB 5NGU, 5NHF, 5NHH, 5NHJ, 5NHL, 5NHO, 5NHP, and 5NHV and related ligands described in Ward, R. A. et al. "Structure-Guided Discovery of Potent and Selective Inhibitors of ERK1/2 from a Modestly Active and Promiscuous Chemical Start Point." *J. Med. Chem.* 60, 3438-3450 (2017); and, the crystal structures PDB 3SHE and 3R1N and related ligands described in Oubrie, A. et al. "Novel ATP competitive MK2 inhibitors with potent biochemical and cell-based activity throughout the series." *Bioorg. Med. Chem. Lett.* 22: 613-618 (2012).

FIG. 8FFF-8III present examples of ABL1 Targeting Ligands wherein R is the point at which the Linker is attached. For additional examples and related ligands, see, the crystal structure PDB 1fpu and 2e2b and related ligands described in Schindler, T., et al. "Structural mechanism for STI-571 inhibition of abelson tyrosine kinase", *Science* 289: 1938-1942 (2000); and Horio, T. et al. "Structural factors contributing to the Abl/Lyn dual inhibitory activity of 3-substituted benzamide derivatives", *Bioorg. Med. Chem. Lett.* 17: 2712-2717 (2007); the crystal structures PDB 2hzn and 2hiw and related ligands described in Cowan-Jacob, S. W. et al. "Structural biology contributions to the discovery of drugs to treat chronic myelogenous leukaemia", *Acta Crystallog.* Sect. D 63: 80-93 (2007) and Okram, B. et al. "A general strategy for creating", *Chem. Biol.* 13: 779-786 (2006); the crystal structure PDB 3cs9 and related ligands described in Weisberg, E. et al. "Characterization of AMN107, a selective inhibitor of native and mutant Bcr-Abl", *Cancer Cell* 7: 129-14 (2005); the crystal structure PDB 3ik3 and related ligands described in O'Hare, T. et al. "AP24534, a pan-BCR-ABL inhibitor for chronic myeloid leukemia, potently inhibits the T315I mutant and overcomes mutation-based resistance", Cancer Cell 16: 401-412 (2009); the crystal structure PDB 3mss and related ligands described in Jahnke, W. et al. "Binding or bending: distinction of allosteric Abl kinase agonists from antagonists by an NMR-based conformational assay", *J Am. Chem. Soc.* 132: 7043-7048 (2010); the crystal structure PDB 3oy3 and related ligands described in Zhou, T. et al. "Structural Mechanism of the Pan-BCR-ABL Inhibitor Ponatinib (AP24534): Lessons for Overcoming Kinase Inhibitor Resistance", *Chem. Biol. Drug Des.* 77: 1-11 (2011); the crystal structures PDB 3qri and 3qrk and related ligands described in Chan, W. W. et al. "Conformational Control Inhibition of the BCR-ABL1 Tyrosine Kinase, Including the Gatekeeper T315I Mutant, by the Switch-Control Inhibitor DCC-2036", Cancer Cell 19: 556-568 (2011); the crystal structure PDB 5hu9 and 2f4j and related ligands described in Liu, F. et al. "Discovery and characterization of a novel potent type II native and mutant BCR-ABL inhibitor (CHMFL-074) for Chronic Myeloid Leukemia (CML)", *Oncotarget* 7: 45562-45574 (2016) and Young, M. A. et al. "Structure of the kinase domain of an imatinib-resistant Abl mutant in complex with the Aurora kinase inhibitor VX-680", *Cancer Res.* 66: 1007-1014 (2006); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006); and Zhou, T. et al. "Crystal Structure of the T 151 Mutant of Abl Kinase", *Chem. Biol. Drug Des.* 70: 171-181 (2007); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006) and Zhou, T. et al. "Crystal Structure of the T315I Mutant of Abl Kinase", *Chem. Biol. Drug Des.* 70: 171-181 (2007); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006) and Zhou, T. et al. "Crystal Structure of the T315I Mutant of Abl Kinase", *Chem. Biol. Drug Des.* 70: 171-181(2007); the crystal structures PDB 3dk3 and 3dk8 and related ligands described in Berkholz, D. S. et al. "Catalytic cycle of human glutathione reductase near 1 A resolution" *J. Mol. Biol.* 382: 371-384 (2008); the crystal structure PDB 3ue4 and related ligands described in Levinson, N. M. et al. "Structural and spectroscopic analysis of the kinase inhibitor bosutinib and an isomer of bosutinib binding to the abl tyrosine kinase domain", *Plos One* 7: e29828-e29828 (2012); the crystal structure PDB 4cy8 and related ligands described in Jensen, C. N. et al. "Structures of the Apo and Fad-Bound Forms of 2-Hydroxybiphenyl 3-Monooxygenase (Hbpa) Locate Activity Hotspots Identified by Using Directed Evolution", *Chembiochem* 16: 968 (2015); the crystal structure PDB 2hz0 and related ligands described in Cowan-Jacob, S. W. et al. "Structural biology contributions to the discovery of drugs to treat chronic myelogenous leukaemia", *Acta Crystallogr D Biol Crystallogr.* 63(Pt 1):80-93 (2007); the crystal structure PDB 3pyy and related ligands described in Yang, J. et al. "Discovery and Characterization of a Cell-Permeable, Small-Molecule c-Abl Kinase Activator that Binds to the Myristoyl Binding Site", *Chem. Biol.* 18: 177-186 (2011); and, the crystal structure PDB 5k5v and related ligands described in Kim, M. K., et al. "Structural basis for dual specificity of yeast N-terminal amidase in the N-end rule pathway", *Proc. Natl. Acad. Sci. U.S.A.* 113: 12438-12443 (2016).

FIG. 8JJJ presents examples of ABL2 Targeting Ligands wherein R is the point at which the Linker is attached. For additional examples and related ligands, see, the crystal structure PDB 2xyn and related ligands described in Salah, E. et al. "Crystal Structures of Abl-Related Gene (Abl2) in Complex with Imatinib, Tozasertib (Vx-680), and a Type I Inhibitor of the Triazole Carbothioamide Class", *J. Med. Chem.* 54: 2359 (2011); the crystal structure PDB 4xli and related ligands described in Ha, B. H. et al. "Structure of the ABL2/ARG kinase in complex with dasatinib" *Acta Crystallogr. Sect. F* 71: 443-448 (2015); and the crystal structure PDB 3gvu and related ligands described in Salah, E. et al. "The crystal structure of human ABL2 in complex with Gleevec", to be published.

FIG. 8KKK-8MMM present examples of AKT1 Targeting Ligands wherein R is the point at which the Linker is attached. For additional examples and related ligands, see, Lippa, B. et al. "Synthesis and structure based optimization of novel Akt inhibitors *Bioorg. Med. Chem. Lett.* 18: 3359-3363 (2008); Freeman-Cook, K. D. et al. "Design of selective, ATP-competitive inhibitors of Akt", *J. Med. Chem.* 53: 4615-4622 (2010); Blake, J. F. et al "Discovery of pyrrolopyrimidine inhibitors of Akt", *Bioorg. Med. Chem. Lett.* 20: 5607-5612 (2010); Kallan, N. C. et al. "Discovery and SAR of spirochromane Akt inhibitors", *Bioorg. Med. Chem. Lett.* 21: 2410-2414 (2011); Lin, K "An ATP-Site On-Off Switch That Restricts Phosphatase Accessibility of Akt", *Sci. Signal.* 5: ra37-ra37 (2012); Addie, M. et al. "Discovery of 4-Amino-N-[(1S)-1-(4-chlorophenyl)-3-hydroxypropyl]-1-(7H-pyrrolo[2,3-d]pyrimidin-4-yl)piperidine-4-carboxamide (AZD5363), an Orally Bioavailable, Potent Inhibitor of Akt Kinases", *J. Med. Chem.* 56: 2059-2073 (2013); Wu, W. I., et al. "Crystal structure of human AKT1 with an allosteric inhibitor reveals a new mode of kinase inhibition. *Plos One* 5: 12913-12913 (2010); Ashwell, M. A. et al. "Discovery and optimization of a series of 3-(3-phenyl-3H-imidazo[4, 5-b]pyridin-2-yl)pyridin-2-amines: orally bioavailable, selective, and potent ATP-independent Akt inhibitors", *J. Med. Chem.* 55: 5291-5310 (2012); and, Lapierre, J. M. et al. "Discovery of 3-(3-(4-(1-Aminocyclobutyl)phenyl)-5-phenyl-3H-imidazo[4,5-b]pyridin-2-yl)pyridin-2-amine (ARQ 092): An Orally Bioavailable, Selective, and Potent Allosteric AKT Inhibitor", *J. Med. Chem.* 59: 6455-6469 (2016).

FIG. 8NNN-8OOO present examples of AKT2 Targeting Ligands wherein R is the point at which the Linker is attached. For additional examples and related ligands, see, the crystal structured PDB 2jdo and 2jdr and related ligands described in Davies, T. G. et al. "A Structural Comparison of Inhibitor Binding to Pkb, Pka and Pka-Pkb Chimera", *J.*

*Mol. Biol.* 367: 882 (2007); the crystal structure PDB 2uw9 and related ligands described in Saxty, G. et al "Identification of Inhibitors of Protein Kinase B Using Fragment-Based Lead Discovery", *J. Med. Chem.* 50: 2293-2296 (2007); the crystal structure PDB 2x39 and 2xh5 and related ligands described in Mchardy, T. et al. "Discovery of 4-Amino-1-(7H-Pyrrolo[2,3-D]Pyrimidin-4-Yl)Piperidine-4-Carboxamides as Selective, Orally Active Inhibitors of Protein Kinase B (Akt)", *J. Med. Chem.* 53: 2239d (2010); the crystal structure PDB 3d03 and related ligands described in Hadler, K. S. et al. "Substrate-promoted formation of a catalytically competent binuclear center and regulation of reactivity in a glycerophosphodiesterase from *Enterobacter aerogenes*', *J. Am. Chem. Soc.* 130: 14129-14138 (2008); and, the crystal structures PDB 3e87, 3e8d and 3e88 and related ligands described in Rouse, M. B. et al. "Aminofurazans as potent inhibitors of AKT kinase" *Bioorg. Med. Chem. Lett.* 19: 1508-1511 (2009).

FIG. 8PPP presents examples of BMX Targeting Ligands wherein R is the point at which the Linker is attached. For additional examples and related ligands, see, the crystal structures PDB 3sxr and 3sxr and related ligands described in Muckelbauer, J. et al. "X-ray crystal structure of bone marrow kinase in the x chromosome: a Tec family kinase", *Chem. Biol. Drug Des.* 78: 739-748 (2011).

FIG. 8QQQ-8SSS present examples of CSF1R Targeting Ligands wherein R is the point at which the Linker is attached. For additional examples and related ligands, see, the crystal structures PDB 2i0v and 2i1m and related ligands described in Schubert, C. et al. "Crystal structure of the tyrosine kinase domain of colony-stimulating factor-1 receptor (cFMS) in complex with two inhibitors", *J. Biol. Chem.* 282: 4094-4101 (2007); the crystal structure PDB 3bea and related ligands described in Huang, H. et al. "Design and synthesis of a pyrido[2,3-d]pyrimidin-5-one class of anti-inflammatory FMS inhibitors", *Bioorg. Med. Chem. Lett.* 18: 2355-2361 (2008); the crystal structure PDB 3dpk and related ligands described in M. T., McKay, D. B. Overgaard, "Structure of the Elastase of *Pseudomonas aeruginosa* Complexed with Phosphoramidon", to be published; the crystal structures PDB 3krj and 3krl and related ligands described in Illig, C. R. et al. "Optimization of a Potent Class of Arylamide Colony-Stimulating Factor-1 Receptor Inhibitors Leading to Anti-inflammatory Clinical Candidate 4-Cyano-N-[2-(1-cyclohexen-1-yl)-4-[1-[(dimethylamino)acetyl]-4-piperidinyl]phenyl]-1H-imidazole-2-carboxamide (JNJ-28312141*", J. Med. Chem.* 54: 7860-7883 (2011); the crystal structure PDB 4r7h and related ligands described in Tap, W. D. et al. "Structure-Guided Blockade of CSF1R Kinase in Tenosynovial Giant-Cell Tumor, *N Engl J Med* 373: 428-437 (2015); the crystal structure PDB 3lcd and 3lcoa and related ligands described in Meyers, M. J. et al. "Structure-based drug design enables conversion of a DFG-in binding CSF-1R kinase inhibitor to a DFG-out binding mod", *Bioorg. Med. Chem. Lett.* 20: 1543-1547 (2010); the crystal structure PDB 4hw7 and related ligands described in Zhang, C. et al. "Design and pharmacology of a highly specific dual FMS and KIT kinase inhibitor", *Proc. Natl. Acad. Sci. USA* 110: 5689-5694 (2013); and, the crystal structure PDB 4r7i and related ligands described in Tap, W. D. et al. "Structure-Guided Blockade of CSF1R Kinase in Tenosynovial Giant-Cell Tumor", *N Engl J Med* 373: 428-437 (2015).

FIG. 8TTT presents examples of CSK Targeting Ligands wherein R is the point at which the Linker is attached. For additional examples and related ligands, see, Levinson, N. M. et al. "Structural basis for the recognition of c-Src by its inactivator Csk", *Cell* 134: 124-134 (2008).

FIG. 8UUU-8YYY present examples of DDR1 Targeting Ligands wherein R is the point at which the Linker is attached. For additional examples and related ligands, see, the crystal structures PDB 3zos and 4bkj and related ligands described in Canning, P. et al. "Structural Mechanisms Determining Inhibition of the Collagen Receptor Ddr1 by Selective and Multi-Targeted Type II Kinase Inhibitors", *J. Mol. Biol.* 426: 2457 (2014); the crystal structure PDB 4ckr and related ligands described in Kim, H. et al. "Discovery of a Potent and Selective Ddr1 Receptor Tyrosine Kinase Inhibitor", *ACS Chem. Biol.* 8: 2145 (2013); the crystal structure PDB 5bvk, 5bvn and 5bvw and related ligands described in Murray, C. W et al. "Fragment-Based Discovery of Potent and Selective DDR1/2 Inhibitors", *ACS Med. Chem. Lett.* 6: 798-803 (2015); the crystal structure PDB 5fdp and related ligands described in Wang, Z. et al. "Structure-Based Design of Tetrahydroisoquinoline-7-carboxamides as Selective Discoidin Domain Receptor 1 (DDR1) Inhibitors", *J. Med. Chem.* 59: 5911-5916 (2016); and, the crystal structure PDB 5fdx and related ligands described in Bartual, S. G. et al. "Structure of DDR1 receptor tyrosine kinase in complex with D2164 inhibitor at 2.65 Angstroms resolution", to be published.

FIG. 8ZZZ-8CCCC present examples of EPHA2 Targeting Ligands wherein R is the point at which the Linker is attached. For additional examples and related ligands, see, the crystal structures PDB 5i9x, 5i9y, 5ia0 and 5ia1 and related ligands described in Heinzlmeir, S. et al. "Chemical Proteomics and Structural Biology Define EPHA2 Inhibition by Clinical Kinase Drug", *ACS Chem. Biol.* 11: 3400-3411 (2016); the crystal structure PDB 5i9z and related ligands described in Heinzlmeir, S. et al. "Crystal Structure of Ephrin A2 (EphA2) Receptor Protein Kinase with danusertib (PHA739358)", *ACS Chem Biol* 11 3400-3411 (2016); and, the crystal structures PDB 5ia2, 5ia3, 5ia4, and 5ia5 and related ligands described in Heinzlmeir, S. et al. "Chemical Proteomics and Structural Biology Define EPHA2 Inhibition by Clinical Kinase Drug", *ACS Chem. Biol.* 11: 3400-3411 (2016).

FIG. 8DDDD-8FFFF present examples of EPHA3 Targeting Ligands wherein R is the point at which the Linker is attached. For additional examples and related ligands, see, the crystal structure PDB 4g2f and related ligands described in Zhao, H. et al. "Discovery of a novel chemotype of tyrosine kinase inhibitors by fragment-based docking and molecular dynamics", *ACSMed. Chem. Lett.* 3: 834-838 (2012); the crystal structure PDB 4gk2 and 4gk3 and related ligands described in Lafleur, K. et al. "Optimization of Inhibitors of the Tyrosine Kinase EphB4. 2. Cellular Potency Improvement and Binding Mode Validation by X-ray Crystallography", *J. Med. Chem.* 56: 84-96 (2013); the crystal structure PDB 4gk3 and related ligands described in Lafleur, K. et al. "Optimization of Inhibitors of the Tyrosine Kinase EphB4. 2. Cellular Potency Improvement and Binding Mode Validation by X-ray Crystallography", *J. Med. Chem.* 56: 84-96 (2013); the crystal structure PDB 4p4c and 4p5q and related ligands described in Unzue, A. et al. "Pyrrolo[3,2-b]quinoxaline Derivatives as Types I1/2 and II Eph Tyrosine Kinase Inhibitors: Structure-Based Design, Synthesis, and in Vivo Validation", *J. Med. Chem.* 57: 6834-6844 (2014); the crystal structure PDB 4p5z and related ligands described in Unzue, A. et al. "Pyrrolo[3,2-b]quinoxaline Derivatives as Types I1/2 and II Eph Tyrosine Kinase Inhibitors: Structure-Based Design, Synthesis, and in Vivo Validation", *J. Med. Chem.* 57: 6834-6844 (2014); the crystal structure PDB 4twn and related ligands described in Dong, J. et al. "Structural Analysis of the Binding of Type I, I1/2, and II Inhibitors to Eph Tyrosine Kinases", *ACS Med. Chem. Lett.* 6: 79-83 (2015); the crystal structure PDB 3dzq and related ligands described in Walker, J. R. "Kinase Domain of Human Ephrin Type-A Receptor 3 (Epha3) in Complex with ALW-II-38-3", to be published.

FIG. 8GGGG presents examples of EPHA4 Targeting Ligands wherein R is the point at which the Linker is attached. For additional examples and related ligands, see, the crystal structure PDB 2y60 and related ligands described in Clifton, I. J. et al. "The Crystal Structure of Isopenicillin N Synthase with Delta((L)-Alpha-Aminoadipoyl)-(L)-Cysteinyl-(D)-Methionine Reveals Thioether Coordination to Iron", *Arch. Biochem. Biophys.* 516: 103 (2011) and the crystal structure PDB 2xyu and related ligands described in Van Linden, O. P et al. "Fragment Based Lead Discovery of Small Molecule Inhibitors for the Epha4 Receptor Tyrosine Kinase", *Eur. J. Med. Chem.* 47: 493 (2012).

FIG. 8HHHH presents examples of EPHA7 Targeting Ligands wherein R is the point at which the Linker is attached. For additional examples and related ligands, see, the crystal structure PDB 3dko and related ligands described in Walker, J. R. et al. "Kinase domain of human ephrin type-a receptor 7 (epha7) in complex with ALW-II-49-7", to be published.

FIG. 8IIII-8LLLL presents examples of EPHB4 Targeting Ligands wherein R is the point at which the Linker is attached. For additional examples and related ligands, see, the crystal structure PDB 2vx1 and related ligands described in Bardelle, C. et al. "Inhibitors of the Tyrosine Kinase Ephb4. *Part* 2: Structure-Based Discovery and Optimisation of 3,5-Bis Substituted Anilinopyrimidines", *Bioorg. Med. Chem. Lett.* 18: 5717(2008); the crystal structure PDB 2x9f and related ligands described in Bardelle, C. et al. "Inhibitors of the Tyrosine Kinase Ephb4. *Part* 3: Identification of Non-Benzodioxole-Based Kinase Inhibitors", *Bioorg. Med. Chem. Lett.* 20: 6242-6245 (2010); the crystal structure PDB 2xvd and related ligands described in Barlaam, B. et al. "Inhibitors of the Tyrosine Kinase Ephb4. Part 4: Discovery and Optimization of a Benzylic Alcohol Series", *Bioorg. Med. Chem. Lett.* 21: 2207 (2011); the crystal structure PDB 3zew and related ligands described in Overman, R. C. et al. "Completing the Structural Family Portrait of the Human Ephb Tyrosine Kinase Domains", *Protein Sci.* 23: 627 (2014); the crystal structure PDB 4aw5 and related ligands described in Kim, M. H. et al. "The Design, Synthesis, and Biological Evaluation of Potent Receptor Tyrosine Kinase Inhibitors", *Bioorg. Med. Chem. Lett.* 22: 4979 (2012); the crystal structure PDB 4bb4 and related ligands described in Vasbinder, M. M. et al. "Discovery and Optimization of a Novel Series of Potent Mutant B-Raf V600E Selective Kinase Inhibitors" *J. Med. Chem.* 56: 1996.", (2013); the crystal structures PDB 2vwu, 2vwv and 2vww and related ligands described in Bardelle, C. et al "Inhibitors of the Tyrosine Kinase Ephb4. *Part* 1: Structure-Based Design and Optimization of a Series of 2,4-Bis-Anilinopyrimidines", *Bioorg. Med. Chem. Lett.* 18: 2776-2780 (2008); the crystal structures PDB 2vwx, 2vwy, and 2vwz and related ligands described in Bardelle, C. et al. "Inhibitors of the Tyrosine Kinase Ephb4. *Part* 2: Structure-Based Discovery and Optimisation of 3,5-Bis Substituted Anilinopyrimidines", *Bioorg. Med. Chem. Lett.* 18: 5717 (2008); and, the crystal structure PDB 2vxo and related ligands described in Welin, M. et al. "Substrate Specificity and Oligomerization of Human Gmp Synthetas", *J. Mol. Biol.* 425: 4323 (2013).

FIG. 8MMMM presents examples of ERBB2 Targeting Ligands wherein R is the point at which the Linker is attached. For additional examples and related ligands, see, the crystal structure and related ligands described in Aertgeerts, K. et al "Structural Analysis of the Mechanism of Inhibition and Allosteric Activation of the Kinase Domain of HER2 Protein", *J. Biol. Chem.* 286: 18756-18765 (2011) and the crystal structure and related ligands described in Ishikawa, T. et al. "Design and Synthesis of Novel Human Epidermal Growth Factor Receptor 2 (HER2)/Epidermal Growth Factor Receptor (EGFR) Dual Inhibitors Bearing a Pyrrolo[3,2-d]pyrimidine Scaffold" *J. Med. Chem.* 54: 8030-8050 (2011).

FIG. 8NNNN presents examples of ERBB3 Targeting Ligands wherein R is the point at which the Linker is attached. For additional examples and related ligands, see, Littlefield, P. et al. "An ATP-Competitive Inhibitor Modulates the Allosteric Function of the HER3 Pseudokinase", *Chem. Biol.* 21: 453-458 (2014).

FIG. 8OOOO presents examples ERBB4 Targeting Ligands wherein R is the point at which the Linker is attached. For additional examples and related ligands, see, Qiu, C. et al. "Mechanism of Activation and Inhibition of the HER4/ErbB4 Kinase", *Structure* 16: 460-467 (2008) and Wood, E. R. et al. "6-Ethynylthieno[3,2-d]- and 6-ethynylthieno[2,3-d]pyrimidin-4-anilines as tunable covalent modifiers of ErbB kinases", *Proc. Natl. Acad. Sci. Usa* 105: 2773-2778 (2008).

FIG. 8PPPP-8QQQQ present examples of FES Targeting Ligands wherein R is the point at which the Linker is attached. For additional examples and related ligands, see, Filippakopoulos, P. et al "Structural Coupling of SH2-Kinase Domains Links Fes and Abl Substrate Recognition and Kinase Activation." *Cell* 134: 793-803 (2008) and Hellwig, S. et al. "Small-Molecule Inhibitors of the c-Fes Protein-Tyrosine Kinase", *Chem. Biol.* 19: 529-540 (2012).

FIG. 8RRRR presents examples of FYN Targeting Ligands wherein R is the point at which the Linker is attached. For additional examples and related ligands, see, Kinoshita, T. et. al. "Structure of human Fyn kinase domain complexed with staurosporine", *Biochem. Biophys. Res. Commun.* 346: 840-844 (2006).

FIG. 8SSSS-8VVVV present examples of GSG2 (Haspin) Targeting Ligands wherein R is the point at which the Linker is attached. For additional examples and related ligands, see, the crystal structures PDB 3e7v, PDB 3f2n, 3fmd and related ligands described in Filippakopoulos, P. et al. "Crystal Structure of Human Haspin with a pyrazolo-pyrimidine ligand", to be published; the crystal structure PDB 3iq7 and related ligands described in Eswaran, J. et al. "Structure and functional characterization of the atypical human kinase haspin", *Proc. Natl. Acad. Sci. USA* 106: 20198-20203 (2009); and, the crystal structure PDB 4qtc and related ligands described in Chaikuad, A. et al. "A unique inhibitor binding site in ERK1/2 is associated with slow binding kinetics", *Nat. Chem. Biol.* 10: 853-860 (2014).

FIG. 8WWWW-8AAAAA present examples of HCK Targeting Ligands wherein R is the point at which the Linker is attached. For additional examples and related ligands, see, the crystal structure PDB 1qcf and related ligands described in Schindler, T. et al. "Crystal structure of Hck in complex with a Src family-selective tyrosine kinase inhibitor", *Mol. Cell* 3: 639-648 (1999); the crystal structure PDB 2c0i and 2c0t and related ligands described in Burchat, A. et al. "Discovery of A-770041, a Src-Family Selective Orally Active Lck Inhibitor that Prevents Organ Allograft Rejection", *Bioorg. Med. Chem. Lett.* 16: 118 (2006); the crystal structure PDB 2hk5 and related ligands described in Sabat, M. et al. "The development of 2-benzimidazole substituted pyrimidine based inhibitors of lymphocyte specific kinase (Lck)", *Bioorg. Med. Chem. Lett.* 16: 5973-5977 (2006); the crystal structures PDB 3vry, 3vs3, 3vs6, and 3vs7 and related ligands described in Saito, Y. et al. "A Pyrrolo-Pyrimidine Derivative Targets Human Primary AML Stem Cells in Vivo", *Sci Transl Med* 5: 181ra52-181ra52 (2013); and, the crystal structure PDB 4lud and related ligands described in Parker, L. J. et al "Kinase crystal identification and ATP-competitive inhibitor screening using the fluorescent ligand SKF86002", *Acta Crystallogr., Sect. D* 70: 392-404 (2014).

FIG. 8BBBBB-8FFFFF present examples of IGF 1R Targeting Ligands wherein R is the point at which the Linker is attached. For additional examples and related ligands, see, the crystal structure PDB 2oj9 and related ligands described in Velaparthi, U. et al. "Discovery and initial SAR of 3-(1H-benzo[d]imidazol-2-yl)pyridin-2(1H)-ones as inhibitors of insulin-like growth factor 1-receptor (IGF-1R)", *Bioorg. Med. Chem. Lett.* 17: 2317-2321 (2007); the crystal structure PDB 3i81 and related ligands described in Wittman, M. D. et al. "Discovery of a 2,4-disubstituted pyrrolo [1,2-f][1,2,4]triazine inhibitor (BMS-754807) of insulin-like growth factor receptor (IGF-1R) kinase in clinical development.", *J. Med. Chem.* 52: 7360-7363 (2009); the crystal structure PDB 3nw5 and related ligands described in Sampognaro, A. J. et al. "Proline isosteres in a series of 2,4-disubstituted pyrrolo[1,2-f][1,2,4]triazine inhibitors of IGF-1R kinase and IR kinase", *Bioorg. Med. Chem. Lett.* 20: 5027-5030 (2010); the crystal structure PDB 3qqu and related ligands described in Buchanan, J. L. et al. "Discovery of 2,4-bis-arylamino-1,3-pyrimidines as insulin-like growth factor-1 receptor (IGF-1R) inhibitors", *Bioorg. Med. Chem. Lett.* 21: 2394-2399 (2011); the crystal structure PDB 4d2r and related ligands described in Kettle, J. G. et al. "Discovery and Optimization of a Novel Series of Dyrk1B Kinase Inhibitors to Explore a Mek Resistance Hypothesis". *J. Med. Chem.* 58: 2834 (2015); the crystal structure PDB 3fxq and related ligands described in Monferrer, D. et al. "Structural studies on the full-length LysR-type regulator TsaR from *Comamonas testosteroni* T-2 reveal a novel open conformation of the tetrameric LTTR fold", *Mol. Microbiol.* 75: 1199-1214 (2010); the crystal structure PDB 5fxs and related ligands described in Degorce, S. et al. "Discovery of Azd9362, a Potent Selective Orally Bioavailable and Efficacious Novel Inhibitor of Igf-R¹", to be published; the crystal structure PDB 2zm3 and related ligands described in Mayer, S. C. et al. "Lead identification to generate isoquinolinedione inhibitors of insulin-like growth factor receptor (IGF-1R) for potential use in cancer treatment", *Bioorg. Med. Chem. Lett.* 18: 3641-3645 (2008); the crystal structure PDB 3f5p and related ligands described in "Lead identification to generate 3-cyanoquinoline inhibitors of insulin-like growth factor receptor (IGF-1R) for potential use in cancer treatment" *Bioorg. Med. Chem. Lett.* 19: 62-66 (2009); the crystal structure PDB 3lvp and related ligands described in Nemecek, C. et al. "Design of Potent IGF1-R Inhibitors Related to Bis-azaindoles" *Chem. Biol. Drug Des.* 76: 100-106 (2010); the crystal structure PDB 3o23 and related ligands described in Lesuisse, D. et al. "Discovery of the first non-ATP competitive IGF-1R kinase inhibitors: Advantages in comparison with competitive inhibitors", *Bioorg. Med. Chem. Lett.* 21: 2224-2228 (2011); the crystal structure PDB 3d94 and related ligands described in Wu, J. et al. "Small-molecule inhibition and activation-loop trans-phosphorylation of the IGF1 receptor", *Embo J.* 27: 1985-1994 (2008); and, the crystal structure PDB 5hzn and related ligands described in Stauffer, F. et al. "Identification of a 5-[3-phenyl-(2-cyclic-ether)-methylether]-4-aminopyrrolo [2,3-d]pyrimidine series of IGF-1R inhibitors", *Bioorg. Med. Chem. Lett.* 26: 2065-2067 (2016).

FIG. 8GGGGG-8JJJJJ present examples of INSR Targeting Ligands wherein R is the point at which the Linker is attached. For additional examples and related ligands, see, the crystal structure PDB 2z8c and related ligands described in Katayama, N. et al. "Identification of a key element for hydrogen-bonding patterns between protein kinases and their inhibitors", *Proteins* 73: 795-801 (2008); the crystal structure PDB 3ekk and related ligands described in Chamberlain, S. D. et al. "Discovery of 4,6-bis-anilino-1H-pyrrolo [2,3-d]pyrimidines: Potent inhibitors of the IGF-1R receptor tyrosine kinase", (2009) *Bioorg. Med. Chem. Lett.* 19: 469-473; the crystal structure PDB 3ekn and related ligands described in Chamberlain, S. D. et al. "Optimization of 4,6-bis-anilino-1H-pyrrolo[2,3-d]pyrimidine IGF-1R tyrosine kinase inhibitors towards JNK selectivity", *Bioorg. Med. Chem. Lett.* 19: 360-364 (2009); the crystal structure PDB 5e1s and related ligands described in Sanderson, M. P. et al. "BI 885578, a Novel IGF1R/INSR Tyrosine Kinase Inhibitor with Pharmacokinetic Properties That Dissociate Antitumor Efficacy and Perturbation of Glucose Homeostasis" *Mol. Cancer Ther.* 14: 2762-2772", (2015); the crystal structure PDB 3eta and related ligands described in Patnaik, S. et al. "Discovery of 3,5-disubstituted-1H-pyrrolo[2,3-b] pyridines as potent inhibitors of the insulin-like growth factor-1 receptor (IGF-1R) tyrosine kinase", *Bioorg. Med. Chem. Lett.* 19: 3136-3140 (2009); the crystal structure PDB 5hhw and related ligands described in Stauffer, F. et al. "Identification of a 5-[3-phenyl-(2-cyclic-ether)-methylether]-4-aminopyrrol o[2,3-d]pyrimidine series of IGF-1R inhibitors", *Bioorg. Med. Chem. Lett.* 26: 2065-2067 (2016); and, the crystal structure PDB 4ibm and related ligands described in Anastassiadis, T. et al. "A highly selective dual insulin receptor (IR)/insulin-like growth factor 1 receptor (IGF-1R) inhibitor derived from an extracellular signal-regulated kinase (ERK) inhibitor", *J. Biol. Chem.* 288: 28068-28077 (2013).

FIG. 8KKKKK-8PPPPP present examples of HBV Targeting Ligands wherein R is the point at which the Linker is attached, Y is methyl or isopropyl, and X is N or C. For additional examples and related ligands, see, Weber, O.; et al. "Inhibition of human hepatitis B virus (HBV) by a novel non-nucleosidic compound in a transgenic mouse model." *Antiviral Res.* 54, 69-78 (2002); Deres, K.; et al. "Inhibition of hepatitis B virus replication by drug-induced depletion of nucleocapsids." *Science,* 299, 893-896 (2003); Stray, S. J.; Zlotnick, A. "BAY 41-4109 has multiple effects on Hepatitis B virus capsid assembly." *J. Mol. Recognit.* 19, 542-548 (2006); Stray, S. J.; et al. "heteroaryldihydropyrimidine activates and can misdirect hepatitis B virus capsid assembly." *Proc. Natl. Acad. Sci. U.S.A,* 102, 8138-8143 (2005); Guan, H.; et al. "The novel compound Z060228 inhibits assembly of the HBV capsid." *Life Sci.* 133, 1-7 (2015); Wang, X. Y.; et al. "In vitro inhibition of HBV replication by a novel compound, GLS4, and its efficacy against adefovir-dipivoxil-resistant HBV mutations." *Antiviral Ther.* 17, 793-803 (2012); Klumpp, K.; et al. "High-resolution crystal structure of a hepatitis B virus replication inhibitor bound to the viral core protein." 112, 15196-15201 (2015); Qiu, Z.; et al. "Design and synthesis of orally bioavailable 4-methyl heteroaryldihydropyrimidine based hepatitis B virus (HBV) capsid inhibitors." *J. Med. Chem.* 59, 7651-7666 (2016); Zhu, X.; et al. "2,4-Diaryl-4,6,7,8-tetrahydroquinazolin-5

(1H)-one derivatives as anti-HBV agents targeting at capsid assembly." *Bioorg. Med. Chem. Lett.* 20, 299-301 (2010); Campagna, M. R.; et al. "Sulfamoylbenzamide derivatives inhibit the assembly of hepatitis B virus nucleocapsids." *J. Virol.* 87, 6931-6942 (2013); Campagna, M. R.; et al. "Sulfamoylbenzamide derivatives inhibit the assembly of hepatitis B virus nucleocapsids." *J. Virol.* 87, 6931-6942 (2013); WO 2013096744 A1 titled "Hepatitis B antiviral agents"; WO 2015138895 titled "Hepatitis B core protein allosteric modulators"; Wang, Y. J.; et al. "A novel pyridazinone derivative inhibits hepatitis B virus replication by inducing genome-free capsid formation." *Antimicrob. Agents Chemother.* 59, 7061-7072 (2015); WO 2014033167 titled "Fused bicyclic sulfamoyl derivatives for the treatment of hepatitis"; U.S. 20150132258 titled "Azepane derivatives and methods of treating hepatitis B infections"; and, WO 2015057945 "Hepatitis B viral assembly effector".

Figure 9:
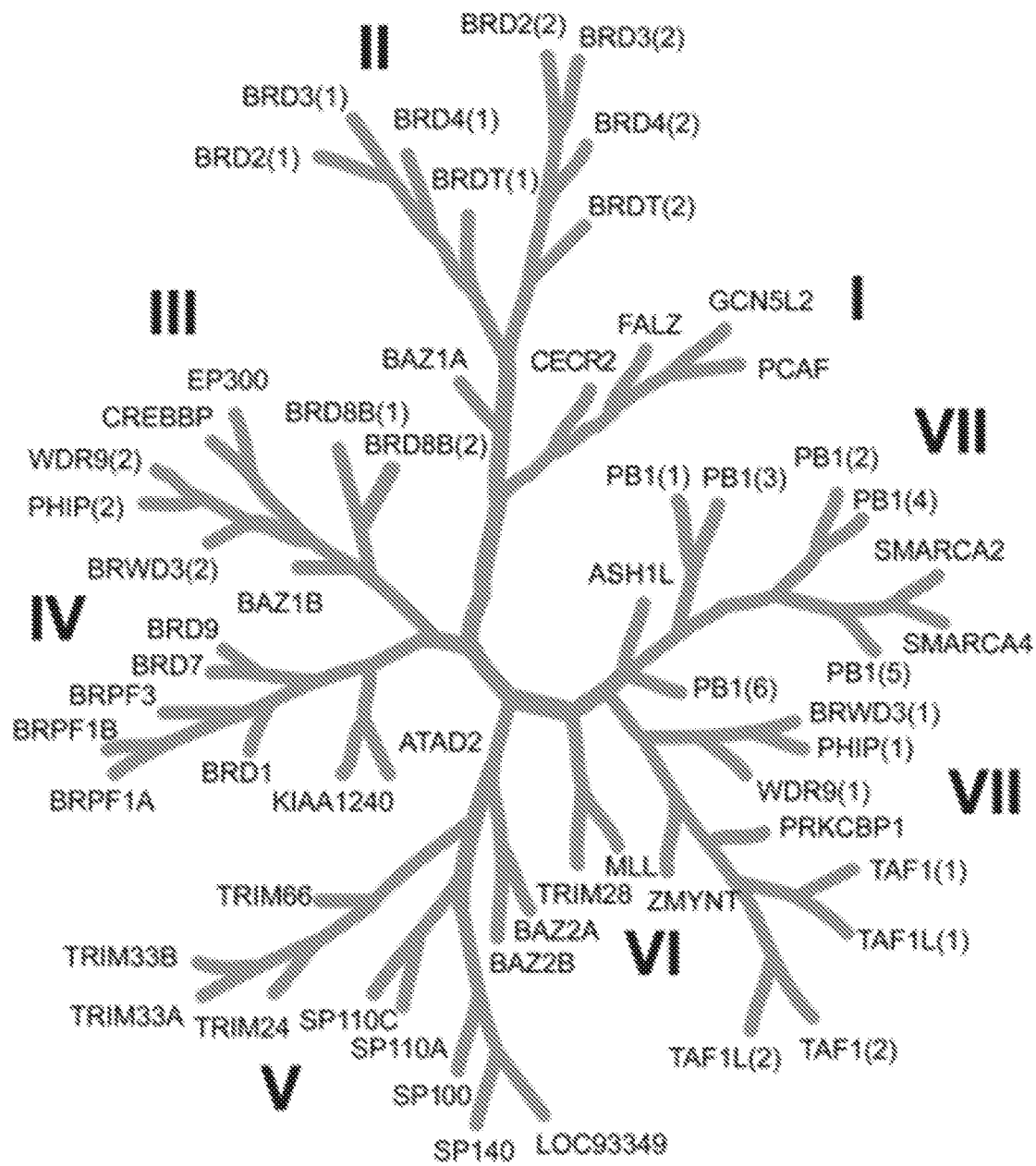

FIG. 9 is a dendrogram of the human bromodomain family of proteins organized into eight subfamilies, which are involved in epigenetic signaling and chromatin biology. Any of the proteins of the bromodomain family in FIG. 9 can be selected as a Target Protein according to the present invention.

Figure 1A:
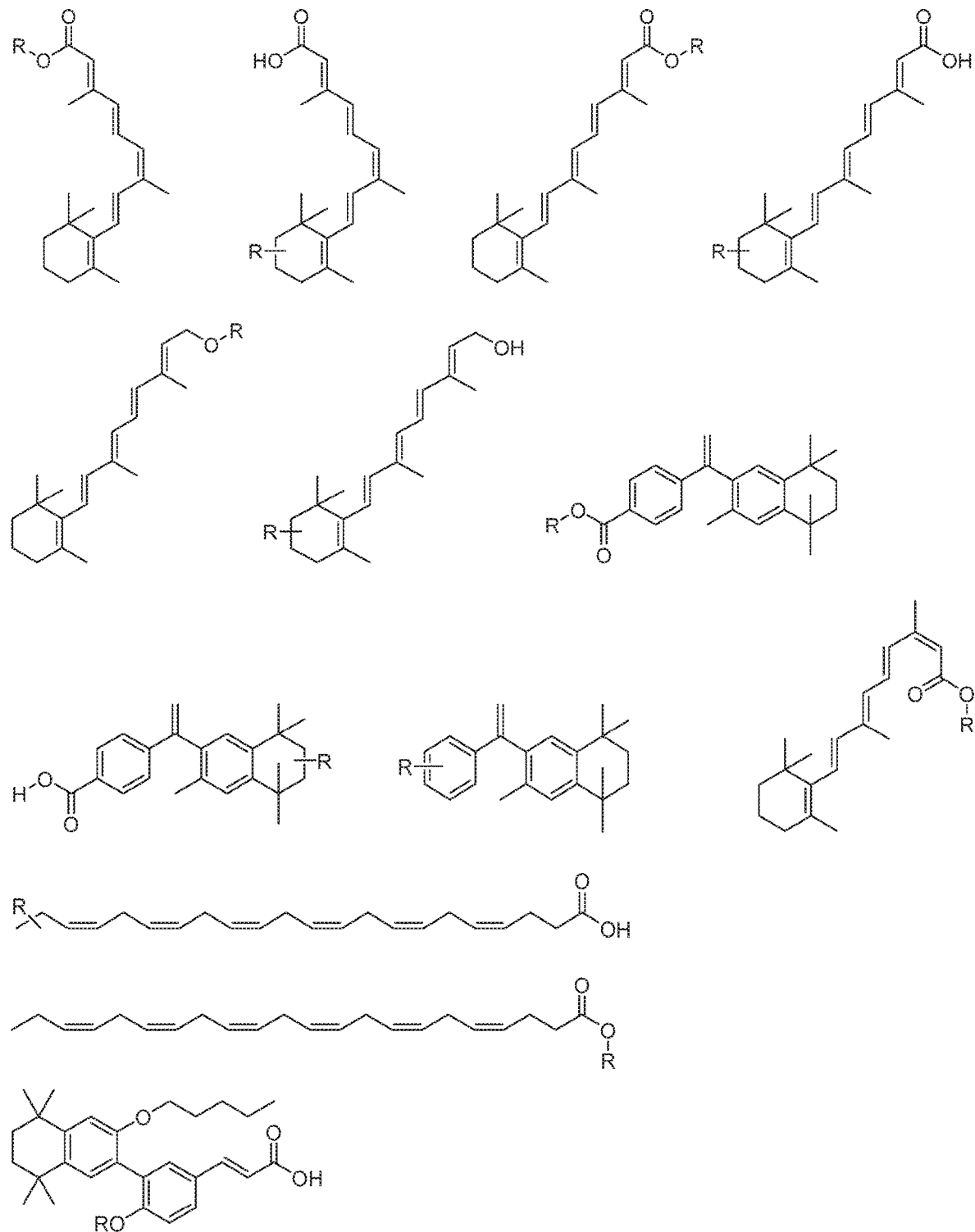
FIG. 1A-1C present examples of Retenoid X Receptor (RXR) Targeting Ligands wherein R is the point at which the Linker is attached.
Figure 1B:
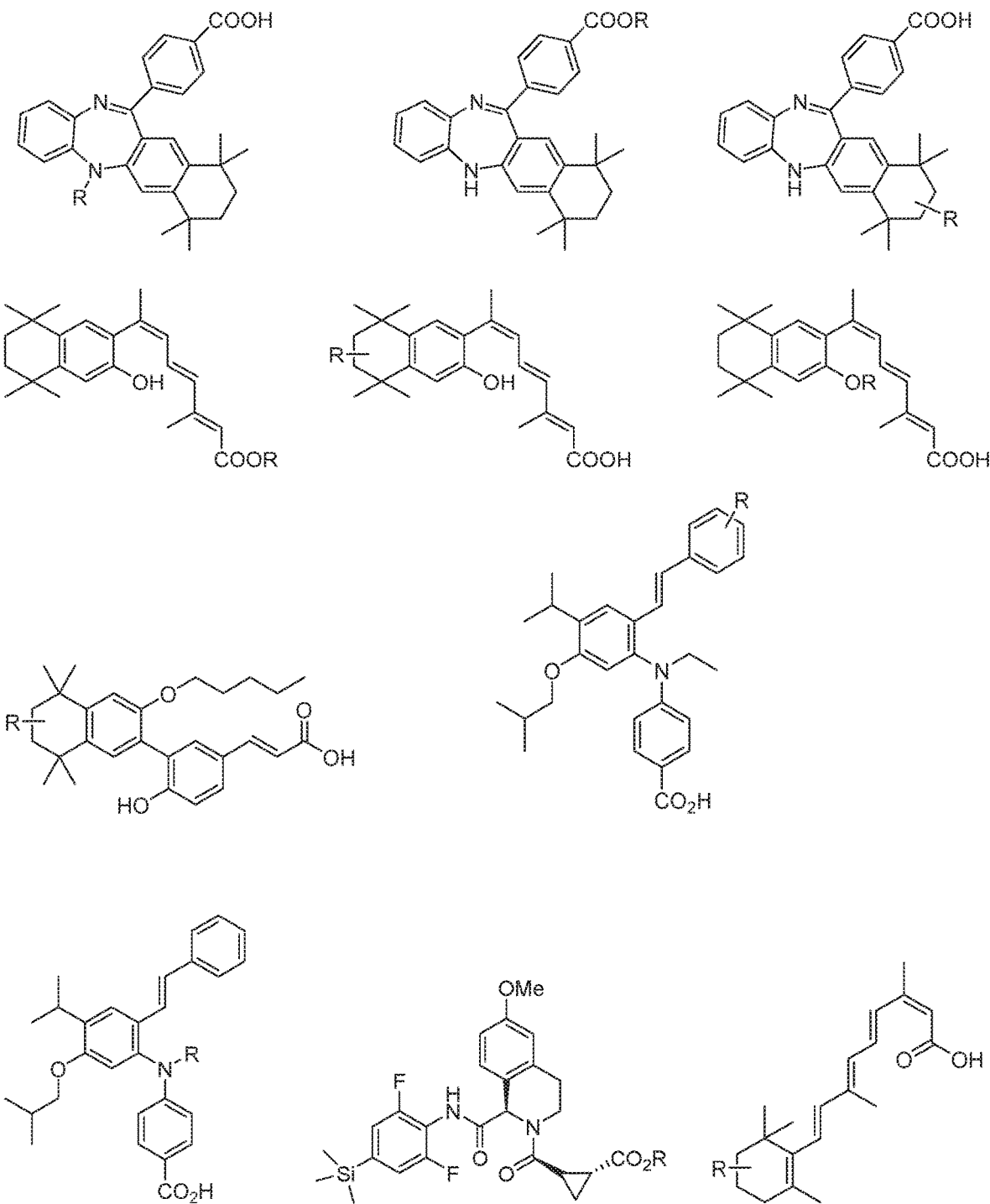
Figure 1C:
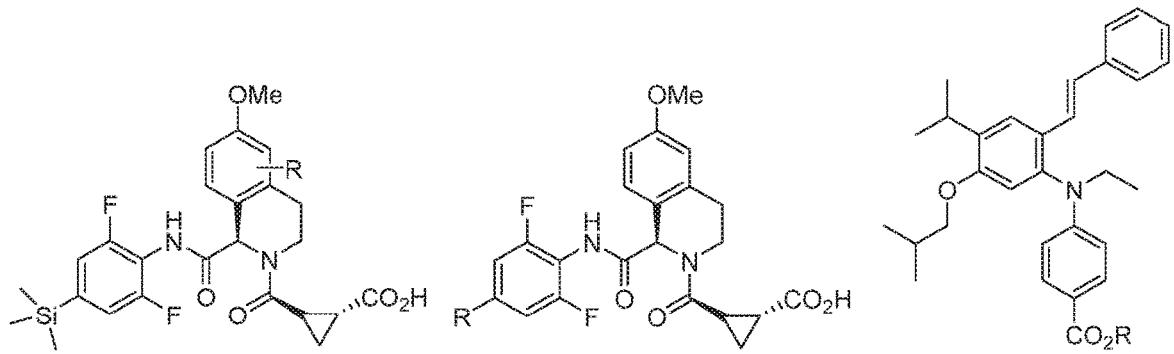
Figure 1D:
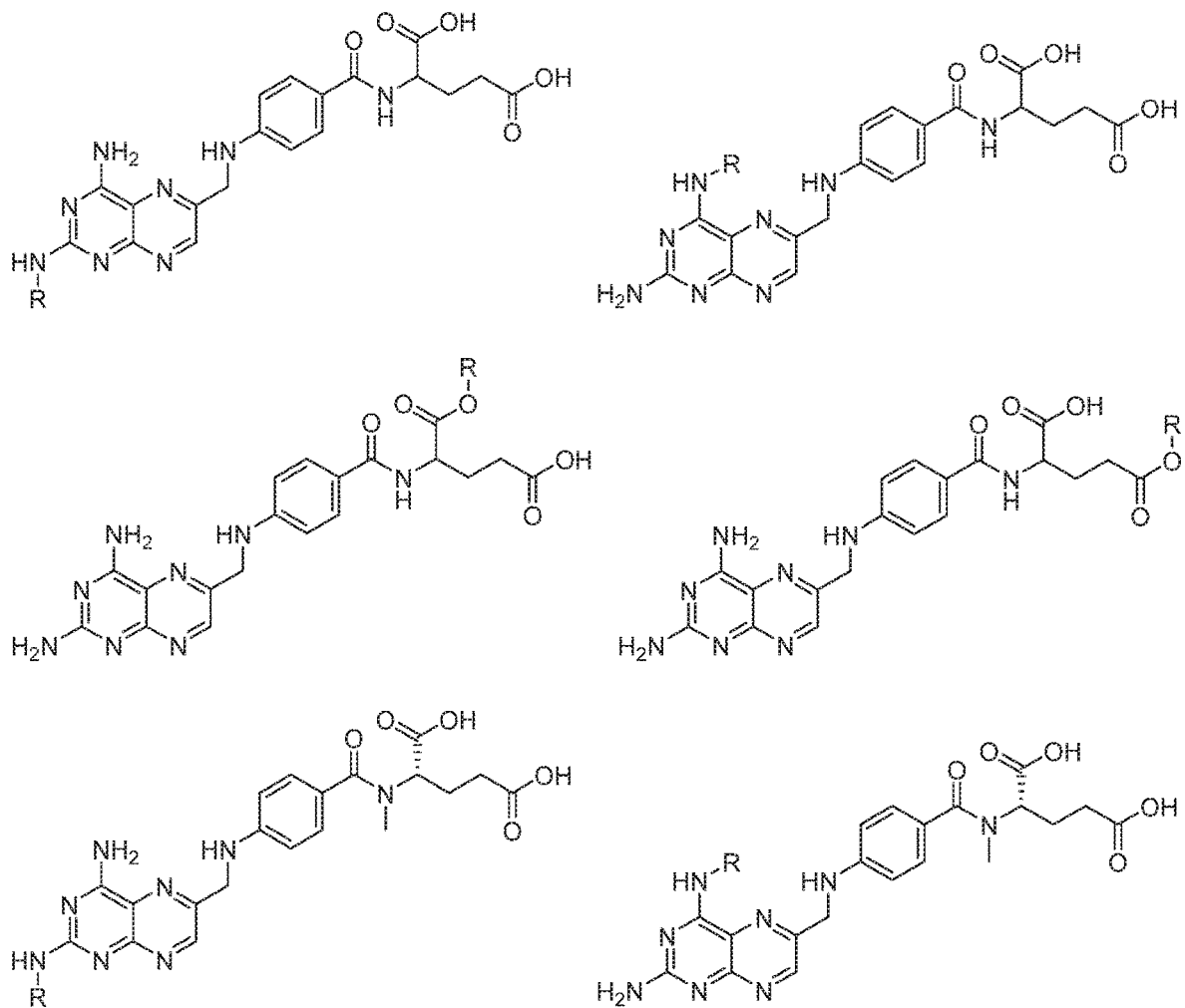
FIG. 1D-1F present examples of general Dihydrofolate reductase (DHFR) Targeting Ligands wherein R is the point at which the Linker is attached.
Figure 1E:
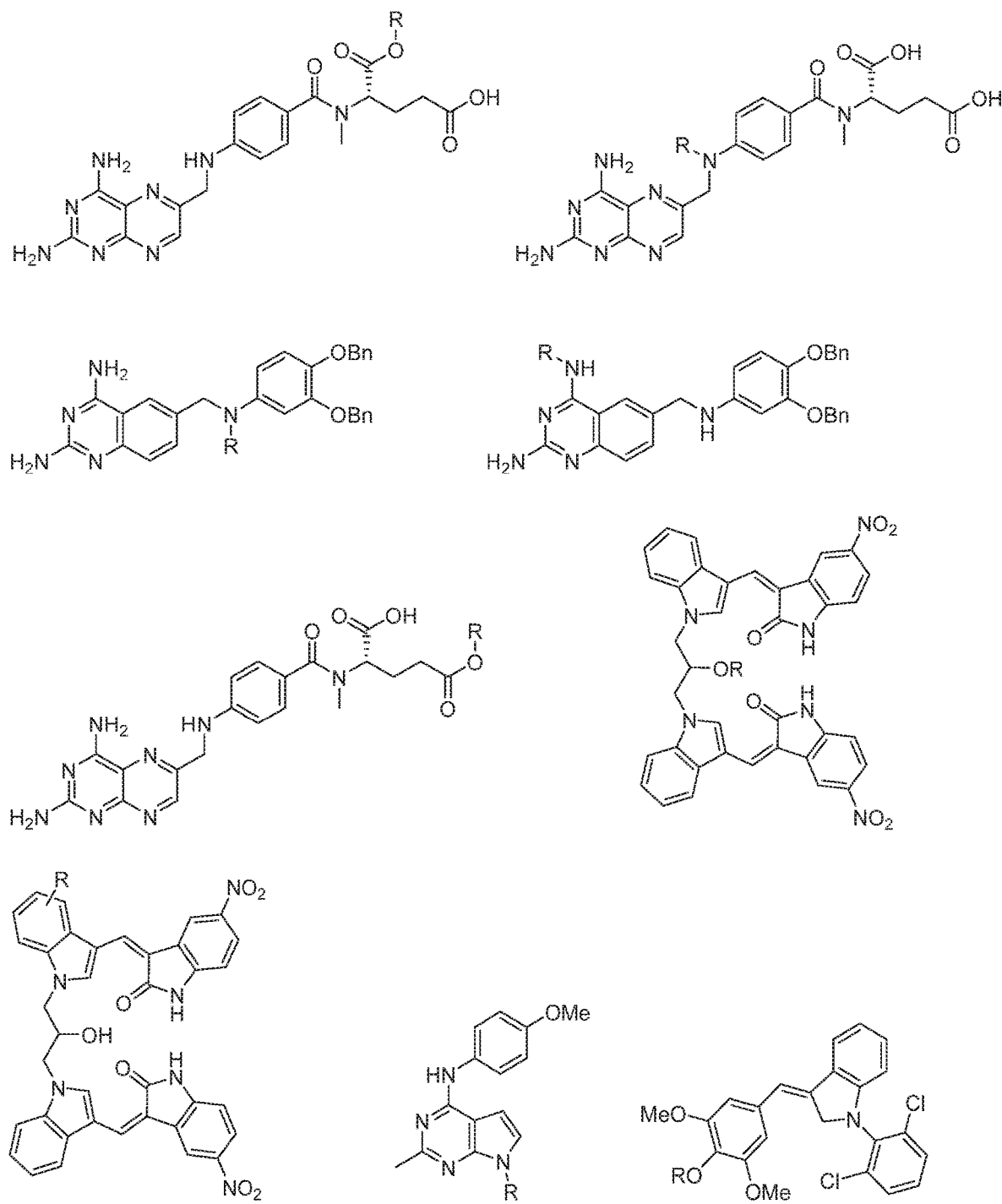
Figure 1F:
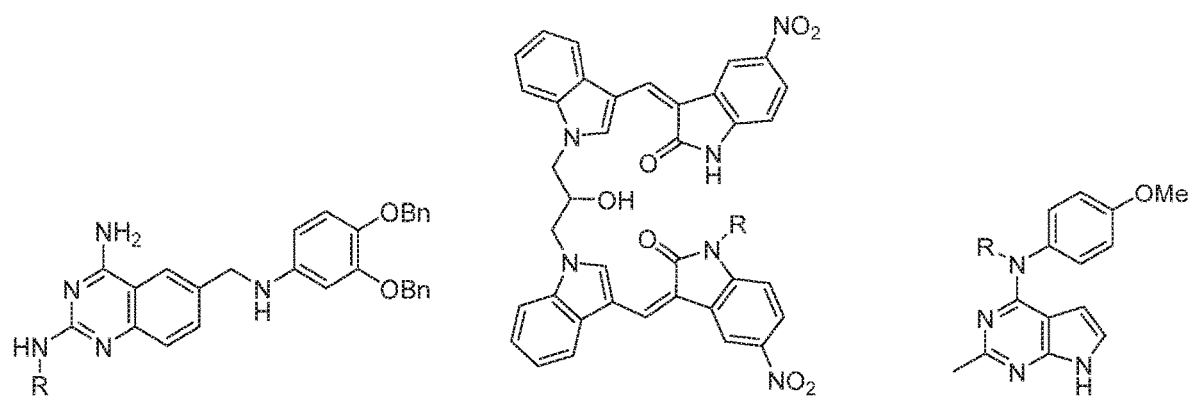
Figure 1G:
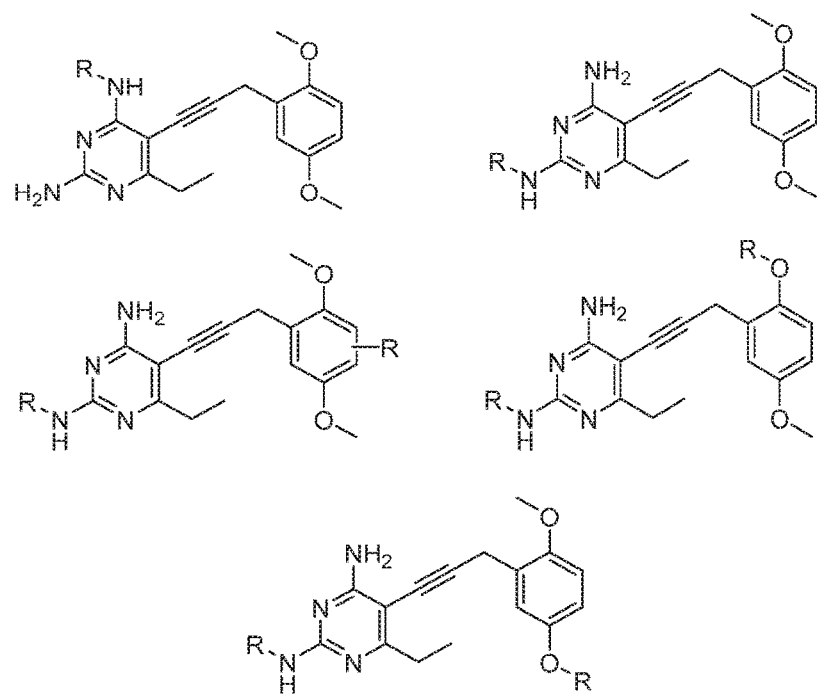
FIG. 1G presents examples of *Bacillus anthracis* Dihydrofolate reductase (BaDHFR) Targeting Ligands wherein R is the point at which the Linker is attached.
Figure 1H:
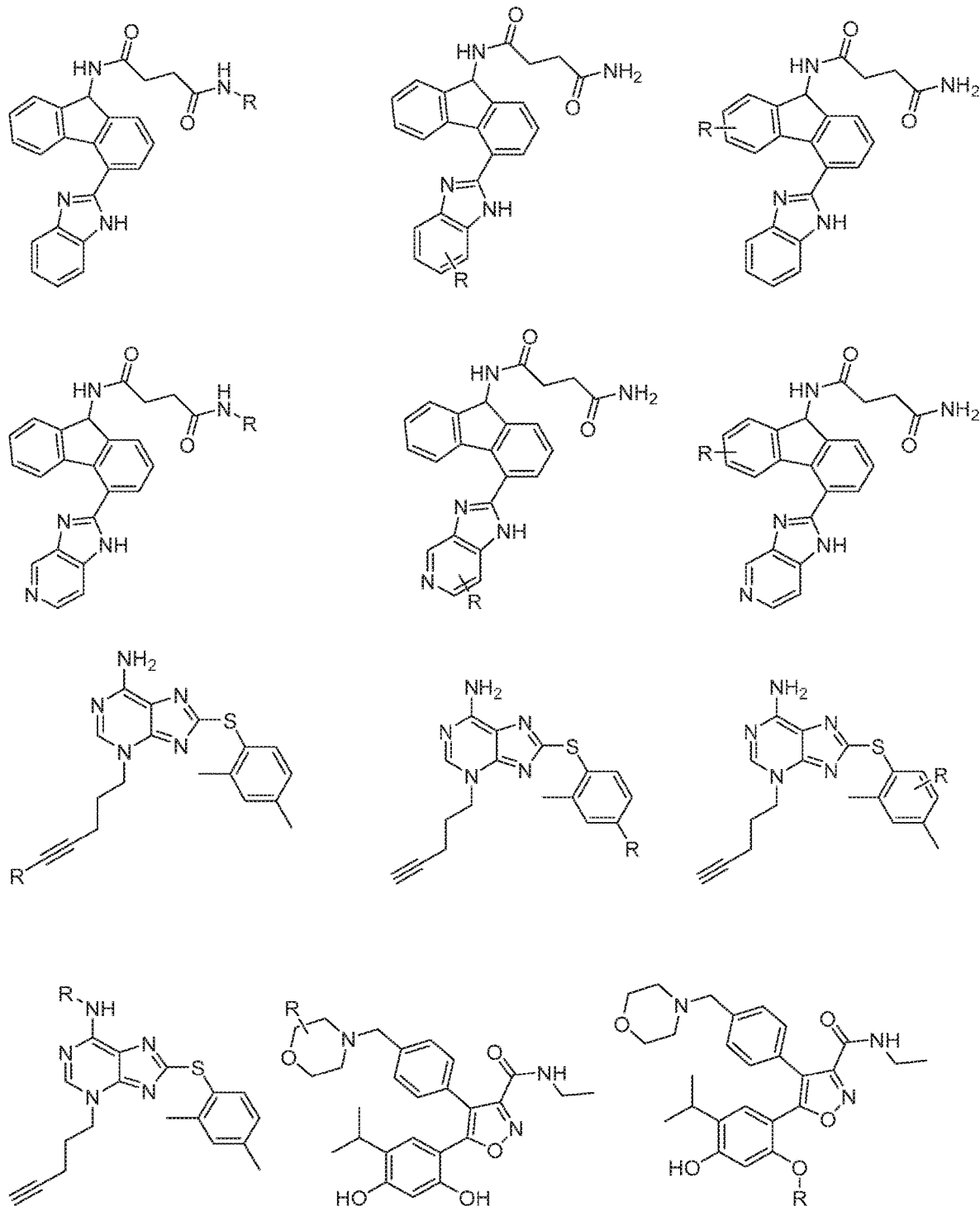
FIG. 1H-1J present examples of Heat Shock Protein 90 (HSP90) Targeting Ligands wherein R is the point at which the Linker is attached.
Figure 1I:
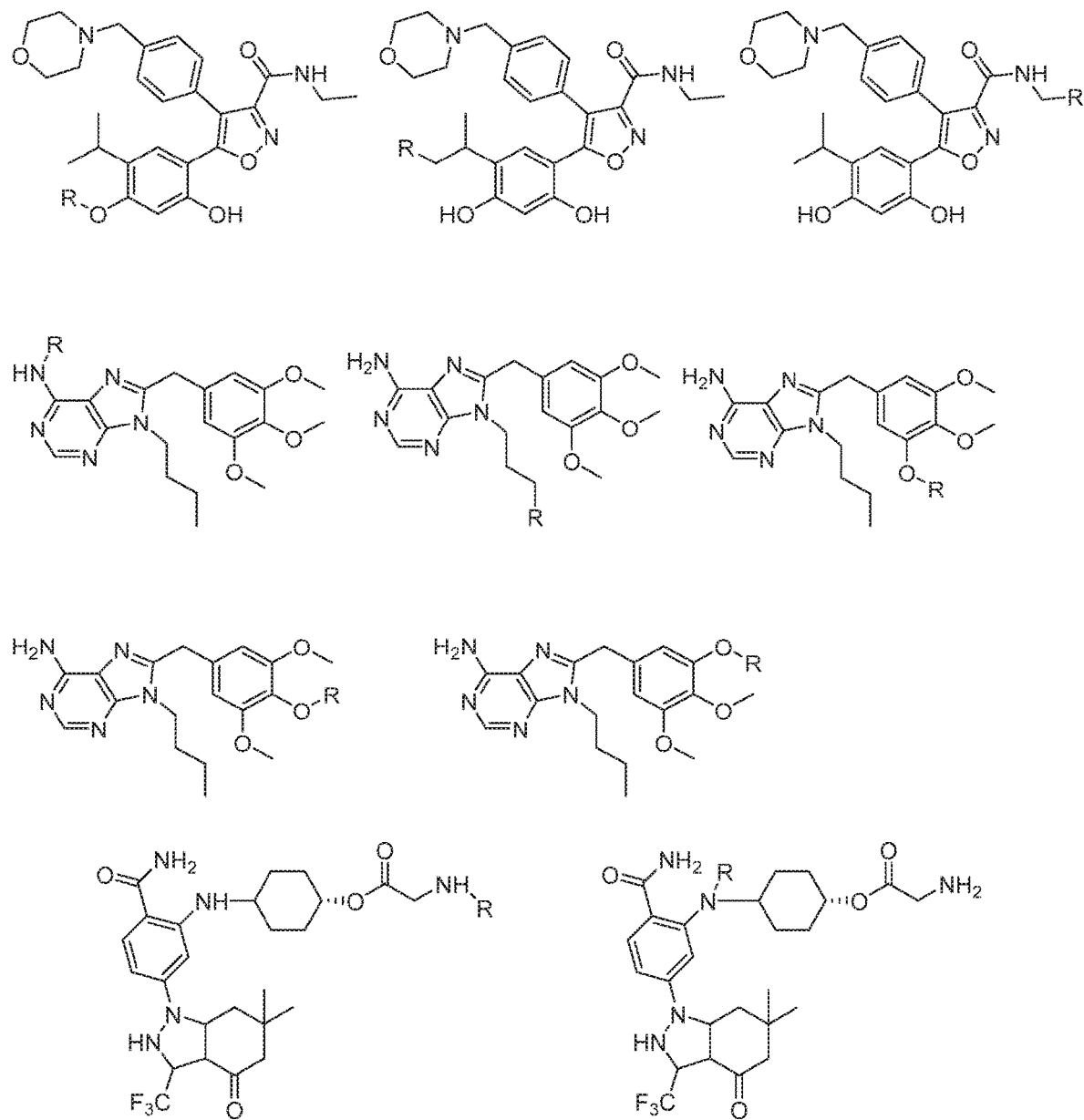
Figure 1J:
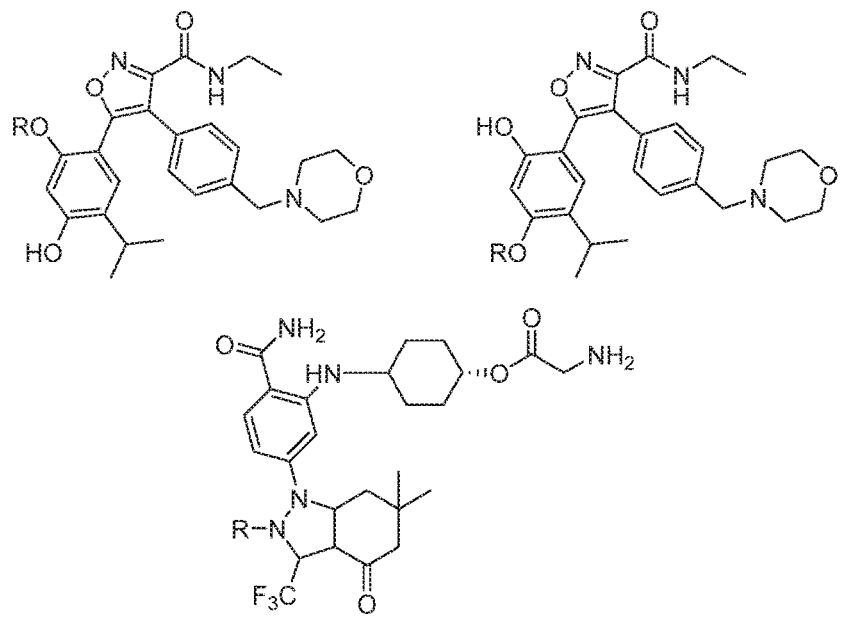
Figure 1K:
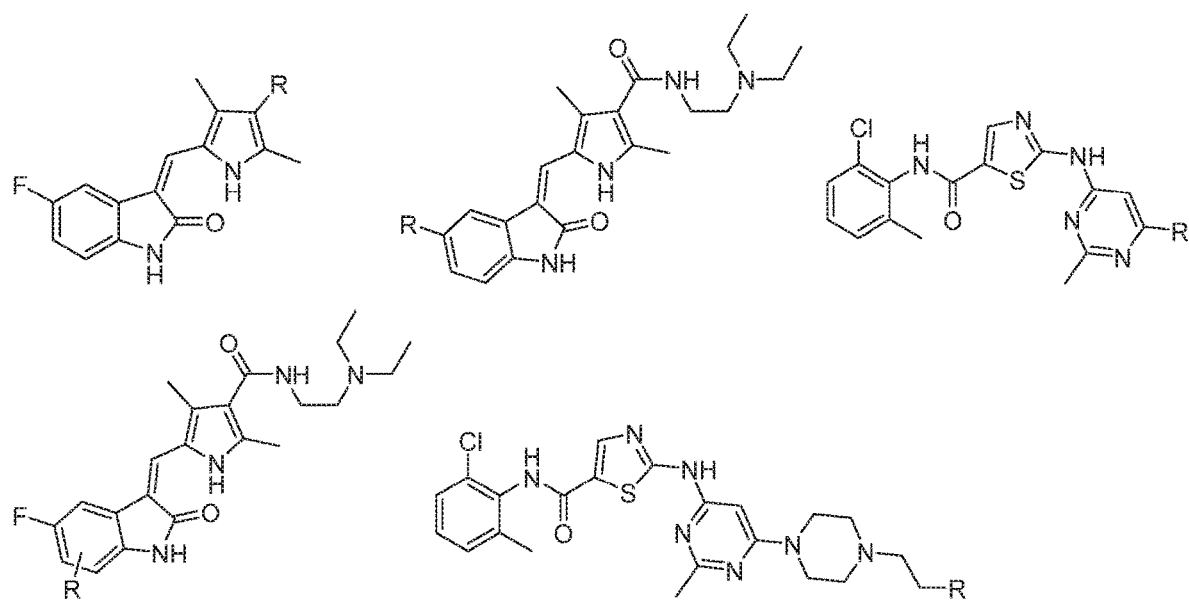
Figure 1L:
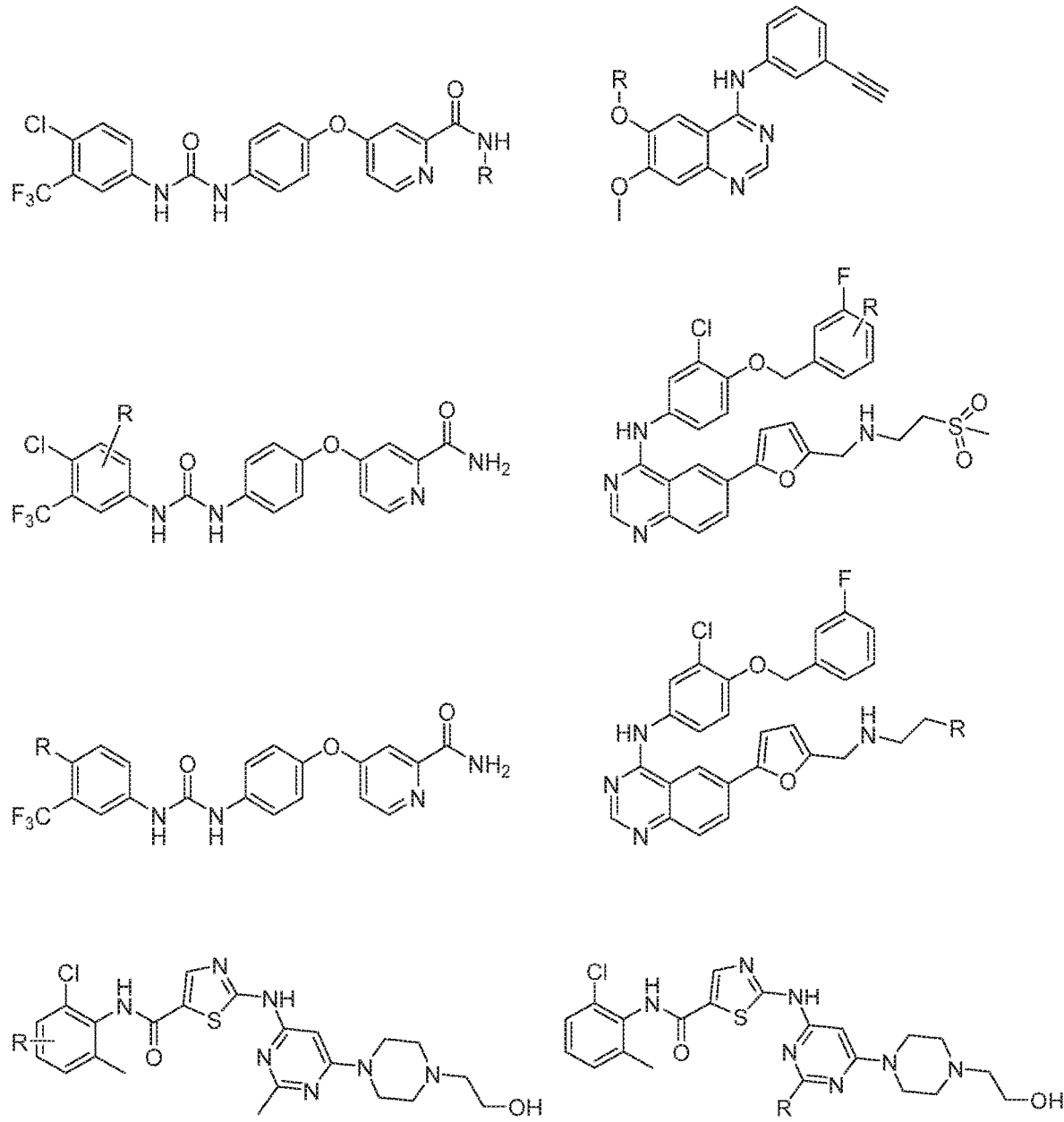
Figure 1M:
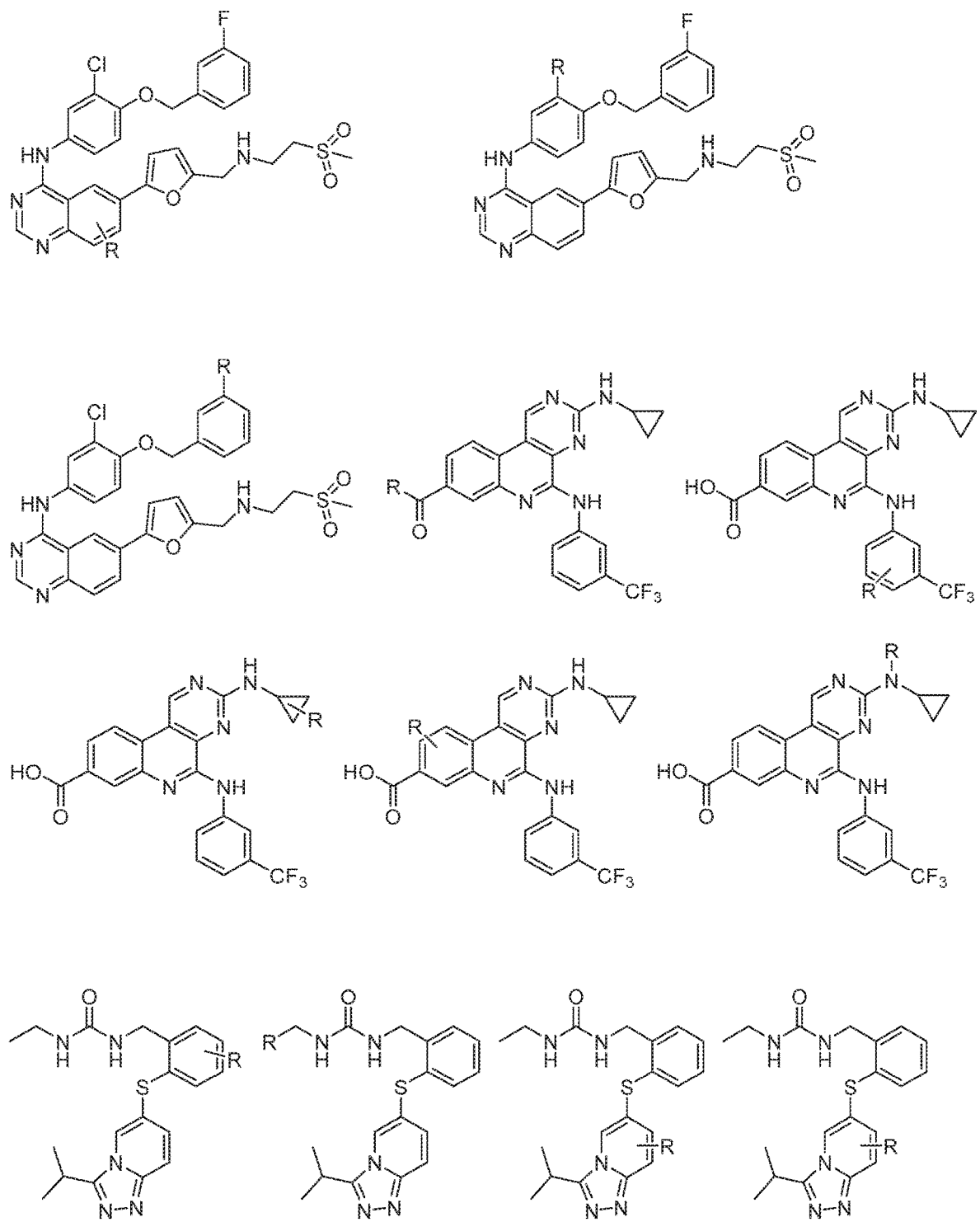
Figure 1N:
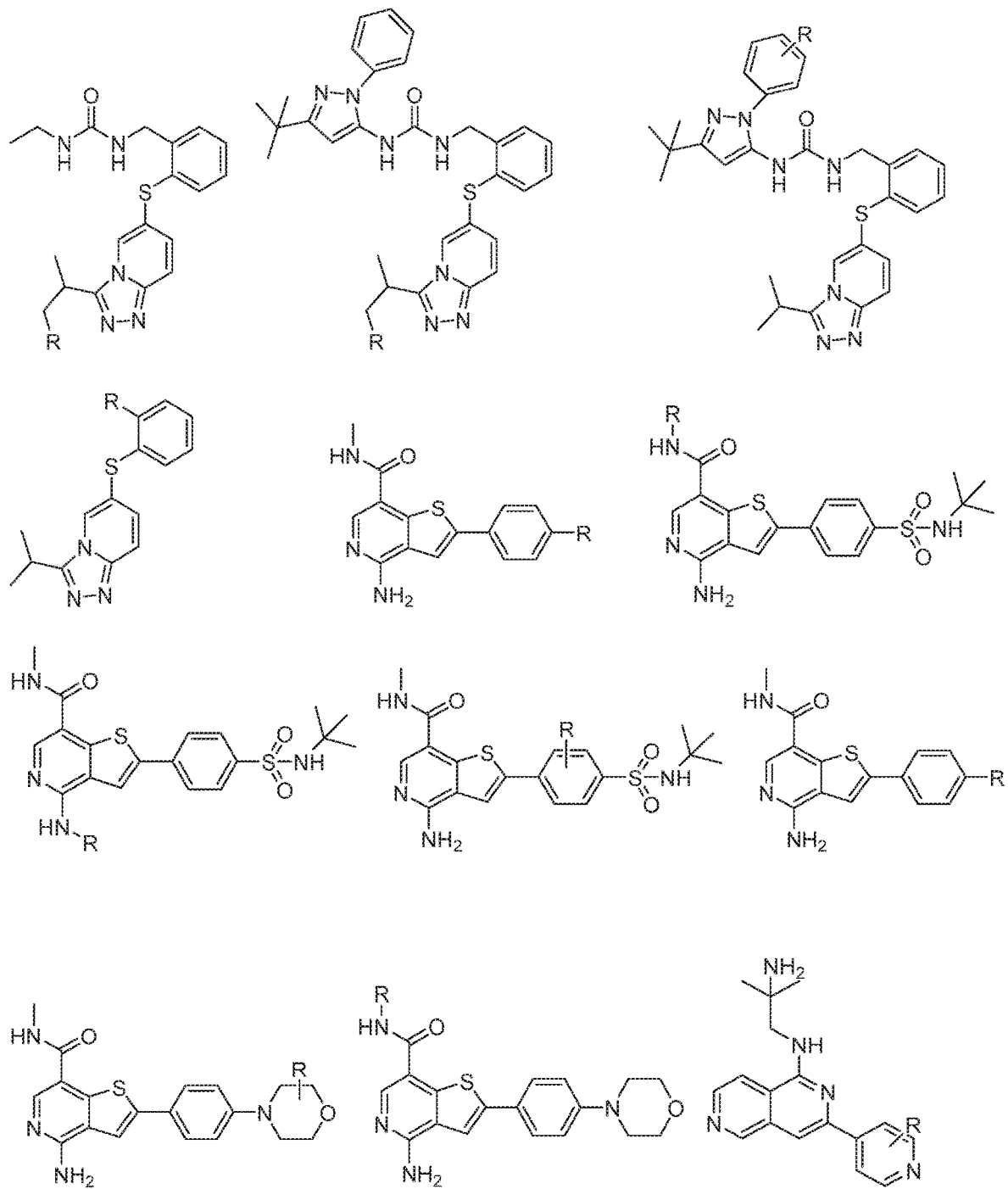
Figure 10:
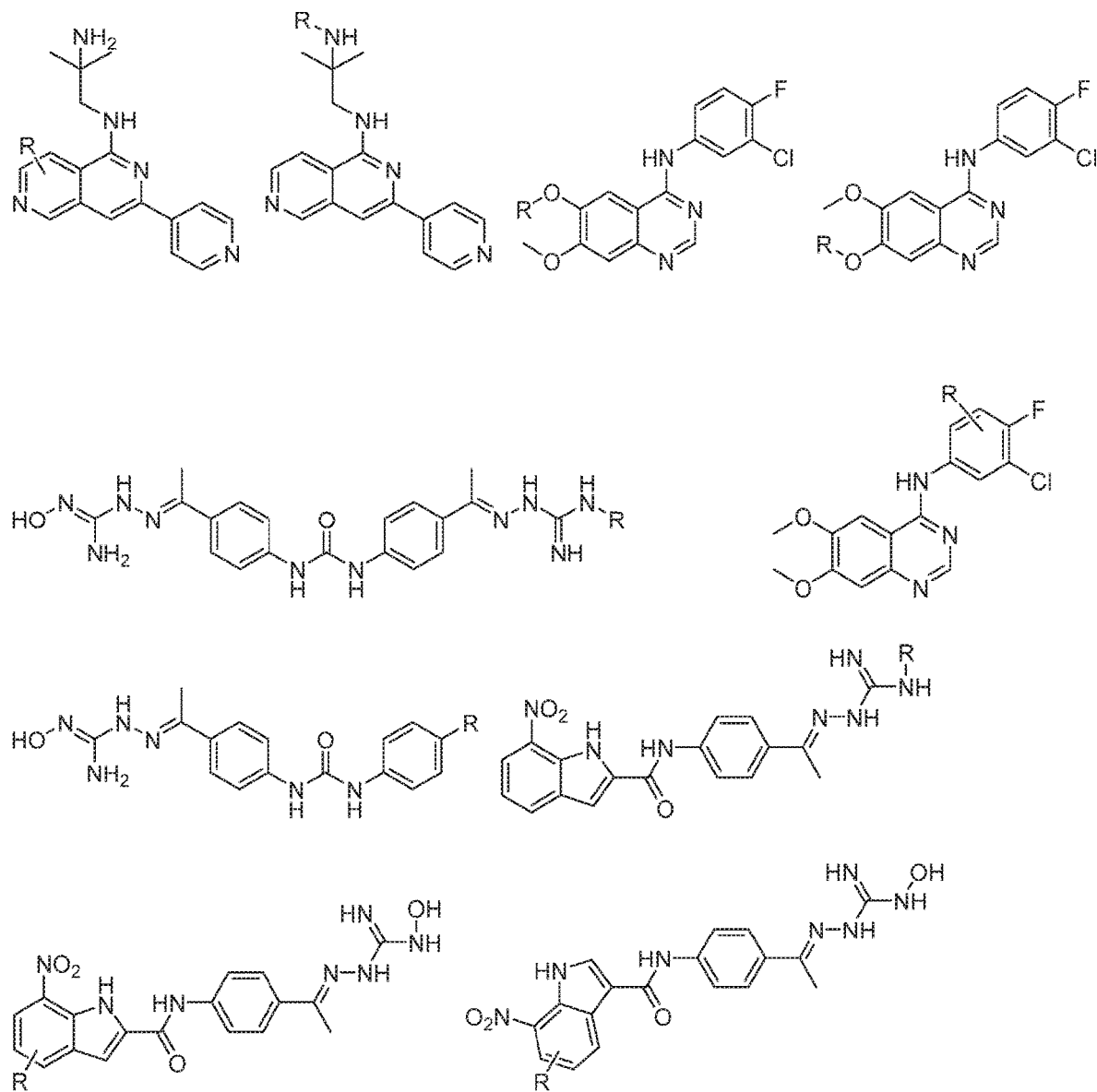

FIG. 10 is Formula I, Formula II, Formula III, and Formula IV.

DETAILED DESCRIPTION OF THE INVENTION

I. Definitions

Compounds are described using standard nomenclature. Unless defined otherwise, all technical and scientific terms used herein have the same meaning as is commonly understood by one of skill in the art to which this invention belongs.

The compounds in any of the Formulas described herein may be in the form of a racemate, enantiomer, mixture of enantiomers, diastereomer, mixture of diastereomers, tautomer, N-oxide, isomer; such as rotamer, as if each is specifically described unless specifically excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes compounds of Formula I, Formula II, Formula III, Formula IV, Formula V, Formula VI, Formula VII, Formula VIII, Formula IX, Formula X, Formula XI, and Formula XII with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^2$H, $^3$H, $^{11}$C, $^{13}$C, $^{14}$C, $^{15}$N, $^{17}$O, $^{18}$O, $^{18}$F $^{31}$P, $^{32}$P, $^{35}$S, $^{36}$Cl, and $^{125}$I respectively. In one non-limiting embodiment, isotopically labelled compounds can be used in metabolic studies (with, for example $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any compound of Formula I, Formula II, Formula III, Formula IV, Formula V, Formula VI, Formula VII, Formula VIII, Formula IX, Formula X, Formula XI, or Formula XII. In one non-limiting embodiment, the substitution of a hydrogen atom for a deuterium atom occurs within one or more groups selected from any of R's or variables described herein, Linker, and Targeting Ligand. For example, when any of the groups are, or contain for example through substitution, methyl, ethyl, or methoxy, the alkyl residue may be deuterated (in non-limiting embodiments, CDH$_2$, CD$_2$H, CD$_3$, CH$_2$CD$_3$, CD$_2$CD$_3$, CHDCH$_2$D, CH$_2$CD$_3$, CHDCHD$_2$, OCDH$_2$, OCD$_2$H, or OCD$_3$ etc.). In certain other embodiments, when two substituents are combined to form a cycle the unsubstituted carbons may be deuterated.

The compound of the present invention may form a solvate with a solvent (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. D$_2$O, d$_6$-acetone, d$_6$-DMSO. A solvate can be in a liquid or solid form.

A dash ("-") that is not between two letters or symbols is used to indicate a point of attachment for a substituent. For example, —(C=O)NH$_2$ is attached through carbon of the carbonyl (C=O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$.

The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species and therefore each subset is considered separately disclosed. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "alkyl" also encompasses cycloalkyl or carbocyclic groups. For example, when a term is used that includes "alk" then "cycloalkyl" or "carbocyclic" can be considered part of the definition, unless unambiguously excluded by the context. For example and without limitation, the terms alkyl, alkoxy, haloalkyl, etc. can all be considered to include the cyclic forms of alkyl, unless unambiguously excluded by context.

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In one embodiment "alkyl" has one carbon.

In one embodiment "alkyl" has two carbons.

In one embodiment "alkyl" has three carbons.

In one embodiment "alkyl" has four carbons.

In one embodiment "alkyl" has five carbons.

In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

In an alternative embodiment "alkyl" is "optionally substituted" with 1, 2, 3, or 4 substituents.

In one embodiment "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_5$cycloalkyl, $C_5$-$C_8$cycloalkyl, or $C_6$-$C_8$cycloalkyl.

In one embodiment "cycloalkyl" has three carbons.

In one embodiment "cycloalkyl" has four carbons.

In one embodiment "cycloalkyl" has five carbons.

In one embodiment "cycloalkyl" has six carbons.

In one embodiment "cycloalkyl" has seven carbons.

In one embodiment "cycloalkyl" has eight carbons.

In one embodiment "cycloalkyl" has nine carbons.

In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

Additional non-limiting examples of "cycloalkyl" include dihydro-indene and tetrahydronaphthalene wherein the point of attachment for each group is on the cycloalkyl ring.

For example

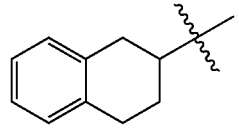 [SMILES: *C1CCc2ccccc2C1]

is an "cycloalkyl" group.

However,

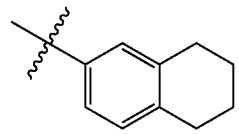 [SMILES: *c1ccc2c(c1)CCCC2]

is an "aryl" group.

In an alternative embodiment "cycloalkyl" is a "optionally substituted" with 1, 2, 3, or 4 substituents.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or carbocyclic groups possessing at least one point of unsaturation. In an alternative embodiment "alkenyl" is "optionally substituted" with 1, 2, 3, or 4 substituents.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or carbocyclic groups possessing at least one triple bond. In an alternative embodiment "alkynyl" is "optionally substituted" with 1, 2, 3, or 4 substituents.

"Alkylene" is a bivalent saturated hydrocarbon. Alkylenes, for example, can be a 1, 2, 3, 4, 5, 6, 7 to 8 carbon moiety, 1 to 6 carbon moiety, or an indicated number of carbon atoms, for example $C_1$-$C_2$alkylene, $C_1$-$C_3$alkylene, $C_1$-$C_4$alkylene, $C_1$-$C_5$alkylene, or $C_1$-$C_6$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, a 2 to 6 carbon moiety, or an indicated number of carbon atoms, for example $C_2$-$C_4$alkynylene.

"Halo" and "Halogen" refers to fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.

In one embodiment "haloalkyl" has one carbon and one halogen.

In one embodiment "haloalkyl" has one carbon and two halogens.

In one embodiment "haloalkyl" has one carbon and three halogens.

In one embodiment "haloalkyl" has two carbons.

In one embodiment "haloalkyl" has three carbons.

In one embodiment "haloalkyl" has four carbons.

In one embodiment "haloalkyl" has five carbons.

In one embodiment "haloalkyl" has six carbons.

Non-limiting examples of "haloalkyl" include:

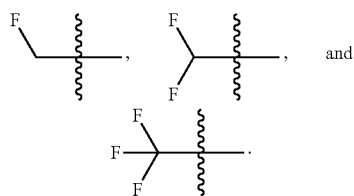

Additional non-limiting examples of "haloalkyl" include:

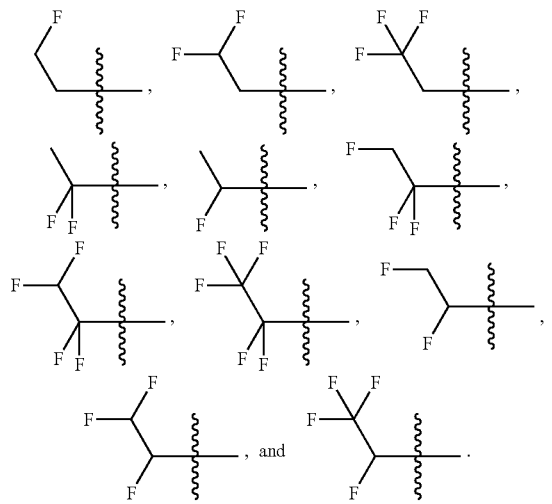

Additional non-limiting examples of "haloalkyl" include:

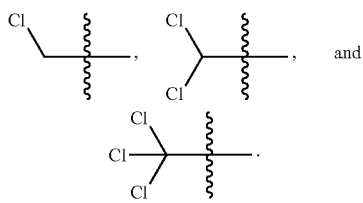

Additional non-limiting examples of "haloalkyl" include:

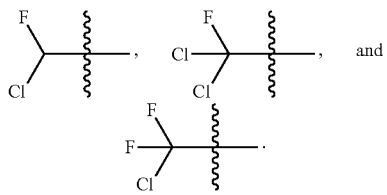

"Chain" indicates a linear chain to which all other chains, long or short or both, may be regarded as being pendant. Where two or more chains could equally be considered to be the main chain, "chain" refers to the one which leads to the simplest representation of the molecule.

"Haloalkoxy" indicates a haloalkyl group as defined herein attached through an oxygen bridge (oxygen of an alcohol radical).

"Heterocycloalkyl" is an alkyl group as defined herein substituted with a heterocyclo group as defined herein.

"Arylalkyl" is an alkyl group as defined herein substituted with an aryl group as defined herein.

Non-limiting examples of "arylalkyl" include:

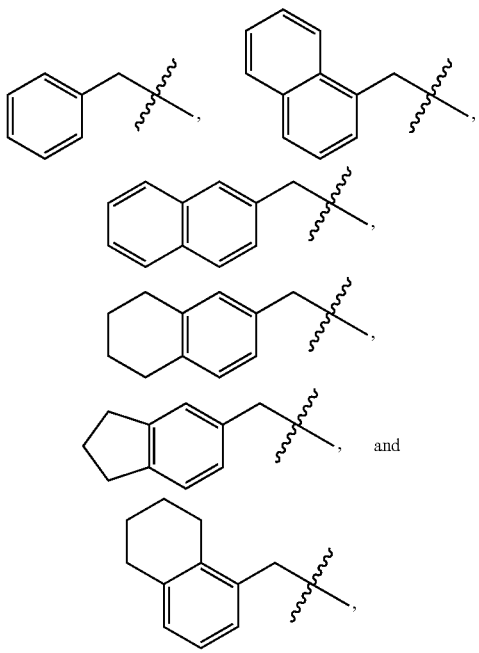

In one embodiment "arylalkyl" is

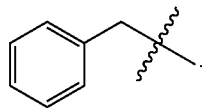

In one embodiment the "arylalkyl" refers to a 2 carbon alkyl group substituted with an aryl group.

Non-limiting examples of "arylalkyl" include:

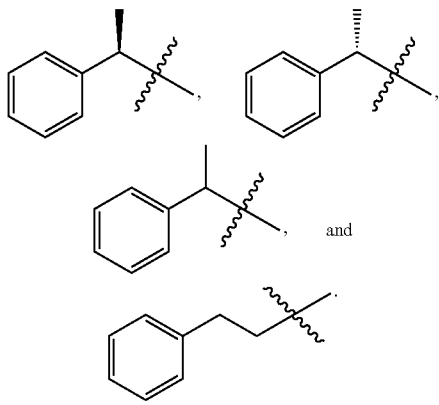

and

In one embodiment the "arylalkyl" refers to a 3 carbon alkyl group substituted with an aryl group.

"Heteroarylalkyl" is an alkyl group as defined herein substituted with a heteroaryl group as defined herein.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. The one or more fused carbocyclyl or heterocyclyl groups can be 4 to 7 or 5 to 7-membered saturated or partially unsaturated carbocyclyl or heterocyclyl groups that optionally contain 1, 2, or 3 heteroatoms independently selected from nitrogen, oxygen, phosphorus, sulfur, silicon and boron, to form, for example, a 3,4-methylenedioxyphenyl group. In one non-limiting embodiment, aryl groups are pendant. An example of a pendant ring is a phenyl group substituted with a phenyl group. In an alternative embodiment, the aryl group is optionally substituted as described above. In certain embodiments, the aryl group is an unsubstituted $C_{6-14}$ aryl. In certain embodiments, the aryl group is a substituted $C_{6-14}$ aryl. An aryl group may be optionally substituted with one or more functional groups that include but are not limited to, halo, hydroxy, nitro, amino, cyano, haloalkyl, aryl, heteroaryl, and heterocyclo.

In one embodiment "aryl" is a 6 carbon aromatic group (phenyl)

In one embodiment "aryl" is a 10 carbon aromatic group (napthyl)

In one embodiment "aryl" is a 6 carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example

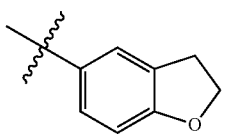 [SMILES: *c1ccc2c(c1)CCO2]

is an "aryl" group.
However,

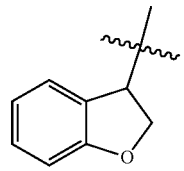 [SMILES: *C1COc2ccccc21]

is a "heterocycle" group.

In one embodiment "aryl" is a 6 carbon aromatic group fused to a cycloalkyl wherein the point of attachment is the aryl ring. Non-limiting examples of "aryl" include dihydroindene and tetrahydronaphthalene wherein the point of attachment for each group is on the aromatic ring.

For example

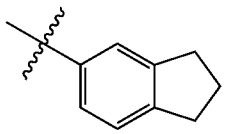 [SMILES: *c1ccc2c(c1)CCC2]

is an "aryl" group.
However,

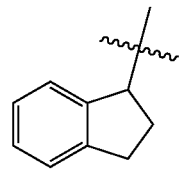 [SMILES: *C1CCc2ccccc21]

is a "cycloalkyl" group.

In an alternative embodiment "aryl" is "optionally substituted" with 1, 2, 3, or 4 substitutents.

The term "heterocyclyl", "heterocycle", and "heterocyclo" includes saturated, and partially saturated heteroatom-containing ring radicals, where the heteroatoms may be selected from nitrogen, sulfur and oxygen. Heterocyclic rings comprise monocyclic 3, 4, 5, 6, 7, 8, 9, or 10 membered rings, as well as 5, 6, 7, 8, 9, 10, 11, 12, 13, 14, 15, or 16 membered bicyclic ring systems (which can include bridged fused and spiro-fused bicyclic ring systems). It does not include rings containing —O—O—, —O—S— or —S—S— portions. Said "heterocyclyl" group may be optionally substituted, for example, with 1, 2, 3, 4 or more substituents that include but are not limited to, hydroxyl, Boc, halo, haloalkyl, cyano, alkyl, aralkyl, oxo, alkoxy, and amino. Examples of saturated heterocyclo groups include saturated 3, 4, 5, or 6-membered heteromonocyclic groups containing 1, 2, 3, or 4 nitrogen atoms [e.g. pyrrolidinyl, imidazolidinyl, piperidinyl, pyrrolinyl, piperazinyl]; saturated 3, 4, 5, or 6-membered heteromonocyclic group containing 1 or 2 oxygen atoms and 1, 2, or 3 nitrogen atoms [e.g. morpholinyl]; saturated 3, 4, 5, or 6-membered heteromonocyclic group containing 1 or 2 sulfur atoms and 1, 2, or 3 nitrogen atoms [e.g., thiazolidinyl]. Examples of partially saturated heterocyclyl radicals include but are not limited to, dihydrothienyl, dihydropyranyl, dihydrofuryl, and dihydrothiazolyl. Examples of partially saturated and saturated heterocyclo groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1X'-benzo[d]isothiazol-6-yl, dihydropyranyl, dihydrofuryl, isoquinolin-1(2H)-onyl, benzo[d]oxazol-2(3H)-onyl, 1,3-dihydro-2H-benzo[d]midazol-2-onyl, benzo[d]thiazole-2(3H)-onyl, 1,2-dihydro-3H-pyrazol-3-onyl, 2(1H)-pyridinonyl, 2-piperazinonyl, indolinyl, and dihydrothiazolyl.

The term"heterocyclyl", "heterocycle", and "heterocyclo" groups also include moieties where heterocyclic radicals are fused/condensed with aryl or heteroaryl radicals: such as unsaturated condensed heterocyclic group containing 1, 2, 3, 4, or 5 nitrogen atoms, for example, indoline, isoindoline, unsaturated condensed heterocyclic group containing 1 or 2 oxygen atoms and 1, 2, or 3 nitrogen atoms, unsaturated condensed heterocyclic group containing 1 or 2 sulfur atoms and 1, 2, or 3 nitrogen atoms, and saturated, partially unsaturated and unsaturated condensed heterocyclic group containing 1 or 2 oxygen or sulfur atoms.

In one embodiment "heterocycle" refers to a cyclic ring with one nitrogen and 3, 4, 5, 6, 7, or 8 carbon atoms.

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocyclic ring.

For example,

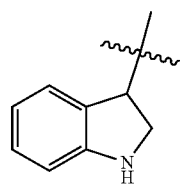 [SMILES: *C1CNc2ccccc21]

is a "heterocycle" group.

However,

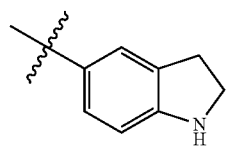 [SMILES: *c1ccc2c(c1)CCN2]

is an "aryl" group.

Non-limiting examples of "heterocycle" also include:

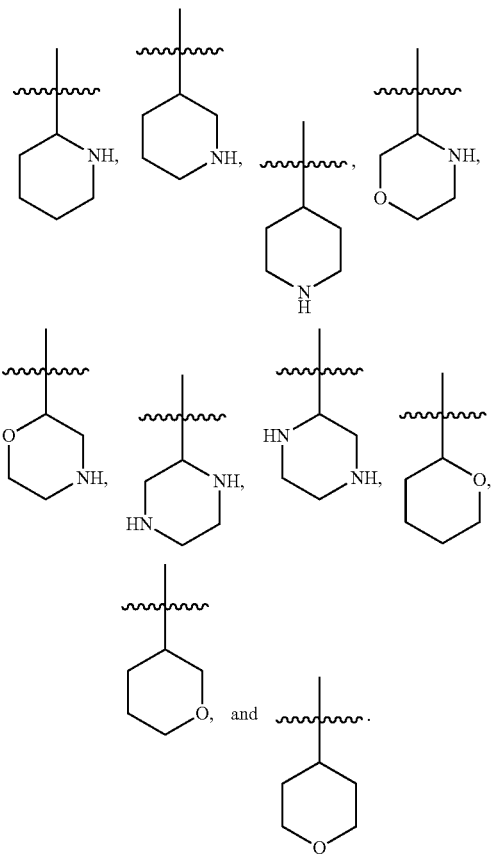

Additional non-limiting examples of "heterocycle" include:
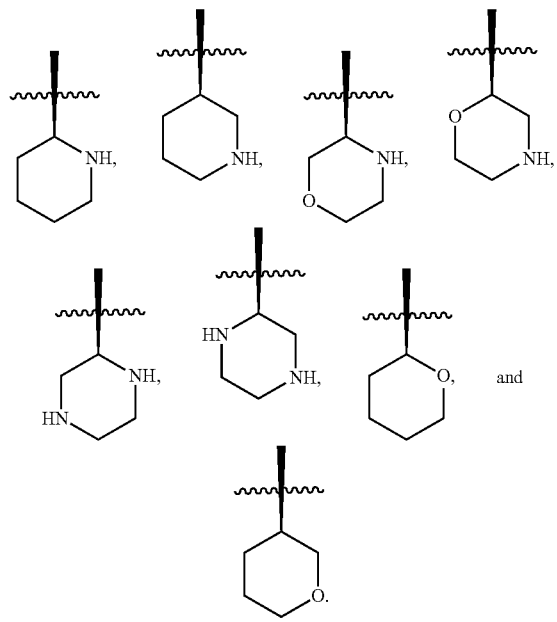
Additional non-limiting examples of "heterocycle" include:
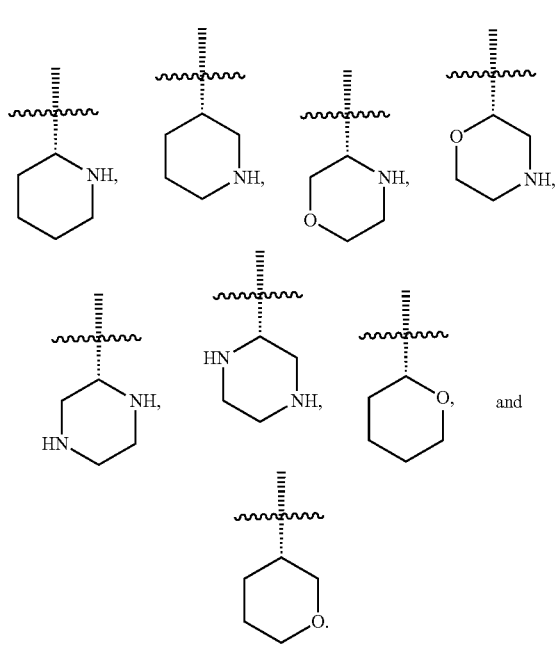
Non-limiting examples of "heterocycle" also include:
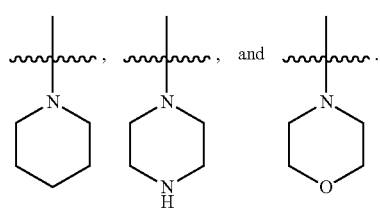
Non-limiting examples of "heterocycle" also include:
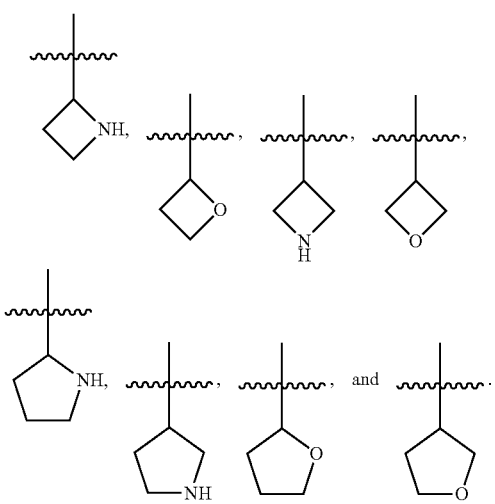
Additional non-limiting examples of "heterocycle" include:
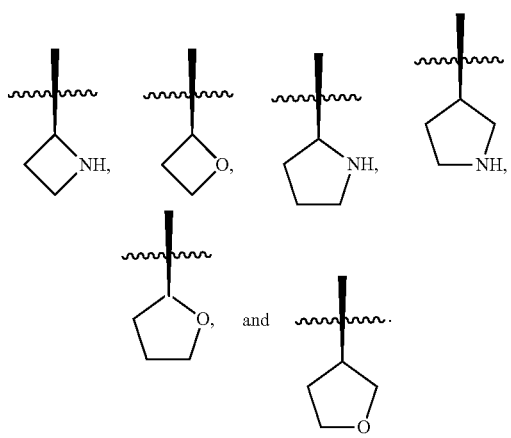
Additional non-limiting examples of "heterocycle" include:
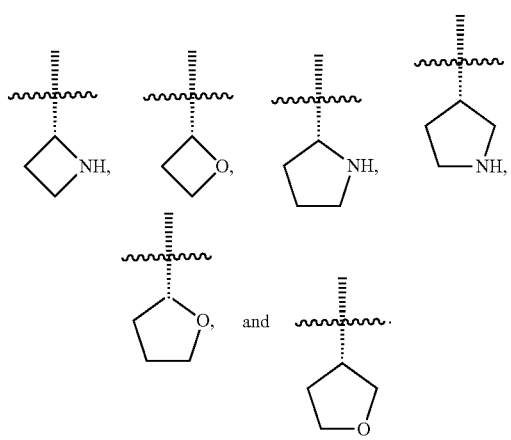

In an alternative embodiment "heterocycle" is "optionally substituted" with 1, 2, 3, or 4 substituents.

The term "heteroaryl" denotes a monocyclic or polycyclic (e.g., bicyclic or tricyclic) 4n+2 aromatic ring system (e.g., having 6, 10, or 14 π electrons shared in a cyclic array) and 1, 2, 3, 4, 5, or 6, heteroatoms independently selected from O, N, and S, wherein the ring nitrogen and sulfur atom(s) are optionally oxidized, and nitrogen atom(s) are optionally quarternized. Examples include but are not limited to, unsaturated 5 to 6 membered heteromonocyclyl groups containing 1, 2, 3, or 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- or 6-membered heteromonocyclic groups containing an oxygen atom, for example, pyranyl, 2-furyl, 3-furyl, etc.; unsaturated 5- or 6-membered heteromonocyclic groups containing a sulfur atom, for example, 2-thienyl, 3-thienyl, etc.; unsaturated 5- or 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 or 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]. Additional examples include 8-, 9-, or 10-membered heteroaryl bicyclic groups such as indazolyl, indolyl, imidazo[1,5-a]pyridinyl, benzimidazolyl, 4(3H)-quinazolinonyl, quinolinyl, isoquinolinyl, isoindolyl, thienothienyl, indolizinyl, benzofuranyl, isobenzofuranyl, benzothienyl, isobenzothienyl, benzoxazolyl, benzothiazolyl, purinyl, coumarinyl, cinnolinyl, and triazolopyridinyl.

In one embodiment "heteroaryl" is a 5 membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

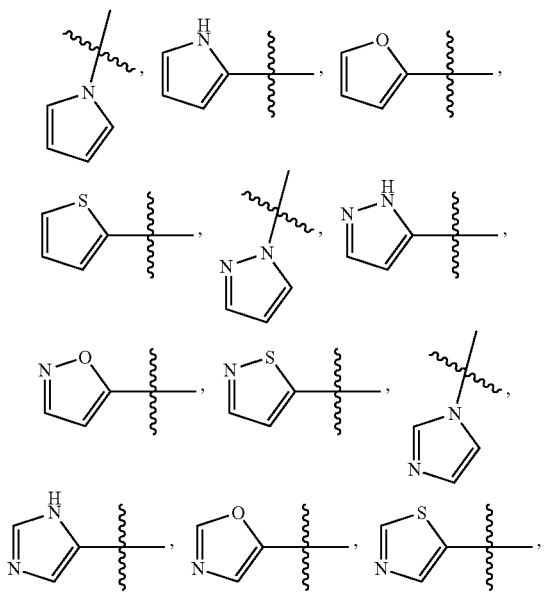

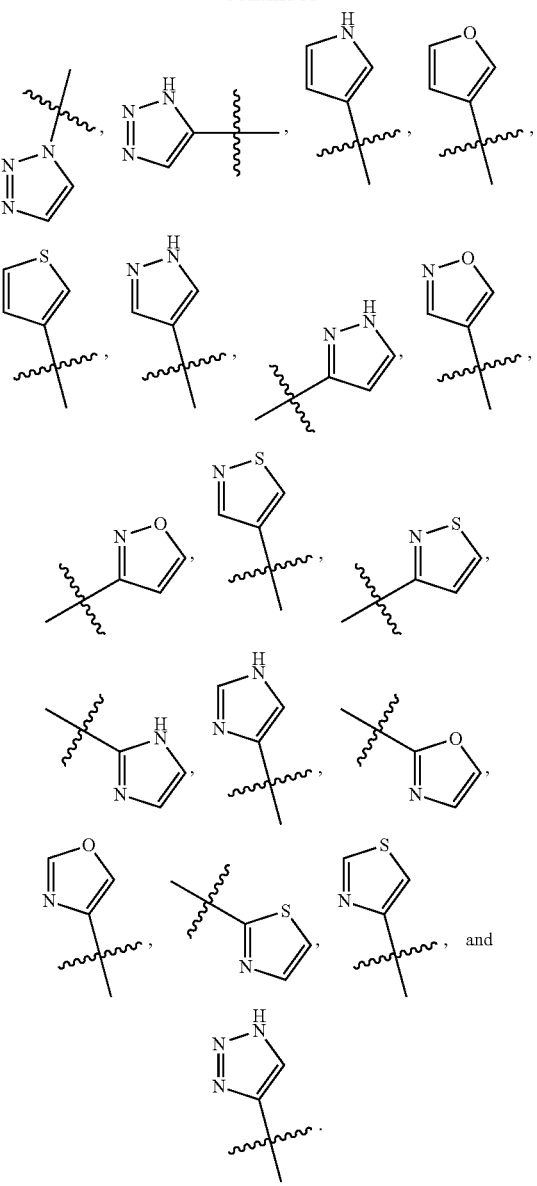

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

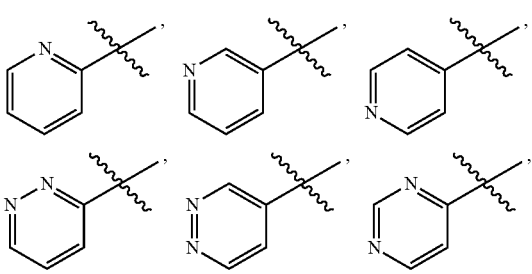

-continued

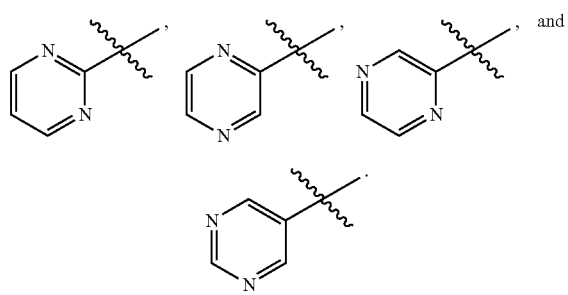

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

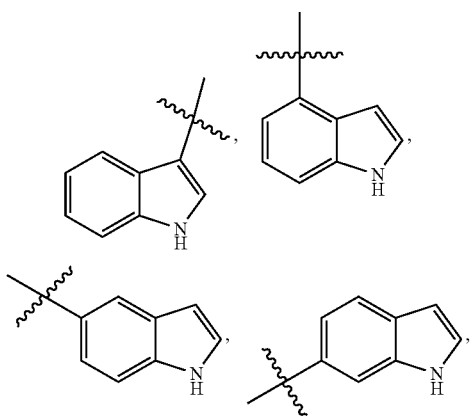

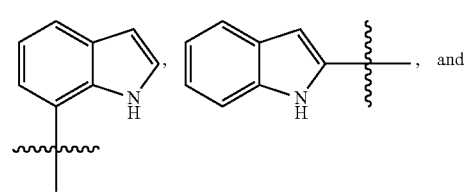

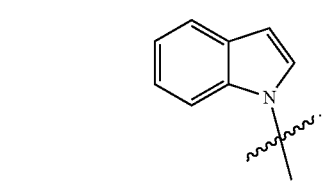

Additional non-limiting examples of "heteroaryl" groups that are bicyclic include:

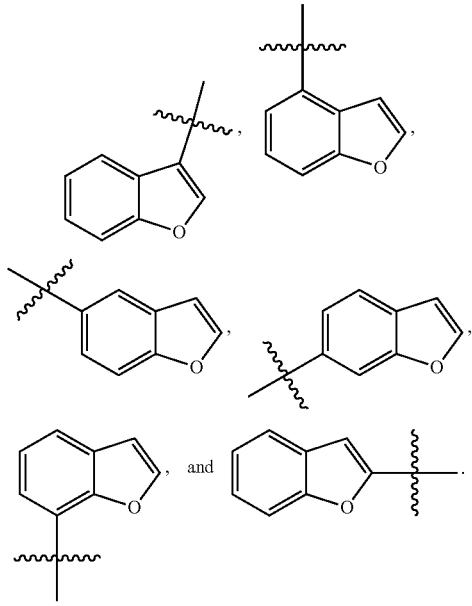

Additional non-limiting examples of "heteroaryl" groups that are bicyclic include:

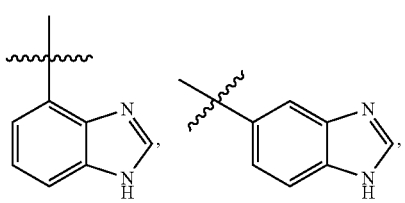

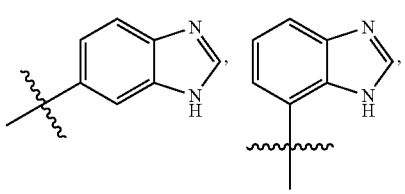

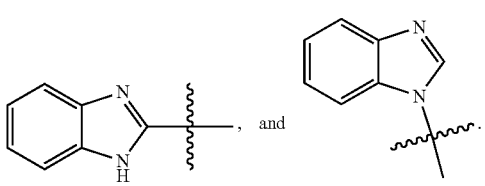

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

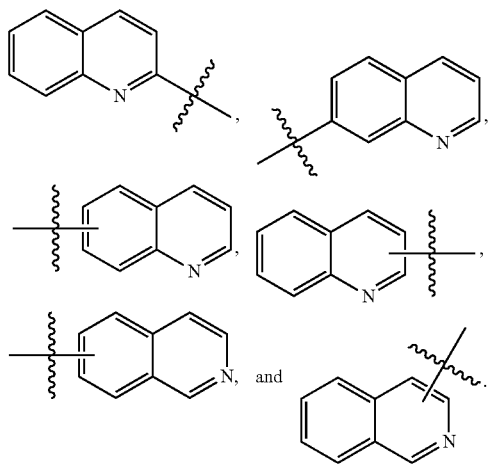

In an alternative embodiment "heteroaryl" is "optionally substituted" with 1, 2, 3, or 4 substituents.

The term "optionally substituted" denotes the substitution of a group herein by a moiety including, but not limited to, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, $C_1$-$C_{12}$ heterocycloalkyl, $C_3$-$C_{12}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{10}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, azido, acyl, thioacyl, acyloxy, carboxyl, and carboxylic ester.

In one alternative embodiment any suitable group may be present on a "substituted" or "optionally substituted" position if indicated that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, —CONH$_2$, alkyl including $C_1$-$C_6$alkyl, alkenyl including $C_2$-$C_6$alkenyl, alkynyl including $C_2$-$C_6$alkynyl, —$C_1$-$C_6$alkoxy, alkanoyl including $C_2$-$C_6$alkanoyl, $C_1$-$C_6$alkylester, (mono- and di-$C_1$-$C_6$alkylamino)$C_0$-$C_2$alkyl, haloalkyl including $C_1$-$C_6$haloalkyl, hydroxy$C_1$-$C_6$alkyl, ester, carbamate, urea, sulfonamide, —$C_1$-$C_6$alkyl(heterocyclo), $C_1$-$C_6$alkyl(heteroaryl), —$C_1$-$C_6$alkyl($C_3$-$C_7$cycloalkyl), O—$C_1$-$C_6$alkyl($C_3$-$C_7$cycloalkyl), B(OH)$_2$, phosphate, phosphonate and haloalkoxy including $C_1$-$C_6$haloalkoxy. In some embodiments, the suitable group present on a "substituted" or "optionally substituted" is divalent including, but not limited to, oxo (=O), =S, =CH$_2$, etc. The suitable group on a "substituted" or "optional substituted" position may be monovalent, divalent, or trivalent such that it forms a stable molecule and meets the desired purpose of the invention.

In one embodiment a group described herein that can be substituted with 1, 2, 3, or 4 substituents is substituted with one substituent.

In one embodiment a group described herein that can be substituted with 1, 2, 3, or 4 substituents is substituted with two substituents.

In one embodiment a group described herein that can be substituted with 1, 2, 3, or 4 substituents is substituted with three substituents.

In one embodiment a group described herein that can be substituted with 1, 2, 3, or 4 substituents is substituted with four substituents.

"Aliphatic" refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, or polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$ or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

The term "heteroaliphatic" refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

An "effective amount" as used herein, means an amount which provides a therapeutic or prophylactic benefit.

As used herein "endogenous" refers to any material from or produced inside an organism, cell, tissue or system.

As used herein, the term "exogenous" refers to any material introduced from or produced outside an organism, cell, tissue or system.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Parenteral" administration of an pharmaceutical composition includes, e.g., subcutaneous (s.c.), intravenous (i.v.), intramuscular (i.m.), intrasternal injection, or infusion techniques.

As used herein, the terms "peptide," "polypeptide," and "protein" are used interchangeably, and refer to a compound comprised of amino acid residues covalently linked by peptide bonds. A protein or peptide must contain at least two amino acids, and the maximum number of amino acids present within the protein or peptide's sequence is typically comparable to up to that found in nature. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

To "treat" a disease as the term is used herein, means to reduce the frequency or severity of at least one sign or symptom of a disease or disorder experienced by a subject (i.e. palliative treatment) or to decrease a cause or effect of the disease or disorder (i.e. disease-modifying treatment).

Throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, "pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, for example that is modulated by a natural (wild-type) or modified (non-wild type) protein that can be degraded according to the present invention, resulting in a therapeutic effect. Typically, the host is a human. A "host" may alternatively refer to for example, a mammal, primate (e.g., human), cow, sheep, goat, horse, dog, cat, rabbit, rat, mice, fish, bird and the like.

A "therapeutically effective amount" of a pharmaceutical composition/combination of this invention means an amount effective, when administered to a host, to provide a therapeutic benefit such as an amelioration of symptoms or reduction or diminution of the disease itself.

II. Compounds of Formula I, Formula II, Formula III, and Formula IV

Non-limiting examples of compounds of Formula I include:

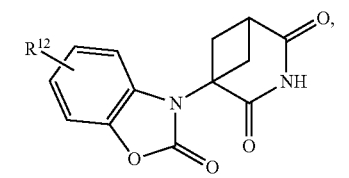
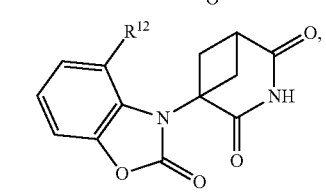
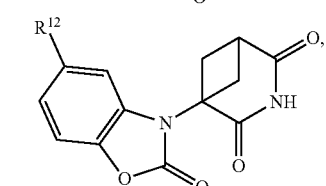
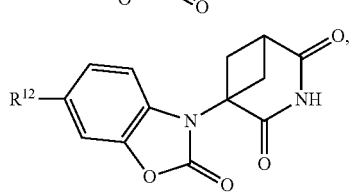
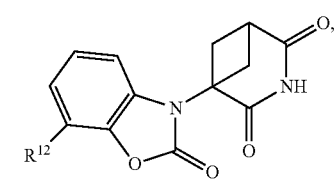
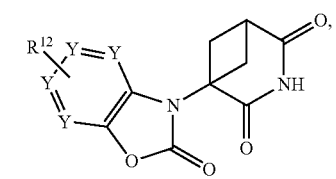
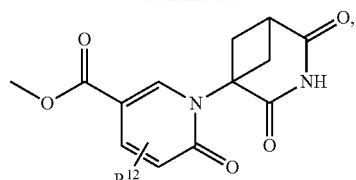
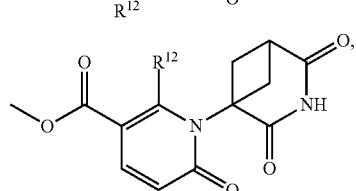
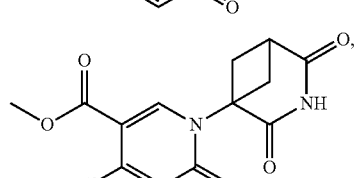
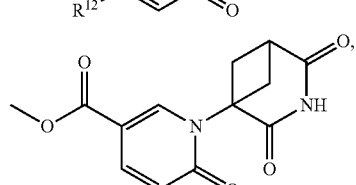
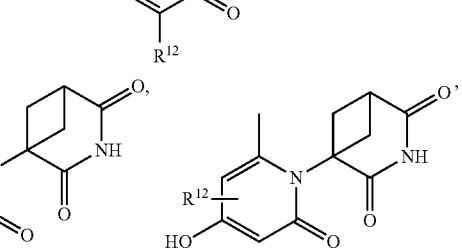
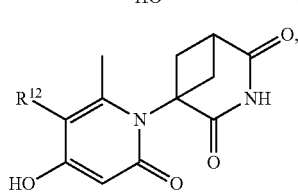
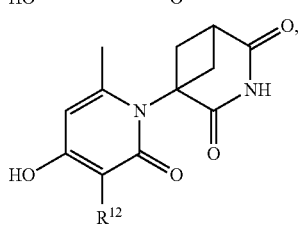
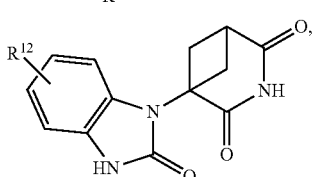
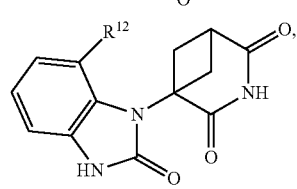

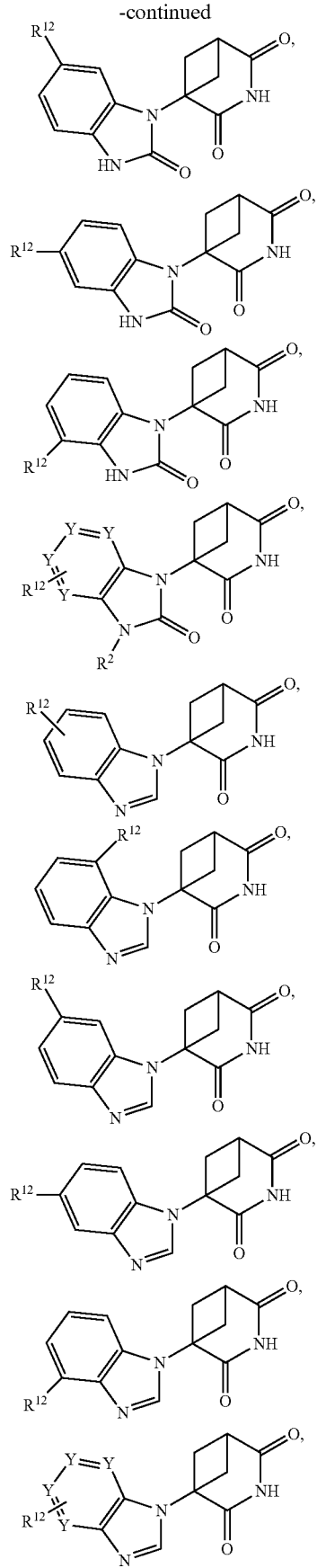
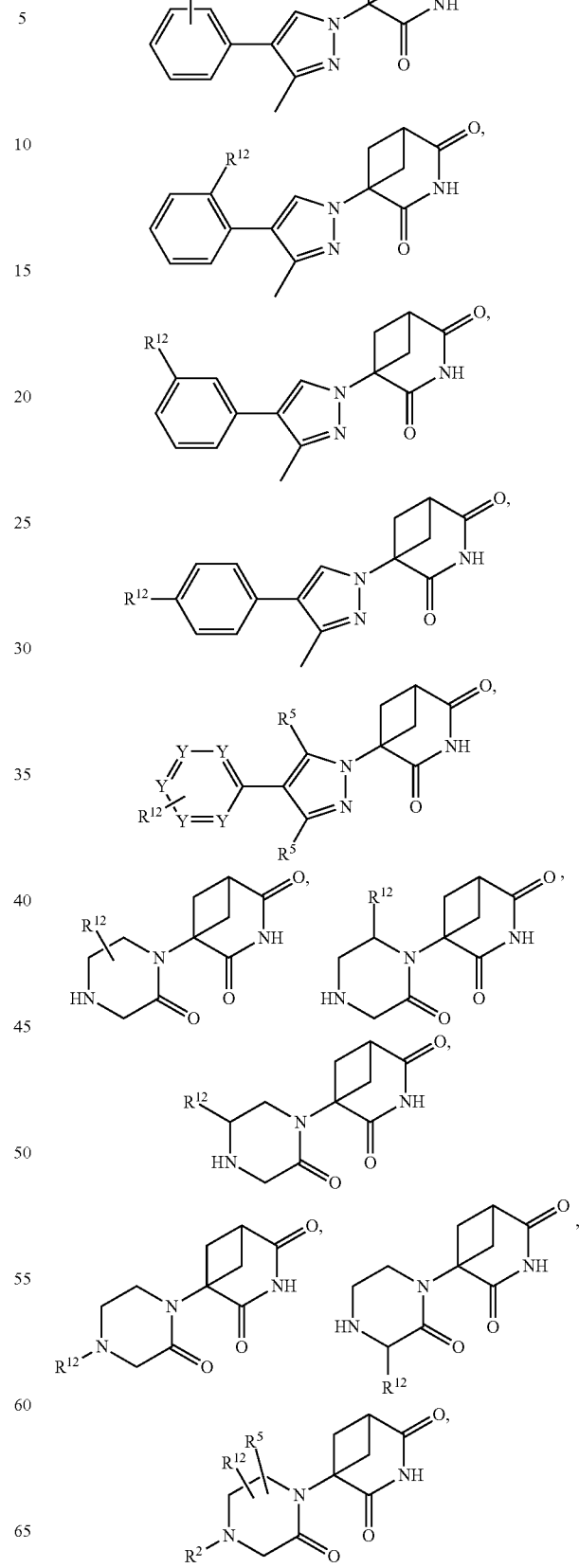

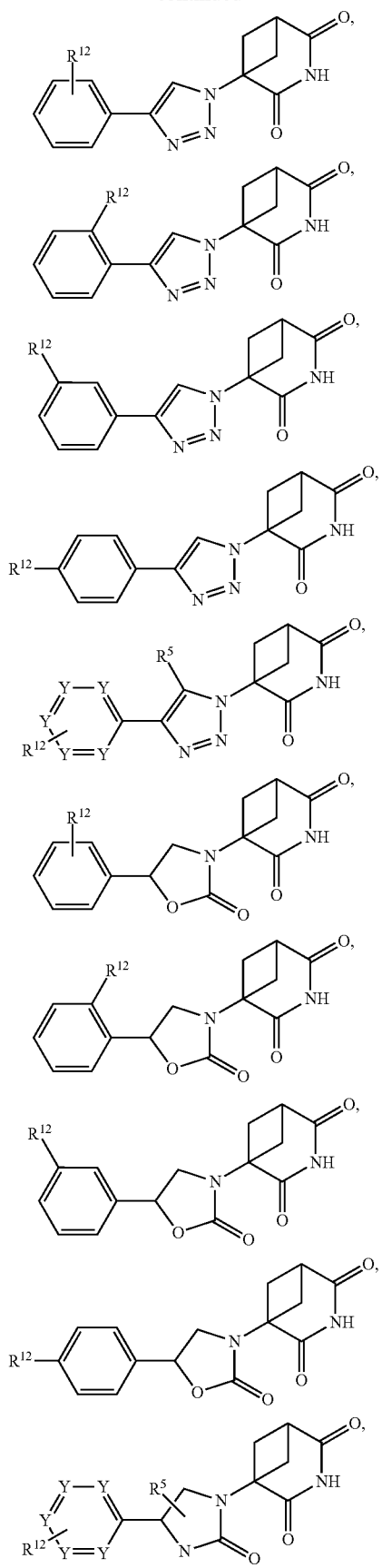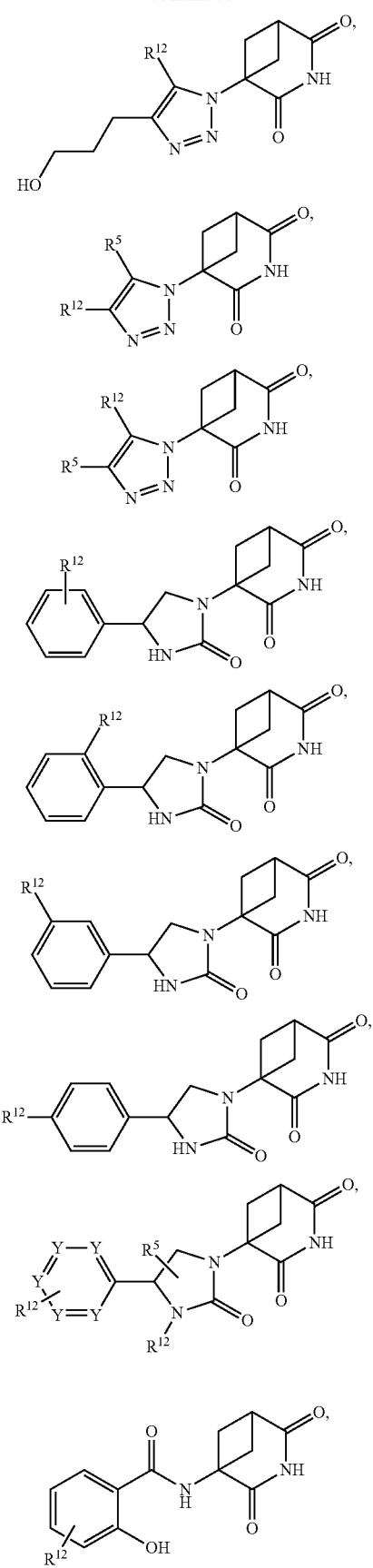

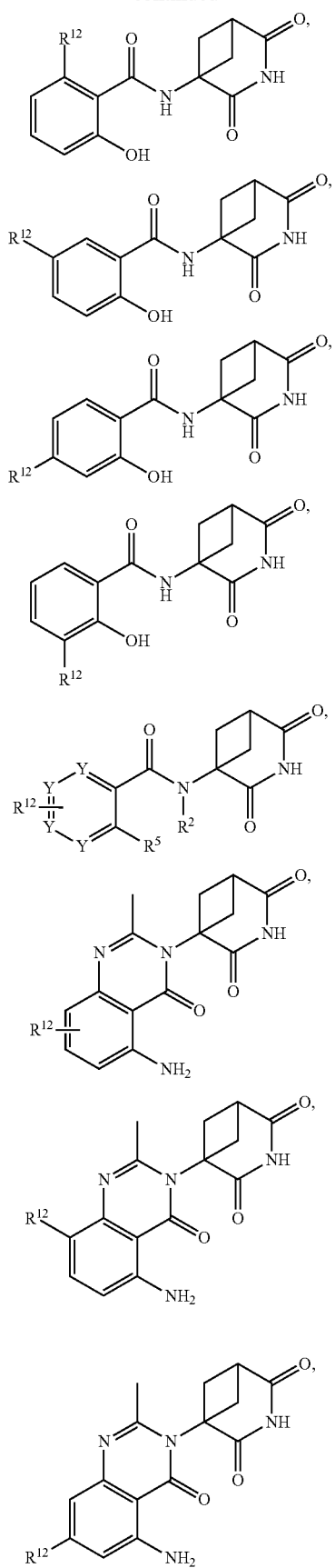
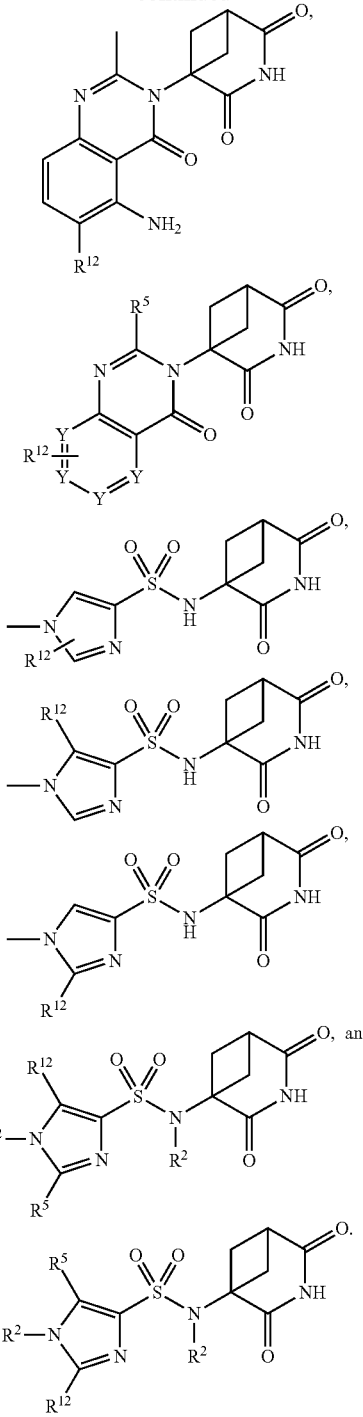
Non-limiting examples of compounds of Formula II include:
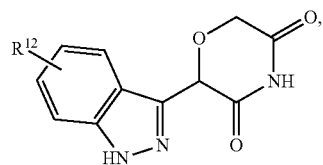

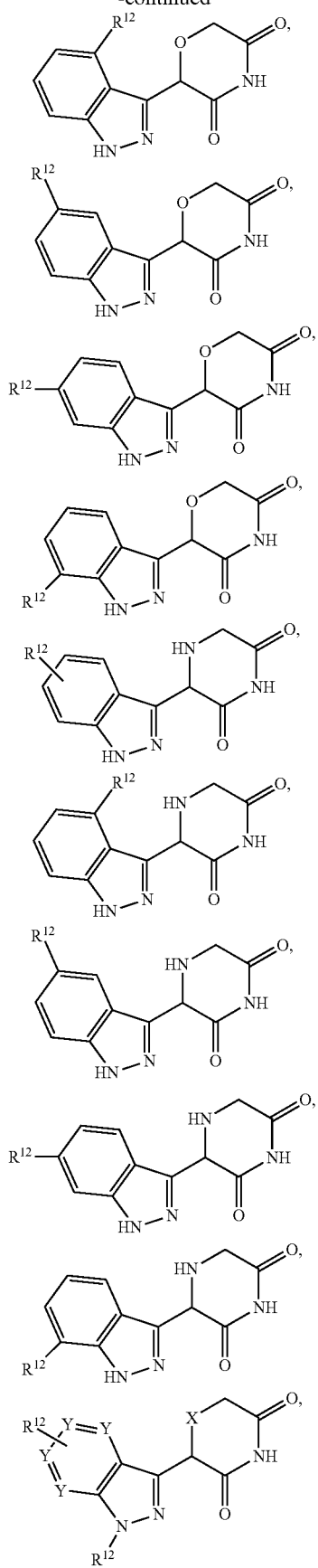
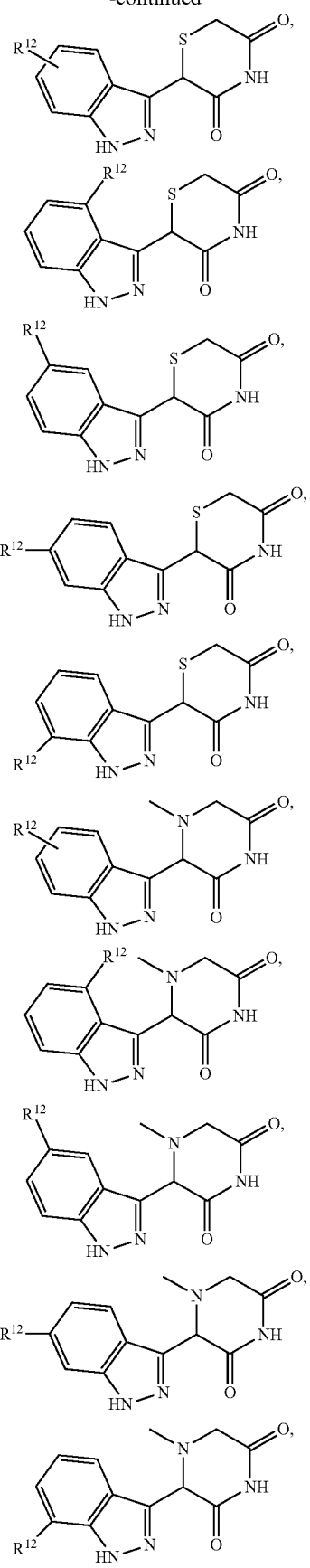

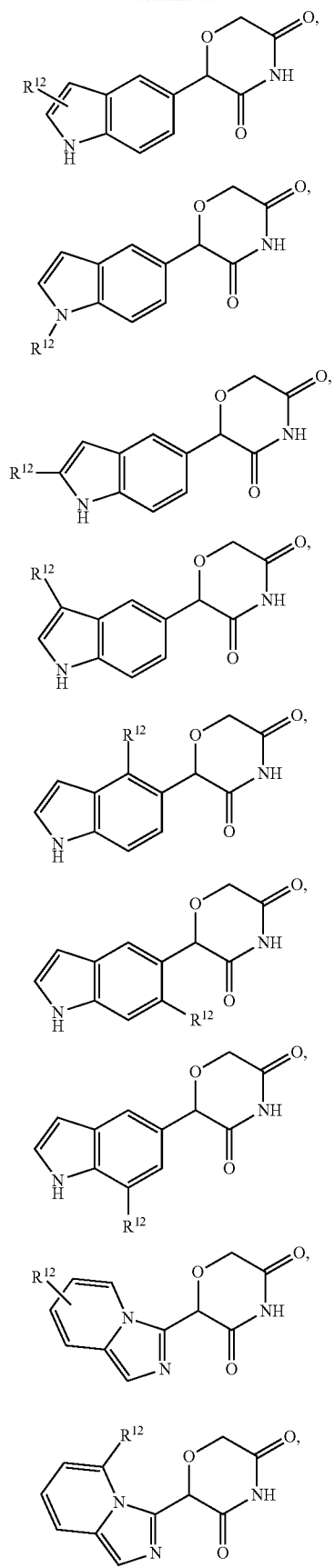
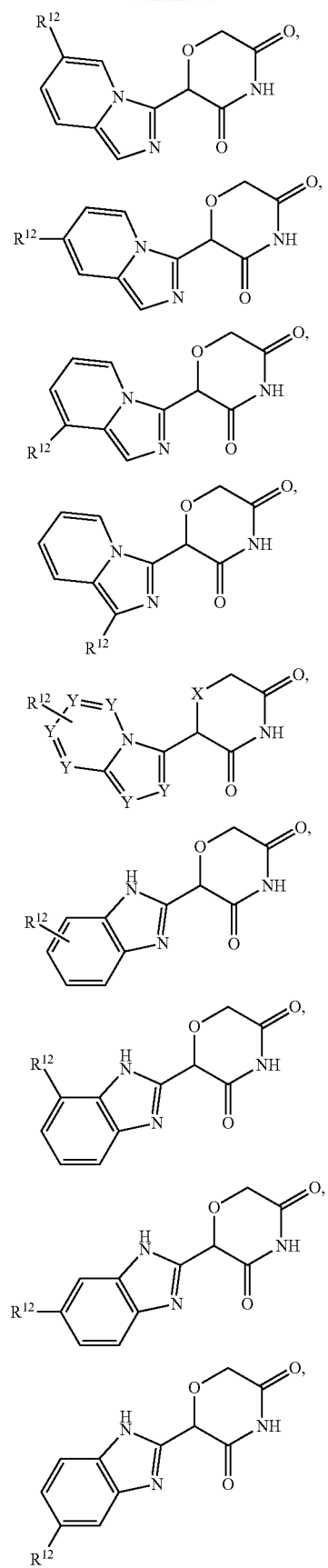

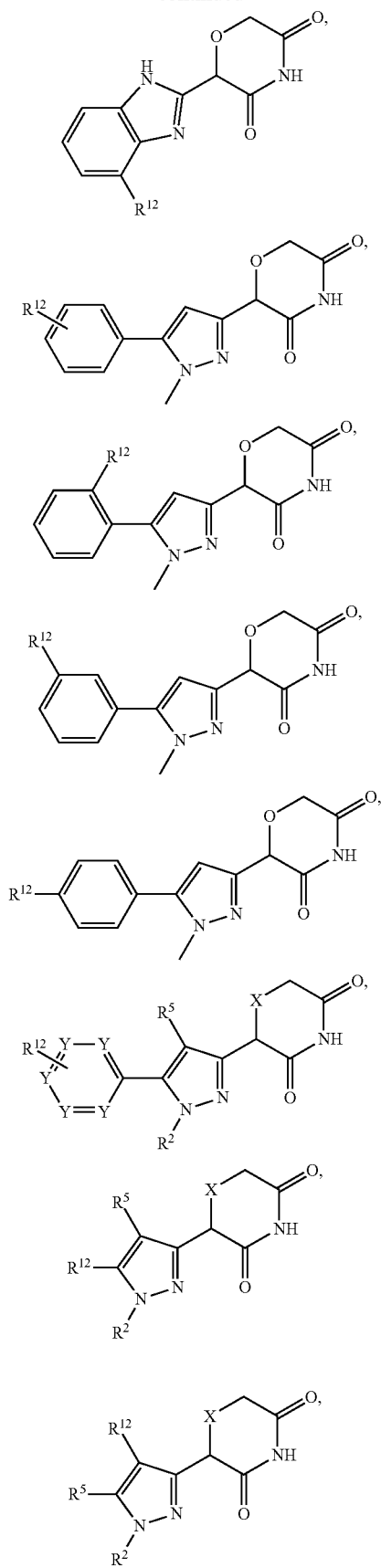
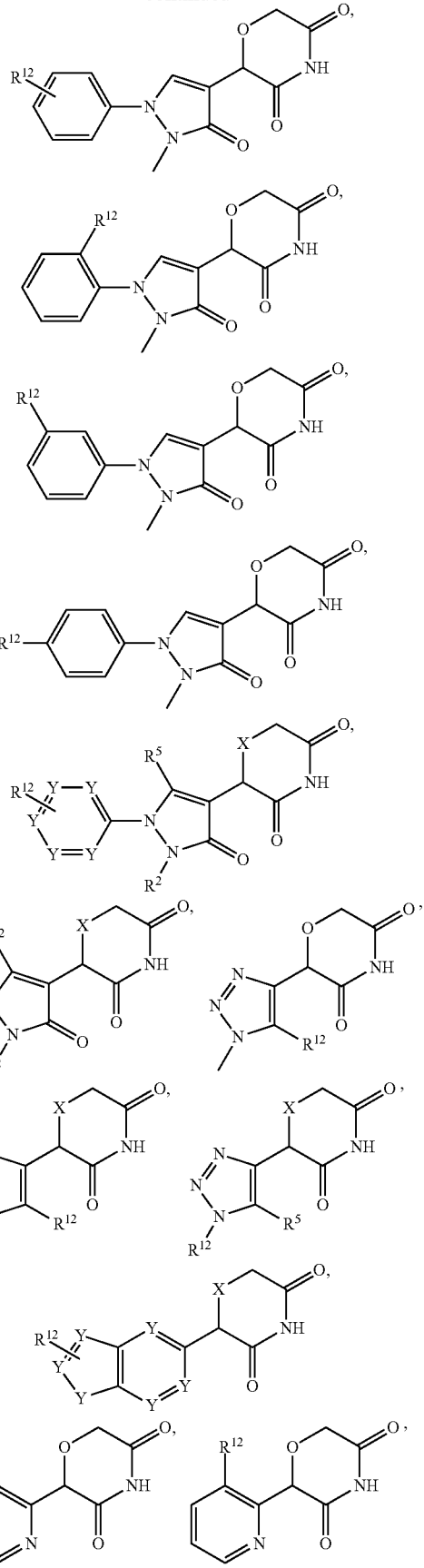

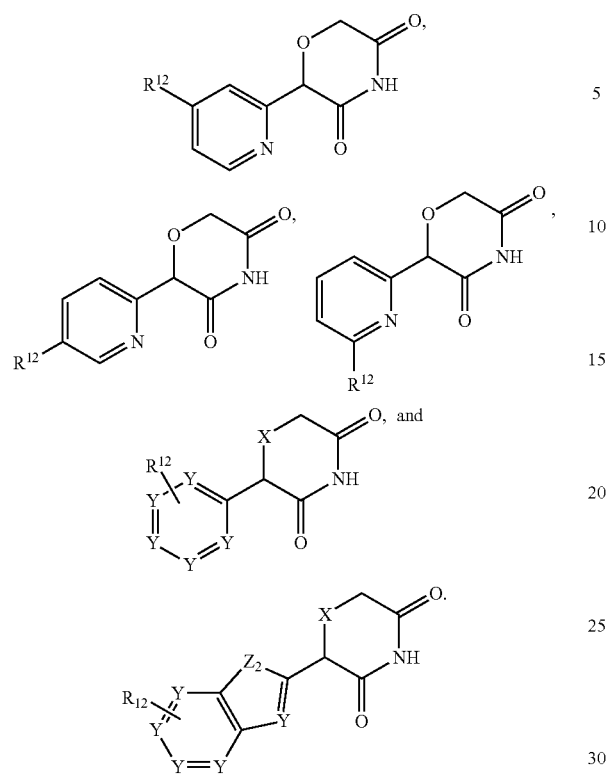
Additional non-limiting examples of compounds of Formula I include:
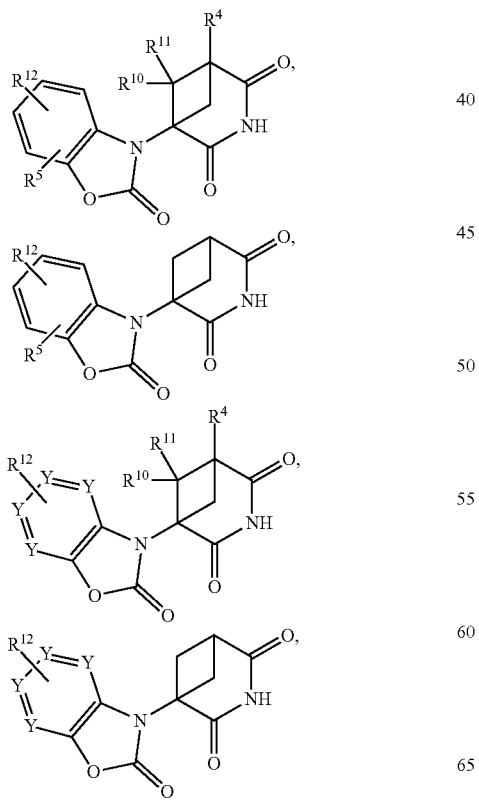
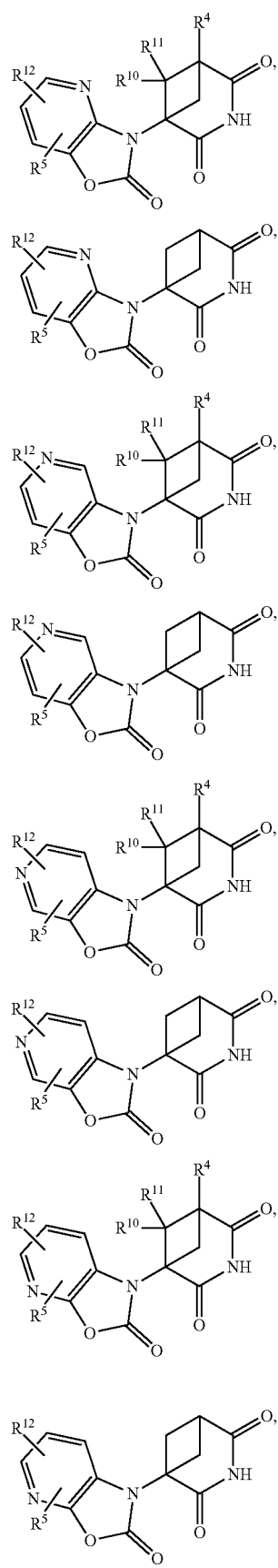

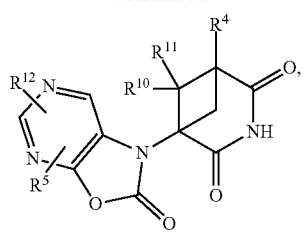
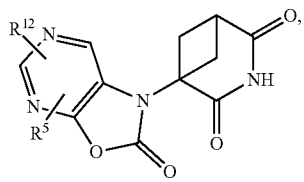
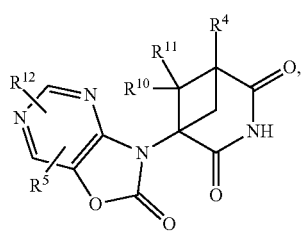
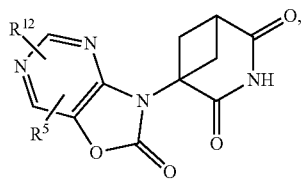
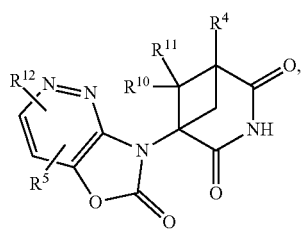
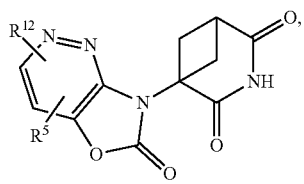
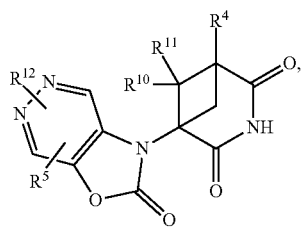
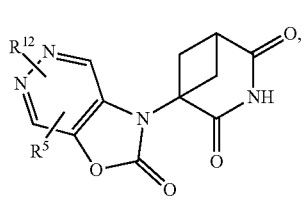
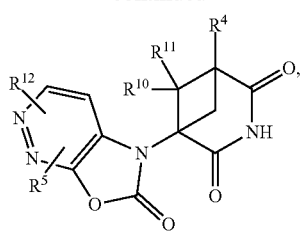
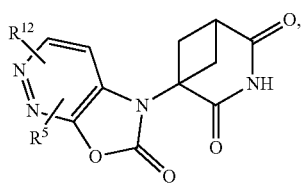
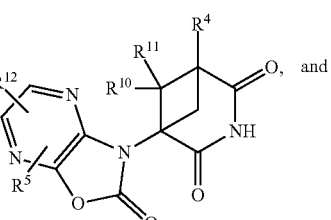
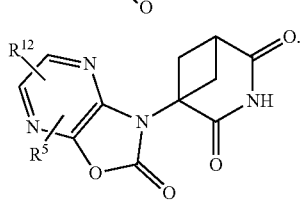
Additional non-limiting examples of compounds of Formula I include:
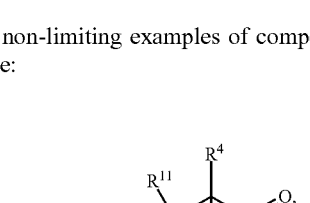
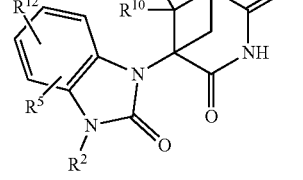
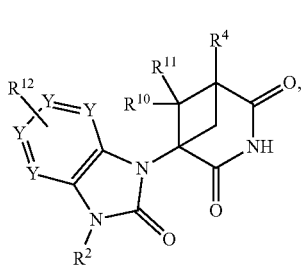

111
-continued
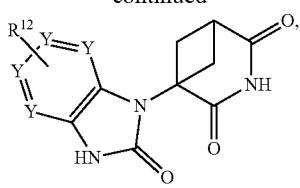
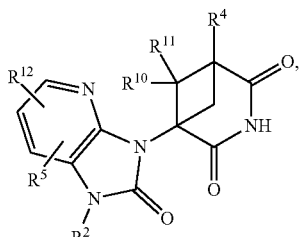
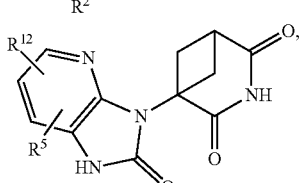
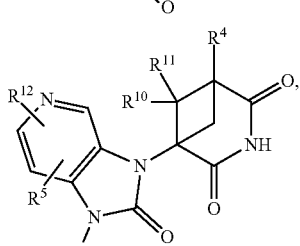
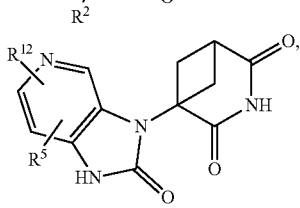
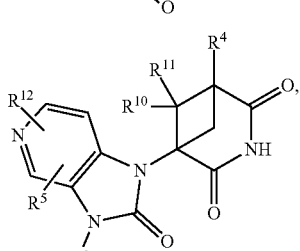
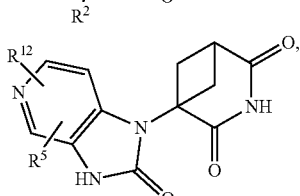
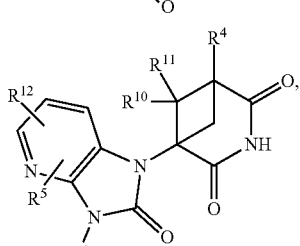
112
-continued
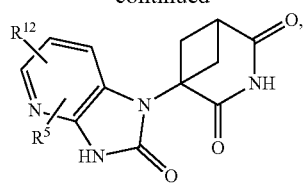
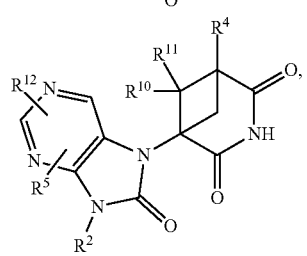
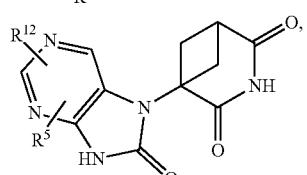
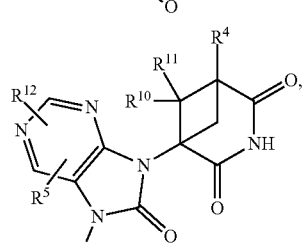
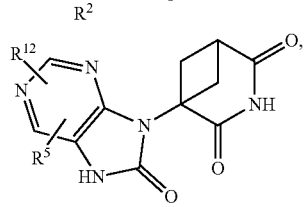
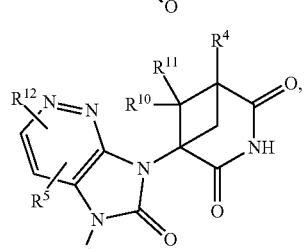
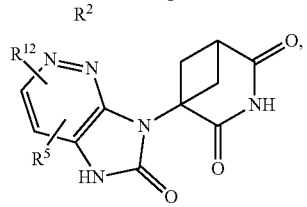
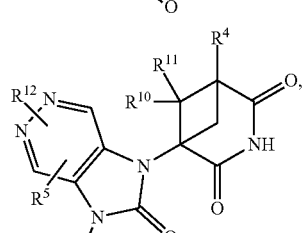

-continued
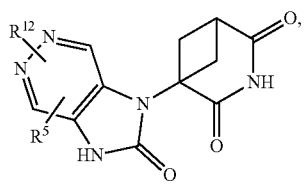
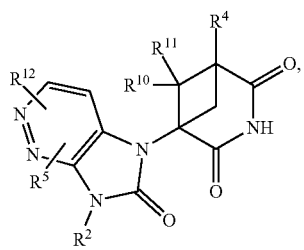
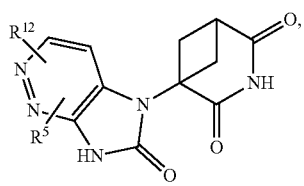
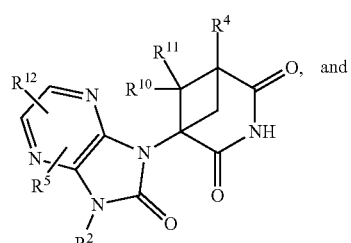
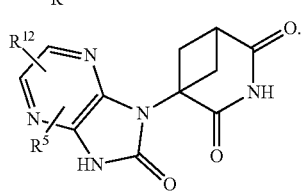
Additional non-limiting examples of compounds of Formula I include:
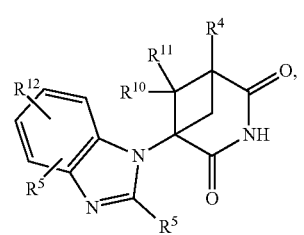
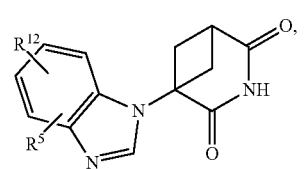
-continued
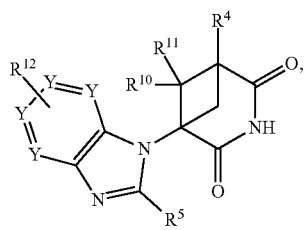
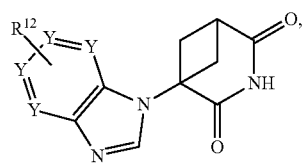
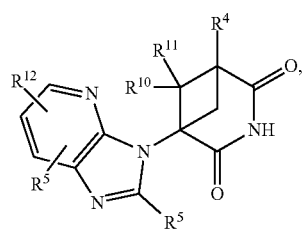
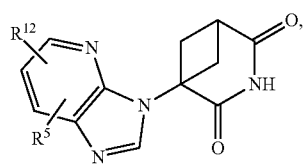
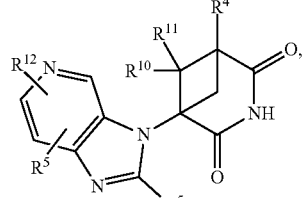
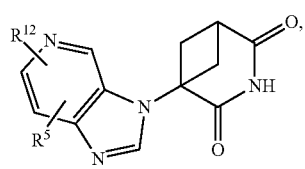
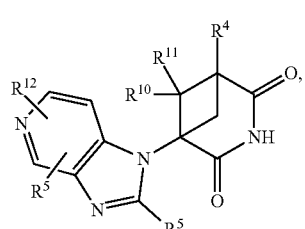
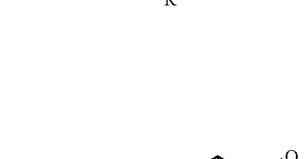
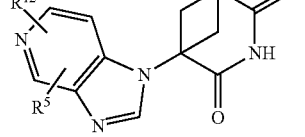

-continued
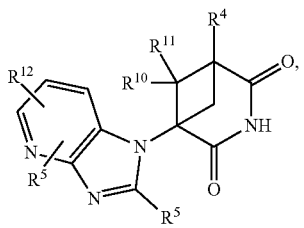
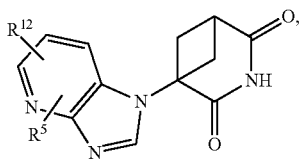
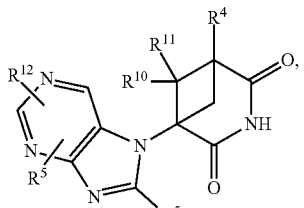
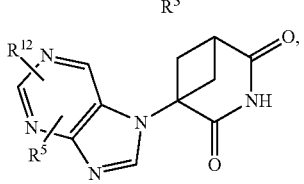
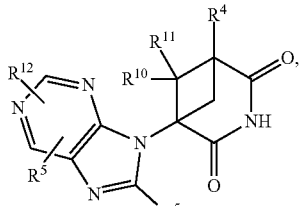
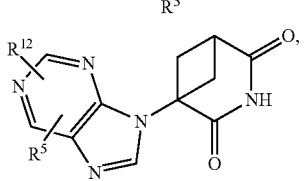
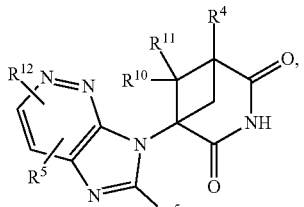
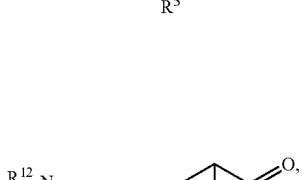
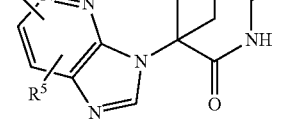
-continued
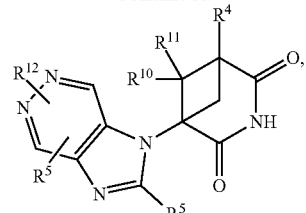
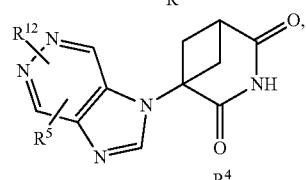
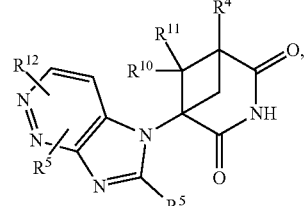
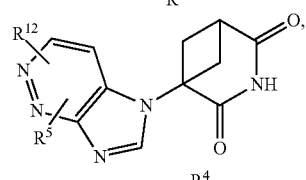
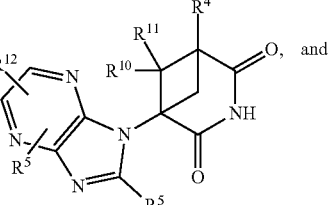, and
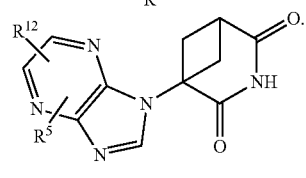.
Additional non-limiting examples of compounds of Formula I include:
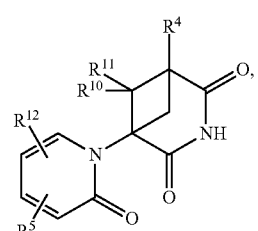
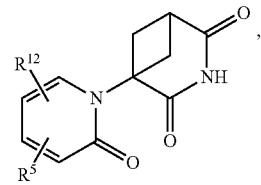
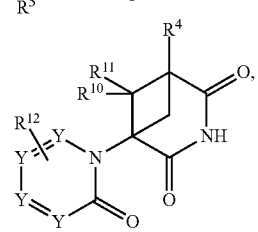
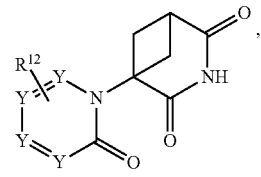

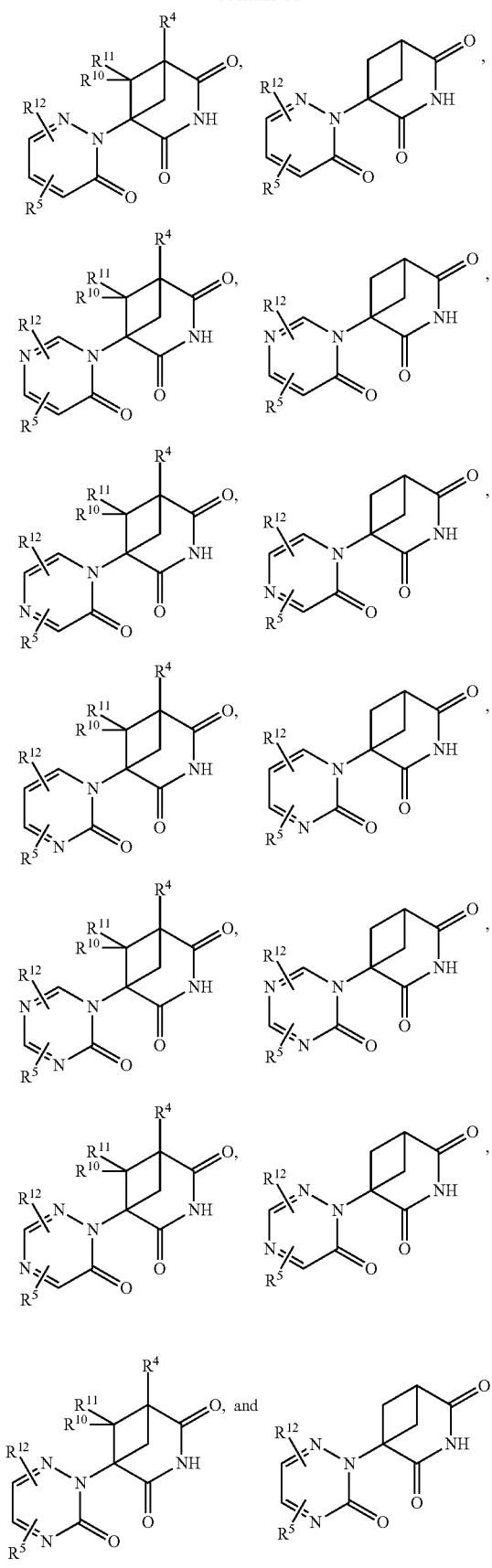
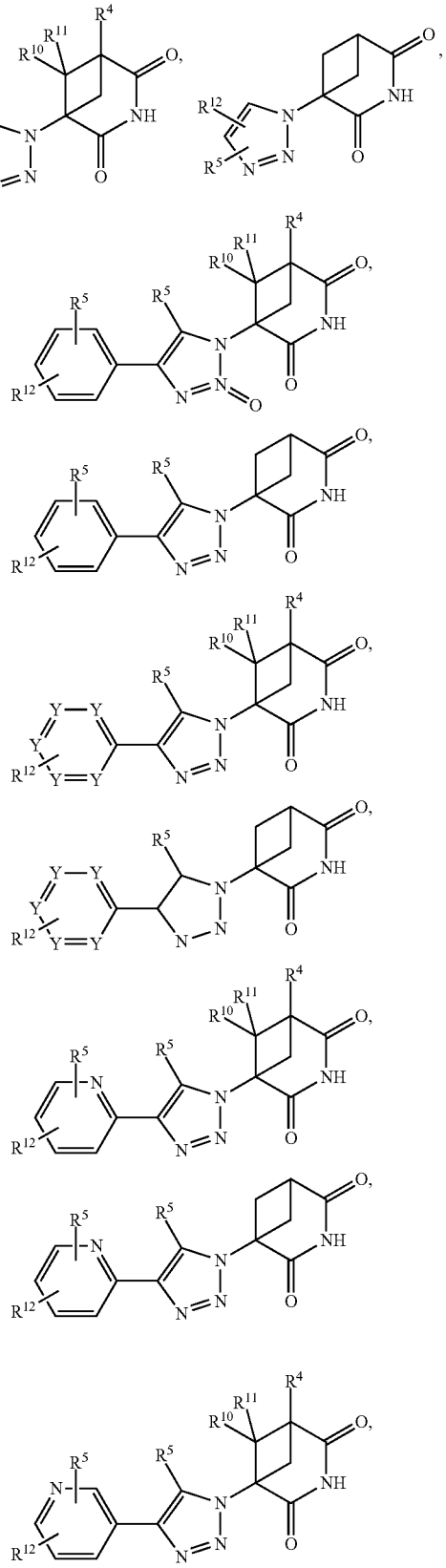
Additional non-limiting examples of compounds of Formula I include:

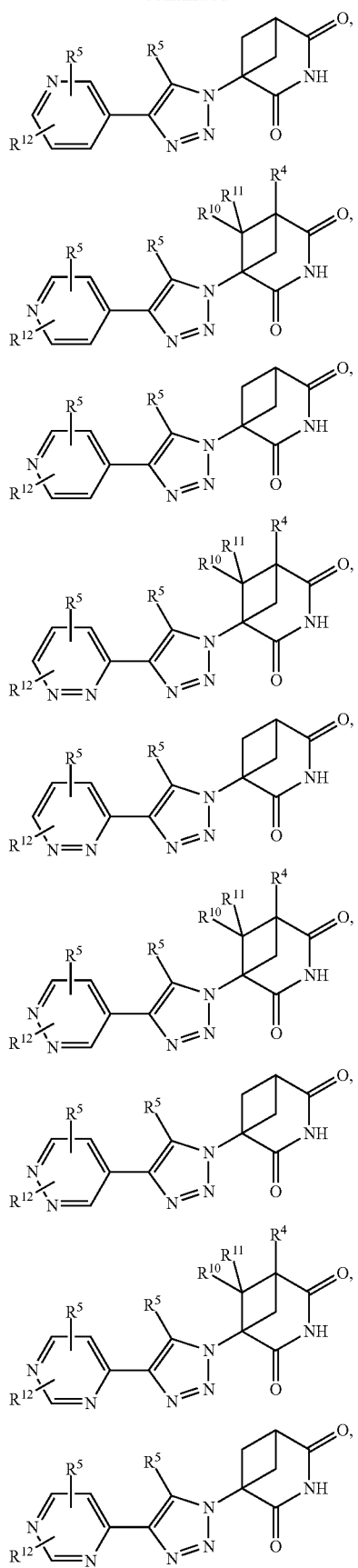
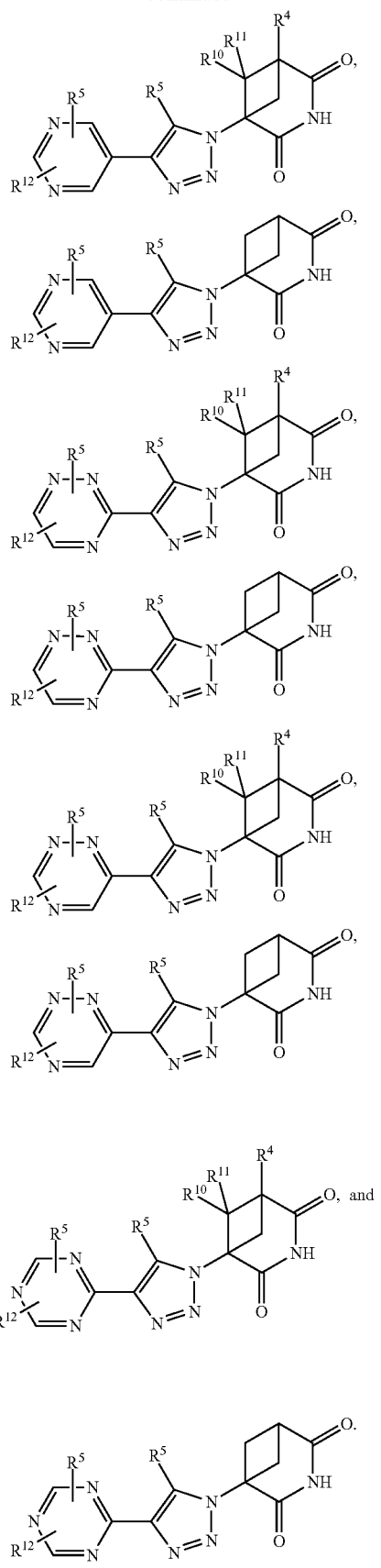

Additional non-limiting examples of compounds of Formula I include:
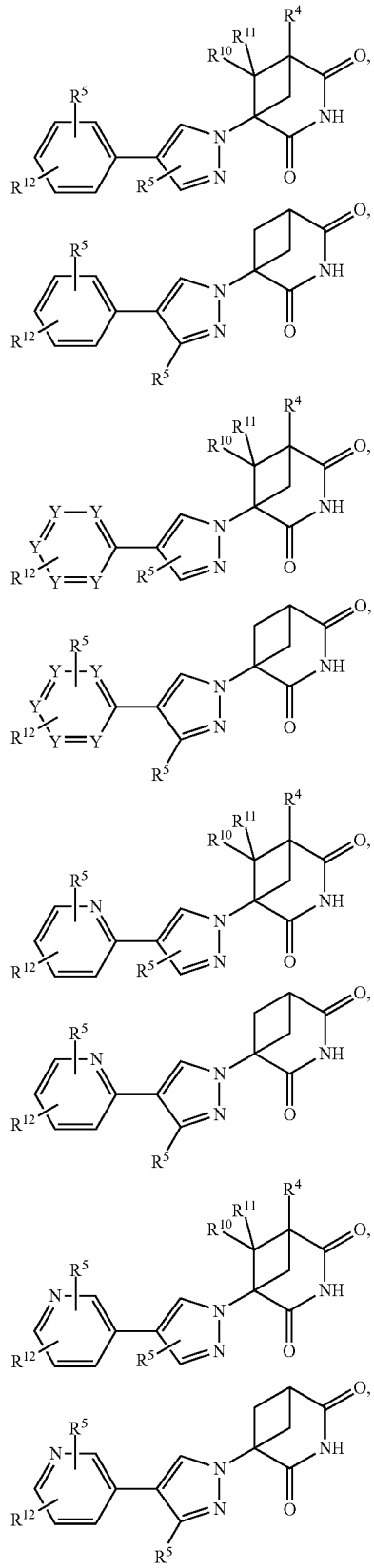
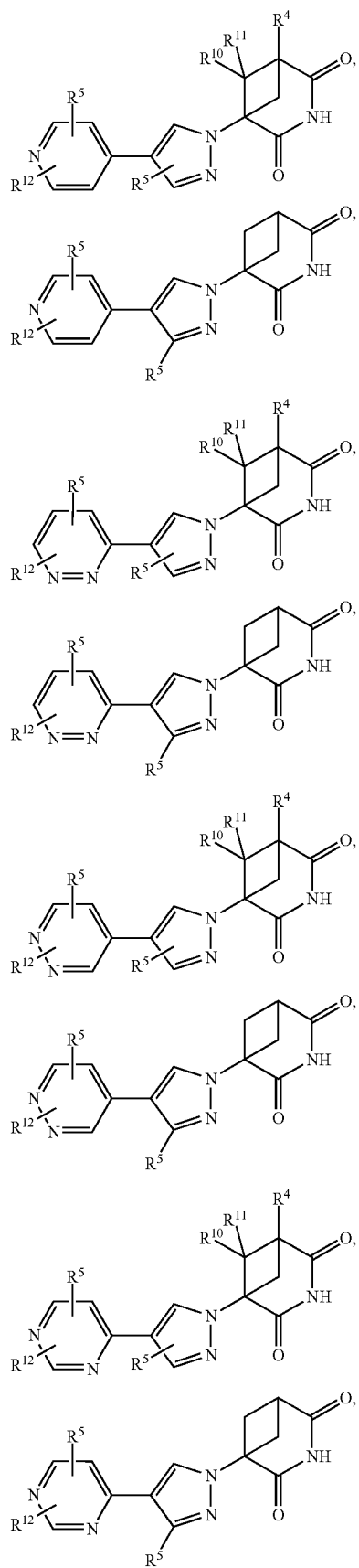

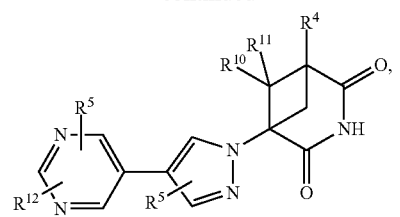
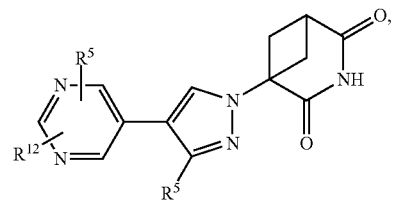
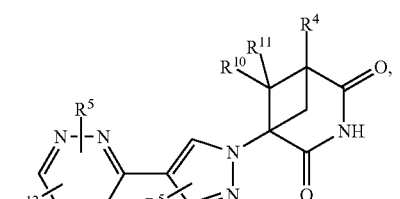
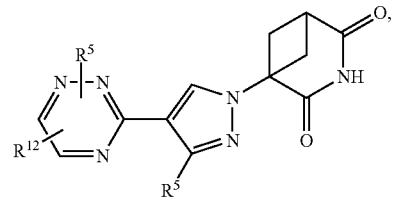
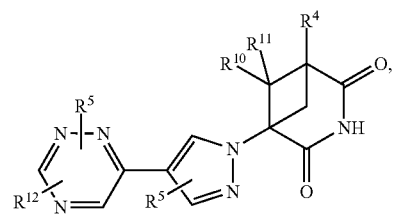
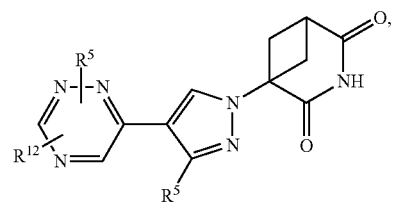
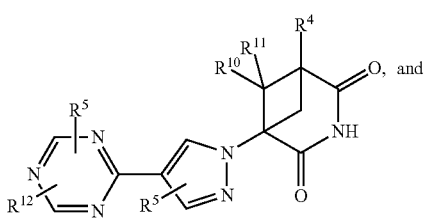
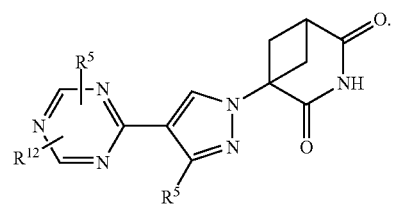
Additional non-limiting examples of compounds of Formula I include:
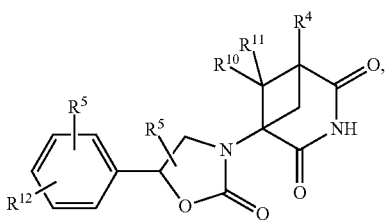
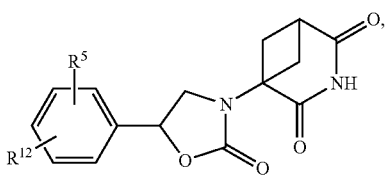
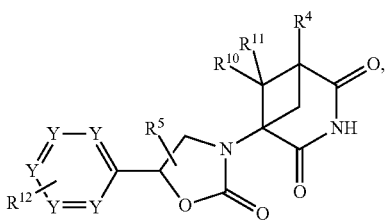
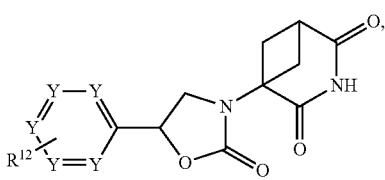
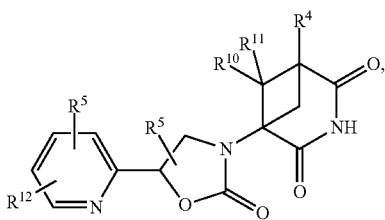
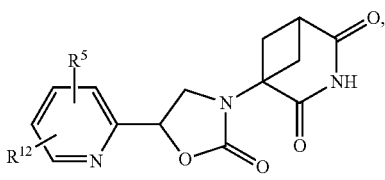
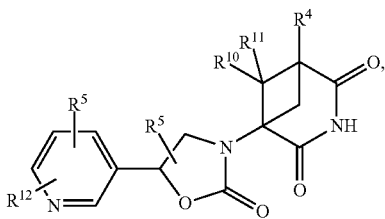
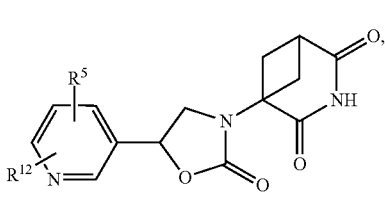

-continued
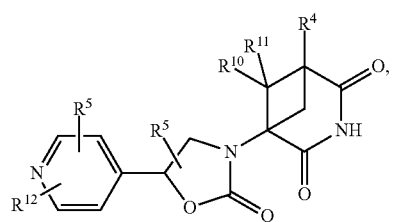
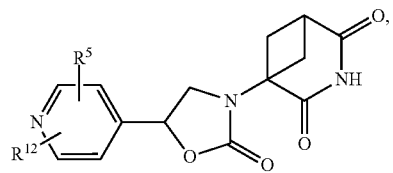
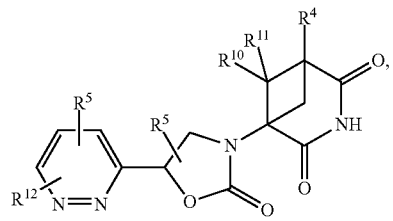
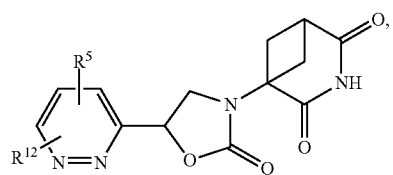
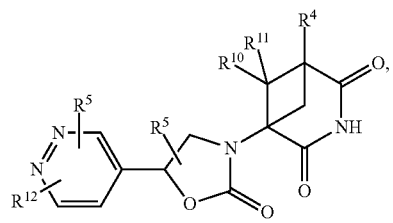
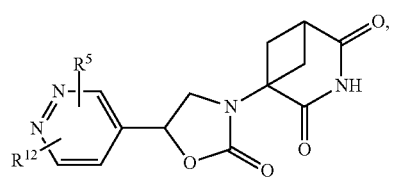
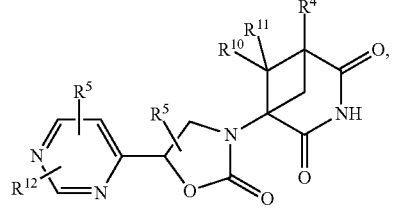
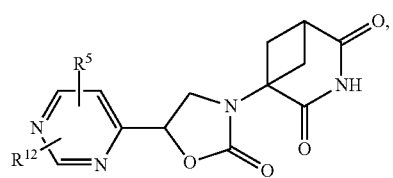
-continued
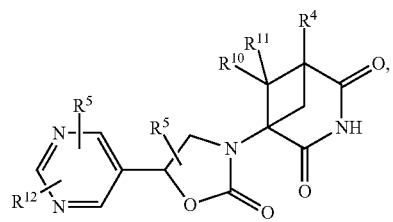
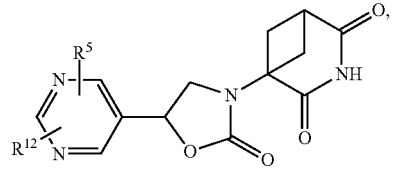
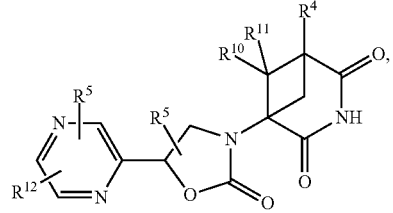
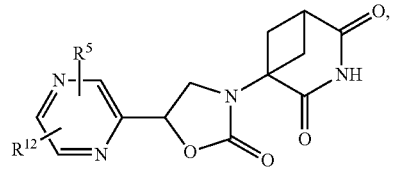
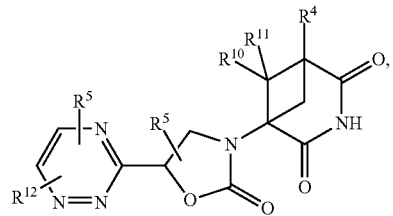
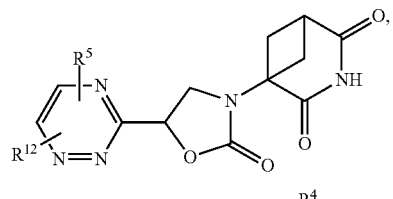
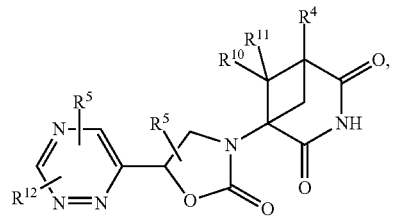
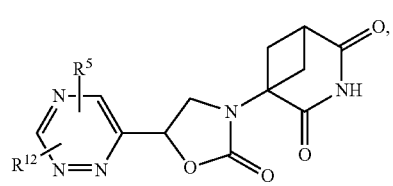

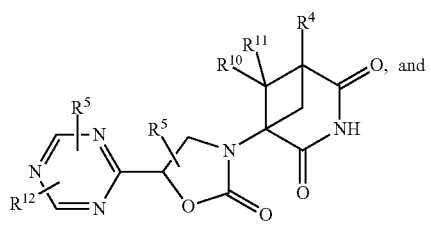
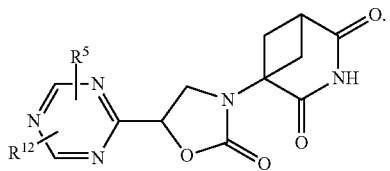
Additional non-limiting examples of compounds of Formula I include:
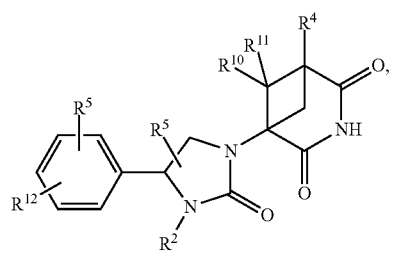
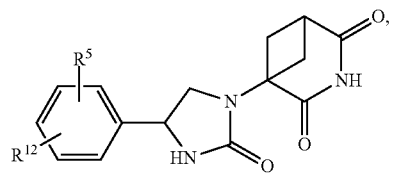
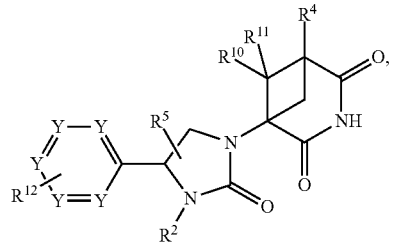
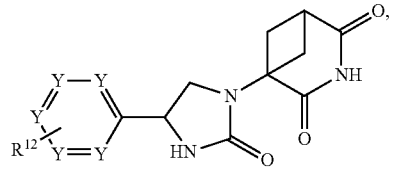
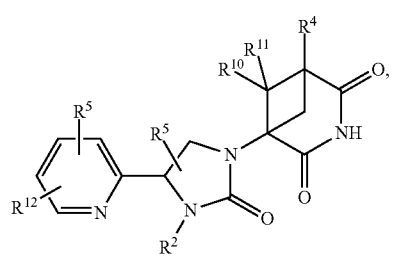
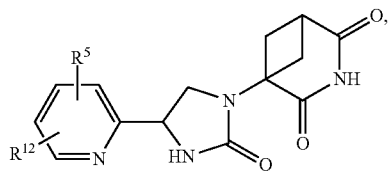
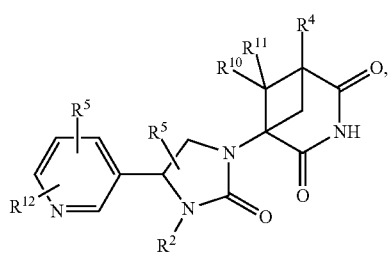
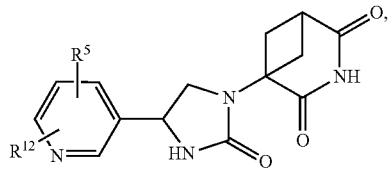
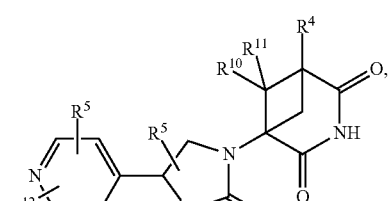
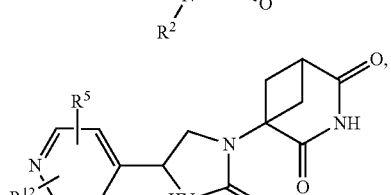
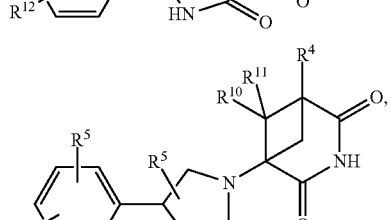
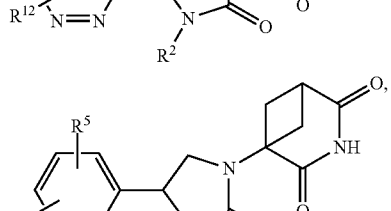
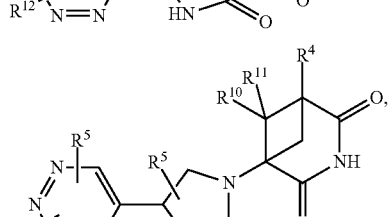

129
-continued
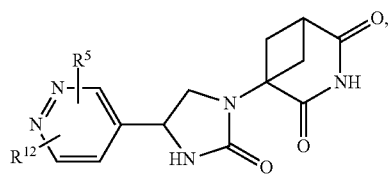
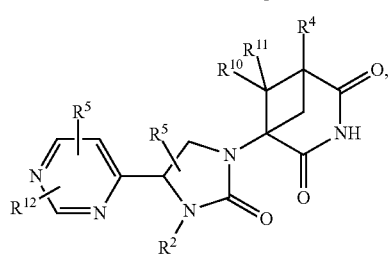
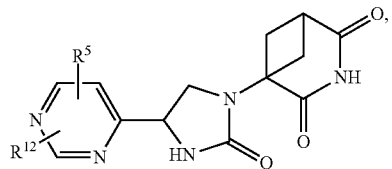
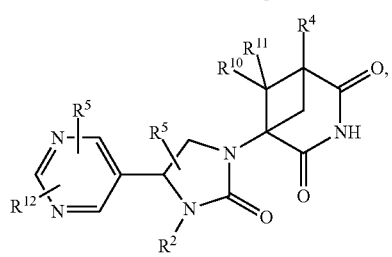
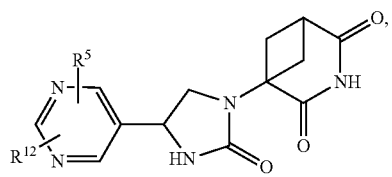
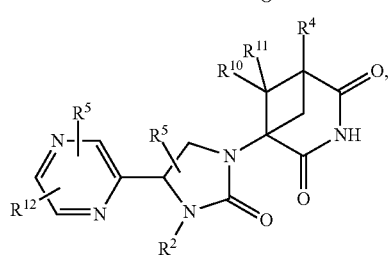
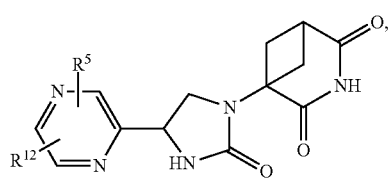
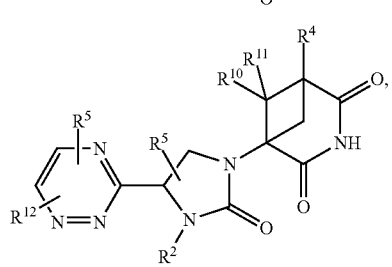
130
-continued
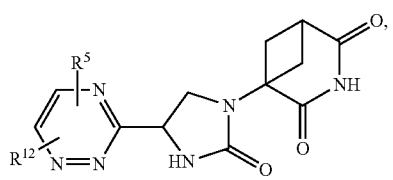
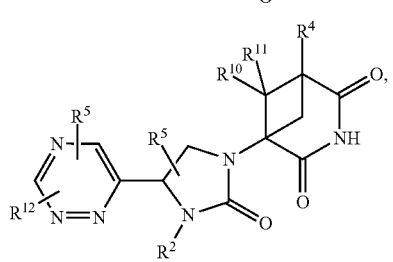
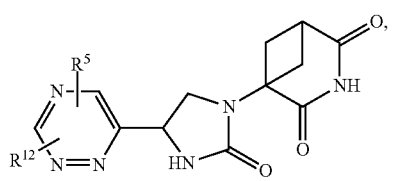
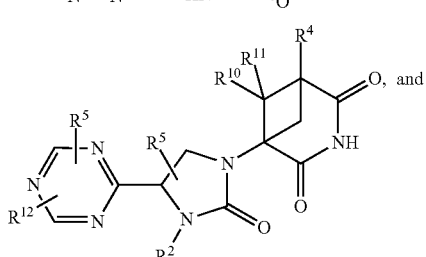
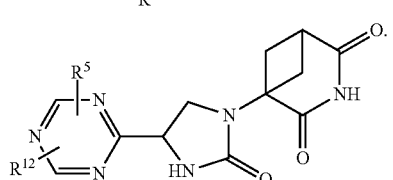
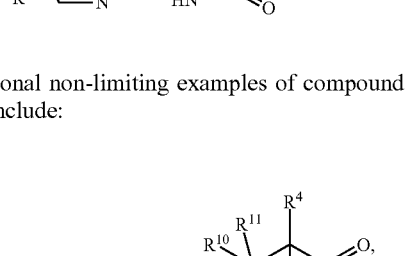
Additional non-limiting examples of compounds of Formula I include:
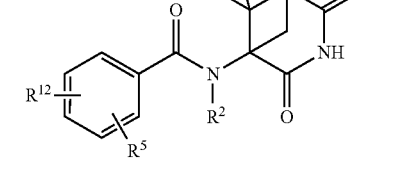
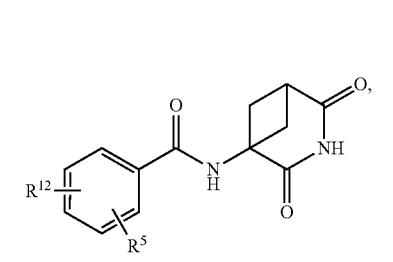

-continued
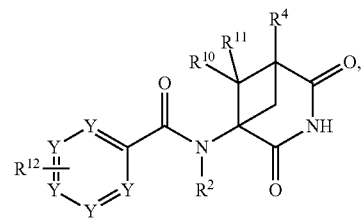
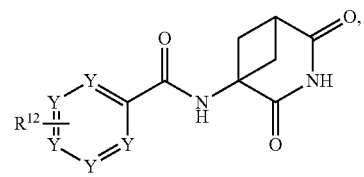
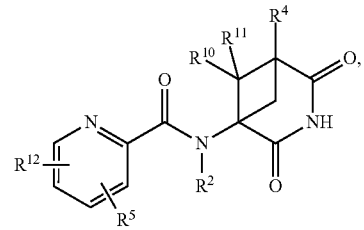
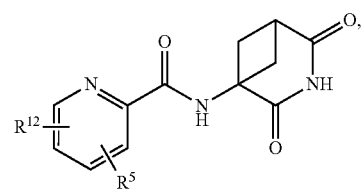
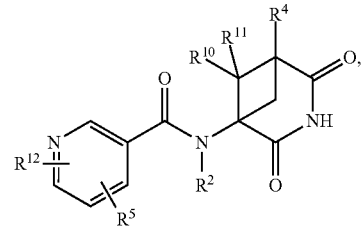
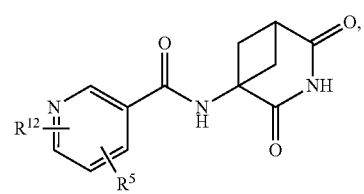
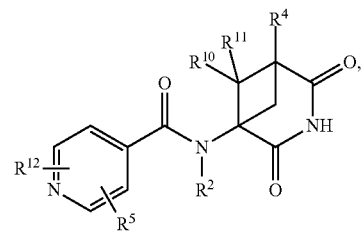
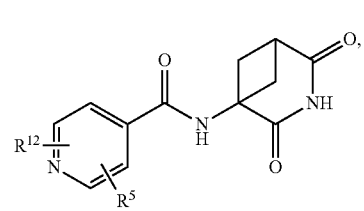
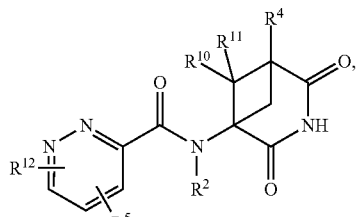
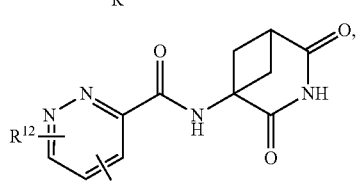
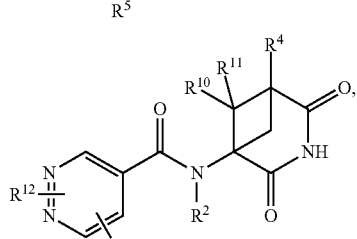
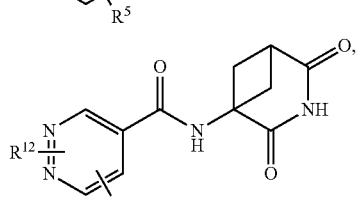
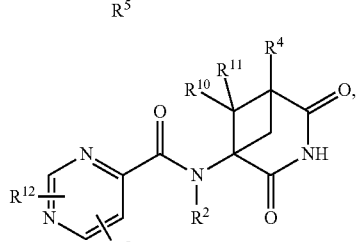
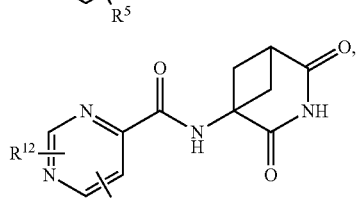
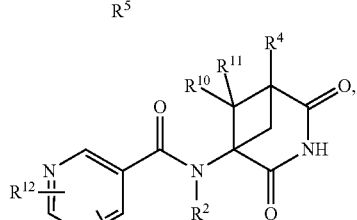
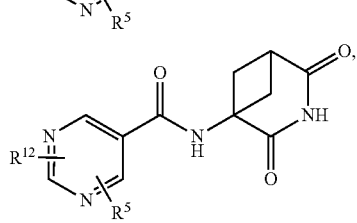

-continued
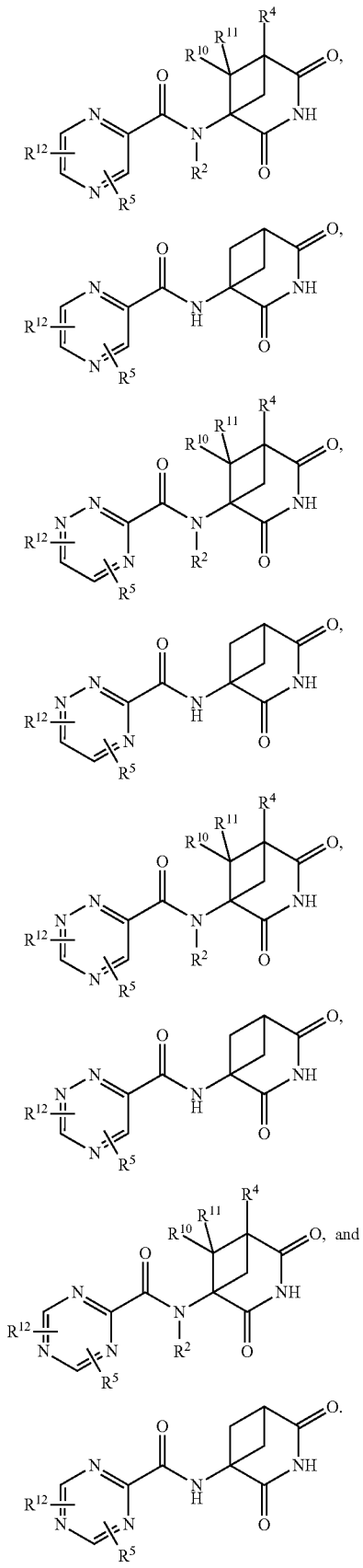
Additional non-limiting examples of compounds of Formula I include:
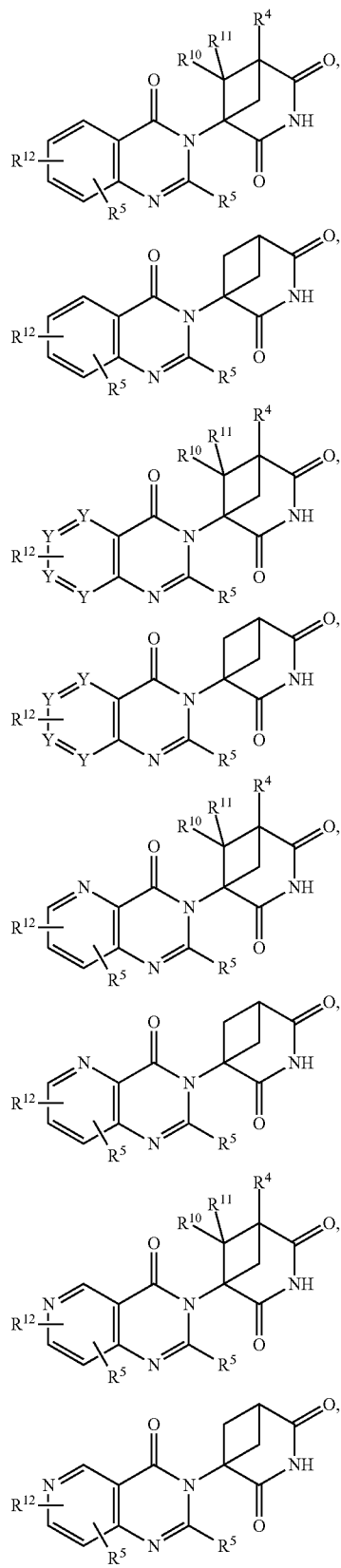

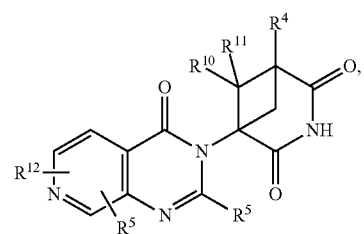
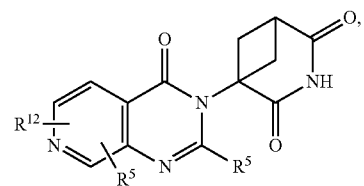
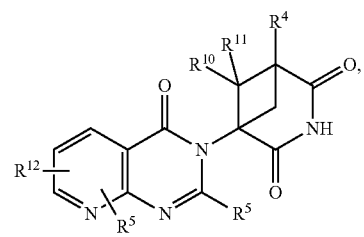
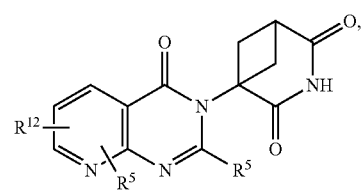
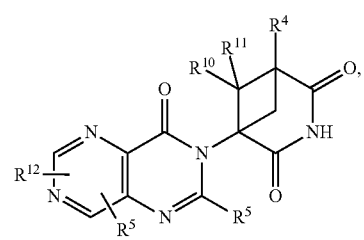
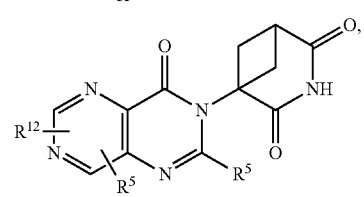
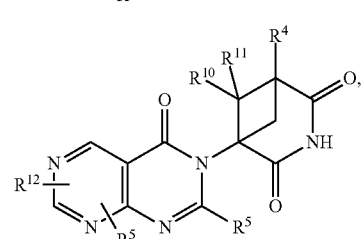
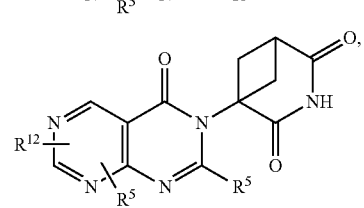
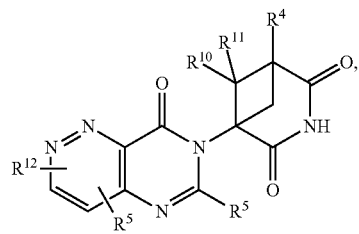
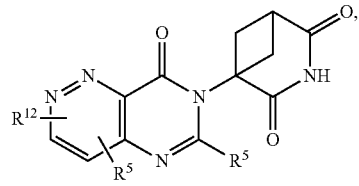
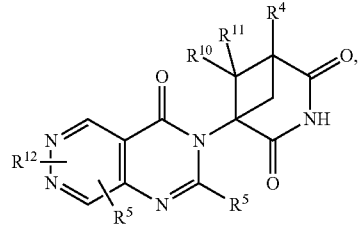
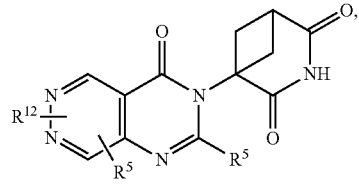
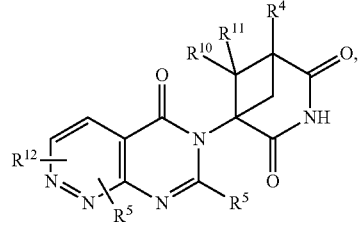
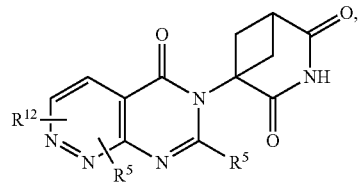
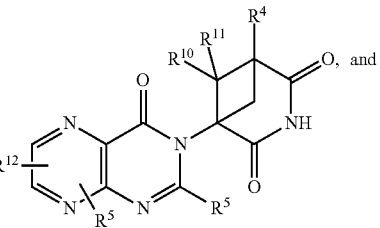
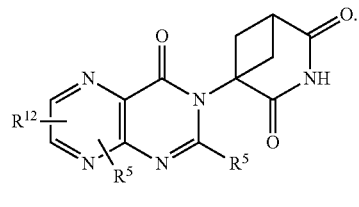

Additional non-limiting examples of compounds of Formula I include:
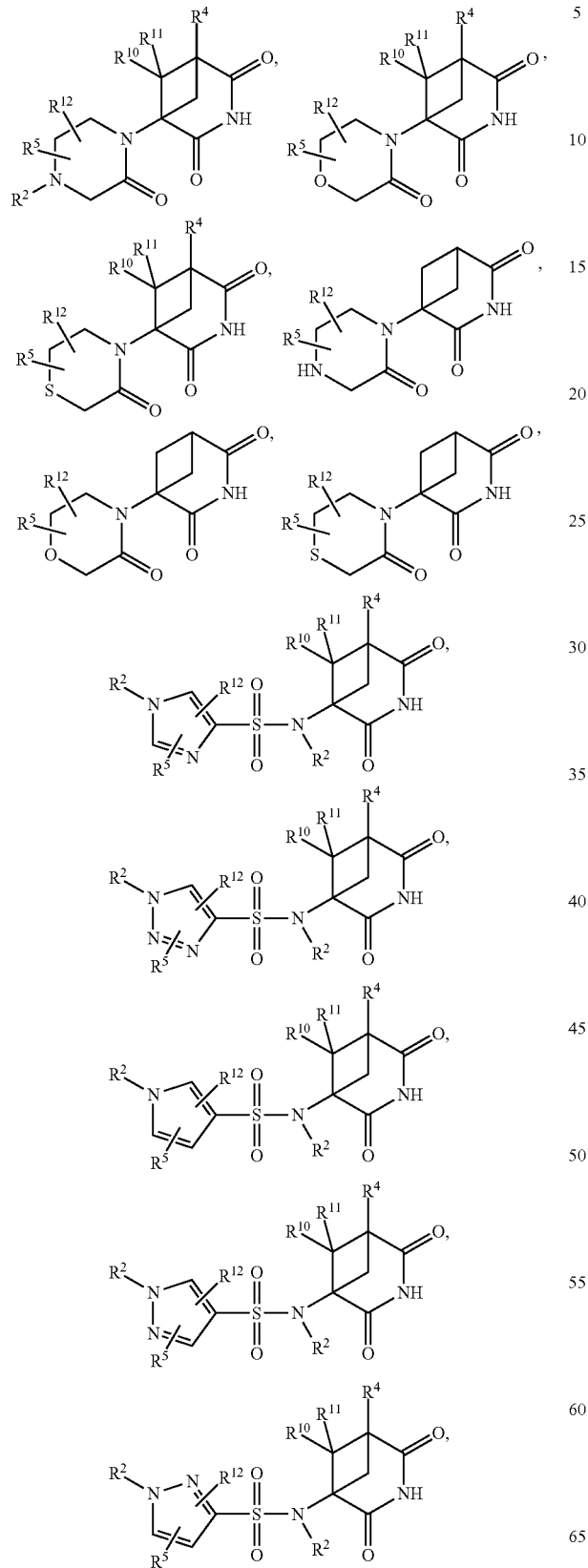
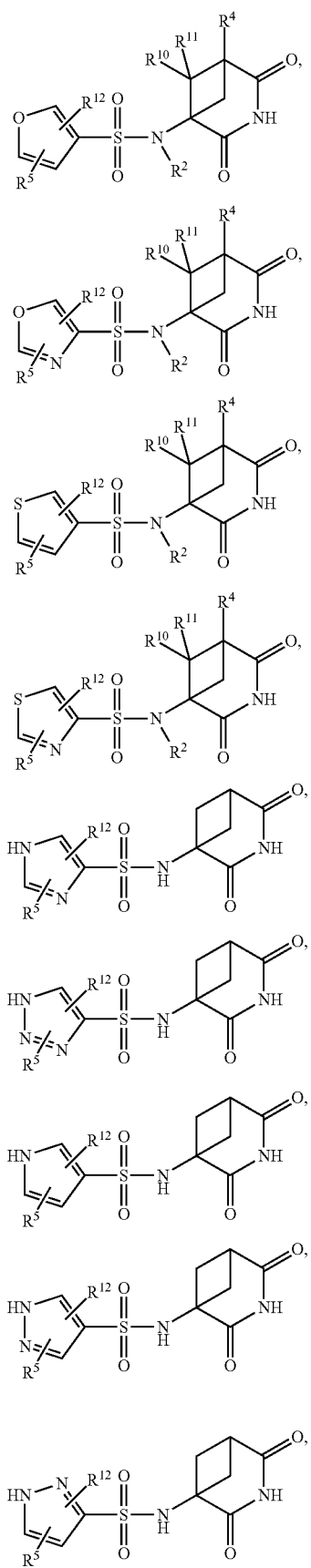

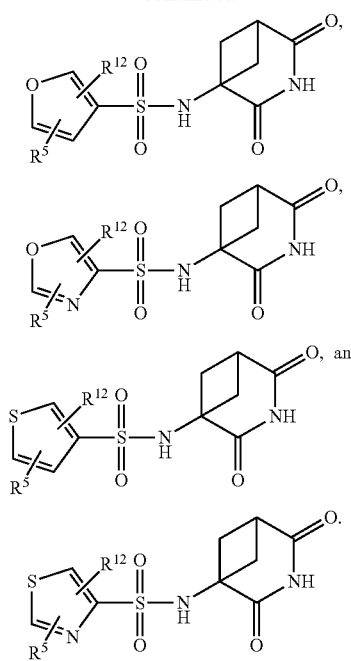
Non-limiting examples of compounds of Formula II include:
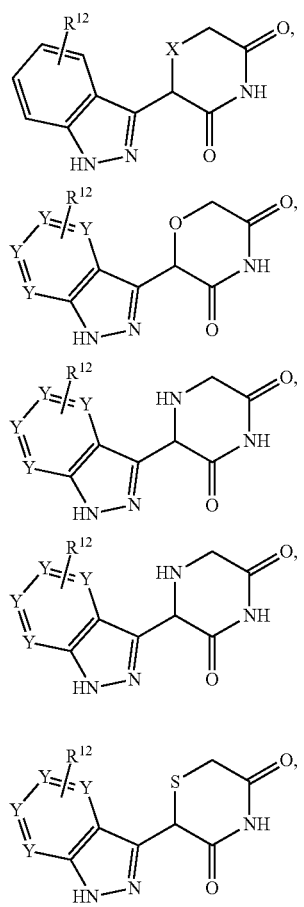
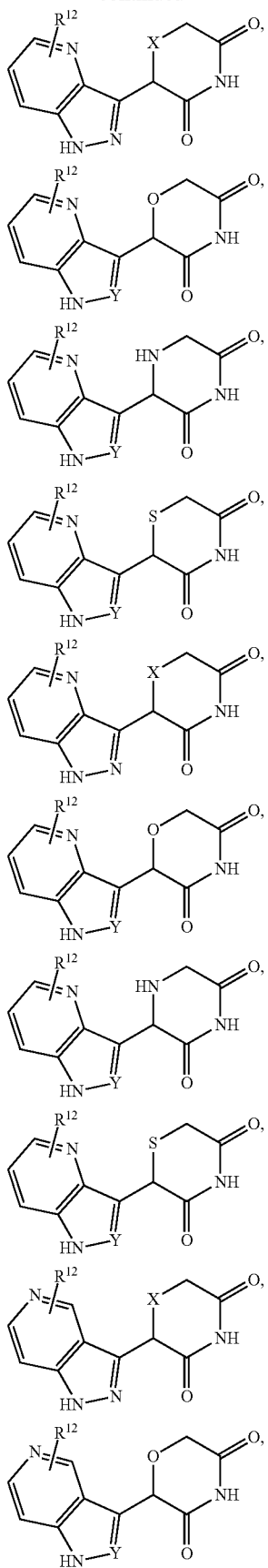

141
-continued
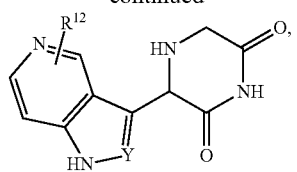
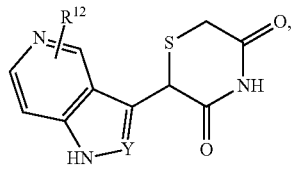
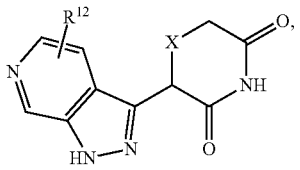
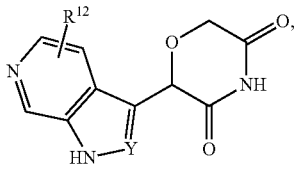
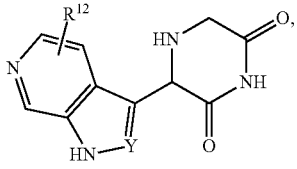
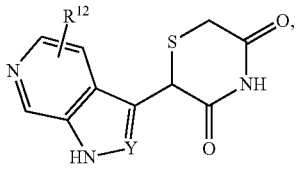
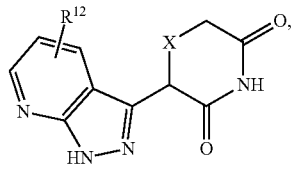
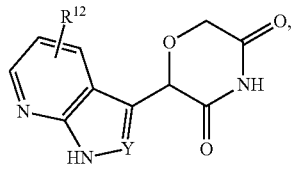
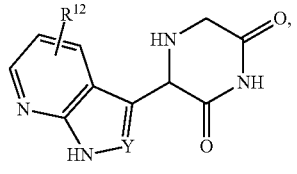
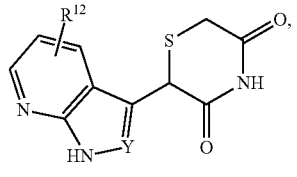
142
-continued
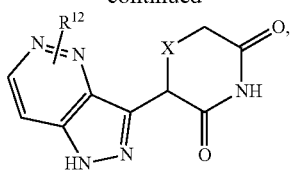
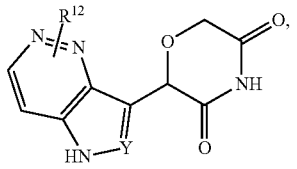
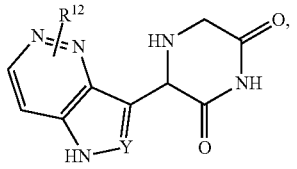
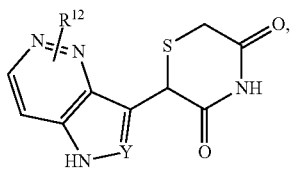
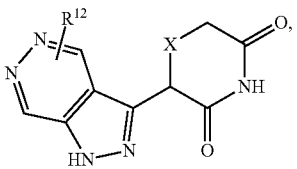
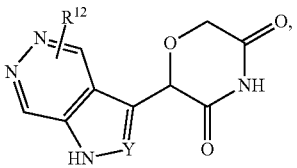
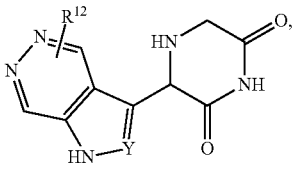
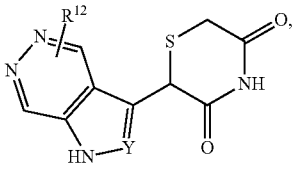
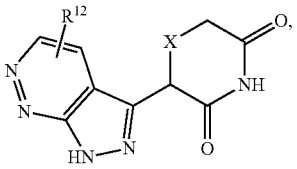
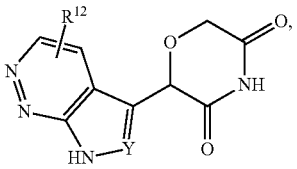

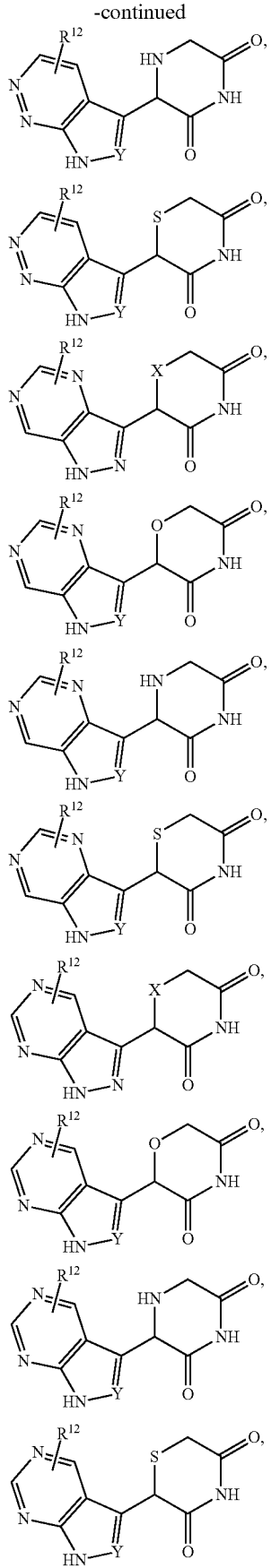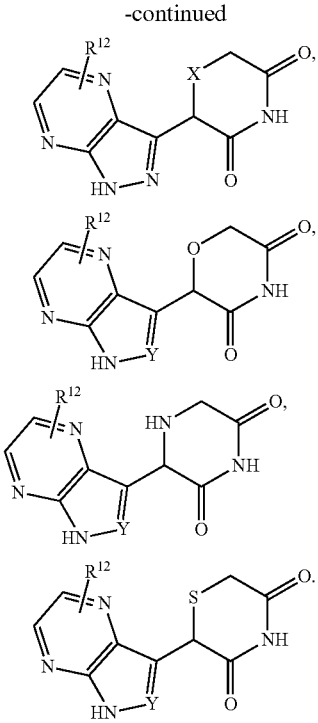
Additional non-limiting examples of compounds of Formula II include:
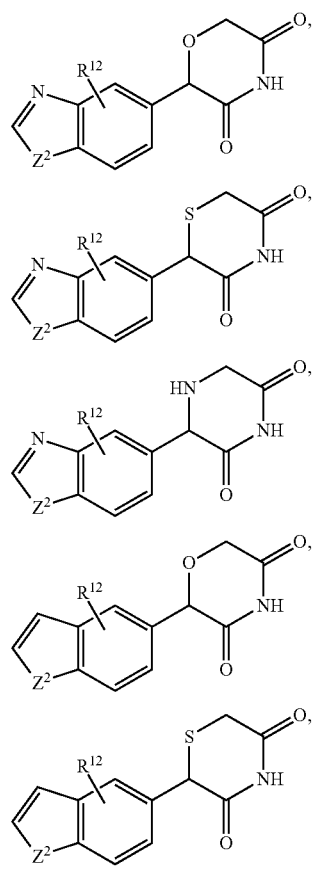

-continued

-continued

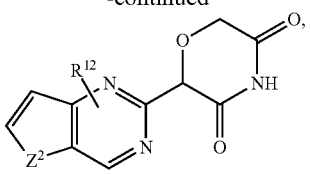
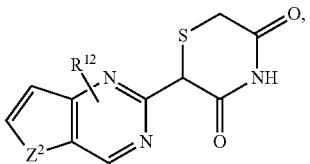
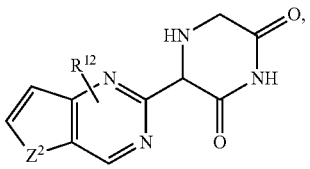
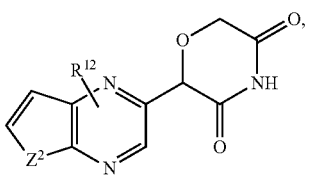
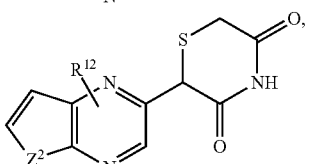
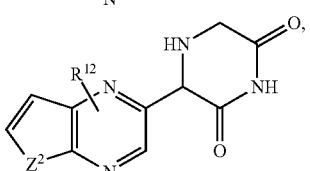
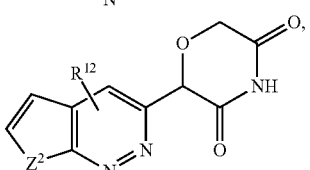
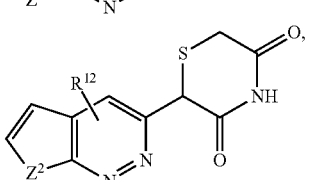
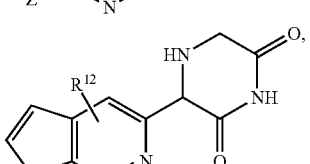
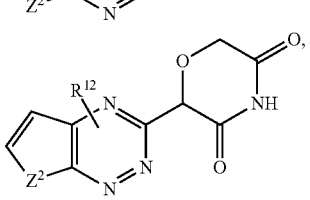
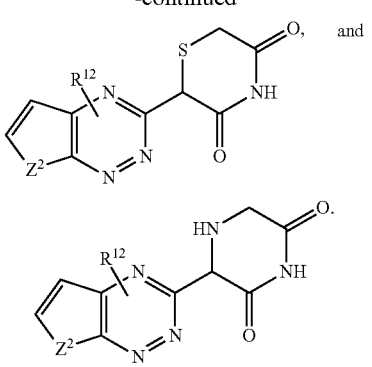
Additional non-limiting examples of compounds of Formula II include:
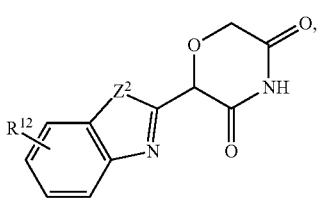
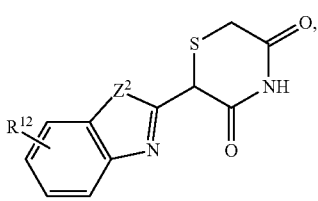
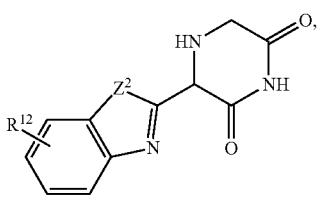
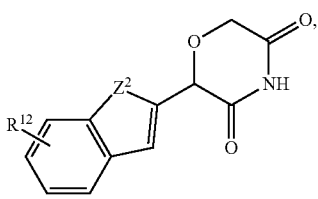
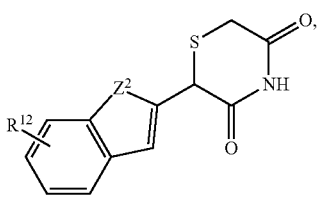
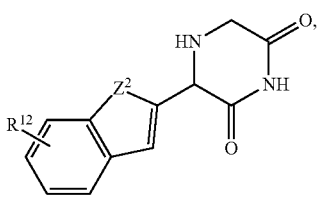

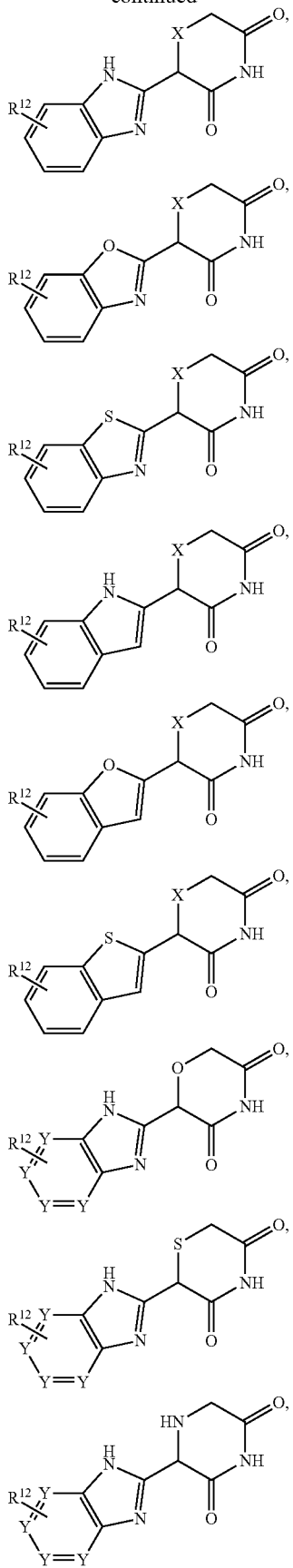
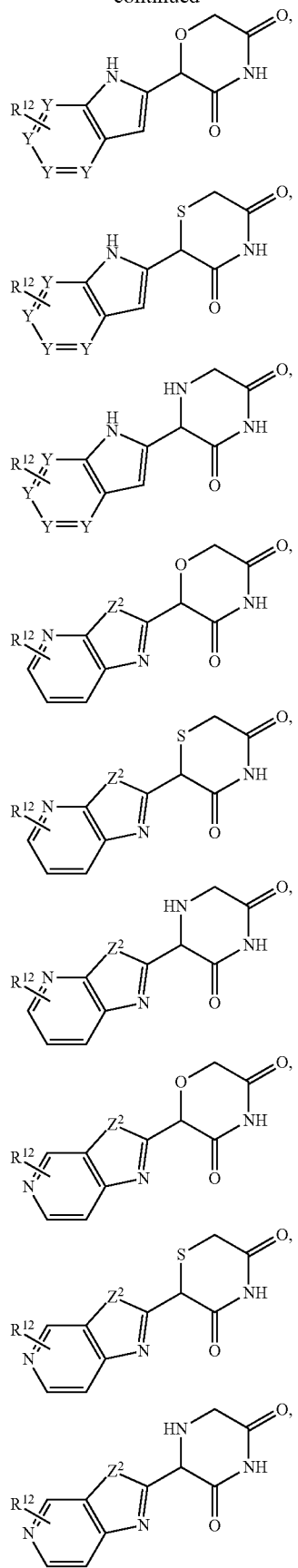

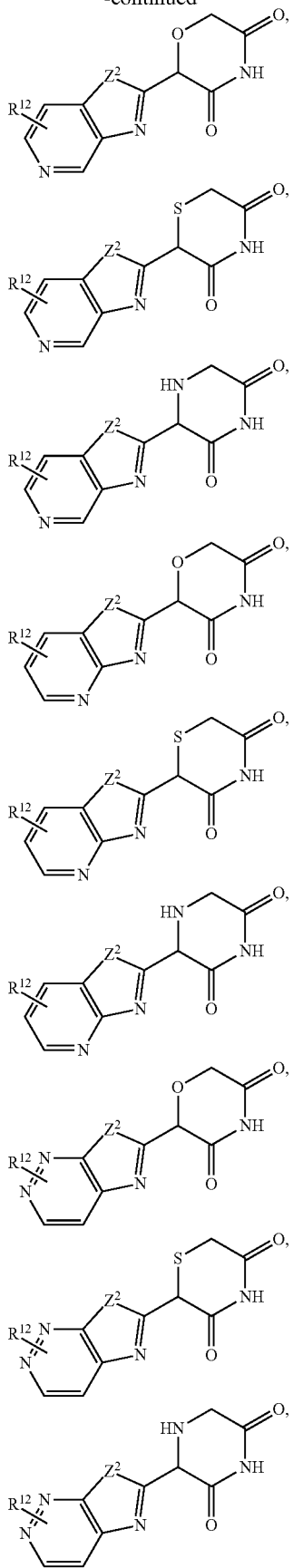
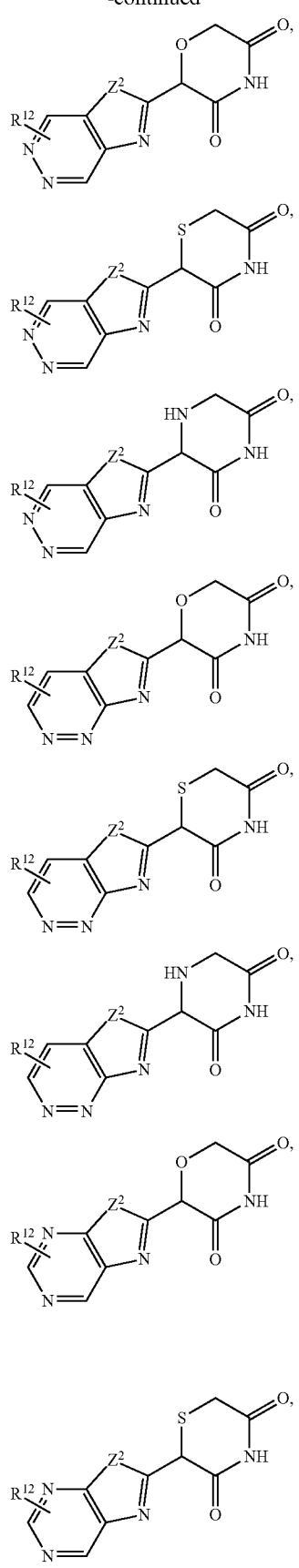

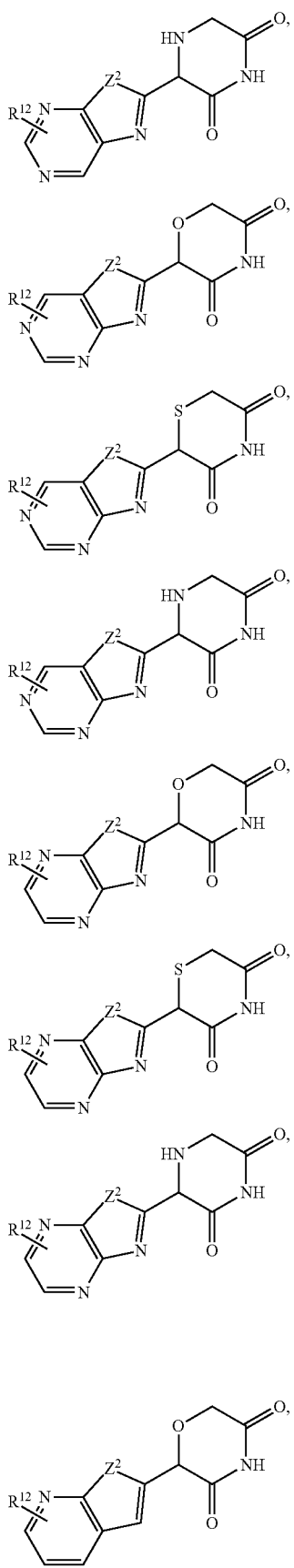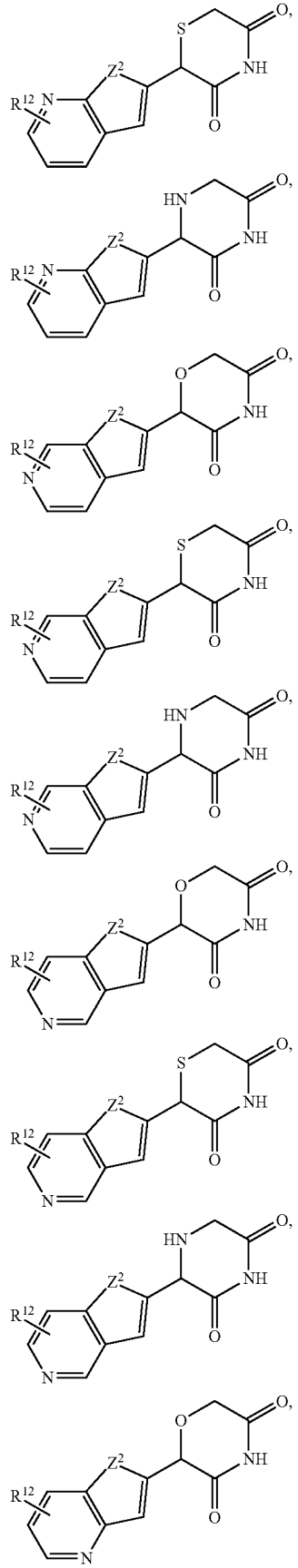

-continued

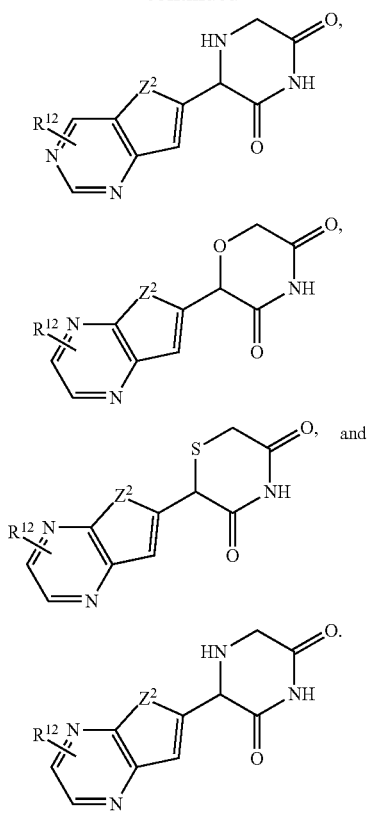
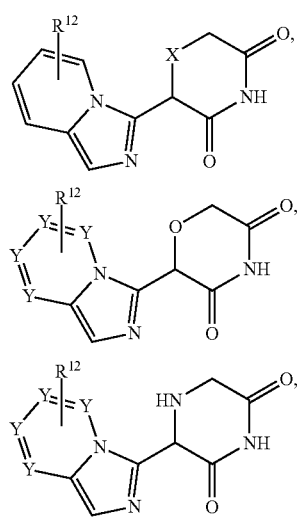
Additional non-limiting examples of compounds of Formula II include:
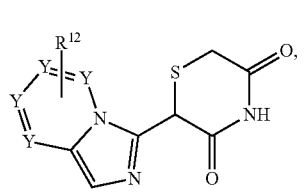
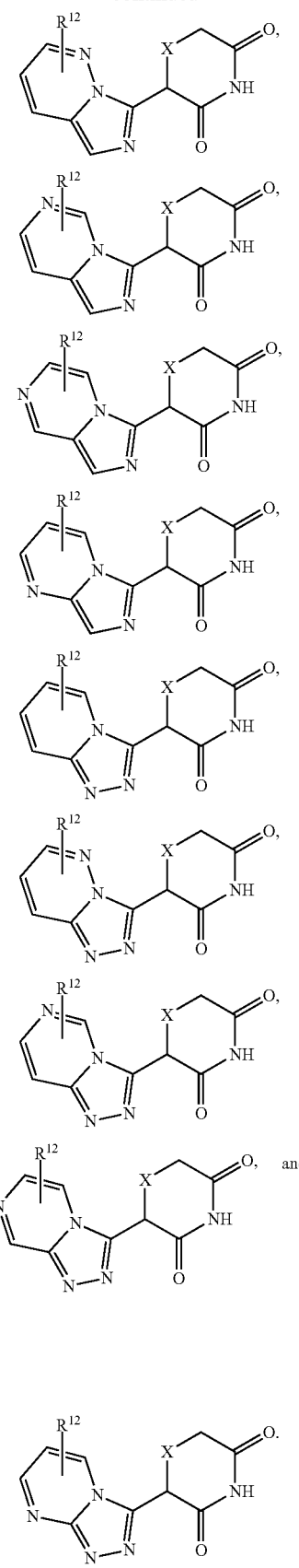

Additional non-limiting examples of compounds of Formula II include:
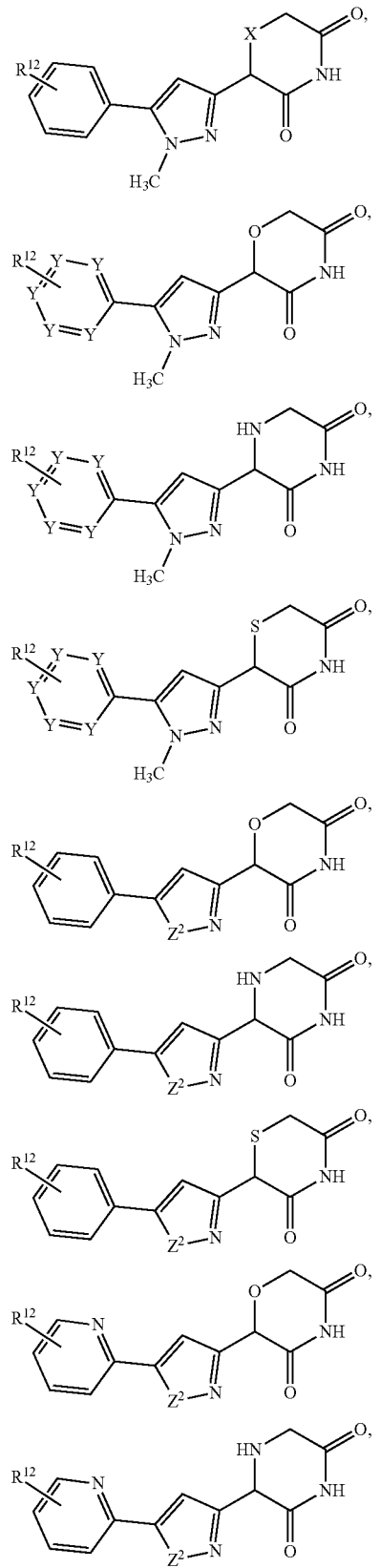
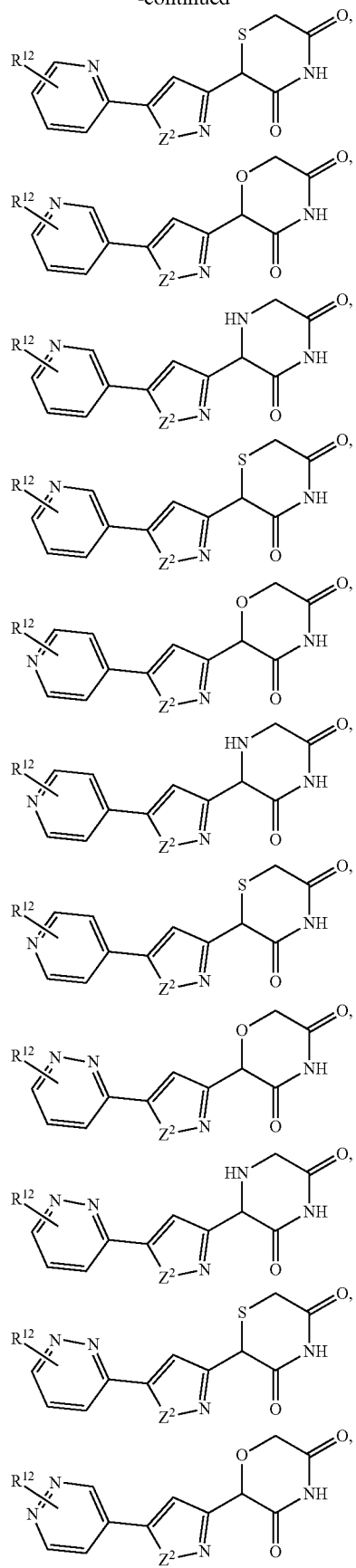

163
-continued
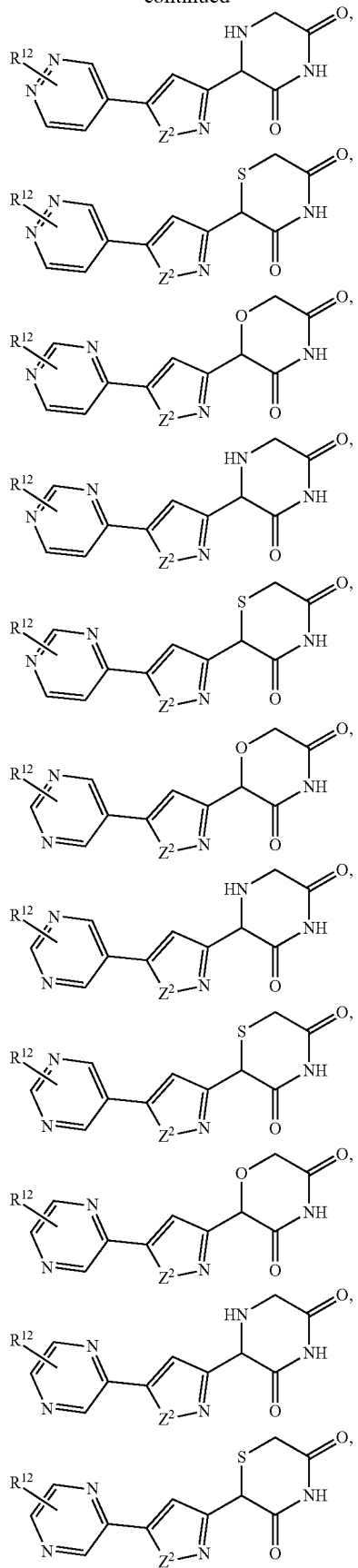
164
-continued
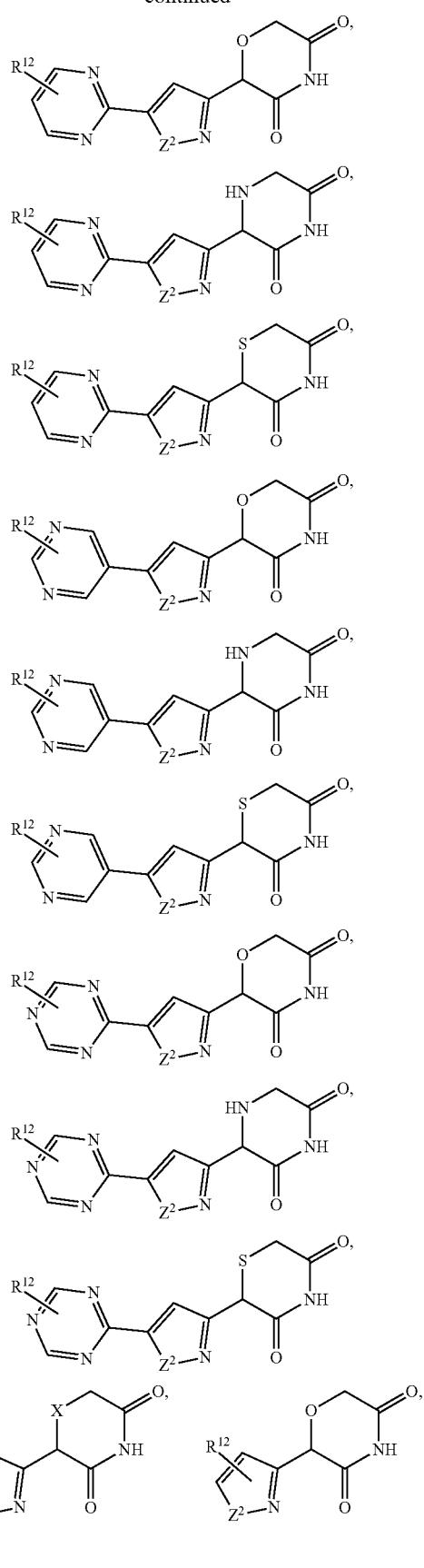

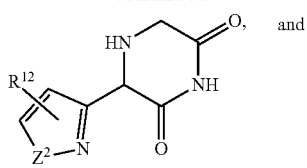
and
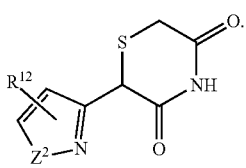
Additional non-limiting examples of compounds of Formula II include:
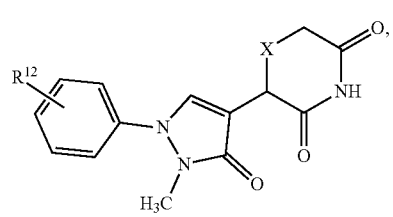
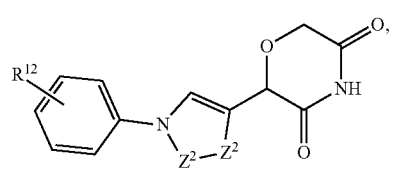
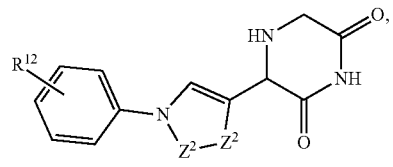
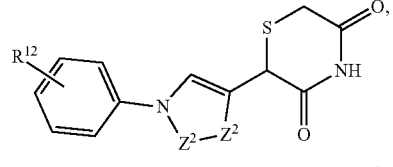
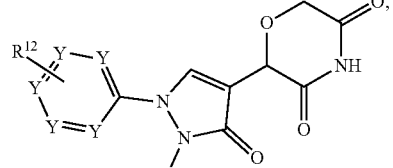
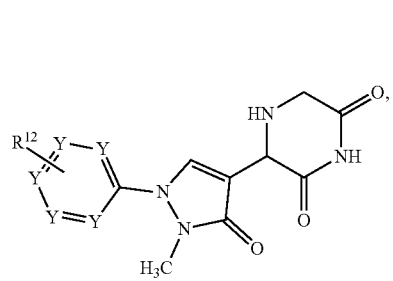
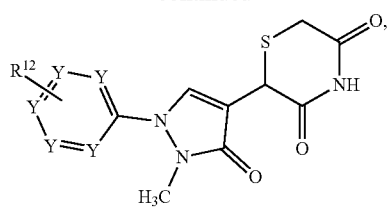
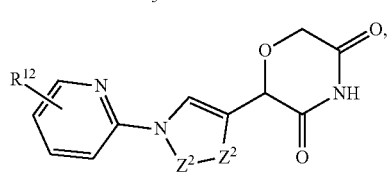
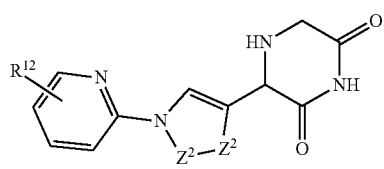
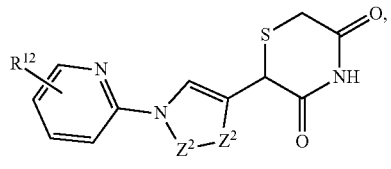
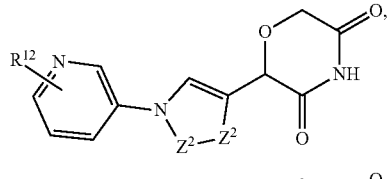
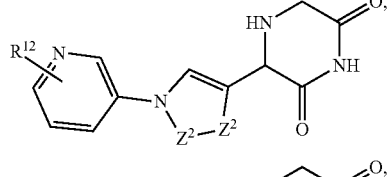
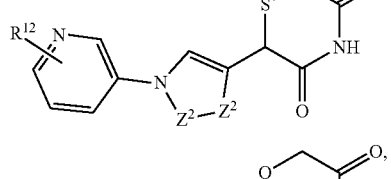
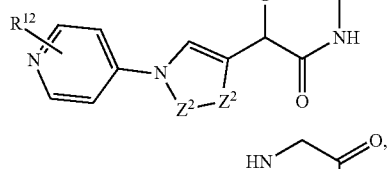
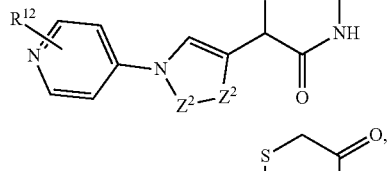
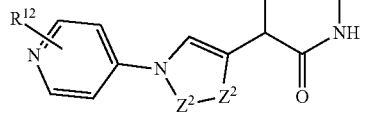

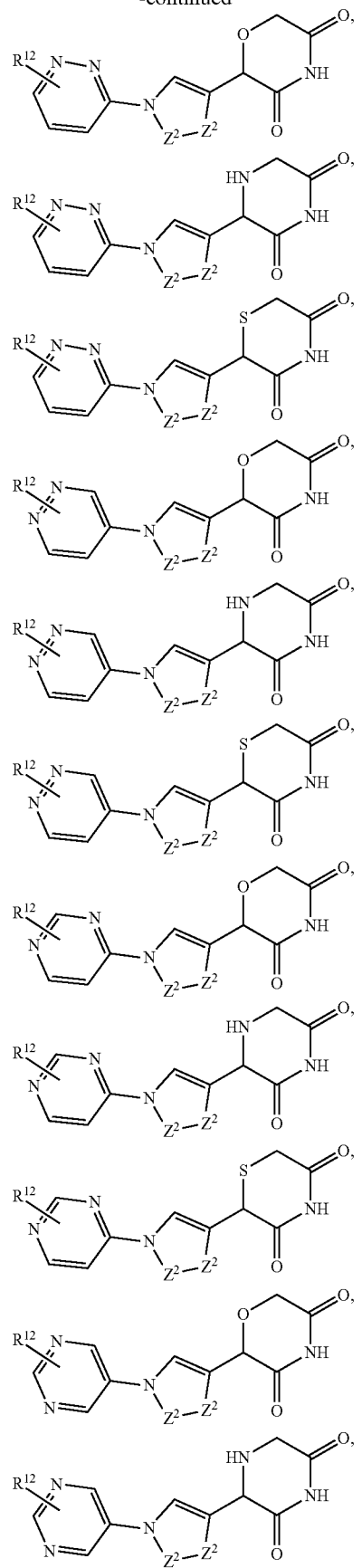
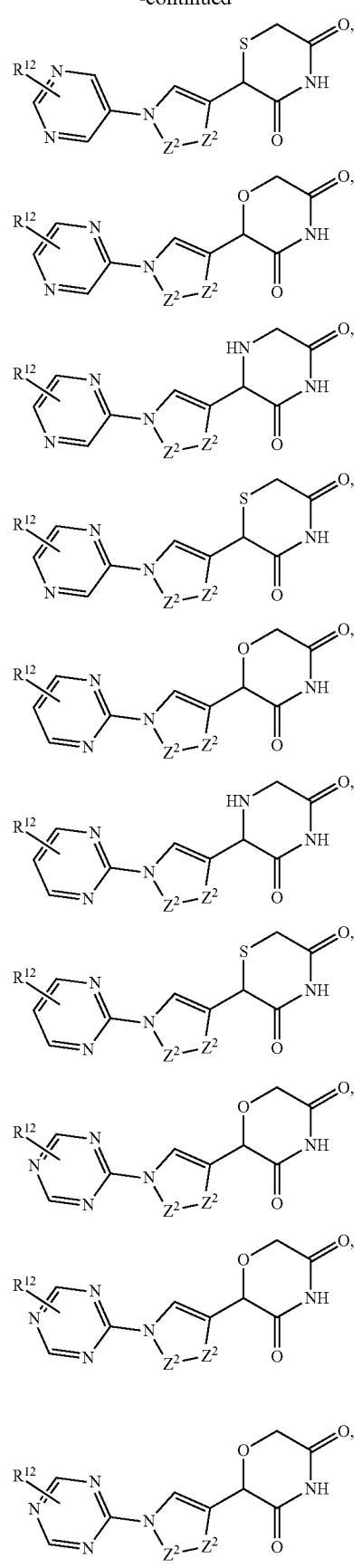

-continued
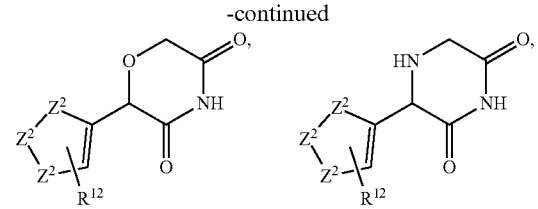
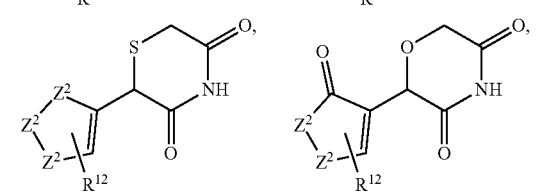
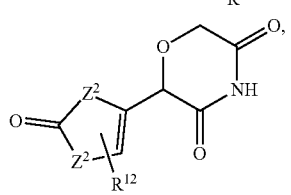
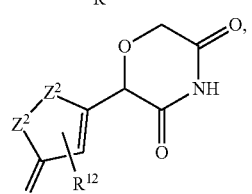
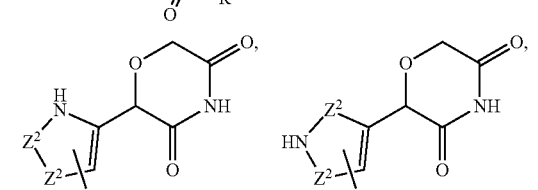
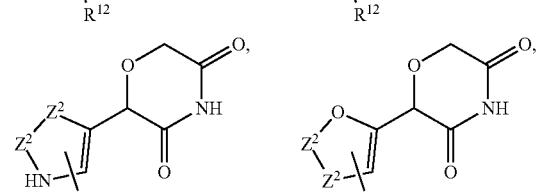
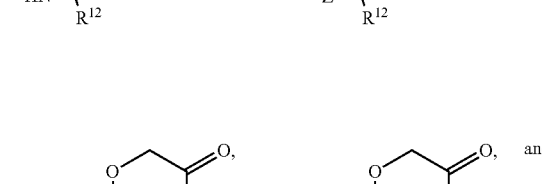
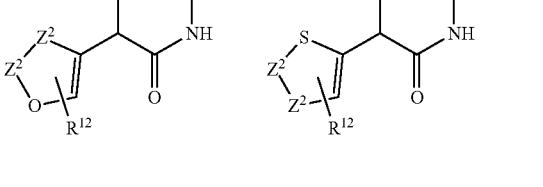
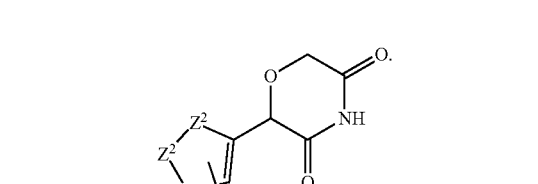
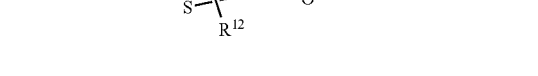
Additional non-limiting examples of compounds of Formula II include:
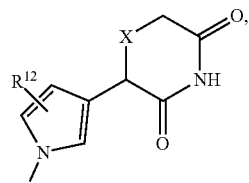
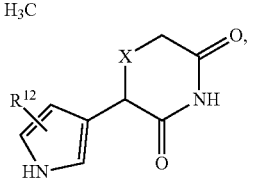
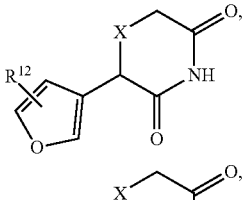
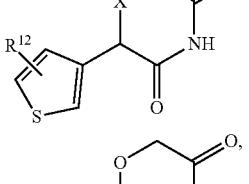
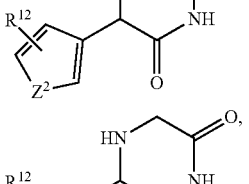
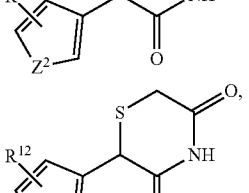
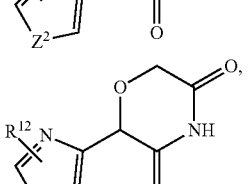
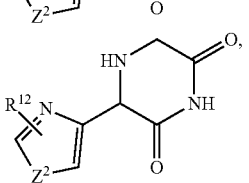
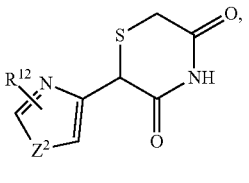

Additional non-limiting examples of compounds of Formula II include:

-continued
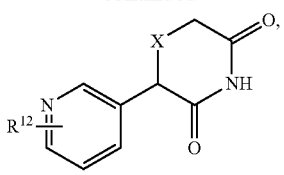
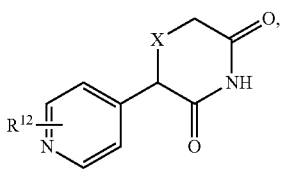
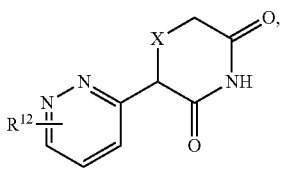
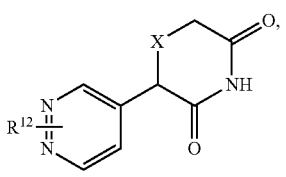
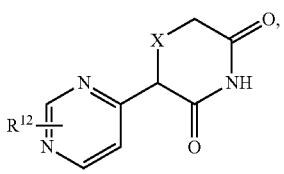
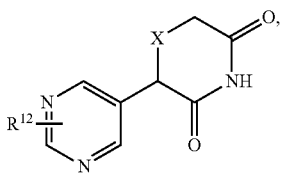
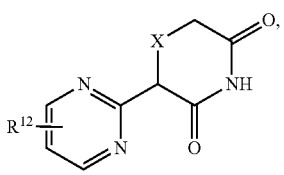
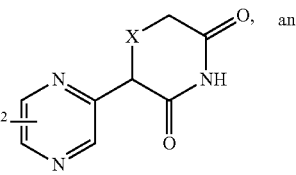
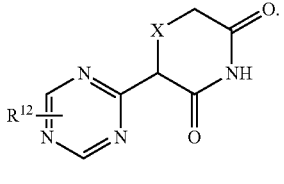
Examples of
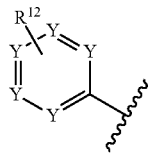
when present in a compound of the present invention include the following:
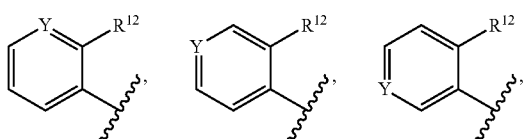
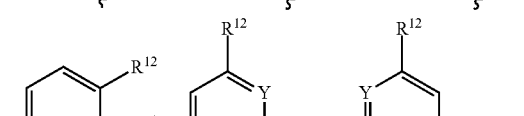
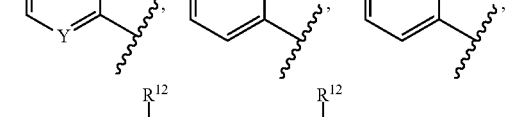
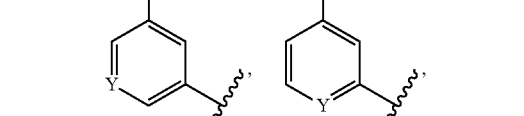
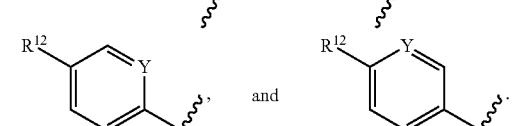
and
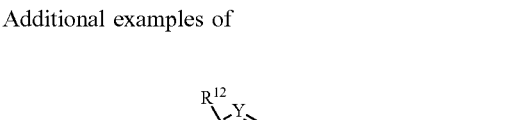
Additional examples of
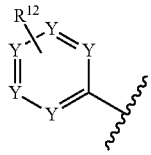
include the following:
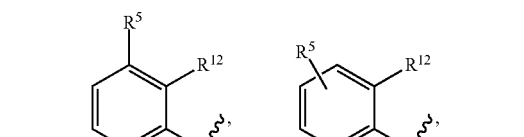
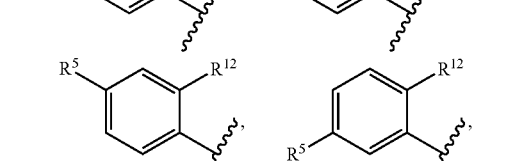

-continued
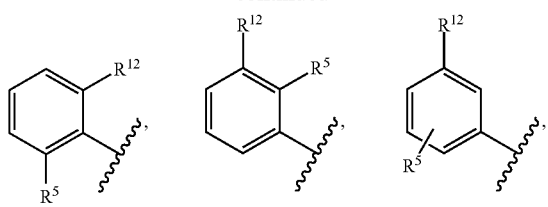
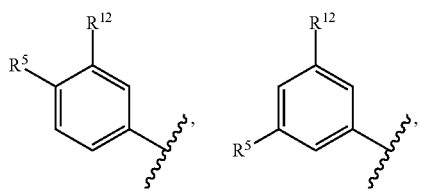
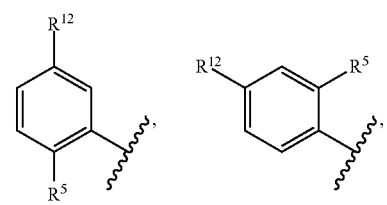
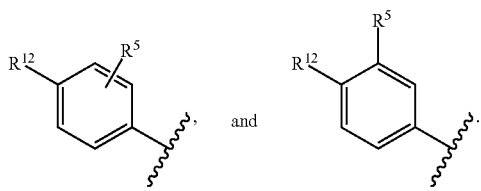
Additional examples
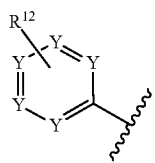
of include the following:
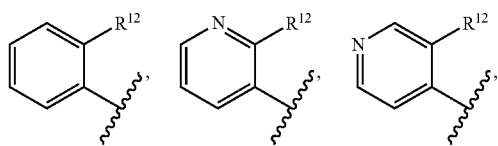
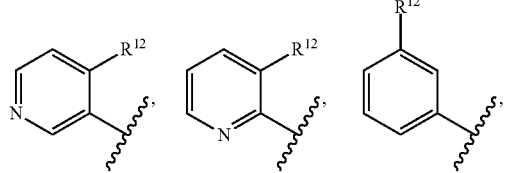
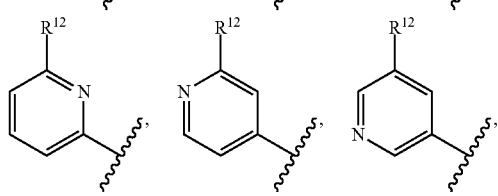
-continued
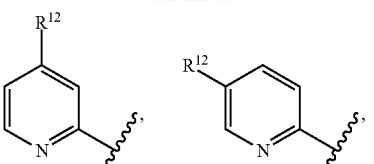
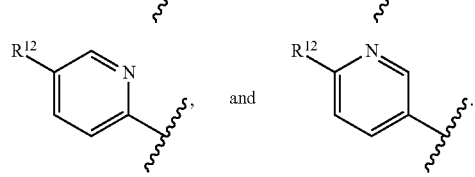 and
Additional examples of
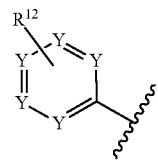
include the following:
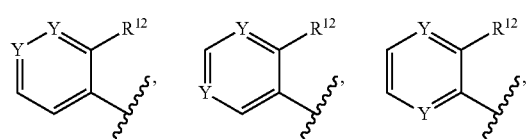
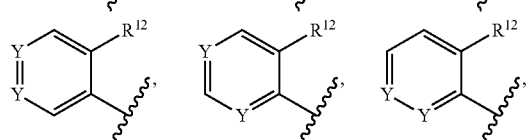
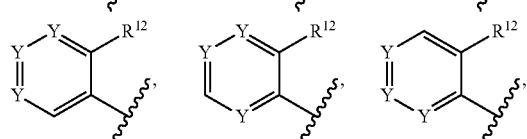
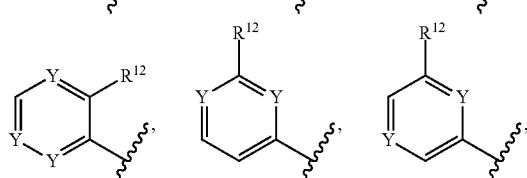
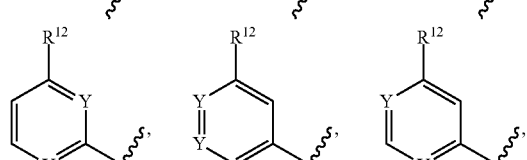
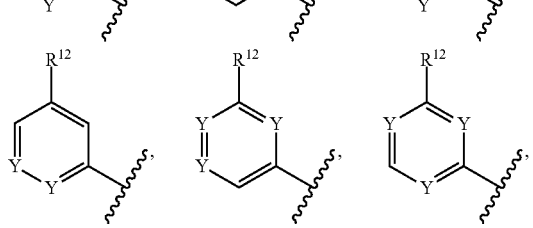

-continued
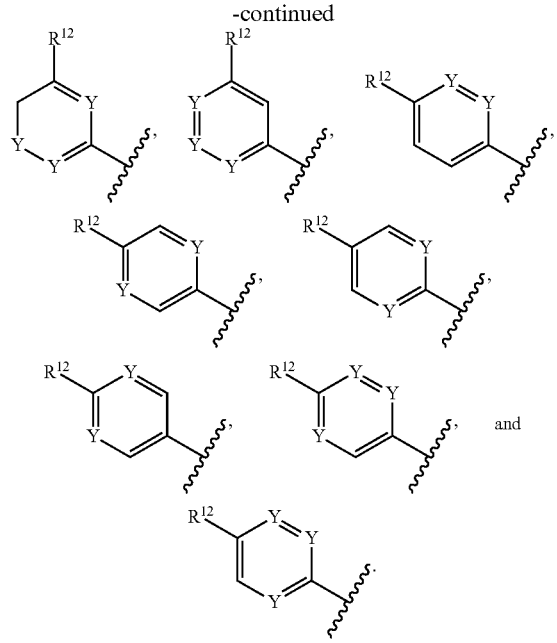
Additional examples of
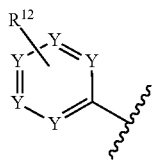
include the following:
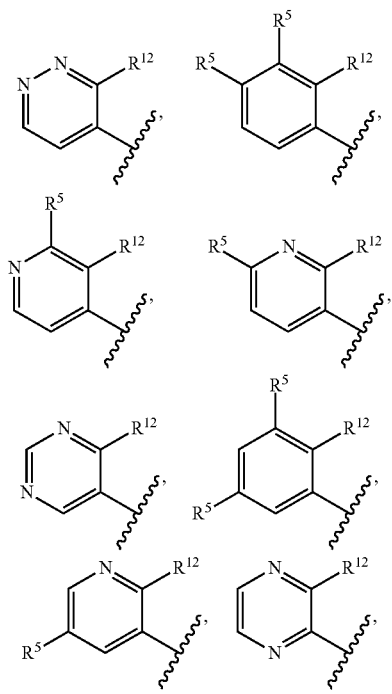
-continued
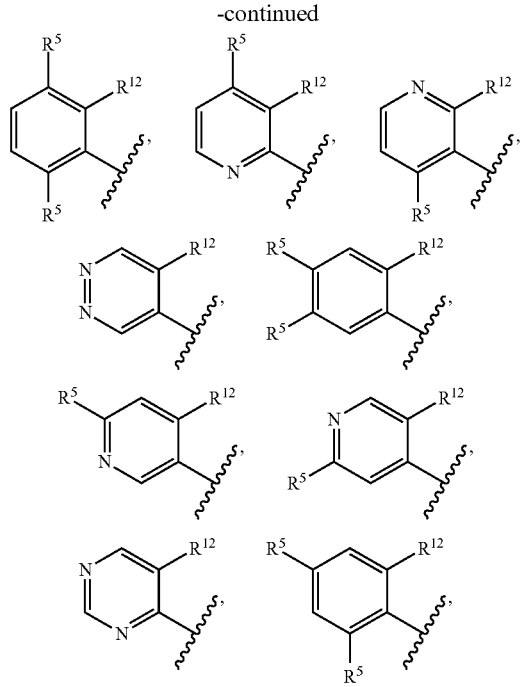
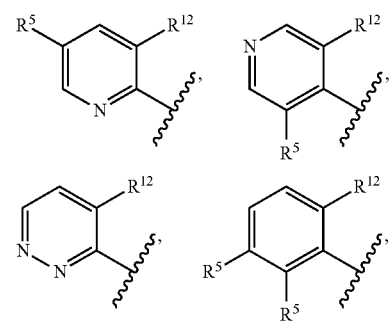

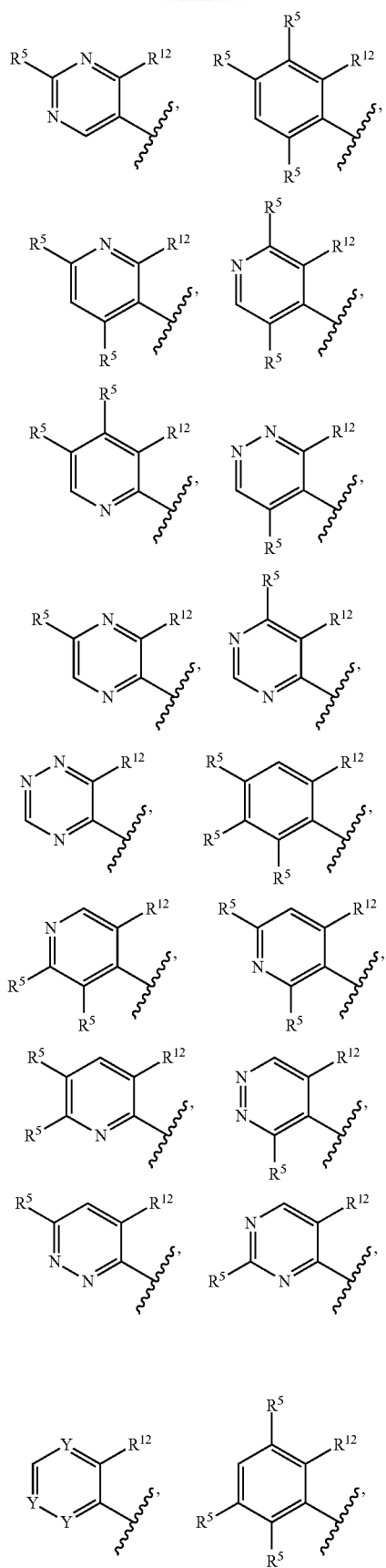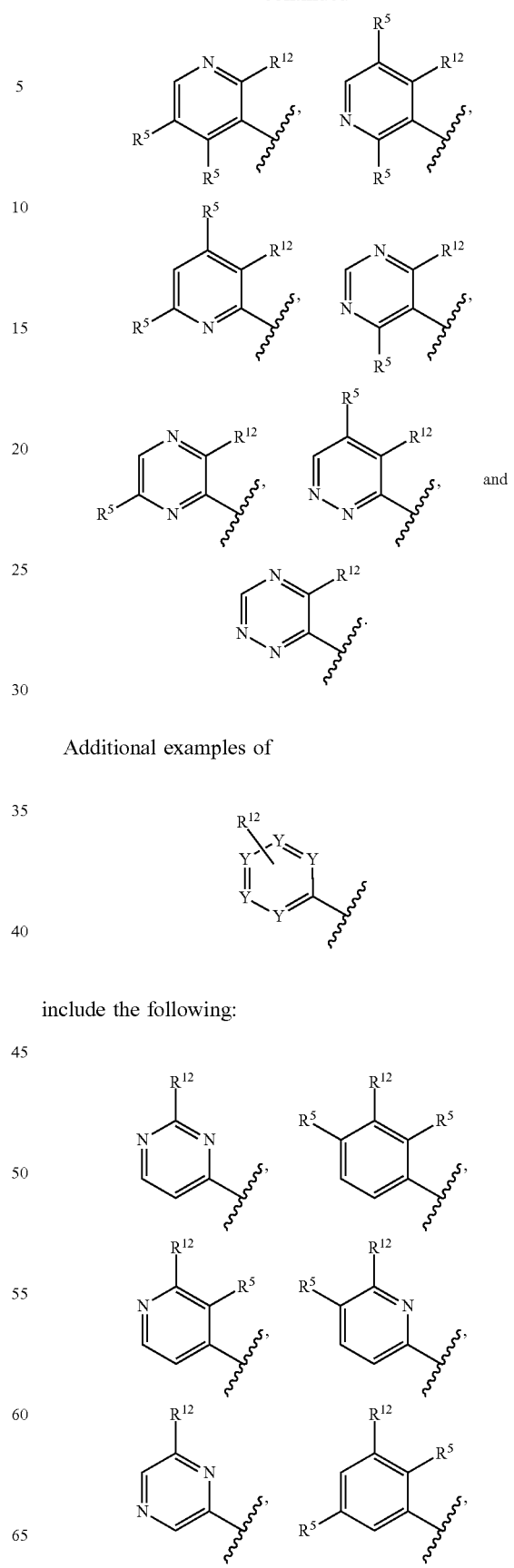
Additional examples of
include the following:

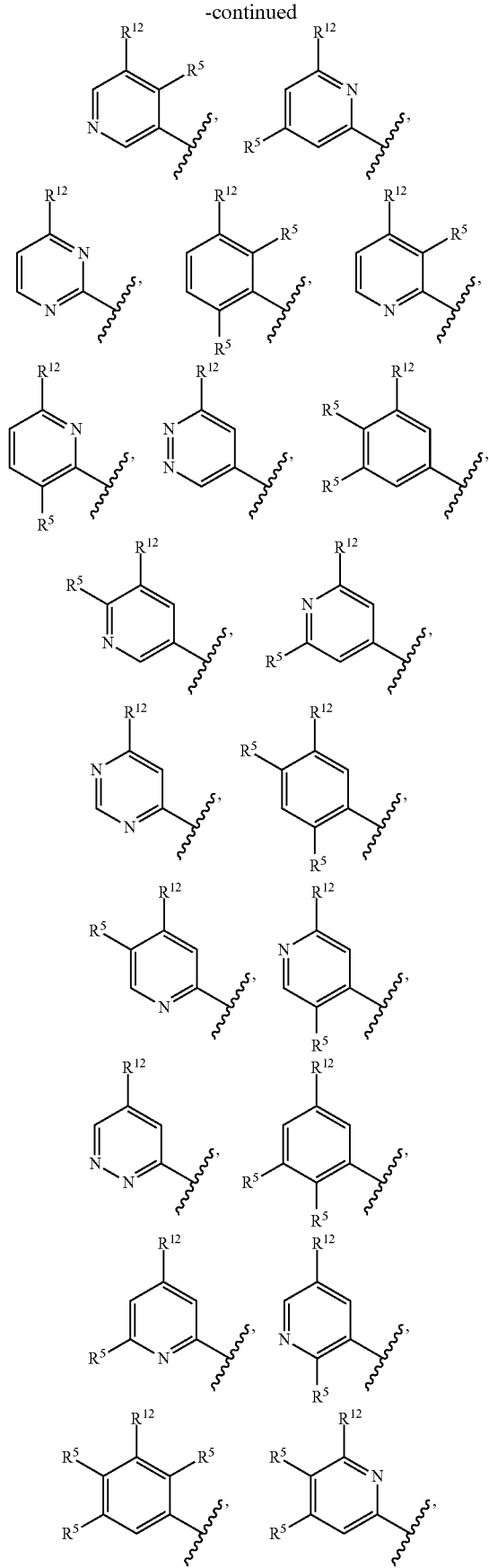
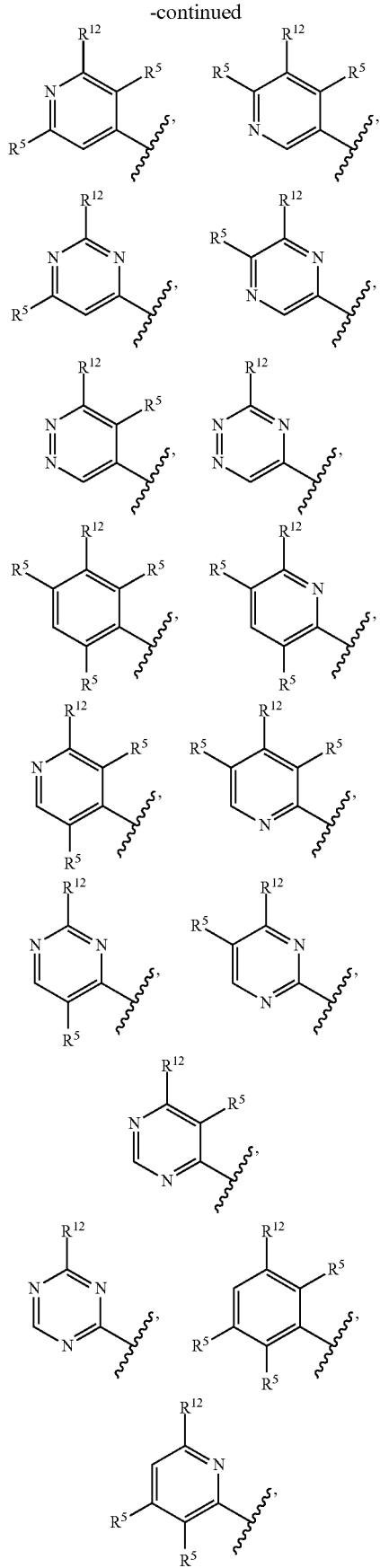

-continued
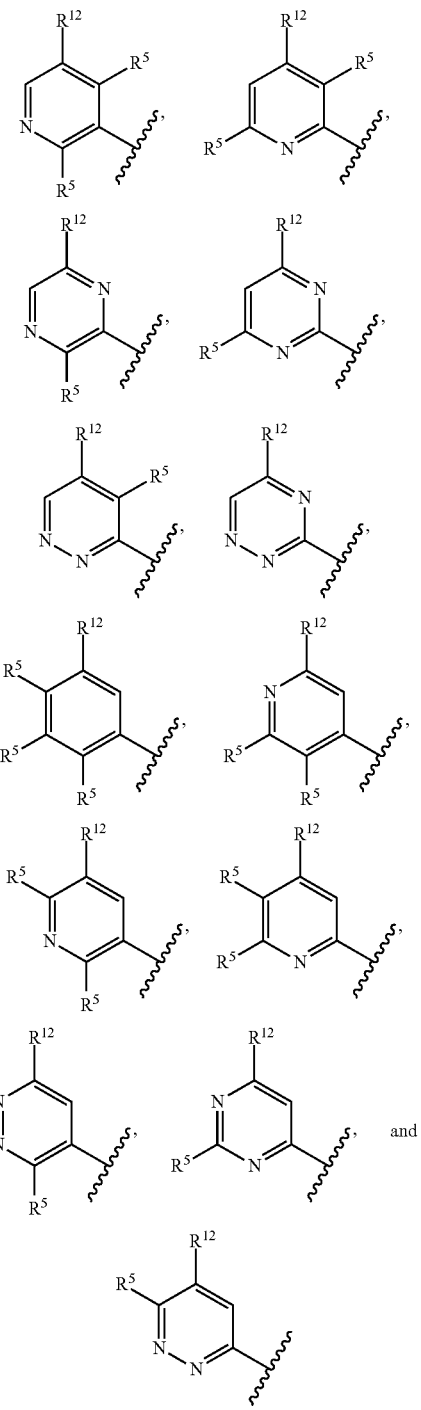
Additional examples of
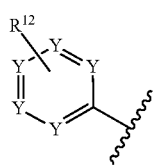
include the following:
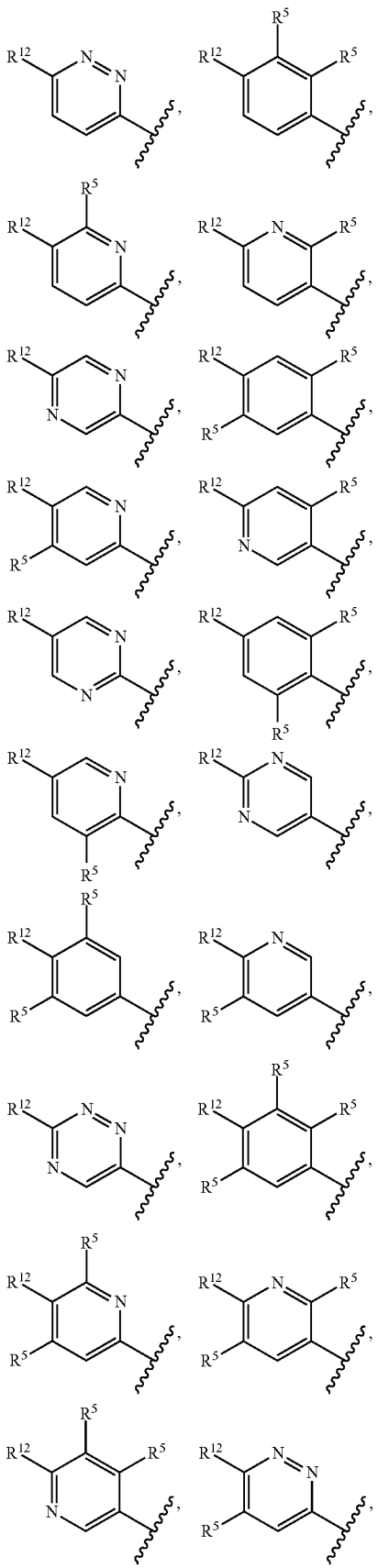

-continued
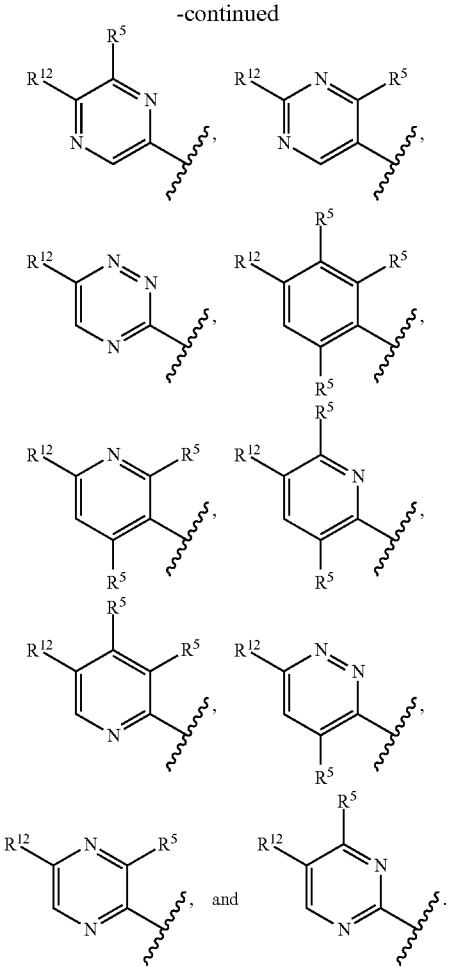
Examples of
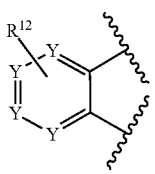
when present within a fused ring system in a moiety described above include the following:
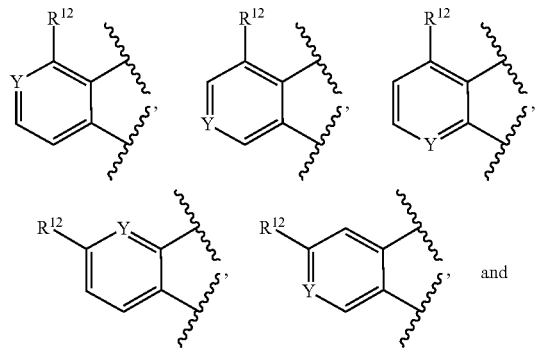
and
-continued
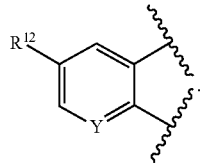
Additional examples of
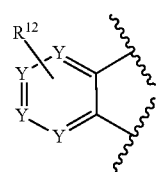
when present within a fused ring system in a moiety described above include the following:
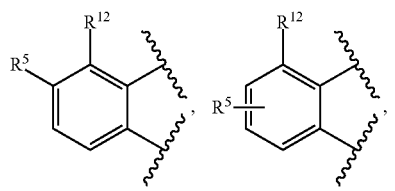
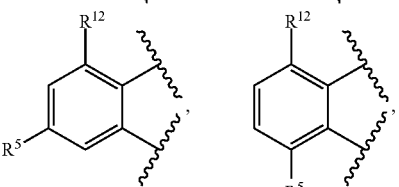
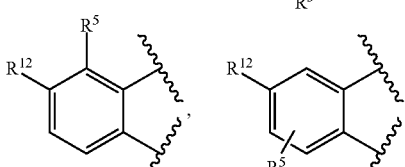
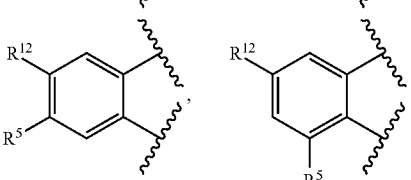
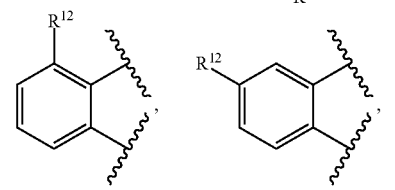
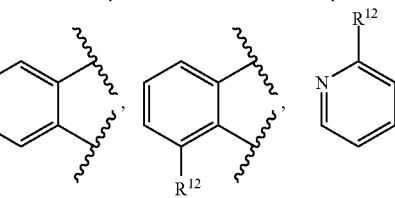

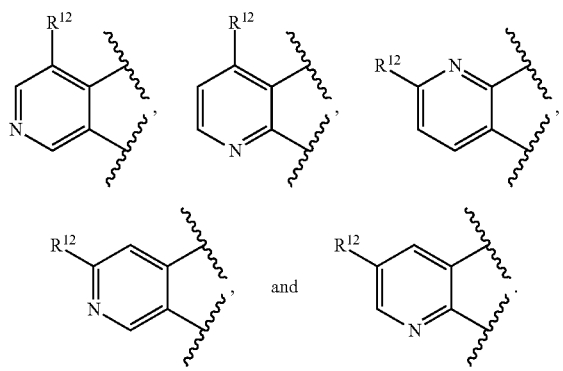
Additional examples of
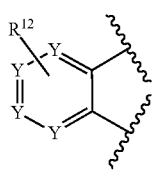
when present within a fused ring system in a moiety described above include the following:
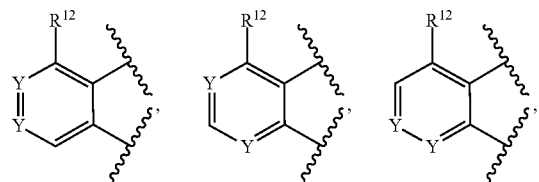
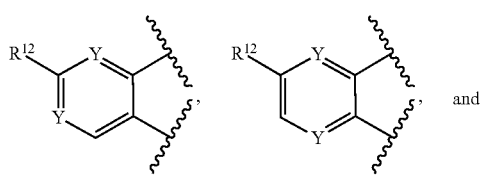
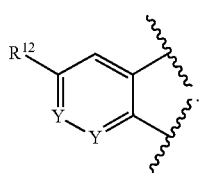
Additional examples of
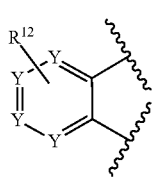
when present within a fused ring system in a moiety described above include the following:
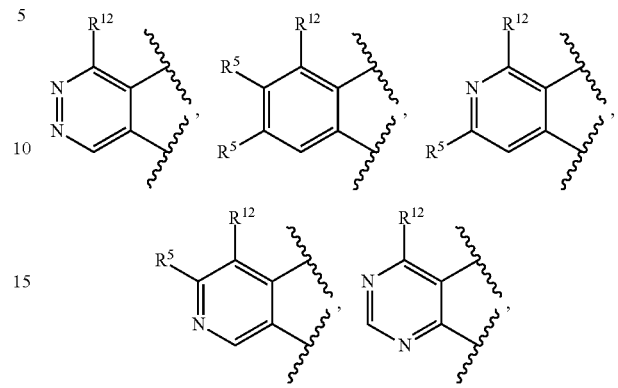
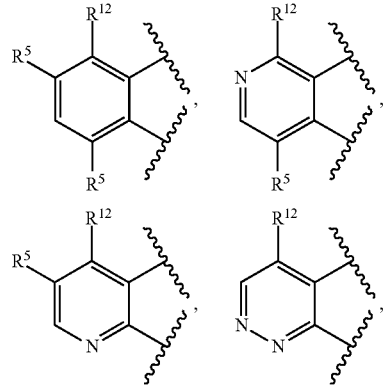
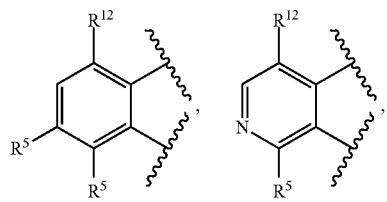
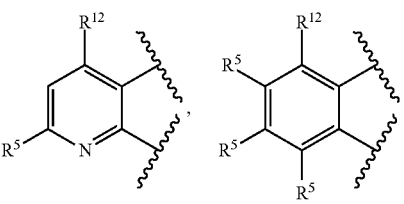
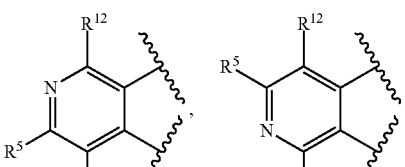
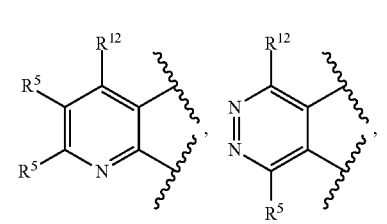

189
-continued
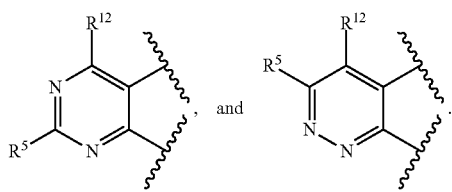, and
Additional examples of
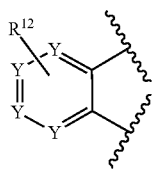
when present within a fused ring system in a moiety described above include the following:
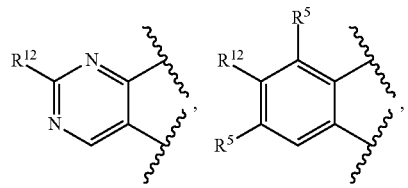
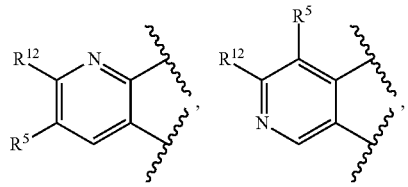
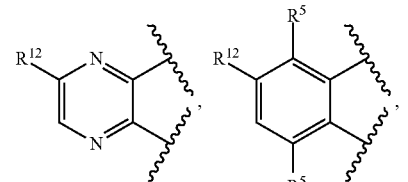
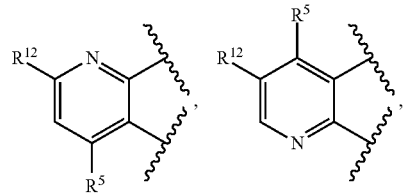
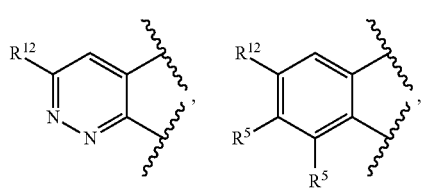
190
-continued
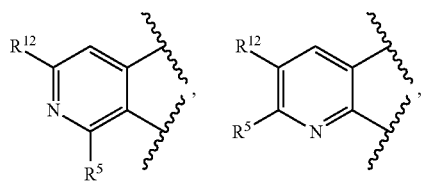
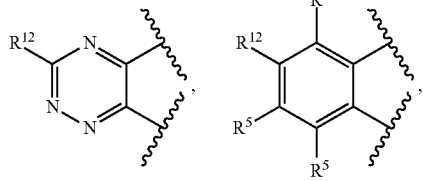
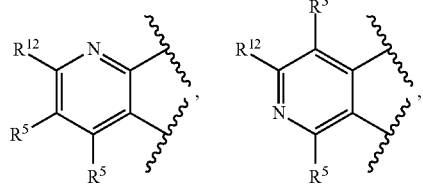
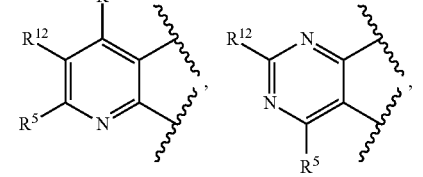
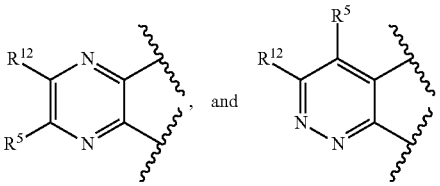, and
Examples of
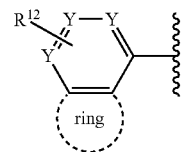
when present in one of the fused systems described above, for example, an illustrated aryl or heteroaryl moiety, includes at least the following:
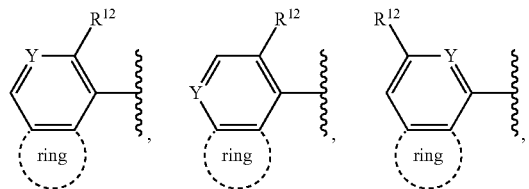

-continued
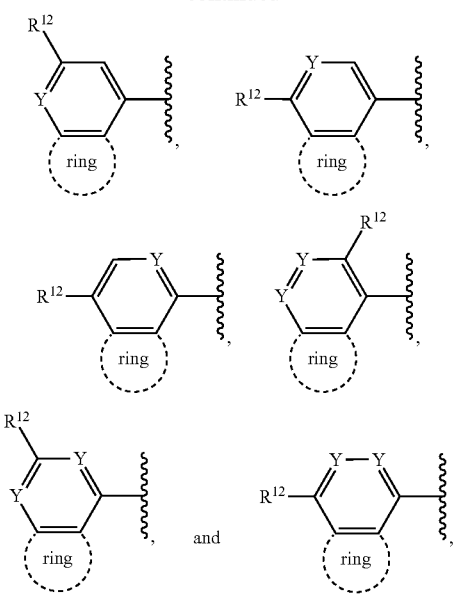
Additional examples of
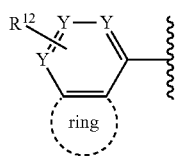
when present in one of the fused systems described above, for example, an illustrated aryl or heteroaryl moiety, includes at least the following:
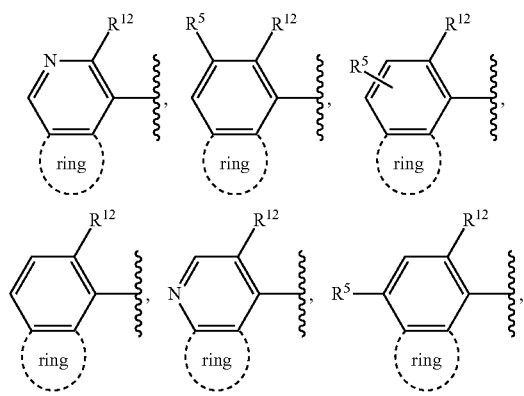
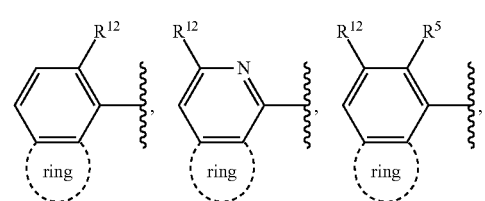
-continued
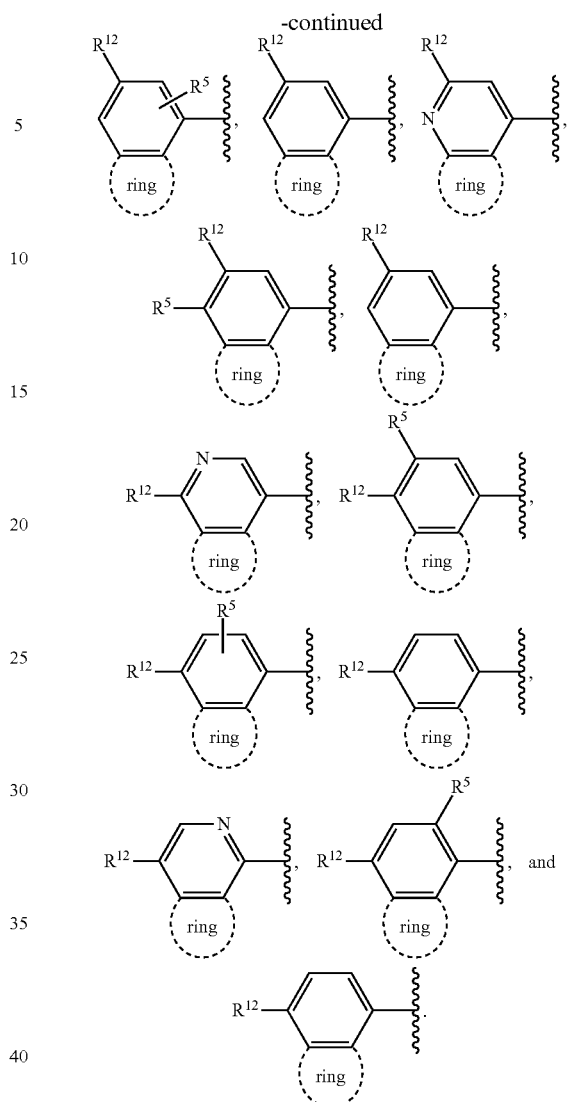
Additional examples of
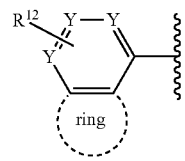
when present in one of the fused systems described above, for example, an illustrated aryl or heteroaryl moiety, includes at least the following:
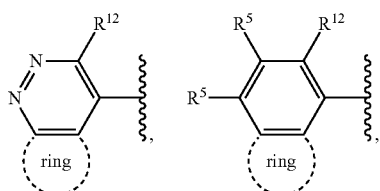

-continued
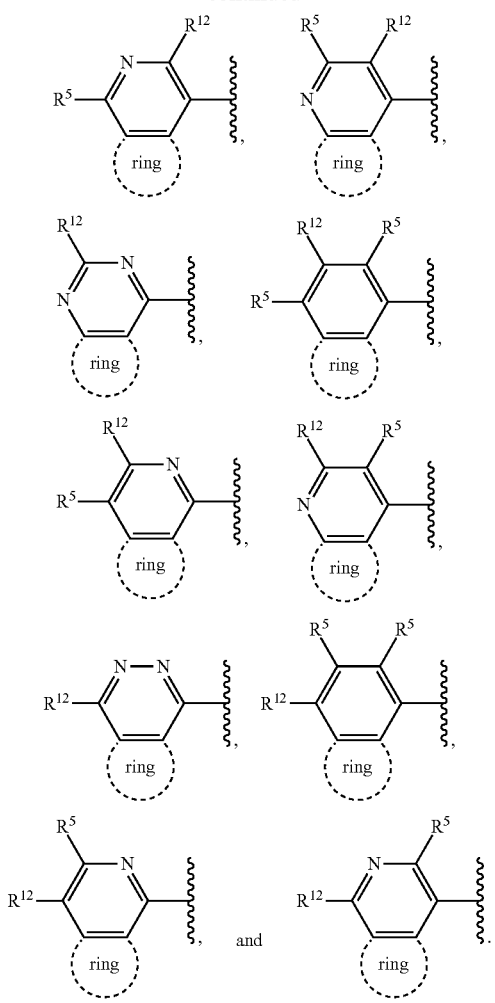
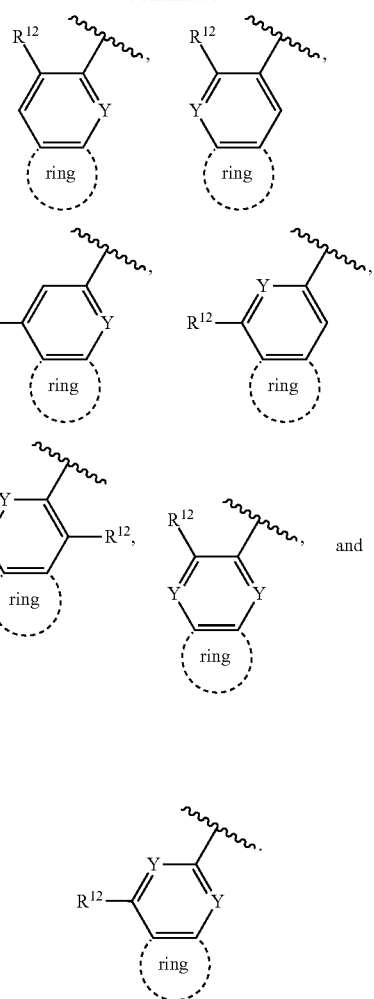
Examples of
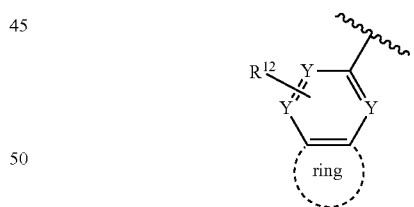
Additional examples of
when present in one of the fused systems described above, for example, an illustrated aryl or heteroaryl moiety, includes at least the following:
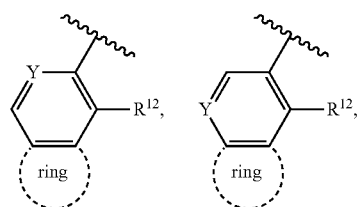
when present in one of the fused systems described above, for example, an illustrated aryl or heteroaryl moiety, includes at least the following:
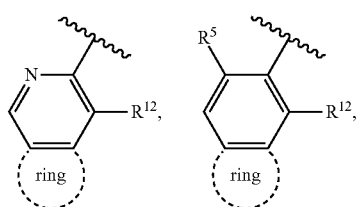

-continued
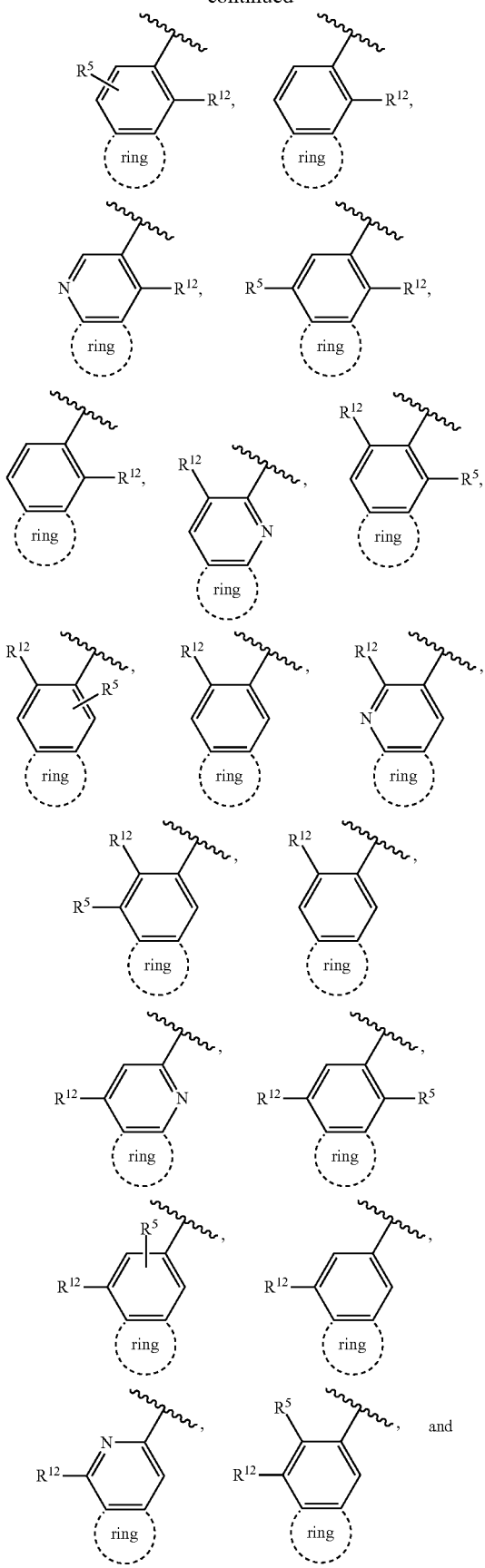
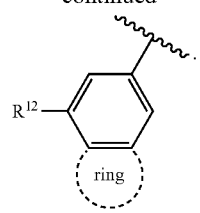
Additional examples of
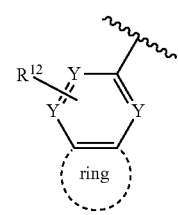
when present in one of the fused systems described above, for example, an illustrated aryl or heteroaryl moiety, includes at least the following:
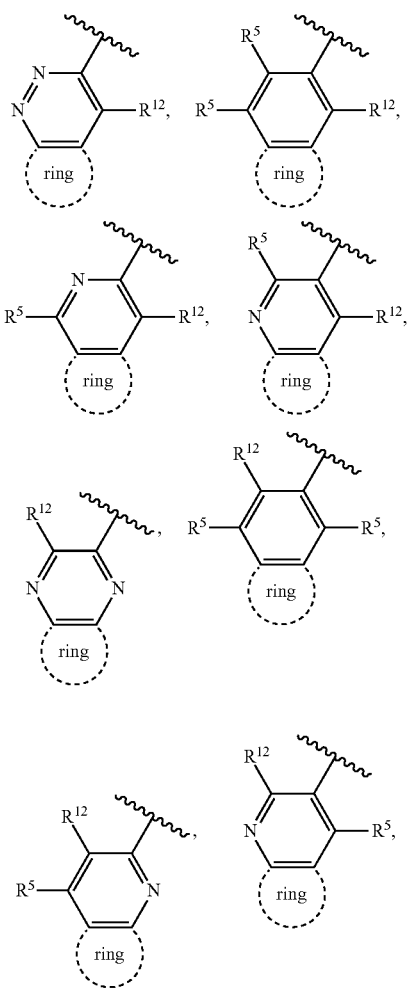

-continued
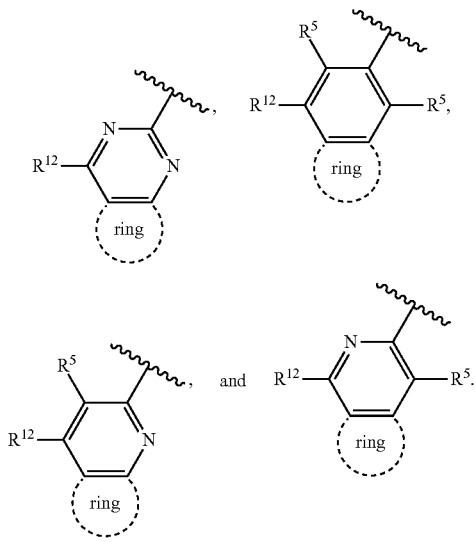
Examples of
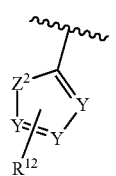
when present in a compound of the present invention include:
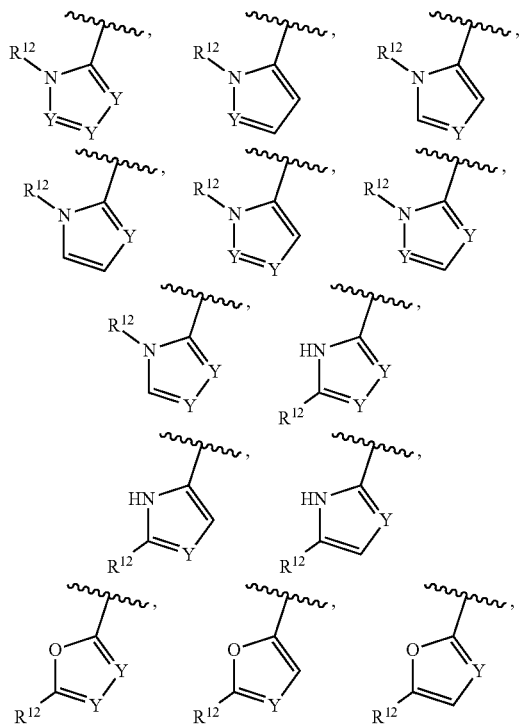
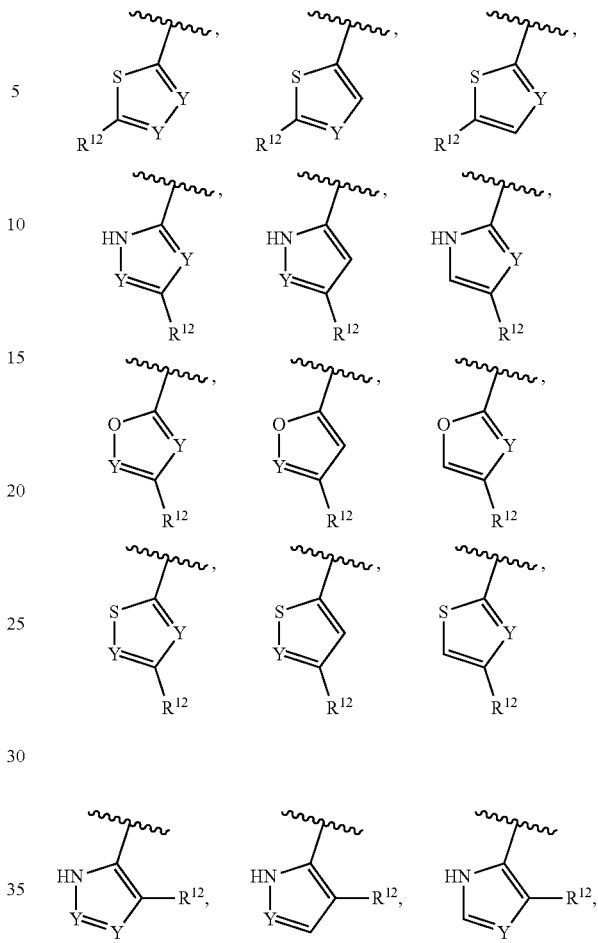
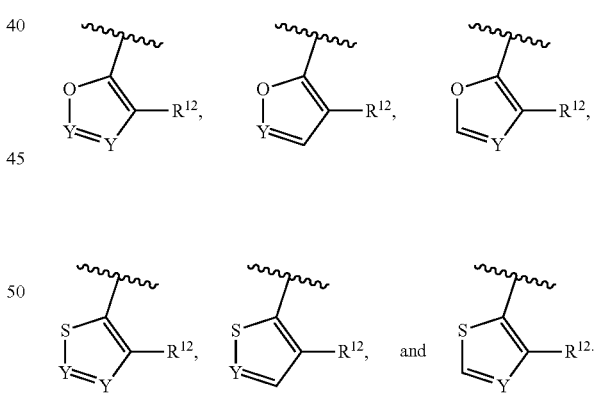
Additional examples of
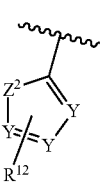

include:
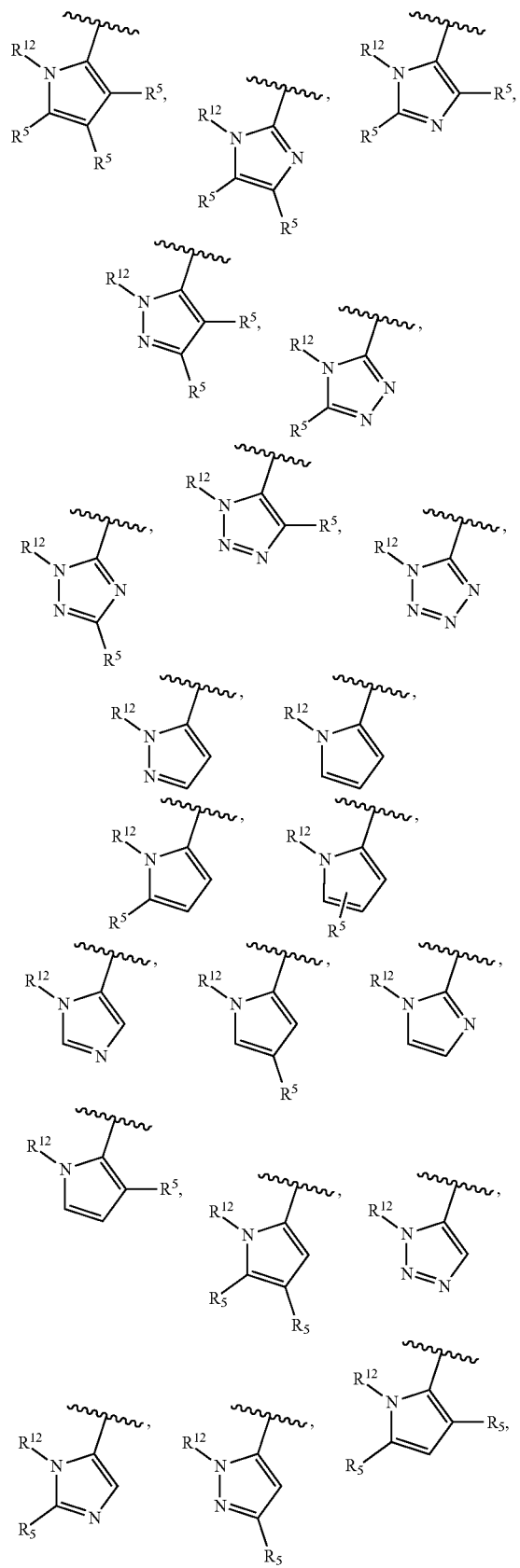
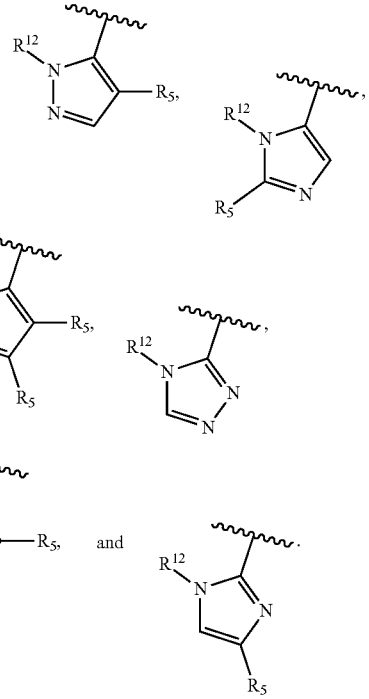
Additional examples of
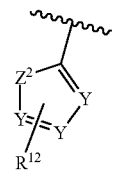
include:
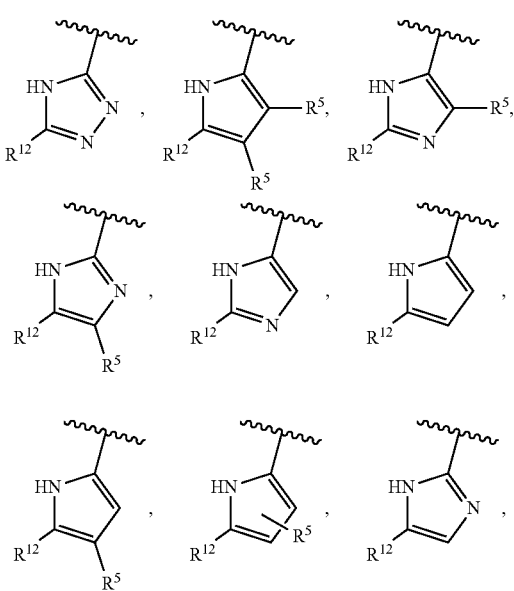

-continued
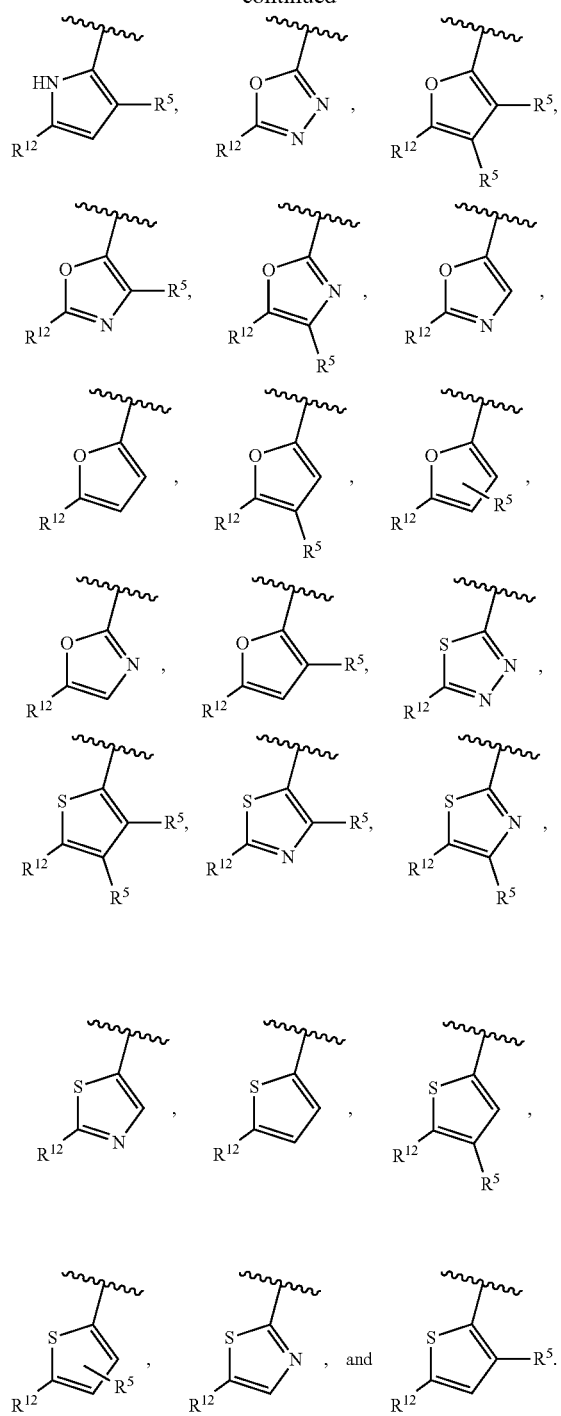
Additional examples of
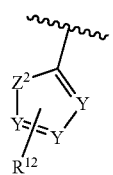
include:
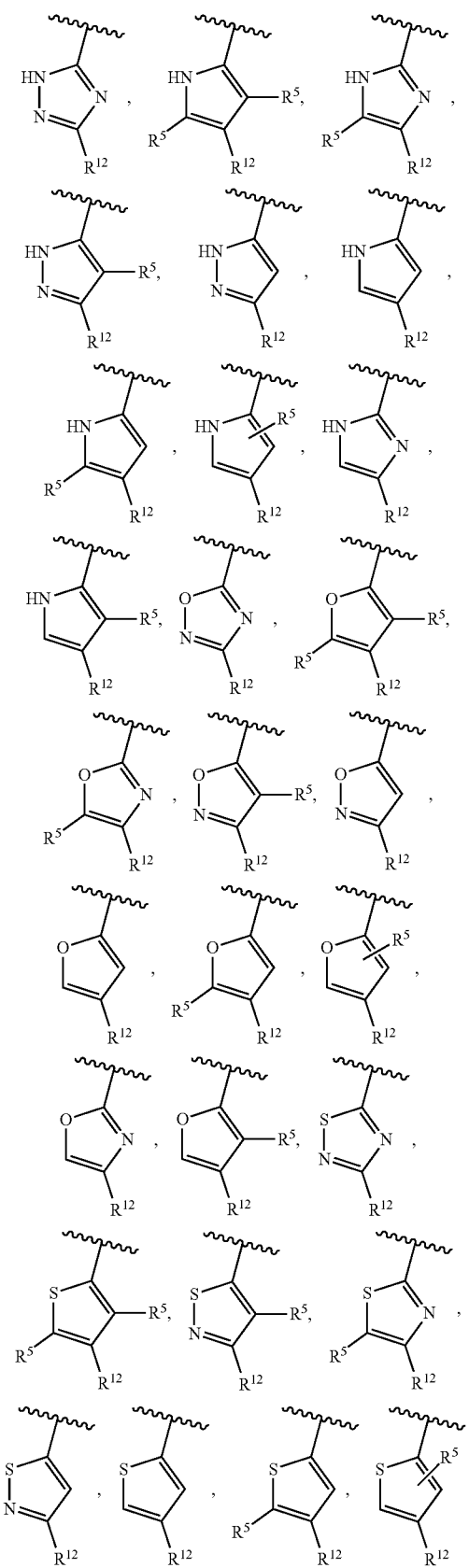

-continued
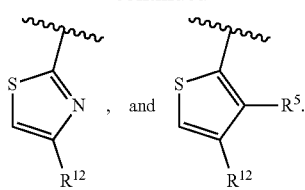
Additional examples of
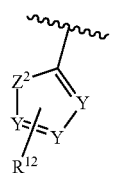
include:
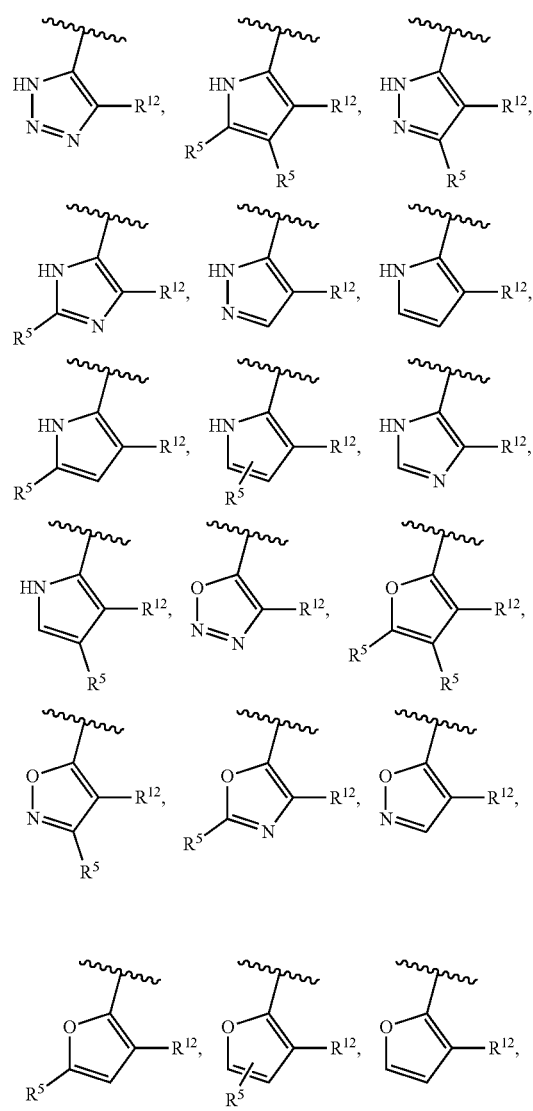
-continued
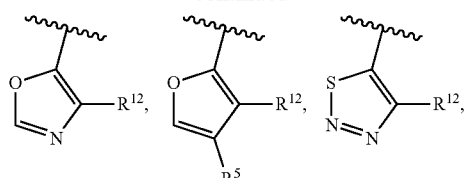
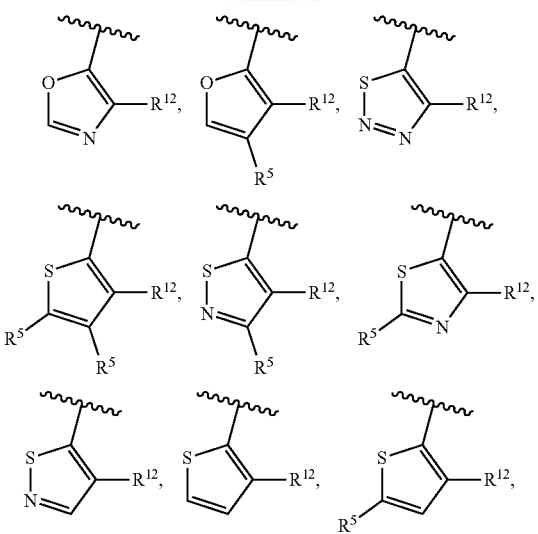
Examples of
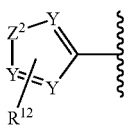
when present in a compound of a present invention include:
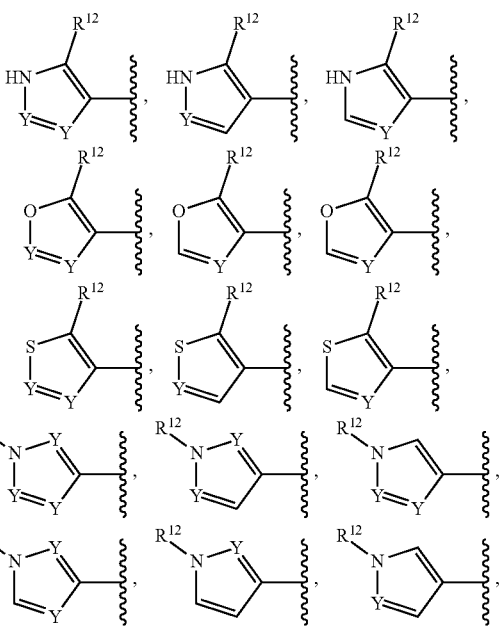

-continued
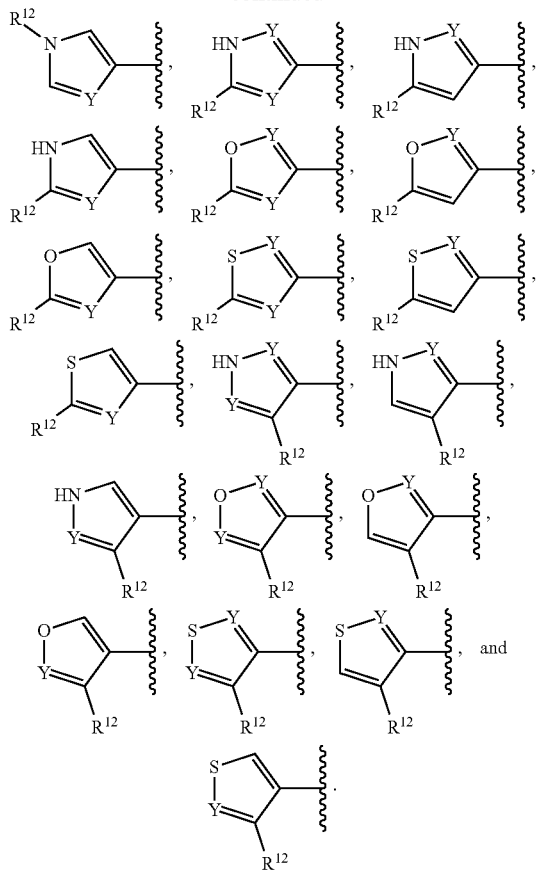
Additional examples of
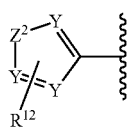
include:
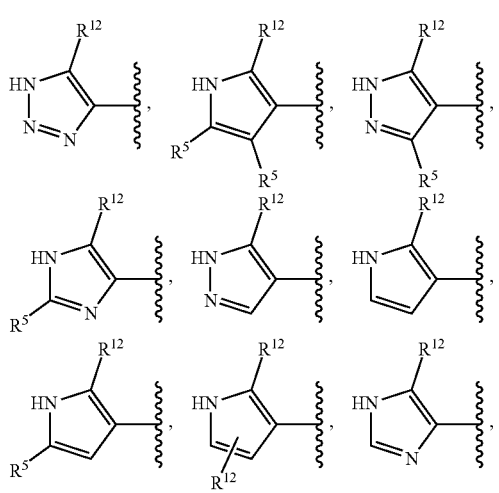
-continued
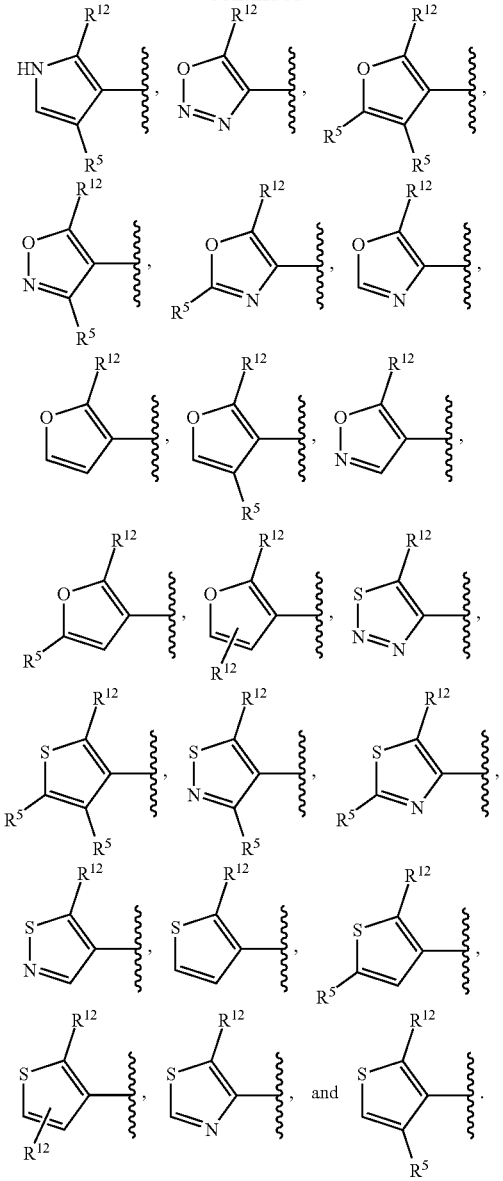
Additional examples of
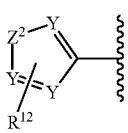
include:
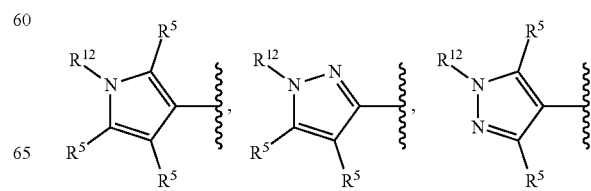

-continued
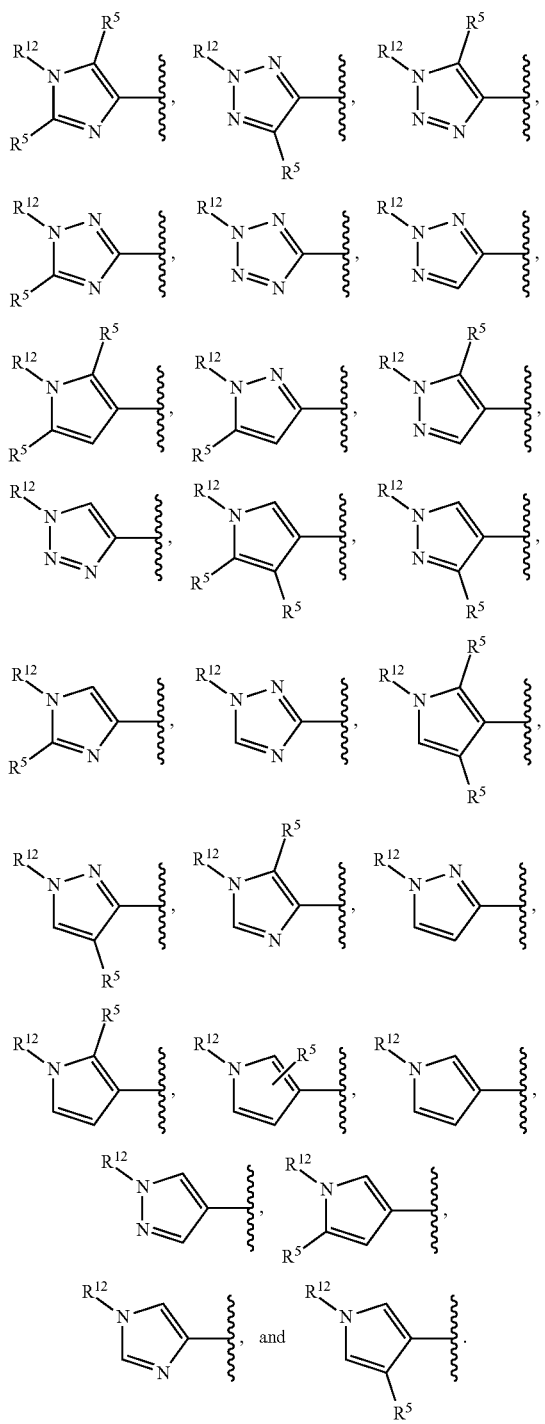
Additional examples of
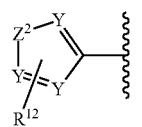
include:
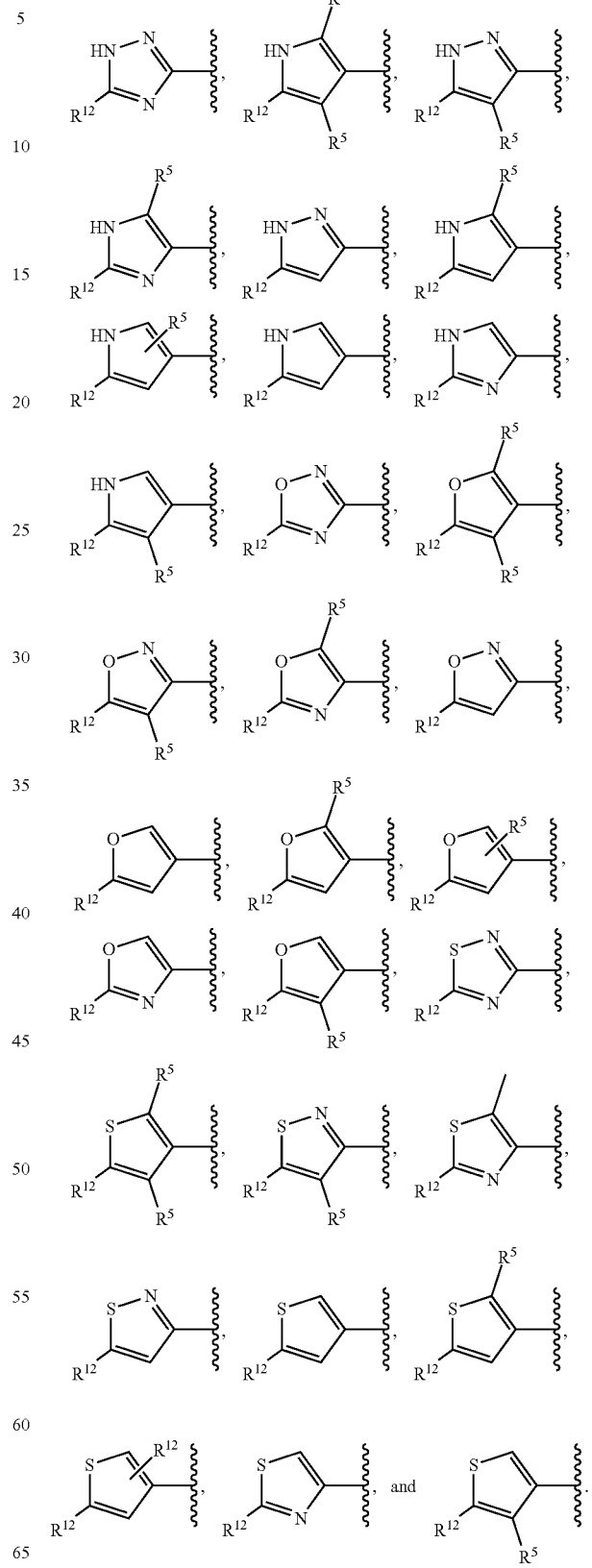

Additional examples of

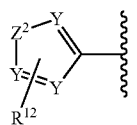

include:

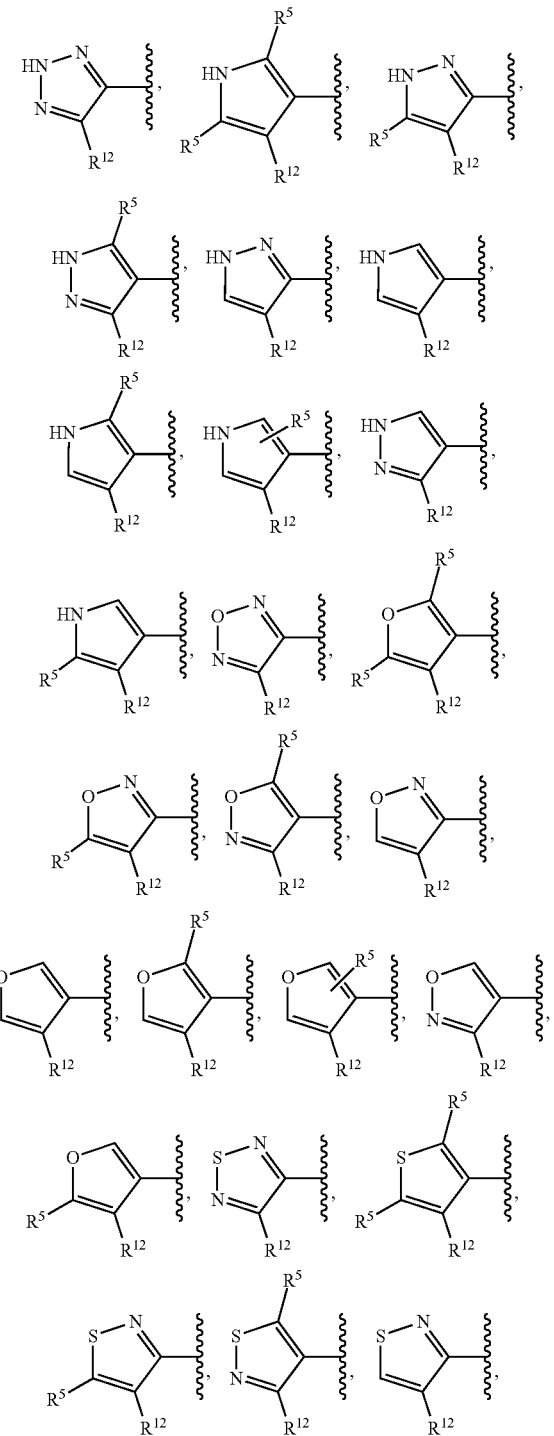

-continued

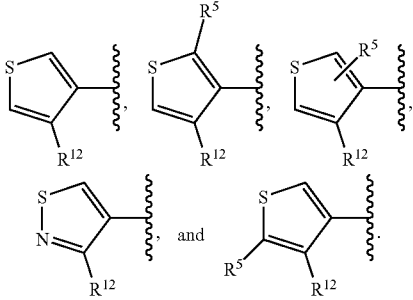

Examples of

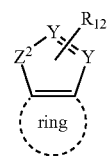

when present in one of the fused systems described above, for example, an illustrated aryl or heteroaryl moiety, includes at least the following:

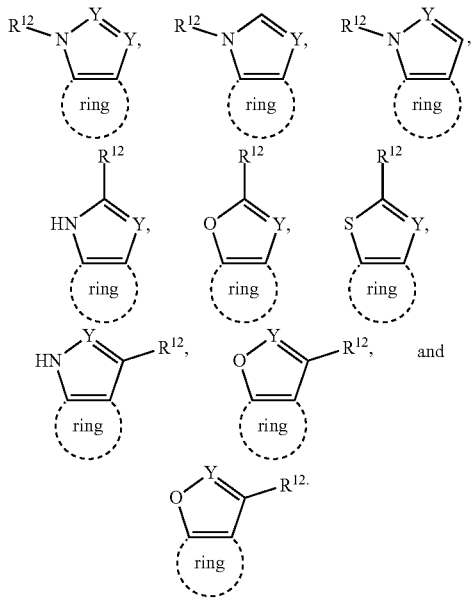

Additional examples of

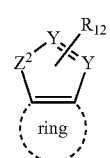

when present in one of the fused systems described above, for example, an illustrated aryl or heteroaryl moiety, includes at least the following:

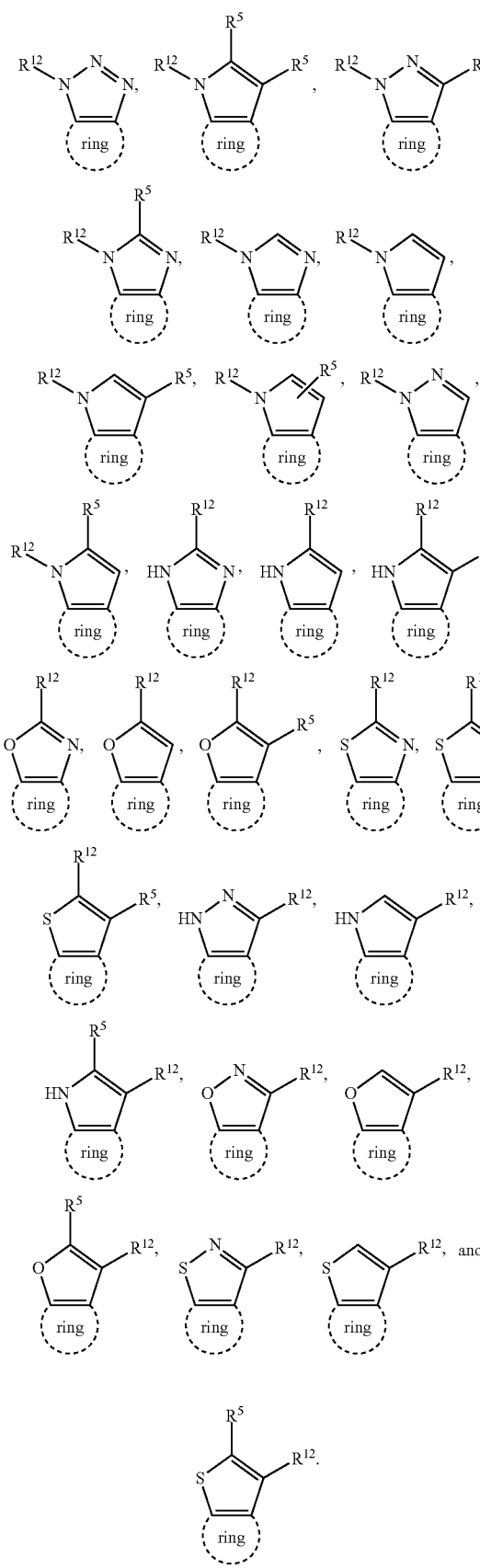
Examples of
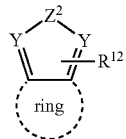
when present in one of the fused systems described above, for example, an illustrated aryl or heteroaryl moiety, includes at least the following:
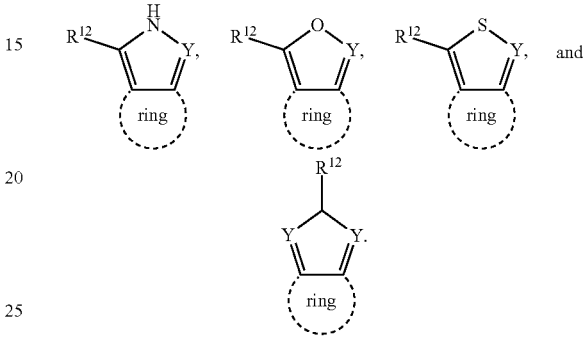
Additional examples of
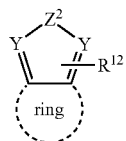
present in one of the fused systems described above, for example, an illustrated aryl or heteroaryl moiety, includes at least the following:
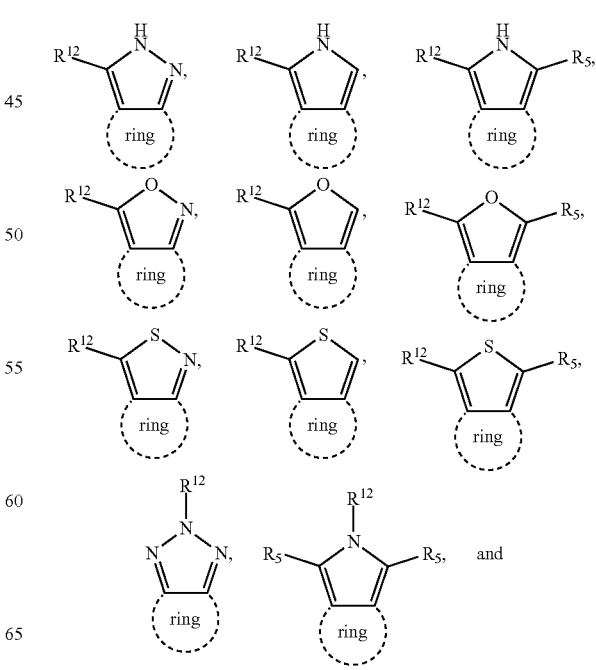

-continued
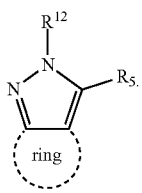
Examples of
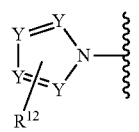
when present in a compound of the present invention include:
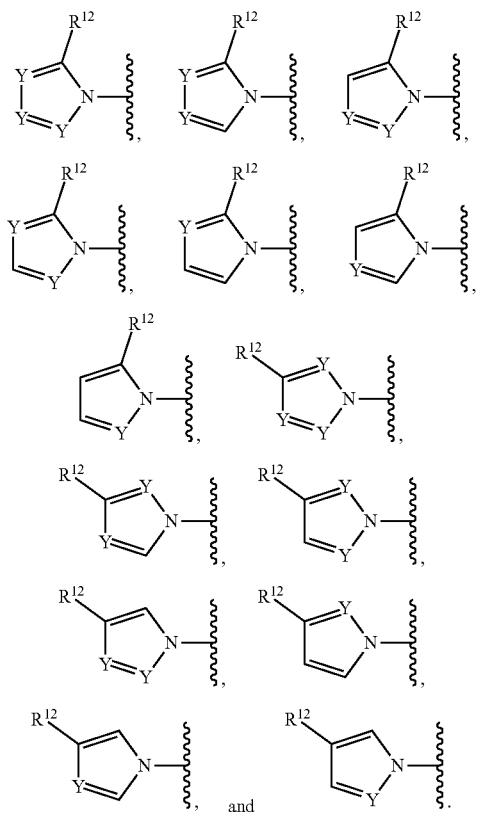
Additional examples of
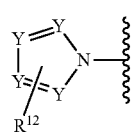
include:
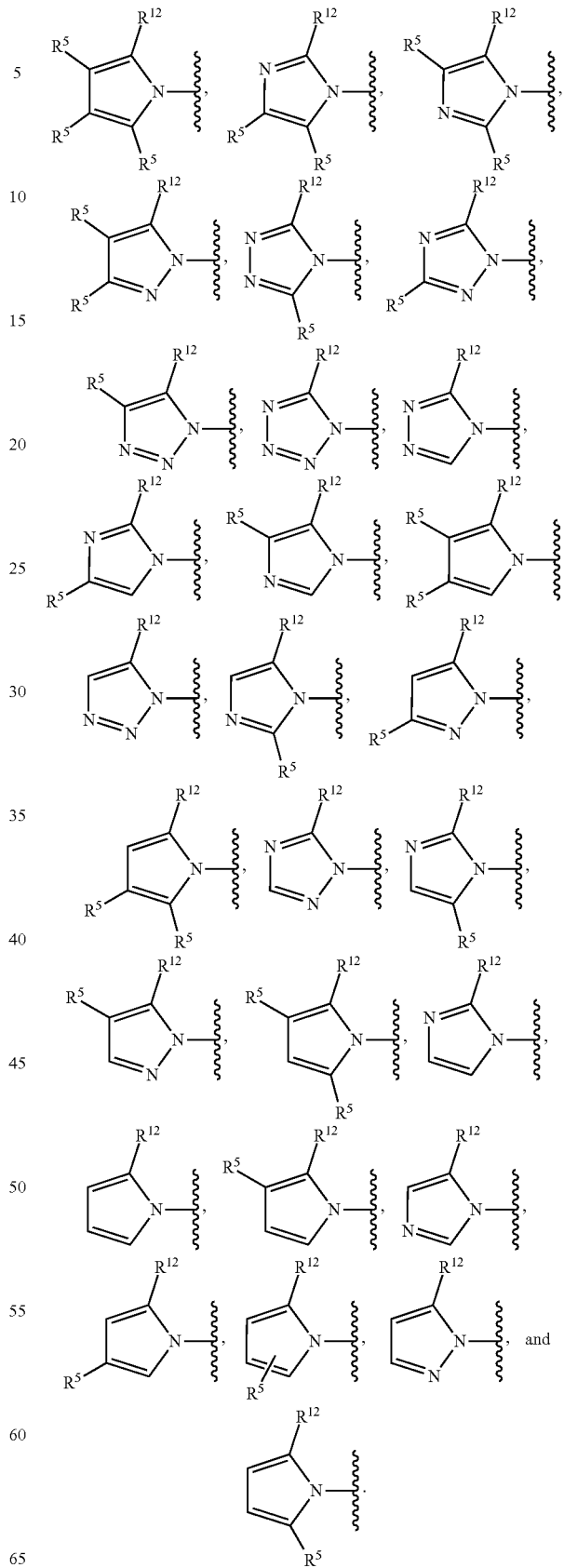

Additional examples of
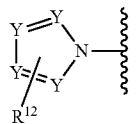
include:
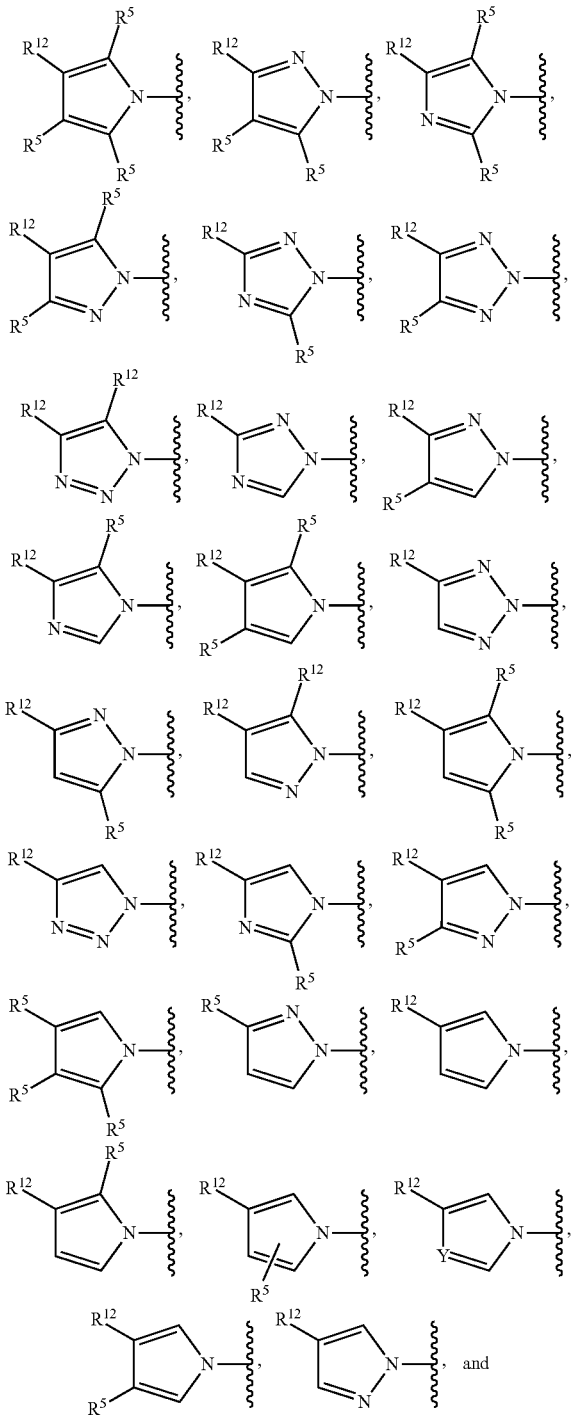
-continued
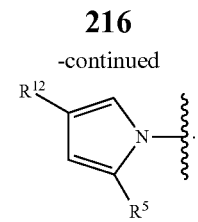
Examples of
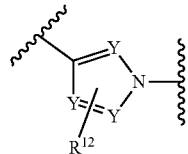
when present in a compound of the present invention include:
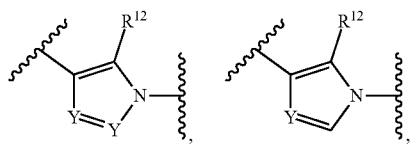
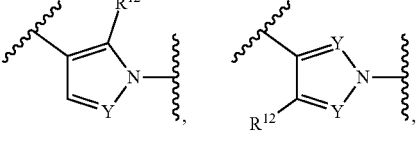
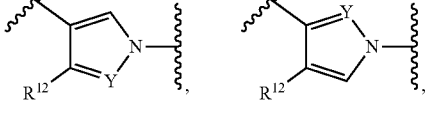
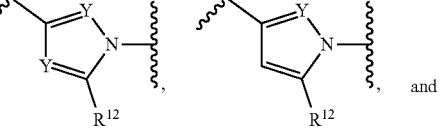, and
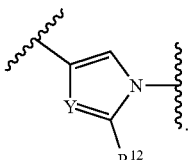
Additional examples of
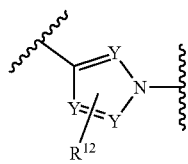

include:
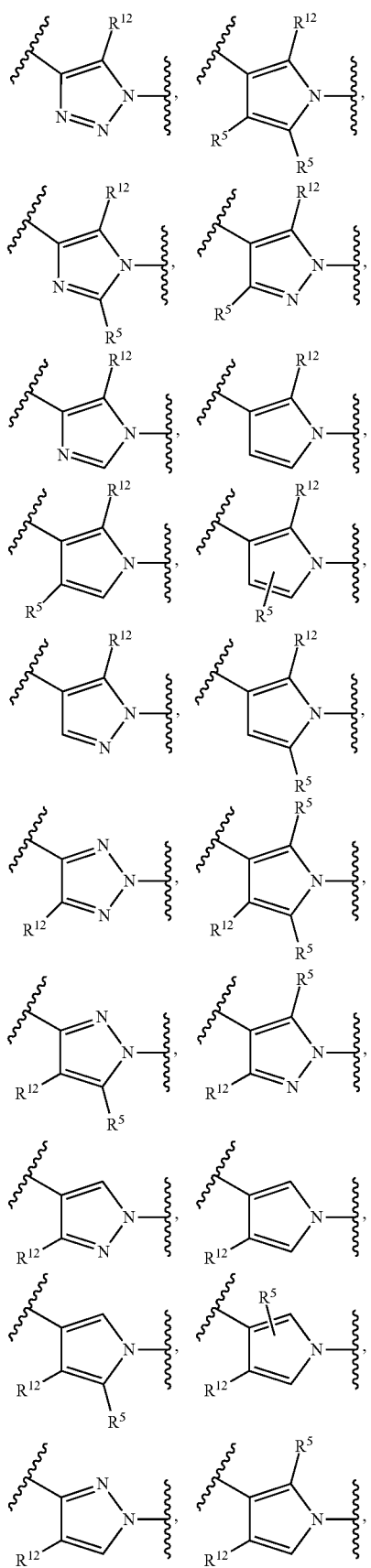
-continued
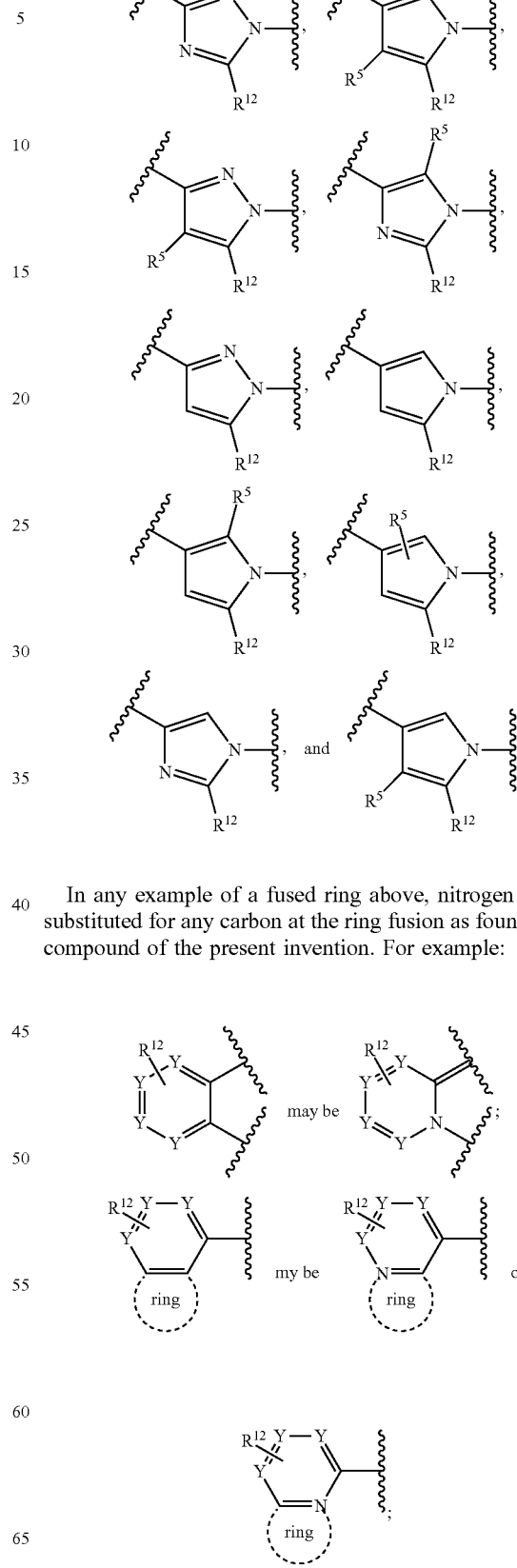
In any example of a fused ring above, nitrogen may be substituted for any carbon at the ring fusion as found in any compound of the present invention. For example:

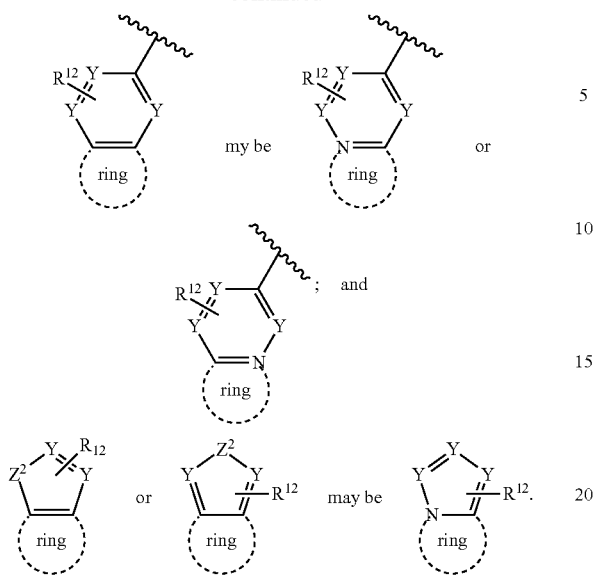

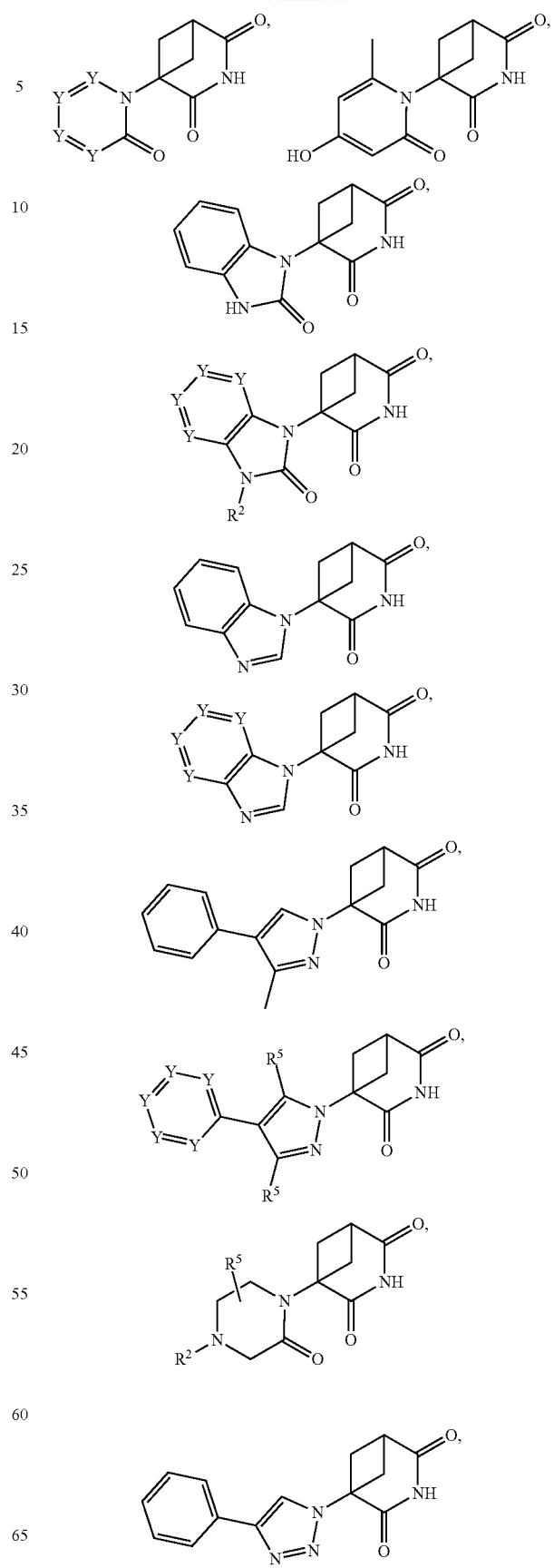

The above structures include compounds that are Degraders when $R^{12}$ is (Linker)$^A$-Targing Ligand and Degrons when $R^{12}$ is (Linker)$^B$. In other embodiments of the above structures, $R^{12}$ is hydrogen or $R^5$. In some embodiments the above structures are included in a compound of Formula V. In some embodiments the above structures are included in a compound of Formula VI. In some embodiments the above structures are included in a compound of Formula VII. In some embodiments the above structures are included in a compound of Formula VIII. In alternative embodiments the above structures are included in a compound of Formula XII.

III. Compounds of Formula V, Formula VI, Formula VII, and Formula VIII

Non-limiting examples of compounds of Formula V include:

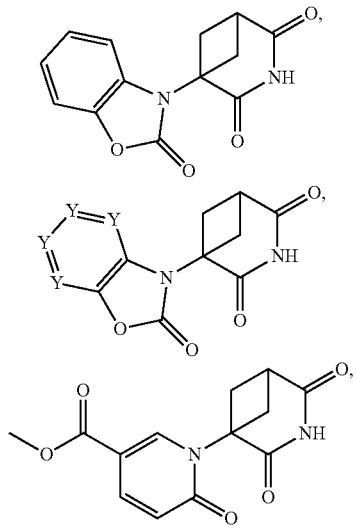

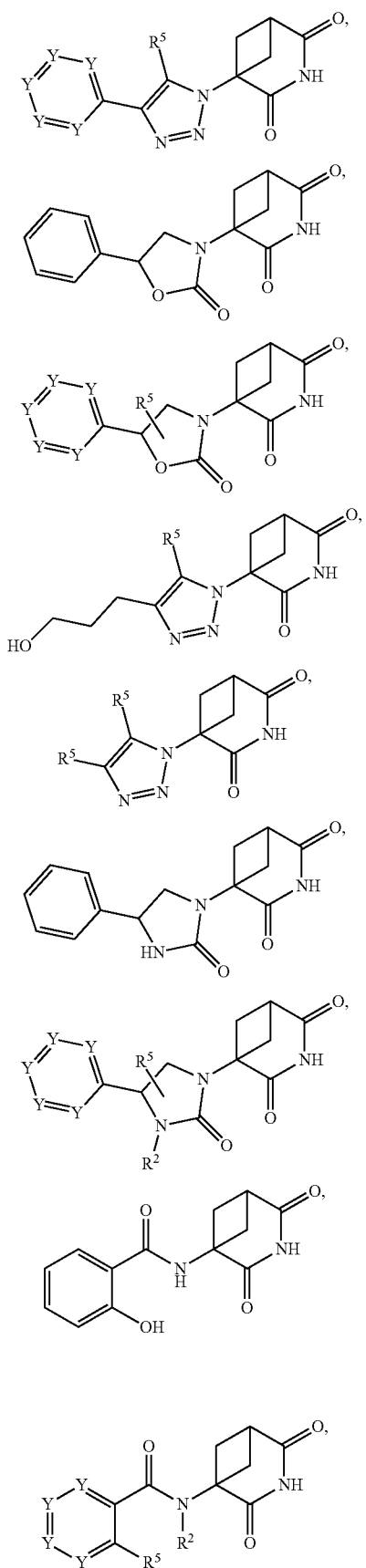
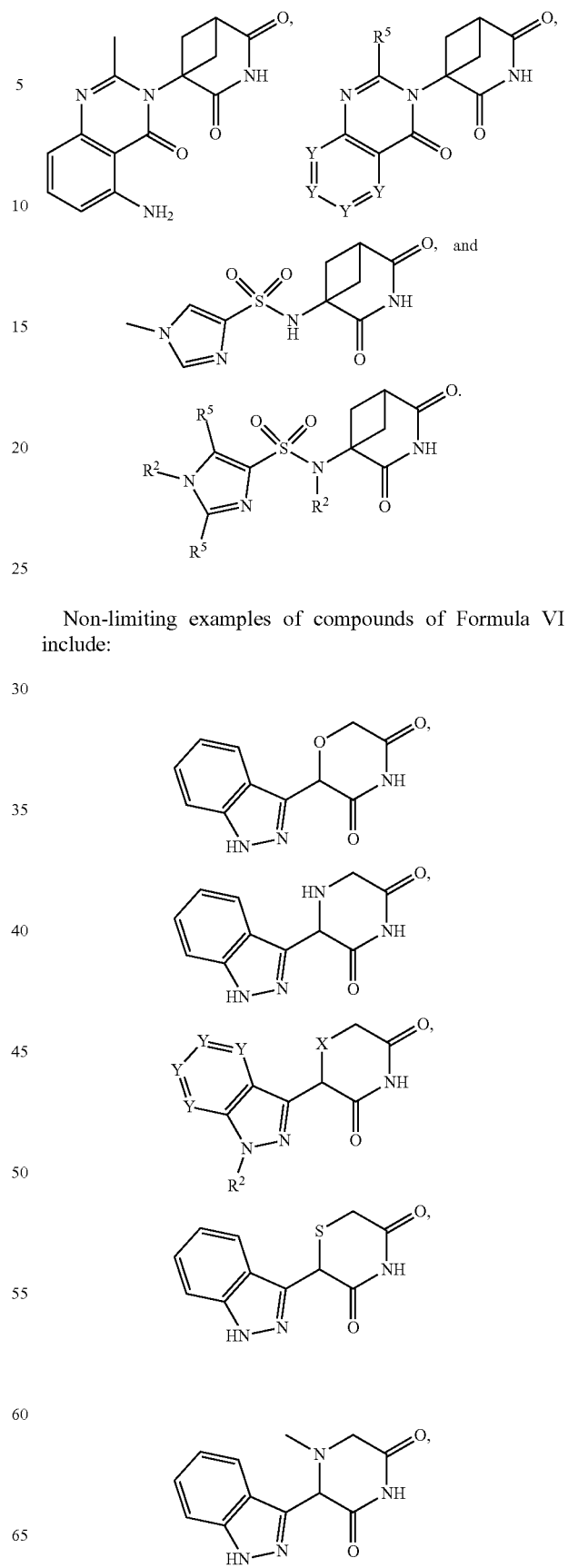
Non-limiting examples of compounds of Formula VI include:

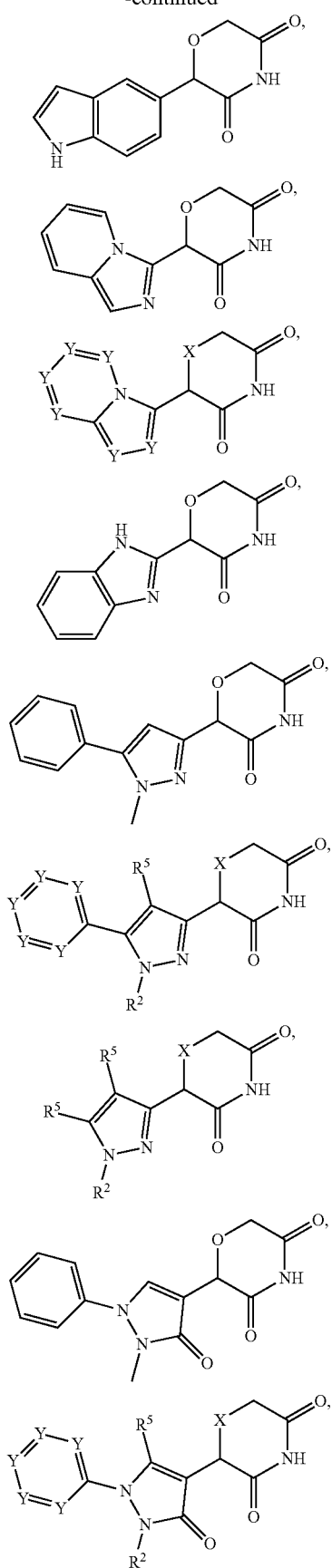
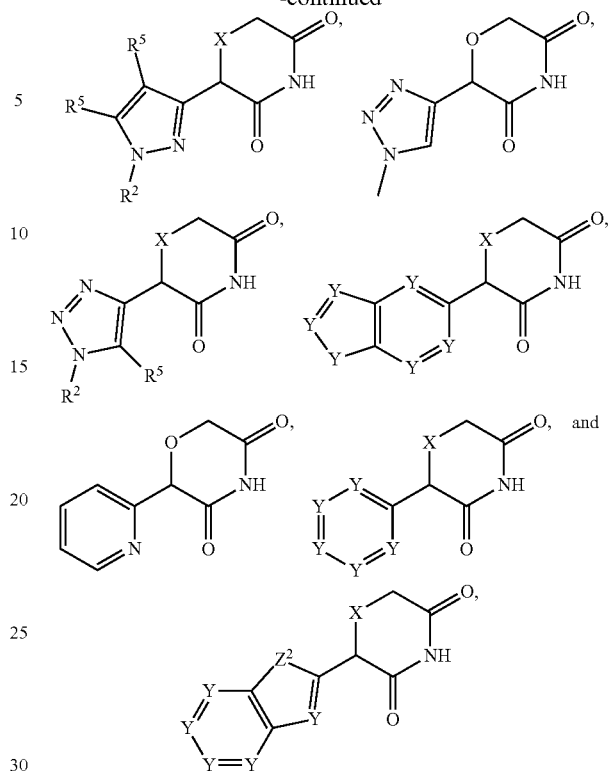
Additional non-limiting examples of compounds of Formula V include:
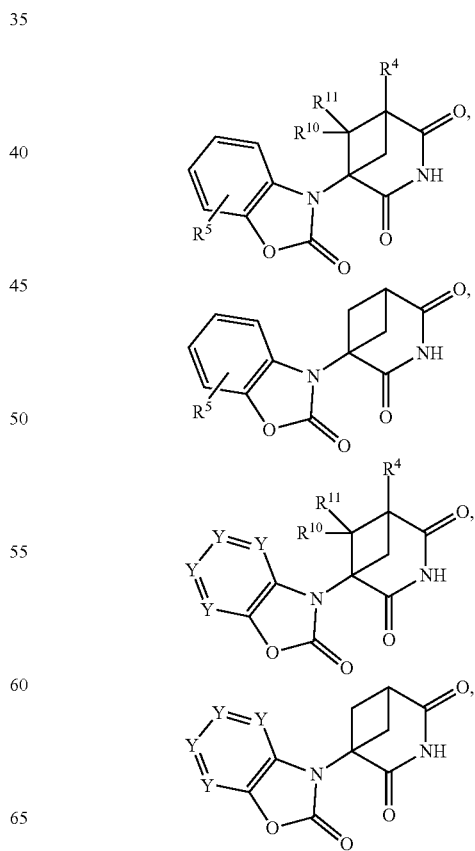

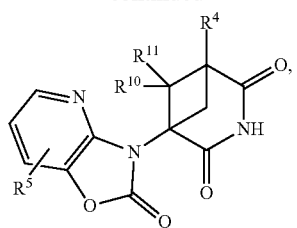
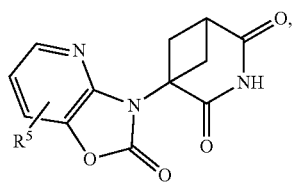
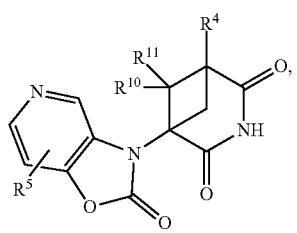
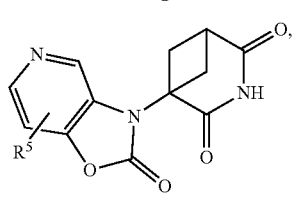
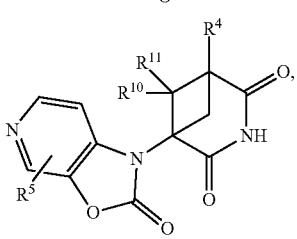
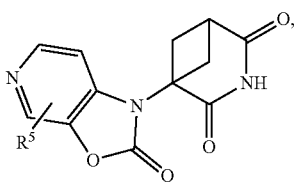
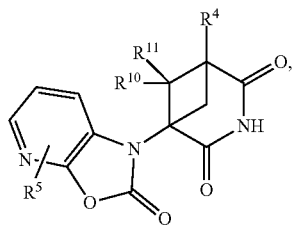
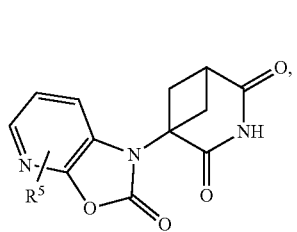
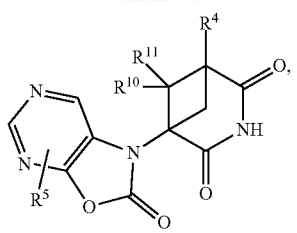
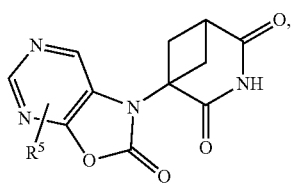
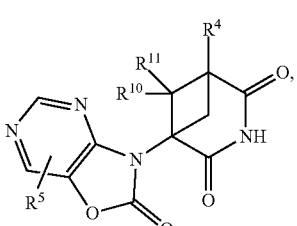
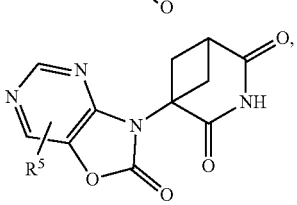
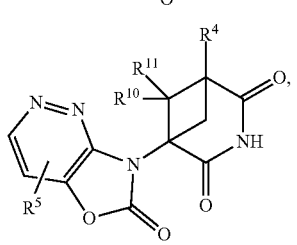
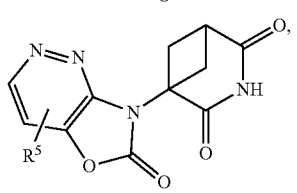
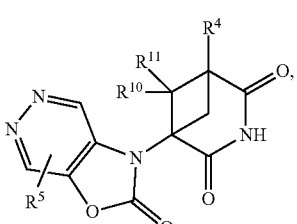
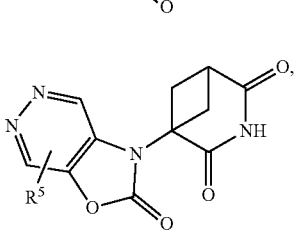

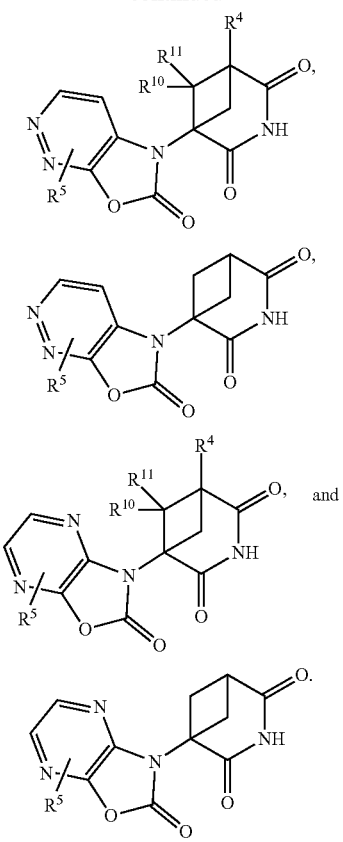
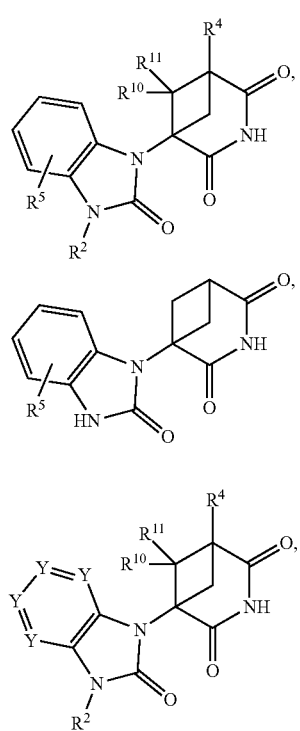
Additional non-limiting examples of compounds of Formula V include:
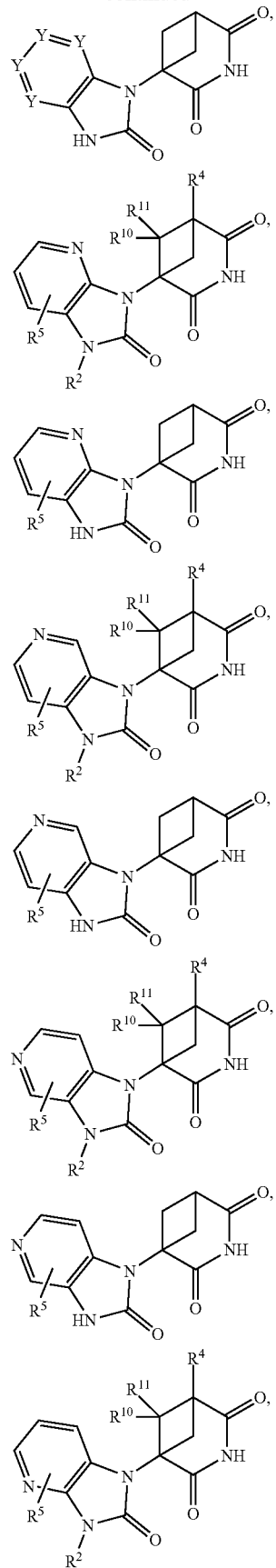

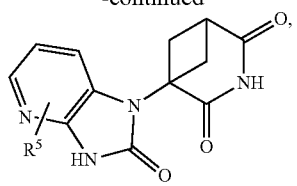
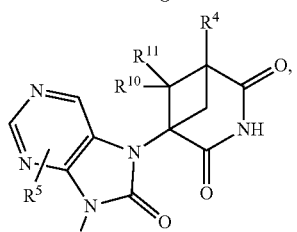
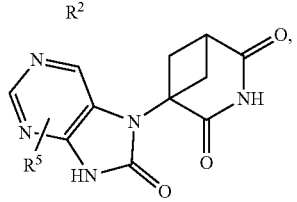
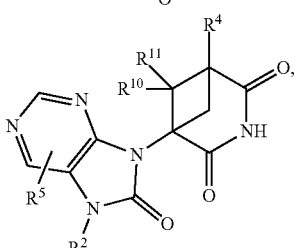
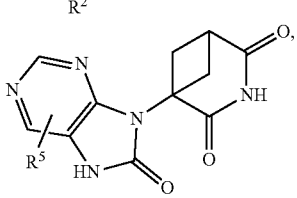
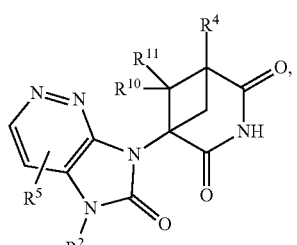
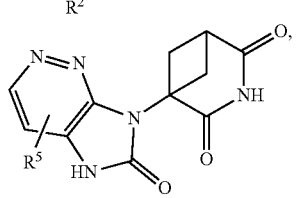
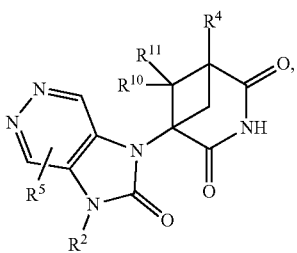
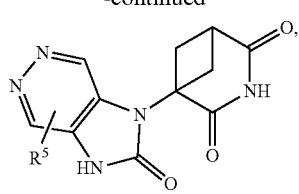
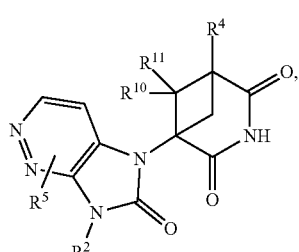
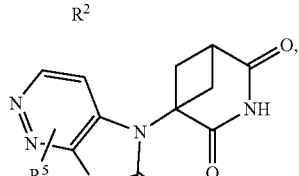
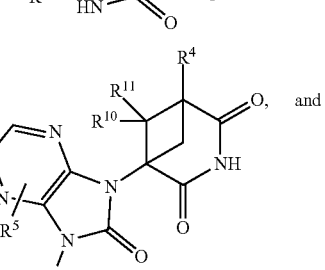
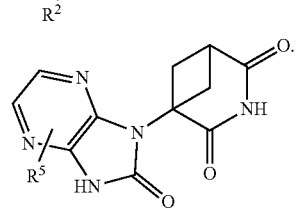
Additional non-limiting examples of compounds of Formula V include:
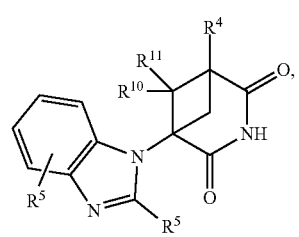
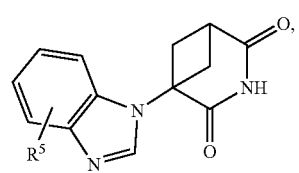

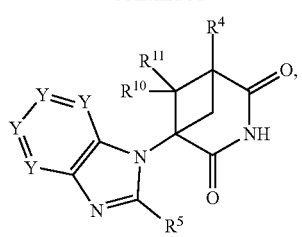
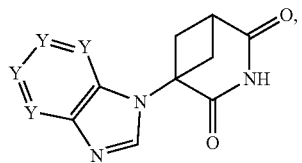
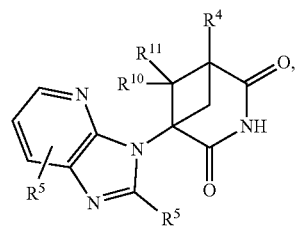
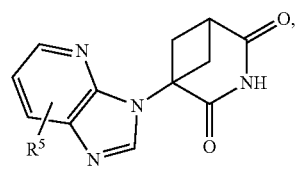
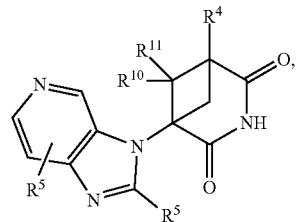
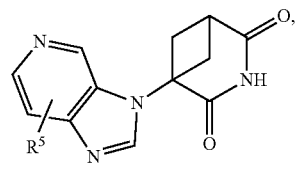
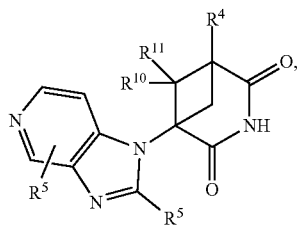
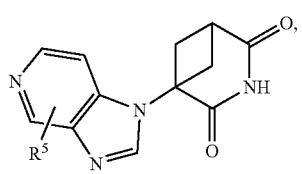
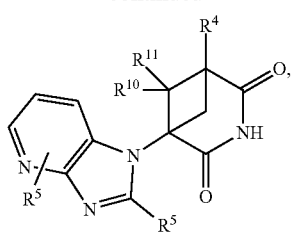
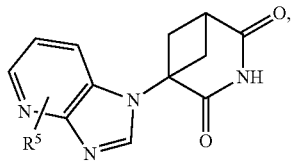
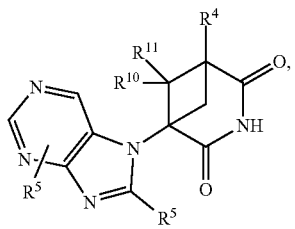
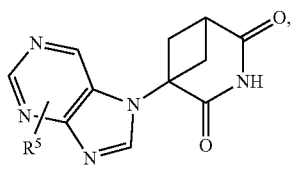
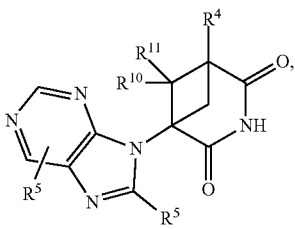
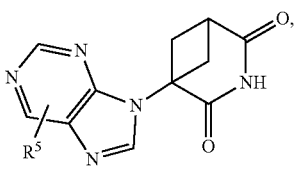
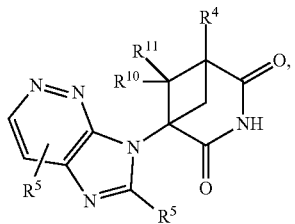
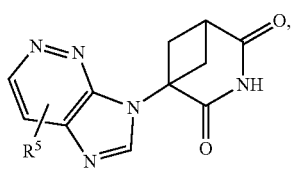

-continued
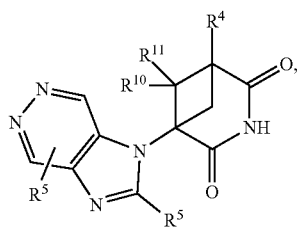
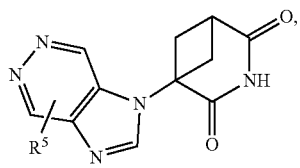
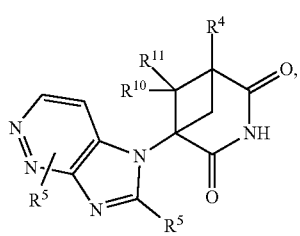
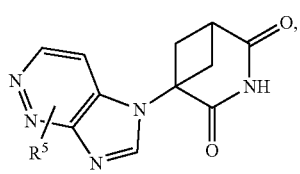
and
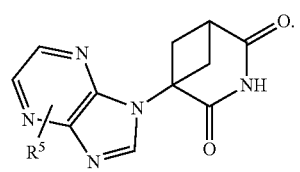
Additional non-limiting examples of compounds of Formula V include:
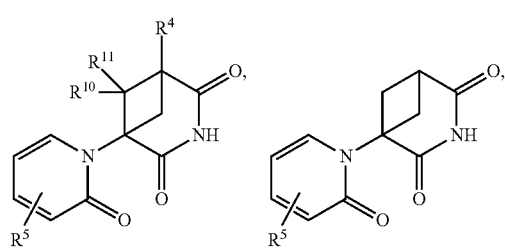
-continued
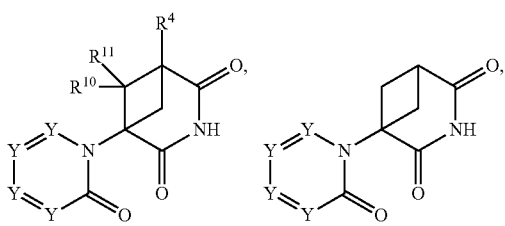
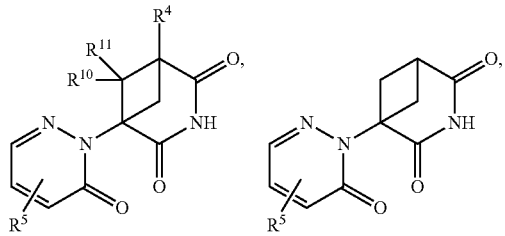
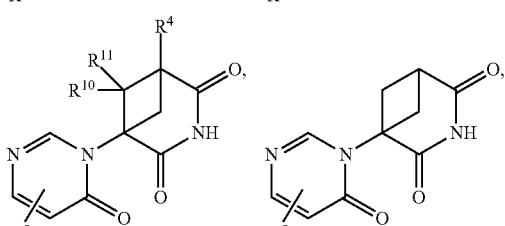
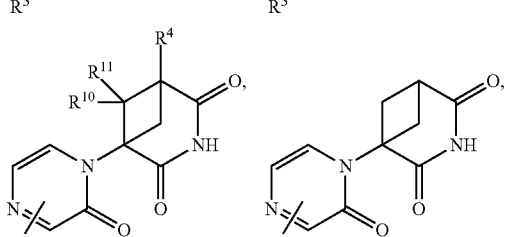
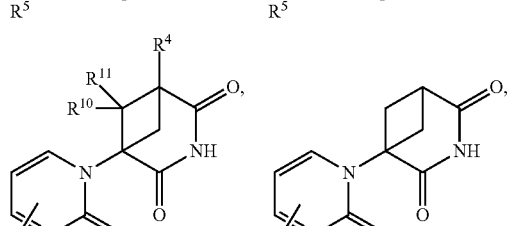
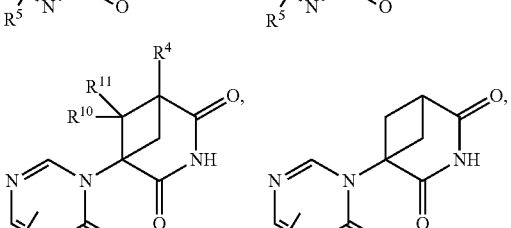
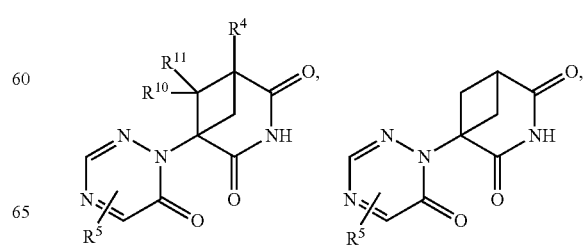

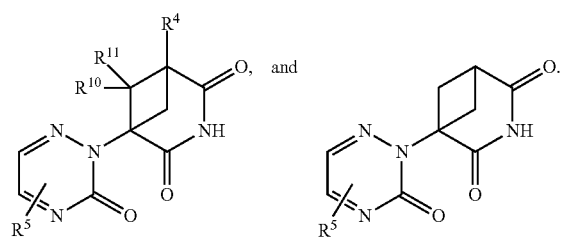
Additional non-limiting examples of compounds of Formula V include:
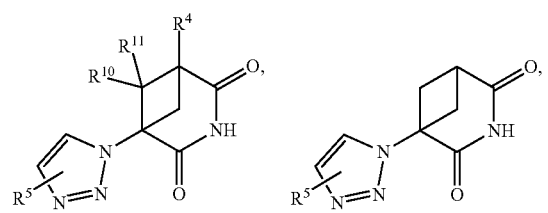
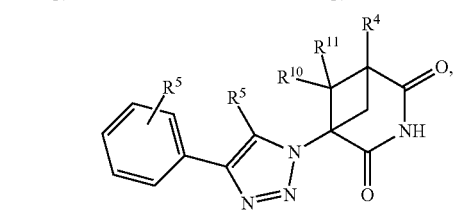
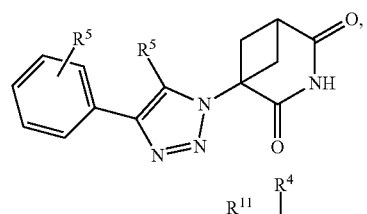
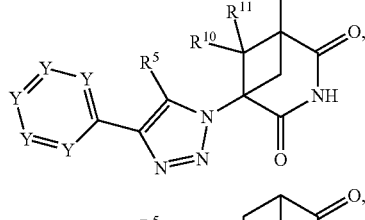
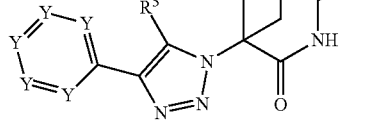
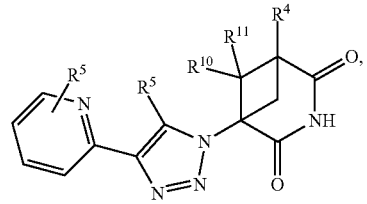
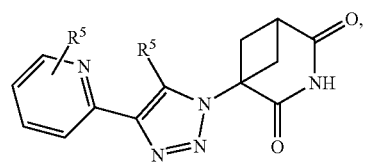
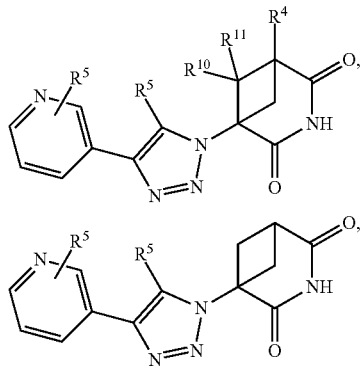
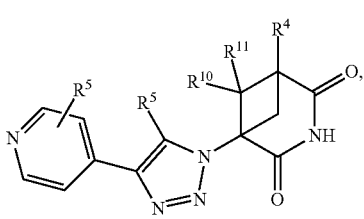
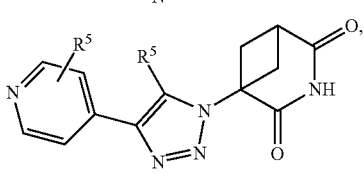
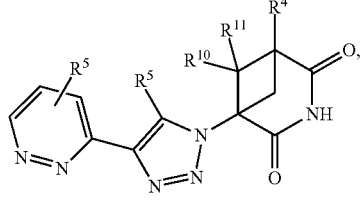
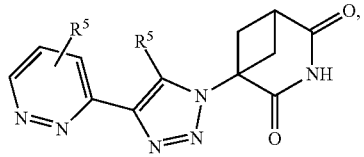
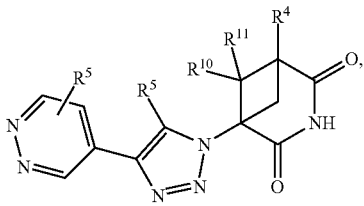
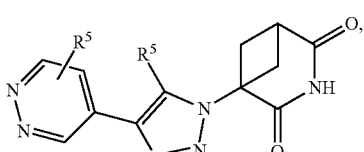
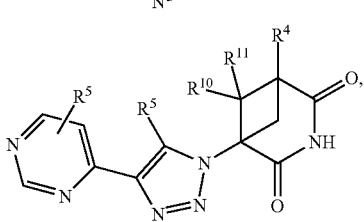

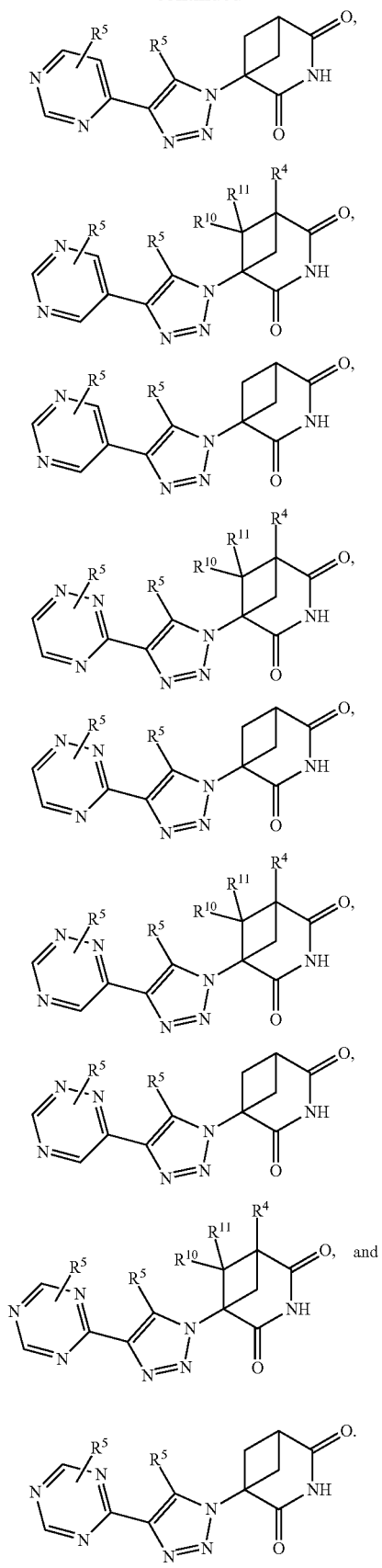
Additional non-limiting examples of compounds of Formula V include:
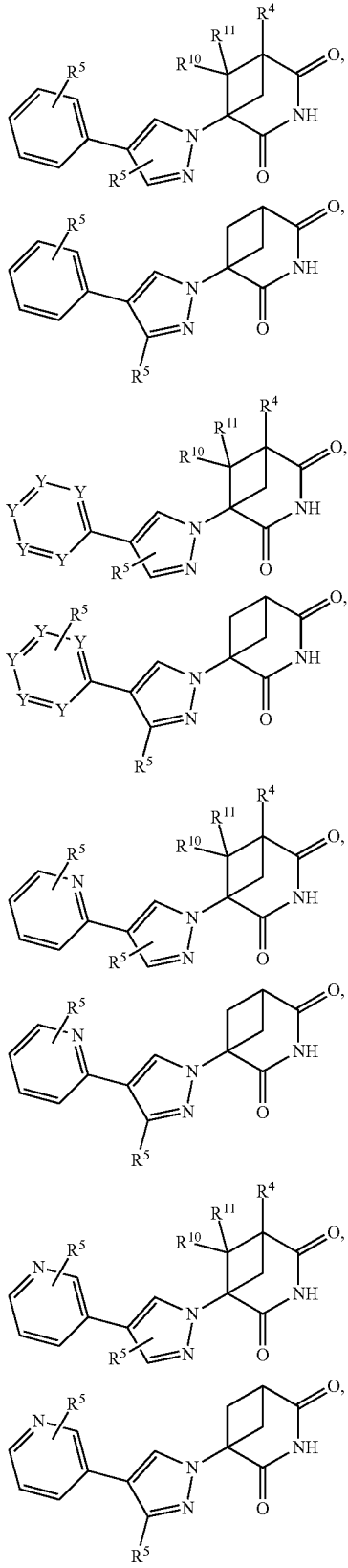

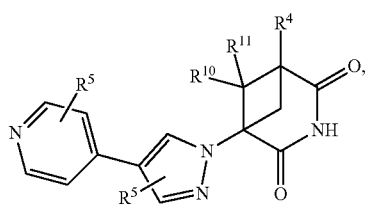
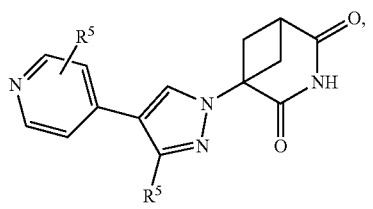
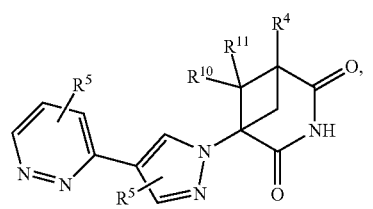
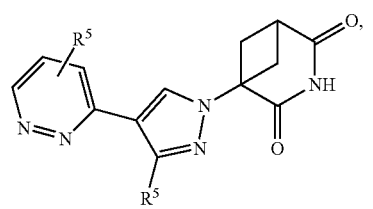
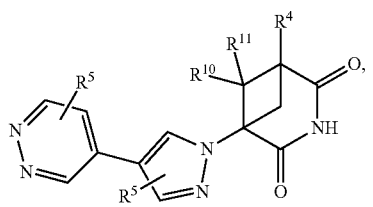
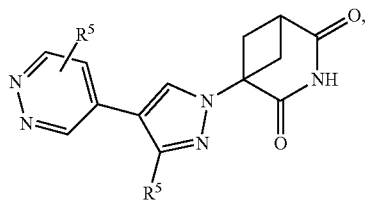
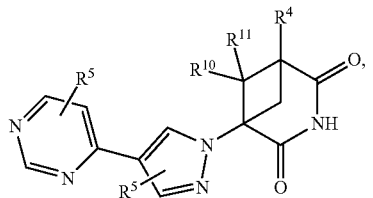
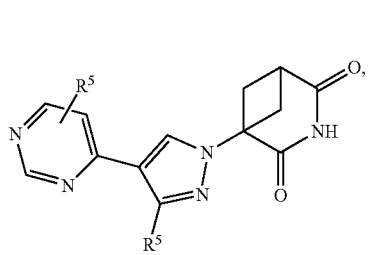
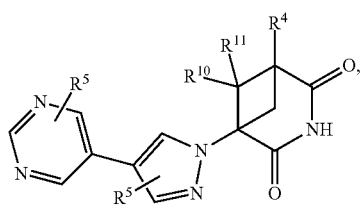
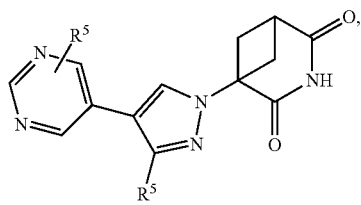
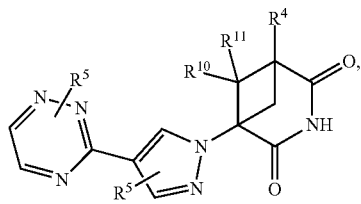
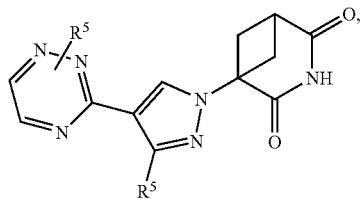
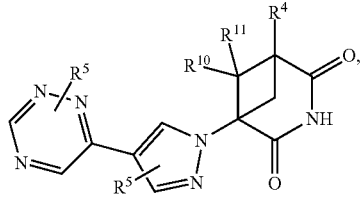
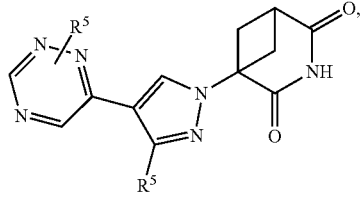
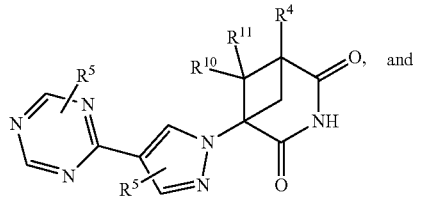
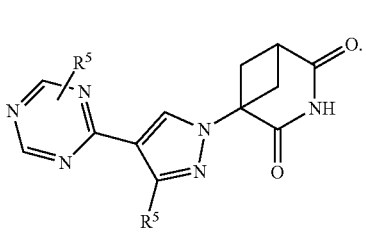

Additional non-limiting examples of compounds of Formula V include:
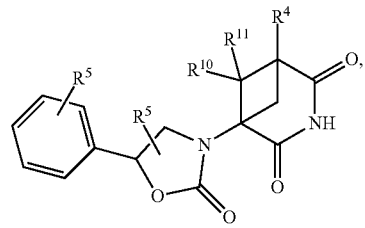
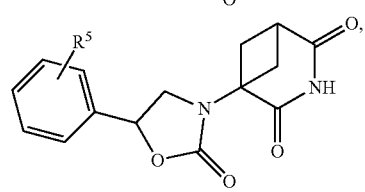
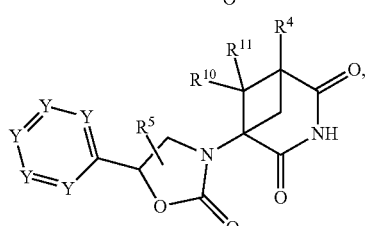
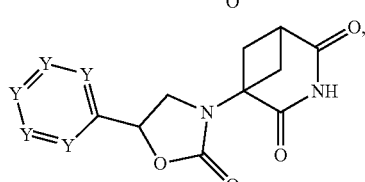
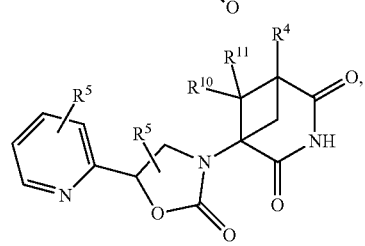
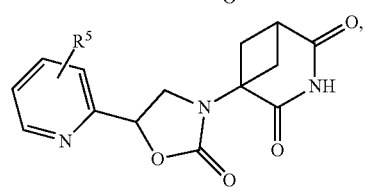
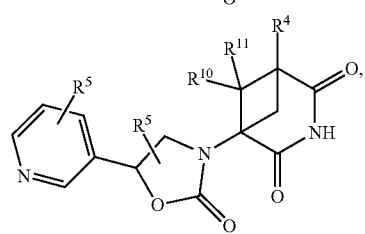
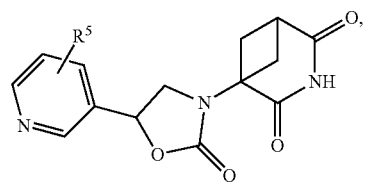
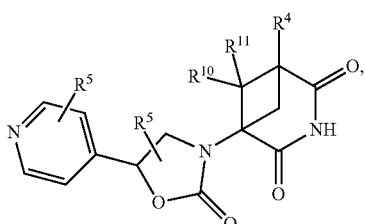
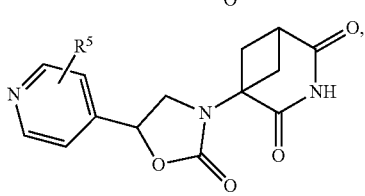
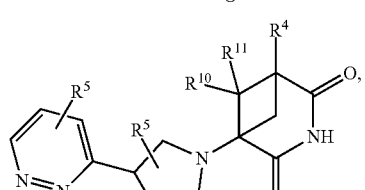
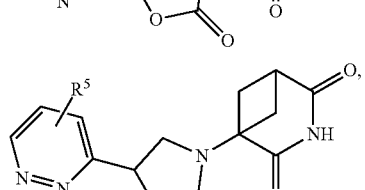
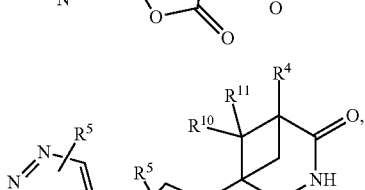
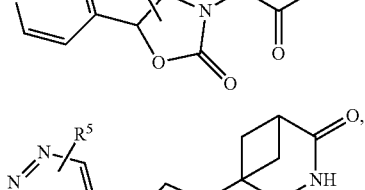
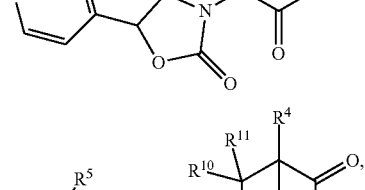
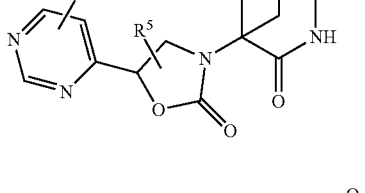
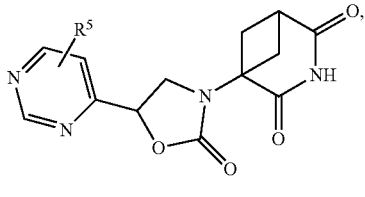

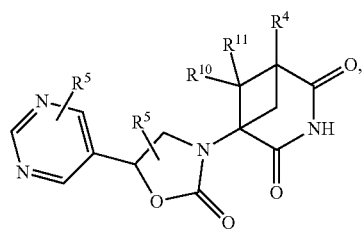
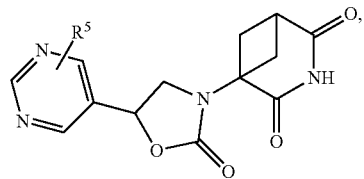
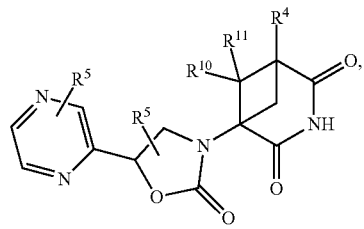
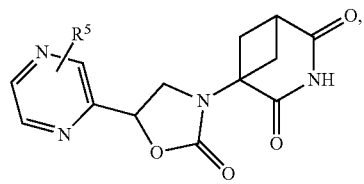
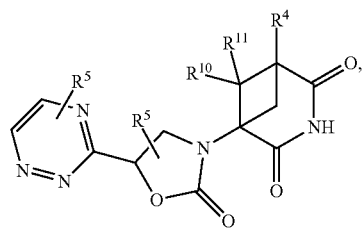
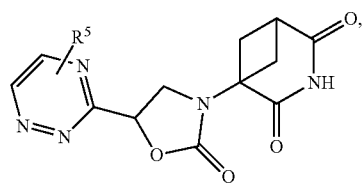
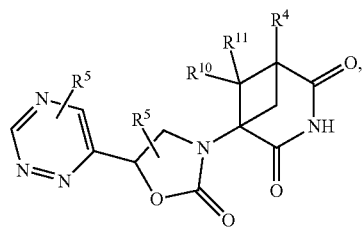
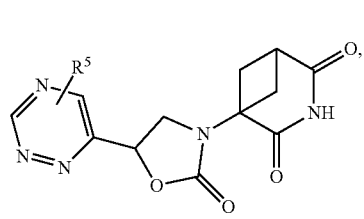
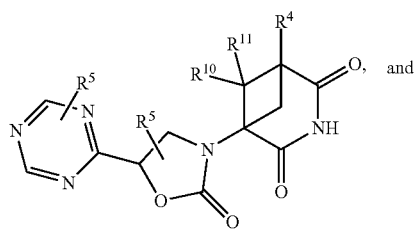
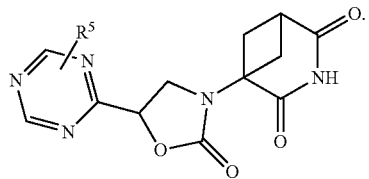
Additional non-limiting examples of compounds of Formula V include:
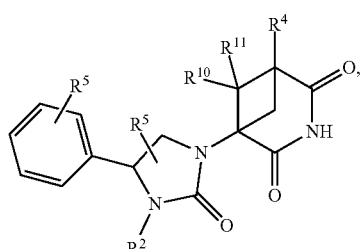
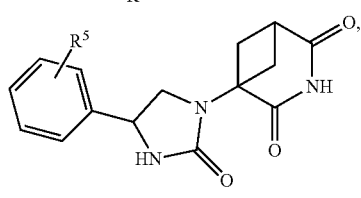
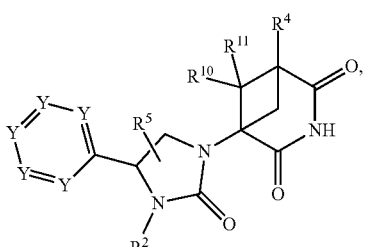
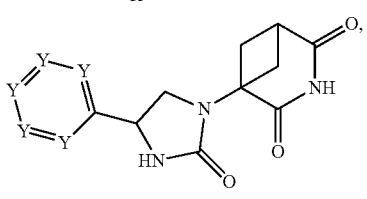
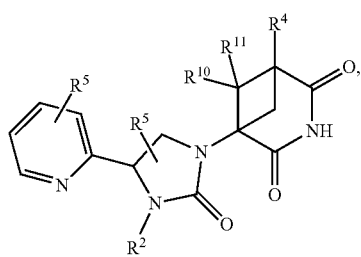

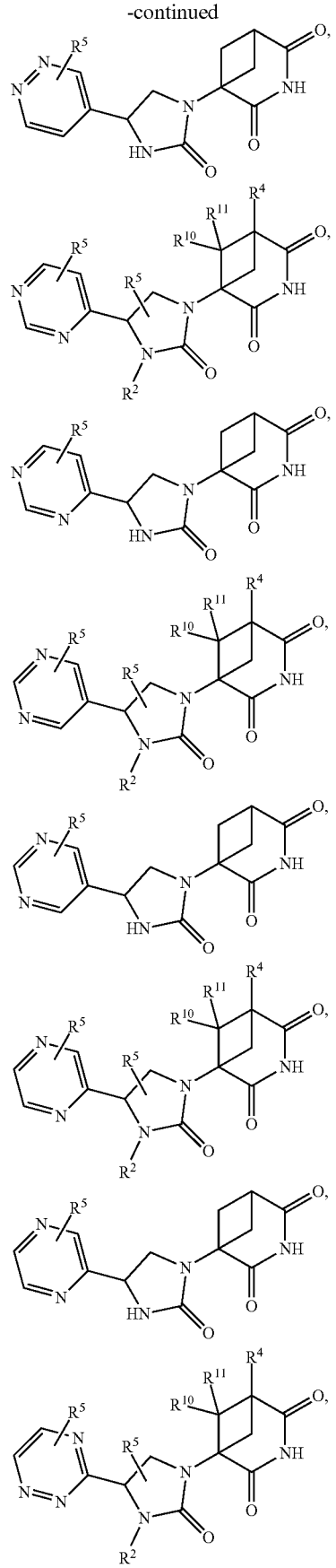

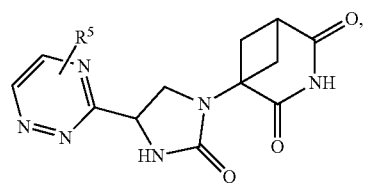
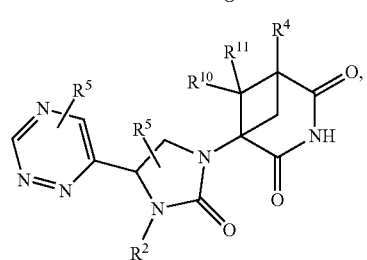
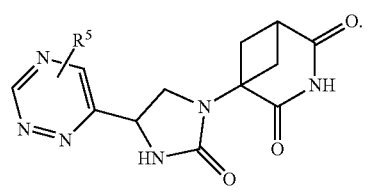
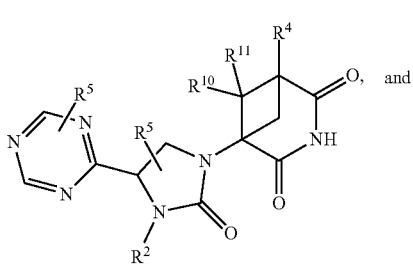
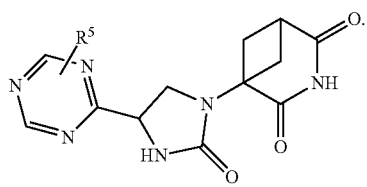
and
Additional non-limiting examples of compounds of Formula V include:
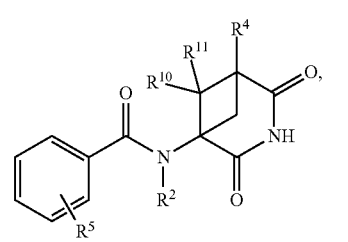
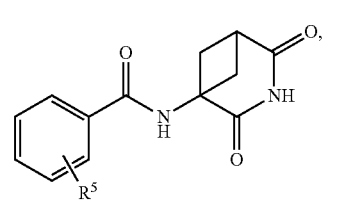
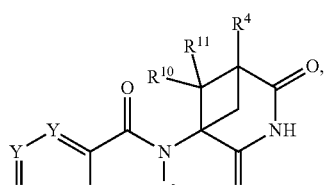
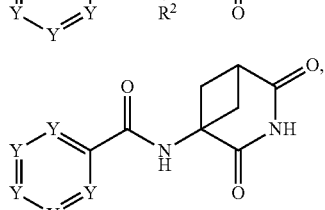
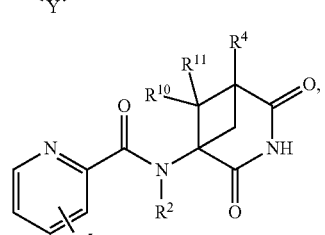
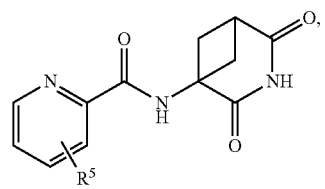
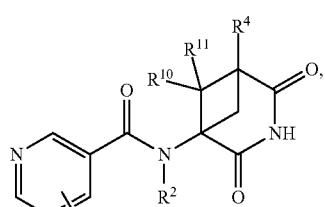
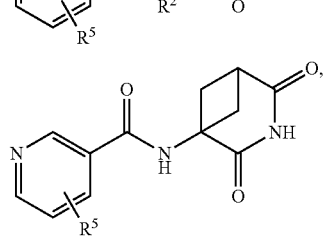
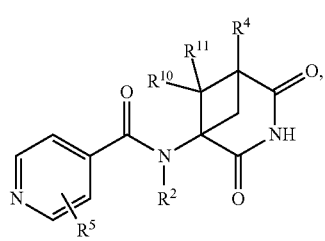
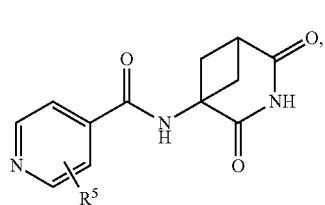

-continued
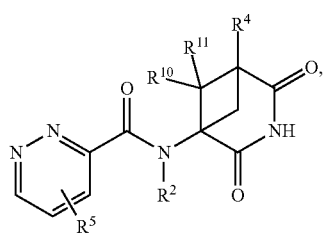
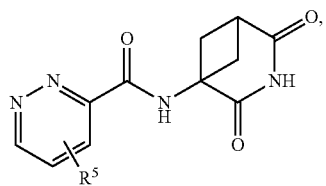
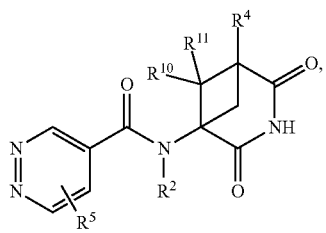
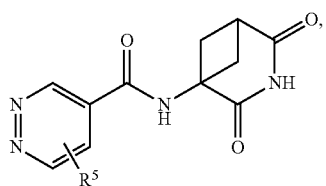
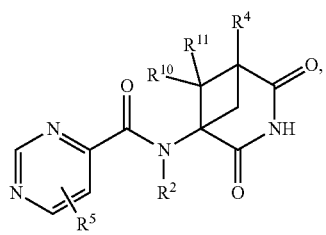
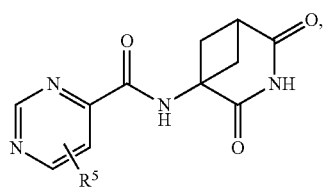
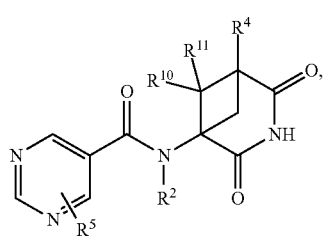
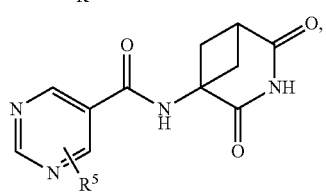
-continued
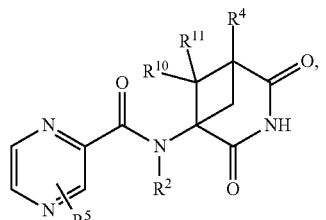
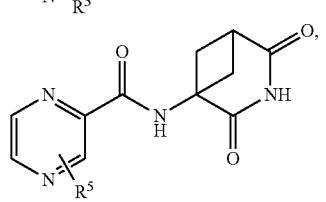
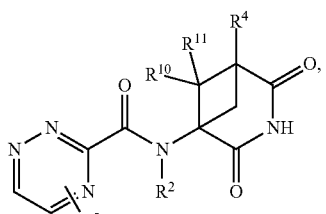
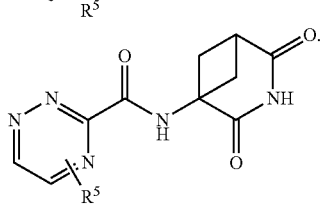
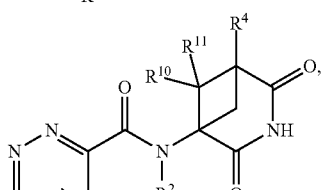
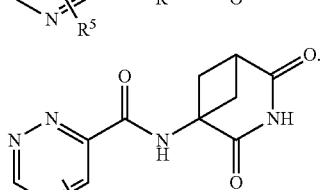
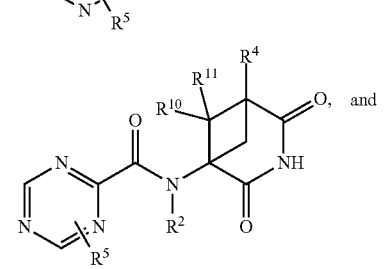
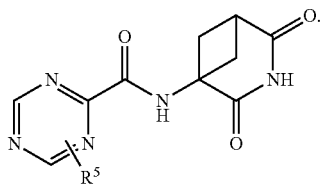

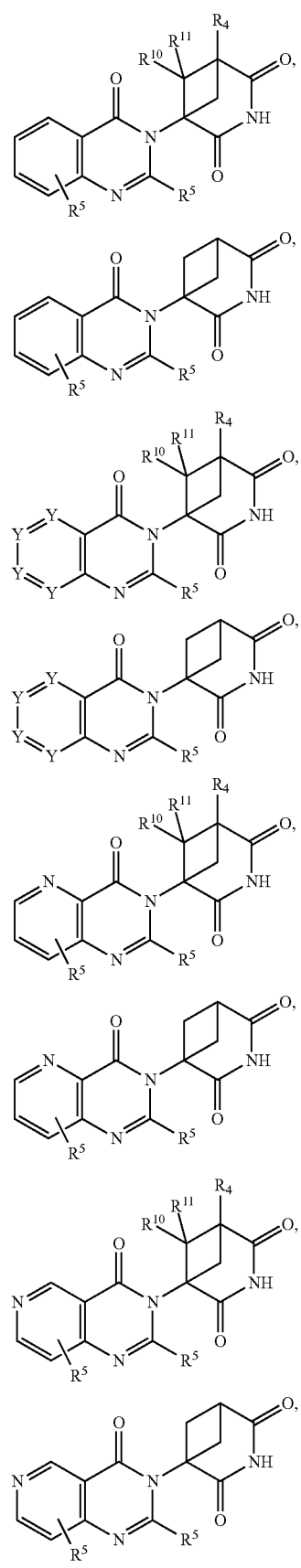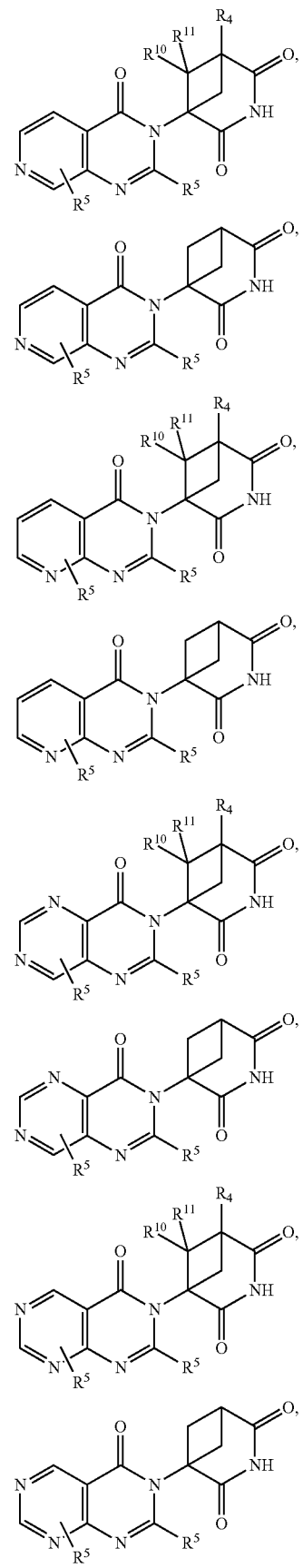

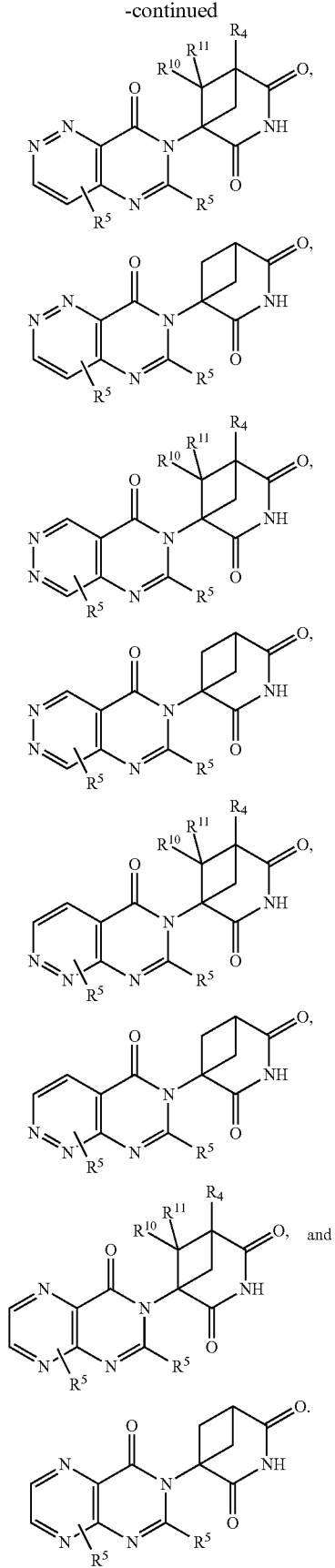
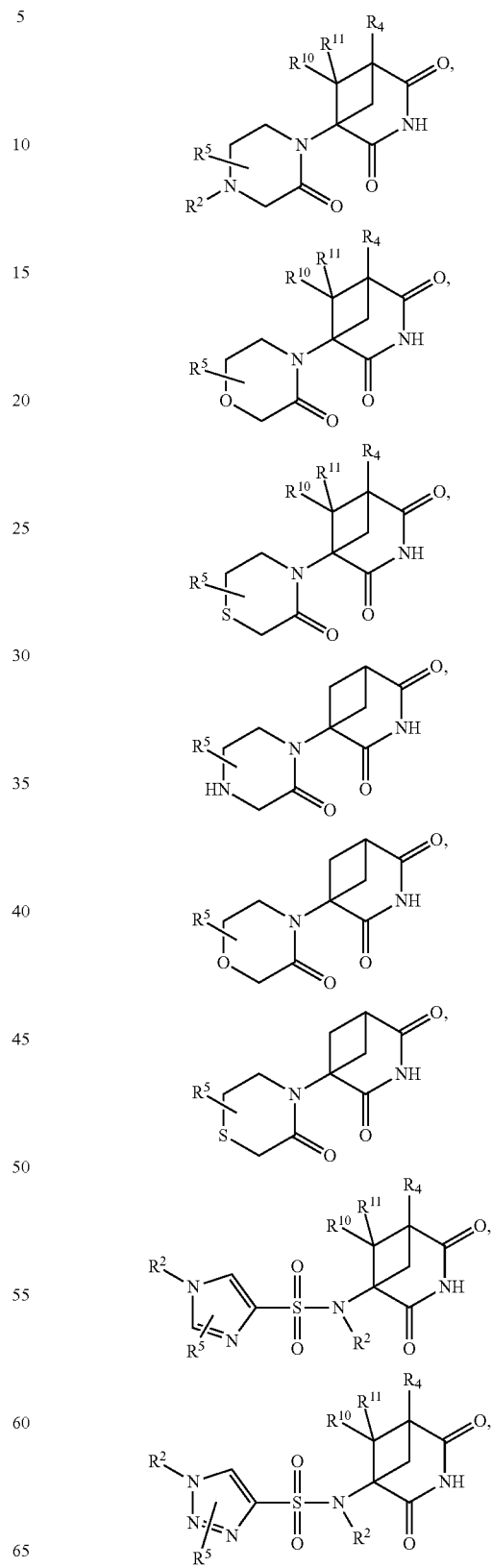
Additional non-limiting examples of compounds of Formula V include:

-continued
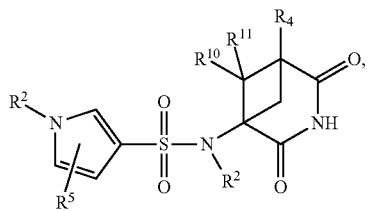
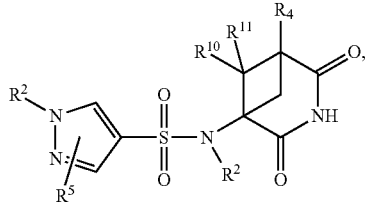
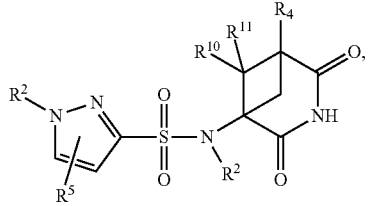
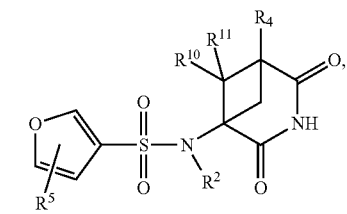
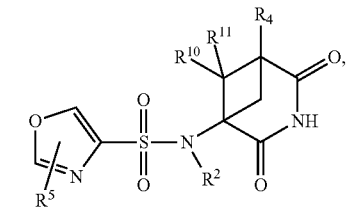
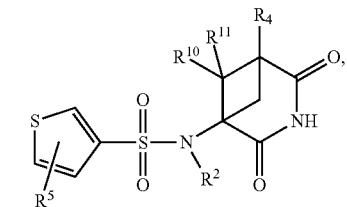
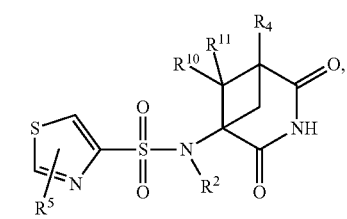
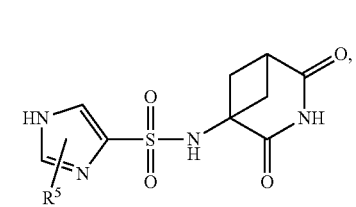
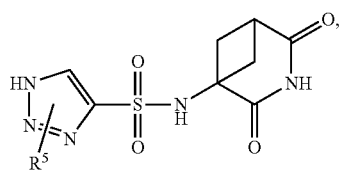
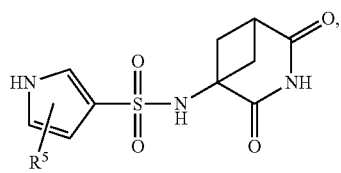
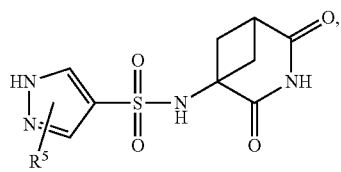
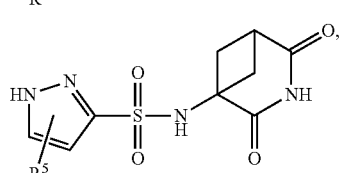
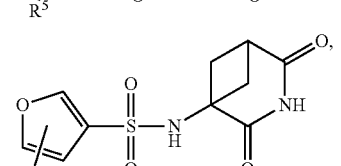
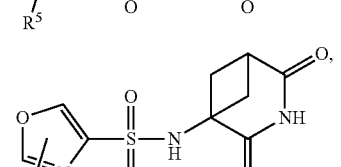
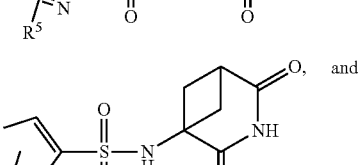
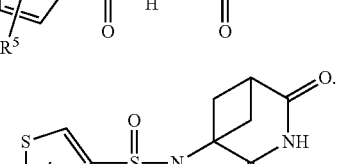
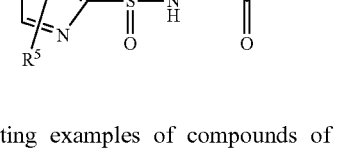
Non-limiting examples of compounds of Formula VI include:
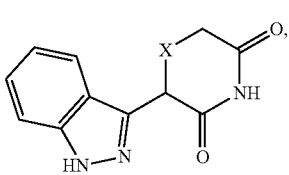

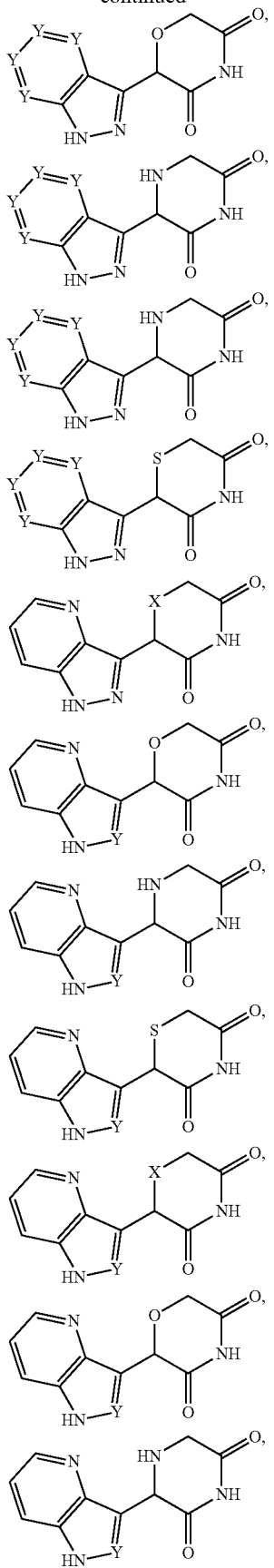
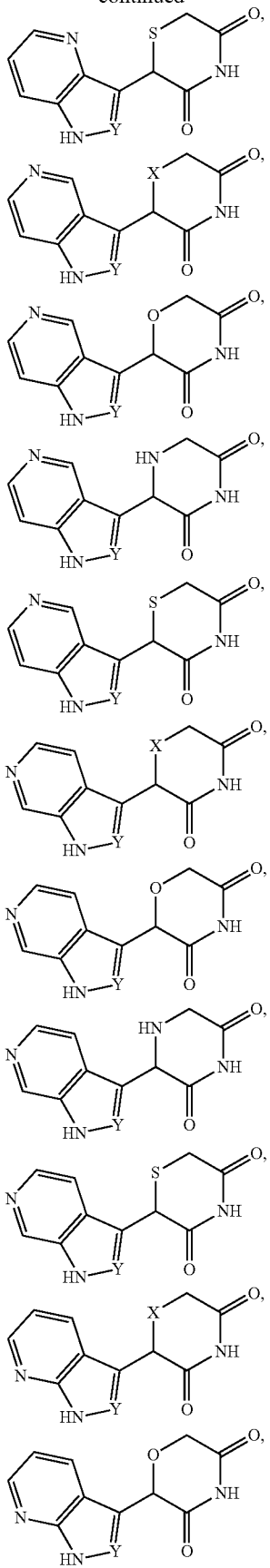

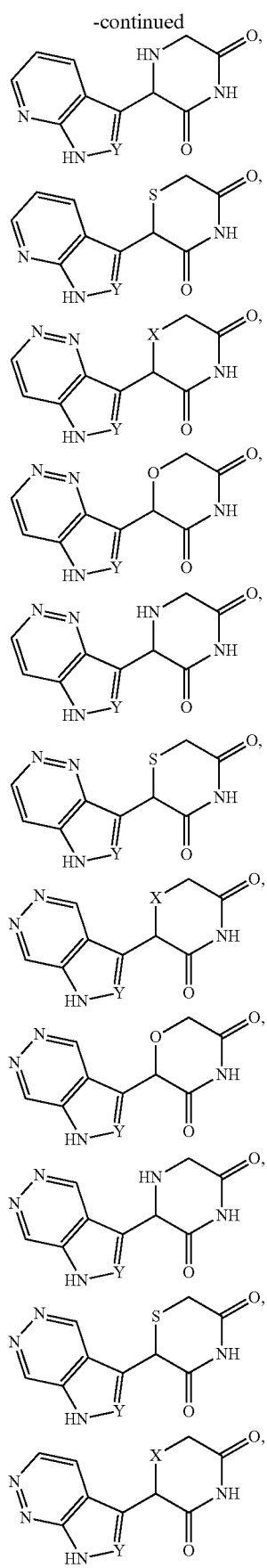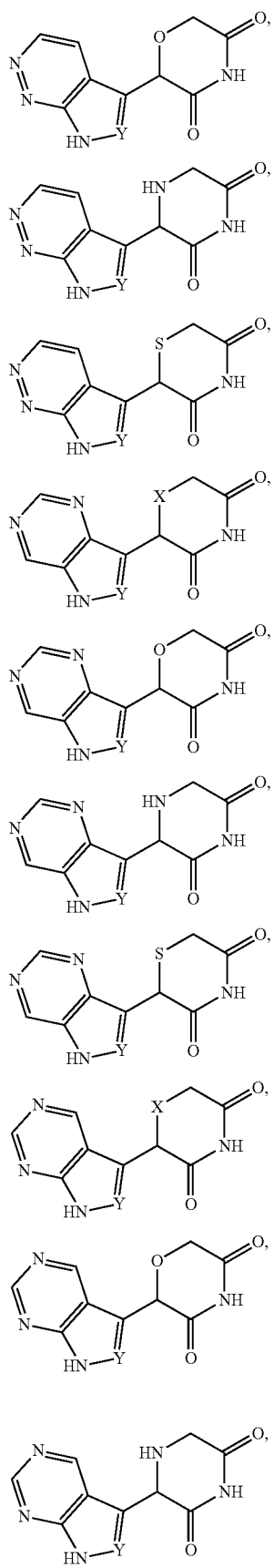

-continued
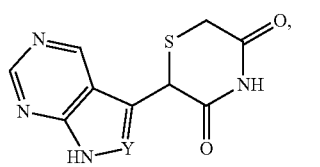
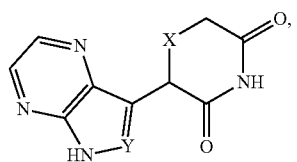
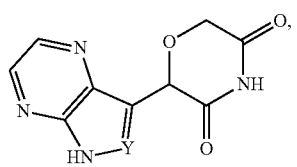
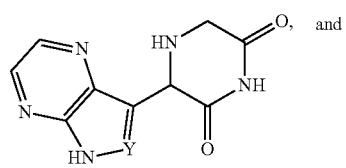 and
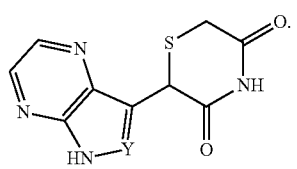
Additional non-limiting examples of compounds of Formula VI include:
-continued
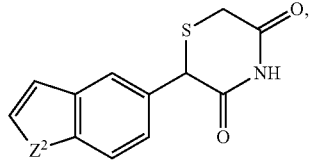
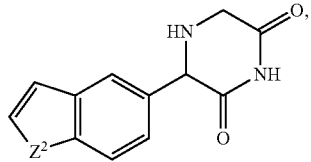
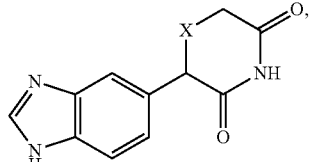
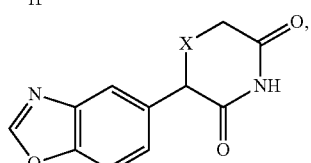
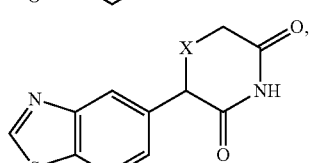
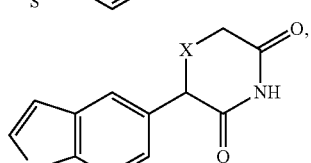
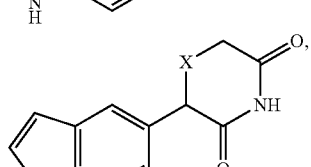
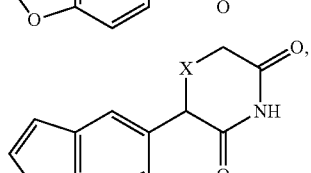
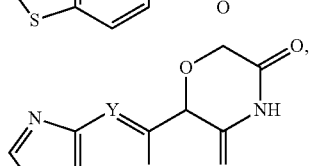

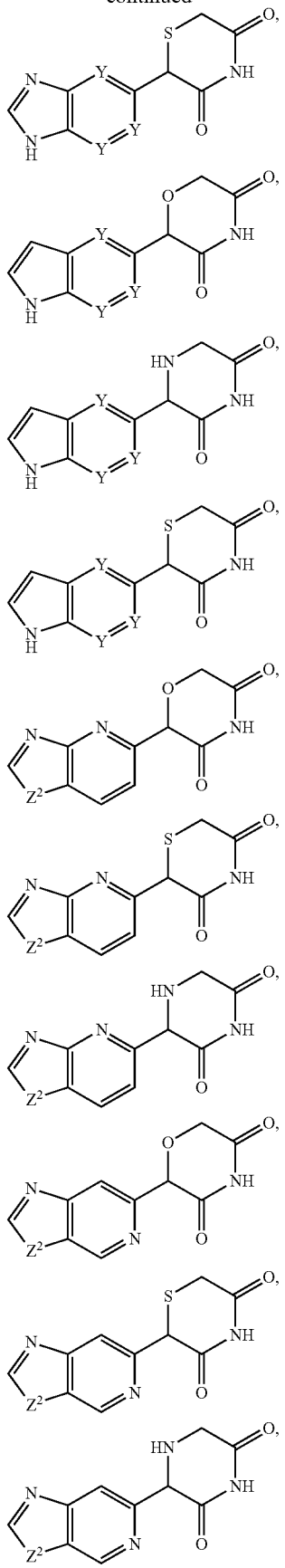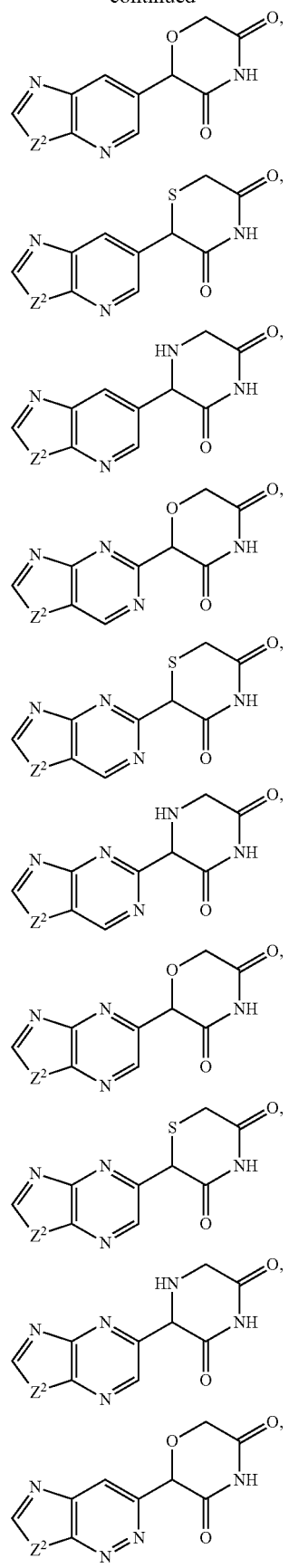

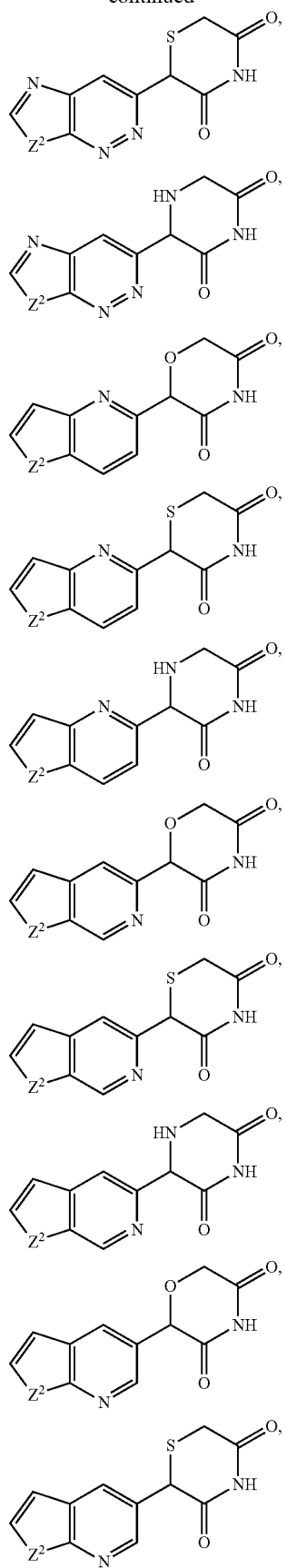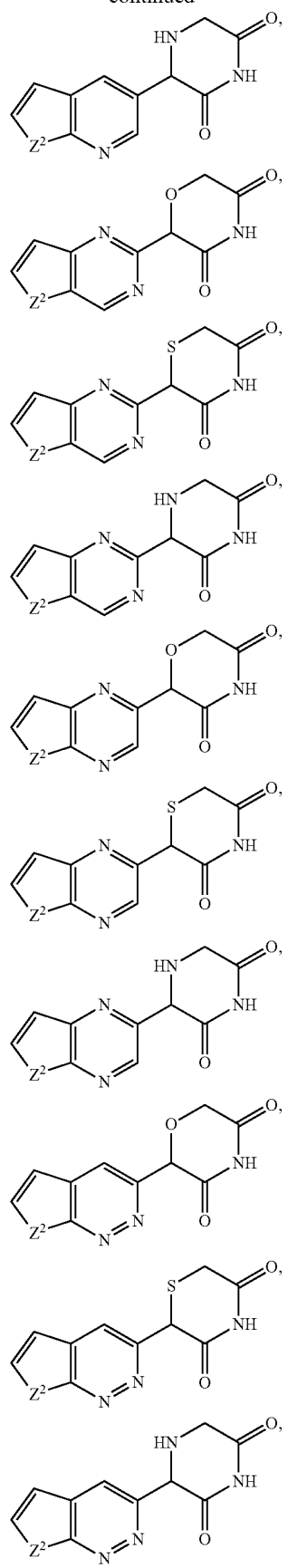

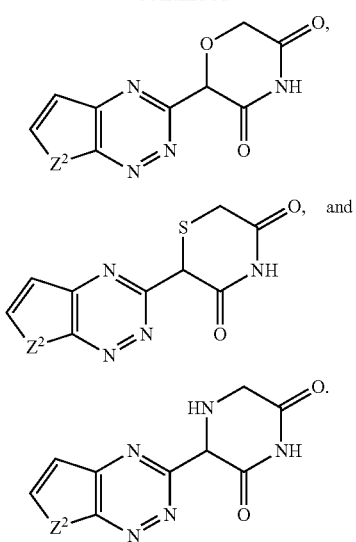
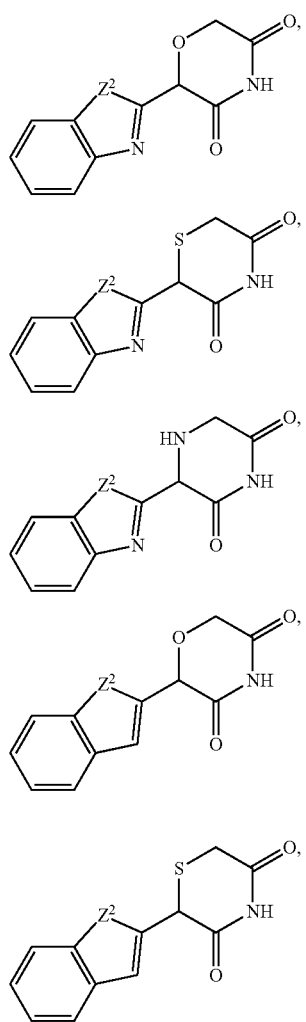
Additional non-limiting examples of compounds of Formula VI include:
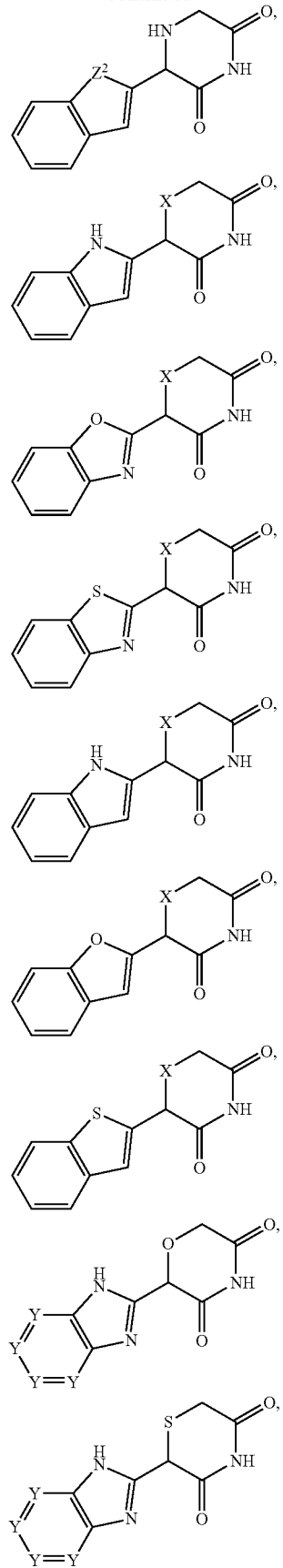

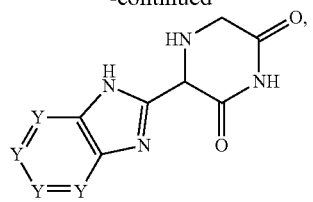
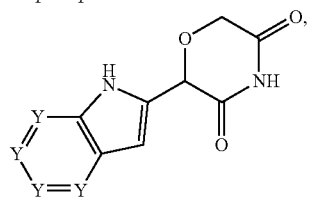
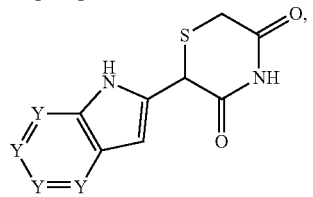
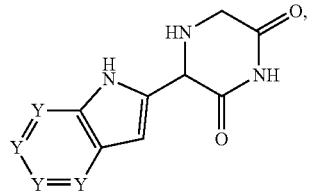
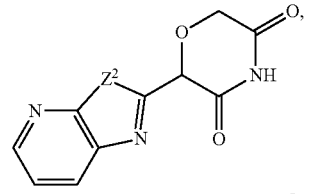
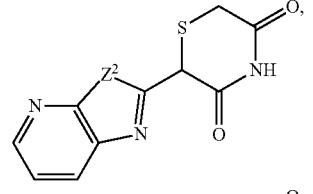
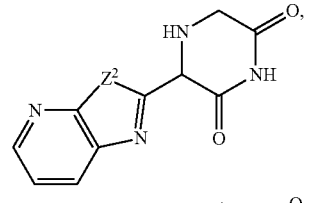
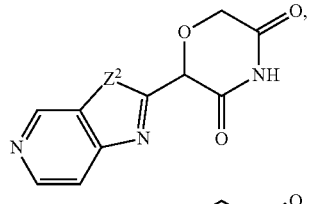
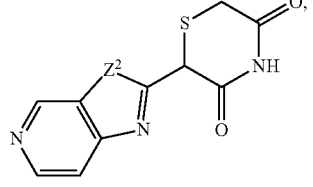
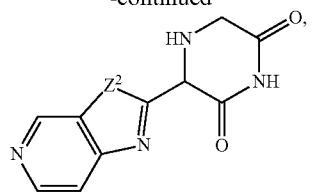
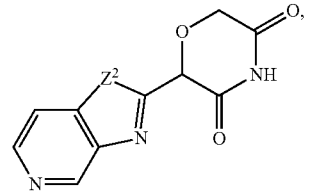
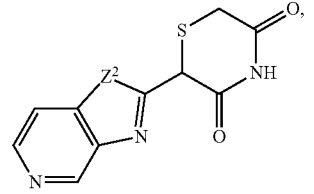
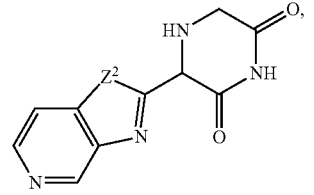
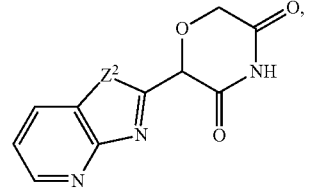
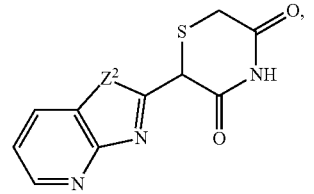
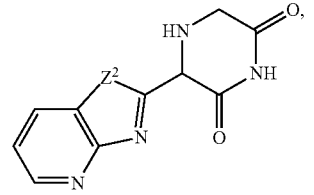
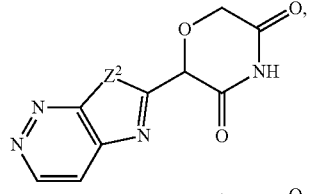
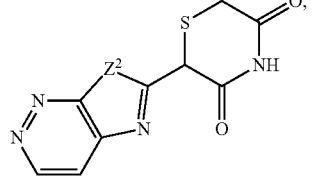

271 -continued

272 -continued

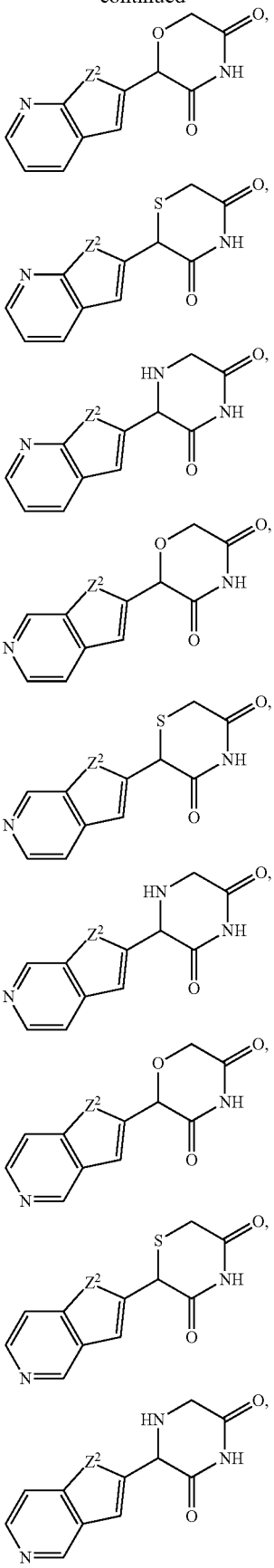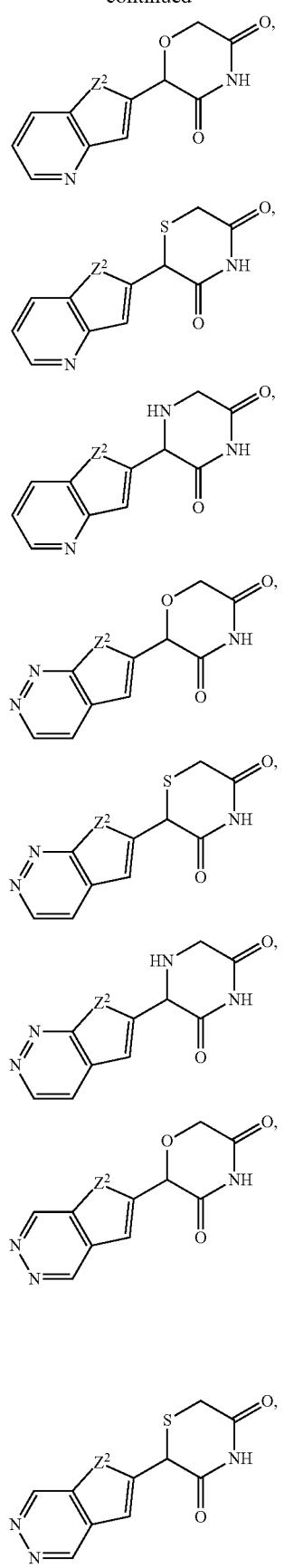

Additional non-limiting examples of compounds of Formula VI include:

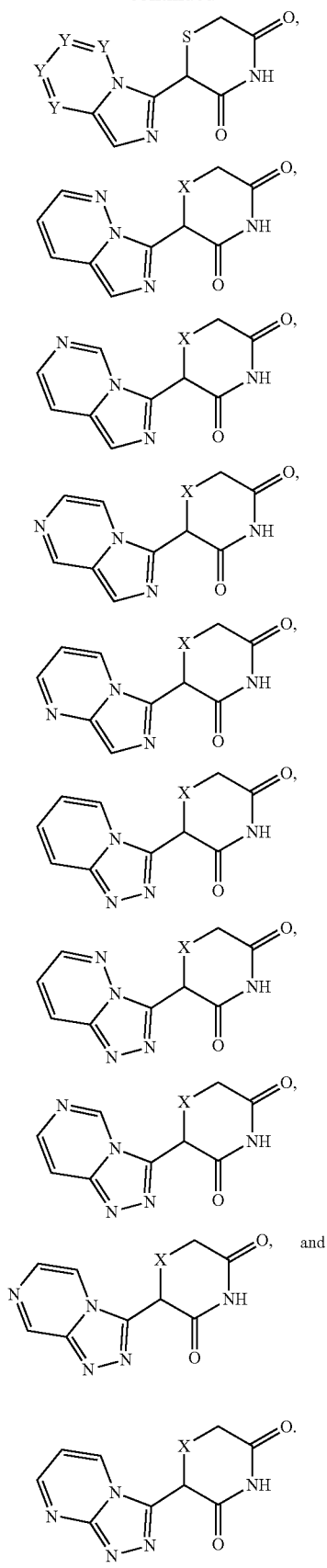
Additional non-limiting examples of compounds of Formula VI include:
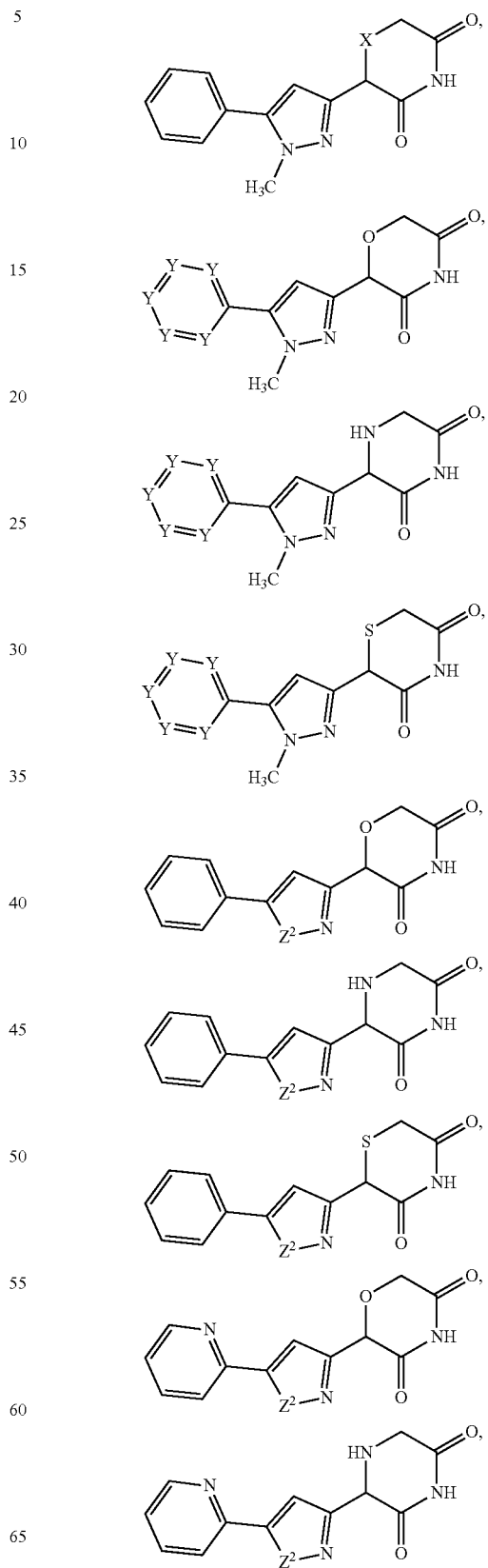

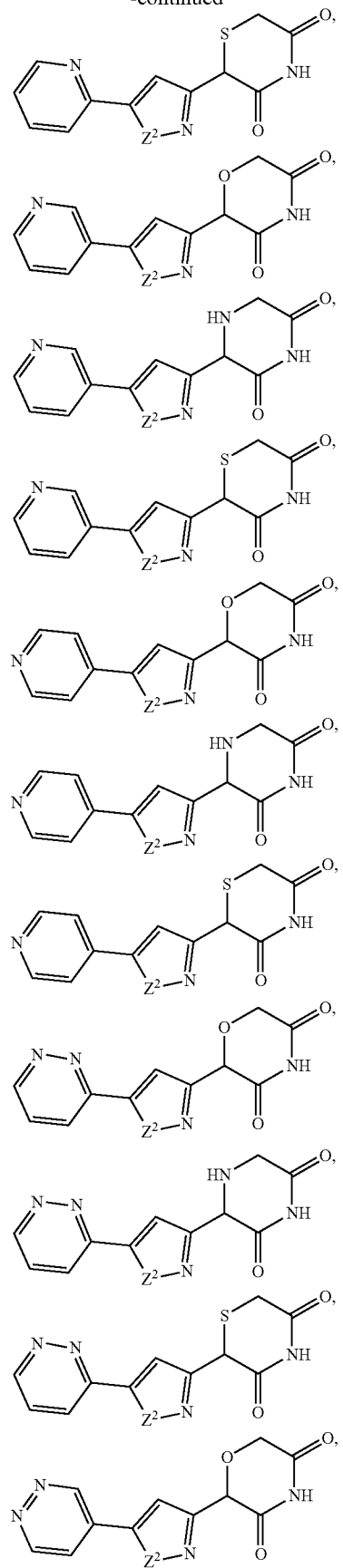
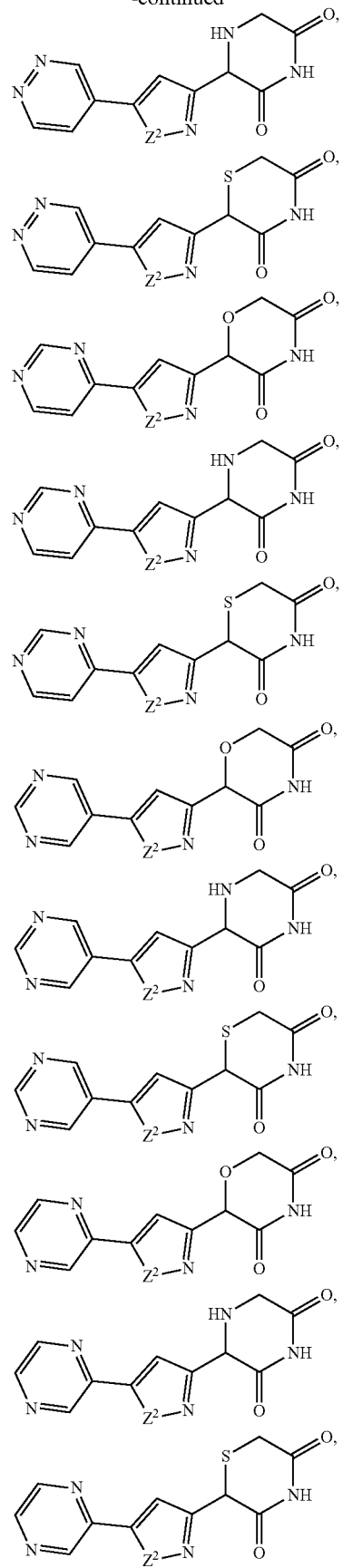

281
-continued
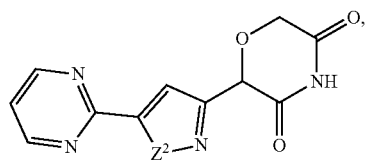
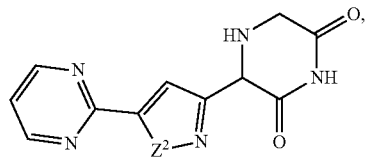
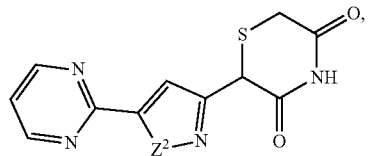
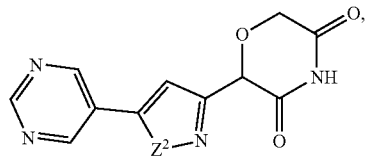
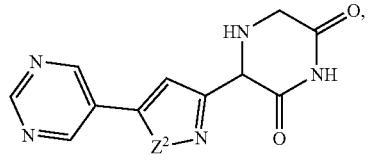
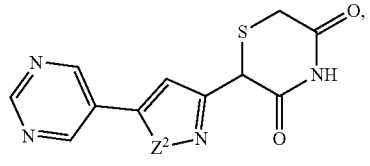
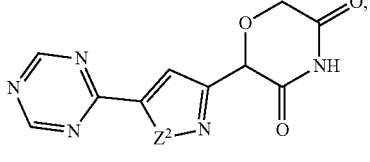
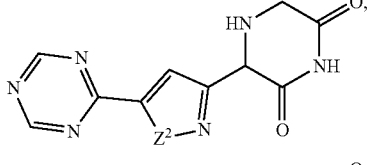
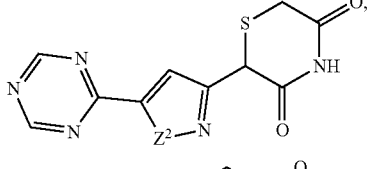
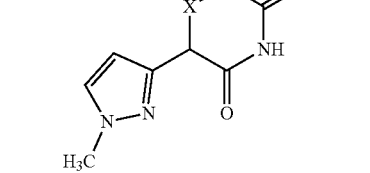
282
-continued
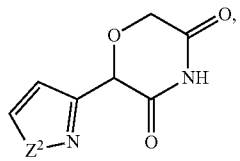
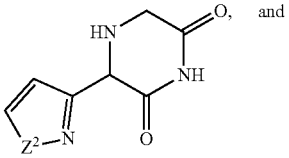
and
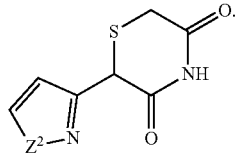
Additional non-limiting examples of compounds of Formula VI include:
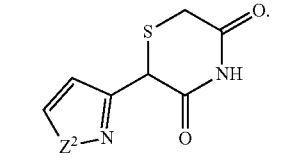
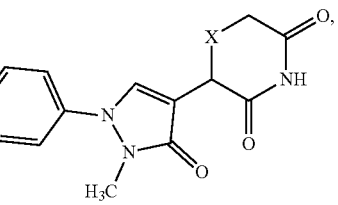
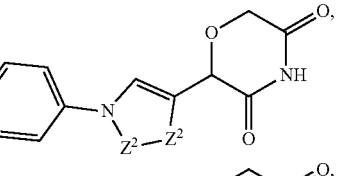
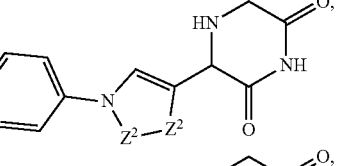
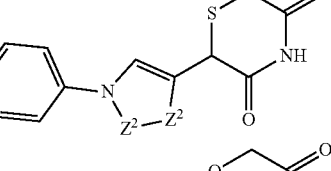
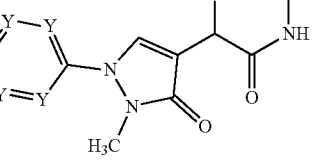
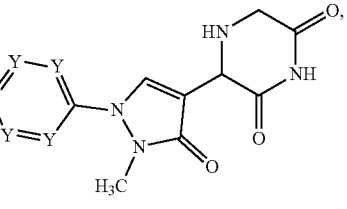

-continued

-continued
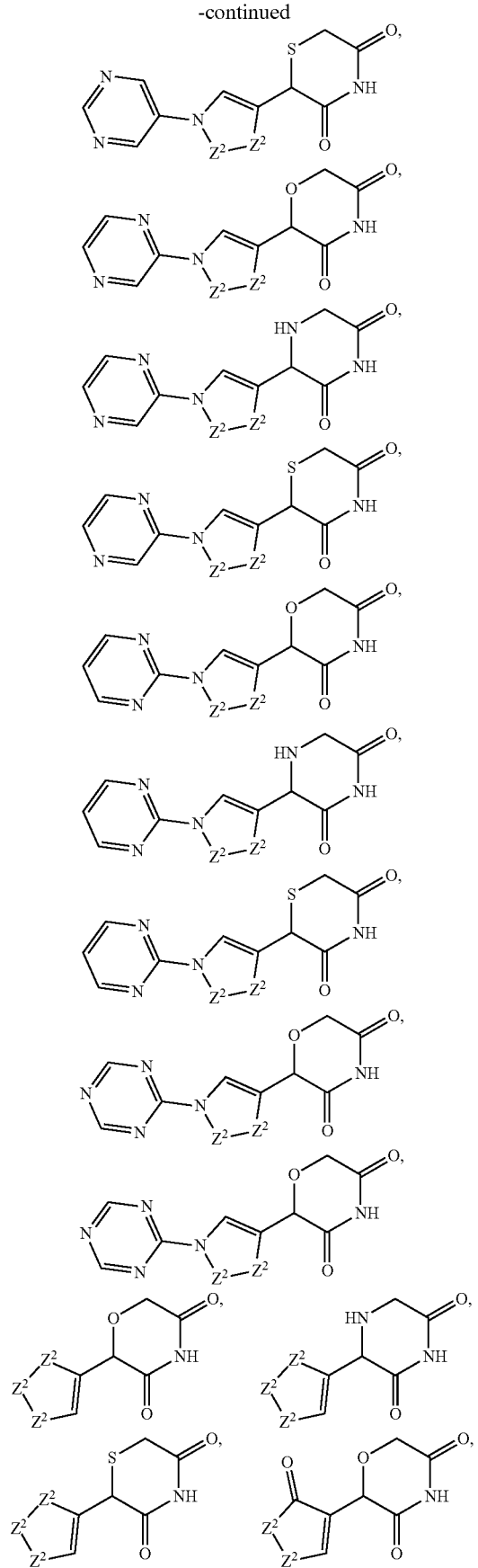
-continued
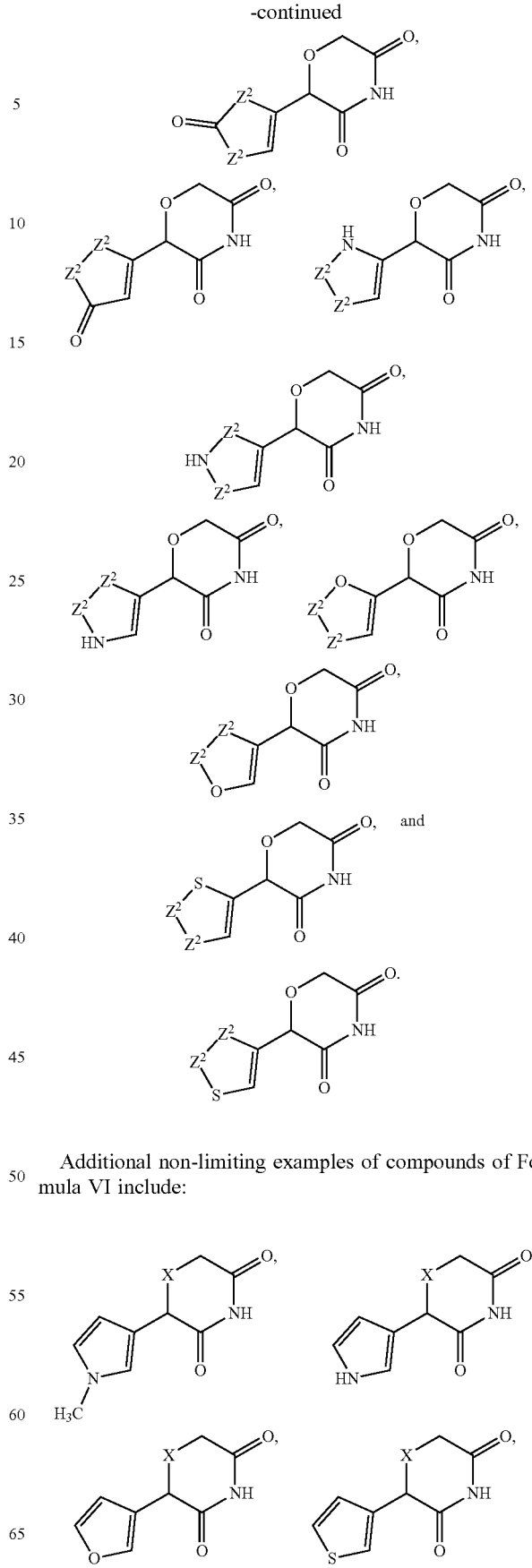
Additional non-limiting examples of compounds of Formula VI include:

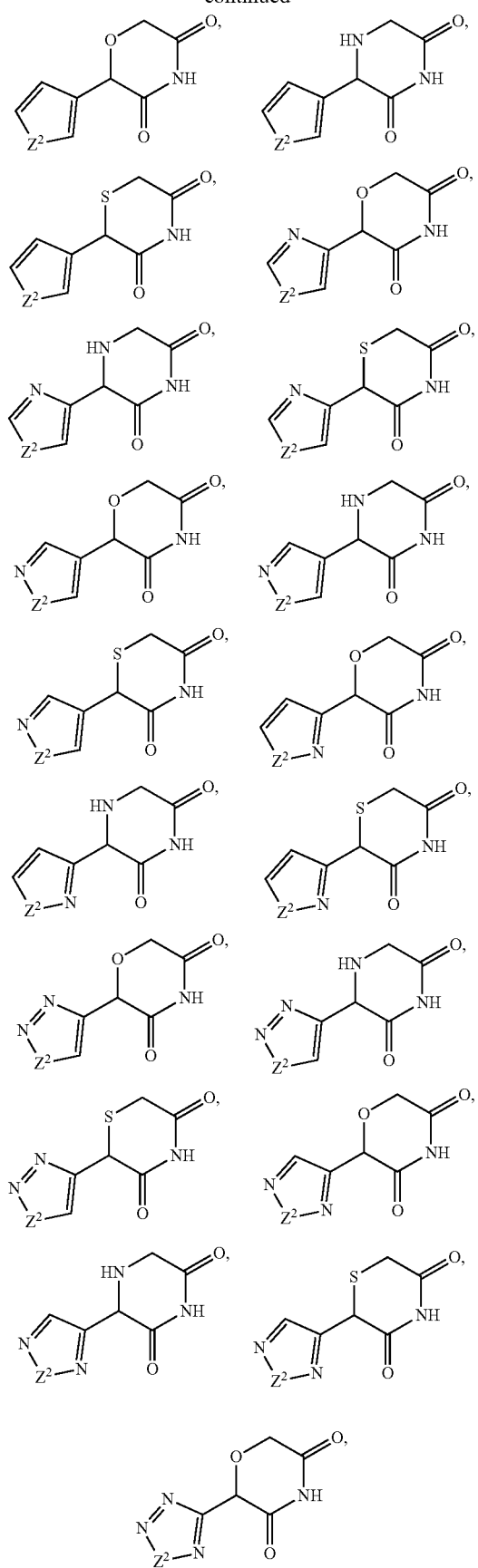
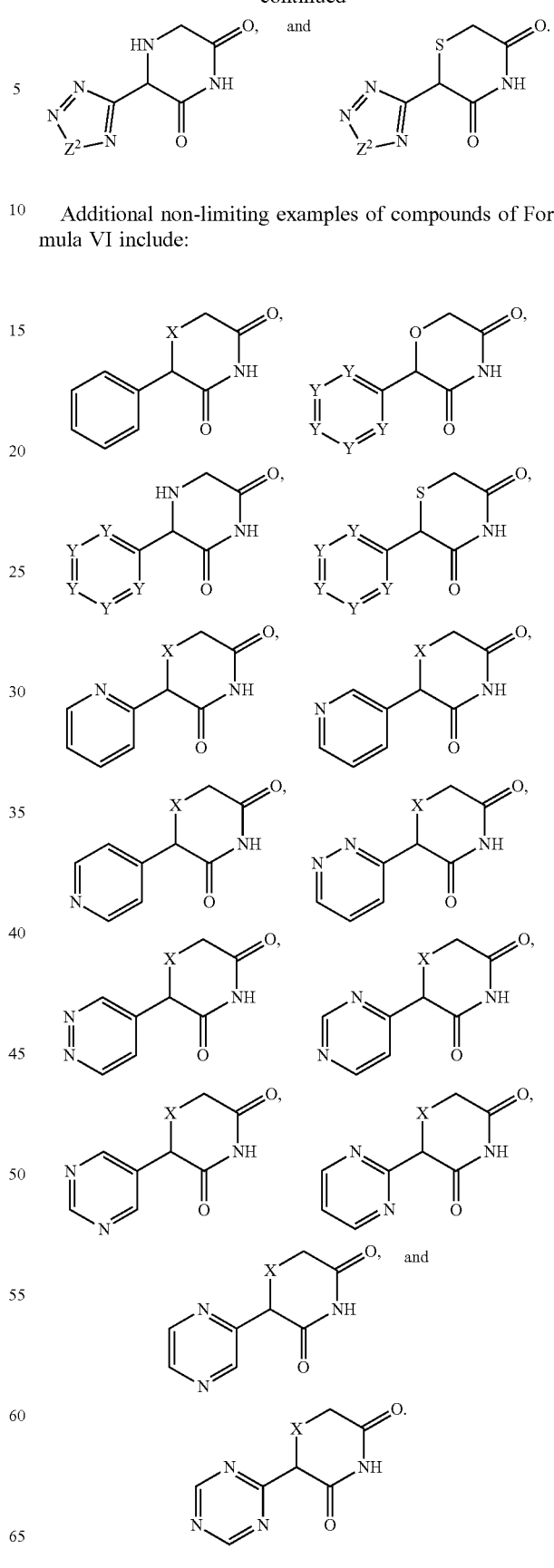
Additional non-limiting examples of compounds of Formula VI include:

In another aspect, the present invention includes a compound of Formula IX or Formula X:

(Formula IX)

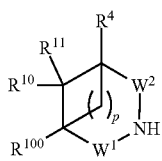

(Formula X)

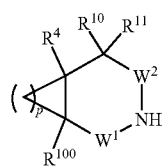

or a pharmaceutically acceptable salt, N-oxide, isotopic derivative, or prodrug thereof, optionally in a pharmaceutically acceptable carrier to form a composition;
wherein:
p is 1, 2, 3, or 4;
$R^{100}$ is selected from $R^{16}$, $R^{17}$, $R^{18}$, and $R^{19}$; and
$W^1$, $W^2$, $R^{10}$, $R^{11}$, $R^4$, $R^{16}$, $R^{17}$, $R^{18}$, and $R^{19}$ are defined above;
In one embodiment $R^{100}$ is $R^{16}$
In one embodiment $R^{100}$ is $R^{17}$.
In one embodiment $R^{100}$ is $R^{18}$.
In one embodiment $R^{100}$ is $R^{19}$.
In one embodiment p is 1.
In one embodiment p is 2.
In one embodiment p is 3.
In one embodiment p is 4.
In one embodiment the compound of the present invention is selected from:

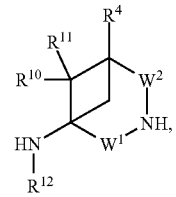 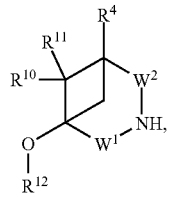

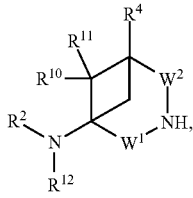 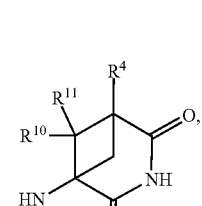

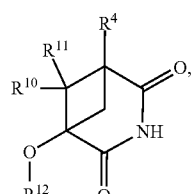 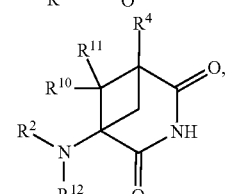

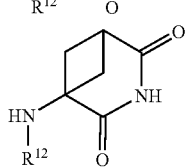 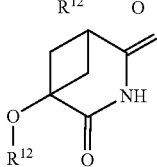 and

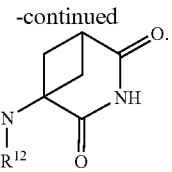
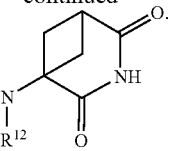

IV. Linkers

A Linker is included in the Degraders of Formula I, Formula II, Formula III, Formula IV, Formula IX, Formula X, and Formula XI. Linker is a bond, a chemically stable bivalent group that attaches a Degron to a Targeting Ligand, or a monovalent moiety attached to the Degron. If the Linker is bivalent, then the Linker is -(Linker)$^A$-. If the Linker is monovalent, then the Linker is -(Linker)$^B$. In some embodiments, Linker can have a closed valence, and thus will contain one or more covalent bonds to ensure a complete valence, which may be to one or more hydrogen atoms, or in the case of carboxyl, sulfonyl, thiol, thiophenol, alcohol, or phenol groups can also be the deprotonated species and salts thereof, and for amines can also be the ammonium species and salts thereof.

The term "Linker" refers to both (Linker)$^A$ and (Linker)$^B$ unless excluded by context.

-(Linker)$^A$- as described herein can be used in either direction, i.e., either the left end is linked to the Degron and the right end to the Target Linker, or the left end is linked to the Target Linker and the right end is linked to the Degron. -(Linker)$^B$ as described herein is attached at the point of open valency shown. In one embodiment, -(Linker)$^A$- is a bivalent chemical group. In another embodiment, -(Linker)$^B$ is a monovalent chemical group. According to the invention, any desired linker can be used as long as the resulting compound has a stable shelf life for at least 2 months, 3 months, 6 months or 1 year as part of a pharmaceutically acceptable dosage form, and itself is pharmaceutically acceptable.

In a typical embodiment, the Linker has a chain of 2 to 14, 15, 16, 17, 18 or 20 or more carbon atoms of which one or more carbons can be replaced by a heteroatom such as O, N, S, or P. In certain embodiments the chain has 2, 3, 4, 5, 6, 7, 8, 9, 10, 11, 12, 13, 14, 15, 16, 17, 18, 19 or 20 contiguous atoms in the chain. For example, the chain may include 1 or more ethylene glycol units that can be contiguous, partially contiguous or non-contiguous (for example, 2, 3, 4, 5, 6, 7, 8, 9, 10, 11 or 12 ethylene glycol units). In certain embodiments the chain has at least 1, 2, 3, 4, 5, 6, 7, or 8 contiguous chains which can have branches which can be independently alkyl, heteroalkyl, aryl, heteroaryl, alkenyl, or alkynyl, aliphatic, heteroaliphatic, cycloalkyl or heterocyclic substituents.

In other embodiments, the linker can include or be comprised of one or more of ethylene glycol, propylene glycol, lactic acid and/or glycolic acid. In general, propylene glycol adds hydrophobicity, while propylene glycol adds hydrophilicity. Lactic acid segments tend to have a longer half-life than glycolic acid segments. Block and random lactic acid-co-glycolic acid moieties, as well as ethylene glycol and propylene glycol, are known in the art to be pharmaceutically acceptable and can be modified or arranged to obtain the desired half-life and hydrophilicity. In certain aspects, these units can be flanked or interspersed with other moieties, such as aliphatic, including alkyl, heteroaliphatic, aryl, heteroaryl, heterocyclic, cycloalkyl, etc., as desired to achieve the appropriate drug properties.

In one aspect, Linker is selected from -(Linker)$^A$-. In one embodiment, -(Linker)$^A$- is a moiety selected from Formula L$^A$I, Formula L$^A$II, Formula L$^A$III, Formula L$^A$IV, Formula L$^A$V, Formula L$^A$VI, and Formula L$^A$VII:

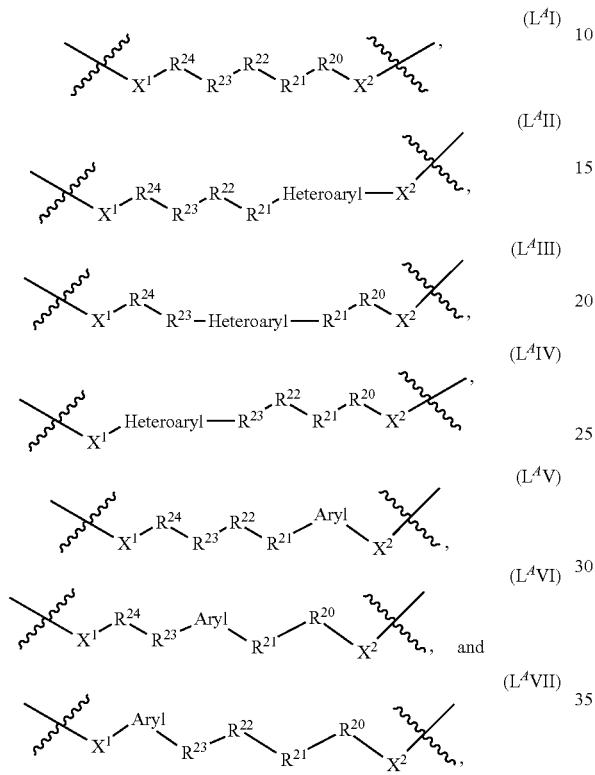

wherein all variables are defined as above.

In an additional embodiment, the Linker is a moiety selected from Formula L$^A$VIII, L$^A$IX, and LAX:

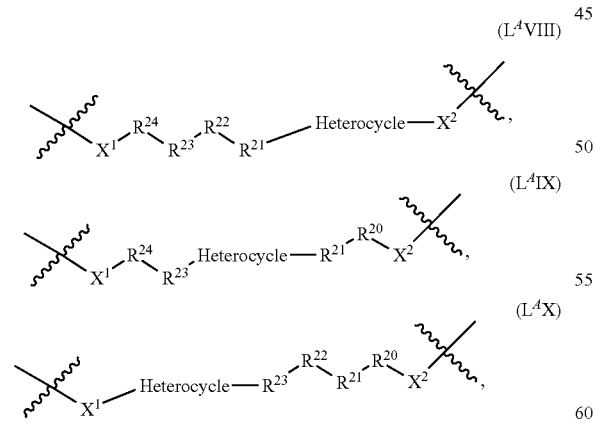

wherein all variables are defined as above. In alternative embodiments of L$^A$VIII, L$^A$IX and L$^A$X, a carbocyclic ring is used in place of the heterocycle.

The following are non-limiting examples of Linkers that can be used in this invention.

Based on this elaboration, those of skill in the art will understand how to use the full breadth of Linkers that will accomplish the goal of the invention.

As certain non-limiting examples, Formula L$^A$I, Formula L$^A$II, Formula L$^A$III, Formula L$^A$IV, Formula L$^A$V, Formula L$^A$VI, or Formula L$^A$VII include:

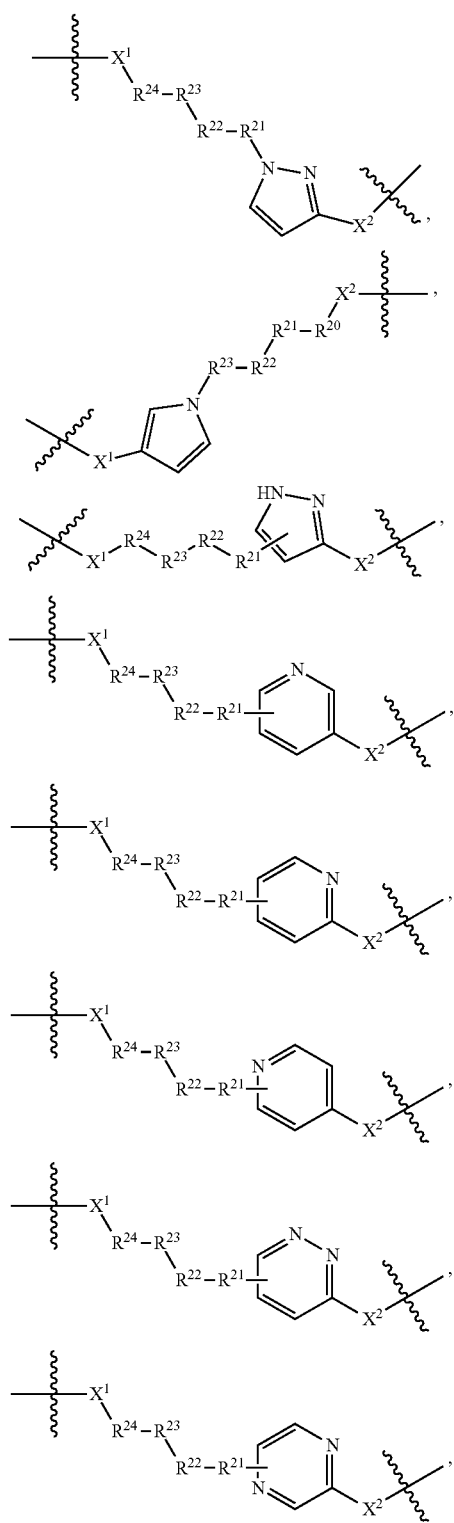

-continued

-continued
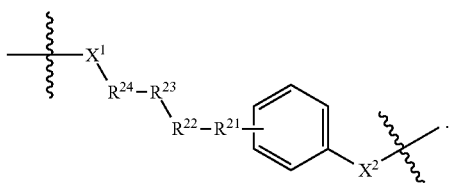
In an additional embodiment -(Linker)$^4$- is selected from:
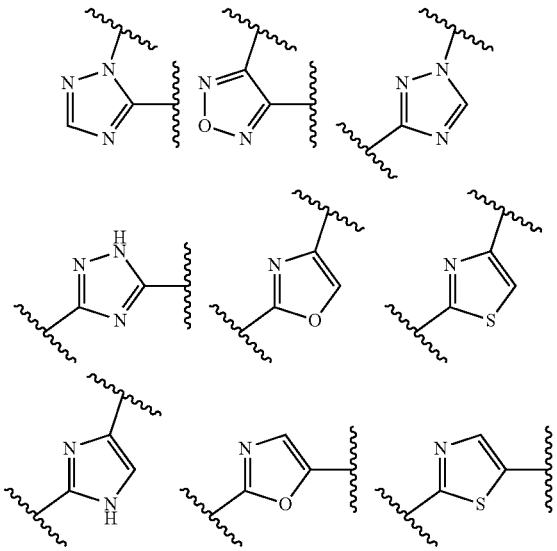
In an additional embodiment -(Linker)$^4$- is selected from:
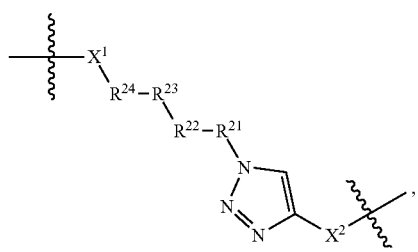
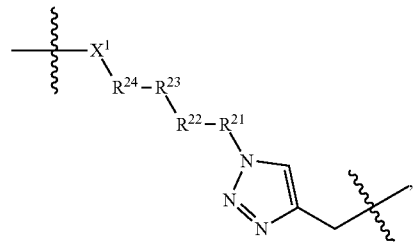
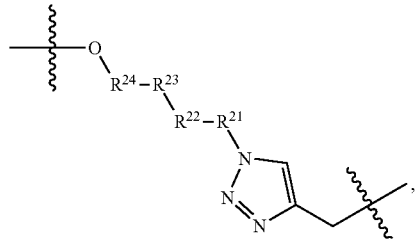
-continued
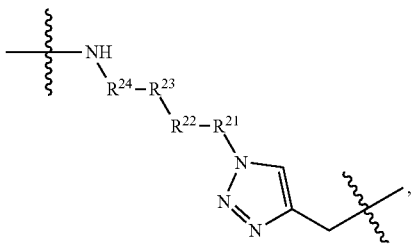
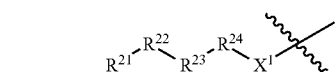
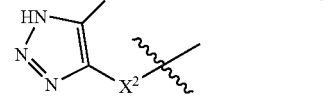
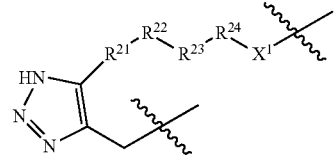
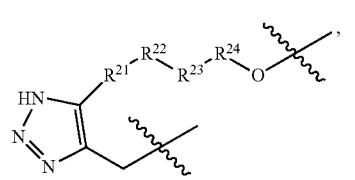
, and
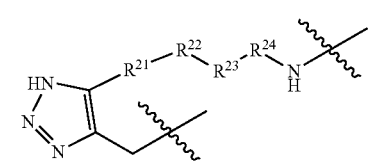
In one embodiment $X^1$ is attached to the Targeting Ligand. In another embodiment $X^2$ is attached to the Targeting Ligand.
Non-limiting examples of moieties of $R^{20}$, $R^{21}$, $R^{22}$, $R^{23}$, and $R^{24}$ include:
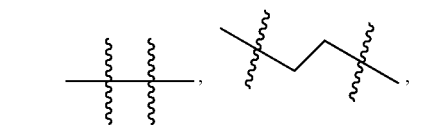
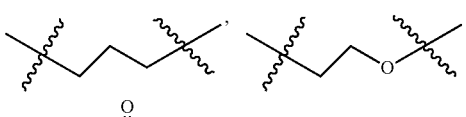
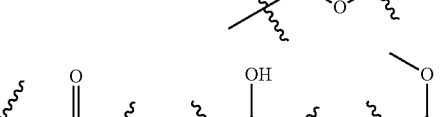
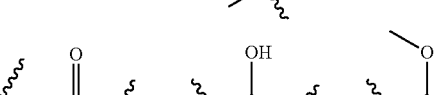

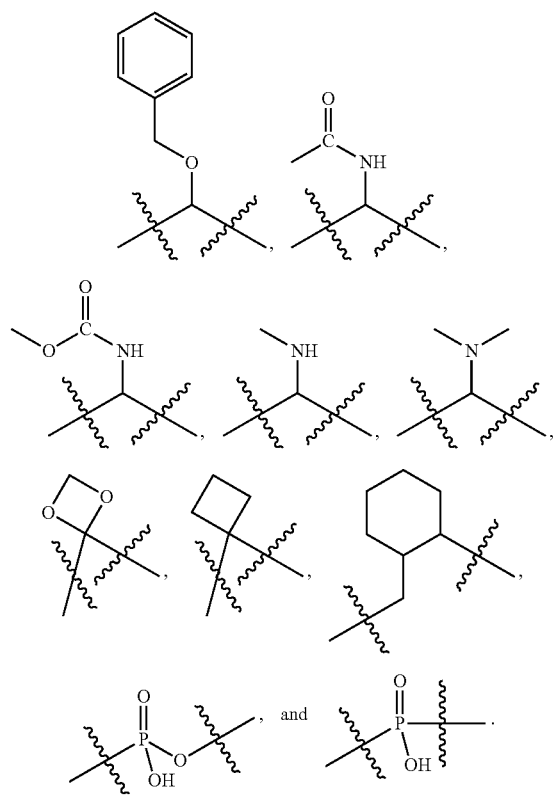
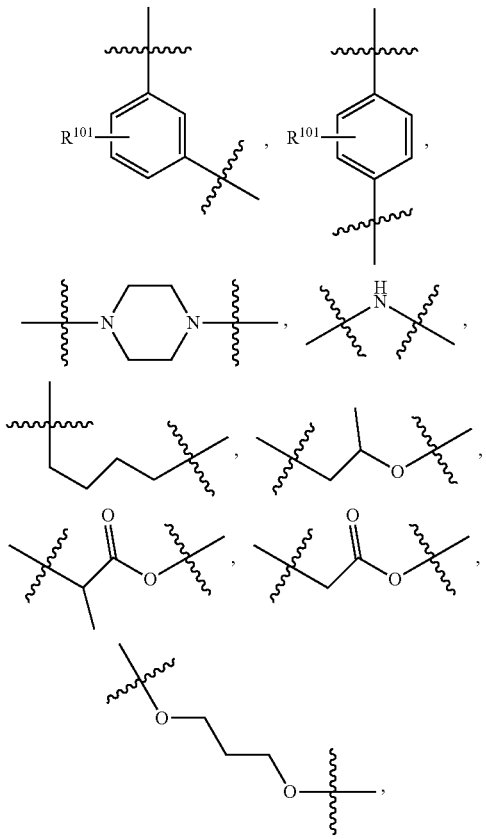
Additional non-limiting examples of moieties of $R^{20}$, $R^{21}$, $R^{22}$, $R^{23}$, and $R^{24}$ include:
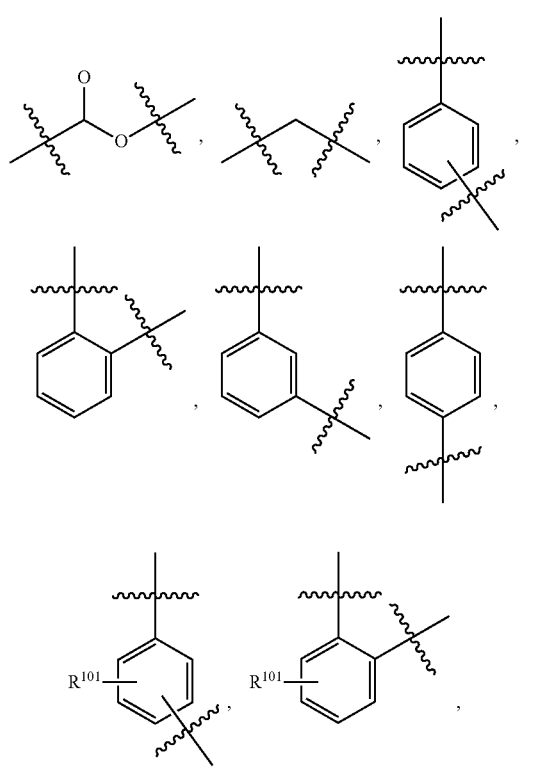
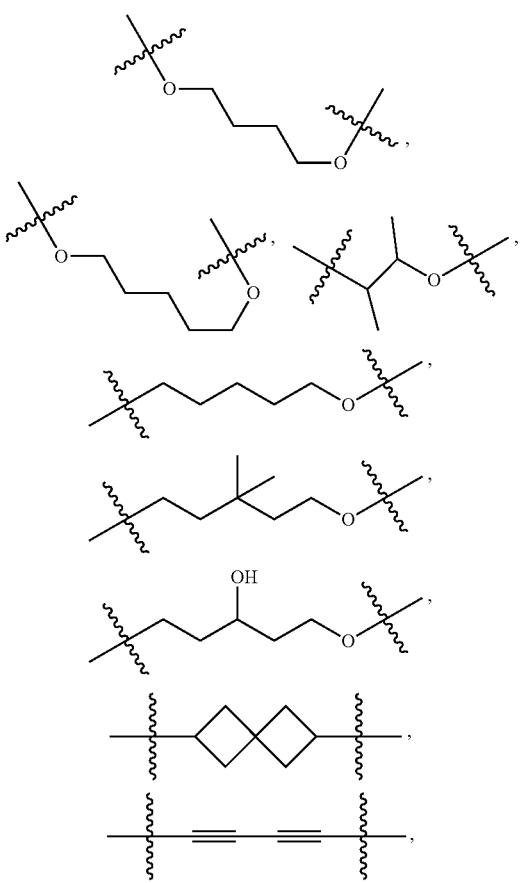

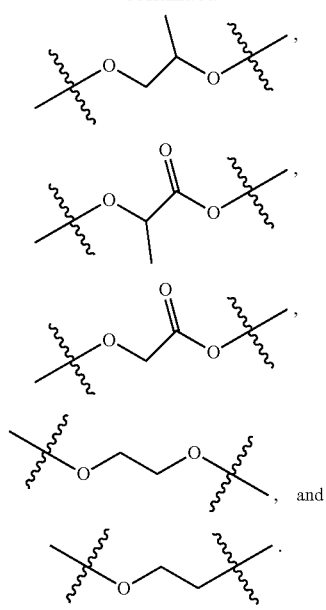
Additional non-limiting examples of moieties of $R^{20}$, $R^{21}$, $R^{22}$, $R^{23}$, and $R^{24}$ include:
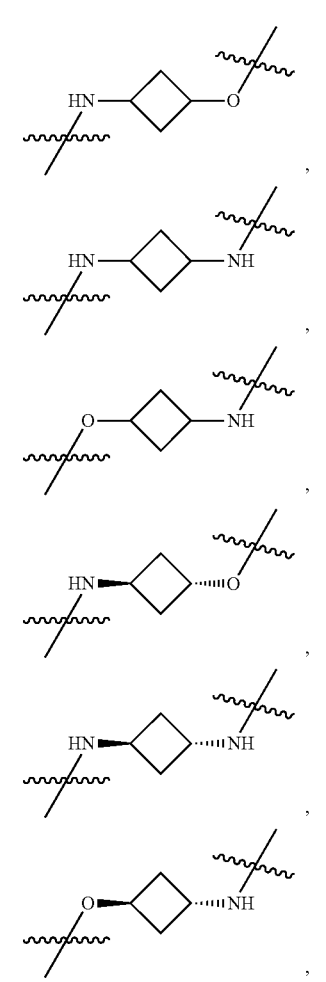
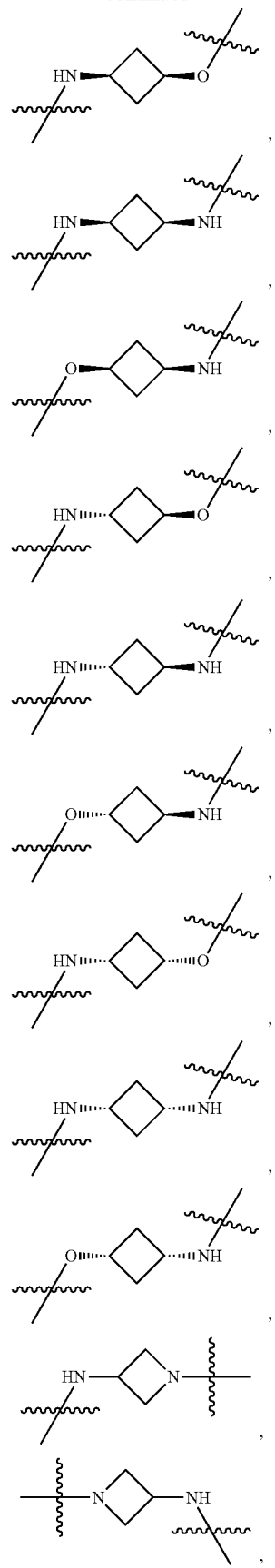

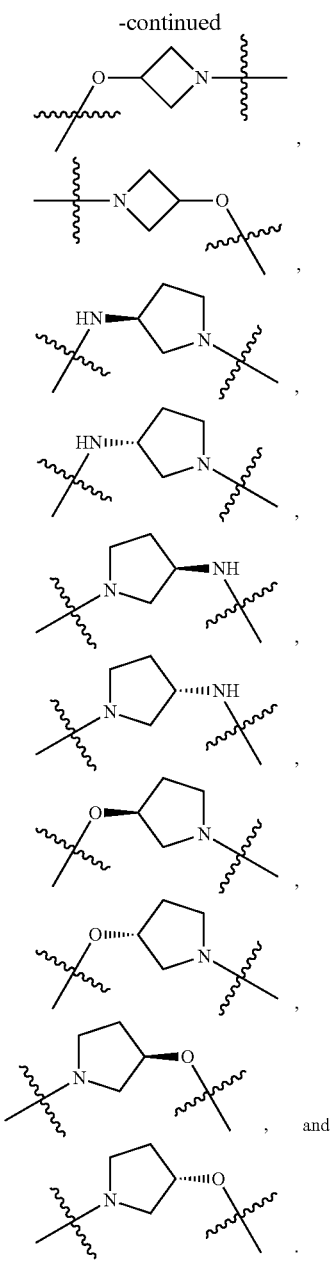
, and

In additional embodiments, the -(Linker)$^A$- moiety is an optionally substituted (poly)ethylene glycol having at least 1, at least 2, at least 3, at least 4, at least 5, at least 6, at least 7, at least 8, at least 9, at least 10, ethylene glycol units, or optionally substituted alkyl groups interspersed with optionally substituted, O, N, S, P or Si atoms. In certain embodiments, -(Linker)$^A$- is flanked, substituted, or interspersed with an aryl, phenyl, benzyl, alkyl, alkylene, or heterocycle group. In certain embodiments, -(Linker)$^A$- may be asymmetric or symmetrical. In some embodiments, -(Linker)$^A$- is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units. In any of the embodiments of the compounds described herein, -(Linker)$^A$- group may be any suitable moiety as described herein.

In additional embodiments, -(Linker)$^A$- is selected from: —NR$^{61}$(CH$_2$)$_{n1}$-(lower alkyl)-, —NR$^{61}$(CH$_2$)$_{n1}$-(lower alkoxyl)-, —NR$^{61}$(CH$_2$)$_{n1}$-(lower alkoxyl)-OCH$_2$—, —NR$^{61}$(CH$_2$)$_{n1}$-(lower alkoxyl)-(lower alkyl)-OCH$_2$—, —NR$^{61}$(CH$_2$)$_{n1}$-(cycloalkyl)-(lower alkyl)-OCH$_2$—, —NR$^{61}$(CH$_2$)$_{n1}$-(heterocycloalkyl)-, —NR$^{61}$(CH$_2$CH$_2$O)$_{n1}$-(lower alkyl)-O—CH$_2$—, —NR$^{61}$(CH$_2$CH$_2$O)$_{n1}$-(heterocycloalkyl)-O—CH$_2$—, —NR$^{61}$(CH$_2$CH$_2$O)$_{n1}$-Aryl-O—CH$_2$—, —NR$^{61}$(CH$_2$CH$_2$O)$_{n1}$-(heteroaryl)-O—CH$_2$—, —NR$^{61}$(CH$_2$CH$_2$O)$_{n1}$-(cycloalkyl)-O-(heteroaryl)-O—CH$_2$—, —NR$^{61}$(CH$_2$CH$_2$O)$_{n1}$-(cycloalkyl)-O-Aryl-O—CH$_2$—, —NR$^{61}$(CH$_2$CH$_2$O)$_{n1}$-(lower alkyl)-NH-Aryl-O—CH$_2$—, —NR$^{61}$(CH$_2$CH$_2$O)$_{n1}$-(lower alkyl)-O-Aryl-CH$_2$, —NR$^{61}$(CH$_2$CH$_2$O)$_{n1}$-cycloalkyl-O-Aryl-, —NR$^{61}$(CH$_2$CH$_2$O)$_{n1}$-cycloalkyl-O-heteroaryl-, —NR$^{61}$(CH$_2$)$_{n1}$-(cycloalkyl)-O-(heterocycle)-CH$_2$, —NR$^{61}$(CH$_2$)$_{n1}$-(heterocycle)-(heterocycle)-CH$_2$, and —NR$^{61}$-(heterocycle)-CH$_2$;

wherein n1 is 0, 1, 2, 3, 4, 5, 6, 7, 8, 9, or 10; and

R$^{61}$ is H, methyl, or ethyl.

In additional embodiments, -(Linker)$^A$- is selected from: —N(R$^{61}$)—(CH$_2$)$_{m1}$—O(CH$_2$)$_{n2}$—O(CH$_2$)$_{o1}$—O(—O(CH$_2$)$_{q1}$—O(CH$_2$)$_{r1}$—OCH$_2$—, —O—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—, —O—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—O—; —N(R$^{61}$)—(CH$_2$)$_{m1}$—O(CH$_2$)$_{n2}$—O(CH$_2$)$_{o1}$—O(CH$_2$)$_{q1}$—O(CH$_2$)$_{r1}$—O—; —(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—O—; —(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—; —O(CH$_2$)$_{m1}$O(CH$_2$)$_{n2}$O(CH$_2$)$_{p1}$O(CH$_2$)$_{q1}$OCH$_2$—; —O(CH$_2$)$_{m1}$O(CH$_2$)$_{n2}$O(CH$_2$)$_{p1}$O(CH$_2$)$_{q1}$OCH$_2$—; wherein m1, n2, o1, p1, q1, and r1 are independently 1, 2, 3, 4, or 5; and R$^{61}$ is H, methyl, or ethyl.

In additional embodiments, -(Linker)$^A$- is selected from:

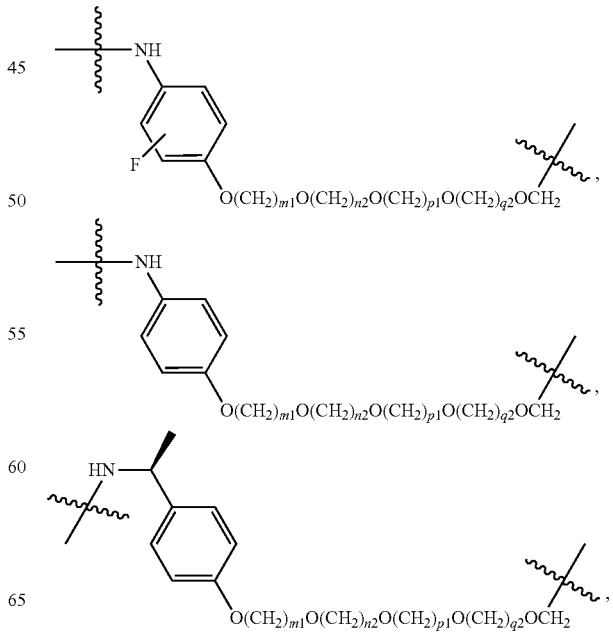

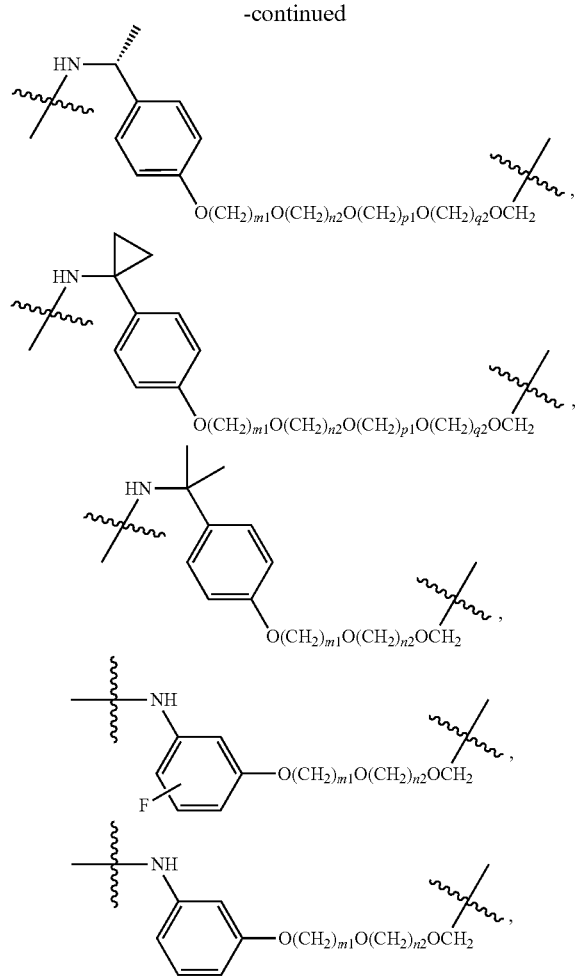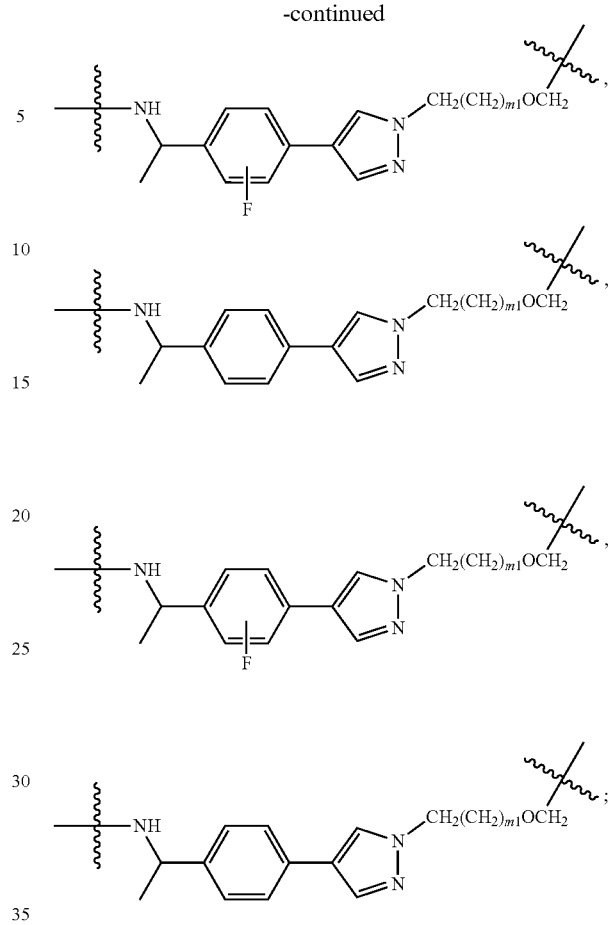
m1, n2, o1, p1, q2, and r1 are independently 1, 2, 3, 4, or 5.
In additional embodiments, -(Linker)$^A$- is selected from:
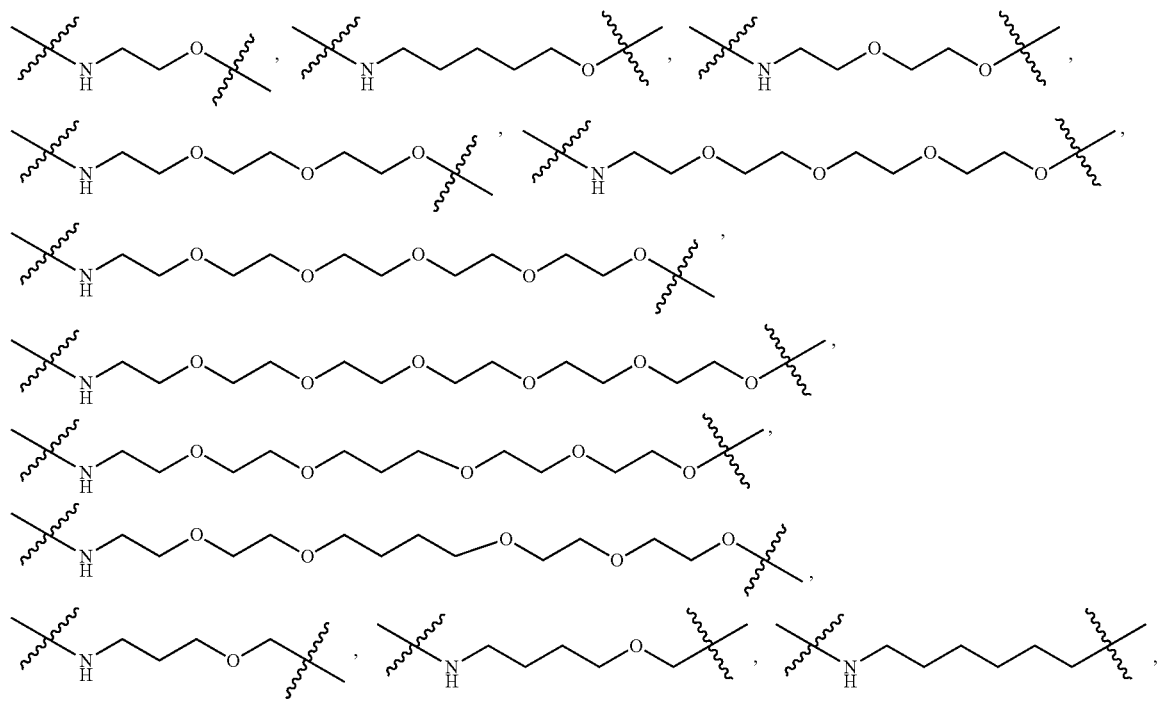

-continued
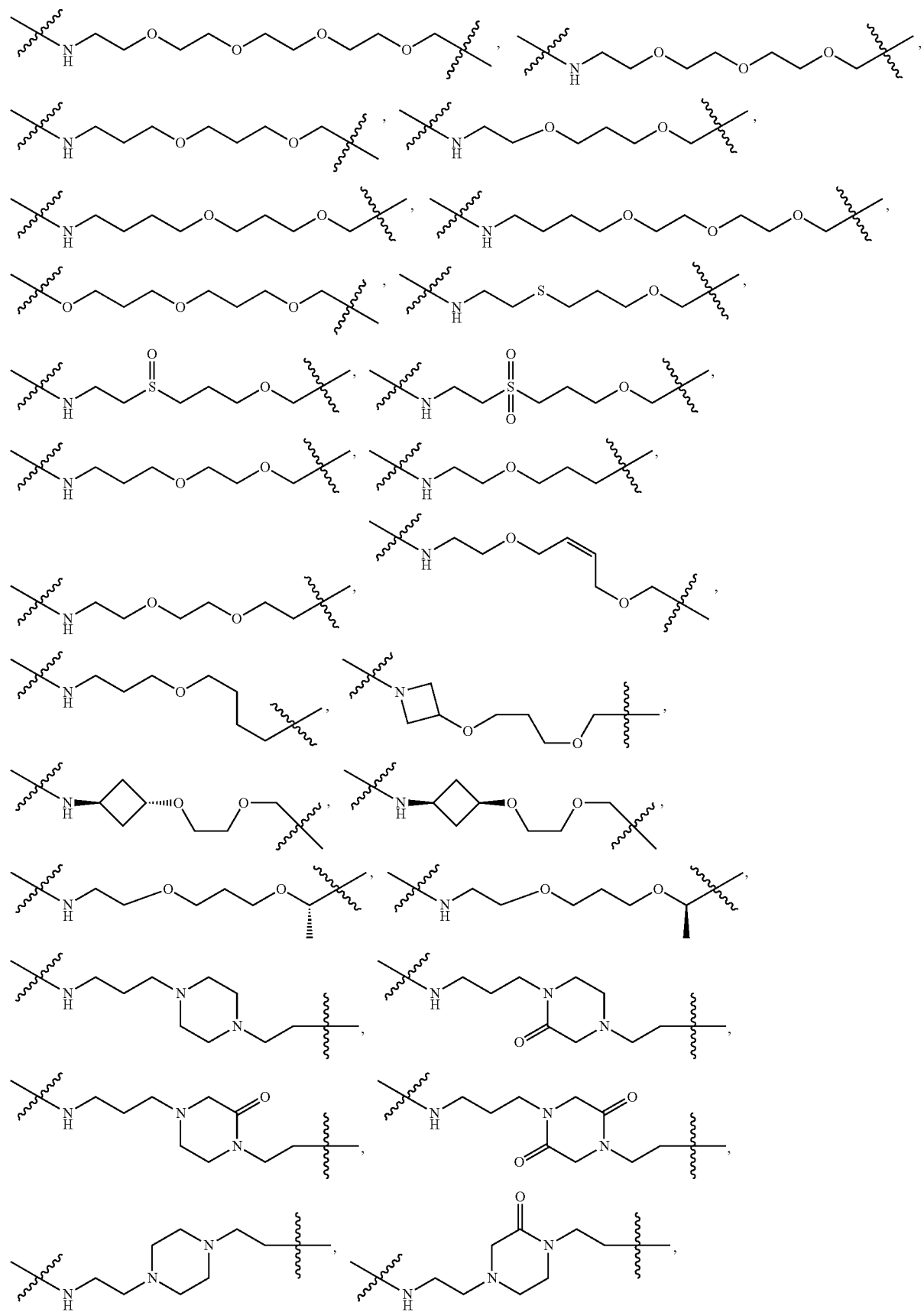

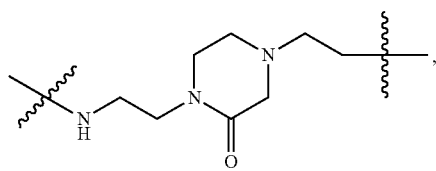
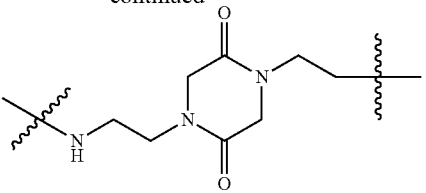
In additional embodiments, -(Linker)$^4$- is selected from:
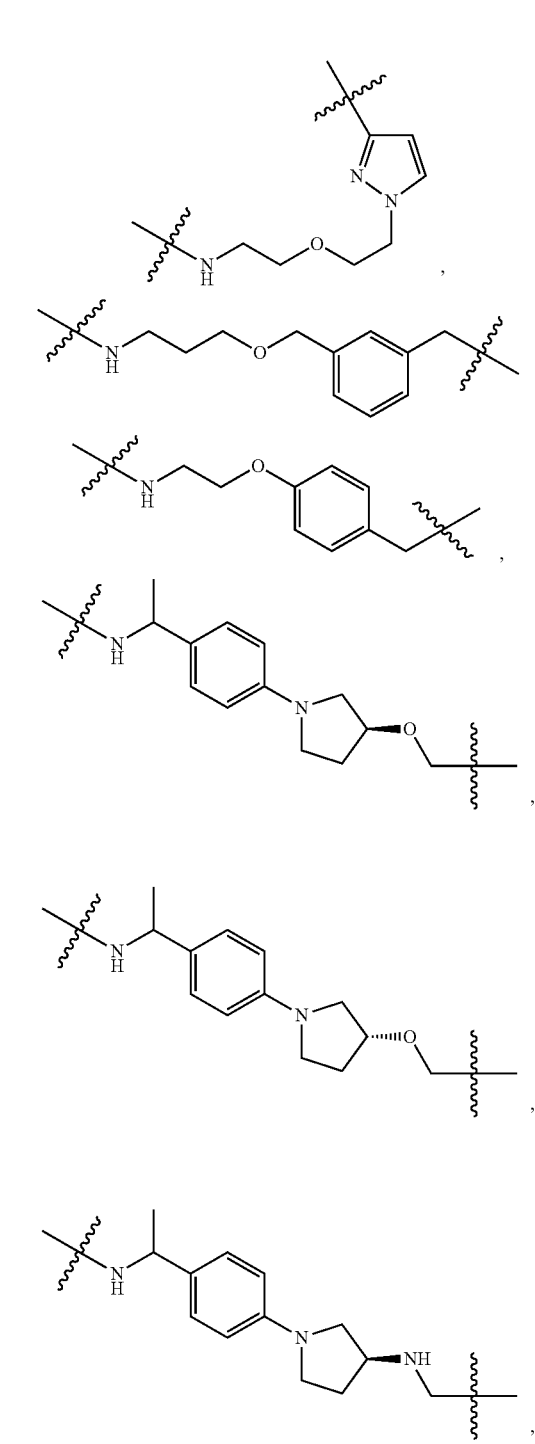
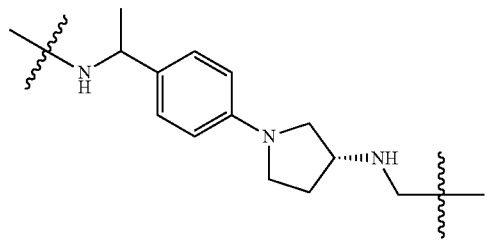
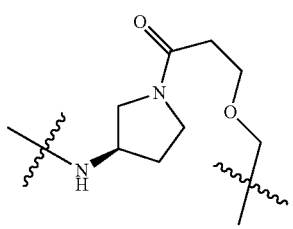
, and In additional embodiments, -(Linker)^A- is selected from:
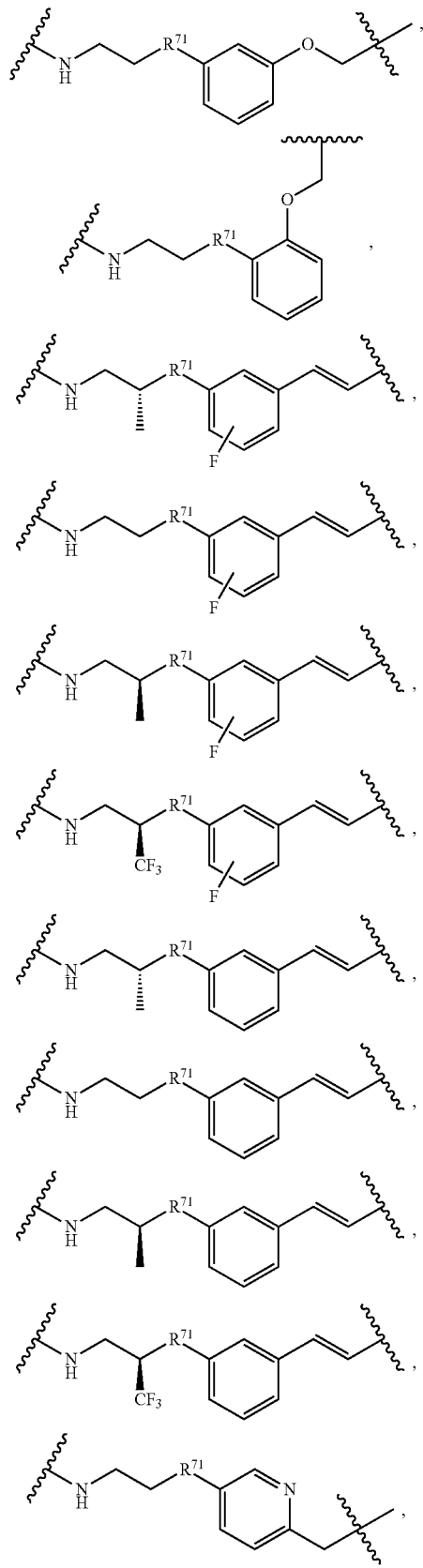
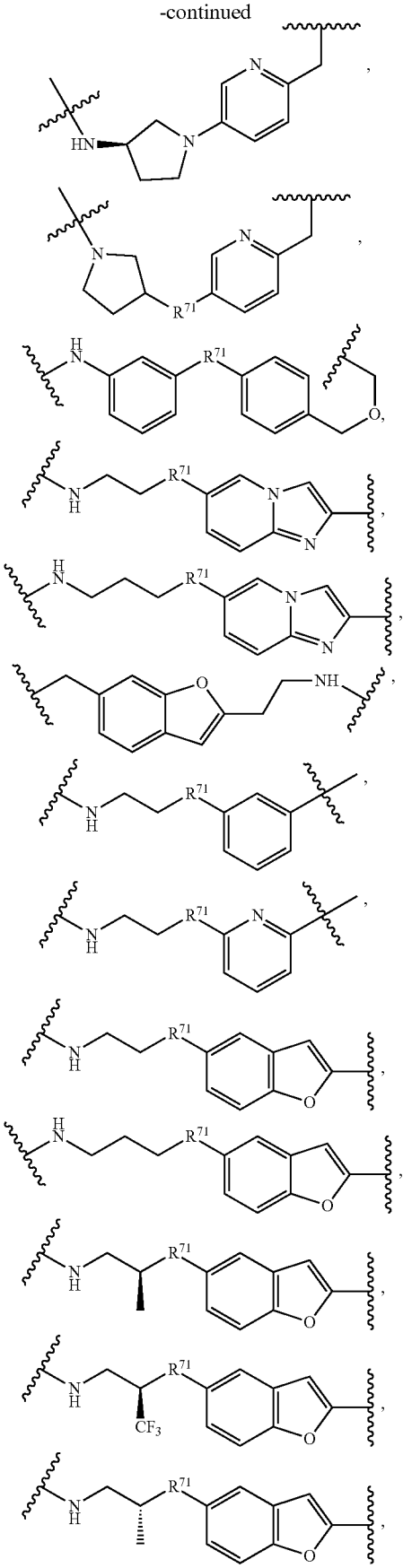

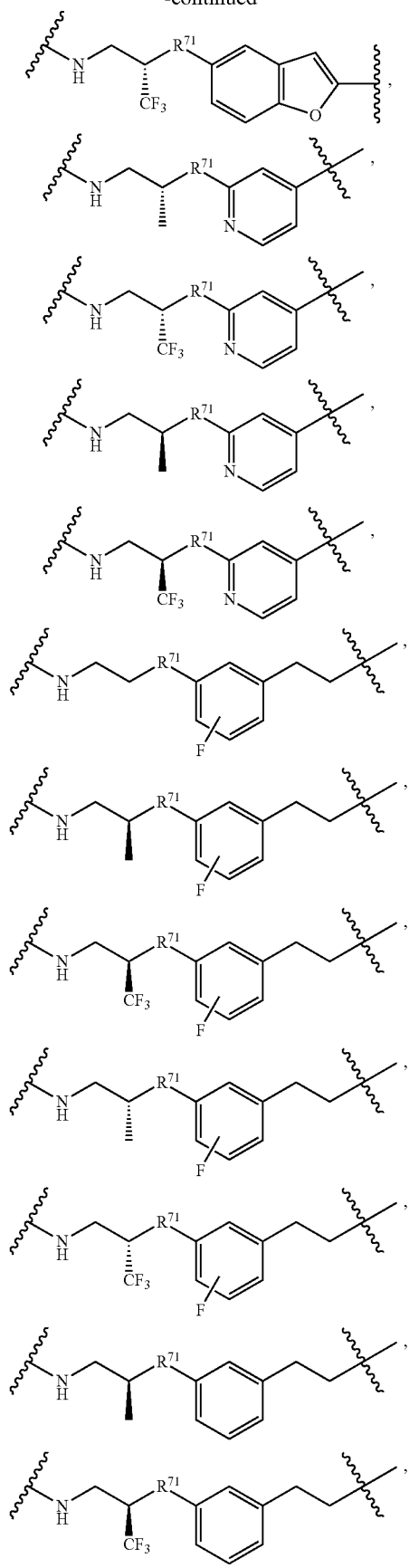
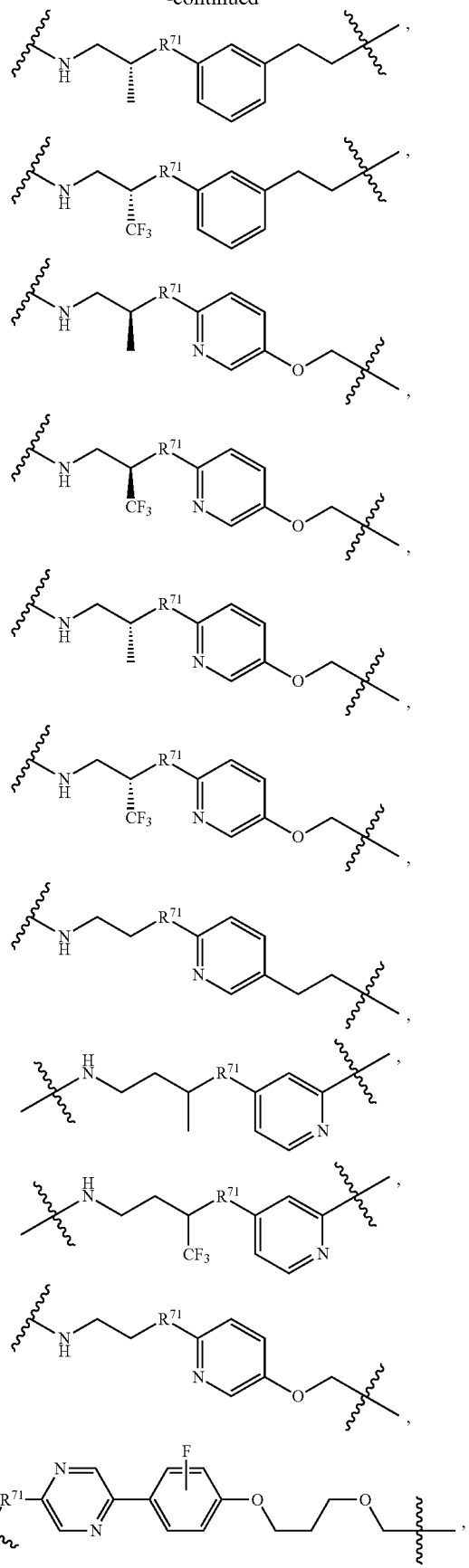

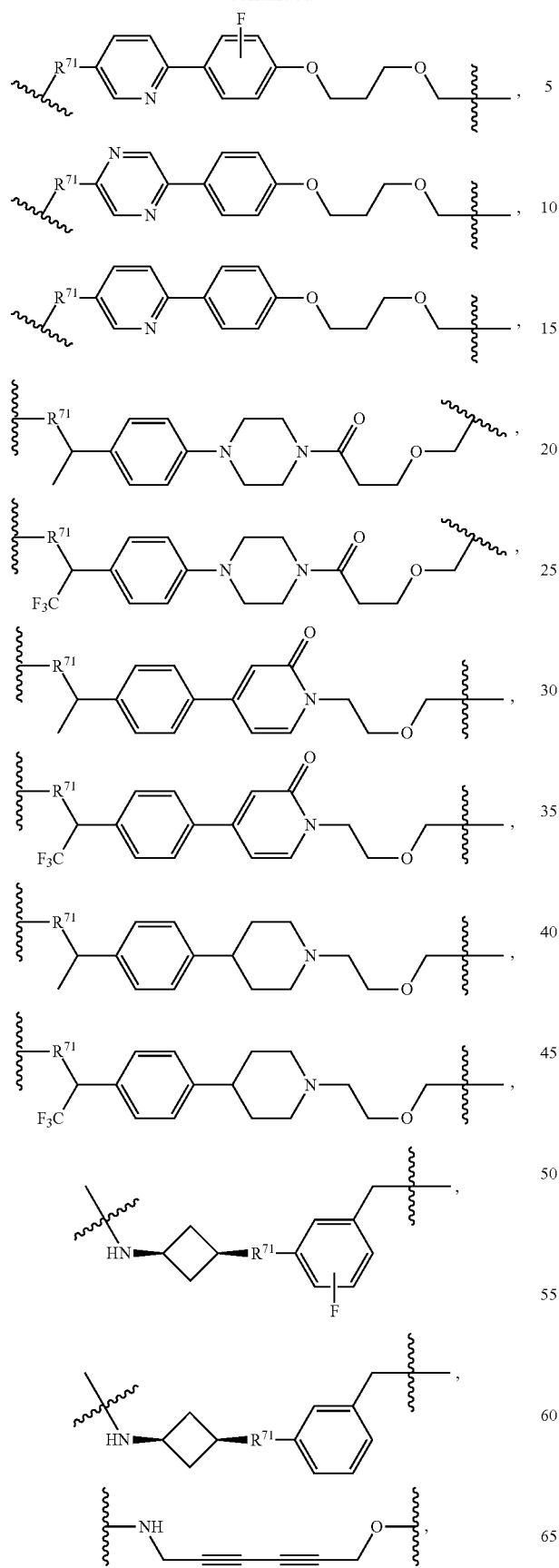
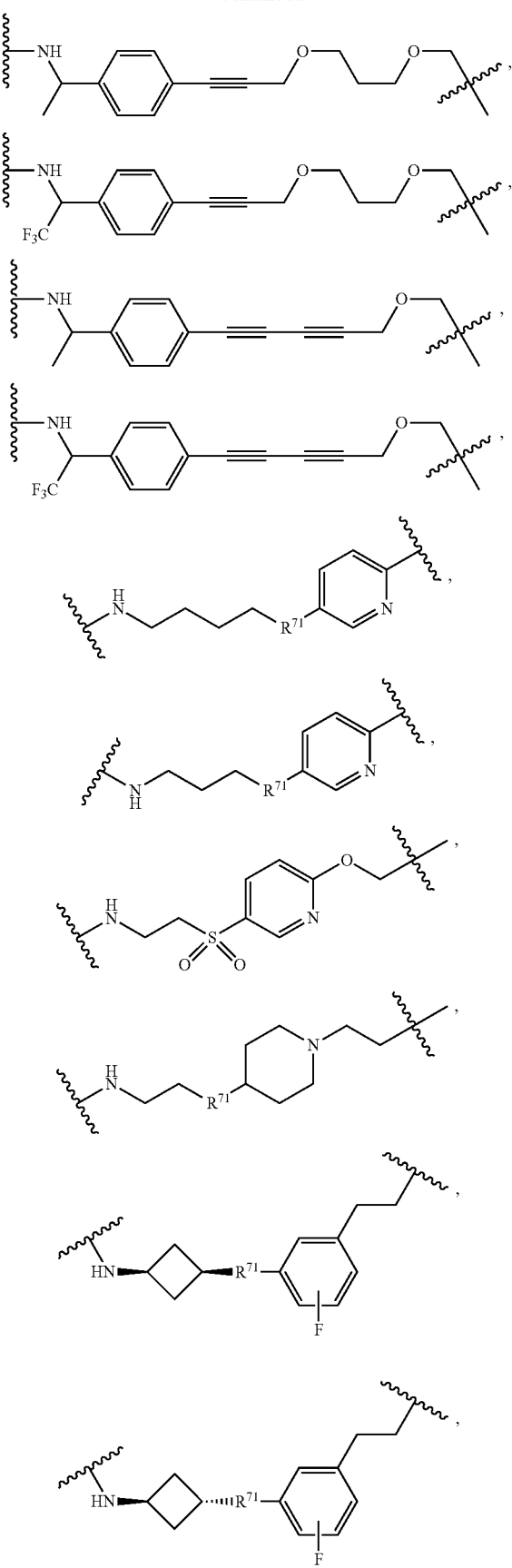

315
-continued
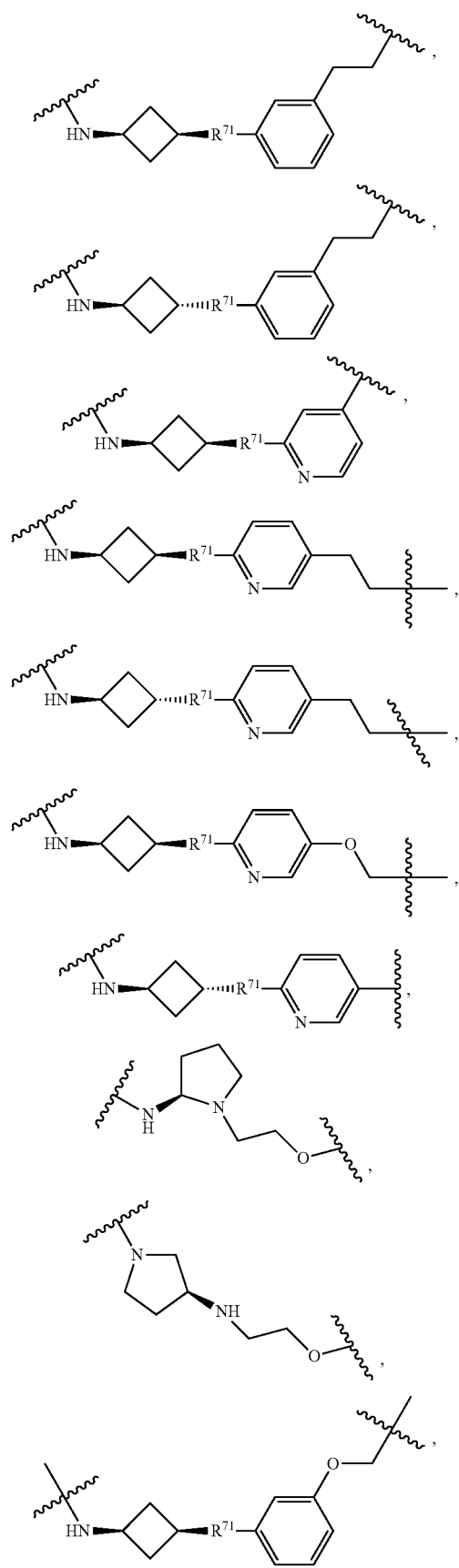
316
-continued
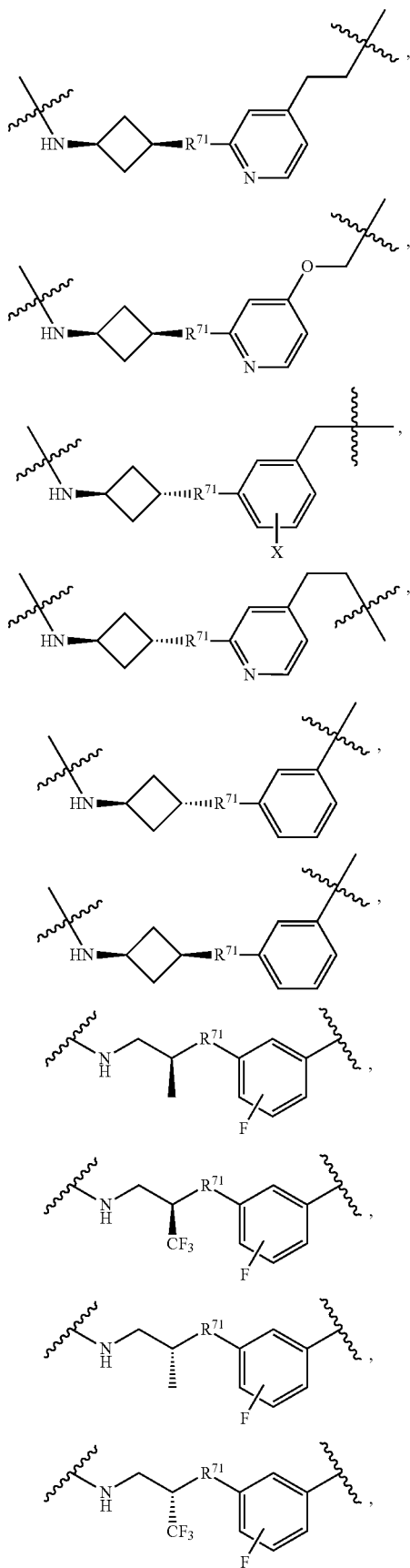

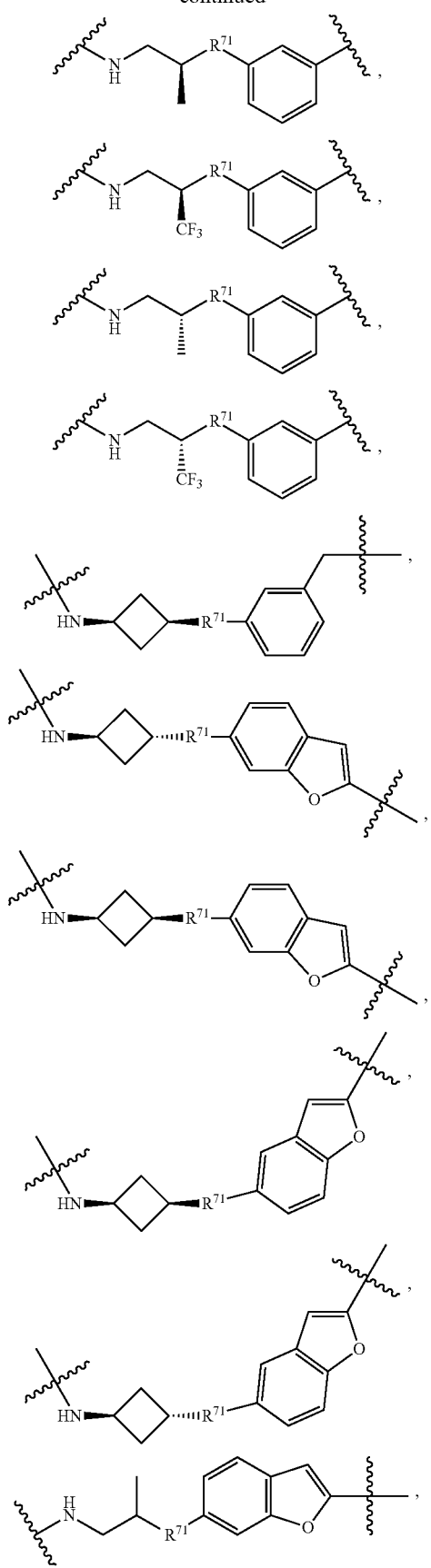
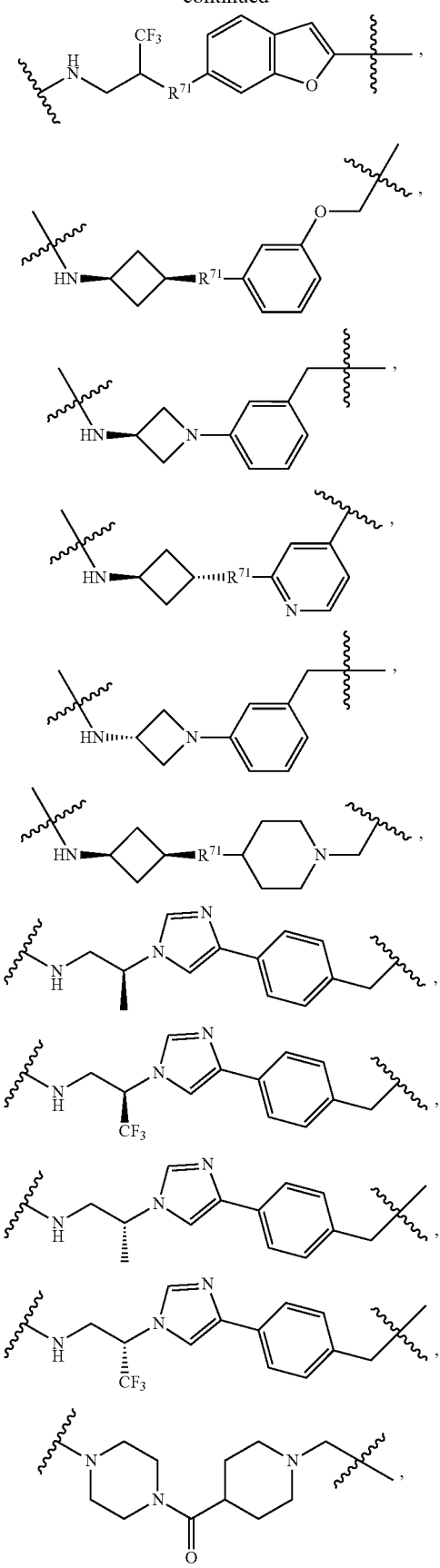

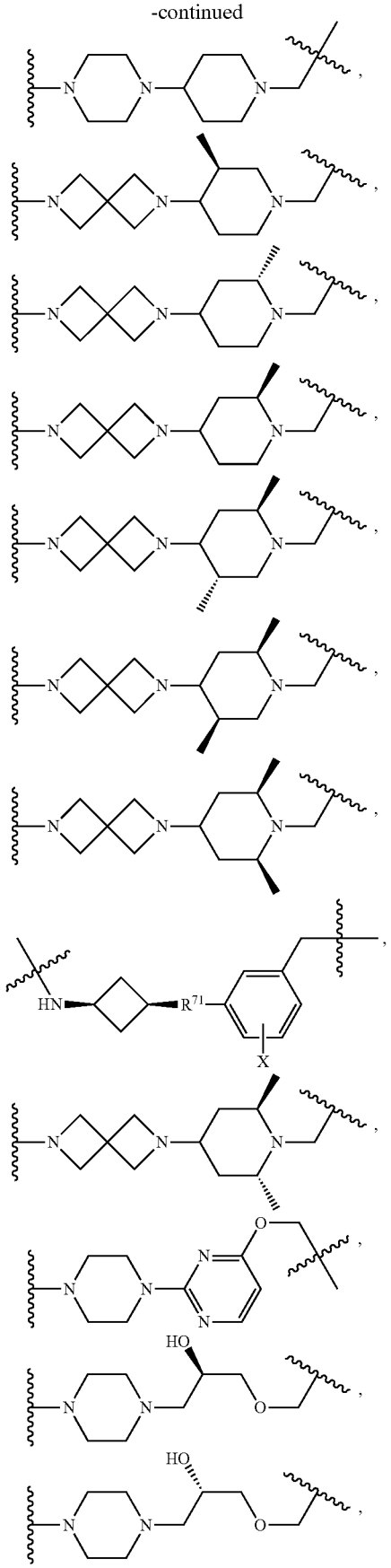
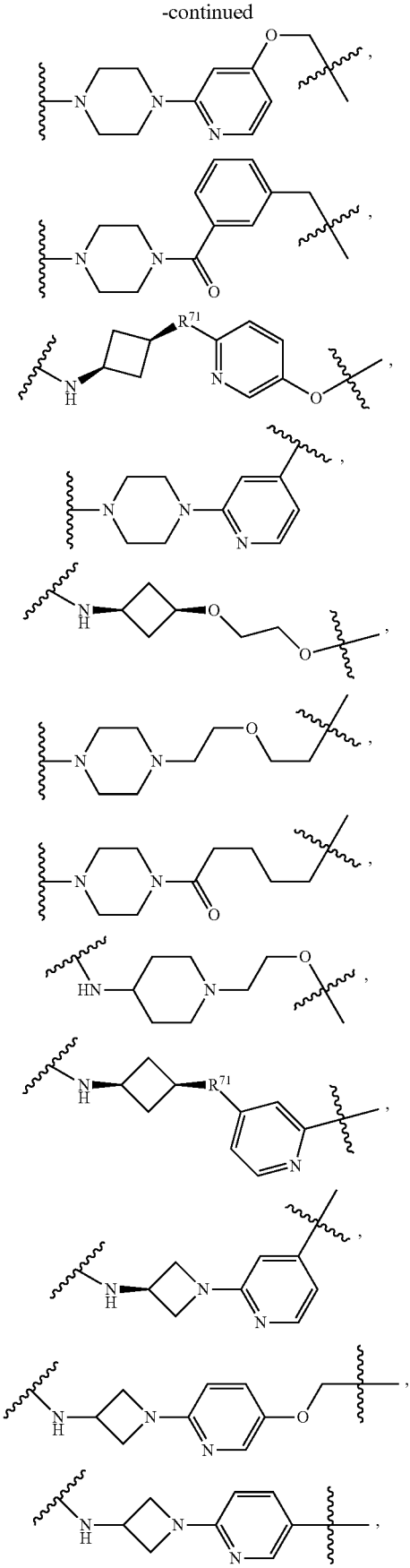

321
-continued
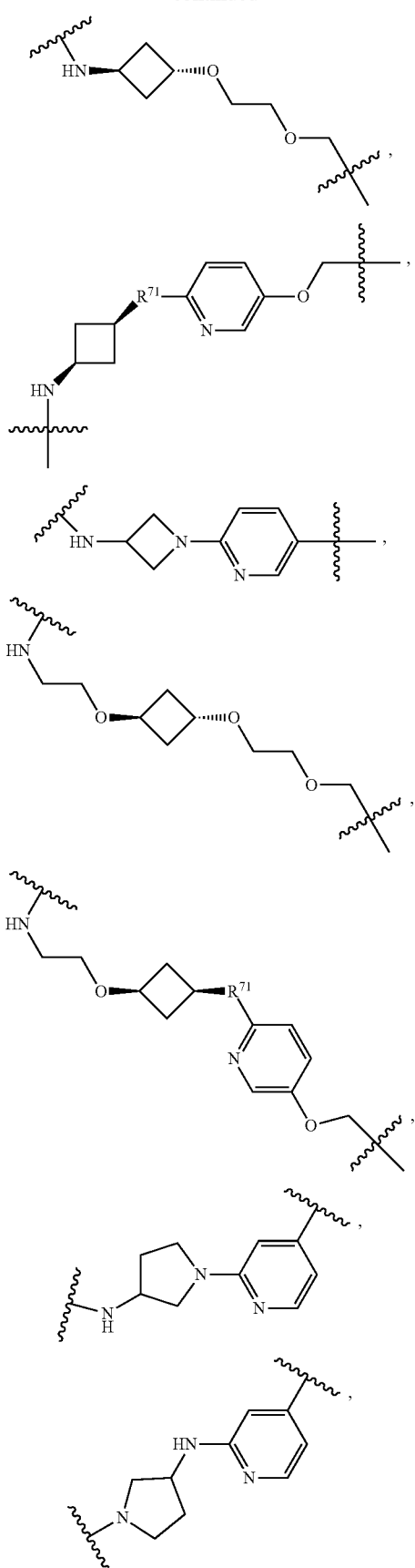
322
-continued
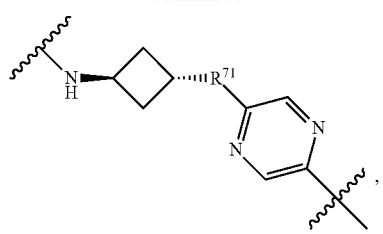
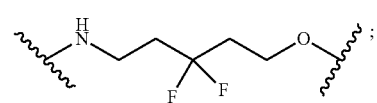
wherein $R^{71}$ is —O—, —NH, Nalkyl, heteroaliphatic, aliphatic, or —NMe
In additional embodiments, -(Linker)$^4$- is selected from:
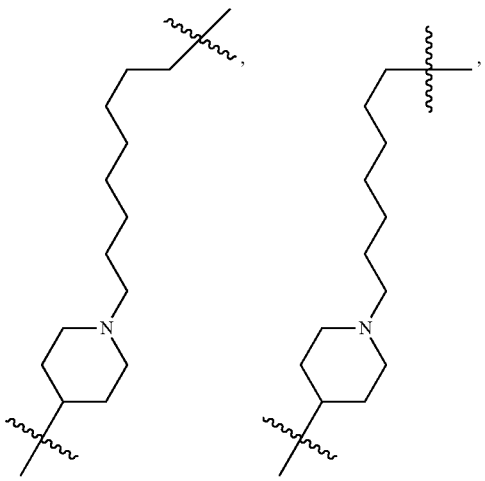
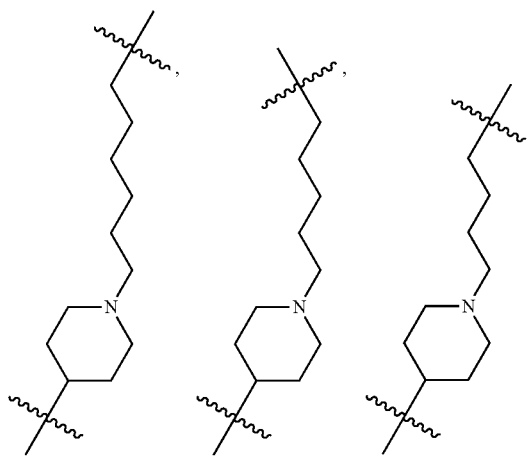

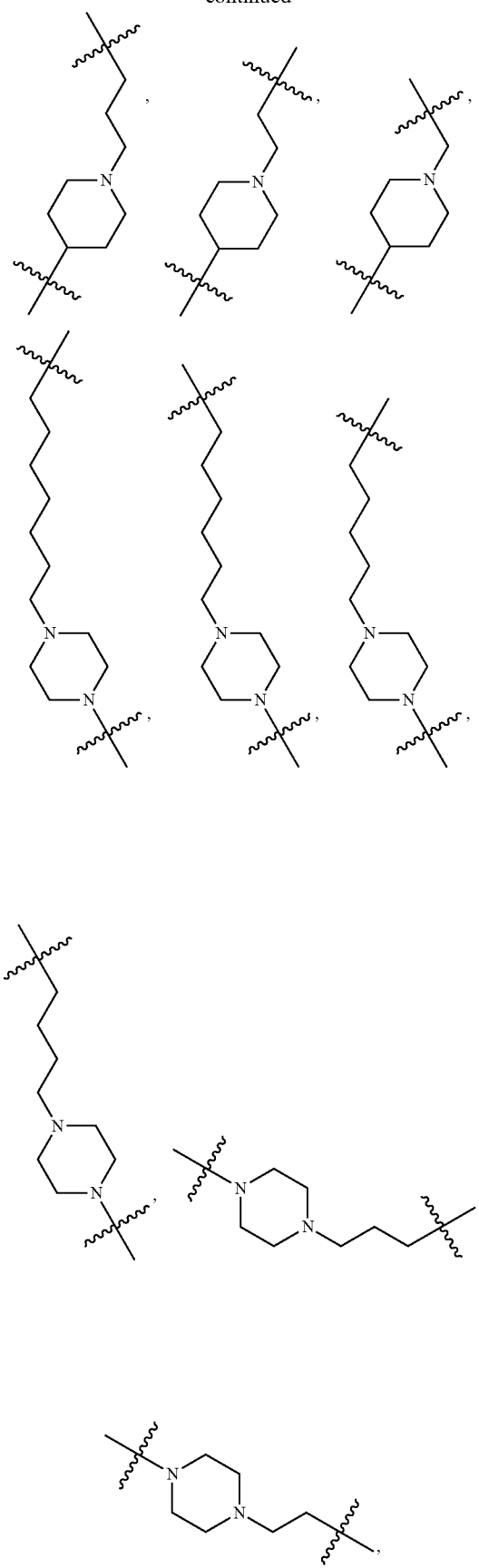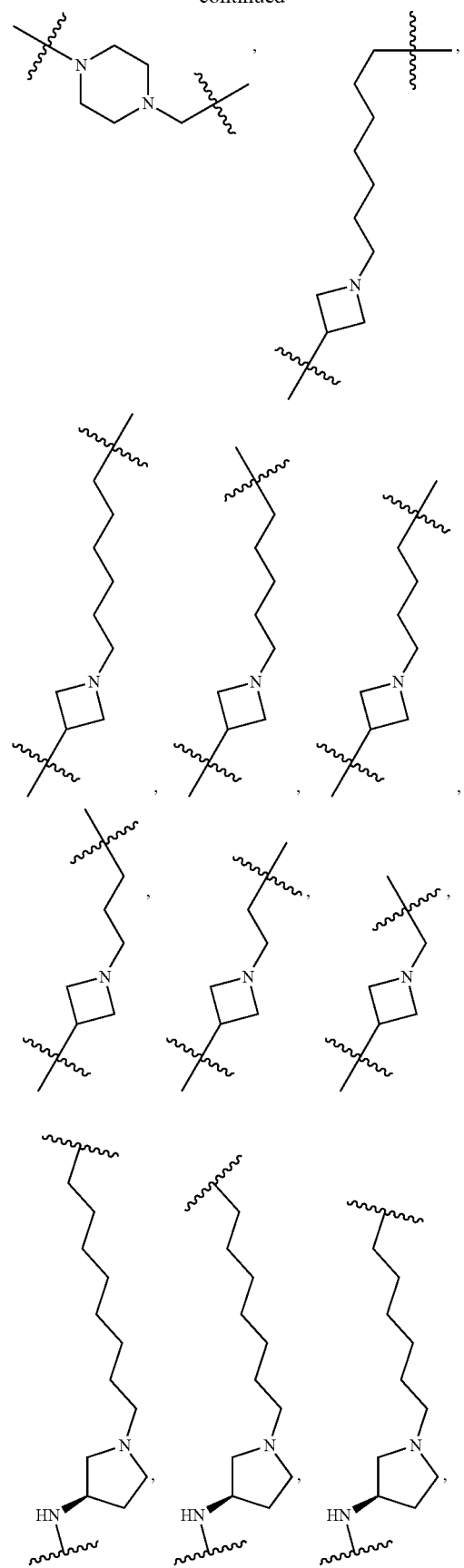

325
-continued
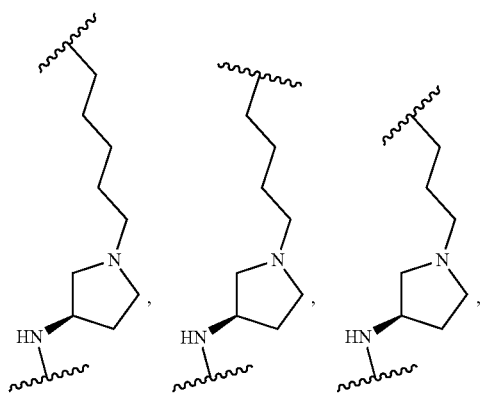
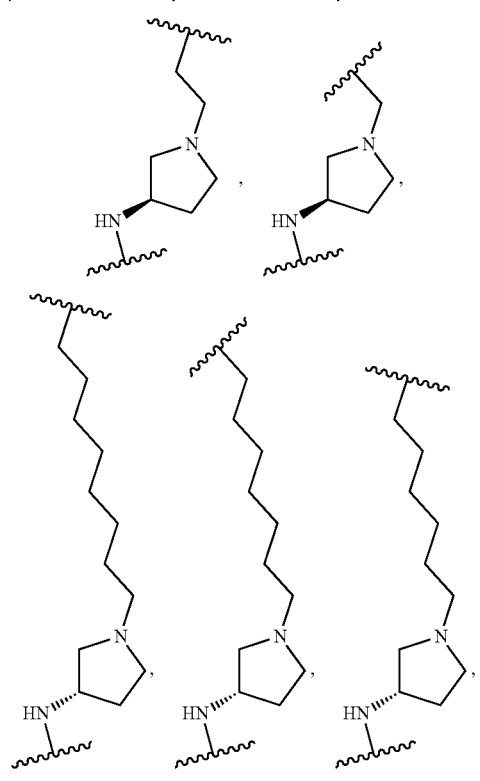
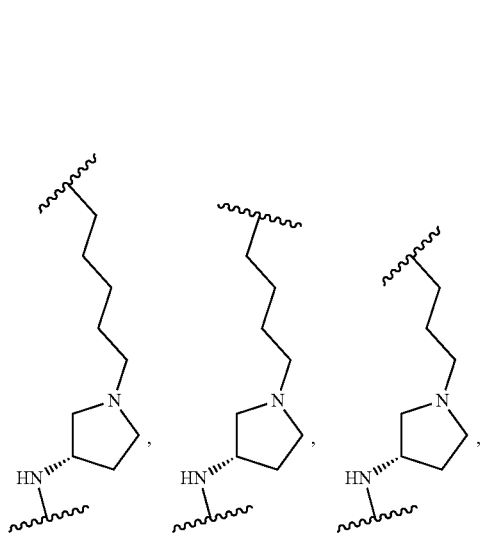
326
-continued
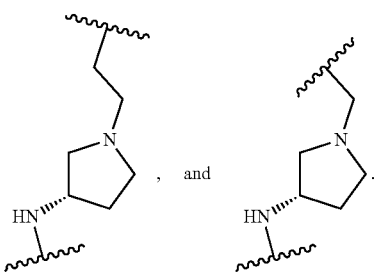 [SMILES: *CCN1CC[C@H](N*)C1 ; *CN1CC[C@H](N*)C1]
, and
In additional embodiments, -(Linker)$^A$- is selected from:
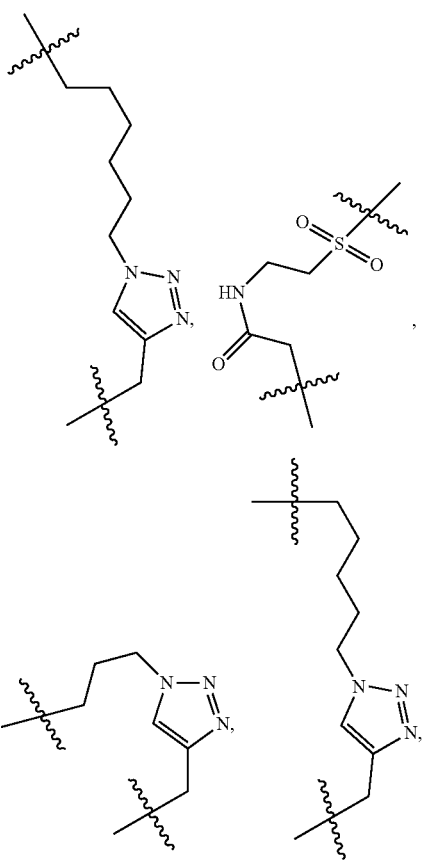
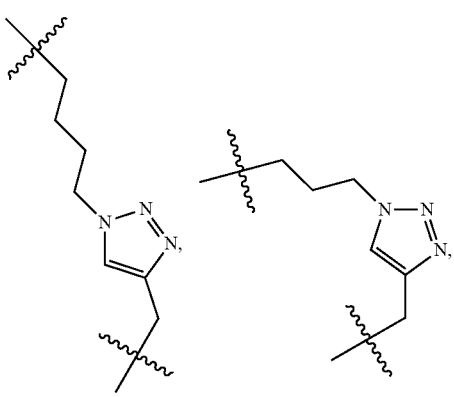

327
-continued
328
-continued
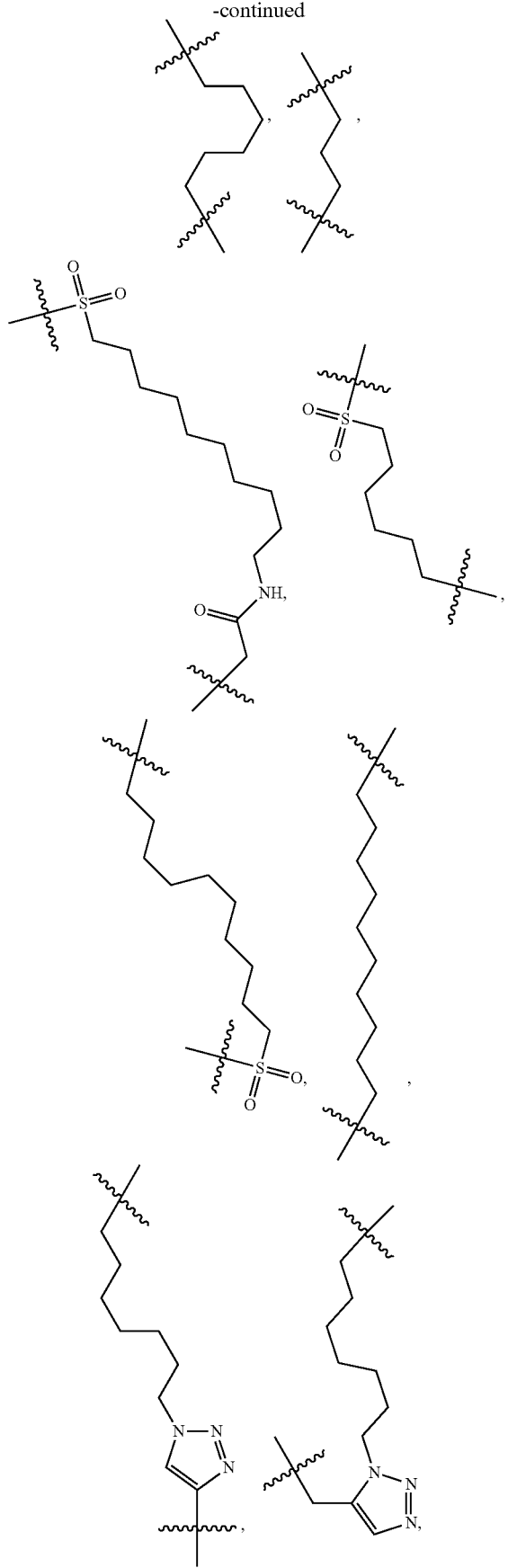
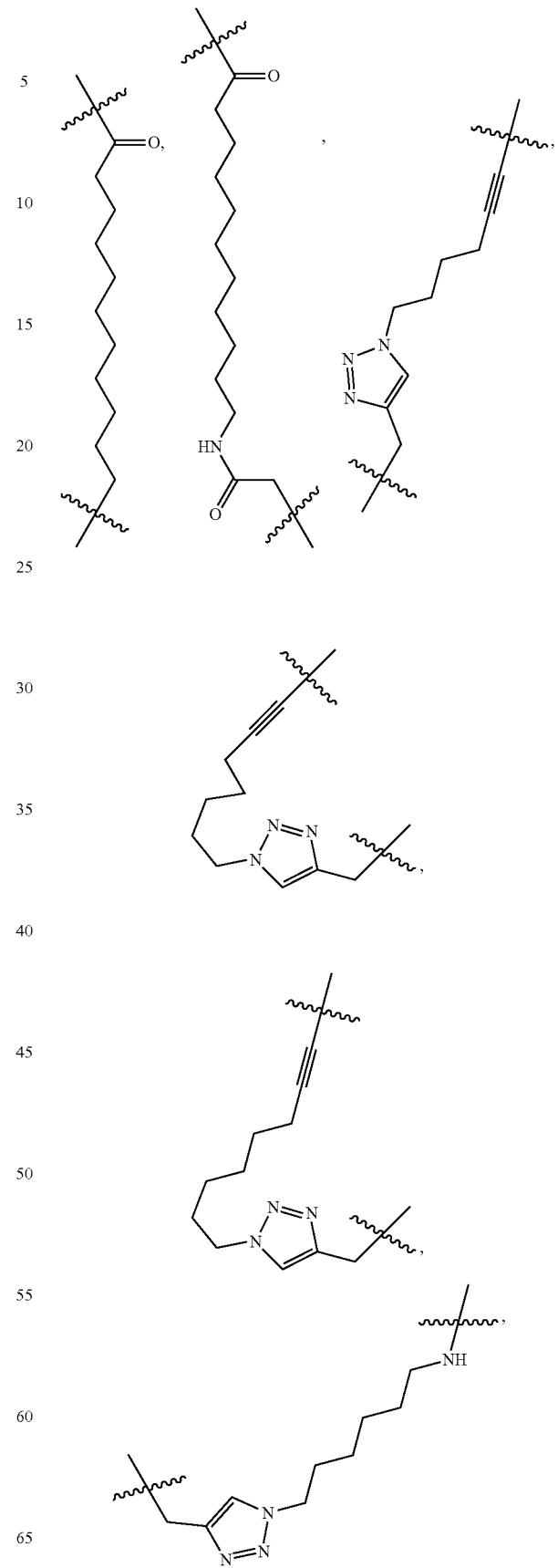

329
-continued
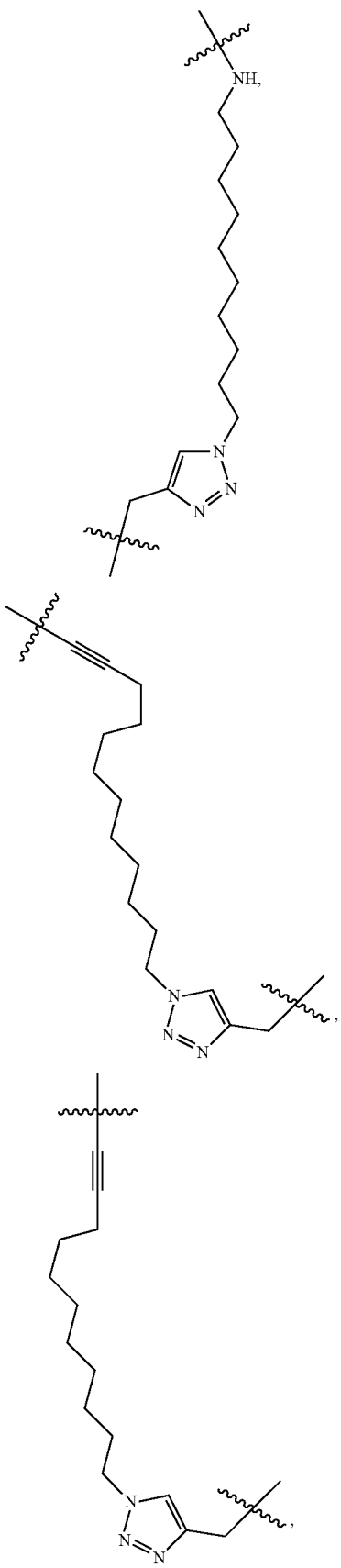 [SMILES: *Cc1cn(CCCCCCCCCCN*)nn1 ; *C#CCCCCCCCCCCn1cc(C*)nn1 ; *C#CCCCCCCCCCn1cc(C*)nn1]
330
-continued
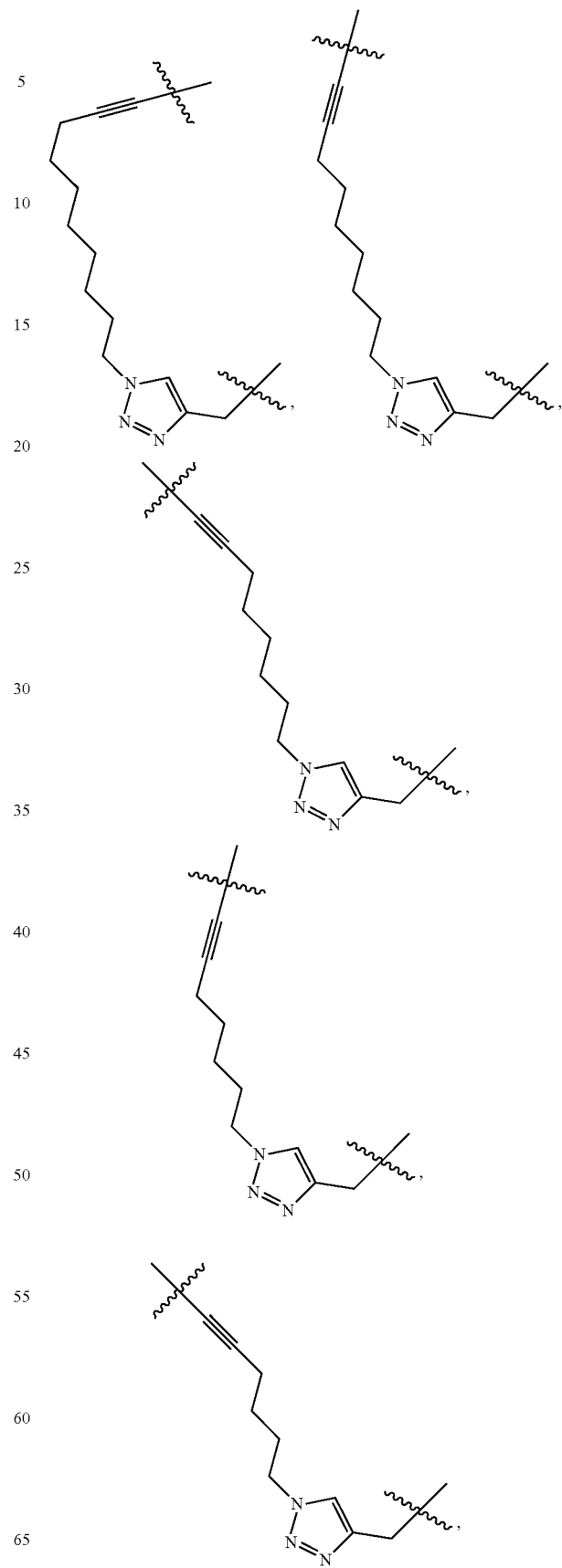

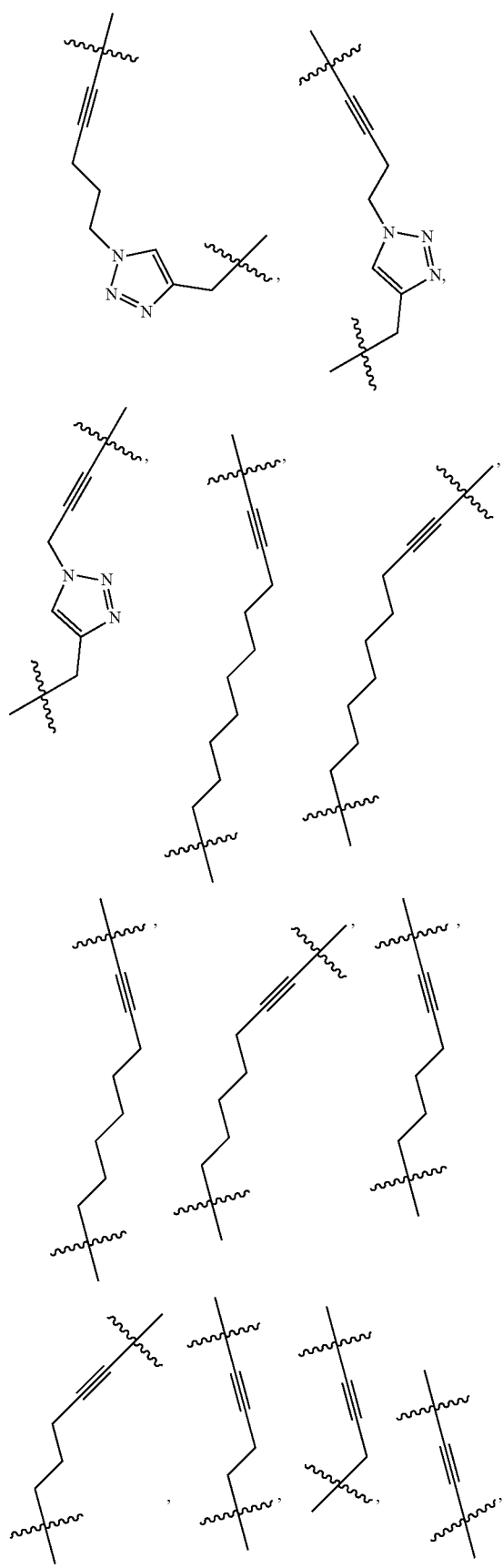
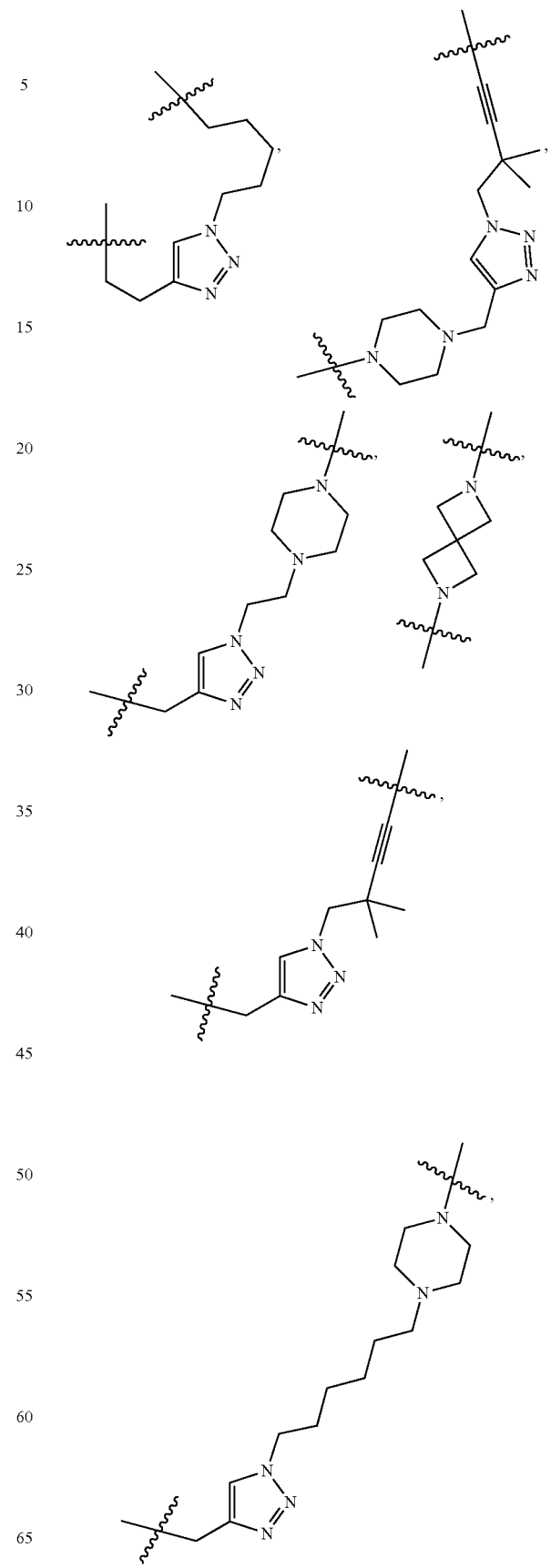

-continued
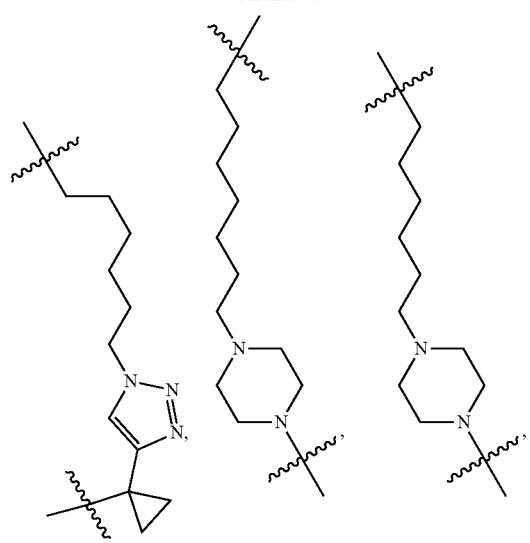
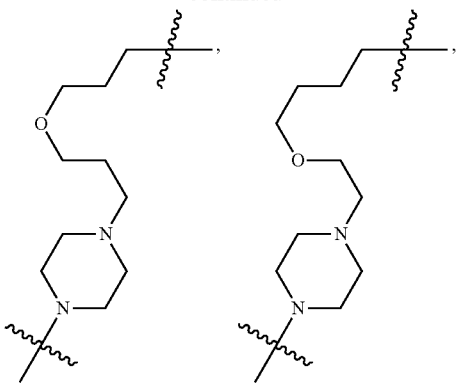
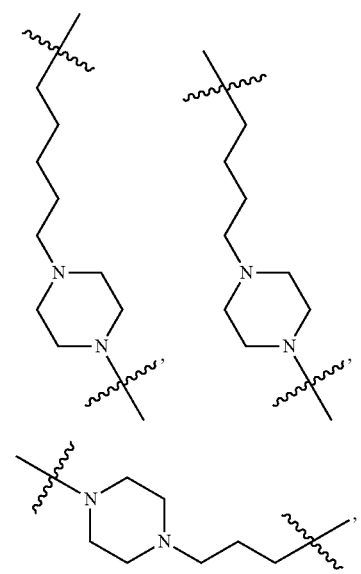
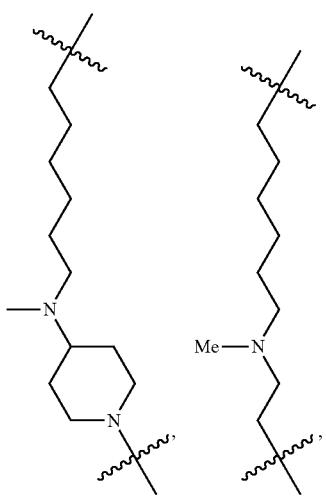
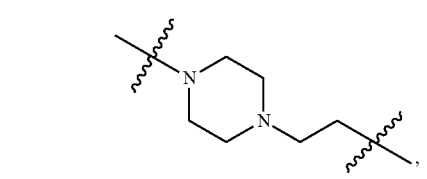
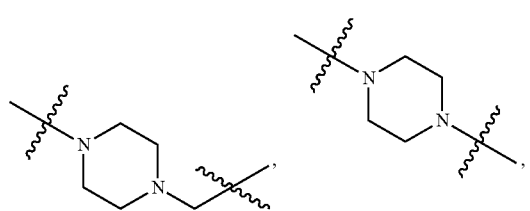
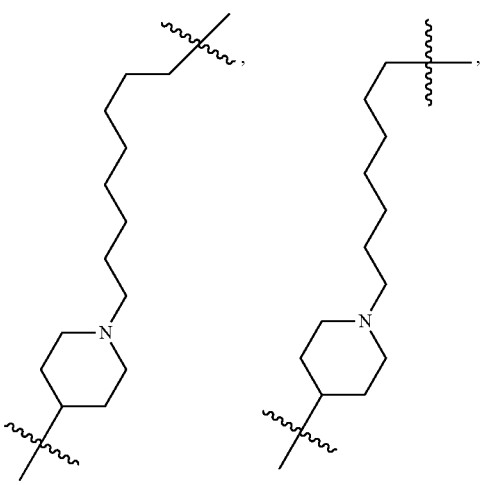

335
-continued
336
-continued
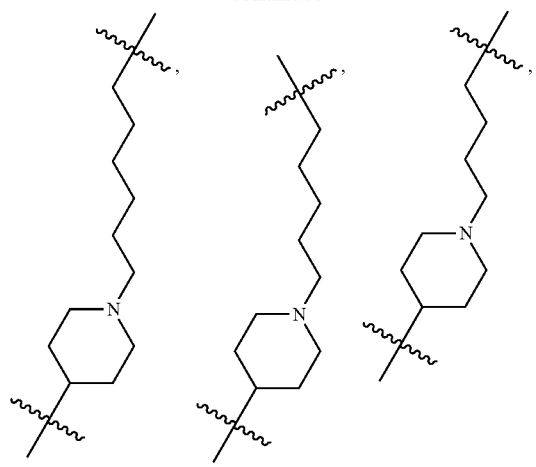
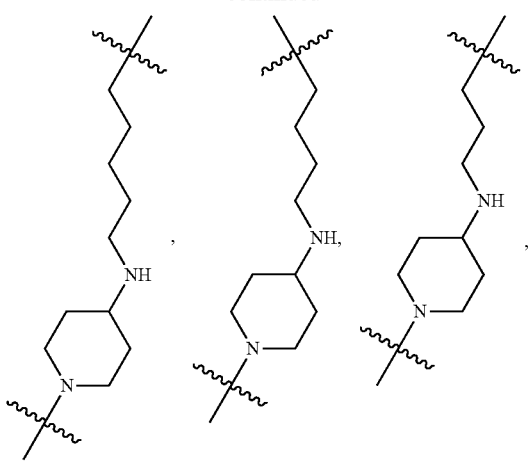
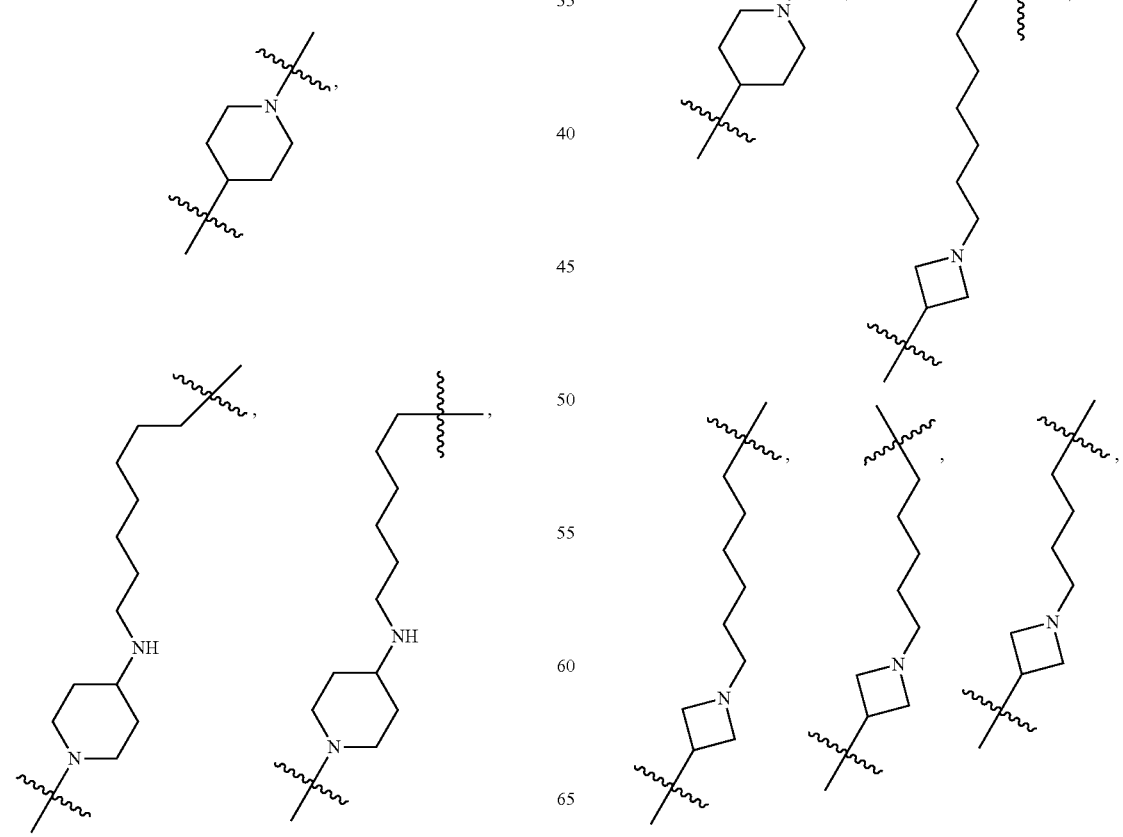

337
-continued
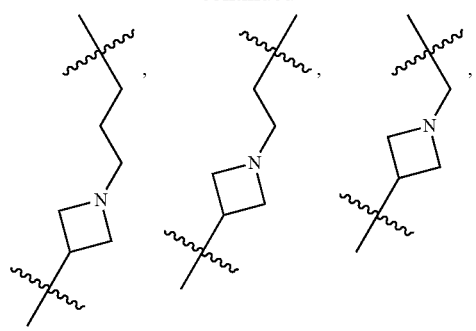
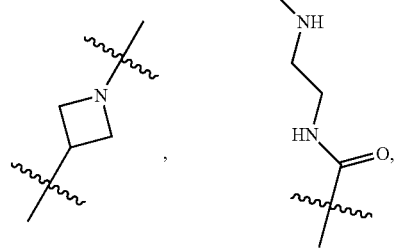
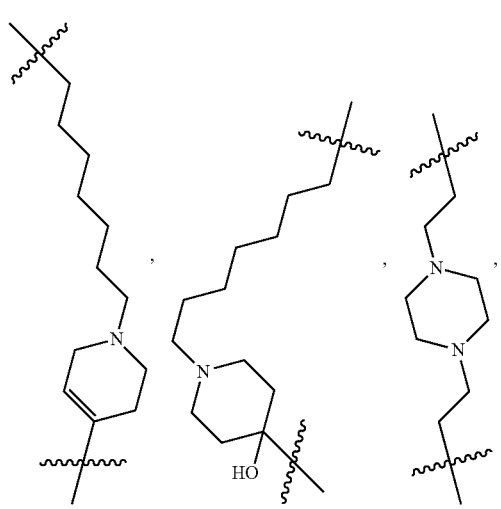
338
-continued
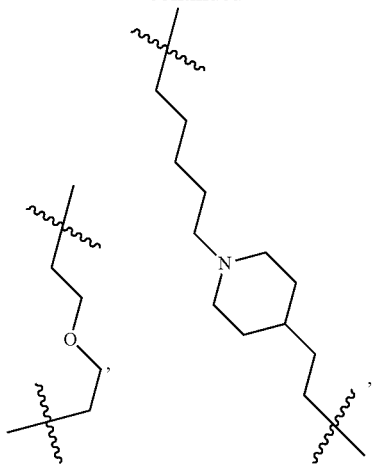
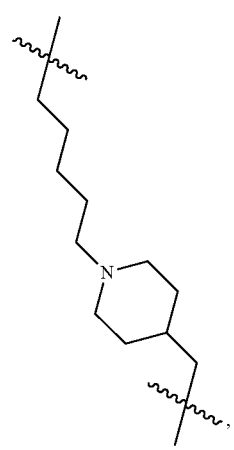
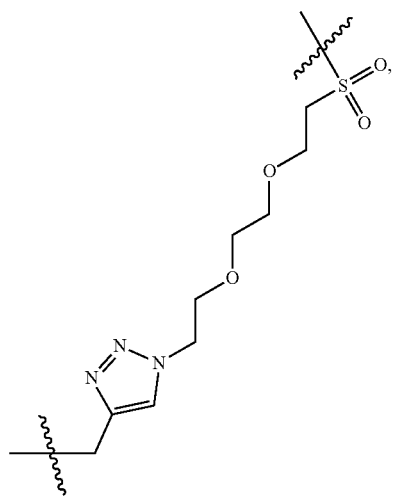

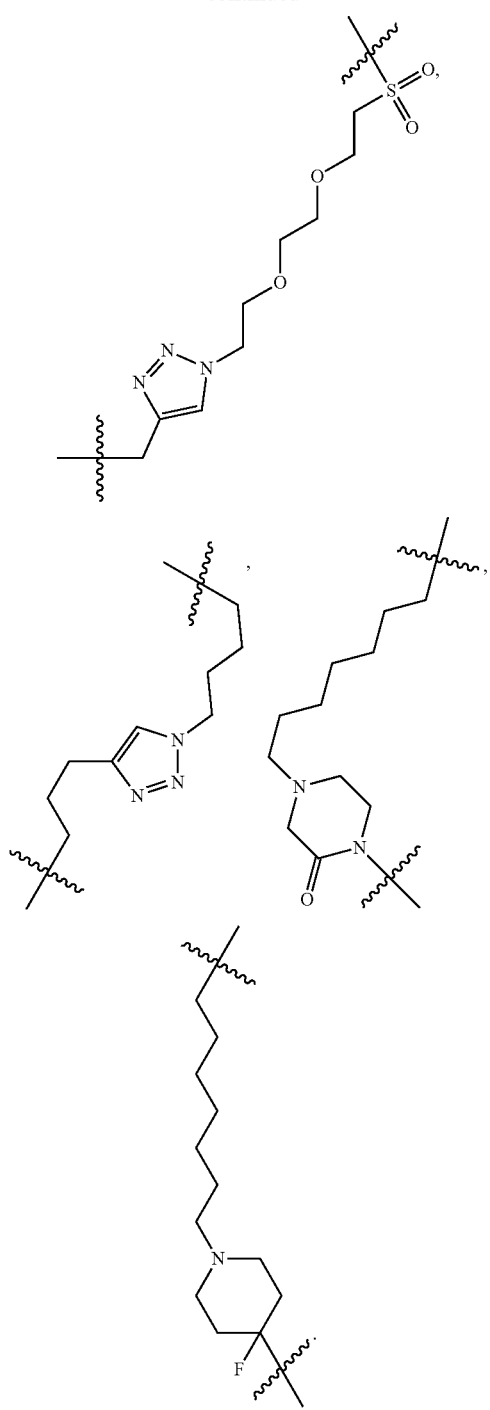
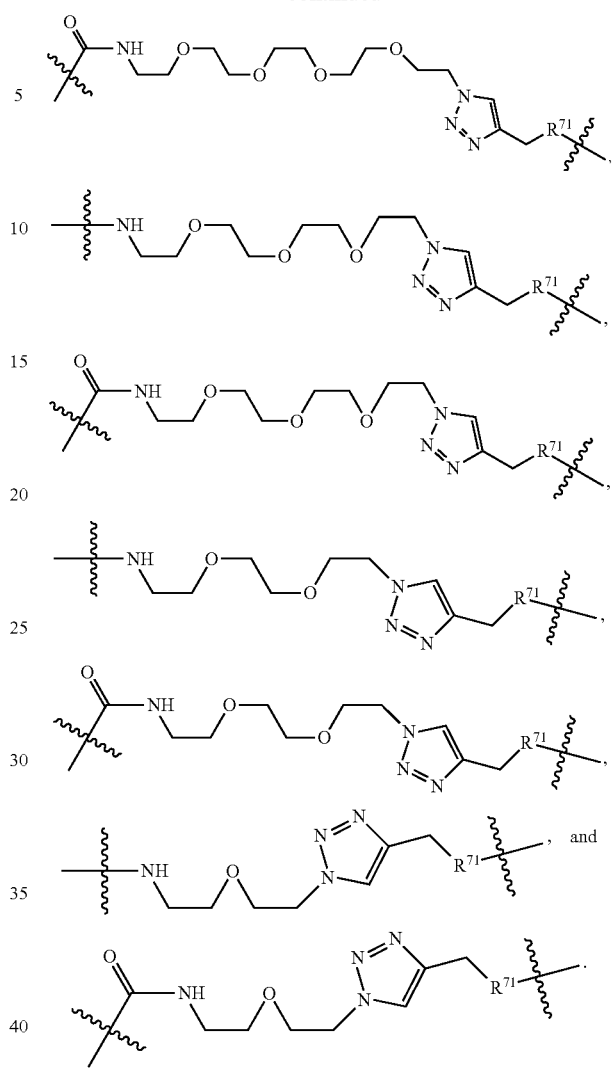
In additional embodiments, -(Linker)$^A$- is selected from:
In an additional embodiment -(Linker)$^A$- is selected from:
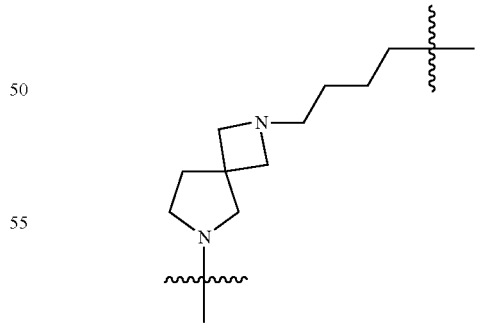
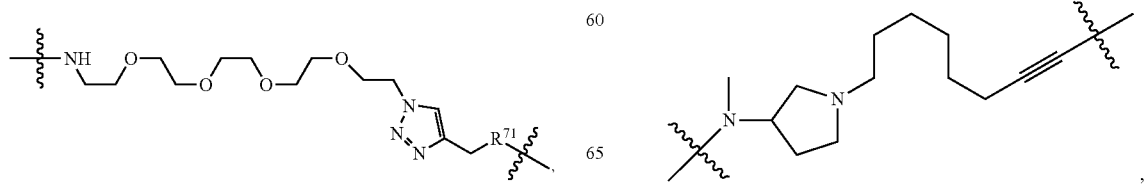

341
-continued
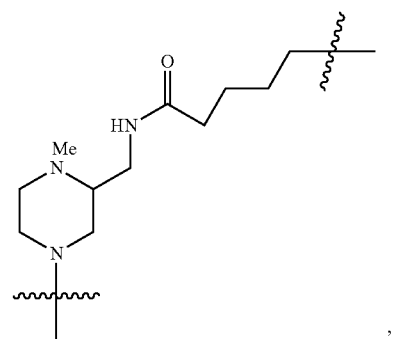
,
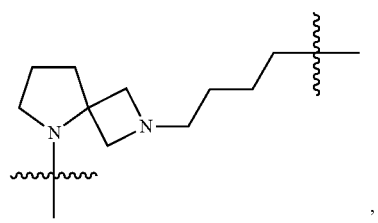
,
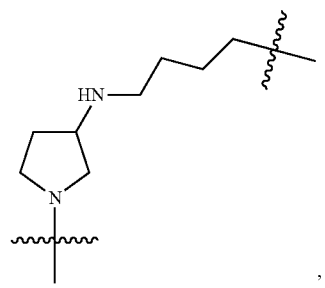
,
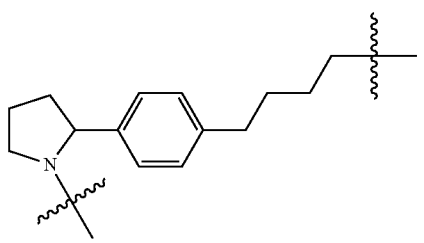
,
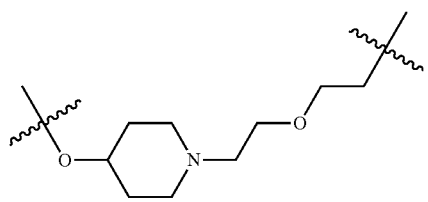
,
342
-continued
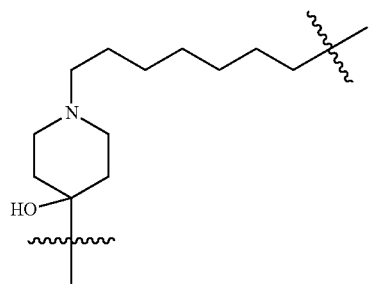
,
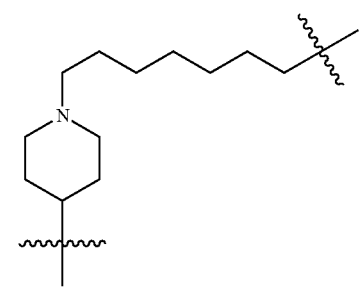
,
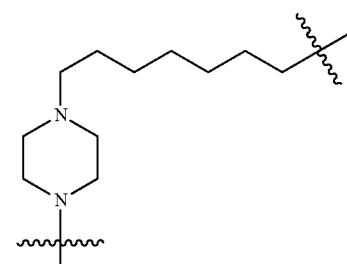
,
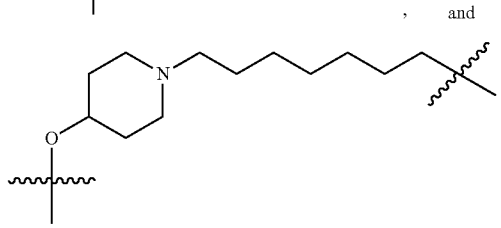 and
In additional embodiments, -(Linker)$^4$- is selected from:
,
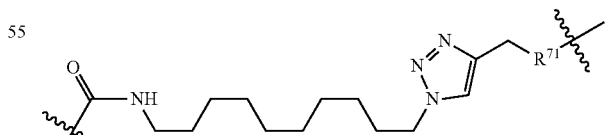
,
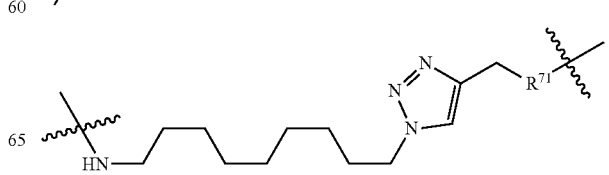
,

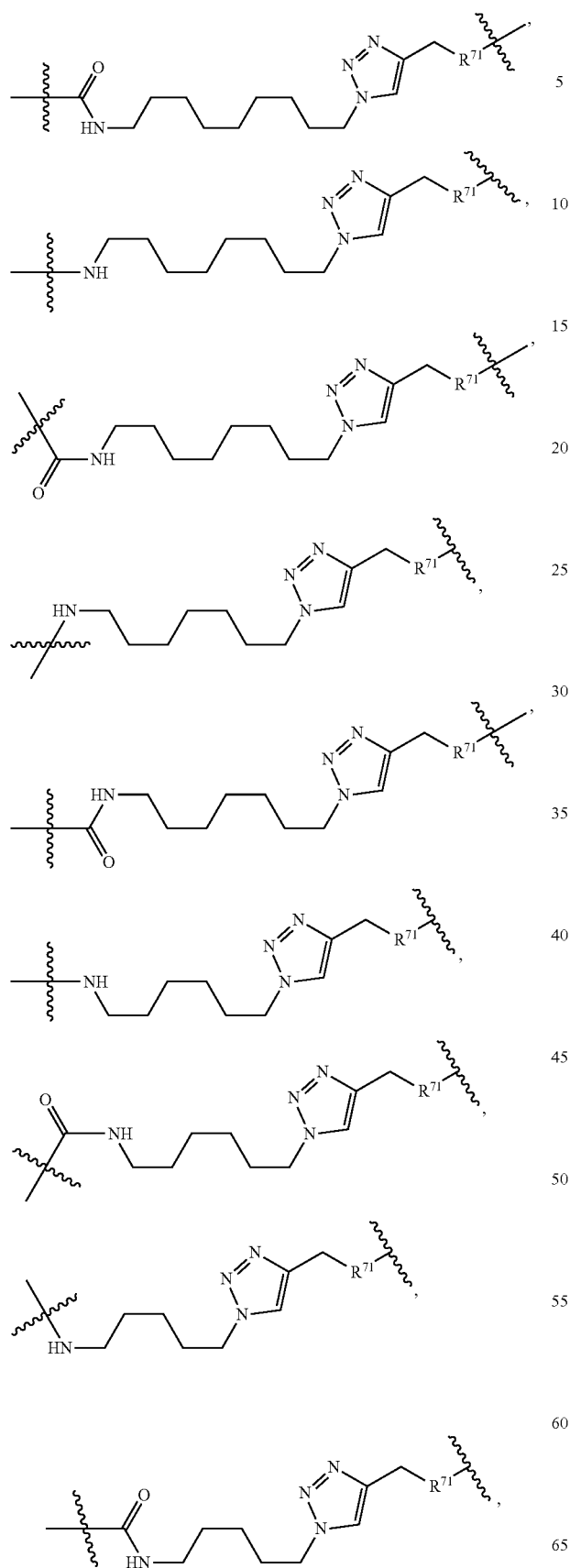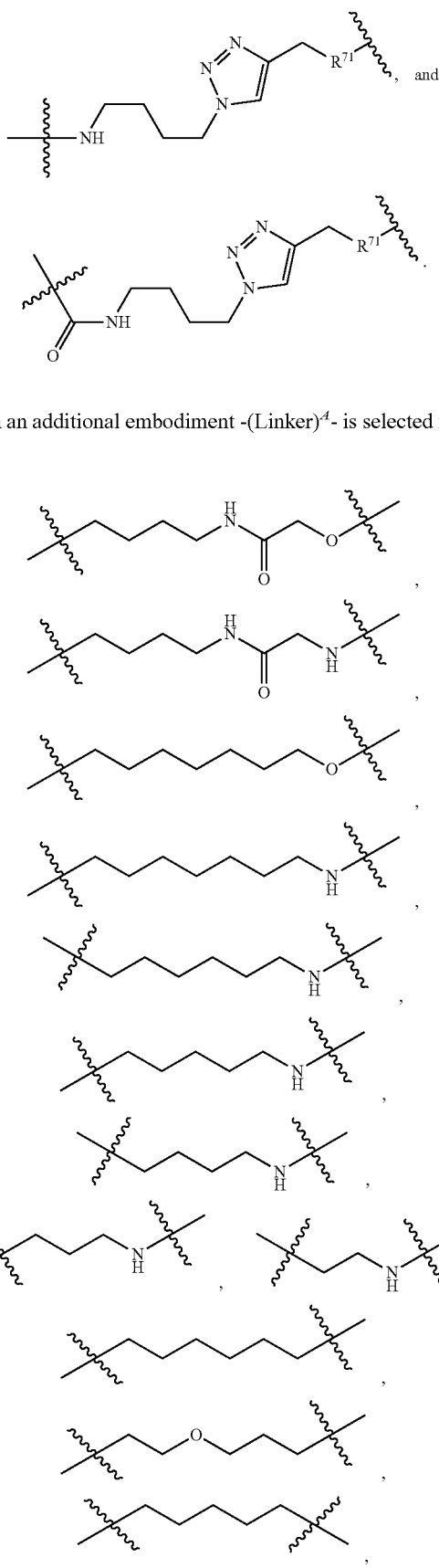
In an additional embodiment -(Linker)$^A$- is selected from:

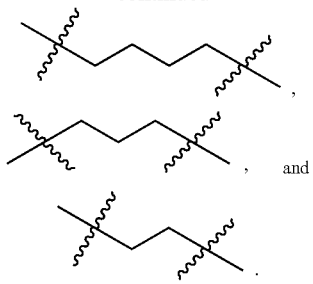
In an additional embodiment -(Linker)$^4$- is selected from:
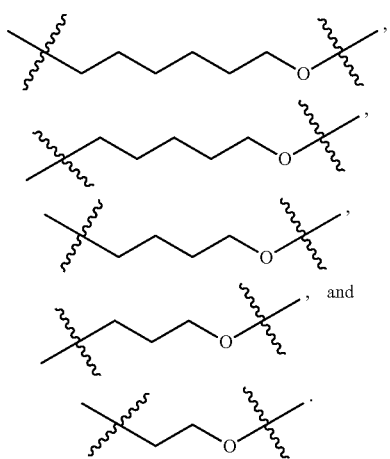
In certain embodiment -(Linker)$^4$- is selected from:
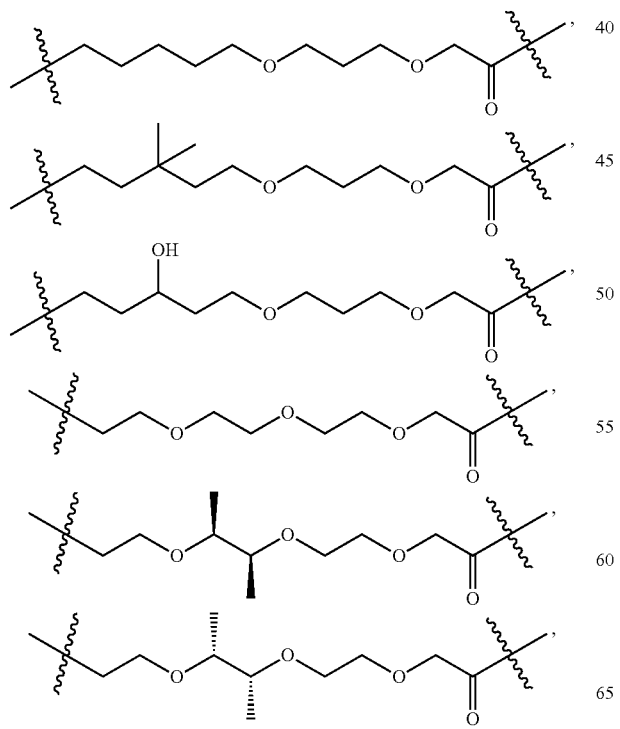
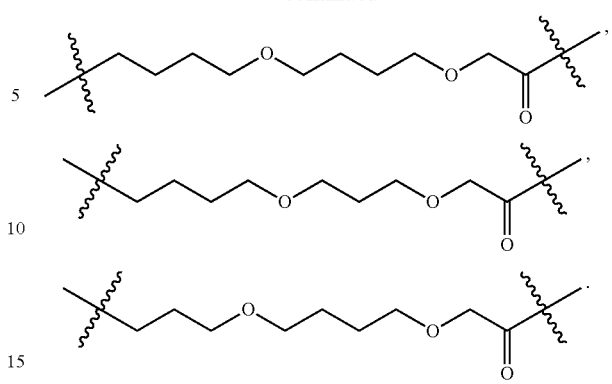
In certain embodiments -(Linker)$^4$- is selected from:
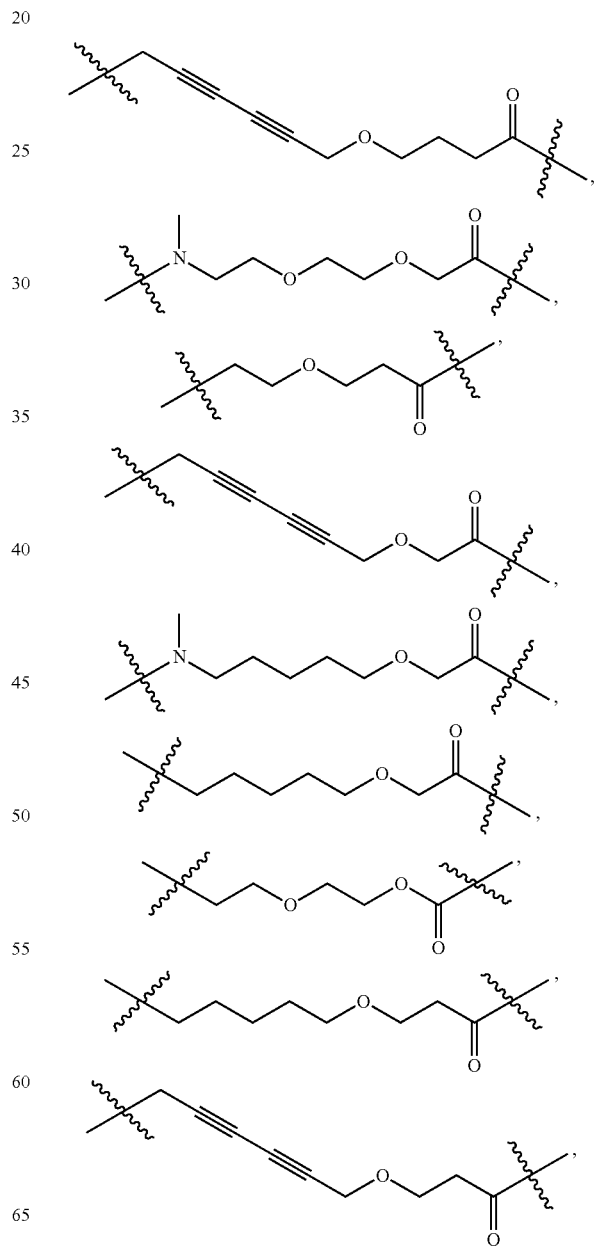

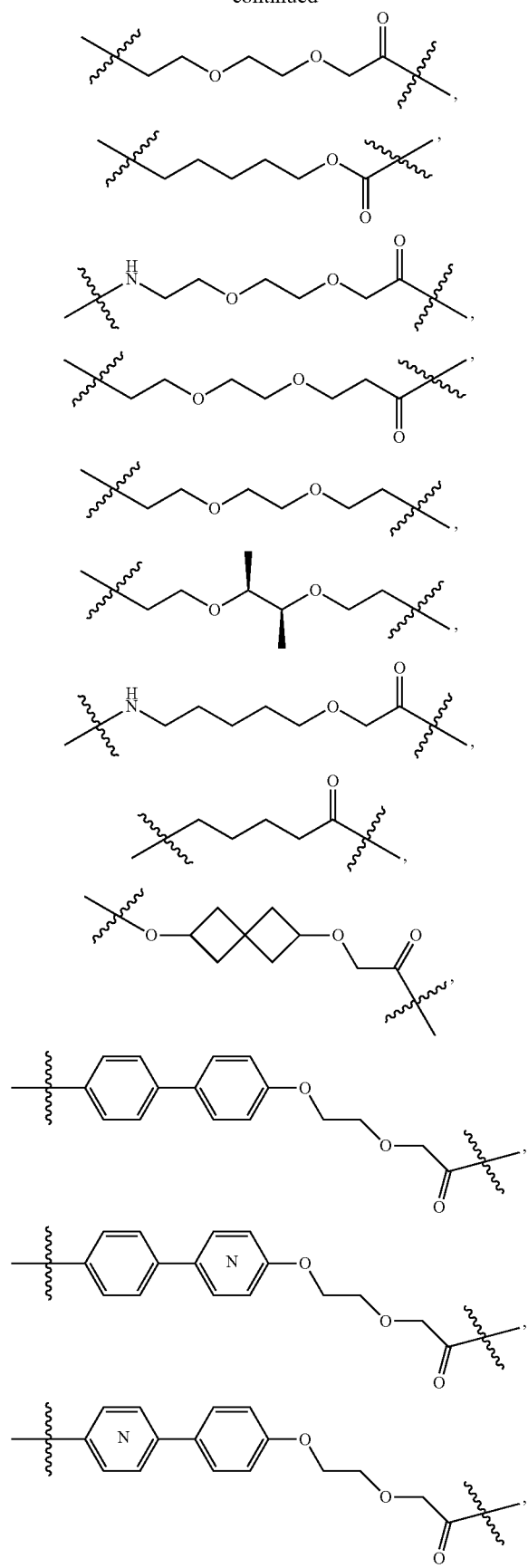
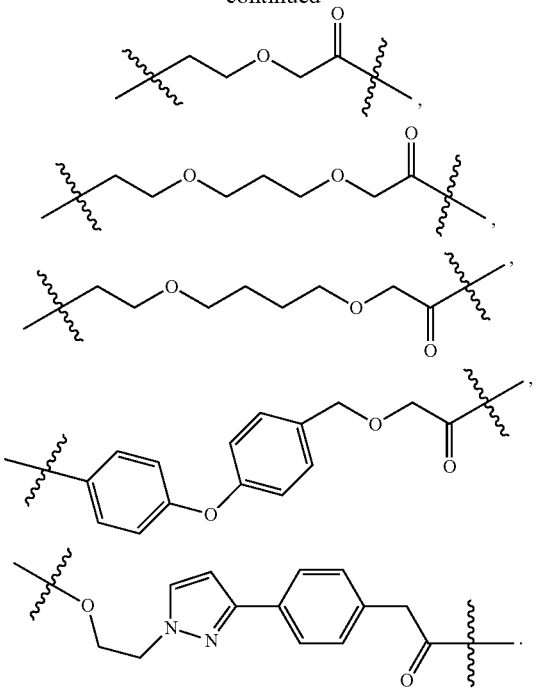
In the above structures
represents
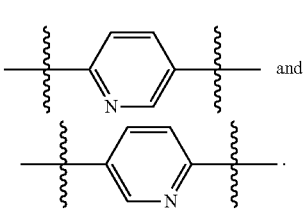
and
In certain embodiments, -(Linker)$^A$- can be a 4-24 carbon atom linear chains, wherein one or more the carbon atoms in the linear chain can be replaced or substituted with oxygen, nitrogen, amide, fluorinated carbon, etc., such as the following:
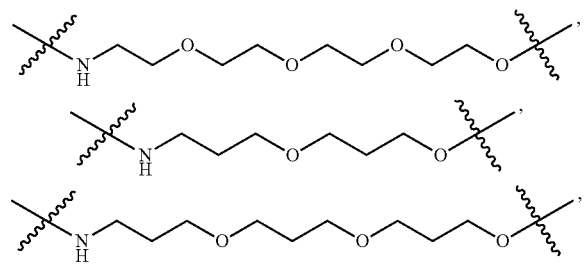

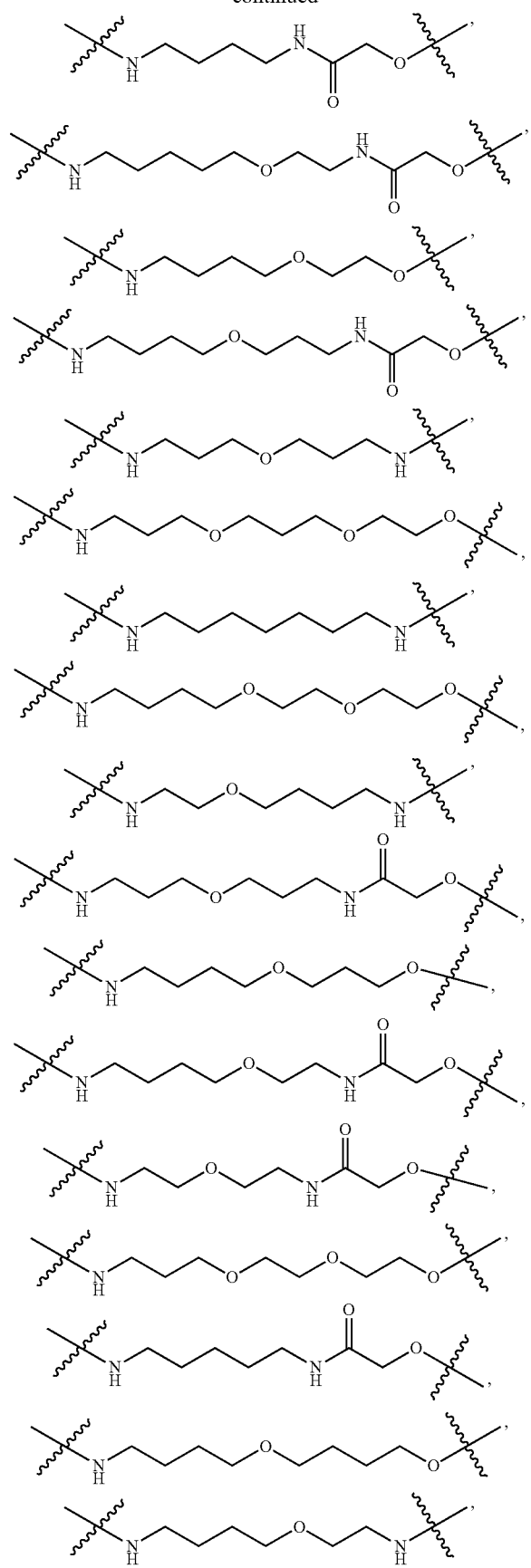
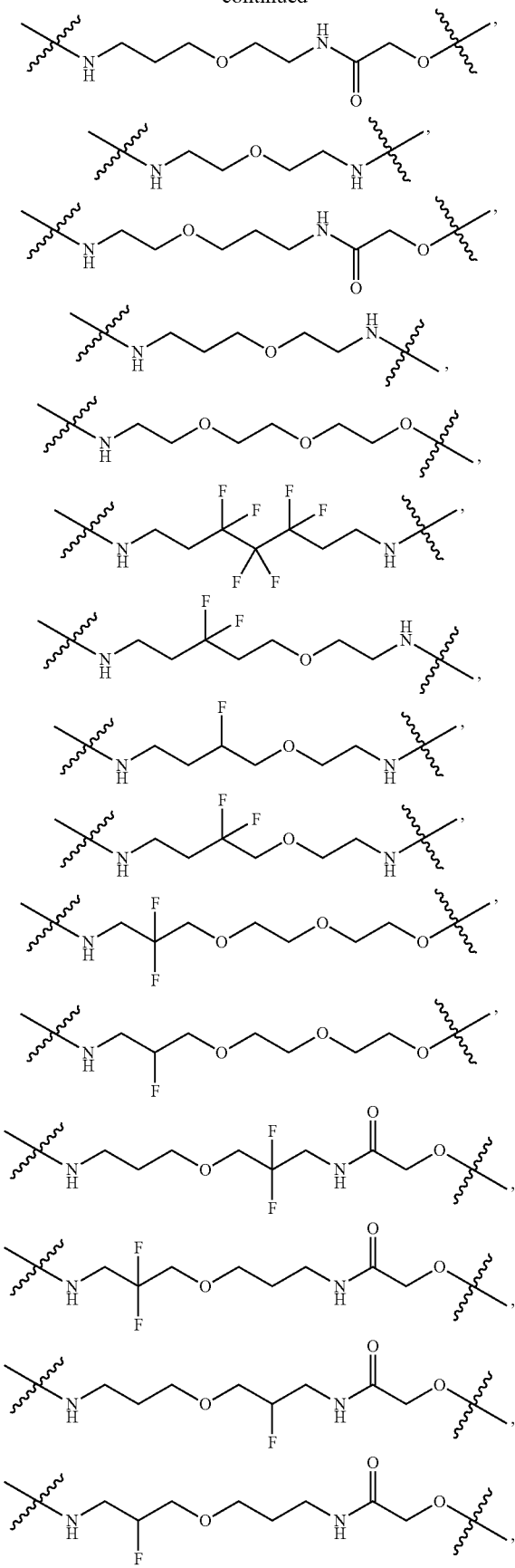

-continued

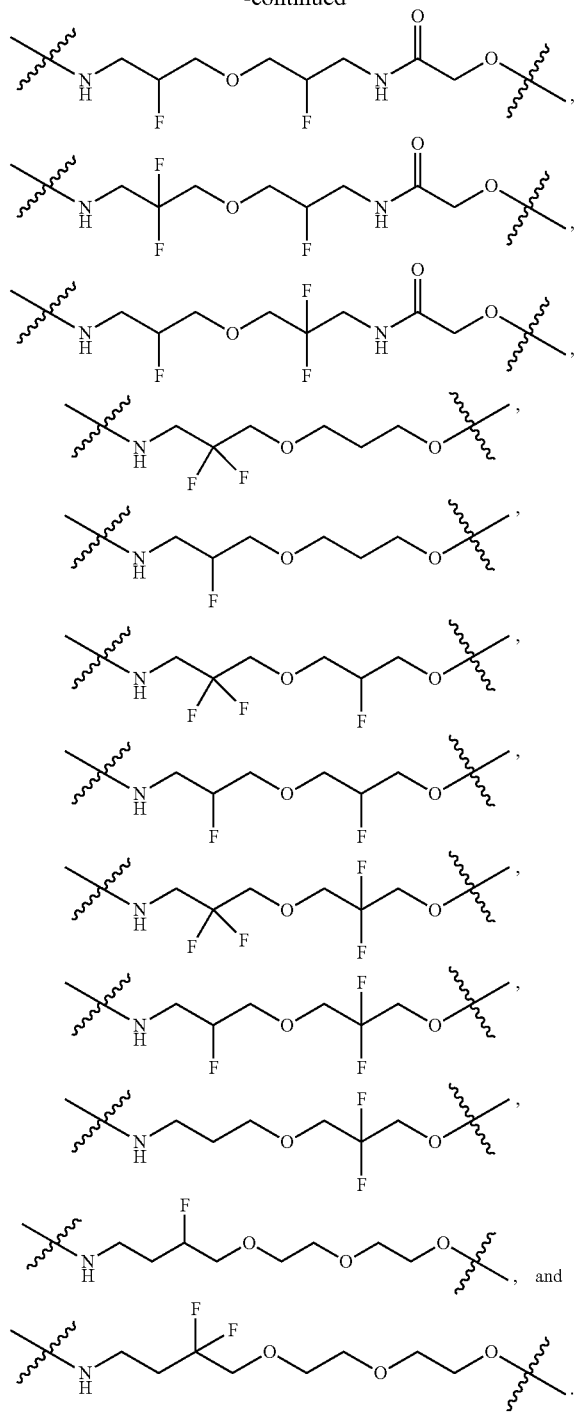

and

In certain embodiments, -(Linker)$^4$- can be a nonlinear chain, and can be, or include, aliphatic or aromatic or heteroaromatic cyclic moieties.

In certain embodiments, -(Linker)$^4$- may include contiguous, partially contiguous or non-contiguous ethylene glycol unit groups ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units, for example, 1, 2, 3, 4, 6, 6, 7, 8, 9, 10, 11 or 12 ethylene glycol units.

In certain embodiments, -(Linker)$^4$- may have 1, 2, 3, 4, 5, 6, 7, 8, 9, 10, 11, 12, 13, 14, or 15 fluorine substituents. In another embodiment -(Linker)$^4$- is perfluorinated. In yet another embodiment -(Linker)$^4$- is a partially or fully fluorinated poly ether. Nonlimiting examples of fluorinated -(Linker)$^4$- moieties include:

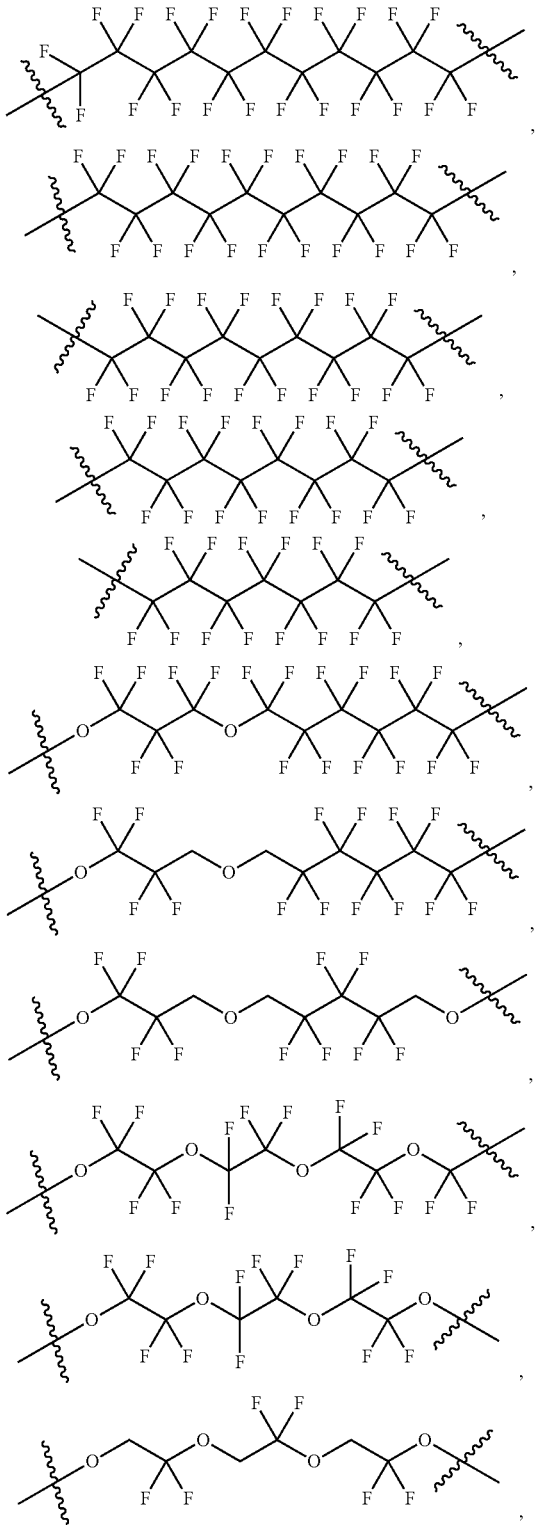

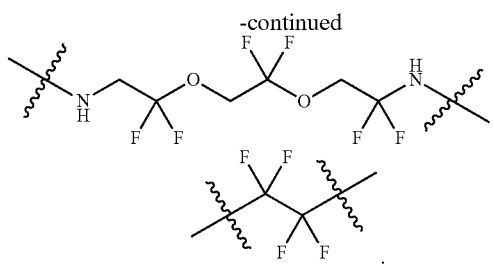

and

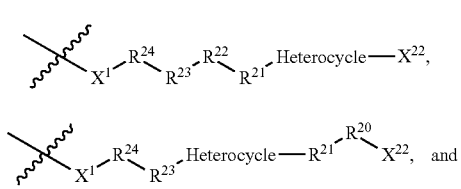

In certain embodiments, where the Target Ligand binds more than one protein (i.e., is not completely selective), selectivity may be enhanced by varying -(Linker)$^A$- length where the ligand binds some of its targets in different binding pockets, e.g., deeper or shallower binding pockets than others. Therefore, the length can be adjusted as desired.

In an alternative aspect, Linker is -(Linker)$^B$. In one embodiment, -(Linker)$^B$ is a moiety selected from Formula L$^B$I, Formula L$^B$II, Formula L$^B$III, Formula L$^B$IV, Formula L$^B$V, Formula L$^B$VI, and Formula L$^B$VII:

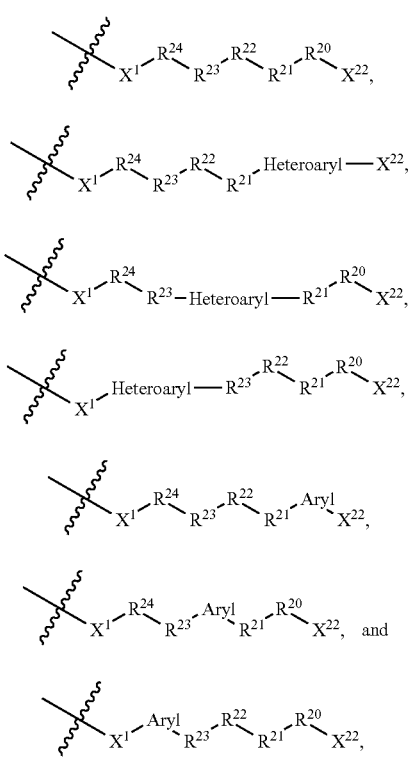

wherein all variables are defined as above.

In an additional embodiment, -(Linker)$^B$ is a moiety selected from Formula L$^B$VIII, L$^B$IX and L$^B$X:

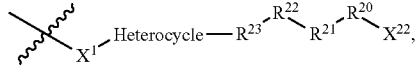

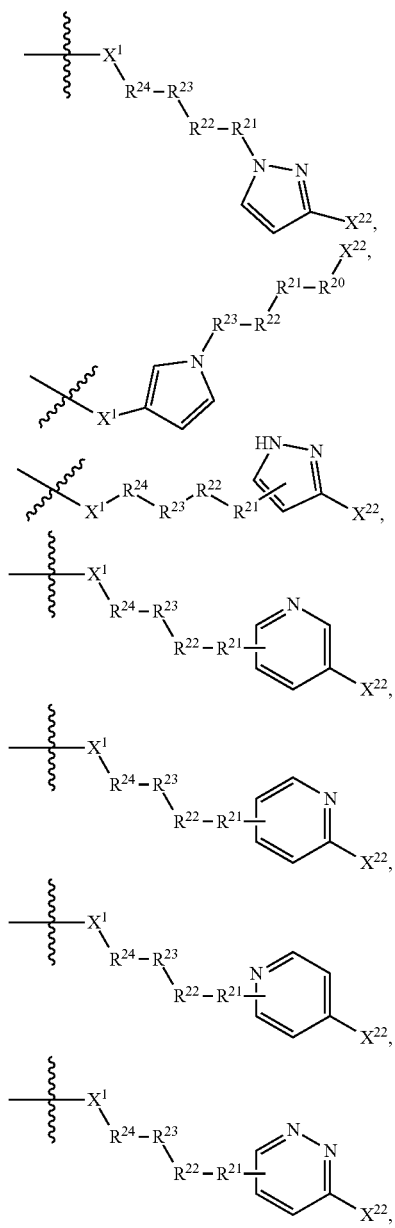

wherein all variables are defined as above. In alternative embodiments of L$^B$VIII, L$^B$IX and L$^B$x, a carbocyclic ring is used in place of the heterocycle.

The following are non-limiting examples of -(Linker)$^B$ moieties that can be used in this invention. Based on this elaboration, those of skill in the art will understand how to use the full breadth of -(Linker)$^B$ moieties that will accomplish the goal of the invention.

As certain non-limiting examples, Formula L$^B$I, Formula L$^B$II, Formula L$^B$III, Formula L$^B$IV, Formula L$^B$V, Formula L$^B$VI, or Formula L$^B$VII include:

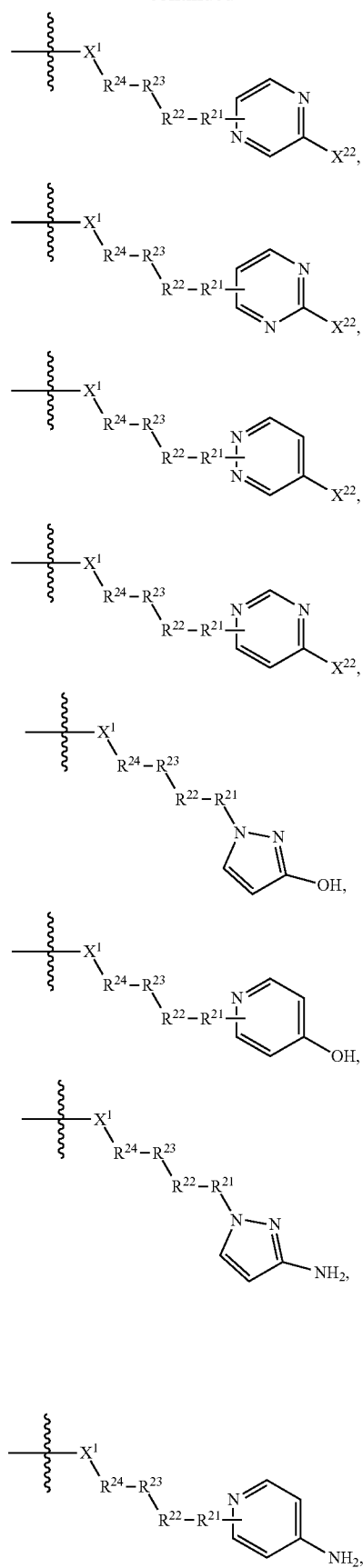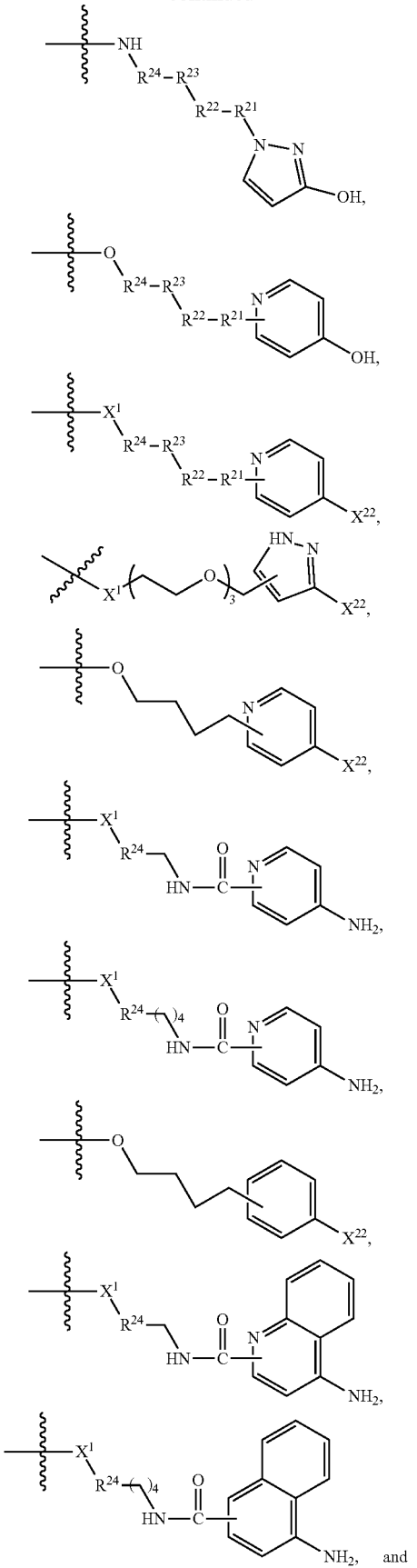

-continued
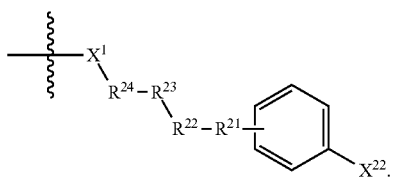
In an additional embodiment -(Linker)$^B$ is selected from:
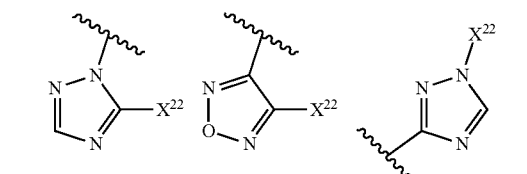
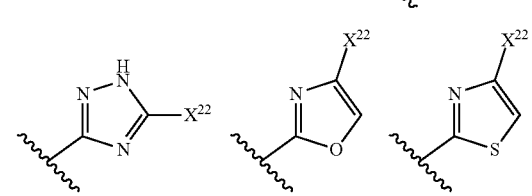
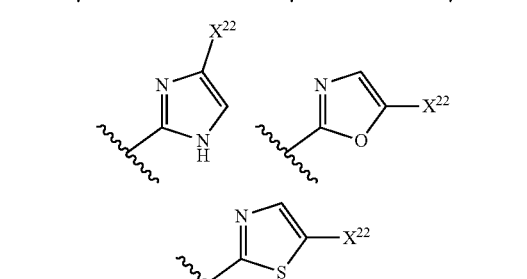
In an additional embodiment -(Linker)$^B$ is selected from:
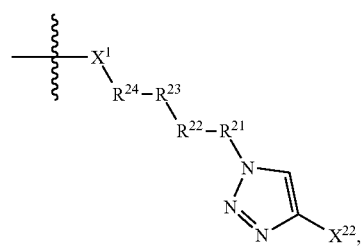
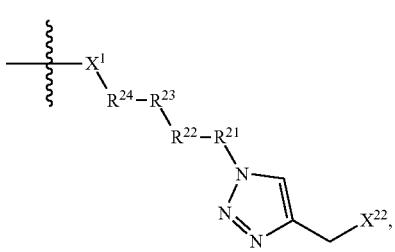
-continued
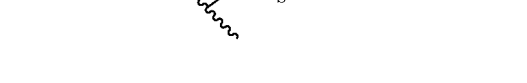
Non-limiting examples of moieties of $R^{20}$, $R^{21}$, $R^{22}$, $R^{23}$, and $R^{24}$ include:
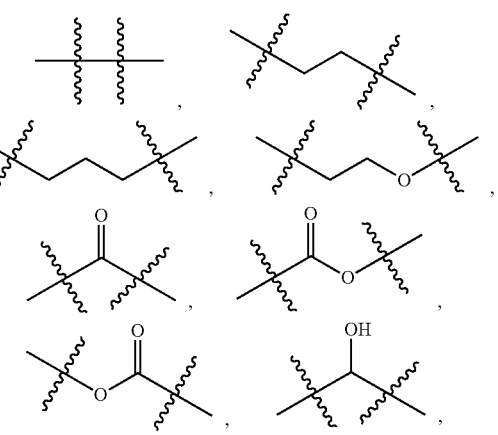

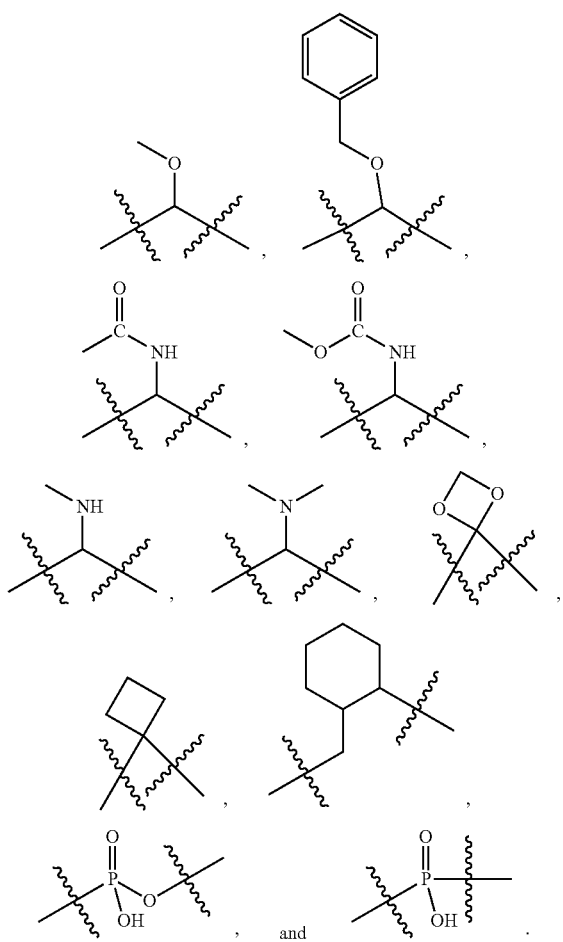
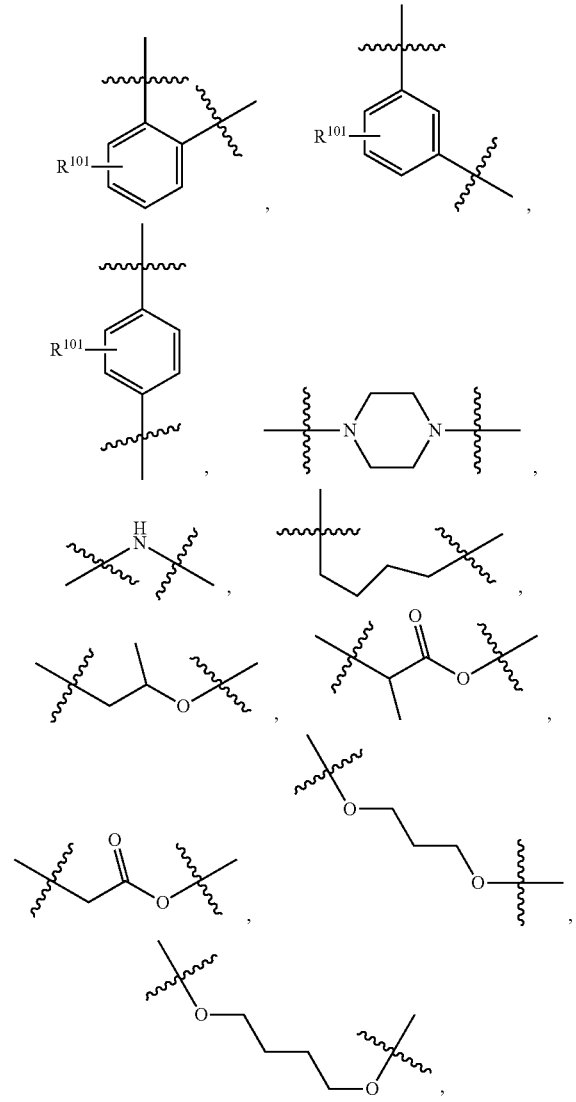
Additional non-limiting examples of moieties of $R^{20}$, $R^{21}$, $R^{22}$, $R^{23}$, and $R^{24}$ include:
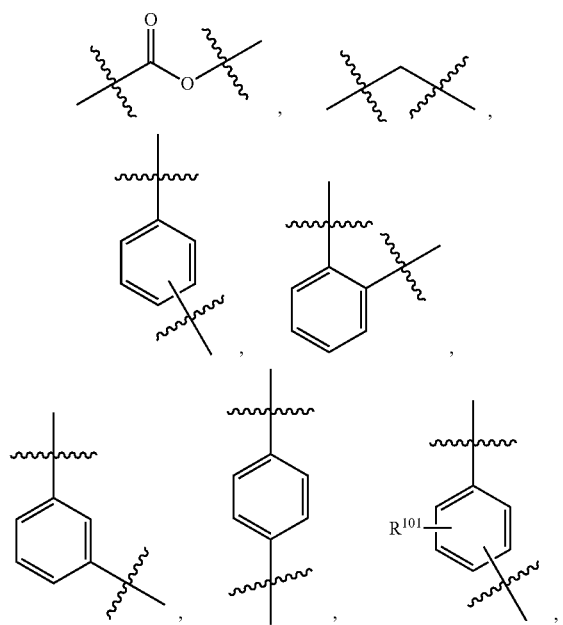
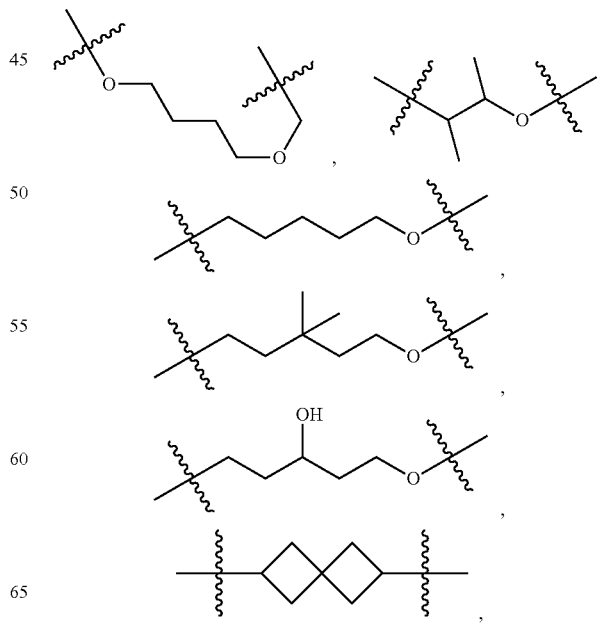

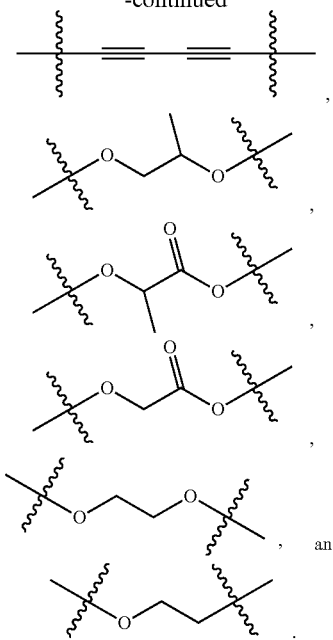
, and
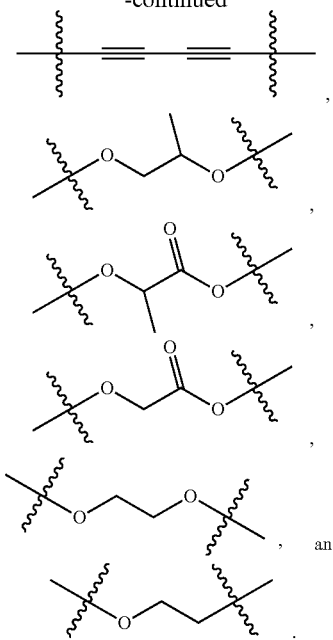
.
Additional non-limiting examples of moieties of $R^{20}$, $R^{21}$, $R^{22}$, $R^{23}$, and $R^{24}$ include:
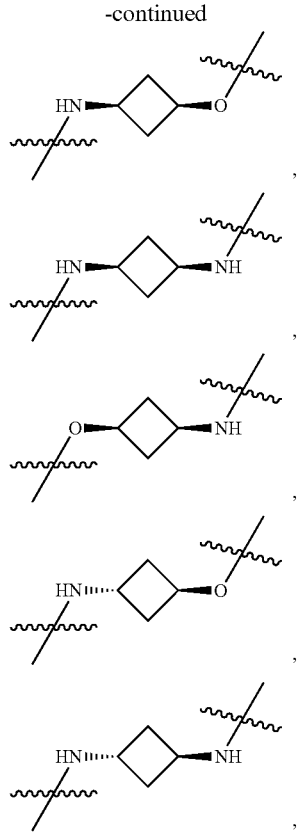
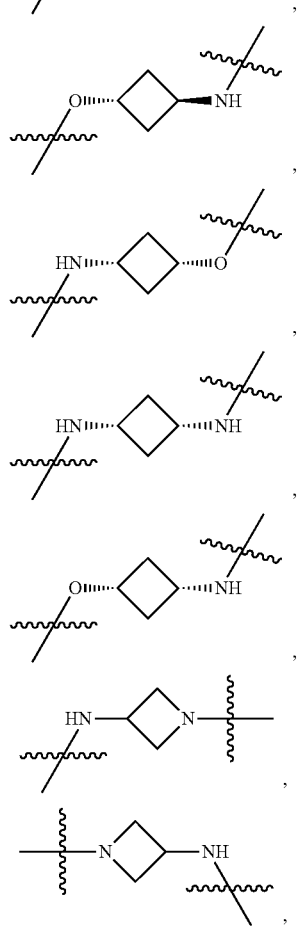

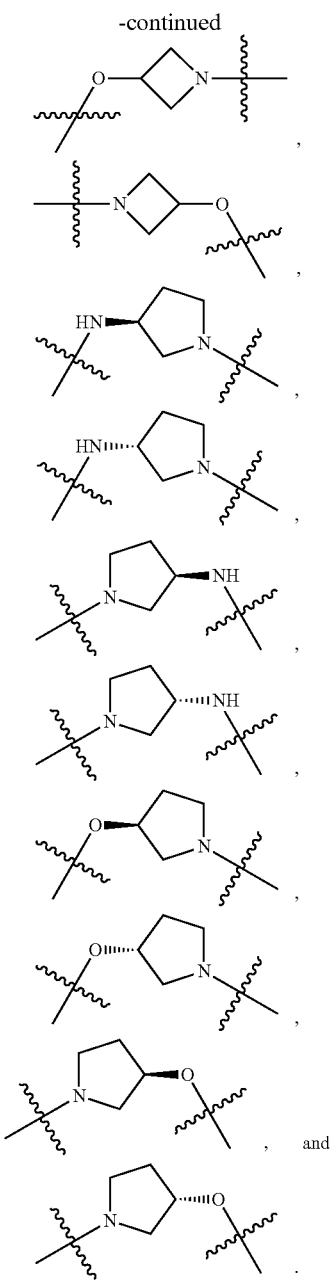
, and

In additional embodiments, -(Linker)$^B$ is an optionally substituted ethylene glycol having at least 1, at least 2, at least 3, at least 4, at least 5, at least 6, at least 7, at least 8, at least 9, at least 10, ethylene glycol units, or optionally substituted alkyl groups interspersed with optionally substituted, O, N, S, P or Si atoms. In certain embodiments, -(Linker)$^B$ is flanked, substituted, or interspersed with an aryl, phenyl, benzyl, alkyl, alkylene, or heterocycle group. In certain embodiments, -(Linker)$^B$ may be asymmetric or symmetrical. In some embodiments, -(Linker)$^B$ is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units. In any of the embodiments of the compounds described herein, -(Linker)$^B$ group may be any suitable moiety as described herein.

In additional embodiments, the -(Linker)$^B$ is selected from: —NR$^{61}$(CH$_2$)$_{n1}$-(lower alkyl)-X$^{22}$, —NR$^{61}$(CH$_2$)$_{n1}$-(lower alkoxyl)-X$^{22}$, —NR$^{61}$(CH$_2$)$_{n1}$-(lower alkoxyl)-OCH$_2$—X$^{22}$, —NR$^{61}$(CH$_2$)$_{n1}$-(lower alkoxyl)-(lower alkyl)-OCH$_2$—X$^{22}$, —NR$^{61}$(CH$_2$)$_{n1}$-(cycloalkyl)-(lower alkyl)-OCH$_2$—X$^{22}$, —NR$^{61}$(CH$_2$)$_{n1}$-(heterocycloalkyl)-X$^{22}$, —NR$^{61}$(CH$_2$CH$_2$O)$_{n1}$-(lower alkyl)-O—CH$_2$—X$^{22}$, —NR$^{61}$(CH$_2$CH$_2$O)$_{n1}$-(heterocycloalkyl)-O—CH$_2$—X$^{22}$, —NR$^{61}$(CH$_2$CH$_2$O)$_{n1}$-Aryl-O—CH$_2$—X$^{22}$, —NR$^{61}$(CH$_2$CH$_2$O)$_{n1}$-(heteroaryl)-O—CH$_2$—X$^{22}$, —NR$^{61}$(CH$_2$CH$_2$O)$_{n1}$-(cycloalkyl)-O-(heteroaryl)-O—CH$_2$—X$^{22}$, —NR$^{61}$(CH$_2$CH$_2$O)$_{n1}$-(cycloalkyl)-O-Aryl-O—CH$_2$—X$^{22}$, —NR$^{61}$(CH$_2$CH$_2$O)$_{n1}$-(lower alkyl)-NH-Aryl-O—CH$_2$—X$^{22}$, —NR$^{61}$(CH$_2$CH$_2$O)$_{n1}$-(lower alkyl)-O-Aryl-CH$_2$—X$^{22}$, —NR$^{61}$(CH$_2$CH$_2$O)$_{n1}$-cycloalkyl-O-Aryl-1-X$^{22}$, —NR$^{61}$(CH$_2$CH$_2$O)$_{n1}$-cycloalkyl-O-heteroaryl-X$^{22}$, —NR$^{61}$(CH$_2$CH$_2$)$_{n1}$-(cycloalkyl)-O-(heterocycle)-CH$_2$—X$^{22}$, —NR$^{61}$(CH$_2$CH$_2$)$_{n1}$-(heterocycle)-(heterocycle)-CH$_2$—X$^{22}$, and —NR$^{61}$-(heterocycle)-CH$_2$—X$^{22}$;

wherein n1 is 0, 1, 2, 3, 4, 5, 6, 7, 8, 9, or 10; and

R$^{61}$ is H, methyl, or ethyl.

In additional embodiments, -(Linker)$^B$ is selected from: —N(R$^{61}$)—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—X$^{22}$, —O—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—X$^{22}$, —O—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OH; —N(R$^{61}$)—(CH$_2$)$_{m1}$—O(—O(CH$_2$)$_{n2}$—O(CH$_2$)$_{o1}$—O(CH$_2$)$_{p1}$—O(CH$_2$)$_{q1}$—O(CH$_2$)$_{r1}$—OH; —(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OH; —(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—X$^{22}$; —O(CH$_2$)$_{m1}$O(CH$_2$)$_{n2}$O(CH$_2$)$_{p1}$O(CH$_2$)$_{q1}$OCH$_2$—X$^{22}$; —O(CH$_2$)$_{m1}$O(CH$_2$)$_{n2}$O(CH$_2$)$_{p1}$O(CH$_2$)$_{q1}$OCH$_2$—X$^{22}$; wherein m1, n2, o1, p1, q1, and r1 are independently 1, 2, 3, 4, or 5; and R$^{61}$ is H, methyl, or ethyl.

In additional embodiments, -(Linker)$^B$ is selected from:

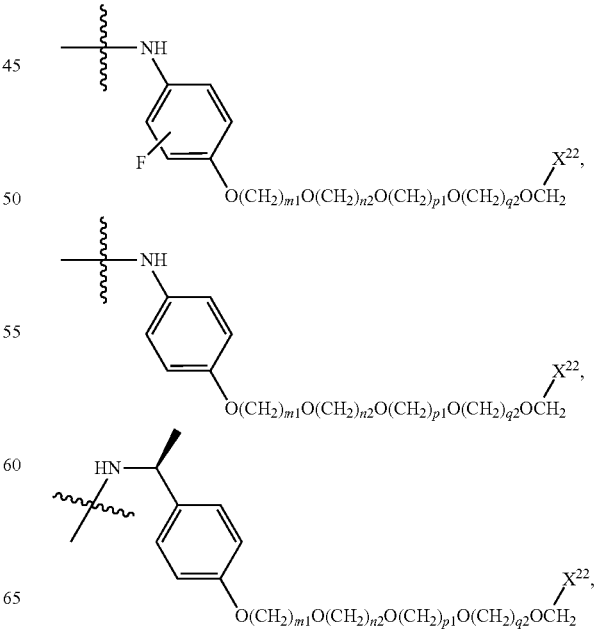

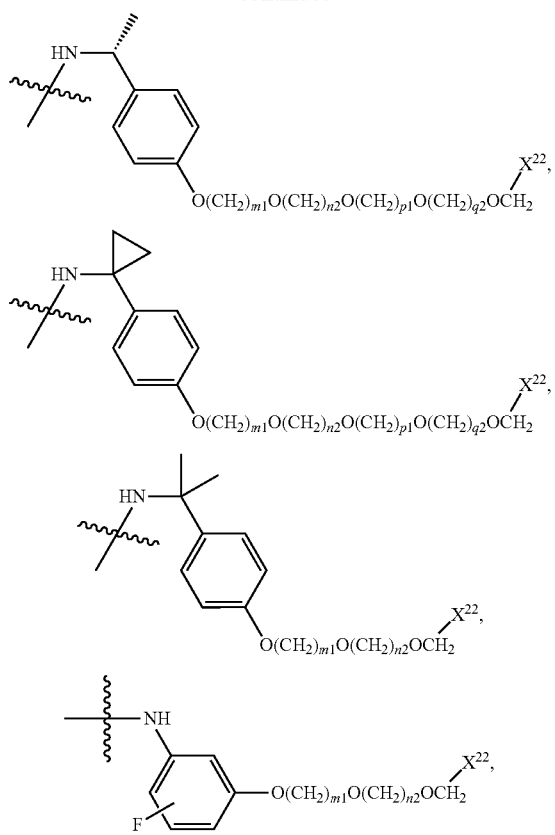
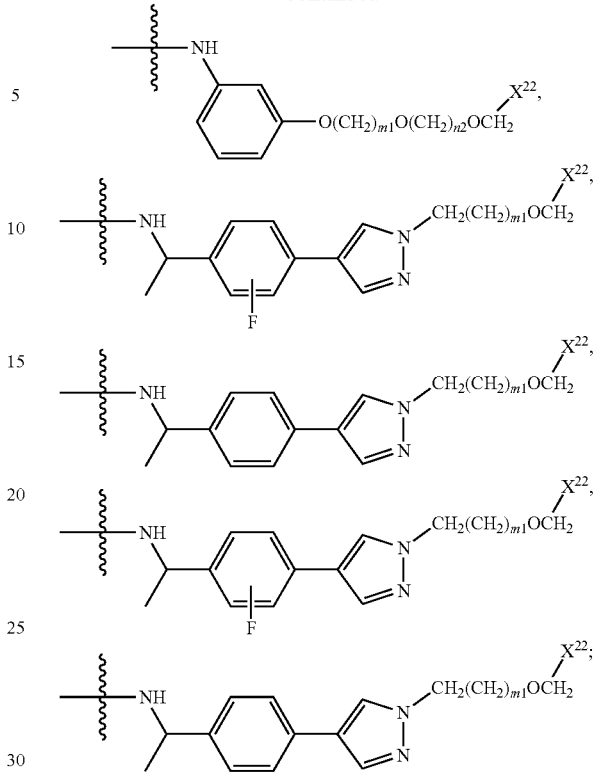
m1, n2, o1, p1, q2, and r1 are independently 1, 2, 3, 4, or 5.
In additional embodiments, -(Linker)$^B$ is selected from:
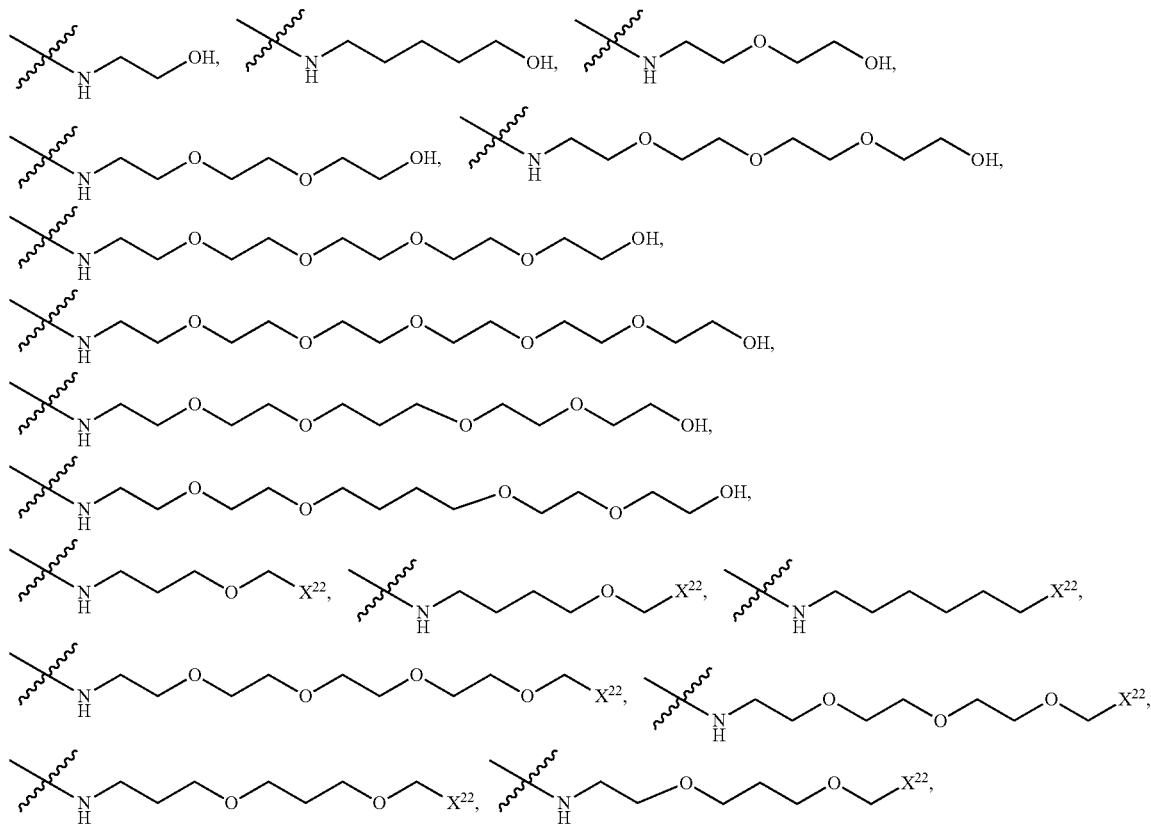

-continued
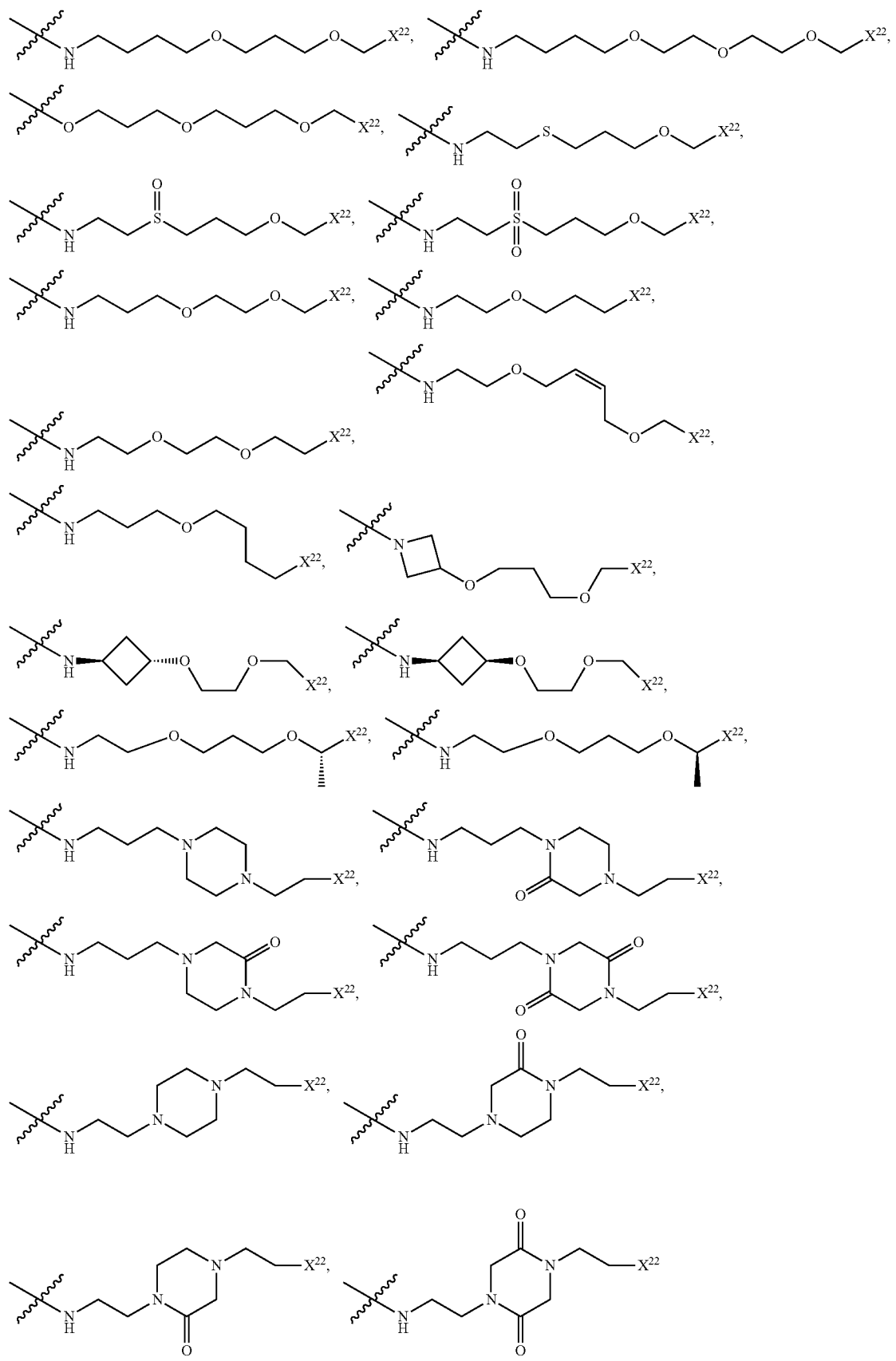

In additional embodiments, -(Linker)$^B$ is selected from:
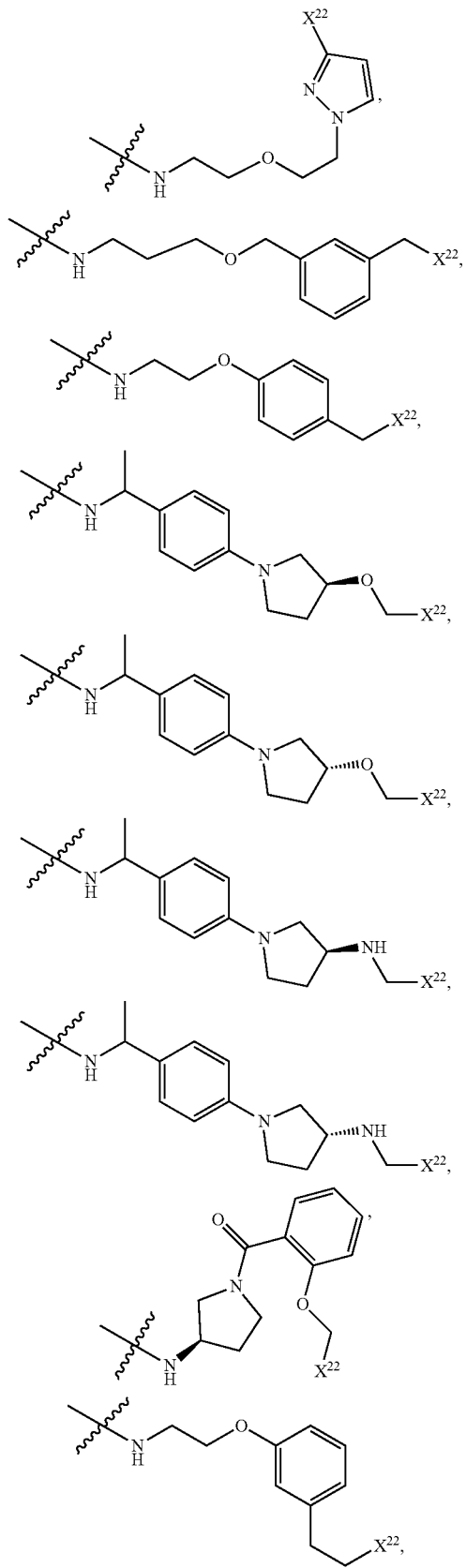
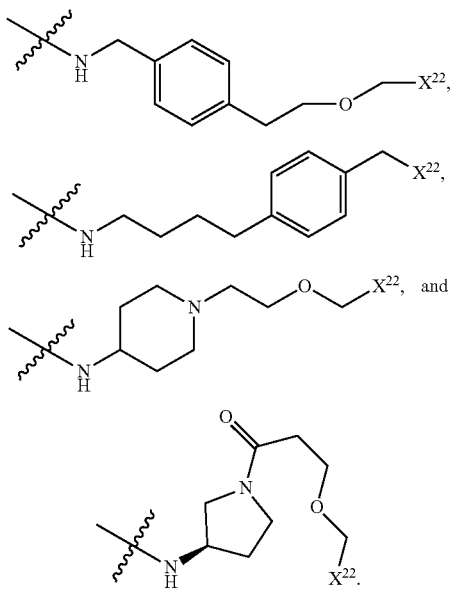
In additional embodiments, -(Linker)$^B$ is selected from:
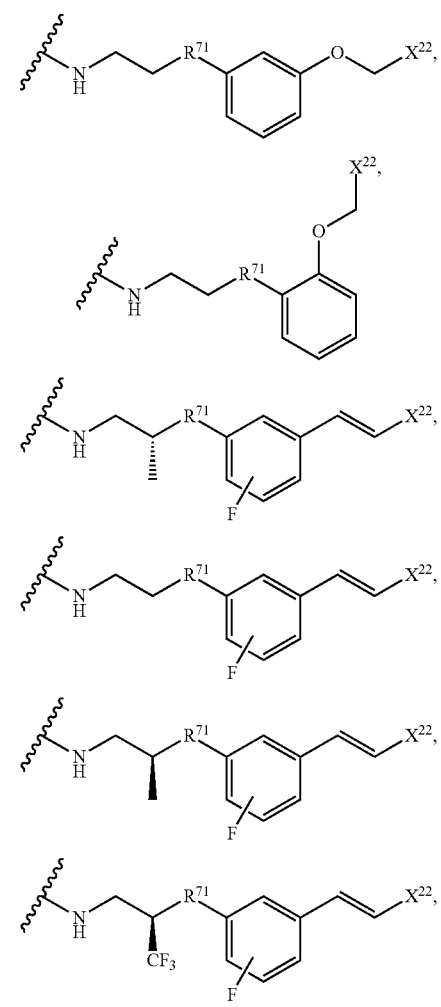

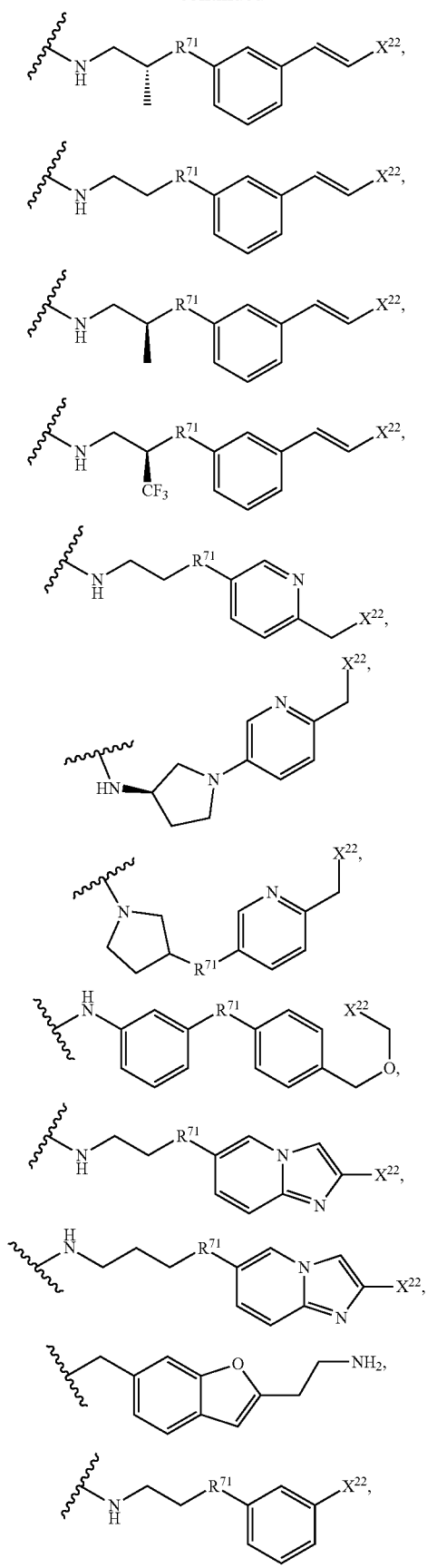
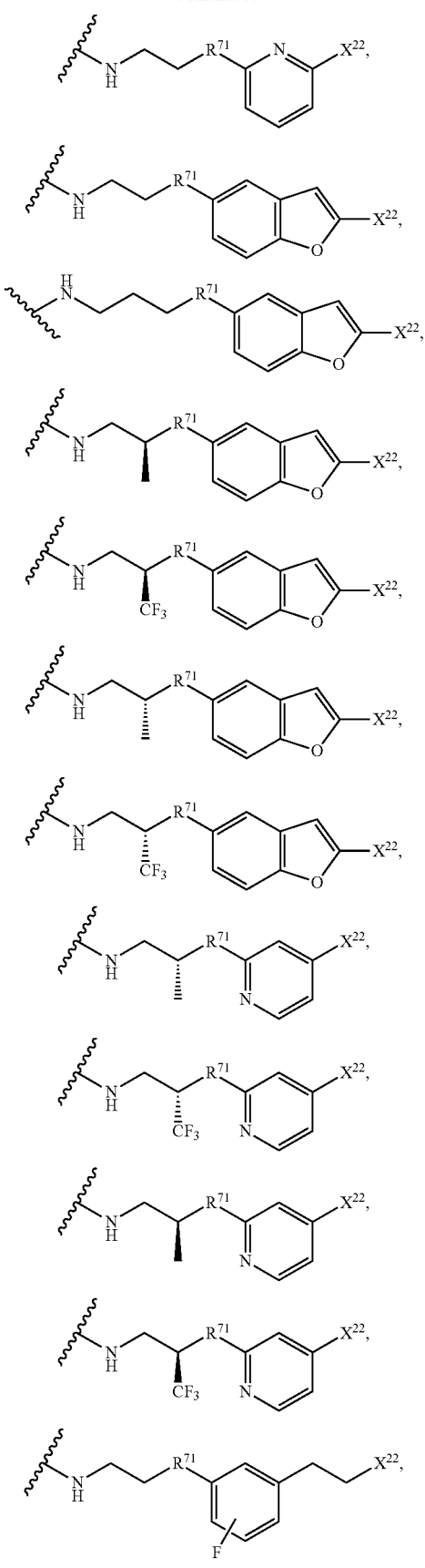

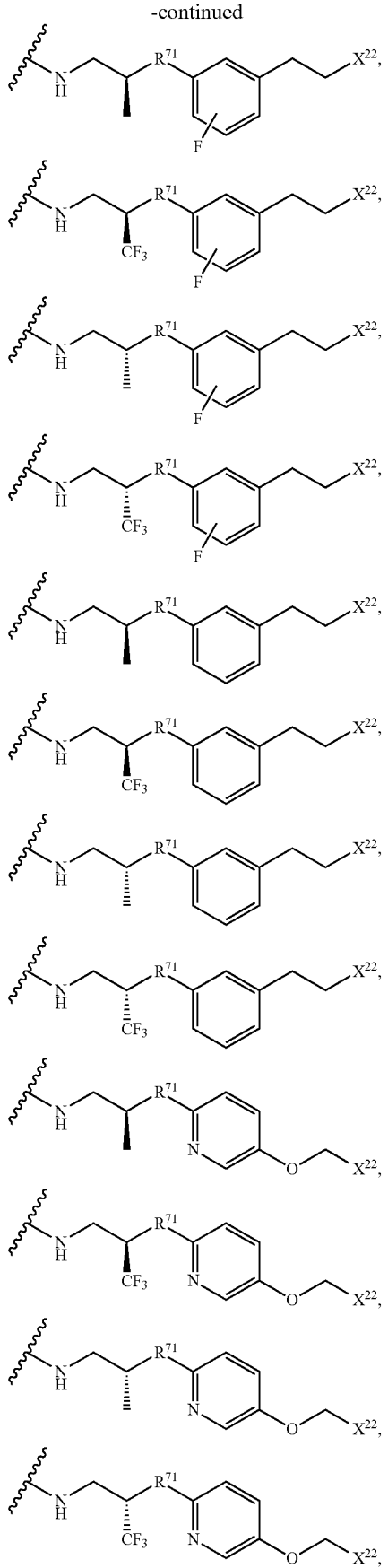
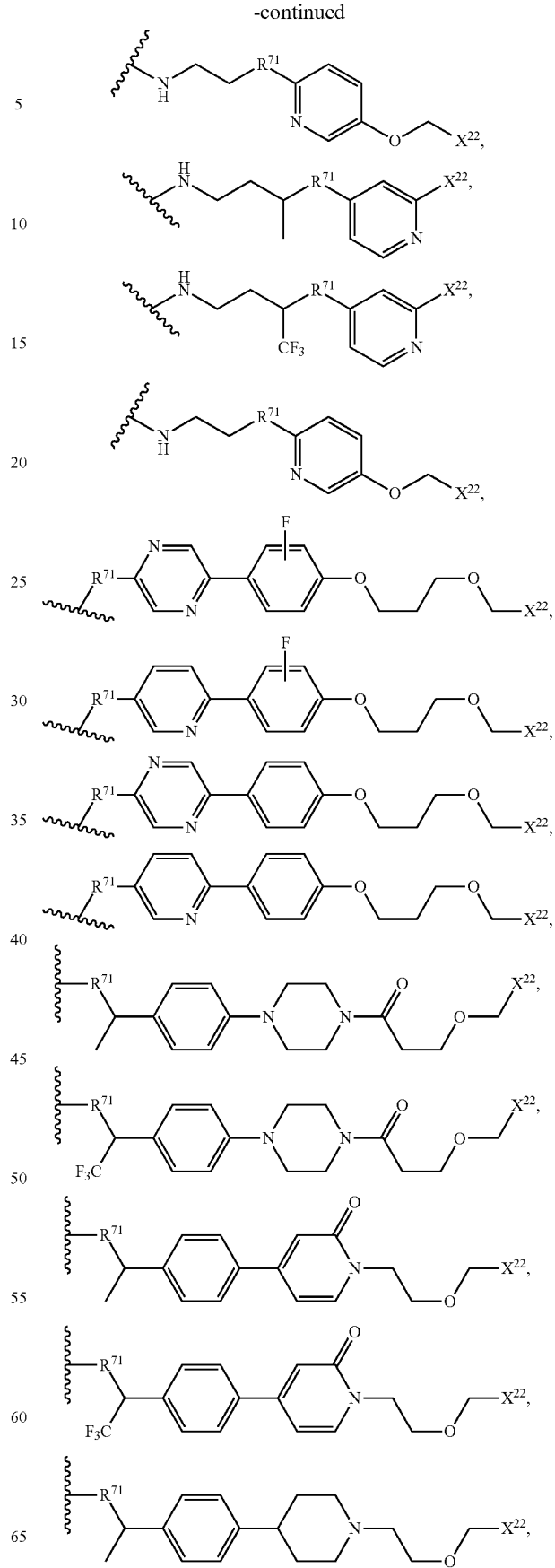

375
-continued
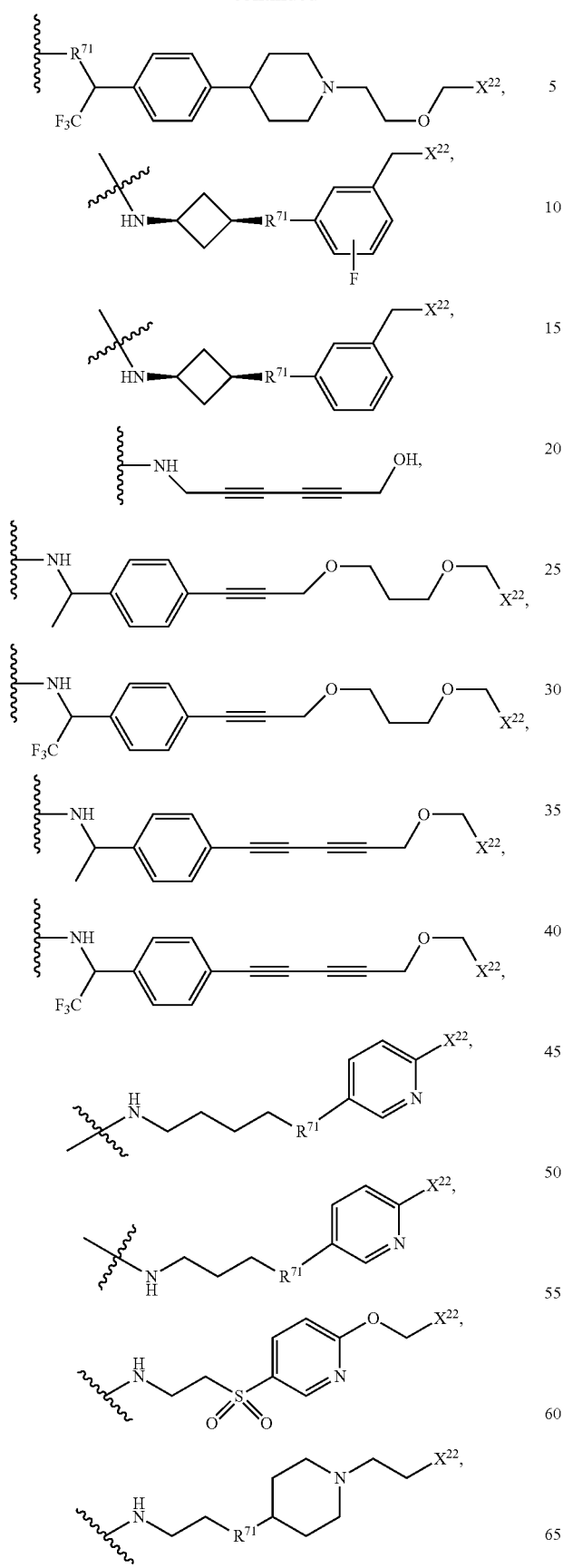
376
-continued
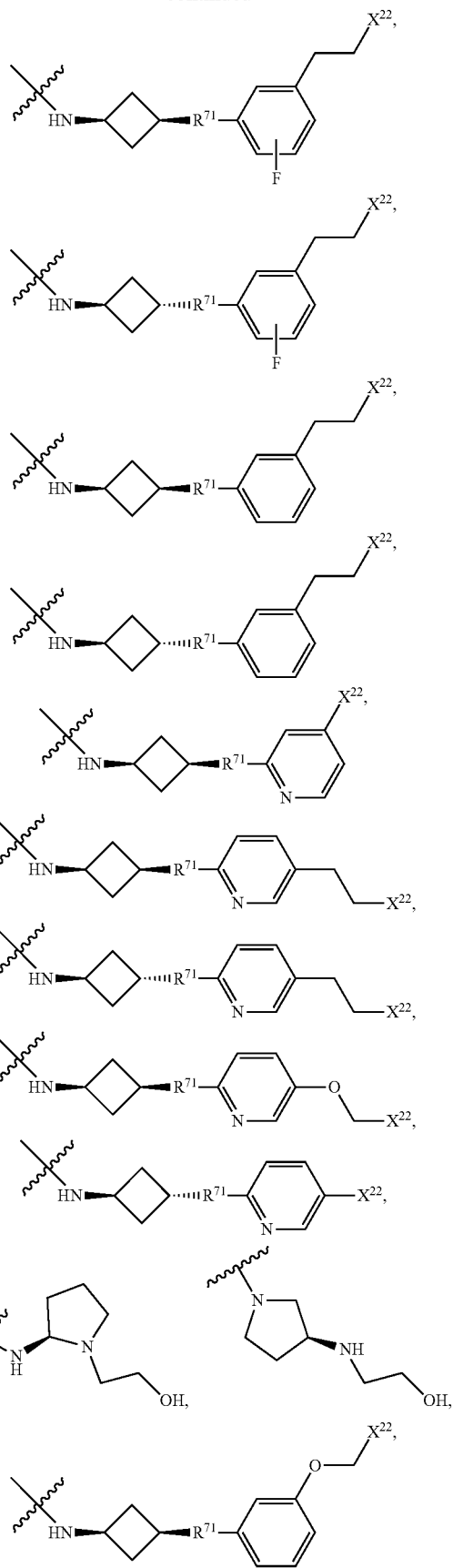

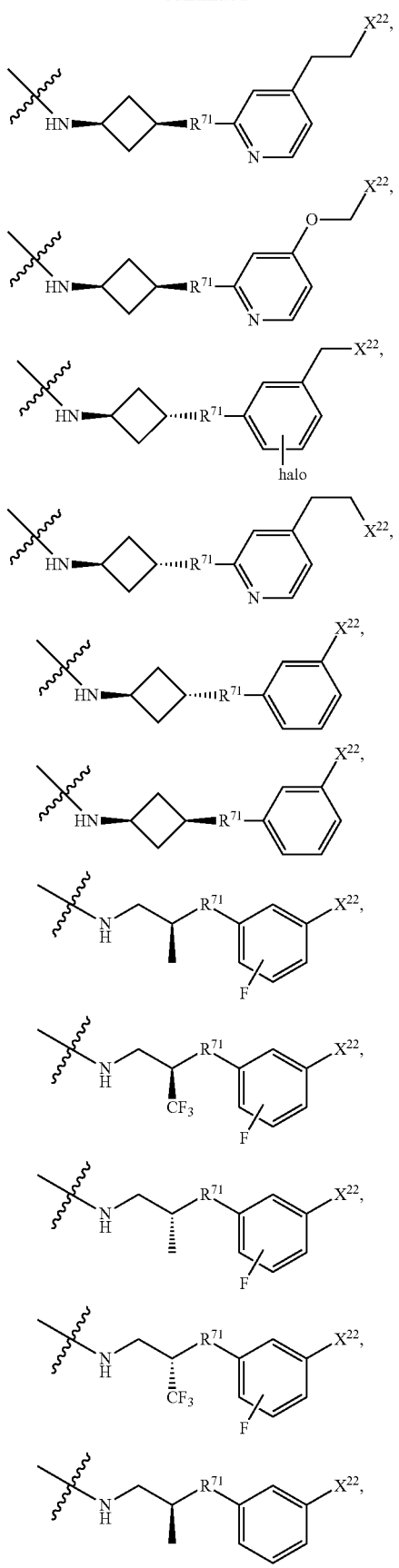
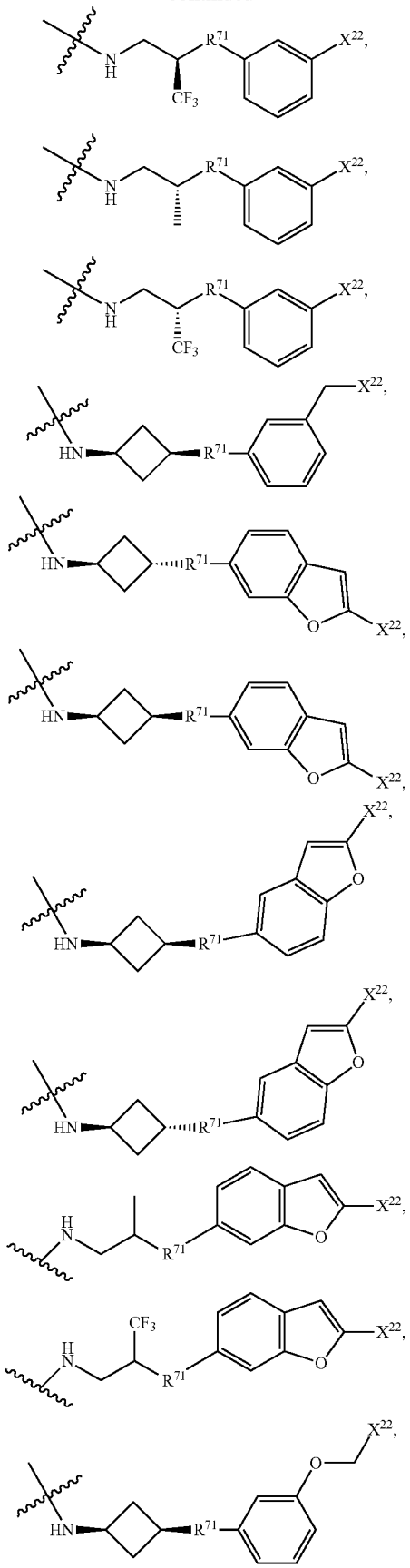

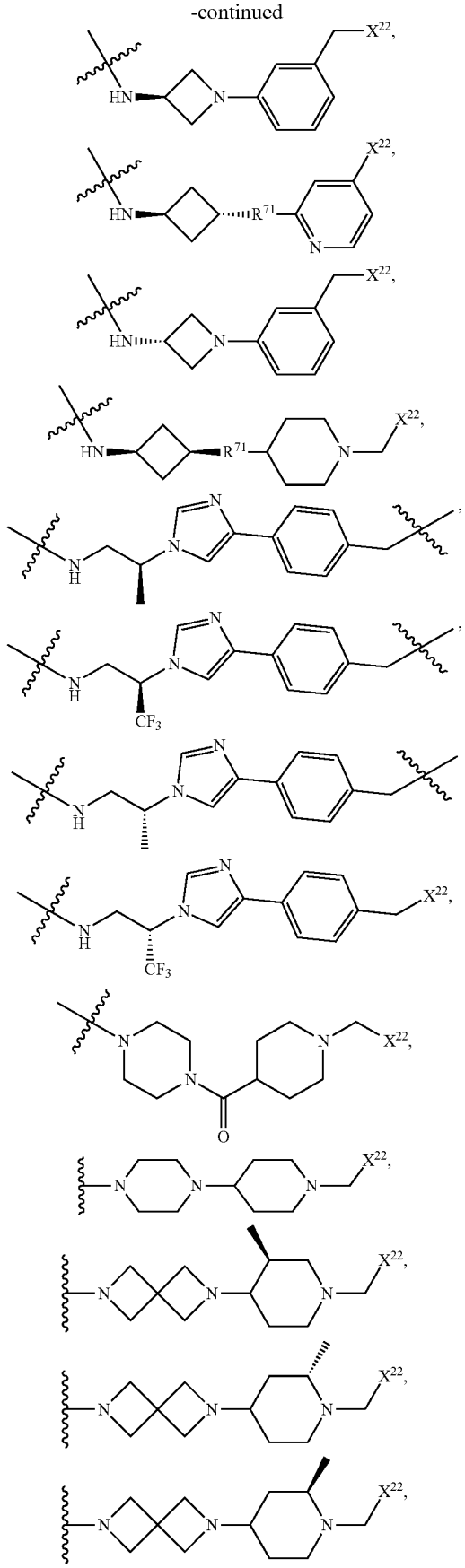
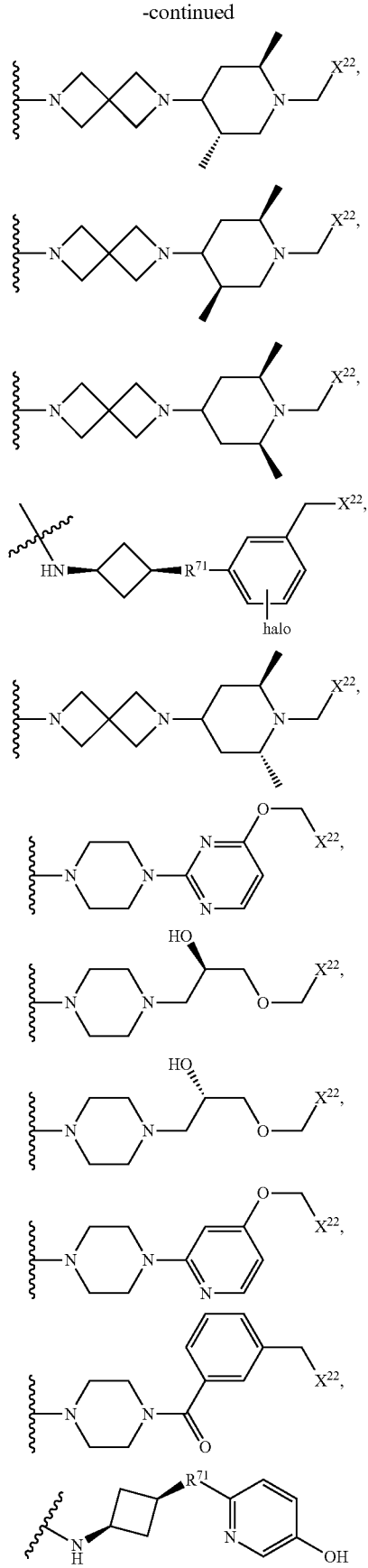

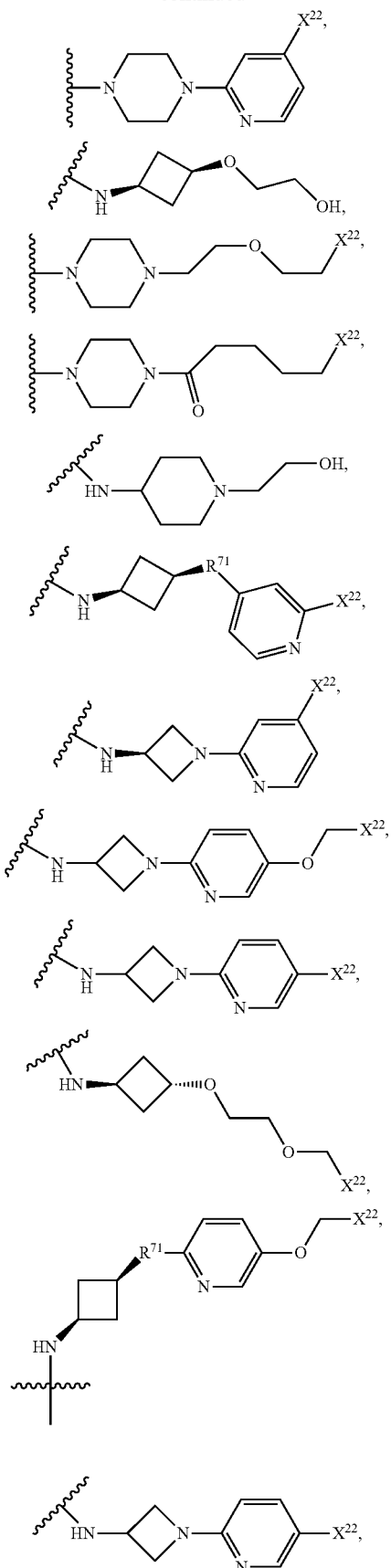
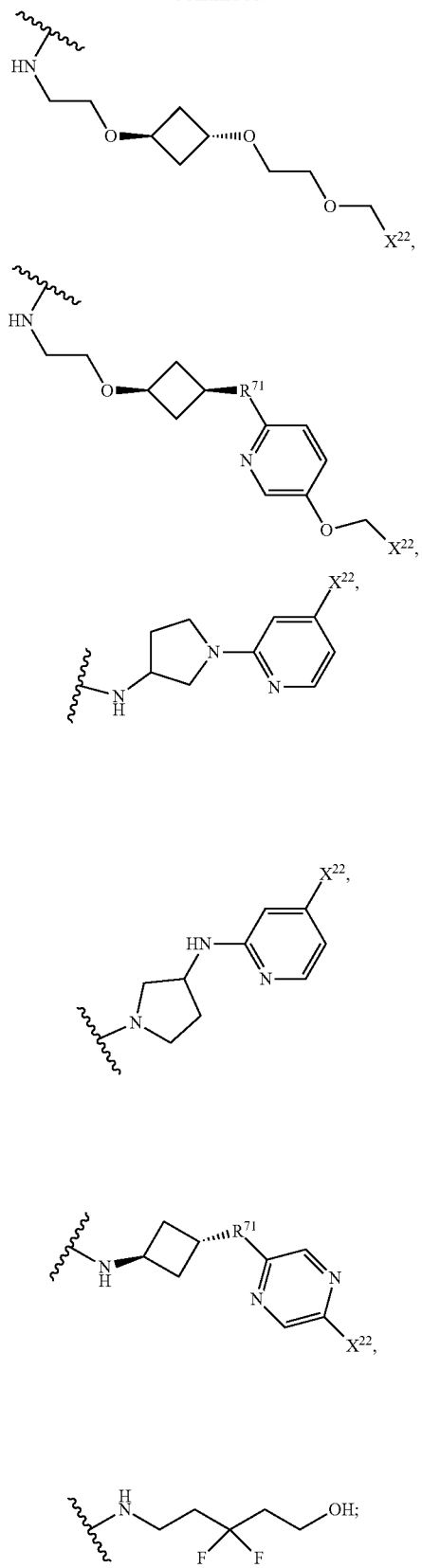
wherein $R^{71}$ is —O—, —NH, Nalkyl, heteroaliphatic, aliphatic, or —NMe.

In additional embodiments, -(Linker)$^B$ is selected from:
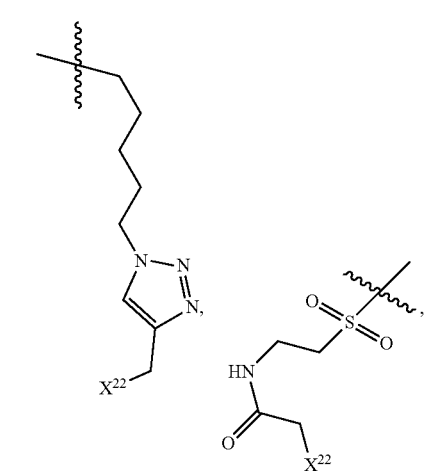
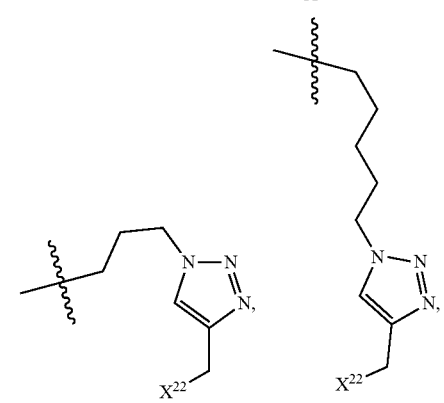
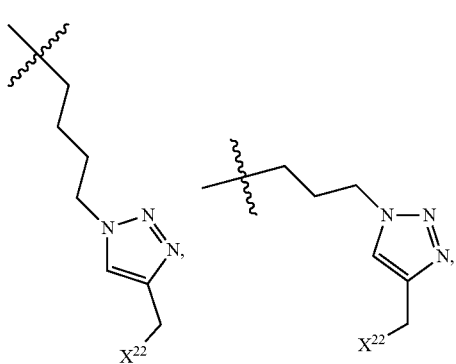
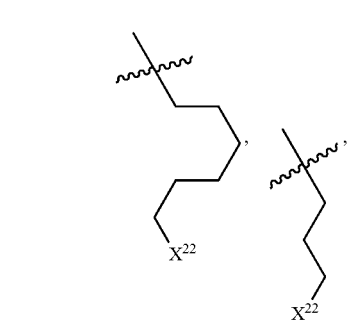
-continued
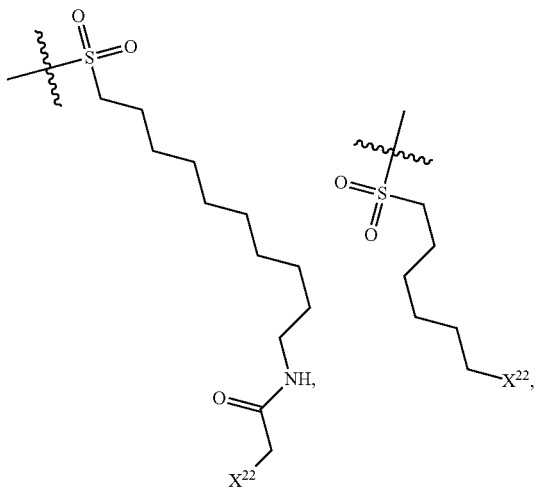
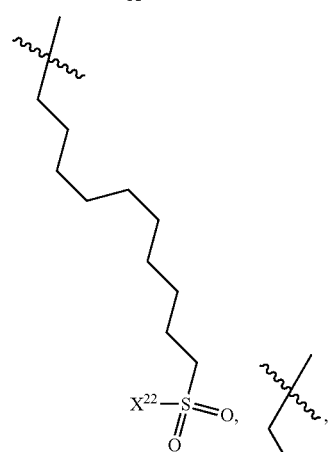
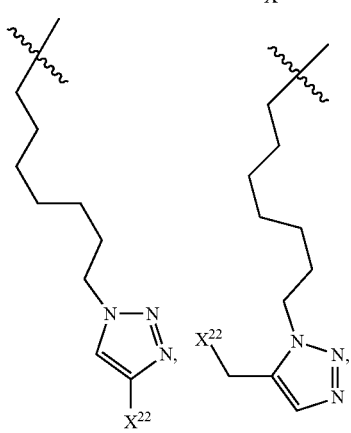

385
-continued
386
-continued
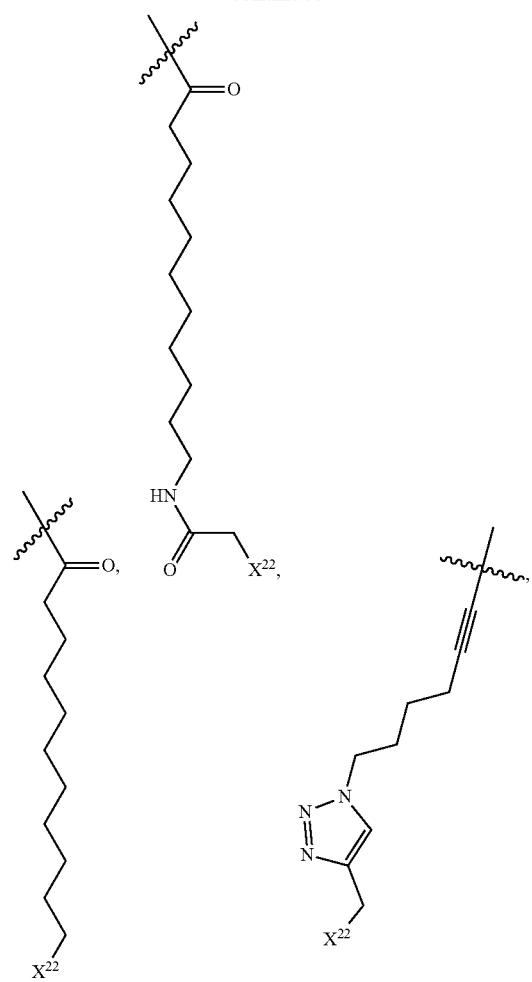
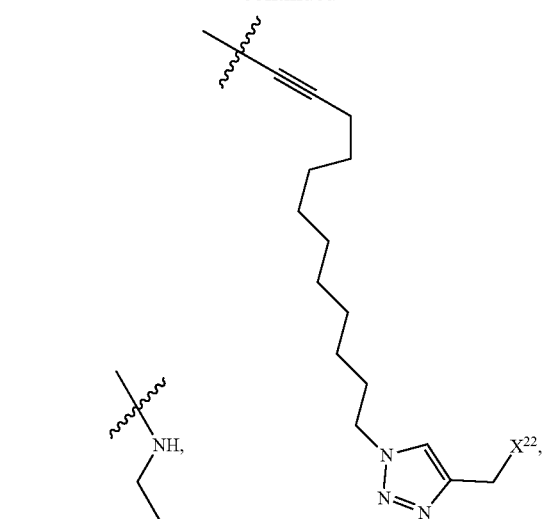
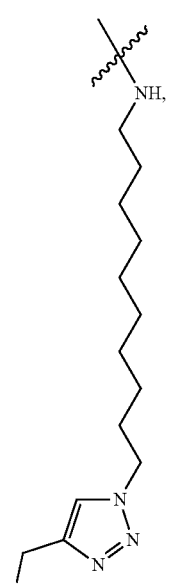
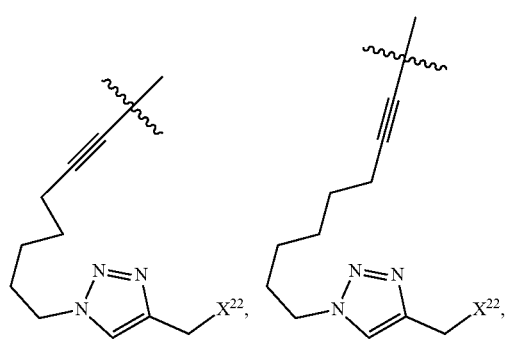
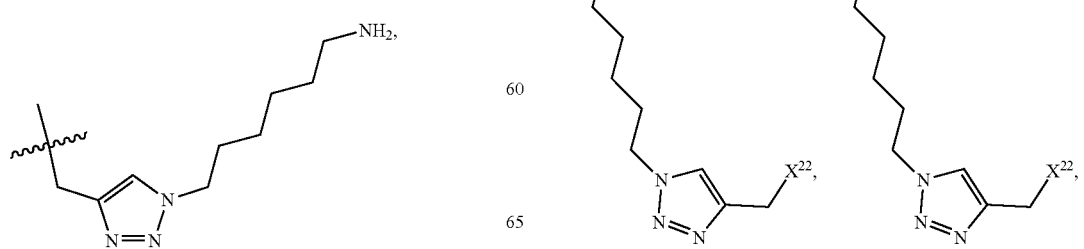

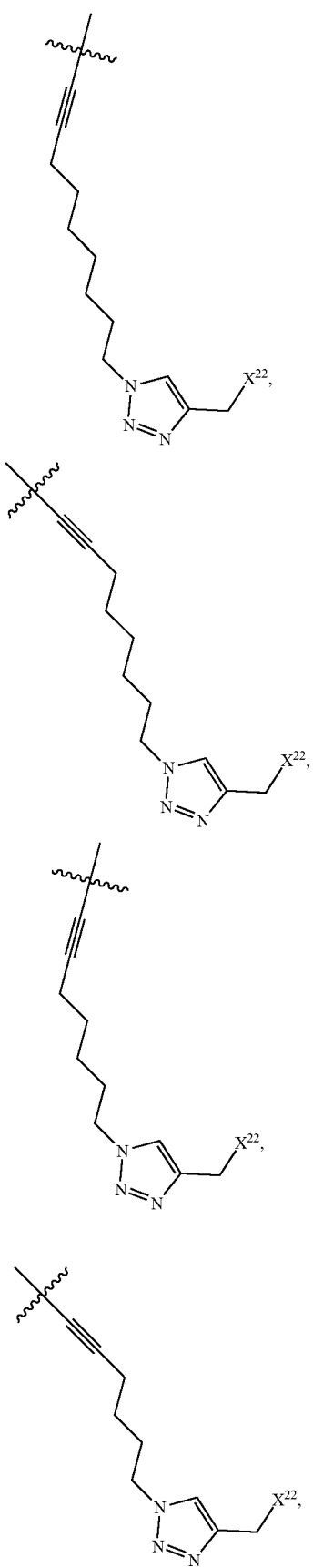
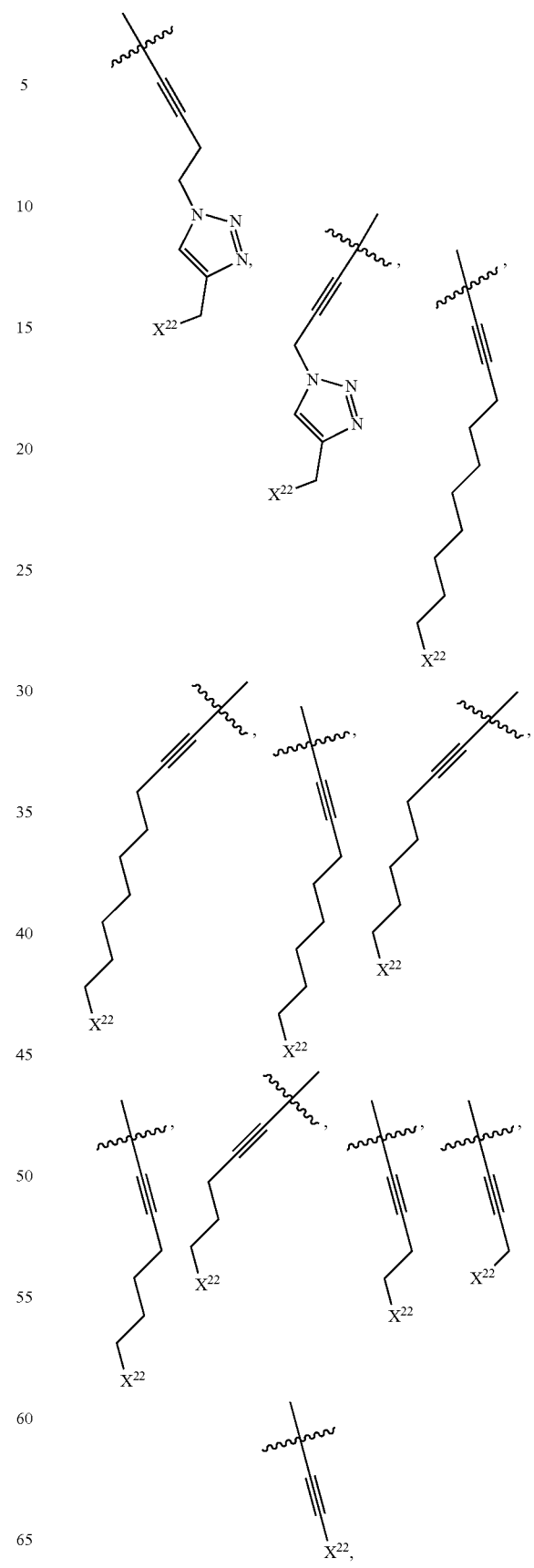

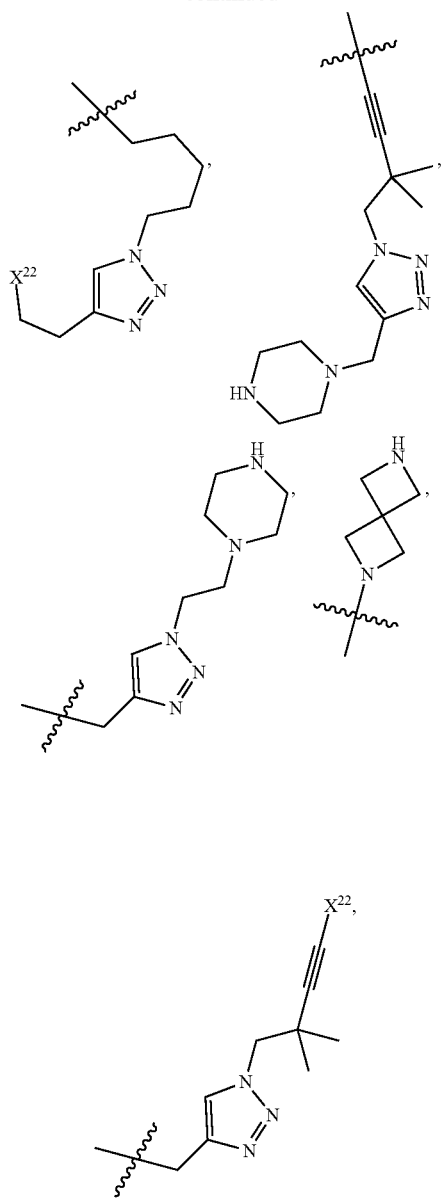
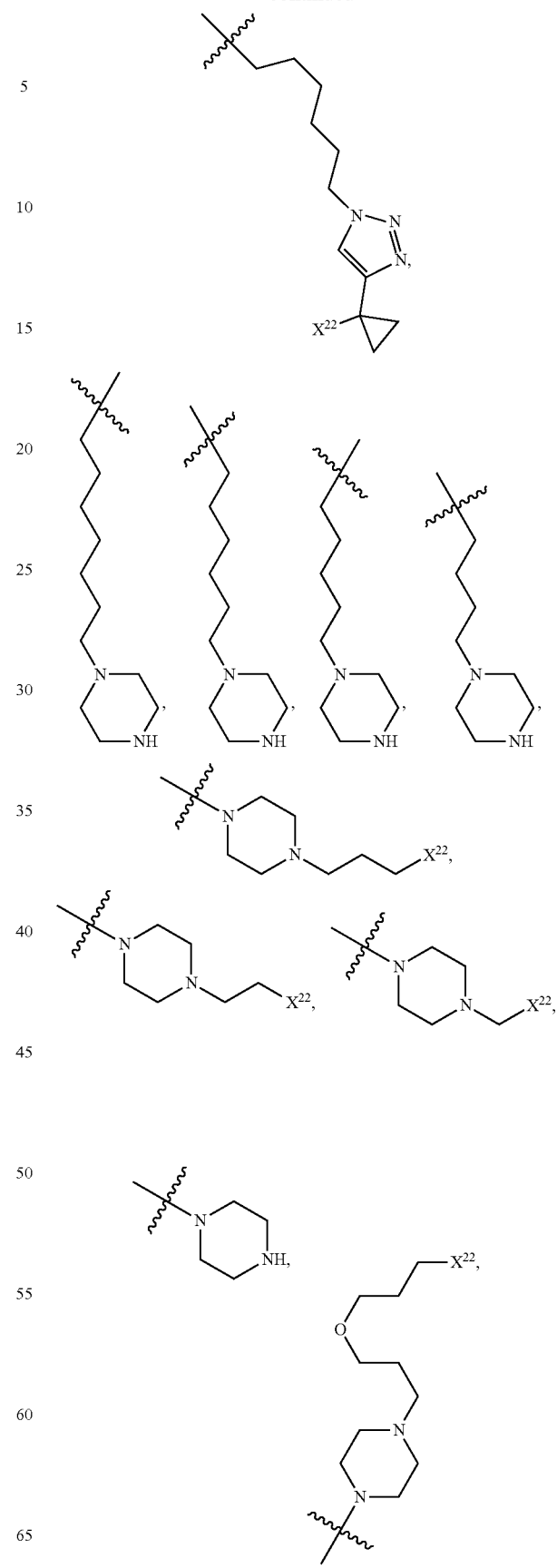

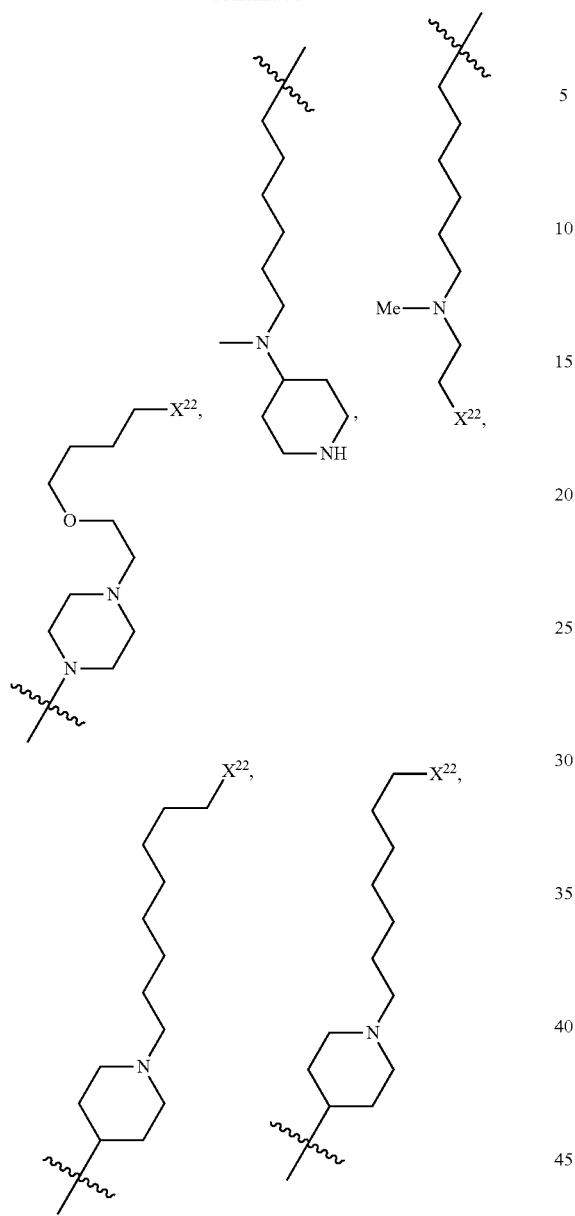
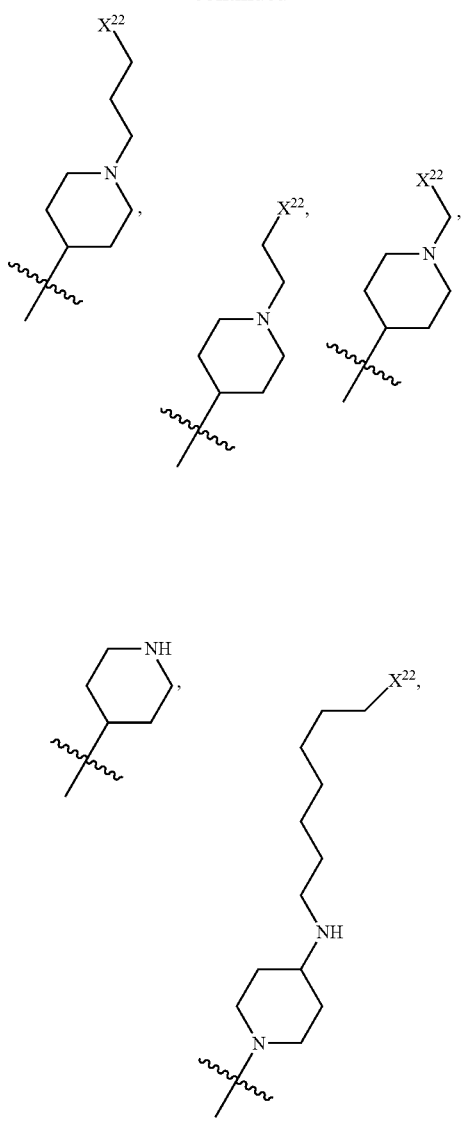
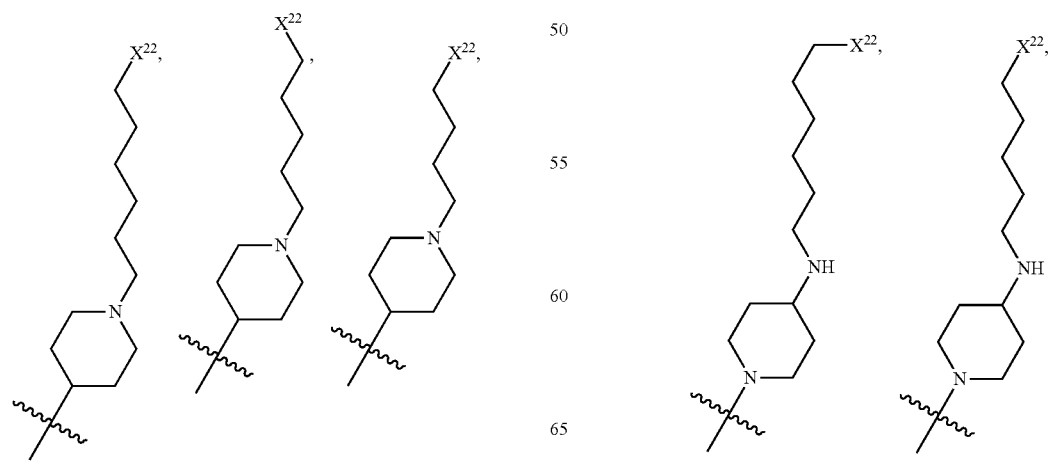

393
-continued
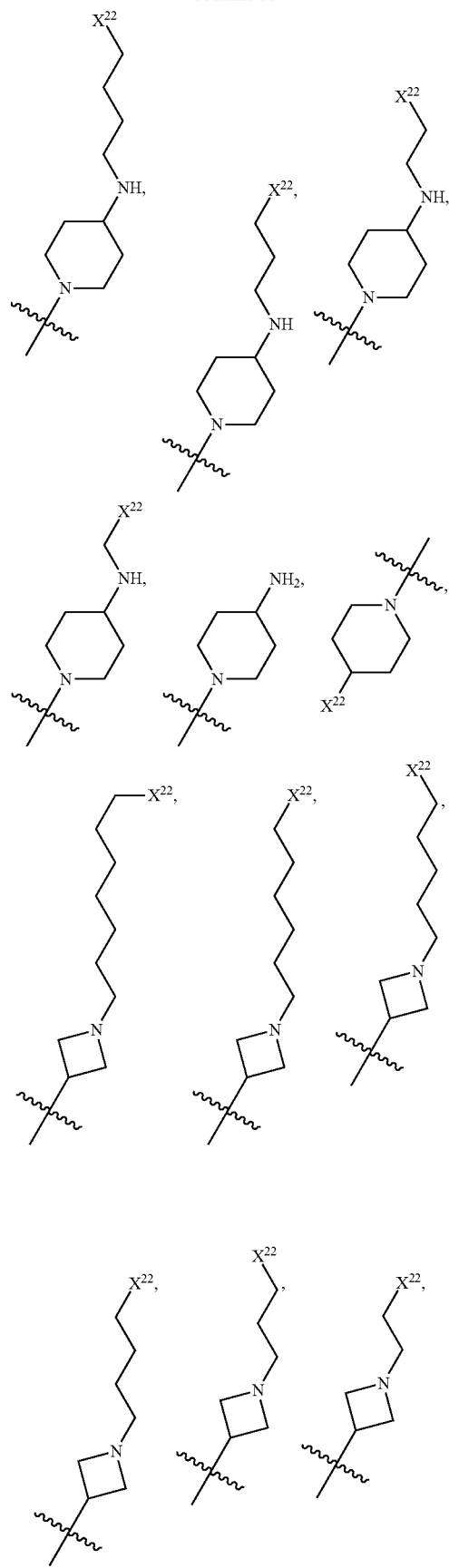
394
-continued
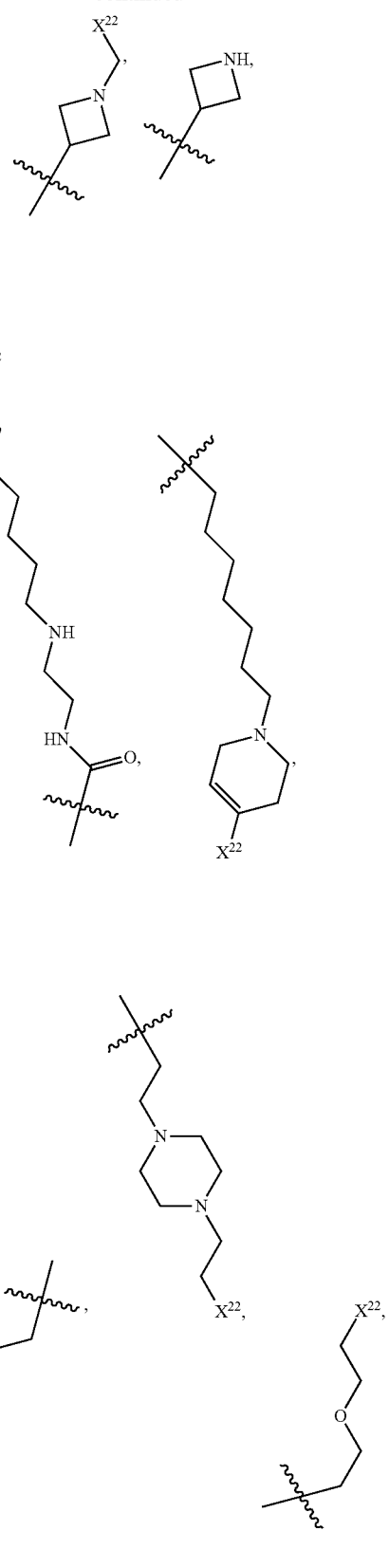

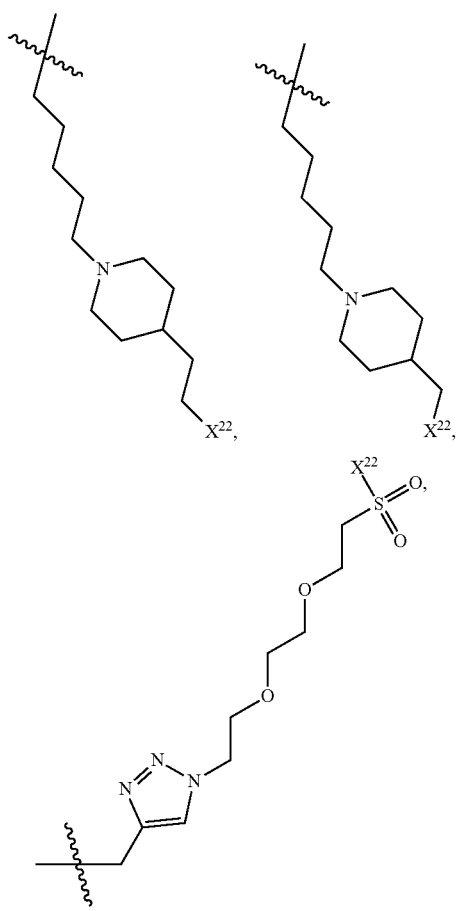
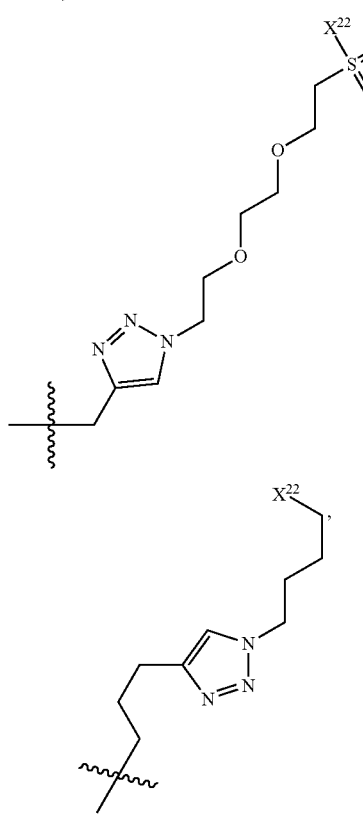
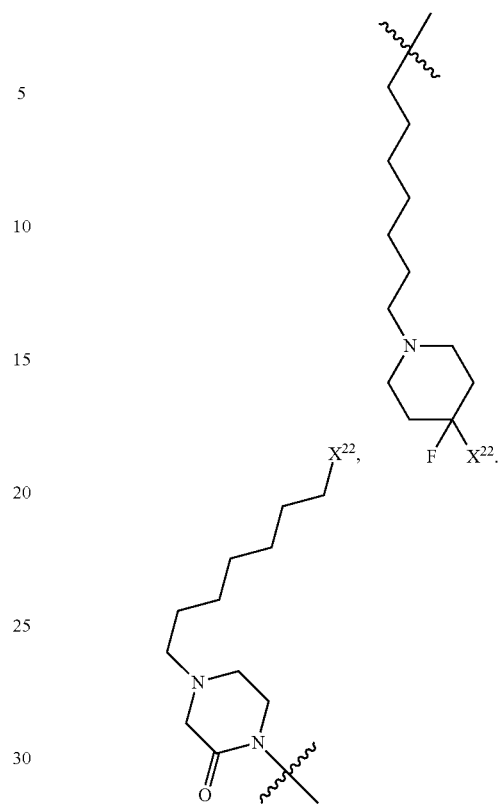
In additional embodiments, -(Linker)$^B$ is selected from:
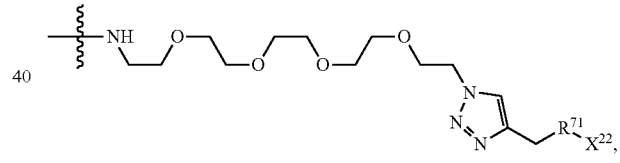
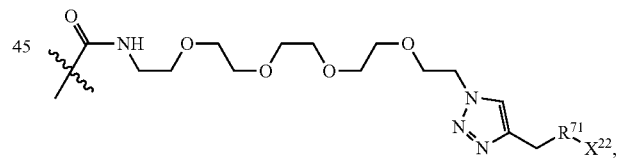
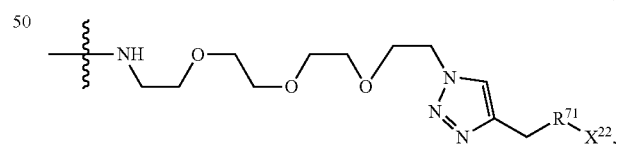
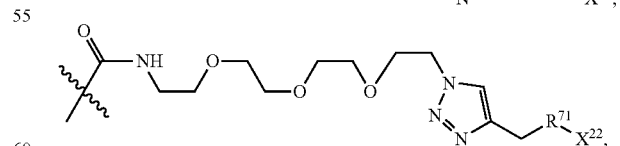
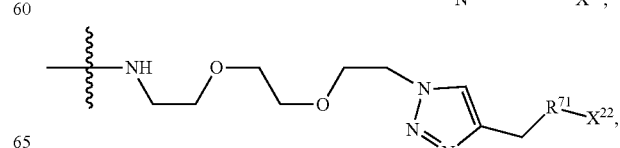

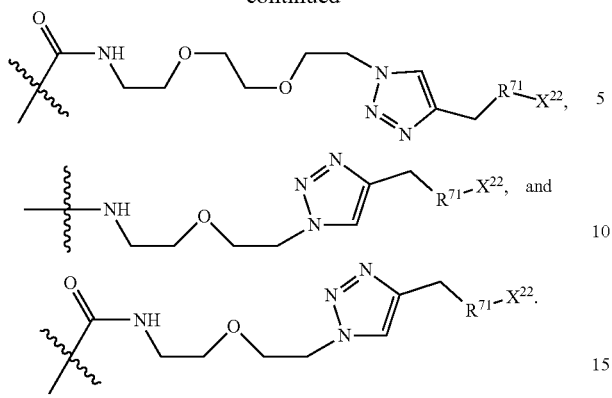
In additional embodiments, -(Linker)$^B$ is selected from:
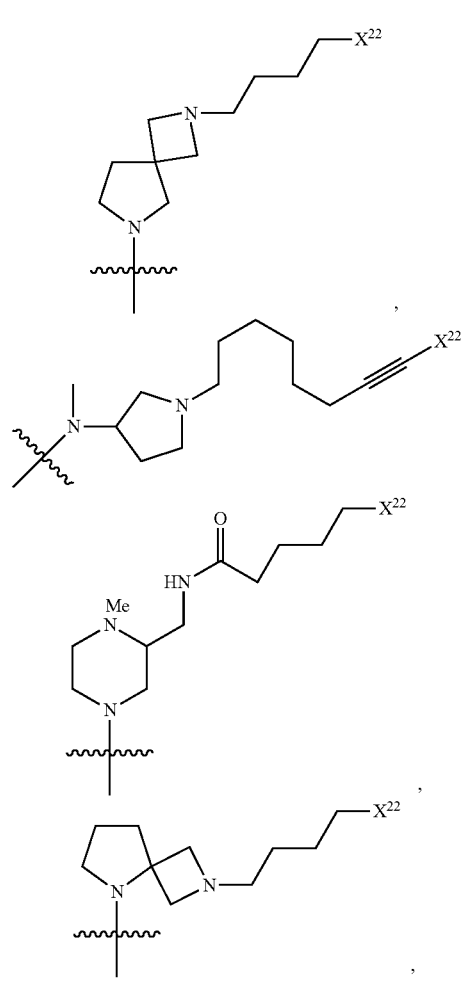
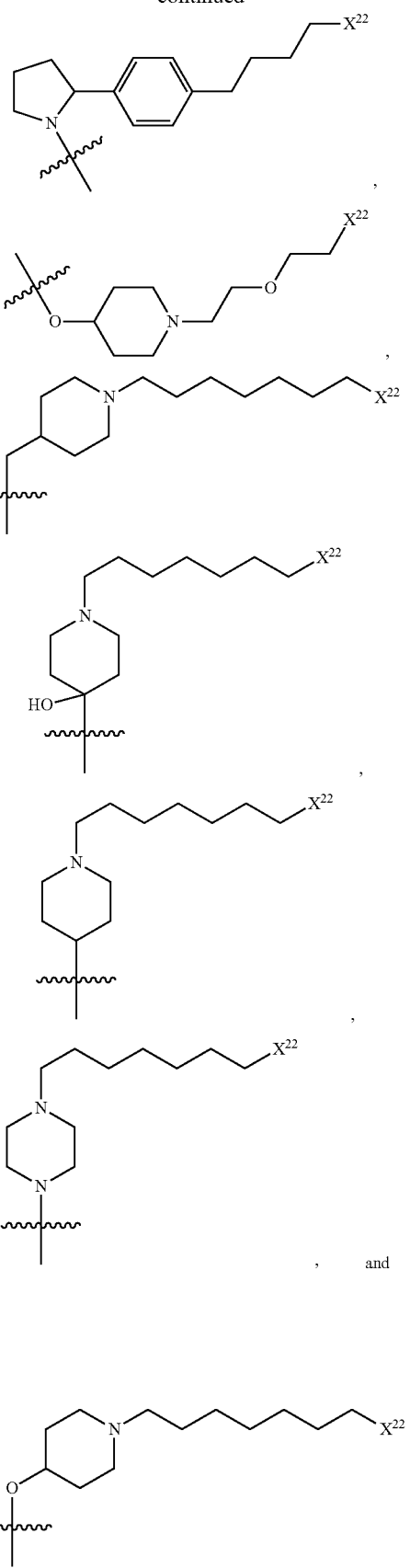
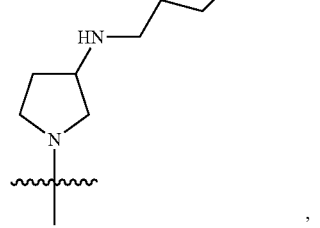

In additional embodiments, -(Linker)$^B$ is selected from:
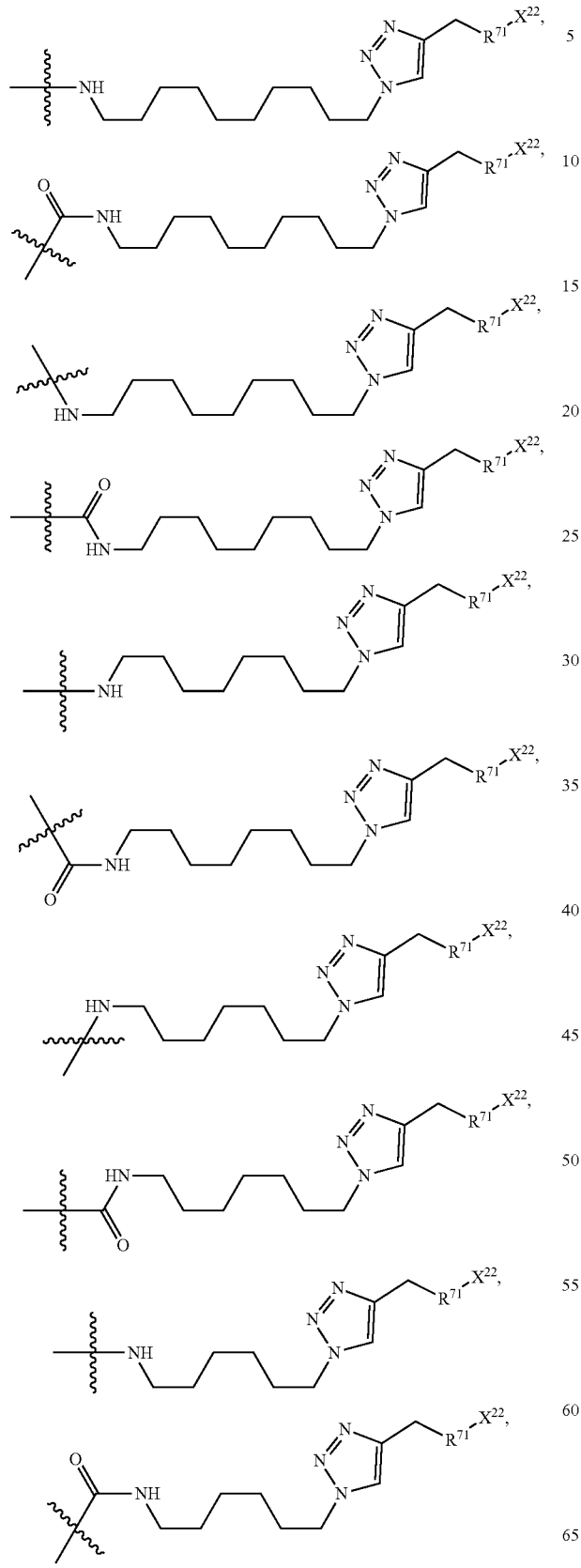
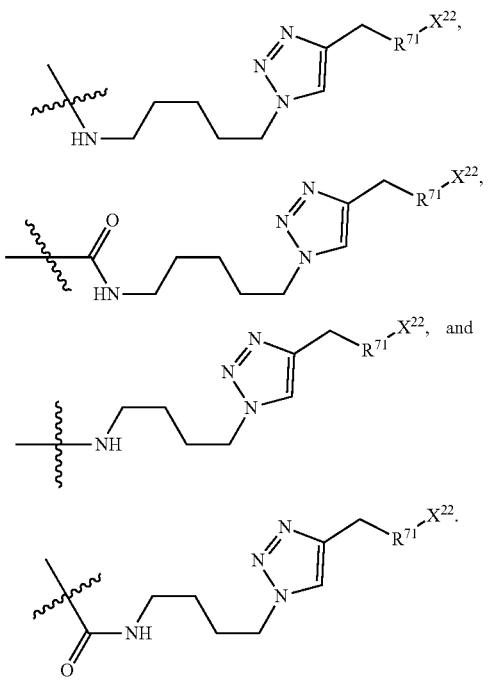
In additional embodiments, -(Linker)$^B$ is selected from:
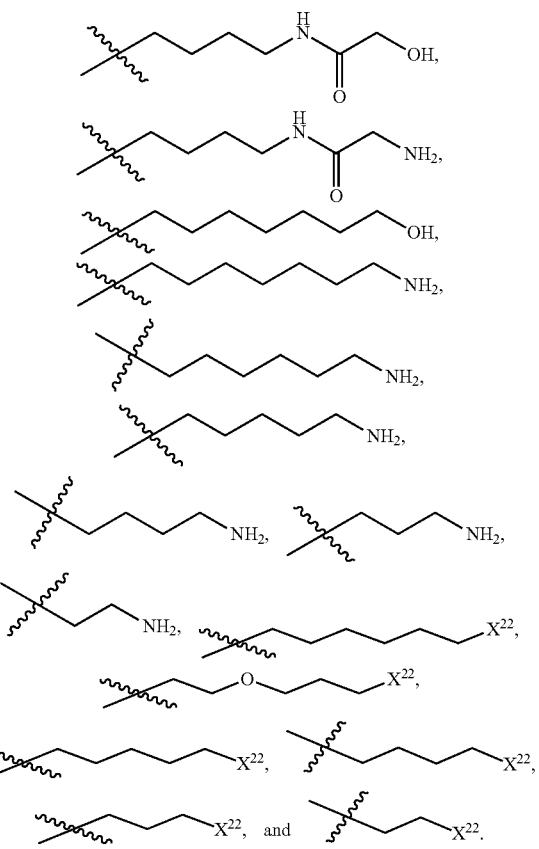
In the above embodiments $X^{22}$ is selected such that a compound sufficiently stable or the intended use results.

In additional embodiments, -(Linker)$^B$ is selected from:
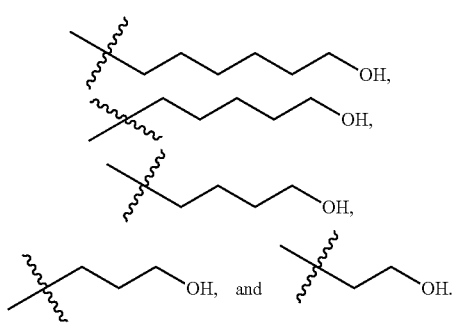
In certain embodiments, -(Linker)$^B$ is selected from:
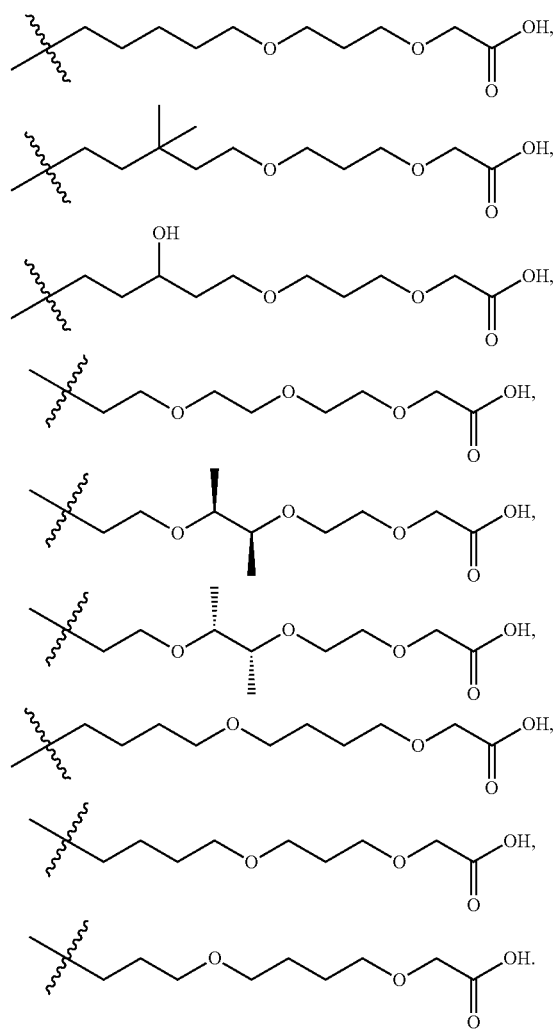
In certain embodiments -(Linker)$^B$ is selected from:
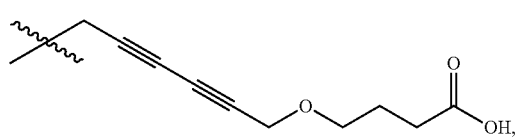
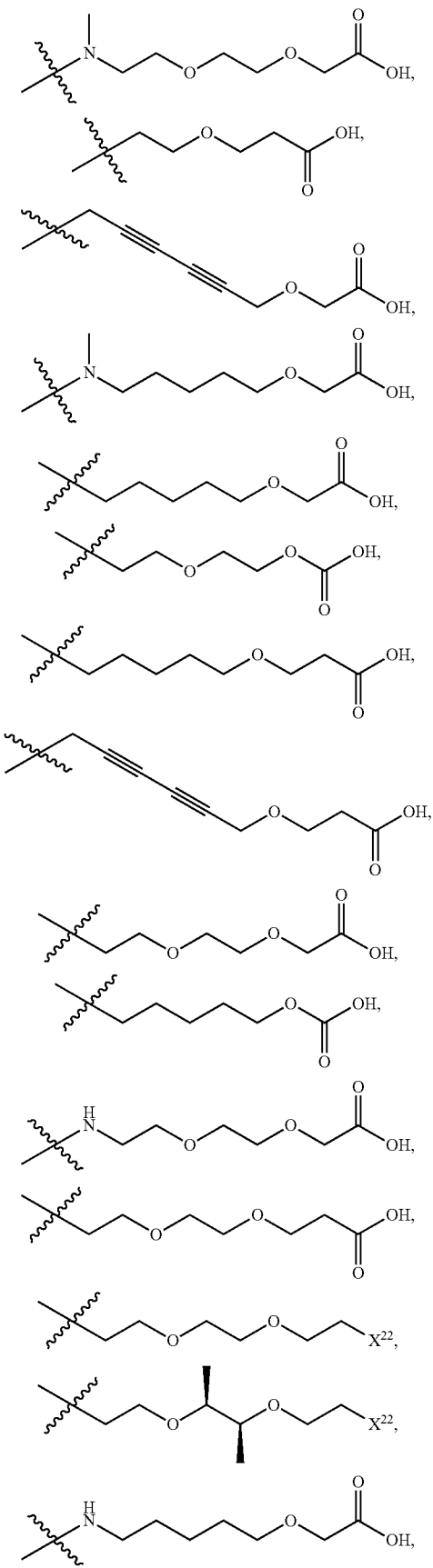

403
-continued
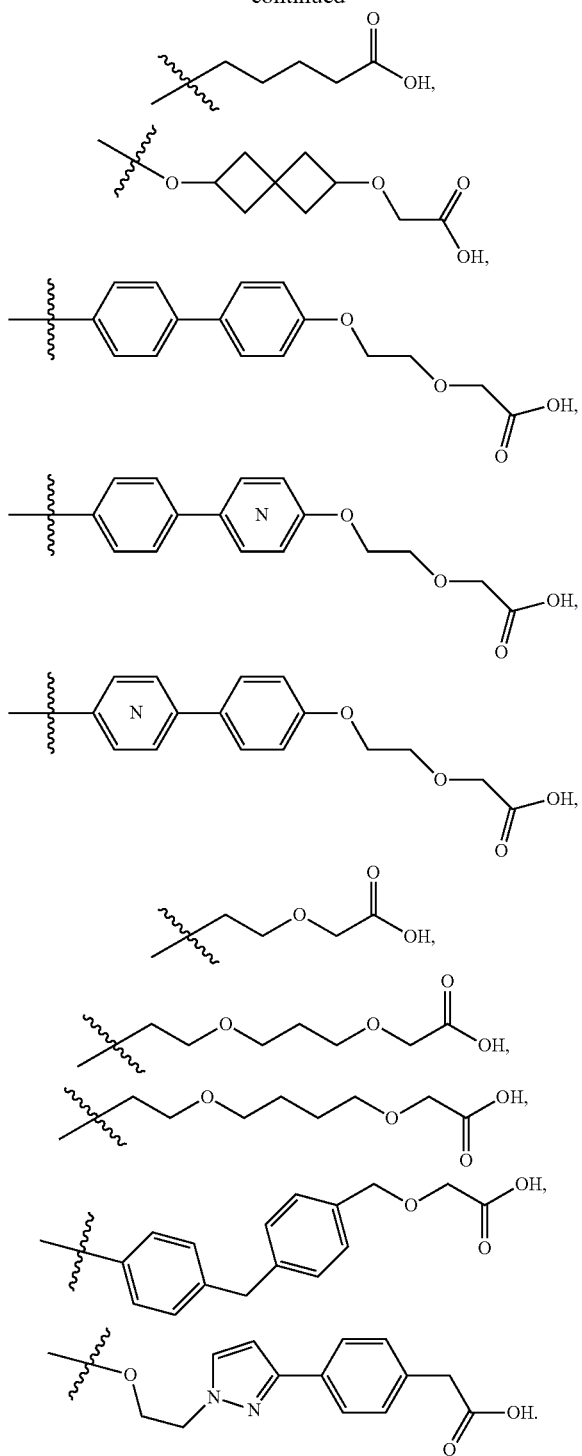
In the above structures
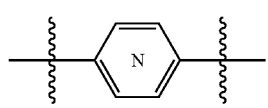
404
represents
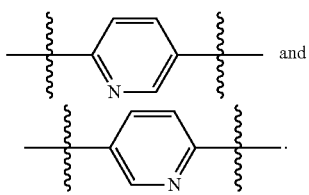
and
In certain embodiments, -(Linker)$^B$ can be a 4-24 carbon atom linear chains, wherein one or more the carbon atoms in the linear chain can be replaced or substituted with oxygen, nitrogen, amide, fluorinated carbon, etc., such as the following:
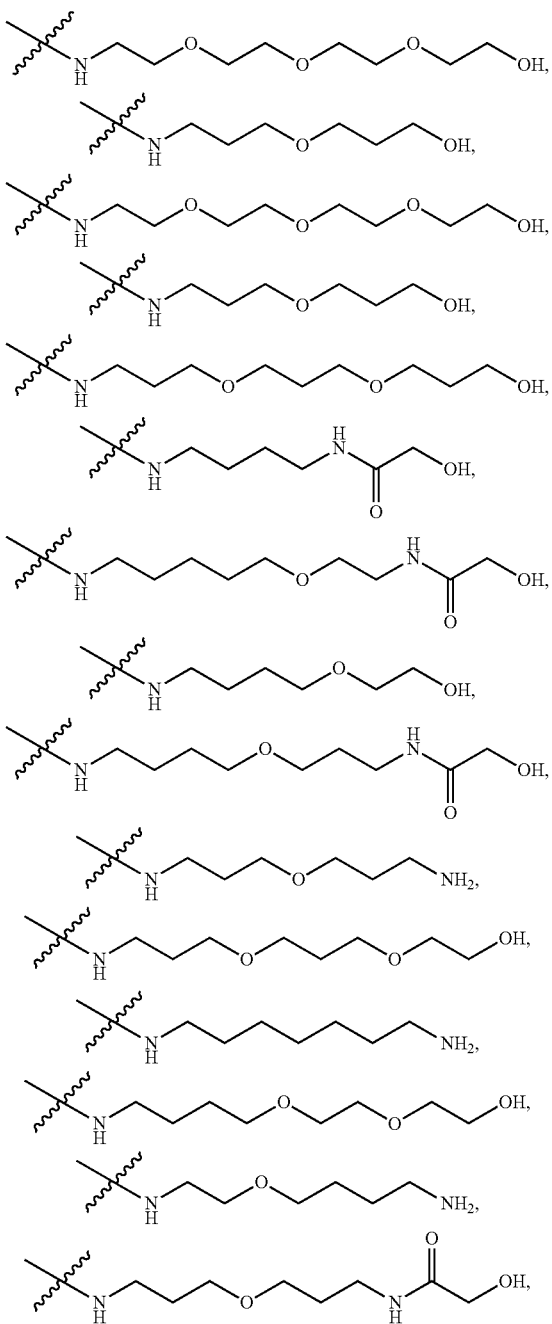

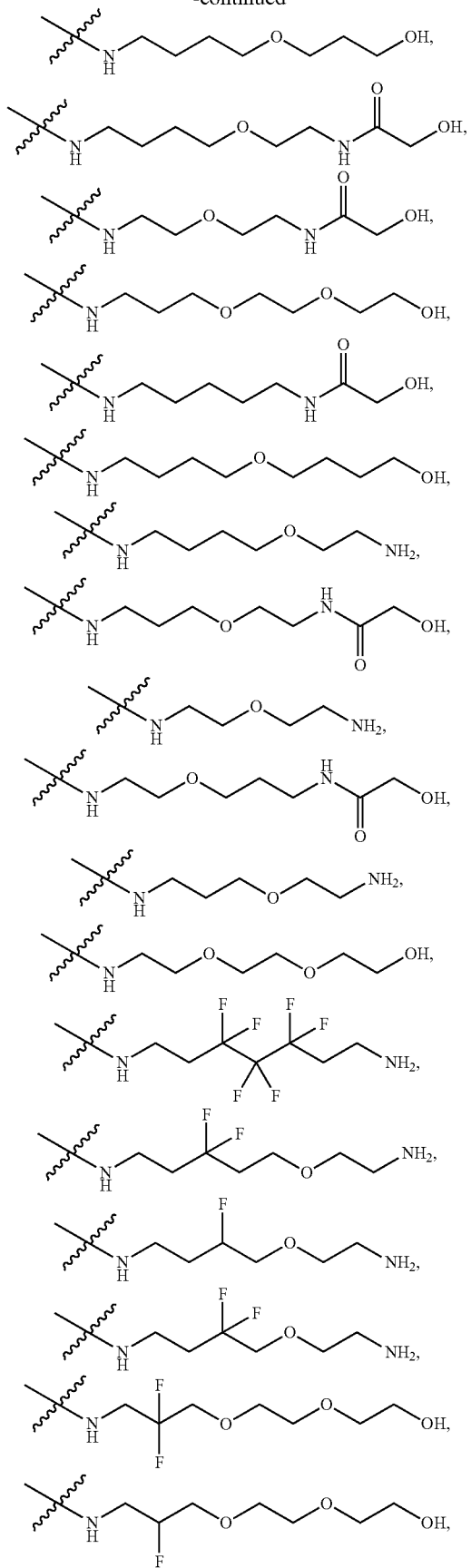
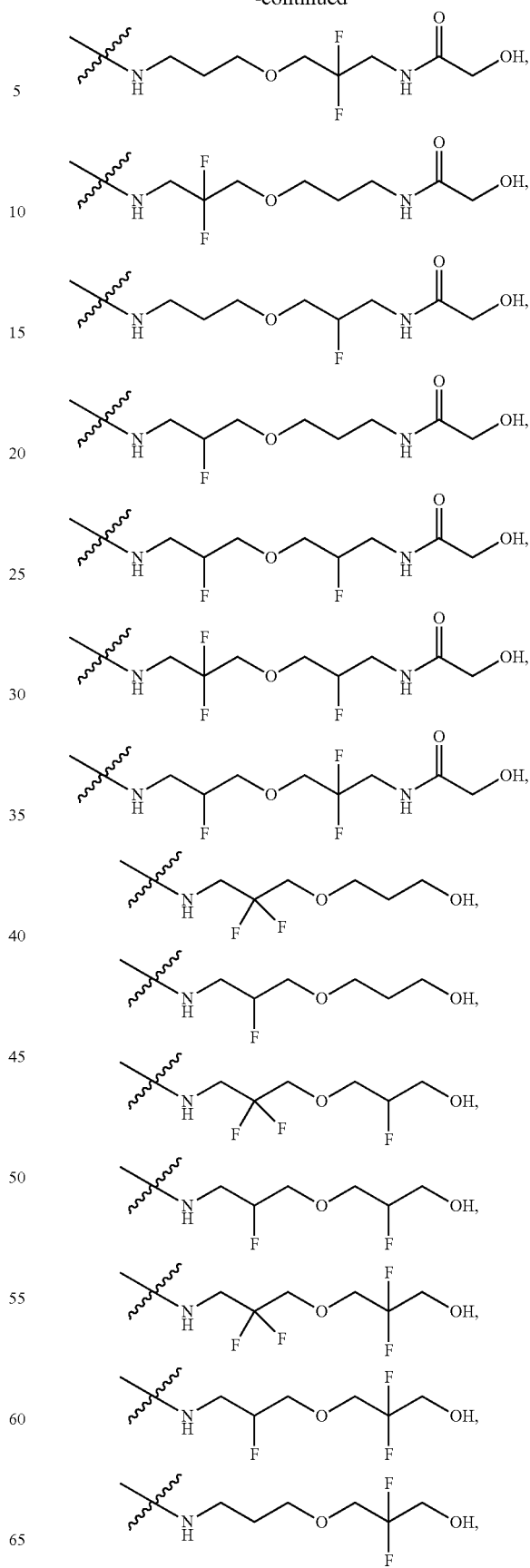

-continued

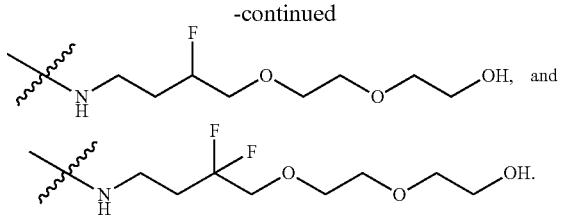

In certain embodiments, -(Linker)$^B$ can be a nonlinear chain, and can be, or include, aliphatic or aromatic or heteroaromatic cyclic moieties.

In certain embodiments, -(Linker)$^B$ may include contiguous, partially contiguous or non-contiguous ethylene glycol unit groups ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units, for example, 1, 2, 3, 4, 6, 6, 7, 8, 9, 10, 11 or 12 ethylene glycol units.

In certain embodiments, -(Linker)$^B$ may have 1, 2, 3, 4, 5, 6, 7, 8, 9, 10, 11, 12, 13, 14, or 15 fluorine substituents. In another embodiment -(Linker)$^B$ is perfluorinated. In yet another embodiment -(Linker)$^B$ is a partially or fully fluorinated poly ether. Nonlimiting examples of fluorinated -(Linker)$^B$ moieties include:

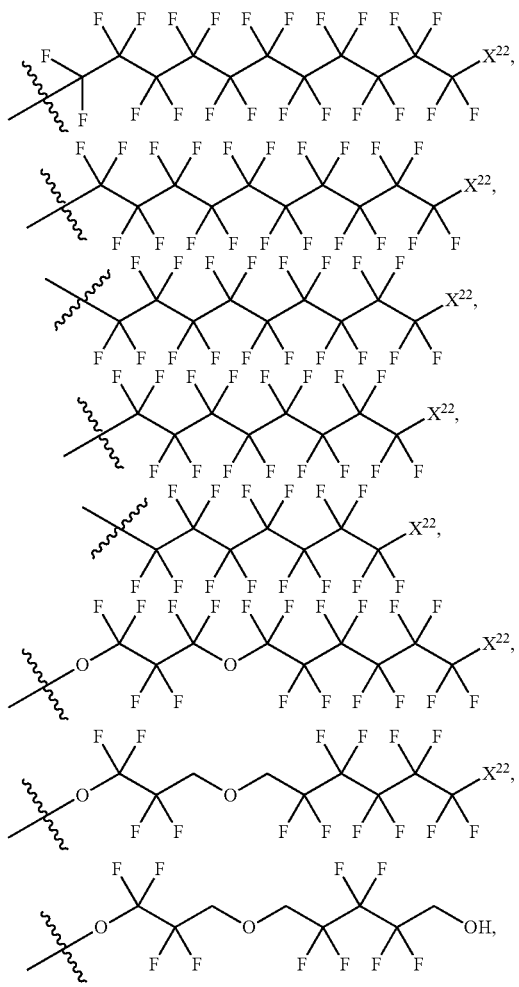

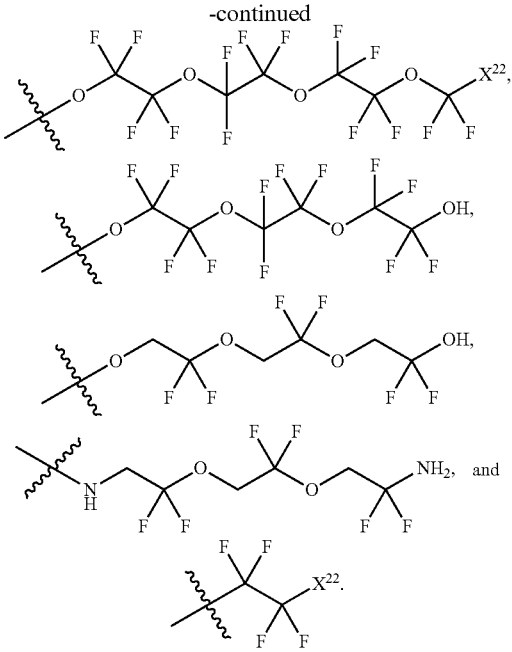

In certain embodiments, the length can be adjusted as desired or as found necessary for the desired application.

In an alternative embodiment, R$^{12}$ can be -(Linker)$^C$, wherein -(Linker)$^C$ is a chemical group that is covalently attached to a Targeting Ligand and one or more, for example 1, 2, 3, or 4, additional Targeting Ligands and/or Degrons. For Example, -(Linker)$^C$ can be covalently attached to a Targeting Ligand and an additional Degron, for example a Degron of Formulas V, VI, VII, VIII, or XII as described herein, or -(Linker)$^C$ can be covalently attached to two Targeting Ligands selected from those described herein.

In one embodiment the compound is selected from:

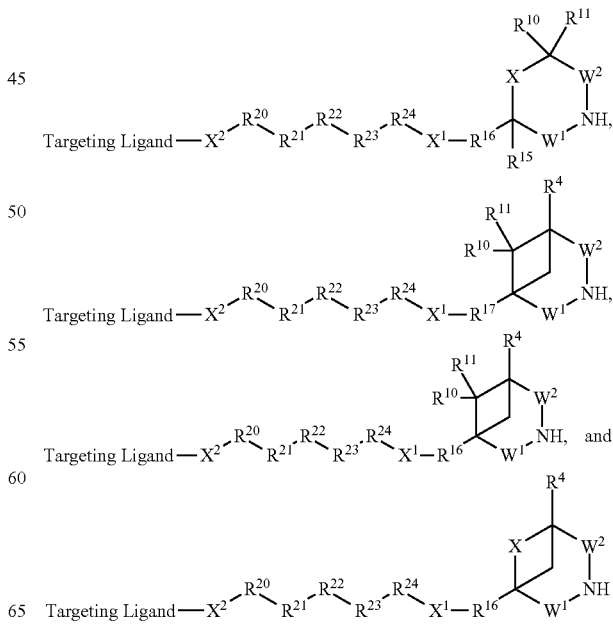

or a pharmaceutically acceptable salt, N-oxide, isotopic derivative, or prodrug thereof, optionally in a pharmaceutically acceptable carrier to form a composition;

wherein $R^{16}$ and $R^{17}$ are defined as above, but do not include an $R^{12}$ substituent; and X, $X^1$, $X^2$, $W^1$, $W^2$, $R^4$, $R^{10}$, $R^{11}$, $R^{20}$, $R^{21}$, $R^{22}$, $R^{23}$, Targeting Ligand and $R^{24}$ are defined as above.

Examples of Degron-Linker-Targeting Ligands of the present invention include the following, wherein a Targeting Ligand is attached to $X^2$:

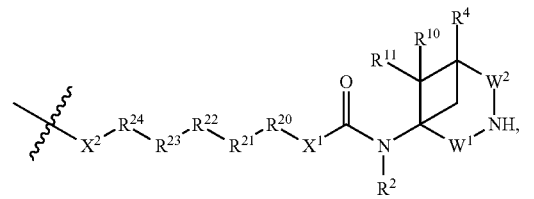

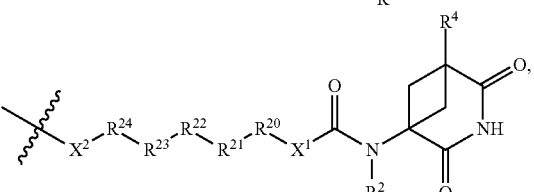

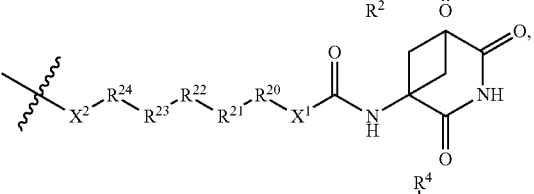

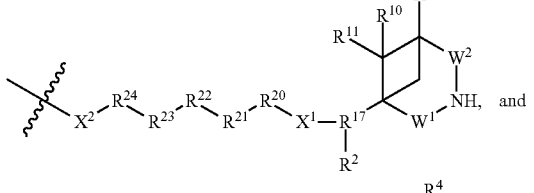

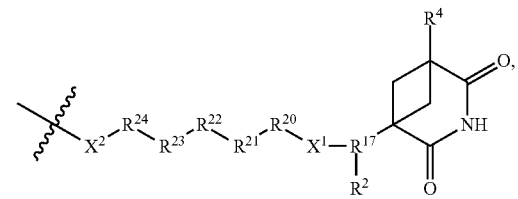

or a pharmaceutically acceptable salt, N-oxide, isotopic derivative, or prodrug thereof, optionally in a pharmaceutically acceptable carrier to form a composition;

wherein X, $X^1$, $X^2$, $W^1$, $W^2$, $R^2$, $R^4$, $R^{10}$, $R^{11}$, $R^{20}$, $R^{21}$, $R^{22}$, $R^{23}$, and $R^{24}$ are defined as above.

In another aspect, the present invention includes a compound of any one of the following formulae, wherein a Targeting Ligand is attached to $X^2$:

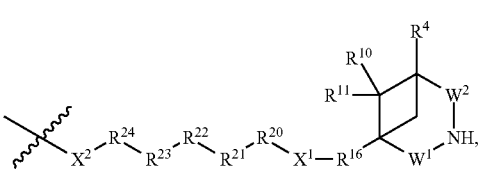

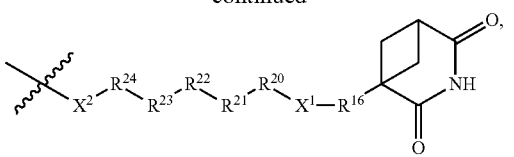

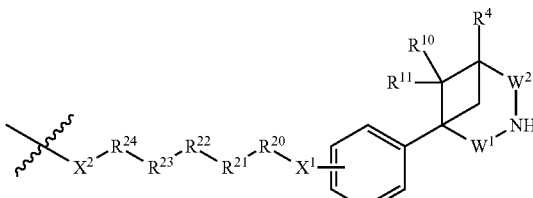

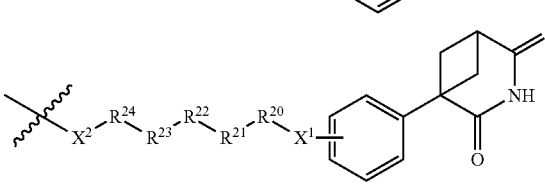

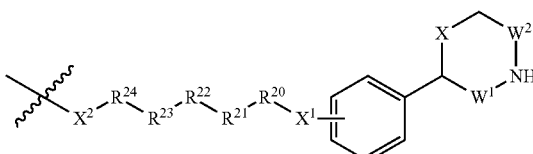

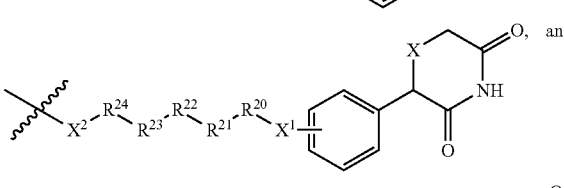

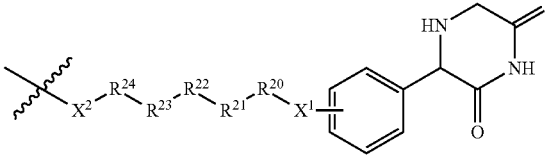

or a pharmaceutically acceptable salt, N-oxide, isotopic derivative, or prodrug thereof, optionally in a pharmaceutically acceptable carrier to form a composition;

wherein X, $X^1$, $X^2$, $W^1$, $W^2$, $R^4$, $R^{10}$, $R^{11}$, $R^{20}$, $R^{21}$, $R^{22}$, $R^{23}$, and $R^{24}$ are defined as above.

V. Linker-Degron Intermediates

The present invention also includes compounds comprising a Degron covalently attached to a monovalent (Linker)$^B$. -(Linker)$^B$ is a monovalent group with a reactive functional group that allows for optional later attachment of a Targeting Ligand.

In one embodiment the compound is selected from:

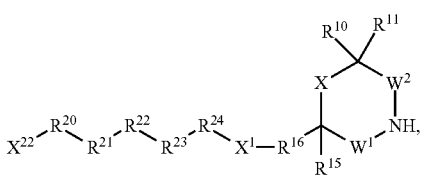

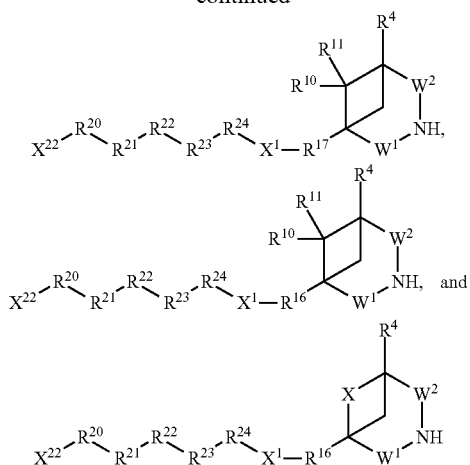

or a pharmaceutically acceptable salt, N-oxide, isotopic derivative, or prodrug thereof, optionally in a pharmaceutically acceptable carrier to form a composition;

wherein $R^{16}$ and $R^{17}$ are defined as above, but do not include an $R^{12}$ substituent; and $X$, $X^1$, $X^{22}$, $W^1$, $W^2$, $R^4$, $R^{10}$, $R^{11}$, $R^{20}$, $R^{21}$, $R^{22}$, $R^{23}$, and $R^{24}$ are defined as above.

In an alternative embodiment, the compound is selected from:

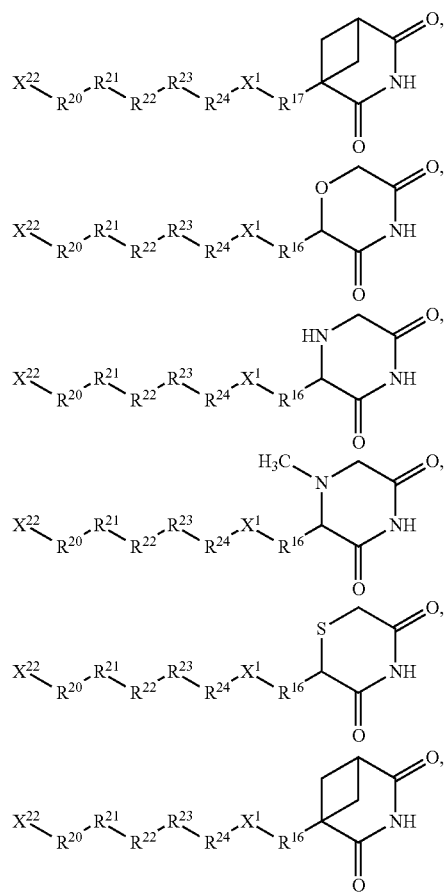

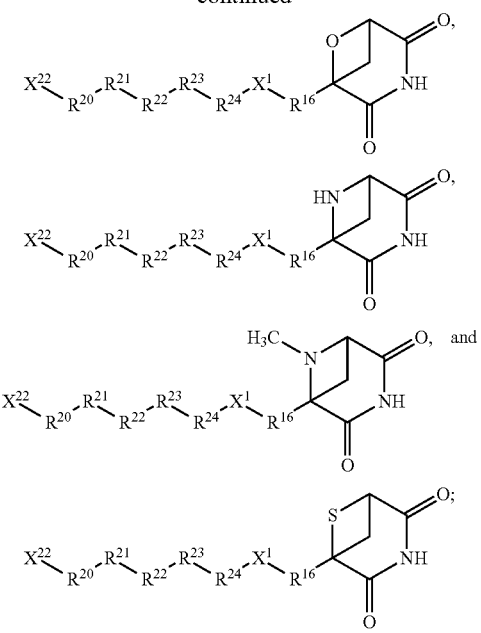

or a pharmaceutically acceptable salt, N-oxide, isotopic derivative, or prodrug thereof, optionally in a pharmaceutically acceptable carrier to form a composition;

wherein $R^{16}$ and $R^{17}$ are defined as above, but do not include an $R^{12}$ substituent; and $X^1$, $X^{22}$, $R^{20}$, $R^{21}$, $R^{22}$, $R^{23}$, and $R^{24}$ are defined as above.

Non-limiting examples of compounds of the present invention include:

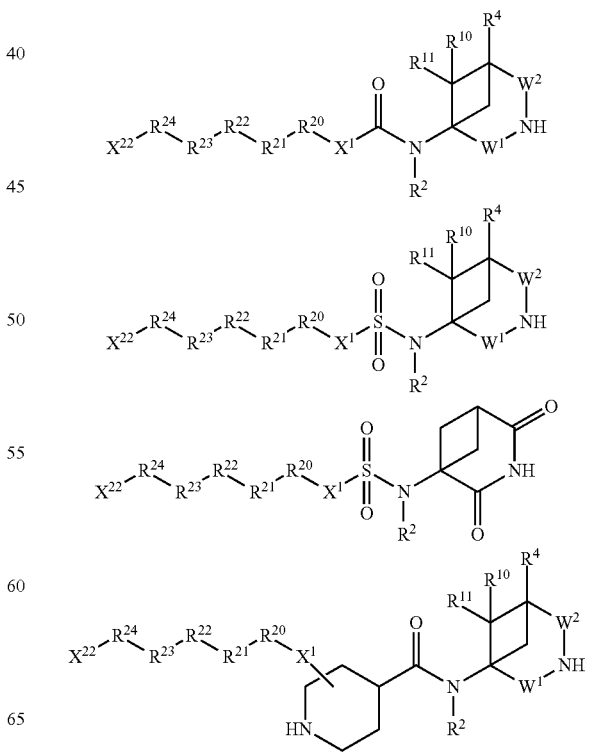

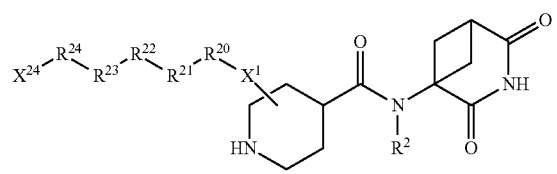
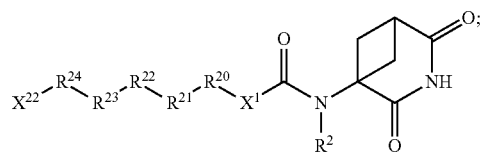
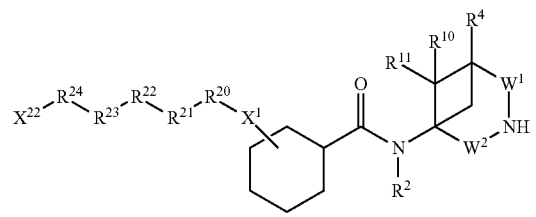
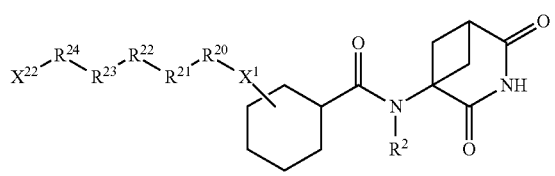
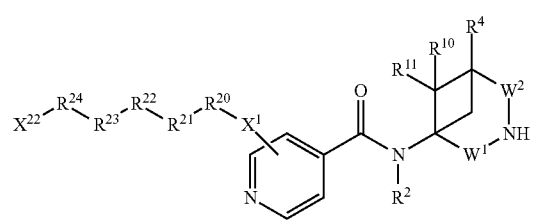
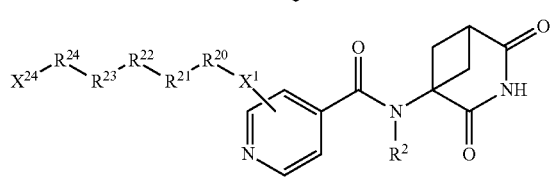
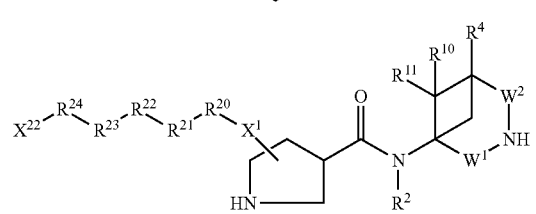
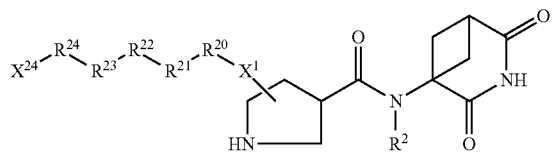
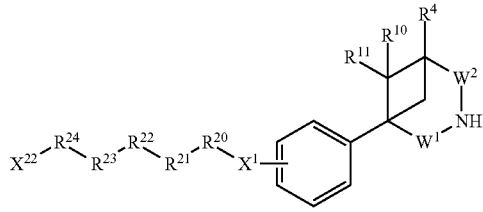
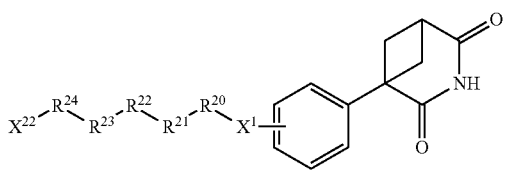
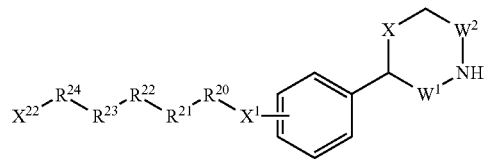
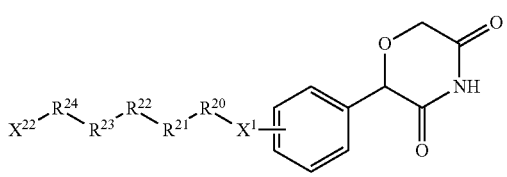
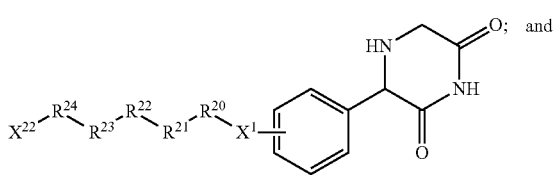
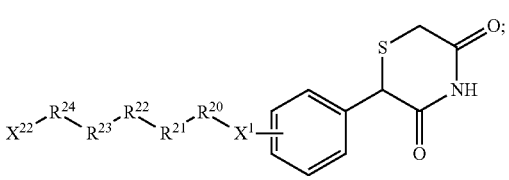
or a pharmaceutically acceptable salt, N-oxide, isotopic derivative, or prodrug thereof, optionally in a pharmaceutically acceptable carrier to form a composition;
wherein X, $X^1$, $X^{22}$, $W^1$, $W^2$, $R^4$, $R^{10}$, $R^{11}$, $R^{20}$, $R^{21}$, $R^{22}$, $R^{23}$, and $R^{24}$ are defined as above.
Additional non-limiting examples of compounds of the present invention include:
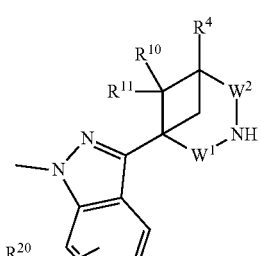
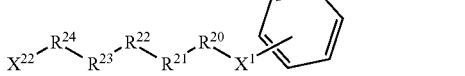
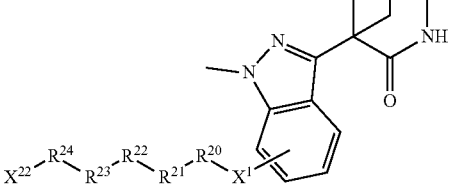

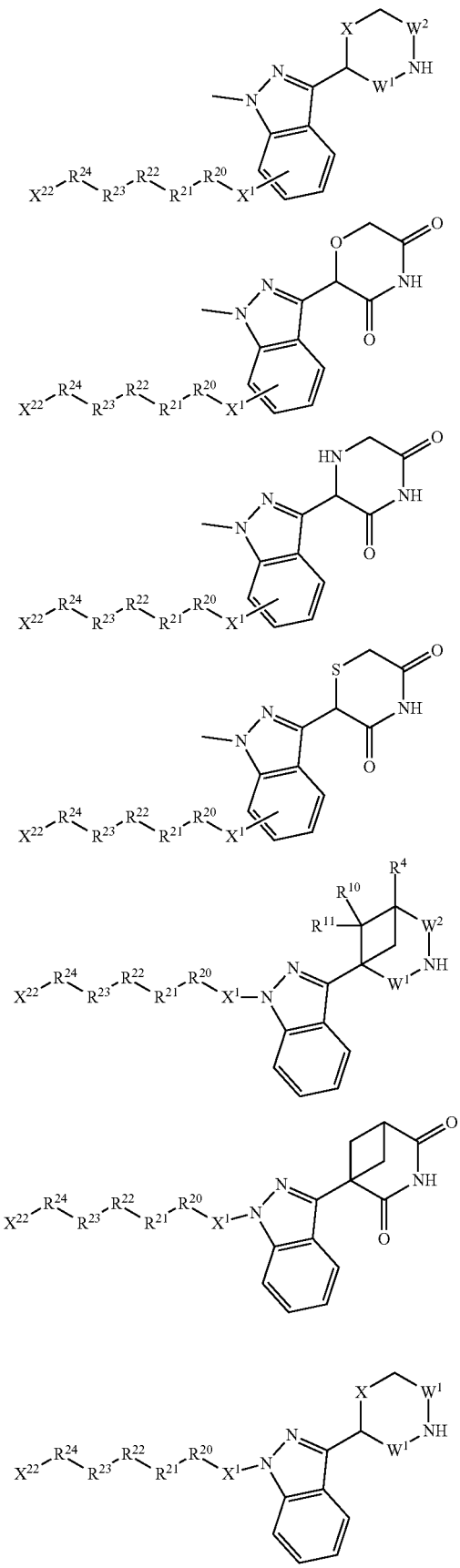

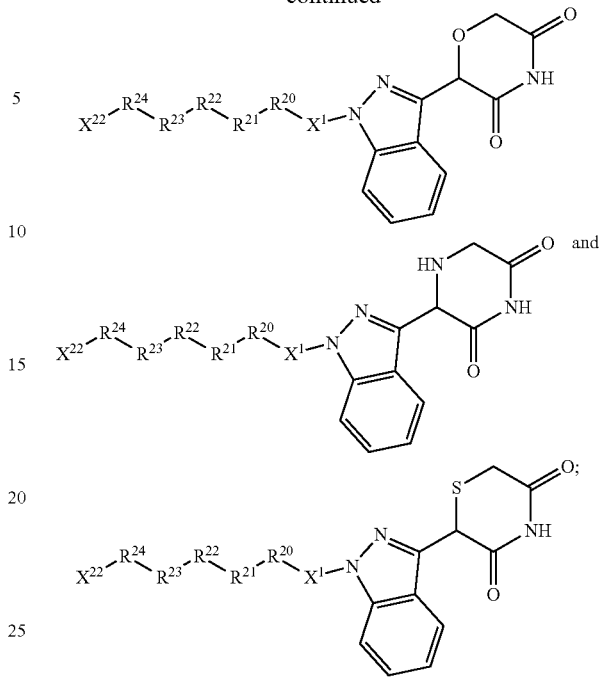

or a pharmaceutically acceptable salt, N-oxide, isotopic derivative, or prodrug thereof, optionally in a pharmaceutically acceptable carrier to form a composition;

wherein all variables are defined as above.

VI. Target Proteins

Degradation of cellular proteins is required for cell homeostasis and normal cell function, such as proliferation, differentiation and cell death. When this system becomes dysfunctional or does not identify and abate abnormal protein behavior in vivo, a disease state can arise in a host, such as a human. A large range of proteins can cause, modulate or amplify diseases in vivo, as well known to those skilled in the art, published in literature and patent filings as well as presented in scientific presentations.

Therefore, in one embodiment, a selected Degrader compound of the present invention can be administered in vivo in an effective amount to a host in need thereof to degrade a selected protein that mediates a disorder to be treated. The selected protein target may modulate a disorder in a human via a mechanism of action such as modification of a biological pathway, pathogenic signaling or modulation of a signal cascade or cellular entry. In one embodiment, the Target Protein is a protein that is not drugable in the classic sense in that it does not have a binding pocket or an active site that can be inhibited or otherwise bound, and cannot be easily allosterically controlled. In another embodiment, the Target Protein is a protein that is drugable in the classic sense, yet for therapeutic purposes, degradation of the protein is preferred to inhibition.

The Target Protein is recruited with a Targeting Ligand, which is a ligand for the Target Protein. Typically the Targeting Ligand binds the Target Protein in a non-covalent fashion. In an alternative embodiment, the Target Protein is covalently bound to the Degron in a manner that can be irreversible or reversible.

In one embodiment, the selected Target Protein is expressed from a gene that has undergone an amplification, translocation, deletion, or inversion event which causes or is caused by a medical disorder. In certain aspects, the selected Target Protein has been post-translationally modified by one, or a combination, of phosphorylation, acetylation, acylation including propionylation and crotylation, N-linked glycosylation, amidation, hydroxylation, methylation and polymethylation, O-linked glycosylation, pyrogultamoylation, myristoylation, farnesylation, geranylgeranylation, ubiquitination, sumoylation, or sulfation which causes or is caused by a medical disorder.

As contemplated herein, the present invention includes an Degrader with a Targeting Ligand that binds to a Target Protein of interest. The Target Protein is any amino acid sequence to which a Degrader can be bound which by degradation thereof, causes a beneficial therapeutic effect in vivo. In one embodiment, the Target Protein is a non-endogenous peptide such as that from a pathogen or toxin. In another embodiment, the Target Protein can be an endogenous protein that mediates a disorder. The endogenous protein can be either the normal form of the protein or an aberrant form. For example, the Target Protein can be a mutant protein found in cancer cells, or a protein, for example, where a partial, or full, gain-of-function or loss-of-function is encoded by nucleotide polymorphisms. In some embodiments, the Degrader targets the aberrant form of the protein and not the normal form of the protein. In another embodiment, the Target Protein can mediate an inflammatory disorder or an immune disorder, including an auto-immune disorder. In one embodiment, the Target Protein is a non-endogenous protein from a virus, as non-limiting examples, HIV, HBV, HCV, RSV, HPV, CMV, flavivirus, pestivirus, coronavirus, noroviridae, etc. In one embodiment, the Target Protein is a non-endogenous protein from a bacteria, which may be for example, a gram positive bacteria, gram negative bacteria or other, and can be a drug-resistant form of bacteria. In one embodiment, the Target Protein is a non-endogenous protein from a fungus. In one embodiment, the Target Protein is a non-endogenous protein from a prion. In one embodiment, the Target Protein is a protein derived from a eukaryotic pathogen, for example a protist, helminth, etc.

In one aspect, the Target Protein mediates chromatin structure and function. The Target Protein may mediate an epigenetic action such as DNA methylation or covalent modification of histones. An example is histone deacetylase (HDAC 1, 2, 3, 4, 5, 6, 7, 8, 9, 10 or 11). Alternatively, the Target Protein may be a bromodomain, which are readers of lysine acetylation (for example, BRD1, 2, 3, 4, 5, 6, 7, 8, 9 and T. FIG. 9 illustrates the proteins of the bromodomain family, which, for example, can act as Target Proteins according to the present invention.

Other nonlimiting examples of Target Proteins are a structural protein, receptor, enzyme, cell surface protein, a protein involved in apoptotic signaling, aromatase, helicase, mediator of a metabolic process (anabolism or catabolism), antioxidant, protease, kinase, oxidoreductase, transferase, hydrolase, lyase, isomerase, ligase, enzyme regulator, signal transducer, structural molecule, binding activity (protein, lipid carbohydrate), cell motility protein, membrane fusion protein, cell communication mediator, regulator of biological processes, behavioral protein, cell adhesion protein, protein involved in cell death, protein involved in transport (including protein transporter activity, nuclear transport, ion transporter, channel transporter, carrier activity, permease, secretase or secretion mediator, electron transporter, chaperone regulator, nucleic acid binding, transcription regulator, extracellular organization and biogenesis regulator, and translation regulator).

In one embodiment, the Target Protein is a modulator of a signaling cascade related to a known disease state. In another embodiment, the Target Protein mediates a disorder by a mechanism different from modulating a signaling cascade. Any protein in a eukaryotic system or a microbial system, including a virus, bacteria or fungus, as otherwise described herein, are targets for proteasomal degradation using the present invention. The Target Protein may be a eukaryotic protein, and in some embodiments, a human protein.

In one embodiment, the Target Protein is RXR, DHFR, Hsp90, a kinase, HDM2, MDM2, BET bromodomain-containing protein, HDAC, IDH1, Mcl-1, human lysine methyltransferase, a nuclear hormone receptor, aryl hydrocarbon receptor (AHR), RAS, RAF, FLT, SMARC, KSR, NF2L, CTNB, CBLB, BCL.

In one embodiment, a bromodomain containing protein has histone acetyl transferase activity.

In one embodiment, the bromodomain containing protein is BRD2, BRD3, BRD4, BRDT or ASH1L.

In one embodiment, the bromodomain containing protein is a non-BET protein.

In one embodiment, the non-BET protein is BRD7 or BRD9.

In one embodiment, the FLT is not FLT 3. In one embodiment, the RAS is not RASK. In one embodiment, the RAF is not RAF 1. In one embodiment, the SMARC is not SMARC2. In one embodiment, the KSR is not KSR1. In one embodiment, the NF2L is not NF2L2. In one embodiment, the CTNB is not CTNB 1. In one embodiment, the BCL is not BCL6.

In one embodiment, the Target Protein is selected from: EGFR, FLT3, RAF 1, SMRCA2, KSR1, NF2L2, CTNB1, CBLB, BCL6, and RASK.

In another embodiment, the Target Protein is not selected from: EGFR, FLT3, RAF1, SMRCA2, KSR1, NF2L2, CTNB1, CBLB, BCL6, and RASK.

In one embodiment, the Targeting Ligand is an EGFR ligand, a FLT3 ligand, a RAF 1 ligand, a SMRCA2 ligand, a KSR1 ligand, a NF2L2 ligand, a CTNB 1 ligand, a CBLB ligand, a BCL6 ligand, or a RASK ligand.

In one embodiment, the Targeting Ligand is not a EGFR ligand, a FLT3 ligand, a RAF 1 ligand, a SMRCA2 ligand, a KSR1 ligand, a NF2L2 ligand, a CTNB 1 ligand, a CBLB ligand, a BCL6 ligand, or a RASK ligand.

The present invention may be used to treat a wide range of disease states and/or conditions, including any disease state and/or condition in which a protein is dysregulated and where a patient would benefit from the degradation of proteins.

For example, a Target Protein can be selected that is a known target for a human therapeutic, and the therapeutic can be used as the Targeting Ligand when incorporated into the Degrader according to the present invention. These include proteins which may be used to restore function in a polygenic disease, including for example B7.1 and B7, TINFR1m, TNFR2, NADPH oxidase, Bcl2/Bax and other partners in the apoptosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, e.g., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuraminidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, neurokinins and receptors, inosine monophosphate dehydrogenase, p38 MAP Kinase, Ras/Raf/MER/ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-2/neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further Target Proteins include Acetyl-CoA carboxylase, adenylosuccinate synthetase, protoporphyrinogen oxidase, and enolpyruvylshikimate-phosphate synthase.

In certain embodiments, the Target Protein is derived from a kinase to which the Targeting Ligand is capable of binding or binds including, but not limited to, a tyrosine kinase (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDGFRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES 1, or ZAP70).

In certain embodiments, the Target Protein is derived from a kinase to which the Targeting Ligand is capable of binding or binds including, but not limited to, a serine/threonine kinase (e.g., casein kinase 2, protein kinase A, protein kinase B, protein kinase C, Raf kinases, CaM kinases, AKT1, AKT2, AKT3, ALK1, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK11, PAK1, PAK2, PAK3, PAK4, PAK5, PAK6, PIM1, PIM2, PLK1, RIP2, RIP5, RSK1, RSK2, SGK2, SGK3, SIK1, STK33, TAO1, TAO2, TGF-beta, TLK2, TSSK1, TSSK2, ULK1, or ULK2).

In certain embodiments, the Target Protein is derived from a kinase to which the Targeting Ligand is capable of binding or binds including, but not limited to a cyclin dependent kinase for example CDK1, CDK2, CDK3, CDK4, CDK5, CDK6, CDK7, CDK8, CDK9, CDK10, CDK11, CDK12, or CDK13.

In certain embodiments, the Target Protein is derived from a kinase to which the Targeting Ligand is capable of binding or binds including, but not limited to a leucine-rich repeat kinase (e.g., LRRK2).

In certain embodiments, the Target Protein is derived from a kinase to which the Targeting Ligand is capable of binding or binds including, but not limited to a lipid kinase (e.g., PIK3CA, PIK3CB) or a sphingosine kinase (e.g. S1P).

In certain embodiments, the Target Protein is derived from a BET bromodomain-containing protein to which the Targeting Ligand is capable of binding or binds including, but not limited to, ASH1L, ATAD2, BAZ1A, BAZ1B, BAZ2A, BAZ2B, BRD1, BRD2, BRD3, BRD4, BRD5, BRD6, BRD7, BRD8, BRD9, BRD10, BRDT, BRPF1, BRPF3, BRWD3, CECR2, CREBBP, EP300, FALZ, GCN5L2, KIAA1240, LOC93349, MLL, PB1, PCAF, PHIP, PRKCBP1, SMARCA2, SMARCA4, SP100, SP110, SP140, TAF1, TAF1L, TIF1a, TRIM28, TRIM33, TRIM66, WDR9, ZMYND11, and MLL4. In certain embodiments, a BET bromodomain-containing protein is BRD4.

In certain embodiments, the Target Protein is derived from a nuclear protein to which the Targeting Ligand is capable of binding or binds including, but not limited to, BRD2, BRD3, BRD4, Antennapedia Homeodomain Protein, BRCA1, BRCA2, CCAAT-Enhanced-Binding Proteins, histones, Polycomb-group proteins, High Mobility Group Proteins, Telomere Binding Proteins, FANCA, FANCD2, FANCE, FANCF, hepatocyte nuclear factors, Mad2, NF-kappa B, Nuclear Receptor Coactivators, CREB-binding protein, p55, p107, p130, Rb proteins, p53, c-fos, c-jun, c-mdm2, c-myc, and c-rel.

In certain embodiments, the Target Protein is a member of the Retinoid X Receptor (RXR) family and the disorder treated is a neuropsychiatric or neurodegenerative disorder.

In certain embodiments, the Target Protein is a member of the Retinoid X Receptor (RXR) family and the disorder treated is schizophrenia.

In certain embodiments, the Target Protein is dihydrofolate reductase (DHFR) and the disorder treated is cancer. In certain embodiments, the Target Protein is dihydrofolate reductase (DHFR) and the disorder treated is microbial.

In certain embodiments, the Target Protein is dihydrofolate reductase from *Bacillus anthracis* (BaDHFR) and the disorder treated is anthrax.

In certain embodiments, the Target Protein is Heat Shock Protein 90 (HSP90) and the disorder treated is cancer.

In certain embodiments, the Target Protein is a kinase or phosphatase and the disorder treated is cancer.

In certain embodiments, the Target Protein is HDM2 and or MDM2 and the disorder treated is cancer.

In certain embodiments, the Target Protein is a BET bromodomain containing protein and the disorder treated is cancer.

In certain embodiments, the Target Protein is a lysine methyltransferase and the disorder treated is cancer.

In certain embodiments, the Target Protein belongs to the RAF family and the disorder treated is cancer.

In certain embodiments, the Target Protein belongs to the FKBP family and the disorder treated is an autoimmune disorder. In certain embodiments, the Target Protein belongs to the FKBP family and the disorder treated is organ rejection. In certain embodiments, the Target Protein belongs to the FKBP family and the compound is given prophylactically to prevent organ failure.

In certain embodiments, the Target Protein is an androgen receptor and the disorder treated is cancer.

In certain embodiments, the Target Protein is an estrogen receptor and the disorder treated is cancer.

In certain embodiments, the Target Protein is a viral protein and the disorder treated is a viral infection. In certain embodiments, the Target Protein is a viral protein and the disorder treated is HIV, HPV, or HCV.

In certain embodiments, the Target Protein is an AP-1 or AP-2 transcription factor and the disorder treated is cancer.

In certain embodiments, the Target Protein is a HIV protease and the disorder treated is a HIV infection. In certain embodiments, the Target Protein is a HIV integrase and the disorder treated is a HIV infection. In certain embodiments, the Target Protein is a HCV protease and the disorder treated is a HCV infection. In certain embodiments, the treatment is prophylactic and the Target Protein is a viral protein.

In certain embodiments, the Target Protein is a member of the histone deacetylase (HDAC) family and the disorder is a neurodegenerative disorder. In certain embodiments, the Target Protein is a member of the histone deacetylase (HDAC) family and the disorder is Huntingon's, Parkinson's, Kennedy disease, amyotropic lateral sclerosis, Rubinstein-Taybi syndrome, or stroke.

In certain embodiments, Targeting Ligand forms a covalent bond with the Target Protein. Non-limiting examples of Target Proteins and Targeting Ligands utilizing a covalent bond include those described in "Covalent Inhibitors Design and Discovery" Eur J Med Chem. 2017 Sep. 29; 138:96-114. doi: 10.1016/j.ejmech.2017.06.019; "Lysine-Targeting Covalent Inhibitors." Angew Chem Int Ed Engl. 2017 Aug. 29. doi: 10.1002/anie.201707630; "Inhibition of Mcl-1 Through Covalent Modification of a Noncatalytic Lysine Side Chain." Nat Chem Biol. 2016 November; 12(11):931-936; "Proteome-wide Map of Targets of T790M-EGFR-Directed Covalent Inhibitors" Cell Chem. Biol. 2016 November: 24:1-13; "Global Profiling of Lysine Reactivity and Ligandability in the Human Proteome" Nat. Chem. 2017 Jul. 31, doi:10.1038/nchem.2826; "The Resurgence of Covalent Drugs" Nat. Rev. Drug Disc. 2011 10, 307-217; U.S. Pat. Nos. 8,008,309; and 9,790,226.

In an alternative embodiment, the Target Protein is selected from DOTL1, CBP, WDR5, BRAF, KRAS, MCL1, PTPN2, HER2, and SHOC2. In another alternative embodiment, the Target Protein is selected from UCHL1, USP6, USP14, and USP30. In another alternative embodiment, the Target Protein is selected from USP 1, USP2, USP4, USP6, USP7, USP8, USP9x, USP10, USP 11, USP13, USP14, USP17, and USP28.

In certain embodiments, the Target Protein as referred to herein is named by the gene that expresses it. The person skilled in the art will recognize that when a gene is referred to as a Target Protein, the protein encoded by the gene is the Target Protein. For example, ligands for the protein SMCA2 which is encoded by SMRCA2 are referred to as SMRCA2 Targeting Ligands.

VII. Targeting Ligands

In certain aspects, the Targeting Ligand is a ligand which covalently or non-covalently binds to a Target Protein which has been selected for proteasomal degradation by the selected Degrader. A Targeting Ligand is a molecule or moiety (for example a peptide, nucleotide, antibody, antibody fragment, aptamer, biomolecule or other chemical structure) that binds to a Target Protein, and wherein the Target Protein is a mediator of disease in a host as described in detail below. Exemplary Target Ligands are provided in FIGS. 1A-8PPPPP.

In one embodiment, the Targeting Ligand binds to an endogenous protein which has been selected for degradation as a means to achieve a therapeutic effect on the host. Illustrative Targeting Ligands include: RXR ligands, DHFR ligands, Hsp90 inhibitors, kinase inhibitors, HDM2 and MDM2 inhibitors, compounds targeting Human BET bromodomain-containing proteins, HDAC inhibitors, ligands of MerTK, ligands of IDH1, ligands of Mcl-1,ligands of SMRCA2, ligands of EGFR, ligands of RAF, ligands of cRAF, human lysine methyltransferase inhibitors, angiogenesis inhibitors, nuclear hormone receptor compounds, immunosuppressive compounds, and compounds targeting the aryl hydrocarbon receptor (AHR), among numerous others. Targeting Ligands also considered to include their pharmaceutically acceptable salts, prodrugs and isotopic derivatives.

In certain aspects, the Targeting Ligand binds to a dehalogenase enzyme in a patient or subject or in a diagnostic assay and is a haloalkane (preferably a $C_1$-$C_{10}$ alkyl group which is substituted with at least one halo group, preferably a halo group at the distal end of the alkyl group (i.e., away from the Linker). In still other embodiments, the Targeting Ligand is a haloalkyl group, wherein said alkyl group generally ranges in size from about 1 or 2 carbons to about 12 carbons in length, often about 2 to 10 carbons in length, often about 3 carbons to about 8 carbons in length, more often about 4 carbons to about 6 carbons in length. The haloalkyl groups are generally linear alkyl groups (although branched-chain alkyl groups may also be used) and are end-capped with at least one halogen group, preferably a single halogen group, often a single chloride group.

Haloalkyl PT, groups for use in the present invention are preferably represented by the chemical structure —$(CH_2)_v$-Halo where v is any integer from 2 to about 12, often about 3 to about 8, more often about 4 to about 6. Halo may be any halogen, but is preferably Cl or Br, more often Cl.

In certain embodiments, the Targeting Ligand is a retinoid X receptor (RXR) agonist or antagonist. Non-limiting examples include retinol, retinoic acid, bexarotene, docosahexenoic acid, compounds disclosed in WO 9929324, the publication by Canan Koch et al. (J. Med. Chem. 1996, 39, 3229-3234) titled "Identification of the First Retinoid X Receptor Homodimer Antagonist", WO 9712853, EP 0947496A1, WO 2016002968, and analogs thereof.

In certain embodiments, the Targeting Ligand is a DHFR agonist or antagonist. Non-limiting examples include folic acid, methotrexate, 8,10-dideazatetrahydrofolate compounds disclosed by Tian et al. (Chem. Biol. Drug Des. 2016, 87, 444-454) titled "Synthesis, Antifolate and Anticancer Activities of N5-Substituted 8,10-Dideazatetrahydrofolate Analogues", compounds prepared by Kaur et al. (Biorg. Med. Chem. Lett. 2016, 26, 1936-1940) titled "Rational Modification of the Lead Molecule: Enhancement in the Anticancer and Dihydrofolate Reductase Inhibitory Activity", WO 2016022890, compounds disclosed by Zhang et al. (Int. J. Antimicrob. Agents 46, 174-182) titled "New Small-Molecule Inhibitors of Dihydrofolate Reductase Inhibit Streptococcus Mutans", modified trimethoprim analogs developed by Singh et al. (J. Med. Chem. 2012, 55, 6381-6390) titled "Mechanism Inspired Development of Rationally Designed Dihydrofolate Reductase Inhibitors as Anticancer Agents", WO20111153310, and analogs thereof.

In certain embodiments, the Targeting Ligand derived from estrogen, an estrogen analog, SERM (selective estrogen receptor modulator), a SERD (selective estrogen receptor degrader), a complete estrogen receptor degrader, or another form of partial or complete estrogen antagonist or agonist. Examples are the partial anti-estrogens raloxifene and tamoxifen and the complete antiestrogen fulvestrant. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703,810, as well as US 2015/0005286, WO 2014/205136, and WO 2014/205138. Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone. Other estrogenic ligands that can be used according to the present invention are described in U.S. Pat. Nos. 4,418,068; 5,478,847; 5,393,763; and 5,457,117, WO2011/156518, U.S. Pat. Nos. 8,455,534 and 8,299,112, 9,078,871; 8,853,423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497, 5,880,137, WO 2012/048058 and WO 2007/087684.

In certain embodiments, the Targeting Ligand is a HSP90 inhibitor identified in Vallee et al. (*J. Med. Chem.* 2011, 54, 7206-7219) titled "Tricyclic Series of Heat Shock Protein 90 (Hsp90) Inhibitors Part I: Discovery of Tricyclic Imidazo[4,5-C]Pyridines as Potent Inhibitors of the Hsp90 Molecular Chaperone", including YKB (N-[4-(3H-imidazo[4,5-C]Pyridin-2-yl)-9H-Fluoren-9-yl]-succinamide), a HSP90 inhibitors (modified) identified in Brough et al. (*J. Med. Chem.* 2008, 51, 196-218) titled "4,5-Diarylisoxazole Hsp90 Chaperone Inhibitors: Potential Therapeutic Agents for the Treatment of Cancer", including compound 2GJ (5-[2,4-dihydroxy-5-(1-methylethyl)phenyl]-n-ethyl-4-[4-(morpholin-4-ylmethyl)phenyl]isoxazole-3-carboxamide), the HSP90 inhibitor geldanamycin ((4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1] (derivatized) or any of its derivatives (e.g. 17-alkylamino-17-desmethoxygeldanamycin ("17-AAG") or 17-(2-dimethylaminoethyl)amino-17-desmethoxygeldanamycin ("17-DMAG")), or a HSP90 inhibitor (modified) identified in Wright et al. (*Chem. Biol.* 2004, 11, 775-785) titled "Structure-Activity Relationships in Purine-Based Inhibitor Binding to Hsp90 Isoforms", including the HSP90 inhibitor PU3. Other non-limiting examples of Hsp90 Targeting Ligands include SNX5422 currently in phase I clinical trials Reddy et al. (*Clin. Lymphoma Myeloma Leuk.* 2013, 13, 385-391) titled "Phase I Trial of the Hsp90 Inhibitor Pf-04929113 (Snx5422) in Adult Patients with Recurrent, Refractory Hematologic Malignancies", or NVP-AUY922 whose anti-cancer activity was assessed by Jensen et al. (*Breast Cancer Research: BCR* 2008, 10, R33-R33) titled "Nvp-Auy922: A Small Molecule Hsp90 Inhibitor with Potent Antitumor Activity in Preclinical Breast Cancer Models".

In certain embodiments, the Targeting Ligand is a kinase inhibitor identified in Millan et al. (*J. Med. Chem.* 2011, 54, 7797-7814) titled "Design and Synthesis of Inhaled P38 Inhibitors for the Treatment of Chronic Obstructive Pulmonary Disease", including the kinase inhibitors Y1W and Y1X, a kinase inhibitor identified in Schenkel et al. (*J. Med. Chem.* 2011, 54, 8440-8450) titled "Discovery of Potent and Highly Selective Thienopyridine Janus Kinase 2 Inhibitors", including the compounds 6TP and OTP, a kinase inhibitor identified in van Eis et al. (*Biorg. Med. Chem. Lett.* 2011, 21, 7367-7372) titled "2,6-Naphthyridines as Potent and Selective Inhibitors of the Novel Protein Kinase C Isozymes", including the kinase inhibitors 07U and YCF identified in Lountos et al. (*J. Struct. Biol.* 2011, 176, 292-301) titled "Structural Characterization of Inhibitor Complexes with Checkpoint Kinase 2 (Chk2), a Drug Target for Cancer Therapy", including the kinase inhibitors XK9 and NXP, afatinib, fostamatinib, gefitinib, lenvatinib, vandetanib, Gleevec, pazopanib, AT-9283, TAE684, nilotanib, NVP-BSK805, crizotinib, JNJ FMS, foretinib, OSI-027, OSI-930, or OSI-906.

In certain embodiments, the Targeting Ligand is a HDM2/MDM2 inhibitor identified in Vassilev et al. (*Science* 2004, 303, 844-848) titled "In Vivo Activation of the P53 Pathway by Small-Molecule Antagonists of Mdm2", and Schneekloth et al. (*Bioorg. Med. Chem. Lett.* 2008, 18, 5904-5908) titled "Targeted Intracellular Protein Degradation Induced by a Small Molecule: En Route to Chemical Proteomics", including the compounds nutlin-3, nutlin-2, and nutlin-1.

In certain embodiments, the Targeting Ligand is a Human BET Bromodomain Targeting Ligand identified in Filippakopoulos et al. (*Nature* 2010, 468, 1067-1073) titled "Selective Inhibition of Bet Bromodomains" such as JQ1; a ligand identified in Nicodeme et al. (*Nature* 2010, 468, 1119-1123) titled "Suppression of Inflammation by a Synthetic Histone Mimic"; Chung et al. (*J. Med. Chem.* 2011, 54, 3827-3838) titled "Discovery and Characterization of Small Molecule Inhibitors of the Bet Family Bromodomains"; a compound disclosed in Hewings et al. (*J. Med. Chem.* 2011, 54, 6761-6770) titled "3,5-Dimethylisoxazoles Act as Acetyl-Lysine-Mimetic Bromodomain Ligands"; a ligand identified in Dawson et al. (*Nature* 2011, 478, 529-533) titled "Inhibition of Bet Recruitment to Chromatin as an Effective Treatment for MLL-Fusion Leukaemia"; or a ligand identified in the following patent applications US 2015/0256700, US 2015/0148342, WO 2015/074064, WO 2015/067770, WO 2015/022332, WO 2015/015318, and WO 2015/011084.

In certain embodiments, the Targeting Ligand is a HDAC Targeting Ligand identified in Finnin et al. (*Nature* 1999, 401, 188-193) titled "Structures of a Histone Deacetylase Homologue Bound to the Tsa and Saha Inhibitors", or a ligand identified as Formula (I) in PCT WO0222577.

In certain embodiments, the Targeting Ligand is a Human Lysine Methyltransferase ligand identified in Chang et al.

(*Nat Struct Mol Biol* 2009, 16, 312-317) titled "Structural Basis for G9a-Like Protein Lysine Methyltransferase Inhibition by Bix-01294", a ligand identified in Liu et al. (*J Med Chem* 2009, 52, 7950-7953) titled "Discovery of a 2,4-Diamino-7-Aminoalkoxyquinazoline as a Potent and Selective Inhibitor of Histone Lysine Methyltransferase G9a", azacitidine, decitabine, or an analog thereof.

In certain embodiments, the Targeting Ligand is an angiogenesis inhibitor. Non-limiting examples of angiogenesis inhibitors include: GA-1, estradiol, testosterone, ovalicin, fumagillin, and analogs thereof.

In certain embodiments, the Targeting Ligand is an immunosuppressive compound. Non-limiting examples of immunosuppressive compounds include: AP21998, hydrocortisone, prednisone, prednisolone, methylprednisolone, beclometasone dipropionate, methotrexate, ciclosporin, tacrolimus, actinomycin, and analogues thereof.

In certain embodiments, the Targeting Ligand is an Aryl Hydrocarbon Receptor (AHR) ligand. Non-limiting examples of AHR ligands include: apigenin, SR1, LGC006, and analogues thereof.

In certain embodiments, the Targeting Ligand is a MerTK or Mer Targeting ligand. Non-limiting examples of MerTK Targeting Ligands are included in WO2013/177168 and WO2014/085225, both titled "Pyrimidine Compounds for the Treatment of Cancer" filed by Wang, et al.

In certain embodiments, the Targeting Ligand is an EGFR ligand. In certain embodiments the Targeting Ligand is an EGRF ligand selected from Afatinib, Dacomitinib, Neratinib, Poziotinib, and Canertinib, or derivatives thereof.

In certain embodiments, the Targeting Ligand is a FLT3 Ligand. In certain embodiments, the Targeting Ligand is a FLT3 ligand selected from Tandutinib, Lestaurtinib, Sorafenib, Midostaurin, Quizartinib, and Crenolanib.

In certain embodiments, the Targeting Ligand is a RAF inhibitor. In certain embodiments the Targeting Ligand is a RAF inhibitor selected from Dabrafenib, Regorafenib, and Vemurafenib. In certain embodiments the Targeting Ligand is a cRAF inhibitor.

In some embodiments, the Targeting Ligand is an Ubc9 SUMO E2 ligase 5F6D Targeting Ligand including but not limited to those described in "Insights Into the Allosteric Inhibition of the SUMO E2 Enzyme Ubc9." by Hewitt, W. M., et. al. (2016) Angew. Chem. Int. Ed. Engl. 55: 5703-5707 In another embodiment, the Targeting Ligand is a Tank1 Targeting Ligand including but not limited to those described in "Structure of human tankyrase 1 in complex with small-molecule inhibitors PJ34 and XAV939." Kirby, C. A., Cheung, A., Fazal, A., Shultz, M. D., Stams, T, (2012) Acta Crystallogr., Sect. F 68: 115-118; and "Structure-Efficiency Relationship of [1,2,4]Triazol-3-ylamines as Novel Nicotinamide Isosteres that Inhibit Tankyrases." Shultz, M. D., et al. (2013) J. Med. Chem. 56: 7049-7059.

In another embodiment, the Targeting Ligand is a SH2 domain of pp60 Src Targeting Ligand including but not limited to those described in "Requirements for Specific Binding of Low Affinity Inhibitor Fragments to the SH2 Domain of pp60Src Are Identical to Those for High Affinity Binding of Full Length Inhibitors," Gudrun Lange, et al., J. Med. Chem. 2003, 46, 5184-5195.

In another embodiment, the Targeting Ligand is a Sec7 domain Targeting Ligand including but not limited to those described in "The Lysosomal Protein Saposin B Binds Chloroquine," Huta, B. P., et al., (2016) Chemmedchem 11: 277.

In another embodiment, the Targeting Ligand is a Saposin-B Targeting Ligand including but not limited to those described in "The structure of cytomegalovirus immune modulator UL 141 highlights structural Ig-fold versatility for receptor binding" I. Nemcovicova and D. M. Zajonc Acta Cryst. (2014). D70, 851-862.

In another embodiment, the Targeting Ligand is a Protein S100-A7 2OWS Targeting Ligand including but not limited to those described in "2WOS STRUCTURE OF HUMAN S100A7 IN COMPLEX WITH 2,6 ANS" DOI: 10.2210/pdb2wos/pdb; and "Identification and Characterization of Binding Sites on S100A7, a Participant in Cancer and Inflammation Pathways." Leon, R., Murray, et al., (2009) Biochemistry 48: 10591-10600.

In another embodiment, the Targeting Ligand is a Phospholipase A2 Targeting Ligand including but not limited to those described in "Structure-based design of the first potent and selective inhibitor of human non-pancreatic secretory phospholipase A2" Schevitz, R. W., et al., *Nat. Struct. Biol.* 1995, 2, 458-465.

In another embodiment, the Targeting Ligand is a PHIP Targeting Ligand including but not limited to those described in "A Poised Fragment Library Enables Rapid Synthetic Expansion Yielding the First Reported Inhibitors of PHIP(2), an Atypical Bromodomain" Krojer, T.; et al. Chem. Sci. 2016, 7, 2322-2330.

In another embodiment, the Targeting Ligand is a PDZ Targeting Ligand including but not limited to those described in "Discovery of Low-Molecular-Weight Ligands for the AF6 PDZ Domain" Mangesh Joshi, et al. Angew. Chem. Int. Ed. 2006, 45, 3790-3795.

In another embodiment, the Targeting Ligand is a PARP15 Targeting Ligand including but not limited to those described in "Structural Basis for Lack of ADP-ribosyltransferase Activity in Poly(ADP-ribose) Polymerase-13/Zinc Finger Antiviral Protein." Karlberg, T., et al., (2015) J. Biol. Chem. 290: 7336-7344.

In another embodiment, the Targeting Ligand is a PARP14 Targeting Ligand including but not limited to those described in "Discovery of Ligands for ADP-Ribosyltransferases via Docking-Based Virtual Screening." Andersson, C. D., et al., (2012) J. Med. Chem. 55: 7706-7718; "Family-wide chemical profiling and structural analysis of PARP and tankyrase inhibitors." Wahlberg, E., et al. (2012) Nat. Biotechnol. 30: 283-288.; "Discovery of Ligands for ADP-Ribosyltransferases via Docking-Based Virtual Screening." Andersson, C. D., et al. (2012) J. Med. Chem. 55: 7706-7718.

In another embodiment, the Targeting Ligand is a MTH1 Targeting Ligand including but not limited to those described in "MTH1 inhibition eradicates cancer by preventing sanitation of the dNTP pool" Helge Gad, et. al. Nature, 2014, 508, 215-221.

In another embodiment, the Targeting Ligand is a mPGES-1 Targeting Ligand including but not limited to those described in "Crystal Structures of mPGES-1 Inhibitor Complexes Form a Basis for the Rational Design of Potent Analgesic and Anti-Inflammatory Therapeutics." Luz, J. G., et al., (2015) J. Med. Chem. 58: 4727-4737.

In another embodiment, the Targeting Ligand is a FLAP-5-lipoxygenase-activating protein Targeting Ligand including but not limited to those described in "Crystal structure of inhibitor-bound human 5-lipoxygenase-activating protein," Ferguson, A. D., McKeever, B. M., Xu, S., Wisniewski, D., Miller, D. K., Yamin, T. T., Spencer, R. H., Chu, L., Ujjainwalla, F., Cunningham, B. R., Evans, J. F., Becker, J. W. (2007) Science 317: 510-512.

In another embodiment, the Targeting Ligand is a FA Binding Protein Targeting Ligand including but not limited to those described in "A Real-World Perspective on Molecular Design." Kuhn, B.; et al. J. Med. Chem. 2016, 59, 4087-4102.

In another embodiment, the Targeting Ligand is a BCL2 Targeting Ligand including but not limited to those described in "ABT-199, a potent and selective BCL-2 inhibitor, achieves antitumor activity while sparing platelets." Souers, A. J., et al. (2013) NAT. MED. (N.Y.) 19: 202-208.

In another embodiment, the Targeting Ligand is a NF2L2 Targeting Ligand.

In another embodiment, the Targeting Ligand is a CTNNB1 Targeting Ligand.

In another embodiment, the Targeting Ligand is a CBLB Targeting Ligand.

In another embodiment, the Targeting Ligand is a BCL6 Targeting Ligand.

In another embodiment, the Targeting Ligand is a RASK Targeting Ligand.

In another embodiment, the Targeting Ligand is a TNIK Targeting Ligand.

In another embodiment, the Targeting Ligand is a MEN1 Targeting Ligand.

In another embodiment, the Targeting Ligand is a PI3Ka Targeting Ligand.

In another embodiment, the Targeting Ligand is a IDO1 Targeting Ligand.

In another embodiment, the Targeting Ligand is a MCL1 Targeting Ligand.

In another embodiment, the Targeting Ligand is a PTPN2 Targeting Ligand.

In another embodiment, the Targeting Ligand is a HER2 Targeting Ligand.

In another embodiment, the Targeting Ligand is an EGFR Targeting Ligand. In one embodiment the Targeting Ligand is selected from erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer). The linker can be placed on these Targeting Ligands in any location that does not interfere with the Ligands binding to EGFR. Non-limiting examples of Linker binding locations are provided in the below tables. In one embodiment, the EGFR Targeting Ligand binds the L858R mutant of EGFR. In another embodiment, the EGFR Targeting Ligand binds the T790M mutant of EGFR. In another embodiment, the EGFR Targeting Ligand binds the C797G or C797S mutant of EGFR. In one embodiment, the EGFR Targeting Ligand is selected from erlotinib, gefitinib, afatinib, neratinib, and dacomitinib and binds the L858R mutant of EGFR. In another embodiment, the EGFR Targeting Ligand is selected from osimertinib, rociletinib, olmutinib, naquotinib, nazartinib, PF-06747775, Icotinib, Neratinib, Avitinib, Tarloxotinib, PF-0645998, Tesevatinib, Transtinib, WZ-3146, WZ8040, and CNX-2006 and binds the T790M mutant of EGFR. In another embodiment, the EGFR Targeting Ligand is EAI045 and binds the C797G or C797S mutant of EGFR.

In one embodiment, the protein target and Targeting Ligand pair are chosen by screening a library of ligands. Such a screening is exemplified in "Kinase Inhibitor Profiling Reveals Unexpected Opportunities to Inhibit Disease-Associated Mutant Kinases" by Duong-Ly et al.; Cell Reports 14, 772-781 Feb. 2, 2016.

In one embodiment, the protein target and Targeting Ligand pair are discovered by screening promiscuous kinase binding ligands for context-specific degradation. Non-limiting examples of targeting ligands are shown below and are found in "Optimized Chemical Proteomics Assay for Kinase Inhibitor Profiling" Guillaume Medard, Fiona Pachl, Benjamin Ruprecht, Susan Klaeger, Stephanie Heinzlmeir, Dominic Helm, Huichao Qiao, Xin Ku, Mathias Wilhelm, Thomas Kuehne, Zhixiang Wu, Antje Dittmann, Carsten Hopf, Karl Kramer, and Bernhard Kuster J. Proteome Res., 2015, 14(3), pp 1574-1586:

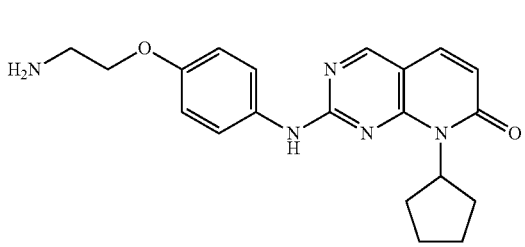

VI16743

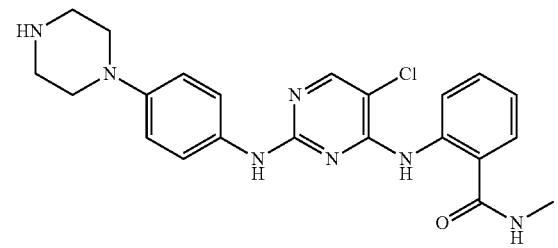

CTx-0294885

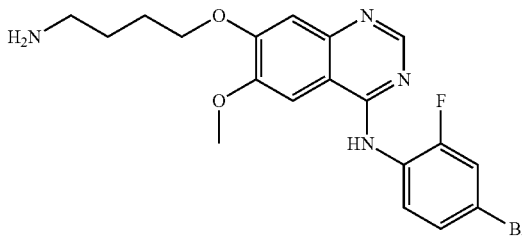

Vandetanib

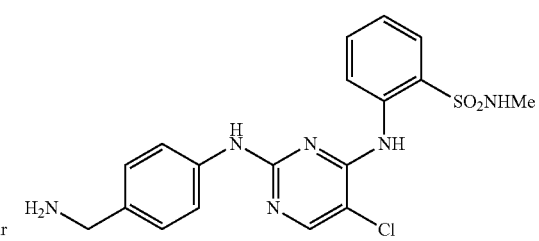

CTx-related

-continued
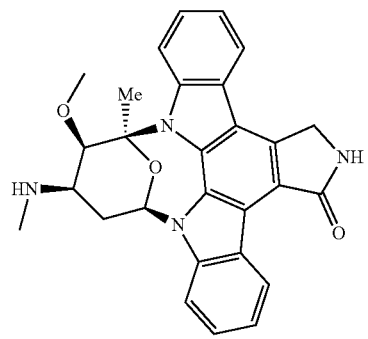
Staurosporine
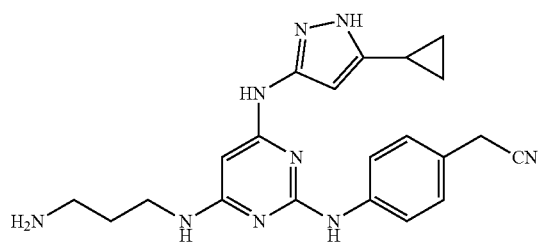
DOI: 10.1021/acschembio.5b00847
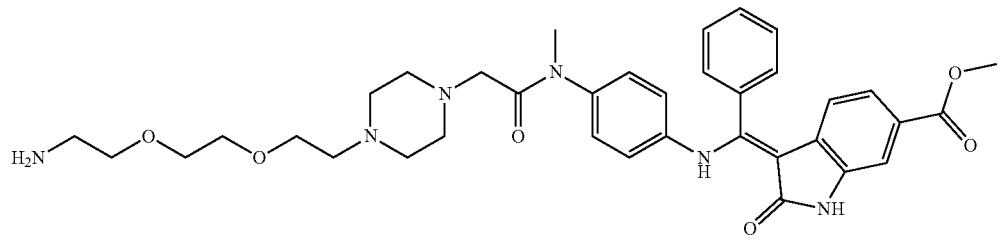
Nintedanib
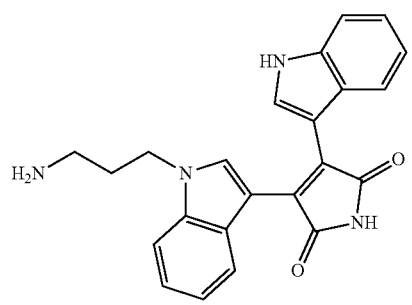
bisindolylmaleimide III
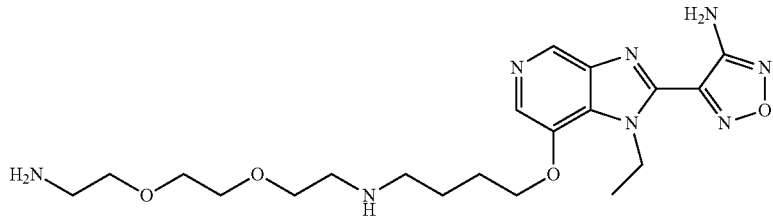
AKT probe
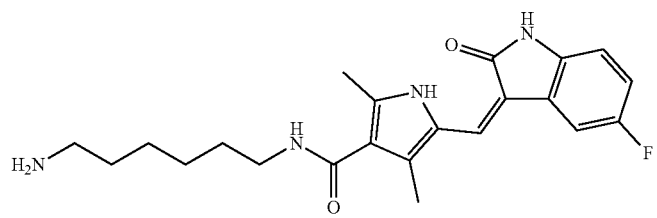
Sunitinib
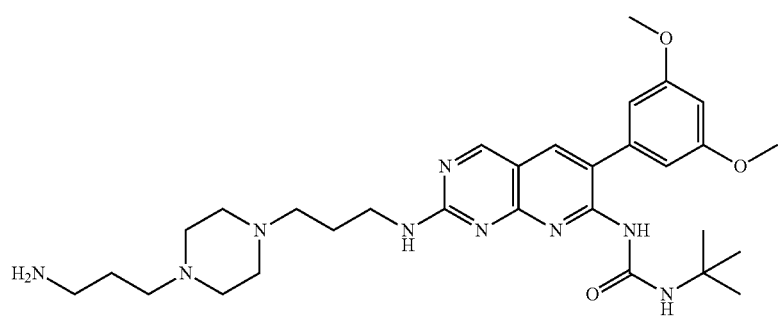
PD173074

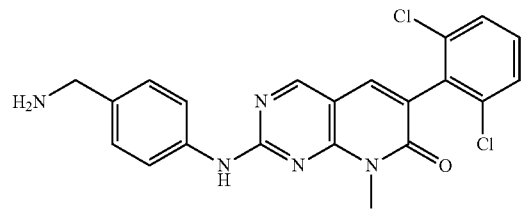
PD173955
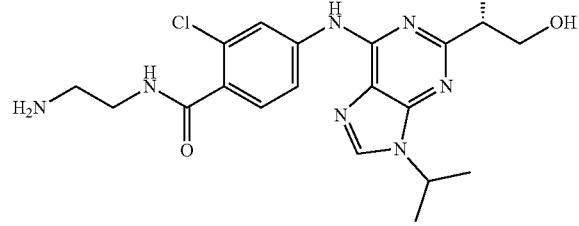
Purvalanol B
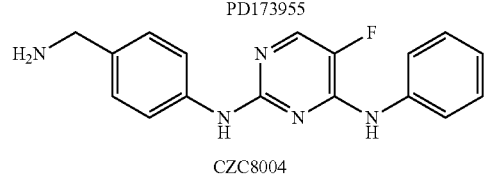
CZC8004
These ligands can be attached to linkers as shown below:
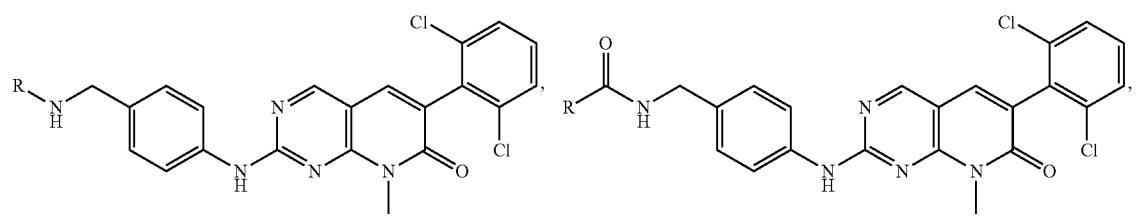
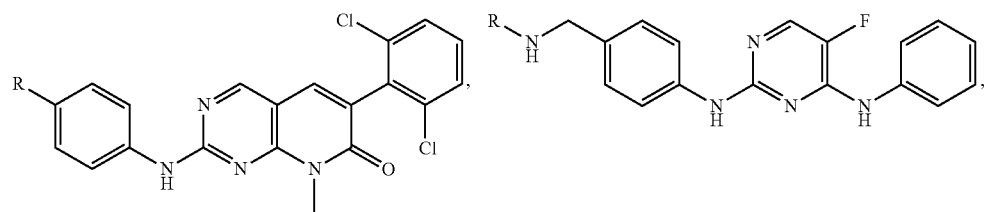
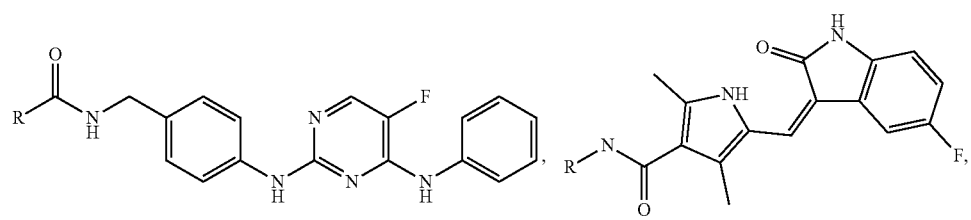
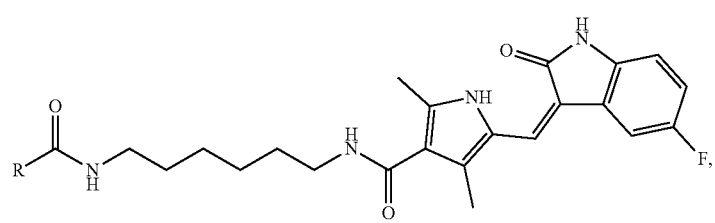

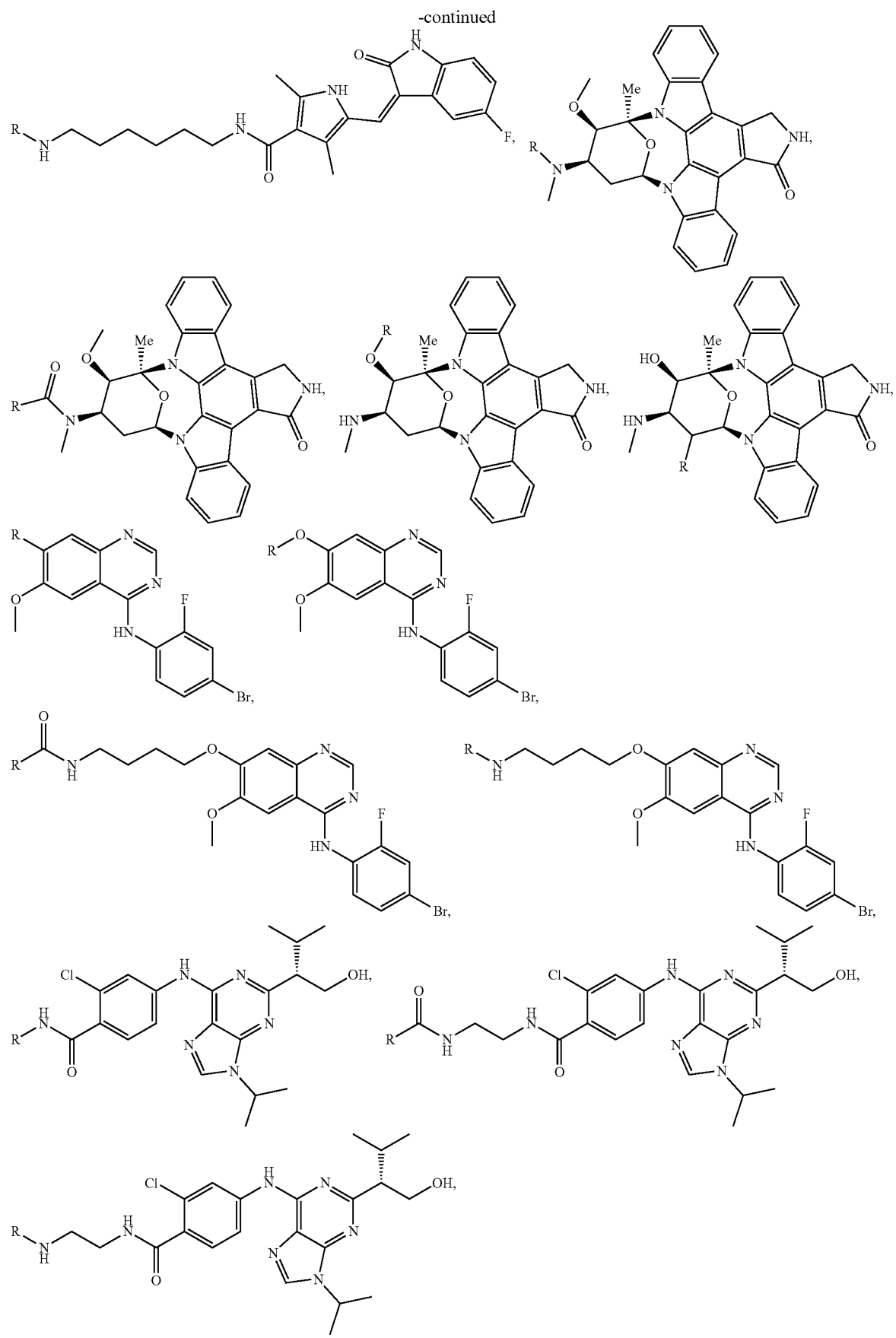

-continued
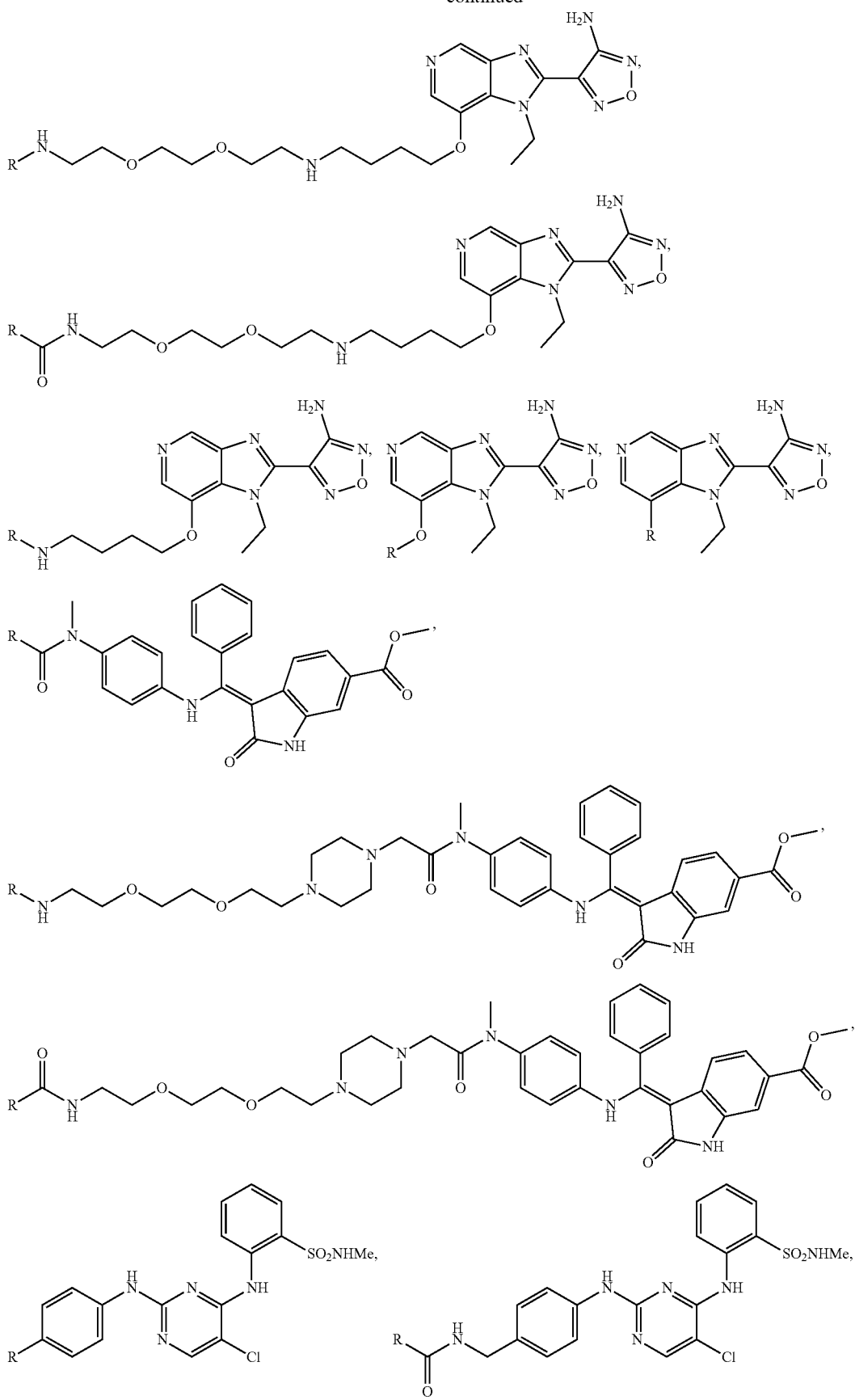

437
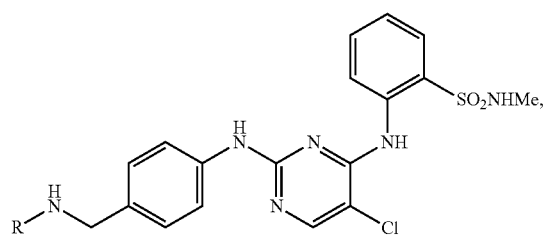
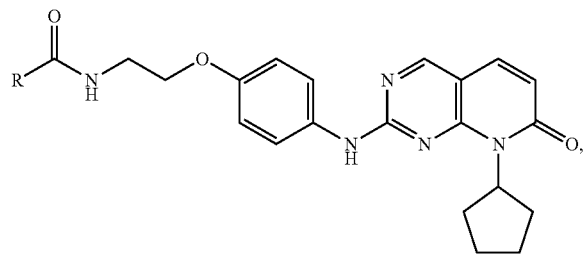
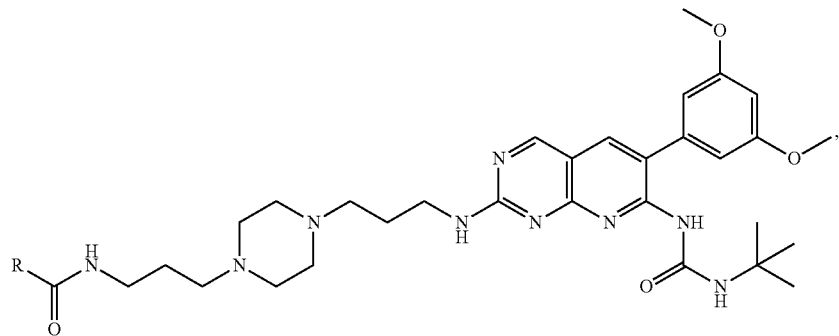
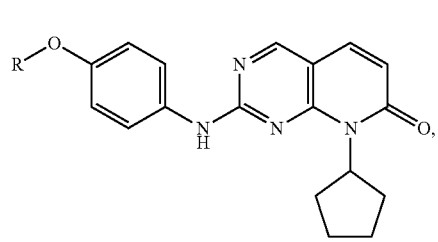
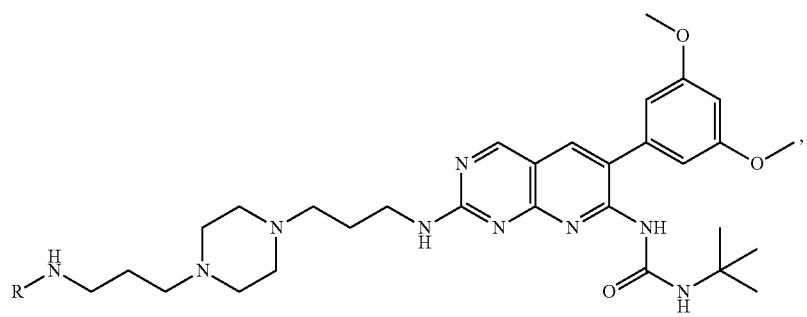
438
-continued
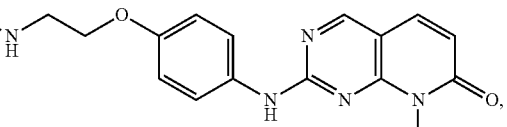
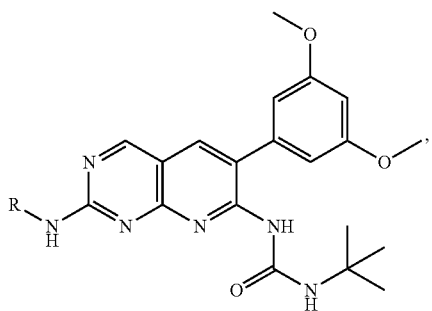
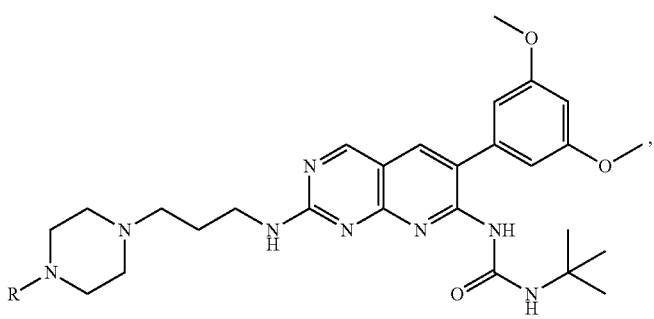

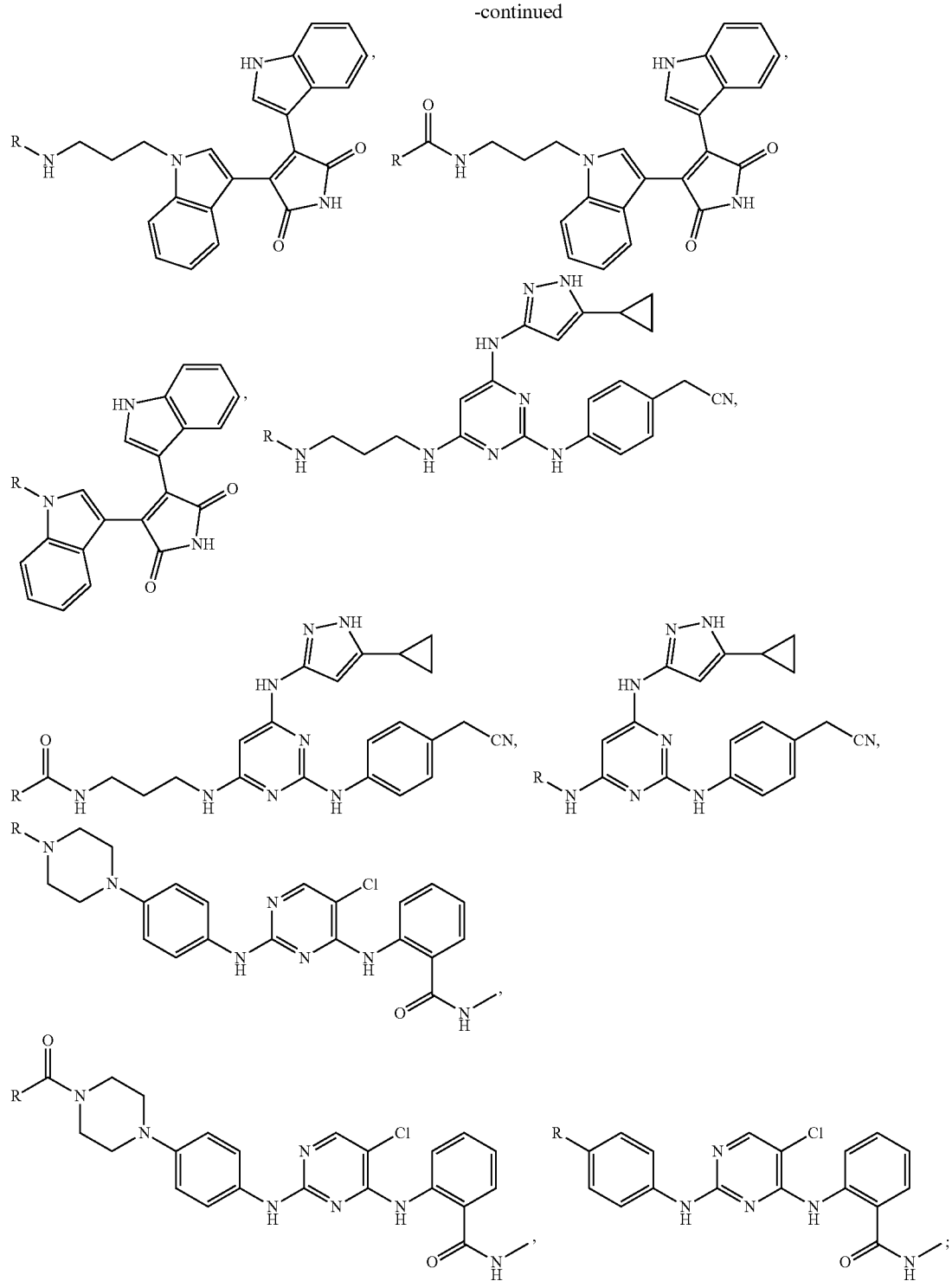

wherein:
R is the point at which the Linker is attached.

In an alternative embodiment, the Targeting Ligand is selected from a DOTL1-Ligand, a CBP Ligand, an ERK1 Ligand, an ERK2 Ligand, a JAK2 Ligand, an FGFR3 Ligand, an FGFR4 Ligand, a WDR5 Ligand, a PAK4 Ligand, a BRAF Ligand, a KRAS Ligand, a BTK Ligand, and a SHOC2 Ligand. In another alternative embodiment, the Targeting Ligand is selected from a UCHL1 Ligan, a USP 1 Ligand, a USP2 Ligand, a USP4 Ligand, a USP6 Ligand, a USP7 Ligand, a USP8 Ligand, a USP9x Ligand, a USP10 Ligand, a USP11 Ligand, a USP13 Ligand, a USP14 Ligand, a USP17 Ligand, and a USP28 Ligand.

According to the present invention, the Targeting Ligand can be covalently bound to the Linker in any manner that achieves the desired results of the Degrader for therapeutic use. In certain non-limiting embodiments, the Targeting Ligand is bound to the Linker with a functional group that does not adversely affect the binding of the Ligand to the Target Protein. The attachment points below are exemplary in nature and one of ordinary skill in the art would be able to determine different appropriate attachment points.

The non-limiting compounds described below exemplify some of the members of these types of Targeting Ligands. In the Tables below, R is the point at which the Linker is attached to the Targeting Ligand.

In certain embodiments, the Targeting Ligand is a compound of Formula TL-I:

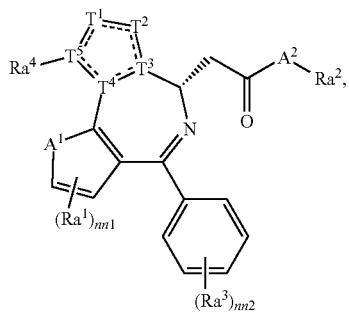

(TL-I)

or a pharmaceutically acceptable salt thereof, wherein:

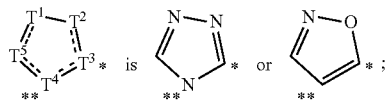

$A^1$ is S or C=C;
$A^2$ is $NRa^5$ or O;
nn1 is 0, 1, or 2;
each $Ra^1$ is independently $C_1$-$C_3$ alkyl, $(CH_2)_{0-3}$—CN, $(CH_2)_{0-3}$-halogen, $(CH_2)_{0-3}$—OH, $(CH_2)_{0-3}$—$C_1$-$C_3$ alkoxy, or R;
$Ra^2$ is H, $C_1$-$C_6$ alkyl, $(CH_2)_{0-3}$-heterocyclyl, $(CH_2)_{0-3}$-phenyl, or R, wherein the heterocyclyl comprises one saturated 5- or 6-membered ring and 1-2 heteroatoms selected from N, O, and S and is optionally substituted with $C_1$-$C_3$ alkyl and wherein the phenyl is optionally substituted with $C_1$-$C_3$ alkyl, CN, halogen, OH, $C_1$-$C_3$ alkoxy;
nn2 is 0, 1, 2, or 3;
each $Ra^3$ is independently $C_1$-$C_3$ alkyl, $(CH_2)_{0-3}$—CN, $(CH_2)_{0-3}$-halogen, or R;
$Ra^4$ is $C_1$-$C_3$ alkyl;
$Ra^5$ is H or $C_1$-$C_3$ alkyl; and
R is the point at which the Linker is attached.
wherein the compound of Formula TL-I is substituted with only one R.

In certain embodiments, the Targeting Ligand is a compound of Formula TL-VIII or Formula TL-IX:

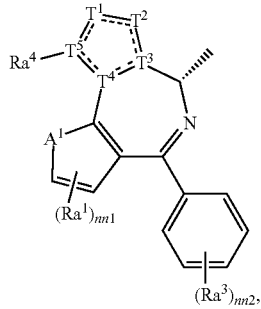

(TL-VIII)

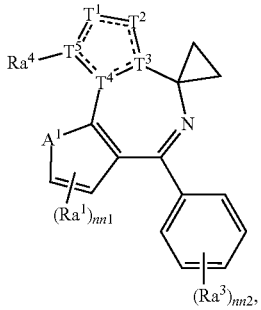

(TL-IX)

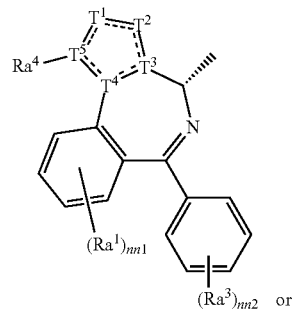

(TL-X)

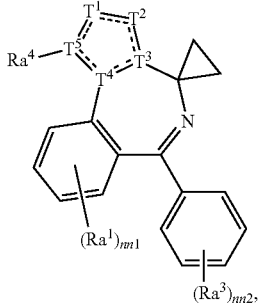

(TL-XI)

wherein the compound of Formula TL-VIII or TL-IX is substituted with only one R.

In certain embodiments,

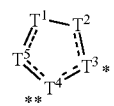

is

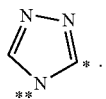

In certain embodiments,

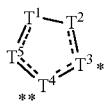

is

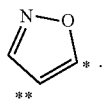

In certain embodiments, $A^1$ is S.

In certain embodiments, $A^1$ is C=C.

In certain embodiments, $A^2$ is $NRa^5$. In further embodiments, $Ra^5$ is H. In other embodiments, $Ra^5$ is $C_1$-$C_3$ alkyl (e.g., methyl, ethyl, propyl, or i-propyl). In further embodiments, $Ra^5$ is methyl.

In certain embodiments, $A^2$ is O.

In certain embodiments, nn1 is 0.

In certain embodiments, nn1 is 1.

In certain embodiments, nn1 is 2.

In certain embodiments, at least one $Ra^1$ is $C_1$-$C_3$ alkyl (e.g., methyl, ethyl, propyl, or i-propyl). In further embodiments, at least one $Ra^1$ is methyl. In further embodiments, two $Ra^1$ are methyl.

In certain embodiments, at least one $Ra^1$ is CN, $(CH_2)$—CN, $(CH_2)_2$—CN, or $(CH_2)_3$—CN. In further embodiments, at least one $Ra^1$ is $(CH_2)$—CN.

In certain embodiments, at least one $Ra^1$ is halogen (e.g., F, Cl, or Br), $(CH_2)$-halogen, $(CH_2)_2$-halogen, or $(CH_2)_3$-halogen. In further embodiments, at least one $Ra^1$ is Cl, $(CH_2)$—Cl, $(CH_2)_2$—Cl, or $(CH_2)_3$—Cl.

In certain embodiments, at least one $Ra^1$ is OH, $(CH_2)$—OH, $(CH_2)_2$—OH, or $(CH_2)_3$—OH.

In certain embodiments, at least one $Ra^1$ is $C_1$-$C_3$ alkoxy (e.g., methoxy, ethoxy, or propoxy), $(CH_2)$—$C_1$-$C_3$ alkoxy, $(CH_2)_2$—$C_1$-$C_3$ alkoxy, or $(CH_2)_3$—$C_1$-$C_3$ alkoxy. In certain embodiments, at least one $Ra^1$ is methoxy.

In further embodiments, $Ra^5$ is H. In other embodiments, $Ra^5$ is $C_1$-$C_3$ alkyl (e.g., methyl, ethyl, propyl, or i-propyl).

In further embodiments, $Ra^5$ is H. In other embodiments, $Ra^5$ is $C_1$-$C_3$ alkyl (e.g., methyl, ethyl, propyl, or i-propyl). In other embodiments, $Ra^5$ is methyl.

In certain embodiments, one $Ra^1$ is R.

In certain embodiments, $Ra^2$ is H.

In certain embodiments, $Ra^2$ is straight-chain $C_1$-$C_6$ or branched $C_3$-$C_6$ alkyl (e.g., methyl, ethyl, propyl, i-propyl, butyl, i-butyl, t-butyl, pentyl, or hexyl). In further embodiments, $Ra^2$ is methyl, ethyl, or t-butyl.

In certain embodiments, $Ra^2$ is heterocyclyl, $(CH_2)$-heterocyclyl, $(CH_2)_2$-heterocyclyl, or $(CH_2)_3$-heterocyclyl. In further embodiments, $Ra^2$ is $(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.

In certain embodiments, the heterocyclyl is substituted with $C_1$-$C_3$ alkyl (e.g., methyl, ethyl, propyl, or i-propyl).

In certain embodiments, $Ra^2$ is phenyl, $(CH_2)$-phenyl, $(CH_2)_2$-phenyl, or $(CH_2)_3$-phenyl. In further embodiments, $Ra^2$ is phenyl.

In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy).

In certain embodiments, $Ra^2$ is R.

In certain embodiments, nn2 is 0.

In certain embodiments, nn2 is 1.

In certain embodiments, nn2 is 2.

In certain embodiments, nn2 is 3.

In certain embodiments, at least one $Ra^3$ is $C_1$-$C_3$ alkyl (e.g., methyl, ethyl, propyl, or i-propyl). In further embodiments, at least one $Ra^3$ is methyl.

In certain embodiments, at least one $Ra^3$ is CN, $(CH_2)$—CN, $(CH_2)_2$—CN, or $(CH_2)_3$—CN. In further embodiments, at least one $Ra^3$ is CN.

In certain embodiments, at least one $Ra^3$ is halogen (e.g., F, Cl, or Br), $(CH_2)$-halogen, $(CH_2)_2$-halogen, or $(CH_2)_3$-halogen. In further embodiments, at least one $Ra^3$ is Cl, $(CH_2)$—Cl, $(CH_2)_2$—Cl, or $(CH_2)_3$—Cl. In further embodiments, at least one $Ra^3$ is $C_1$.

In certain embodiments, one $Ra^3$ is R.

In further embodiments, $Ra^5$ is H. In other embodiments, $Ra^5$ is $C_1$-$C_3$ alkyl (e.g., methyl, ethyl, propyl, or i-propyl).

In certain embodiments, $Ra^4$ is $C_1$-$C_3$ alkyl (e.g., methyl, ethyl, propyl, or i-propyl). In further embodiments, $Ra^4$ is methyl.

In certain embodiments, $Ra^5$ is H.

In certain embodiments, $Ra^5$ is $C_1$-$C_3$ alkyl (e.g., methyl, ethyl, propyl, or i-propyl). In further embodiments, $Ra^5$ is methyl.

In certain embodiments,

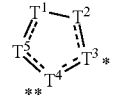

is

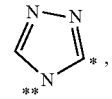

and $A^1$ is S.

In certain embodiments,

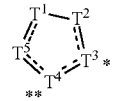

is

and A¹ is C=C.

In certain embodiments,

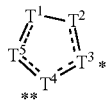

is

and A¹ is C=C.

In certain embodiments, A² is NH, and $Ra^2$ is $(CH_2)_{0-3}$-heterocyclyl. In further embodiments, $Ra^2$ is $(CH_2)_3$-heterocyclyl.

In certain embodiments, A² is NH, and $Ra^2$ is $(CH_2)_{0-3}$-phenyl. In further embodiments, $Ra^2$ is phenyl. In further embodiments, the phenyl is substituted with OH.

In certain embodiments, A² is NH, and $Ra^2$ is R.

In certain embodiments, A² is NH, and $Ra^2$ is H or $C_1$-$C_6$ alkyl. In further embodiments, $Ra^2$ is $C_1$-$C_4$ alkyl.

In certain embodiments, A² is O, and $Ra^2$ is H or $C_1$-$C_6$ alkyl. In further embodiments, $Ra^2$ is $C_1$-$C_4$ alkyl.

In one embodiment, the Targeting Ligand binds to ASH1L. For example, the ASH1L small molecule inhibitor may be as described in WO2017/197240, the entirety of which is incorporated herein by reference. In one embodiment, the Targeting Ligand is

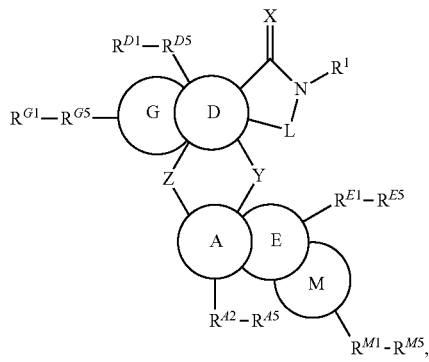

wherein all variables are as defined in WO2017/197240. As described in the '240 application, in some embodiments, any of formulas provided therein may be converted to bifunctional compounds composed of ASH1L inhibitor and an E3 ubiquitin ligase ligand connected with a linker, which function to bind ASH1L and recruit an E ubiquitin ligase (Cereblon, VHL ligase, etc.) complex to ubiquitinate and induce proteasome-mediated degradation of ASH1L. In the present invention, the linker is a Linker as defined herein covalently bound to a Degron as described herein.

In an alternative embodiment, the Targeting Ligand is a deubiquitylating enzyme (DUB) inhibitor as described in WO2018/065768, WO2018/060742, WO2018/060691, WO2018/060689, WO2017/163078, WO2017/158388, WO2017/158381, WO2017/141036, WO2018/103614, WO2017/093718, WO2017/009650, WO2016/156816, or WO2016/046530.

In an alternative embodiment, any of the Targeting Ligands as described herein may be optionally substituted with one or more, for example 1, 2, 3, 4, or 5, groups selected from $R^{101}$ VIII. Methods of Treatment The compounds of Formula I, Formula II, Formula III, Formula IV, Formula V, Formula VI, Formula VII, Formula VIII, Formula IX, Formula X, Formula XI, or Formula XII can be used in an effective amount to treat a host, including a human, in need thereof, optionally in a pharmaceutically acceptable carrier to treat any of the disorders described herein.

The terms "treat", "treating", and "treatment", etc., as used herein, refer to any action providing a benefit to a patient for which the present compounds may be administered, including the treatment of any disease state or condition which is modulated through the protein to which the present compounds bind. Illustrative non-limiting disease states or conditions, including cancer, which may be treated using compounds according to the present invention are set forth hereinabove.

The Degraders of Formula I, Formula II, Formula III, Formula IV, Formula IX, Formula X, Formula XI, and Formula XII and compositions as described herein can be used to degrade a Target Protein which is a mediator of the disorder affecting the patient, such as a human. The control of protein level afforded by the Formula I, Formula II, Formula III, Formula IV, Formula IX, Formula X, and Formula XI Degraders of the present invention provides treatment of a disease state or condition, which is modulated through the Target Protein by lowering the level of that protein in the cell, e.g., cell of a patient. In certain embodiments, the method comprises administering an effective amount of the compound as described herein, optionally including a pharmaceutically acceptable excipient, carrier, adjuvant, i.e., a pharmaceutically acceptable composition, optionally in combination with another bioactive agent or combination of agents.

The term "disease state or condition" when used in connection with a Formula I, Formula II, Formula III, Formula IV, Formula IX, Formula X, or Formula XI compound is meant to refer to any disease state or condition wherein protein dysregulation (i.e., the amount of protein expressed in a patient is elevated) occurs via a Target Protein and where degradation of such protein in a patient may provide beneficial therapy or relief of symptoms to a patient in need thereof. In certain instances, the disease state or condition may be cured. The compounds of Formula I, Formula II, Formula III, Formula IV, Formula IX, Formula X, and Formula XI are for example useful as therapeutic agents when administered in an effective amount to a host, including a human, to treat a myelo- or lymphoproliferative disorder such as B- or T-cell lymphomas, multiple myeloma, Waldenstrom's macroglobulinemia, Wiskott-Aldrich syndrome, or a post-transplant lymphoproliferative disorder; an immune disorder, including autoimmune disorders such as Addison disease, Celiac disease, dermatomyositis, Graves disease, thyroiditis, multiple sclerosis, pernicious anemia, reactive arthritis, lupus, or type I diabetes; a disease of cardiologic malfunction, including hypercholesterolemia; an infectious disease, including viral and/or bacterial infections; an inflammatory condition, including asthma, chronic peptic ulcers, tuberculosis, rheumatoid arthritis, periodontitis, ulcerative colitis, Crohn's disease, or hepatitis.

The term "disease state or condition" when used in connection with a Formula V, Formula VI, Formula VII, Formula VIII, or Formula XII compound for example, refers to any therapeutic indication which can be treated by decreasing the activity of cereblon or a cereblon-containing E3 Ligase, including but not limited to uses known for the cereblon binders thalidomide, pomalidomide or lenalidomide. Nonlimiting examples of uses for cereblon binders are multiple myeloma, a hematological disorder such as myelodysplastic syndrome, cancer, tumor, abnormal cellular proliferation, HIV/AIDS, HBV, HCV, hepatitis, Crohn's disease, sarcoidosis, graft-versus-host disease, rheumatoid arthritis, Behcet's disease, tuberculosis, and myelofibrosis. Other indications include a myelo- or lymphoproliferative disorder such as B- or T-cell lymphomas, Waldenstrom's macroglobulinemia, Wiskott-Aldrich syndrome, or a post-transplant lymphoproliferative disorder; an immune disorder, including autoimmune disorders such as Addison disease, Celiac disease, dermatomyositis, Graves disease, thyroiditis, multiple sclerosis, pernicious anemia, arthritis, and in particular rheumatoid arthritis, lupus, or type I diabetes; a disease of cardiologic malfunction, including hypercholesterolemia; an infectious disease, including viral and/or bacterial infection, as described generally herein; an inflammatory condition, including asthma, chronic peptic ulcers, tuberculosis, rheumatoid arthritis, periodontitis and ulcerative colitis.

In certain embodiments, the present invention provides for administering a compound of Formula I, Formula II, Formula III, Formula IV, Formula V, Formula VI, Formula VII, Formula VIII, Formula IX, Formula X, Formula XI, or Formula XII to a patient, for example, a human, having an infectious disease, wherein the therapy targets a protein of the infectious agent, optionally in combination with another bioactive agent. The disease state or condition may be a disease caused by a microbial agent or other exogenous agent such as a virus (as non-limiting examples, HIV, HBV, HCV, HSV, HPV, RSV, CMV, Ebola, Flavivirus, Pestivirus, Rotavirus, Influenza, Coronavirus, EBV, viral pneumonia, drug-resistant viruses, Bird flu, RNA virus, DNA virus, adenovirus, poxvirus, Picornavirus, Togavirus, Orthomyxovirus, Retrovirus or Hepadnovirus), bacteria (Gram-negative, Gram-positive, fungus, protozoa, helminth, worms, prion, parasite, or other microbe or may be a disease state, which is caused by overexpression of a protein, which leads to a disease state and/or condition.

In certain embodiments, the condition treated with a compound of the present invention is a disorder related to abnormal cellular proliferation. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis.

Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver.

An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells.

Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease 1 (PKD1) or 2 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis *Coli*, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alstrom syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome # arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dube syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia-familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysylhydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alstrom syndrome), Vrolik disease, Waardenburg syndrome, Warburg Sjo Fledelius Syndrome, Weissenbacher-Zweymuller syndrome, Wolf-Hirschhorn syndrome, Wolff Periodic disease, Weissenbacher-Zweymfiller syndrome and Xeroderma pigmentosum, among others.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In one embodiment the cancer is NUT midline cardinioma.

In one embodiment the cancer is adenoid cystic carcinoma.

The term "bioactive agent" is used to describe an agent, other than a compound according to the present invention, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

IX. Combination Therapy

The compounds of Formula I, Formula II, Formula III, Formula IV, Formula V, Formula VI, Formula VII, Formula VIII, Formula IX, Formula X, Formula XI, and Formula XII can be used in an effective amount alone or in combination to treat a host such as a human with a disorder as described herein.

The disclosed compounds described herein can be used in an effective amount alone or in combination with another compound of the present invention or another bioactive agent to treat a host such as a human with a disorder as described herein.

The term "bioactive agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, the compound of the present invention and the bioactive agent are administered to a host in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb).

CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors, include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In yet another embodiment, one of the active compounds described herein can be administered in an effective amount for the treatment of abnormal tissue of the female reproductive system such as breast, ovarian, endometrial, or uterine cancer, in combination or alternation with an effective amount of an estrogen inhibitor including but not limited to a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703, 810, as well as US 2015/0005286, WO 2014/205136, and WO 2014/205138. Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestratnt; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone. Other estrogenic ligands that can be used according to the present invention are described in U.S. Pat. Nos. 4,418,068; 5,478, 847; 5,393,763; and 5,457,117, WO2011/156518, U.S. Pat. Nos. 8,455,534 and 8,299,112, 9,078,871; 8,853,423; 8,703, 810; US 2015/0005286; and WO 2014/205138, US2016/ 0175289, US2015/0258080, WO 2014/191726, WO 2012/ 084711; WO 2002/013802; WO 2002/004418; WO 2002/ 003992; WO 2002/003991; WO 2002/003990; WO 2002/ 003989; WO 2002/003988; WO 2002/003986; WO 2002/ 003977; WO 2002/003976; WO 2002/003975; WO 2006/ 078834; U.S. Pat. No. 6,821,989; US 2002/0128276; U.S. Pat. No. 6,777,424; US 2002/0016340; U.S. Pat. Nos. 6,326, 392; 6,756,401; US 2002/0013327; U.S. Pat. Nos. 6,512, 002; 6,632,834; US 2001/0056099; U.S. Pat. Nos. 6,583, 170; 6,479,535; WO 1999/024027; U.S. Pat. No. 6,005,102; EP 0802184; U.S. Pat. Nos. 5,998,402; 5,780,497; 5,880, 137, WO 2012/048058 and WO 2007/087684.

In another embodiment, an active compounds described herein can be administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one embodiment, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In one embodiment, the bioactive agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer).

In one embodiment, the bioactive agent is an HER-2 inhibitor. Examples of HER-2 inhibitors include trastuzumab, lapatinib, ado-trastuzumab emtansine, and pertuzumab.

In one embodiment, the bioactive agent is a CD20 inhibitor. Examples of CD20 inhibitors include obinutuzumab, rituximab, fatumumab, ibritumomab, tositumomab, and ocrelizumab.

In one embodiment, the bioactive agent is a JAK3 inhibitor. Examples of JAK3 inhibitors include tasocitinib.

In one embodiment, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[((2R)-4-(dimethylamino)-1-phenyl sulfanylbutan-2-yl] amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl) phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In one embodiment, the bioactive agent is a kinase inhibitor. In one embodiment, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((+)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl) benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl) amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S])-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl) phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4] triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d] pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl] phenyl}propanenitrile) (dactolisib), XL-765 (N-(3-(N-(3-(3,5-dimethoxyphenylamino)quinoxalin-2-yl)sulfamoyl) phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis (prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-10-yl] acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structure described in WO2014/071109 having the formula:

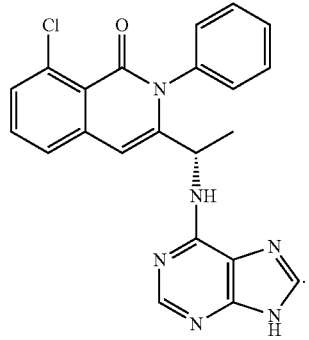

Compound 292

Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl) phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo [h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors include, for example, Cerdulatinib (4-(cyclopropylamino)-2-((4-(4-(ethylsulfonyl)piperazin-1-yl) phenyl)amino)pyrimidine-5-carboxamide), entospletinib (6-(1H-indazol-6-yl)-N-(4-morpholinophenyl)imidazo[1,2-a] pyrazin-8-amine), fostamatinib ([6-({5-Fluoro-2-[(3,4,5-trimethoxyphenyl)amino]-4-pyrimidinyl}amino)-2,2- dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4]oxazin-3 (4H)-one), piceatannol (3-Hydroxyresveratol), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, *J. Med. Chem.* 2012, 55, 3614-3643 incorporated in its entirety herein).

In one embodiment, the bioactive agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-l(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEAl 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H, 8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), RO5126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2yl)methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In one embodiment, the bioactive agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3 (trifluoroMethyl)phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, the bioactive agent is an AKT inhibitor, including but not limited to, MK-2206, GSK690693, Perifosine, (KRX-0401), GDC-0068, Triciribine, AZD5363, Honokiol, PF-04691502, and Miltefosine, a FLT-3 inhibitor, including but not limited to, P406, Dovitinib, Quizartinib (AC220), Amuvatinib (MP-470), Tandutinib (MLN518), ENMD-2076, and KW-2449, or a combination thereof.

In one embodiment, the bioactive agent is an mTOR inhibitor. Examples of mTOR inhibitors include but are not limited to rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6, 8-dimethyl-2,4,7-trioxo-3,4,6,7-tetrahydropyrido[4,3-d]pyrimidin-l(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol) (cobimetinib), refametinib/BAY869766/RDEAl19 (N-(3,4-difluoro-2-(2-fluoro-4-iodophenylamino)-6-methoxyphenyl)-1-(2,3- dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), RO5126766 (3-[[3-Fluoro-2-(methylsulfamoylamino)-4-pyridyl]methyl]-4-methyl-7-pyrimidin-2-yloxychromen-2-one), WX-554, RO4987655/CH$_{4987655}$ (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide).

In one embodiment, the bioactive agent is a RAS inhibitor. Examples of RAS inhibitors include but are not limited to Reolysin and siG12D LODER.

In one embodiment, the bioactive agent is a HSP inhibitor. HSP inhibitors include but are not limited to Geldanamycin or 17-N-Allylamino-17-demethoxygeldanamycin (17AAG), and Radicicol.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an aurora kinase inhibitor, a PIK-1 modulator, an HDAC inhbitor, a c-MET inhibitor, a PARP inhibitor, a Cdk inhibitor, an IGFR-TK inhibitor, an anti-HGF antibody, a focal adhesion kinase inhibitor, a Map kinase kinase (mek) inhibitor, a VEGF trap antibody, pemetrexed, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRiKRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethyl stilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatinib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In one embodiment, the bioactive agent is selected from, but are not limited to, Imatinib mesylate (Gleevac®), Dasatinib (Sprycel®), Nilotinib (Tasigna®), Bosutinib (Bosulif®), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilzomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the bioactive agent is an anti-inflammatory agent, a chemotherapeutic agent, a radiotherapeutic, an additional therapeutic agent, or an immunosuppressive agent.

Suitable chemotherapeutic bioactive agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents that can be administered in combination with a Degrader disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one aspect of the invention, the disclosed compound is administered in combination with an anti-infective agent, for example but not limited to an anti-HIV agent, anti-HCV agent, anti-HBV agent, or other anti-viral or anti-bacterial agent. In one embodiment, the anti-HIV agent can be, but is not limited to, for example, a nucleoside reverse transcriptase inhibitor (NRTI), other non-nucleoeside reverse transcriptase inhibitor, protease inhibitor, fusion inhibitor, among others. Nucleoside/Nucleotide Reverse Transcriptase Inhibitors (NRTIs) include, but are not limited to, Abacavir or ABC (Ziagen), Didanosine or ddI (Videx), Emtricitabine or FTC (Emtriva), Lamivudine or 3TC (Epivir), ddC (zalcitabine), Stavudine or d4T (Zerit), Tenofovircor TDF (Viread), D-D4FC (Reverset), and Zidovudine or AZT or ZDV (Retrovir). Non-nucleoside Reverse Transcriptase Inhibitors (NNRTIs) include, but are not limited to, Delavirdine (Rescriptor), Efavirenz (Sustiva), Etravirine (Intelence), Nevirapine (Viramune), and Rilpivirine (Edurant). Anti-HIV Protease Inhibitors (PIs) include, but are not limited to, Atazanavir or ATV (Reyataz), Darunavir or DRV (Prezista), Fosamprenavir or FPV (Lexiva), Indinavir or IDV (Crixivan), Lopinavir+ritonavir, or LPV/r (Kaletra), Nelfinavir or NFV (Viracept), Ritonavir or RTV (Norvir), Saquinavir or SQV (Invirase), Tipranavir, or TPV (Aptivus), Cobicistat (Tybost), Atazanavir+cobicistat, or ATV/COBI (Evotaz), Darunavir+cobicistat, or DRV/COBI (Prezcobix). Anti-HIV Fusion Inhibitors include, but are not limited to, Enfuvirtide or ENF or T-(Fuzeon). Anti-HIV also include, but are not limited to, Maraviroc or MVC (Selzentry). Anti-HIV Integrase Inhibitors include, but are not limited to Dolutegravir (Tivicay), Elvitegravir (Vitekta), Raltegravir (Isentress). Anti-HIV combinations agents include Abacavir+Dolutegravir+lamivudine, or ABC/DTG/3TC (Triumeq), Abacavir+lamivudine or ABC/3TC (Epzicom), Abacavir+lamivudine+zidovudine, or ABC/3TC/ZDV (Trizivir), Efavirenz+emtricitabine+tenofovir or EFV/FTC/TDF (Atripla, Tribuss), elvitegravir, cobicistat, emtricitabine, tenofovir alafenamide or EVG/COBI/FTC/TAF or ECF/TAF (Genvoya; (Stribild), emtricitabine+rilpivirine+tenofovir or FTC/RPV/TAF (Odefsey); Emtricitabine+rilpivirine+tenofovir or FTC/RPV/TDF (Complera), Emtricitabine+tenofovir or TAF/FTC (Descovy), emtricitabine and tenofovir disoproxil fumarate (Truvada), and Lamivudine+zidovudine or 3TC/ZDV (Combivir). Other anti-HIV compounds include, but are not limited to Racivir, L-FddC, L-FD4C, SQVM (Saquinavir mesylate), IDV (Indinavir), SQV (Saquinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in co-administration with the disclosed compounds according to the present invention. NNRTIs may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furan-carbothiamide), etravirine (TMC125), Trovirdine (Ly300046.HCl), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl)phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl]piperazine, 1-[3-(Ethylamino)-2-[pyridinyl]-4-[(5-hydroxy-2-indolyl)carbonyl]piperazine, 1-[(6-Formyl-2-indolyl)carbonyl]-4-[3-(isopropylamino)-2-pyridinyl]piperazine, 1-[[5-(Methylsulfonyloxy)-2-indolyl)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 342-(4, 7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amino]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5 (9bH)-one, Tivirapine (R86183), UC-38 and UC-84, among others.

In one aspect of the invention, the disclosed compound when used to treat an HCV infection can be administered in combination with another anti-HCV agent. Anti-HCV agents are known in the art. To date, a number of fixed dose drug combinations have been approved for the treatment of HCV. Harvoni® (Gilead Sciences, Inc.) contains the NS5A inhibitor ledipasvir and the NS5B inhibitor sofosbuvir. Technivie™ (AbbVie, Inc.) is a fixed-dose combination containing ombitasvir, an NS5A inhibitor; paritaprevir, an NS3/4A protease inhibitor; and ritonavir, a CYP3A inhibitor. Daklinza™ (daclatasvir, Bristol-Myers Squibb) is a HCV NS5A inhibitor indicated for use with sofosbuvir for the treatment of chronic genotype 3 infection. Zepatier™ (Merck & Co.) has recently been approved for the treatment of chronic HCV genotypes 1 and 4. Zepatier™ is a fixed-dose combination product containing elbasvir, an HCV NS5A inhibitor, and grazoprevir, an HCV NS3/4A protease inhibitor. Zepatier™ is indicated with or without ribavirin. Epclusa® (Gilead Sciences, Inc.) is a fixed-dose combination tablet containing sofosbuvir and velpatasvir. Additional anti-HCV agents and combinations thereof include those described in U.S. Pat. Nos. 9,382,218; 9,321,753; 9,249,176; 9,233,974; 9,221,833; 9,211,315; 9,194,873; 9,186,369; 9,180,193; 9,156,823; 9,138,442; 9,133,170; 9,108,999; 9,090,559; 9,079,887; 9,073,943; 9,073,942; 9,056,090; 9,051,340; 9,034,863; 9,029,413; 9,011,938; 8,987,302; 8,945,584; 8,940,718; 8,927,484; 8,921,341; 8,884,030; 8,841,278; 8,822,430; 8,772,022; 8,765,722; 8,742,101; 8,741,946; 8,674,085; 8,673,288; 8,669,234; 8,663,648; 8,618,275; 8,580,252; 8,575,195; 8,575,135; 8,575,118; 8,569,302; 8,524,764; 8,513,298; 8,501,714; 8,404,651; 8,273,341; 8,257,699; 8,197,861; 8,158,677; 8,105,586; 8,093,353; 8,088,368; 7,897,565; 7,871,607; 7,846,431; 7,829,081; 7,829,077; 7,824,851; 7,572,621; and 7,326,536; patents assigned to Alios: U.S. Pat. Nos. 9,365,605; 9,346,848; 9,328,119; 9,278,990; 9,249,174; 9,243,022; 9,073,960; 9,012,427; 8,980,865; 8,895,723; 8,877,731; 8,871,737; 8,846,896 and 8,772,474; Achillion U.S. Pat. Nos. 9,273, 082; 9,233,136; 9,227,952; 9,133,115; 9,125,904; 9,115, 175; 9,085,607; 9,006,423; 8,946,422; 8,835,456; 8,809, 313; 8,785,378; 8,614,180; 8,445,430; 8,435,984; 8,183, 263; 8,173,636; 8,163,693; 8,138,346; 8,114,888; 8,106, 209; 8,088,806; 8,044,204; 7,985,541; 7,906,619; 7,902, 365; 7,767,706; 7,741,334; 7,718,671; 7,659,399; 7,476, 686; 7,439,374; 7,365,068; 7,199,128; and 7,094,807; Cocrystal Pharma Inc. 9,181,227; 9,173,893; 9,040,479 and 8,771,665; Gilead Sciences U.S. Pat. Nos. 9,353,423; 9,346, 841; 9,321,800; 9,296,782; 9,296,777; 9,284,342; 9,238, 039; 9,216,996; 9,206,217; 9,161,934; 9,145,441; 9,139, 604; 9,090,653; 9,090,642; 9,085,573; 9,062,092; 9,056,860; 9,045,520; 9,045,462; 9,029,534; 8,980,878; 8,969,588; 8,962,652; 8,957,046; 8,957,045; 8,946,238; 8,933,015; 8,927,741; 8,906,880; 8,889,159; 8,871,785; 8,841,275; 8,815,858; 8,809,330; 8,809,267; 8,809,266; 8,779,141; 8,765,710; 8,759,544; 8,759,510; 8,735,569; 8,735,372; 8,729,089; 8,722,677; 8,716,264; 8,716,263; 8,716,262; 8,697,861; 8,664,386; 8,642,756; 8,637,531; 8,633,309; 8,629,263; 8,618,076; 8,592,397; 8,580,765; 8,569,478; 8,563,530; 8,551,973; 8,536,187; 8,513,186; 8,513,184; 8,492,539; 8,486,938; 8,481,713; 8,476,225; 8,420,597; 8,415,322; 8,338,435; 8,334,270; 8,329,926; 8,329,727; 8,324,179; 8,283,442; 8,263,612; 8,232,278; 8,178,491; 8,173,621; 8,163,718; 8,143,394; patents assigned to Idenix, acquired by Merck, include U.S. Pat. Nos. 9,353,100; 9,309,275; 9,296,778; 9,284,307; 9,249,173; 9,243,025; 9,211,300; 9,187,515; 9,187,496, 9,109,001; 8,993,595; 8,951,985; 8,691,788; 8,680,071; 8,637,475; 8,507,460; 8,377,962; 8,362,068; 8,343,937; 8,299,038; 8,193,372; 8,093,379; 7,951,789; 7,932,240; 7,902,202; 7,662,798; 7,635,689; 7,625,875; 7,608,600; 7,608,597; 7,582,618; 7,547,704; 7,456,155; 7,384,924; 7,365,057; 7,192,936; 7,169,766; 7,163,929; 7,157,441; 7,148,206; 7,138,376; 7,105,493; 6,914,054 and 6,812,219; patents assigned to Merck include U.S. Pat. Nos. 9,364,482; 9,339,541; 9,328,138; 9,265,773; 9,254,292; 9,243,002; 9,242,998; 9,242,988; 9,242,917; 9,238,604; 9,156,872; 9,150,603; 9,139,569; 9,120,818; 9,090,661; 9,073,825; 9,061,041; 8,987,195; 8,980,920; 8,927,569; 8,871,759; 8,828,930; 8,772,505; 8,715,638; 8,697,694; 8,637,449; 8,609,635; 8,557,848; 8,546,420; 8,541,434; 8,481,712; 8,470,834; 8,461,107; 8,404,845; 8,377,874; 8,377,873; 8,354,518; 8,309,540; 8,278,322; 8,216,999; 8,148,349; 8,138,164; 8,080,654; 8,071,568; 7,973,040; 7,935,812; 7,915,400; 7,879,815; 7,879,797; 7,632,821; 7,569,374; 7,534,767; 7,470,664 and 7,329,732; patent application publication US 2013/0029904 to Boehringer Ingelheim GMBH and US 2014/0113958 to Stella Aps.

In one embodiment, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

In one aspect of the present invention, the bioactive agent is an immunosuppressive agent. The immunosuppressive agent can be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELL-CEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-$CD_{25}$, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA41g (Abatacept), belatacept, LFA31g, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

X. Pharmaceutical Compositions

The compounds of Formula I, Formula II, Formula III, Formula IV, Formula V, Formula VI, Formula VII, Formula VIII, Formula IX, Formula X, Formula XI, and Formula XII as disclosed herein can be administered as the neat chemical, but are more typically administered as a pharmaceutical composition, that includes an effective amount for a host, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, or 750 mg of active compound, or its salt. The pharmaceutical composition may also include a molar ratio of the active compound and an additional active agent. For example the pharmaceutical composition may contain a molar ratio of about 0.5:1, about 1:1, about 2:1, about 3:1 or from about 1.5:1 to about 4:1 of an anti-inflammatory or immunosuppressing agent. Compounds disclosed herein may be administered orally, topically, parenterally, by inhalation or spray, sublingually, via implant, including ocular implant, transdermally, via buccal administration, rectally, as an ophthalmic solution, injection, including ocular injection, intraveneous, intra-aortal, intracranial, subdermal, intraperitioneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, subretinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

Formulations suitable for rectal administration are typically presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Many methods and devices for drug delivery are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277, 830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

XI. General Synthesis

The compounds described herein can be prepared by methods known by those skilled in the art. In one non-limiting example, the disclosed compounds can be made using the schemes below.

Compounds of the present invention with stereocenters may be drawn without stereochemistry for convenience. One skilled in the art will recognize that pure enantiomers and diastereomers can be prepared by methods known in the art. Examples of methods to obtain optically active materials include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the enantiomer is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step in the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e. chirality) in the product, which may be achieved by chiral catalysts or chiral auxiliaries;

vi) diastereomer separations—a technique whereby a racemic compound is reaction with an enantiomerically pure reagent (the chiral auxiliary) that converts the individual enantiomers to diastereomers. The resulting diastereomers are then separated by chromatography or crystallization by virtue of their now more distinct structural differences the chiral auxiliary later removed to obtain the desired enantiomer;

vii) first- and second-order asymmetric transformations—a technique whereby diastereomers from the racemate quickly equilibrate to yield a preponderance in solution of the diastereomer from the desired enantiomer of where preferential crystallization of the diastereomer from the desired enantiomer perturbs the equilibrium such that eventually in principle all the material is converted to the crystalline diastereomer from the desired enantiomers. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including vial chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is place in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through;

xiv) simulated moving bed chromatography is used in one embodiment. A wide variety of chiral stationary phases are commercially available.

General Scheme 1

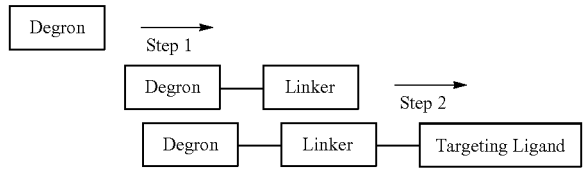

General Scheme 2

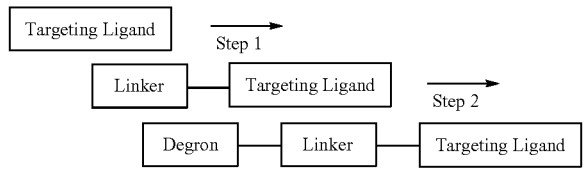

As shown in General Scheme 1, compounds for use in the present invention can be prepared by chemically combining a Degron and a Linker followed by subsequent addition of a Targeting Ligand. Similarly in General Scheme 2, compounds for use in the present invention are prepared by chemically combining a Targeting Ligand and Linker first, followed by subsequent addition of a Degron. As illustrated in the above and following schemes, compounds for use in the present invention can be readily synthesized by one skilled in the art using a variety of methods and chemical reactions.

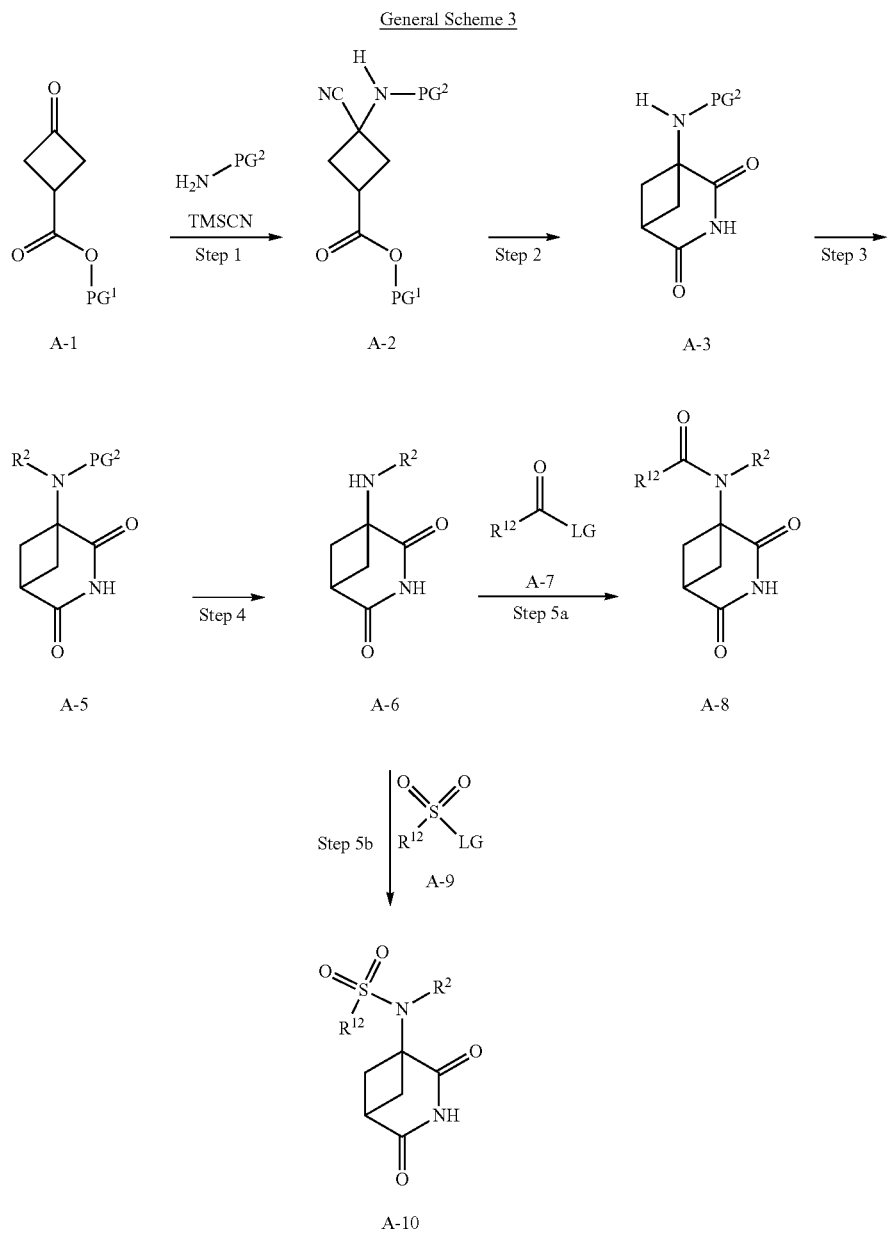

As demonstrated in the non-limiting illustrative example in Scheme 3, compounds falling within Formula I can be prepared by methods known to those skilled in the art. In Step 1, reaction of A-1 with $PG^2$-$NH_2$ and trimethylsilyl-cyanide provides A-2. In some embodiments, $PG^1$ is methyl. In some embodiments, $PG^2$ is 4-methoxybenzyl. In Step 2, A-2 is cyclized in the presence of catalytic acid to provide A-3. In some embodiments, the catalytic acid is sulfuric acid. In Step 3, A-3 is reacted with the appropriate reagent to provide A-5. In some embodiment, $R^2$ is methyl. In some embodiments, $R^2$ as methyl is introduced by reaction of A-3 with formaldehyde and sodium cyanoborohydride under acidic conditions. In Step 4, protecting group $PG^2$ is removed to provide A-6. In some embodiments, $PG^2$ as 4-methoxybenzyl is removed by reaction of A-5 with molecular hydrogen and an organometallic catalyst, wherein the organometallic catalyst is typically palladium on carbon. In Step 5a, A-6 is coupled with A-7 using a coupling reagent to provide A-8. In some embodiments, LG on A-7 is hydroxyl. In some embodiments, the coupling agent is a typical amide coupling agent known to those skilled in the art. Alternatively in Step 5b, A-6 is reacted with A-9 in the presence of base to provide A-10. In some embodiments, LG on A-9 is chloro. In some embodiments, the base is triethylamine.

General Scheme 4

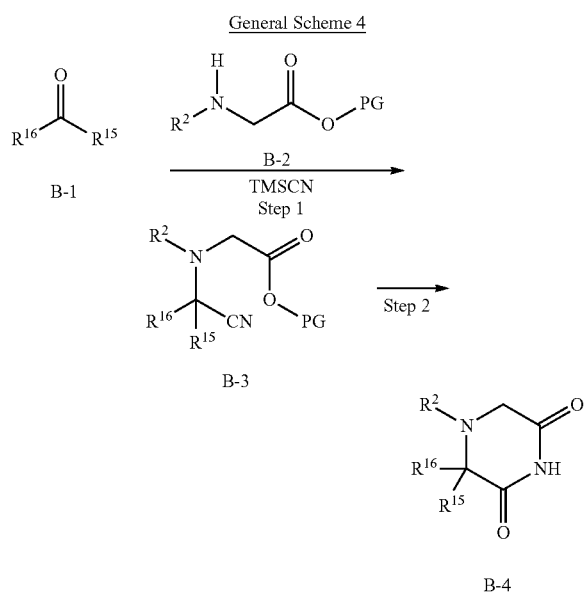

As demonstrated in the non-limiting illustrative example in Scheme 4, compounds falling within Formula II can be prepared by methods known to those skilled in the art. In Step 1, reaction of B-1 with B-2 and trimethylsilyl cyanide provides B-3. In some embodiments, PG is methyl. In Step 2, B-3 is cyclized in the presence of catalytic acid to provide B-4. In some embodiments, the catalytic acid is sulfuric acid.

General Scheme 5

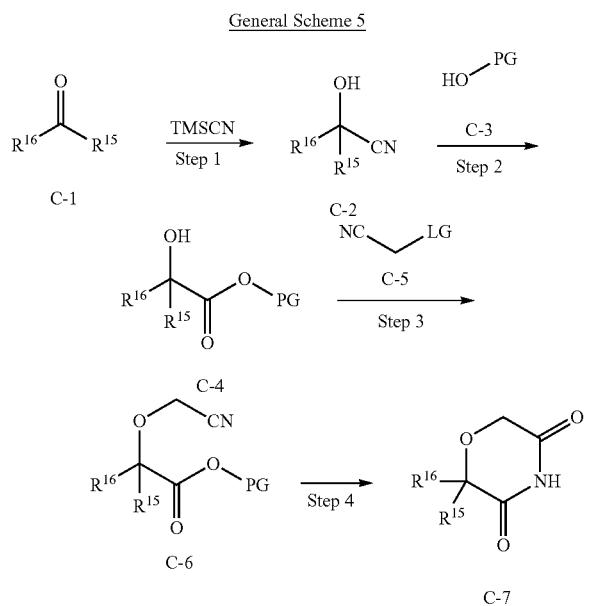

As demonstrated in the non-limiting illustrative example in Scheme 5, compounds falling within Formula II can be prepared by methods known to those skilled in the art. In Step 1, reaction of C-1 with trimethylsilylcyanide provides cyanohydrin C-2. In Step 2, Reaction of C-2 with C-3 under acidic conditions provides C-4. In some embodiments, PG is ethyl. In some embodiments, the acidic conditions in Step 2 involve the use of ethanolic hydrogen chloride. In Step 3, reaction of C-4 with C-5 by nucleophilic displacement of LG in the presence of base provides C-6. In some embodiments, LG is bromo. In some embodiments, the base in Step 3 is sodium hydride. In Step 4, C-6 is cyclized in the presence of catalytic acid to provide C-7. In some embodiments, the catalytic acid is sulfuric acid

General Scheme 6

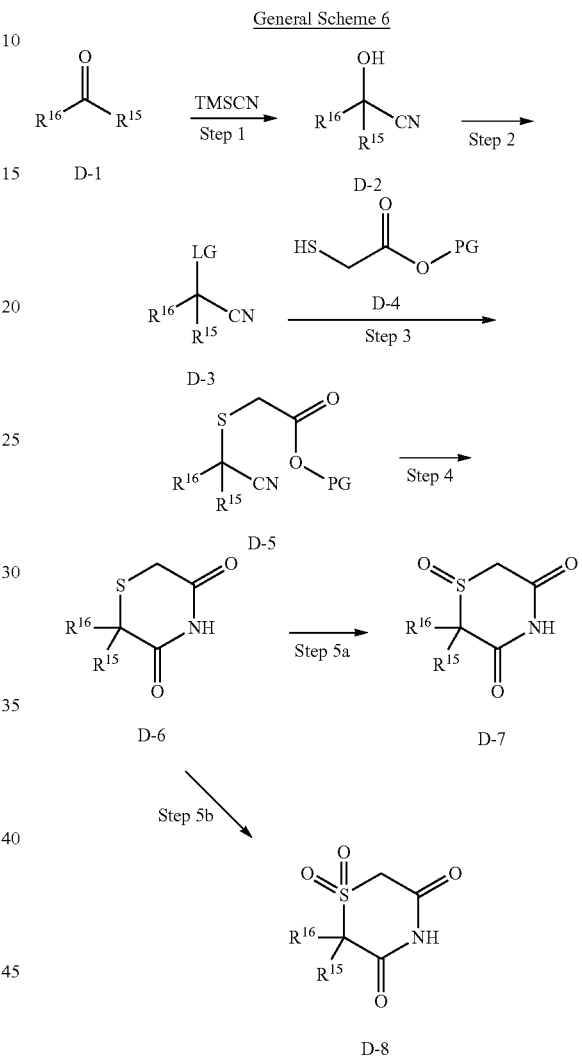

As demonstrated in the non-limiting illustrative example in Scheme 4, compounds falling within Formula II can be prepared by methods known to those skilled in the art. In Step 1, reaction of D-1 with trimethylsilyl cyanide provide cyanohydrin D-2. In Step 2, the alcohol in D-2 is converted into LG to provide D-3. In some embodiments, Step 2 involves the conversion of the alcohol in D-2 into a sulfonate by reaction with a corresponding sulfonyl chloride in the presence of base. In some embodiments, the sulfonate is 4-toluenesulfonate. In Step 3, nucleophilic displacement of LG in D-3 with D-4 provides D-5. In some embodiments, PG is methyl. In Step 4, cyclization of D-5 in the presence of catalytic acid provides D-6. In some embodiments, the catalytic acid is sulfuric acid. In Step 5a, reaction of an oxidant and D-6 at low temperature provides D-7. In some embodiments, the oxidant is 3-chlorobenzene-1-carboperoxoic acid. In some embodiments, the temperature is −20°

C. Alternatively in Step 5b, reactive of an oxidant and D-6 at room temperature provides D-8. In some embodiments, the oxidant is 3-chlorobenzene-1-carboperoxoic acid.

XII. Exemplary Methods for the Synthesis of the Disclosed Compounds

Example 1: Synthesis of Methyl 1-(2,4-Dioxo-3-azabicyclo[3.1.1]heptan-1-yl)-6-oxo-1,6-dihydropyridine-3-carboxylate

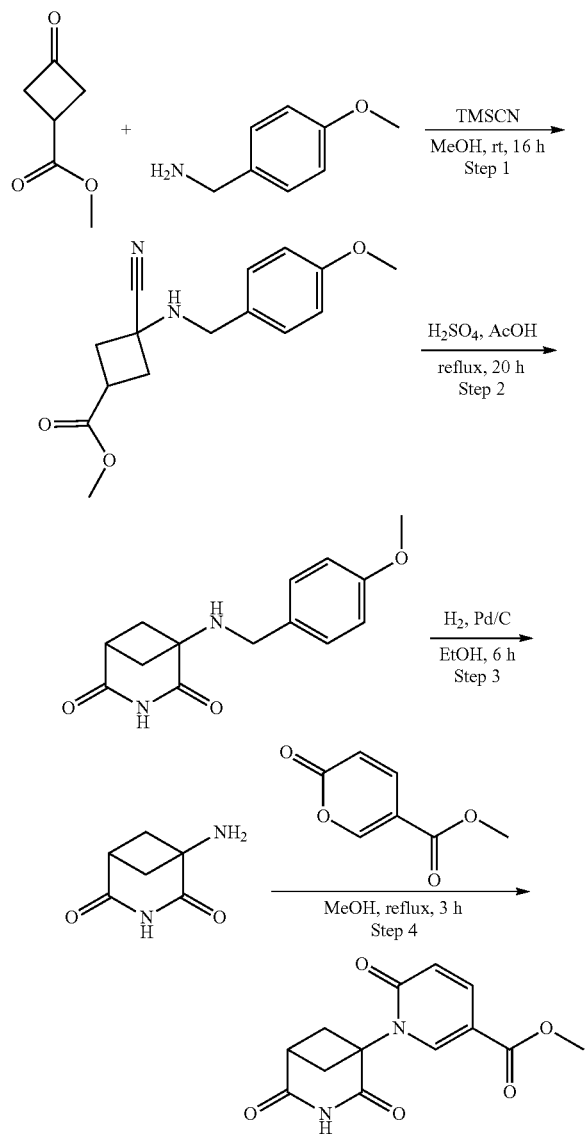

Step 1: Preparation of Methyl 3-Cyano-3-((4-methoxybenzyl)amino)cyclobutane-1-carboxylate To a stirred solution of methyl 3-oxocyclobutane-1-carboxylate (5.0 g, 39.02 mmol) in methanol (50.0 mL) was added (4-methoxyphenyl)methanamine (5.89 g, 42.96 mmol, 5.61 mL), and the reaction was stirred at room temperature for one hour. Trimethylsilyl cyanide (7.98 g, 80.39 mmol, 10.10 mL) was then added drop-wise to the reaction mixture at 0° C. The reaction mixture was then stirred at room temperature for 16 hours. The reaction mixture was concentrated under reduced pressure. The crude material was purified by silica gel column chromatography (0-10% ethyl acetate/hexanes) to afford methyl 3-cyano-3-((4-methoxybenzyl)amino)cyclobutane-1-carboxylate (7.5 g, 27.34 mmol, 70% yield) as a light yellow oil. LC MS (ES+): 275.3.

Step 2: Preparation of 1-((4-Methoxybenzyl)amino)-3-azabicyclo[3.1.1]heptane-2,4-dione To a stirred solution of afford methyl 3-cyano-3-((4-methoxybenzyl)amino)cyclobutane-1-carboxylate (4.5 g, 16.40 mmol) in acetic acid (26.60 g, 442.92 mmol, 25.33 mL) was added sulfuric acid (5.63 g, 57.42 mmol, 3.06 mL), and the reaction mixture was refluxed for 16 hours.

The reaction mixture was concentrated under reduced pressure and diluted with ethyl acetate. The organic layer was washed with saturated aqueous $NaHCO_3$ solution, water, and brine, dried over sodium sulfate, and concentrated under reduced pressure. The crude material was purified by silica gel column chromatography (0-2% methanol/$CH_2Cl_2$) to afford 1-((4-methoxybenzyl)amino)-3-azabicyclo[3.1.1]heptane-2,4-dione (1.0 g, 3.84 mmol, 23.42% yield) as a light brown solid. LC MS (ES+): 261.3.

Step 3: Preparation of 1-Amino-3-azabicyclo[3.1.1]heptane-2,4-dione

A stirred solution of 1-((4-methoxybenzyl)amino)-3-azabicyclo[3.1.1]heptane-2,4-dione (1.0 g, 3.84 mmol) in ethanol (25.0 mL) was degassed for 15 minutes under argon. 10% palladium on carbon (Type 487, dry, 408.86 mg, 3.84 mmol) was added, and the reaction mixture was placed under a balloon of hydrogen gas for six hours. The reaction mixture was filtered through a pad of celite, and the filter pad was washed with ethanol. The combined filtrated was concentrated to afford 1-amino-3-azabicyclo[3.1.1]heptane-2,4-dione (500.0 mg, 3.57 mmol, 92.97% yield) as a white solid. LC MS (ES+): 141.0.

Step 4: Preparation of Methyl 1-(2,4-Dioxo-3-azabicyclo[3.1.1]heptan-1-yl)-6-oxo-1,6-dihydropyridine-3-carboxylate To a stirred solution of methyl 2-oxo-2H-pyran-5-carboxylate (100.0 mg, 648.84 umol) in methanol (2 mL) was added 1-amino-3-azabicyclo[3.1.1]heptane-2,4-dione (109.11 mg, 778.61 umol) and the reaction mixture was heated at 80° C. for three hours. The reaction mixture was evaporated under reduced pressure. The crude material was purified by preparative TLC (developed with 2% methanol/$CH_2Cl_2$) to afford methyl 1-(2,4-dioxo-3-azabicyclo[3.1.1]heptan-1-yl)-6-oxo-1,6-dihydropyridine-3-carboxylate (32.0 mg, 115.84 umol, 17.85% yield), as a white solid. $^1$H NMR (400 MHz, DMSO-$d_6$) δ 11.07 (s, 1H), 7.94 (s, 1H), 7.83-7.80 (m, 1H), 6.43-6.40 (m, 1H), 3.77 (s, 3H), 3.06-3.00 (m, 3H), 2.86-2.80 (m, 2H); LC MS (ES+): 277.2.

Example 2: Synthesis of 1-(4-Hydroxy-6-methyl-2-oxopyridin-1(2H)-yl)-3-azabicyclo[3.1.1]heptane-2,4-dione

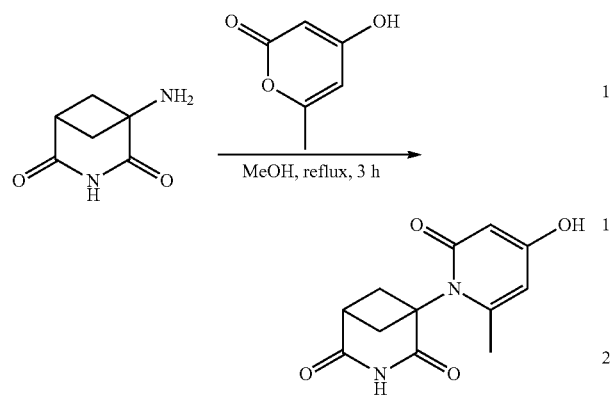

To a stirred solution of 4-hydroxy-6-methyl-2H-pyran-2-one (648.85 umol) in methanol (2 mL) is added 1-amino-3-azabicyclo[3.1.1]heptane-2,4-dione (109.11 mg, 778.61 umol), and the reaction mixture is heated at 80° C. for three hours. The reaction mixture is evaporated under reduced pressure. The crude material is purified by preparative TLC (developed with 2% methanol/$CH_2Cl_2$) to afford 1-(4-hydroxy-6-methyl-2-oxopyridin-1(2H)-yl)-3-azabicyclo[3.1.1]heptane-2,4-dione.

Example 3: Synthesis of 1-(4-Phenyl-1H-1,2,3-triazol-1-yl)-3-azabicyclo[3.1.1]heptane-2,4-dione

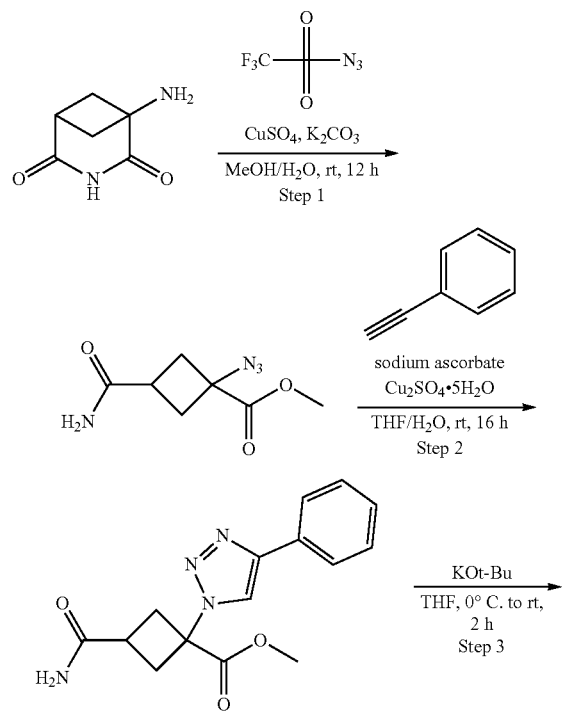

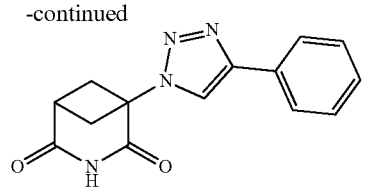

Step 1: Preparation of Methyl 1-Azido-3-carbamoylcyclobutane-1-carboxylate

Triflyl Azide Preparation:

To a stirred solution of sodium azide (10.0 equiv) in toluene/water (2:1) was added triflic anhydride (2.0 equiv) over 5 minutes at 0° C. The reaction mixture was stirred for two hours, and the layers were then separated. The organic layer was washed with saturated aqueous $Na_2CO_3$ solution and used directly in the next step.

To a stirred solution of 1-amino-3-azabicyclo[3.1.1]heptane-2,4-dione (100 mg, 713.57 umol) in methanol (6.0 mL) and water (3.0 mL) was added granular potassium carbonate (147.93 mg, 1.07 mmol, 64.60 uL) and copper(II) sulfate pentahydrate (17.82 mg, 73.16 umol) at 0° C. Triflyl azide solution in toluene (713.57 umol) was then added slowly, and the reaction mixture was stirred at room temperature for 16 hours. The reaction mixture was concentrated under reduced pressure and diluted with ethyl acetate. The organic layer was separated, dried over sodium sulfate, and concentrated under reduced pressure to provide methyl 1-azido-3-carbamoylcyclobutane-1-carboxylate (115.0 mg, 692.20 umol, 84.00% yield) as an off-white semisolid which was used directly in the next step.

Step 2: Preparation of Methyl 3-Carbamoyl-1-(4-phenyl-1H-1,2,3-triazol-1-yl)cyclobutane-1-carboxylate To a stirred solution of methyl 1-azido-3-carbamoylcyclobutane-1-carboxylate (115.0 mg, 692.20 umol) in THF (3.0 mL) was added ethynylbenzene (77.77 mg, 761.42 umol, 83.62 uL). To the reaction mixture was added copper (II) sulfate pentahydrate (17.28 mg, 69.22 umol) in water (1.0 mL). The reaction mixture was stirred at room temperature for ten minutes. Sodium ascorbate (54.85 mg, 276.88 umol) was then added, and the reaction mixture was stirred at room temperature for 16 hours. The reaction mixture was filtered through a pad of celite, and the filtrate was concentrated under reduced pressure. The crude material was purified by silica gel column chromatography (0-1.5% methanol/$CH_2Cl_2$) to provide methyl 3-carbamoyl-1-(4-phenyl-1H-1,2,3-triazol-1-yl)cyclobutane-1-carboxylate (25.0 mg, 83.25 umol, 12.03% yield) as an off-white solid. LC MS (ES+): 301.2.

Step 3: Preparation of 1-(4-Phenyl-1H-1,2,3-triazol-1-yl)-3-azabicyclo[3.1.1]heptane-2,4-dione To a stirred solution of methyl 3-carbamoyl-1-(4-phenyl-1H-1,2,3-triazol-1-yl)cyclobutane-1-carboxylate (50.0 mg, 166.49 umol) in THF (3.0 mL) was added potassium tert-butoxide (18.68 mg, 166.49 umol) at 0° C., and the reaction mixture was stirred at room temperature for two hours. Upon formation of a new spot by TLC, the reaction mixture was diluted with ethyl acetate. The organic layer was washed with water and brine, dried over sodium sulfate, and concentrated under reduced pressure. The crude material was triturated with ether/pentane to afford 1-(4-phenyl-1H-1,2,3-triazol-1-yl)-3-azabicyclo[3.1.1]heptane-2,4-dione (20.0 mg, 74.55 umol, 44.78% yield) as an off-white solid. $^1$H NMR (400 MHz, DMSO-$d_6$) δ 11.29 (s, 1H), 8.68 (s, 1H), 7.87 (m, 2H), 7.46 (m, 2H), 7.35 (m, 1H), 3.13-3.09 (m, 5H); LC MS (ES+): 269.2.

Example 4: Synthesis of 1-(Methylamino)-3-azabicyclo[3.1.1]heptane-2,4-dione

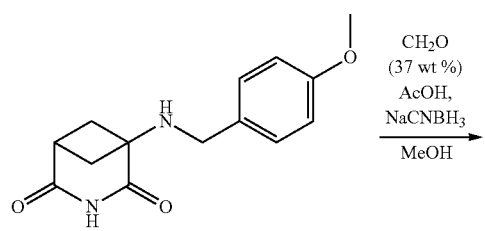

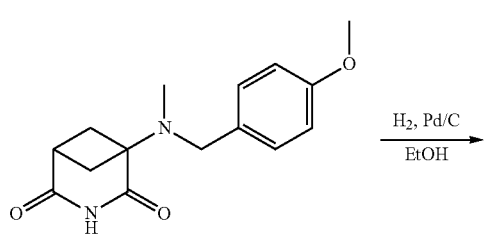

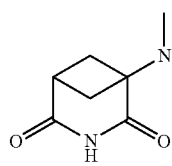

To a solution of 1-((4-methoxybenzyl)amino)-3-azabicyclo[3.1.1]heptane-2,4-dione (0.4 mmol) in methanol is added formaldehyde (37 wt % in water, 16.2 mmol), acetic acid (2.4 mmol), and sodium cyanoborohydride (1.60 mmol). The reaction mixture stirred at room temperature overnight, and the solvent is removed under reduced pressure. The residue is partitioned between ethyl acetate and saturated aqueous NaHCO$_3$, and the layers are separated. The organic layer is washed with saturated aqueous NaHCO$_3$, brine, dried over sodium sulfate, and concentrated under reduced pressure to provide 1-((4-methoxybenzyl)(methyl)amino)-3-azabicyclo[3.1.1]heptane-2,4-dione.

A stirred solution of 1-((4-methoxybenzyl)(methyl)amino)-3-azabicyclo[3.1.1]heptane-2,4-dione (3.84 mmol) in ethanol (25.0 mL) is degasses for 15 minutes under argon. To this solution is added 10% palladium on carbon (Type 487, dry, 3.84 mmol) and the reaction mixture is placed under a balloon of hydrogen gas for six hours. The solution is filtered through a pad of celite, and the filter pad is washed with ethanol. The combined filtrate is concentrated to afford 1-(methylamino)-3-azabicyclo[3.1.1]heptane-2,4-dione.

Example 5: Synthesis of 1-(4-(3-Hydroxypropyl)-1H-1,2,3-triazol-1-yl)-3-azabicyclo[3.1.1]heptane-2,4-dione

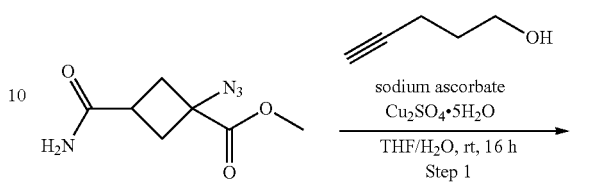

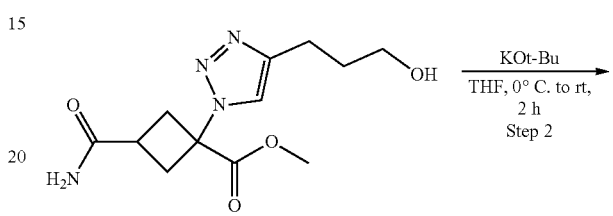

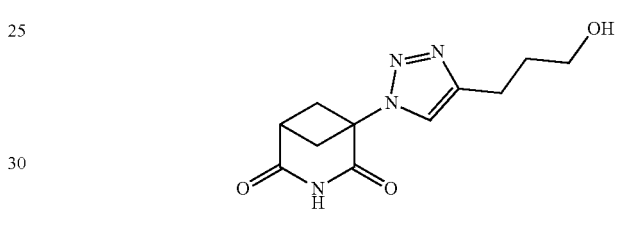

Step 1: Preparation of Methyl 1-(4-Butyl-1H-1,2,3-triazol-1-yl)-3-carbamoylcyclobutane-1-carboxylate To a stirred solution of methyl 1-azido-3-carbamoylcyclobutane-1-carboxylate (692.20 umol) in THF (3.0 mL) is added pent-4-yn-1-ol (761.42 umol). Copper(II) sulfate pentahydrate (69.22 umol) in water (1.0 mL) is added, and the reaction mixture is stirred at room temperature for ten minutes. Sodium ascorbate (276.88 umol) is then added, and the reaction mixture is stirred at room temperature for 16 hours. The reaction mixture is filtered through a pad of celite, and the filtrate is concentrated. The crude material is purified by silica gel column chromatography (0-1.5% MeOH/CH$_2$Cl$_2$) to provide methyl 1-(4-butyl-1H-1,2,3-triazol-1-yl)-3-carbamoylcyclobutane-1-carboxylate.

Step 2: Preparation of 1-(4-(3-Hydroxypropyl)-1H-1,2,3-triazol-1-yl)-3-azabicyclo[3.1.1]heptane-2,4-dione To a stirred solution of methyl 1-(4-butyl-1H-1,2,3-triazol-1-yl)-3-carbamoylcyclobutane-1-carboxylate (166.49 umol) in THF (3.0 mL) is added potassium tert-butoxide (166.49 umol) at 0° C., and the reaction mixture is stirred at room temperature for two hours. The reaction is diluted with ethyl acetate, washed with water and brine, dried over sodium sulfate, and concentrated under reduced pressure. The crude material is triturated with ether/pental to afford 1-(4-(3-Hydroxypropyl)-1H-1,2,3-triazol-1-yl)-3-azabicyclo[3.1.1]heptane-2,4-dione.

Example 6: Synthesis of N-(2,4-dioxo-3-azabicyclo[3.1.1]heptan-1-yl)-N,1-dimethyl-1H-imidazole-4-sulfonamide

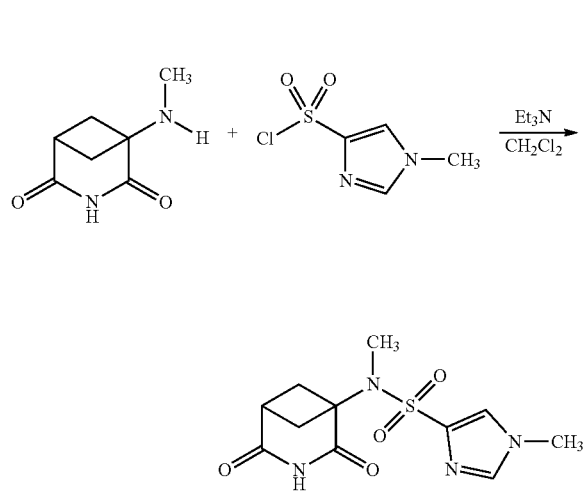

To a mixture of 1-(methylamino)-3-azabicyclo[3.1.1]heptane-2,4-dione (100 mg) in CH$_2$Cl$_2$ (3 mL) on an ice bath is added triethylamine (3 equiv) and 1-methyl-1H-imidazole-4-sulfonyl chloride (1.1 equiv), and the reaction mixture is stirred at room temperature for 16 hours. The reaction mixture is concentrated under reduced pressure and brought up in DMF. The crude material is purified by preparatory HPLC to provide N-(2,4-dioxo-3-azabicyclo[3.1.1]heptan-1-yl)-N,1-dimethyl-1H-imidazole-4-sulfonamide.

Example 7: Synthesis of N-(2,4-dioxo-3-azabicyclo[3.1.1]heptan-1-yl)-2-hydroxybenzamide

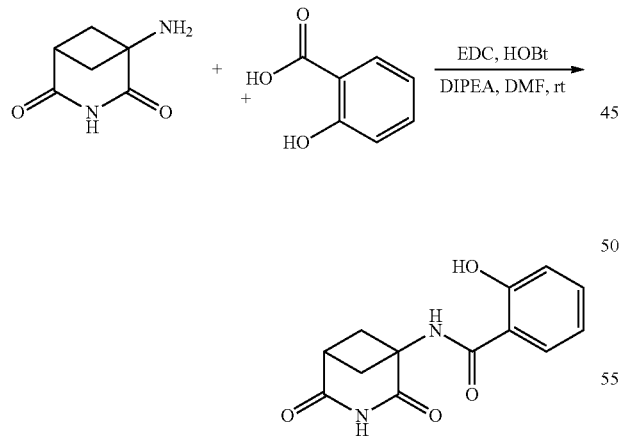

To a mixture of 1-amino-3-azabicyclo[3.1.1]heptane-2,4-dione (100 mg) and 2-hydroxybenzoic acid (1.1 equiv) in DMF (2 mL) is added EDC-HCl (2.5 equiv) and HOBt (1.5 equiv). DIPEA (3 equiv) is then added, and the reaction mixture is stirred at room temperature for 16 hours. Upon completion, the crude material is purified by preparative HPLC to provide N-(2,4-dioxo-3-azabicyclo[3.1.1]heptan-1-yl)-2-hydroxybenzamide.

Example 8: Synthesis of 1-(3-Methyl-4-phenyl-1H-pyrazol-1-yl)-3-azabicyclo[3.1.1]heptane-2,4-dione

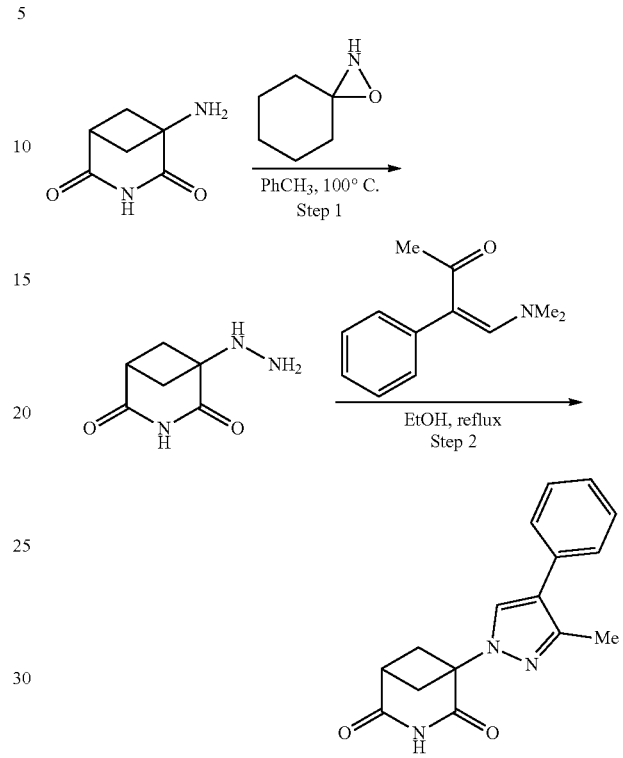

Step 1: Preparation of 1-Hydrazineyl-3-azabicyclo[3.1.1]heptane-2,4-dione

To a suspension of 1-amino-3-azabicyclo[3.1.1]heptane-2,4-dione (1.5 mmol) in toluene (34 mL) is added 1-oxa-2-azaspiro[2.5]octane (4 m/m %, 5 mL, 1.8 mmol) over 50 minutes at a temperature between 100 and 105° C. The reaction mixture is stirred at 100° C. for 30 minutes and then cooled to 5° C. until crystals form. The crystals are filtered off and wash with toluene (400 mL) and water (400 mL) to provide 1-hydrazineyl-3-azabicyclo[3.1.1]heptane-2,4-dione.

Step 2: Preparation of 1-(3-Methyl-4-phenyl-1H-pyrazol-1-yl)-3-azabicyclo[3.1.1]heptane-2,4-dione To a solution of (Z)-4-(dimethylamino)-3-phenylbut-3-en-2-one in ethanol (4 mL) is added 1-hydrazineyl-3-azabicyclo[3.1.1]heptane-2,4-dione (0.135 g, 1.09 mmol), and the reaction mixture is heated to 75° C. for 18 hours. The reaction mixture is then cooled to room temperature and stirred for 38 hours. The reaction mixture is concentrated under reduced pressure, and the residue is partitioned between ethyl acetate and saturated aqueous NaHCO$_3$ solution. The aqueous layer is extracted with ethyl acetate. The combined organic layer is washed with brine, dried over sodium sulfate, filtered, and concentrated under reduced pressure to afford 1-(3-methyl-4-phenyl-1H-pyrazol-1-yl)-3-azabicyclo[3.1.1]heptane-2,4-dione.

Example 9: Synthesis of 1-(2-Oxobenzo[d]oxazol-3(2H)-yl)-3-azabicyclo[3.1.1]heptane-2,4-dione

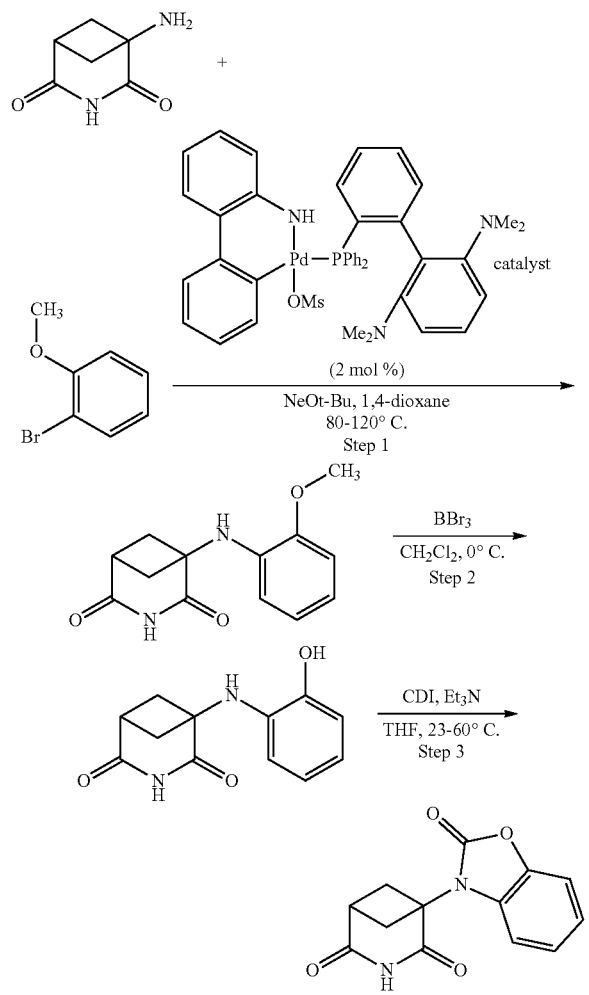

Step 1: Preparation of 1-((2-Methoxyphenyl)amino)-3-azabicyclo[3.1.1]heptane-2,4-dione A reaction tube equipped with a stir bar and a Teflon septum is charged with 1-bromo-2-methoxybenzene (1.0 equiv), 1-amino-3-azabicyclo[3.1.1]heptane-2,4-dione (1.2 equiv), precatalyst (1-2 mol %, see *J. Am. Chem. Soc.* 2015, 137, 3085). The reaction tube is evacuated and backfilled with argon three times. 1,4-Dioxane (1 M solution) is added, and the Teflon septum is replaced with a new septum under a positive pressure of argon. The reaction mixture is placed in a preheated oil bath at 80-120° C. and stirred for 6-24 hours. Upon completion, the reaction mixture is filtered through a pad of celite and concentrated under reduced pressure. The crude mixture is purified by silica gel column chromatography to provide 1-((2-methoxyphenyl)amino)-3-azabicyclo[3.1.1]heptane-2,4-dione.

Step 2: Preparation of 1-((2-Hydroxyphenyl)amino)-3-azabicyclo[3.1.1]heptane-2,4-dione A stirred solution of 1-((2-methoxyphenyl)amino)-3-azabicyclo[3.1.1]heptane-2,4-dione (1 equiv) in $CH_2Cl_2$ is cooled to 0° C. Borontribromide (1 equiv, 1M in $CH_2Cl_2$) is added, and the reaction mixture is stirred until all starting material is consumed. The reaction mixture is then adsorbed onto silica gel and purified by silica gel column chromatography to provide 1-((2-hydroxyphenyl)amino)-3-azabicyclo[3.1.1]heptane-2,4-dione.

Step 3: Preparation of 1-(2-Oxobenzo[d]oxazol-3(2H)-yl)-3-azabicyclo[3.1.1]heptane-2,4-dione A round bottom flashed charged with 1-((2-hydroxyphenyl)amino)-3-azabicyclo[3.1.1]heptane-2,4-dione (1 equiv) is sealed with a septum and cycled between vacuum and nitrogen atmosphere three times. THF (0.3M solution), triethylamine (2.5 equiv), and CDI (1.1 equiv) are then added, and the reaction mixture is stirred until starting material is no longer observed. The crude mixture is adsorbed onto silica gel and purified by silica gel column chromatography to provide 1-(2-oxobenzo[d]oxazol-3(2H)-yl)-3-azabicyclo[3.1.1]heptane-2,4-dione.

Example 10: Synthesis of 1-(2-Oxo-2,3-dihydro-1H-benzo[d]imidazol-1-yl)-3-azabicyclo[3.1.1]heptane-2,4-dione

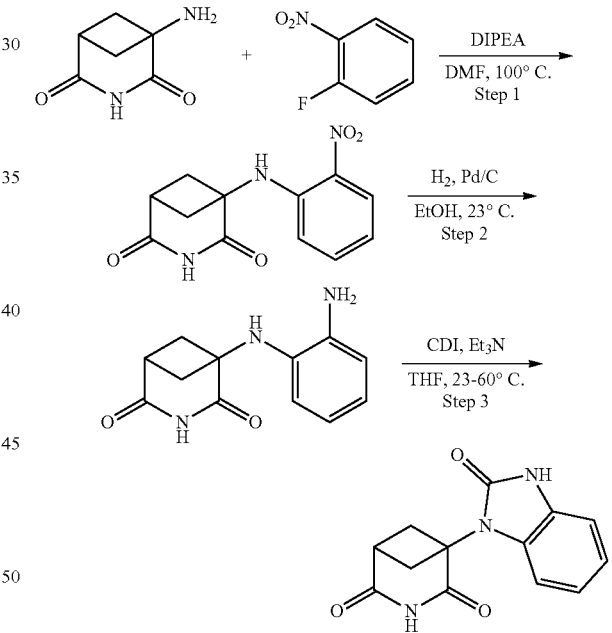

Step 1: Preparation of 1-((2-Nitrophenyl)amino)-3-azabicyclo[3.1.1]heptane-2,4-dione A round bottom flask is charged with 1-amino-3-azabicyclo[3.1.1]heptane-2,4-dione (1 equiv), purged with nitrogen, and sealed. DIPEA (1.5 equiv) and DMF (0.3M solution) are added, and the reaction is heated to 100° C. Upon completion of the reaction, the reaction mixture is cooled to room temperature and concentrated under reduced pressure. The crude mixture is purified by silica gel column chromatography to provide 1-((2-nitrophenyl)amino)-3-azabicyclo[3.1.1]heptane-2,4-dione.

Step 2: Preparation of 1-((2-Aminophenyl)amino)-3-azabicyclo[3.1.1]heptane-2,4-dione A solution of 1-((2-nitrophenyl)amino)-3-azabicyclo[3.1.1]heptane-2,4-dione in anhydrous ethanol is purged with nitrogen. Palladium on carbon (0.1 equiv by weight) is added, and the solution is purged again with nitrogen. The solution and flask are then purged with hydrogen, and a balloon of hydrogen is affixed to the top of the flask. Upon completion of the reaction, the solution is purged with nitrogen and filtered through a pad of celite, and the filter cake is washed with 1:1 $CH_2Cl_2$/MeOH. The filtrate is concentrated under reduced pressure, and the crude residue is purified by silica gel column chromatography to provide 1-((2-aminophenyl)amino)-3-azabicyclo[3.1.1]heptane-2,4-dione.

Step 3: Preparation of 1-(2-Oxo-2,3-dihydro-1H-benzo[d]imidazol-1-yl)-3-azabicyclo[3.1.1]heptane-2,4-dione To a solution of 1-((2-aminophenyl)amino)-3-azabicyclo[3.1.1]heptane-2,4-dione (1 equiv) in THF is added triethylamine (2.5 equiv) and carbonyldiimidazole (1.0 equiv) sequentially, and the reaction mixture is heated to 60° C. Upon consumption of the starting material, the reaction is concentrated under reduced pressure. The crude mixture is purified by silica gel column chromatography to provide 1-(2-oxo-2,3-dihydro-1H-benzo[d]imidazol-1-yl)-3-azabicyclo[3.1.1]heptane-2,4-dione.

Example 11: Synthesis of 1-(1H-benzo[d]imidazol-1-yl)-3-azabicyclo[3.1.1]heptane-2,4-dione

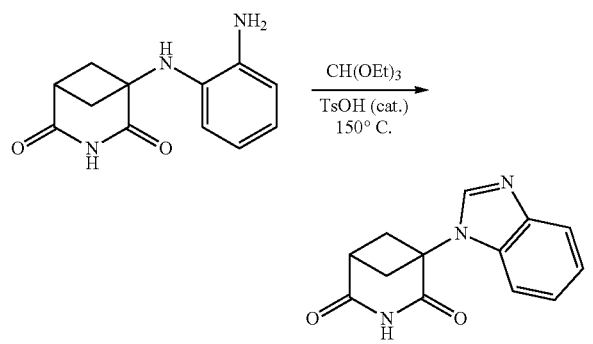

A reaction vial is charged with 1-((2-aminophenyl)amino)-3-azabicyclo[3.1.1]heptane-2,4-dione (1 equiv), TsOH (0.1 equiv), and triethylorthoformate (0.3 M solution), and the reaction mixture is heated to 150° C. Upon consumption of the starting material, the reaction is concentrated under reduced pressure. The crude mixture is purified by silica gel column chromatography to provide 1-(1H-benzo[d]imidazol-1-yl)-3-azabicyclo[3.1.1]heptane-2,4-dione.

Example 12: Synthesis of 1-(2-Oxopiperazin-1-yl)-3-azabicyclo[3.1.1]heptane-2,4-dione

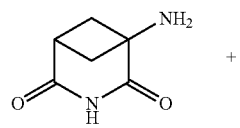

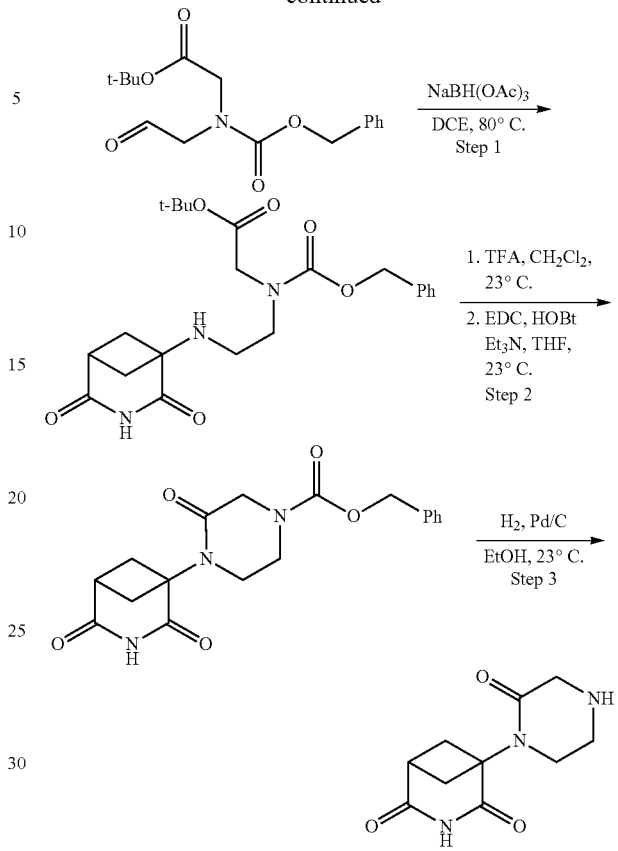

Step 1: Preparation of Tert-butyl N-((benzyloxy)carbonyl)-N-(2-((2,4-dioxo-3-azabicyclo[3.1.1]heptan-1-yl)amino)ethyl)glycinate To a solution of 1-amino-3-azabicyclo[3.1.1]heptane-2,4-dione (1 equiv) and tert-butyl N-((benzyloxy)carbonyl)-N-(2-oxoethyl)glycinate (1 equiv, see *Tetrahedron* 1993, 49, 3479) in anhydrous 1,2-dichloroethane is added sodium triacetoxyborohydride (2 equiv), and the reaction mixture is heated to 80° C. Upon consumption of the starting material, the reaction is concentrated under reduced pressure. The crude mixture is purified by silica gel column chromatography to provide tert-butyl N-((benzyloxy)carbonyl)-N-(2-((2,4-dioxo-3-azabicyclo[3.1.1]heptan-1-yl)amino)ethyl)glycinate.

Step 2: Preparation of Benzyl 4-(2,4-Dioxo-3-azabicyclo[3.1.1]heptan-1-yl)-3-oxopiperazine-1-carboxylate A solution of tert-butyl N-((benzyloxy)carbonyl)-N-(2-((2,4-dioxo-3-azabicyclo[3.1.1]heptan-1-yl)amino)ethyl)glycinate in $CH_2Cl_2$ is treated with trifluoroacetic acid (20 equiv) at room temperature. Upon consumption of the starting material, the reaction mixture is azeotroped with toluene three times. The crude residue is then brought up in THF (0.3 M solution), and EDC (1.2 equiv), triethylamine (1 equiv), and HOBt (0.2 equiv) are added. Upon consumption of the starting material, the reaction mixture is concentrated under reduced pressure. The crude mixture is purified by silica gel column chromatography to provide benzyl 4-(2,4-dioxo-3-azabicyclo[3.1.1]heptan-1-yl)-3-oxopiperazine-1-carboxylate.

Step 3: Preparation of 1-(2-Oxopiperazin-1-yl)-3-azabicyclo[3.1.1]heptane-2,4-dione A solution of benzyl 4-(2,4-dioxo-3-azabicyclo[3.1.1]heptan-1-yl)-3-oxopiperazine-1-carboxylate in anhydrous ethanol is purged with nitrogen. Palladium on carbon (0.1 equiv by weight) is added, and the solution is purged again with nitrogen. The solution and flask are then purged with hydrogen, and a balloon of hydrogen is affixed to the top of the flask. Upon completion of the reaction, the solution is purged with nitrogen and filtered through a pad of celite, and the filter cake is washed with 1:1 CH$_2$Cl$_2$/MeOH. The filtrate is concentrated under reduced pressure, and the crude residue is purified by silica gel column chromatography to provide 1-(2-oxopiperazin-1-yl)-3-azabicyclo[3.1.1]heptane-2,4-dione.

Example 13: Synthesis of 1-(2-Oxo-5-phenyloxazolidin-3-yl)-3-azabicyclo[3.1.1]heptane-2,4-dione

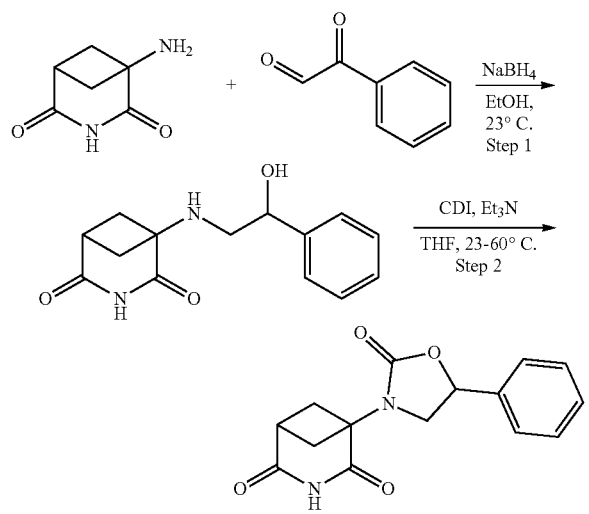

Step 1: Preparation of 1-((2-Hydroxy-2-phenylethyl)amino)-3-azabicyclo[3.1.1]heptane-2,4-dione A solution of 1-amino-3-azabicyclo[3.1.1]heptane-2,4-dione (1 equiv) and 2-oxo-2-phenylacetaldehyde (1 equiv) is mixed in ethanol (0.3M solution) until both starting materials are consumed. Sodium borohydride is then added, and the reaction mixture is stirred at room temperature. Upon completion of the reaction, the mixture is concentrated under reduced pressure and adsorbed onto silica gel. The crude mixture is purified by silica gel column chromatography to provide 1-((2-hydroxy-2-phenylethyl)amino)-3-azabicyclo[3.1.1]heptane-2,4-dione.

Step 2: Preparation of 1-(2-Oxo-5-phenyloxazolidin-3-yl)-3-azabicyclo[3.1.1]heptane-2,4-dione To a solution of 1-((2-hydroxy-2-phenylethyl)amino)-3-azabicyclo[3.1.1]heptane-2,4-dione (1 equiv) in THF is added triethylamine (2.5 equiv) and carbonyldiimidazole (1.0 equiv) sequentially, and the reaction is heated to 60° C. Upon consumption of the starting material, the reaction is cooled to room temperature and concentrated under reduced pressure. The crude residue is purified by silica gel column chromatography to provide 1-(2-oxo-5-phenyloxazolidin-3-yl)-3-azabicyclo[3.1.1]heptane-2,4-dione.

Example 14: Synthesis of 1-(2-Oxo-4-phenylimidazolidin-1-yl)-3-azabicyclo[3.1.1]heptane-2,4-dione

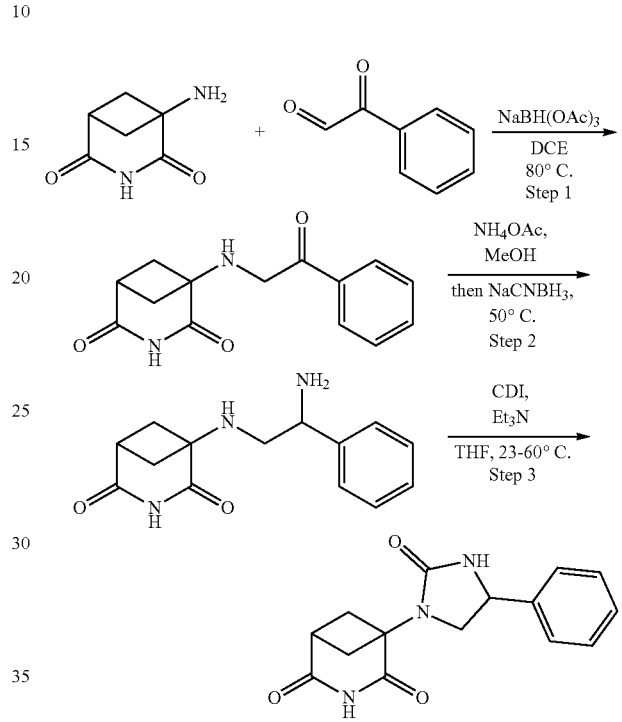

Step 1: Preparation of 1-((2-Oxo-2-phenylethyl)amino)-3-azabicyclo[3.1.1]heptane-2,4-dione To a solution of 1-amino-3-azabicyclo[3.1.1]heptane-2,4-dione (1 equiv) and 2-oxo-2-phenylacetaldehyde (1 equiv) in anhydrous 1,2-dichloroethane is added sodium triacetoxyborohydride (2 equiv), and the reaction mixture is heated to 80° C. Upon consumption of the starting material, the reaction mixture is concentrated under reduced pressure. The crude mixture is purified by silica gel column chromatography to provide 1-((2-oxo-2-phenylethyl)amino)-3-azabicyclo[3.1.1]heptane-2,4-dione.

Step 2: Preparation of 1-((2-Amino-2-phenylethyl)amino)-3-azabicyclo[3.1.1]heptane-2,4-dione A solution of 1-((2-oxo-2-phenylethyl)amino)-3-azabicyclo[3.1.1]heptane-2,4-dione (1 equiv) and ammonium acetate (10 equiv) in methanol is mixed for one hour. Sodium cyanoborohydride (1.4 equiv) is then added, and the reaction is heated to 40° C. Upon completion of the reaction, the solution is treated with aqueous 6M sodium hydroxide (1.4 equiv), stirred for one hour, and then neutralized with 6M hydrochloric acid (1.4 equiv). The reaction mixture is concentrated under reduced pressure. The crude residue is purified by silica gel column chromatography to provide 1-((2-amino-2-phenylethyl)amino)-3-azabicyclo[3.1.1]heptane-2,4-dione.

Step 3: Preparation of 1-(2-Oxo-4-phenylimidazolidin-1-yl)-3-azabicyclo[3.1.1]heptane-2,4-dione To a solution of 1-((2-amino-2-phenylethyl)amino)-3-azabicyclo[3.1.1]heptane-2,4-dione (1 equiv) in THF is added triethylamine (2.5 equiv) and carbonyldiimidazole (1.0 equiv) sequentially, and the reaction mixture is then heated to 60° C. Upon consumption of the starting material, the reaction mixture is concentrated under reduced pressure. The crude residue is purified by silica gel column chromatography to provide 1-(2-oxo-4-phenylimidazolidin-1-yl)-3-azabicyclo[3.1.1]heptane-2,4-dione.

Example 15: Synthesis of 1-(5-Amino-2-methyl-4-oxoquinazolin-3(4H)-yl)-3-azabicyclo[3.1.1]heptane-2,4-dione

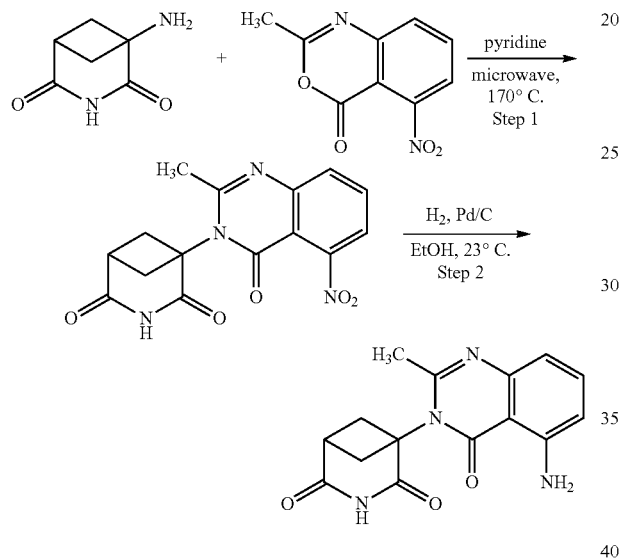

Step 1: Preparation of 1-(2-Methyl-5-nitro-4-oxoquinazolin-3(4H)-yl)-3-azabicyclo[3.1.1]heptane-2,4-dione A solution of 1-amino-3-azabicyclo[3.1.1]heptane-2,4-dione (1 equiv), 2-methyl-5-nitro-4H-benzo[d][1,3]oxazin-4-one (1 equiv), and pyridine (30 volume equiv) is heated to 170° C. in a microwave reactor. Upon consumption of the starting materials, the reaction mixture is concentrated under reduced pressure. The crude residue is purified by silica gel column chromatography to provide 1-(2-methyl-5-nitro-4-oxoquinazolin-3 (4H)-yl)-3-azabicyclo[3.1.1]heptane-2,4-dione.

Step 2: Preparation of 1-(5-Amino-2-methyl-4-oxoquinazolin-3(4H)-yl)-3-azabicyclo[3.1.1]heptane-2,4-dione A solution of 1-(2-methyl-5-nitro-4-oxoquinazolin-3 (4H)-yl)-3-azabicyclo[3.1.1]heptane-2,4-dione in anhydrous ethanol is purged with nitrogen. Palladium on carbon (0.1 equiv by weight) is added, and the solution is purged again with nitrogen. The solution and flask are then purged with hydrogen, and a balloon of hydrogen is affixed to the top of the flask. Upon completion of the reaction, the solution is purged with nitrogen and filtered through a pad of celite, and the filter cake is washed with 1:1 $CH_2Cl_2$/MeOH. The filtrate is concentrated under reduced pressure, and the crude residue is purified by silica gel column chromatography to provide 1-(5-amino-2-methyl-4-oxoquinazolin-3 (4H)-yl)-3-azabicyclo[3.1.1]heptane-2,4-dione.

Example 16: Synthesis of 2-(1,5-Dimethyl-3-oxo-2-phenyl-2,3-dihydro-1H-pyrazol-4-yl)morpholine-3,5-dione

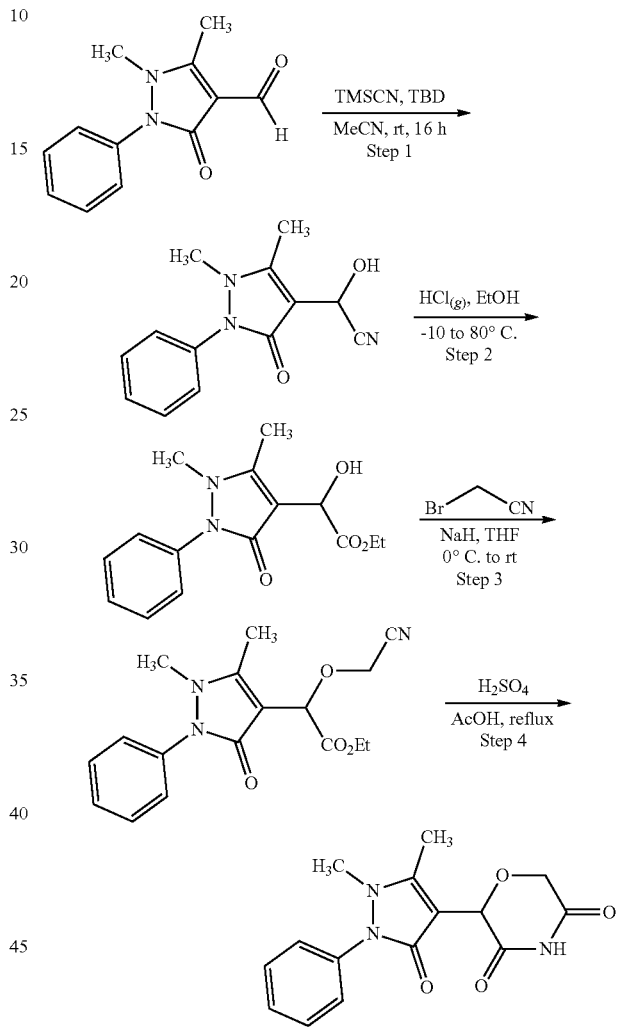

Step 1: Preparation of 2-(1,5-Dimethyl-3-oxo-2-phenyl-2,3-dihydro-1H-pyrazol-4-yl)-2-hydroxyacetonitrile A solution of trimethysilyl cyanide (1.1 equiv) in acetonitrile (0.1 M) is added to a solution of 1,5-dimethyl-3-oxo-2-phenyl-2,3-dihydro-1H-pyrazole-4-carbaldehyde (1 equiv) and 1,5,7-Triazabicyclo[4.4.0]dec-5-ene (1 equiv) in acetonitrile (0.1 M), and the reaction mixture is stirred for three hours. The crude mixture is diluted with 1N aqueous hydrochloric acid solution and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/ hexanes) to afford 2-(1,5-dimethyl-3-oxo-2-phenyl-2,3-dihydro-1H-pyrazol-4-yl)-2-hydroxyacetonitrile.

Step 2: Preparation of Ethyl 2-(1,5-Dimethyl-3-oxo-2-phenyl-2,3-dihydro-1H-pyrazol-4-yl)-2-hydroxyacetate A stirred solution of 2-(1,5-dimethyl-3-oxo-2-phenyl-2,3-dihydro-1H-pyrazol-4-yl)-2-hydroxyacetonitrile (1 equiv) in ethanol (0.5 M) is cooled to −10 to −5° C. Hydrogen chloride gas (prepared from sodium chloride and sulfuric acid) is introduced into the reaction mixture. The reaction is carried out at low temperature for two hours and is subsequently heated to reflux for another two hours. The mixture is cooled, and the resulting ammonium chloride is filtered off. The filtrate is distilled out, basified with saturated aqueous sodium bicarbonate solution, and diluted with ethyl acetate. The layers are separated, and the organic layer is washed with water and brine, dried over sodium sulfate, filtered, and concentrated under reduced pressure. The crude material is purified by silica gel column chromatography (0-10% ethyl acetate/hexanes) to afford ethyl 2-(1,5-dimethyl-3-oxo-2-phenyl-2,3-dihydro-1H-pyrazol-4-yl)-2-hydroxyacetate.

Step 3: Preparation of Ethyl 2-(Cyanomethoxy)-2-(1,5-dimethyl-3-oxo-2-phenyl-2,3-dihydro-1H-pyrazol-4-yl)acetate A stirred solution of ethyl 2-(1,5-dimethyl-3-oxo-2-phenyl-2,3-dihydro-1H-pyrazol-4-yl)-2-hydroxyacetate (1 equiv) in THF (0.3 M) is cooled to 0° C. Sodium hydride (60% dispersion in mineral oil, 1.2 equiv) is added in portions, and the reaction mixture is stirred for 15 minutes. A solution of 2-bromoacetonitrile (1.2 equiv) in THF (0.3 M) is added, and the mixture is stirred at room temperature for two hours. The reaction mixture is diluted with water and ethyl acetate, and the layers are separated. The organic layer is washed with brine, dried over sodium sulfate, filtered, and concentrated under reduced pressure. The crude material is purified by silica gel column chromatography (0-30% ethyl acetate/hexanes) to afford ethyl 2-(cyanomethoxy)-2-(1,5-dimethyl-3-oxo-2-phenyl-2,3-dihydro-1H-pyrazol-4-yl)acetate.

Step 4: Preparation of 2-(1,5-Dimethyl-3-oxo-2-phenyl-2,3-dihydro-1H-pyrazol-4-yl)morpholine-3,5-dione To a stirred solution of ethyl 2-(cyanomethoxy)-2-(1,5-dimethyl-3-oxo-2-phenyl-2,3-dihydro-1H-pyrazol-4-yl)acetate (1 equiv) in acetic acid (0.7 M) is added sulfuric acid (2 equiv), and the reaction mixture is heated to 110° C. for five hours. The mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to provide 2-(1,5-dimethyl-3-oxo-2-phenyl-2,3-dihydro-1H-pyrazol-4-yl)morpholine-3,5-dione.

Example 17: Synthesis of 2-(1-Methyl-1H-indazol-3-yl)morpholine-3,5-dione

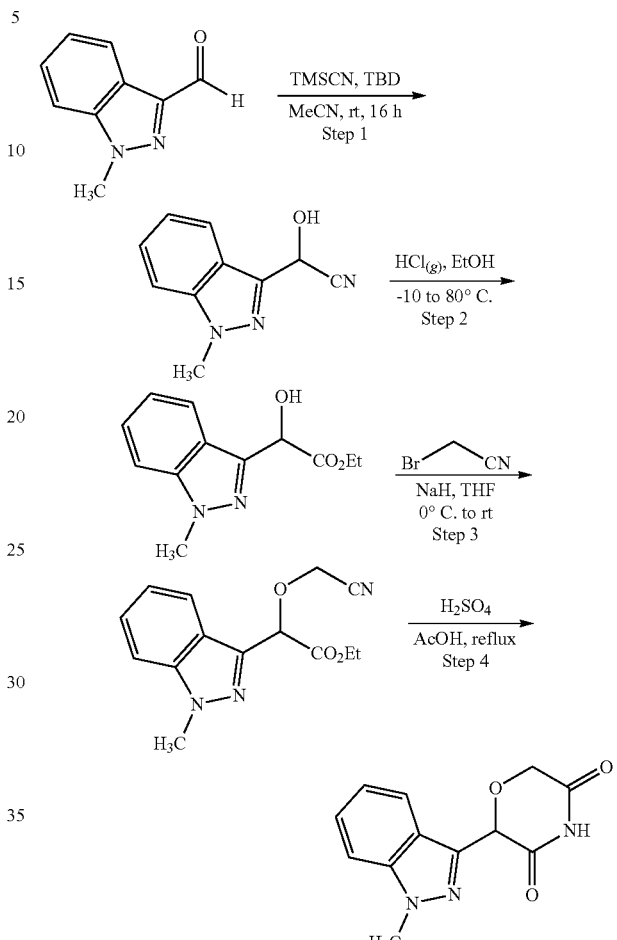

Step 1: Preparation of 2-Hydroxy-2-(1-methyl-1H-indazol-3-yl)acetonitrile

A solution of trimethylsilyl cyanide (422.41 mg, 4.26 mmol, 532.68 uL) in acetonitrile (5 mL) was added to a solution of 1-methyl-1H-indazole-3-carbaldehyde 620 mg, 3.87 mmol) and 1,5,7-triazabicyclo[4.4.0]dec-5-ene (53.88 mg, 387.09 umol), and the reaction mixture was stirred at room temperature for 3 hours. The reaction mixture was diluted with 1N aqueous hydrochloric acid solution and ethyl acetate followed by addition of saturated aqueous sodium bicarbonate solution, and the layers were separated. The organic layer was washed with brine, dried over sodium sulfate, filtered, and concentrated under reduced pressure. The crude material was purified by silica gel column chromatography (0-50% ethyl acetate/hexanes) to provide 2-hydroxy-2-(1-methyl-1H-indazol-3-yl)acetonitrile 9520 mg, 2.78 mmol, 71.76% yield) as a yellow solid. LC MS (ES+): 188.

Step 2: Preparation of Ethyl 2-Hydroxy-2-(1-methyl-1H-indazol-3-yl)acetate

A stirred solution of 2-hydroxy-2-(1-methyl-1H-indazol-3-yl)acetonitrile (520 mg, 2.78 mmol) in ethanol (5 mL) was cooled to −10 to −5° C. Hydrogen chloride gas (prepared from sodium chloride and sulfuric acid) was introduced into the reaction mixture. The reaction was carried out at low temperature for two hours and subsequently was heated to reflux for another two hours. The mixture was cooled, and the resulting ammonium chloride was filtered off. The filtrate was distilled out, basified with saturated aqueous sodium bicarbonate solution, and diluted with ethyl acetate. The layers were separated, and the organic layer was washed with water and brine, dried over sodium sulfate, filtered, and concentrated under reduced pressure. The crude material was purified by silica gel column chromatography (0-10% ethyl acetate/hexanes) to afford ethyl 2-hydroxy-2-(1-methyl-1H-indazol-3-yl)acetate (500 mg, 2.13 mmol, 76.84% yield) as a colorless liquid. LC MS (ES+): 235.2

Step 3: Preparation of Ethyl 2-(Cyanomethoxy)-2-(1-methyl-1H-indazol-3-yl)acetate A stirred solution of ethyl 2-hydroxy-2-(1-methyl-1H-indazol-3-yl)acetate (500 mg, 2.13 mmol) in THF (6 mL) was cooled to 0° C. Sodium hydride (60% dispersion in mineral oil, 98.14 mg, 2.56 mmol) was added in portions, and the reaction mixture was stirred for 15 minutes. A solution of 2-bromoacetonitrile (1.2 equiv) in THF (0.3 M) was added, and the mixture was stirred at room temperature for two hours. The reaction mixture was diluted with water and ethyl acetate, and the layers were separated. The organic layer was washed with brine, dried over sodium sulfate, filtered, and concentrated under reduced pressure. The crude material was purified by silica gel column chromatography (0-30% ethyl acetate/hexanes) to afford ethyl 2-(cyanomethoxy)-2-(1-methyl-1H-indazol-3-yl)acetate (120 mg, 439.10 umol, 20.57% yield) as a red liquid. LC MS (ES+): 274.2.

Step 4: Preparation of 2-(1-Methyl-1H-indazol-3-yl)morpholine-3,5-dione

To a stirred solution of ethyl 2-(cyanomethoxy)-2-(1-methyl-1H-indazol-3-yl)acetate (100.0 mg, 365.92 umol) in acetic acid (532.19 uL) was added sulfuric acid (71.78 mg, 731.83 umol, 39.01 uL), and the reaction mixture was heated to 110° C. for five hours. The mixture was cooled to room temperature and concentrated under reduced pressure. The crude residue was diluted with ethyl acetate and saturated aqueous sodium bicarbonate solution, and the layers were separated. The organic layer was washed with water and brine, dried over sodium sulfate, filtered, and concentrated under reduced pressure. The crude material was purified by silica gel column chromatography (1.5% methanol/dichloromethane) to 2-(1-methyl-1H-indazol-3-yl)morpholine-3,5-dione (8.0 mg, 32.62 umol, 8.92% yield) as a yellow solid. $^1$H NMR (400 MHz, DMSO-d$_6$) δ 11.68 (s, 1H), 7.72-7.66 (m, 2H), 7.44 (t, J=7.24 Hz, 1H), 7.18 (t, J=7.44 Hz, 1H), 5.88 (s, 1H), 4.45 (d, J=16.64 Hz, 1H), 4.28 (d, J=16.64 Hz, 1H); LC MS (ES+): 246.0.

Example 18: Synthesis of 2-(Imidazo[1,5-a]pyridin-3-yl)morpholine-3,5-dione

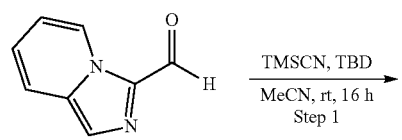

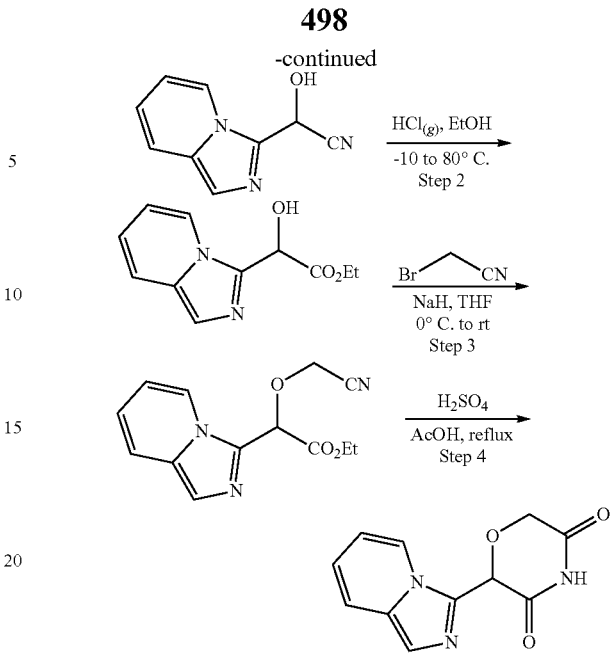

Step 1: Preparation of 2-Hydroxy-2-(imidazo[1,5-a]pyridin-3-yl)acetonitrile

A solution of trimethysilylcyanide (1.1 equiv) in acetonitrile (0.1 M) is added to a solution of imidazo[1,5-a]pyridine-3-carbaldehyde (1 equiv) and 1,5,7-Triazabicyclo[4.4.0]dec-5-ene (1 equiv) in acetonitrile (0.1 M), and the reaction mixture is stirred for three hours. The crude mixture is diluted with 1N aqueous hydrochloric acid solution and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/hexanes) to afford 2-hydroxy-2-(imidazo[1,5-a]pyridin-3-yl)acetonitrile.

Step 2: Preparation of Ethyl 2-Hydroxy-2-(imidazo[1,5-a]pyridin-3-yl)acetate

A stirred solution of 2-hydroxy-2-(imidazo[1,5-a]pyridin-3-yl)acetonitrile (1 equiv) in ethanol (0.5 M) is cooled to −10 to −5° C. Hydrogen chloride gas (prepared from sodium chloride and sulfuric acid) is introduced into the reaction mixture. The reaction is carried out at low temperature for two hours and is subsequently heated to reflux for another two hours. The mixture is cooled, and the resulting ammonium chloride is filtered off. The filtrate is distilled out, basified with saturated aqueous sodium bicarbonate solution, and diluted with ethyl acetate. The layers are separated, and the organic layer is washed with water and brine, dried over sodium sulfate, filtered, and concentrated under reduced pressure. The crude material is purified by silica gel column chromatography (0-10% ethyl acetate/hexanes) to afford ethyl 2-hydroxy-2-(imidazo[1,5-a]pyridin-3-yl)acetate.

Step 3: Preparation of Ethyl 2-(Cyanomethoxy)-2-(imidazo[1,5-a]pyridin-3-yl)acetate A stirred solution of ethyl 2-hydroxy-2-(imidazo[1,5-a]pyridin-3-yl)acetate (1 equiv) in THF (0.3 M) is cooled to 0°

C. Sodium hydride (60% dispersion in mineral oil, 1.2 equiv) is added in portions, and the reaction mixture is stirred for 15 minutes. A solution of 2-bromoacetonitrile (1.2 equiv) in THF (0.3 M) is added, and the mixture is stirred at room temperature for two hours. The reaction mixture is diluted with water and ethyl acetate, and the layers are separated. The organic layer is washed with brine, dried over sodium sulfate, filtered, and concentrated under reduced pressure. The crude material is purified by silica gel column chromatography (0-30% ethyl acetate/hexanes) to afford ethyl 2-(cyanomethoxy)-2-(imidazo[1,5-a]pyridin-3-yl)acetate.

Step 4: Preparation of 2-(Imidazo[1,5-a]pyridin-3-yl)morpholine-3,5-dione

To a stirred solution of ethyl 2-(cyanomethoxy)-2-(imidazo[1,5-a]pyridin-3-yl)acetate (1 equiv) in acetic acid (0.7 M) is added sulfuric acid (2 equiv), and the reaction mixture is heated to 110° C. for five hours. The mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to provide 2-(imidazo[1,5-a]pyridin-3-yl)morpholine-3,5-dione.

Example 19: Synthesis of 2-(1-Methyl-5-phenyl-1H-pyrazol-3-yl)morpholine-3,5-dione

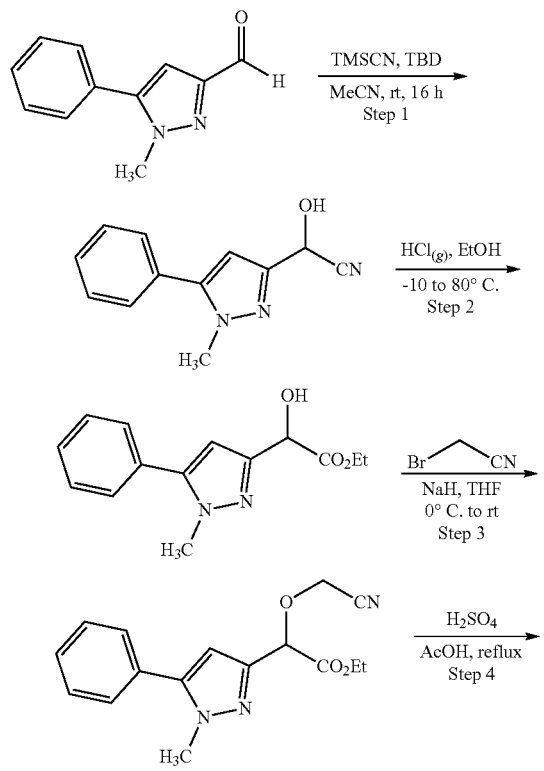

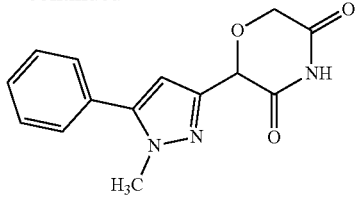

Step 1: Preparation of 2-Hydroxy-2-(1-methyl-5-phenyl-1H-pyrazol-3-yl)acetonitrile A solution of trimethysilylcyanide (1.1 equiv) in acetonitrile (0.1 M) is added to a solution of 1-methyl-5-phenyl-1H-pyrazole-3-carbaldehyde (1 equiv) and 1,5,7-Triazabicyclo[4.4.0]dec-5-ene (1 equiv) in acetonitrile (0.1 M), and the reaction mixture is stirred for three hours. The crude mixture is diluted with 1N aqueous hydrochloric acid solution and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/hexanes) to afford 2-hydroxy-2-(1-methyl-5-phenyl-1H-pyrazol-3-yl)acetonitrile.

Step 2: Preparation of Ethyl 2-Hydroxy-2-(1-methyl-5-phenyl-1H-pyrazol-3-yl)acetate A stirred solution of 2-hydroxy-2-(1-methyl-5-phenyl-1H-pyrazol-3-yl)acetonitrile (1 equiv) in ethanol (0.5 M) is cooled to −10 to −5° C. Hydrogen chloride gas (prepared from sodium chloride and sulfuric acid) is introduced into the reaction mixture. The reaction is carried out at low temperature for two hours and is subsequently heated to reflux for another two hours. The mixture is cooled, and the resulting ammonium chloride is filtered off. The filtrate is distilled out, basified with saturated aqueous sodium bicarbonate solution, and diluted with ethyl acetate. The layers are separated, and the organic layer is washed with water and brine, dried over sodium sulfate, filtered, and concentrated under reduced pressure. The crude material is purified by silica gel column chromatography (0-10% ethyl acetate/hexanes) to afford ethyl 2-hydroxy-2-(1-methyl-5-phenyl-1H-pyrazol-3-yl)acetate.

Step 3: Preparation of Ethyl 2-(Cyanomethoxy)-2-(1-methyl-5-phenyl-1H-pyrazol-3-yl)acetate A stirred solution of ethyl 2-hydroxy-2-(1-methyl-5-phenyl-1H-pyrazol-3-yl)acetate (1 equiv) in THF (0.3 M) is cooled to 0° C. Sodium hydride (60% dispersion in mineral oil, 1.2 equiv) is added in portions, and the reaction mixture is stirred for 15 minutes. A solution of 2-bromoacetonitrile (1.2 equiv) in THF (0.3 M) is added, and the mixture is stirred at room temperature for two hours. The reaction mixture is diluted with water and ethyl acetate, and the layers are separated. The organic layer is washed with brine, dried over sodium sulfate, filtered, and concentrated under reduced pressure. The crude material is purified by silica gel column chromatography (0-30% ethyl acetate/hexanes) to afford ethyl 2-(cyanomethoxy)-2-(1-methyl-5-phenyl-1H-pyrazol-3-yl)acetate.

Step 4: Preparation of 2-(1-Methyl-5-phenyl-1H-pyrazol-3-yl)morpholine-3,5-dione To a stirred solution of ethyl 2-(cyanomethoxy)-2-(1-methyl-5-phenyl-1H-pyrazol-3-yl)acetate (1 equiv) in acetic acid (0.7 M) is added sulfuric acid (2 equiv), and the reaction mixture is heated to 110° C. for five hours. The mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to provide 2-(1-methyl-5-phenyl-1H-pyrazol-3-yl)morpholine-3,5-dione.

Example 20: Synthesis of 2-(1-Methyl-1H-1,2,3-triazol-4-yl)morpholine-3,5-dione

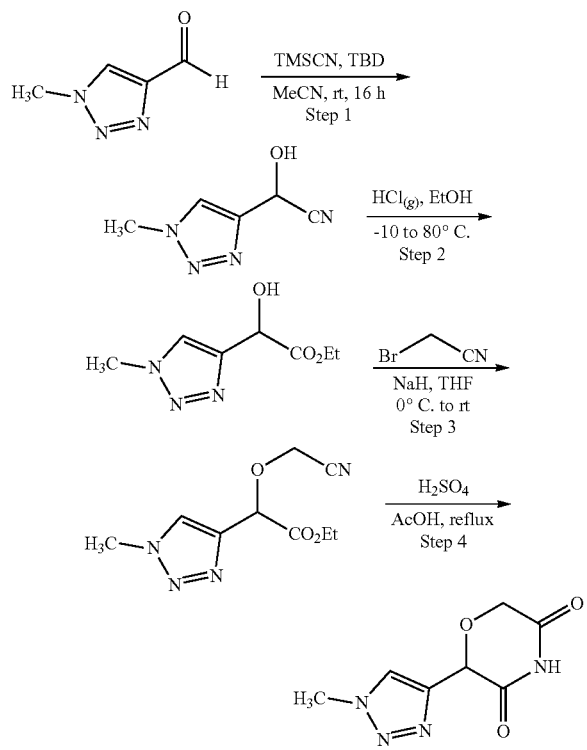

Step 1: Preparation of 2-Hydroxy-2-(1-methyl-1H-1,2,3-triazol-4-yl)acetonitrile A solution of trimethysilylcyanide (1.1 equiv) in acetonitrile (0.1 M) is added to a solution of 1-methyl-1H-1,2,3-triazole-4-carbaldehyde (1 equiv) and 1,5,7-Triazabicyclo[4.4.0]dec-5-ene (1 equiv) in acetonitrile (0.1 M), and the reaction mixture is stirred for three hours. The crude mixture is diluted with 1N aqueous hydrochloric acid solution and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/hexanes) to afford 2-hydroxy-2-(1-methyl-1H-1,2,3-triazol-4-yl)acetonitrile.

Step 2: Preparation of Ethyl 2-Hydroxy-2-(1-methyl-1H-1,2,3-triazol-4-yl)acetate A stirred solution of 2-hydroxy-2-(1-methyl-1H-1,2,3-triazol-4-yl)acetonitrile (1 equiv) in ethanol (0.5 M) is cooled to −10 to −5° C. Hydrogen chloride gas (prepared from sodium chloride and sulfuric acid) is introduced into the reaction mixture. The reaction is carried out at low temperature for two hours and is subsequently heated to reflux for another two hours. The mixture is cooled, and the resulting ammonium chloride is filtered off. The filtrate is distilled out, basified with saturated aqueous sodium bicarbonate solution, and diluted with ethyl acetate. The layers are separated, and the organic layer is washed with water and brine, dried over sodium sulfate, filtered, and concentrated under reduced pressure. The crude material is purified by silica gel column chromatography (0-10% ethyl acetate/hexanes) to afford ethyl 2-hydroxy-2-(1-methyl-1H-1,2,3-triazol-4-yl)acetate.

Step 3: Preparation of Ethyl 2-(Cyanomethoxy)-2-(1-methyl-1H-1,2,3-triazol-4-yl)acetate A stirred solution of ethyl 2-hydroxy-2-(1-methyl-1H-1,2,3-triazol-4-yl)acetate (1 equiv) in THF (0.3 M) is cooled to 0° C. Sodium hydride (60% dispersion in mineral oil, 1.2 equiv) is added in portions, and the reaction mixture is stirred for 15 minutes. A solution of 2-bromoacetonitrile (1.2 equiv) in THF (0.3 M) is added, and the mixture is stirred at room temperature for two hours. The reaction mixture is diluted with water and ethyl acetate, and the layers are separated. The organic layer is washed with brine, dried over sodium sulfate, filtered, and concentrated under reduced pressure. The crude material is purified by silica gel column chromatography (0-30% ethyl acetate/hexanes) to afford ethyl 2-(cyanomethoxy)-2-(1-methyl-1H-1,2,3-triazol-4-yl)acetate.

Step 4: Preparation of 2-(1-Methyl-1H-1,2,3-triazol-4-yl)morpholine-3,5-dione To a stirred solution of ethyl 2-(cyanomethoxy)-2-(1-methyl-1H-1,2,3-triazol-4-yl)acetate (1 equiv) in acetic acid (0.7 M) is added sulfuric acid (2 equiv), and the reaction mixture is heated to 110° C. for five hours. The mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to provide 2-(1-methyl-1H-1,2,3-triazol-4-yl)morpholine-3,5-dione.

Example 21: Synthesis of 2-(1-Methyl-1H-benzo[d]imidazol-2-yl)morpholine-3,5-dione

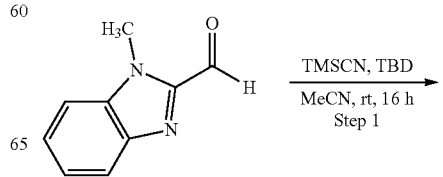

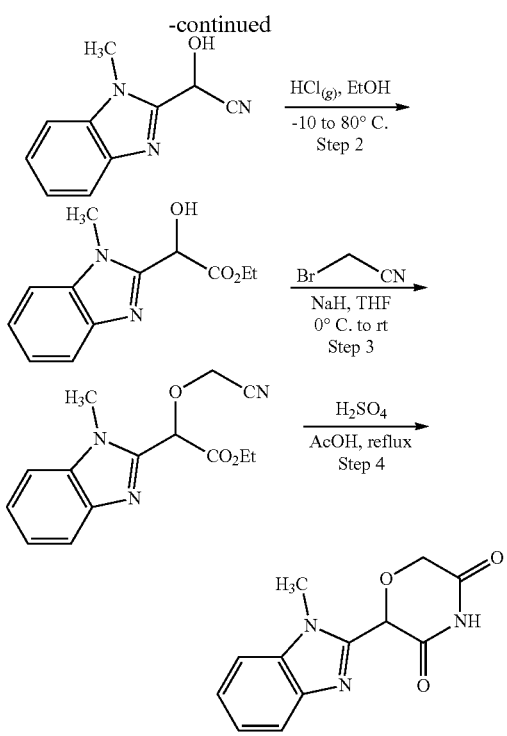

Step 1: Preparation of 2-Hydroxy-2-(1-methyl-1H-benzo[d]imidazol-2-yl)acetonitrile A solution of trimethysilylcyanide (1.1 equiv) in acetonitrile (0.1 M) is added to a solution of 1-methyl-1H-benzo[d]imidazole-2-carbaldehyde (1 equiv) and 1,5,7-Triazabicyclo[4.4.0]dec-5-ene (1 equiv) in acetonitrile (0.1 M), and the reaction mixture is stirred for three hours. The crude mixture is diluted with 1N aqueous hydrochloric acid solution and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/hexanes) to afford 2-hydroxy-2-(1-methyl-1H-benzo[d]imidazol-2-yl)acetonitrile.

Step 2: Preparation of Ethyl 2-Hydroxy-2-(1-methyl-1H-benzo[d]imidazol-2-yl)acetate A stirred solution 2-hydroxy-2-(1-methyl-1H-benzo[d]imidazol-2-yl)acetonitrile (1 equiv) in ethanol (0.5 M) is cooled to −10 to −5° C. Hydrogen chloride gas (prepared from sodium chloride and sulfuric acid) is introduced into the reaction mixture. The reaction is carried out at low temperature for two hours and is subsequently heated to reflux for another two hours. The mixture is cooled, and the resulting ammonium chloride is filtered off. The filtrate is distilled out, basified with saturated aqueous sodium bicarbonate solution, and diluted with ethyl acetate. The layers are separated, and the organic layer is washed with water and brine, dried over sodium sulfate, filtered, and concentrated under reduced pressure. The crude material is purified by silica gel column chromatography (0-10% ethyl acetate/hexanes) to afford ethyl 2-hydroxy-2-(1-methyl-1H-benzo[d]imidazol-2-yl)acetate.

Step 3: Preparation of Ethyl 2-(Cyanomethoxy)-2-(1-methyl-1H-benzo[d]imidazol-2-yl)acetate A stirred solution of ethyl 2-hydroxy-2-(1-methyl-1H-benzo[d]imidazol-2-yl)acetate (1 equiv) in THF (0.3 M) is cooled to 0° C. Sodium hydride (60% dispersion in mineral oil, 1.2 equiv) is added in portions, and the reaction mixture is stirred for 15 minutes. A solution of 2-bromoacetonitrile (1.2 equiv) in THF (0.3 M) is added, and the mixture is stirred at room temperature for two hours. The reaction mixture is diluted with water and ethyl acetate, and the layers are separated. The organic layer is washed with brine, dried over sodium sulfate, filtered, and concentrated under reduced pressure. The crude material is purified by silica gel column chromatography (0-30% ethyl acetate/hexanes) to afford ethyl 2-(cyanomethoxy)-2-(1-methyl-1H-benzo[d]imidazol-2-yl)acetate.

Step 4: Preparation of 2-(1-Methyl-1H-benzo[d]imidazol-2-yl)morpholine-3,5-dione To a stirred solution ethyl 2-(cyanomethoxy)-2-(1-methyl-1H-benzo[d]imidazol-2-yl)acetate (1 equiv) in acetic acid (0.7 M) is added sulfuric acid (2 equiv), and the reaction mixture is heated to 110° C. for five hours. The mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to 2-(1-methyl-1H-benzo[d]imidazol-2-yl)morpholine-3,5-dione.

Example 22: Synthesis of 2-(2-Methylpyrimidin-4-yl)morpholine-3,5-dione

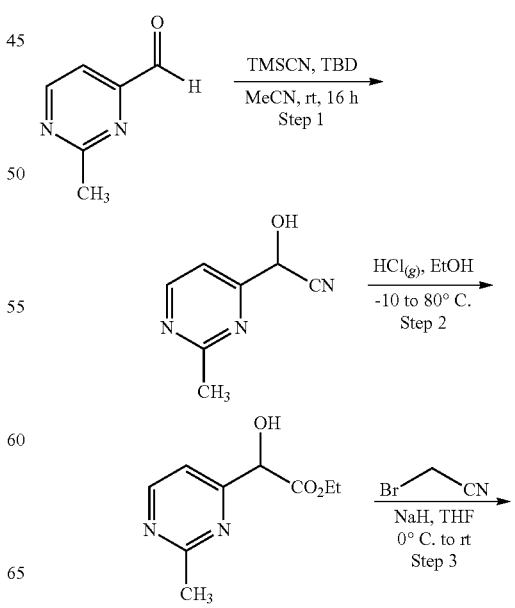

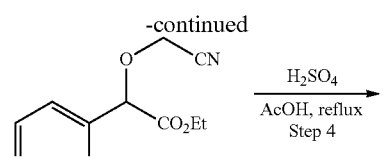

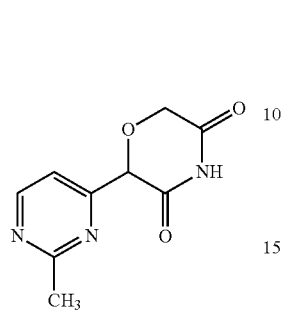

Step 1: Preparation of 2-Hydroxy-2-(2-ethylpyrimidin-4-yl)acetonitrile

A solution of trimethysilylcyanide (1.1 equiv) in acetonitrile (0.1 M) is added to a solution of 2-methylpyrimidine-4-carbaldehyde (1 equiv) and 1,5,7-Triazabicyclo[4.4.0]dec-5-ene (1 equiv) in acetonitrile (0.1 M), and the reaction mixture is stirred for three hours. The crude mixture is diluted with 1N aqueous hydrochloric acid solution and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/hexanes) to afford 2-hydroxy-2-(2-methylpyrimidin-4-yl)acetonitrile.

Step 2: Preparation of Ethyl 2-Hydroxy-2-(2-methylpyrimidin-4-yl)acetate

A stirred solution 2-hydroxy-2-(2-methylpyrimidin-4-yl)acetonitrile (1 equiv) in ethanol (0.5 M) is cooled to −10 to −5° C. Hydrogen chloride gas (prepared from sodium chloride and sulfuric acid) is introduced into the reaction mixture. The reaction is carried out at low temperature for two hours and is subsequently heated to reflux for another two hours. The mixture is cooled, and the resulting ammonium chloride is filtered off. The filtrate is distilled out, basified with saturated aqueous sodium bicarbonate solution, and diluted with ethyl acetate. The layers are separated, and the organic layer is washed with water and brine, dried over sodium sulfate, filtered, and concentrated under reduced pressure. The crude material is purified by silica gel column chromatography (0-10% ethyl acetate/hexanes) to afford ethyl 2-hydroxy-2-(2-methylpyrimidin-4-yl)acetate.

Step 3: Preparation of Ethyl 2-(Cyanomethoxy)-2-(2-methylpyrimidin-4-yl)acetate A stirred solution of ethyl 2-hydroxy-2-(2-methylpyrimidin-4-yl)acetate (1 equiv) in THF (0.3 M) is cooled to 0° C. Sodium hydride (60% dispersion in mineral oil, 1.2 equiv) is added in portions, and the reaction mixture is stirred for 15 minutes. A solution of 2-bromoacetonitrile (1.2 equiv) in THF (0.3 M) is added, and the mixture is stirred at room temperature for two hours. The reaction mixture is diluted with water and ethyl acetate, and the layers are separated. The organic layer is washed with brine, dried over sodium sulfate, filtered, and concentrated under reduced pressure. The crude material is purified by silica gel column chromatography (0-30% ethyl acetate/hexanes) to afford ethyl 2-(cyanomethoxy)-2-(2-methylpyrimidin-4-yl)acetate.

Step 4: Preparation of 2-(2-Methylpyrimidin-4-yl)morpholine-3,5-dione

To a stirred solution ethyl 2-(cyanomethoxy)-2-(2-methylpyrimidin-4-yl)acetate (1 equiv) in acetic acid (0.7 M) is added sulfuric acid (2 equiv), and the reaction mixture is heated to 110° C. for five hours. The mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to 2-(2-methylpyrimidin-4-yl)morpholine-3,5-dione.

Example 23: Synthesis of 3-(1-Methyl-1H-indazol-3-yl)piperazine-2,6-dione

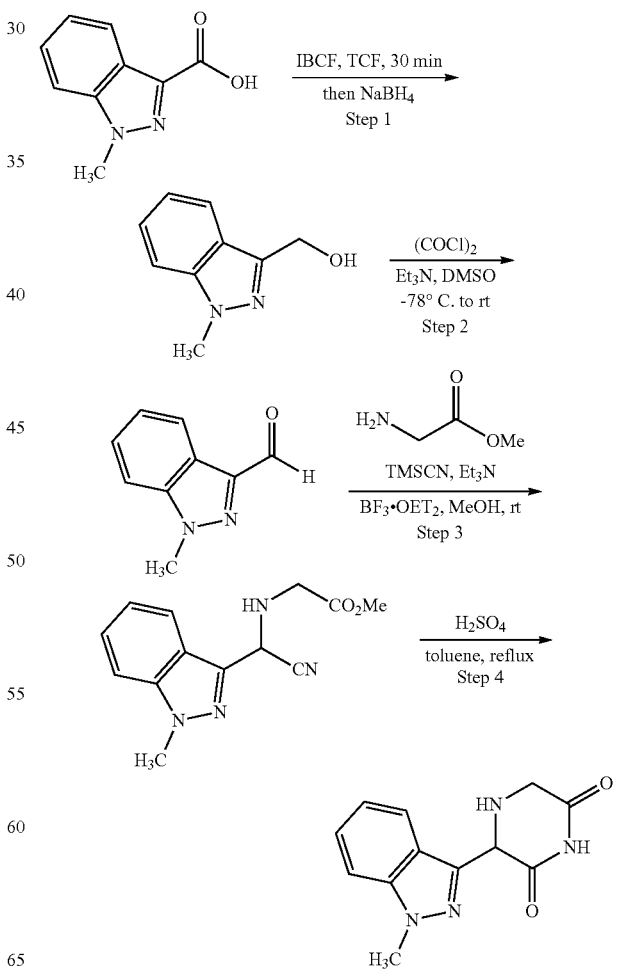

Step 1: Preparation of (1-Methyl-1H-indazol-3-yl)methanol

To a stirred solution of 1-methyl-1H-indazole-3-carboxylic acid (1 g, 5.68 mmol) in THF (15 mL) at −18° C. was added isobutyl chloroformate (852.77 mg, 6.24 mmol), and the mixture was stirred for 30 minutes. Sodium borohydride (644.24 mg, 17.03 mmol) and a few drops of water were added, and the reaction mixture was stirred for one hour. The mixture was quenched by the slow addition of 20 mL of water, and the aqueous phase was extracted with ethyl acetate. The combined organic layer was washed with brine, dried over sodium sulfate, filtered, and concentrated under reduced pressure to afford (1-methyl-1H-indazol-3-yl)methanol (500 mg, 3.08 mmol, 54.31% yield) as a colorless liquid. LC MS (ES+): 163.2.

Step 2: Preparation of 1-Methyl-1H-indazole-3-carbaldehyde

Dimethyl sulfoxide (242.80 mg, 3.11 mmol) was added to a solution of oxalyl chloride (394.42 mg, 3.11 mmol) in dichloromethane (7 mL) at −78° C., and the reaction was stirred for 20 minutes. A solution of (1-methyl-1H-indazol-3-yl)methanol (420 mg, 2.59 mmol) in dichloromethane was then added slowly to the reaction mixture, and the resultant solution was stirred for one hour. The reaction mixture was then treated with triethylamine (1.31 g, 12.95 mmol, 1.80 mL), warmed up to room temperature, and stirred for 30 minutes. The reaction mixture was diluted with dichloromethane and water, and the layers were separated. The aqueous phase was extracted with dichloromethane. The combined organic layer was washed with brine, dried over sodium sulfate, filtered, and concentrated under reduced pressure to provide 1-methyl-1H-indazole-3-carbaldehyde (300 mg, 1.87 mmol, 72.33% yield) as a gummy solid. LC MS (ES+): 161.1.

Step 3: Preparation of Methyl (Cyano(1-methyl-1H-indazol-3-yl)methyl)glycinate To a stirred solution of 1-methyl-1H-indazole-3-carbaldehyde (570 mg, 3.56 mmol) and methyl glycinate (670.21 mg, 5.34 mmol) in methanol (15 mL) at room temperature was added triethylamine (540.15 mg, 5.34 mmol), and the mixture was stirred for five minutes. Borontrifluoride diethyletherate (757.62 mg, 5.34 mmol) and trimethylsilyl cyanide (529.58 mg, 5.34 mmol) were then added. Upon consumption of the aldehyde starting material, the reaction mixture was partitioned between ethyl acetate and water. The layers were separated, and the aqueous phase was extracted with ethyl acetate. The combined organic layer was washed with brine, dried over sodium sulfate, filtered, and concentrated under reduced pressure. Purification by silica gel column chromatography provided methyl (cyano(1-methyl-1H-indazol-3-yl)methyl)glycinate (200 mg, 774.37 umol, 21.76% yield) as a yellow liquid. LC MS (ES+): 259.3.

Step 4: Preparation of 3-(1-Methyl-1H-indazol-3-yl)piperazine-2,6-dione

A solution of methyl (cyano(1-methyl-1H-indazol-3-yl)methyl)glycinate (200 mg, 774.37 umol) in toluene (1.2 mL) was treated with sulfuric acid (0.8 mL), and the mixture was heated in a sealed tube at 100° C. Upon consumption of the starting material, the reaction mixture was cooled to room temperature and partitioned between ethyl acetate and saturated aqueous sodium bicarbonate solution. The layers were separated, and the aqueous phase was extracted with ethyl acetate. The combined organic layer was washed with brine, dried over sodium sulfate, filtered, and concentrated under reduced pressure. The crude material was purified by silica gel column chromatography to afford 3-(1-methyl-1H-indazol-3-yl)piperazine-2,6-dione (12 mg, 47.66 umol, 6.15% yield) as a white solid. $^1$H NMR (400 MHz, DMSO-$d_6$) δ 11.07 (s, 1H), 7.80-7.78 (d, J=8.16 Hz, 1H), 7.63-7.61 (d, J=8.44 Hz, 1H), 7.43-7.39 (t, J=7.08 Hz, 1H), 7.16-7.12 (t, J=7.52 Hz, 1H), 5.09-5.08 (d, J=6.44 Hz, 1H), 4.00 (s, 3H), 3.70-3.68 (m, 1H), 3.48-3.47 (d, J=6.12 Hz, 1H), 3.41-3.39 (m, 1H); LC MS (ES+): 245.2.

Example 24: Synthesis of 4-Methyl-3-(1-methyl-5-phenyl-1H-pyrazol-3-yl)piperazine-2,6-dione

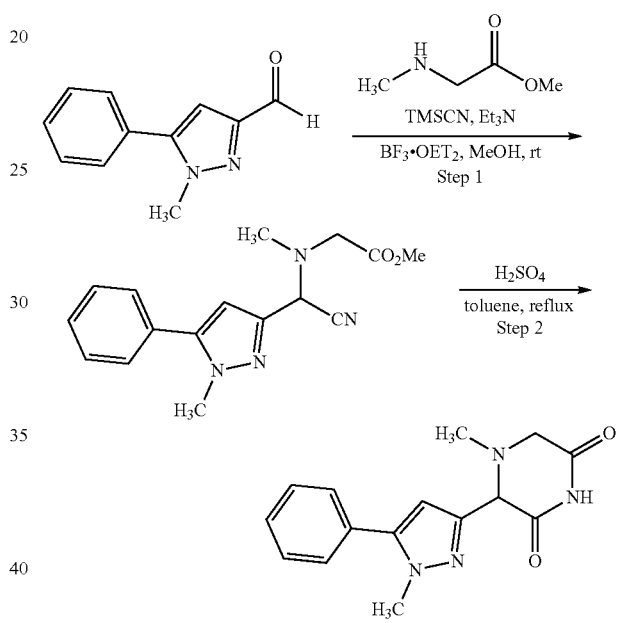

Step 1: Preparation of Methyl N-(Cyano(1-methyl-5-phenyl-1H-pyrazol-3-yl)methyl)-N-methylglycinate To a stirred solution of 1-methyl-5-phenyl-1H-pyrazole-3-carbaldehyde (1 equiv) and methyl glycinate (1.5 equiv) in methanol (0.2 M) at room temperature is added triethylamine (1.5 equiv), and the mixture is stirred for five minutes. Borontrifluoride diethyletherate (1.5 equiv) and trimethylsilyl cyanide (1.5 equiv) is then added. Upon consumption of the aldehyde starting material, the reaction mixture is partitioned between ethyl acetate and water. The layers are separated, and the aqueous phase is extracted with ethyl acetate. The combined organic layer is washed with brine, dried over sodium sulfate, filtered, and concentrated under reduced pressure. Purification by silica gel column chromatography provides methyl N-(cyano(1-methyl-5-phenyl-1H-pyrazol-3-yl)methyl)-N-methylglycinate.

Step 2: Preparation of 4-Methyl-3-(1-methyl-5-phenyl-1H-pyrazol-3-yl)piperazine-2,6-dione A solution of methyl N-(cyano(1-methyl-5-phenyl-1H-pyrazol-3-yl)methyl)-N-methylglycinate (1 equiv) in toluene (0.5 M) is treated with sulfuric acid (2 equiv), and the mixture is heated in a sealed tube at 100° C. Upon consumption of the starting material, the reaction mixture is cooled to room temperature and partitioned between ethyl acetate and saturated aqueous sodium bicarbonate solution. The layers are separated, and the aqueous phase is extracted with ethyl acetate. The combined organic layer is washed with brine, dried over sodium sulfate, filtered, and concentrated under reduced pressure. The crude material is purified by silica gel column chromatography to afford 4-methyl-3-(1-methyl-5-phenyl-1H-pyrazol-3-yl)piperazine-2,6-dione.

Example 25: Synthesis of 3-(1-Phenyl-1H-1,2,3-triazol-4-yl)piperazine-2,6-dione

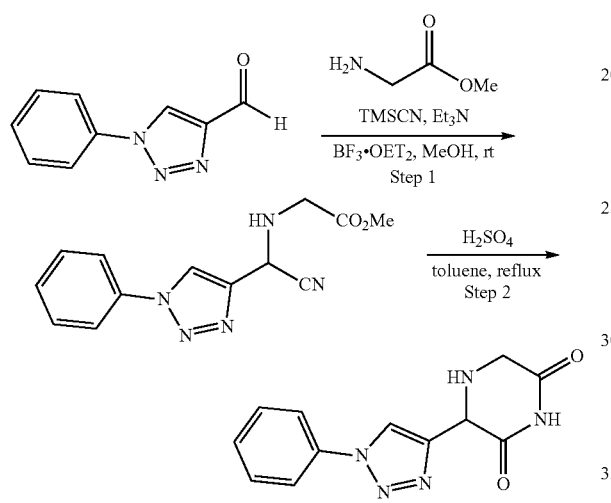

Step 1: Preparation of Methyl (Cyano(1-phenyl-1H-1,2,3-triazol-4-yl)methyl)glycinate To a stirred solution of 1-phenyl-1H-1,2,3-triazole-4-carbaldehyde (1 equiv) and methyl glycinate (1.5 equiv) in methanol (0.2 M) at room temperature is added triethylamine (1.5 equiv), and the mixture is stirred for five minutes. Borontrifluoride diethyletherate (1.5 equiv) and trimethylsilyl cyanide (1.5 equiv) is then added. Upon consumption of the aldehyde starting material, the reaction mixture is partitioned between ethyl acetate and water. The layers are separated, and the aqueous phase is extracted with ethyl acetate. The combined organic layer is washed with brine, dried over sodium sulfate, filtered, and concentrated under reduced pressure. Purification by silica gel column chromatography provides methyl N-(cyano(1-methyl-5-phenyl-1H-pyrazol-3-yl)methyl)-N-methylglycinate.

Step 2: Preparation of 3-(1-Phenyl-1H-1,2,3-triazol-4-yl)piperazine-2,6-dione

A solution of methyl N-(cyano(1-methyl-5-phenyl-1H-pyrazol-3-yl)methyl)-N-methylglycinate (1 equiv) in toluene (0.5 M) is treated with sulfuric acid (2 equiv), and the mixture is heated in a sealed tube at 100° C. Upon consumption of the starting material, the reaction mixture is cooled to room temperature and partitioned between ethyl acetate and saturated aqueous sodium bicarbonate solution. The layers are separated, and the aqueous phase is extracted with ethyl acetate. The combined organic layer is washed with brine, dried over sodium sulfate, filtered, and concentrated under reduced pressure. The crude material is purified by silica gel column chromatography to afford 3-(1-phenyl-1H-1,2,3-triazol-4-yl)piperazine-2,6-dione.

Example 26: Synthesis of 3-(5-Bromobenzo[d]oxazol-2-yl)piperazine-2,6-dione

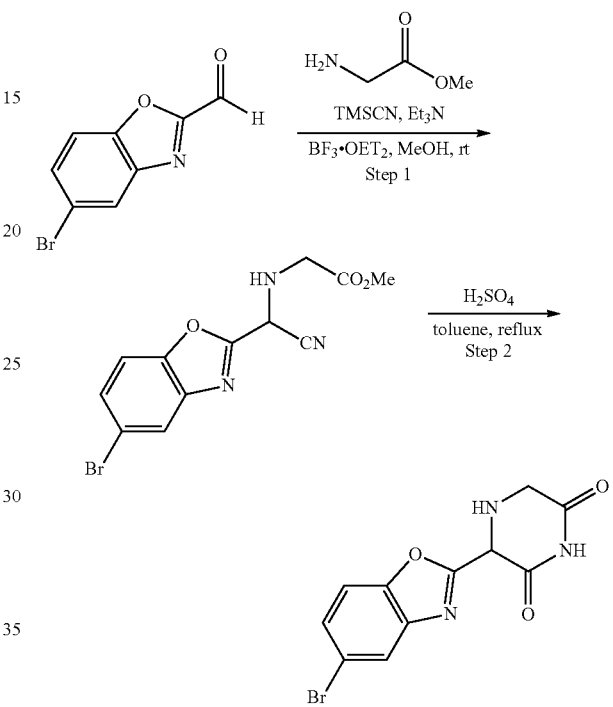

Step 1: Preparation of Methyl ((5-Bromobenzo[d]oxazol-2-yl)(cyano)methyl)glycinate To a stirred solution of 5-bromobenzo[d]oxazole-2-carbaldehyde (1 equiv) and methyl glycinate (1.5 equiv) in methanol (0.2 M) at room temperature is added triethylamine (1.5 equiv), and the mixture is stirred for five minutes. Borontrifluoride diethyletherate (1.5 equiv) and trimethylsilyl cyanide (1.5 equiv) is then added. Upon consumption of the aldehyde starting material, the reaction mixture is partitioned between ethyl acetate and water. The layers are separated, and the aqueous phase is extracted with ethyl acetate. The combined organic layer is washed with brine, dried over sodium sulfate, filtered, and concentrated under reduced pressure. Purification by silica gel column chromatography provides methyl ((5-bromobenzo[d]oxazol-2-yl)(cyano)methyl)glycinate.

Step 2: Preparation of 3-(5-Bromobenzo[d]oxazol-2-yl)piperazine-2,6-dione

A solution of methyl ((5-bromobenzo[d]oxazol-2-yl)(cyano)methyl)glycinate (1 equiv) in toluene (0.5 M) is treated with sulfuric acid (2 equiv), and the mixture is heated in a sealed tube at 100° C. Upon consumption of the starting material, the reaction mixture is cooled to room temperature and partitioned between ethyl acetate and saturated aqueous sodium bicarbonate solution. The layers are separated, and the aqueous phase is extracted with ethyl acetate. The combined organic layer is washed with brine, dried over sodium sulfate, filtered, and concentrated under reduced pressure. The crude material is purified by silica gel column chromatography to afford 3-(5-bromobenzo[d]oxazol-2-yl)piperazine-2,6-dione.

Example 27: Synthesis of 3-(3-Bromo-5-fluorophenyl)piperazine-2,6-dione

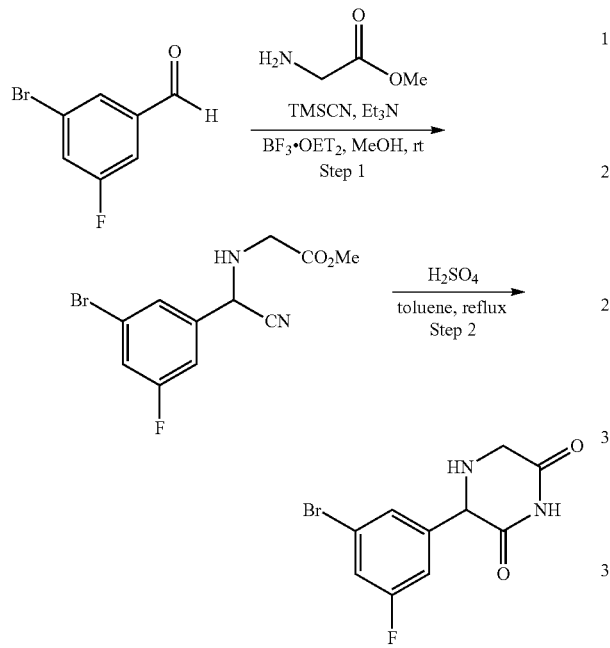

Step 1: Preparation of Methyl ((3-Bromo-5-fluorophenyl)(cyano)methyl)glycinate

To a stirred solution of 3-bromo-5-fluorobenzaldehyde (1 equiv) and methyl glycinate (1.5 equiv) in methanol (0.2 M) at room temperature is added triethylamine (1.5 equiv), and the mixture is stirred for five minutes. Borontrifluoride diethyletherate (1.5 equiv) and trimethylsilyl cyanide (1.5 equiv) is then added. Upon consumption of the aldehyde starting material, the reaction mixture is partitioned between ethyl acetate and water. The layers are separated, and the aqueous phase is extracted with ethyl acetate. The combined organic layer is washed with brine, dried over sodium sulfate, filtered, and concentrated under reduced pressure. Purification by silica gel column chromatography provides methyl ((3-bromo-5-fluorophenyl)(cyano)methyl)glycinate.

Step 2: Preparation of 3-(3-Bromo-5-fluorophenyl)piperazine-2,6-dione

A solution of methyl ((3-bromo-5-fluorophenyl)(cyano)methyl)glycinate (1 equiv) in toluene (0.5 M) is treated with sulfuric acid (2 equiv), and the mixture is heated in a sealed tube at 100° C. Upon consumption of the starting material, the reaction mixture is cooled to room temperature and partitioned between ethyl acetate and saturated aqueous sodium bicarbonate solution. The layers are separated, and the aqueous phase is extracted with ethyl acetate. The combined organic layer is washed with brine, dried over sodium sulfate, filtered, and concentrated under reduced pressure. The crude material is purified by silica gel column chromatography to afford 3-(3-bromo-5-fluorophenyl)piperazine-2,6-dione.

Example 28: Synthesis of 3-(1,5-Dimethyl-3-oxo-2-phenyl-2,3-dihydro-1H-pyrazol-4-yl)piperazine-2,6-dione

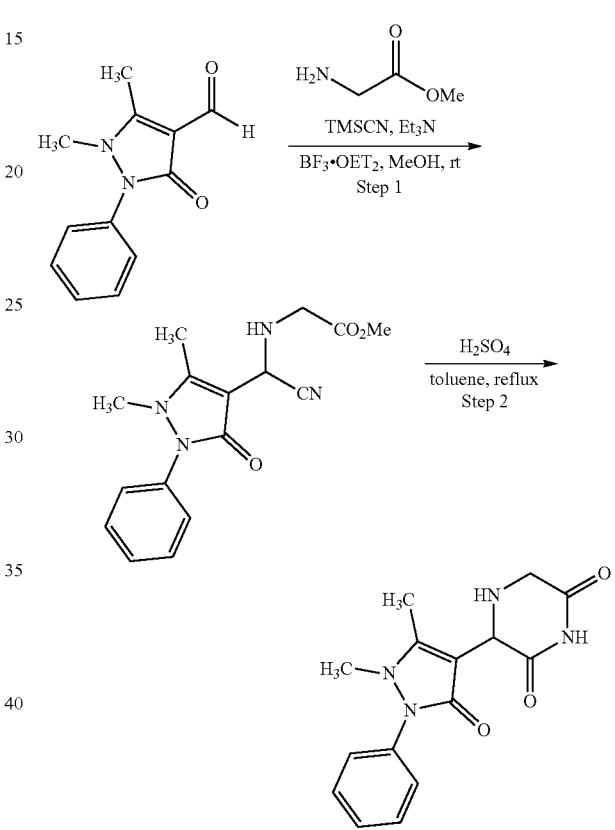

Step 1: Preparation of Methyl (Cyano(1,5-dimethyl-3-oxo-2-phenyl-2,3-dihydro-1H-pyrazol-4-yl)methyl)glycinate To a stirred solution of 1,5-dimethyl-3-oxo-2-phenyl-2,3-dihydro-1H-pyrazole-4-carbaldehyde (1 equiv) and methyl glycinate (1.5 equiv) in methanol (0.2 M) at room temperature is added triethylamine (1.5 equiv), and the mixture is stirred for five minutes. Borontrifluoride diethyletherate (1.5 equiv) and trimethylsilyl cyanide (1.5 equiv) is then added. Upon consumption of the aldehyde starting material, the reaction mixture is partitioned between ethyl acetate and water. The layers are separated, and the aqueous phase is extracted with ethyl acetate. The combined organic layer is washed with brine, dried over sodium sulfate, filtered, and concentrated under reduced pressure. Purification by silica gel column chromatography provides methyl (cyano(1,5-dimethyl-3-oxo-2-phenyl-2,3-dihydro-1H-pyrazol-4-yl)methyl)glycinate.

Step 2: Preparation of 3-(1,5-Dimethyl-3-oxo-2-phenyl-2,3-dihydro-1H-pyrazol-4-yl)piperazine-2,6-dione A solution of methyl (cyano(1,5-dimethyl-3-oxo-2-phenyl-2,3-dihydro-1H-pyrazol-4-yl)methyl)glycinate (1 equiv) in toluene (0.5 M) is treated with sulfuric acid (2 equiv), and the mixture is heated in a sealed tube at 100° C. Upon consumption of the starting material, the reaction mixture is cooled to room temperature and partitioned between ethyl acetate and saturated aqueous sodium bicarbonate solution. The layers are separated, and the aqueous phase is extracted with ethyl acetate. The combined organic layer is washed with brine, dried over sodium sulfate, filtered, and concentrated under reduced pressure. The crude material is purified by silica gel column chromatography to afford 3-(1,5-dimethyl-3-oxo-2-phenyl-2,3-dihydro-1H-pyrazol-4-yl)piperazine-2,6-dione.

Example 29: Synthesis of 4-Methyl-3-(1-methyl-1H-pyrrolo[2,3-c]pyridin-5-yl)piperazine-2,6-dione

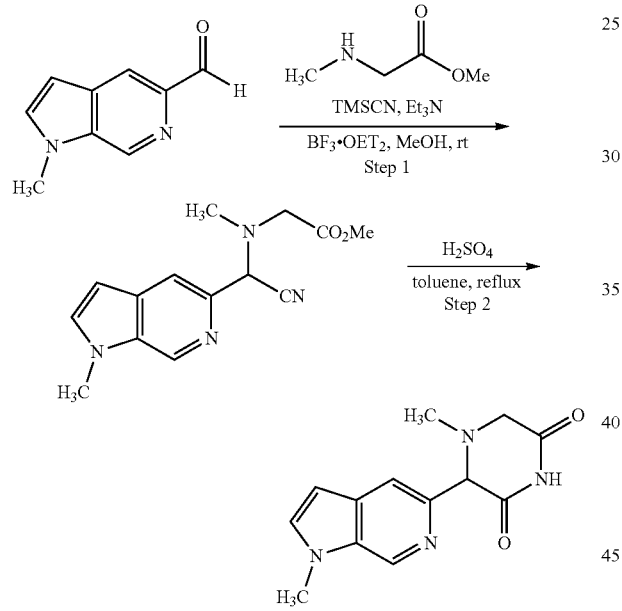

Step 1: Preparation of Methyl N-(Cyano(1-methyl-1H-pyrrolo[2,3-c]pyridin-5-yl)methyl)-N-methylglycinate To a stirred solution of 1-methyl-1H-pyrrolo[2,3-c]pyridine-5-carbaldehyde (1 equiv) and methyl methylglycinate (1.5 equiv) in methanol (0.2 M) at room temperature is added triethylamine (1.5 equiv), and the mixture is stirred for five minutes. Borontrifluoride diethyletherate (1.5 equiv) and trimethylsilyl cyanide (1.5 equiv) is then added. Upon consumption of the aldehyde starting material, the reaction mixture is partitioned between ethyl acetate and water. The layers are separated, and the aqueous phase is extracted with ethyl acetate. The combined organic layer is washed with brine, dried over sodium sulfate, filtered, and concentrated under reduced pressure. Purification by silica gel column chromatography provides methyl N-(cyano(1-methyl-1H-pyrrolo[2,3-c]pyridin-5-yl)methyl)-N-methylglycinate.

Step 2: Preparation of 4-Methyl-3-(1-methyl-1H-pyrrolo[2,3-c]pyridin-5-yl)piperazine-2,6-dione A solution of methyl N-(cyano(1-methyl-1H-pyrrolo[2,3-c]pyridin-5-yl)methyl)-N-methylglycinate (1 equiv) in toluene (0.5 M) is treated with sulfuric acid (2 equiv), and the mixture is heated in a sealed tube at 100° C. Upon consumption of the starting material, the reaction mixture is cooled to room temperature and partitioned between ethyl acetate and saturated aqueous sodium bicarbonate solution. The layers are separated, and the aqueous phase is extracted with ethyl acetate. The combined organic layer is washed with brine, dried over sodium sulfate, filtered, and concentrated under reduced pressure. The crude material is purified by silica gel column chromatography to afford 4-methyl-3-(1-methyl-1H-pyrrolo[2,3-c]pyridin-5-yl)piperazine-2,6-dione.

Example 30: Synthesis of 3-(6-Bromoimidazo[1,5-a]pyridin-3-yl)piperazine-2,6-dione

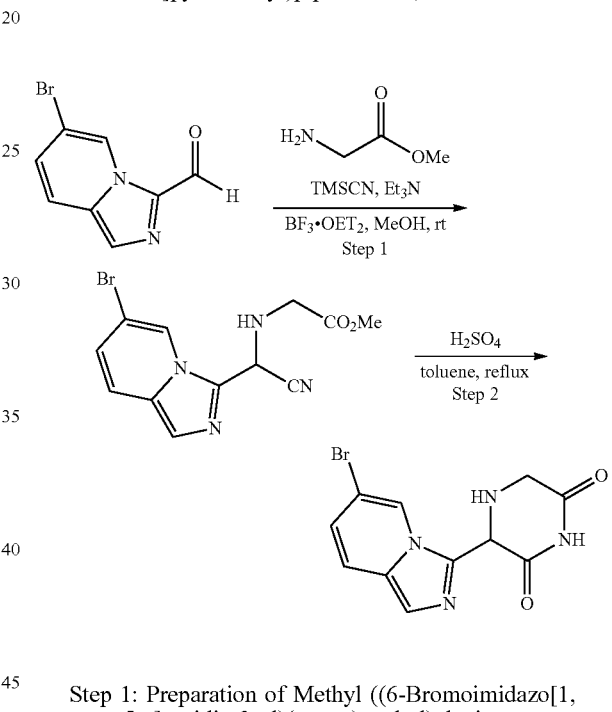

Step 1: Preparation of Methyl ((6-Bromoimidazo[1,5-a]pyridin-3-yl)(cyano)methyl)glycinate To a stirred solution of 6-bromoimidazo[1,5-a]pyridine-3-carbaldehyde (1 equiv) and methyl methylglycinate (1.5 equiv) in methanol (0.2 M) at room temperature is added triethylamine (1.5 equiv), and the mixture is stirred for five minutes. Borontrifluoride diethyletherate (1.5 equiv) and trimethylsilyl cyanide (1.5 equiv) is then added. Upon consumption of the aldehyde starting material, the reaction mixture is partitioned between ethyl acetate and water. The layers are separated, and the aqueous phase is extracted with ethyl acetate. The combined organic layer is washed with brine, dried over sodium sulfate, filtered, and concentrated under reduced pressure. Purification by silica gel column chromatography provides methyl ((6-bromoimidazo[1,5-a]pyridin-3-yl)(cyano)methyl)glycinate.

Step 2: Preparation of 3-(6-Bromoimidazo[1,5-a]pyridin-3-yl)piperazine-2,6-dione A solution of methyl ((6-bromoimidazo[1,5-a]pyridin-3-yl)(cyano)methyl)glycinate (1 equiv) in toluene (0.5 M) is treated with sulfuric acid (2 equiv), and the mixture is heated in a sealed tube at 100° C. Upon consumption of the starting material, the reaction mixture is cooled to room temperature and partitioned between ethyl acetate and saturated aqueous sodium bicarbonate solution. The layers are separated, and the aqueous phase is extracted with ethyl acetate. The combined organic layer is washed with brine, dried over sodium sulfate, filtered, and concentrated under reduced pressure. The crude material is purified by silica gel column chromatography to afford 3-(6-bromoimidazo[1,5-a]pyridin-3-yl)piperazine-2,6-dione.

Example 31: Synthesis of 2-(1,5-Dimethyl-3-oxo-2-phenyl-2,3-dihydro-1H-pyrazol-4-yl)thiomorpholine-3,5-dione

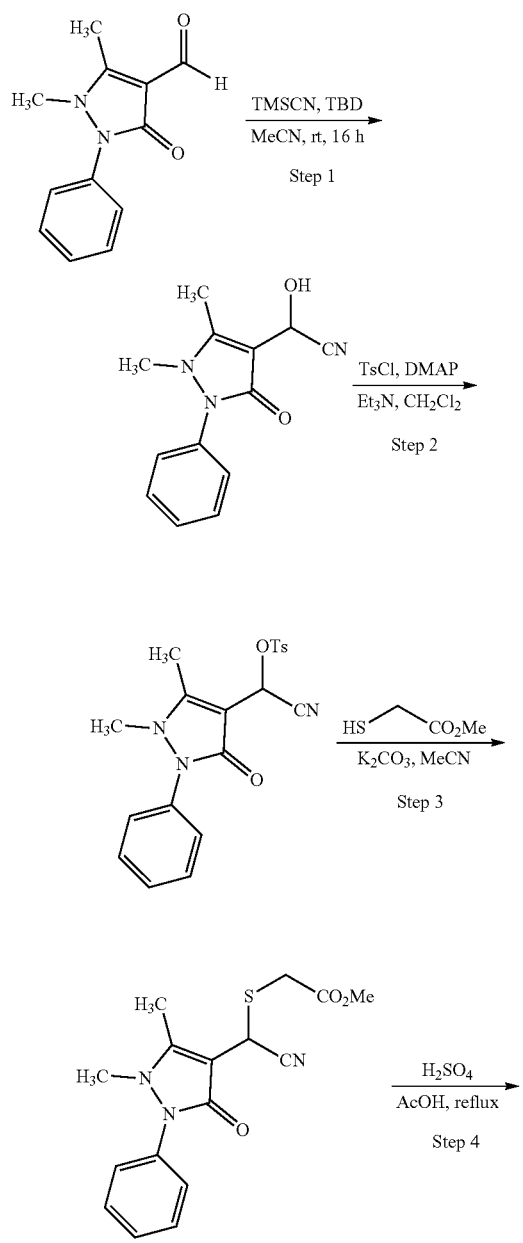

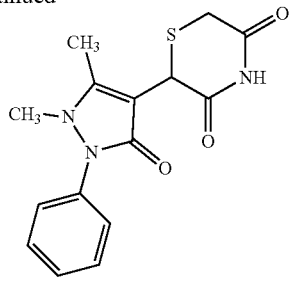

Step 1: Preparation of 2-(1,5-Dimethyl-3-oxo-2-phenyl-2,3-dihydro-1H-pyrazol-4-yl)-2-hydroxyacetonitrile A solution of trimethylsilyl cyanide (1.1 equiv) in acetonitrile (0.1 M) is added to a solution of 1,5-dimethyl-3-oxo-2-phenyl-2,3-dihydro-1H-pyrazole-4-carbaldehyde (1 equiv) and 1,5,7-triazabicyclo[4.4.0]dec-5-ene (1 equiv) in acetonitrile (0.1 M), and the reaction mixture is stirred at room temperature for three hours. The reaction mixture is diluted with 1N aqueous hydrochloric acid and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/hexanes) to afford 2-(1,5-dimethyl-3-oxo-2-phenyl-2,3-dihydro-1H-pyrazol-4-yl)-2-hydroxyacetonitrile.

Step 2: Preparation of Cyano(1,5-dimethyl-3-oxo-2-phenyl-2,3-dihydro-1H-pyrazol-4-yl)methyl 4-Methylbenzenesulfonate To a solution of 2-(1,5-dimethyl-3-oxo-2-phenyl-2,3-dihydro-1H-pyrazol-4-yl)-2-hydroxyacetonitrile (1 equiv) in dichloromethane (0.1 M) at 0° C. is added triethylamine (1.2 equiv) and N,N-dimethylpyridin-4-amine (0.1 equiv). 4-Methylbenzenesulfonyl chloride (1 equiv) is then added, and the solution is stirred until complete consumption of the starting material. The reaction mixture is quenched with water, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide cyano(1,5-dimethyl-3-oxo-2-phenyl-2,3-dihydro-1H-pyrazol-4-yl)methyl 4-methylbenzenesulfonate.

Step 3: Preparation of Methyl 2-((Cyano(1,5-dimethyl-3-oxo-2-phenyl-2,3-dihydro-1H-pyrazol-4-yl)methyl)thio)acetate To a solution of cyano(1,5-dimethyl-3-oxo-2-phenyl-2,3-dihydro-1H-pyrazol-4-yl)methyl 4-methylbenzenesulfonate (1 equiv) in acetonitrile (0.2 M) is added potassium carbonate (3 equiv) and methyl 2-mercaptoacetate (1 equiv), and the reaction mixture is stirred until full consumption of the starting material. The reaction is concentrated under reduced pressure and brought up in ethyl acetate. Water is added, and the layers are separated. The aqueous layer is extracted with ethyl acetate. The combined organic layer is washed with brine, dried over sodium sulfate, filtered, and concentrated under reduced pressure. The crude material is purified by silica gel column chromatography to provide methyl 2-((cyano(1,5-dimethyl-3-oxo-2-phenyl-2,3-dihydro-1H-pyrazol-4-yl)methyl)thio)acetate.

Step 4: Preparation of 2-(1,5-Dimethyl-3-oxo-2-phenyl-2,3-dihydro-1H-pyrazol-4-yl)thiomorpholine-3,5-dione To a solution of methyl 2-((cyano(1,5-dimethyl-3-oxo-2-phenyl-2,3-dihydro-1H-pyrazol-4-yl)methyl)thio)acetate (1 equiv) in acetic acid (0.7 M) is added sulfuric acid (2 equiv), and the reaction mixture is heated to 110° C. for five hours. The reaction mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to provide 2-(1,5-dimethyl-3-oxo-2-phenyl-2,3-dihydro-1H-pyrazol-4-yl)thiomorpholine-3,5-dione.

Example 32: Synthesis of 2-(1,5-Dimethyl-3-oxo-2-phenyl-2,3-dihydro-1H-pyrazol-4-yl)thiomorpholine-3,5-dione 1-Oxide

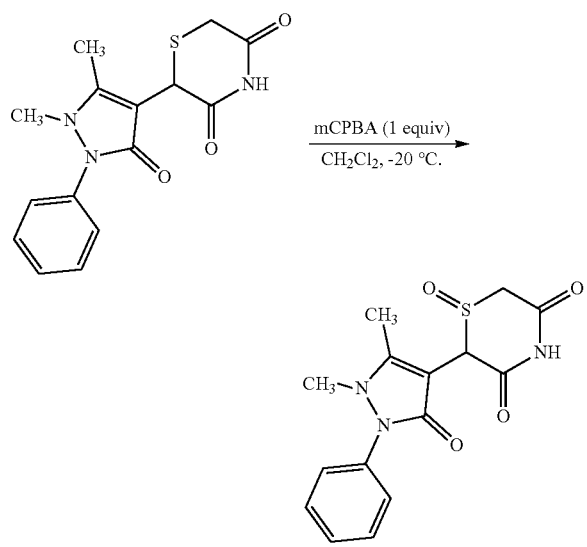

To a solution of 2-(1,5-dimethyl-3-oxo-2-phenyl-2,3-dihydro-1H-pyrazol-4-yl)thiomorpholine-3,5-dione (1 equiv) in CH$_2$Cl$_2$ (0.1 M) at −20° C. is added 3-chlorobenzoperoxoic acid (1 equiv), and the reaction is stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(1,5-dimethyl-3-oxo-2-phenyl-2,3-dihydro-1H-pyrazol-4-yl)thiomorpholine-3,5-dione 1-oxide.

Example 33: Synthesis of 2-(1,5-Dimethyl-3-oxo-2-phenyl-2,3-dihydro-1H-pyrazol-4-yl)thiomorpholine-3,5-dione 1,1-Dioxide

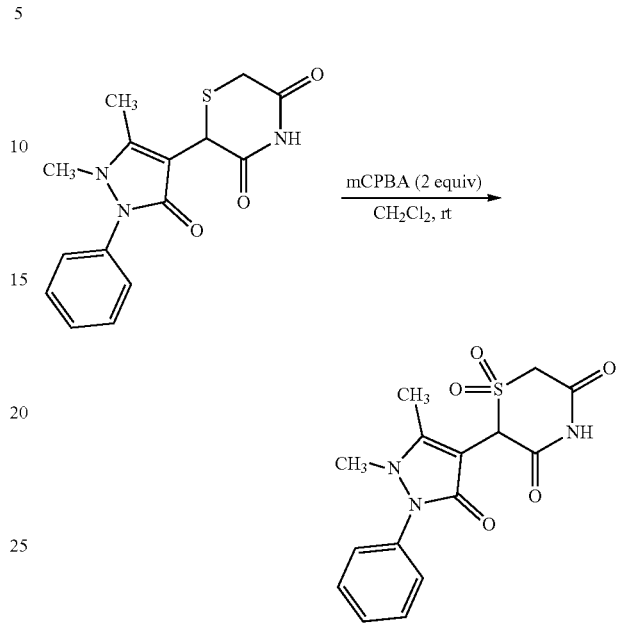

To a solution of 2-(1,5-dimethyl-3-oxo-2-phenyl-2,3-dihydro-1H-pyrazol-4-yl)thiomorpholine-3,5-dione (1 equiv) in CH$_2$Cl$_2$ (0.1 M) at 0° C. is added 3-chlorobenzoperoxoic acid (2 equiv), and the reaction is slowly warmed up to room temperature and stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(1,5-dimethyl-3-oxo-2-phenyl-2,3-dihydro-1H-pyrazol-4-yl)thiomorpholine-3,5-dione 1,1-dioxide.

Example 34: Synthesis of 2-(1-Methyl-1H-indazol-3-yl)thiomorpholine-3,5-dione

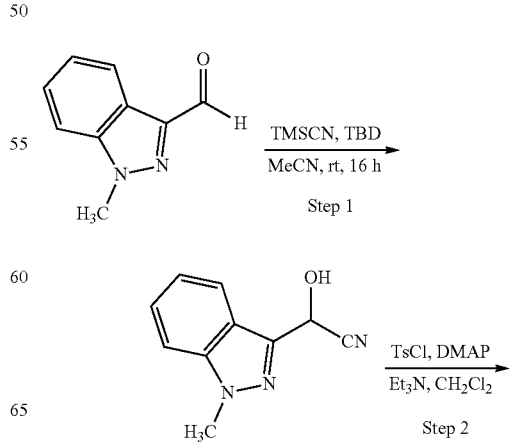

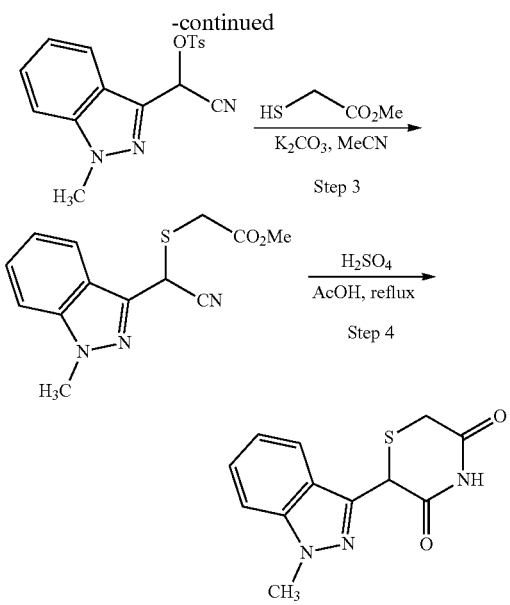

Step 1: Preparation of 2-Hydroxy-2-(1-methyl-1H-indazol-3-yl)acetonitrile

A solution of trimethylsilyl cyanide (1.1 equiv) in acetonitrile (0.1 M) is added to a solution of 1-methyl-1H-indazole-3-carbaldehyde (1 equiv) and 1,5,7-triazabicyclo[4.4.0]dec-5-ene (1 equiv) in acetonitrile (0.1 M), and the reaction mixture is stirred at room temperature for three hours. The reaction mixture is diluted with 1N aqueous hydrochloric acid and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/hexanes) to 2-hydroxy-2-(1-methyl-1H-indazol-3-yl)acetonitrile.

Step 2: Preparation of Cyano(1-methyl-1H-indazol-3-yl)methyl 4-Methylbenzenesulfonate To a solution of 2-hydroxy-2-(1-methyl-1H-indazol-3-yl)acetonitrile (1 equiv) in dichloromethane (0.1 M) at 0° C. is added triethylamine (1.2 equiv) and N,N-dimethylpyridin-4-amine (0.1 equiv). 4-Methylbenzenesulfonyl chloride (1 equiv) is then added, and the solution is stirred until complete consumption of the starting material. The reaction mixture is quenched with water, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide cyano(1-methyl-1H-indazol-3-yl)methyl 4-methylbenzenesulfonate.

Step 3: Preparation of Methyl 2-((Cyano(1-methyl-1H-indazol-3-yl)methyl)thio)acetate To a solution of cyano(1-methyl-1H-indazol-3-yl)methyl 4-methylbenzenesulfonate (1 equiv) in acetonitrile (0.2 M) is added potassium carbonate (3 equiv) and methyl 2-mercaptoacetate (1 equiv), and the reaction mixture is stirred until full consumption of the starting material. The reaction is concentrated under reduced pressure and brought up in ethyl acetate. Water is added, and the layers are separated. The aqueous layer is extracted with ethyl acetate. The combined organic layer is washed with brine, dried over sodium sulfate, filtered, and concentrated under reduced pressure. The crude material is purified by silica gel column chromatography to provide methyl 2-((cyano(1-methyl-1H-indazol-3-yl)methyl)thio)acetate.

Step 4: Preparation of 2-(1-Methyl-1H-indazol-3-yl)thiomorpholine-3,5-dione

To a solution of methyl 2-((cyano(1-methyl-1H-indazol-3-yl)methyl)thio)acetate (1 equiv) in acetic acid (0.7 M) is added sulfuric acid (2 equiv), and the reaction mixture is heated to 110° C. for five hours. The reaction mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to provide 2-(1-methyl-1H-indazol-3-yl)thiomorpholine-3,5-dione.

Example 35: Synthesis of 2-(1-Methyl-1H-indazol-3-yl)thiomorpholine-3,5-dione 1-Oxide

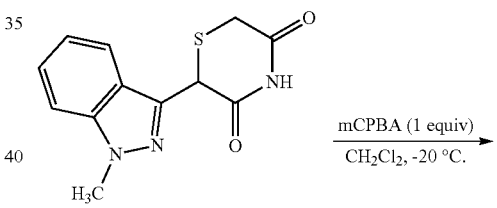

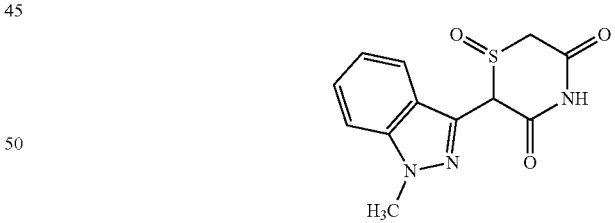

To a solution of 2-(1-methyl-1H-indazol-3-yl)thiomorpholine-3,5-dione (1 equiv) in $CH_2Cl_2$ (0.1 M) at −20° C. is added 3-chlorobenzoperoxoic acid (1 equiv), and the reaction is stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(1-methyl-1H-indazol-3-yl)thiomorpholine-3,5-dione 1-oxide.

Example 36: Synthesis of 2-(1-Methyl-1H-indazol-3-yl)thiomorpholine-3,5-dione 1,1-Dioxide

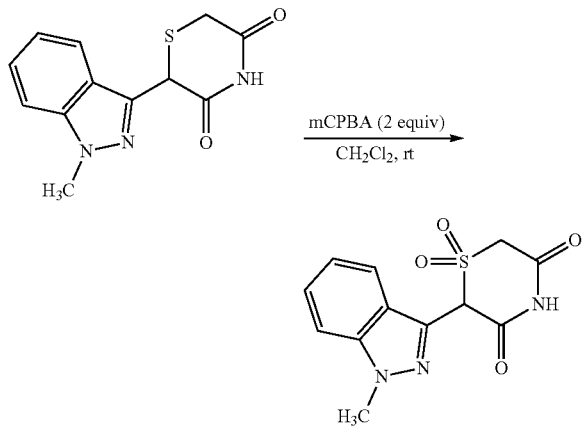

To a solution of 2-(1-methyl-1H-indazol-3-yl)thiomorpholine-3,5-dione (1 equiv) in CH$_2$Cl$_2$ (0.1 M) at 0° C. is added 3-chlorobenzoperoxoic acid (2 equiv), and the reaction is slowly warmed up to room temperature and stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(1-methyl-1H-indazol-3-yl)thiomorpholine-3,5-dione 1,1-dioxide.

Example 37: Synthesis of 2-(Benzo[d]oxazol-5-yl)thiomorpholine-3,5-dione

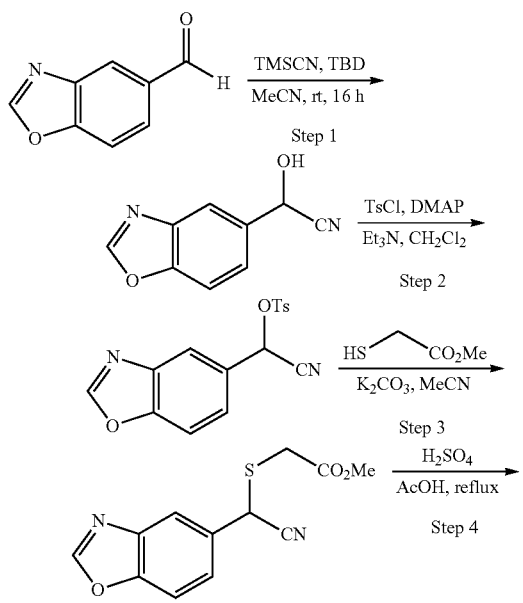

-continued

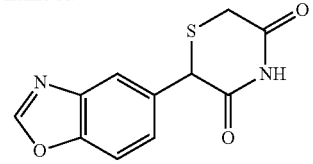

Step 1: Preparation of 2-(Benzo[d]oxazol-5-yl)-2-hydroxyacetonitrile

A solution of trimethylsilyl cyanide (1.1 equiv) in acetonitrile (0.1 M) is added to a solution of benzo[d]oxazole-5-carbaldehyde (1 equiv) and 1,5,7-triazabicyclo[4.4.0]dec-5-ene (1 equiv) in acetonitrile (0.1 M), and the reaction mixture is stirred at room temperature for three hours. The reaction mixture is diluted with 1N aqueous hydrochloric acid and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/hexanes) to afford 2-(benzo[d]oxazol-5-yl)-2-hydroxyacetonitrile.

Step 2: Preparation of Benzo[d]oxazol-5-yl(cyano)methyl 4-Methylbenzenesulfonate To a solution of 2-(benzo[d]oxazol-5-yl)-2-hydroxyacetonitrile (1 equiv) in dichloromethane (0.1 M) at 0° C. is added triethylamine (1.2 equiv) and N,N-dimethylpyridin-4-amine (0.1 equiv). 4-Methylbenzenesulfonyl chloride (1 equiv) is then added, and the solution is stirred until complete consumption of the starting material. The reaction mixture is quenched with water, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide benzo[d]oxazol-5-yl(cyano)methyl 4-methylbenzenesulfonate.

Step 3: Preparation of Methyl 2-((Benzo[d]oxazol-5-yl(cyano)methyl)thio)acetate To a solution of benzo[d]oxazol-5-yl(cyano)methyl 4-methylbenzenesulfonate (1 equiv) in acetonitrile (0.2 M) is added potassium carbonate (3 equiv) and methyl 2-mercaptoacetate (1 equiv), and the reaction mixture is stirred until full consumption of the starting material. The reaction is concentrated under reduced pressure and brought up in ethyl acetate. Water is added, and the layers are separated. The aqueous layer is extracted with ethyl acetate. The combined organic layer is washed with brine, dried over sodium sulfate, filtered, and concentrated under reduced pressure. The crude material is purified by silica gel column chromatography to provide methyl 2-((benzo[d]oxazol-5-yl(cyano)methyl)thio)acetate.

Step 4: Preparation of 2-(Benzo[d]oxazol-5-yl)thiomorpholine-3,5-dione

To a solution of methyl 2-((benzo[d]oxazol-5-yl(cyano)methyl)thio)acetate (1 equiv) in acetic acid (0.7 M) is added sulfuric acid (2 equiv), and the reaction mixture is heated to 110° C. for five hours. The reaction mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to provide 2-(benzo[d]oxazol-5-yl)thiomorpholine-3,5-dione.

Example 38: Synthesis of 2-(Benzo[d]oxazol-5-yl)thiomorpholine-3,5-dione 1-Oxide

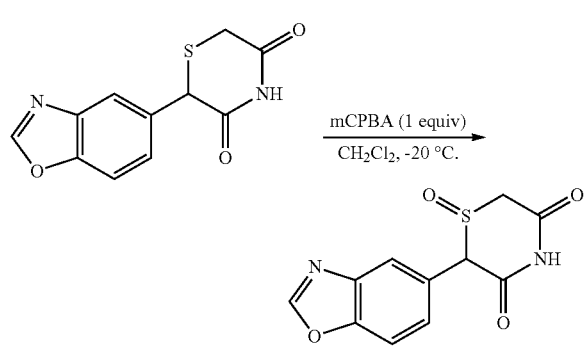

To a solution of 2-(benzo[d]oxazol-5-yl)thiomorpholine-3,5-dione (1 equiv) in CH$_2$Cl$_2$ (0.1 M) at −20° C. is added 3-chlorobenzoperoxoic acid (1 equiv), and the reaction is stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(benzo[d]oxazol-5-yl)thiomorpholine-3,5-dione 1-oxide.

Example 39: Synthesis of 2-(Benzo[d]oxazol-5-yl)thiomorpholine-3,5-dione 1,1-Dioxide

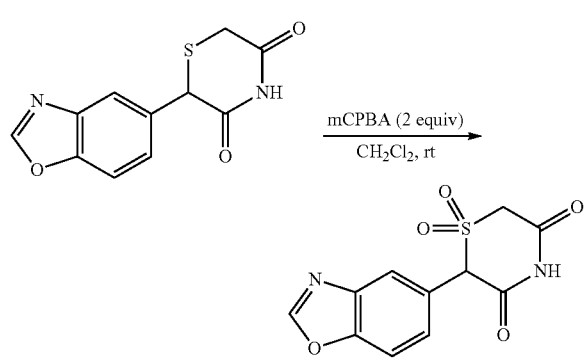

To a solution of 2-(benzo[d]oxazol-5-yl)thiomorpholine-3,5-dione (1 equiv) in CH$_2$Cl$_2$ (0.1 M) at 0° C. is added 3-chlorobenzoperoxoic acid (2 equiv), and the reaction is slowly warmed up to room temperature and stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(benzo[d]oxazol-5-yl)thiomorpholine-3,5-dione 1,1-dioxide.

Example 40: Synthesis of 2-(Imidazo[1,5-a]pyridin-3-yl)thiomorpholine-3,5-dione

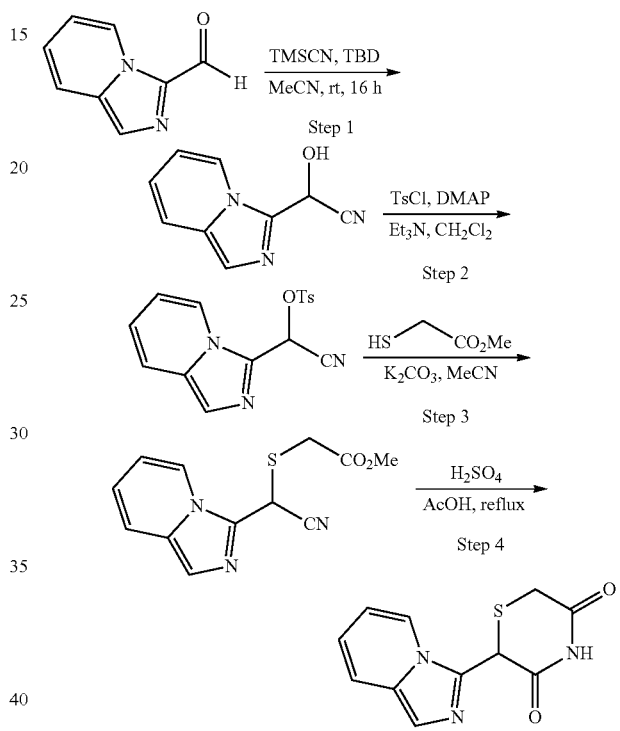

Step 1: Preparation of 2-Hydroxy-2-(imidazo[1,5-a]pyridin-3-yl)acetonitrile

A solution of trimethylsilyl cyanide (1.1 equiv) in acetonitrile (0.1 M) is added to a solution of imidazo[1,5-a]pyridine-3-carbaldehyde (1 equiv) and 1,5,7-triazabicyclo[4.4.0]dec-5-ene (1 equiv) in acetonitrile (0.1 M), and the reaction mixture is stirred at room temperature for three hours. The reaction mixture is diluted with 1N aqueous hydrochloric acid and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/hexanes) to afford 2-hydroxy-2-(imidazo[1,5-a]pyridin-3-yl)acetonitrile.

Step 2: Preparation of Cyano(imidazo[1,5-a]pyridin-3-yl)methyl 4-Methylbenzenesulfonate To a solution of 2-hydroxy-2-(imidazo[1,5-a]pyridin-3-yl)acetonitrile (1 equiv) in dichloromethane (0.1 M) at 0° C.

is added triethylamine (1.2 equiv) and N,N-dimethylpyridin-4-amine (0.1 equiv). 4-Methylbenzenesulfonyl chloride (1 equiv) is then added, and the solution is stirred until complete consumption of the starting material. The reaction mixture is quenched with water, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide cyano(imidazo[1,5-a]pyridin-3-yl)methyl 4-methylbenzenesulfonate.

Step 3: Preparation of Methyl 2-((Cyano(imidazo[1,5-a]pyridin-3-yl)methyl)thio)acetate To a solution of cyano(imidazo[1,5-a]pyridin-3-yl)methyl 4-methylbenzenesulfonate (1 equiv) in acetonitrile (0.2 M) is added potassium carbonate (3 equiv) and methyl 2-mercaptoacetate (1 equiv), and the reaction mixture is stirred until full consumption of the starting material. The reaction is concentrated under reduced pressure and brought up in ethyl acetate. Water is added, and the layers are separated. The aqueous layer is extracted with ethyl acetate. The combined organic layer is washed with brine, dried over sodium sulfate, filtered, and concentrated under reduced pressure. The crude material is purified by silica gel column chromatography to provide methyl 2-((cyano(imidazo[1,5-a]pyridin-3-yl)methyl)thio)acetate.

Step 4: Preparation of 2-(Imidazo[1,5-a]pyridin-3-yl)thiomorpholine-3,5-dione

To a solution of methyl 2-((cyano(imidazo[1,5-a]pyridin-3-yl)methyl)thio)acetate (1 equiv) in acetic acid (0.7 M) is added sulfuric acid (2 equiv), and the reaction mixture is heated to 110° C. for five hours. The reaction mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to provide 2-(imidazo[1,5-a]pyridin-3-yl)thiomorpholine-3,5-dione.

Example 41: Synthesis of 2-(Imidazo[1,5-a]pyridin-3-yl)thiomorpholine-3,5-dione 1-Oxide

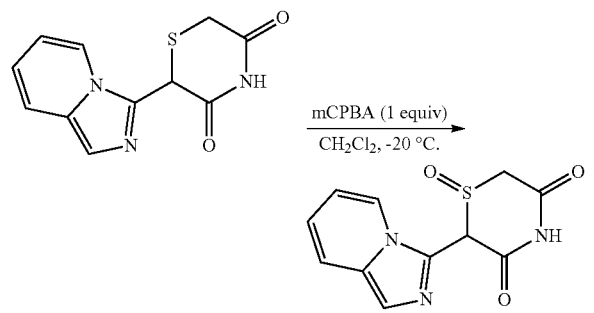

To a solution of 2-(imidazo[1,5-a]pyridin-3-yl)thiomorpholine-3,5-dione (1 equiv) in CH$_2$Cl$_2$ (0.1 M) at −20° C. is added 3-chlorobenzoperoxoic acid (1 equiv), and the reaction is stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(imidazo[1,5-a]pyridin-3-yl)thiomorpholine-3,5-dione 1-oxide.

Example 42: Synthesis of 2-(Imidazo[1,5-a]pyridin-3-yl)thiomorpholine-3,5-dione 1,1-Dioxide

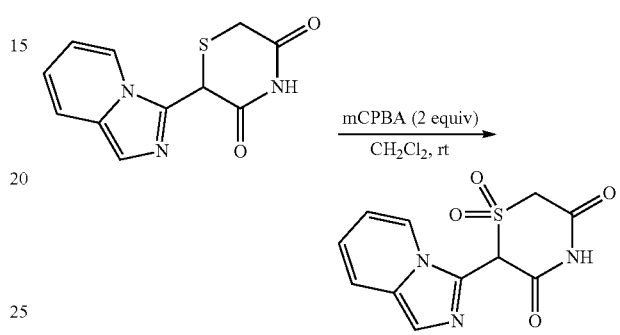

To a solution of 2-(imidazo[1,5-a]pyridin-3-yl)thiomorpholine-3,5-dione (1 equiv) in CH$_2$Cl$_2$ (0.1 M) at 0° C. is added 3-chlorobenzoperoxoic acid (2 equiv), and the reaction is slowly warmed up to room temperature and stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(imidazo[1,5-a]pyridin-3-yl)thiomorpholine-3,5-dione 1,1-dioxide.

Example 43: Synthesis of 2-(1-Methyl-5-phenyl-1H-pyrazol-3-yl)thiomorpholine-3,5-dione

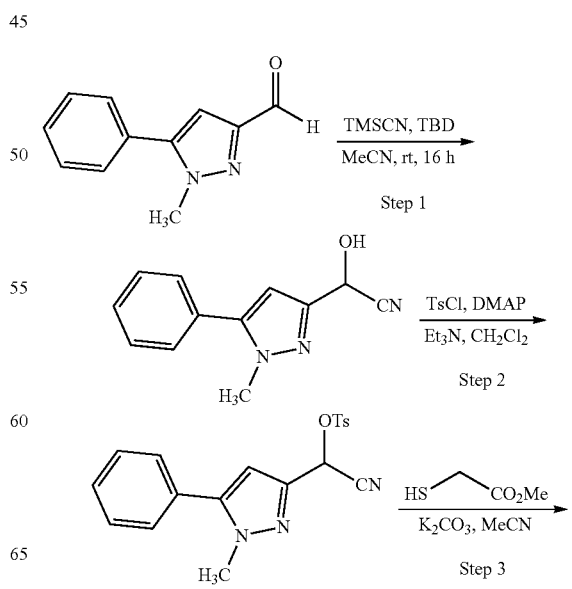

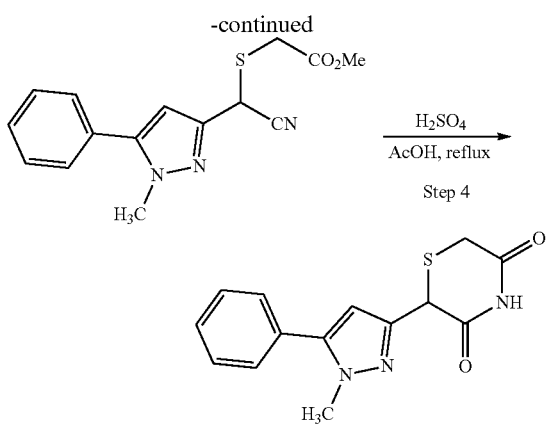

Step 1: Preparation of 2-Hydroxy-2-(1-methyl-5-phenyl-1H-pyrazol-3-yl)acetonitrile A solution of trimethylsilyl cyanide (1.1 equiv) in acetonitrile (0.1 M) is added to a solution of imidazo[1,5-a]pyridine-3-carbaldehyde (1 equiv) and 1,5,7-triazabicyclo[4.4.0]dec-5-ene (1 equiv) in acetonitrile (0.1 M), and the reaction mixture is stirred at room temperature for three hours. The reaction mixture is diluted with 1N aqueous hydrochloric acid and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/hexanes) to afford 2-hydroxy-2-(1-methyl-5-phenyl-1H-pyrazol-3-yl)acetonitrile.

Step 2: Preparation of Cyano(1-methyl-5-phenyl-1H-pyrazol-3-yl)methyl 4-Methylbenzenesulfonate To a solution of 2-hydroxy-2-(1-methyl-5-phenyl-1H-pyrazol-3-yl)acetonitrile (1 equiv) in dichloromethane (0.1 M) at 0° C. is added triethylamine (1.2 equiv) and N,N-dimethylpyridin-4-amine (0.1 equiv). 4-Methylbenzenesulfonyl chloride (1 equiv) is then added, and the solution is stirred until complete consumption of the starting material. The reaction mixture is quenched with water, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide cyano(1-methyl-5-phenyl-1H-pyrazol-3-yl)methyl 4-methylbenzenesulfonate.

Step 3: Preparation of Methyl 2-((Cyano(1-methyl-5-phenyl-1H-pyrazol-3-yl)methyl)thio)acetate To a solution of cyano(1-methyl-5-phenyl-1H-pyrazol-3-yl)methyl 4-methylbenzenesulfonate (1 equiv) in acetonitrile (0.2 M) is added potassium carbonate (3 equiv) and methyl 2-mercaptoacetate (1 equiv), and the reaction mixture is stirred until full consumption of the starting material. The reaction is concentrated under reduced pressure and brought up in ethyl acetate. Water is added, and the layers are separated. The aqueous layer is extracted with ethyl acetate. The combined organic layer is washed with brine, dried over sodium sulfate, filtered, and concentrated under reduced pressure. The crude material is purified by silica gel column chromatography to provide methyl 2-((cyano(1-methyl-5-phenyl-1H-pyrazol-3-yl)methyl)thio)acetate.

Step 4: Preparation of 2-(1-Methyl-5-phenyl-1H-pyrazol-3-yl)thiomorpholine-3,5-dione To a solution of methyl 2-((cyano(1-methyl-5-phenyl-1H-pyrazol-3-yl)methyl)thio)acetate (1 equiv) in acetic acid (0.7 M) is added sulfuric acid (2 equiv), and the reaction mixture is heated to 110° C. for five hours. The reaction mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to provide 2-(1-methyl-5-phenyl-1H-pyrazol-3-yl)thiomorpholine-3,5-dione.

Example 44: Synthesis of 2-(1-Methyl-5-phenyl-1H-pyrazol-3-yl)thiomorpholine-3,5-dione 1-Oxide

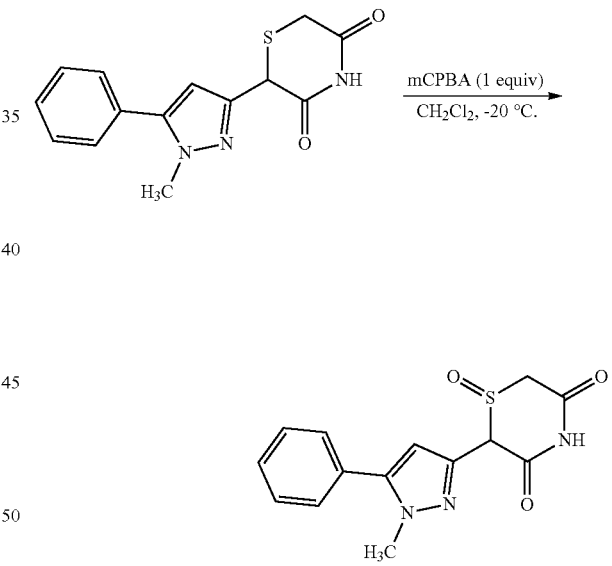

To a solution of 2-(1-methyl-5-phenyl-1H-pyrazol-3-yl)thiomorpholine-3,5-dione (1 equiv) in $CH_2Cl_2$ (0.1 M) at −20° C. is added 3-chlorobenzoperoxoic acid (1 equiv), and the reaction is stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(1-methyl-5-phenyl-1H-pyrazol-3-yl)thiomorpholine-3,5-dione 1-oxide.

Example 45: Synthesis of 2-(1-Methyl-5-phenyl-1H-pyrazol-3-yl)thiomorpholine-3,5-dione 1,1-Dioxide

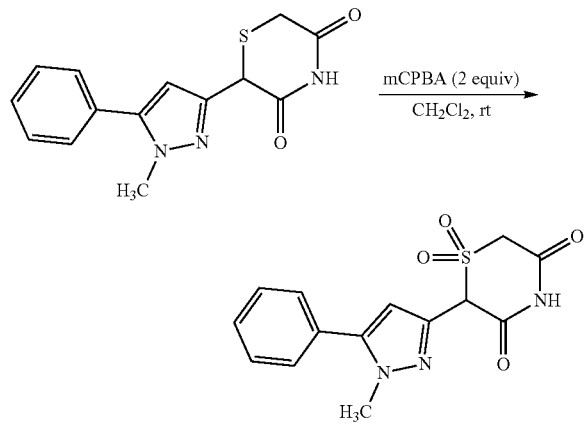

To a solution of 2-(1-methyl-5-phenyl-1H-pyrazol-3-yl) thiomorpholine-3,5-dione (1 equiv) in CH₂Cl₂ (0.1 M) at 0° C. is added 3-chlorobenzoperoxoic acid (2 equiv), and the reaction is slowly warmed up to room temperature and stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(1-methyl-5-phenyl-1H-pyrazol-3-yl)thiomorpholine-3,5-dione 1,1-dioxide.

Example 46: Synthesis of 2-(1-Methyl-1H-1,2,3-triazol-4-yl)thiomorpholine-3,5-dione

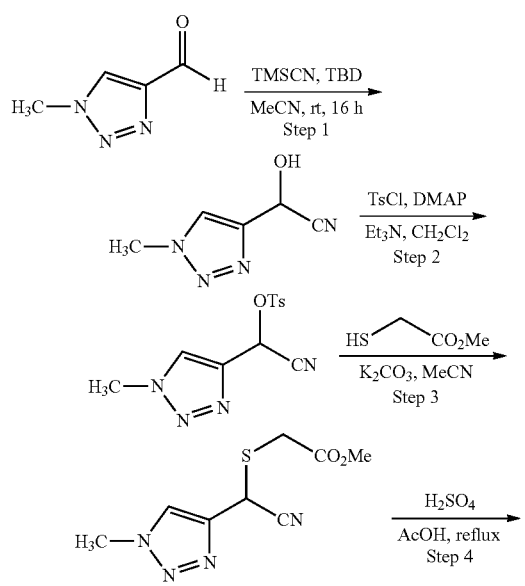

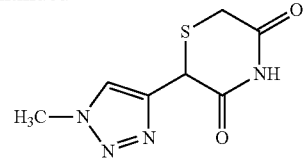

Step 1: Preparation of 2-Hydroxy-2-(1-methyl-1H-1,2,3-triazol-4-yl)acetonitrile A solution of trimethylsilyl cyanide (1.1 equiv) in acetonitrile (0.1 M) is added to a solution of 1-methyl-1H-1,2,3-triazole-4-carbaldehyde (1 equiv) and 1,5,7-triazabicyclo [4.4.0]dec-5-ene (1 equiv) in acetonitrile (0.1 M), and the reaction mixture is stirred at room temperature for three hours. The reaction mixture is diluted with 1N aqueous hydrochloric acid and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/hexanes) to afford 2-hydroxy-2-(1-methyl-1H-1,2,3-triazol-4-yl)acetonitrile.

Step 2: Preparation of Cyano(1-methyl-1H-1,2,3-triazol-4-yl)methyl 4-Methylbenzenesulfonate To a solution of afford 2-hydroxy-2-(1-methyl-1H-1,2,3-triazol-4-yl)acetonitrile (1 equiv) in dichloromethane (0.1 M) at 0° C. is added triethylamine (1.2 equiv) and N,N-dimethylpyridin-4-amine (0.1 equiv). 4-Methylbenzenesulfonyl chloride (1 equiv) is then added, and the solution is stirred until complete consumption of the starting material. The reaction mixture is quenched with water, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide cyano(1-methyl-1H-1,2,3-triazol-4-yl)methyl 4-methylbenzenesulfonate.

Step 3: Preparation of Methyl 2-((Cyano(1-methyl-1H-1,2,3-triazol-4-yl)methyl)thio)acetate To a solution of cyano(1-methyl-1H-1,2,3-triazol-4-yl) methyl 4-methylbenzenesulfonate (1 equiv) in acetonitrile (0.2 M) is added potassium carbonate (3 equiv) and methyl 2-mercaptoacetate (1 equiv), and the reaction mixture is stirred until full consumption of the starting material. The reaction is concentrated under reduced pressure and brought up in ethyl acetate. Water is added, and the layers are separated. The aqueous layer is extracted with ethyl acetate. The combined organic layer is washed with brine, dried over sodium sulfate, filtered, and concentrated under reduced pressure. The crude material is purified by silica gel column chromatography to provide methyl 2-((cyano(1-methyl-1H-1,2,3-triazol-4-yl)methyl)thio)acetate.

Step 4: Preparation of 2-(1-Methyl-1H-1,2,3-triazol-4-yl)thiomorpholine-3,5-dione To a solution of methyl 2-((cyano(1-methyl-1H-1,2,3-triazol-4-yl)methyl)thio)acetate (1 equiv) in acetic acid (0.7

M) is added sulfuric acid (2 equiv), and the reaction mixture is heated to 110° C. for five hours. The reaction mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to provide 2-(1-methyl-1H-1,2,3-triazol-4-yl)thiomorpholine-3,5-dione.

Example 47: Synthesis of 2-(1-Methyl-1H-1,2,3-triazol-4-yl)thiomorpholine-3,5-dione 1-Oxide

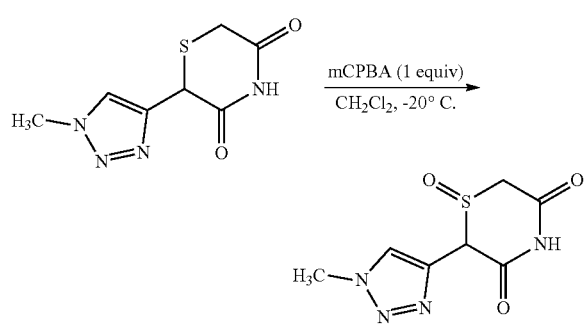

To a solution of 2-(1-methyl-1H-1,2,3-triazol-4-yl)thiomorpholine-3,5-dione (1 equiv) in CH$_2$Cl$_2$ (0.1 M) at −20° C. is added 3-chlorobenzoperoxoic acid (1 equiv), and the reaction is stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(1-methyl-1H-1,2,3-triazol-4-yl)thiomorpholine-3,5-dione 1-oxide.

Example 48: Synthesis of 2-(1-Methyl-1H-1,2,3-triazol-4-yl)thiomorpholine-3,5-dione 1,1-Dioxide

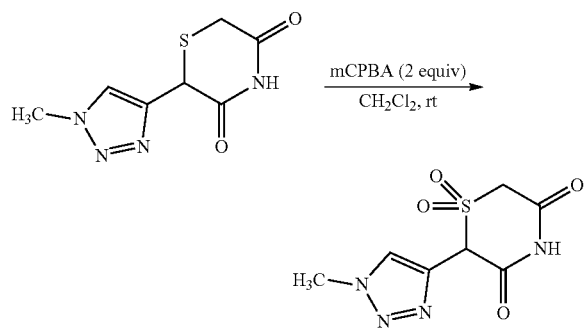

To a solution of 2-(1-methyl-1H-1,2,3-triazol-4-yl)thiomorpholine-3,5-dione (1 equiv) in CH$_2$Cl$_2$ (0.1 M) at 0° C. is added 3-chlorobenzoperoxoic acid (2 equiv), and the reaction is slowly warmed up to room temperature and stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(1-methyl-1H-1,2,3-triazol-4-yl)thiomorpholine-3,5-dione 1,1-dioxide.

Example 49: Synthesis of 2-(1-Methyl-1H-benzo[d]imidazol-2-yl)thiomorpholine-3,5-dione

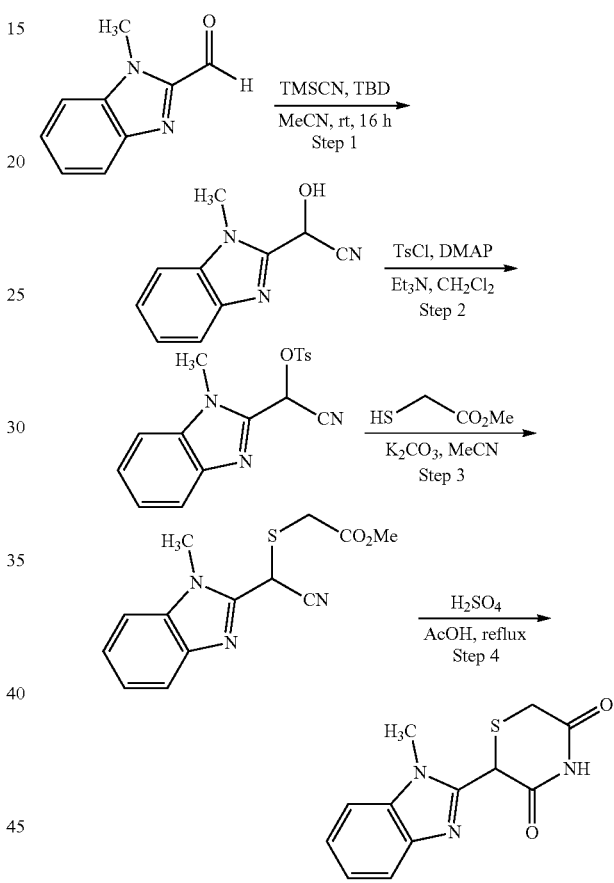

Step 1: Preparation of 2-Hydroxy-2-(1-methyl-1H-benzo[d]imidazol-2-yl)acetonitrile A solution of trimethylsilyl cyanide (1.1 equiv) in acetonitrile (0.1 M) is added to a solution of 1-methyl-1H-benzo[d]imidazole-2-carbaldehyde (1 equiv) and 1,5,7-triazabicyclo[4.4.0]dec-5-ene (1 equiv) in acetonitrile (0.1 M), and the reaction mixture is stirred at room temperature for three hours. The reaction mixture is diluted with 1N aqueous hydrochloric acid and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/hexanes) to afford 2-hydroxy-2-(1-methyl-1H-benzo[d]imidazol-2-yl)acetonitrile.

Step 2: Preparation of Cyano(1-methyl-1H-benzo[d]imidazol-2-yl)methyl 4-Methylbenzenesulfonate To a solution of afford 2-hydroxy-2-(1-methyl-1H-benzo[d]imidazol-2-yl)acetonitrile (1 equiv) in dichloromethane (0.1 M) at 0° C. is added triethylamine (1.2 equiv) and N,N-dimethylpyridin-4-amine (0.1 equiv). 4-Methylbenzenesulfonyl chloride (1 equiv) is then added, and the solution is stirred until complete consumption of the starting material. The reaction mixture is quenched with water, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide cyano(1-methyl-1H-benzo[d]imidazol-2-yl)methyl 4-methylbenzenesulfonate.

Step 3: Preparation of Methyl 2-((Cyano(1-methyl-1H-benzo[d]imidazol-2-yl)methyl)thio)acetate To a solution of cyano(1-methyl-1H-benzo[d]imidazol-2-yl)methyl 4-methylbenzenesulfonate (1 equiv) in acetonitrile (0.2 M) is added potassium carbonate (3 equiv) and methyl 2-mercaptoacetate (1 equiv), and the reaction mixture is stirred until full consumption of the starting material. The reaction is concentrated under reduced pressure and brought up in ethyl acetate. Water is added, and the layers are separated. The aqueous layer is extracted with ethyl acetate. The combined organic layer is washed with brine, dried over sodium sulfate, filtered, and concentrated under reduced pressure. The crude material is purified by silica gel column chromatography to methyl 2-((cyano(1-methyl-1H-benzo[d]imidazol-2-yl)methyl)thio)acetate.

Step 4: Preparation of 2-(1-Methyl-1H-benzo[d]imidazol-2-yl)thiomorpholine-3,5-dione To a solution of methyl 2-((cyano(1-methyl-1H-benzo[d]imidazol-2-yl)methyl)thio)acetate (1 equiv) in acetic acid (0.7 M) is added sulfuric acid (2 equiv), and the reaction mixture is heated to 110° C. for five hours. The reaction mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to provide 2-(1-methyl-1H-benzo[d]imidazol-2-yl)thiomorpholine-3,5-dione.

Example 50: Synthesis of 2-(1-Methyl-1H-benzo[d]imidazol-2-yl)thiomorpholine-3,5-dione 1-Oxide

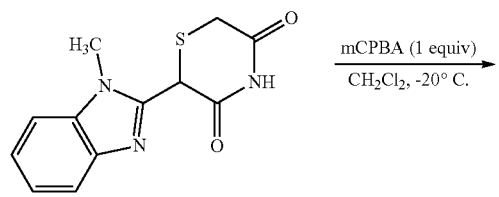

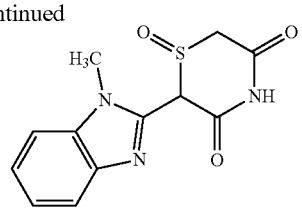

To a solution 2-(1-methyl-1H-benzo[d]imidazol-2-yl)thiomorpholine-3,5-dione (1 equiv) in $CH_2Cl_2$ (0.1 M) at −20° C. is added 3-chlorobenzoperoxoic acid (1 equiv), and the reaction is stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(1-methyl-1H-benzo[d]imidazol-2-yl)thiomorpholine-3,5-dione 1-oxide.

Example 51: Synthesis of 2-(1-Methyl-1H-benzo[d]imidazol-2-yl)thiomorpholine-3,5-dione 1,1-Dioxide

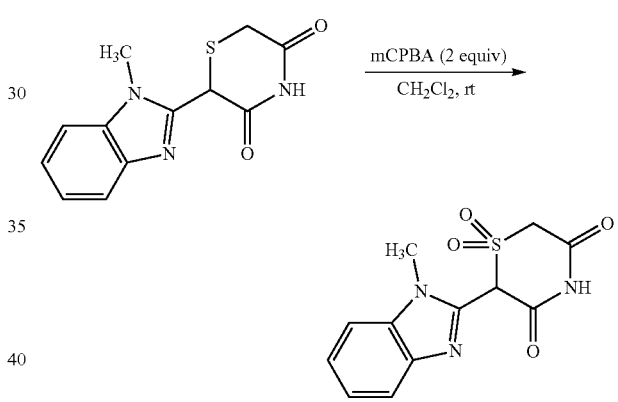

To a solution 2-(1-methyl-1H-benzo[d]imidazol-2-yl)thiomorpholine-3,5-dione (1 equiv) in $CH_2Cl_2$ (0.1 M) at 0° C. is added 3-chlorobenzoperoxoic acid (2 equiv), and the reaction is slowly warmed up to room temperature and stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(1-methyl-1H-benzo[d]imidazol-2-yl)thiomorpholine-3,5-dione 1,1-dioxide.

Example 52: Synthesis of 2-(Pyridin-2-yl)thiomorpholine-3,5-dione

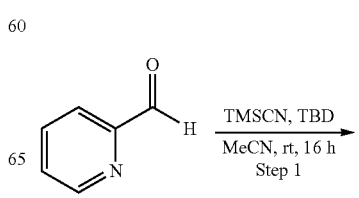

535

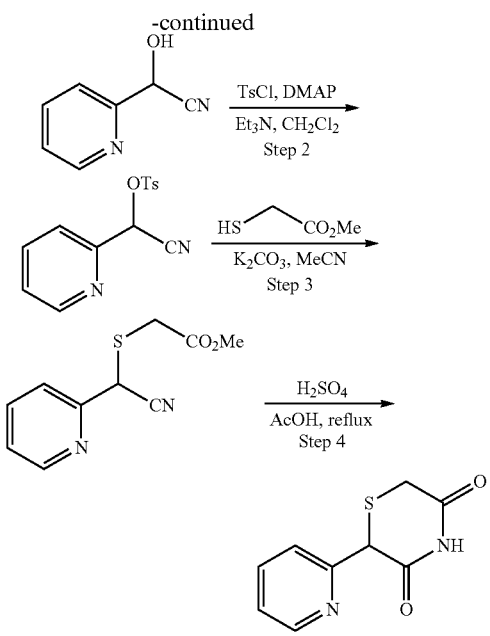

Step 1: Preparation of 2-Hydroxy-2-(pyridin-2-yl)acetonitrile

A solution of trimethylsilyl cyanide (1.1 equiv) in acetonitrile (0.1 M) is added to a solution of picolinaldehyde (1 equiv) and 1,5,7-triazabicyclo[4.4.0]dec-5-ene (1 equiv) in acetonitrile (0.1 M), and the reaction mixture is stirred at room temperature for three hours. The reaction mixture is diluted with 1N aqueous hydrochloric acid and ethyl acetate followed by addition of saturated aqueous sodium bicarbonate solution, and the layers are separated. The organic layer is washed with brine, dried over sodium sulfate, filtered, and concentrated under reduced pressure. The crude material is purified by silica gel column chromatography (0-50% ethyl acetate/hexanes) to afford 2-hydroxy-2-(pyridin-2-yl)acetonitrile.

Step 2: Preparation of Cyano(pyridin-2-yl)methyl 4-Methylbenzenesulfonate

To a solution of afford 2-hydroxy-2-(pyridin-2-yl)acetonitrile (1 equiv) in dichloromethane (0.1 M) at 0° C. is added triethylamine (1.2 equiv) and N,N-dimethylpyridin-4-amine (0.1 equiv). 4-Methylbenzenesulfonyl chloride (1 equiv) is then added, and the solution is stirred until complete consumption of the starting material. The reaction mixture is quenched with water, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide cyano(pyridin-2-yl)methyl 4-methylbenzenesulfonate.

Step 3: Preparation of Methyl 2-((Cyano(pyridin-2-yl)methyl)thio)acetate

To a solution of cyano(pyridin-2-yl)methyl 4-methylbenzenesulfonate (1 equiv) in acetonitrile (0.2 M) is added potassium carbonate (3 equiv) and methyl 2-mercaptoacetate (1 equiv), and the reaction mixture is stirred until full consumption of the starting material. The reaction is concentrated under reduced pressure and brought up in ethyl acetate. Water is added, and the layers are separated. The aqueous layer is extracted with ethyl acetate. The combined organic layer is washed with brine, dried over sodium sulfate, filtered, and concentrated under reduced pressure. The crude material is purified by silica gel column chromatography to methyl 2-((cyano(pyridin-2-yl)methyl)thio)acetate.

Step 4: Preparation of 2-(Pyridin-2-yl)thiomorpholine-3,5-dione

To a solution of to methyl 2-((cyano(pyridin-2-yl)methyl)thio)acetate (1 equiv) in acetic acid (0.7 M) is added sulfuric acid (2 equiv), and the reaction mixture is heated to 110° C. for five hours. The reaction mixture is cooled to room temperature and concentrated under reduced pressure. The crude residue is diluted with ethyl acetate and saturated aqueous sodium bicarbonate solution, and the layers are separated. The organic layer is washed with water and brine, dried over sodium sulfate, filtered, and concentrated under reduced pressure. The crude material is purified by silica gel column chromatography to provide 2-(pyridin-2-yl)thiomorpholine-3,5-dione.

Example 53: Synthesis of 2-(Pyridin-2-yl)thiomorpholine-3,5-dione 1-Oxide

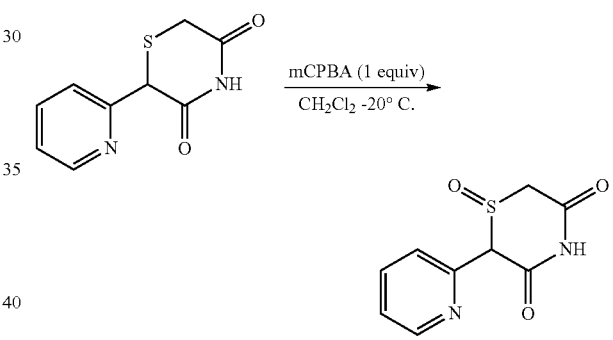

To a solution 2-(pyridin-2-yl)thiomorpholine-3,5-dione (1 equiv) in $CH_2Cl_2$ (0.1 M) at −20° C. is added 3-chlorobenzoperoxoic acid (1 equiv), and the reaction is stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(pyridin-2-yl)thiomorpholine-3,5-dione 1-oxide.

Example 54: Synthesis of 2-(Pyridin-2-yl)thiomorpholine-3,5-dione 1,1-Dioxide

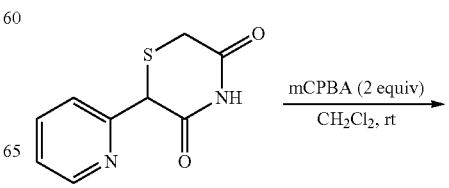

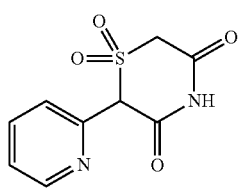

To a solution 2-(pyridin-2-yl)thiomorpholine-3,5-dione (1 equiv) in CH$_2$Cl$_2$ (0.1 M) at 0° C. is added 3-chlorobenzoperoxoic acid (2 equiv), and the reaction is slowly warmed up to room temperature and stirred until consumption of the starting material. The reaction is quenched with saturated aqueous sodium bicarbonate solution, and the layers are separated. The aqueous layer is extracted with dichloromethane. The combined organic layer is washed with brine, dried over sodium sulfate, filtered, and concentrated under reduced pressure. The crude material is purified by silica gel column chromatography to provide 2-(pyridin-2-yl)thiomorpholine-3,5-dione 1,1-dioxide.

Example 55. Synthesis of {4-[4-(2,4-Dioxo-3-azabicyclo[3.1.1]hept-1-ylamino)-phenyl]-cyclohexyl}-carbamic Acid tert-Butyl Ester

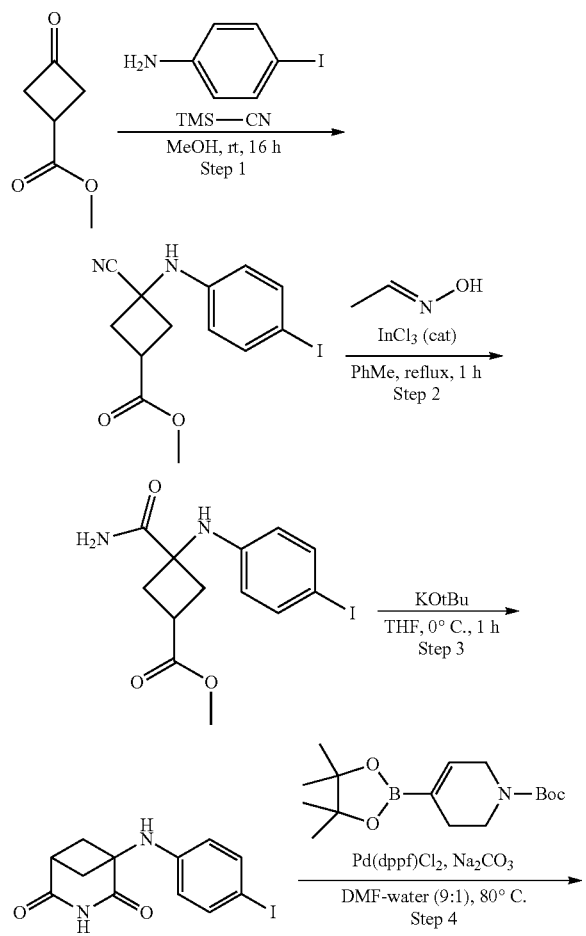

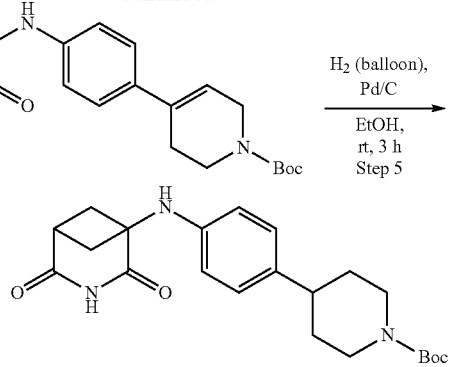

Step 1: Preparation of 3-Cyano-3-(4-iodo-phenylamino)-cyclobutanecarboxylic Acid Methyl Ester To a stirred solution of methyl 3-oxocyclobutanecarboxylate (5.0 g, 39.02 mmol) in methanol (10 mL) was added 4-iodoaniline (9.40 g, 42.93 mmol), and to this solution was added TMSCN (18.71 g, 78.05 mmol 23.60 mL). The reaction mixture was stirred for 16 hours at room temperature. The reaction mixture was evaporated under reduced pressure to provide a crude residue. The crude material was purified by silica gel (100-200 mesh) column chromatography (0%-30% ethyl acetate in hexane) to provide methyl 3-cyano-3-(4-iodoanilino)cyclobutanecarboxylate (11.5 g, 32.29 mmol, 82.74% yield) as an off-white solid. LC MS: ES+ 357.2.

Step 2: Preparation of 3-Carbamoyl-3-(4-iodo-phenylamino)-cyclobutanecarboxylic Acid Methyl Ester A stirred solution of methyl 3-cyano-3-(4-iodoanilino) cyclobutanecarboxylate (4 g, 11.23 mmol), (1Z)-acetaldehyde oxime (1.99 g, 33.69 mmol) and indium(III) chloride (24.84 mg, 112.31 umol) in toluene (20 mL) was heated to reflux for 3 h. After complete consumption of the starting material as monitored by TLC, the resulting precipitate was filtered off and washed with toluene/ether to obtain methyl 3-carbamoyl-3-(4-iodoanilino)cyclobutanecarboxylate (3 g, 8.02 mmol, 71.39% yield) which was sufficiently pure to use in the next step. LC MS: ES+ 375.2.

Step 3: Synthesis of 1-(4-Iodo-phenylamino)-3-azabicyclo[3.1.1]heptane-2,4-dione To a stirred solution of methyl 3-carbamoyl-3-(4-iodoanilino)cyclobutanecarboxylate (600 mg, 1.60 mmol) in THF (10 mL), potassium tert-butoxide (359.87 mg, 3.21 mmol) was added at 0° C. and stirred for 30 minutes at same temperature. The reaction mixture was neutralized with 1M citric acid solution (to adjust pH-6) and diluted with ethyl acetate (25 mL). The combined organic layer was separated, dried over sodium sulfate and concentrated under reduced pressure. The resulting crude residue was purified by column chromatography using (0%-40% ethyl acetate/hexane as eluent) to afford 5-(4-iodoanilino)-3-azabicyclo[3.1.1]heptane-2,4-dione (300 mg, 876.85 umol, 54.68% yield). LC MS: ES+ 343.0.

Step 4: Synthesis of tert-Butyl 4-[4-[(2,4-Dioxo-3-azabicyclo[3.1.1]heptan-5-yl)amino]phenyl]-3,6-dihydro-2H-pyridine-1-carboxylate To a mixture of 5-(4-iodoanilino)-3-azabicyclo[3.1.1]heptane-2,4-dione (1.6 g, 4.68 mmol) and tert-butyl 4-(4,4,5,5- tetramethyl-1,3,2-dioxaborolan-2-yl)-3,6-dihydro-2H-pyridine-1-carboxylate (2.89 g, 9.35 mmol) in DMF (4 mL) and water (0.5 mL) was added sodium carbonate (495.66 mg, 4.68 mmol, 195.91 μL) and the resulting solution was degassed with N2 for 15 minutes followed by the addition of PdCl₂(dppf)-DCM (3.82 g, 4.68 mmol). After complete addition, the reaction mixture was heated at 90° C. for 5 hours in a sealed tube. The reaction mixture was filtered through a celite bed. The filtrate was collected and added to ice cooled water. The aqueous fraction was extracted with ethyl acetate (3×30 mL), separated, dried over sodium sulfate and concentrated. The crude residue was purified using column chromatography to provide tert-butyl 4-[4-[(2,4-dioxo-3-azabicyclo[3.1.1]heptan-5-yl)amino]phenyl]-3,6-dihydro-2H-pyridine-1-carboxylate (1.3 g, 3.27 mmol, 69.94% yield) as a white solid. LC MS: ES+ 398.0.

Step 5: Synthesis of {4-[4-(2,4-Dioxo-3-aza-bicyclo [3.1.1]hept-1-ylamino)-phenyl]-cyclohexyl}-carbamic Acid tert-Butyl Ester A thoroughly degassed solution of tert-butyl 4-[4-[(2,4-dioxo-3-azabicyclo[3.1.1]heptan-5-yl)amino]phenyl]-3,6-dihydro-2H-pyridine-1-carboxylate (1.4 g, 3.52 mmol) in ethanol (20 mL) was hydrogenated under balloon pressure in the presence of 10% palladium on carbon (374.84 mg, 3.52 mmol) at room temperature for 3 hours. The reaction mixture was filtered through a celite bed; the filtrate was collected and evaporated under reduced pressure. The crude residue was purified by column chromatography to afford tert-butyl 4-[4-[(2,4-dioxo-3-azabicyclo[3.1.1]heptan-5-yl)amino]phenyl]piperidine-1-carboxylate (900 mg, 2.25 mmol, 63.96% yield, 100% purity) as an off-white solid. 1H NMR (d₆-DMSO, 400 MHZ) 6 10.69 (s, 1H), 6.90 (d, J=8.36 Hz, 2H), 6.39 (d, J=8.36 Hz, 2H), 6.08 (s, 1H), 4.05-4.01 (m, 2H), 2.96-2.93 (m, 1H), 2.77-2.66 (m, 4H), 2.49-2.45 (m, 2H), 1.69-1.64 (m, 2H), 1.40 (s, 9H), 1.39-1.33 (m, 2H); LC MS: ES+ 400.2.

Example 56. Synthesis of tert-Butyl N-[1-[4-[(2,4-dioxo-3-azabicyclo[3.1.1]heptan-5-yl)amino]phenyl]-4-piperidyl]carbamate

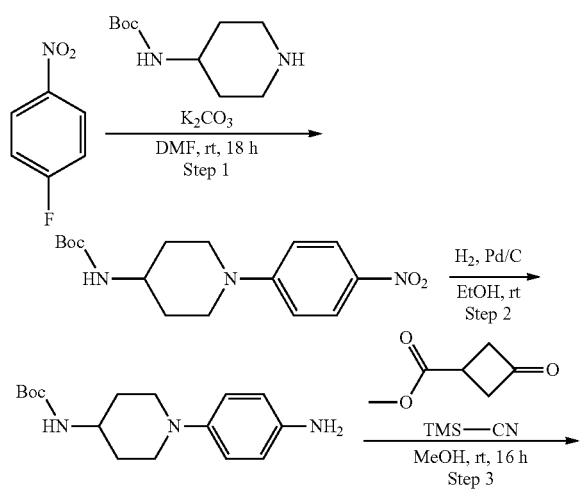

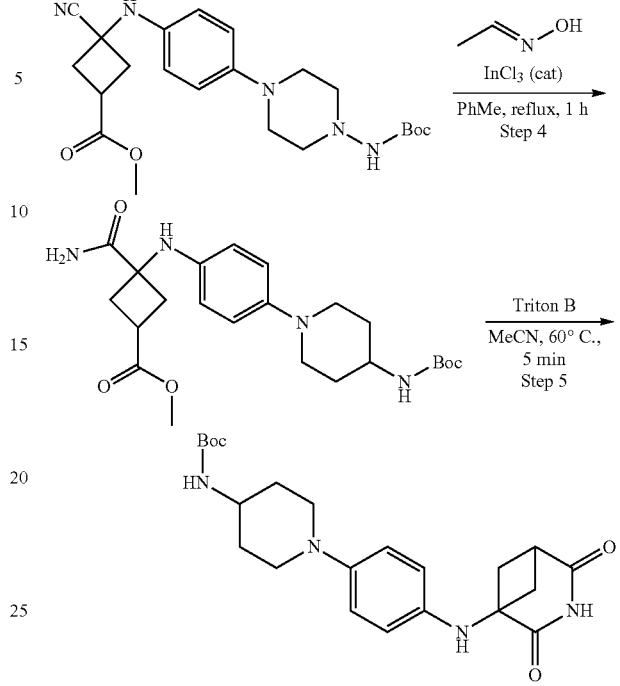

Step 1: Synthesis of [1-(4-Nitrophenyl)-piperidin-4-yl]-carbamic Acid tert-Butyl Ester To a stirred solution of 1-fluoro-4-nitro-benzene (800 mg, 5.67 mmol, 601.50 uL) in DMF (10 mL) was added tert-butyl N-(4-piperidyl)carbamate (1.03 g, 5.15 mmol), K₂CO₃ (3.25 g, 15.46 mmol) and the reaction mixture was heated at 80° C. for 16 hours. The reaction mixture was diluted with ethyl acetate, washed with water and brine, dried over Na₂SO₄ and concentrated. The crude mixture was purified by column chromatography using 0-30% ethyl acetate: hexane to afford tert-butyl N-[1-(4-nitrophenyl)-4-piperidyl] carbamate (1.6 g, 4.98 mmol, 96.59% yield) as a yellow solid. LC MS: ES+ 322.4.

Step 2: Synthesis of [1-(4-Amino-phenyl)-piperidin-4-yl]-carbamic Acid tert-Butyl Ester To a thoroughly degassed solution of tert-butyl N-[1-(4-nitrophenyl)-4-piperidyl]carbamate (1.6 g, 4.98 mmol) in ethanol (50 mL) was added wet 10% palladium on carbon (635.80 mg, 5.97 mmol) and the solution was stirred under a hydrogen atmosphere (Balloon) for 16 hours. The reaction mixture was filtered through a celite bed and washed with ethanol. The filtrate was concentrated. The crude mixture was purified by column chromatography using (0%-20% ethyl acetate/hexane) to afford tert-butyl N-[1-(4-aminophenyl)-4-piperidyl]carbamate (1.1 g, 3.78 mmol, 75.82% yield) as a light brown solid. LC MS: ES+ 292.3.

Step 3: Synthesis of 3-[4-(4-tert-Butoxycarbonylamino-piperidin-1-yl)-phenylamino]-3-cyano-cyclobutanecarboxylic Acid Methyl Ester To a stirred solution of methyl 3-oxocyclobutanecarboxylate (2.6 g, 20.29 mmol, 2.13 mL) in methanol (50 mL) was added tert-butyl N-[1-(4-aminophenyl)-4-piperidyl]carbamate (6.50 g, 22.32 mmol) and reaction mixture was stirred at room temperature for 1 hour. TMSCN (9.73 g, 40.59 mmol, 12.27 mL) was then added to the reaction mixture and the reaction mixture was stirred for 16 hours at room temperature. The reaction mixture was concentrated under reduced pressure and the crude material was purified by column chromatography using (0%-30% ethyl acetate/hexane) to afford methyl 3-[4-[4-(tert-butoxycarbonylamino)-1-piperidyl]anilino]-3-cyano-cyclobutanecarboxylate (4 g, 9.33 mmol, 46.00% yield) as a light brown solid. LC MS: ES+ 429.4.

Step 4: Synthesis of tert-Butyl 4-[4-[(1-Carbamoyl-3-methoxycarbonyl-cyclobutyl)amino]phenyl]piperazine-1-carboxylate A stirred solution of tert-butyl 4-[4-[(1-cyano-3-methoxycarbonyl-cyclobutyl)amino]phenyl]piperazine-1-carboxylate (6.5 g, 15.68 mmol), (1Z)-acetaldehyde oxime (2.78 g, 47.04 mmol) and indium(III) chloride (1.04 g, 4.70 mmol) in toluene (20 mL) was heated to reflux for 3 hours. The resulting precipitate was filtered off and washed with toluene/ether to obtain tert-butyl 4-[4-[(1-carbamoyl-3-methoxycarbonyl-cyclobutyl)amino]phenyl]piperazine-1-carboxylate (4.7 g, 10.87 mmol, 69.30% yield) which was sufficiently pure to use in the next step. LC MS: ES+ 447.4.

Step 5: Synthesis of tert-Butyl N-[1-[4-[(2,4-Dioxo-3-azabicyclo[3.1.1]heptan-5-yl)amino]phenyl]-4-piperidyl]carbamate A solution of tert-butyl 4-[4-[(1-carbamoyl-3-methoxycarbonyl-cyclobutyl)amino]phenyl]piperazine-1-carboxylate (800 mg, 1.79 mmol) in acetonitrile (5 mL) was heated at 60° C. under inert atmosphere while a solution of Triton B [40% in MeOH (2.69 mmol)] in acetonitrile (5 mL) was added drop-wise to this pre-heated reaction mixture. After complete addition, the reaction mixture was kept at the same temperature for a further 10 minutes. After completion of the reaction, as evidenced from LC-MS, the reaction mixture was cooled to room temperature and concentrated under vacuum. The oily residue was directly purified by column chromatography to afford tert-butyl N-[1-[4-[(2,4-dioxo-3-azabicyclo[3.1.1]heptan-5-yl)amino]phenyl]-4-piperidyl]carbamate (375 mg, 904.71 umol, 50.50% yield) as a light brown solid. 1H NMR (d$_6$-DMSO, 400 MHZ) δ 10.67 (s, 1H), 6.80 (d, J=7.44 Hz, 1H), 6.71 (d, J=8.72 Hz, 2H), 6.41 (d, J=8.6 Hz, 2H), 5.69 (s, 1H), 3.33-3.31 (m, 2H), 2.92 (t, J=6.24 Hz, 1H), 2.68-2.63 (m, 2H), 2.55-2.42 (m, 4H), 1.76-1.74 (m, 2H), 1.52-1.46 (m, 2H), 1.38 (s, 9H); LC MS: ES+ 415.2.

Example 57. Synthesis of {4-[4-(2,4-Dioxo-3-azabicyclo[3.1.1]hept-1-ylamino)-phenyl]-cyclohexyl}-carbamic Acid tert-Butyl Ester

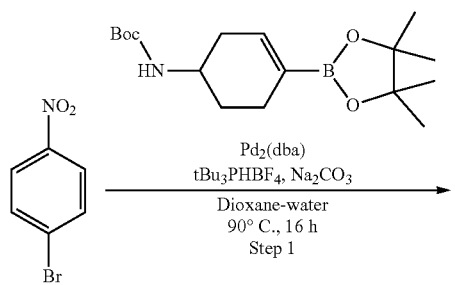

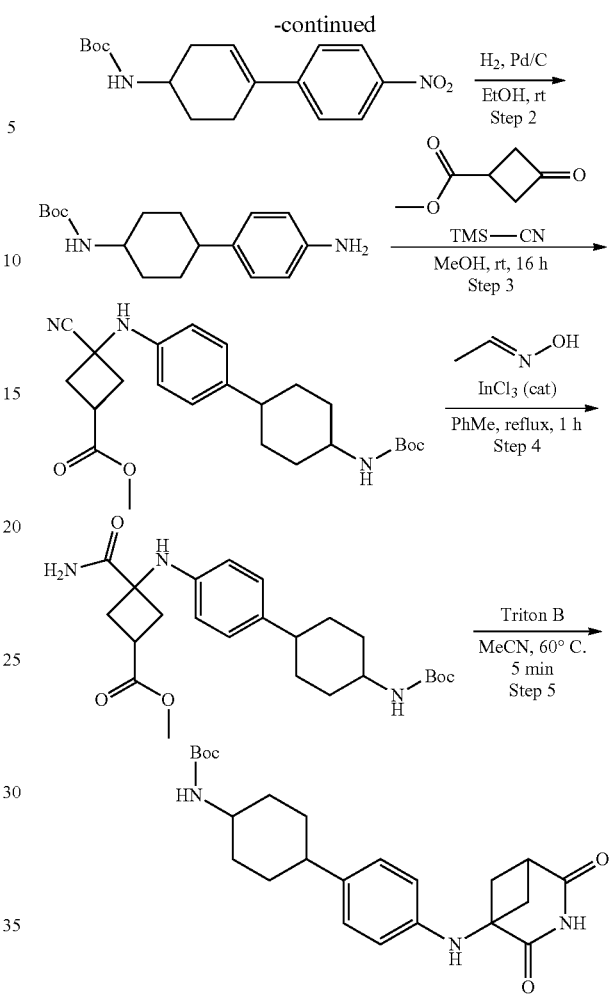

Step 1: Synthesis of [4-(4-Nitro-phenyl)-cyclohex-3-enyl]-carbamic Acid tert-Butyl Ester A stirred solution of 1-bromo-4-nitro-benzene (315 mg, 1.56 mmol, 161.54 uL) and tert-butyl N-[4-(4,4,5,5-tetramethyl-1,3,2-dioxaborolan-2-yl)cyclohex-3-en-1-yl]carbamate (504.04 mg, 1.56 mmol) in dioxane (3.2 mL) and water (0.8 mL) in a sealed tube was purged with argon. To this mixture was added sodium carbonate (495.83 mg, 4.68 mmol, 195.98 uL) followed by tri-tert-butylphosphonium tetrafluoroborate (90.48 mg, 311.87 umol) and Pd$_2$(dba)$_3$ (142.79 mg, 155.94 umol), the reaction mixture was closed tightly and was allowed to stir for 14 hours at 90° C. The reaction mixture was cooled and concentrated under reduced pressure to afford the crude product. The crude product thus obtained was purified by column chromatography over silica gel to elute tert-butyl N-[4-(4-nitrophenyl)cyclohex-3-en-1-yl]carbamate (450 mg, 1.41 mmol, 90.64% yield) as light yellow solid. LC MS: ES+ 319.2.

Step 2: Synthesis of [4-(4-Amino-phenyl)-cyclohexyl]-carbamic Acid tert-Butyl Ester A stirred suspension of tert-butyl N-[4-(4-nitrophenyl)cyclohex-3-en-1-yl]carbamate (700.0 mg, 2.20 mmol) in ethanol (12.0 mL) was degassed with nitrogen. 10% palladium on carbon, (Type 487, dry, 491.37 mg, 461.73 umol, 10% purity) was added and the reaction mixture was stirred at room temperature under a hydrogen balloon for 2 hours. The reaction mixture was filtered through a celite bed, and the filtrate was concentrated to afford tert-butyl N-[4-(4-aminophenyl)cyclohexyl]carbamate (500.0 mg, 1.72 mmol, 78.31% yield) as white solid. LC MS: ES+ 291.2.

Step 3: Synthesis of 3-[4-(4-tert-Butoxycarbonylamino-cyclohexyl)-phenylamino]-3-cyano-cyclobutanecarboxylic Acid Methyl Ester The same procedure was followed as in Step 3 of Example 56. Yield-80.83%, LC MS: ES+ 428.3

Step 4. Synthesis of Methyl 3-((4-(4-((tert-Butoxycarbonyl)amino)cyclohexyl)phenyl)amino)-3-carbamoylcyclobutane-1-carboxylate The same procedure was followed as in Step 4 of Example 56. The product was used without further purification in the next step.

Step 4: {4-[4-(2,4-Dioxo-3-aza-bicyclo[3.1.1]hept-1-ylamino)-phenyl]-cyclohexyl}-carbamic Acid tert-Butyl Ester A solution of methyl 3-((4-(4-((tert-butoxycarbonyl)amino)cyclohexyl)phenyl)amino)-3-carbamoylcyclobutane-1-carboxylate (550 mg, 1.27 mmol) in acetonitrile (10 mL) was heated at 60° C. under inert atmosphere while a solution of Triton B [40% in MeOH (1.91 mmol)] in acetonitrile (5 mL) was added drop-wise to this pre-heated reaction mixture. After complete addition, the reaction mixture was maintained at the same temperature for a further 10 minutes. After completion of reaction as evidenced from LC-MS, the reaction mixture was cooled to room temperature and concentrated under vacuum. The oily residue was directly purified by column chromatography to afford methyl 3-((4-(4-((tert-butoxycarbonyl)amino)cyclohexyl)phenyl)amino)-3-carbamoylcyclobutane-1-carboxylate (210 mg, ~48% yield) as of white solid. 1H NMR ($d_6$-DMSO, 400 MHZ) δ isolated as a mixture of Cis- and Trans-isomers; ES (M+H) 414.3.

Example 58. Synthesis of 4-[4-(2,4-Dioxo-3-aza-bicyclo[3.1.1]hept-1-ylamino)-phenyl]-piperazine-1-carboxylic Acid tert-Butyl Ester

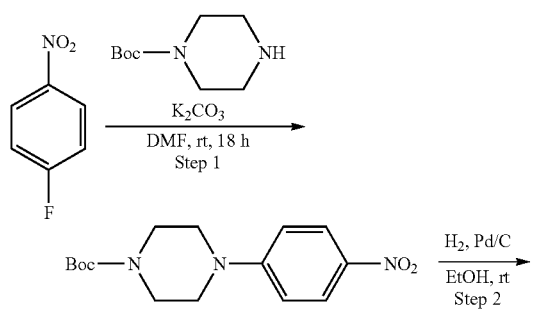

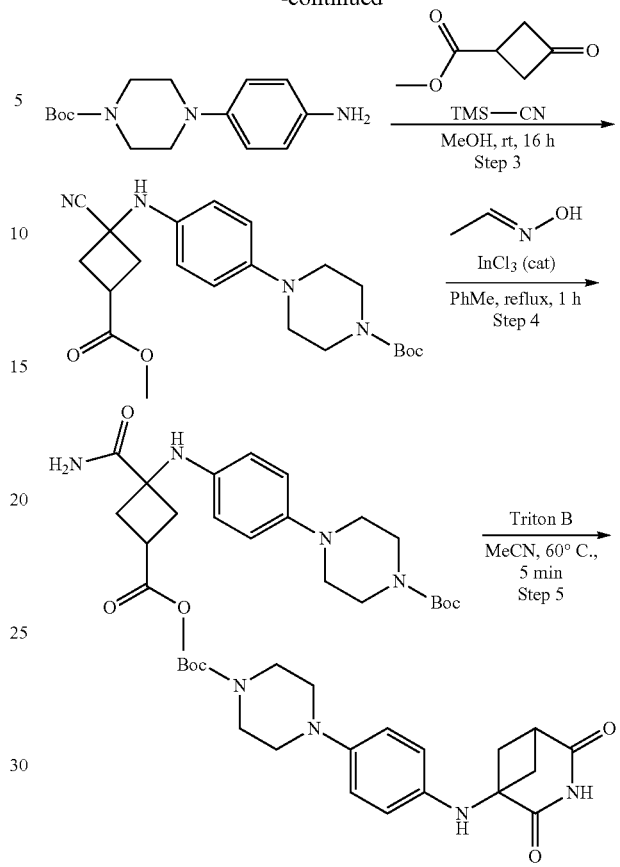

Step 1: Synthesis of 4-(4-Nitrophenyl)-piperazine-1-carboxylic Acid tert-Butyl Ester The same procedure was used as in Step 1 of Example 56. Yield—75.39%, LC MS: ES+ 308.2.

Step 2: Synthesis of 4-(4-Aminophenyl)-piperazine-1-carboxylic Acid tert-Butyl Ester The same procedure was used as in Step 2 of Example 56. Yield-89.36%, LC MS: ES+ 278.1.

Step 3: Synthesis of 4-[4-(1-Cyano-3-methoxycarbonyl-cyclobutylamino)-phenyl]-piperazine-1-carboxylic Acid tert-Butyl Ester The same procedure was used as in Step 3 of Example 56. Yield—7.42%, LC MS: ES+ 415.2.

Step 4: Synthesis of 4-[4-(1-Carbamoyl-3-methoxycarbonyl-cyclobutylamino)-phenyl]-piperazine-1-carboxylic Acid tert-Butyl Ester The same procedure was used as in Step 4 of Example 56. Yield-79.86%, LC MS: ES+ 433.2.

Step 5: Synthesis of 4-[4-(2,4-Dioxo-3-aza-bicyclo[3.1.1]hept-1-ylamino)-phenyl]-piperazine-1-carboxylic acid tert-Butyl Ester The same procedure was used as in Step 5 of Example 56. Yield-%, 1H NMR ($d_6$-DMSO, 400 MHZ) δ 10.68 (s, 1H), 6.73 (d, J=8.4 Hz, 2H), 6.42 (d, J=8.4 Hz, 2H), 5.79 (s, 1H), 3.42 (brs, 4H), 2.95-2.91 (m, 1H), 2.85 (brs, 4H), 2.67-2.64 (m, 2H), 2.49-2.45 (m, 2H), 1.41 (s, 9H); LC MS: ES+ 401.2.

TABLE 1

Representative Compounds of the Present Invention

| Compound | Structure |
|---|---|
| 1 | 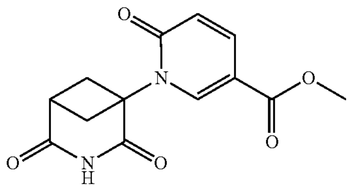 [SMILES: COC(=O)c1ccc(=O)n(C23CC(C2)C(=O)NC3=O)c1] |
| 2 | 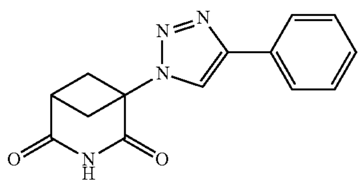 [SMILES: O=C1NC(=O)C2(n3cc(-c4ccccc4)nn3)CC1C2] |
| 3 | 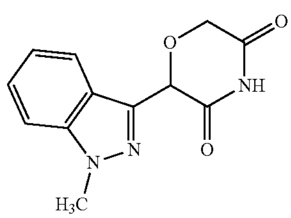 [SMILES: Cn1nc(C2OCC(=O)NC2=O)c2ccccc21] |
| 4 | 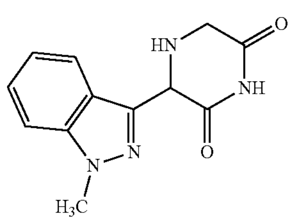 [SMILES: Cn1nc(C2NCC(=O)NC2=O)c2ccccc21] |

TABLE 2

Additional Compounds of the Present Invention

| Compound | Structure |
|---|---|
| 5 | 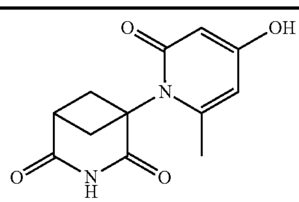 |
| 6 | 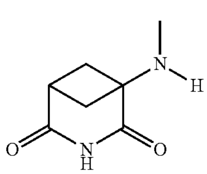 |

TABLE 2-continued

Additional Compounds of the Present Invention

| Compound | Structure |
|---|---|
| 7 | 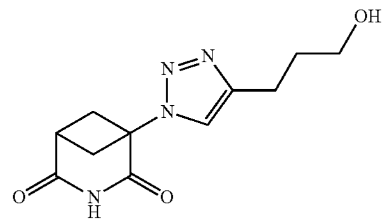 [SMILES: O=C1NC(=O)C2(n3cc(CCCO)nn3)CC1C2] |
| 8 | 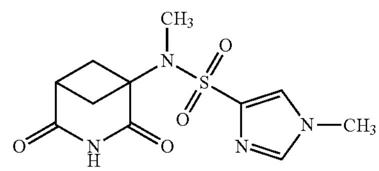 [SMILES: CN(C12CC(C1)C(=O)NC2=O)S(=O)(=O)c1cn(C)cn1] |
| 9 | 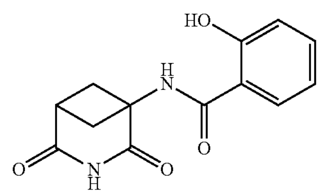 [SMILES: O=C(NC12CC(C1)C(=O)NC2=O)c1ccccc1O] |
| 10 | 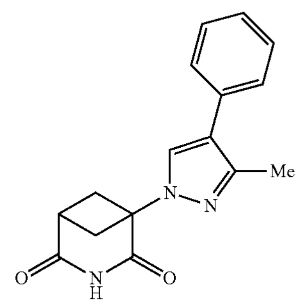 [SMILES: Cc1nn(C23CC(C2)C(=O)NC3=O)cc1-c1ccccc1] |
| 11 | 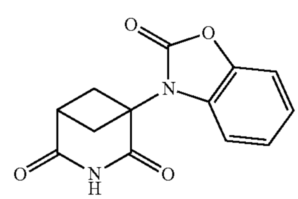 [SMILES: O=C1NC(=O)C2(n3c(=O)oc4ccccc43)CC1C2] |
| 12 | 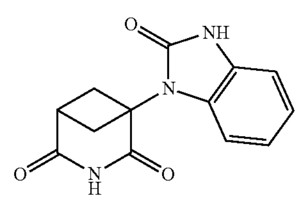 [SMILES: O=C1NC(=O)C2(n3c(=O)[nH]c4ccccc43)CC1C2] |
| 13 | 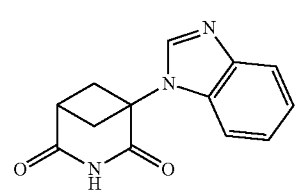 [SMILES: O=C1NC(=O)C2(n3cnc4ccccc43)CC1C2] |

TABLE 2-continued

Additional Compounds of the Present Invention

| Compound | Structure |
|---|---|
| 14 | (structure) |
| 15 | (structure) |
| 16 | (structure) |
| 17 | (structure) |
| 18 | (structure) |
| 19 | (structure) |
| 20 | (structure) |
| 21 | (structure) |
| 22 | (structure) |
| 23 | (structure) |
| 24 | (structure) |
| 25 | (structure) |
| 26 | (structure) |
| 27 | (structure) |

TABLE 2-continued

Additional Compounds of the Present Invention

| Compound | Structure |
|---|---|
| 28 | |
| 29 | |
| 30 | |
| 31 | |
| 32 | |
| 33 | |
| 34 | 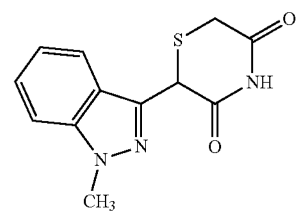 [SMILES: Cn1nc(C2SCC(=O)NC2=O)c2ccccc21] |
| 35 | 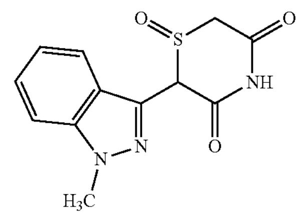 [SMILES: Cn1nc(C2C(=O)NC(=O)CS2=O)c2ccccc21] |
| 36 | 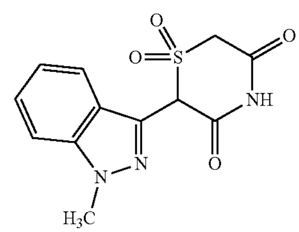 [SMILES: Cn1nc(C2C(=O)NC(=O)CS2(=O)=O)c2ccccc21] |
| 37 | 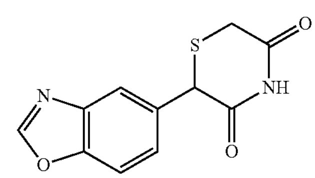 [SMILES: O=C1CSC(c2ccc3ocnc3c2)C(=O)N1] |
| 38 | 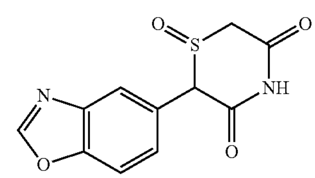 [SMILES: O=C1CS(=O)C(c2ccc3ocnc3c2)C(=O)N1] |
| 39 | 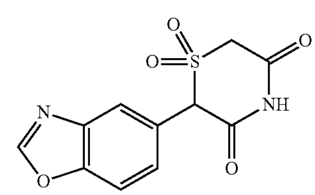 [SMILES: O=C1CS(=O)(=O)C(c2ccc3ocnc3c2)C(=O)N1] |
| 40 | 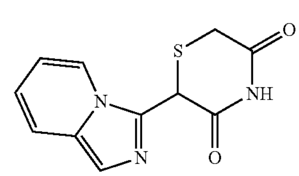 [SMILES: O=C1CSC(c2ncc3ccccn23)C(=O)N1] |

TABLE 2-continued
Additional Compounds of the Present Invention
| Compound | Structure |
|---|---|
| 41 | 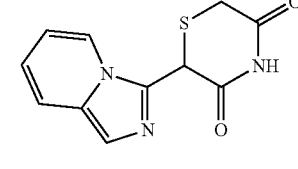 |
| 42 | 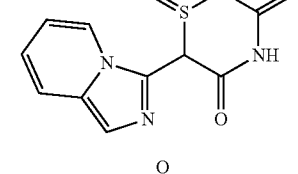 |
| 43 | 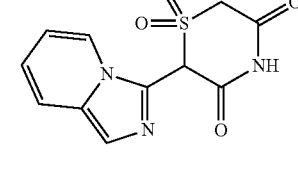 |
| 44 | 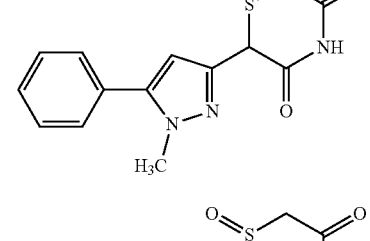 |
| 45 | 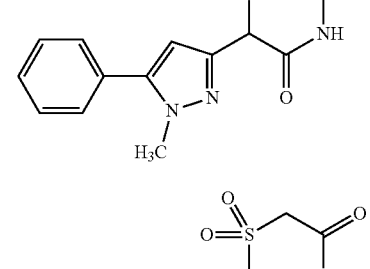 |
| 46 | 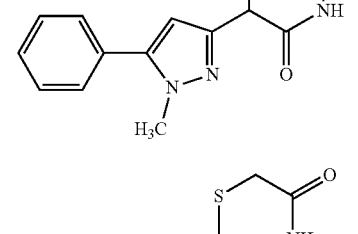 |
| 47 | 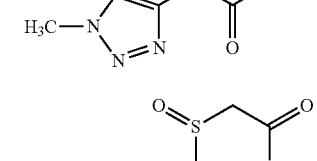 |
| 48 | 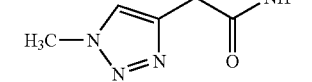 |
| 49 | |
| 50 | |
| 51 | |
| 52 | |
| 53 | |
| 54 | |
| 55 | |

TABLE 3

Additional Representative Compounds of the Present Invention

| Compound | Structure |
|---|---|
| 56 | 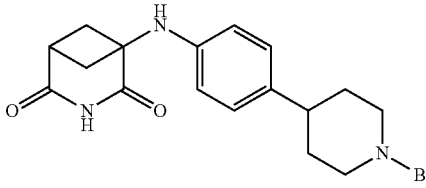 |
| 57 | 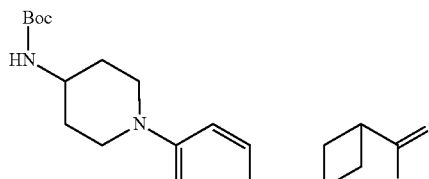 |
| 58 | 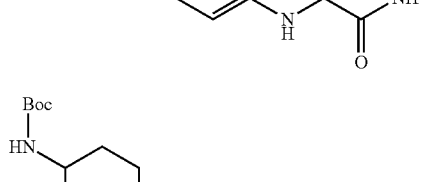 |
| 59 | 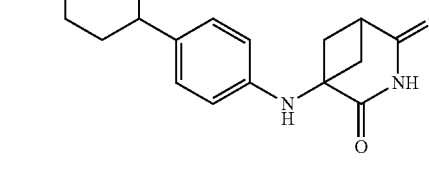 |

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modification may be made thereto without departing from the spirit or scope of the invention as defined in the appended claims.

We claim:

1. A compound of Formula:

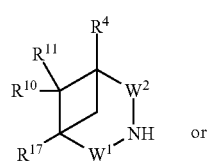

(I)

or

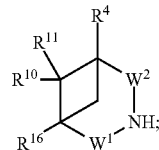

(III)

or a pharmaceutically acceptable salt thereof;

wherein:

$W^1$ is C=O;

$W^2$ is C=O;

$R^2$ is selected at each instance from the group consisting of hydrogen, alkyl, heteroalkyl, aliphatic, heteroaliphatic, heterocyclic, aryl, heteroaryl, —C(O)H, —C(O)OH, —C(O)alkyl, —C(O)Oalkyl, —C(O)(aliphatic, aryl, heteroaliphatic or heteroaryl), —C(O)O(aliphatic, aryl, heteroaliphatic, or heteroaryl), alkene, and alkyne;

$R^4$ is selected from the group consisting of hydrogen, aliphatic, heterocyclic, and heteroaliphatic;

$R^5$ is selected at each instance from the group consisting of hydrogen, alkyl, alkene, alkyne, halogen, hydroxyl, alkylhydroxyl, alkoxy, azide, amino, alkylamino, cyano, —NH(aliphatic), —N(aliphatic)$_2$, —NHSO$_2$(aliphatic), —N(aliphatic)SO$_2$alkyl, —NHSO$_2$(aryl, heteroaryl, or heterocyclic), —N(alkyl)SO$_2$(aryl, heteroaryl, or heterocyclic), —NHSO$_2$alkenyl, —N(alkyl)SO$_2$alkenyl, —NHSO$_2$alkynyl, —N(alkyl)SO$_2$alkynyl, haloalkyl, aliphatic, heteroaliphatic, heteroalkyl, carbocyclic, C(O)R$^{40}$, aryl, aryloxy, heterocyclo, heteroaryl, arylalkyl, O-arylalkyl, nitro, nitroso, sulfone, sulfoxide, thioalkyl, thiol, haloalkyl, and cycloalkyl;

$R^{10}$ and $R^{11}$ are independently selected from the group consisting of hydrogen, alkyl, aliphatic, heteroaliphatic, carbocyclic, heterocyclic, aryl, heteroaryl, halo, azide, cyano, hydroxyl, alkoxy, amine, —NH(aliphatic), and —N(aliphatic)$_2$;

or $R^{10}$ and $R^{11}$ together with the carbon to which they are bound form a 3-, 4-, 5-, or 6-membered spirocarbocycle, or a 4-, 5-, or 6-membered spiroheterocycle comprising 1 or 2 heteroatoms selected from N, O, and S;

$R^{13}$ and $R^{14}$ are independently selected from the group consisting of hydrogen, alkyl, alkenyl, alkynyl, alkoxy, haloalkoxy, hydroxy, amino, —NHalkyl, and —N(alkyl)$_2$;

or $R^{13}$ and $R^{14}$ together with the carbon atom to which they are attached form C(O), C(S), C=CH$_2$, a 3-, 4-, 5-, or 6-membered spirocarbocycle, or a 4-, 5-, or 6-membered spiroheterocycle comprising 1 or 2 heteroatoms selected from N and O;

$R^{16}$ is selected from the group consisting of:

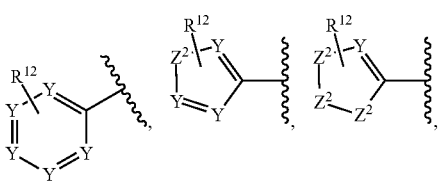

-continued

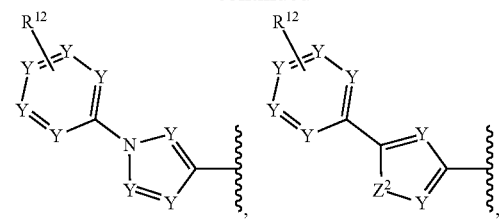

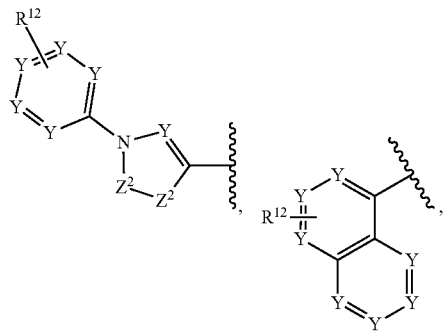

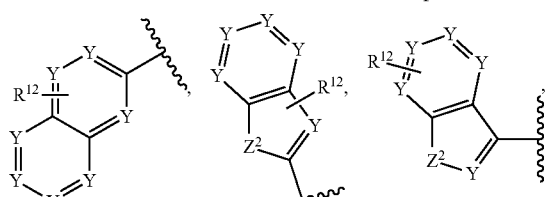

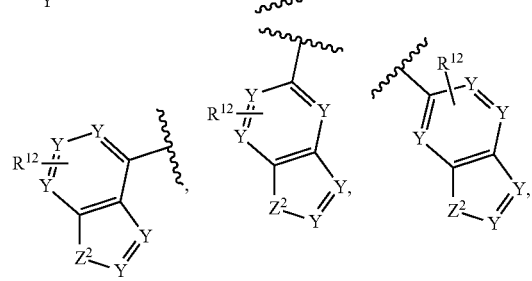

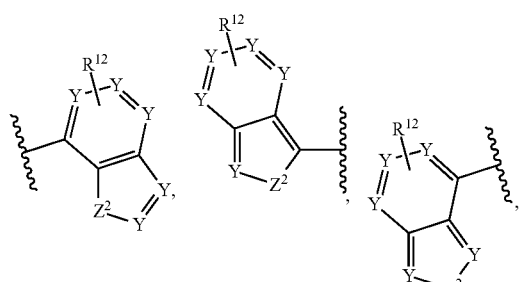

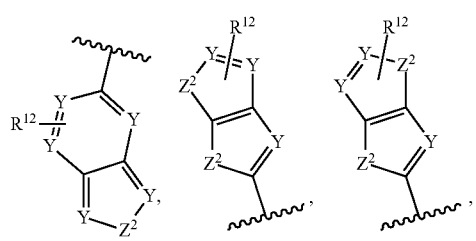

-continued

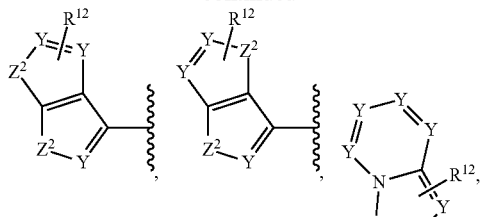

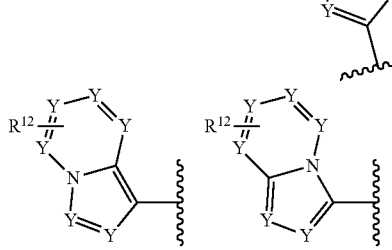

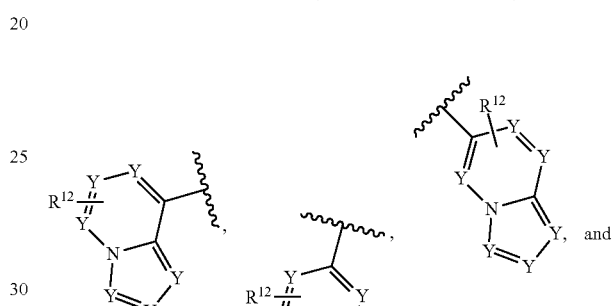

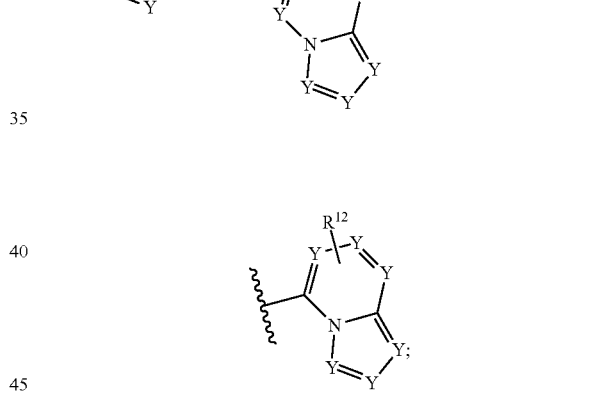

or $R^{16}$ is a 4, 5, 6, 7, 8, 9, or 10 membered carbocyclo or aryl moiety, wherein the carbocyclo or aryl moiety is substituted with $R^{12}$ at any desired position; wherein the carbocyclo or aryl moiety is optionally further substituted with one or more substituents selected from $R^5$; and wherein the carbocyclo or aryl moiety is attached through a carbon atom;

or $R^{16}$ is

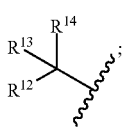

$R^{17}$ is selected from the group consisting of $R^{17a}$, $R^{17b}$, and $R^{17c}$;

R$^{17a}$ is selected from the group consisting of:

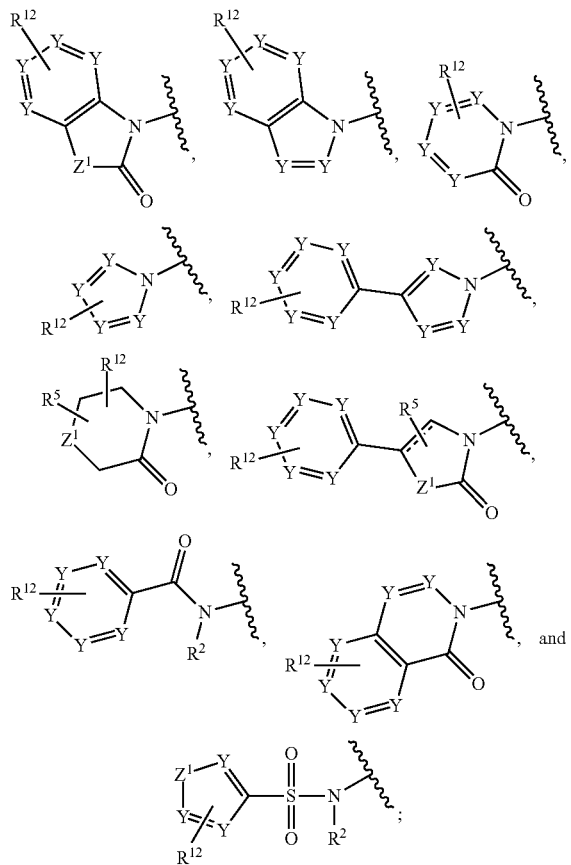

or R$^{17a}$ is selected from the group consisting of

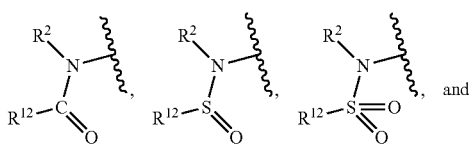

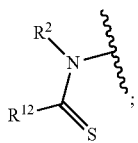

or R$^{17a}$ is a 3, 4, 5, 6, 7, 8, or 10 membered heterocyclo or heteroaryl moiety containing at least one nitrogen atom through which it is directly attached, wherein the heterocyclo or heteroaryl moiety is substituted with R$^{12}$ at any desired position, wherein the heterocyclo or heteroaryl moiety is optionally further substituted with one or more substituents selected from R$^5$; and the heterocyclo or heteroaryl moiety is optionally further substituted with one or more oxo groups at a position allowed by valence;

or R$^{17a}$ is selected from the group consisting of:

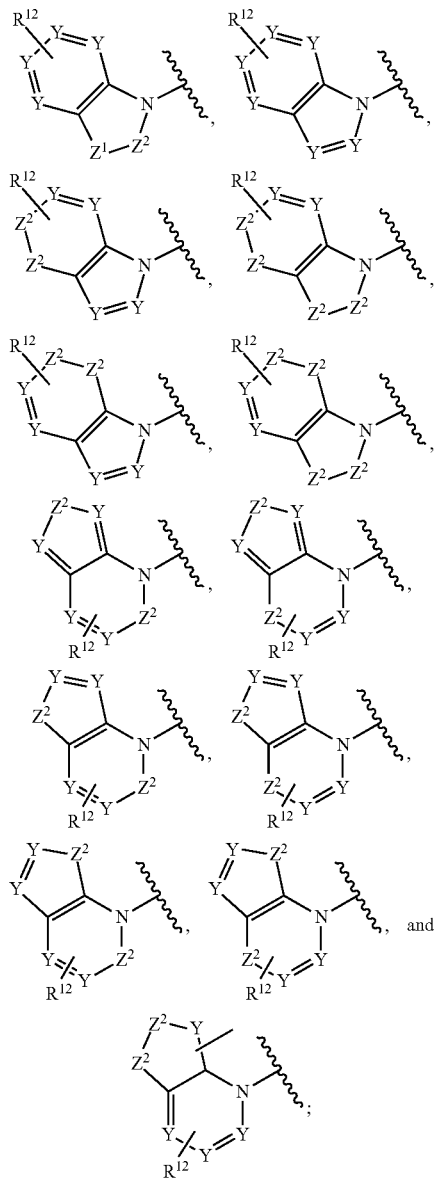

R$^{17b}$ is selected from the group consisting of:

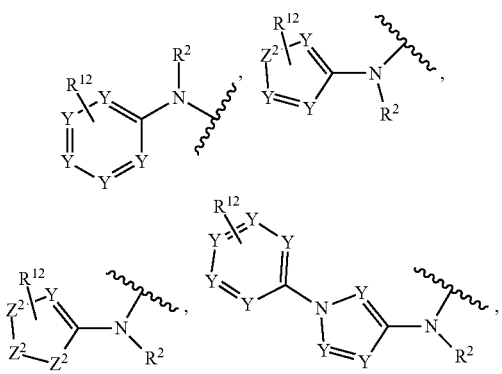

-continued
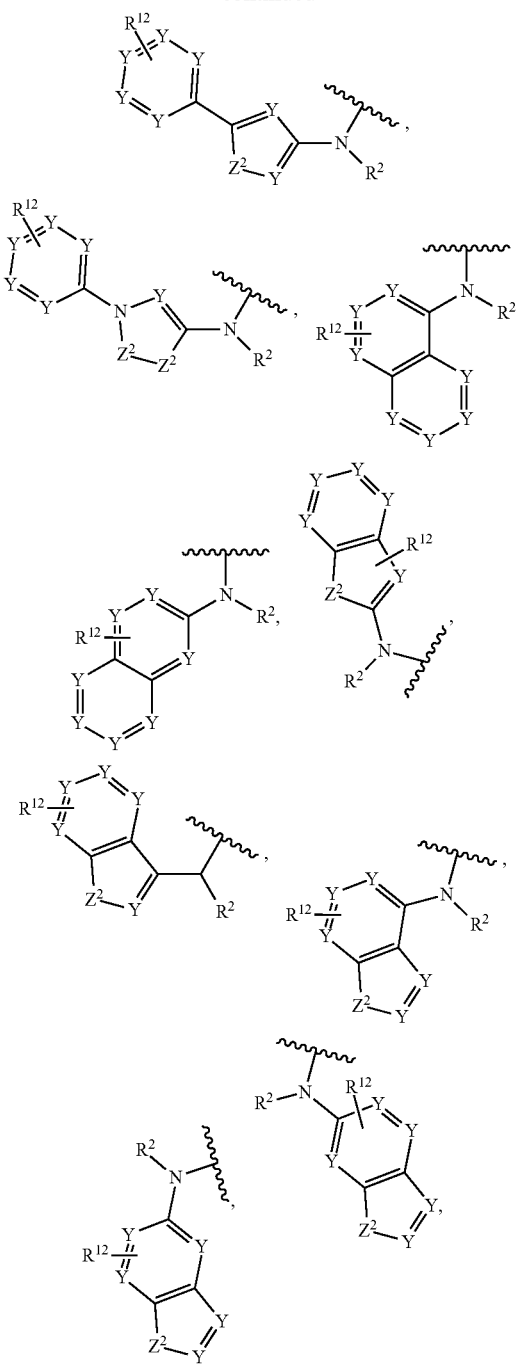
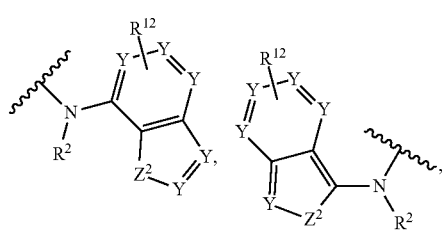
-continued
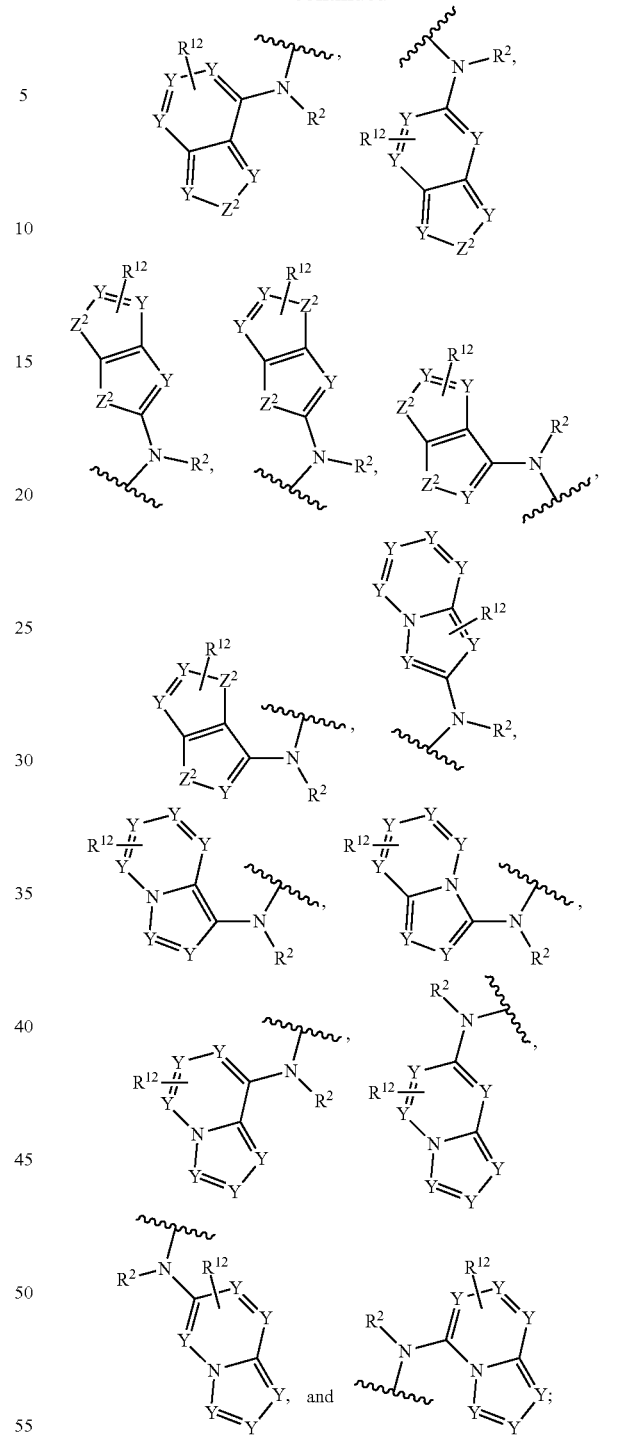
or R$^{17b}$ is
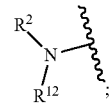
or R$^{17b}$ is —NR$^2$aryl, —NR$^2$heteroaryl, or NR$^2$carbocycle, wherein the aryl, heteroaryl, and carbocycle moieties are substituted with a $R^{12}$ at any desired position, wherein the aryl, heteroaryl, and carbocycle moieties are optionally further substituted with one or more substituents selected from $R^5$; and wherein the aryl, heteroaryl, and carbocycle moieties are optionally further substituted with one or more oxo groups at a position allowed by valence;

$R^{17c}$ is selected from the group consisting of:

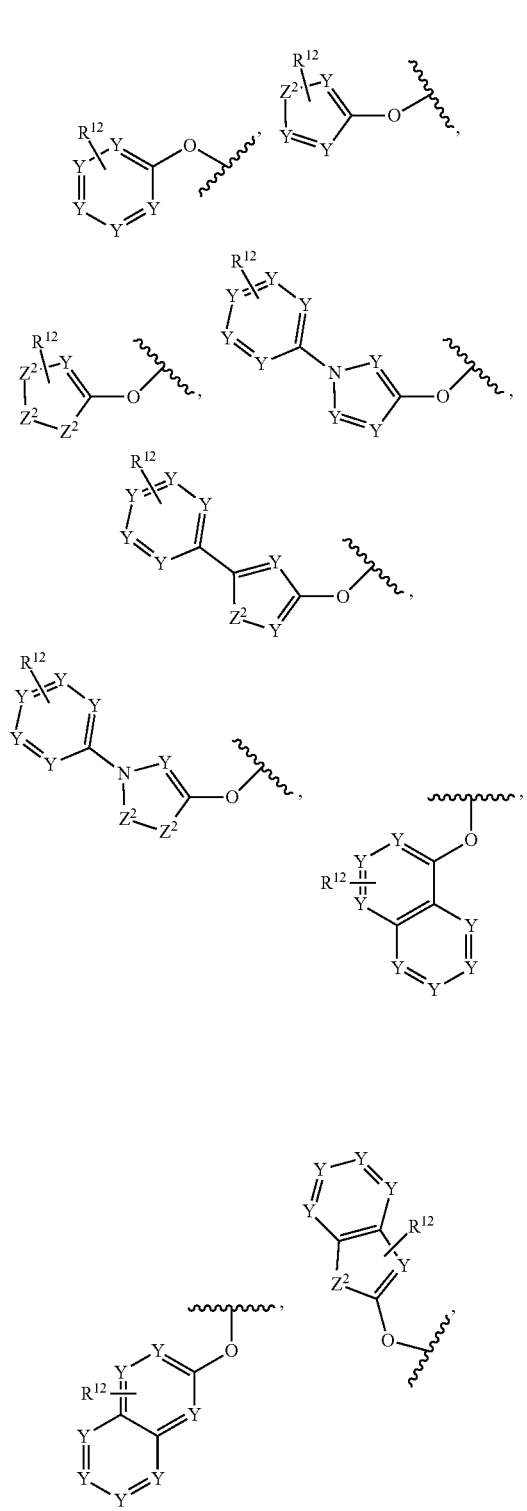

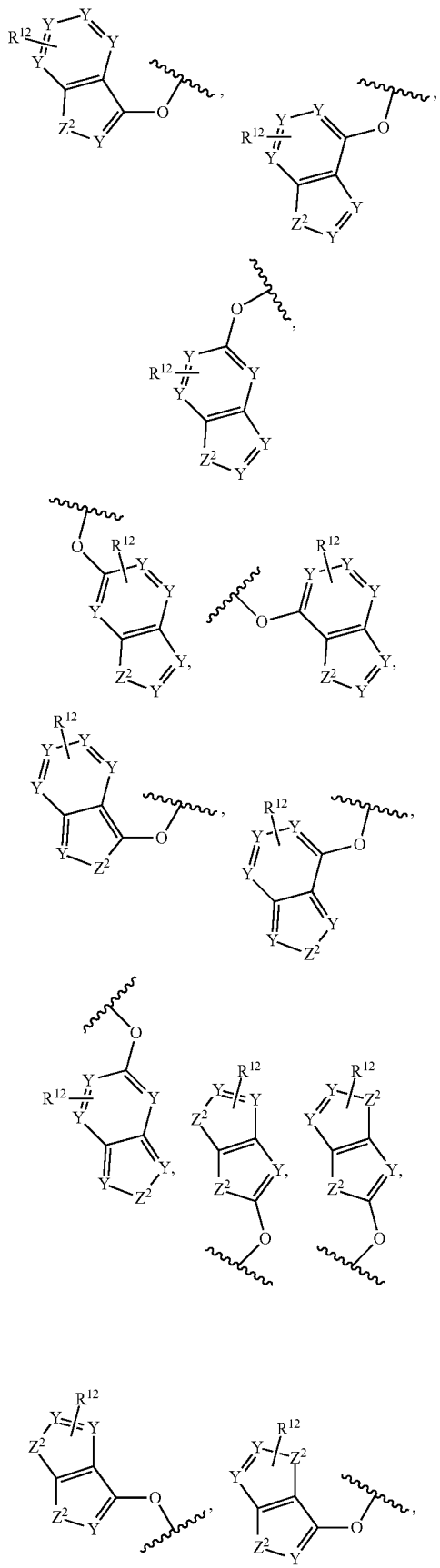

563

-continued

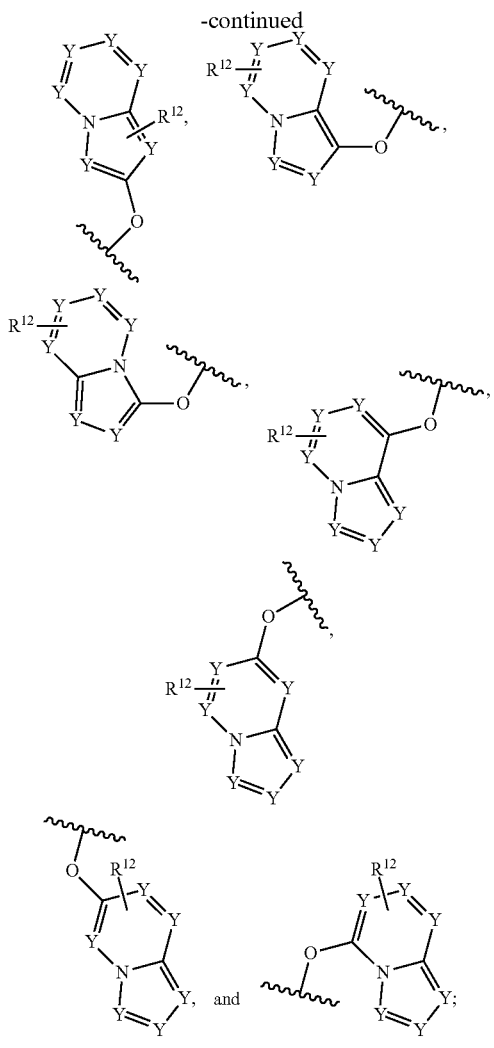

or $R^{17c}$ is

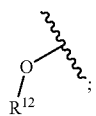

or $R^{17c}$ is —O-aryl, —O-heteroaryl, or —O-carbocycle, wherein the aryl, heteroaryl, and carbocycle moieties are substituted with a $R^{12}$ at any desired position, wherein the aryl, heteroaryl, and carbocycle moieties are optionally further substituted with one or more substituents selected from $R^5$; and wherein the aryl, heteroaryl, and carbocycle moieties are optionally further substituted with one or more oxo groups at a position allowed by valence;

$R^{40}$ is selected at each instance from the group consisting of: hydrogen, alkyl, alkene, alkyne, halogen, hydroxyl, alkoxy, azide, amino, cyano, —NH(aliphatic), —N(aliphatic)$_2$, —NHSO$_2$(aliphatic), —N(aliphatic)SO$_2$alkyl, —NHSO$_2$(aryl, heteroaryl or heterocyclic), —N(alkyl)SO$_2$(aryl, heteroaryl or heterocyclic) —NHSO$_2$alkenyl, —N(alkyl) SO$_2$alkenyl, —NHSO$_2$alkynyl, —N(alkyl)

564

SO$_2$alkynyl, haloalkyl, aliphatic, heteroaliphatic, aryl, heteroaryl, heteroalkyl, heterocyclic and carbocyclic;

═ is selected from the group consisting of a single and a double bond;

Y is independently selected from the group consisting of N, CH, or $CR^5$;

$Z^1$ is selected from the group consisting of $CH_2$, $CHR^2$, $C(R^2)_2$, $NR^2$, O, and S;

$Z^2$ is selected from the group consisting of NH, O, S, $NR^2$, C═O, S═O, and SO$_2$;

wherein when $R^{12}$ is bonded to a Y, then Y is $CR^{12}$; when $R^{12}$ is bonded to a $Z^1$ that is nitrogen, then $Z^1$ is $NR^{12}$; when $R^{12}$ is bonded to $Z^1$ that is carbon, then $Z^1$ is $CR^2R^{12}$; when $R^{12}$ is bonded to a $Z^2$, then $Z^2$ is $NR^{12}$;

$R^{12}$ is -(Linker)$^4$-Targeting Ligand;

(Linker)$^4$ is a bivalent chemical group; and

Figure 1P:
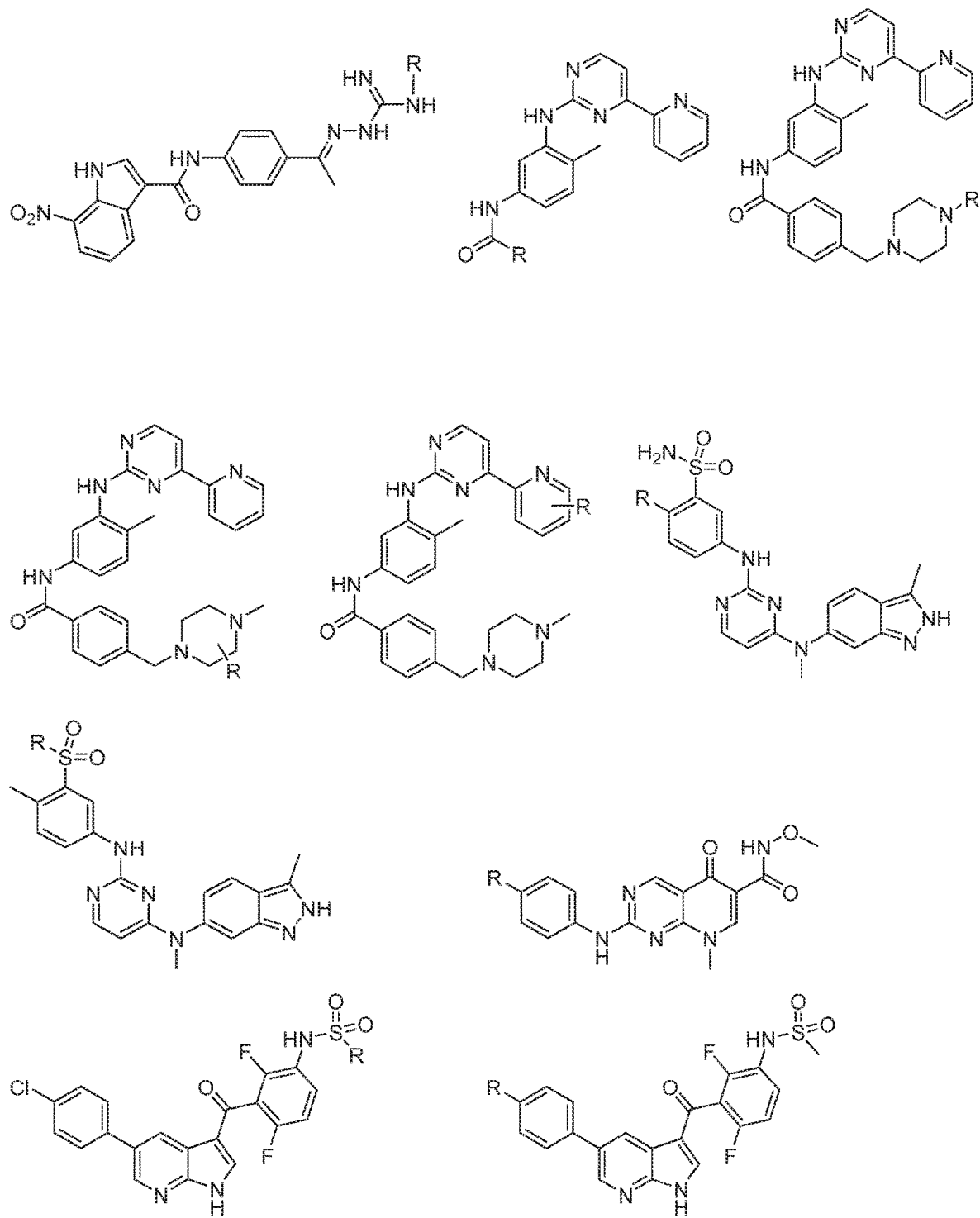
Figure 1S:
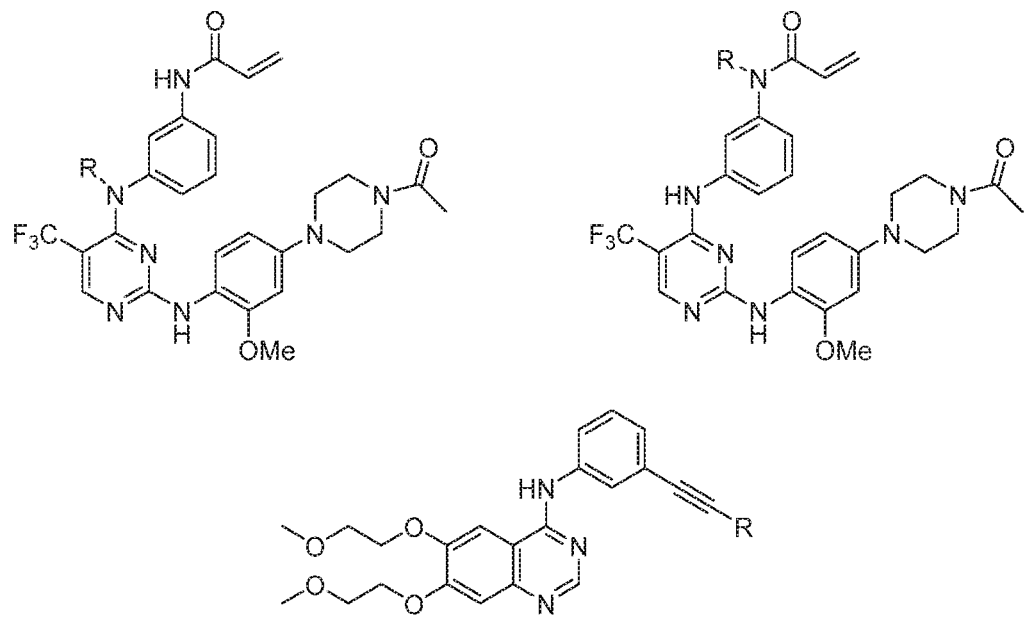
FIG. 1R-1S present examples of Tyrosine Kinase Targeting Ligands wherein R is the point at which the Linker is attached.
Figure 1T:
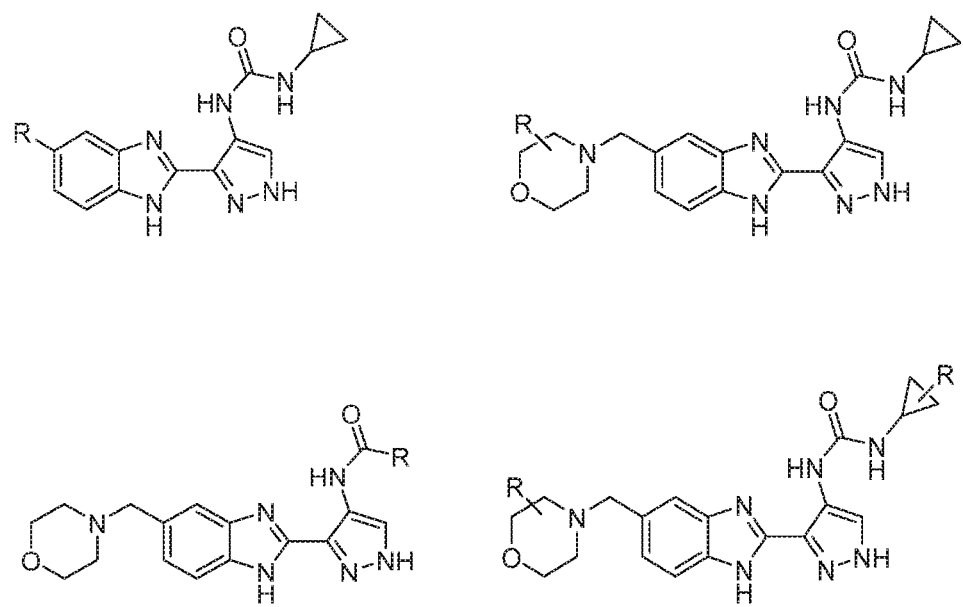
FIG. 1T presents examples of Aurora Kinase Targeting Ligands wherein R is the point at which the Linker is attached.
Figure 1U:
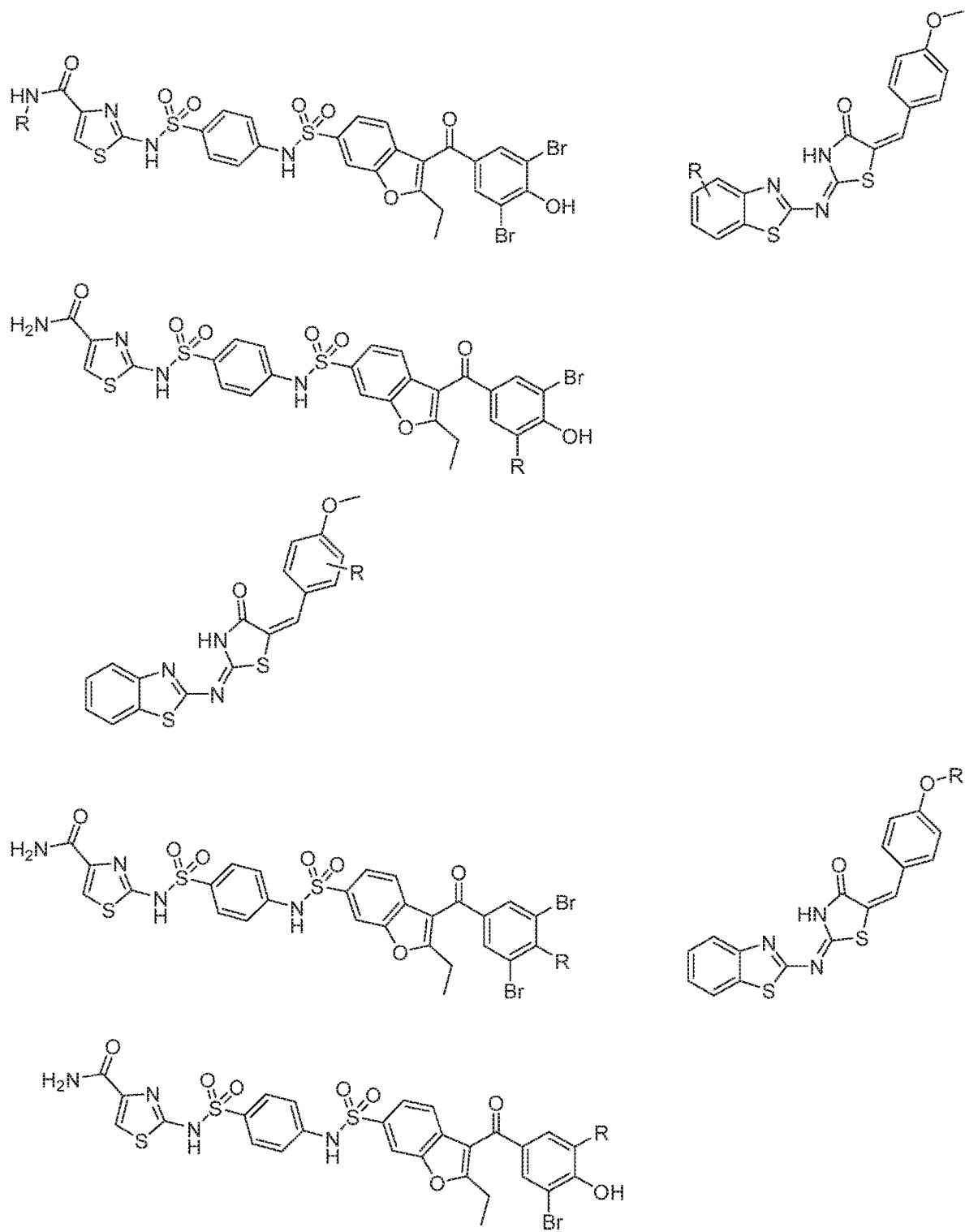
FIG. 1U presents examples of Protein Tyrosine Phosphatase Targeting Ligands wherein R is the point at which the Linker is attached.
Figure 1V:
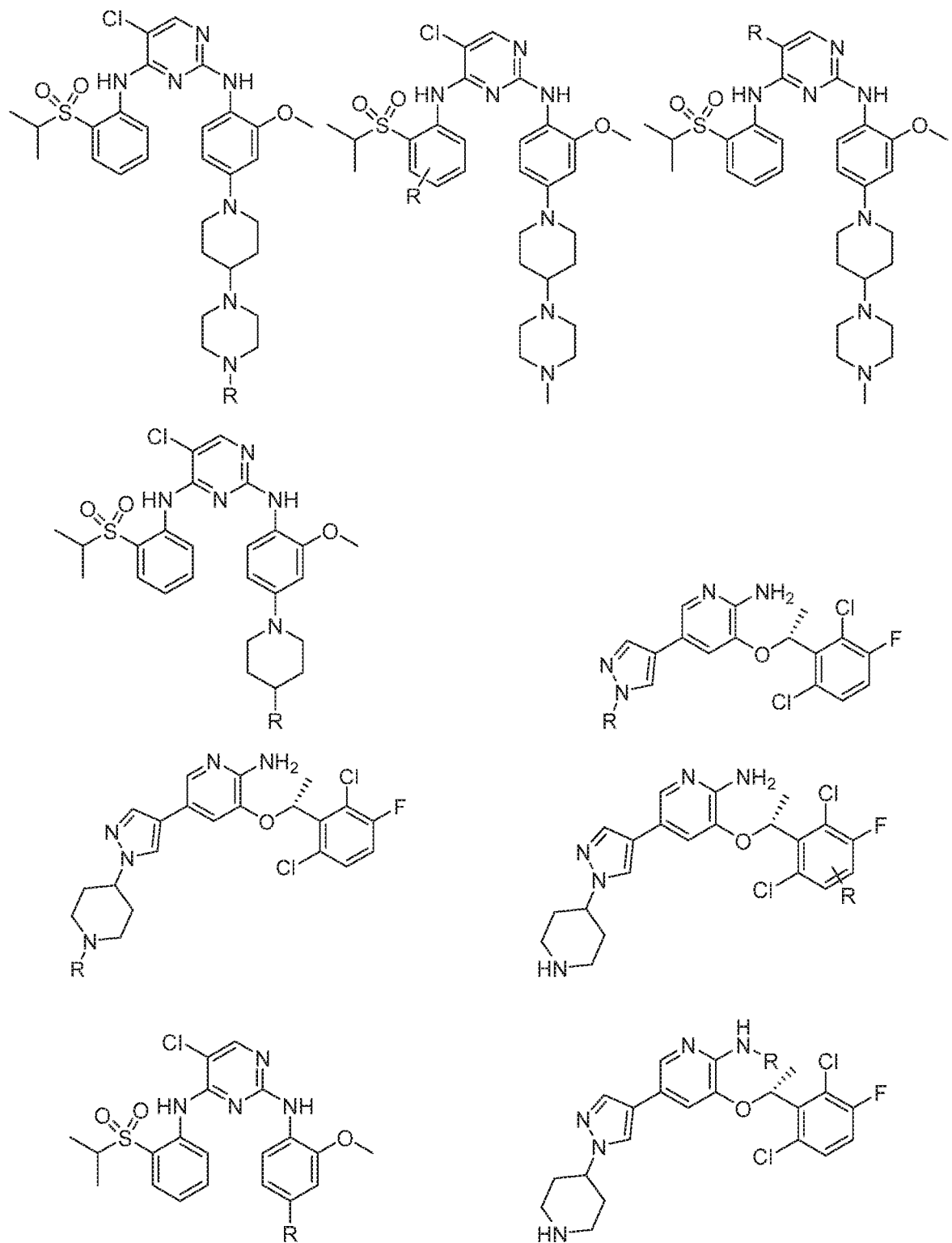
FIG. 1V presents examples of ALK Targeting Ligands wherein R is the point at which the Linker is attached.
Figure 1W:
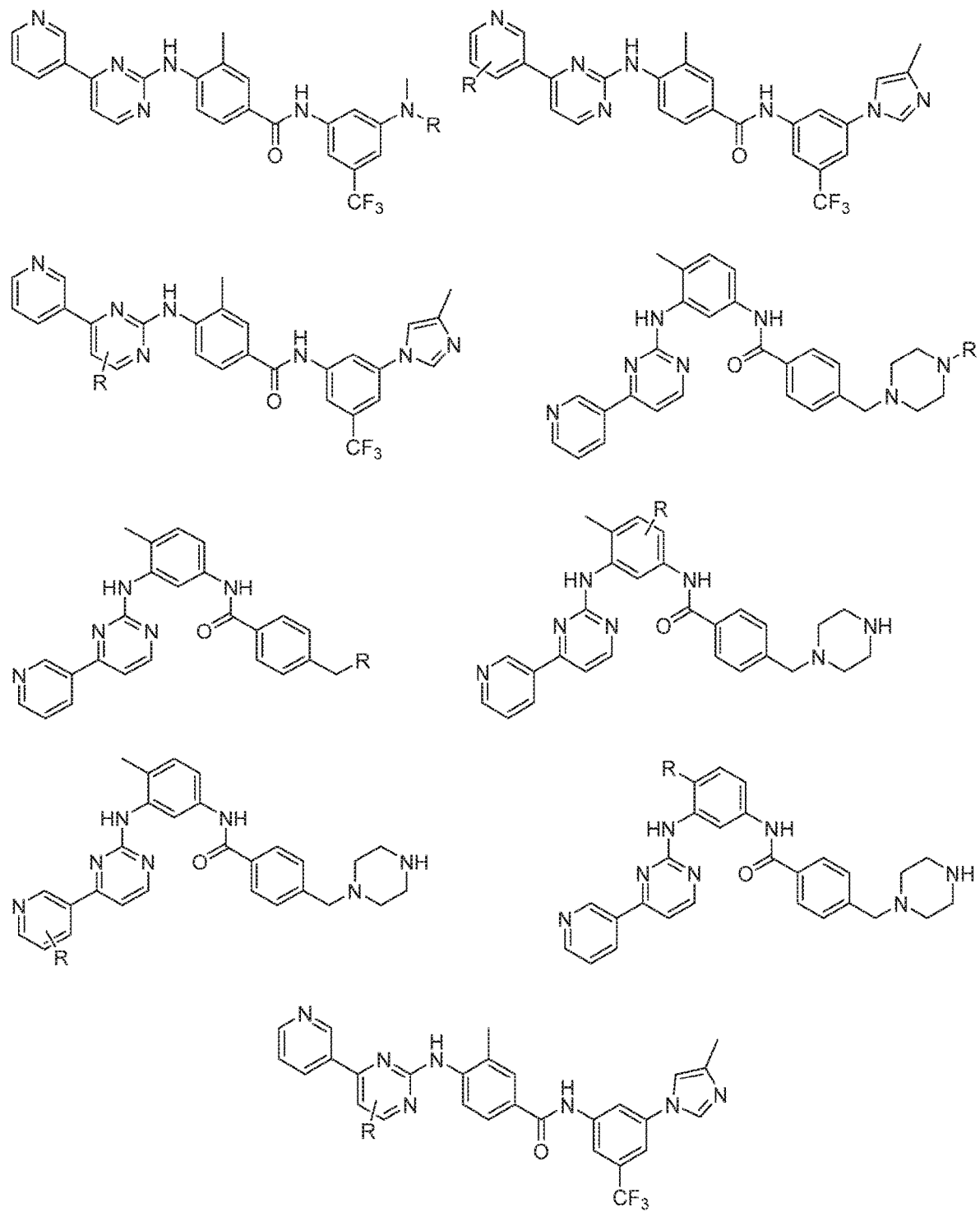
FIG. 1W presents examples of ABL Targeting Ligands wherein R is the point at which the Linker is attached.
Figure 1X:
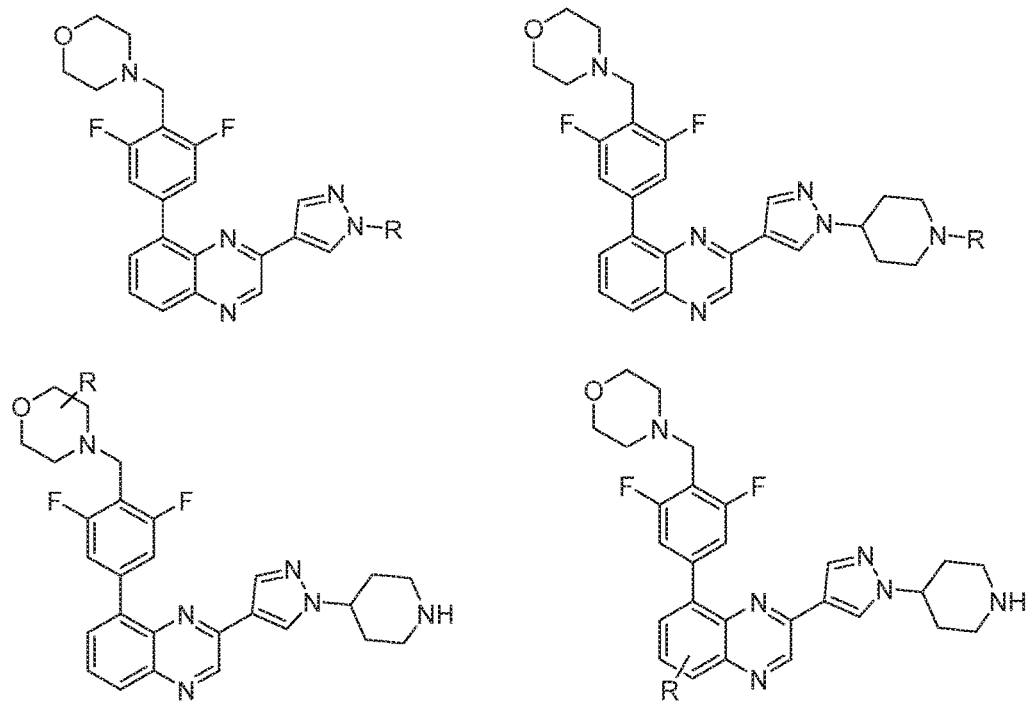
FIG. 1X presents examples of JAK2 Targeting Ligands wherein R is the point at which the Linker is attached.
Figure 1Y:
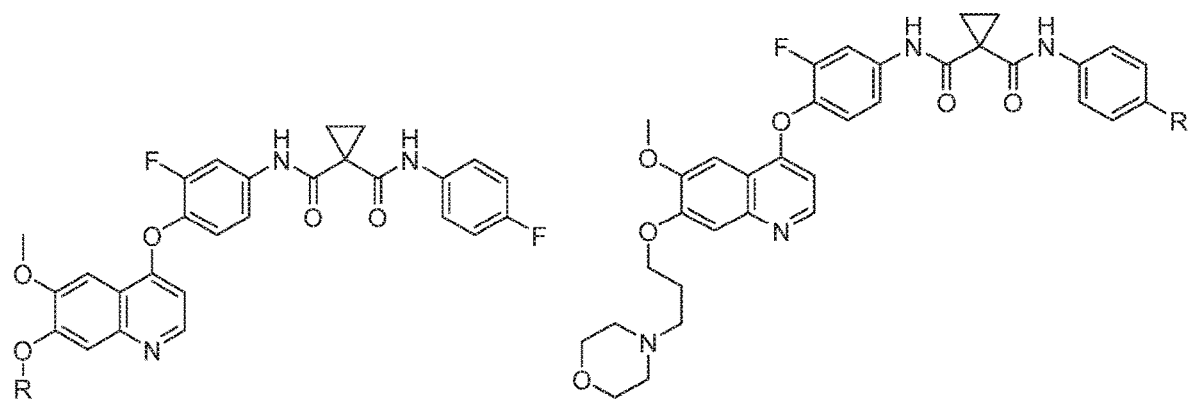
FIG. 1Y-1Z present examples of MET Targeting Ligands wherein R is the point at which the Linker is attached.
Figure 1Z:
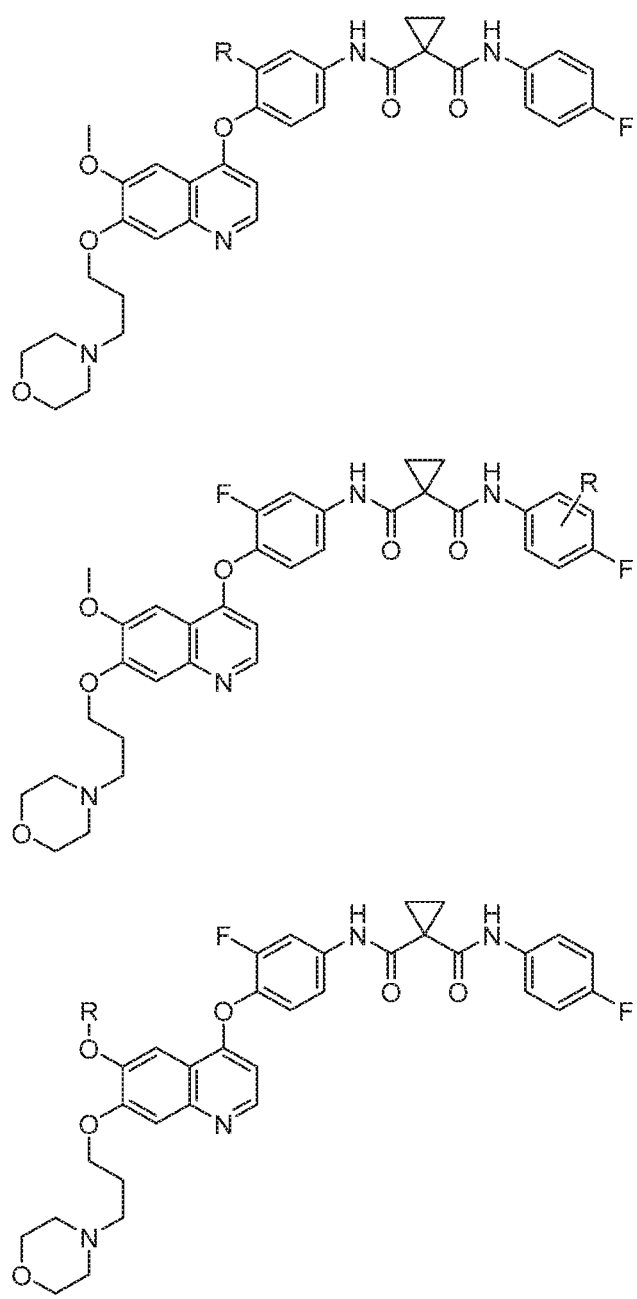
Figure 1A:
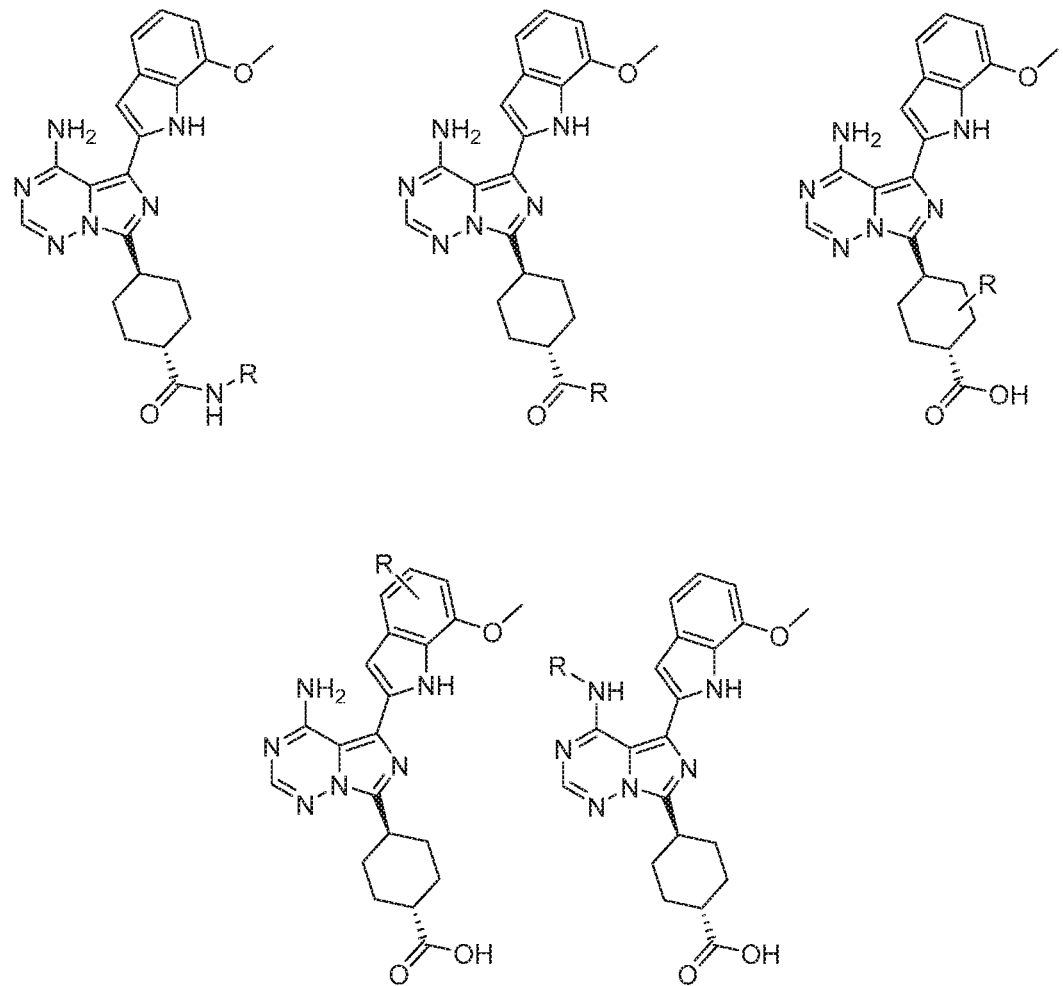
Figure 1B:
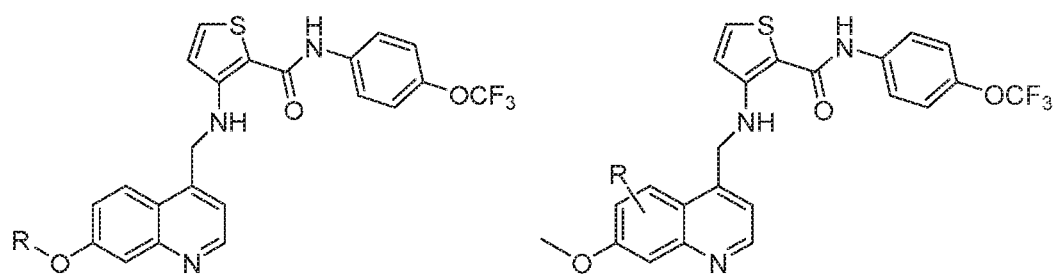
Figure 1C:
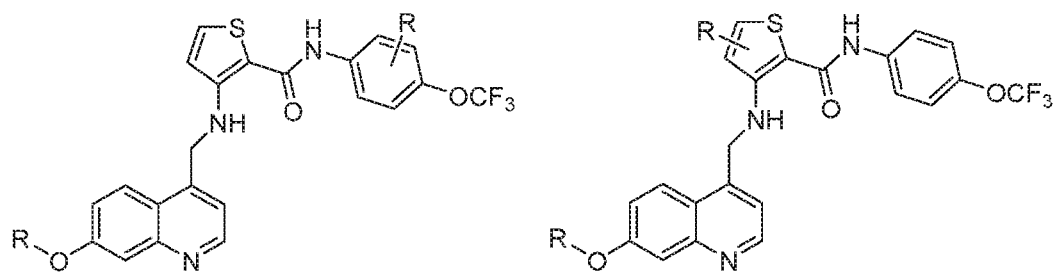
Figure 1D:
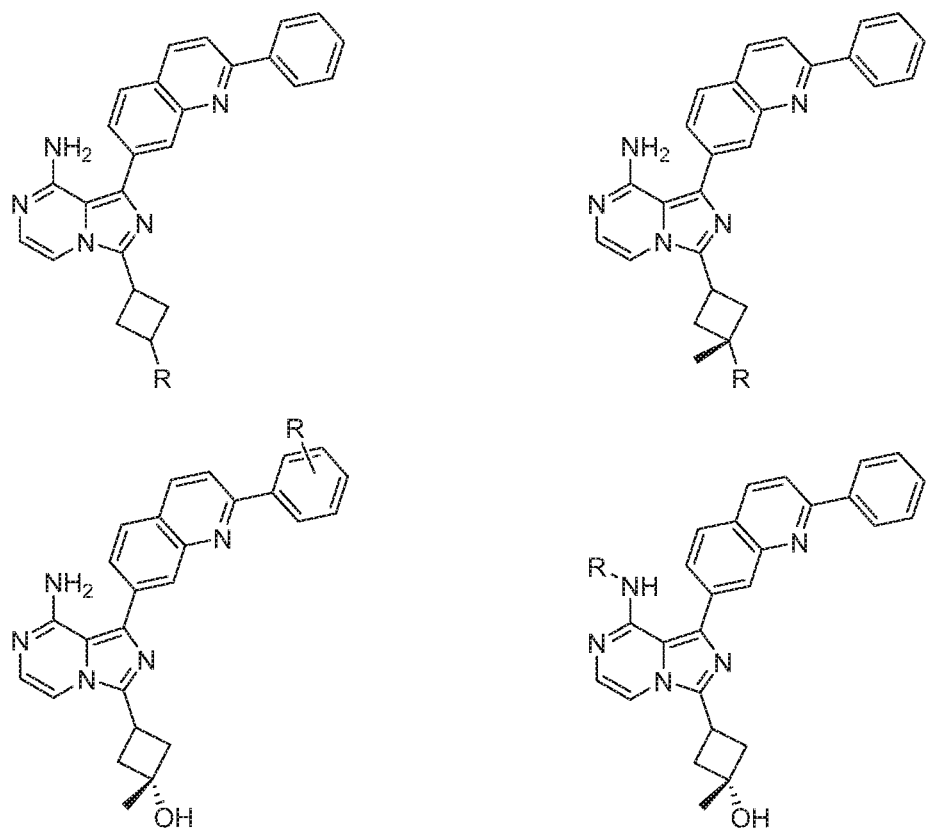
Figure 1F:
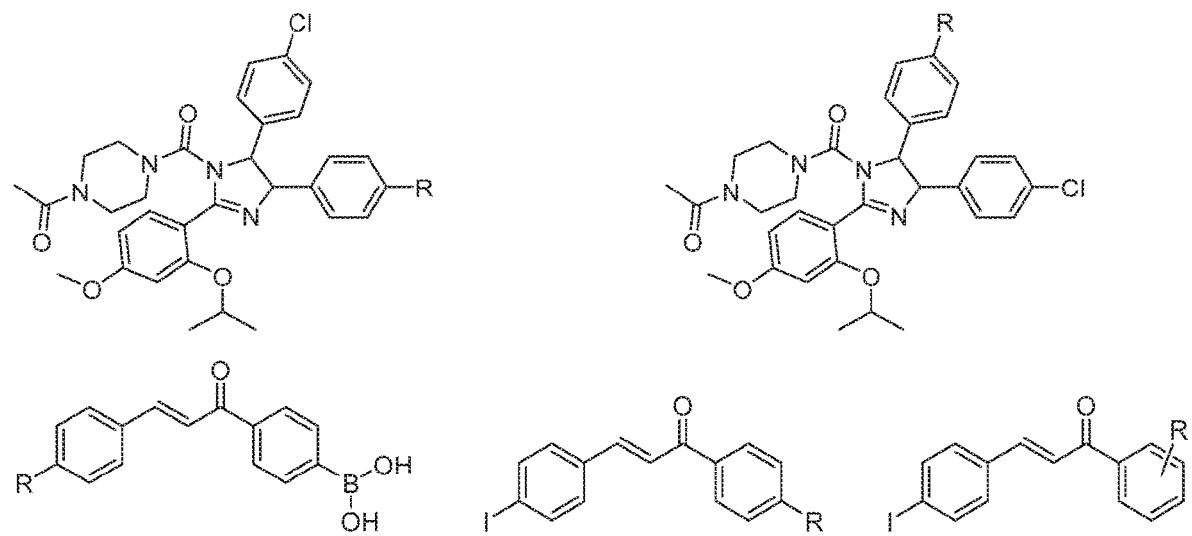
Figure 1G:
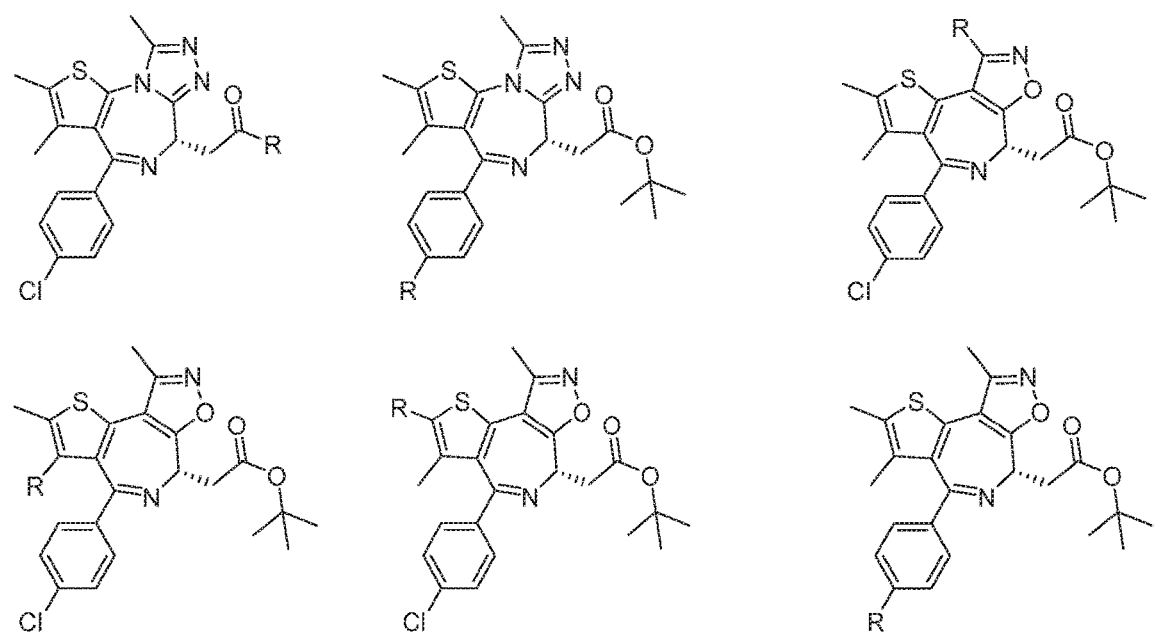
Figure 1H:
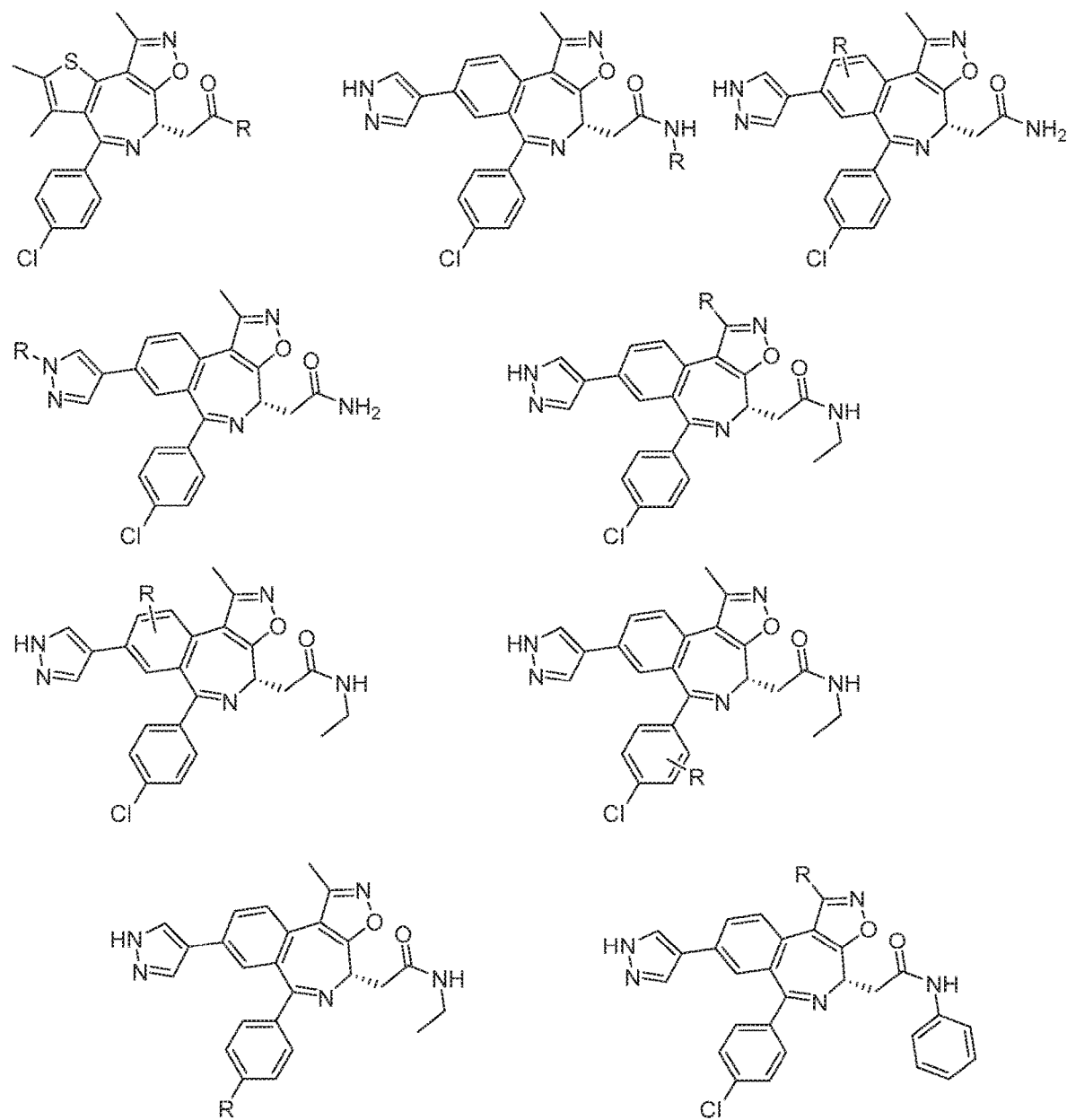
Figure 1I:
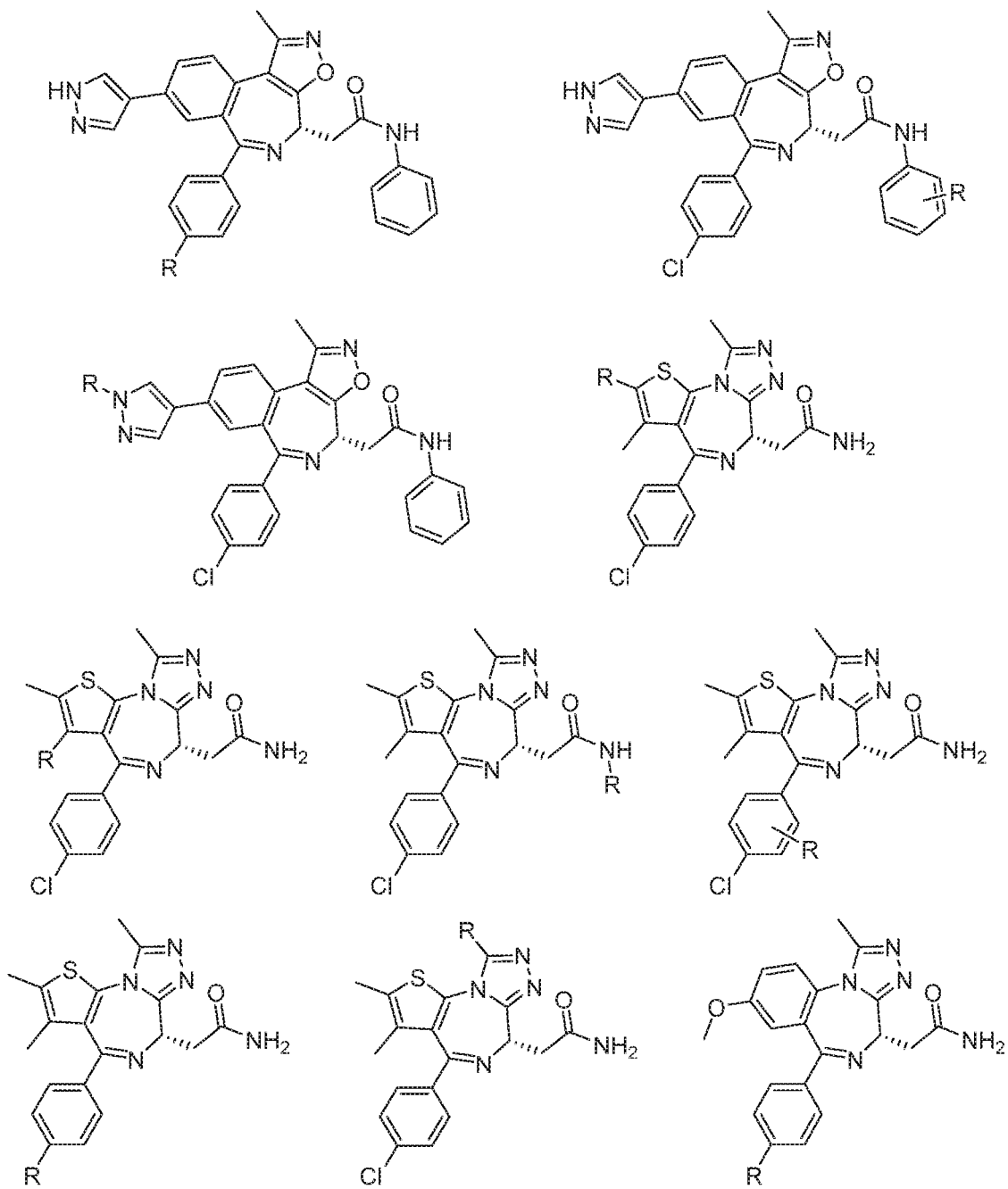
Figure 1J:
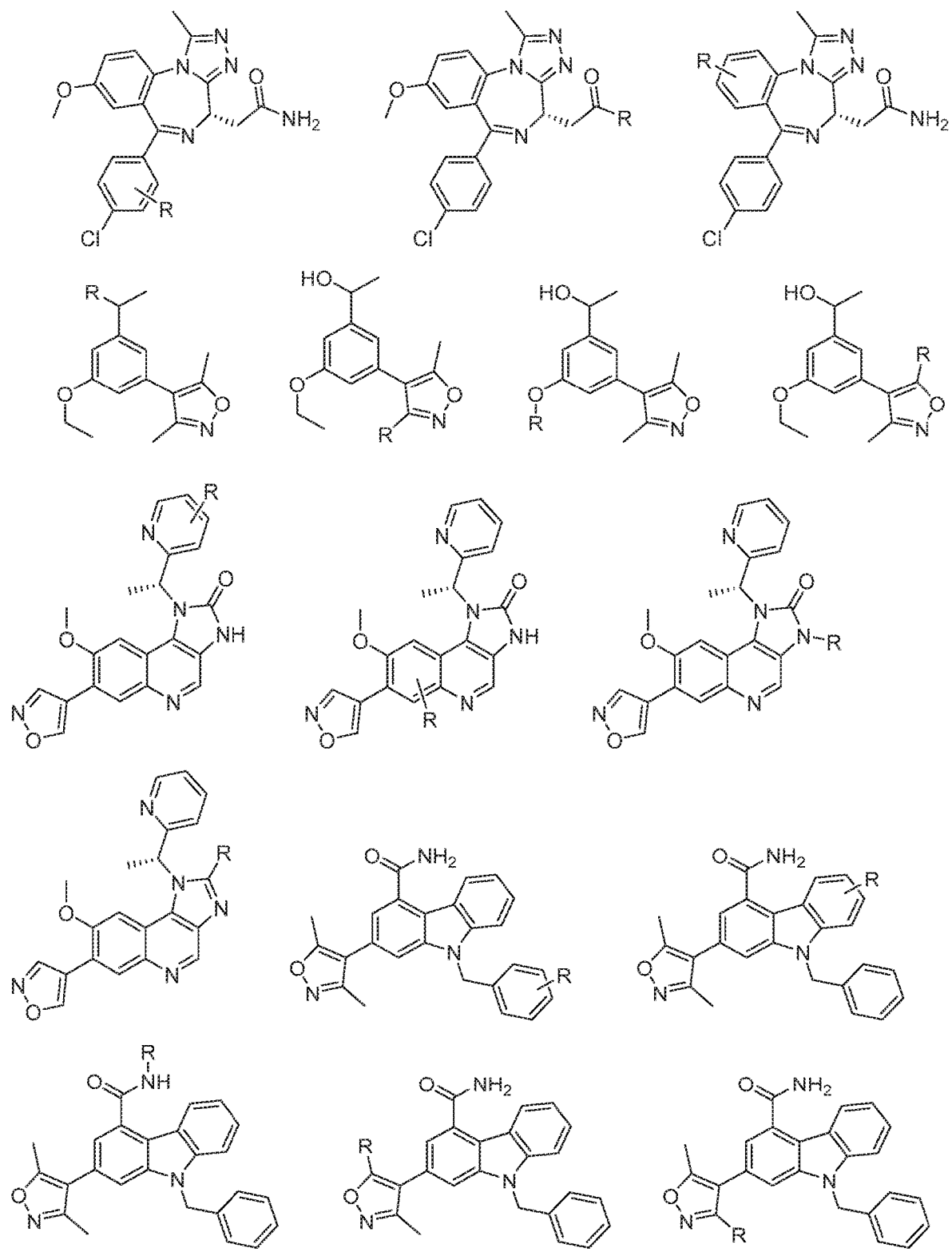
Figure 1K:
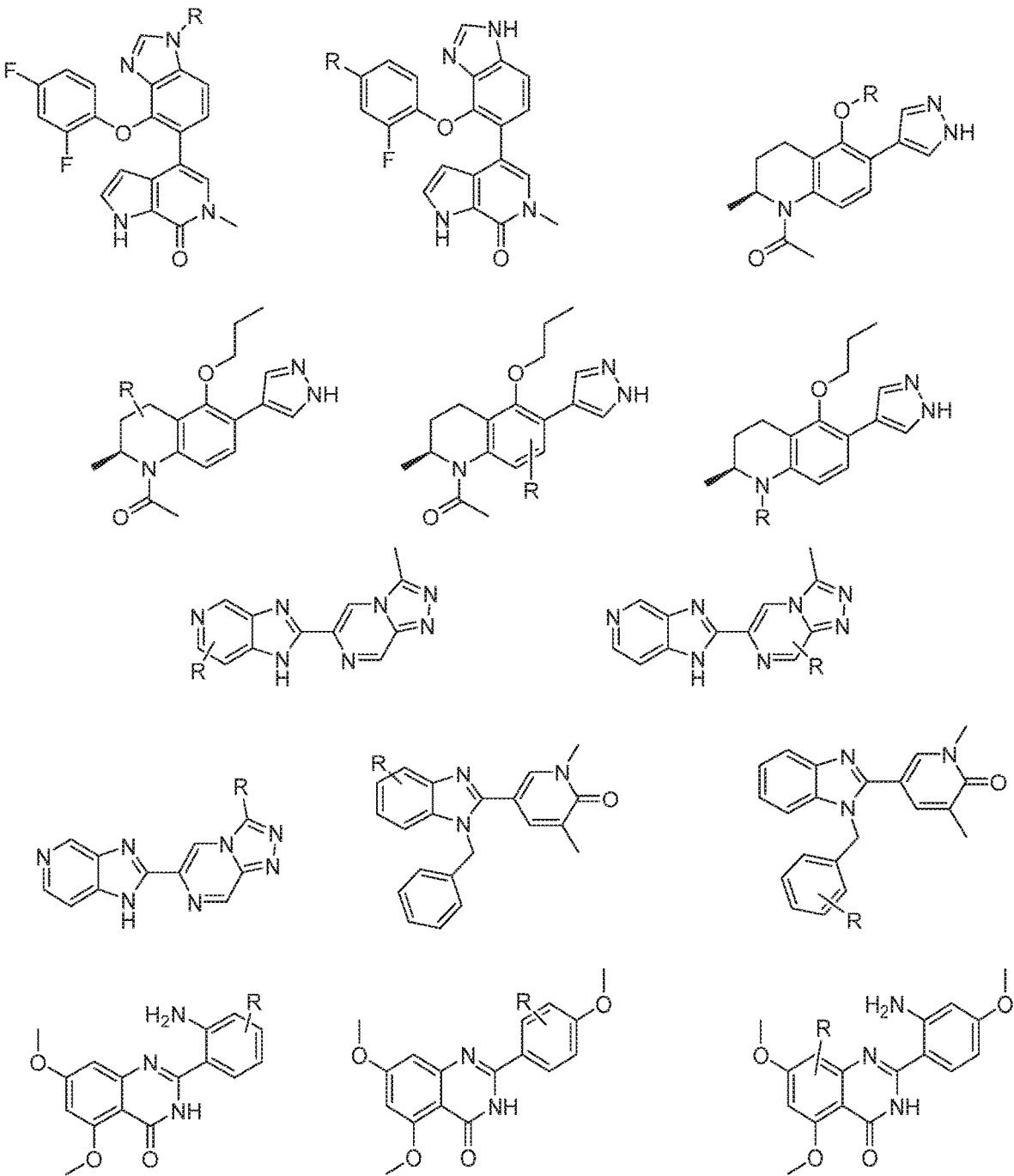
Figure 1M:
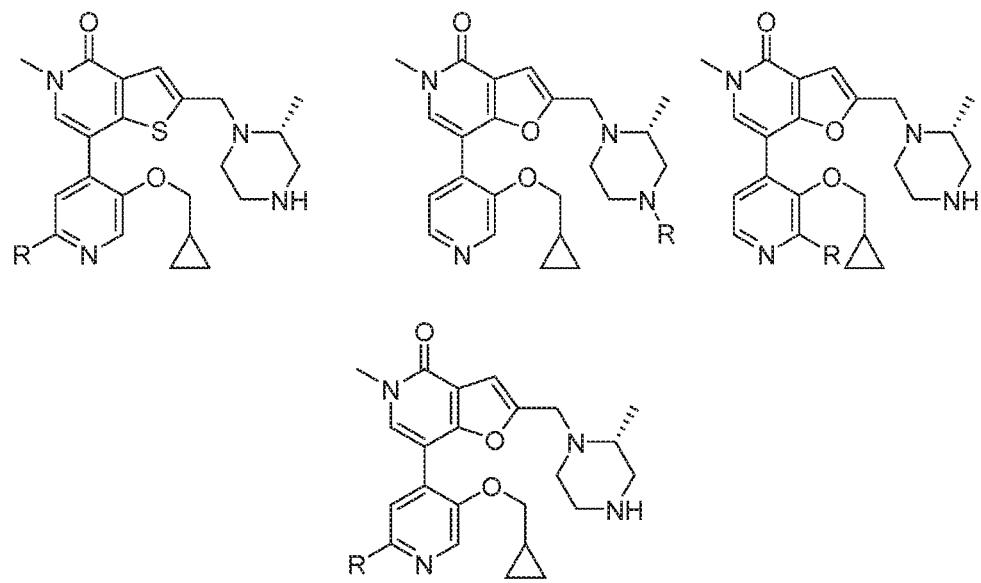
Figure 1N:
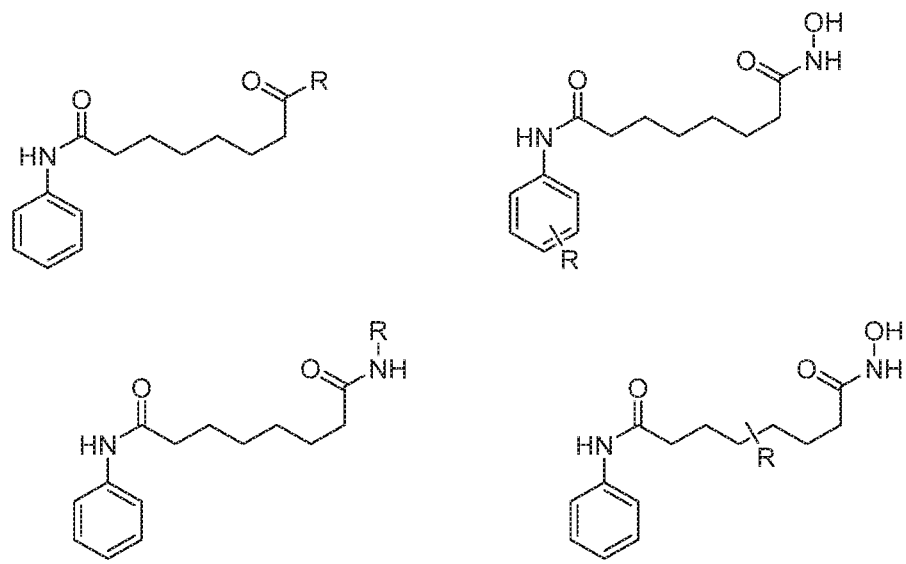
Figure 100:
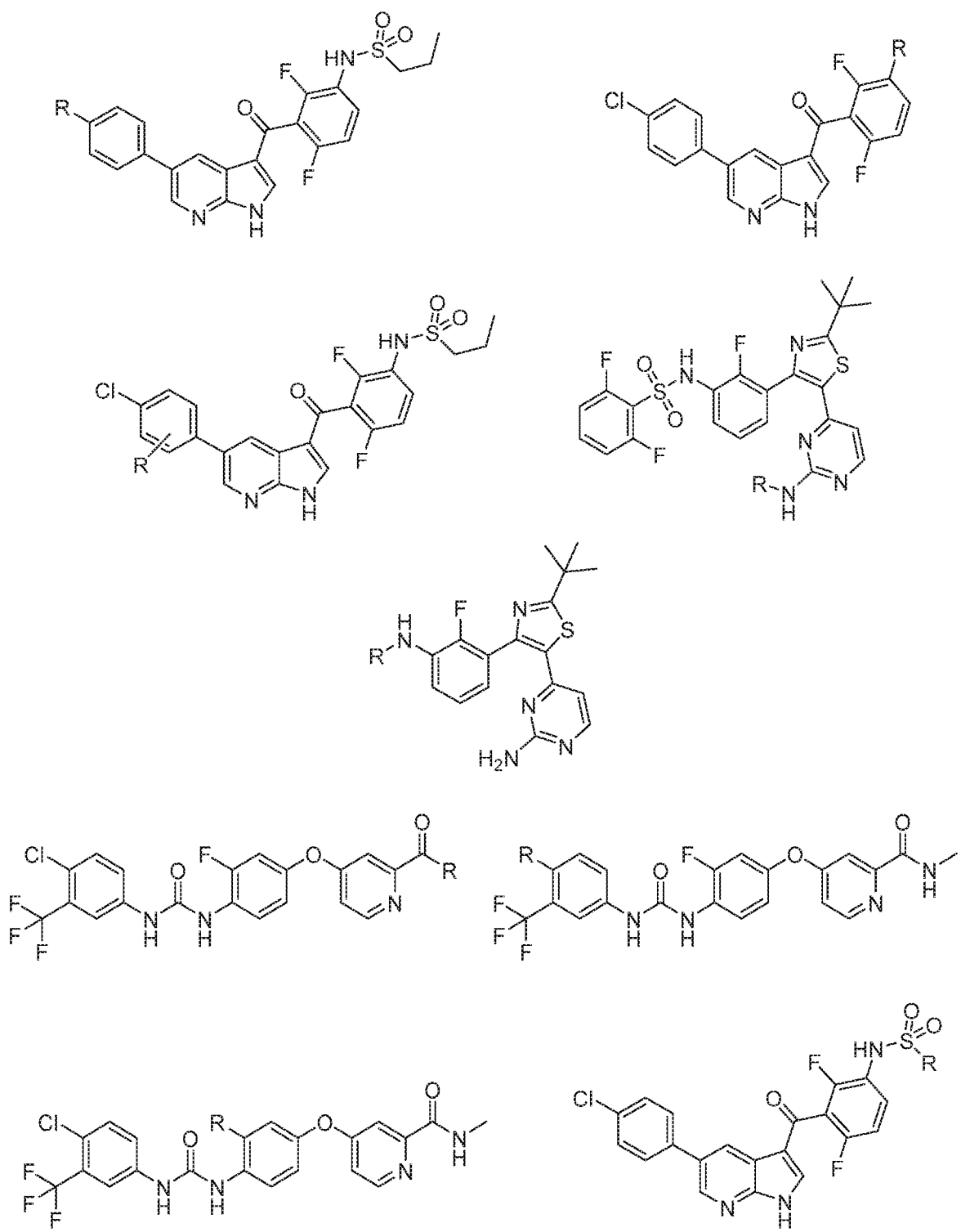
Figure 1R:
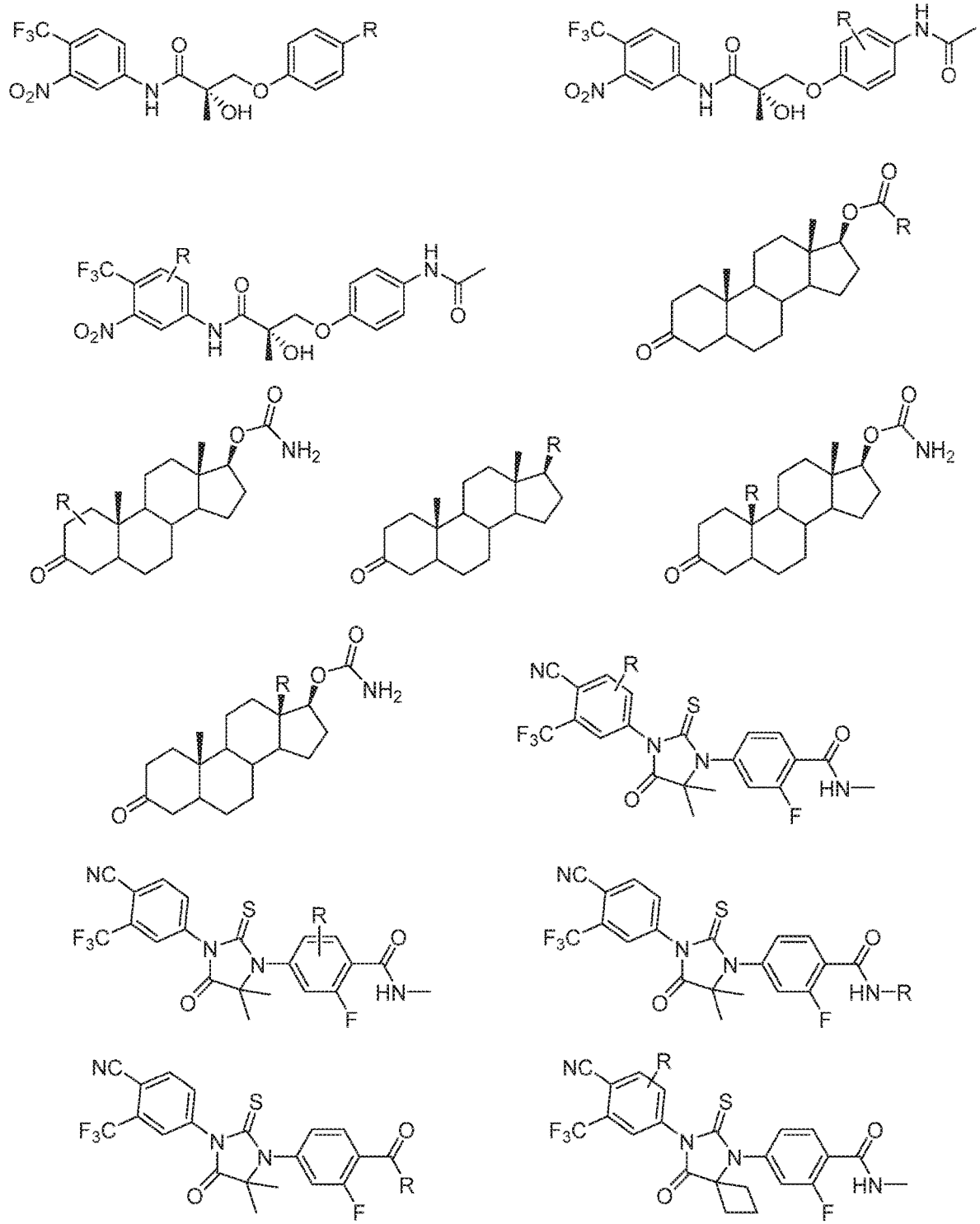
Figure 1S:
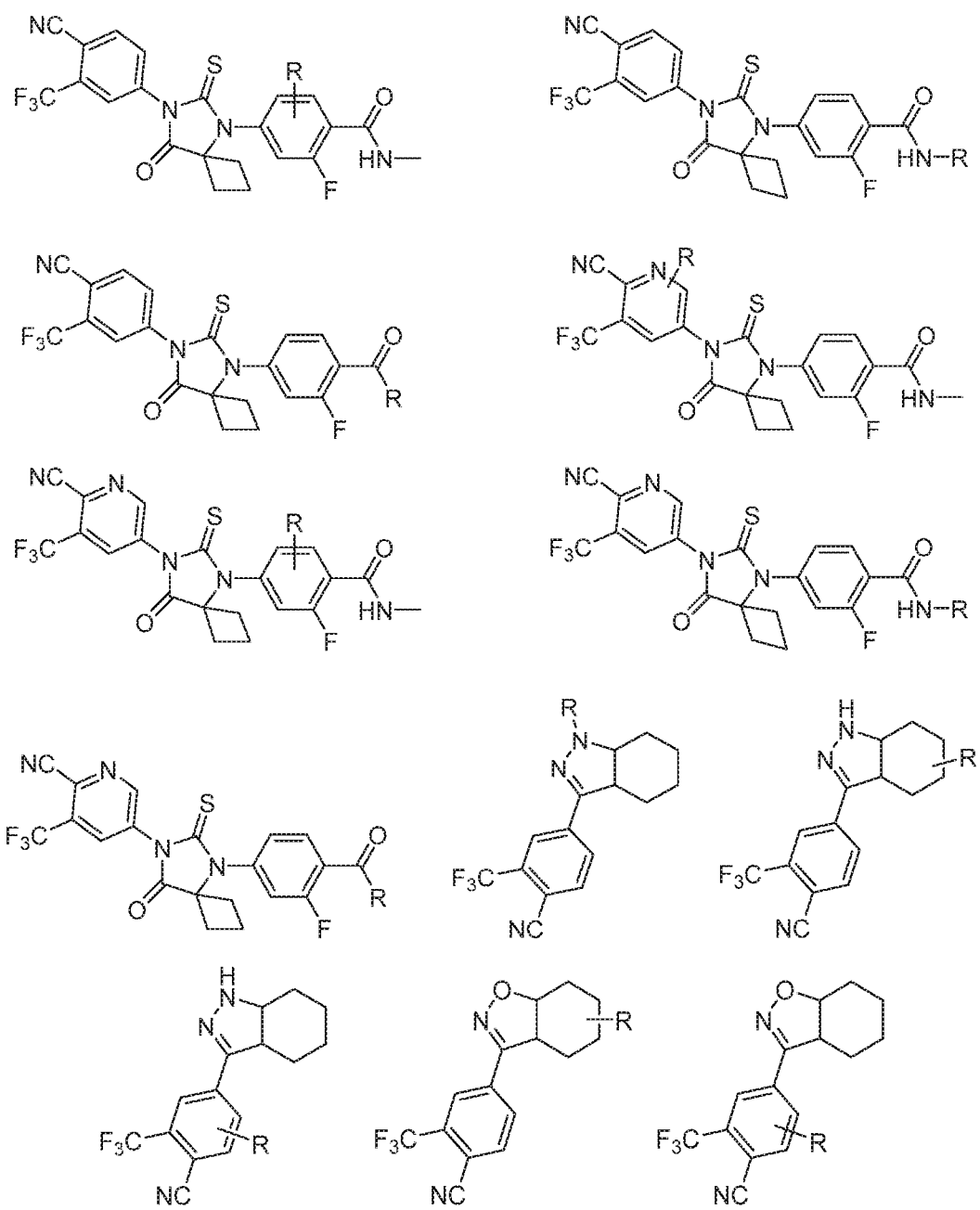
Figure 1Y:
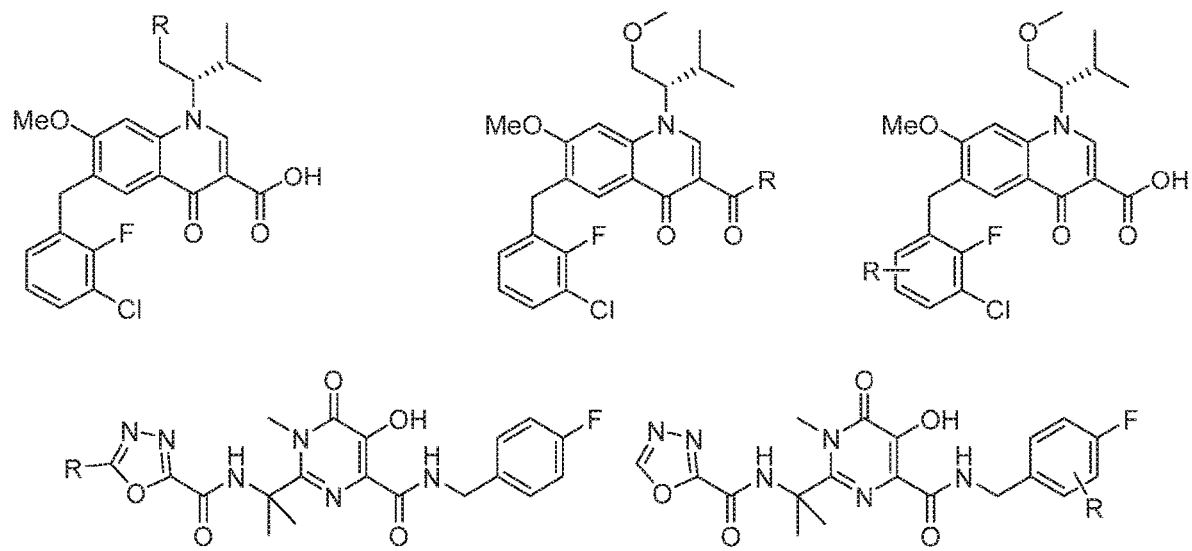
Figure 1Z:
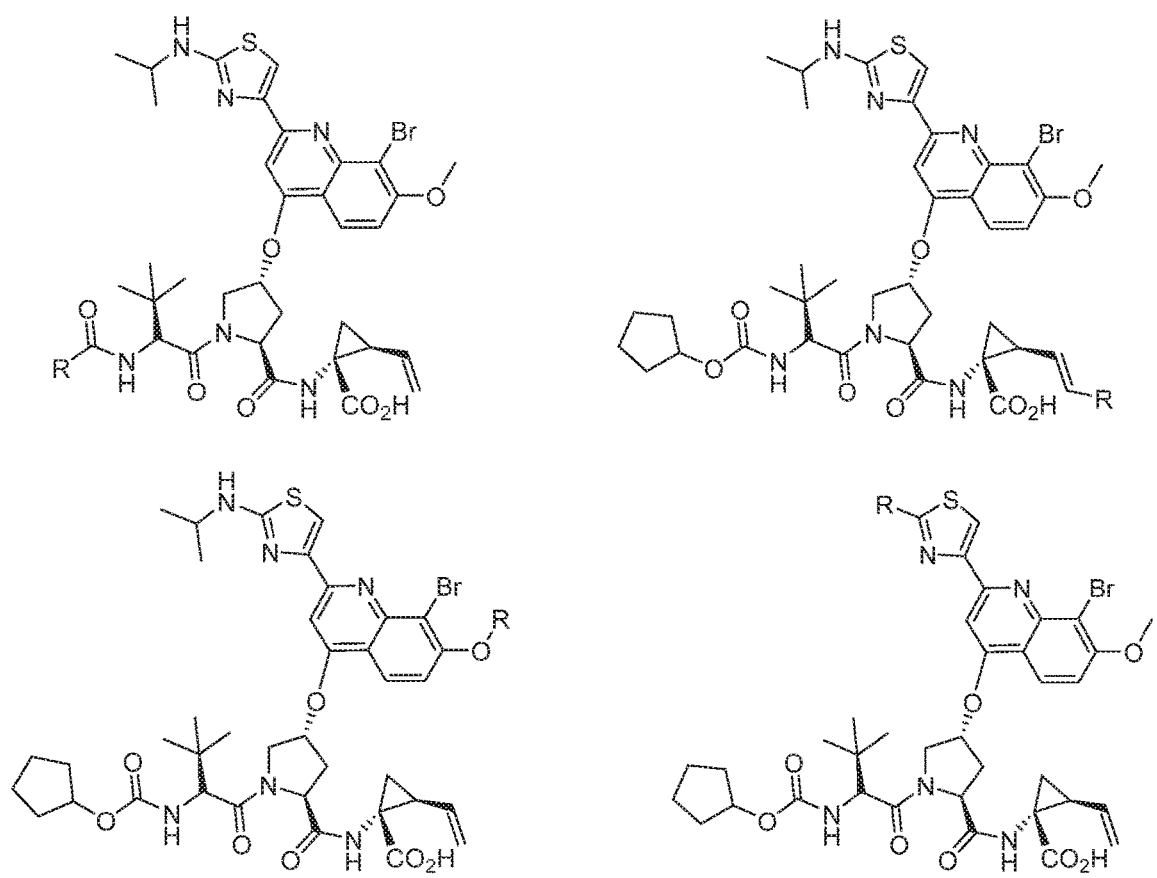

Targeting Ligand is a small molecule that binds to a Target Protein, wherein the Target Protein is a mediator of a disease in a host in need of such therapy, and wherein the Targeting Ligand has a structure described in FIG. 1QQ, FIG. 1RR, FIG. 1SS, FIG. 1TT, FIG. 1UU, FIG. 3IIIII, FIG. 4T, FIG. 4U, FIG. 4V, FIG. 4W, FIG. 4X, FIG. 4Y, FIG. 4Z, FIG. 4AA, FIG. 4BB, FIG. 4CC, FIG. 4DD, FIG. 4EE, FIG. 6R, FIG. 6S, FIG. 6T, or FIG. 6U.

2. The compound of claim 1, wherein the Target Protein is selected from the group consisting of androgen receptor, ATF2, estrogen receptor, KDM4, KDM5, LSD1, and histone lysine demethylases.

3. The compound of claim 1, wherein Linker$^4$ is selected from formula:

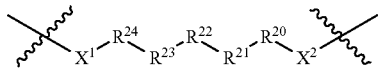

wherein:

$X^1$ and $X^2$ are independently selected from the group consisting of bond, NH, $NR^2$, $CH_2$, $CHR^2$, $C(R^2)_2$, O, and S;

$R^{20}$, $R^{21}$, $R^{22}$, $R^{23}$, and $R^{24}$ are independently selected from the group consisting of bond, alkyl, —C(O)—, —C(O)O—, —OC(O)—, —C(O)alkyl, —C(O)Oalkyl, —C(S)—, —SO$_2$—, —S(O)—, —C(S)—, —C(O)NH—, —NHC(O)—, —N(alkyl)C(O)—, —C(O)N(alkyl)-, —O—, —S—, —NH—, —N(alkyl)-, —CH(—O—$R^{26}$)—, —CH(—NHR$^2$)—, —CH(—NH$_2$)—, —CH(—NR$^2_2$)—, —C(—O—$R^{26}$)alkyl-, —C(—NHR$^2$)alkyl-, —C(—NR$^2_2$)alkyl-, —C(R$^{40}$R$^{40}$)—, -alkyl(R$^{27}$)-alkyl(R$^{28}$)—, —C(R$^{27}$R$^{28}$)—, —P(O)(OR$^{26}$)O—, —P(O)(OR$^{26}$)—, —NHC(O)NH—, —N(R$^2$)C(O)N(R$^2$)—, —N(H)C(O)N(R$^2$)—, polyethylene glycol, poly(lactic-co-glycolic acid), alkene, haloalkyl, alkoxy, alkyneheteroarylalkyl, aryl, arylalkyl, heterocycle, aliphatic, heteroaliphatic, heteroaryl, polypropylene glycol, lactic acid, glycolic acid, carbocycle, —O—(CH$_2$)$_{1-12}$—O—, —NH—(CH$_2$)$_{1-12}$—NH—, —NH—(CH$_2$)$_{1-12}$—O—, —O—(CH$_2$)$_{1-12}$—NH—, —S—(CH$_2$)$_{1-12}$—O—, —O—(CH$_2$)$_{1-12}$—S—, —S—(CH$_2$)$_{1-12}$—S—, —S—(CH$_2$)$_{1-12}$—NH—, and —NH—(CH$_2$)$_{1-12}$—S—;

each of which $R^{20}$, $R^{21}$, $R^{22}$, $R^{23}$, and $R^{24}$ is optionally substituted with one or more substituents selected from $R^{101}$;

R²⁶ is selected from the group consisting of hydrogen, alkyl, silane, arylalkyl, heteroarylalkyl, alkene, alkyne, aryl, heteroaryl, heterocyclic, aliphatic and heteroaliphatic;

R²⁷ and R²⁸ are independently selected from the group consisting of hydrogen, alkyl, amine, or together with the carbon atom to which they are attached, form C(O), C(S), C=CH₂, a C3-C6 spirocarbocycle, or a 4-, 5-, or 6-membered spiroheterocycle comprising 1 or 2 heteroatoms selected from N and O, or form a 1 or 2 carbon bridged ring; and R¹⁰¹ is independently selected at each occurrence from the group consisting of hydrogen, alkyl, alkene, alkyne, haloalkyl, alkoxy, hydroxyl, aryl, heteroaryl, heterocycle, arylalkyl, heteroarylalkyl, heterocycloalkyl, aryloxy, heteroaryloxy, CN, —COOalkyl, COOH, NO2, F, Cl, Br, I, CF₃, NH₂, NHalkyl, N(alkyl)₂, aliphatic, and heteroaliphatic.

4. The compound of claim 1, wherein R² is hydrogen.

5. The compound of claim 1, wherein R⁴ is hydrogen.

6. The compound of claim 1, wherein R¹⁰ and R¹¹ are both hydrogen.

7. The compound of claim 1, wherein R¹³ and R¹⁴ are both hydrogen.

8. The compound of claim 1, wherein the compound is selected from the group consisting of:

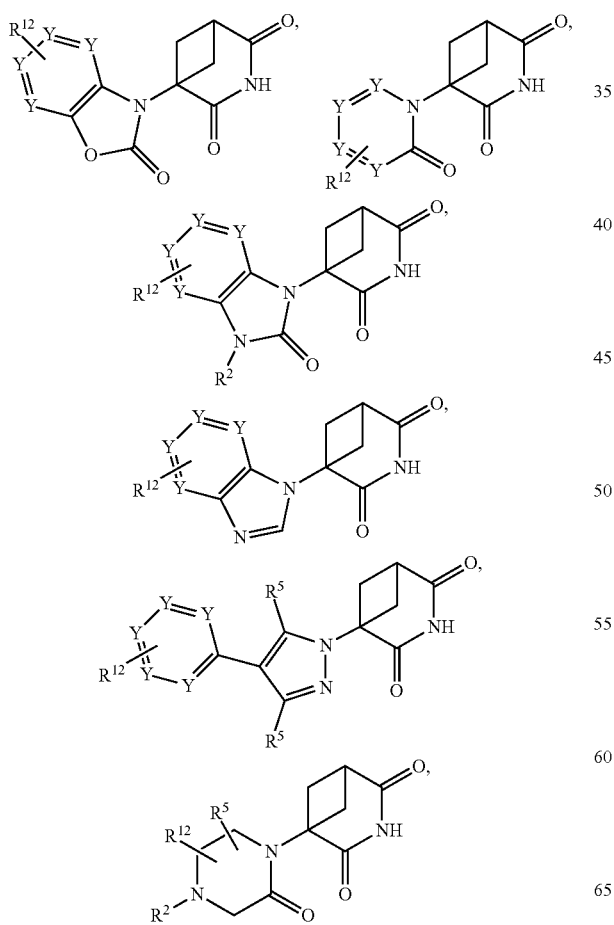

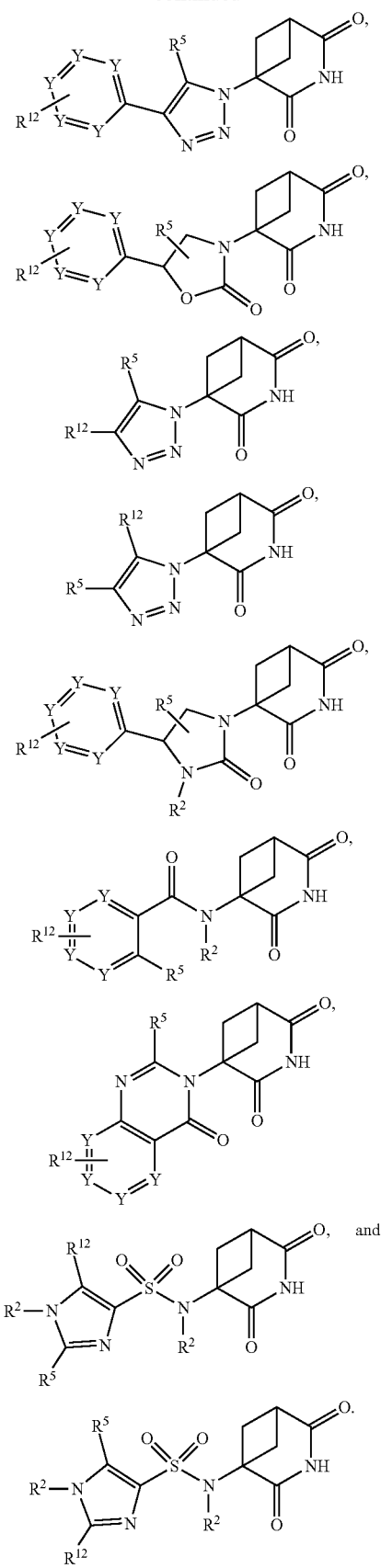

9. The compound of claim 1, wherein the compound is selected from the group consisting of:
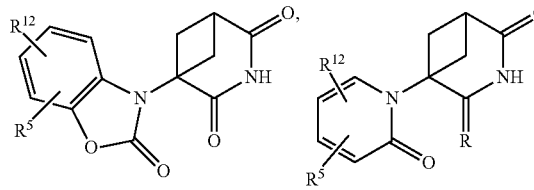
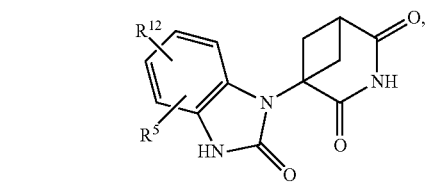
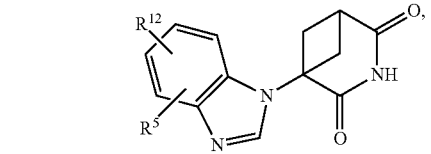
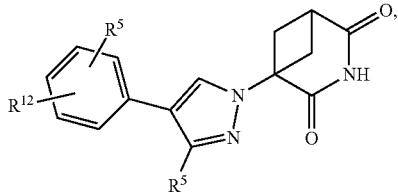
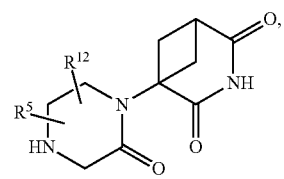
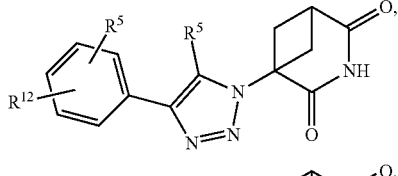
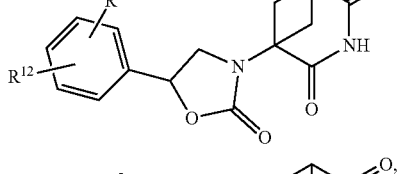
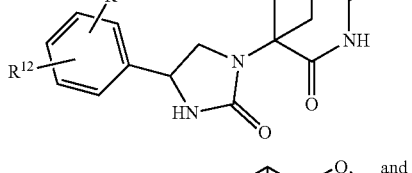
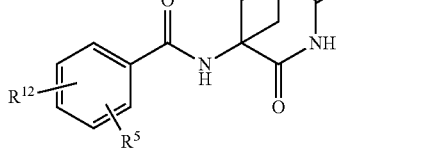 and
-continued
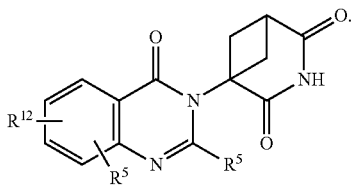
10. The compound of claim 1, wherein $R^{17}$ is
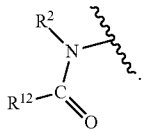
11. The compound of claim 1, wherein $R^{17}$ is
12. The compound of claim 1, wherein $R^{17}$ is
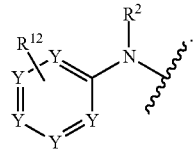
13. The compound of claim 1, wherein $R^{17}$ is selected from the group consisting of:
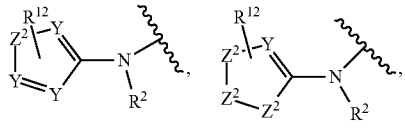
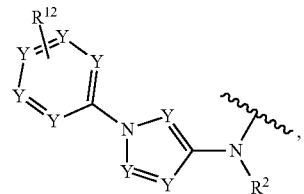
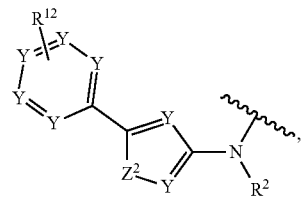

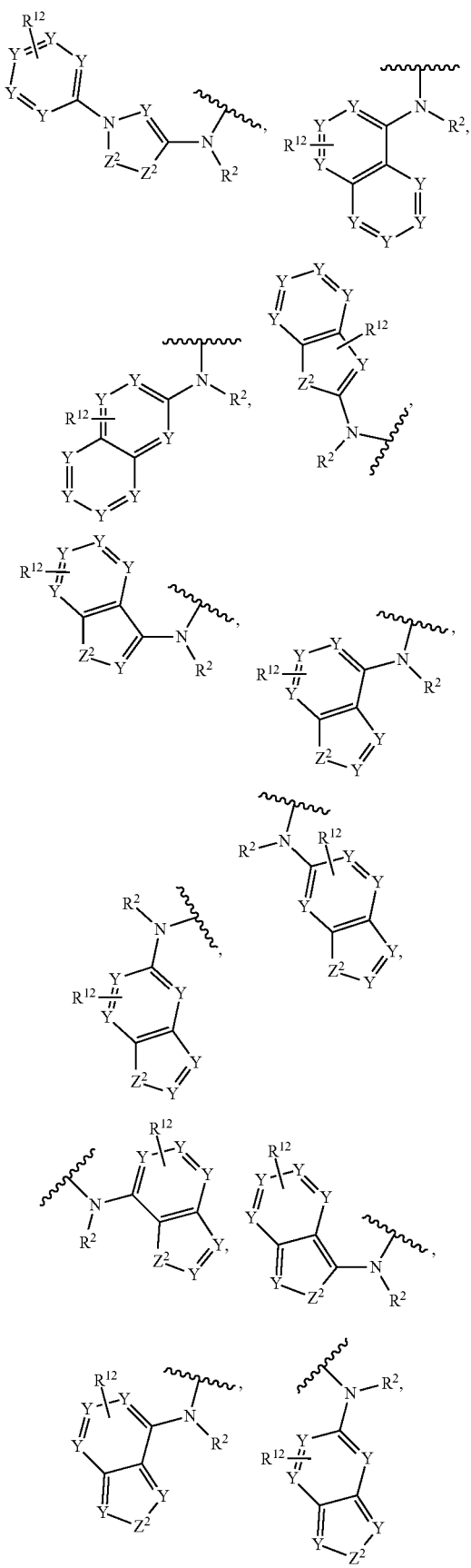

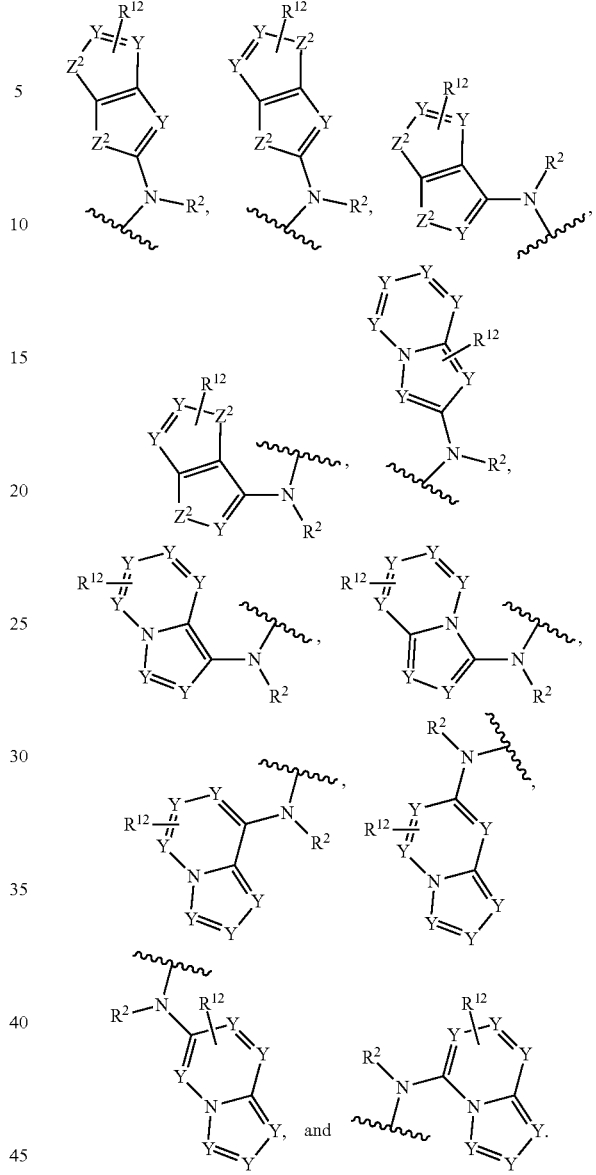

14. The compound of claim 1, wherein the Target Protein is the androgen receptor.

15. The compound of claim 1, wherein the Target Protein is the estrogen receptor.

16. A pharmaceutical composition comprising an effective amount of a compound of claim 1, or a pharmaceutically acceptable salt thereof, and a pharmaceutically acceptable carrier.

17. A method for treating a human with a medical disorder comprising administering an effective amount of a compound of claim 1, or a pharmaceutically acceptable salt thereof, optionally in a pharmaceutically acceptable carrier, wherein the medical disorder is a cancer mediated by the Target Protein, wherein the cancer is selected from prostate cancer, breast cancer, testicular cancer, colon cancer, and melanoma.

18. The method of claim 17, wherein the cancer is selected from the group consisting of colon cancer, prostate cancer, breast cancer, and testicular cancer.

* * * * *